United States Patent
Naito et al.

(10) Patent No.: US 11,185,594 B2
(45) Date of Patent: *Nov. 30, 2021

(54) (ANTI-HER2 ANTIBODY)-DRUG CONJUGATE

(71) Applicant: DAIICHI SANKYO COMPANY, LIMITED, Tokyo (JP)

(72) Inventors: Hiroyuki Naito, Tokyo (JP); Takeshi Masuda, Tokyo (JP); Takashi Nakada, Tokyo (JP); Masao Yoshida, Tokyo (JP); Shinji Ashida, Tokyo (JP); Hideki Miyazaki, Tokyo (JP); Yuji Kasuya, Tokyo (JP); Koji Morita, Tokyo (JP); Yusuke Ogitani, Tokyo (JP); Yuki Abe, Tokyo (JP)

(73) Assignee: DAIICHI SANKYO COMPANY, LIMITED, Tokyo (JP)

(*) Notice: Subject to any disclaimer, the term of this patent is extended or adjusted under 35 U.S.C. 154(b) by 495 days.

This patent is subject to a terminal disclaimer.

(21) Appl. No.: 15/302,803

(22) PCT Filed: Apr. 6, 2015

(86) PCT No.: PCT/JP2015/001922
§ 371 (c)(1),
(2) Date: Oct. 7, 2016

(87) PCT Pub. No.: WO2015/155976
PCT Pub. Date: Oct. 15, 2015

(65) Prior Publication Data
US 2017/0035906 A1    Feb. 9, 2017

(30) Foreign Application Priority Data
Apr. 10, 2014  (JP) .............................. JP2014-081180

(51) Int. Cl.
| | | |
|---|---|---|
| A61K 47/68 | (2017.01) | |
| A61K 31/4745 | (2006.01) | |
| C07K 7/06 | (2006.01) | |
| C07K 16/32 | (2006.01) | |
| A61K 39/395 | (2006.01) | |
| C07K 16/30 | (2006.01) | |

(52) U.S. Cl.
CPC ...... *A61K 47/6871* (2017.08); *A61K 31/4745* (2013.01); *A61K 39/395* (2013.01); *A61K 47/6803* (2017.08); *C07K 7/06* (2013.01); *C07K 16/30* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3061* (2013.01); *C07K 16/3069* (2013.01); *C07K 16/32* (2013.01)

(58) Field of Classification Search
None
See application file for complete search history.

(56) References Cited

U.S. PATENT DOCUMENTS

| | | |
|---|---|---|
| 5,677,171 A | 10/1997 | Hudziak et al. |
| 5,821,337 A | 10/1998 | Carter et al. |
| 5,834,476 A | 11/1998 | Terasawa et al. |

(Continued)

FOREIGN PATENT DOCUMENTS

| | | |
|---|---|---|
| CA | 2927832 A1 | 11/2011 |
| CA | 2859255 A1 | 6/2013 |

(Continued)

OTHER PUBLICATIONS

Russian Office Action dated Mar. 5, 2019 in corresponding application No. 2016143351.
Sievers et al, Antibody-Drug Conjugates in Cancer Therapy, Annual Review of Medicine, 2013, vol. 64, No. 1, pp. 15-29.
United States Office Action dated Apr. 5, 2019 in U.S. Appl. No. 15/821,697.
Taiwanese Patent Office, "Allowance", issued in connection with Taiwanese Patent Application No. 104103127,dated Apr. 11, 2018.
Canadian Office Action dated Apr. 13, 2018 in corresponding application No. 2939802.
Burke, Patrick J. et al., Design, Synthesis, and Biological Evaluation of Antibody—Drug Conjugates Comprised of Potent Camptothecin Analogues, Bioconjugate Chemistry, Jun. 17, 2009, vol. 20, No. 6, pp. 1242-1250.

(Continued)

*Primary Examiner* — Patricia Duffy
(74) *Attorney, Agent, or Firm* — Foley & Lardner LLP

(57) ABSTRACT

As an antitumor drug which is excellent in terms of antitumor effect and safety and has an excellent therapeutic effect, there is provided an antibody-drug conjugate in which an antitumor compound represented by the following formula is conjugated to an anti-HER2 antibody via a linker having a structure represented by the formula: $L^1$-$L^2$-$L^P$-NH—$(CH_2)n^1$-$L^a$-$L^b$-$L^c$ or -$L^1$-$L^2$-$L^P$- wherein the anti-HER2 antibody is connected to the terminal $L^1$, and the antitumor compound is connected to the terminal $L^c$ or $L^P$ with the nitrogen atom of the amino group at position 1 as the connecting position.

[Formula 1]

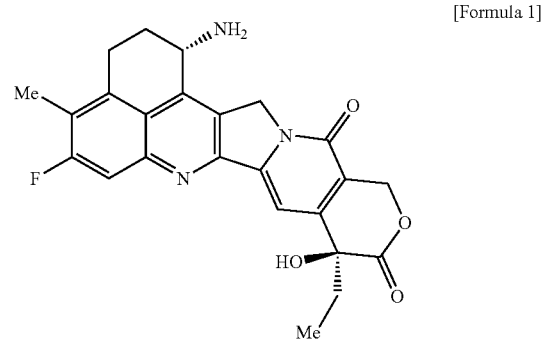

11 Claims, 5 Drawing Sheets
Specification includes a Sequence Listing.

(56) References Cited

U.S. PATENT DOCUMENTS

| | | | |
|---|---|---|---|
| 5,837,673 | A | 11/1998 | Tsujihara et al. |
| 5,892,043 | A | 4/1999 | Tsujihara et al. |
| 6,214,345 | B1 | 4/2001 | Firestone et al. |
| 6,291,671 | B1 | 9/2001 | Inoue et al. |
| 6,835,807 | B1 | 12/2004 | Susaki et al. |
| 7,449,184 | B2 | 11/2008 | Allison et al. |
| 7,585,491 | B2 | 9/2009 | Govindan |
| 7,837,980 | B2 | 11/2010 | Alley et al. |
| 8,802,820 | B2 * | 8/2014 | Chamberlain ....... C07K 16/082 530/350 |
| 2003/0148931 | A1 | 8/2003 | Takahashi et al. |
| 2003/0166513 | A1 | 9/2003 | Imura et al. |
| 2004/0185053 | A1 | 9/2004 | Govindan |
| 2005/0123536 | A1 | 6/2005 | Law et al. |
| 2005/0271671 | A1 | 12/2005 | Griffiths |
| 2005/0276812 | A1 | 12/2005 | Ebens et al. |
| 2006/0018899 | A1 | 1/2006 | Kao et al. |
| 2006/0193865 | A1 | 8/2006 | Govindan |
| 2007/0071764 | A1 | 3/2007 | Sullivan et al. |
| 2008/0050310 | A1 | 2/2008 | Ebens et al. |
| 2008/0131363 | A1 | 6/2008 | Govindan et al. |
| 2008/0161245 | A1 | 7/2008 | Kratz et al. |
| 2008/0305044 | A1 | 12/2008 | McDonagh et al. |
| 2009/0274713 | A1 | 11/2009 | Chari et al. |
| 2009/0286258 | A1 | 11/2009 | Kaur et al. |
| 2011/0059076 | A1 | 3/2011 | McDonagh et al. |
| 2011/0070248 | A1 | 3/2011 | Ichikawa et al. |
| 2011/0293513 | A1 | 12/2011 | Govindan et al. |
| 2012/0121615 | A1 | 5/2012 | Flygare et al. |
| 2012/0171201 | A1 | 7/2012 | Sapra |
| 2012/0201809 | A1 | 8/2012 | Bhat et al. |
| 2013/0123178 | A1 | 5/2013 | Dimarchi et al. |
| 2015/0297748 | A1 | 10/2015 | Masuda et al. |
| 2015/0352224 | A1 | 12/2015 | Naito et al. |
| 2016/0287722 | A1 | 10/2016 | Govindan |

FOREIGN PATENT DOCUMENTS

| | | |
|---|---|---|
| CN | 101023100 A | 8/2007 |
| CN | 101490087 A | 7/2009 |
| CN | 102481364 A | 5/2012 |
| EP | 0 495 432 A1 | 7/1992 |
| EP | 0 737 686 A1 | 10/1996 |
| EP | 0 916 348 A1 | 5/1999 |
| EP | 1 155 702 A1 | 11/2001 |
| EP | 2 907 824 A1 | 8/2015 |
| JP | H05-059061 A | 3/1993 |
| JP | H08-337584 A | 12/1996 |
| JP | H10-095802 A | 4/1998 |
| JP | H1171280 A | 3/1999 |
| JP | H11-092405 A | 4/1999 |
| JP | 2002-060351 A | 2/2002 |
| JP | 2005-511627 A | 4/2005 |
| JP | 2006-511526 A | 4/2006 |
| JP | 2008-521828 A | 6/2008 |
| JP | 2009-538629 A | 11/2009 |
| JP | 2011-519864 A | 7/2011 |
| JP | 2011-524001 A | 8/2011 |
| JP | 2012-509259 A | 4/2012 |
| JP | 2012-100671 A | 5/2012 |
| JP | 2013-500253 A | 1/2013 |
| JP | 2013-534535 A | 9/2013 |
| JP | 2013-534906 A | 9/2013 |
| KR | 1020010052385 A | 6/2001 |
| KR | 1020110044808 A | 4/2011 |
| RU | 2404810 C2 | 7/2008 |
| TW | I232930 | 5/2005 |
| TW | 200817434 | 4/2008 |
| WO | WO-97/46260 A1 | 12/1997 |
| WO | WO-00/25825 A1 | 5/2000 |
| WO | WO-01/00244 A2 | 1/2001 |
| WO | WO-02/00734 A1 | 1/2002 |
| WO | WO 03/043583 A2 | 5/2003 |
| WO | WO-2005/112919 A2 | 12/2005 |
| WO | WO 2006/065533 A2 | 6/2006 |
| WO | WO 2006/092230 A2 | 9/2006 |
| WO | WO-2011/011474 A1 | 1/2011 |
| WO | WO-2011/068845 A1 | 6/2011 |
| WO | WO 2013/163229 A1 | 10/2013 |
| WO | WO 2013/188740 A1 | 12/2013 |
| WO | WO-2014/057687 A1 | 4/2014 |
| WO | WO-2014/061277 A1 | 4/2014 |
| WO | WO-2014/107024 A1 | 7/2014 |

OTHER PUBLICATIONS

Extended European Search Report issued in corresponding Application No. 15743738.5 dated Aug. 9, 2017.

Extended European Search Report issued in corresponding Application No. 15776810.2 dated Aug. 11, 2017.

Behrens et al, Methods for site-specific drug conjugation to antibodies, mAbs, 2014, vol. 6, No. 1. pp. 46-53.

Korean Office Action dated May 1, 2018 in corresponding application No. 10-2016-7015961.

Shen et al, Conjugation site modulates the in vivo stability and therapeutic activity of antibody-drug conjugates, Nature Biotechnology, 2012, vol. 30, pp. 184-189.

Taiwanese Office Action dated Jul. 30, 2018 in corresponding application No. 104111534.

Acchione et al, Impact of linker and conjugation chemistry on antigen binding, Fc receptor binding and thermal stability of model antibody-drug conjugates, mAbs, 2012, pp. 362-372.

Colombian Reconsideration Petition dated Mar. 15, 2018 in corresponding application No. NC2016/0000187.

Rowinsky, Preclinical and Clinical Development of Exatecan(DX-8951f), Camptothecins in Cancer Therapy, 2005, pp. 317-318.

Office Action issued in U.S. Appl. No. 15/187,179 dated Oct. 21, 2016.

Office Action issued in Chinese Application No. 201380053256.2 dated Nov. 1, 2016.

Notice of Allowance issued in Japanese Application No. 2016-166850 dated Oct. 18, 2016.

Office Action issued in Japanese Application No. 2016-540705 dated Dec. 6, 2016.

Russian Office Action dated Oct. 11, 2018 in corresponding application No. 2016123597.

Barok et al, Trastuzumab-DM1 is highly effective in preclinical models of HER2-positive gastric cancer, Cancer Letters, 2011, vol. 306, No. 2, pp. 172-179.

Oguma et al, Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry, Biomedical Chromatography, 2005, vol. 19, No. 1, pp. 19-26.

Adams et al., "Humanization of a recombinant monoclonal antibody to produce a therapeutic HER dimerization inhibitor, pertuzumab," Cancer Immunol. Immunother. 55:717-727 (2006).

Alley et al., "Antibody-drug conjugates: targeted drug delivery for cancer," Current Opinion in Chemical Biology 14:529-537 (2010).

Barginear et al., "Trastuzumab-DM1: A Review of the Novel Immuno-Conjugate for HER2-Overexpressing Breast Cancer," The Open Breast Cancer Journal 1:25-30 (2009).

Baselga et al., "Phase II Study of Weekly Intravenous Recombinant Humanized Anti-p185$^{HER2}$ Monoclonal Antibody in Patients with HER2/neu-Overexpressing Metastatic Breast Cancer," J. Clin. Oncol. 14(3):737-744 (Mar. 1996).

Beck, Alain, "The Next Generation of Antibody-drug Conjugates Comes of Age," Discovery Medicine 10(53):329-339 (Oct. 16, 2010).

Burris, III et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," J. Clin. Oncol. 29(4):398-405 (Feb. 2011).

Coussens et al., "Tyrosine Kinase Receptor with Extensive Homology to EGF Receptor Shares Chromosomal Location with neu Oncogene," Science 230(4730):1132-1139 (Dec. 1985).

(56) References Cited

OTHER PUBLICATIONS

Damle, Nitin K., "Tumour-targeted chemotherapy with immunoconjugates of calicheamicin," Expert Opin. Biol. Ther. 4(9):1445-1452 (2004).
De Jager et al., "DX-8951f: Summary of Phase I Clinical Trials," Ann. N.Y. Acad. Sci. 922:260-273 (2000).
Di Fiore et al., "erbB-2 Is a Potent Oncogene When Overexpressed in NIH/3T3 Cells," Science 237:178-182 (Jul. 1987).
Ducry et al., "Antibody—Drug Conjugates: Linking Cytotoxic Payloads to Monoclonal Antibodies," Bioconjugate Chem. 21:5-13 (2010).
Fendly et al., "Characterization of Murine Monoclonal Antibodies Reactive to Either the Human Epidermal Growth Factor Receptor or HER2/neu Gene Product," Cancer Research 50:1550-1558 (1990).
Fukushige et al., "Localization of a Novel v-erbB-Related Gene, c-erbB-2, on Human Chromosome 17 and Its Amplification in a Gastric Cancer Cell Line," Mol. Cell. Biol. 6(3):955-958 (1986).
Graus-Porta et al., "ERbB-2, the preferred heterodimerization partner of all ErbB receptors, is a mediator of lateral signaling," EMBO J. 16(7):1647-1655 (1997).
Gravalos et al., "HER2 in gastric cancer: a new prognostic factor and a novel therapeutic target," Ann. Oncol. 19:1523-1529 (2008).
Hardwick et al., "Immunohistochemical detection of p53 and c-erbB-2 in oesophageal carcinoma; no correlation with prognosis," Eur. J. Surg. Oncol. 23:30-35 (1997).
Hudis, M.D., Clifford A., "Trastuzumab—Mechanism of Action and Use in Clinical Practice," N. Engl. J. Med. 357(1):39-51 (2007).
Hudziak et al., "Increased expression of the putative growth factor receptor p185$^{HER2}$ causes transformation and tumorigenesis of NIH 3T3 cells," Proc. Natl. Acad. Sci. USA 84:7159-7163 (1987).
Inoue et al., "CM-Dextran-Polyalcohol-Camptothecin Conjugate: DE-310 with a Novel Carrier System and Its Preclinical Data," Polymer Drugs in the Clinical Stage, 145-153 (2003).
Joto et al., "DX-8951F, A Water-Soluble Camptothecin Analog, Exhibits Potent Antitumor Activity Against a Human Lung Cancer Cell Line and its SN-38-Resistant Variant," Int. J. Cancer 72:680-686 (1997).
Kaptain et al., "Her-2/neu and Breast Cancer," Diagn. Mol. Pathol. 10(3):139-152 (2001).
Karunagaran et al., "ErbB-2 is a common auxiliary subunit of NDF and EGF receptors: implications for breast cancer," EMBO J. 15(2):254-264 (1996).
Korkaya et al., "HER2 regulates the mammary stem/progenitor cell population driving tumorigenesis and invasion," Oncogene 27:6120-6130 (2008).
Kumazawa et al., "Antitumor activity of DX-8951f: a new camptothecin derivative," Exp. Opin. Invest. Drugs 7(4):625-632 (1998).
Kumazawa et al., "De-310, a novel macromolecular carrier system for the camptothecin analog DX-8951f: Potent antitumor activities in various murine tumor models," Cancer Sci. 95(2):168-175 (Feb. 2004).
Kumazawa et al., "Potent and broad antitumor effects of DX-8951f, a water-soluble camptothecin derivative, against various human tumors xenografted in nude mice," Cancer Chemother. Pharmacol. 42:210-220 (1998).
Mitsui et al., "A New Water-soluble Camptothecin Derivative, DX-8951f, Exhibits Potent Antitumor Activity against Human Tumors in vitro and in vivo," Jpn. J. Cancer Res. 86:776-782 (Aug. 1995).
Nakada et al., "Novel antibody drug conjugates containing exatecan derivative-based cytotoxic payloads," Bioorganic & Medical Chemistry Letters 26(6):1542-1545 (2016).
Senter et al., "The discovery and development of brentuximab vedotin for use in relapsed Hodgkin lymphoma and systemic anaplastic large cell lymphoma," Nature Biotechnology 30(7):631-637 (Jul. 2012).
Slamon et al., "Human Breast Cancer: Correlation of Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Sliwkowski et al., "Coexpression of erbB2 and erbB3 Proteins Reconstitutes a High Affinity Receptor for Heregulin." J. Biol. Chem. 269(20):14661-14665 (1994).
Sliwkowski et al., "Nonclinical Studies Addressing the Mechanism of Action of Trastuzumab (Herceptin)," Semin. Oncol. 26(4) Suppl. 12:60-70 (Aug. 1999).
Soepenberg et al., "Phase I and Pharmacokinetic Study of DE-310 in Patients with Advanced Solid Tumors," Clin. Cancer Res. 11:703-711 (Jan. 15, 2005).
Takiguchi et al., "Antitumor Effect of DX-8951, a Novel Camptothecin Analog, on Human Pancreatic Tumor Cells and Their CPT-11-resistant Variants Cultured in vitro and Xeografted in Nude Mice," Jpn. J. Cancer Res. 88:760-769 (Aug. 1997).
Vogel et al., "Efficacy and Safety of Trastuzumab as a Single Agent in First-Line Treatment of HER2-Overexpressing Metastatic Breast Cancer," J. Clin. Oncol. 20(3):719-726 (Feb. 2002).
Wente et al., "DE-310, a macromolecular prodrug of the topoisomerase-1-inhibitor exatecan (DX-8951), in patients with operable solid tumors," Investigational New Drugs 23:339-347 (2005).
Yano et al., "Comparison of HER2 gene amplification assessed by fluorescence in situ hybridization and HER2 protein expression assessed by immunohistochemistry in gastric cancer," Oncol. Rep. 15:65-71 (2006).
International Search Report issued in International Patent Application No. PCT/JP2015/001922 dated May 26, 2015.
Esteva et al., A Phase II Study of Intravenous Exatecan Mesylate (DX-8951f) Administered Daily for 5 Days Every 3 Weeks to Patients with Metastatic Breast Carcinoma, American Cancer Society, 2003,900-907.
International Search Report dated Nov. 21, 2017 on corresponding application No. PCT/JP2017/036215.
Office Action dated Jul. 7, 2017 in U.S. Appl. No. 15/221,851.
Office Action dated May 15, 2017 in Taiwanese Patent Application No. 102136742.
European Search Report issued in corresponding application No. 14874745 dated May 10, 2017.
N. Masucuchi, "Pharmacokinetics of DE-310, a novel macromolecular carrier system for the camptothecin analog DX-8951f, in tumor-bearing mice," Pharmazie 59: 374-377 (2004).
Office Action issued in Canada Application No. 2885800 dated Mar. 28, 2017.
Office Action issued in Colombia Application No. NC2016/0000187 dated May 9, 2017.
Otto Soepenberg, "Liquid chromatographic assays for DE-310, a novel camptothecin analog, and two major enzymatic products in human matrices," Journal of Chromatography B, 799, 15-22 (2004).
Thomas M. Cardillo, "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research vol. 17, No. 10, Mar. 3, 2011, pp. 3157-3169.
Yoshinobu Shiose, "Systematic Research of Peptide Spacers Controlling Drug Release from Macromolecular Prodrug System, Carboxymethyldextran Polyalcohol-Peptide-Drug Conjugates," Bioconjugate Chem. 20, 60-70 (2009).
Yusuke Ochi, "A possible mechanism for the long-lasting antitumor effect of the macromolecular conjugate DE-310: mediation by cellular uptake and drug release of its active camptothecin analog DX-8951," Cancer Chemother Pharmacol (2005) 55: 323-332.
India Office Action issued in the corresponding Indian Patent Application Ser. No. 201647013640, dated Jul. 19, 2019 (6 pages).

* cited by examiner

FIG.1

SEQ ID NO 1 : - Amino acid sequence of heavy chain of humanized anti-HER2 monoclonal antibody
EVQLVESGGGLVQPGGSLRLSCAASGFNIKDTYIHWVRQAPGKGLEWVARIYPTNGYTRYADS
VKGRFTISADTSKNTAYLQMNSLRAEDTAVYYCSRWGGDGFYAMDYWGQGTLVTVSSASTKG
PSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEALHNHYT
QKSLSLSPGK

FIG. 2

SEQ ID NO 2 :- Amino acid sequence of light chain of humanized anti-HER2 monoclonal antibody
DIQMTQSPSSLSASVGDRVTITCRASQDVNTAVAWYQQKPGKAPKLLIYSASFLYSGVPSRFS
GSRSGTDFTLTISSLQPEDFATYYCQQHYTTPPTFGQGTKVEIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC

(ANTI-HER2 ANTIBODY)-DRUG CONJUGATE

CROSS-REFERENCE TO RELATED APPLICATIONS

The present application is a U.S. national stage application of International Patent Application No. PCT/JP2015/001922, filed Apr. 6, 2015, which claims the benefit of priority to Japanese Patent Application No. 2014-081180, filed Apr. 10, 2014, the entireties of which are hereby incorporated by reference.

SEQUENCE LISTING

The instant application contains a Sequence Listing which has been submitted electronically in ASCII format and is hereby incorporated by reference in its entirety. Said ASCII copy, created on Apr. 13, 2017, is named 111119-0110_SL.txt and is 10,223 bytes in size.

TECHNICAL FIELD

The present invention relates to an antibody-drug conjugate having an antitumor drug conjugated to an anti-HER2 antibody via a linker structure moiety, the conjugate being useful as an antitumor drug.

BACKGROUND ART

An antibody-drug conjugate (ADC) having a drug with cytotoxicity conjugated to an antibody, whose antigen is expressed on the surface of cancer cells and which also binds to an antigen capable of cellular internalization, and therefore can deliver the drug selectively to cancer cells, is thus expected to cause accumulation of the drug within cancer cells and to kill the cancer cells (see, Non-patent Literatures 1 to 3). As an ADC, Mylotarg (registered trademark; Gemtuzumab ozogamicin) in which calicheamicin is conjugated to an anti-CD33 antibody is approved as a therapeutic agent for acute myeloid leukemia. Further, Adcetris (registered trademark; Brentuximab vedotin), in which auristatin E is conjugated to an anti-CD30 antibody, has recently been approved as a therapeutic agent for Hodgkin's lymphoma and anaplastic large cell lymphoma (see, Non-patent Literature 4). The drugs contained in ADCs which have been approved until now target DNA or tubulin.

With regard to an antitumor agent, camptothecin derivatives, low-molecular-weight compounds that inhibit topoisomerase I to exhibit an antitumor effect, are known. Among these, an antitumor compound represented by the formula below

[Formula 1]

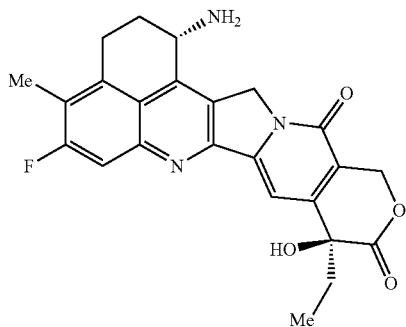

(exatecan, chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13(9H,15H)-dione) is known (Patent Literatures 1 and 2). Unlike irinotecan currently used in clinical settings, this compound does not require activation by an enzyme for exhibiting its antitumor effect. Further, its inhibitory activity on topoisomerase I was observed to be higher than SN-38 which is the main pharmaceutically active substance of irinotecan and topotecan also used in clinical settings, and higher in vitro cytocidal activity was confirmed against various cancer cells. In particular, it was confirmed to have the effect against cancer cells that have resistance to SN-38 or the like due to expression of P-glycoprotein. Further, in a human tumor subcutaneously transplanted mouse model, it was confirmed to have a potent antitumor effect, and thus has undergone clinical studies, but has not been placed on the market yet (see, Non-patent Literatures 5 to 10). It remains unclear whether or not exatecan acts effectively as an ADC.

DE-310 is a complex in which exatecan is conjugated to a biodegradable carboxymethyldextran polyalcohol polymer via a GGFG peptide spacer (SEQ ID NO: 3) (Patent Literature 3). By converting exatecan into the form of a polymer prodrug, a high blood retention property can be maintained and also a high targeting property to tumor areas is passively increased by utilizing the increased permeability of newly formed blood vessels within tumors and retention property in tumor tissues. With DE-310, through cleavage of the peptide spacer by enzyme, exatecan and exatecan with glycine connected to an amino group are continuously released as main active substance, and as a result, the pharmacokinetics are improved. DE-310 was found to have higher effectiveness than exatecan administered alone even though the total dosage of exatecan contained in D310 is lower than in the case of administration of exatecan alone according to various tumor evaluation models in non-clinical studies. A clinical study was conducted for DE-310, and effective cases were also confirmed, including a report suggesting that the main active substance accumulates in tumors more than in normal tissues. However, there is also a report indicating that accumulation of DE-310 and the main active substance in tumors is not much different from accumulation in normal tissues in humans, and thus no passive targeting is observed in humans (see, Non-patent Literatures 11 to 14). As a result, DE-310 was not also commercialized, and it remains unclear whether or not exatecan effectively acts as a drug directed to such targeting.

As a compound relating to DE-310, a complex in which a structure moiety represented by —NH—(CH$_2$)$_4$—C(=O)— is inserted between the -GGFG (SEQ ID NO: 3)-spacer and exatecan to form -GGFG (SEQ ID NO: 3)-NH—(CH$_2$)$_4$—C(=O)— used as a spacer structure is also known (Patent Literature 4). However, the antitumor effect of said complex is not known at all.

HER2 is one of the products of a typical growth factor receptor type oncogene identified as human epidermal cell growth factor receptor 2-related oncogene, and is a transmembrane receptor protein having a molecular weight of 185 kDa and having a tyrosine kinase domain (Non-patent Literature 15). The DNA sequence and amino acid sequence of HER2 are disclosed on a public database, and can be referred to, for example, under Accession No. M11730 (GenBank), NP_004439.2 (NCBI), or the like.

HER2 (neu, ErbB-2) is one of the members of the EGFR (epidermal growth factor receptor) family and is activated by autophosphorylation at intracellular tyrosine residues by its homodimer formation or heterodimer formation with another EGFR receptor HER1 (EGFR, ErbB-1), HER3 (ErbB-3), or HER4 (ErbB-4) (Non-patent Literatures 16 to 18), thereby playing an important role in cell growth, differentiation, and survival in normal cells and cancer cells (Non-patent Literatures 19 and 20). HER2 is overexpressed in various cancer types such as breast cancer, gastric cancer, and ovarian cancer (Non-patent Literatures 21 to 26) and has been reported to be a negative prognosis factor for breast cancer (Non-patent Literatures 27 and 28).

Trastuzumab is a humanized antibody of a mouse anti-HER2 antibody 4D5 (Non-patent Literature 29 and Patent Literature 5), named as recombinant humanized anti-HER2 monoclonal antibody (huMAb4D5-8, rhuMAb HER2, Herceptin®) (Patent Literature 6). Trastuzumab specifically binds to the extracellular domain IV of HER2 and induces antibody-dependent cellular cytotoxicity (ADCC) or exerts an anticancer effect via the inhibition of signal transduction from HER2 (Non-patent Literatures 30 and 31). Trastuzumab is highly effective for tumors overexpressing HER2 (Non-patent Literature 32) and as such, was launched in 1999 in the USA and in 2001 in Japan as a therapeutic agent for patients with metastatic breast cancer overexpressing HER2.

Although the therapeutic effect of trastuzumab on breast cancer has been adequately proven (Non-patent Literature 33), allegedly about 15% of patients with breast cancer overexpressing HER2 who have received a wide range of conventional anticancer therapies are responders to trastuzumab. About 85% of patients of this population have no or merely weak response to trastuzumab treatment.

Thus, the need for a therapeutic agent targeting HER2 expression-related diseases has been recognized for patients affected by tumors overexpressing HER2 with no or weak response to trastuzumab or HER2-related disorders. T-DM1 (trastuzumab emtansine, Kadcyla®; Non-patent Literature 34) having an antitumor drug conjugated to trastuzumab via a linker structure, and pertuzumab (Perjeta®; Non-patent Literature 35 and Patent Literature 7) designed to target the extracellular domain II of HER2 and inhibit heterodimer formation have been developed. However, their responsiveness, activity strength, and accepted indications are still insufficient, and there are unsatisfied medical needs for therapeutic targeting HER2.

CITATION LIST

Patent Literatures

[Patent Literature 1] Japanese Patent Laid-Open No. 5-59061
[Patent Literature 2] Japanese Patent Laid-Open No. 8-337584
[Patent Literature 3] International Publication No. WO 1997/46260
[Patent Literature 4] International Publication No. WO 2000/25825
[Patent Literature 5] U.S. Pat. No. 5,677,171
[Patent Literature 6] U.S. Pat. No. 5,821,337
[Patent Literature 7] International Publication No. WO 01/00244

Non-Patent Literatures

[Non-patent Literature 1] Ducry, L., et al., Bioconjugate Chem. (2010) 21, 5-13.
[Non-patent Literature 2] Alley, S. C., et al., Current Opinion in Chemical Biology (2010) 14, 529-537.
[Non-patent Literature 3] Damle N. K. Expert Opin. Biol. Ther. (2004) 4, 1445-1452.
[Non-patent Literature 4] Senter P. D., et al., Nature Biotechnology (2012) 30, 631-637.
[Non-patent Literature 5] Kumazawa, E., Tohgo, A., Exp. Opin. Invest. Drugs (1998) 7, 625-632.
[Non-patent Literature 6] Mitsui, I., et al., Jpn J. Cancer Res. (1995) 86, 776-782.
[Non-patent Literature 7] Takiguchi, S., et al., Jpn J. Cancer Res. (1997) 88, 760-769.
[Non-patent Literature 8] Joto, N. et al. Int J Cancer (1997) 72, 680-686.
[Non-patent Literature 9] Kumazawa, E. et al., Cancer Chemother. Pharmacol. (1998) 42, 210-220.
[Non-patent Literature 10] De Jager, R., et al., Ann N Y Acad Sci (2000) 922, 260-273.
[Non-patent Literature 11] Inoue, K. et al., Polymer Drugs in the Clinical Stage, Edited by Maeda et al. (2003) 145-153.
[Non-patent Literature 12] Kumazawa, E. et al., Cancer Sci (2004) 95, 168-175.
[Non-patent Literature 13] Soepenberg, O. et al; Clinical Cancer Research, (2005) 11, 703-711.
[Non-patent Literature 14] Wente M. N. et al., Investigational New Drugs (2005) 23, 339-347.
[Non-patent Literature 15] Coussens L, et al., Science. 1985; 230 (4730):1132-1139.
[Non-patent Literature 16] Graus-Porta G, et al., EMBO J. 1997; 16; 647-1655.
[Non-patent Literature 17] Karnagaran D, et al., EMBO J. 1996; 15: 254-264.
[Non-patent Literature 18] Sliwkowski M X, et al., J. Biol. Chem. 1994; 269: 14661-14665.
[Non-patent Literature 19] Di Fore P P, et al., Science. 1987; 237: 178-182.
[Non-patent Literature 20] Hudziak R M, et al., Proc Natl Acad Sci USA. 1987; 84: 7159-7163.
[Non-patent Literature 21] Hardwick R, et al., Eur. J Surg Oncol. 1997 (23): 30-35.
[Non-patent Literature 22] Korkaya H, et al., Oncogene. 2008/27 (47): 6120-6130.
[Non-patent Literature 23] Yano T, et al., Oncol Rep. 2006; 15(1): 65-71.
[Non-patent Literature 24] Slamon D J, et al., Science. 1987; 235: 177-182.
[Non-patent Literature 25] Gravalos C, et al., Ann Oncol 19: 1523-1529, 2008.
[Non-patent Literature 26] Fukushige S et al., Mol Cell Biol 6: 955-958, 1986.
[Non-patent Literature 27] Slamon D J, et al. Science. 1989; 244: 707-712.
[Non-patent Literature 28] Kaptain S et al., Diagn Mol Pathol 10: 139-152, 2001.
[Non-patent Literature 29] Fendly. et al., Cancer Research 1990 (50): 1550-1558.
[Non-patent Literature 30] Sliwkowski M X, et al., Semin Oncol. 1999; 26 (4,Suppl 12): 60-70.
[Non-patent Literature 31] Hudis C A, et al., N Engl J Med. 357: 39-51, 2007.
[Non-patent Literature 32] Vogel C L, et al., J Clin Oncol. 2002; 20 (3):719-726.
[Non-patent Literature 33] Baselga et al., J. Clin. Oncol. 14: 737-744 (1996).
[Non-patent Literature 34] Howard A. et al., J Clin Oncol 2011; 29: 398-405.
[Non-patent Literature 35] Adams C W, et al., Cancer Immunol Immunother. 2006; 6: 717-727.

SUMMARY OF INVENTION

Technical Problem

With regard to the treatment of tumors by antibodies, an insufficient antitumor effect may be observed even when the antibody recognizes an antigen to bind to tumor cells, and there are cases in which a more effective antitumor antibody is needed. Further, many antitumor low-molecular-weight compounds have problems in safety like side effects and toxicity even if the compounds have an excellent antitumor effect. It has remained an objective to achieve a superior therapeutic effect by further enhancing safety. Thus, an object of the present invention is to provide an antitumor drug having an excellent therapeutic effect, which is excellent in terms of antitumor effect and safety.

Solution to Problem

The inventors considered that an anti-HER2 antibody is an antibody which is capable of targeting tumor cells, that is, having a property of recognizing tumor cells, a property of binding to tumor cells, a property of internalizing within tumor cells, a cytotoxic activity against tumor cells, a cytocidal activity against tumor cells, or the like; thus, when the antitumor compound exatecan is converted into an antibody-drug conjugate, via a linker structure moiety, by conjugation to this antibody, the antitumor compound can be more surely delivered to tumor cells to specifically exhibit the antitumor effect of the compound in tumor cells, and thus the antitumor effect can be surely exhibited and also an enhanced cytocidal effect of the anti-HER2 antibody can be expected, and the dose of the antitumor compound can be reduced compared to the case of administering the compound alone, and thus influences of the antitumor compound on normal cells can be alleviated so that a higher safety can be achieved.

In this connection, the inventors created a linker with a specific structure and succeeded in obtaining an antibody-drug conjugate in which the anti-HER2 antibody and exatecan are conjugated to each other via the linker, and confirmed an excellent antitumor effect exhibited by the conjugate to thereby complete the present invention.

Specifically, the present invention relates to the following.

[1] An antibody-drug conjugate wherein an antitumor compound represented by the following formula:

[Formula 2]

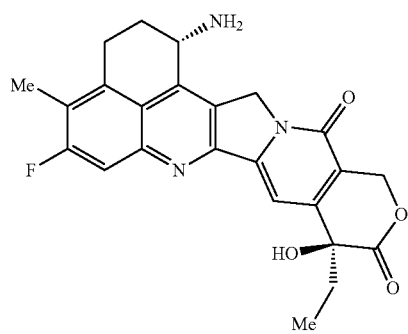

is conjugated to an anti-HER2 antibody via a linker having a structure represented by the following formula:

-$L^1$-$L^2$-$L^P$-NH—(CH$_2$)$n^1$-$L^a$-$L^b$-$L^c$- or -$L^1$-$L^2$-$L^P$-.

Here, the anti-HER2 antibody is connected to the terminal $L^1$, the antitumor compound is connected to the terminal $L^c$ or $L^P$ with the nitrogen atom of the amino group at position 1 as the connecting position, wherein $n^1$ represents an integer of 0 to 6, $L^1$ represents -(Succinimid-3-yl-N)—(CH$_2$)$n^2$-C(=O)—, -(Succinimid-3-yl-N)—CH[—(CH$_2$)$n^3$-COOH]—C(=O)—, -(Succinimid-3-yl-N)—CH$_2$CH$_2$—[N(—CH$_2$—COOH)]—CH$_2$—(C=O)—, —CH$_2$—C(=O)—NH—(CH$_2$)$n^4$-C(=O)—, —C(=O)-cyc.Hex (1,4)-CH$_2$—(N-ly-3-diminiccuS)-, or —C(=O)—(CH$_2$)$n^5$-C(=O)—, wherein $n^2$ represents an integer of 2 to 8, $n^3$ represents an integer of 1 to 8, $n^4$ represents an integer of 1 to 8, and $n^5$ represents an integer of 1 to 8, $L^2$ represents —NH—(CH$_2$CH$_2$—O)$n^6$-CH$_2$CH$_2$—C(=O)—, —N[—(CH$_2$CH$_2$—O)$n^7$-CH$_2$CH$_2$—OH]—CH$_2$—C(=O)—, —NH—CH$_2$CH$_2$—[N(—CH$_2$—COOH)]—CH$_2$—(C=O)—, —NH—[CH(—CH$_2$—COOH)]—CH$_2$—(C=O)—, —NH—[CH(—CH$_2$—COOH)]—CH$_2$—O—CH$_2$—(C=O)—, —S—(CH$_2$)$n^8$-C(=O)—, or a single bond, wherein $n^6$ represents an integer of 0 to 6, $n^7$ represents an integer of 1 to 4, and $n^8$ represents an integer of 1 to 6, $L^P$ represents a peptide residue consisting of 2 to 8 amino acids, $L^a$ represents —C(=O)—NH—, —NR$^1$—(CH$_2$)$n^9$-, —O—, or a single bond, wherein $n^9$ represents an integer of 1 to 6, R$^1$ represents a hydrogen atom, an alkyl group having 1 to 6 carbon atoms, —(CH$_2$)$n^a$-COOH, or —(CH$_2$)$n^b$-OH, $n^a$ represents an integer of 1 to 4, and $n^b$ represents an integer of 1 to 6, $L^b$ represents —CR$^2$(—R$^3$)—, —O—, —NR$^4$—, or a single bond, wherein R$^2$ and R$^3$ each independently represent a hydrogen atom, an alkyl group having 1 to 6 carbon atoms, —(CH$_2$)$n^c$-NH$_2$, —(CH$_2$)$n^d$-COOH, or —(CH$_2$)$n^e$-OH, R$^4$ represents a hydrogen atom or an alkyl group having 1 to 6 carbon atoms, $n^c$ represents an integer of 0 to 6, $n^d$ represents an integer of 1 to 4, $n^e$ represents an integer of 1 to 4, and when $n^c$ is 0, R$^2$ and R$^3$ are not the same, $L^c$ represents —CH$_2$— or —C(=O)—, -(Succinimid-3-yl-N)— has a structure represented by the following formula:

[Formula 3]

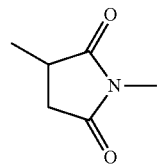

which is connected to the antibody at position 3 thereof and is connected to the methylene group in the linker structure containing this structure on the nitrogen atom at position 1, —(N-ly-3-diminiccuS)- has a structure represented by the following formula:

[Formula 4]

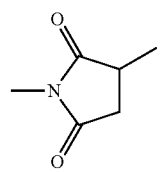

which is connected to $L^2$ at position 3 thereof and is connected to the methylene group in the linker structure containing this structure on the nitrogen atom at position 1, cyc.Hex(1,4) represents a 1,4-cyclohexylene group, and when $L^2$ is —S—$(CH_2)n^8$-C(=O)—, $L^1$ is —C(=O)-cyc.Hex (1,4)-$CH_2$—(N-ly-3-diminiccuS)-.

The present invention further relates to each of the following.

[2] The antibody-drug conjugate according to [1], wherein the linker is a linker having a structure represented by -$L^1$-$L^2$-$L^P$-NH—$(CH_2)n^1$-$L^a$-$L^b$-$L^c$-.

[3] The antibody-drug conjugate according to [2], wherein $L^c$ is —C(=O)—.

[4] The antibody-drug conjugate according to [2] or [3], wherein —NH—$(CH_2)n^1$-$L^a$-$L^b$-in the linker is a structure selected from the following group:
—NH—$CH_2$—,
—NH—$CH_2CH_2$—,
—NH—$CH_2$—O—$CH_2$—,
—NH—$CH_2CH_2$—O—,
—NH—$CH_2CH_2$—O—$CH_2$—,
—NH—$CH_2CH_2$—NH—,
—NH—$CH_2CH_2$—NH—$CH_2$—,
—NH—$CH_2CH_2$—N(—$CH_2$—COOH)—$CH_2$—,
—NH—$CH_2CH_2$—N(—$CH_2CH_2$—OH)—$CH_2CH_2$—,
—NH—$CH_2CH_2CH_2$—C(=O)—NH—CH(—$CH_2$—COOH)—,
—NH—$CH_2CH_2CH_2$—,
—NH—$CH_2CH_2CH_2CH_2$—, and
—NH—$CH_2CH_2CH_2CH_2CH_2$—.

[5] The antibody-drug conjugate according to [2] or [3], wherein —NH—$(CH_2)n^1$-$L^a$-$L^b$-in the linker is a structure selected from the following group:
—NH—$CH_2$—,
—NH—$CH_2CH_2$—,
—NH—$CH_2CH_2CH_2$—,
—NH—$CH_2$—O—$CH_2$—, and
—NH—$CH_2CH_2$—O—$CH_2$—.

[6] The antibody-drug conjugate according to [1], wherein the linker is a linker having a structure represented by -$L^1$-$L^2$-$L^P$-.

[7] The antibody-drug conjugate according to any one of [1] to [6], wherein $L^1$ is -(Succinimid-3-yl-N)—$(CH_2)n^2$-C(=O)—, and $L^2$ is a single bond or is —NH—$CH_2CH_2$—O)$n^6$-$CH_2CH_2$—C(=O)—, —N[—$(CH_2CH_2$—O)$n^7$-$CH_2CH_2$—OH]—$CH_2$—C(=O)—, —NH—[CH(—$CH_2$—COOH)]—$CH_2$—(C=O)—, —NH—$CH_2CH_2$—[N(—$CH_2$—COOH)]—$CH_2$—(C=O)—, or —NH—[CH(—$CH_2$—COOH)]—$CH_2$—O—$CH_2$—(C=O)—.

[8] The antibody-drug conjugate according to any one of [1] to [6], wherein $L^1$ is -(Succinimid-3-yl-N)—$(CH_2)n^2$-C(=O)—, and $L^2$ is a single bond or is —NH—$(CH_2CH_2$—O)$n^6$-$CH_2CH_2$—C(=O)—.

[9] The antibody-drug conjugate according to [8], wherein $n^2$ is 2 or 5, and $L^2$ is a single bond.

[10] The antibody-drug conjugate according to [9], wherein $n^2$ is 5, and $L^2$ is a single bond.

[11] The antibody-drug conjugate according to [8], wherein $n^2$ is 2 or 5, $L^2$ is —NH—$(CH_2CH_2$—O)$n^6$-$CH_2CH_2$—C(=O)—, and $n^6$ is 2 or 4.

[12] The antibody-drug conjugate according to [11], wherein $n^2$ is 2, $L^2$ is —NH—$(CH_2CH_2$—O)$n^6$-$CH_2CH_2$—C(=O)—, and $n^6$ is 2 or 4.

[13] The antibody-drug conjugate according to any one of [1] to [6], wherein $L^1$ is -(Succinimid-3-yl-N)—$(CH_2)n^2$-C(=O)—, and $L^2$ is —NH—[CH(—$CH_2$—COOH)]—$CH_2$—(C=O)—.

[14] The antibody-drug conjugate according to [13], wherein $n^2$ is 2 or 5.

[15] The antibody-drug conjugate according to [13], wherein $n^2$ is 5.

[16] The antibody-drug conjugate according to any one of [1] to [6], wherein $L^1$ is -(Succinimid-3-yl-N)—$(CH_2)n^2$-C(=O)—, and $L^2$ is —NH—$CH_2CH_2$—[N(—$CH_2$—COOH)]—$CH_2$—(C=O)—.

[17] The antibody-drug conjugate according to [16], wherein $n^2$ is 2 or 5.

[18] The antibody-drug conjugate according to [16], wherein $n^2$ is 5.

[19] The antibody-drug conjugate according to any one of [1] to [6], wherein $L^1$ is -(Succinimid-3-yl-N)—$(CH_2)n^2$-C(=O)—, and $L^2$ is —NH—[CH(—$CH_2$—COOH)]—$CH_2$—O—$CH_2$—(C=O)—.

[20] The antibody-drug conjugate according to [19], wherein $n^2$ is 2 or 5.

[21] The antibody-drug conjugate according to [19], wherein $n^2$ is 5.

[22] The antibody-drug conjugate according to any one of [1] to [6], wherein $L^1$ is -(Succinimid-3-yl-N)—CH[—$(CH_2)n^3$-COOH]—C(=O)—, and $L^2$ is a single bond or —NH—$(CH_2CH_2$—O)$n^6$-$CH_2CH_2$—C(=O)—.

[23] The antibody-drug conjugate according to [22], wherein $n^3$ is 2 to 4, and $L^2$ is a single bond.

[24] The antibody-drug conjugate according to [22], wherein $n^3$ is 2, and $L^2$ is a single bond.

[25] The antibody-drug conjugate according to [22], wherein $n^3$ is 2 to 4, $L^2$ is —NH—$(CH_2CH_2$—O)$n^6$-$CH_2CH_2$—C(=O)—, and $n^6$ is 2 or 4.

[26] The antibody-drug conjugate according to [25], wherein $n^3$ is 2, $L^2$ is —NH—$(CH_2CH_2$—O)$n^6$-$CH_2CH_2$—C(=O)—, and $n^6$ is 2 or 4.

[27] The antibody-drug conjugate according to any one of [1] to [6], wherein $L^1$ is -(Succinimid-3-yl-N)—$CH_2CH_2$—[N(—$CH_2$—COOH)]—$CH_2$—(C=O)—, and $L^2$ is a single bond.

[28] The antibody-drug conjugate according to any one of [1] to [6], wherein $L^1$ is —$CH_2$—C(=O)—NH—$(CH_2)n^4$-C(=O)—, and $L^2$ is a single bond.

[29] The antibody-drug conjugate according to [28], wherein $n^4$ is 2 to 6.

[30] The antibody-drug conjugate according to [28], wherein $n^4$ is 2.

[31] The antibody-drug conjugate according to any one of [1] to [6], wherein $L^1$ is —C(=O)—$(CH_2)n^5$-C(=O)—, and $L^2$ is —NH—$(CH_2CH_2$—O)$n^6$-$CH_2CH_2$—C(=O)— or a single bond.

[32] The antibody-drug conjugate according to [31], wherein $n^5$ is 2 to 6, and $L^2$ is a single bond.

[33] The antibody-drug conjugate according to [31], wherein $n^5$ is 6.

[34] The antibody-drug conjugate according to any one of [1] to [6], wherein $L^1$ is —C(=O)-cyc.Hex(1,4)-$CH_2$—(N-ly-3-diminiccuS)-, and $L^2$ is —S—$(CH_2)n^8$-C(=O)—.

[35] The antibody-drug conjugate according to [34], wherein $n^8$ is 2 to 4.

[36] The antibody-drug conjugate according to [34], wherein $n^8$ is 2.

[37] The antibody-drug conjugate according to any one of [1] to [36], wherein $L^P$ is a peptide residue comprising an amino acid selected from the amino acid group consisting of phenylalanine, leucine, glycine, alanine, valine, citrulline, aspartic acid, glutamic acid, lysine, serine, threonine, glutamine, asparagine, histidine, tyrosine, and arginine.

[38] The antibody-drug conjugate according to any one of [1] to [36], wherein $L^P$ is a peptide residue comprising an amino acid selected from the amino acid group consisting of phenylalanine, glycine, valine, lysine, citrulline, serine, glutamic acid, and aspartic acid.

[39] The antibody-drug conjugate according to any one of [1] to [36], wherein $L^P$ is VK, VC, GFG, GGFG (SEQ ID NO: 3), GGFGG (SEQ ID NO: 4), GGFGS (SEQ ID NO: 5), GGFGGG (SEQ ID NO: 6), GGFGGE (SEQ ID NO: 7), GGFGGGFG (SEQ ID NO: 8), DGGF (SEQ ID NO: 9), DGGFG (SEQ ID NO: 10), $D^d$GGFG, $DG^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) ($^d$ of $D^d$ indicates that the amino acid is in a D-form, and $^{Me}$ of $G^{Me}$ indicates that the amino acid is N-methylated at its α-amino group).

[40] The antibody-drug conjugate according to any one of [1] to [36], wherein $L^P$ is GGFG (SEQ ID NO: 3), GGFGG (SEQ ID NO: 4), GGFGS (SEQ ID NO: 5), GGFGGE (SEQ ID NO: 7), DGGF (SEQ ID NO: 9), DGGFG (SEQ ID NO: 10), $D^d$GGFG, $DG^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17).

[41] The antibody-drug conjugate according to any one of [1] to [36], wherein $L^P$ is GGFG (SEQ ID NO: 3), GDGGF (SEQ ID NO: 18), DGGFG (SEQ ID NO: 10), $D^d$GGFG, $DG^{Me}$GFG (SEQ ID NO: 11), DGGFS (SEQ ID NO: 12), DDGGFG (SEQ ID NO: 13), or KDGGFG (SEQ ID NO: 14).

[42] The antibody-drug conjugate according to any one of [1] to [36], wherein $L^P$ is GGFG (SEQ ID NO: 3), DGGFG (SEQ ID NO: 10), $D^d$GGFG, or $DG^{Me}$GFG (SEQ ID NO: 11).

[43] The antibody-drug conjugate according to any one of [2] to [5], wherein $L^P$ is GGFG (SEQ ID NO: 3) or DGGFG (SEQ ID NO: 10).

[44] The antibody-drug conjugate according to [6], wherein $L^P$ is GGFG (SEQ ID NO: 3), GDGGF (SEQ ID NO: 18), DGGFG (SEQ ID NO: 10), $D^d$GGFG, $DG^{Me}$GFG (SEQ ID NO: 11), DGGFS (SEQ ID NO: 12), DDGGFG (SEQ ID NO: 13), or KDGGFG (SEQ ID NO: 14).

[45] The antibody-drug conjugate according to [6], wherein $L^P$ is DGGFG (SEQ ID NO: 10), $D^d$GGFG, or $DG^{Me}$GFG (SEQ ID NO: 11).

[46] The antibody-drug conjugate according to any one of [1] to [45], wherein the average number of units of the antitumor compound conjugated per antibody molecule is in the range of from 1 to 10.

[47] The antibody-drug conjugate according to any one of [1] to [45], wherein the average number of units of the antitumor compound conjugated per antibody molecule is in the range of from 1 to 8.

[48] The antibody-drug conjugate according to any one of [1] to [45], wherein the average number of units of the antitumor compound conjugated per antibody molecule is in the range of from 3 to 8.

[49] The antibody-drug conjugate according to any one of [1] to [48], wherein the antibody is an antibody having one or more of a property of recognizing target cells, a property of binding to target cells, a property of internalizing within target cells, and a property of damaging target cells.

[50] The antibody-drug conjugate according to [49], wherein the target cells are tumor cells.

[51] The antibody-drug conjugate according to [49], wherein the target cells are cells derived from lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

[52] A drug containing the antibody-drug conjugate according to any one of [1] to [45], or a salt thereof or a hydrate thereof.

[53] An antitumor drug and/or anticancer drug containing the antibody-drug conjugate according to any one of [1] to [45], a salt thereof or a hydrate thereof.

[54] The antitumor drug and/or anticancer drug according to [53], which is for use against lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

[55] A pharmaceutical composition containing the antibody-drug conjugate according to any one of [1] to [45], a salt thereof or a hydrate thereof as an active component, and a pharmaceutically acceptable formulation component.

[56] The pharmaceutical composition according to [55], which is for use against lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

[57] A method for treating tumor and/or cancer comprising administering the antibody-drug conjugate according to any one of [1] to [45], a salt thereof or a hydrate thereof.

[58] The treatment method according to [57], which is for use against lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

[59] An antibody-drug conjugate wherein an antitumor compound represented by the following formula:

[Formula 5]

is conjugated to an anti-HER2 antibody via a linker having a structure represented by the following formula:

-L$^1$-L$^2$-L$^P$-NH—(CH$_2$)$n^1$-L$^a$-L$^b$-L$^c$- or -L$^1$-L$^2$-L$^P$-.

Here, the anti-HER2 antibody is connected to the terminal L$^1$, the antitumor compound is connected to the terminal L$^c$ or L$^P$ with the nitrogen atom of the amino group at position 1 as the connecting position, wherein n$^1$ represents an integer of 0 to 6, L$^1$ represents -(Succinimid-3-yl-N)—(CH$_2$)n$^2$-C(=O)—, -(Succinimid-3-yl-N)—CH[—(CH$_2$)n$^3$-COOH]—C(=O)—, -(Succinimid-3-yl-N)—CH$_2$CH$_2$—[N(—CH$_2$—COOH)]—CH$_2$—(C=O)—, or —CH$_2$—C(=O)—NH—(CH$_2$)n$^4$-C(=O)—, which is connected via a thioether bond at a disulfide bond moiety in the hinge part of the antibody, wherein n$^2$ represents an integer of 2 to 8, n$^3$ represents an integer of 1 to 8, and n$^4$ represents an integer of 1 to 8, L$^2$ represents —NH—(CH$_2$CH$_2$—O)n$^6$-CH$_2$CH$_2$—C(=O)—, —N[—(CH$_2$CH$_2$—O)n$^7$-CH$_2$CH$_2$—OH]—CH$_2$—C(=O)—, —NH—CH$_2$CH$_2$—[N(—CH$_2$—COOH)]—CH$_2$—(C=O)—, —NH—[CH(—COOH)]—CH$_2$—(C=O)—NH—[CH(—CH$_2$—COOH)]—CH$_2$—O—CH$_2$—(C=O)—, or a single bond, wherein n$^6$ represents an integer of 0 to 6, and n$^7$ represents an integer of 1 to 4, L$^P$ represents a peptide residue consisting of 2 to 8 amino acids, L$^a$ represents —C(=O)—NH—, —NR$^1$—(CH$_2$)n$^9$-, —O—, or a single bond, wherein n$^9$ represents an integer of 1 to 6, R$^1$ represents a hydrogen atom, an alkyl group having 1 to 6 carbon atoms, —(CH$_2$)n$^a$-COOH, or —(CH$_2$)n$^b$-OH, n$^a$ represents an integer of 1 to 4, and n$^b$ represents an integer of 1 to 6, L$^b$ represents —CR$^2$(—R$^3$)—, —O—, —NR$^4$—, or a single bond, wherein R$^2$ and R$^3$ each independently represent a hydrogen atom, an alkyl group having 1 to 6 carbon atoms, —(CH$_2$)n$^c$-NH$_2$, —(CH$_2$)n$^d$-COOH, or —(CH$_2$)n$^e$-OH, R$^4$ represents a hydrogen atom or an alkyl group having 1 to 6 carbon atoms, n$^c$ represents an integer of 0 to 6, n$^d$ represents an integer of 1 to 4, n$^e$ represents an integer of 1 to 4, and when n$^c$ is 0, R$^2$ and R$^3$ are not the same, L$^c$ represents —CH$_2$— or —C(=O)—, and -(Succinimid-3-yl-N)— has a structure represented by the following formula:

[Formula 6]

which is connected to the antibody at position 3 thereof and is connected to the methylene group in the linker structure containing this structure on the nitrogen atom at position 1.

[60] An antibody-drug conjugate wherein an antitumor compound represented by the following formula:

[Formula 7]

is conjugated to an anti-HER2 antibody via a linker having a structure represented by the following formula:

-L$^1$-L$^2$-L$^P$-NH—(CH$_2$)$n^1$-L$^a$-L$^b$-L$^c$- or -L$^1$-L$^2$-L$^P$-.

Here, the anti-HER2 antibody is connected to the terminal L$^1$, the antitumor compound is connected to the terminal L$^c$ or L$^P$ with the nitrogen atom of the amino group at position 1 as the connecting position, wherein n$^1$ represents an integer of 0 to 6, L$^1$ represents —C(=O)-cyc.Hex(1,4)-CH$_2$—(N-ly-3-diminiccuS)-, or —C(=O)—(CH$_2$)n$^5$-C(=O)—, which is connected to the antibody via an amide bond, wherein n$^5$ represents an integer of 1 to 8, L$^2$ represents —NH—(CH$_2$CH$_2$—O)n$^6$-CH$_2$CH$_2$—C(=O)—, —S—(CH$_2$)n$^8$-C(=O)—, or a single bond, when L$^2$ is —S—(CH$_2$)n$^8$-C(=O)—, L$^1$ is —C(=O)-cy-c.Hex (1,4)-CH$_2$—(N-ly-3-diminiccuS)-, wherein n$^6$ represents an integer of 0 to 6, and n$^8$ represents an integer of 1 to 6, L$^P$ represents a peptide residue consisting of 2 to 8 amino acids, L$^a$ represents —C(=O)—NH—, —NR$^1$—(CH$_2$)n$^9$-, —O—, or a single bond, wherein n$^9$ represents an integer of 1 to 6, R$^1$ represents a hydrogen atom, an alkyl group having 1 to 6 carbon atoms, —(CH$_2$)n$^a$-COOH, or —(CH$_2$)n$^b$-OH, n$^a$ represents an integer of 1 to 4, and n$^b$ represents an integer of 1 to 6, L$^b$ represents —CR$^2$(—R$^3$)—, —O—, —NR$^4$—, or a single bond, wherein R$^2$ and R$^3$ each independently represent a hydrogen atom, an alkyl group having 1 to 6 carbon atoms, —(CH$_2$)n$^c$-NH$_2$, —(CH$_2$)n$^d$-COOH, or —(CH$_2$)n$^e$-OH, R$^4$ represents a hydrogen atom or an alkyl group having 1 to 6 carbon atoms, n$^c$ represents an integer of 0 to 6, n$^d$ represents an integer of 1 to 4, n$^e$ represents an integer of 1 to 4, and when n$^c$ is 0, R$^2$ and R$^3$ are not the same, $L^c$ represents —CH$_2$— or —C(=O)—,
wherein —(N-ly-3-diminiccuS)- has a structure represented by the following formula:

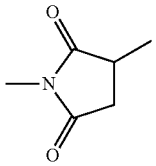

[Formula 8]

which is connected to $L^2$ at position 3 thereof and is connected to the methylene group in the linker structure containing this structure on the nitrogen atom at position 1, and
cyc.Hex(1,4) represents a 1,4-cyclohexylene group.
[61] A drug-linker intermediate compound represented by the following formula:

Q-L$^{1a}$-(CH$_2$)n$^Q$-C(=O)-L$^{2a}$-L$^P$-NH—(CH$_2$)n$^1$-L$^a$-L$^b$-L$^c$-(NH-DX) or

Q-L$^{1a}$-(CH$_2$)n$^Q$-C(=O)-L$^{2a}$-L$^P$-(NH-DX)

wherein Q represents (maleimid-N-yl)-, HS—, X—CH$_2$—C(=O)—NH—, or (Pyrrolidine-2,5-dione-N-yl)-O—C(=O)—,
X represents a bromine atom or an iodine atom,
$L^{1a}$ represents —CH[—(CH$_2$)n$^3$-COOH]—, —CH$_2$CH$_2$—[N(—CH$_2$—COOH)]—, or a single bond,
  wherein n$^3$ represents an integer of 1 to 8,
n$^Q$ represents an integer of 0 to 8,
$L^{2a}$ represents —NH—(CH$_2$CH$_2$—O)n$^6$-CH$_2$CH$_2$—C(=O)—, —N[—(CH$_2$CH$_2$—O)n$^7$-CH$_2$CH$_2$—OH]—CH$_2$—C(=O)—, —NH—CH$_2$CH$_2$—[N(—CH$_2$—COOH)]—CH$_2$—(C=O)—, —NH—[CH(—COOH)]—CH$_2$—(C=O)—, —NH—[CH(—CH$_2$—COOH)]—CH$_2$—O—CH$_2$—(C=O)—, or a single bond,
  wherein n$^6$ represents an integer of 0 to 6, and n$^7$ represents an integer of 1 to 4,
$L^P$ represents a peptide residue consisting of 2 to 8 amino acids,
n$^1$ represents an integer of 0 to 6,
$L^a$ represents —C(=O)—NH—, —NR$^1$—(CH$_2$)n$^9$-, —O—, or a single bond,
  wherein n$^9$ represents an integer of 1 to 6, R$^1$ represents a hydrogen atom, an alkyl group having 1 to 6 carbon atoms, —(CH$_2$)n$^a$-COOH, or —(CH$_2$)n$^b$-OH, n$^a$ represents an integer of 1 to 4, and n$^b$ represents an integer of 1 to 6,
$L^b$ represents —CR$^2$(—R$^3$)—, —O—, —NR$^4$—, or a single bond,
  wherein R$^2$ and R$^3$ each independently represent a hydrogen atom, an alkyl group having 1 to 6 carbon atoms, —(CH$_2$)n$^c$-NH$_2$, —(CH$_2$)n$^d$-COOH, or —(CH$_2$)n$^e$-OH, R$^4$ represents a hydrogen atom or an alkyl group having 1 to 6 carbon atoms, n$^c$ represents an integer of 0 to 6, n$^d$ represents an integer of 1 to 4, n$^e$ represents an integer of 1 to 4, and when n$^c$ is 0, R$^2$ and R$^3$ are not the same,
$L^c$ represents —CH$_2$— or —C(=O)—,
wherein (maleimid-N-yl)- is a group represented by the following formula:

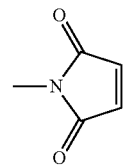

[Formula 9]

wherein the nitrogen atom is the connecting position, (Pyrrolidine-2,5-dione-N-yl) is a group represented by the following formula:

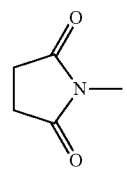

[Formula 10]

wherein the nitrogen atom is the connecting position, and —(NH-DX) is a group derived from a compound represented by the following formula:

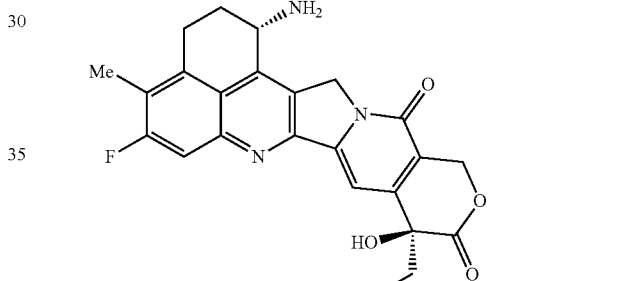

[Formula 11]

wherein the nitrogen atom of the amino group at position 1 is the connecting position. [62] A drug-linker intermediate compound represented by any of the following formulas:

Q-L$^{1a}$-(CH$_2$)n$^Q$-C(=O)-L$^{2a}$-L$^P$-NH—(CH$_2$)n$^1$-L$^a$-L$^b$-L$^c$-(NH-DX), or

Q-L$^{1a}$-(CH$_2$)n$^Q$-C(=O)-L$^{2a}$-L$^P$-(NH-DX)

wherein
Q represents (maleimid-N-yl)-, HS—, X—CH$_2$—C(=O)—NH—, or (Pyrrolidine-2,5-dione-N-yl)-O—C(=O)—,
X represents a bromine atom or an iodine atom,
$L^{1a}$ represents —CH [—(CH$_2$)n$^3$-COOH]—, —CH$_2$CH$_2$—[N(—CH$_2$—COOH)]—,
or a single bond,
  wherein n$^3$ represents an integer of 1 to 8,
n$^Q$ represents an integer of 0 to 8,
$L^{2a}$ represents —NH—(CH$_2$—CH$_2$—O)n$^6$-CH$_2$—CH$_2$—C(=O)—, —N[—(CH$_2$CH$_2$—O)n$^7$-CH$_2$CH$_2$—OH]—CH$_2$—C(=O)—, —NH—CH$_2$CH$_2$—[N(—CH$_2$—COOH)]—CH$_2$—(C=O)—, —NH—[CH(—COOH)]—CH$_2$—(C=O)—, —NH—[CH(—CH$_2$—COOH)]—CH$_2$—O—CH$_2$—(C=O)—, or a single bond,
  wherein n$^6$ represents an integer of 0 to 6, and n$^7$ represents an integer of 1 to 4, $L^P$ represents a peptide residue consisting of 3 to 8 amino acids,
$n^1$ represents an integer of 0 to 6,
$L^a$ and $L^b$ each represent a single bond,
$L^c$ represents —C(=O)—,
wherein (maleimid-N-yl)- is a group represented by the following formula:

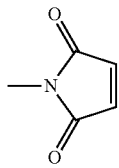

[Formula 12]

wherein the nitrogen atom is the connecting position, (Pyrrolidine-2,5-dione-N-yl) is a group represented by the following formula:

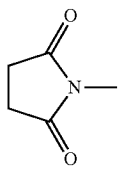

[Formula 13]

wherein the nitrogen atom is the connecting position, —(NH-DX) is a group derived from a compound represented by the following formula:

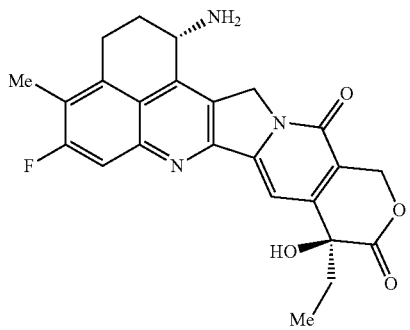

[Formula 14]

wherein the nitrogen atom of the amino group at position 1 is the connecting position

[63] A linker having a structure represented by any of the following formulas:

-$L^1$-$L^2$-$L^P$-NH—(CH$_2$)$n^1$-$L^a$-$L^b$-$L^c$- or

-$L^1$-$L^2$-$L^P$- for obtaining an antibody-drug conjugate wherein an antitumor compound is conjugated to an antibody via the linker, wherein
the antibody is connected to the terminal $L^1$, the antitumor compound is connected to the terminal $L^c$ or $L^P$ wherein $n^1$ represents an integer of 0 to 6,
$L^1$ represents -(Succinimid-3-yl-N)—(CH$_2$)$n^2$-C(=O)—, -(Succinimid-3-yl-N)—CH[—(CH$_2$)$n^3$-COOH]—C(=O)—, -(Succinimid-3-yl-N)—CH$_2$CH$_2$—[N(—CH$_2$—COOH)]—CH$_2$—(C=O)—, —CH$_2$—C(=O)—NH—(CH$_2$)$n^4$-C(=O)—, —C(=O)-cyc.Hex(1,4)-CH$_2$—(N-ly-3-diminiccuS)-, or —C(=O)—(CH$_2$)$n^5$-C(=O)—,
wherein $n^2$ represents an integer of 2 to 8, $n^3$ represents an integer of 1 to 8, $n^4$ represents an integer of 1 to 8, and $n^5$ represents an integer of 1 to 8, $L^2$ represents —NH—(CH$_2$CH$_2$—O)$n^6$-CH$_2$CH$_2$—C(=O)—, —N[—(CH$_2$CH$_2$—O)$n^7$-CH$_2$CH$_2$—OH]—CH$_2$—C(=O)—, —NH—CH$_2$CH$_2$—[N(—CH$_2$—COOH)]—CH$_2$—(C=O)—, —NH—[CH(—COOH)]—CH$_2$—(C=O)—, —NH—[CH(—CH$_2$—COOH)]—CH$_2$—O—CH$_2$—(C=O)—, —S—(CH$_2$)$n^8$-C(=O)—, or a single bond,
wherein $n^6$ represents an integer of 0 to 6, $n^7$ represents an integer of 1 to 4, and $n^8$ represents an integer of 1 to 6,
$L^P$ represents a peptide residue consisting of 2 to 8 amino acids,
$L^a$ represents —C(=O)—NH—, —NR$^1$—(CH$_2$)$n^9$-, —O—, or a single bond,
wherein $n^9$ represents an integer of 1 to 6, $R^1$ represents a hydrogen atom, an alkyl group having 1 to 6 carbon atoms, —(CH$_2$)$n^a$-COOH, or —(CH$_2$)$n^b$-OH, $n^a$ represents an integer of 1 to 4, and $n^b$ represents an integer of 1 to 6,
$L^b$ represents —CR$^2$(—R$^3$)—, —O—, —NR$^4$—, or a single bond,
wherein $R^2$ and $R^3$ each independently represent a hydrogen atom, an alkyl group having 1 to 6 carbon atoms, —(CH$_2$)$n^c$-NH$_2$, —(CH$_2$)$n^d$-COOH, or —(CH$_2$)$n^e$-OH, $R^4$ represents a hydrogen atom or an alkyl group having 1 to 6 carbon atoms, $n^c$ represents an integer of 0 to 6, $n^d$ represents an integer of 1 to 4, $n^e$ represents an integer of 1 to 4, and when $n^c$ is 0, $R^2$ and $R^3$ are not the same,
$L^c$ represents —CH$_2$— or —C(=O)—,
-(Succinimid-3-yl-N)— has a structure represented by the following formula:

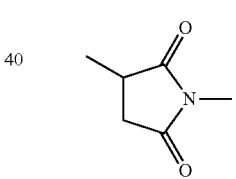

[Formula 15]

which is connected to the antibody at position 3 thereof and is connected to the methylene group in the linker structure containing this structure on the nitrogen atom at position 1, —(N-ly-3-diminiccuS)- has a structure represented by the following formula:

[Formula 16]

which is connected to $L^2$ at position 3 thereof and is connected to the methylene group in the linker structure containing this structure on the nitrogen atom at position 1, cyc.Hex(1,4) represents a 1,4-cyclohexylene group, and when $L^2$ is —S—(CH$_2$)$n^8$-C(=O)—, $L^1$ is —C(=O)-cyc.Hex (1,4)-CH$_2$—(N-ly-3-diminiccuS)-.

[64] The linker according to [63], wherein the linker structure is a linker structure selected from forms according to [2] to [45].

[65] An antibody-drug conjugate having the linker structure according to [63].

[66] The antibody-drug conjugate according to [65], wherein the linker structure is a linker structure selected from forms according to [2] to [45].

[67] Use of the linker structure according to [63] in an antibody-drug conjugate. [68] The use according to [67], wherein the linker structure is a linker structure selected from forms according to [2] to [45].

[69] A method for producing an antibody-drug conjugate comprising reacting a compound represented by any of the following formulas:

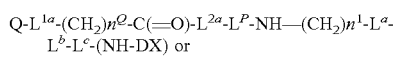

or

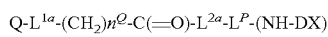

with an anti-HER2 antibody or a reactive derivative thereof and conjugating a drug-linker moiety to the antibody by a method for forming a thioether bond at a disulfide bond site present in the hinge part of the antibody, or a method for forming an amide bond at an amino group present on a side chain of an amino acid constituting the antibody or at the terminal amino group.

In the formula,

Q represents (maleimid-N-yl)-, HS—, X—CH$_2$—C(=O)—NH—, or (Pyrrolidine-2,5-dione-N-yl)-O—C(=O)—, X represents a bromine atom or an iodine atom, $L^{1a}$ represents —CH[—(CH$_2$)n$^3$-COOH]— or a single bond, wherein n$^3$ represents an integer of 1 to 8, n$^Q$ represents an integer of 0 to 8, $L^{2a}$ represents —NH—(CH$_2$CH$_2$—O)n$^6$-CH$_2$CH$_2$—C(=O)—, —N[—(CH$_2$CH$_2$—O)n$^7$-CH$_2$CH$_2$—OH]—CH$_2$—C(=O)—, or a single bond, wherein n$^6$ represents an integer of 0 to 6, and n$^7$ represents an integer of 1 to 4, $L^P$ represents a peptide residue consisting of 2 to 8 amino acids, n$^1$ represents an integer of 0 to 6, $L^a$ represents —C(=O)—NH—, —NR$^1$—(CH$_2$)n$^9$-, —O—, or a single bond, wherein n$^9$ represents an integer of 1 to 6, R$^1$ represents a hydrogen atom, an alkyl group having 1 to 6 carbon atoms, —(CH$_2$)n$^a$-COOH, or —(CH$_2$)n$^b$-OH, n$^a$ represents an integer of 1 to 4, and n$^b$ represents an integer of 1 to 6, $L^b$ represents —CR$^2$(—R$^3$)—, —O—, —NR$^4$—, or a single bond, wherein R$^2$ and R$^3$ each independently represent a hydrogen atom, an alkyl group having 1 to 6 carbon atoms, —(CH$_2$)n$^c$-NH$_2$, —(CH$_2$)n$^d$-COOH, or —(CH$_2$)n$^e$-OH, R$^4$ represents a hydrogen atom or an alkyl group having 1 to 6 carbon atoms, n$^c$ represents an integer of 0 to 6, n$^d$ represents an integer of 1 to 4, n$^e$ represents an integer of 1 to 4, and when n$^c$ is 0, R$^2$ and R$^3$ are not the same, $L^c$ represents —CH$_2$— or —C(=O)—, wherein (maleimid-N-yl)- is a group represented by the following formula:

[Formula 17]

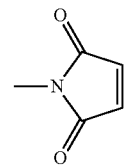

wherein the nitrogen atom is the connecting position, (Pyrrolidine-2,5-dione-N-yl) is a group represented by the following formula:

[Formula 18]

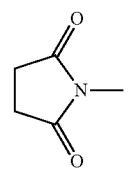

wherein the nitrogen atom is the connecting position, and —(NH-DX) is a group derived from a compound represented by the following formula:

[Formula 19]

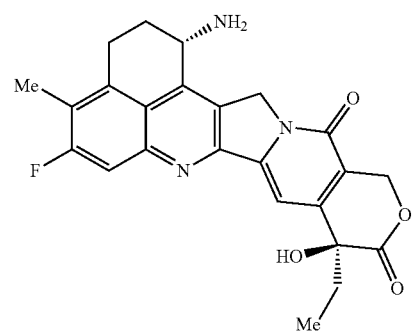

wherein the nitrogen atom of the amino group at position 1 is the connecting position.

[70] The method for producing an antibody-drug conjugate according to [69], wherein the method for conjugating a drug-linker moiety to an antibody is a method of reducing the antibody, followed by reaction with a compound in which Q is a maleimidyl group or X—CH$_2$—C(=O)—NH— to form a thioether bond, a method of reacting the antibody with a compound in which Q is (Pyrrolidine-2,5-dione-N-yl)-O—C(=O)— to form an amide bond, or a method of reacting the antibody with a compound represented by the formula Q$^1$-L$^{1b}$-(CH$_2$)n$^Q$-C(=O)-Q$^2$ wherein Q$^1$ represents (Pyrrolidine-2,5-dione-N-yl)-O—C(=O)—, (3-Sulfo-pyrrolidine-2,5-dione-N-yl)-O—C(=O)—, R$^Q$—O—C(=N)—, or O=C=N—, $L^{1b}$ represents -cyc.Hex(1,4)-CH$_2$—, an alkylene group having 1 to 10 carbon atoms, a phenylene group, —(CH$_2$)n$^4$-C(=O)—, —(CH$_2$)n$^{4a}$-NH—C(=O)—(CH$_2$)n$^{4b}$-, or —(CH$_2$)n$^{4a}$-NH—C(=O)-cyc.Hex(1,4)-CH$_2$—, wherein R$^Q$ represents an alkyl group having 1 to 6 carbon atoms, n$^4$ represents an integer of 1 to 8, n$^{4a}$ represents an integer of 0 to 6, and n$^{4b}$ represents an integer of 1 to 6, n$^Q$ represents an integer of 0 to 8, Q² represents (maleimid-N-yl), a halogen atom, or —S—S-(2-Pyridyl),
wherein (3-Sulfo-pyrrolidine-2,5-dione-N-yl)- is a group represented by the following formula:

[Formula 20]

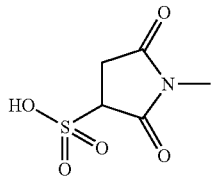

wherein the nitrogen atom is the connecting position, and this sulfonic acid is capable of forming a lithium salt, a sodium salt, or a potassium salt, cyc.Hex(1,4) represents a 1,4-cyclohexylene group, and (2-Pyridyl) represents a 2-pyridyl group, followed by reaction with a compound in which Q is HS— to form a drug-linker structure via an amide bond.
[71] An antibody-drug conjugate produced by the production method according to [69] or [70].
[72] The antibody-drug conjugate according to [71], wherein the linker structure is a linker structure selected from forms according to [2] to [45].

Advantageous Effects of Invention

With an anti-HER2 antibody-drug conjugate having the antitumor compound exatecan conjugated via a linker with a specific structure, an excellent antitumor effect and safety can be achieved.

BRIEF DESCRIPTION OF DRAWINGS

FIG. 1 shows an amino acid sequence of a heavy chain of a humanized anti-HER2 monoclonal antibody (SEQ ID NO: 1).
FIG. 2 shows an amino acid sequence of a light chain of a humanized anti-HER2 monoclonal antibody (SEQ ID NO: 2).

DESCRIPTION OF EMBODIMENTS

Figure 3:
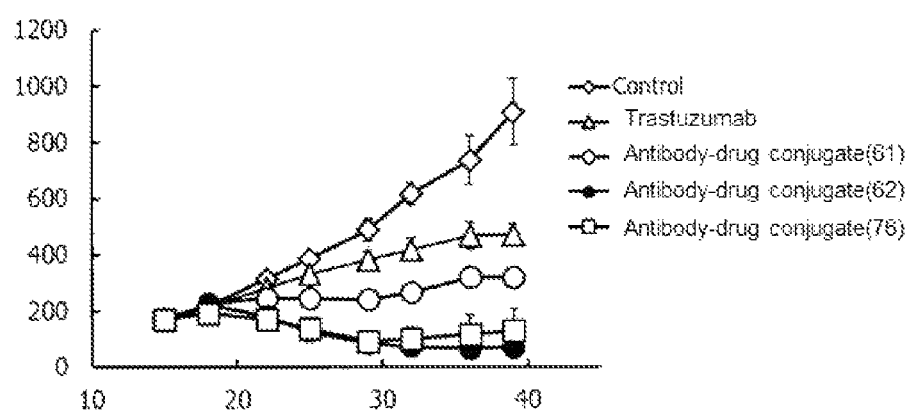
FIG. 3 is a diagram showing the antitumor effect of an antibody-drug conjugate (61), (62), (76), or trastuzumab on a nude mouse with subcutaneously transplanted human breast cancer line KPL-4 cells. In the drawing, the abscissa depicts days after tumor inoculation, and the ordinate depicts tumor volume.

Hereinafter, preferred modes for carrying out the present invention are described with reference to the drawings. The embodiments described below are given merely for illustrating one example of a typical embodiment of the present invention and are not intended to limit the scope of the present invention.

The anti-HER2 antibody-drug conjugate of the present invention is an antitumor drug in which an anti-HER2 antibody is conjugated to an antitumor compound via a linker structure moiety and is explained in detail hereinbelow.

[Antibody]

The anti-HER2 antibody used in the anti-HER2 antibody-drug conjugate of the present invention may be derived from any species, and preferred examples of the species can include humans, rats, mice, and rabbits. In case when the antibody is derived from other than human species, it is preferably chimerized or humanized using a well known technique. The antibody of the present invention may be a polyclonal antibody or a monoclonal antibody and is preferably a monoclonal antibody.

The anti-HER2 antibody is the antibody, which is capable of targeting tumor cells, that is, possesses a property of recognizing a tumor cell, a property of binding to a tumor cell, a property of internalizing in a tumor cell, cytocidal activity against tumor cells, or the like, and can be conjugated with a drug having antitumor activity via a linker to form an antibody-drug conjugate.

The binding activity of the antibody against tumor cells can be confirmed using flow cytometry. The internalization of the antibody into tumor cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring a fluorescence intensity incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000). As the immunotoxin, a recombinant complex protein of a diphtheria toxin catalytic domain and protein G may be used.

The antitumor activity of the antibody can be confirmed in vitro by determining inhibitory activity against cell growth. For example, a cancer cell line overexpressing a target protein for the antibody is cultured, and the antibody is added at varying concentrations into the culture system to determine an inhibitory activity against focus formation, colony formation, and spheroid growth. The antitumor activity can be confirmed in vivo, for example, by administering the antibody to a nude mouse with a transplanted tumor cell line highly expressing the target protein, and determining change in the cancer cell.

Since the compound conjugated in the antibody-drug conjugate exerts an antitumor effect, it is preferred but not essential that the antibody itself should have an antitumor effect. For the purpose of specifically and selectively exerting the cytotoxic activity of the antitumor compound against tumor cells, it is important and also preferred that the antibody should have the property of internalizing to migrate into tumor cells.

The anti-HER2 antibody can be obtained by a procedure known in the art. For example, the antibody of the present invention can be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat and the like. In this case, the cross-reactivity of antibodies binding to the obtained heterologous antigen with human antigens can be tested to screen for an antibody applicable to a human disease.

Alternatively, antibody-producing cells which produce antibodies against the antigen are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can in turn be obtained.

The antigen can be obtained by genetically engineering host cells to produce a gene encoding the antigenic protein. Specifically, vectors that permit expression of the antigen gene are prepared and transferred to host cells so that the gene is expressed. The antigen thus expressed can be purified. The antibody can also be obtained by a method of immunizing animals with the above-described genetically engineered antigen-expressing cells or a cell line expressing the antigen.

The anti-HER2 antibody can be obtained by a procedure known in the art.

The anti-HER2 antibodies that can be used in the present invention are not particularly limited and are preferably, for example, those having properties as described below.

(1) An anti-HER2 antibody having the following properties:
  (a) specifically binding to HER2, and
  (b) having an activity of internalizing in HER2-expressing cells by binding to HER2.
(2) The antibody according to (1) above, wherein the antibody binds to the extracellular domain of HER2.
(3) The antibody according to (1) or (2) above, wherein the antibody is a monoclonal antibody.
(4) The antibody according to any of (1) to (3) above, wherein the antibody has an antibody-dependent cellular cytotoxicity (ADCC) activity and/or a complement-dependent cytotoxicity (CDC) activity
(5) The antibody according to any of (1) to (4) above, wherein the antibody is a mouse monoclonal antibody, a chimeric monoclonal antibody, or a humanized monoclonal antibody.
(6) The antibody according to any of (1) to (5) above, wherein the antibody is a humanized monoclonal antibody comprising a heavy chain consisting of the amino acid sequence represented by SEQ ID NO: 1 and a light chain consisting of the amino acid sequence represented by SEQ ID NO: 2.
(7) The antibody according to any of (1) to (6) above, wherein the antibody lacks a lysine residue at the carboxyl terminus of the heavy chain.
(8) The antibody according to (7) above, wherein the antibody comprises a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.
(9) An antibody obtained by a method for producing the antibody according to any of (1) to (8) above, the method comprising the steps of: culturing a host cell transformed with an expression vector containing a polynucleotide encoding the antibody; and collecting the antibody of interest from the cultures obtained in the preceding step.

Hereinafter, the anti-HER2 antibody used in the invention is described.

The terms "cancer" and "tumor" as used herein are used with the same meaning.

The term "gene" as used herein includes not only DNA, but also mRNA thereof, cDNA thereof and cRNA thereof.

The term "polynucleotide" as used herein is used with the same meaning as a nucleic acid and also includes DNA, RNA, probes, oligonucleotides, and primers.

The terms "polypeptide", "protein" and "protein" as used herein are used without distinction.

The term "cell" as used herein also includes cells in an animal individual and cultured cells.

The term "HER2" as used herein is used with the same meaning as HER2 protein.

Examples of the anti-HER2 antibody as used herein can include, but not particularly limited to, pertuzumab (International Patent Publication No. WO 01/00245) and trastuzumab (U.S. Pat. No. 5,821,337). Trastuzumab is preferred. However, the anti-HER2 antibody of the present invention is not limited thereto as long as it is an anti-HER2 antibody specifically binding to HER2, and more preferably having an activity of internalizing in HER2-expressing cells by binding to HER2.

The term "trastuzumab" as used herein is also called HERCEPTIN®, huMAb4D5-8, or rhuMAb4D5-8 and is a humanized antibody comprising a heavy chain consisting of an amino acid sequence consisting of amino acid residues 1 to 449 of SEQ ID NO: 1 (FIG. 1) and a light chain consisting of an amino acid sequence consisting of amino acid residues 1 to 214 of SEQ ID NO: 2 (FIG. 2).

The term "specifically binding" as used herein means binding that is not nonspecific adsorption. Examples of the criterion for determining whether the binding is specific or not can include dissociation constant (hereinafter referred to as "KD"). The KD value of the antibody for the HER2 protein is preferably $1\times10^{-5}$ M or smaller, $5\times10^{-6}$ M or smaller, $2\times10^{-6}$ M or smaller, or $1\times10^{-6}$ M or smaller, more preferably $5\times10^{-7}$ M or smaller, $2\times10^{-7}$ M or smaller, or $1\times10^{-7}$ M or smaller, further preferably $5\times10^{-8}$ M or smaller, $2\times10^{-8}$ M or smaller, or $1\times10^{-8}$ M or smaller, and most preferably $5\times10^{-9}$ M or smaller, $2\times10^{-9}$ M or smaller, or $1\times10^{-9}$ M or smaller. The binding between the HER2 protein and the antibody can be measured using a method known in the art, such as surface plasmon resonance, ELISA, or RIA.

The term "CDR" as used herein refers to a complementarity determining region (CDR). It is known that each heavy and light chain of an antibody molecule has three complementarity determining regions (CDRs). The CDR is also called the hypervariable domain, and is present in a variable region of each heavy and light chain of an antibody. It is a site which has unusually high variability in its primary structure, and there are three separate CDRs in the primary structure of each heavy and light polypeptide chain. In this specification, as for the CDRs of an antibody, the CDRs of the heavy chain are represented by CDRH1, CDRH2, and CDRH3 from the amino-terminal side of the amino acid sequence of the heavy chain, and the CDRs of the light chain are represented by CDRL1, CDRL2, and CDRL3 from the amino-terminal side of the amino acid sequence of the light chain. These sites are proximate to one another in the tertiary structure and determine the specificity for an antigen to which the antibody binds.

The phrase "hybridization is performed under stringent conditions" as used herein refers to a process in which hybridization is performed under conditions under which identification can be achieved by performing hybridization at 68° C. in a commercially available hybridization solution ExpressHyb Hybridization Solution (manufactured by Clontech, Inc.) or by performing hybridization at 68° C. in the presence of 0.7 to 1.0 M NaCl using a filter having DNA immobilized thereon, followed by performing washing at 68° C. using 0.1 to 2×SSC solution (1×SSC solution is composed of 150 mM NaCl and 15 mM sodium citrate) or under conditions equivalent thereto.

1. HER2

HER2 is one of the oncogene products of a typical growth factor receptor oncogene identified as human epidermal cell growth factor receptor 2-related oncogene, and is a transmembrane receptor protein having a molecular weight of 185 kDa and having a tyrosine kinase domain. HER2 is a member of the EGFR family consisting of HER1 (EGFR, ErbB-1), HER2 (neu, ErbB-2), HER3 (ErbB-3), and HER4 (ErbB-4) and is known to be autophosphorylated at intracellular tyrosine residues by its homodimer formation or heterodimer formation with another EGFR receptor HER1, HER3, or HER4 and is itself activated in that manner, thereby playing an important role in cell growth, differentiation, and survival in normal cells and tumor cells.

As for the HER2 protein to be used in the present invention, the HER2 protein can be directly purified from HER2-expressing cells of a human or a non-human mammal (such as a rat or a mouse) and used, or a cell membrane fraction of the above-described cells can be prepared and used. Further, HER2 can also be obtained by in vitro synthesis thereof or production thereof in a host cell through genetic engineering. In the genetic engineering, specifically, after HER2 cDNA is integrated into a vector capable of expressing HER2 cDNA, the HER2 protein can be obtained by synthesizing it in a solution containing an enzyme, a substrate and an energy substance required for transcription and translation, or by expressing HER2 in another prokaryotic or eucaryotic transformed host cell. Alternatively, the above-described genetically engineered HER2-expressing cells, or a cell line expressing HER2 may be used as the HER2 protein.

The DNA sequence and amino acid sequence of HER2 are disclosed on a public database, and can be referred to, for example, under Accession No. M11730 (GenBank), NP_004439.2 (NCBI), or the like.

Further, a protein which consists of an amino acid sequence wherein one or several amino acids are substituted, deleted and/or added in any of the above-described amino acid sequences of HER2 and also has a biological activity equivalent to that of the protein is also included in HER2.

Human HER2 protein is composed of a signal sequence consisting of N-terminal 22 amino acid residues, an extracellular domain consisting of 630 amino acid residues, a transmembrane domain consisting of 23 amino acid residues, and an intracellular domain consisting of 580 amino acid residues.

2. Production of Anti-HER2 Antibody

The antibody against HER2 of the present invention can be obtained according to, for example, a method usually carried out in the art, which involves immunizing animals with HER2 or an arbitrary polypeptide selected from the amino acid sequence of HER2 and collecting and purifying antibodies produced in vivo. The biological species of HER2 to be used as an antigen is not limited to being human, and an animal can be immunized with HER2 derived from an animal other than humans such as a mouse or a rat or with rat p185neu. In this case, by examining the cross-reactivity between an antibody binding to the obtained heterologous HER2 and human HER2, an antibody applicable to a human disease can be selected.

Further, a monoclonal antibody can be obtained from a hybridoma established by fusing antibody-producing cells which produce an antibody against HER2 with myeloma cells according to a known method (for example, Kohler and Milstein, Nature, (1975) 256, pp. 495-497; Kennet, R. ed., Monoclonal Antibodies, pp. 365-367, Plenum Press, N.Y. (1980)).

HER2 to be used as an antigen can be obtained by expressing HER2 gene in a host cell using genetic engineering.

Specifically, a vector capable of expressing HER2 gene is produced, and the resulting vector is transfected into a host cell to express the gene, and then, the expressed HER2 is purified.

Alternatively, the above-described genetically engineered HER2-expressing cells, or a cell line expressing HER2 may be used as the HER2 protein. The anti-HER2 antibody can be obtained by a procedure known in the art. Hereinafter, a method of obtaining an antibody against HER2 is specifically described.

(1) Preparation of Antigen

Examples of the antigen to be used for producing the anti-HER2 antibody include HER2, or a polypeptide consisting of a partial amino acid sequence comprising at least 6 consecutive amino acids of HER2, or a derivative obtained by adding a given amino acid sequence or carrier thereto.

HER2 can be purified directly from human tumor tissues or tumor cells and used. Further, HER2 can be obtained by synthesizing it in vitro or by producing it in a host cell by genetic engineering.

With respect to the genetic engineering, specifically, after HER2 cDNA is integrated into a vector capable of expressing HER2 cDNA, HER2 can be obtained by synthesizing it in a solution containing an enzyme, a substrate and an energy substance required for transcription and translation, or by expressing HER2 in another prokaryotic or eucaryotic transformed host cell.

Further, the antigen can also be obtained as a secretory protein by expressing a fusion protein obtained by ligating the extracellular domain of HER2, which is a membrane protein, to the constant region of an antibody in an appropriate host-vector system.

HER2 cDNA can be obtained by, for example, a so-called PCR method in which a polymerase chain reaction is performed using a cDNA library expressing HER2 cDNA as a template and primers which specifically amplify HER2 cDNA (PCR; Saiki, R. K., et al., Science, (1988) 239, pp. 487-489).

As the in vitro synthesis of the polypeptide, for example, Rapid Translation System (RTS) manufactured by Roche Diagnostics, Inc. can be exemplified, but it is not limited thereto.

Examples of the prokaryotic host cells include *Escherichia coli* and *Bacillus subtilis*. In order to transform the host cells with a target gene, the host cells are transformed by a plasmid vector comprising a replicon, i.e., a replication origin derived from a species compatible with the host, and a regulatory sequence. Further, the vector preferably has a sequence capable of imposing phenotypic selectivity on the transformed cell.

Examples of the eucaryotic host cells include vertebrate cells, insect cells, and yeast cells. As the vertebrate cells, for example, simian COS cells (Gluzman, Y., Cell, (1981) 23, pp. 175-182, ATCC CRL-1650; ATCC: American Type Culture Collection), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61); and the like are often used, however, the cells are not limited thereto.

The thus obtained transformant can be cultured according to a method usually carried out in the art, and by the culturing of the transformant, a target polypeptide is produced intracellularly or extracellularly.

A suitable medium to be used for the culturing can be selected from various commonly used culture media depending on the employed host cells. If *Escherichia coli* is employed, for example, an LB medium supplemented with an antibiotic such as ampicillin or IPMG as needed can be used.

A recombinant protein produced intracellularly or extracellularly by the transformant through such culturing can be separated and purified by any of various known separation methods utilizing the physical or chemical property of the protein.

Specific examples of the methods include treatment with a common protein precipitant, ultrafiltration, various types of liquid chromatography such as molecular sieve chromatography (gel filtration), adsorption chromatography, ion exchange chromatography, and affinity chromatography, dialysis, and a combination thereof.

Further, by attaching a tag of six histidine residues to a recombinant protein to be expressed, the protein can be efficiently purified with a nickel affinity column. Alternatively, by attaching the IgG Fc region to a recombinant protein to be expressed, the protein can be efficiently purified with a protein A column.

By combining the above-described methods, a large amount of a target polypeptide can be easily produced in high yield and high purity.

The above-described transformant itself may be used as the antigen. A cell line expressing HER2 may also be used as the antigen. Examples of such a cell line can include human breast cancer lines SK-BR-3, BT-474, KPL-4, and JIMT-1, a human gastric cancer line NCI-N87, and a human ovarian cancer line SK-OV-3. The cell line of the present invention is not limited to these cell lines as long as it expresses HER2.

(2) Production of Anti-HER2 Monoclonal Antibody

Examples of the antibody specifically bind to HER2 include a monoclonal antibody specifically bind to HER2, and a method of obtaining such antibody is as described below.

The production of a monoclonal antibody generally requires the following operational steps of:

(a) purifying a biopolymer to be used as an antigen, or preparing antigen-expressing cells;

(b) preparing antibody-producing cells by immunizing an animal by injection of the antigen, collecting the blood, assaying its antibody titer to determine when the spleen is excised;

(c) preparing myeloma cells (hereinafter referred to as "myeloma");

(d) fusing the antibody-producing cells with the myeloma;

(e) screening a group of hybridomas producing a desired antibody;

(f) dividing the hybridomas into single cell clones (cloning);

(g) optionally, culturing the hybridoma or rearing an animal implanted with the hybridoma for producing a large amount of monoclonal antibody;

(h) examining the thus produced monoclonal antibody for biological activity and binding specificity, or assaying the same for properties as a labeled reagent; and the like.

Hereinafter, the method of producing a monoclonal antibody will be described in detail following the above steps, however, the method is not limited thereto, and, for example, antibody-producing cells other than spleen cells and myeloma can be used.

(a) Purification of Antigen

As the antigen, HER2 prepared by the method as described above or a partial peptide thereof can be used.

Further, a membrane fraction prepared from recombinant cells expressing HER2 or the recombinant cells expressing HER2 themselves, and also a partial peptide of the protein of the invention chemically synthesized by a method known to those skilled in the art can also be used as the antigen.

Furthermore, a HER2-expressing cell line can also be used as the antigen.

(b) Preparation of Antibody-Producing Cells

The antigen obtained in the step (a) is mixed with an adjuvant such as Freund's complete or incomplete adjuvant or auxiliary agent such as aluminum potassium sulfate and the resulting mixture is used as an immunogen to immunize an experimental animal. Another method involves immunizing an experimental animal with antigen-expressing cells as an immunogen. As the experimental animal, any animal used in a known hybridoma production method can be used without hindrance. Specifically, for example, a mouse, a rat, a goat, sheep, cattle, a horse, or the like can be used. However, from the viewpoint of ease of availability of myeloma cells to be fused with the extracted antibody-producing cells, a mouse or a rat is preferably used as the animal to be immunized.

Further, the strain of a mouse or a rat to be used is not particularly limited, and in the case of a mouse, for example, various strains such as A, AKR, BALB/c, BDP, BA, CE, C3H, 57BL, C57BL, C57L, DBA, FL, HTH, HT1, LP, NZB, NZW, RF, R III, SJL, SWR, WB, and 129 and the like can be used, and in the case of a rat, for example, Wistar, Low, Lewis, Sprague, Dawley, ACI, BN, Fischer and the like can be used.

These mice and rats are commercially available from breeders/distributors of experimental animals, for example, CLEA Japan, Inc. and Charles River Laboratories Japan, Inc.

As the animal to be immunized, in consideration of compatibility of fusing with myeloma cells described below, in the case of a mouse, BALB/c strain, and in the case of a rat, Wistar and Low strains are particularly preferred.

Further, in consideration of antigenic homology between humans and mice, it is also preferred to use a mouse having decreased biological function to remove auto-antibodies, that is, a mouse with an autoimmune disease.

The age of such mouse or rat at the time of immunization is preferably 5 to 12 weeks of age, more preferably 6 to 8 weeks of age.

In order to immunize an animal with HER2 or a recombinant thereof, for example, a known method described in detail in, for example, Weir, D. M., Handbook of Experimental Immunology Vol. I. II. III., Blackwell Scientific Publications, Oxford (1987); Rabat, E. A. and Mayer, M. M., Experimental Immunochemistry, Charles C Thomas Publisher Springfield, Ill. (1964) or the like can be used.

Among these immunization methods, a preferred specific method in the present invention is, for example, as follows.

That is, first, a membrane protein fraction serving as the antigen or cells caused to express the antigen is/are intradermally or intraperitoneally administrated to an animal. However, the combination of both routes of administration is preferred for increasing the immunization efficiency, and when intradermal administration is performed in the first half and intraperitoneal administration is performed in the latter half or only at the last dosing, the immunization efficiency can be particularly increased.

The administration schedule of the antigen varies depending on the type of animal to be immunized, individual difference or the like. However, in general, an administration schedule in which the frequency of administration of the antigen is 3 to 6 times and the dosing interval is 2 to 6 weeks is preferred, and an administration schedule in which the frequency of administration of the antigen is 3 to 4 times and the dosing interval is 2 to 4 weeks is more preferred.

Further, the dose of the antigen varies depending on the type of animal, individual differences or the like, however, the dose is generally set to 0.05 to 5 mg, preferably about 0.1 to 0.5 mg.

A booster immunization is performed 1 to 6 weeks, preferably 1 to 4 weeks, more preferably 1 to 3 weeks after the administration of the antigen as described above. When the immunogen is cells, $1 \times 10^6$ to $1 \times 10^7$ cells are used.

The dose of the antigen at the time of performing the booster immunization varies depending on the type or size of animal or the like, however, in the case of, for example, a mouse, the dose is generally set to 0.05 to 5 mg, preferably 0.1 to 0.5 mg, more preferably about 0.1 to 0.2 mg. When the immunogen is cells, $1 \times 10^6$ to $1 \times 10^7$ cells are used.

Spleen cells or lymphocytes including antibody-producing cells are aseptically removed from the immunized animal after 1 to 10 days, preferably 2 to 5 days, more preferably 2 to 3 days from the booster immunization. At this time, the antibody titer is measured, and if an animal having a sufficiently increased antibody titer is used as a supply source of the antibody-producing cells, the subsequent procedure can be carried out more efficiently.

Examples of the method of measuring the antibody titer to be used here include an RIA method and an ELISA method, but the method is not limited thereto. For example, if an ELISA method is employed, the measurement of the antibody titer in the invention can be carried out according to the procedures as described below.

First, a purified or partially purified antigen is adsorbed to the surface of a solid phase such as a 96-well plate for ELISA, and the surface of the solid phase having no antigen adsorbed thereto is covered with a protein unrelated to the antigen such as bovine serum albumin (BSA). After washing the surface, the surface is brought into contact with a serially-diluted sample (for example, mouse serum) as a primary antibody to allow the antibody in the sample to bind to the antigen.

Further, as a secondary antibody, an antibody labeled with an enzyme against a mouse antibody is added and is allowed to bind to the mouse antibody. After washing, a substrate for the enzyme is added and a change in absorbance which occurs due to color development induced by degradation of the substrate or the like is measured and the antibody titer is calculated based on the measurement.

The separation of the antibody-producing cells from the spleen cells or lymphocytes of the immunized animal can be carried out according to a known method (for example, Kohler et al., Nature (1975), 256, p. 495; Kohler et al., Eur. J. Immunol. (1977), 6, p. 511; Milstein et al., Nature (1977), 266, p. 550; Walsh, Nature (1977), 266, p. 495). For example, in the case of spleen cells, a general method in which the antibody-producing cells are separated by homogenizing the spleen to obtain the cells through filtration with a stainless steel mesh and suspending the cells in Eagle's Minimum Essential Medium (MEM) can be employed.

(c) Preparation of Myeloma Cells (Hereinafter Referred to as "Myeloma")

The myeloma cells to be used for cell fusion are not particularly limited and suitable cells can be selected from known cell lines. However, in consideration of convenience when a hybridoma is selected from fused cells, it is preferred to use an HGPRT (hypoxanthine-guanine phosphoribosyl transferase) deficient strain whose selection procedure has been established.

More specifically, examples of the HGPRT-deficient strain include X63-Ag8(X63), NS1-ANS/1(NS1), P3X63-Ag8.U1(P3U1), X63-Ag8.653(X63.653), SP2/0-Ag14(SP2/0), MPC11-45.6TG1.7(45.6TG), FO, S149/5XXO, and BU.1 derived from mice; 210.RSY3.Ag.1.2.3 (Y3) derived from rats; and U266AR (SKO-007), GM1500-GTG-A12 (GM1500), UC729-6, LICR-LOW-HMy2(HMy2) and 8226AR/NIP4-1(NP41) derived from humans. These HGPRT-deficient strains are available from, for example, ATCC or the like.

These cell strains are subcultured in an appropriate medium such as an 8-azaguanine medium [a medium obtained by adding 8-azaguanine to an RPMI 1640 medium supplemented with glutamine, 2-mercaptoethanol, gentamicin, and fetal calf serum (hereinafter referred to as "FCS")], Iscove's Modified Dulbecco's Medium (hereinafter referred to as "IMDM"), or Dulbecco's Modified Eagle Medium (hereinafter referred to as "DMEM"). In this case, 3 to 4 days before performing cell fusion, the cells are subcultured in a normal medium (for example, an ASF104 medium (manufactured by Ajinomoto Co., Ltd.) containing 10% FCS) to ensure not less than $2 \times 10^7$ cells on the day of cell fusion.

(d) Cell Fusion

Fusion between the antibody-producing cells and the myeloma cells can be appropriately performed according to a known method (Weir, D. M. Handbook of Experimental Immunology Vol. I. II. III., Blackwell Scientific Publications, Oxford (1987); Rabat, E. A. and Mayer, M. M., Experimental Immunochemistry, Charles C Thomas Publisher, Springfield, Ill. (1964), etc.), under conditions such that the survival rate of cells is not excessively reduced.

As such a method, for example, a chemical method in which the antibody-producing cells and the myeloma cells are mixed in a solution containing a polymer such as polyethylene glycol at a high concentration, a physical method using electric stimulation, or the like can be used. Among these methods, a specific example of the chemical method is as described below.

That is, in the case where polyethylene glycol is used in the solution containing a polymer at a high concentration, the antibody-producing cells and the myeloma cells are mixed in a solution of polyethylene glycol having a molecular weight of 1500 to 6000, more preferably 2000 to 4000 at a temperature of from 30 to 40° C., preferably from 35 to 38° C. for 1 to 10 minutes, preferably 5 to 8 minutes.

(e) Selection of a Group of Hybridomas

The method of selecting hybridomas obtained by the above-described cell fusion is not particularly limited. Usually, an HAT (hypoxanthine, aminopterin, thymidine) selection method (Kohler et al., Nature (1975), 256, p. 495; Milstein et al., Nature (1977), 266, p. 550) can be used.

This method is effective when hybridomas are obtained using the myeloma cells of an HGPRT-deficient strain which cannot survive in the presence of aminopterin. That is, by culturing unfused cells and hybridomas in an HAT medium, only hybridomas resistant to aminopterin are selectively allowed to survive and proliferate.

(f) Division into Single Cell Clone (Cloning)

As a cloning method for hybridomas, a known method such as a methylcellulose method, a soft agarose method, or a limiting dilution method can be used (see, for example, Barbara, B. M. and Stanley, M. S.: Selected Methods in Cellular Immunology, W. H. Freeman and Company, San Francisco (1980)). Among these methods, particularly, a three-dimensional culture method such as a methylcellulose method is preferred. For example, the group of hybridomas produced by cell fusion are suspended in a methylcellulose medium such as ClonaCell-HY Selection Medium D (manufactured by StemCell Technologies, Inc., #03804) and cultured. Then, the formed hybridoma colonies are collected, whereby monoclonal hybridomas can be obtained. The collected respective hybridoma colonies are cultured, and a hybridoma which has been confirmed to have a stable antibody titer in an obtained hybridoma culture supernatant is selected as a HER2 monoclonal antibody-producing hybridoma strain.

(g) Preparation of Monoclonal Antibody by Culturing Hybridoma

By culturing the thus selected hybridoma, a monoclonal antibody can be efficiently obtained. However, prior to culturing, it is preferred to perform screening of a hybridoma which produces a target monoclonal antibody.

In such screening, a known method can be employed.

The measurement of the antibody titer in the invention can be carried out by, for example, an ELISA method explained in item (b) described above.

The hybridoma obtained by the method described above can be stored in a frozen state in liquid nitrogen or in a freezer at −80° C. or below.

After completion of cloning, the medium is changed from an HT medium to a normal medium, and the hybridoma is cultured.

Large-scale culture is performed by rotation culture using a large culture bottle or by spinner culture. From the supernatant obtained by the large-scale culture, a monoclonal antibody which specifically binds to the protein of the invention can be obtained by purification using a method known to those skilled in the art such as gel filtration.

Further, the hybridoma is injected into the abdominal cavity of a mouse of the same strain as the hybridoma (for example, the above-described BALB/c) or a Nu/Nu mouse to proliferate the hybridoma, whereby the ascites containing a large amount of the monoclonal antibody of the invention can be obtained.

In the case where the hybridoma is administered in the abdominal cavity, if a mineral oil such as 2,6,10,14-tetramethyl pentadecane (pristane) is administered 3 to 7 days prior thereto, a larger amount of the ascites can be obtained.

For example, an immunosuppressant is previously injected into the abdominal cavity of a mouse of the same strain as the hybridoma to inactivate T cells. 20 days thereafter, $10^6$ to $10^7$ hybridoma clone cells are suspended in a serum-free medium (0.5 ml), and the suspension is administrated in the abdominal cavity of the mouse. In general, when the abdomen is expanded and filled with the ascites, the ascites is collected from the mouse. By this method, the monoclonal antibody can be obtained at a concentration which is about 100 times or much higher than that in the culture solution.

The monoclonal antibody obtained by the above-described method can be purified by a method described in, for example, Weir, D. M.: Handbook of Experimental Immunology Vol. I, II, III, Blackwell Scientific Publications, Oxford (1978).

The thus obtained monoclonal antibody has high antigen specificity for HER2. Examples of the monoclonal antibody of the present invention can include, but are not particularly limited to, a mouse monoclonal antibody 4D5 (ATCC CRL 10463).

(h) Assay of Monoclonal Antibody

The isotype and subclass of the thus obtained monoclonal antibody can be determined as follows.

First, examples of the identification method include an Ouchterlony method, an ELISA method, and an RIA method.

An Ouchterlony method is simple, but when the concentration of the monoclonal antibody is low, a condensation operation is required.

On the other hand, when an ELISA method or an RIA method is used, by directly reacting the culture supernatant with an antigen-adsorbed solid phase and using antibodies corresponding to various types of immunoglobulin isotypes and subclasses as secondary antibodies, the isotype and subclass of the monoclonal antibody can be identified.

In addition, as a simpler method, a commercially available identification kit (for example, Mouse Typer Kit manufactured by Bio-Rad Laboratories, Inc.) or the like can also be used.

Further, the quantitative determination of a protein can be performed by the Folin Lowry method and a method of calculation based on the absorbance at 280 nm (1.4 ($OD_{280}$) =Immunoglobulin 1 mg/ml).

Further, even when the monoclonal antibody is separately and independently obtained by performing again the steps of (a) to (h) in (2), it is possible to obtain an antibody having a cytotoxic activity equivalent to that of the HER2 antibody obtained in the step of (g). As one example of such an antibody, an antibody which binds to the same epitope as the HER2 antibody obtained in the step of (g) can be exemplified. If a newly produced monoclonal antibody binds to a partial peptide or a partial tertiary structure to which the anti-HER2 antibody binds, it can be determined that the monoclonal antibody binds to the same epitope as the anti-HER2 antibody. Further, by confirming that the monoclonal antibody competes with the anti-HER2 antibody for the binding to HER2 (that is, the monoclonal antibody inhibits the binding between the anti-HER2 antibody and HER2), it can be determined that the monoclonal antibody binds to the same epitope as the anti-HER2 antibody even if the specific epitope sequence or structure has not been determined. When it is confirmed that the monoclonal antibody binds to the same epitope as the anti-HER2 antibody, the monoclonal antibody is strongly expected to have an antigen-binding affinity or biological activity equivalent to that of the anti-HER2 antibody.

(3) Other Antibodies

The antibody of the invention includes not only the above-described monoclonal antibody against HER2 but also a recombinant antibody obtained by artificial modification for the purpose of decreasing heterologous antigenicity to humans such as a chimeric antibody, a humanized antibody and a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region can be exemplified (see Proc. Natl. Acad. Sci. USA, 81, 6851-6855, (1984)). Examples of the chimeric antibody of the present invention can include, but are not particularly limited to, a chimeric antibody 4D5 comprising a heavy chain constant region of human IgG1 or IgG2.

As the humanized antibody, an antibody obtained by integrating only a complementarity determining region (CDR) into a human-derived antibody (see Nature (1986) 321, pp. 522-525), and an antibody obtained by grafting a part of the amino acid residues of the framework as well as the CDR sequence to a human antibody by a CDR-grafting method (WO 90/07861), and an antibody humanized using gene conversion mutagenesis strategy (U.S. Pat. No. 5,821,337) can be exemplified.

The term "several" as used herein refers to 1 to 10, 1 to 9, 1 to 8, 1 to 7, 1 to 6, 1 to 5, 1 to 4, 1 to 3, or 1 or 2.

As the amino acid substitution in this specification, a conservative amino acid substitution is preferred. The conservative amino acid substitution refers to a substitution occurring within a group of amino acids related to amino acid side chains. Preferred amino acid groups are as follows: an acidic group (aspartic acid and glutamic acid); a basic group (lysine, arginine, and histidine); a non-polar group (alanine, valine, leucine, isoleucine, proline, phenylalanine, methionine, and tryptophan); and an uncharged polar family (glycine, asparagine, glutamine, cysteine, serine, threonine, and tyrosine). More preferred amino acid groups are as follows: an aliphatic hydroxy group (serine and threonine); an amide-containing group (asparagine and glutamine); an aliphatic group (alanine, valine, leucine, and isoleucine); and an aromatic group (phenylalanine, tryptophan, and tyrosine). Such an amino acid substitution is preferably performed within a range which does not impair the properties of a substance having the original amino acid sequence.

By combining a sequence having a high homology with the above-described heavy chain amino acid sequence with a sequence having a high homology with the above-described light chain amino acid sequence, it is possible to select an antibody having a biological activity equivalent to that of each of the above-described antibodies. Such a homology is generally a homology of 80% or more, preferably a homology of 90% or more, more preferably a homology of 95% or more, most preferably a homology of 99% or more. Further, by combining an amino acid sequence wherein one to several amino acid residues are substituted, deleted or added in the heavy chain or light chain amino acid sequence, it is also possible to select an antibody having a biological activity equivalent to that of each of the above-described antibodies. The term "homology" as used herein is used with the same meaning as "identity".

The homology between two amino acid sequences can be determined using default parameters of Blast algorithm version 2.2.2 (Altschul, Stephen F., Thomas L. Madden, Alejandro A. Schaeffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm can be used also through the Internet by accessing the site www.ncbi.nlm.nih.gov/blast.

Further, the antibody of the invention includes a human antibody which binds to HER2. An anti-HER2 human antibody refers to a human antibody having only a sequence of an antibody derived from a human chromosome. The anti-HER2 human antibody can be obtained by a method using a human antibody-producing mouse having a human chromosome fragment comprising heavy and light chain genes of a human antibody (see Tomizuka, K. et al; Nature Genetics (1997) 16, pp. 133-143; Kuroiwa, Y. et al., Nucl. Acids Res. (1998) 26, pp. 3447-3448; Yoshida, H. et al., Animal Cell Technology: Basic and Applied Aspects vol. 10, pp. 69-73 (Kitagawa, Y., Matuda, T. and Iijima, S. eds.), Kluwer Academic Publishers, 1999; Tomizuka, K. et al., Proc. Natl. Acad. Sci. USA (2000) 97, pp. 722-727, etc.).

Such a human antibody-producing mouse can be created specifically as follows. A genetically modified animal in which endogenous immunoglobulin heavy and light chain gene loci have been disrupted, and instead, human immunoglobulin heavy and light chain gene loci have been introduced via a yeast artificial chromosome (YAC) vector or the like is created by producing a knockout animal and a transgenic animal and mating these animals.

Further, according to a recombinant DNA technique, by using cDNAs encoding each of such a heavy chain and a light chain of a human antibody, and preferably a vector comprising such cDNAs, eukaryotic cells are transformed, and a transformant cell which produces a recombinant human monoclonal antibody is cultured, whereby the antibody can also be obtained from the culture supernatant.

Here, as the host, for example, eukaryotic cells, preferably mammalian cells such as CHO cells, lymphocytes, or myeloma cells can be used.

Further, a method of obtaining a phage display-derived human antibody selected from a human antibody library (see Wormstone, I. M. et al., Investigative Ophthalmology & Visual Science (2002), 43 (7), pp. 2301-2308; Carmen, S. et al., Briefings in Functional Genomics and Proteomics (2002), 1 (2), pp. 189-203; Siriwardena, D. et al., Ophthalmology (2002), 109 (3), pp. 427-431, etc.) is also known.

For example, a phage display method in which a variable region of a human antibody is expressed on the surface of a phage as a single-chain antibody (scFv), and a phage which binds to an antigen is selected (Nature Biotechnology (2005), 23(9), pp. 1105-1116) can be used.

By analyzing the gene of the phage selected based on the binding to an antigen, a DNA sequence encoding the variable region of a human antibody which binds to an antigen can be determined.

If the DNA sequence of scFv which binds to an antigen is determined, a human antibody can be obtained by preparing an expression vector comprising the sequence and introducing the vector into an appropriate host to express it (WO 92/01047, WO 92/20791, WO 93/06213, WO 93/11236, WO 93/19172, WO 95/01438, WO 95/15388; Annu. Rev. Immunol. (1994) 12, pp. 433-455, Nature Biotechnology (2005), 23 (9), pp. 1105-1116).

As one example of another index for use in the comparison of the properties of antibodies, the stability of antibodies can be exemplified. The differential scanning calorimetry (DSC) is a device capable of quickly and accurately measuring a thermal denaturation midpoint temperature (Tm) to be used as a favorable index of the relative conformational stability of proteins. By measuring the Tm values using DSC and comparing the values, a difference in thermal stability can be compared. It is known that the storage stability of antibodies shows some correlation with the thermal stability of antibodies (Lori Burton, et. al., Pharmaceutical Development and Technology (2007), 12, pp. 265-273), and a preferred antibody can be selected by using thermal stability as an index. Examples of other indices for selecting antibodies include the following features: the yield in an appropriate host cell is high; and the aggregability in an aqueous solution is low. For example, an antibody which shows the highest yield does not always show the highest thermal stability, and therefore, it is necessary to select an antibody most suitable for the administration to humans by making comprehensive evaluation based on the above-described indices.

In the present invention, a modified variant of the antibody is also included. The modified variant refers to a variant obtained by subjecting the antibody of the present invention to chemical or biological modification. Examples of the chemically modified variant include variants chemically modified by linking a chemical moiety to an amino acid skeleton, variants chemically modified with an N-linked or O-linked carbohydrate chain, etc. Examples of the biologically modified variant include variants obtained by post-translational modification (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell. Further, an antibody labeled so as to enable the detection or isolation of the antibody or an antigen of the invention, for example, an enzyme-labeled antibody, a fluorescence-labeled antibody, and an affinity-labeled antibody are also included in the meaning of the modified variant. Such a modified variant of the antibody of the invention is useful for improving the stability and blood retention of the antibody, reducing the antigenicity thereof, detecting or isolating an antibody or an antigen, and so on.

Further, by regulating the modification of a glycan which is linked to the antibody of the invention (glycosylation, defucosylation, etc.), it is possible to enhance an antibody-dependent cellular cytotoxic activity. As the technique for regulating the modification of a glycan of antibodies, WO 99/54342, WO 00/61739, WO 02/31140, etc. are known. However, the technique is not limited thereto. In the antibody of the present invention, an antibody in which the modification of a glycan is regulated is also included.

In the case where an antibody is produced by first isolating an antibody gene and then introducing the gene into an appropriate host, a combination of an appropriate host and an appropriate expression vector can be used. Specific examples of the antibody gene include a combination of a gene encoding a heavy chain sequence of an antibody described in this specification and a gene encoding a light chain sequence thereof. When a host cell is transformed, it is possible to insert the heavy chain sequence gene and the light chain sequence gene into the same expression vector, and also into different expression vectors separately.

In the case where eukaryotic cells are used as the host, animal cells, plant cells, and eukaryotic microorganisms can be used. As the animal cells, mammalian cells, for example, simian COS cells (Gluzman, Y., Cell, (1981), 23, pp. 175-182, ATCC CRL-1650), murine fibroblasts NIH3T3 (ATCC No. CRL-1658), and dihydrofolate reductase-deficient strains (Urlaub, G. and Chasin, L. A., Proc. Natl. Acad. Sci. USA (1980), 77, pp. 4126-4220) of Chinese hamster ovarian cells (CHO cells; ATCC: CCL-61) can be exemplified.

In the case where prokaryotic cells are used, for example, *Escherichia coli* and *Bacillus subtilis* can be exemplified.

By introducing a desired antibody gene into these cells through transformation, and culturing the thus transformed cells in vitro, the antibody can be obtained. In the above-described culture method, the yield may sometimes vary depending on the sequence of the antibody, and therefore, it is possible to select an antibody which is easily produced as a pharmaceutical by using the yield as an index among the antibodies having an equivalent binding activity. Therefore, in the antibody of the present invention, an antibody obtained by a method of producing an antibody, characterized by including a step of culturing the transformed host cell and a step of collecting a desired antibody from a cultured product obtained in the culturing step is also included.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (the activation of a complement, the antibody-dependent cellular cytotoxicity, etc.) of the antibody. Therefore, in the antibody according to the present invention, an antibody subjected to such modification and a functional fragment of the antibody is also included, and a deletion variant in which one or two amino acids have been deleted at the carboxyl terminus of the heavy chain, a variant obtained by amidation of the deletion variant (for example, a heavy chain in which the carboxyl terminal proline residue has been amidated), and the like are also included. The type of deletion variant having a deletion at the carboxyl terminus of the heavy chain of the antibody according to the invention is not limited to the above variants as long as the antigen-binding affinity and the effector function are conserved. The two heavy chains constituting the antibody according to the invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the invention and the culture conditions, however, a case where one amino acid residue at the carboxyl terminus has been deleted in both of the two heavy chains contained as main components in the antibody according to the invention can be exemplified.

As isotype of the antibody of the invention, for example, IgG (IgG1, IgG2, IgG3, IgG4) can be exemplified, and IgG1 or IgG2 can be exemplified preferably.

As the biological activity of the antibody, generally an antigen-binding activity, an activity of internalizing in cells expressing an antigen by binding to the antigen, an activity of neutralizing the activity of an antigen, an activity of enhancing the activity of an antigen, an antibody-dependent cellular cytotoxicity (ADCC) activity, a complement-dependent cytotoxicity (CDC) activity, and an antibody-dependent cell-mediated phagocytosis (ADCP) can be exemplified. The biological activity of the antibody of the present invention is a binding activity to HER2, and preferably an activity of internalizing in HER2-expressing cells by binding to HER2. Further, the antibody of the present invention may have an ADCC activity, a CDC activity, and/or an ADCP activity in addition to an activity of internalizing in cells.

The obtained antibody can be purified to homogeneity. The separation and purification of the antibody may be performed employing a conventional protein separation and purification method. For example, the antibody can be separated and purified by appropriately selecting and combining column chromatography, filter filtration, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of such chromatography include affinity chromatography, ion exchange chromatography, hydrophobic chromatography, gel filtration chromatography, reverse phase chromatography, and adsorption chromatography.

Such chromatography can be performed employing liquid chromatography such as HPLC or FPLC.

As a column to be used in affinity chromatography, a Protein A column and a Protein G column can be exemplified. For example, as a column using a Protein A column, Hyper D, POROS, Sepharose FF (Pharmacia Corporation) and the like can be exemplified.

Further, by using a carrier having an antigen immobilized thereon, the antibody can also be purified utilizing the binding property of the antibody to the antigen.

The antibody in the antibody-drug conjugate needs only to be the antibody, which is capable of targeting tumor cells. That is, the antibody can possess a property of recognizing tumor cells, a property of binding to tumor cells, and a property of internalizing in tumor cells and more preferably possesses even cytocidal activity against tumor cells. Such an antibody can be conjugated with an antitumor drug via the linker structure of the present invention to obtain an excellent antibody-drug conjugate. Specifically, the antibody used in the antibody-drug conjugate of the present invention is not limited to the anti-HER2 antibody, and examples thereof can include, but not limited to, anti-A33 antibodies, anti-B7-H3 antibodies, anti-CanAg antibodies, anti-CD20 antibodies, anti-CD22 antibodies, anti-CD30 antibodies, anti-CD33 antibodies, anti-CD56 antibodies, anti-CD70 antibodies, anti-CD98 antibodies, anti-CEA antibodies, anti-Cripto antibodies, anti-EphA2 antibodies, anti-G250 antibodies, anti-GPNMB antibodies, anti-HER3 antibodies, anti-Integrin antibodies, anti-Mesothelin antibodies, anti-MUC1 antibodies, anti-PSMA antibodies, anti-SLC44A4 antibodies, anti-Tenascin-C antibodies, and anti-TROP2 antibodies.

[Antitumor Compound]

The antitumor compound to be conjugated to the anti-HER2 antibody-drug conjugate of the present invention is explained. The antitumor compound used in the present invention is not particularly limited provided it is a compound having an antitumor effect and a substituent group or a partial structure allowing connection to a linker structure. When a part or whole linker is cleaved in tumor cells, the antitumor compound moiety is released to exhibit the antitumor effect of the antitumor compound. As the linker is cleaved at a connecting position to the drug, the antitumor compound is released in an unmodified structure to exhibit its intrinsic antitumor effect.

As the antitumor compound used in the present invention, exatecan (((1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione; shown in the following formula), one of the camptothecin derivatives, can be preferably used.

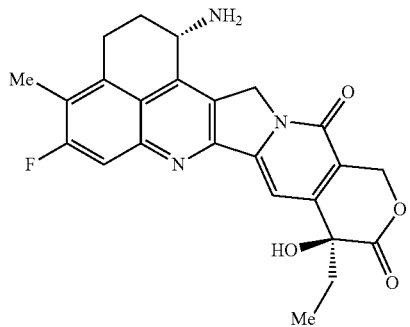

[Formula 21]

Although having an excellent antitumor effect, exatecan has not been commercialized as an antitumor drug. The compound can be easily obtained by a known method and the amino group at position 1 can be preferably used as the connecting position to the linker structure. Further, although exatecan can be also released in tumor cells while part of the linker is still attached thereto, it is an excellent compound exhibiting an excellent antitumor effect even in such a structure.

Because exatecan has a camptothecin structure, it is known that the equilibrium shifts to a structure with a closed lactone ring (closed ring) in an aqueous acidic medium (for example, pH 3 or so) but it shifts to a structure with an open lactone ring (open ring) in an aqueous basic medium (for example, pH 10 or so). A drug conjugate being introduced with an exatecan residue corresponding to the closed ring structure and the open ring structure is also expected to have the same antitumor effect and it is needless to say that any of these structures is within the scope of the present invention.

Further examples of the antitumor compound can include doxorubicin, daunorubicin, mitomycin C, bleomycin, cyclocytidine, vincristine, vinblastine, methotrexate, platinum-based antitumor agent (cisplatin or derivatives thereof), taxol or derivatives thereof, and other camptothecins or derivatives thereof (antitumor agent described in Japanese Patent Laid-Open No. 6-87746).

With regard to the antibody-drug conjugate, the number of conjugated drug molecules per antibody molecule is a key factor having an influence on efficacy and safety. Production of the antibody-drug conjugate is performed by defining the reaction conditions including the amounts of raw materials and reagents used for the reaction so as to have a constant number of conjugated drug molecules. A mixture containing different numbers of conjugated drug molecules is generally obtained unlike the chemical reaction of a low-molecular-weight compound. The number of drugs conjugated in an antibody molecule is expressed or specified by the average value, that is, the average number of conjugated drug molecules. Unless specifically described otherwise as a principle, the number of conjugated drug molecules means the average value except in the case in which it represents an antibody-drug conjugate having a specific number of conjugated drug molecules that is included in an antibody-drug conjugate mixture having different numbers of conjugated drug molecules.

The number of exatecan molecules conjugated to an antibody molecule is controllable, and as the average number of conjugated drug molecules per antibody molecule, about 1 to 10 exatecans can be connected. Preferably, it is 2 to 8, and more preferably 3 to 8. Meanwhile, a person skilled in the art can design a reaction for conjugating a required number of drug molecules to an antibody molecule based on the description of the Examples of the present application and can obtain an antibody-drug conjugate conjugated with a controlled number of exatecan molecules.

[Linker Structure]

1. Linker

Hereinafter, the linker of the present invention is described. The linker of the present invention has a structure of any of the following formulas:

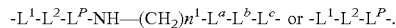

-$L^1$-$L^2$-$L^P$-NH—(CH$_2$)$n^1$-$L^a$-$L^b$-$L^c$- or -$L^1$-$L^2$-$L^P$-.

The antibody is connected to the terminal $L^1$, which is a terminal opposite to the connection to $L^2$. The antitumor drug is connected to the terminal $L^c$, which is a terminal opposite to the connection of $L^b$, or the terminal $L^P$, which is a terminal opposite to the connection to $L^2$.

As for the structure moiety represented by —NH—(CH$_2$)$n^1$- in the linker, $n^1$ is an integer of 0 to 6 and is preferably an integer of 1 to 5, and more preferably 1 to 3. The amino group moiety of this moiety is connected to the C terminal of $L^P$.

2. $L^P$

In the linker, $L^P$ is a peptide consisting of 2 to 8 amino acids. Each amino acid constituting the peptide can be an amino acid such as phenylalanine (Phe; F), leucine (Leu; L), glycine (Gly; G), alanine (Ala; A), valine (Val; V), or citrulline (Cit). The amino acid constituting the peptide may be a hydrophilic amino acid having a hydrophilic structure moiety or may be aspartic acid (Asp; D), glutamic acid (Glu; E), lysine (Lys; K), serine (Ser; S), threonine (Thr; T), glutamine (Gln; Q), asparagine (Asn; N), histidine (His; H), tyrosine (Tyr; Y), or arginine (Arg; R). The amino acid constituting $L^P$ can be an L- or a D-amino acid and is preferably an L-amino acid. It can be β-alanine, ε-aminocaproic acid, γ-aminobutyric acid, or the like in addition to an α-amino acid, and further, it can be, for example, a non-natural type amino acid such as an amino acid N-methylated at its α-amino group. Among these amino acids, preferred examples thereof can include phenylalanine, glycine, valine, lysine, citrulline, serine, glutamic acid, and aspartic acid.

Examples of a sequence preferred as $L^P$ can include a tripeptide of GFG and a tetrapeptide of GGFG (SEQ ID NO: 3). Among these, GGFG (SEQ ID NO: 3) is more preferred.

These peptides, particularly GGFG (SEQ ID NO: 3), can be converted to other sequences by the substitution or addition of a constituting amino acid. A hydrophilic amino acid can be preferably used as the amino acid for such substitution or addition. Any of the hydrophilic amino acids shown above can be used, and preferred examples thereof can include aspartic acid, glutamic acid, lysine, and serine. Examples of a sequence in which the hydrophilic amino acid is added can include a sequence in which one or two amino acids are added to the N terminal of the linker peptide. In the case of adding two hydrophilic amino acids, one of them is preferably aspartic acid. Examples of such a sequence can include DGGFG (SEQ ID NO: 10), KGGFG (SEQ ID NO: 15), EGGFG (SEQ ID NO: 16), SGGFG (SEQ ID NO: 17), DDGGFG (SEQ ID NO: 13), KDGGFG (SEQ ID NO: 14), EDGGFG (SEQ ID NO: 19), and SDGGFG (SEQ ID NO: 20). Peptides obtained by the removal of C-terminal glycine from these can be also preferably used. Among them, DGGF (SEQ ID NO: 9) is preferred. This is particularly preferred when the linker has a structure represented by -$L^1$-$L^2$-$L^P$-.

Serine may be added the C terminal of the linker peptide. Examples thereof can include GGFGS (SEQ ID NO: 5) and DGGFS (SEQ ID NO: 12).

Glycine is also classified as a hydrophilic amino acid and is also known to be hydrophilic. A peptide in which two or three or more glycine residues are consecutively connected may be added. Preferred examples of such a form of glycine can include a di- or tripeptide of glycine. For the linker peptide containing such a sequence, it is preferred that this sequence should be present at the C terminal. Examples thereof can include GGFGG (SEQ ID NO: 4) and GGFGGG (SEQ ID NO: 6). In the peptide having such glycine residues, an additional amino acid may be connected to the C terminal, and examples thereof can include GGFGGE (SEQ ID NO: 7) and GGFGGGFG (SEQ ID NO: 8).

Examples of the minimum linker peptide can include VC and VA in addition to a dipeptide of VK containing lysine having a hydrophilic structure.

Examples of the peptide containing a D-amino acid can include $D^d$GGFG in which aspartic acid in the peptide of DGGFG (SEQ ID NO: 10) is substituted with D-aspartic acid (referred to as $D^d$). Examples of the N-methylamino acid can include DG$^{Me}$GFG (SEQ ID NO: 11) in which glycine as the 2nd amino acid (1st glycine) counted from the N terminal of DGGFG (SEQ ID NO: 10) is converted to N-methylglycine (sarcosine; referred to as $G^{Me}$) by the methylation of α-amino group thereof. Selection of such a D-amino acid, selection of an N-methylated amino acid, and further, selection of the position of such an amino acid within the peptide are not limited to these examples.

In view of the above, examples of the peptide that can be preferably used as $L^P$ in the present invention can include VK, VC, GFG, GGFG (SEQ ID NO: 3), GGFGG (SEQ ID NO: 4), GGFGS (SEQ ID NO: 5), GGFGGG (SEQ ID NO: 6), GGFGGE (SEQ ID NO: 7), GGFGGGFG (SEQ ID NO: 8), DGGF (SEQ ID NO: 9), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), and SGGFG (SEQ ID NO: 17). Among these, GGFG (SEQ ID NO: 3), GGFGG (SEQ ID NO: 4), GGFGS (SEQ ID NO: 5), GGFGGE (SEQ ID NO: 7), GDGGF (SEQ ID NO: 18), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) is preferred. GGFG (SEQ ID NO: 3), GDGGF (SEQ ID NO: 18), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), or KDGGFG (SEQ ID NO: 14) is more preferred. GGFG (SEQ ID NO: 3), DGGFG (SEQ ID NO: 10), $D^d$GGFG, or DG$^{Me}$GFG (SEQ ID NO: 11) is further preferred.

When the linker structure is -$L^1$-$L^2$-$L^P$-NH—(CH$_2$)$n^1$-$L^a$-$L^b$-$L^c$-, $L^P$ is preferably GGFG (SEQ ID NO: 3) or DGGFG (SEQ ID NO: 10), more preferably GGFG (SEQ ID NO: 3). When the linker structure is -$L^1$-$L^2$-$L^P$-lacking —NH—(CH$_2$)$n^1$-$L^a$-$L^b$-$L^c$-, $L^P$ can be GGFG (SEQ ID NO: 3), GDGGF (SEQ ID NO: 18), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), or KDGGFG (SEQ ID NO: 14), but is preferably GGFG (SEQ ID NO: 3) or contains aspartic acid, more preferably DGGFG (SEQ ID NO: 10), $D^d$GGFG, or DG$^{Me}$GFG (SEQ ID NO: 11), further preferably GGFG (SEQ ID NO: 3) or DGGFG (SEQ ID NO: 10).

3. $L^1$

In the linker, $L^1$ has a structure represented by
-(Succinimid-3-yl-N)—(CH$_2$)$n^2$-C(=O)—,
-(Succinimid-3-yl-N)—CH[—(CH$_2$)$n^3$-COOH]—C(=O)—, -(Succinimid-3-yl-N)—CH$_2$CH$_2$—[N(—CH$_2$—COOH)]—CH$_2$—(C=O)—,
—CH$_2$—C(=O)—NH—(CH$_2$)n$^4$-C(=O)—,
—C(=O)-cyc.Hex(1,4)-CH$_2$—(N-ly-3-diminiccuS)-, or
—C(=O)—(CH$_2$)n$^5$-C(=O)—, Here, n$^2$ is an integer of 2 to 8, n$^3$ is an integer of 1 to 8, n$^4$ is an integer of 1 to 8, and n$^5$ is an integer of 1 to 8.

In the structure represented by -(Succinimid-3-yl-N)—(CH$_2$)n$^2$-C(=O)— of L$^1$, "-(Succinimid-3-yl-N)—" is a structure represented by the following formula.

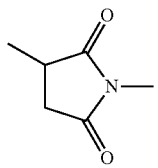

[Formula 22]

Position 3 of the above partial structure is the connecting position to the antibody. The bond to the antibody at position 3 is characterized by bonding with thioether formation at a disulfide bond site in the hinge part of the antibody. On the other hand, the nitrogen atom at position 1 of the structure moiety is connected to the carbon atom of the methylene which is present within the linker including the structure. Specifically, antibody-S-(Succinimid-3-yl-N)—(CH$_2$)n$^2$-C(=O)-L$^2$- is a structure represented by the following formula (herein, "antibody-S—" originates from an antibody).

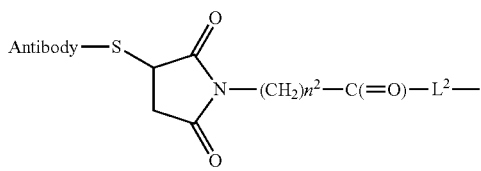

[Formula 23]

n$^2$ is an integer of 2 to 8 and is preferably 2 to 5.

The structure represented by -(Succinimid-3-yl-N)—CH[—(CH$_2$)n$^3$-COOH]—C(=O)— of L$^1$ is a hydrophilic structure. n$^3$ is an integer of 1 to 8 and is preferably 2 to 4, more preferably 2. In —(CH$_2$)n$^3$-COOH of this hydrophilic structure moiety, the carboxy group moiety may be a hydroxyl group or an amino group. When L$^1$ is -(Succinimid-3-yl-N)—CH[—(CH$_2$)n$^3$-COOH]—C(=O)—, —NH—(CH$_2$CH$_2$—O)n$^6$-CH$_2$CH$_2$—C(=O)— is preferably selected as L$^2$, and n$^6$ is preferably 0 to 4.

The structure represented by -(Succinimid-3-yl-N)—CH$_2$CH$_2$—[N(—CH$_2$—COOH)]—CH$_2$—(C=O)— of L$^1$ is also a hydrophilic structure.

In the structure represented by —CH$_2$—C(=O)—NH—(CH$_2$)n$^4$-C(=O)— of L$^1$, n$^4$ is an integer of 1 to 8 and is preferably 2 to 6. This structure is connected to the antibody via the carbon atom of the terminal methylene and forms the following structure by bonding with thioether formation, as in the above (herein, "antibody-S—" originates from an antibody).
Antibody-S—CH$_2$—C(=O)—NH—(CH$_2$)n$^4$-C(=O)-L$^2$-.

In the structure represented by —C(=O)-cyc.Hex (1,4)-CH$_2$—(N-ly-3-diminiccuS)- of L$^1$, "—(N-ly-3-diminiccuS)-" is a structure represented by the following formula.

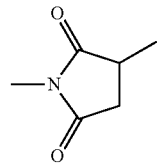

[Formula 24]

In this structure moiety, the nitrogen atom at position 1 is connected to the carbon atom of the methylene which is present within the linker including the structure. The carbon atom at position 3 is connected to the terminal sulfur atom of —S—(CH$_2$)n$^8$-C(=O)— of L$^2$. This structure —S—(CH$_2$)n$^8$-C(=O)— of L$^2$ is combined only with —C(=O)-cyc.Hex(1,4)-CH$_2$—(N-ly-3-diminiccuS)- of L$^1$ to form a linker structure. Herein, "-cyc.Hex(1,4)-" contained in the linker represents a 1,4-cyclohexylene group. The carbon atom of the terminal carbonyl in the structure —C(=O)-cyc.Hex(1,4)-CH$_2$—(N-ly-3-diminiccuS)- forms an amide bond with the antibody to form a structure represented by the following formula.

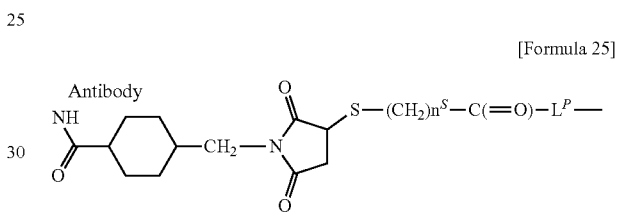

[Formula 25]

The amino group of the antibody for forming the amide bond can be a side chain amino group of a lysine residue of the antibody or the N-terminal amino group of the antibody. This structure can be also connected to the antibody by forming an ester bond with the hydroxyl group of an amino acid of the antibody, in addition to an amide bond.

The "-cyc.Hex(1,4)-" structure moiety of this structure may be a 1,4-cyclohexylene group or any of other divalent saturated cyclic alkylene groups, that is, a divalent cyclic saturated hydrocarbon group such as a cyclobutylene group, a cyclopentylene group, a cycloheptylene group, or a cyclooctylene group. Alternatively, it may be a divalent aromatic hydrocarbon group such as a phenylene group or a naphthylene group, or may be a divalent heterocyclic group containing one or two heteroatoms, which is a 5- or 6-membered saturated, partially saturated, or aromatic ring. Further, it may be a divalent alkylene group having 1 to 4 carbon atoms. The positions of the divalent bonding may be adjacent positions or may be distant positions.

In the structure represented by —C(=O)—(CH$_2$)n$^5$-C(=O)— of L$^1$, n$^5$ is an integer of 1 to 8 and is preferably 2 to 6. The terminal carbonyl group in this structure also forms an amide bond, as in the above structure, with the amino group of an amino acid of the antibody to form a structure represented by the following formula (herein, "antibody-NH—" originates from an antibody).
Antibody-NH—C(=O)—(CH$_2$)n$^5$-C(=O)-L$^2$-.

Specific examples of L$^1$ can include ones having the following structures:
-(Succinimid-3-yl-N)—CH$_2$CH$_2$—C(=O)
-(Succinimid-3-yl-N)—CH$_2$CH$_2$CH$_2$—C(=O)—,
-(Succinimid-3-yl-N)—CH$_2$CH$_2$CH$_2$CH$_2$—C(=O)—,
-(Succinimid-3-yl-N)—CH$_2$CH$_2$CH$_2$CH$_2$CH$_2$—C(=O)—, -(Succinimid-3-yl-N)—CH₂CH₂CH₂CH₂CH₂CH₂—C(=O)—,
-(Succinimid-3-yl-N)—CH₂CH₂CH₂CH₂CH₂CH₂CH₂—C(=O)—,
-(Succinimid-3-yl-N)—CH₂CH₂CH₂CH₂CH₂CH₂CH₂CH₂—C(=O)—,
-(Succinimid-3-yl-N)—CH(—CH₂—COOH)—C(=O)—,
-(Succinimid-3-yl-N)—CH(—CH₂CH₂—COOH)—C(=O)—,
-(Succinimid-3-yl-N)—CH(—CH₂CH₂CH₂—COOH)—C(=O)—,
-(Succinimid-3-yl-N)—CH(—CH₂CH₂CH₂CH₂—COOH)—C(=O)—,
-(Succinimid-3-yl-N)—CH(—CH₂CH₂CH₂CH₂CH₂—COOH)—C(=O)—,
-(Succinimid-3-yl-N)—CH(—CH₂CH₂CH₂CH₂CH₂CH₂—COOH)—C(=O)—,
-(Succinimid-3-yl-N)—CH(—CH₂CH₂CH₂CH₂CH₂CH₂CH₂—COOH)—C(=O)—,
-(Succinimid-3-yl-N)—CH(—CH₂CH₂CH₂CH₂CH₂CH₂CH₂CH₂—COOH)—C(=O)—,
(Succinimid-3-yl-N)—CH₂CH₂—[N(—CH₂—COOH)]—CH₂—(C=O)—,
—CH₂—C(=O)—NH—CH₂—C(=O)—,
—CH₂—C(=O)—NH—CH₂CH₂—C(=O)—,
—CH₂—C(=O)—NH—CH₂CH₂CH₂—C(=O)—,
—CH₂—C(=O)—NH—CH₂CH₂CH₂CH₂—C(=O)—,
—CH₂—C(=O)—NH—CH₂CH₂CH₂CH₂CH₂—C(=O)—,
—CH₂—C(=O)—NH—CH₂CH₂CH₂CH₂CH₂CH₂—C(=O)—,
—CH₂—C(=O)—NH—CH₂CH₂CH₂CH₂CH₂CH₂CH₂—C(=O)—,
—CH₂—C(=O)—NH—CH₂CH₂CH₂CH₂CH₂CH₂CH₂CH₂—C(=O)—,
—C(=O)-cyc.Hex(1,4)-CH₂—(N-ly-3-diminiccuS)-,
—C(=O)-Aryl(2)-CH₂—(N-ly-3-diminiccuS)-,
—C(=O)-cyc.Het(2)-CH₂—(N-ly-3-diminiccuS)-,
—C(=O)—CH₂—C(=O)—,
—C(=O)—CH₂CH₂—C(=O)—,
—C(=O)—CH₂CH₂CH₂—C(=O)—,
—C(=O)—CH₂CH₂CH₂CH₂—C(=O)—,
—C(=O)—CH₂CH₂CH₂CH₂CH₂—C(=O)—,
—C(=O)—CH₂CH₂CH₂CH₂CH₂CH₂—C(=O)—,
—C(=O)—CH₂CH₂CH₂CH₂CH₂CH₂CH₂—C(=O)—,
—C(=O)—CH₂CH₂CH₂CH₂CH₂CH₂CH₂CH₂—C(=O)—.
(In the above formulas, Aryl(2) represents a divalent aromatic hydrocarbon group, and cyc.Het(2) represents a divalent cyclic heterocyclic group.)

Among these, preferred are the following:
-(Succinimid-3-yl-N)—CH₂CH₂—C(=O)—,
-(Succinimid-3-yl-N)—CH₂CH₂CH₂—C(=O)—,
-(Succinimid-3-yl-N)—CH₂CH₂CH₂CH₂—C(=O)—,
-(Succinimid-3-yl-N)—CH₂CH₂CH₂CH₂CH₂—C(=O)—,
-(Succinimid-3-yl-N)—CH(—CH₂CH₂—COOH)—C(=O)—,
-(Succinimid-3-yl-N)—CH(—CH₂CH₂CH₂—COOH)—C(=O)—,
-(Succinimid-3-yl-N)—CH(—CH₂CH₂CH₂CH₂—COOH)—C(=O)—,
-(Succinimid-3-yl-N)—CH₂CH₂—[N(—CH₂—COOH)]—CH₂—(C=O)—,
—CH₂—C(=O)—NH—CH₂CH₂—C(=O)—,
—CH₂—C(=O)—NH—CH₂CH₂CH₂—C(=O)—,
—CH₂—C(=O)—NH—CH₂CH₂CH₂CH₂—C(=O)—,
—CH₂—C(=O)—NH—CH₂CH₂CH₂CH₂CH₂—C(=O)—,
—CH₂—C(=O)—NH—CH₂CH₂CH₂CH₂CH₂CH₂—C(=O)—,
—C(=O)-cyc.Hex(1,4)-CH₂—(N-ly-3-diminiccuS)-,
—C(=O)—CH₂CH₂—C(=O)—,
—C(=O)—CH₂CH₂CH₂—C(=O)—,
—C(=O)—CH₂CH₂CH₂CH₂—C(=O)—,
—C(=O)—CH₂CH₂CH₂CH₂CH₂—C(=O)—,
—C(=O)—CH₂CH₂CH₂CH₂CH₂CH₂—C(=O)—.

4. $L^2$

In the linker, $L^2$ has a structure represented by
—NH—(CH₂CH₂—O)$n^6$-CH₂CH₂—C(=O)—,
—N[—(CH₂CH₂—O)$n^7$-CH₂CH₂—OH]—CH₂—C(=O)—,
—NH—CH₂CH₂—[N(—CH₂—COOH)]—CH₂—(C=O)—,
—NH—[CH(—CH₂—COOH)]—CH₂—(C=O)—,
—NH—[CH(—CH₂—COOH)]—CH₂—O—CH₂—(C=O)—, or
—S—(CH₂)$n^8$-C(=O)—,
or $L^2$ may not be present, and in such a case, $L^2$ is a single bond. $n^6$ is an integer of 0 to 6, $n^7$ is an integer of 1 to 4, and $n^8$ is an integer of 1 to 6. These structures of $L^2$ except for —S—(CH₂)$n^8$-C(=O)— are hydrophilic structures.

In the structure represented by —NH—(CH₂CH₂—O)$n^6$-CH₂CH₂—C(=O)— of $L^2$, $n^6$ is an integer of 0 to 6 and is preferably 2 to 4. Also, 0 is preferred. This structure is connected to $L^1$ via the nitrogen atom of the terminal amino group and connected to the N terminal of $L^P$ via the terminal carbonyl group on the opposite side. When $L^1$ is -(Succinimid-3-yl-N)—CH[—(CH₂)$n^3$-COOH]—C(=O)—, it is connected only to —NH—(CH₂CH₂—O)$n^6$-CH₂CH₂—C(=O)— as $L^2$, and $n^6$ is 0.

$L^2$ may have a structure represented by —N[—(CH₂CH₂—O)$n^7$-CH₂CH₂—OH]—CH₂—(C(=O)—.
Here, $n^7$ is an integer of 1 to 4 and is preferably 3 or 4. This structure is connected to $L^1$ via the terminal amino group and connected to the N terminal of $L^P$ via the terminal carbonyl group on the opposite side.

Further examples of $L^2$ can include ones having a structure of —NH—CH₂CH₂—[N(—CH₂—COOH)]—CH₂—(C=O)—, —NH—[CH(—CH₂—COOH)]—CH₂—(C=O)—, or —NH[CH(—CH₂—COOH)]—CH₂—O—CH₂—(C=O)—. Any of these are connected to $L^1$ via the terminal amino group and connected to the N terminal of $L^P$ via the terminal carbonyl group on the opposite side.

In —S—(CH₂)$n^8$-C(=O)— of $L^2$, $n^8$ is an integer of 1 to 6 and is preferably 2 to 4.

Specific examples of $L^2$ can include ones having the following structures:
—NH—CH₂CH₂—C(=O)—,
—NH—CH₂CH₂O—CH₂CH₂—C(=O)—,
—NH—CH₂CH₂O—CH₂CH₂O—CH₂CH₂—C(=O)—,
—NH—CH₂CH₂O—CH₂CH₂O—CH₂CH₂O—CH₂CH₂—C(=O)—,
—NH—CH₂CH₂O—CH₂CH₂O—CH₂CH₂O—CH₂CH₂O—CH₂CH₂—C(=O)—,
—NH—CH₂CH₂O—CH₂CH₂O—CH₂CH₂O—CH₂CH₂O—CH₂CH₂O—CH₂CH₂—C(=O)—,
—NH—CH₂CH₂O—CH₂CH₂O—CH₂CH₂O—CH₂CH₂O—CH₂CH₂O—CH₂CH₂O—CH₂CH₂—C(=O)—,
—N(—CH₂CH₂—O—CH₂CH₂—OH)—CH₂—C(=O)—N(—CH₂CH₂—O—CH₂CH₂—O—CH₂CH₂—OH)—CH₂—C(=O)—
—N(—CH₂CH₂—O—CH₂CH₂—O—CH₂CH₂—OH)—CH₂—C(=O)—

—N(—CH$_2$CH$_2$—O—CH$_2$CH$_2$—O—CH$_2$CH$_2$—O—CH$_2$CH$_2$—O—CH$_2$CH$_2$—OH)—CH$_2$—C(=O)
—NH—CH$_2$CH$_2$—[N(—CH$_2$—COOH)]—CH$_2$—(C=O)—,
—NH—[CH(—CH$_2$—COOH)]—CH$_2$—(C=O)
—NH—[CH(—CH$_2$—COOH)]—CH$_2$—O—CH$_2$—(C=O)—.

Among these, preferred are the following:
—NH—CH$_2$CH$_2$—C(=O)—,
—NH—CH$_2$CH$_2$O—CH$_2$CH$_2$O—CH$_2$CH$_2$—C(=O)—,
—NH—CH$_2$CH$_2$O—CH$_2$CH$_2$O—CH$_2$CH$_2$O—CH$_2$CH$_2$—C(=O)—,
—NH—CH$_2$CH$_2$O—CH$_2$CH$_2$O—CH$_2$CH$_2$O—CH$_2$CH$_2$O—CH$_2$CH$_2$—C(=O)—,
—N(—CH$_2$CH$_2$—O—CH$_2$CH$_2$—O—CH$_2$CH$_2$—O—CH$_2$CH$_2$—OH)—CH$_2$—C(=O)
—N(—CH$_2$CH$_2$—O—CH$_2$CH$_2$—O—CH$_2$CH$_2$—O—CH$_2$CH$_2$—O—CH$_2$CH$_2$—OH)—CH$_2$—C(=O)
—NH—CH$_2$CH$_2$—[N(—CH$_2$—COOH)]—CH$_2$—(C=O)—,
—NH—[CH(—CH$_2$—COOH)]—CH$_2$—(C=O)—,
—NH—[CH(—CH$_2$—COOH)]—CH$_2$—O—CH$_2$—(C=O)—.

When L$^2$ is —S—(CH$_2$)n$^8$-C(=O)—, L$^1$ to be combined is —C(=O)-cyc.Hex(1,4)-CH$_2$—(N-ly-3-diminiccuS)-. Therefore, specific examples of -L$^1$-L$^2$-can include ones having the following structures:
—C(=O)-cyc.Hex(1,4)-CH$_2$—(N-ly-3-diminiccuS)—S—CH$_2$—C(=O)—,
—C(=O)-cyc.Hex(1,4)-CH$_2$—(N-ly-3-diminiccuS)—S—CH$_2$CH$_2$—C(=O)—,
—C(=O)-cyc.Hex(1,4)-CH$_2$—(N-ly-3-diminiccuS)-S—CH$_2$CH$_2$CH$_2$—C(=O)—,
—C(=O)-cyc.Hex(1,4)-CH$_2$—(N-ly-3-diminiccuS)—S—CH$_2$CH$_2$CH$_2$CH$_2$—C(=O)—,
—C(=O)-cyc.Hex(1,4)-CH$_2$—(N-ly-3-diminiccuS)—S—CH$_2$CH$_2$CH$_2$CH$_2$CH$_2$—C(=O)—,
—C(=O)-cyc.Hex(1,4)-CH$_2$—(N-ly-3-diminiccuS)—S—CH$_2$CH$_2$CH$_2$CH$_2$CH$_2$CH$_2$—C(=O)—.

Among these, preferred are the following:
—C(=O)-cyc.Hex(1,4)-CH$_2$—(N-ly-3-diminiccuS)—S—CH$_2$CH$_2$—C(=O)—,
—C(=O)-cyc.Hex(1,4)-CH$_2$—(N-ly-3-diminiccuS)-S—CH$_2$CH$_2$CH$_2$—C(=O)—,
—C(=O)-cyc.Hex(1,4)-CH$_2$—(N-ly-3-diminiccuS)—S—CH$_2$CH$_2$CH$_2$CH$_2$—C(=O)—.

5. L$^a$

L$^a$ has any of structures of —C(=O)—NH—, —NR$^1$—(CH$_2$)n$^9$-, and —O—, or is a single bond, n$^9$ is an integer of 1 to 6, R$^1$ is a hydrogen atom, an alkyl group having 1 to 6 carbon atoms, —(CH$_2$)n$^a$-COOH, or —(CH$_2$)n$^b$-OH, n$^a$ is an integer of 1 to 4, and n$^b$ is an integer of 1 to 6.

The amide structure —C(=O)—NH— of L$^a$ is connected to L$^b$ via the nitrogen atom. In the —NR$^1$—(CH$_2$)n$^9$-structure moiety of L$^a$, n$^9$ is an integer of 1 to 6 and is preferably 1 to 3. The moiety is connected to L$^b$ via the methylene.

R$^1$ may be a hydrogen atom or an alkyl group having 1 to 6 carbon atoms. The alkyl group having 1 to 6 carbon atoms may be linear or branched. Examples thereof can include a methyl group, an ethyl group, a propyl group, an isopropyl group, a butyl group, an isobutyl group, a sec-butyl group, a tert-butyl group, a pentyl group, an isopentyl group, a 2-methylbutyl group, a neopentyl group, a 1-ethylpropyl group, a hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, and a 2-ethylbutyl group. Among these, a methyl group or an ethyl group is preferred.

When R$^1$ has a structure represented by —(CH$_2$)n$^a$-COOH, n$^a$ is an integer of 1 to 4 and is preferably 1 or 2.

When R$^1$ has a structure represented by —(CH$_2$)n$^b$-OH, n$^b$ is an integer of 1 to 6 and is preferably 1 or 2.

R$^1$ is preferably a hydrogen atom, a methyl group, an ethyl group, —CH$_2$—COOH, —CH$_2$CH$_2$—COOH, or —CH$_2$CH$_2$—OH, more preferably a hydrogen atom, a methyl group, or —CH$_2$—COOH, further preferably a hydrogen atom.

L$^a$ may be —O— or a single bond.

5. L$^b$

L$^b$ has a structure of —CR$^2$(—R$^3$)—, —O—, or —NR$^4$—, or is a single bond. Here, R$^2$ and R$^3$ are each independently a hydrogen atom, an alkyl group having 1 to 6 carbon atoms, —(CH$_2$)n$^c$-NH$_2$, —(CH$_2$)n$^d$-COOH, or —(CH$_2$)n$^e$-OH, R$^4$ is a hydrogen atom or an alkyl group having 1 to 6 carbon atoms, n$^c$ is an integer of 0 to 6, n$^d$ is an integer of 1 to 4, n$^e$ is an integer of 0 to 4, and when n$^c$ or n$^e$ is 0, R$^2$ and R$^3$ are not the same.

When each of R$^2$ and R$^3$ is an alkyl group, this alkyl group is an alkyl group as defined in the alkyl group for R$^1$. When each of R$^2$ and R$^3$ has a structure of —(CH$_2$)n$^c$-NH$_2$, n$^c$ is an integer of 0 to 6 and is preferably 0, or is 3 to 5. When n$^c$ is 0, R$^2$ and R$^3$ are not the same. When each of R$^2$ and R$^3$ has a structure of —(CH$_2$)n$^d$-COOH, n$^d$ is an integer of 1 to 4 and is preferably 1 or 2. When each of R$^2$ and R$^3$ has a structure of —(CH$_2$)n$^e$-OH, n$^e$ is an integer of 0 to 4 and is preferably 1 or 2.

Each of R$^2$ and R$^3$ is preferably a hydrogen atom, a methyl group, an ethyl group, —NH$_2$, —CH$_2$CH$_2$CH$_2$—NH$_2$, —CH$_2$CH$_2$CH$_2$CH$_2$—NH$_2$, —CH$_2$CH$_2$CH$_2$CH$_2$CH$_2$CH$_2$—NH$_2$, —CH$_2$—COOH, —CH$_2$CH$_2$—COOH, —CH$_2$—OH, or —CH$_2$CH$_2$—OH, more preferably a hydrogen atom, a methyl group, —NH$_2$, —CH$_2$CH$_2$CH$_2$CH$_2$—NH$_2$, —CH$_2$—COOH, —CH$_2$CH$_2$—COOH, —CH$_2$—OH, or —CH$_2$CH$_2$—OH, further preferably a hydrogen atom.

When R$^4$ is an alkyl group having 1 to 6 carbon atoms, this alkyl group is an alkyl group as defined in the alkyl group for R$^1$. R$^4$ is preferably a hydrogen atom or a methyl group, more preferably a hydrogen atom.

Specific examples of the structure represented by —NH—(CH$_2$)n$^1$-L$^a$-L$^b$-can include ones having the following structures:
—NH—CH$_2$—,
—NH—CH(-Me)-,
—NH—C(-Me)$_2$-,
—NH—CH$_2$—CH(-Me)-,
—NH—CH(—CH$_2$—OH)—,
—NH—CH(—CH$_2$—COOH)—,
—NH—CH(—CH$_2$CH$_2$—COOH)—,
—NH—CH(—CH$_2$CH$_2$CH$_2$CH$_2$—NH$_2$)—,
—NH—CH$_2$CH$_2$—,
—NH—CH$_2$—O—CH$_2$—,
—NH—CH$_2$CH$_2$—O—,
—NH—CH$_2$CH$_2$—O—CH$_2$—,
—NH—CH$_2$CH$_2$C(-Me)$_2$-,
—NH—CH$_2$CH$_2$—NH—,
—NH—CH$_2$CH$_2$—NH—CH$_2$—,
—NH—CH$_2$CH$_2$—N(-Me)-CH$_2$—,
—NH—CH$_2$CH$_2$—N(-Me)-CH$_2$CH$_2$—,
—NH—CH$_2$CH$_2$—NH—CH$_2$CH$_2$—,
—NH—CH$_2$CH$_2$—N(-Me)-CH$_2$CH$_2$—,
—NH—CH$_2$CH$_2$—N(—CH$_2$—COOH)—CH$_2$—, —NH—CH$_2$CH$_2$—N(—CH$_2$COOH)—CH$_2$CH$_2$—,
—NH—CH$_2$CH$_2$—N(—CH$_2$CH$_2$—OH)—CH$_2$—,
—NH—CH$_2$CH$_2$—N(—CH$_2$CH$_2$—OH)—CH$_2$CH$_2$—,
—NH—CH$_2$CH$_2$CH$_2$—C(=O)—NH—CH(—CH$_2$—OH)—,
—NH—CH$_2$CH$_2$CH$_2$—C(=O)—NH—CH(—CH$_2$—COOH)
—NH—CH$_2$CH$_2$CH$_2$—C(=O)—NH—CH(—CH$_2$CH$_2$CH$_2$CH$_2$—NH$_2$)—,
—NH—CH$_2$CH$_2$CH$_2$—,
—NH—CH$_2$CH$_2$CH$_2$CH$_2$—,
—NH—CH$_2$CH$_2$CH$_2$CH$_2$CH$_2$—,
—NH—CH$_2$CH$_2$CH$_2$CH$_2$CH(—NH$_2$)—.

Among these, preferred are the following structures:
—NH—CH$_2$—,
—NH—CH$_2$—CH(-Me)-,
—NH—CH(—CH$_2$—OH)—,
—NH—CH(—CH$_2$CH$_2$—COOH)—,
—NH—CH$_2$CH$_2$—,
—NH—CH$_2$—O—CH$_2$—,
—NH—CH$_2$CH$_2$—O—,
—NH—CH$_2$CH$_2$—O—CH$_2$—,
—NH—CH$_2$CH$_2$C(-Me)$_2$-,
—NH—CH$_2$CH$_2$—NH—,
—NH—CH$_2$CH$_2$—NH—CH$_2$—,
—NH—CH$_2$CH$_2$—N(-Me)-CH$_2$—,
—NH—CH$_2$CH$_2$—N(-Me)-CH$_2$CH$_2$—,
—NH—CH$_2$CH$_2$—N(—CH$_2$—COOH)—CH$_2$—,
—NH—CH$_2$CH$_2$—N(—CH$_2$CH$_2$—OH)—CH$_2$—,
—NH—CH$_2$CH$_2$—N(—CH$_2$CH$_2$—OH)—CH$_2$CH$_2$—,
—NH—CH$_2$CH$_2$CH$_2$—C(=O)—NH—CH(—CH$_2$—OH)—,
—NH—CH$_2$CH$_2$CH$_2$—C(=O)—NH—CH(—CH$_2$—COOH)—,
—NH—CH$_2$CH$_2$CH$_2$—,
—NH—CH$_2$CH$_2$CH$_2$CH$_2$—,
—NH—CH$_2$CH$_2$CH$_2$CH$_2$CH$_2$—.

More preferred are the following structures:
—NH—CH$_2$—,
—NH—CH$_2$CH$_2$—,
—NH—CH$_2$—O—CH$_2$—,
—NH—CH$_2$CH$_2$—O—,
—NH—CH$_2$CH$_2$—O—CH$_2$—,
—NH—CH$_2$CH$_2$—NH—,
—NH—CH$_2$CH$_2$—NH—CH$_2$—,
—NH—CH$_2$CH$_2$—N(—CH$_2$—COOH)—CH$_2$—,
—NH—CH$_2$CH$_2$—N(—CH$_2$CH$_2$—OH)—CH$_2$CH$_2$—,
—NH—CH$_2$CH$_2$CH$_2$—C(=O)—NH—CH(—CH$_2$—COOH)
—NH—CH$_2$CH$_2$CH$_2$—,
—NH—CH$_2$CH$_2$CH$_2$CH$_2$—,
—NH—CH$_2$CH$_2$CH$_2$CH$_2$CH$_2$—.

Further preferred are the following structures:
—NH—CH$_2$—,
—NH—CH$_2$CH$_2$—,
—NH—CH$_2$CH$_2$CH$_2$—,
—NH—CH$_2$—O—CH$_2$—,
—NH—CH$_2$CH$_2$—O—CH$_2$—.

6. $L^c$ $L^c$ has a structure represented by —CH$_2$— or —C(=O)—. This structure is connected to the antitumor compound. $L^c$ in the linker is preferably —C(=O)—.

7. Linker and Drug Activity

With regard to the antibody-drug conjugate of the present invention, when it is transferred to the inside of tumor cells, it has been suggested that the linker moiety is cleaved and the drug derivative having a structure represented by NH$_2$—(CH$_2$)n$^1$-L$^a$-L$^b$-L$^c$-(NH-DX) is released to express an antitumor action. Examples of the antitumor derivative exhibiting an antitumor effect by releasing from the antibody-drug conjugate of the present invention include an antitumor derivative having a structure moiety in which a terminal of $L^c$ which is connected to the structure represented by —NH—(CH$_2$)n$^1$-L$^a$-L$^b$-of the linker has an amino group, and those particularly preferred include the following:
NH$_2$—CH$_2$—C(=O)—(NH-DX),
NH$_2$—CH$_2$CH$_2$—C(=O)—(NH-DX),
NH$_2$—CH$_2$CH$_2$CH$_2$—C(=O)—(NH-DX),
NH$_2$—CH$_2$—O—CH$_2$—C(=O)—(NH-DX),
NH$_2$—CH$_2$CH$_2$—O—CH$_2$—C(=O)—(NH-DX).

Meanwhile, in case of NH$_2$—CH$_2$—O—CH$_2$—C(=O)—(NH-DX), as the aminal structure in the molecule is unstable, it again undergoes a self-degradation to release the following
HO—CH$_2$—C(=O)—(NH-DX). Those compounds can be also preferably used as a production intermediate of the antibody-drug conjugate of the present invention.

8. -L$^1$-L$^2$-L$^P$- or -L$^1$-L$^2$-L$^P$-NH—(CH$_2$)n$^1$-L$^a$-L$^b$-L$^c$-

In the antibody-drug conjugate of the present invention, the average conjugated number of the drug-linker structure moieties per antibody molecule can be 1 to 10 and is preferably 2 to 8, more preferably 3 to 8. The drug-linker structure moiety is preferably a drug connected to a linker structure moiety having a structure described below. The structure of the linker can be a structure of -L$^1$-L$^2$-L$^P$-NH—(CH$_2$)n$^1$-L$^a$-L$^b$-L$^c$-, or is a structure of -L$^1$-L$^2$-L$^P$-, L$^P$ of which is directly connected to the drug.

When the drug-linker structure moiety is conjugated to the antibody via a thioether bond, a structure represented by
-(Succinimid-3-yl-N)—(CH$_2$)n$^2$-C(=O)—
-(Succinimid-3-yl-N)—CH [—(CH$_2$)n$^3$-COOH]—C(=O)—, -(Succinimid-3-yl-N)—CH$_2$CH$_2$—[N(—CH$_2$—COOH)]—CH$_2$—(C=O)—, or —CH$_2$—C(=O)—NH—(CH$_2$)n$^4$-C(=O)—
can be used as L$^1$. When the drug-linker structure moiety is conjugated to the antibody via an amide bond, a structure represented by
—C(=O)-cyc.Hex(1,4)-CH$_2$—(N-ly-3-diminiccuS)- or
—C(=O)—(CH$_2$)n$^5$-C(=O)—
can be used as L$^1$.

When L$^1$ is -(Succinimid-3-yl-N)—(CH$_2$)n$^2$-C(=O)—, L$^2$ is a single bond, or is —NH—(CH$_2$CH$_2$—O)n$^6$-CH$_2$CH$_2$—C(=O)—, —N[—(CH$_2$CH$_2$—O)n$^7$-CH$_2$CH$_2$—OH]—CH$_2$—C(=O)—, —NH—[CH(—CH$_2$—COOH)]—CH$_2$—(C=O)—, —NH—CH$_2$CH$_2$—[N(—CH$_2$—COOH)]—CH$_2$—(C=O)—, or —NH—[CH(—CH$_2$—COOH)]—CH$_2$—O—CH$_2$—(C=O)—. For such L$^1$ and L$^2$, specific examples of -L$^1$-L$^2$-L$^P$-can include ones having the following structures:
-(Succinimid-3-yl-N)—CH$_2$CH$_2$—C(=O)-L$^P$-,
-(Succinimid-3-yl-N)—CH$_2$CH$_2$CH$_2$—C(=O)-L$^P$-,
-(Succinimid-3-yl-N)—CH$_2$CH$_2$CH$_2$CH$_2$—C(=O)-L$^P$-,
-(Succinimid-3-yl-N)—CH$_2$CH$_2$CH$_2$CH$_2$CH$_2$—C(=O)-L$^P$-,
-(Succinimid-3-yl-N)—CH$_2$CH$_2$CH$_2$CH$_2$CH$_2$CH$_2$—C(=O)-L$^P$-,
-(Succinimid-3-yl-N)—CH$_2$CH$_2$CH$_2$CH$_2$CH$_2$CH$_2$CH$_2$—C(=O)-L$^P$-,
-(Succinimid-3-yl-N)—CH$_2$CH$_2$CH$_2$CH$_2$CH$_2$CH$_2$CH$_2$CH$_2$—C(=O)-L$^P$-,
-L$^1$-NH—CH$_2$CH$_2$—C(=O)-L$^P$-,
-L$^1$-NH—CH$_2$CH$_2$—O—CH$_2$CH$_2$—C(=O)-L$^P$-,
-L$^1$-NH—CH$_2$CH$_2$—O—CH$_2$CH$_2$—O—CH$_2$CH$_2$—C(=O)-L$^P$-, -L$^1$-NH—CH$_2$CH$_2$—O—CH$_2$CH$_2$—O—CH$_2$CH$_2$—C(=O)-L$^P$-,
-L$^1$-NH—CH$_2$CH$_2$—O—CH$_2$CH$_2$—O—CH$_2$CH$_2$—O—CH$_2$CH$_2$—C(=O)-L$^P$-,
-L$^1$-NH—CH$_2$CH$_2$—O—CH$_2$CH$_2$—O—CH$_2$CH$_2$—O—CH$_2$CH$_2$—O—CH$_2$CH$_2$—C(=O)-L$^P$-,
L$^1$-NH—CH$_2$CH$_2$—O—CH$_2$CH$_2$—O—CH$_2$CH$_2$—O—CH$_2$CH$_2$—O—CH$_2$CH$_2$—O—CH$_2$CH$_2$—C(=O)-L$^P$-,
-L$^1$-NH—CH$_2$CH$_2$—O—CH$_2$CH$_2$—O—CH$_2$CH$_2$—O—CH$_2$CH$_2$—O—CH$_2$CH$_2$—O—CH$_2$CH$_2$—O—CH$_2$CH$_2$—C(=O)-L$^P$-,
-L$^1$-NH—CH$_2$CH$_2$—O—CH$_2$CH$_2$—O—CH$_2$CH$_2$—O—CH$_2$CH$_2$—O—CH$_2$CH$_2$—O—CH$_2$CH$_2$—O—CH$_2$—CH$_2$—C(=O)-L$^P$-,
-L$^1$-N[—CH$_2$CH$_2$—O—CH$_2$CH$_2$—OH]—CH$_2$—C(=O)-L$^P$-,
-L$^1$-N[—CH$_2$CH$_2$—O—CH$_2$CH$_2$—O—CH$_2$CH$_2$—OH]—CH$_2$—C(=O)-L$^P$-,
-L$^1$-N[—CH$_2$CH$_2$—O—CH$_2$CH$_2$—O—CH$_2$CH$_2$—O—CH$_2$CH$_2$—OH]—CH$_2$—C(=O)-L$^P$-,
-L$^1$-N[—CH$_2$CH$_2$—O—CH$_2$CH$_2$—O—CH$_2$CH$_2$—O—CH$_2$CH$_2$—O—CH$_2$CH$_2$—OH]—CH$_2$—C(=O)-L$^P$-,
-L$^1$-NH—CH$_2$CH$_2$—[N(—CH$_2$—COOH)]—CH$_2$—(C=O)-L$^P$-,
-L$^1$-NH—[CH(—CH$_2$—COOH)]—CH$_2$—O—CH$_2$—(C=O)-L$^P$-.

Here, L$^1$ preferably has the following structure in which n$^2$ is 2 or 3:
-(Succinimid-3-yl-N)—CH$_2$CH$_2$—C(=O)—, or -(Succinimid-3-yl-N)—CH$_2$CH$_2$CH$_2$CH$_2$—C(=O)—.

Thus, -L$^1$-L$^2$-L$^P$-preferably has any of the following structures having the structure of L$^1$ as follows:
-(Succinimid-3-yl-N)—CH$_2$CH$_2$—C(=O)-L$^P$-,
-(Succinimid-3-yl-N)—CH$_2$CH$_2$CH$_2$CH$_2$—C(=O)-L$^P$-,
-(Succinimid-3-yl-N)—CH$_2$CH$_2$—C(=O)—NH—CH$_2$—CH$_2$—C(=O)-L$^P$-,
-(Succinimid-3-yl-N)—CH$_2$CH$_2$CH$_2$CH$_2$—C(=O)—NH—CH$_2$—CH$_2$—C(=O)-L$^P$-,
-(Succinimid-3-yl-N)—CH$_2$CH$_2$—C(=O)—NH—CH$_2$—O—CH$_2$CH$_2$—O—CH$_2$CH$_2$—C(=O)-L$^P$-,
-(Succinimid-3-yl-N)—CH$_2$CH$_2$CH$_2$CH$_2$—C(=O)—NH—CH$_2$CH$_2$—O—CH$_2$CH$_2$—O—CH$_2$CH$_2$—C(=O)-L$^P$-,
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—C(=O)-L$^P$-,
-(Succinimid-3-yl-N)—CH$_2$CH$_2$CH$_2$CH$_2$—C(=O)—NH—CH$_2$CH$_2$—O—CH$_2$CH$_2$—O—CH$_2$CH$_2$—O—CH$_2$CH$_2$—C(=O)-L$^P$-,
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-L$^P$-,
-(Succinimid-3-yl-N)—CH$_2$CH$_2$CH$_2$CH$_2$—C(=O)—NH—CH$_2$CH$_2$—O—CH$_2$CH$_2$—O—CH$_2$CH$_2$—O—CH$_2$CH$_2$—O—CH$_2$—CH$_2$—C(=O)-L$^P$-,
-(Succinimid-3-yl-N)—CH$_2$CH$_2$—C(=O)—N[—CH$_2$CH$_2$—O—CH$_2$CH$_2$—O—CH$_2$CH$_2$—OH]—CH$_2$—C(=O)-L$^P$-,
-(Succinimid-3-yl-N)—CH$_2$CH$_2$CH$_2$CH$_2$—C(=O)—N[—CH$_2$CH$_2$—O—CH$_2$CH$_2$—O—CH$_2$CH$_2$—OH]—CH$_2$—C(=O)-L$^P$-,
-(Succinimid-3-yl-N)—CH$_2$CH$_2$—C(=O)—N[—CH$_2$CH$_2$—O—CH$_2$CH$_2$—O—CH$_2$CH$_2$—O—CH$_2$CH$_2$—OH]—CH$_2$—C(=O)-L$^P$-,
-(Succinimid-3-yl-N)—CH$_2$CH$_2$CH$_2$CH$_2$—C(=O)—N[—CH$_2$CH$_2$—O—CH$_2$CH$_2$—O—CH$_2$CH$_2$—O—CH$_2$CH$_2$—OH]—CH$_2$—C(=O)-L$^P$-,
-(Succinimid-3-yl-N)—CH$_2$CH$_2$—C(=O)—N[—CH$_2$CH$_2$—O—CH$_2$CH$_2$—O—CH$_2$CH$_2$—O—CH$_2$CH$_2$—O—CH$_2$CH$_2$—OH]—CH$_2$—C(=O)-L$^P$-,
-(Succinimid-3-yl-N)—CH$_2$CH$_2$CH$_2$CH$_2$—C(=O)—N[—CH$_2$CH$_2$—O—CH$_2$CH$_2$—O—CH$_2$CH$_2$—O—CH$_2$CH$_2$—O—CH$_2$CH$_2$—OH]—CH$_2$—C(=O)-L$^P$-,
-(Succinimid-3-yl-N)—CH$_2$CH$_2$—C(=O)—NH—CH$_2$CH$_2$—[N(—CH$_2$—COOH)]—CH$_2$—(C=O)-L$^P$-,
-(Succinimid-3-yl-N)—CH$_2$CH$_2$CH$_2$CH$_2$—C(=O)—NH—CH$_2$CH$_2$—[N(—CH$_2$—COOH)]—CH$_2$—(C=O)-L$^P$-,
-(Succinimid-3-yl-N)—CH$_2$CH$_2$—C(=O)—NH—[CH(—CH$_2$—COOH)]—CH$_2$—O—CH$_2$—(C=O)-L$^P$-,
-(Succinimid-3-yl-N)—CH$_2$CH$_2$CH$_2$CH$_2$—C(=O)—NH—[CH(—CH$_2$—COOH)]—CH$_2$—O—CH$_2$—(C=O)-L$^P$-.

Among these, further preferred are the following structures:
-(Succinimid-3-yl-N)—CH$_2$CH$_2$CH$_2$CH$_2$—C(=O)-L$^P$-,
-(Succinimid-3-yl-N)—CH$_2$CH$_2$—C(=O)—NH—CH$_2$—CH$_2$—C(=O)-L$^P$-,
-(Succinimid-3-yl-N)—CH$_2$CH$_2$CH$_2$CH$_2$—C(=O)—NH—CH$_2$—CH$_2$—C(=O)-L$^P$-,
-(Succinimid-3-yl-N)—CH$_2$CH$_2$—C(=O)—NH—CH$_2$CH$_2$—O—CH$_2$CH$_2$—O—CH$_2$CH$_2$—C(=O)-L$^P$-,
-(Succinimid-3-yl-N)—CH$_2$CH$_2$CH$_2$CH$_2$—C(=O)—NH—CH$_2$CH$_2$—O—CH$_2$CH$_2$—O—CH$_2$CH$_2$—C(=O)-L$^P$-,
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—C(=O)-L$^P$-,
-(Succinimid-3-yl-N)—CH$_2$CH$_2$CH$_2$CH$_2$—C(=O)—NH—CH$_2$CH$_2$—O—CH$_2$CH$_2$—O—CH$_2$CH$_2$—O—CH$_2$CH$_2$—O—CH$_2$—CH$_2$—C(=O)-L$^P$-,
-(Succinimid-3-yl-N)—CH$_2$CH$_2$—C(=O)—N[—CH$_2$CH$_2$—O—CH$_2$CH$_2$—O—CH$_2$CH$_2$—OH]—CH$_2$—C(=O)-L$^P$-,
-(Succinimid-3-yl-N)—CH$_2$CH$_2$CH$_2$CH$_2$—C(=O)—N[—CH$_2$CH$_2$—O—CH$_2$CH$_2$—O—CH$_2$CH$_2$—OH]—CH$_2$—C(=O)-L$^P$-,
-(Succinimid-3-yl-N)—CH$_2$CH$_2$—C(=O)—N[—CH$_2$CH$_2$—O—CH$_2$CH$_2$—O—CH$_2$CH$_2$—O—CH$_2$CH$_2$—OH]—CH$_2$—C(=O)-L$^P$-,
-(Succinimid-3-yl-N)—CH$_2$CH$_2$CH$_2$CH$_2$—C(=O)—N[—CH$_2$CH$_2$—O—CH$_2$CH$_2$—O—CH$_2$CH$_2$—O—CH$_2$CH$_2$—OH]—CH$_2$—C(=O)-L$^P$-,
-(Succinimid-3-yl-N)—CH$_2$CH$_2$—C(=O)—N[—CH$_2$CH$_2$—O—CH$_2$CH$_2$—O—CH$_2$CH$_2$—O—CH$_2$CH$_2$—OH]—CH$_2$—C(=O)-L$^P$-,
-(Succinimid-3-yl-N)—CH$_2$CH$_2$CH$_2$CH$_2$—C(=O)—N[—CH$_2$CH$_2$—O—CH$_2$CH$_2$—O—CH$_2$CH$_2$—O—CH$_2$CH$_2$—OH]—CH$_2$—C(=O)-L$^P$-,
-(Succinimid-3-yl-N)—CH$_2$CH$_2$—C(=O)—NH—CH$_2$CH$_2$—[N(—CH$_2$—COOH)]—CH$_2$—(C=O)-L$^P$-,
-(Succinimid-3-yl-N)—CH$_2$CH$_2$CH$_2$CH$_2$—C(=O)—NH—CH$_2$CH$_2$—[N(—CH$_2$—COOH)]—CH$_2$—(C=O)-L$^P$-,
-(Succinimid-3-yl-N)—CH$_2$CH$_2$—C(=O)—NH—[CH(—CH$_2$—COOH)]—CH$_2$—O—CH$_2$—(C=O)-L$^P$-,
-(Succinimid-3-yl-N)—CH$_2$CH$_2$CH$_2$CH$_2$—C(=O)—NH—[CH(—CH$_2$—COOH)]—CH$_2$—O—CH$_2$—(C=O)-L$^P$-.

When L$^1$ is -(Succinimid-3-yl-N)—CH [—(CH$_2$)n$^3$-COOH]—C(=O)—, L$^2$ is a single bond or —NH—(CH$_2$CH$_2$—O)n$^6$-CH$_2$CH$_2$—C(=O)—. For such L$^1$ and L$^2$, specifically, -L$^1$-L$^2$-L$^P$-preferably has any of the following structures:

-(Succinimid-3-yl-N)—CH(—CH$_2$—COOH)—C(=O)-L$^P$-,
-(Succinimid-3-yl-N)—CH(—CH$_2$CH$_2$—COOH)—C(=O)-L$^P$-,
-(Succinimid-3-yl-N)—CH(—CH$_2$CH$_2$CH$_2$—COOH)—C(=O)-L$^P$-,
-(Succinimid-3-yl-N)—CH(—CH$_2$CH$_2$CH$_2$CH$_2$—COOH)—C(=O)-L$^P$-,
-(Succinimid-3-yl-N)—CH(—CH$_2$CH$_2$CH$_2$CH$_2$CH$_2$—COOH)—C(=O)-L$^P$-,
-(Succinimid-3-yl-N)—CH(—CH$_2$CH$_2$CH$_2$CH$_2$CH$_2$CH$_2$—COOH)—C(=O)-L$^P$-,
-(Succinimid-3-yl-N)—CH(—CH$_2$CH$_2$CH$_2$CH$_2$CH$_2$CH$_2$CH$_2$—COOH)—C(=O)-L$^P$-,
-(Succinimid-3-yl-N)—CH(—CH$_2$CH$_2$CH$_2$CH$_2$CH$_2$CH$_2$CH$_2$CH$_2$—COOH)—C(=O)-L$^P$-,
-(Succinimid-3-yl-N)—CH [—(CH$_2$)n$^3$-COOH]—C(=O)—NH—CH$_2$CH$_2$—C(=O)-L$^P$-,
-(Succinimid-3-yl-N)—CH [—(CH$_2$)n$^3$-COOH]—C(=O)—NH—CH$_2$CH$_2$—O—CH$_2$CH$_2$—C(=O)-L$^P$-,
-(Succinimid-3-yl-N)—CH [—(CH$_2$)n$^3$-COOH]—C(=O)—NH—CH$_2$CH$_2$—O—CH$_2$CH$_2$—O—CH$_2$CH$_2$—C(=O)-L$^P$-,
-(Succinimid-3-yl-N)—CH [—(CH$_2$)n$^3$-COOH]—C(=O)—NH—CH$_2$CH$_2$—O—CH$_2$CH$_2$—O—CH$_2$CH$_2$—O—CH$_2$CH$_2$—C(=O)-L$^P$-,
-(Succinimid-3-yl-N)—CH [—(CH$_2$)n$^3$-COOH]—C(=O)—NH—CH$_2$CH$_2$—O—CH$_2$CH$_2$—O—CH$_2$CH$_2$—O—CH$_2$CH$_2$—O—CH$_2$CH$_2$—C(=O)-L$^P$-.

Among these, preferred are the following structures in which n$^3$ is 2 to 4:

-(Succinimid-3-yl-N)—CH(—CH$_2$CH$_2$—COOH)—C(=O)-L$^P$-,
-(Succinimid-3-yl-N)—CH(—CH$_2$CH$_2$CH$_2$—COOH)—C(=O)-L$^P$-,
-(Succinimid-3-yl-N)—CH(—CH$_2$CH$_2$CH$_2$CH$_2$—COOH)—C(=O)-L$^P$-, -(Succinimid-3-yl-N)—CH(—CH$_2$CH$_2$—COOH)—C(=O)—NH—CH$_2$CH$_2$—C(=O)-L$^P$-,
-(Succinimid-3-yl-N)—CH(—CH$_2$CH$_2$—COOH)—C(=O)—NH—CH$_2$CH$_2$—O—CH$_2$CH$_2$—C(=O)-L$^P$-,
-(Succinimid-3-yl-N)—CH(—CH$_2$CH$_2$—COOH)—C(=O)—NH—CH$_2$CH$_2$—O—CH$_2$CH$_2$—O—CH$_2$CH$_2$—C(=O)-L$^P$-,
-(Succinimid-3-yl-N)—CH(—CH$_2$CH$_2$—COOH)—C(=O)—NH—CH$_2$CH$_2$—O—CH$_2$CH$_2$—O—CH$_2$CH$_2$—O—CH$_2$CH$_2$—C(=O)-L$^P$-,
-(Succinimid-3-yl-N)—CH(—CH$_2$CH$_2$—COOH)—C(=O)—NH—CH$_2$CH$_2$—O—CH$_2$CH$_2$—O—CH$_2$CH$_2$—O—CH$_2$CH$_2$—O—CH$_2$—CH$_2$—C(=O)-L$^P$-,
-(Succinimid-3-yl-N)—CH(—CH$_2$CH$_2$CH$_2$—COOH)—C(=O)—NH—CH$_2$CH$_2$—C(=O)-L$^P$-,
-(Succinimid-3-yl-N)—CH(—CH$_2$CH$_2$CH$_2$—COOH)—C(=O)—NH—CH$_2$CH$_2$—O—CH$_2$CH$_2$—C(=O)-L$^P$-,
-(Succinimid-3-yl-N)—CH(—CH$_2$CH$_2$CH$_2$—COOH)—C(=O)—NH—CH$_2$CH$_2$—O—CH$_2$CH$_2$—O—CH$_2$CH$_2$—C(=O)-L$^P$-,
-(Succinimid-3-yl-N)—CH(—CH$_2$CH$_2$CH$_2$—COOH)—C(=O)—NH—CH$_2$CH$_2$—O—CH$_2$CH$_2$—O—CH$_2$CH$_2$—O—CH$_2$—CH$_2$—C(=O)-L$^P$-,
-(Succinimid-3-yl-N)—CH(—CH$_2$CH$_2$CH$_2$CH$_2$—COOH)—C(=O)—NH—CH$_2$CH$_2$—C(=O)-L$^P$-,
-(Succinimid-3-yl-N)—CH(—CH$_2$CH$_2$CH$_2$CH$_2$—COOH)—C(=O)—NH—CH$_2$CH$_2$—O—CH$_2$CH$_2$—C(=O)-L$^P$-,
-(Succinimid-3-yl-N)—CH(—CH$_2$CH$_2$CH$_2$CH$_2$—COOH)—C(=O)—NH—CH$_2$CH$_2$—O—CH$_2$CH$_2$—O—CH$_2$CH$_2$—C(=O)-L$^P$-,
-(Succinimid-3-yl-N)—CH(—CH$_2$CH$_2$CH$_2$CH$_2$—COOH)—C(=O)—NH—CH$_2$CH$_2$—O—CH$_2$CH$_2$—O—CH$_2$CH$_2$—O—CH$_2$—CH$_2$—C(=O)-L$^P$-.

Among these, more preferred are the following structures in which n$^3$ is 2:

-(Succinimid-3-yl-N)—CH(—CH$_2$CH$_2$—COOH)—C(=O)-L$^P$-, -(Succinimid-3-yl-N)—CH(—CH$_2$CH$_2$—COOH)—C(=O)—NH—CH$_2$CH$_2$—C(=O)-L$^P$-,
-(Succinimid-3-yl-N)—CH(—CH$_2$CH$_2$—COOH)—C(=O)—NH—CH$_2$CH$_2$—O—CH$_2$CH$_2$—C(=O)-L$^P$-,
-(Succinimid-3-yl-N)—CH(—CH$_2$CH$_2$—COOH)—C(=O)—NH—CH$_2$CH$_2$—O—CH$_2$CH$_2$—O—CH$_2$CH$_2$—C(=O)-L$^P$-, -(Succinimid-3-yl-N)—CH(—CH$_2$CH$_2$—COOH)—C(=O)—NH—CH$_2$CH$_2$—O—CH$_2$CH$_2$—O—CH$_2$CH$_2$—O—CH$_2$CH$_2$—C(=O)-L$^P$-,
-(Succinimid-3-yl-N)—CH(—CH$_2$CH$_2$—COOH)—C(=O)—NH—CH$_2$CH$_2$—O—CH$_2$CH$_2$—O—CH$_2$CH$_2$—O—CH$_2$CH$_2$—C(=O)-L$^P$-.

A form in which n$^6$ is 0 is also preferred, that is, a structure represented by -(Succinimid-3-yl-N)—CH [—(CH$_2$)n$^3$-COOH]—C(=O)—NH—CH$_2$—CH$_2$—C(=O)-L$^P$- is preferred. Specifically, preferred are the following structures:

-(Succinimid-3-yl-N)—CH(—CH$_2$CH$_2$—COOH)—C(=O)—NH—CH$_2$CH$_2$—C(=O)-L$^P$-,
-(Succinimid-3-yl-N)—CH(—CH$_2$CH$_2$CH$_2$—COOH)—C(=O)—NH—CH$_2$CH$_2$—C(=O)-L$^P$-,
-(Succinimid-3-yl-N)—CH(—CH$_2$CH$_2$CH$_2$CH$_2$—COOH)—C(=O)—NH—CH$_2$CH$_2$—C(=O)-L$^P$-.

When L$^1$ is -(Succinimid-3-yl-N)—CH$_2$CH$_2$—[N(—CH$_2$—COOH)]—CH$_2$—(C=O)—, L$^2$ can be a single bond. For such L$^1$ and L$^2$, specifically, -L$^1$-L$^2$-L$^P$-has a structure represented by -(Succinimid-3-yl-N)—CH$_2$CH$_2$—[N(—CH$_2$—COOH)]—CH$_2$—(C=O)-L$^P$-.

When L$^1$ is —CH$_2$—C(=O)—NH—(CH$_2$)n$^4$-C(=O)—, L$^2$ can be a single bond. For such L$^1$ and L$^2$, specifically, L$^1$-L$^2$-L$^P$-has any of the following structures:

—CH$_2$—C(=O)—NH—CH$_2$—C(=O)-L$^P$-,
—CH$_2$—C(=O)—NH—CH$_2$CH$_2$—C(=O)-L$^P$-,
—CH$_2$—C(=O)—NH—CH$_2$CH$_2$CH$_2$—C(=O)-L$^P$-,
—CH$_2$—C(=O)—NH—CH$_2$CH$_2$CH$_2$CH$_2$—C(=O)-L$^P$-,
—CH$_2$—C(=O)—NH—CH$_2$CH$_2$CH$_2$CH$_2$CH$_2$—C(=O)-L$^P$-,
—CH$_2$—C(=O)—NH—CH$_2$CH$_2$CH$_2$CH$_2$CH$_2$CH$_2$—C(=O)-L$^P$-,
—CH$_2$—C(=O)—NH—CH$_2$CH$_2$CH$_2$CH$_2$CH$_2$CH$_2$CH$_2$—C(=O)-L$^P$-,
—CH$_2$—C(=O)—NH—CH$_2$CH$_2$CH$_2$CH$_2$CH$_2$CH$_2$CH$_2$CH$_2$—C(=O)-L$^P$-.

When L$^1$ is —C(=O)—(CH$_2$)n$^5$-C(=O)—, L$^2$ is selected from —NH—(CH$_2$CH$_2$—O)n$^6$-CH$_2$CH$_2$—C (=O)— and a single bond. For such $L^1$ and $L^2$, specifically, $L^1$-$L^2$-$L^P$-has any of the following structures:

—C(=O)—CH$_2$—C(=O)-$L^P$-,
—C(=O)—CH$_2$CH$_2$—C(=O)-$L^P$-,
—C(=O)—CH$_2$CH$_2$CH$_2$—C(=O)-$L^P$-,
—C(=O)—CH$_2$CH$_2$CH$_2$CH$_2$—C(=O)-$L^P$-,
—C(=O)—CH$_2$CH$_2$CH$_2$CH$_2$CH$_2$—C(=O)-$L^P$-,
—C(=O)—CH$_2$CH$_2$CH$_2$CH$_2$CH$_2$CH$_2$—C(=O)-$L^P$-,
—C(=O)—CH$_2$CH$_2$CH$_2$CH$_2$CH$_2$CH$_2$CH$_2$—C(=O)-$L^P$-,
—C(=O)—CH$_2$CH$_2$CH$_2$CH$_2$CH$_2$CH$_2$CH$_2$CH$_2$—C(=O)-$L^P$-,
—C(=O)—(CH$_2$)n$^5$-C(=O)—NH—CH$_2$CH$_2$—C(=O)-$L^P$-,
—C(=O)—(CH$_2$)n$^5$-C(=O)—NH—CH$_2$CH$_2$—O—CH$_2$CH$_2$—C(=O)-$L^P$-,
—C(=O)—(CH$_2$)n$^5$-C(=O)—NH—CH$_2$CH$_2$—O—CH$_2$CH$_2$—O—CH$_2$CH$_2$—C(=O)-$L^P$-,
—C(=O)—(CH$_2$)n$^5$-C(=O)—NH—CH$_2$CH$_2$—O—CH$_2$CH$_2$—O—CH$_2$CH$_2$—C(=O)-$L^P$-,
—C(=O)—(CH$_2$)n$^5$-C(=O)—NH—CH$_2$CH$_2$—O—CH$_2$CH$_2$—O—CH$_2$CH$_2$—O—CH$_2$CH$_2$—C(=O)-$L^P$-,
—C(=O)—(CH$_2$)n$^5$-C(=O)—NH—CH$_2$CH$_2$—O—CH$_2$CH$_2$—O—CH$_2$CH$_2$—O—CH$_2$CH$_2$—O—CH$_2$CH$_2$—C(=O)-$L^P$-,
—C(=O)—(CH$_2$)n$^5$-C(=O)—NH—CH$_2$CH$_2$—O—CH$_2$CH$_2$—O—CH$_2$CH$_2$—O—CH$_2$CH$_2$—O—CH$_2$CH$_2$—C(=O)-$L^P$-,
—C(=O)—(CH$_2$)n$^5$-C(=O)—NH—CH$_2$CH$_2$—O—CH$_2$CH$_2$—O—CH$_2$CH$_2$—O—CH$_2$CH$_2$—O—CH$_2$CH$_2$—O—CH$_2$CH$_2$—C(=O)-$L^P$-,
—C(=O)—(CH$_2$)n$^5$-C(=O)—NH—CH$_2$CH$_2$—O—CH$_2$CH$_2$—O—CH$_2$CH$_2$—O—CH$_2$CH$_2$—O—CH$_2$—H$_2$—O—CH$_2$—H$_2$—O—CH$_2$—H$_2$—O—CH$_2$—CH$_2$—C(=O)-$L^P$-.

$L^2$ having a structure represented by —S—(CH$_2$)n$^8$-C(=O)— is used in combination with —C(=O)-cyc.Hex(1,4)-CH$_2$—(N-ly-3-diminiccuS)- of $L^1$. For such $L^1$ and $L^2$, specifically, $L^1$-$L^2$-$L^P$-has any of the following structures:
—C(=O)-cyc.Hex(1,4)-CH$_2$—(N-ly-3-diminiccuS)—S—CH$_2$—C(=O)-$L^P$-,
—C(=O)-cyc.Hex(1,4)-CH$_2$—(N-ly-3-diminiccuS)—S—CH$_2$CH$_2$—C(=O)-$L^P$-,
—C(=O)-cyc.Hex(1,4)-CH$_2$—(N-ly-3-diminiccuS)-S—CH$_2$CH$_2$CH$_2$—C(=O)-$L^P$-,
—C(=O)-cyc.Hex(1,4)-CH$_2$—(N-ly-3-diminiccuS)—S—CH$_2$CH$_2$CH$_2$CH$_2$—C(=O)-$L^P$-,
—C(=O)-cyc.Hex(1,4)-CH$_2$—(N-ly-3-diminiccuS)—S—CH$_2$CH$_2$CH$_2$CH$_2$CH$_2$—C(=O)-$L^P$-,
—C(=O)-cyc.Hex(1,4)-CH$_2$—(N-ly-3-diminiccuS)—S—CH$_2$CH$_2$CH$_2$CH$_2$CH$_2$CH$_2$—C(=O)-$L^P$-.

In each of the above linker structures, the peptide of the $L^P$ moiety can be selected from the group consisting of VK, VC, GFG, GGFG (SEQ ID NO: 3), GGFGG (SEQ ID NO: 4), GGFGS (SEQ ID NO: 5), GGFGGG (SEQ ID NO: 6), GGFGGE (SEQ ID NO: 7), GGFGGGFG (SEQ ID NO: 8), DGGF (SEQ ID NO: 9), DGGFG (SEQ ID NO: 10), D$^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), and SGGFG (SEQ ID NO: 17). Among these $L^P$, GGFG (SEQ ID NO: 3), GGFGG (SEQ ID NO: 4), GGFGS (SEQ ID NO: 5), GGFGGE (SEQ ID NO: 7), GDGGF (SEQ ID NO: 18), DGGFG (SEQ ID NO: 10), D$^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) is preferred. GGFG (SEQ ID NO: 3), GDGGF (SEQ ID NO: 18), DGGFG (SEQ ID NO: 10), D$^d$GGFG, DG$^{Me}$GFG (SEQ ID NO: 11), DGGFS (SEQ ID NO: 12), DDGGFG (SEQ ID NO: 13), or KDGGFG (SEQ ID NO: 14) is more preferred. GGFG (SEQ ID NO: 3), DGGFG (SEQ ID NO: 10), D$^d$GGFG, or DG$^{Me}$GFG (SEQ ID NO: 11) is further preferred.

When the —NH—(CH$_2$)n$^1$-$L^a$-$L^b$-$L^c$-moiety is connected to the above -$L^1$-$L^2$-$L^P$-, the —NH—(CH$_2$)n$^1$-$L^a$-$L^b$-$L^c$-moiety preferably has a chain length of 3 to 7 atoms. It more preferably has a chain length of 4 to 7 atoms, further preferably a chain length of 5 or 6 atoms. Although specific examples of the —NH—(CH$_2$)n$^1$-$L^a$-$L^b$-moiety in the linker are as described above, —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)— is particularly preferred.

[Linker-Drug Structure]

As the ADC of the Present Invention, ADC Expressing excellent properties can be obtained by conjugating the linker-drug moiety having each of structures shown below to the antibody.

a. A linker-drug moiety excellent as a linker-drug moiety having a structure of -$L^1$-$L^2$-$L^P$-NH—(CH$_2$)n$^1$-$L^a$-$L^b$-$L^c$-(NH-DX), which is conjugated to the antibody via a sulfide bond, wherein $L^P$ is GGFG (SEQ ID NO: 3), is as follows:
-(Succinimid-3-yl-N)—CH$_2$CH$_2$CH$_2$CH$_2$CH$_2$—C(=O)-GGFG (SEQ ID NO: 3)-NH—CH$_2$CH$_2$—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$CH$_2$—(NH-DX),
—CH$_2$—C(=O)—NH—CH$_2$CH$_2$—C(=O)-GGFG (SEQ ID NO: 3)-NH—CH$_2$CH$_2$CH$_2$—C(=O)—(NH-DX).

b. A linker-drug moiety excellent as a linker-drug moiety having a structure of -$L^1$-$L^2$-$L^P$-NH—(CH$_2$)n$^1$-$L^a$-$L^b$-$L^c$-(NH-DX), which is conjugated to the antibody via a sulfide bond, wherein $L^P$ is GGFG (SEQ ID NO: 3) and -$L^a$-$L^b$-$L^c$-has an alkyl branched chain, is as follows:
-(Succinimid-3-yl-N)—CH$_2$CH$_2$CH$_2$CH$_2$CH$_2$—C(=O)-GGFG (SEQ ID NO: 3)-NH—CH$_2$CMe(-H)—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH(-Me)-C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$C(-Me) 2-C(=O)—(NH-DX).

c. A linker-drug moiety excellent as a linker-drug moiety having a structure of -$L^1$-$L^2$-$L^P$-NH—(CH$_2$)n$^1$-$L^a$-$L^b$-$L^c$-(NH-DX), which is conjugated to the antibody via a sulfide bond, wherein $L^P$ is GGFG (SEQ ID NO: 3) and -$L^a$-$L^b$-$L^c$-has a nitrogen atom, is as follows:
-(Succinimid-3-yl-N)—CH$_2$CH$_2$CH$_2$CH$_2$CH$_2$—C(=O)-GGFG (SEQ ID NO: 3)-NH—CH$_2$CH$_2$—NH—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—NH—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(-Me)-CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(-Me)-CH$_2$CH$_2$—C(=O)—(NH-DX).

d. A linker-drug moiety excellent as a linker-drug moiety having a structure of -$L^1$-$L^2$-$L^P$-NH—(CH$_2$)n$^1$-$L^a$-$L^b$-$L^c$-(NH-DX), which is conjugated to the antibody via a sulfide bond, wherein L$^P$ is GGFG (SEQ ID NO: 3) and further has a branched chain moiety having a hydrophilic substituent, is as follows:
-(Succinimid-3-yl-N)—CH(—CH$_2$CH$_2$—COOH)—C(=O)-GGFG (SEQ ID NO: 3)-NH—CH$_2$CH$_2$CH$_2$—C(=O)—(NH-DX),
-(Succinimid-3-yl-N)—CH(—CH$_2$CH$_2$—COOH)—C(=O)—NH—CH$_2$CH$_2$—C(=O)-GGFG (SEQ ID NO: 3)-CH$_2$CH$_2$CH$_2$—C(=O)—(NH-DX),
-(Succinimid-3-yl-N)—CH$_2$CH$_2$—[N(—CH$_2$—COOH)]—CH$_2$—(C=O)-GGFG (SEQ ID NO: 3)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)—NH—CH$_2$CH$_2$—N [—CH$_2$—COOH]—CH$_2$—C(=O)-GGFG (SEQ ID NO: 3)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)—NH—[CH(—CH$_2$—COOH)]—CH$_2$—O—CH$_2$—(C=O)-GFG-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$CH$_2$—OH)—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$CH$_2$—OH)—CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$—COOH)—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$—COOH)—CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$—C(=O)—NH—CH(—CH$_2$—OH)—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$—C(=O)—NH—CH(—CH$_2$—COOH)—C(=O)—(NH-DX).

e. A linker-drug moiety excellent as a linker-drug moiety having a structure of -L$^1$-L$^2$-L$^P$-NH—(CH$_2$)n$^1$-L$^a$-L$^b$-L$^c$-(NH-DX), which is conjugated to the antibody via an amide bond, wherein L$^P$ is GGFG (SEQ ID NO: 3), is as follows:
—C(=O)—CH$_2$CH$_2$CH$_2$CH$_2$CH$_2$CH$_2$—C(=O)-GGFG (SEQ ID NO: 3)-NH—CH$_2$CH$_2$CH$_2$—C(=O)—(NH-DX),
—C(=O)-cyc.Hex(1,4)-CH$_2$—(N-ly-3-diminiccuS)—S—CH$_2$CH$_2$—C(=O)-GGFG (SEQ ID NO: 3)-NH—CH$_2$CH$_2$CH$_2$—C(=O)—(NH-DX).

f. A linker-drug moiety excellent as a linker-drug moiety having a structure of -L$^1$-L$^2$-L$^P$-NH—(CH$_2$)n$^1$-L$^a$-L$^b$-L$^c$-(NH-DX), which is conjugated to the antibody via a sulfide bond, wherein L$^P$ is GFG, is as follows:
-(Succinimid-3-yl-N)—CH$_2$CH$_2$CH$_2$CH$_2$CH$_2$—C(=O)—NH—[CH(—CH$_2$—COOH)]—CH$_2$—O—CH$_2$—(C=O)-GFG-(NH-DX).

g. A linker-drug moiety excellent as a linker-drug moiety having a structure of -L$^1$-L$^2$-L$^P$-NH—(CH$_2$)n$^1$-L$^a$-L$^b$-L$^c$-(NH-DX), which is conjugated to the antibody via a sulfide bond, wherein L$^P$ contains 4 or more glycine residues, is as follows:
-(Succinimid-3-yl-N)—CH$_2$CH$_2$CH$_2$CH$_2$CH$_2$—C(=O)—NH-GGFGG (SEQ ID NO: 4)-(NH-DX),
-(Succinimid-3-yl-N)—CH$_2$CH$_2$CH$_2$CH$_2$CH$_2$—C(=O)—NH-GGFGGG (SEQ ID NO: 6)-(NH-DX),
-(Succinimid-3-yl-N)—CH$_2$CH$_2$CH$_2$CH$_2$CH$_2$—C(=O)—NH-GGFGGGFG (SEQ ID NO: 8)-(NH-DX).

h. A linker-drug moiety excellent as a linker-drug moiety having a structure of -L$^1$-L$^2$-L$^P$-NH—(CH$_2$)n$^1$-L$^a$-L$^b$-L$^c$-(NH-DX), which is conjugated to the antibody via a sulfide bond, wherein L$^P$ has a C-terminal hydrophilic amino acid, is as follows:
-(Succinimid-3-yl-N)—CH$_2$CH$_2$CH$_2$CH$_2$CH$_2$—C(=O)—NH-GGFGS (SEQ ID NO: 5)-(NH-DX), and
-(Succinimid-3-yl-N)—CH$_2$CH$_2$CH$_2$CH$_2$CH$_2$—C(=O)—NH-GGFGE (SEQ ID NO: 7)-(NH-DX).

i. A linker-drug moiety excellent as a linker-drug moiety having a structure of -L$^1$-L$^2$-L$^P$-(NH-DX), which is conjugated to the antibody via a sulfide bond, wherein L$^P$ is GGFG (SEQ ID NO: 3), is as follows:
-(Succinimid-3-yl-N)—CH$_2$CH$_2$CH$_2$CH$_2$CH$_2$—C(=O)-GGFG (SEQ ID NO: 3)-(NH-DX), and
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-(NH-DX).

j. A linker-drug moiety excellent as a linker-drug moiety having a structure of -L$^1$-L$^2$-L$^P$-(NH-DX), which is conjugated to the antibody via a sulfide bond, wherein L$^P$ is GGFG (SEQ ID NO: 3) and further has a branched chain moiety having a hydrophilic substituent, is as follows:
-(Succinimid-3-yl-N)—CH$_2$CH$_2$—[N(—CH$_2$—COOH)]—CH$_2$—(C=O)-GGFG (SEQ ID NO: 3)-(NH-DX),
-(Succinimid-3-yl-N)—CH$_2$CH$_2$CH$_2$CH$_2$CH$_2$—C(=O)—NH—[CH(—CH$_2$—COOH)]—CH$_2$—(C=O)-GGFG (SEQ ID NO: 3)-(NH-DX),
-(Succinimid-3-yl-N)—CH$_2$CH$_2$CH$_2$CH$_2$CH$_2$—C(=O)—NH—CH$_2$CH$_2$—[N(—CH$_2$—COOH)]—CH$_2$—(C=O)-GGFG (SEQ ID NO: 3)-(NH-DX).

k. A linker-drug moiety excellent as a linker-drug moiety having a structure of -L$^1$-L$^2$-L$^P$-(NH-DX), which is conjugated to the antibody via an amide bond, wherein L$^P$ is GGFG (SEQ ID NO: 3), is as follows:
—C(=O)-cyc.Hex(1,4)-CH$_2$—(N-ly-3-diminiccuS)—S—CH$_2$CH$_2$—C(=O)-GGFG (SEQ ID NO: 3)-(NH-DX).

l. A linker-drug moiety excellent as a linker-drug moiety having a structure of -L$^1$-L$^2$-L$^P$-NH—(CH$_2$)n$^1$-L$^a$-L$^b$-L$^c$-(NH-DX), which is conjugated to the antibody via a sulfide bond, wherein L$^P$ is a peptide residue containing aspartic acid, lysine, glutamic acid, and/or serine, which are hydrophilic amino acids, in particular, a peptide residue having N-terminal aspartic acid, is as follows:
-(Succinimid-3-yl-N)—CH$_2$CH$_2$—C(=O)-DGGFG (SEQ ID NO: 10)-NH—CH$_2$CH$_2$—C(=O)—(NH-DX),
-(Succinimid-3-yl-N)—CH$_2$CH$_2$—C(=O)-DGGFG (SEQ ID NO: 10)-NH—CH$_2$CH$_2$CH$_2$—C(=O)—(NH-DX),
-(Succinimid-3-yl-N)—CH$_2$CH$_2$CH$_2$—C(=O)-DGGFG (SEQ ID NO: 10)-NH—CH$_2$CH$_2$—C(=O)—(NH-DX),
-(Succinimid-3-yl-N)—CH$_2$CH$_2$CH$_2$—C(=O)-DGGFG (SEQ ID NO: 10)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-DGGF (SEQ ID NO: 9)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-DGGFG (SEQ ID NO: 10)-NH—CH$_2$CH$_2$—C(=O)—(NH-DX),
-(Succinimid-3-yl-N)—CH$_2$CH$_2$CH$_2$CH$_2$CH$_2$—C(=O)-DGGFG (SEQ ID NO: 10)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-DGGFG (SEQ ID NO: 10)-NH—CH$_2$CH$_2$CH$_2$CH$_2$—C(=O)—(NH-DX).
-(Succinimid-3-yl-N)—CH$_2$CH$_2$—C(=O)—NH—CH$_2$CH$_2$—O—CH$_2$CH$_2$—O—CH$_2$CH$_2$—C(=O)-DGGFG (SEQ ID NO: 10)-NH—CH$_2$CH$_2$—C(=O)—(NH-DX), -(Succinimid-3-yl-N)—CH$_2$CH$_2$—C(=O)—NH—CH$_2$CH$_2$—O—CH$_2$CH$_2$—O—CH$_2$CH$_2$—C(=O)-DGGFG (SEQ ID NO: 10)-NH—CH$_2$CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-DGGFG (SEQ ID NO: 10)-NH—CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-DGGFG (SEQ ID NO: 10)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-DGGFG (SEQ ID NO: 10)-NH—CH$_2$CH$_2$C(Me)$_2$-C(=O)—(NH-DX),
-(Succinimid-3-yl-N)—CH$_2$CH$_2$CH$_2$CH$_2$CH$_2$—C(=O)-DG$^{Me}$GFG (SEQ ID NO: 11)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-DGGFG (SEQ ID NO: 10)-NH—CH$_2$—O—CH$_2$—C(=O)—(NH-DX),
-(Succinimid-3-yl-N)—CH$_2$CH$_2$CH$_2$CH$_2$CH$_2$—C(=O)-DDGGFG (SEQ ID NO: 13)-NH—CH$_2$CH$_2$CH$_2$—C(=O)—(NH-DX).

m. A linker-drug moiety excellent as a linker-drug moiety having a structure of -L$^1$-L$^2$-L$^P$-NH—(CH$_2$)n$^1$-L$^a$-L$^b$-L$^c$-(NH-DX), which is conjugated to the antibody via a sulfide bond, wherein L$^P$ is a peptide residue containing aspartic acid, lysine, glutamic acid, and/or serine, which are hydrophilic amino acids, in particular, a peptide residue having an N-terminal hydrophilic amino acid other than aspartic acid, is as follows:
-(Succinimid-3-yl-N)—CH$_2$CH$_2$CH$_2$CH$_2$CH$_2$—C(=O)-KGGFG (SEQ ID NO: 15)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-EGGFG (SEQ ID NO: 16)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-KDGGFG (SEQ ID NO: 14)-NH—CH$_2$CH$_2$CH$_2$—C(=O)—(NH-DX).

n. A linker-drug moiety excellent as a linker-drug moiety having a structure of -L$^1$-L$^2$-L$^P$-NH—(CH$_2$)n$^1$-L$^a$-L$^b$-L$^c$-(NH-DX), which is conjugated to the antibody via an amide bond, wherein L$^P$ is a peptide residue containing aspartic acid, lysine, glutamic acid, and/or serine, which are hydrophilic amino acids, in particular, a peptide residue containing aspartic acid as a hydrophilic amino acid, is as follows:
—C(=O)-cyc.Hex(1,4)-CH$_2$—(N-ly-3-diminiccuS)—S—CH$_2$CH$_2$—C(=O)-DGGFG (SEQ ID NO: 10)-NH—CH$_2$CH$_2$CH$_2$—C(=O)—(NH-DX).

o. A linker-drug moiety excellent as a linker-drug moiety having a structure of -L$^1$-L$^2$-L$^P$-(NH-DX), which is conjugated to the antibody via a sulfide bond, wherein L$^P$ is a peptide residue containing aspartic acid, lysine, glutamic acid, and/or serine, which are hydrophilic amino acids, in particular, a peptide residue having N-terminal aspartic acid, is as follows:
-(Succinimid-3-yl-N)—CH$_2$CH$_2$—C(=O)—NH-DGGFG (SEQ ID NO: 10)-(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-DGGFG (SEQ ID NO: 10)-(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-DGGFG (SEQ ID NO: 10)-(NH-DX),
-(Succinimid-3-yl-N)—CH$_2$CH$_2$CH$_2$—C(=O)—NH-DGGFG (SEQ ID NO: 10)-(NH-DX),
-(Succinimid-3-yl-N)—CH$_2$CH$_2$CH$_2$CH$_2$—C(=O)—NH-DGGFG (SEQ ID NO: 10)-(NH-DX),
-(Succinimid-3-yl-N)—CH$_2$CH$_2$CH$_2$CH$_2$CH$_2$—C(=O)—NH-DDGGFG (SEQ ID NO: 13)-(NH-DX),
-(Succinimid-3-yl-N)—CH$_2$CH$_2$CH$_2$CH$_2$CH$_2$—C(=O)—NH-DG$^{Me}$GFG (SEQ ID NO: 11)-(NH-DX),
-(Succinimid-3-yl-N)—CH$_2$CH$_2$CH$_2$CH$_2$CH$_2$—C(=O)—NH-DGGFS (SEQ ID NO: 12)-(NH-DX).

p. A linker-drug moiety excellent as a linker-drug moiety having a structure of -L$^1$-L$^2$-L$^P$-NH—(CH$_2$)n$^1$-(NH-DX), which is conjugated to the antibody via a sulfide bond, wherein L$^P$ is a peptide residue containing aspartic acid, lysine, glutamic acid, and/or serine, which are hydrophilic amino acids, in particular, a peptide residue having no aspartic acid at the N terminal, is as follows:
-(Succinimid-3-yl-N)—CH$_2$CH$_2$CH$_2$CH$_2$CH$_2$—C(=O)—NH-KGGFG (SEQ ID NO: 15)-(NH-DX),
-(Succinimid-3-yl-N)—CH$_2$CH$_2$CH$_2$CH$_2$CH$_2$—C(=O)—NH-SGGFG (SEQ ID NO: 17)-(NH-DX),
-(Succinimid-3-yl-N)—CH$_2$CH$_2$CH$_2$CH$_2$CH$_2$—C(=O)—NH-EGGFG (SEQ ID NO: 16)-(NH-DX).

q. A linker-drug moiety excellent as a linker-drug moiety having a structure of -L$^1$-L$^2$-L$^P$-NH—(CH$_2$)n$^1$-(NH-DX), which is conjugated to the antibody via a sulfide bond, wherein L$^P$ is a peptide residue of dipeptide, is as follows:
-(Succinimid-3-yl-N)—CH$_2$CH$_2$CH$_2$CH$_2$CH$_2$—C(=O)—VK—NH—CH$_2$CH$_2$CH$_2$—C(=O)—(NH-DX), and
-(Succinimid-3-yl-N)—CH$_2$CH$_2$CH$_2$CH$_2$CH$_2$—C(=O)—VC—NH—CH$_2$CH$_2$CH$_2$—C(=O)—(NH-DX).

In the ADC of the present invention, a linker-drug moiety having any of structures shown below is preferably conjugated to the antibody.

A. As for the linker-drug moiety of the present invention, a preferred linker-drug moiety having a structure of -L$^1$-L$^2$-L$^P$-NH—(CH$_2$)n$^1$-L$^a$-L$^b$-L$^c$-(NH-DX) wherein L$^P$ is GGGF (SEQ ID NO: 21) is shown below.

A-1. When L$^1$ is -(Succinimid-3-yl-N)—(CH$_2$)n$^2$-C(=O)— and L$^2$ is a single bond;
-(Succinimid-3-yl-N)—CH$_2$CH$_2$—C(=O)-GGFG (SEQ ID NO: 3)-NH—CH$_2$CH$_2$—(NH-DX),
-(Succinimid-3-yl-N)—CH$_2$CH$_2$—C(=O)-GGFG (SEQ ID NO: 3)-NH—CH$_2$CH$_2$CH$_2$—(NH-DX),
-(Succinimid-3-yl-N)—CH$_2$CH$_2$—C(=O)-GGFG (SEQ ID NO: 3)-NH—CH$_2$CH$_2$CH$_2$—CH$_2$—(NH-DX),
-(Succinimid-3-yl-N)—CH$_2$CH$_2$CH$_2$CH$_2$—C(=O)-GGFG (SEQ ID NO: 3)-NH—CH$_2$CH$_2$—(NH-DX),
-(Succinimid-3-yl-N)—CH$_2$CH$_2$CH$_2$CH$_2$—C(=O)-GGFG (SEQ ID NO: 3)-NH—CH$_2$CH$_2$CH$_2$—(NH-DX),
-(Succinimid-3-yl-N)—CH$_2$CH$_2$CH$_2$CH$_2$—C(=O)-GGFG (SEQ ID NO: 3)-NH—CH$_2$CH$_2$CH$_2$CH$_2$—(NH-DX).

Among these, more preferred are the following:
-(Succinimid-3-yl-N)—CH$_2$CH$_2$CH$_2$CH$_2$CH$_2$—C(=O)-GGFG (SEQ ID NO: 3)-NH—CH$_2$CH$_2$—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$CH$_2$—(NH-DX).

A-2. When L$^1$ is -(Succinimid-3-yl-N)—(CH$_2$)n$^2$-C(=O)— and L$^2$ is —NH—(CH$_2$—O)n$^6$-CH$_2$CH$_2$—C(=O)—;
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$—(NH-DX), -(Succinimid-3-yl-N)—CH$_2$CH$_2$—C(=O)—NH—CH$_2$CH$_2$—O—

CH₂CH₂—O—CH₂CH₂—C(=O)-GGFG (SEQ ID NO: 3)-NH—CH₂CH₂CH₂—(NH-DX),
-(Succinimid-3-yl-N)—CH₂CH₂—C(=O)—NH—CH₂CH₂—O—CH₂CH₂—O—CH₂CH₂—C(=O)-GGFG (SEQ ID NO: 3)-NH—CH₂CH₂CH₂—CH₂—(NH-DX),
-(Succinimid-3-yl-N)—CH₂CH₂CH₂CH₂CH₂—C(=O)—NH—CH₂CH₂—O—CH₂CH₂—O—CH₂CH₂—C(=O)-GGFG (SEQ ID NO: 3)-NH—CH₂CH₂—(NH-DX),
-(Succinimid-3-yl-N)—CH₂CH₂CH₂CH₂CH₂—C(=O)—NH—CH₂CH₂—O—CH₂CH₂—O—CH₂CH₂—C(=O)-GGFG (SEQ ID NO: 3)-NH—CH₂CH₂CH₂—(NH-DX),
-(Succinimid-3-yl-N)—CH₂CH₂CH₂CH₂CH₂—C(=O)—NH—CH₂CH₂—O—CH₂CH₂—O—CH₂CH₂—C(=O)-GGFG (SEQ ID NO: 3)-NH—CH₂CH₂CH₂CH₂—(NH-DX),
-(Succinimid-3-yl-N)—CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂—(NH-DX),
-(Succinimid-3-yl-N)—CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂CH₂—(NH-DX),
-(Succinimid-3-yl-N)—CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂CH₂—CH₂—(NH-DX),
-(Succinimid-3-yl-N)—CH₂CH₂CH₂CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂—(NH-DX),
-(Succinimid-3-yl-N)—CH₂CH₂CH₂CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂CH₂—(NH-DX),
-(Succinimid-3-yl-N)—CH₂CH₂CH₂CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂CH₂CH₂—(NH-DX).

A-3. When $L^1$ is -(Succinimid-3-yl-N)—CH [—(CH₂)$n^3$-COOH]—C(=O)— and $L^2$ is a single bond;
-(Succinimid-3-yl-N)—CH(—CH₂—COOH)—C(=O)-GGFG (SEQ ID NO: 3)-NH—CH₂CH₂—C(=O)—(NH-DX),
-(Succinimid-3-yl-N)—CH(—CH₂—COOH)—C(=O)-GGFG (SEQ ID NO: 3)-NH—CH₂CH₂CH₂—C(=O)—(NH-DX),
-(Succinimid-3-yl-N)—CH(—CH₂—COOH)—C(=O)-GGFG (SEQ ID NO: 3)-NH—CH₂CH₂CH₂CH₂—C(=O)—(NH-DX),
-(Succinimid-3-yl-N)—CH(—CH₂CH₂—COOH)—C(=O)-GGFG (SEQ ID NO: 3)-NH—CH₂CH₂—C(=O)—(NH-DX),
-(Succinimid-3-yl-N)—CH(—CH₂CH₂—COOH)—C(=O)-GGFG (SEQ ID NO: 3)-NH—CH₂CH₂CH₂—C(=O)—(NH-DX),
-(Succinimid-3-yl-N)—CH(—CH₂CH₂—COOH)—C(=O)-GGFG (SEQ ID NO: 3)-NH—CH₂CH₂CH₂CH₂—C(=O)—(NH-DX).

Among these, more preferred are the following:
-(Succinimid-3-yl-N)—CH(—CH₂CH₂—COOH)—C(=O)-GGFG (SEQ ID NO: 3)-NH—CH₂CH₂—C(=O)—(NH-DX),
-(Succinimid-3-yl-N)—CH(—CH₂CH₂—COOH)—C(=O)-GGFG (SEQ ID NO: 3)-NH—CH₂CH₂CH₂—C(=O)—(NH-DX),
-(Succinimid-3-yl-N)—CH(—CH₂CH₂—COOH)—C(=O)-GGFG (SEQ ID NO: 3)-NH—CH₂CH₂CH₂CH₂—C(=O)—(NH-DX).

A-4. When $L^1$ is -(Succinimid-3-yl-N)—CH [—(CH₂)$n^3$-COOH]—C(=O)— and $L^2$ is —NH—(CH₂CH₂—O)$n^6$-CH₂CH₂—C(=O)—;
-(Succinimid-3-yl-N)—CH(—CH₂—COOH)—C(=O)—NH—CH₂CH₂—C(=O)-GGFG (SEQ ID NO: 3)-CH₂CH₂—C(=O)—(NH-DX),
-(Succinimid-3-yl-N)—CH(—CH₂—COOH)—C(=O)—NH—CH₂CH₂—C(=O)-GGFG (SEQ ID NO: 3)-CH₂CH₂CH₂—C(=O)—(NH-DX),
-(Succinimid-3-yl-N)—CH(—CH₂—COOH)—C(=O)—NH—CH₂CH₂—C(=O)-GGFG (SEQ ID NO: 3)-CH₂CH₂CH₂CH₂—C(=O)—(NH-DX),
-(Succinimid-3-yl-N)—CH(—CH₂CH₂—COOH)—C(=O)—NH—CH₂CH₂—C(=O)-GGFG (SEQ ID NO: 3)-CH₂CH₂—C(=O)—(NH-DX),
-(Succinimid-3-yl-N)—CH(—CH₂CH₂—COOH)—C(=O)—NH—CH₂CH₂—C(=O)-GGFG (SEQ ID NO: 3)-CH₂CH₂CH₂—C(=O)—(NH-DX),
-(Succinimid-3-yl-N)—CH(—CH₂CH₂—COOH)—C(=O)—NH—CH₂CH₂—C(=O)-GGFG (SEQ ID NO: 3)-CH₂CH₂CH₂CH₂—C(=O)—(NH-DX).

Among these, more preferred are the following:
-(Succinimid-3-yl-N)—CH(—CH₂CH₂—COOH)—C(=O)—NH—CH₂CH₂—C(=O)-GGFG (SEQ ID NO: 3)-CH₂CH₂—C(=O)—(NH-DX),
-(Succinimid-3-yl-N)—CH(—CH₂CH₂—COOH)—C(=O)—NH—CH₂CH₂—C(=O)-GGFG (SEQ ID NO: 3)-CH₂CH₂CH₂—C(=O)—(NH-DX),
-(Succinimid-3-yl-N)—CH(—CH₂CH₂—COOH)—C(=O)—NH—CH₂CH₂—C(=O)-GGFG (SEQ ID NO: 3)-CH₂CH₂CH₂CH₂—C(=O)—(NH-DX).

A-5. When $L^1$ is -(Succinimid-3-yl-N)—CH₂CH₂—[N(—CH₂—COOH)]—CH₂—(C=O)— and $L^2$ is a single bond;
-(Succinimid-3-yl-N)—CH₂CH₂—[N(—CH₂—COOH)]—CH₂—(C=O)-GGFG (SEQ ID NO: 3)-NH—CH₂CH₂—C(=O)—(NH-DX),
-(Succinimid-3-yl-N)—CH₂CH₂—[N(—CH₂—COOH)]—CH₂—(C=O)-GGFG (SEQ ID NO: 3)-NH—CH₂CH₂CH₂—C(=O)—(NH-DX),
-(Succinimid-3-yl-N)—CH₂CH₂—[N(—CH₂—COOH)]—CH₂—(C=O)-GGFG (SEQ ID NO: 3)-NH—CH₂CH₂CH₂CH₂—C(=O)—(NH-DX).

A-6. When $L^1$ is -(Succinimid-3-yl-N)—(CH₂)$n^2$-C(=O)— and $L^2$ is —NH—(CH₂—CH₂—O)$n^6$-CH₂—CH₂—C(=O)—;
-(Succinimid-3-yl-N)—CH₂CH₂—C(=O)—NH—CH₂CH₂—O—CH₂CH₂—O—CH₂CH₂—C(=O)-GGFG (SEQ ID NO: 3)-NH—CH₂CH₂—(NH-DX),
-(Succinimid-3-yl-N)—CH₂CH₂—C(=O)—NH—CH₂CH₂—O—CH₂CH₂—O—CH₂CH₂—C(=O)-GGFG (SEQ ID NO: 3)-NH—CH₂CH₂CH₂—(NH-DX),
-(Succinimid-3-yl-N)—CH₂CH₂—C(=O)—NH—CH₂CH₂—O—CH₂CH₂—O—CH₂CH₂—C(=O)-GGFG (SEQ ID NO: 3)-NH—CH₂CH₂CH₂—CH₂—(NH-DX),
-(Succinimid-3-yl-N)—CH₂CH₂CH₂CH₂CH₂—C(=O)—NH—CH₂CH₂—O—CH₂CH₂—O—CH₂CH₂—C(=O)-GGFG (SEQ ID NO: 3)-NH—CH₂CH₂—(NH-DX),
-(Succinimid-3-yl-N)—CH₂CH₂CH₂CH₂CH₂—C(=O)—NH—CH₂CH₂—O—CH₂CH₂—O—CH₂CH₂—C(=O)-GGFG (SEQ ID NO: 3)-NH—CH₂CH₂CH₂—(NH-DX),
-(Succinimid-3-yl-N)—CH₂CH₂CH₂CH₂CH₂—C(=O)—NH—CH₂CH₂—O—CH₂CH₂—O—CH₂CH₂—C(=O)-GGFG (SEQ ID NO: 3)-NH—CH₂CH₂CH₂—CH₂—(NH-DX), -(Succinimid-3-yl-N)—CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂—(NH-DX),
-(Succinimid-3-yl-N)—CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂CH₂—(NH-DX),
-(Succinimid-3-yl-N)—CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂CH₂—CH₂—(NH-DX),
-(Succinimid-3-yl-N)—CH₂CH₂CH₂CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂—(NH-DX),
-(Succinimid-3-yl-N)—CH₂CH₂CH₂CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂CH₂—(NH-DX), -(Succinimid-3-yl-N)-CH₂CH₂CH₂CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂CH₂—CH₂—(NH-DX).

A-7. When $L^1$ is -(Succinimid-3-yl-N)—(CH₂)n²-C(=O)—, $L^2$ is a single bond, and -$L^a$-$L^b$-$L^c$-has an alkyl branched chain;
-(Succinimid-3-yl-N)—CH₂CH₂—C(=O)-GGFG (SEQ ID NO: 3)-NH—CH₂CMe(-H)—C(=O)—(NH-DX),
-(Succinimid-3-yl-N)—CH₂CH₂—C(=O)-GGFG (SEQ ID NO: 3)-NH—CH₂CH(-Me)-C(=O)—(NH-DX),
-(Succinimid-3-yl-N)—CH₂CH₂—C(=O)-GGFG (SEQ ID NO: 3)-NH—CH₂C(-Me)₂-C(=O)—(NH-DX),
-(Succinimid-3-yl-N)—CH₂CH₂—C(=O)-GGFG (SEQ ID NO: 3)-NH—CH₂CH₂CMe(-H)—C(=O)—(NH-DX),
-(Succinimid-3-yl-N)—CH₂CH₂—C(=O)-GGFG (SEQ ID NO: 3)-NH—CH₂CH₂CH(-Me)-C(=O)—(NH-DX),
-(Succinimid-3-yl-N)—CH₂CH₂—C(=O)-GGFG (SEQ ID NO: 3)-NH—CH₂CH₂C(-Me)₂-C(=O)—(NH-DX),
-(Succinimid-3-yl-N)—CH₂CH₂CH₂CH₂CH₂—C(=O)-GGFG (SEQ ID NO: 3)-NH—CH₂CMe(-H)—C(=O)—(NH-DX),
-(Succinimid-3-yl-N)—CH₂CH₂CH₂CH₂CH₂—C(=O)-GGFG (SEQ ID NO: 3)-NH—CH₂CH(-Me)-C(=O)—(NH-DX),
-(Succinimid-3-yl-N)—CH₂CH₂CH₂CH₂CH₂—C(=O)-GGFG (SEQ ID NO: 3)-NH—CH₂C(-Me)₂-C(=O)—(NH-DX),
-(Succinimid-3-yl-N)—CH₂CH₂CH₂CH₂CH₂—C(=O)-GGFG (SEQ ID NO: 3)-NH—CH₂CH₂CMe(-H)—C(=O)—(NH-DX),
-(Succinimid-3-yl-N)—CH₂CH₂CH₂CH₂CH₂—C(=O)-GGFG (SEQ ID NO: 3)-NH—CH₂CH₂CH(-Me)-C(=O)—(NH-DX),
-(Succinimid-3-yl-N)—CH₂CH₂CH₂CH₂CH₂—C(=O)-GGFG (SEQ ID NO: 3)-NH—CH₂CH₂C(-Me)₂-C(=O)—(NH-DX).

Among these, preferred are the following:
-(Succinimid-3-yl-N)—CH₂CH₂CH₂CH₂CH₂—C(=O)-GGFG (SEQ ID NO: 3)-NH—CH₂CMe(-H)—C(=O)—(NH-DX),
-(Succinimid-3-yl-N)—CH₂CH₂CH₂CH₂CH₂—C(=O)-GGFG (SEQ ID NO: 3)-NH—CH₂CH(-Me)-C(=O)—(NH-DX),
-(Succinimid-3-yl-N)—CH₂CH₂CH₂CH₂CH₂—C(=O)-GGFG (SEQ ID NO: 3)-NH—CH₂C(-Me)₂-C(=O)—(NH-DX),
-(Succinimid-3-yl-N)—CH₂CH₂CH₂CH₂CH₂—C(=O)-GGFG (SEQ ID NO: 3)-NH—CH₂CH₂CMe(-H)—C(=O)—(NH-DX),
-(Succinimid-3-yl-N)—CH₂CH₂CH₂CH₂CH₂—C(=O)-GGFG (SEQ ID NO: 3)-NH—CH₂CH₂CH(-Me)-C(=O)—(NH-DX),
-(Succinimid-3-yl-N)—CH₂CH₂CH₂CH₂CH₂—C(=O)-GGFG (SEQ ID NO: 3)-NH—CH₂CH₂C(-Me)₂-C(=O)—(NH-DX).

Further preferred are the following:
-(Succinimid-3-yl-N)—CH₂CH₂CH₂CH₂CH₂—C(=O)-GGFG (SEQ ID NO: 3)-NH—CH₂CMe(-H)—C(=O)—(NH-DX),
-(Succinimid-3-yl-N)—CH₂CH₂CH₂CH₂CH₂—C(=O)-GGFG (SEQ ID NO: 3)-NH—CH₂CH(-Me)-C(=O)—(NH-DX),
-(Succinimid-3-yl-N)—CH₂CH₂CH₂CH₂CH₂—C(=O)-GGFG (SEQ ID NO: 3)-NH—CH₂CH₂C(-Me)₂-C(=O)—(NH-DX).

A-8. When $L^1$ is -(Succinimid-3-yl-N)—(CH₂)n²-C(=O)—, $L^2$ is a single bond, and the -$L^a$-$L^b$-$L^c$-chain has a nitrogen atom;
-(Succinimid-3-yl-N)—CH₂CH₂—C(=O)-GGFG (SEQ ID NO: 3)-NH—CH₂CH₂—NH—C(=O)—(NH-DX),
-(Succinimid-3-yl-N)—CH₂CH₂—C(=O)-GGFG (SEQ ID NO: 3)-NH—CH₂CH₂—NMe-C(=O)—(NH-DX),
-(Succinimid-3-yl-N)—CH₂CH₂—C(=O)-GGFG (SEQ ID NO: 3)-NH—CH₂CH₂—NH—CH₂—C(=O)—(NH-DX),
-(Succinimid-3-yl-N)—CH₂CH₂—C(=O)-GGFG (SEQ ID NO: 3)-NH—CH₂CH₂—NMe-CH₂—C(=O)—(NH-DX),
-(Succinimid-3-yl-N)—CH₂CH₂—C(=O)-GGFG (SEQ ID NO: 3)-NH—CH₂CH₂—NH—CH₂CH₂—C(=O)—(NH-DX),
-(Succinimid-3-yl-N)—CH₂CH₂—C(=O)-GGFG (SEQ ID NO: 3)-NH—CH₂CH₂—NMe-CH₂CH₂—C(=O)—(NH-DX),
-(Succinimid-3-yl-N)—CH₂CH₂CH₂CH₂CH₂—C(=O)-GGFG (SEQ ID NO: 3)-NH—CH₂CH₂—NH—C(=O)—(NH-DX),
-(Succinimid-3-yl-N)—CH₂CH₂CH₂CH₂CH₂—C(=O)-GGFG (SEQ ID NO: 3)-NH—CH₂CH₂—NMe-C(=O)—(NH-DX),
-(Succinimid-3-yl-N)—CH₂CH₂CH₂CH₂CH₂—C(=O)-GGFG (SEQ ID NO: 3)-NH—CH₂CH₂—NH—CH₂—C(=O)—(NH-DX),
-(Succinimid-3-yl-N)—CH₂CH₂CH₂CH₂CH₂—C(=O)-GGFG (SEQ ID NO: 3)-NH—CH₂CH₂—NMe-CH₂—C(=O)—(NH-DX), -(Succinimid-3-yl-N)—CH₂CH₂CH₂CH₂CH₂—C(=O)-GGFG (SEQ ID NO: 3)-NH—CH₂CH₂—NH—CH₂CH₂—C(=O)—(NH-DX),
-(Succinimid-3-yl-N)—CH₂CH₂CH₂CH₂CH₂—C(=O)-GGFG (SEQ ID NO: 3)-NH—CH₂CH₂-NMe-CH₂CH₂—C(=O)—(NH-DX).

Among these, more preferred are the following:
-(Succinimid-3-yl-N)—CH₂CH₂CH₂CH₂CH₂—C(=O)-GGFG (SEQ ID NO: 3)-NH—CH₂CH₂—NH—C(=O)—(NH-DX),
-(Succinimid-3-yl-N)—CH₂CH₂CH₂CH₂CH₂—C(=O)-GGFG (SEQ ID NO: 3)-NH—CH₂CH₂—NMe-C(=O)—(NH-DX),
-(Succinimid-3-yl-N)—CH₂CH₂CH₂CH₂CH₂—C(=O)-GGFG (SEQ ID NO: 3)-NH—CH₂CH₂—NH—CH₂—C(=O)—(NH-DX),
-(Succinimid-3-yl-N)—CH₂CH₂CH₂CH₂CH₂—C(=O)-GGFG (SEQ ID NO: 3)-NH—CH₂CH₂—NMe-CH₂—C(=O)—(NH-DX), -(Succinimid-3-yl-N)—CH$_2$CH$_2$CH$_2$CH$_2$CH$_2$—C(=O)-GGFG (SEQ ID NO: 3)-NH—CH$_2$CH$_2$—NH—CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—NMe-CH$_2$CH$_2$—C(=O)—(NH-DX).

A-9. When L$^1$ is -(Succinimid-3-yl-N)—(CH$_2$)n$^2$-C(=O)—, L$^2$ is a single bond, and -L$^a$-L$^b$-L$^c$-has a nitrogen atom and has a branched chain moiety having a hydroxyl group;
-(Succinimid-3-yl-N)—CH$_2$CH$_2$—C(=O)-GGFG (SEQ ID NO: 3)-NH—CH$_2$CH$_2$—N(—CH$_2$CH$_2$—OH)—CH$_2$—C(=O)—(NH-DX),
-(Succinimid-3-yl-N)—CH$_2$CH$_2$—C(=O)-GGFG (SEQ ID NO: 3)-NH—CH$_2$CH$_2$—N(—CH$_2$CH$_2$—OH)—CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$CH$_2$—OH)—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$CH$_2$—OH)—CH$_2$CH$_2$—C(=O)—(NH-DX).

Among these, more preferred are the following:
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$CH$_2$—OH)—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$CH$_2$—OH)—CH$_2$CH$_2$—C(=O)—(NH-DX).

A-10. When L$^1$ is -(Succinimid-3-yl-N)—(CH$_2$)n$^2$-C(=O)—, L$^2$ is a single bond, and the -L$^a$-L$^b$-L$^c$-chain has a nitrogen atom and has a branched moiety having a carboxy group;
-(Succinimid-3-yl-N)—CH$_2$CH$_2$—C(=O)-GGFG (SEQ ID NO: 3)-NH—CH$_2$CH$_2$—N(—CH$_2$—COOH)—CH$_2$—C(=O)—(NH-DX),
-(Succinimid-3-yl-N)—CH$_2$CH$_2$—C(=O)-GGFG (SEQ ID NO: 3)-NH—CH$_2$CH$_2$—N(—CH$_2$—COOH)—CH$_2$CH$_2$—C(=O)—(NH-DX),
-(Succinimid-3-yl-N)—CH$_2$CH$_2$—C(=O)-GGFG (SEQ ID NO: 3)-NH—CH$_2$CH$_2$—N(—CH$_2$CH$_2$—COOH)—CH$_2$—C(=O)—(NH-DX),
-(Succinimid-3-yl-N)—CH$_2$CH$_2$—C(=O)-GGFG (SEQ ID NO: 3)-NH—CH$_2$CH$_2$—N(—CH$_2$CH$_2$—COOH)—CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$—COOH)—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$—COOH)—CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$CH$_2$—COOH)—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$CH$_2$—COOH)—CH$_2$CH$_2$—C(=O)—(NH-DX).

Among these, more preferred are the following:
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$—COOH)—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$—COOH)—CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$CH$_2$—COOH)—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$CH$_2$—COOH)—CH$_2$CH$_2$—C(=O)—(NH-DX).

Further preferred are the following:
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$—COOH)—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—N(—CH$_2$—COOH)—CH$_2$CH$_2$—C(=O)—(NH-DX).

A-11. When L$^1$ is -(Succinimid-3-yl-N)—(CH$_2$)n$^2$-C(=O)—, L$^2$ is a single bond, -L$^a$-L$^b$-L$^c$-has a branched moiety having a hydroxyl group or a carboxy group;
-(Succinimid-3-yl-N)—CH$_2$CH$_2$—C(=O)-GGFG (SEQ ID NO: 3)-NH—CH$_2$CH$_2$—C(=O)—NH—CH(—CH$_2$—OH)—C(=O)—(NH-DX),
-(Succinimid-3-yl-N)—CH$_2$CH$_2$—C(=O)-GGFG (SEQ ID NO: 3)-NH—CH$_2$CH$_2$—C(=O)—NH—CH(—CH$_2$CH$_2$—OH)—C(=O)—(NH-DX),
-(Succinimid-3-yl-N)—CH$_2$CH$_2$—C(=O)-GGFG (SEQ ID NO: 3)-NH—CH$_2$CH$_2$—C(=O)—NH—CH(—CH$_2$—COOH)—C(=O)—(NH-DX),
-(Succinimid-3-yl-N)—CH$_2$CH$_2$—C(=O)-GGFG (SEQ ID NO: 3)-NH—CH$_2$CH$_2$—C(=O)—NH—CH(—CH$_2$CH$_2$—COOH)—C(=O)—(NH-DX),
-(Succinimid-3-yl-N)—CH$_2$CH$_2$—C(=O)-GGFG (SEQ ID NO: 3)-NH—CH$_2$CH$_2$CH$_2$—C(=O)—NH—CH(—CH$_2$—OH)—C(=O)—(NH-DX),
-(Succinimid-3-yl-N)—CH$_2$CH$_2$—C(=O)-GGFG (SEQ ID NO: 3)-NH—CH$_2$CH$_2$CH$_2$—C(=O)—NH—CH(—CH$_2$CH$_2$—OH)—C(=O)—(NH-DX),
-(Succinimid-3-yl-N)—CH$_2$CH$_2$—C(=O)-GGFG (SEQ ID NO: 3)-NH—CH$_2$CH$_2$CH$_2$—C(=O)—NH—CH(—CH$_2$—COOH)—C(=O)—(NH-DX),
-(Succinimid-3-yl-N)—CH$_2$CH$_2$—C(=O)-GGFG (SEQ ID NO: 3)-NH—CH$_2$CH$_2$CH$_2$—C(=O)—NH—CH(—CH$_2$CH$_2$—COOH)—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—C(=O)—NH—CH(—CH$_2$—OH)—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—C(=O)—NH—CH(—CH$_2$CH$_2$—OH)—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—C(=O)—NH—CH(—CH$_2$—COOH)—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—C(=O)—NH—CH(—CH$_2$CH$_2$—COOH)—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$—C(=O)—NH—CH(—CH$_2$—OH)—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$—C(=O)—NH—CH(—CH$_2$CH$_2$—OH)—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$—C(=O)—NH—CH(—CH$_2$—COOH)—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$—C(=O)—NH—CH(—CH$_2$CH$_2$—COOH)—C(=O)—(NH-DX).

Among these, more preferred are the following:
-(Succinimid-3-yl-N)—CH$_2$CH$_2$CH$_2$CH$_2$CH$_2$—C(=O)-GGFG (SEQ ID NO: 3)-NH—CH$_2$CH$_2$—C(=O)—NH—CH(—CH$_2$—OH)—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—C(=O)—NH—

CH(—CH₂CH₂—OH)—C(=O)—(NH-DX), -(Succinimid-3-yl-N)—CH₂CH₂CH₂CH₂CH₂—C(=O)-GGFG (SEQ ID NO: 3)-NH—CH₂CH₂—C(=O)—NH—CH(—CH₂—COOH)—C(=O)—(NH-DX),
-(Succinimid-3-yl-N)—CH₂CH₂CH₂CH₂CH₂—C(=O)-GGFG (SEQ ID NO: 3)-NH—CH₂CH₂—C(=O)—NH—CH(—CH₂CH₂—COOH)—C(=O)—(NH-DX),
-(Succinimid-3-yl-N)—CH₂CH₂CH₂CH₂CH₂—C(=O)-GGFG (SEQ ID NO: 3)-NH—CH₂CH₂CH₂—C(=O)—NH—CH(—CH₂—OH)—C(=O)—(NH-DX),
-(Succinimid-3-yl-N)—CH₂CH₂CH₂CH₂CH₂—C(=O)-GGFG (SEQ ID NO: 3)-NH—CH₂CH₂CH₂—C(=O)—NH—CH(—CH₂CH₂—OH)—C(=O)—(NH-DX),
-(Succinimid-3-yl-N)—CH₂CH₂CH₂CH₂CH₂—C(=O)-GGFG (SEQ ID NO: 3)-NH—CH₂CH₂CH₂—C(=O)—NH—CH(—CH₂—COOH)—C(=O)—(NH-DX),
-(Succinimid-3-yl-N)—CH₂CH₂CH₂CH₂CH₂—C(=O)-GGFG (SEQ ID NO: 3)-NH—CH₂CH₂CH₂—C(=O)—NH—CH(—CH₂CH₂—COOH)—C(=O)—(NH-DX).

Further preferred are the following:
-(Succinimid-3-yl-N)—CH₂CH₂CH₂CH₂CH₂—C(=O)-GGFG (SEQ ID NO: 3)-NH—CH₂CH₂CH₂—C(=O)—NH—CH(—CH₂—OH)—C(=O)—(NH-DX),
-(Succinimid-3-yl-N)—CH₂CH₂CH₂CH₂CH₂—C(=O)-GGFG (SEQ ID NO: 3)-NH—CH₂CH₂CH₂—C(=O)—NH—CH(—CH₂CH₂—OH)—C(=O)—(NH-DX),
-(Succinimid-3-yl-N)—CH₂CH₂CH₂CH₂CH₂—C(=O)-GGFG (SEQ ID NO: 3)-NH—CH₂CH₂CH₂—C(=O)—NH—CH(—CH₂—COOH)—C(=O)—(NH-DX),
-(Succinimid-3-yl-N)—CH₂CH₂CH₂CH₂CH₂—C(=O)-GGFG (SEQ ID NO: 3)-NH—CH₂CH₂CH₂—C(=O)—NH—CH(—CH₂CH₂—COOH)—C(=O)—(NH-DX).

Among these, preferred are the following:
-(Succinimid-3-yl-N)—CH₂CH₂CH₂CH₂CH₂—C(=O)-GGFG (SEQ ID NO: 3)-NH—CH₂CH₂CH₂—C(=O)—NH—CH(—CH₂—OH)—C(=O)—(NH-DX),
-(Succinimid-3-yl-N)—CH₂CH₂CH₂CH₂CH₂—C(=O)-GGFG (SEQ ID NO: 3)-NH—CH₂CH₂CH₂—C(=O)—NH—CH(—CH₂—COOH)—C(=O)—(NH-DX).

A-12. When $L^1$ is -(Succinimid-3-yl-N)—CH₂CH₂—[N(—CH₂—COOH)]—CH₂—C(=O)—, $L^2$ is a single bond, and -$L^a$-$L^b$-$L^c$-has an alkyl branched chain;
-(Succinimid-3-yl-N)—CH₂CH₂—[N(—CH₂—COOH)]—CH₂—C(=O)-GGFG (SEQ ID NO: 3)-NH—CH₂CMe(-H)—C(=O)—(NH-DX),
-(Succinimid-3-yl-N)—CH₂CH₂—[N(—CH₂—COOH)]—CH₂—C(=O)-GGFG (SEQ ID NO: 3)-NH—CH₂CH(-Me)-C(=O)—(NH-DX),
-(Succinimid-3-yl-N)—CH₂CH₂—[N(—CH₂—COOH)]—CH₂—C(=O)-GGFG (SEQ ID NO: 3)-NH—CH₂C(-Me)₂-C(=O)—(NH-DX), -(Succinimid-3-yl-N)—CH₂CH₂—[N(—CH₂—COOH)]—CH₂—C(=O)-GGFG (SEQ ID NO: 3)-NH—CH₂CH₂CMe(-H)—C(=O)—(NH-DX),
-(Succinimid-3-yl-N)—CH₂CH₂—[N(—CH₂—COOH)]—CH₂—C(=O)-GGFG (SEQ ID NO: 3)-NH—CH₂CH₂CH(-Me)-C(=O)—(NH-DX),
-(Succinimid-3-yl-N)—CH₂CH₂—[N(—CH₂—COOH)]—CH₂—C(=O)-GGFG (SEQ ID NO: 3)-NH—CH₂CH₂C(-Me)₂-C(=O)—(NH-DX).

A-13. In -$L^1$-$L^2$-$L^P$-NH—(CH₂)n¹-$L^a$-$L^b$-$L^c$-, when $L^1$ is —CH₂—C(=O)—NH—(CH₂)n⁴-C(=O)— and $L^2$ is a single bond;
—CH₂—C(=O)—NH—CH₂CH₂—C(=O)-GGFG (SEQ ID NO: 3)-NH—CH₂CH₂—C(=O)—(NH-DX),
—CH₂—C(=O)—NH—CH₂CH₂CH₂—C(=O)-GGFG (SEQ ID NO: 3)-NH—CH₂CH₂—C(=O)—(NH-DX),
—CH₂—C(=O)—NH—CH₂CH₂CH₂CH₂—C(=O)-GGFG (SEQ ID NO: 3)-NH—CH₂CH₂—C(=O)—(NH-DX),
—CH₂—C(=O)—NH—CH₂CH₂CH₂CH₂CH₂—C(=O)-GGFG (SEQ ID NO: 3)-NH—CH₂CH₂—C(=O)—(NH-DX),
—CH₂—C(=O)—NH—CH₂CH₂CH₂CH₂CH₂CH₂—C(=O)-GGFG (SEQ ID NO: 3)-NH—CH₂CH₂—C(=O)—(NH-DX),
—CH₂—C(=O)—NH—CH₂CH₂—C(=O)-GGFG (SEQ ID NO: 3)-NH—CH₂CH₂CH₂—C(=O)—(NH-DX),
—CH₂—C(=O)—NH—CH₂CH₂CH₂—C(=O)-GGFG (SEQ ID NO: 3)-NH—CH₂CH₂CH₂—C(=O)—(NH-DX),
—CH₂—C(=O)—NH—CH₂CH₂CH₂CH₂—C(=O)-GGFG (SEQ ID NO: 3)-NH—CH₂CH₂CH₂—C(=O)—(NH-DX),
—CH₂—C(=O)—NH—CH₂CH₂CH₂CH₂CH₂—C(=O)-GGFG (SEQ ID NO: 3)-NH—CH₂CH₂CH₂—C(=O)—(NH-DX),
—CH₂—C(=O)—NH—CH₂CH₂CH₂CH₂CH₂CH₂—C(=O)-GGFG (SEQ ID NO: 3)-NH—CH₂CH₂CH₂—C(=O)—(NH-DX),
—CH₂—C(=O)—NH—CH₂CH₂—C(=O)-GGFG (SEQ ID NO: 3)-NH—CH₂CH₂CH₂CH₂—C(=O)—(NH-DX),
—CH₂—C(=O)—NH—CH₂CH₂CH₂—C(=O)-GGFG (SEQ ID NO: 3)-NH—CH₂CH₂CH₂CH₂—C(=O)—(NH-DX),
—CH₂—C(=O)—NH—CH₂CH₂CH₂CH₂—C(=O)-GGFG (SEQ ID NO: 3)-NH—CH₂CH₂CH₂CH₂—C(=O)—(NH-DX),
—CH₂—C(=O)—NH—CH₂CH₂CH₂CH₂CH₂—C(=O)-GGFG (SEQ ID NO: 3)-NH—CH₂CH₂CH₂CH₂—C(=O)—(NH-DX),
—CH₂—C(=O)—NH—CH₂CH₂CH₂CH₂CH₂CH₂—C(=O)-GGFG (SEQ ID NO: 3)-NH—CH₂CH₂CH₂CH₂—C(=O)—(NH-DX).

Among these, more preferred are the following:
—CH₂—C(=O)—NH—CH₂CH₂—C(=O)-GGFG (SEQ ID NO: 3)-NH—CH₂CH₂—C(=O)—(NH-DX),
—CH₂—C(=O)—NH—CH₂CH₂—C(=O)-GGFG (SEQ ID NO: 3)-NH—CH₂CH₂CH₂—C(=O)—(NH-DX),
—CH₂—C(=O)—NH—CH₂CH₂—C(=O)-GGFG (SEQ ID NO: 3)-NH—CH₂CH₂CH₂CH₂—C(=O)—(NH-DX).

A-14. When $L^1$ is —CH₂—C(=O)—NH—(CH₂)n⁴-C(=O)— and $L^2$ is —NH—(CH₂CH₂—O)n⁶-CH₂CH₂—C(=O)—;
—CH₂—C(=O)—NH—CH₂CH₂—C(=O)—CH₂CH₂—O—CH₂CH₂—O—CH₂CH₂—C(=O)-GGFG (SEQ ID NO: 3)-NH—CH₂CH₂—C(=O)—(NH-DX),
—CH₂—C(=O)—NH—CH₂CH₂CH₂—C(=O)—CH₂CH₂—O—CH₂CH₂—O—CH₂CH₂—C(=O)-GGFG (SEQ ID NO: 3)-NH—CH₂CH₂—C(=O)—(NH-DX),
—CH₂—C(=O)—NH—CH₂CH₂CH₂CH₂—C(=O)—CH₂CH₂—O—CH₂CH₂—O—CH₂CH₂—C(=O)-GGFG (SEQ ID NO: 3)-NH—CH₂CH₂—C(=O)—(NH-DX),
—CH₂—C(=O)—NH—CH₂CH₂CH₂CH₂CH₂—C(=O)—CH₂CH₂—O—CH₂CH₂—O—CH₂CH₂—C(=O)-GGFG (SEQ ID NO: 3)-NH—CH₂CH₂—C(=O)—(NH-DX),
—CH₂—C(=O)—NH—CH₂CH₂CH₂CH₂CH₂CH₂—C(=O)—CH₂CH₂—O—CH₂CH₂—O—CH₂CH₂—C(=O)-GGFG (SEQ ID NO: 3)-NH—CH₂CH₂—C(=O)—(NH-DX),
—CH₂—C(=O)—NH—CH₂CH₂—C(=O)—CH₂CH₂—O—CH₂CH₂—O—CH₂CH₂—C(=O)-GGFG (SEQ ID NO: 3)-NH—CH₂CH₂CH₂—C(=O)—(NH-DX), —CH$_2$—C(=O)—NH—CH$_2$CH$_2$CH$_2$—C(=O)—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX),
—CH$_2$—C(=O)—NH—CH$_2$CH$_2$CH$_2$CH$_2$—C(=O)—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX),
—CH$_2$—C(=O)—NH—CH$_2$CH$_2$CH$_2$CH$_2$CH$_2$—C(=O)—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX),
—CH$_2$—C(=O)—NH—CH$_2$CH$_2$CH$_2$CH$_2$CH$_2$CH$_2$—C(=O)—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX),
—CH$_2$—C(=O)—NH—CH$_2$CH$_2$—C(=O)—CH$_2$CH$_2$—O—CH$_2$CH$_2$—O—CH$_2$CH$_2$—C(=O)-GGFG (SEQ ID NO: 3)-NH—CH$_2$CH$_2$CH$_2$CH$_2$—C(=O)—(NH-DX),
—CH$_2$—C(=O)—NH—CH$_2$CH$_2$CH$_2$—C(=O)—CH$_2$CH$_2$—O—CH$_2$CH$_2$—O—CH$_2$CH$_2$—C(=O)-GGFG (SEQ ID NO: 3)-NH—CH$_2$CH$_2$CH$_2$CH$_2$—C(=O)—(NH-DX),
—CH$_2$—C(=O)—NH—CH$_2$CH$_2$CH$_2$CH$_2$—C(=O)—CH$_2$CH$_2$—O—CH$_2$CH$_2$—O—CH$_2$CH$_2$—C(=O)-GGFG (SEQ ID NO: 3)-NH—CH$_2$CH$_2$CH$_2$CH$_2$—C(=O)—(NH-DX),
—CH$_2$—C(=O)—NH—CH$_2$CH$_2$CH$_2$CH$_2$CH$_2$—C(=O)—CH$_2$CH$_2$—O—CH$_2$CH$_2$—O—CH$_2$CH$_2$—C(=O)-GGFG (SEQ ID NO: 3)-NH—CH$_2$CH$_2$CH$_2$CH$_2$—C(=O)—(NH-DX),
—CH$_2$—C(=O)—NH—CH$_2$CH$_2$CH$_2$CH$_2$CH$_2$CH$_2$—C(=O)—CH$_2$CH$_2$—O—CH$_2$CH$_2$—O—CH$_2$CH$_2$—C(=O)-GGFG (SEQ ID NO: 3)-NH—CH$_2$CH$_2$CH$_2$CH$_2$—C(=O)—(NH-DX).

Among these, more preferred are the following:
—CH$_2$—C(=O)—NH—CH$_2$CH$_2$—C(=O)—CH$_2$CH$_2$—O—CH$_2$CH$_2$—O—CH$_2$CH$_2$—C(=O)-GGFG (SEQ ID NO: 3)-NH—CH$_2$CH$_2$—C(=O)—(NH-DX),
—CH$_2$—C(=O)—NH—CH$_2$CH$_2$—C(=O)—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX),
—CH$_2$—C(=O)—NH—CH$_2$CH$_2$—C(=O)—CH$_2$CH$_2$—O—CH$_2$CH$_2$—O—CH$_2$CH$_2$—C(=O)-GGFG (SEQ ID NO: 3)-NH—CH$_2$CH$_2$CH$_2$CH$_2$—C(=O)—(NH-DX).

A-15. When L$^1$ is —C(=O)—(CH$_2$)n$^5$-C(=O)— and L$^2$ is a single bond;
—C(=O)—CH$_2$CH$_2$—C(=O)-GGFG (SEQ ID NO: 3)-NH—CH$_2$CH$_2$—C(=O)—(NH-DX),
—C(=O)—CH$_2$CH$_2$CH$_2$—C(=O)-GGFG (SEQ ID NO: 3)-NH—CH$_2$CH$_2$—C(=O)—(NH-DX),
—C(=O)—CH$_2$CH$_2$CH$_2$CH$_2$—C(=O)-GGFG (SEQ ID NO: 3)-NH—CH$_2$CH$_2$—C(=O)—(NH-DX),
—C(=O)—CH$_2$CH$_2$CH$_2$CH$_2$CH$_2$—C(=O)-GGFG (SEQ ID NO: 3)-NH—CH$_2$CH$_2$—C(=O)—(NH-DX),
—C(=O)—CH$_2$CH$_2$CH$_2$CH$_2$CH$_2$CH$_2$—C(=O)-GGFG (SEQ ID NO: 3)-NH—CH$_2$CH$_2$—C(=O)—(NH-DX),
—C(=O)—CH$_2$CH$_2$—C(=O)-GGFG (SEQ ID NO: 3)-NH—CH$_2$CH$_2$CH$_2$—C(=O)—(NH-DX),
—C(=O)—CH$_2$CH$_2$CH$_2$—C(=O)-GGFG (SEQ ID NO: 3)-NH—CH$_2$CH$_2$CH$_2$—C(=O)—(NH-DX),
—C(=O)—CH$_2$CH$_2$CH$_2$CH$_2$—C(=O)-GGFG (SEQ ID NO: 3)-NH—CH$_2$CH$_2$CH$_2$—C(=O)—(NH-DX),
—C(=O)—CH$_2$CH$_2$CH$_2$CH$_2$CH$_2$—C(=O)-GGFG (SEQ ID NO: 3)-NH—CH$_2$CH$_2$CH$_2$—C(=O)—(NH-DX),
—C(=O)—CH$_2$CH$_2$CH$_2$CH$_2$CH$_2$CH$_2$—C(=O)-GGFG (SEQ ID NO: 3)-NH—CH$_2$CH$_2$CH$_2$—C(=O)—(NH-DX),
—C(=O)—CH$_2$CH$_2$—C(=O)-GGFG (SEQ ID NO: 3)-NH—CH$_2$CH$_2$CH$_2$CH$_2$—C(=O)—(NH-DX),
—C(=O)—CH$_2$CH$_2$CH$_2$—C(=O)-GGFG (SEQ ID NO: 3)-NH—CH$_2$CH$_2$CH$_2$CH$_2$—C(=O)—(NH-DX),
—C(=O)—CH$_2$CH$_2$CH$_2$CH$_2$—C(=O)-GGFG (SEQ ID NO: 3)-NH—CH$_2$CH$_2$CH$_2$CH$_2$—C(=O)—(NH-DX),
—C(=O)—CH$_2$CH$_2$CH$_2$CH$_2$CH$_2$—C(=O)-GGFG (SEQ ID NO: 3)-NH—CH$_2$CH$_2$CH$_2$CH$_2$—C(=O)—(NH-DX),
—C(=O)—CH$_2$CH$_2$CH$_2$CH$_2$CH$_2$CH$_2$—C(=O)-GGFG (SEQ ID NO: 3)-NH—CH$_2$CH$_2$CH$_2$CH$_2$—C(=O)—(NH-DX).

Among these, more preferred are the following:
—C(=O)—CH$_2$CH$_2$CH$_2$CH$_2$CH$_2$CH$_2$—C(=O)-GGFG (SEQ ID NO: 3)-NH—CH$_2$CH$_2$—C(=O)—(NH-DX),
—C(=O)—CH$_2$CH$_2$CH$_2$CH$_2$CH$_2$CH$_2$—C(=O)-GGFG (SEQ ID NO: 3)-NH—CH$_2$CH$_2$CH$_2$—C(=O)—(NH-DX),
—C(=O)—CH$_2$CH$_2$CH$_2$CH$_2$CH$_2$CH$_2$—C(=O)-GGFG (SEQ ID NO: 3)-NH—CH$_2$CH$_2$CH$_2$CH$_2$—C(=O)—(NH-DX).

A-16. When L$^1$ is —C(=O)-cyc.Hex(1,4)-CH$_2$—(N-ly-3-diminiccuS)- and L$^2$ is —S—(CH$_2$)n$^8$-C(=O)—;
—C(=O)-cyc.Hex(1,4)-CH$_2$—(N-ly-3-diminiccuS)—S—CH$_2$CH$_2$—C(=O)-GGFG (SEQ ID NO: 3)-NH—CH$_2$CH$_2$—C(=O)—(NH-DX),
—C(=O)-cyc.Hex(1,4)-CH$_2$—(N-ly-3-diminiccuS)—S—CH$_2$CH$_2$—C(=O)-GGFG (SEQ ID NO: 3)-NH—CH$_2$CH$_2$CH$_2$—C(=O)—(NH-DX),
—C(=O)-cyc.Hex(1,4)-CH$_2$—(N-ly-3-diminiccuS)—S—CH$_2$CH$_2$—C(=O)-GGFG (SEQ ID NO: 3)-NH—CH$_2$CH$_2$CH$_2$CH$_2$—C(=O)—(NH-DX),
—C(=O)-cyc.Hex(1,4)-CH$_2$—(N-ly-3-diminiccuS)-S—CH$_2$CH$_2$CH$_2$—C(=O)-GGFG (SEQ ID NO: 3)-NH—CH$_2$CH$_2$—C(=O)—(NH-DX),
—C(=O)-cyc.Hex(1,4)-CH$_2$—(N-ly-3-diminiccuS)-S—CH$_2$CH$_2$CH$_2$—C(=O)-GGFG (SEQ ID NO: 3)-NH—CH$_2$CH$_2$CH$_2$—C(=O)—(NH-DX),
—C(=O)-cyc.Hex(1,4)-CH$_2$—(N-ly-3-diminiccuS)-S—CH$_2$CH$_2$CH$_2$—C(=O)-GGFG (SEQ ID NO: 3)-NH—CH$_2$CH$_2$CH$_2$CH$_2$—C(=O)—(NH-DX),
—C(=O)-cyc.Hex(1,4)-CH$_2$—(N-ly-3-diminiccuS)—S—CH$_2$CH$_2$CH$_2$CH$_2$—C(=O)-GGFG (SEQ ID NO: 3)-NH—CH$_2$CH$_2$—C(=O)—(NH-DX),
—C(=O)-cyc.Hex(1,4)-CH$_2$—(N-ly-3-diminiccuS)—S—CH$_2$CH$_2$CH$_2$CH$_2$—C(=O)-GGFG (SEQ ID NO: 3)-NH—CH$_2$CH$_2$CH$_2$—C(=O)—(NH-DX),
—C(=O)-cyc.Hex(1,4)-CH$_2$—(N-ly-3-diminiccuS)—S—CH$_2$CH$_2$CH$_2$CH$_2$—C(=O)-GGFG (SEQ ID NO: 3)-NH—CH$_2$CH$_2$CH$_2$CH$_2$—C(=O)—(NH-DX).

Among these, more preferred are the following:
—C(=O)-cyc.Hex(1,4)-CH$_2$—(N-ly-3-diminiccuS)—S—CH$_2$CH$_2$—C(=O)-GGFG (SEQ ID NO: 3)-NH—CH$_2$CH$_2$—C(=O)—(NH-DX),
—C(=O)-cyc.Hex(1,4)-CH$_2$—(N-ly-3-diminiccuS)—S—CH$_2$CH$_2$—C(=O)-GGFG (SEQ ID NO: 3)-NH—CH$_2$CH$_2$CH$_2$—C(=O)—(NH-DX),
—C(=O)-cyc.Hex(1,4)-CH$_2$—(N-ly-3-diminiccuS)—S—CH$_2$CH$_2$—C(=O)-GGFG (SEQ ID NO: 3)-NH—CH$_2$CH$_2$CH$_2$CH$_2$—C(=O)—(NH-DX).

A-17. When L$^1$ is -(Succinimid-3-yl-N)—CH$_2$CH$_2$—[N(—CH$_2$—COOH)]—CH$_2$—(C=O)— and L$^2$ is —NH—CH$_2$CH$_2$—[N(—CH$_2$—COOH)]—CH$_2$—(C=O)—;
-(Succinimid-3-yl-N)—CH$_2$CH$_2$—C(=O)—NH—CH$_2$CH$_2$—N(—CH$_2$—COOH)—CH$_2$—C(=O)-GGFG (SEQ ID NO: 3)-NH—CH$_2$CH$_2$—C(=O)—(NH-DX),
-(Succinimid-3-yl-N)—CH$_2$CH$_2$—C(=O)—NH—CH$_2$CH$_2$—N(—CH$_2$—COOH)—CH$_2$—C(=O)-GGFG (SEQ ID NO: 3)-NH—CH$_2$CH$_2$CH$_2$—C(=O)—(NH-DX), -(Succinimid-3-yl-N)—CH$_2$CH$_2$—C(=O)—NH—CH$_2$CH$_2$—N(—CH$_2$—COOH)—CH$_2$—C(=O)-GGFG (SEQ ID NO: 3)-NH—CH$_2$CH$_2$CH$_2$CH$_2$—C(=O)—(NH-DX),
-(Succinimid-3-yl-N)—CH$_2$CH$_2$CH$_2$CH$_2$CH$_2$—C(=O)—NH—CH$_2$CH$_2$—N(—CH$_2$—COOH)—CH$_2$—C(=O)-GGFG (SEQ ID NO: 3)-NH—CH$_2$CH$_2$—C(=O)—(NH-DX),
-(Succinimid-3-yl-N)—CH$_2$CH$_2$CH$_2$CH$_2$CH$_2$—C(=O)—NH—CH$_2$CH$_2$—N(—CH$_2$—COOH)—CH$_2$—C(=O)-GGFG (SEQ ID NO: 3)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)—NH—CH$_2$CH$_2$—N(—CH$_2$—COOH)—CH$_2$—C(=O)-GGFG (SEQ ID NO: 3)-NH—CH$_2$CH$_2$CH$_2$CH$_2$—C(=O)—(NH-DX).

Among these, more preferred are the following:
-(Succinimid-3-yl-N)—CH$_2$CH$_2$CH$_2$CH$_2$CH$_2$—C(=O)—NH—CH$_2$CH$_2$—N(—CH$_2$—COOH)—CH$_2$—C(=O)-GGFG (SEQ ID NO: 3)-NH—CH$_2$CH$_2$—C(=O)—(NH-DX),
-(Succinimid-3-yl-N)—CH$_2$CH$_2$CH$_2$CH$_2$CH$_2$—C(=O)—NH—CH$_2$CH$_2$—N(—CH$_2$—COOH)—CH$_2$—C(=O)-GGFG (SEQ ID NO: 3)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)—NH—CH$_2$CH$_2$—N(—CH$_2$—COOH)—CH$_2$—C(=O)-GGFG (SEQ ID NO: 3)-NH—CH$_2$CH$_2$CH$_2$CH$_2$—C(=O)—(NH-DX).

A-18. When L$^1$ is -(Succinimid-3-yl-N)—CH$_2$CH$_2$—[N(—CH$_2$—COOH)]—CH$_2$—(C=O)— and L$^2$ is —NH—[CH(—CH$_2$—COOH)]—CH$_2$—O—CH$_2$—(C=O)—;
-(Succinimid-3-yl-N)—CH$_2$CH$_2$—C(=O)—NH—[CH(—CH$_2$—COOH)]—CH$_2$—O—CH$_2$—(C=O)-GFG-NH—CH$_2$CH$_2$—C(=O)—(NH-DX),
-(Succinimid-3-yl-N)—CH$_2$CH$_2$—C(=O)—NH—[CH(—CH$_2$—COOH)]—CH$_2$—O—CH$_2$—(C=O)-GFG-NH—CH$_2$CH$_2$CH$_2$—C(=O)—(NH-DX),
-(Succinimid-3-yl-N)—CH$_2$CH$_2$—C(=O)—NH—[CH(—CH$_2$—COOH)]—CH$_2$—O—CH$_2$—(C=O)-GFG-NH—CH$_2$CH$_2$CH$_2$CH$_2$—C(=O)—(NH-DX),
-(Succinimid-3-yl-N)—CH$_2$CH$_2$CH$_2$CH$_2$CH$_2$—C(=O)—NH—[CH(—CH$_2$—COOH)]—CH$_2$—O—CH$_2$—(C=O)-GFG-NH—CH$_2$CH$_2$—C(=O)—(NH-DX),
-(Succinimid-3-yl-N)—CH$_2$CH$_2$CH$_2$CH$_2$CH$_2$—C(=O)—NH—[CH(—CH$_2$—COOH)]—CH$_2$—O—CH$_2$—(C=O)-GFG-NH—CH$_2$CH$_2$CH$_2$—C(=O)—(NH-DX),
-(Succinimid-3-yl-N)—CH$_2$CH$_2$CH$_2$CH$_2$CH$_2$—C(=O)—NH—[CH(—CH$_2$—COOH)]—CH$_2$—O—CH$_2$—(C=O)-GFG-NH—CH$_2$CH$_2$CH$_2$CH$_2$—C(=O)—(NH-DX).

Among these, more preferred are the following:
-(Succinimid-3-yl-N)—CH$_2$CH$_2$CH$_2$CH$_2$CH$_2$—C(=O)—NH—[CH(—CH$_2$—COOH)]—CH$_2$—O—CH$_2$—(C=O)-GFG-NH—CH$_2$CH$_2$—C(=O)—(NH-DX),
-(Succinimid-3-yl-N)—CH$_2$CH$_2$CH$_2$CH$_2$CH$_2$—C(=O)—NH—[CH(—CH$_2$—COOH)]—CH$_2$—O—CH$_2$—(C=O)-GFG-NH—CH$_2$CH$_2$CH$_2$—C(=O)—(NH-DX), -(Succinimid-3-yl-N)—CH$_2$CH$_2$CH$_2$CH$_2$CH$_2$—C(=O)—NH—[CH(—CH$_2$—COOH)]—CH$_2$—O—CH$_2$—(C=O)-GFG-NH—CH$_2$CH$_2$CH$_2$CH$_2$—C(=O)—(NH-DX).

A-19. Other preferred linkers analogous to linkers having the GGFG (SEQ ID NO: 3) peptide are as shown below.
When L$^1$ is -(Succinimid-3-yl-N)—(CH$_2$)n$^2$-C(=O)—, L$^2$ is a single bond, and the peptide residue is GFG;
-(Succinimid-3-yl-N)—CH$_2$CH$_2$—C(=O)—NH—[CH(—CH$_2$—COOH)]—CH$_2$—O—CH$_2$—(C=O)-GFG-(NH-DX),
-(Succinimid-3-yl-N)—CH$_2$CH$_2$CH$_2$CH$_2$CH$_2$—C(=O)—NH—[CH(—CH$_2$—COOH)]—CH$_2$—O—CH$_2$—(C=O)-GFG-(NH-DX).

A-20. When L$^1$ is -(Succinimid-3-yl-N)—(CH$_2$)n$^2$-C(=O)—, L$^2$ is a single bond, and the peptide residue contains 4 or more glycine residues;
-(Succinimid-3-yl-N)—CH$_2$CH$_2$—C(=O)—NH-GGFGG (SEQ ID NO: 4)-(NH-DX),
-(Succinimid-3-yl-N)—CH$_2$CH$_2$—C(=O)—NH-GGFGGG (SEQ ID NO: 6)-(NH-DX),
-(Succinimid-3-yl-N)—CH$_2$CH$_2$—C(=O)—NH-GGFGGGFG (SEQ ID NO: 8)-(NH-DX),
-(Succinimid-3-yl-N)—CH$_2$CH$_2$CH$_2$CH$_2$CH$_2$—C(=O)—NH-GGFGG (SEQ ID NO: 4)-(NH-DX),
-(Succinimid-3-yl-N)—CH$_2$CH$_2$CH$_2$CH$_2$CH$_2$—C(=O)—NH-GGFGGG (SEQ ID NO: 6)-(NH-DX),
-(Succinimid-3-yl-N)—CH$_2$CH$_2$CH$_2$CH$_2$CH$_2$—C(=O)—NH-GGFGGGFG (SEQ ID NO: 8)-(NH-DX).

Among these, more preferred are the following:
-(Succinimid-3-yl-N)—CH$_2$CH$_2$CH$_2$CH$_2$CH$_2$—C(=O)—NH-GGFGG (SEQ ID NO: 4)-(NH-DX),
-(Succinimid-3-yl-N)—CH$_2$CH$_2$CH$_2$CH$_2$CH$_2$—C(=O)—NH-GGFGGG (SEQ ID NO: 6)-(NH-DX),
-(Succinimid-3-yl-N)—CH$_2$CH$_2$CH$_2$CH$_2$CH$_2$—C(=O)—NH-GGFGGGFG (SEQ ID NO: 8)-(NH-DX).

A-21. When L$^1$ is -(Succinimid-3-yl-N)—(CH$_2$)n$^2$-C(=O)—, L$^2$ is a single bond, and the C terminal includes a hydrophilic amino acid;
-(Succinimid-3-yl-N)—CH$_2$CH$_2$—C(=O)—NH-GGFGS (SEQ ID NO: 5)-(NH-DX),
-(Succinimid-3-yl-N)—CH$_2$CH$_2$—C(=O)—NH-GGFGE (SEQ ID NO: 7)-(NH-DX),
-(Succinimid-3-yl-N)—CH$_2$CH$_2$CH$_2$CH$_2$CH$_2$—C(=O)—NH-GGFGS (SEQ ID NO: 5)-(NH-DX),
-(Succinimid-3-yl-N)—CH$_2$CH$_2$CH$_2$CH$_2$CH$_2$—C(=O)—NH-GGFGE (SEQ ID NO: 7)-(NH-DX).

Among these, more preferred are the following:
-(Succinimid-3-yl-N)—CH$_2$CH$_2$CH$_2$CH$_2$CH$_2$—C(=O)—NH-GGFGS (SEQ ID NO: 5)-(NH-DX), and
-(Succinimid-3-yl-N)—CH$_2$CH$_2$CH$_2$CH$_2$CH$_2$—C(=O)—NH-GGFGE (SEQ ID NO: 7)-(NH-DX).

B. A preferred linker-drug moiety having a structure of -L$^1$-L$^2$-L$^P$-(NH-DX) wherein L$^P$ is GGGF (SEQ ID NO: 21) is as shown below.
B-0. When L$^1$ is -(Succinimid-3-yl-N)—(CH$_2$)n$^2$-C(=O)— and L$^2$ is a single bond;
-(Succinimid-3-yl-N)—CH$_2$CH$_2$—C(=O)-GGFG (SEQ ID NO: 3)-(NH-DX), and
-(Succinimid-3-yl-N)—CH$_2$CH$_2$CH$_2$CH$_2$CH$_2$—C(=O)-GGFG (SEQ ID NO: 3)-(NH-DX).

B-1. When L$^1$ is -(Succinimid-3-yl-N)—(CH$_2$)n$^2$-C(=O)— and L$^2$ is —NH—(CH$_2$—CH$_2$—O)n$^6$-CH$_2$—CH$_2$—C(=O)—;
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-GGFG (SEQ ID NO: 3)-(NH-DX),
-(Succinimid-3-yl-N)—CH$_2$CH$_2$CH$_2$CH$_2$CH$_2$—C(=O)—NH—CH$_2$CH$_2$—O—CH$_2$CH$_2$—O—CH$_2$CH$_2$—C(=O)-GGFG (SEQ ID NO: 3)-(NH-DX),
-(Succinimid-3-yl-N)—CH$_2$CH$_2$CH$_2$CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-GGFG (SEQ ID NO: 3)-(NH-DX).

Among these, more preferred are the following:
-(Succinimid-3-yl-N)—CH₂CH₂—C(=O)—NH—CH₂CH₂—O—CH₂CH₂—O—CH₂CH₂—C(=O)-GGFG (SEQ ID NO: 3)-(NH-DX),
-(Succinimid-3-yl-N)—CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-(NH-DX).

B-2. When L¹ is -(Succinimid-3-yl-N)—CH [—(CH₂)n³-COOH]—C(=O)— and L² is a single bond,
-(Succinimid-3-yl-N)—CH₂CH₂—[N(—CH₂—COOH)]—CH₂—(C=O)-GGFG (SEQ ID NO: 3)-(NH-DX)
is preferred.

B-3. When L¹ is —C(=O)-cyc.Hex(1,4)-CH₂—(N-ly-3-diminiccuS)- and L² is —S—(CH₂)n⁸-C(=O)—,
—C(=O)-cyc.Hex(1,4)-CH₂—(N-ly-3-diminiccuS)-S—CH₂CH₂—C(=O)-GGFG (SEQ ID NO: 3)-(NH-DX)
is preferred.

B-4. When L¹ is -(Succinimid-3-yl-N)—CH₂CH₂—[N(—CH₂—COOH)]—CH₂—(C=O)— and L² is —NH—[CH(—CH₂—COOH)]—CH₂—O—CH₂—(C=O)—;
-(Succinimid-3-yl-N)—CH₂CH₂—C(=O)—NH—[CH(—CH₂—COOH)]—CH₂—(C=O)-GGFG (SEQ ID NO: 3)-(NH-DX),
-(Succinimid-3-yl-N)—CH₂CH₂CH₂CH₂CH₂—C(=O)—NH—[CH(—CH₂—COOH)]—CH₂—(C=O)-GGFG (SEQ ID NO: 3)-(NH-DX).

More preferred is
-(Succinimid-3-yl-N)—CH₂CH₂CH₂CH₂CH₂—C(=O)—NH—[CH(—CH₂—COOH)]—CH₂—(C=O)-GGFG (SEQ ID NO: 3)-(NH-DX).

B-5. When L¹ is -(Succinimid-3-yl-N)—CH₂CH₂—[N(—CH₂—COOH)]—CH₂—(C=O)— and L² is —NH—CH₂CH₂—[N(—CH₂—COOH)]—CH₂—(C=O)—;
-(Succinimid-3-yl-N)—CH₂CH₂—C(=O)—NH—CH₂CH₂—[N(—CH₂—COOH)]—CH₂—(C=O)-GGFG (SEQ ID NO: 3)-(NH-DX),
-(Succinimid-3-yl-N)—CH₂CH₂CH₂CH₂CH₂—C(=O)—NH—CH₂CH₂—[N(—CH₂—COOH)]—CH₂—(C=O)-GGFG (SEQ ID NO: 3)-(NH-DX).

More preferred is
-(Succinimid-3-yl-N)—CH₂CH₂CH₂CH₂CH₂—C(=O)—NH—CH₂CH₂—[N(—CH₂—COOH)]—CH₂—(C=O)-GGFG (SEQ ID NO: 3)-(NH-DX).

C. A preferred linker-drug moiety having a structure of -L¹-L²-Lᴾ-NH—(CH₂)n¹-Lᵃ-Lᵇ-Lᶜ-(NH-DX) wherein Lᴾ contains aspartic acid, lysine, glutamic acid, and/or serine, which are hydrophilic amino acids, in particular, aspartic acid is shown below.

C-1. When L¹ is -(Succinimid-3-yl-N)—(CH₂)n²-C(=O)— and L² is a single bond;
-(Succinimid-3-yl-N)—CH₂CH₂—C(=O)-DGGF (SEQ ID NO: 9)-NH—CH₂CH₂—C(=O)—(NH-DX),
-(Succinimid-3-yl-N)—CH₂CH₂—C(=O)-DGGF (SEQ ID NO: 9)-NH—CH₂CH₂CH₂—C(=O)—(NH-DX),
-(Succinimid-3-yl-N)—CH₂CH₂—C(=O)-DGGF (SEQ ID NO: 9)-NH—CH₂CH₂CH₂CH₂—C(=O)—(NH-DX),
-(Succinimid-3-yl-N)—CH₂CH₂CH₂CH₂CH₂—C(=O)-DGGF (SEQ ID NO: 9)-NH—CH₂CH₂—C(=O)—(NH-DX),
-(Succinimid-3-yl-N)—CH₂CH₂CH₂CH₂CH₂—C(=O)-DGGF (SEQ ID NO: 9)-NH—CH₂CH₂CH₂—C(=O)—(NH-DX),
-(Succinimid-3-yl-N)—CH₂CH₂CH₂CH₂CH₂—C(=O)-DGGF (SEQ ID NO: 9)-NH—CH₂CH₂CH₂CH₂—C(=O)—(NH-DX).

Among these, more preferred are the following:
-(Succinimid-3-yl-N)—CH₂CH₂CH₂CH₂CH₂—C(=O)-DGGF (SEQ ID NO: 9)-NH—CH₂CH₂—C(=O)—(NH-DX),
-(Succinimid-3-yl-N)—CH₂CH₂CH₂CH₂CH₂—C(=O)-DGGF (SEQ ID NO: 9)-NH—CH₂CH₂CH₂—C(=O)—(NH-DX),
-(Succinimid-3-yl-N)—CH₂CH₂CH₂CH₂CH₂—C(=O)-DGGF (SEQ ID NO: 9)-NH—CH₂CH₂CH₂CH₂—C(=O)—(NH-DX).

C-2. When L¹ is -(Succinimid-3-yl-N)—(CH₂)n²-C(=O)— and L² is a single bond;
-(Succinimid-3-yl-N)—CH₂CH₂—C(=O)-DGGFG (SEQ ID NO: 10)-NH—CH₂CH₂—C(=O)—(NH-DX),
-(Succinimid-3-yl-N)—CH₂CH₂—C(=O)-DGGFG (SEQ ID NO: 10)-NH—CH₂CH₂CH₂—C(=O)—(NH-DX),
-(Succinimid-3-yl-N)—CH₂CH₂—C(=O)-DGGFG (SEQ ID NO: 10)-NH—CH₂CH₂CH₂CH₂—C(=O)—(NH-DX),
-(Succinimid-3-yl-N)—CH₂CH₂CH₂—C(=O)-DGGFG (SEQ ID NO: 10)-NH—CH₂CH₂—C(=O)—(NH-DX),
-(Succinimid-3-yl-N)—CH₂CH₂CH₂—C(=O)-DGGFG (SEQ ID NO: 10)-NH—CH₂CH₂CH₂—C(=O)—(NH-DX),
-(Succinimid-3-yl-N)—CH₂CH₂CH₂—C(=O)-DGGFG (SEQ ID NO: 10)-NH—CH₂CH₂CH₂CH₂—C(=O)—(NH-DX),
-(Succinimid-3-yl-N)—CH₂CH₂CH₂CH₂CH₂—C(=O)-DGGFG (SEQ ID NO: 10)-NH—CH₂CH₂—C(=O)—(NH-DX),
-(Succinimid-3-yl-N)—CH₂CH₂CH₂CH₂CH₂—C(=O)-DGGFG (SEQ ID NO: 10)-NH—CH₂CH₂CH₂—C(=O)—(NH-DX),
-(Succinimid-3-yl-N)—CH₂CH₂CH₂CH₂CH₂—C(=O)-DGGFG (SEQ ID NO: 10)-NH—CH₂CH₂CH₂CH₂—C(=O)—(NH-DX).

Among these, preferred are the following:
-(Succinimid-3-yl-N)—CH₂CH₂—C(=O)-DGGFG (SEQ ID NO: 10)-NH—CH₂CH₂—C(=O)—(NH-DX),
-(Succinimid-3-yl-N)—CH₂CH₂—C(=O)-DGGFG (SEQ ID NO: 10)-NH—CH₂CH₂CH₂—C(=O)—(NH-DX),
-(Succinimid-3-yl-N)—CH₂CH₂CH₂—C(=O)-DGGFG (SEQ ID NO: 10)-NH—CH₂CH₂—C(=O)—(NH-DX),
-(Succinimid-3-yl-N)—CH₂CH₂CH₂—C(=O)-DGGFG (SEQ ID NO: 10)-NH—CH₂CH₂CH₂—C(=O)—(NH-DX),
-(Succinimid-3-yl-N)—CH₂CH₂CH₂CH₂CH₂—C(=O)-DGGFG (SEQ ID NO: 10)-NH—CH₂CH₂—C(=O)—(NH-DX), -(Succinimid-3-yl-N)-CH₂CH₂CH₂CH₂CH₂—C(=O)-DGGFG (SEQ ID NO: 10)-NH—CH₂CH₂CH₂—C(=O)—(NH-DX),
-(Succinimid-3-yl-N)—CH₂CH₂CH₂CH₂CH₂—C(=O)-DGGFG (SEQ ID NO: 10)-NH—CH₂CH₂CH₂CH₂—C(=O)—(NH-DX).

C-3. When L¹ is -(Succinimid-3-yl-N)—(CH₂)n²-C(=O)— and L² is —NH—(CH₂CH₂—O)n⁶-CH₂CH₂—C(=O)—;
-(Succinimid-3-yl-N)—CH₂CH₂—C(=O)—NH—CH₂CH₂—O—CH₂CH₂—O—CH₂CH₂—C(=O)-DGGFG (SEQ ID NO: 10)-NH—CH₂CH₂—C(=O)—(NH-DX),
-(Succinimid-3-yl-N)—CH₂CH₂—C(=O)—NH—CH₂CH₂—O—CH₂CH₂—O—CH₂CH₂—C(=O)-DGGFG (SEQ ID NO: 10)-NH—CH₂CH₂CH₂—C(=O)—(NH-DX),
-(Succinimid-3-yl-N)—CH₂CH₂—C(=O)—NH—CH₂CH₂—O—CH₂CH₂—O—CH₂CH₂—C(=O)-DGGFG (SEQ ID NO: 10)-NH—CH₂CH₂CH₂CH₂—C(=O)—(NH-DX),
-(Succinimid-3-yl-N)—CH₂CH₂—C(=O)—NH—CH₂CH₂—O—CH₂CH₂—O—CH₂CH₂—O—CH₂CH₂—

O—CH₂CH₂—C(=O)-DGGFG (SEQ ID NO: 10)-NH—CH₂CH₂—C(=O)—(NH-DX),
-(Succinimid-3-yl-N)—CH₂CH₂—C(=O)—NH—CH₂CH₂—O—CH₂CH₂—O—CH₂CH₂—O—CH₂CH₂—O—CH₂CH₂—C(=O)-DGGFG (SEQ ID NO: 10)-NH—CH₂CH₂CH₂—C(=O)—(NH-DX),
-(Succinimid-3-yl-N)—CH₂CH₂—C(=O)—NH—CH₂CH₂—O—CH₂CH₂—O—CH₂CH₂—O—CH₂CH₂—O—CH₂CH₂—C(=O)-DGGFG (SEQ ID NO: 10)-NH—CH₂CH₂CH₂CH₂—C(=O)—(NH-DX),
-(Succinimid-3-yl-N)—CH₂CH₂CH₂CH₂CH₂—C(=O)—NH—CH₂CH₂—O—CH₂CH₂—O—CH₂CH₂—C(=O)-DGGFG (SEQ ID NO: 10)-NH—CH₂CH₂—C(=O)—(NH-DX),
-(Succinimid-3-yl-N)—CH₂CH₂CH₂CH₂CH₂—C(=O)—NH—CH₂CH₂—O—CH₂CH₂—O—CH₂CH₂—C(=O)-DGGFG (SEQ ID NO: 10)-NH—CH₂CH₂CH₂—C(=O)—(NH-DX),
-(Succinimid-3-yl-N)—CH₂CH₂CH₂CH₂CH₂—C(=O)—NH—CH₂CH₂—O—CH₂CH₂—O—CH₂CH₂—C(=O)-DGGFG (SEQ ID NO: 10)-NH—CH₂CH₂CH₂CH₂—C(=O)—(NH-DX),
-(Succinimid-3-yl-N)—CH₂CH₂CH₂CH₂CH₂—C(=O)—NH—CH₂CH₂—O—CH₂CH₂—O—CH₂CH₂—O—CH₂CH₂—O—CH₂CH₂—C(=O)-DGGFG (SEQ ID NO: 10)-NH—CH₂CH₂—C(=O)—(NH-DX),
-(Succinimid-3-yl-N)—CH₂CH₂CH₂CH₂CH₂—C(=O)—NH—CH₂CH₂—O—CH₂CH₂—O—CH₂CH₂—O—CH₂CH₂—C(=O)-DGGFG (SEQ ID NO: 10)-NH—CH₂CH₂CH₂—C(=O)—(NH-DX),
-(Succinimid-3-yl-N)—CH₂CH₂CH₂CH₂CH₂—C(=O)—NH—CH₂CH₂—O—CH₂CH₂—O—CH₂CH₂—O—CH₂CH₂—C(=O)-DGGFG (SEQ ID NO: 10)-NH—CH₂CH₂CH₂CH₂—C(=O)—(NH-DX).

Among these, preferred are the following:
-(Succinimid-3-yl-N)—CH₂CH₂—C(=O)—NH—CH₂CH₂—O—CH₂CH₂—O—CH₂CH₂—C(=O)-DGGFG (SEQ ID NO: 10)-NH—CH₂CH₂—C(=O)—(NH-DX),
-(Succinimid-3-yl-N)—CH₂CH₂—C(=O)—NH—CH₂CH₂—O—CH₂CH₂—O—CH₂CH₂—C(=O)-DGGFG (SEQ ID NO: 10)-NH—CH₂CH₂CH₂—C(=O)—(NH-DX),
-(Succinimid-3-yl-N)—CH₂CH₂—C(=O)—NH—CH₂CH₂—O—CH₂CH₂—O—CH₂CH₂—C(=O)-DGGFG (SEQ ID NO: 10)-NH—CH₂CH₂CH₂CH₂—C(=O)—(NH-DX),
-(Succinimid-3-yl-N)—CH₂CH₂—C(=O)—NH—CH₂CH₂—O—CH₂CH₂—O—CH₂CH₂—O—CH₂CH₂—O—CH₂CH₂—C(=O)-DGGFG (SEQ ID NO: 10)-NH—CH₂CH₂—C(=O)—(NH-DX),
-(Succinimid-3-yl-N)—CH₂CH₂—C(=O)—NH—CH₂CH₂—O—CH₂CH₂—O—CH₂CH₂—O—CH₂CH₂—O—CH₂CH₂—C(=O)-DGGFG (SEQ ID NO: 10)-NH—CH₂CH₂CH₂—C(=O)—(NH-DX),
-(Succinimid-3-yl-N)—CH₂CH₂—C(=O)—NH—CH₂CH₂—O—CH₂CH₂—O—CH₂CH₂—O—CH₂CH₂—O—CH₂CH₂—C(=O)-DGGFG (SEQ ID NO: 10)-NH—CH₂CH₂CH₂CH₂—C(=O)—(NH-DX).

C-4. When $L^1$ is -(Succinimid-3-yl-N)—(CH₂)n²-C(=O)—, $L^2$ is a single bond, and -$L^a$-$L^b$-$L^c$-contains an alkyl branched chain, preferred are the following:
-(Succinimid-3-yl-N)—CH₂CH₂—C(=O)-DGGFG (SEQ ID NO: 10)-NH—CH₂CH₂C(-Me)₂-C(=O)—(NH-DX), and
-(Succinimid-3-yl-N)—CH₂CH₂CH₂CH₂CH₂—C(=O)-DGGFG (SEQ ID NO: 10)-NH—CH₂CH₂C(-Me)₂-C(=O)—(NH-DX).

More preferred is
-(Succinimid-3-yl-N)—CH₂CH₂CH₂CH₂CH₂—C(=O)-DGGFG (SEQ ID NO: 10)-NH—CH₂CH₂C(-Me)₂-C(=O)—(NH-DX).

C-5. When $L^1$ is -(Succinimid-3-yl-N)—(CH₂)n²-C(=O)—, $L^2$ is a single bond, and the peptide residue contains sarcosine;
-(Succinimid-3-yl-N)—CH₂CH₂—C(=O)-DG$^{Me}$GFG (SEQ ID NO: 11)-NH—CH₂CH₂—C(=O)—(NH-DX),
-(Succinimid-3-yl-N)—CH₂CH₂—C(=O)-DG$^{Me}$GFG (SEQ ID NO: 11)-NH—CH₂CH₂CH₂—C(=O)—(NH-DX),
-(Succinimid-3-yl-N)—CH₂CH₂—C(=O)-DG$^{Me}$GFG (SEQ ID NO: 11)-NH—CH₂CH₂CH₂CH₂—C(=O)—(NH-DX),
-(Succinimid-3-yl-N)—CH₂CH₂CH₂CH₂CH₂—C(=O)-DG$^{Me}$GFG (SEQ ID NO: 11)-NH—CH₂CH₂—C(=O)—(NH-DX),
-(Succinimid-3-yl-N)—CH₂CH₂CH₂CH₂CH₂—C(=O)-DG$^{Me}$GFG (SEQ ID NO: 11)-NH—CH₂CH₂CH₂—C(=O)—(NH-DX),
-(Succinimid-3-yl-N)—CH₂CH₂CH₂CH₂CH₂—C(=O)-DG$^{Me}$GFG (SEQ ID NO: 11)-NH—CH₂CH₂CH₂CH₂—C(=O)—(NH-DX).

Among these, more preferred are the following:
-(Succinimid-3-yl-N)—CH₂CH₂CH₂CH₂CH₂—C(=O)-DG$^{Me}$GFG (SEQ ID NO: 11)-NH—CH₂CH₂—C(=O)—(NH-DX),
-(Succinimid-3-yl-N)—CH₂CH₂CH₂CH₂CH₂—C(=O)-DG$^{Me}$GFG (SEQ ID NO: 11)-NH—CH₂CH₂CH₂—C(=O)—(NH-DX),
-(Succinimid-3-yl-N)—CH₂CH₂CH₂CH₂CH₂—C(=O)-DG$^{Me}$GFG (SEQ ID NO: 11)-NH—CH₂CH₂CH₂CH₂—C(=O)—(NH-DX).

C-6. When $L^1$ is -(Succinimid-3-yl-N)—(CH₂)n²-C(=O)—, $L^2$ is a single bond, and the peptide residue contains lysine;
-(Succinimid-3-yl-N)—CH₂CH₂—C(=O)—KGGFG (SEQ ID NO: 15)-NH—CH₂CH₂—C(=O)—(NH-DX),
-(Succinimid-3-yl-N)—CH₂CH₂—C(=O)—KGGFG (SEQ ID NO: 15)-NH—CH₂CH₂CH₂—C(=O)—(NH-DX),
-(Succinimid-3-yl-N)—CH₂CH₂—C(=O)—KGGFG (SEQ ID NO: 15)-NH—CH₂CH₂CH₂CH₂—C(=O)—(NH-DX),
-(Succinimid-3-yl-N)—CH₂CH₂CH₂CH₂CH₂—C(=O)-KGGFG (SEQ ID NO: 15)-NH—CH₂CH₂—C(=O)—(NH-DX),
-(Succinimid-3-yl-N)—CH₂CH₂CH₂CH₂CH₂—C(=O)-KGGFG (SEQ ID NO: 15)-NH—CH₂CH₂CH₂—C(=O)—(NH-DX),
-(Succinimid-3-yl-N)—CH₂CH₂CH₂CH₂CH₂—C(=O)-KGGFG (SEQ ID NO: 15)-NH—CH₂CH₂CH₂CH₂—C(=O)—(NH-DX).

Among these, more preferred are the following:
-(Succinimid-3-yl-N)—CH₂CH₂CH₂CH₂CH₂—C(=O)-KGGFG (SEQ ID NO: 15)-NH—CH₂CH₂—C(=O)—(NH-DX),
-(Succinimid-3-yl-N)—CH₂CH₂CH₂CH₂CH₂—C(=O)-KGGFG (SEQ ID NO: 15)-NH—CH₂CH₂CH₂—C(=O)—(NH-DX),
-(Succinimid-3-yl-N)—CH₂CH₂CH₂CH₂CH₂—C(=O)-KGGFG (SEQ ID NO: 15)-NH—CH₂CH₂CH₂CH₂—C(=O)—(NH-DX).

C-7. When $L^1$ is -(Succinimid-3-yl-N)—(CH₂)n²-C(=O)—, $L^2$ is a single bond, and the peptide residue contains glutamic acid;

-(Succinimid-3-yl-N)—CH$_2$CH$_2$—C(=O)-EGGFG (SEQ ID NO: 16)-NH—CH$_2$CH$_2$—C(=O)—(NH-DX),
-(Succinimid-3-yl-N)—CH$_2$CH$_2$—C(=O)-EGGFG (SEQ ID NO: 16)-NH—CH$_2$CH$_2$CH$_2$—C(=O)—(NH-DX),
-(Succinimid-3-yl-N)—CH$_2$CH$_2$—C(=O)-EGGFG (SEQ ID NO: 16)-NH—CH$_2$CH$_2$CH$_2$CH$_2$—C(=O)—(NH-DX),
-(Succinimid-3-yl-N)—CH$_2$CH$_2$CH$_2$CH$_2$—C(=O)-EGGFG (SEQ ID NO: 16)-NH—CH$_2$CH$_2$—C(=O)—(NH-DX),
-(Succinimid-3-yl-N)—CH$_2$CH$_2$CH$_2$CH$_2$—C(=O)-EGGFG (SEQ ID NO: 16)-NH—CH$_2$CH$_2$CH$_2$—C(=O)—(NH-DX),
-(Succinimid-3-yl-N)—CH$_2$CH$_2$CH$_2$CH$_2$—C(=O)-EGGFG (SEQ ID NO: 16)-NH—CH$_2$CH$_2$CH$_2$CH$_2$—C(=O)—(NH-DX).

Among these, more preferred are the following:
-(Succinimid-3-yl-N)—CH$_2$CH$_2$CH$_2$CH$_2$—C(=O)-EGGFG (SEQ ID NO: 16)-NH—CH$_2$CH$_2$—C(=O)—(NH-DX),
-(Succinimid-3-yl-N)—CH$_2$CH$_2$CH$_2$CH$_2$—C(=O)-EGGFG (SEQ ID NO: 16)-NH—CH$_2$CH$_2$CH$_2$—C(=O)—(NH-DX),
-(Succinimid-3-yl-N)—CH$_2$CH$_2$CH$_2$CH$_2$—C(=O)-EGGFG (SEQ ID NO: 16)-NH—CH$_2$CH$_2$CH$_2$CH$_2$—C(=O)—(NH-DX).

C-8. When $L^1$ is -(Succinimid-3-yl-N)—(CH$_2$)n$^2$-C(=O)—, $L^2$ is —NH—(CH$_2$CH$_2$—O)n$^6$-CH$_2$CH$_2$—C(=O)—, and -L$^a$-L$^b$-L$^c$-contains an oxygen atom, preferred are the following:
-(Succinimid-3-yl-N)—CH$_2$CH$_2$—C(=O)-DGGFG (SEQ ID NO: 10)-NH—CH$_2$—O—CH$_2$—C(=O)—(NH-DX), and
-(Succinimid-3-yl-N)—CH$_2$CH$_2$CH$_2$CH$_2$—C(=O)-DGGFG (SEQ ID NO: 10)-NH—CH$_2$—O—CH$_2$—C(=O)—(NH-DX).

More preferred is
-(Succinimid-3-yl-N)—CH$_2$CH$_2$CH$_2$CH$_2$—C(=O)-DGGFG (SEQ ID NO: 10)-NH—CH$_2$—O—CH$_2$—C(=O)—(NH-DX).

C-9. When $L^1$ is -(Succinimid-3-yl-N)—(CH$_2$)n$^2$-C(=O)—, $L^2$ is a single bond, and the peptide residue contains a plurality of hydrophilic amino acids, preferred are the followings:
-(Succinimid-3-yl-N)—CH$_2$CH$_2$—C(=O)-DDGGFG (SEQ ID NO: 13)-NH—CH$_2$CH$_2$—C(=O)—(NH-DX),
-(Succinimid-3-yl-N)—CH$_2$CH$_2$—C(=O)-DDGGFG (SEQ ID NO: 13)-NH—CH$_2$CH$_2$CH$_2$—C(=O)—(NH-DX),
-(Succinimid-3-yl-N)—CH$_2$CH$_2$—C(=O)-DDGGFG (SEQ ID NO: 13)-NH—CH$_2$CH$_2$CH$_2$CH$_2$—C(=O)—(NH-DX),
-(Succinimid-3-yl-N)—CH$_2$CH$_2$CH$_2$CH$_2$—C(=O)-DDGGFG (SEQ ID NO: 13)-NH—CH$_2$CH$_2$—C(=O)—(NH-DX),
-(Succinimid-3-yl-N)—CH$_2$CH$_2$CH$_2$CH$_2$—C(=O)-DDGGFG (SEQ ID NO: 13)-NH—CH$_2$CH$_2$CH$_2$—C(=O)—(NH-DX),
-(Succinimid-3-yl-N)—CH$_2$CH$_2$CH$_2$CH$_2$—C(=O)-DDGGFG (SEQ ID NO: 13)-NH—CH$_2$CH$_2$CH$_2$CH$_2$—C(=O)—(NH-DX),
-(Succinimid-3-yl-N)—CH$_2$CH$_2$—C(=O)—KDGGFG (SEQ ID NO: 14)-NH—CH$_2$CH$_2$—C(=O)—(NH-DX),
-(Succinimid-3-yl-N)—CH$_2$CH$_2$—C(=O)—KDGGFG (SEQ ID NO: 14)-NH—CH$_2$CH$_2$CH$_2$—C(=O)—(NH-DX),
-(Succinimid-3-yl-N)—CH$_2$CH$_2$—C(=O)—KDGGFG (SEQ ID NO: 14)-NH—CH$_2$CH$_2$CH$_2$CH$_2$—C(=O)—(NH-DX),
-(Succinimid-3-yl-N)—CH$_2$CH$_2$CH$_2$CH$_2$CH$_2$—C(=O)-KDGGFG (SEQ ID NO: 14)-NH—CH$_2$CH$_2$—C(=O)—(NH-DX),
-(Succinimid-3-yl-N)—CH$_2$CH$_2$CH$_2$CH$_2$CH$_2$—C(=O)-KDGGFG (SEQ ID NO: 14)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-KDGGFG (SEQ ID NO: 14)-NH—CH$_2$CH$_2$CH$_2$CH$_2$—C(=O)—(NH-DX).

Among these, more preferred are the following:
-(Succinimid-3-yl-N)—CH$_2$CH$_2$CH$_2$CH$_2$CH$_2$—C(=O)-DDGGFG (SEQ ID NO: 13)-NH—CH$_2$CH$_2$—C(=O)—(NH-DX),
-(Succinimid-3-yl-N)—CH$_2$CH$_2$CH$_2$CH$_2$CH$_2$—C(=O)-DDGGFG (SEQ ID NO: 13)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-DDGGFG (SEQ ID NO: 13)-NH—CH$_2$CH$_2$CH$_2$CH$_2$—C(=O)—(NH-DX),
-(Succinimid-3-yl-N)—CH$_2$CH$_2$CH$_2$CH$_2$CH$_2$—C(=O)-KDGGFG (SEQ ID NO: 14)-NH—CH$_2$CH$_2$—C(=O)—(NH-DX),
-(Succinimid-3-yl-N)—CH$_2$CH$_2$CH$_2$CH$_2$CH$_2$—C(=O)-KDGGFG (SEQ ID NO: 14)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-KDGGFG (SEQ ID NO: 14)-NH—CH$_2$CH$_2$CH$_2$CH$_2$—C(=O)—(NH-DX).

Further preferred are
-(Succinimid-3-yl-N)—CH$_2$CH$_2$CH$_2$CH$_2$CH$_2$—C(=O)-DDGGFG (SEQ ID NO: 13)-NH—CH$_2$CH$_2$CH$_2$—C(=O)—(NH-DX), and
-(Succinimid-3-yl-N)—CH$_2$CH$_2$CH$_2$CH$_2$CH$_2$—C(=O)-KDGGFG (SEQ ID NO: 14)-NH—CH$_2$CH$_2$CH$_2$—C(=O)—(NH-DX).

C-10. When $L^1$ is —C(=O)-cyc.Hex (1,4)-CH$_2$—(N-ly-3-diminiccuS)- and $L^2$ is —S—(CH$_2$)n$^8$-C(=O)—, preferred are the following:
—C(=O)-cyc.Hex(1,4)-CH$_2$—(N-ly-3-diminiccuS)—S—CH$_2$CH$_2$—C(=O)-DGGFG (SEQ ID NO: 10)-NH—CH$_2$CH$_2$—C(=O)—(NH-DX),
—C(=O)-cyc.Hex(1,4)-CH$_2$—(N-ly-3-diminiccuS)—S—CH$_2$CH$_2$—C(=O)-DGGFG (SEQ ID NO: 10)-NH—CH$_2$CH$_2$CH$_2$—C(=O)—(NH-DX),
—C(=O)-cyc.Hex(1,4)-CH$_2$—(N-ly-3-diminiccuS)—S—CH$_2$CH$_2$—C(=O)-DGGFG (SEQ ID NO: 10)-NH—CH$_2$CH$_2$CH$_2$CH$_2$—C(=O)—(NH-DX),
—C(=O)-cyc.Hex(1,4)-CH$_2$—(N-ly-3-diminiccuS)-S—CH$_2$CH$_2$CH$_2$—C(=O)-DGGFG (SEQ ID NO: 10)-NH—CH$_2$CH$_2$—C(=O)—(NH-DX),
—C(=O)-cyc.Hex(1,4)-CH$_2$—(N-ly-3-diminiccuS)-S—CH$_2$CH$_2$CH$_2$—C(=O)-DGGFG (SEQ ID NO: 10)-NH—CH$_2$CH$_2$CH$_2$—C(=O)—(NH-DX),
—C(=O)-cyc.Hex(1,4)-CH$_2$—(N-ly-3-diminiccuS)-S—CH$_2$CH$_2$CH$_2$—C(=O)-DGGFG (SEQ ID NO: 10)-NH—CH$_2$CH$_2$CH$_2$CH$_2$—C(=O)—(NH-DX),
—C(=O)-cyc.Hex(1,4)-CH$_2$—(N-ly-3-diminiccuS)-S-CH$_2$CH$_2$CH$_2$CH$_2$—C(=O)-DGGFG (SEQ ID NO: 10)-NH—CH$_2$CH$_2$—C(=O)—(NH-DX),
—C(=O)-cyc.Hex(1,4)-CH$_2$—(N-ly-3-diminiccuS)—S—CH$_2$CH$_2$CH$_2$CH$_2$—C(=O)-DGGFG (SEQ ID NO: 10)-NH—CH$_2$CH$_2$CH$_2$—C(=O)—(NH-DX), —C(=O)-cyc.Hex(1,4)-CH$_2$—(N-ly-3-diminiccuS)—S—CH$_2$CH$_2$CH$_2$CH$_2$—C(=O)-DGGFG (SEQ ID NO: 10)-NH—CH$_2$CH$_2$CH$_2$CH$_2$—C(=O)—(NH-DX).

Among these, preferred are the following:
—C(=O)-cyc.Hex(1,4)-CH$_2$—(N-ly-3-diminiccuS)—S—CH$_2$CH$_2$—C(=O)-DGGFG (SEQ ID NO: 10)-NH—CH$_2$CH$_2$—C(=O)—(NH-DX),
—C(=O)-cyc.Hex(1,4)-CH$_2$—(N-ly-3-diminiccuS)—S—CH$_2$CH$_2$—C(=O)-DGGFG (SEQ ID NO: 10)-NH—CH$_2$CH$_2$CH$_2$—C(=O)—(NH-DX),
—C(=O)-cyc.Hex(1,4)-CH$_2$—(N-ly-3-diminiccuS)—S—CH$_2$CH$_2$—C(=O)-DGGFG (SEQ ID NO: 10)-NH—CH$_2$CH$_2$CH$_2$CH$_2$—C(=O)—(NH-DX).

D. A preferred linker-drug moiety having a structure of -L$^1$-L$^2$-L$^P$-(NH-DX) wherein L$^P$ contains aspartic acid, lysine, glutamic acid, and/or serine, which are hydrophilic amino acids, in particular, aspartic acid is shown below.

D-1. When L$^1$ is -(Succinimid-3-yl-N)—(CH$_2$)n$^2$-C(=O)— and L$^2$ is —NH—(CH$_2$CH$_2$—O)n$^6$-CH$_2$CH$_2$—C(=O)—;
-(Succinimid-3-yl-N)—CH$_2$CH$_2$—C(=O)—NH-DGGFG (SEQ ID NO: 10)-(NH-DX),
-(Succinimid-3-yl-N)—CH$_2$CH$_2$CH$_2$CH$_2$CH$_2$—C(=O)—NH-DGGFS (SEQ ID NO: 12)-(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-DGGFG (SEQ ID NO: 10)-(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-DGGFG (SEQ ID NO: 10)-(NH-DX),
-(Succinimid-3-yl-N)—CH$_2$CH$_2$CH$_2$CH$_2$CH$_2$—C(=O)—NH-DGGFG (SEQ ID NO: 10)-(NH-DX),
-(Succinimid-3-yl-N)—CH$_2$CH$_2$CH$_2$CH$_2$CH$_2$—C(=O)—NH—CH$_2$CH$_2$—O—CH$_2$CH$_2$—O—CH$_2$CH$_2$—C(=O)-DGGFG (SEQ ID NO: 10)-(NH-DX),
-(Succinimid-3-yl-N)—CH$_2$CH$_2$CH$_2$CH$_2$CH$_2$—C(=O)—NH—CH$_2$CH$_2$—O—CH$_2$CH$_2$—O—CH$_2$CH$_2$—O—CH$_2$CH$_2$—C(=O)-DGGFG (SEQ ID NO: 10)-(NH-DX).

Among these, more preferred are the following:
-(Succinimid-3-yl-N)—CH$_2$CH$_2$—C(=O)—NH-DGGFG (SEQ ID NO: 10)-(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-DGGFG (SEQ ID NO: 10)-(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—C(=O)-DGGFG (SEQ ID NO: 10)-(NH-DX).

D-2. When L$^1$ is -(Succinimid-3-yl-N)—(CH$_2$)n$^2$-C(=O)— and L$^2$ is a single bond, preferred are the following:
-(Succinimid-3-yl-N)—CH$_2$CH$_2$—C(=O)—NH-DGGFG (SEQ ID NO: 10)-(NH-DX),
-(Succinimid-3-yl-N)—CH$_2$CH$_2$CH$_2$—C(=O)—NH-DGGFG (SEQ ID NO: 10)-(NH-DX),
-(Succinimid-3-yl-N)—CH$_2$CH$_2$CH$_2$CH$_2$CH$_2$—C(=O)—NH-DGGFG (SEQ ID NO: 10)-(NH-DX).

D-3. When L$^1$ is -(Succinimid-3-yl-N)—(CH$_2$)n$^2$-C(=O)— and L$^2$ is a single bond, preferred are the following:
-(Succinimid-3-yl-N)—CH$_2$CH$_2$—C(=O)—NH-DDGGFG (SEQ ID NO: 13)-(NH-DX), and
-(Succinimid-3-yl-N)—CH$_2$CH$_2$CH$_2$CH$_2$CH$_2$—C(=O)—NH-DDGGFG (SEQ ID NO: 13)-(NH-DX)
in which the aspartic acid is D-aspartic acid.

D-4. When L$^1$ is -(Succinimid-3-yl-N)—(CH$_2$)n$^2$-C(=O)— and L$^2$ is a single bond, preferred are the following:

-(Succinimid-3-yl-N)—CH$_2$CH$_2$—C(=O)—NH-DG-$^{Me}$GFG (SEQ ID NO: 11)-(NH-DX), and
-(Succinimid-3-yl-N)—CH$_2$CH$_2$CH$_2$CH$_2$CH$_2$—C(=O)—NH-DG$^{Me}$GFG (SEQ ID NO: 11)-(NH-DX)
in which glycine is in the form of sarcosine.

D-5. When L$^1$ is -(Succinimid-3-yl-N)—(CH$_2$)n$^2$-C(=O)—, L$^2$ is a single bond, the peptide residue contains a hydrophilic amino acid other than aspartic acid, preferred are the following:
-(Succinimid-3-yl-N)—CH$_2$CH$_2$—C(=O)—NH—KGGFG (SEQ ID NO: 15)-(NH-DX),
-(Succinimid-3-yl-N)—CH$_2$CH$_2$—C(=O)—NH—SGGFG (SEQ ID NO: 17)-(NH-DX),
-(Succinimid-3-yl-N)—CH$_2$CH$_2$—C(=O)—NH-EGGFG (SEQ ID NO: 16)-(NH-DX),
-(Succinimid-3-yl-N)—CH$_2$CH$_2$—C(=O)—NH-DGGFS (SEQ ID NO: 12)-(NH-DX),
-(Succinimid-3-yl-N)—CH$_2$CH$_2$CH$_2$CH$_2$CH$_2$—C(=O)—NH-KGGFG (SEQ ID NO: 15)-(NH-DX),
-(Succinimid-3-yl-N)—CH$_2$CH$_2$CH$_2$CH$_2$CH$_2$—C(=O)—NH-SGGFG (SEQ ID NO: 17)-(NH-DX),
-(Succinimid-3-yl-N)—CH$_2$CH$_2$CH$_2$CH$_2$CH$_2$—C(=O)—NH-EGGFG (SEQ ID NO: 16)-(NH-DX).

Among these, more preferred are the following:
-(Succinimid-3-yl-N)—CH$_2$CH$_2$CH$_2$CH$_2$CH$_2$—C(=O)—NH-KGGFG (SEQ ID NO: 15)-(NH-DX),
-(Succinimid-3-yl-N)—CH$_2$CH$_2$CH$_2$CH$_2$CH$_2$—C(=O)—NH-SGGFG (SEQ ID NO: 17)-(NH-DX),
-(Succinimid-3-yl-N)—CH$_2$CH$_2$CH$_2$CH$_2$CH$_2$—C(=O)—NH-EGGFG (SEQ ID NO: 16)-(NH-DX),
-(Succinimid-3-yl-N)—CH$_2$CH$_2$CH$_2$CH$_2$CH$_2$—C(=O)—NH-DGGFS (SEQ ID NO: 12)-(NH-DX).

E. A preferred linker-drug moiety having a structure of -L$^1$-L$^2$-L$^P$-NH—(CH$_2$)n$^1$-L$^a$-L$^b$-L$^c$-(NH-DX) wherein L$^1$ is -(Succinimid-3-yl-N)—(CH$_2$)n$^2$-C(=O)—, L$^2$ is a single bond, and the peptide residue is a dipeptide is shown below.
-(Succinimid-3-yl-N)—CH$_2$CH$_2$—C(=O)—VK—NH—CH$_2$CH$_2$—C(=O)—(NH-DX),
-(Succinimid-3-yl-N)—CH$_2$CH$_2$—C(=O)—VC—NH—CH$_2$CH$_2$—C(=O)—(NH-DX),
-(Succinimid-3-yl-N)—CH$_2$CH$_2$—C(=O)—VK—NH—CH$_2$CH$_2$CH$_2$—C(=O)—(NH-DX),
-(Succinimid-3-yl-N)—CH$_2$CH$_2$—C(=O)—VC—NH—CH$_2$CH$_2$CH$_2$—C(=O)—(NH-DX),
-(Succinimid-3-yl-N)—CH$_2$CH$_2$—C(=O)—VK—NH—CH$_2$CH$_2$CH$_2$CH$_2$CH$_2$—C(=O)—(NH-DX),
-(Succinimid-3-yl-N)—CH$_2$CH$_2$—C(=O)—VC—NH—CH$_2$CH$_2$CH$_2$CH$_2$CH$_2$—C(=O)—(NH-DX),
-(Succinimid-3-yl-N)—CH$_2$CH$_2$CH$_2$CH$_2$CH$_2$—C(=O)—VK—NH—CH$_2$CH$_2$—C(=O)—(NH-DX),
-(Succinimid-3-yl-N)—CH$_2$CH$_2$CH$_2$CH$_2$CH$_2$—C(=O)—VC—NH—CH$_2$CH$_2$—C(=O)—(NH-DX),
-(Succinimid-3-yl-N)—CH$_2$CH$_2$CH$_2$CH$_2$CH$_2$—C(=O)—VK—NH—CH$_2$CH$_2$CH$_2$—C(=O)—(NH-DX),
-(Succinimid-3-yl-N)—CH$_2$CH$_2$CH$_2$CH$_2$CH$_2$—C(=O)—VC—NH—CH$_2$CH$_2$CH$_2$—C(=O)—(NH-DX),
-(Succinimid-3-yl-N)—CH$_2$CH$_2$CH$_2$CH$_2$CH$_2$—C(=O)—VK—NH—CH$_2$CH$_2$CH$_2$CH$_2$CH$_2$—C(=O)—(NH-DX),
-(Succinimid-3-yl-N)—CH$_2$CH$_2$CH$_2$CH$_2$CH$_2$—C(=O)—VC—NH—CH$_2$CH$_2$CH$_2$CH$_2$CH$_2$—C(=O)—(NH-DX).

Among these, more preferred are the following:
-(Succinimid-3-yl-N)—CH$_2$CH$_2$CH$_2$CH$_2$CH$_2$—C(=O)—VK—NH—CH$_2$CH$_2$—C(=O)—(NH-DX),
-(Succinimid-3-yl-N)—CH$_2$CH$_2$CH$_2$CH$_2$CH$_2$—C(=O)—VC—NH—CH$_2$CH$_2$—C(=O)—(NH-DX),
-(Succinimid-3-yl-N)—CH$_2$CH$_2$CH$_2$CH$_2$CH$_2$—C(=O)—VK—NH—CH$_2$CH$_2$CH$_2$—C(=O)—(NH-DX), -(Succinimid-3-yl-N)—CH$_2$CH$_2$CH$_2$CH$_2$CH$_2$—C(=O)—
VC—NH—CH$_2$CH$_2$CH$_2$—C(=O)—(NH-DX),
-(Succinimid-3-yl-N)—CH$_2$CH$_2$CH$_2$CH$_2$CH$_2$—C(=O)—
VK—NH—CH$_2$CH$_2$CH$_2$CH$_2$CH$_2$—C(=O)—(NH-DX),
-(Succinimid-3-yl-N)—CH$_2$CH$_2$CH$_2$CH$_2$CH$_2$—C(=O)—
VC—NH—CH$_2$CH$_2$CH$_2$CH$_2$CH$_2$—C(=O)—(NH-DX).

Further preferred are
-(Succinimid-3-yl-N)—CH$_2$CH$_2$CH$_2$CH$_2$CH$_2$—C(=O)—
VK—NH—CH$_2$CH$_2$CH$_2$—C(=O)—(NH-DX), and
-(Succinimid-3-yl-N)—CH$_2$CH$_2$CH$_2$CH$_2$CH$_2$—C(=O)—
VC—NH—CH$_2$CH$_2$CH$_2$—C(=O)—(NH-DX).

The excellent properties of the anti-HER2 antibody-drug conjugate of the present invention are achieved by adequately exerting properties possessed by the anti-HER2 antibody and exatecan by the linker connected thereto. Thus, an antibody-drug conjugate having excellent properties can be obtained by adopting the linker having the structure of the present invention. The linker structure of the present invention can be easily connected to the antibody by forming a thioether bond or an amide bond according to a method known in the art. For the antibody, there are no particular requirements for connecting the antibody to the linker of the present invention. Also, the linker structure of the present invention can be also connected to the antitumor drug as long as it is a compound having a functional group capable of forming an amide bond, an ether bond, an ester bond, a carbon-carbon alkyl bond, or the like. In this way, an antibody other than the anti-HER2 antibody can be conjugated to a drug other than exatecan via the linker structure of the present invention to obtain an excellent antibody-drug conjugate.

[Compound Reactive with Antibody]

For the above linker-drug structure, as a compound for introducing it to the antibody, 1. a compound in which, in the case of using a (Succinimid-3-yl-N) group at the terminal of the linker-drug structure, the moiety is a maleimidyl group,
2. a compound in which, in the case of connecting the —CH$_2$—C(=O)—NH— group of the linker-drug structure to the antibody via a sulfide bond, the methylene group is a halogenomethyl group,
3. a compound in which, in the case of connecting the —C(=O)—CH$_2$CH$_2$—C(=O) of the linker-drug structure to the antibody via an amide bond, the terminal is converted to an active ester with a (Pyrrolidine-2,5-dione-N-yl)-O— group, or
4. a compound which, in the case of connecting the —C(=O)-cyc.Hex(1,4)-CH$_2$—(N-ly-3-diminiccuS)- of the linker-drug structure to the antibody, has the structure represented by L$^2$ at the terminal in which S of this moiety is HS can be preferably used. Any of these compounds corresponding to each of the above structures can be used.

[Production Method]

Next, explanations are given for the representative method for producing the antibody-drug conjugate of the present invention or a production intermediate thereof. Meanwhile, the compounds are hereinbelow described with the compound number shown in each reaction formula. Specifically, they are referred to as a "compound of the formula (1)", a "compound (1)", or the like. The compounds with numbers other than those are also described similarly.

1. Production Method 1

The antibody-drug conjugate represented by the formula (1) in which the antibody is connected to the drug-linker structure via thioether can be produced by the following method, for example.

[Formula 26]

$$L^{1'}—L^2—L^P—NH—(CH_2)n^1—L^a—L^b—L^c—(NH—DX) \quad AB$$
$$\text{or}$$
$$L^{1'}—L^2—L^P—(NH—DX)$$
2
$$AB—L^1—L^2—L^P—NH—(CH_2)n^1—L^a—L^b—L^c—(NH—DX)$$
$$\text{or}$$
$$AB—L^1—L^2—L^P—(NH—DX)$$
1

$$\xrightarrow{3a}$$

[In the formula, AB represents an antibody having a sulfhydryl group, and L$^{1'}$ represents L$^1$ linker structure in which the terminal is converted to a maleimidyl group (formula shown below)

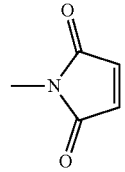

[Formula 27]

(in the formula, the nitrogen atom is the connecting position), or a linker structure in which the terminal is converted to halogen. It is, for example, a group in which the -(Succinimid-3-yl-N)— moiety in a structure such as -(Succinimid-3-yl-N)—(CH$_2$)n$^2$-C(=O)— represented as L$^1$ is a maleimidyl group, or a Halogen-CH$_2$—C—(=O)—NH—(CH$_2$)n$^4$-C(=O)— group in which the terminal methylene of —CH$_2$C(=O) NH—(CH$_2$)n$^4$-C(=O)— represented as L$^1$ is haloacetamide by halogenation. Further, the —(NH-DX) represents a structure represented by the following formula:

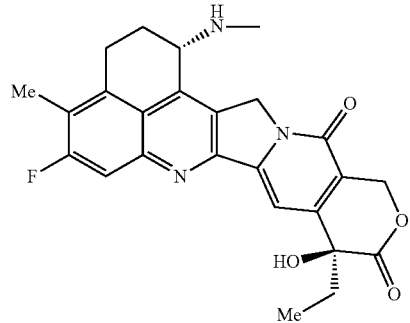

[Formula 28]

and it represents a group that is derived by removing one hydrogen atom of the amino group at position 1 of the antitumor drug. Further, the compound of the formula (1) in the above reaction formula is described as a structure in which one structure moiety corresponding from the drug to the linker terminal connects to one antibody. However, it is only a description given for the sake of convenience, and there are actually many cases in which a plurality of the structure moieties are connected to one antibody molecule. The same applies to the explanation of the production method described below.]

That is, the antibody-drug conjugate (1) can be produced by reacting the compound (2), which is obtainable by the method described below, with the antibody (3a) having a sulfhydryl group.

The antibody (3a) having a sulfhydryl group can be obtained by a method well known in the art (Hermanson, G. T, Bioconjugate Techniques, pp. 56-136, pp. 456-493, Academic Press (1996)). Examples include: Traut's reagent is reacted with the amino group of the antibody; N-succinimidyl S-acetylthioalkanoates are reacted with the amino group of the antibody followed by reaction with hydroxylamine; after reacting it with N-succinimidyl 3-(pyridyldithio)propionate, the antibody is reacted with a reducing agent; the antibody is reacted with a reducing agent such as dithiothreitol, 2-mercaptoethanol, and tris(2-carboxyethyl)phosphine hydrochloride (TCEP) to reduce the disulfide bond in the hinge part in the antibody, but it is not limited thereto.

Specifically, a dimethyl sulfoxide solution of the compound (2) can be added to a phosphate-buffered saline solution (pH 7.2) containing the antibody (3a) having a sulfhydryl group to produce the antibody-drug conjugate (1). Thereafter, the reactivity of unreacted compound (2) is deactivated by the addition of N-acetyl-L-cysteine (NAC) as usually used in reaction for forming antibody-drug bonding. The produced antibody-drug conjugate (1) can, after concentration, buffer exchange, purification, measurement of antibody concentration and average number of conjugated drug molecules per antibody molecule, and calculation of aggregate content according to procedures described below, be subjected to identification of the antibody-drug conjugate (1).

Common Procedure A: Concentration of Aqueous Solution of Antibody or Antibody-Drug Conjugate To an Amicon Ultra (50,000 MWCO, Millipore Corporation) container, a solution of antibody or antibody-drug conjugate was added and the solution of the antibody or antibody-drug conjugate was concentrated by centrifugation (centrifuge for 5 to 20 minutes at 2000 to 3800 G) using a centrifuge (Allegra X-15R, Beckman Coulter, Inc.).

Common Procedure B: Measurement of Antibody Concentration

Using a UV detector (Nanodrop 1000, Thermo Fisher Scientific Inc.), measurement of the antibody concentration was performed according to the method defined by the manufacturer. At that time, a 280 nm absorption coefficient different for each antibody was used (1.3 to 1.8/mg/mL).

Common Procedure C-1: Buffer Exchange for Antibody

NAP-25 column (Cat. No. 17-0852-02, GE Healthcare Japan Corporation) using Sephadex G-25 carrier was equilibrated with phosphate buffer (10 mM, pH 6.0; it is referred to as PBS6.0/EDTA in the specification) containing sodium chloride (137 mM) and ethylene diamine tetraacetic acid (EDTA; 5 mM) according to the method defined by the manufacturer. Aqueous solution of the antibody was applied in an amount of 2.5 mL to single NAP-25 column, and then the fraction (3.5 mL) eluted with 3.5 mL of PBS6.0/EDTA was collected. The resulting fraction was concentrated by the Common procedure A. After measuring the concentration of the antibody using the Common procedure B, the antibody concentration was adjusted to 10 mg/mL using PBS6.0/EDTA.

Common Procedure C-2: Buffer Exchange for Antibody

NAP-25 column (Cat. No. 17-0852-02, GE Healthcare Japan Corporation) using Sephadex G-25 carrier was equilibrated with phosphate buffer (50 mM, pH 6.5; it is referred to as PBS6.5/EDTA in the specification) containing sodium chloride (50 mM) and EDTA (2 mM) according to the method defined by the manufacturer. Aqueous solution of the antibody was applied in an amount of 2.5 mL to single NAP-25 column, and then the fraction (3.5 mL) eluted with 3.5 mL of PBS6.5/EDTA was collected. The resulting fraction was concentrated by the Common procedure A. After measuring the concentration of the antibody using the Common procedure B, the antibody concentration was adjusted to 20 mg/mL using PBS6.5/EDTA.

Common Procedure D-1: Purification of Antibody-Drug Conjugate

NAP-25 column was equilibrated with any buffer selected from commercially available phosphate buffer (PBS7.4, Cat. No. 10010-023, Invitrogen), sodium phosphate buffer (10 mM, pH 6.0; it is referred to as PBS6.0 in the specification) containing sodium chloride (137 mM), and acetate buffer containing sorbitol (5%) (10 mM, pH 5.5; it is referred to as ABS in the specification). Aqueous solution of the antibody-drug conjugate reaction was applied in an amount of about 1.5 mL to the NAP-25 column, and then eluted with the buffer in an amount defined by the manufacturer to collect the antibody fraction. The collected fraction was again applied to the NAP-25 column and, by repeating 2 to 3 times in total the gel filtration purification process for eluting with buffer, the antibody-drug conjugate excluding non-conjugated drug linker and a low-molecular-weight compound (tris(2-carboxyethyl)phosphine hydrochloride (TCEP), N-acetyl-L-cysteine (NAC), and dimethyl sulfoxide) was obtained.

Common Procedure D-2: Purification of Succinimidyl-4-(N-maleimidylmethyl)-cyclohexane-1-carboxylate (SMCC)-Derivatized Antibody NAP-25 column was equilibrated with PBS6.5/EDTA. Reaction solution containing a succinimidyl-4-(N-maleimidylmethyl)-cyclohexane-1-carboxylate (referred to as SMCC in the specification)-derivatized antibody was applied in an amount of about 0.5 mL to the NAP-25 column, and then eluted with the buffer in an amount defined by the manufacturer to collect the antibody fraction, followed by purification.

Common Procedure E: Measurement of Antibody Concentration in Antibody-Drug Conjugate and Average Number of Conjugated Drug Molecules Per Antibody Molecule The conjugated drug concentration in the antibody-drug conjugate can be calculated by measuring UV absorbance of an aqueous solution of the antibody-drug conjugate at, for example, two wavelengths of 280 nm and 370 nm, followed by performing the calculation shown below.

Because the total absorbance at any wavelength is equal to the sum of the absorbance of every light-absorbing chemical species that are present in the system [additivity of absorbance], when the molar absorption coefficients of the antibody and the drug remain the same before and after conjugation between the antibody and the drug, the antibody concentration and the drug concentration in the antibody-drug conjugate are expressed by the following equations.

$$A_{280} = A_{D,280} + A_{A,280} = \varepsilon_{D,280} C_D + \varepsilon_{A,280} C_A \quad \text{Equation (I)}$$

$$A_{370} = A_{D,370} + A_{A,370} = \varepsilon_{D,370} C_D + \varepsilon_{A,370} C_A \quad \text{Equation (II)}$$

In the above, $A_{280}$ represents the absorbance of an aqueous solution of the antibody-drug conjugate at 280 nm, $A_{370}$ represents the absorbance of an aqueous solution of the antibody-drug conjugate at 370 nm, $A_{A,280}$ represents the absorbance of an antibody at 280 nm, $A_{A,370}$ represents the absorbance of an antibody at 370 nm, $A_{D,280}$ represents the absorbance of a conjugate precursor at 280 nm, $A_{D,370}$ represents the absorbance of a conjugate precursor at 370 nm, $\varepsilon_{A,280}$ represents the molar absorption coefficient of an antibody at 280 nm, $\varepsilon_{A,370}$ represents the molar absorption coefficient of an antibody at 370 nm, $\varepsilon_{D,280}$ represents the molar absorption coefficient of a conjugate precursor at 280 nm, $\varepsilon_{D,370}$ represents the molar absorption coefficient of a conjugate precursor at 370 nm, $C_A$ represents the antibody concentration in an antibody-drug conjugate, and $C_D$ represent the drug concentration in an antibody-drug conjugate.

$\varepsilon_{A,280}$, $\varepsilon_{A,370}$, $\varepsilon_{D,280}$, and $\varepsilon_{D,370}$ in the above are known by previous measurement. By measuring $A_{280}$ and $A_{370}$ of an aqueous solution of the antibody-drug conjugate and solving the simultaneous equations (I) and (II) using the values, $C_A$ and $C_D$ can be obtained. Further, by dividing $C_D$ by $C_A$, the average number of conjugated drug molecules per antibody molecule can be obtained.

The compound represented by the formula (2) used as an intermediate compound in Production method 1 is described below. The compound is, for example, a compound having the following structure:

[Formula 29]

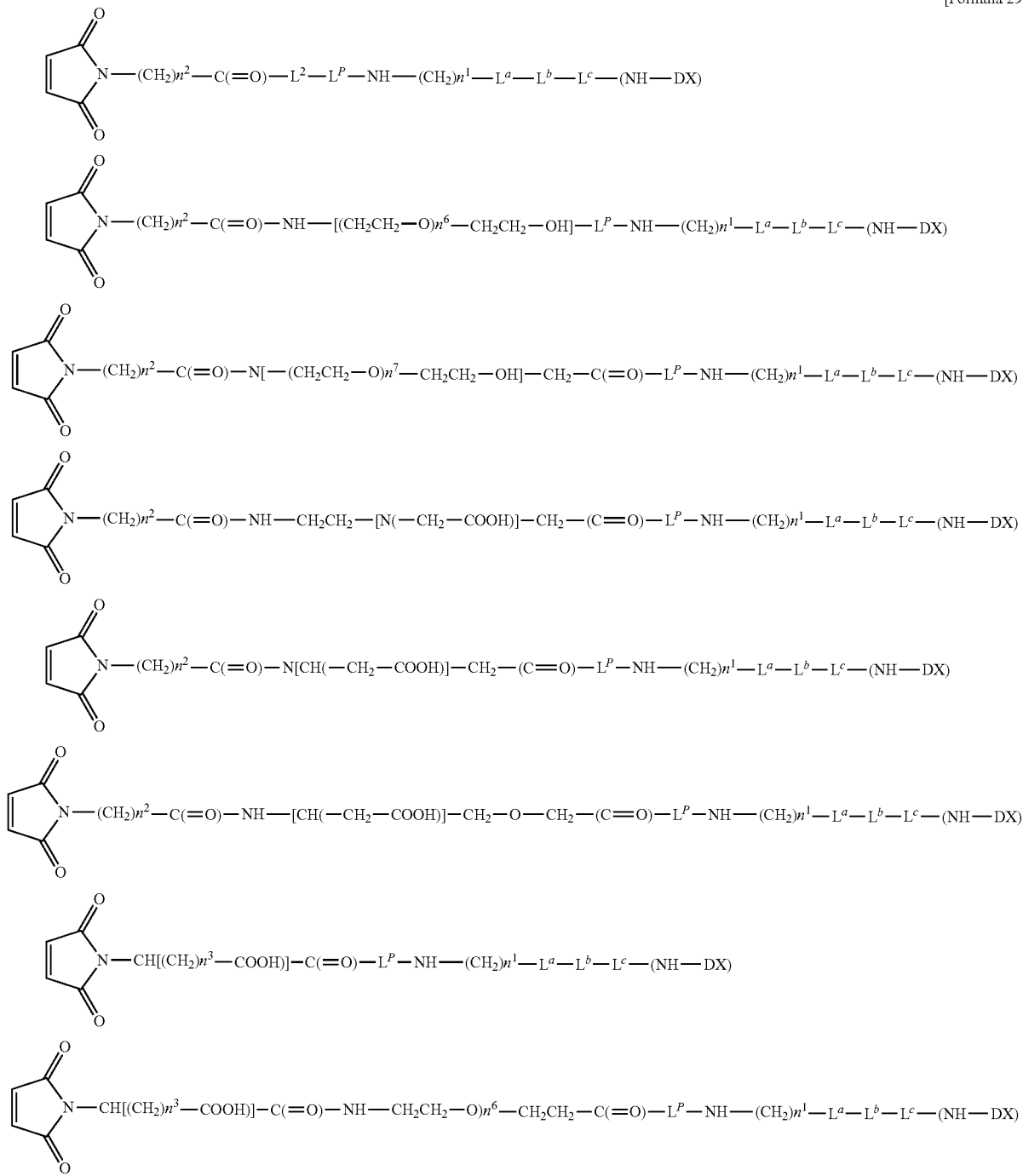

-continued

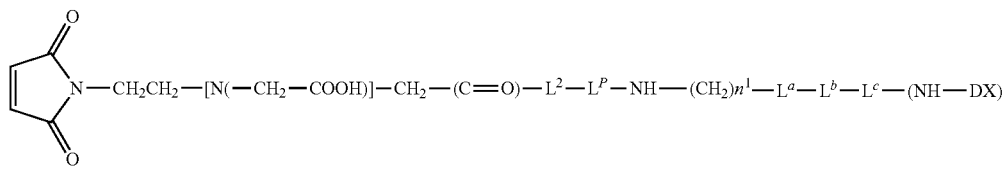

Halogen-CH$_2$C(=O)NH—(CH$_2$)$n^3$—C(=O)—L$^2$—L$^P$—NH—(CH$_2$)$n^1$—L$^a$—L$^b$—L$^c$—(NH—DX)

Halogen-CH$_2$C(=O)NH—(CH$_2$)$n^3$—C(=O)—NH—[(CH$_2$CH$_2$—O)$n^6$—CH$_2$CH$_2$—OH]—L$^P$—NH—(CH$_2$)$n^1$—L$^a$—L$^b$—L$^c$—(NH—DX)

[Formula 30]

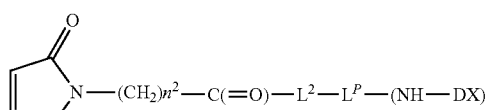—(CH$_2$)$n^2$—C(=O)—L$^2$—L$^P$—(NH—DX)

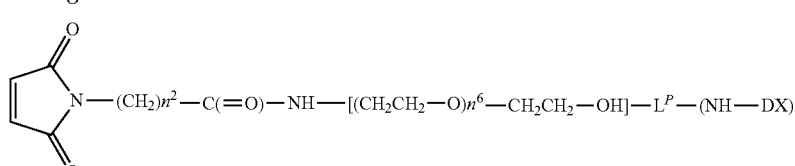—(CH$_2$)$n^2$—C(=O)—NH—[(CH$_2$CH$_2$—O)$n^6$—CH$_2$CH$_2$—OH]—L$^P$—(NH—DX)

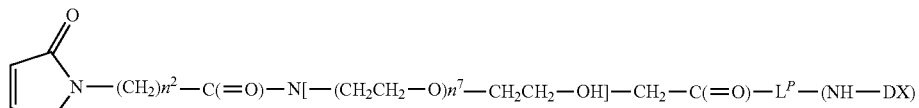—(CH$_2$)$n^2$—C(=O)—N[—(CH$_2$CH$_2$—O)$n^7$—CH$_2$CH$_2$—OH]—CH$_2$—C(=O)—L$^P$—(NH—DX)

—(CH$_2$)$n^2$—C(=O)—NH—CH$_2$CH$_2$—[N(—CH$_2$—COOH)]—CH$_2$—(C=O)—L$^P$—(NH—DX)

—(CH$_2$)$n^2$—C(=O)—N[CH(—CH$_2$—COOH)]—CH$_2$—(C=O)—L$^P$—(NH—DX)

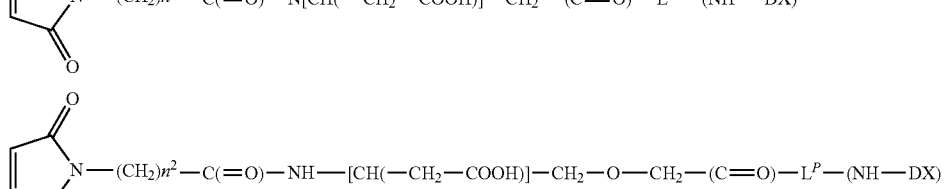—(CH$_2$)$n^2$—C(=O)—NH—[CH(—CH$_2$—COOH)]—CH$_2$—O—CH$_2$—(C=O)—L$^P$—(NH—DX)

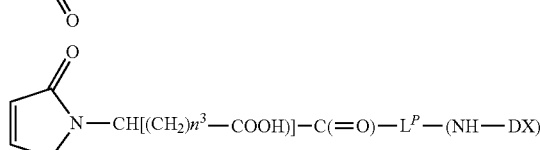—CH[(CH$_2$)$n^3$—COOH)]—C(=O)—L$^P$—(NH—DX)

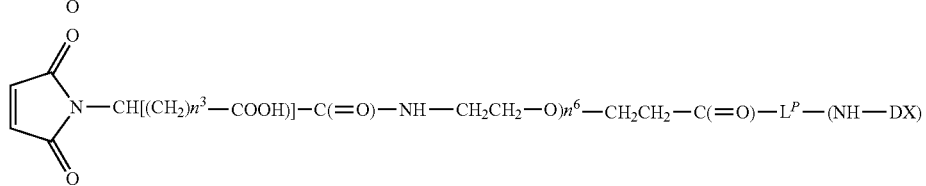—CH[(CH$_2$)$n^3$—COOH)]—C(=O)—NH—CH$_2$CH$_2$—O)$n^6$—CH$_2$CH$_2$—C(=O)—L$^P$—(NH—DX)

-continued

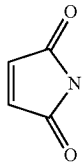
N—CH$_2$CH$_2$—[N(—CH$_2$—COOH)]—CH$_2$—(C=O)—L$^2$—L$^P$—(NH—DX)

Halogen-CH$_2$C(=O)NH—(CH$_2$)$n^3$—C(=O)—L$^2$—L$^P$—(NH—DX)

Halogen-CH$_2$C(=O)NH—(CH$_2$)$n^3$—C(=O)—NH—[(CH$_2$CH$_2$—O)$n^6$—CH$_2$CH$_2$—OH]—L$^P$—(NH—DX)

In the above formula, $n^1$, $n^2$, $n^3$, $n^4$, $n^7$, $L^2$, $L^P$, $L^a$, $L^b$, and $L^c$ are as already defined, and the terminal of $L^P$ or $L^c$ is the connecting position with the drug.

In a preferred intermediate useful in the production of such an antibody-drug conjugate of the present invention $n^2$ is an integer of 2 to 5.

When $L^1$ is -(Succinimid-3-yl-N)—(CH$_2$)$n^2$-C(=O)—, $L^2$ is preferably any of —NH—(CH$_2$CH$_2$—O)$n^6$-CH$_2$CH$_2$—C(=O)— wherein $n^6$ is 2 to 4, —N[—(CH$_2$CH$_2$—O)$n^7$-CH$_2$CH$_2$—OH]—CH$_2$—C(=O)— wherein $n^7$ is 3 or 4, —NH—CH$_2$CH$_2$—[N(—CH$_2$—COOH)]—CH$_2$—(C=O)—, —NH—[CH(—CH$_2$—COOH)]—CH$_2$—(C=O)—, or —NH—[CH(—CH$_2$—COOH)]—CH$_2$—O—CH$_2$—(C=O)—, or is a single bond.

When $L^1$ is -(Succinimid-3-yl-N)—CH [—(CH$_2$)$n^3$-COOH]—C(=O)—, $n^3$ is preferably an integer of 1 to 4, more preferably 1 or 2, $L^2$ is —NH—(CH$_2$CH$_2$—O)$n^6$-CH$_2$CH$_2$—C(=O)—, and $n^6$ is preferably 0 to 4, more preferably $n^6$ is 0 or a single bond.

When $L^1$ is -(Succinimid-3-yl-N)—CH$_2$CH$_2$—[N(—CH$_2$—COOH)]—CH$_2$—(C=O)—, $L^2$ is preferably a single bond.

When $L^1$ is —CH$_2$—C(=O)—NH—(CH$_2$)$n^4$-C(=O)—, $n^4$ is preferably 2, and $L^2$ is preferably a single bond.

$L^P$ can be VK, VC, GFG, GGFG (SEQ ID NO: 3), GGFGG (SEQ ID NO: 4), GGFGS (SEQ ID NO: 5), GGFGGG (SEQ ID NO: 6), GGFGGE (SEQ ID NO: 7), GGFGGGFG (SEQ ID NO: 8), DGGF (SEQ ID NO: 9), DGGFG (SEQ ID NO: 10), D$^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17). Among these, GGFG (SEQ ID NO: 3), GGFGG (SEQ ID NO: 4), GGFGS (SEQ ID NO: 5), GGFGGE (SEQ ID NO: 7), GDGGF (SEQ ID NO: 18), DGGFG (SEQ ID NO: 10), D$^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) is preferred. GGFG (SEQ ID NO: 3), GDGGF (SEQ ID NO: 18), DGGFG (SEQ ID NO: 10), D$^d$GGFG, DG$^{Me}$GFG (SEQ ID NO: 11), DGGFS (SEQ ID NO: 12), DDGGFG (SEQ ID NO: 13), or KDGGFG (SEQ ID NO: 14) is more preferred. GGFG (SEQ ID NO: 3), DGGFG (SEQ ID NO: 10), D$^d$GGFG, or DG$^{Me}$GFG (SEQ ID NO: 11) is further preferred.

The —NH—(CH$_2$)$n^1$-L$^a$-L$^b$-L$^c$-moiety can be —NH—CH$_2$CH$_2$—C(=O)—, —NH—CH$_2$CH$_2$CH$_2$—C(=O)—, —NH—CH$_2$CH$_2$CH$_2$CH$_2$—C(=O)—, —NH—CH$_2$CH(-Me)-C(=O)—, —NH—CH$_2$C(-Me)H—C(=O)—, —NH—CH$_2$CH$_2$C(-Me)$_2$-C(=O)—, —NH—CH$_2$CH$_2$—NH—C(=O)—, —NH—CH$_2$CH$_2$—NH—CH$_2$—C(=O)—, —NH—CH$_2$CH$_2$—NMe-CH$_2$—C(=O)—, —NH—CH$_2$—O—CH$_2$—C(=O)—, —NH—CH$_2$CH$_2$—N(—CH$_2$CH$_2$—OH)—CH$_2$—C(=O)—, —NH—CH$_2$CH$_2$—N(—CH$_2$CH$_2$—OH)—CH$_2$CH$_2$—C(=O)—, —NH—CH$_2$CH$_2$—N(—CH$_2$—COOH)—CH$_2$—C(=O)—, —NH—CH$_2$CH$_2$CH$_2$—C(=O)—NH—CH(—CH$_2$—COOH)—C(=O)—, —NH—CH$_2$CH$_2$CH$_2$—C(=O)—NH—CH(—CH$_2$—OH)—C(=O)—, —NH—CH$_2$CH$_2$—, or —NH—CH$_2$CH$_2$CH$_2$—. Among these, a partial structure of —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)— is preferred.

Specific examples of these compounds can include the following [herein, (maleimid-N-yl) represents a maleimidyl group (2,5-dioxo-2,5-dihydro-1H-pyrrol-1-yl group)].

When $L^1$ is -(Succinimid-3-yl-N)—(CH$_2$)$n^2$-C(=O)—, $L^2$ is —NH—(CH$_2$CH$_2$—O)$n^6$-CH$_2$CH$_2$—C(=O)—, —N[—(CH$_2$CH$_2$—O)$n^7$-CH$_2$CH$_2$—OH]-CH$_2$—C(=O)—, —NH—[CH(—CH$_2$—COOH)]—CH$_2$—(C=O)—, —NH—CH$_2$CH$_2$—[N(—CH$_2$—COOH)]—CH$_2$—(C=O)—, or a single bond. Therefore, as a production intermediate, a compound having a structure preferably represented by the following formula:

(maleimid-N-yl)-(CH$_2$)$n^2$-C(=O)-L$^P$-NH—(CH$_2$)$n_1$-L$^a$-L$^b$-L$^c$-(NH-DX), (maleimid-N-yl)-(CH$_2$)$n^2$-C(=O)—NH—(CH$_2$CH$_2$—O)$n^6$-CH$_2$CH$_2$—C(=O)-L$^P$-NH—(CH$_2$)$n^1$-L$^a$-L$^b$-L$^c$-(NH-DX) wherein $n^6$ is 2 to 4, (maleimid-N-yl)-(CH$_2$)$n^2$-C(=O)—N[—(CH$_2$CH$_2$—O)$n^7$-CH$_2$CH$_2$—OH]-CH$_2$—C(=O)-L$^P$-NH—(CH$_2$)$n^1$-L$^a$-L$^b$-L$^c$-(NH-DX) wherein $n^7$ is 3 or 4, (maleimid-N-yl)-(CH$_2$)$n^2$-C(=O)—NH—CH$_2$CH$_2$—[N(—CH$_2$—COOH)]—CH$_2$—(C=O)-L$^P$-NH—(CH$_2$)$n^1$-L$^a$-L$^b$-L$^c$-(NH-DX), (maleimid-N-yl)-(CH$_2$)$n^2$-C(=O)—NH—[CH(—CH$_2$—COOH)]—CH$_2$—(C=O)-L$^P$-NH—(CH$_2$)$n^1$-L$^a$-L$^b$-L$^c$-(NH-DX), or (maleimid-N-yl)-(CH$_2$)$n^2$-C(=O)—NH—[CH(—CH$_2$—COOH)]—CH$_2$—O—CH$_2$—(C=O)-L$^P$-NH—(CH$_2$)$n^1$-L$^a$-L$^b$-L$^c$-(NH-DX)

can be preferably used.

Here, preferably, $n^2$ is 2 to 5, and the —NH—(CH$_2$)$n^1$-L$^a$-L$^b$-L$^c$-moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—.

As $L^P$, VK, GFG, GGFG (SEQ ID NO: 3), GGFGG (SEQ ID NO: 4), GGFGS (SEQ ID NO: 5), GGFGGG (SEQ ID NO: 6), GGFGGE (SEQ ID NO: 7), GGFGGGFG (SEQ ID NO: 8), DGGF (SEQ ID NO: 9), DGGFG (SEQ ID NO: 10), D$^d$GGFG, DG$^{Me}$GFG (SEQ ID NO: 11), DGGFS (SEQ ID NO: 12), DDGGFG (SEQ ID NO: 13), KDGGFG (SEQ ID

NO: 14), KGGFG (SEQ ID NO: 15), EGGFG (SEQ ID NO: 16), or SGGFG (SEQ ID NO: 17) can be preferably used. Among these, GGFG (SEQ ID NO: 3), GGFGG (SEQ ID NO: 4), GGFGS (SEQ ID NO: 5), GGFGGE (SEQ ID NO: 7), GDGGF (SEQ ID NO: 18), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) is preferred. GGFG (SEQ ID NO: 3), GDGGF (SEQ ID NO: 18), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), or KDGGFG (SEQ ID NO: 14) is more preferred. GGFG (SEQ ID NO: 3), DGGFG (SEQ ID NO: 10), $D^d$GGFG, or DG$^{Me}$GFG (SEQ ID NO: 11) is further preferred. Also preferably, $L^P$ is directly connected to the drug.

When $L^1$ is -(Succinimid-3-yl-N)—CH[—(CH$_2$)n$^3$-COOH]—C(=O)—, $L^2$ is —NH—(CH$_2$CH$_2$—O)n$^6$-CH$_2$CH$_2$—C(=O)— or a single bond. Therefore, as a production intermediate, a compound having a structure represented by the following formula:

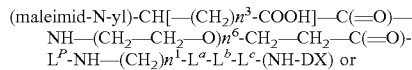

can be preferably used. Here, n$^6$ is 0 to 6 and is particularly preferably 0. Preferably, n$^3$ is 2 to 4, and the —NH—(CH$_2$)n$^1$-L$^a$-L$^b$-L$^c$-moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—.

As $L^P$, VK, VC, GFG, GGFG (SEQ ID NO: 3), GGFGG (SEQ ID NO: 4), GGFGS (SEQ ID NO: 5), GGFGGG (SEQ ID NO: 6), GGFGGE (SEQ ID NO: 7), GGFGGGFG (SEQ ID NO: 8), DGGF (SEQ ID NO: 9), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) can be preferably used. Among these, GGFG (SEQ ID NO: 3), GGFGG (SEQ ID NO: 4), GGFGS (SEQ ID NO: 5), GGFGGE (SEQ ID NO: 7), GDGGF (SEQ ID NO: 18), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) is preferred. GGFG (SEQ ID NO: 3), GDGGF (SEQ ID NO: 18), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), or KDGGFG (SEQ ID NO: 14) is more preferred. GGFG (SEQ ID NO: 3), DGGFG (SEQ ID NO: 10), $D^d$GGFG, or DG$^{Me}$GFG (SEQ ID NO: 11) is further preferred. Also preferably, $L^P$ is directly connected to the drug. $L^P$ is preferably GGFG (SEQ ID NO: 3).

When $L^1$ is —CH$_2$—C(=O)—NH—(CH$_2$)n$^4$-C(=O)— and $L^2$ is a single bond, as a production intermediate, a compound having a halogenoacetyl group and having a structure represented by the following formula:

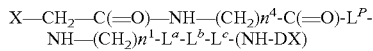

can be preferably used.

Here, preferably n$^4$ is 2 to 5, and the —NH—(CH$_2$)n$^1$-L$^a$-L$^b$-L$^c$-moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—.

As $L^P$, VK, VC, GFG, GGFG (SEQ ID NO: 3), GGFGG (SEQ ID NO: 4), GGFGS (SEQ ID NO: 5), GGFGGG (SEQ ID NO: 6), GGFGGE (SEQ ID NO: 7), GGFGGGFG (SEQ ID NO: 8), DGGF (SEQ ID NO: 9), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) can be preferably used. Among these, GGFG (SEQ ID NO: 3), GGFGG (SEQ ID NO: 4), GGFGS (SEQ ID NO: 5), GGFGGE (SEQ ID NO: 7), GDGGF (SEQ ID NO: 18), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) is preferred. GGFG (SEQ ID NO: 3), GDGGF (SEQ ID NO: 18), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), or KDGGFG (SEQ ID NO: 14) is more preferred. GGFG (SEQ ID NO: 3), DGGFG (SEQ ID NO: 10), $D^d$GGFG, or DG$^{Me}$GFG (SEQ ID NO: 11) is further preferred. Also preferably, $L^P$ is directly connected to the drug. X is preferably bromine or iodine.

Here, X in the above formula represents a bromine atom or an iodine atom. Any of such a bromine compound and iodine compound can be preferably used as a production intermediate.

When $L^1$ is —CH$_2$—C(=O)—NH—(CH$_2$)n$^4$-C(=O)— and $L^2$ is —N[—(CH$_2$CH$_2$—O)n$^7$-CH$_2$CH$_2$—OH]—CH$_2$—C(=O)—, as a production intermediate, a compound having a structure represented by the following formula:

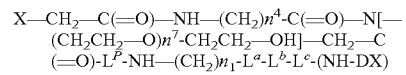

can be preferably used.

Here, preferably, n$^4$ is 2 to 5, n$^7$ is 3 or 4, and the —NH—(CH$_2$)n$^1$-L$^a$-L$^b$-L$^c$-moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—.

As $L^P$, VK, VC, GFG, GGFG (SEQ ID NO: 3), GGFGG (SEQ ID NO: 4), GGFGS (SEQ ID NO: 5), GGFGGG (SEQ ID NO: 6), GGFGGE (SEQ ID NO: 7), GGFGGGFG (SEQ ID NO: 8), DGGF (SEQ ID NO: 9), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) can be preferably used. Among these, GGFG (SEQ ID NO: 3), GGFGG (SEQ ID NO: 4), GGFGS (SEQ ID NO: 5), GGFGGE (SEQ ID NO: 7), GDGGF (SEQ ID NO: 18), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) is preferred. GGFG (SEQ ID NO: 3), GDGGF (SEQ ID NO: 18), DGGFG (SEQ ID NO: 10), $D^d$GGFG, DG$^{Me}$GFG (SEQ ID NO: 11), DGGFS (SEQ ID NO: 12), DDGGFG (SEQ ID NO: 13), or KDGGFG (SEQ ID NO: 14) is more preferred. GGFG (SEQ ID NO: 3), DGGFG (SEQ ID NO: 10), $D^d$GGFG, or DG$^{Me}$GFG (SEQ ID NO: 11) is further preferred. Also preferably, $L^P$ is directly connected to the drug. $L^P$ is preferably GGFG (SEQ ID NO: 3).

In order to secure the amount of the conjugate, a plurality of conjugates obtained under similar production conditions to have an equivalent number of drugs (e.g., about ±1) can be mixed to prepare new lots. In this case, the average number of drugs falls between the average numbers of drugs in the conjugates before the mixing.

2. Production Method 2

The antibody-drug conjugate represented by the formula (1) in which the bond to the antibody is an amide bond, the linker is a linker having a thioether bond, and -$L^1$-$L^2$- is a structure of —C(=O)-cyc.Hex(1,4)-$CH_2$—(N-ly-3-diminiccuS)-S—$(CH_2)^8$-C(=O)—, or a pharmacologically acceptable salt thereof can be also produced by the following method.

[Formula 31]

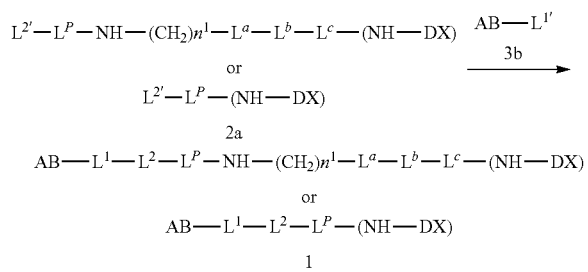

In the formula, AB-$L^{1'}$ represents a compound having a structure in which the antibody is connected to linker $L^1$ via an amide bond and further, the terminal of $L^1$ is converted to an N-maleimidyl group. That is, it is a structure in which -(N-ly-3-diminiccuS)- in AB—C(=O)-cyc.Hex(1,4)-$CH_2$—(N-ly-3-diminiccuS)-, is converted to a maleimidyl group. $L^{21}$ represents a group represented by HS—$(CH_2)^8$-C(=O)— having a terminal mercapto group, and AB represents an antibody.

That is, the antibody-drug conjugate (1) can be produced by reacting the compound (2a), which is obtainable by the method described below, with the linker-connected antibody (3b) having a maleimidyl group.

The antibody (3b) having a maleimidyl group can be also obtained by a method well known in the art (Hermanson, G. T, Bioconjugate Techniques, pp. 56-136, pp. 456-493, Academic Press (1996)). Examples can include a bifunctional linker such as succinimidyl 4-(N-maleimidomethyl)cyclohexane-1-carboxylate (SMCC) capable of binding to an amino group or a hydroxyl group and having a maleimidyl group is reacted with the amino group of the antibody to introduce the maleimidyl group, but it is not limited thereto.

For example, a compound in which a reactive moiety for an amino group and a reactive moiety for a thiol group are connected via a linker can be preferably used. Herein, the reactive moiety for an amino group can be active ester, imide ester, or the like, and the thiol reactive moiety can be maleimidyl, acetyl halide, alkyl halide, dithiopyridyl, or the like.

Examples of a method for constructing the antibody-drug conjugate via an amide bond at the amino group or hydroxyl group, particularly, amino group, of the amino acid constituting the antibody include a method using the linker-connected antibody (3b) of the present invention having a maleimidyl group. As a compound that is reacted with the antibody for obtaining this compound, a compound known in the art and represented by the following formula:

$Q^1$-$L^{1a}$-$Q^2$

[in the formula, $Q^1$ represents (Pyrrolidine-2,5-dione-N-yl)-O—C(=O)—, (3-Sulfo-pyrrolidine-2,5-dione-N-yl)-O—C(=O)—, $R^Q$—O—C(=N)—, or O=C=N—, $L^{1a}$-represents -cyc.Hex(1,4)-$CH_2$—, an alkylene group having 1 to 10 carbon atoms, a phenylene group, —$(CH_2)$$n^4$-C(=O)—, —$(CH_2)_{n^{4a}}$-NH—C(=O)—$(CH_2)_{n^{4b}}$-, or —$(CH_2)_{n^{4a}}$-NH—C(=O)-cyc.Hex(1,4)-$CH_2$—, $Q^2$ represents (maleimid-N-yl), a halogen atom, or —S—S-(2-Pyridyl), $R^Q$ represents an alkyl group having 1 to 6 carbon atoms, $n^4$ represents an integer of 1 to 8, $n^{4a}$ represents an integer of 0 to 6, and $n^{4b}$ represents an integer of 1 to 6]

can be preferably used.

Here, $R^Q$ can be an alkyl group having 1 to 6 carbon atoms and is more preferably a methyl group or an ethyl group.

The alkylene group of $L^{1a}$ can have 1 to 10 carbon atoms. The phenylene group may be ortho-, meta-, or para-phenylene and is more preferably para- or meta-phenylene.

Preferred examples of $L^{1a}$ can include -cyc.Hex(1,4)-$CH_2$—, —$(CH_2)_5$—NH—C(=O)-cyc.Hex(1,4)—$CH_2$—, —$(CH_2)_2$—NH—C(=O)—$CH_2$—, —$(CH_2)_5$—NH—C(=O)—$(CH_2)_2$—, —$CH_2$—, —$(CH_2)_2$—, —$(CH_2)_3$—, —$(CH_2)_5$—, —$(CH_2)_{10}$—, -(para-Ph)-, -(meta-Ph)-, -(para-Ph)-CH(-Me)-, —$(CH_2)_3$-(meta-Ph)-, and -(meta-Ph)-NH—C(=O)—$CH_2$—.

$Q^1$ is preferably (Pyrrolidine-2,5-dione-N-yl)-O—C(=O)—, and $Q^2$ is preferably (maleimid-N-yl). In order to form a disulfide bond, —S—S-(2-Pyridyl) can be used.

Here, (Pyrrolidine-2,5-dione-N-yl)- is a group represented by the following formula:

[Formula 32]

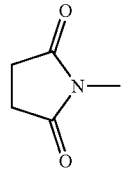

wherein the nitrogen atom is the connecting position, (3-Sulfo-pyrrolidine-2,5-dione-N-yl)- is a group represented by the following formula:

[Formula 33]

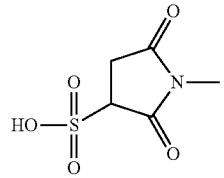

wherein the nitrogen atom is the connecting position, and this sulfonic acid is capable of forming a lithium salt, a sodium salt, or a potassium salt, preferably a sodium salt, cyc.Hex(1,4) represents a 1,4-cyclohexylene group, (maleimid-N-yl) is a group represented by the following formula:

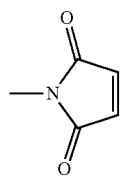

[Formula 34]

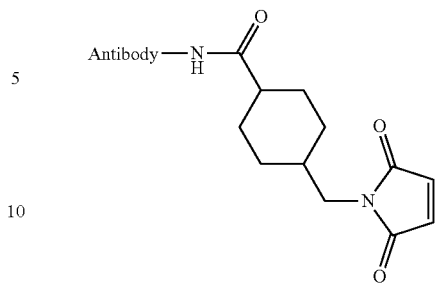

[Formula 35]

wherein the nitrogen atom is the connecting position, (2-Pyridyl) represents a 2-pyridyl group, (para-Ph) represents a para-phenylene group, and (meta-Ph) represents a meta-phenylene group.

As such a compound, in addition to the above compound, sulfosuccinimidyl 4-(N-maleimidylmethyl)cyclohexane-1-carboxylate (sulfo-SMCC), N-succinimidyl-(N-maleimidylmethyl)-cyclohexane-1-carboxy-(6-amidocaproate) (LC-SMCC), κ-maleimidylundecanoic acid N-succinimidyl ester (KMUA), γ-maleimidylbutyric acid N-succinimidyl ester (GMBS), ε-maleimidylcaproic acid N-hydroxysuccinimide ester (EMCS), m-maleimidylbenzoyl-N-hydroxysuccinimide ester (MBS), N-(α-maleimidylacetoxy)-succinimide ester (AMAS), succinimidyl-6-(β-maleimidylpropionamido)hexanoate (SMPH), N-succinimidyl 4-(p-maleimidylphenyl)-butyrate (SMPB), N-(p-maleimidylphenyl)isocyanate (PMPI), N-succinimidyl-4-(iodoacetyl)-aminobenzoate (SIAB), N-succinimidyl iodoacetate (SIA), N-succinimidyl bromoacetate (SBA), N-succinimidyl 3-(bromoacetamide)propionate (SBAP), N-succinimidyl-3-(2-pyridodithio)propionate (SPDP), and succinimidyloxycarbonyl-α-methyl-α-(2-pyridyldithio)toluene (SMPT), for example, may be used.

Specifically, for example, the antibody (3) can be reacted with 2 to 6 equivalents of SMCC in a phosphate buffer of pH 6 to 7 at room temperature for 1 to 6 hours so that the active ester of SMCC is reacted with the antibody to obtain the antibody (3b) having a maleimidyl group. The obtained antibody (3b) can be purified by the Common procedure D-2 below and used for the next reaction with the compound (2a).

The amino group and the hydroxyl group of the antibody to be connected with the linker moiety indicate, for example, the N-terminal amino group of the antibody and/or an amino group of a lysine residue of the antibody, and a hydroxyl group of a serine residue of the antibody, respectively, but they are not limited thereto.

The produced antibody-drug conjugate (1) can, after concentration, buffer exchange, purification, measurement of antibody concentration and average number of conjugated drug molecules per antibody molecule, and calculation of aggregate content, be subjected to identification of the antibody-drug conjugate (1) as mentioned in Production method 1.

In Production method 2, the compound represented by the formula (3b) has the following structure (in the structure of the following formula, "Antibody-NH-" originates from an antibody).

A compound having the above structure, which is an intermediate for producing the antibody-drug conjugate of the present invention, is as follows (in the formula, n is an integer of 1 to 10 and is preferably 2 to 8, more preferably 3 to 8).

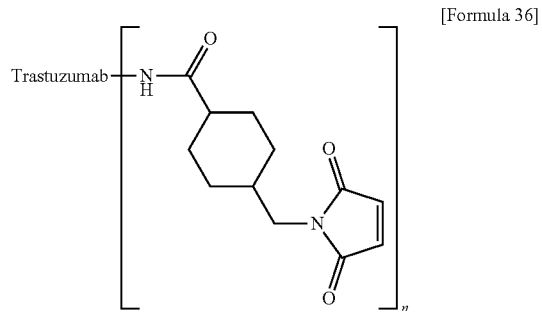

[Formula 36]

As a compound having a linker-drug moiety for reaction with the above intermediate, in which $L^1$-$L^2$-has a structure of —C(=O)-cyc.Hex(1,4)-CH$_2$—(N-ly-3-diminiccuS)-S—(CH$_2$)n$^8$-C(=O)— and the terminal for constructing the antibody-drug conjugate is a mercapto group, a compound having a structure represented by the following formula:

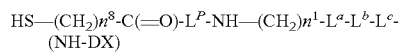

can be preferably used.

Here, preferably, $n^8$ is 2 to 5, and the —NH—(CH$_2$)n$^1$-$L^a$-$L^b$-$L^c$-moiety is —NH—CH$_2$CH$_2$—C(=O)—, —NH—CH$_2$CH$_2$CH$_2$—C(=O)—, —NH—CH$_2$—O—CH$_2$—C(=O)—, or —NH—CH$_2$CH$_2$—O—CH$_2$—C(=O)—.

As $L^p$, VK, VC, GFG, GGFG (SEQ ID NO: 3), GGFGG (SEQ ID NO: 4), GGFGS (SEQ ID NO: 5), GGFGGG (SEQ ID NO: 6), GGFGGE (SEQ ID NO: 7), GGFGGGFG (SEQ ID NO: 8), DGGF (SEQ ID NO: 9), DGGFG (SEQ ID NO: 10), D$^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) can be preferably used. Among these, GGFG (SEQ ID NO: 3), GGFGG (SEQ ID NO: 4), GGFGS (SEQ ID NO: 5), GGFGGE (SEQ ID NO: 7), GDGGF (SEQ ID NO: 18), DGGFG (SEQ ID NO: 10), D$^d$GGFG, DG$^{Me}$GFG (SEQ ID NO: 11), DGGFS (SEQ ID NO: 12), DDGGFG (SEQ ID NO: 13), KDGGFG (SEQ ID NO: 14), KGGFG (SEQ ID NO: 15), EGGFG (SEQ ID NO: 16), or SGGFG (SEQ ID NO: 17) is preferred. GGFG (SEQ ID NO: 3), GDGGF (SEQ ID NO: 18), DGGFG (SEQ ID NO: 10), D$^d$GGFG, DG$^{Me}$GFG (SEQ ID NO: 11), DGGFS (SEQ ID NO: 12), DDGGFG (SEQ ID NO: 13), or KDGGFG (SEQ ID NO: 14) is more preferred. GGFG (SEQ ID NO: 3), DGGFG (SEQ ID NO: 10), D$^d$GGFG, or DG$^{Me}$GFG (SEQ ID NO: 11) is further preferred. Also preferably, L$^P$ is directly connected to the drug.

3. Production Method 3

The antibody-drug conjugate represented by the formula (1) in which the drug linker moiety is connected to the antibody via an amide bond, or a pharmacologically acceptable salt thereof can be produced by a method described below. When L$^1$ is, for example, —C(=O)—(CH$_2$)n$^5$-C(=O)—, L$^{1\prime}$ in which it is further converted to active ester, for example, (Pyrrolidine-2,5-dione-N-yl)-O—C(=O)—(CH$_2$)n$^5$-C(=O)—, can be preferably used. When L$^2$ is a single bond, the antibody-drug conjugate can be produced by the following method, for example.

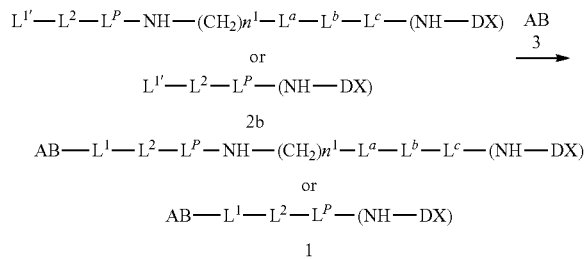

[Formula 37]

That is, the antibody-drug conjugate (1) can be produced by reacting the compound (2b), which is obtainable by the method described below, with the antibody (3).

The compound (2b) is capable of binding to an amino group or a hydroxyl group of the antibody. The amino group and the hydroxyl group of the antibody, as described in Production method 2, indicate, for example, the N-terminal amino group of the antibody and/or an amino group of a lysine residue of the antibody, and a hydroxyl group of a serine residue of the antibody, respectively, but they are not limited thereto.

Although the compound (2b) is an active ester containing an N-hydroxysuccinimidyl ester group, other active esters, for example, a sulfosuccinimidyl ester group, N-hydroxyphthalimidyl ester, N-hydroxysulfophthalimidyl ester, ortho-nitrophenyl ester, para-nitrophenyl ester, 2,4-dinitrophenyl ester, 3-sulfonyl-4-nitrophenyl ester, 3-carboxy-4-nitrophenyl ester, or pentafluorophenyl ester may be used.

Using 2 to 20 molar equivalents of the compound (2b) per the antibody (3) in the reaction between the compound (2b) and the antibody (3), the antibody-drug conjugate (1) in which 1 to 10 drug molecules are conjugated per antibody molecule can be produced. Specifically, the solution containing the compound (2b) dissolved therein can be added to a buffer solution containing the antibody (3) for the reaction to produce the antibody-drug conjugate (1). Herein, examples of the buffer solution which may be used include sodium acetate solution, sodium phosphate, and sodium borate. The pH for the reaction is 5 to 9, and more preferably the reaction is performed near pH 7. Examples of the solvent for dissolving the compound (2b) include an organic solvent such as dimethyl sulfoxide (DMSO), dimethylformamide (DMF), dimethylacetamide (DMA), and N-methyl-2-pyridone (NMP). It is sufficient that the organic solvent solution containing the compound (2b) dissolved therein is added at 1 to 20% v/v to a buffer solution containing the antibody (3) for the reaction. The reaction temperature is 0 to 37° C., more preferably 10 to 25° C., and the reaction time is 0.5 to 20 hours.

The produced antibody-drug conjugate (1) can, after concentration, buffer exchange, purification, and measurement of antibody concentration and average number of conjugated drug molecules per antibody molecule, be subjected to identification of the antibody-drug conjugate (1) in the same manner as Production method 1.

In Production method 3, (Pyrrolidine-2,5-dione-N-yl)-O—C(=O)—(CH$_2$)n$^5$-C(=O)— has the following structure.

[Formula 38]

When L$^1$ is —C(=O)—(CH$_2$)n$^5$-C(=O)—, examples of the compound for connecting the linker-drug moiety to the antibody via an amide bond can include a linker-drug compound having a structure having the above structure moiety at the terminal.

4. Production Method 4

The compound represented by the formula (2) or (2b) as an intermediate used in the previous production method or a pharmacologically acceptable salt thereof can be produced by the following method, for example.

[Formula 39]

NH$_2$—DX

4

↓ P$^1$—NH—(CH$_2$)n$^1$—L$^a$—L$^b$—L$^c$—OH

5

P$^1$—NH—(CH$_2$)n$^1$—L$^a$—L$^a$—L$^b$—(NH—DX)

6

↓

NH$_2$—(CH$_2$)n$^1$—L$^a$—L$^b$—L$^c$—OP$^3$

12

↓ P$^2$—L$^p$—OH

8

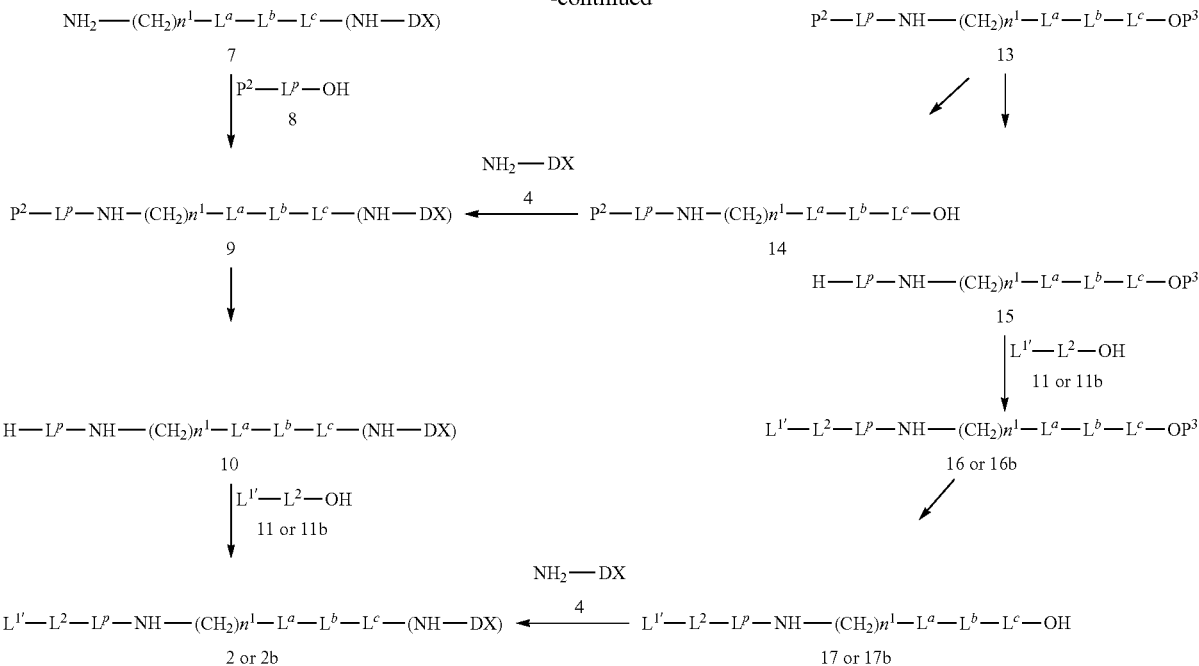

In the formula, $L^c$ is —C(=O)— and is connected to —(NH-DX) by forming an amide bond, $L^{11}$ corresponds to $L^1$ having a structure in which the terminal is converted to a maleimidyl group, a haloacetyl group, or (Pyrrolidine-2,5-dione-N-yl)-O—C(=O)—(CH$_2$)n$^4$-C(=O)—, and $P^1$, $P^2$ and $P^3$ each represent a protecting group.

The compound (6) can be produced by derivatizing the carboxylic acid (5) into an active ester, mixed acid anhydride, acid halide, or the like and reacting it with NH$_2$-DX [which indicates exatecan; chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione] (4) or a pharmacologically acceptable salt thereof. Also, a suitable base may be added.

Reaction reagents and conditions that are commonly used for peptide synthesis can be employed for the reaction. There are various kinds of active ester. For example, it can be produced by reacting phenols such as p-nitrophenol, N-hydroxybenzotriazole, N-hydroxysuccinimide, or the like, with the carboxylic acid (5) using a condensing agent such as N,N'-dicyclohexylcarbodiimide or 1-ethyl-3-(3-dimethylaminopropyl)carbodiimide hydrochloride. Further, the active ester can be also produced by a reaction of the carboxylic acid (5) with pentafluorophenyl trifluoroacetate or the like; a reaction of the carboxylic acid (5) with 1-benzotriazolyl oxytripyrrolidinophosphonium hexafluorophosphite; a reaction of the carboxylic acid (5) with diethyl cyanophosphonate (salting-in method); a reaction of the carboxylic acid (5) with triphenylphosphine and 2,2'-dipyridyl disulfide (Mukaiyama's method); a reaction of the carboxylic acid (5) with a triazine derivative such as 4-(4,6-dimethoxy-1,3,5-triazin-2-yl)-4-methylmorpholinium chloride (DMTMM); or the like. Further, the reaction can be also performed by, e.g., an acid halide method by which the carboxylic acid (5) is treated with an acid halide such as thionyl chloride and oxalyl chloride. By reacting the active ester, mixed acid anhydride, or acid halide of the carboxylic acid (5) obtained as above with the compound (4) in the presence of a suitable base in an inert solvent at −78° C. to 150° C., the compound (6) can be produced. (Meanwhile, "inert solvent" indicates a solvent which does not inhibit a reaction for which the solvent is used). Also, a suitable base may be added.

Specific examples of the base used for each step described above include a carbonate of an alkali metal or an alkali earth metal, an alkali metal alkoxide, and an alkali metal hydroxide or hydride, such as sodium carbonate, potassium carbonate, sodium ethoxide, potassium butoxide, sodium hydroxide, potassium hydroxide, sodium hydride, and potassium hydride; an organometallic base represented by an alkyl lithium such as n-butyl lithium, or dialkylamino lithium such as lithium diisopropylamide; an organometallic base of bissilylamine such as lithium bis(trimethylsilyl) amide; and an organic base such as pyridine, 2,6-lutidine, collidine, 4-dimethylaminopyridine, triethylamine, N-methyl morpholine, diisopropylethylamine, and diazabicyclo[5.4.0]undec-7-ene (DBU).

Examples of the inert solvent which is used for the reaction of the present invention include a halogenated hydrocarbon solvent such as dichloromethane, chloroform, and carbon tetrachloride; an ether solvent such as tetrahydrofuran, 1,2-dimethoxyethane, and dioxane; an aromatic hydrocarbon solvent such as benzene and toluene; and an amide solvent such as N,N-dimethylformamide, N,N-dimethylacetamide, and N-methylpyrrolidin-2-one. In addition to these, a sulfoxide solvent such as dimethyl sulfoxide and sulfolane; an alcohol solvent such as methanol and ethanol; and a ketone solvent such as acetone and methyl ethyl ketone may be used in some cases.

In $L^a$ and $L^b$ of the compound (6), as described below, a hydroxyl group, carboxy group, amino group, or the like thereof may be protected with a protecting group which is generally used for organic compound synthesis. Specifically, examples of the protecting group for a hydroxyl group can include an alkoxymethyl group such as a methoxymethyl group; an arylmethyl group such as a benzyl group, a 4-methoxybenzyl group, and a triphenylmethyl group; an alkanoyl group such as an acetyl group; an aroyl group such as a benzoyl group; and a silyl group such as a tert-butyl diphenylsilyl group. A carboxy group can be protected, e.g., as an ester with an alkyl group such as a methyl group, an ethyl group, and a tert-butyl group, an allyl group, or an arylmethyl group such as a benzyl group. An amino group can be protected with a protecting group for an amino group which is generally used for peptide synthesis, for example, an alkyloxy carbonyl group such as a tert-butyloxy carbonyl group, a methoxycarbonyl group, and an ethoxycarbonyl group; an arylmethyl group such as allyloxycarbonyl, a 9-fluorenylmethyloxy carbonyl group, a benzyloxy carbonyl group, a paramethoxybenzyloxy carbonyl group, and a para (or ortho)nitrobenzyloxy carbonyl group; an alkanoyl group such as an acetyl group; an arylmethyl group such as a benzyl group and a triphenyl methyl group; an aroyl group such as a benzoyl group; and an aryl sulfonyl group such as a 2,4-dinitrobenzene sulfonyl group or an orthonitrobenzene sulfonyl group. The above protecting groups can be introduced and removed according to a method usually carried out.

As for the protecting group $P^1$ for the terminal amino group of the compound (6), a protecting group for an amino group which is generally used for peptide synthesis, for example, a tert-butyloxy carbonyl group, a 9-fluorenylmethyloxy carbonyl group, or a benzyloxy carbonyl group, can be used. Examples of other protecting groups for an amino group include an alkanoyl group such as an acetyl group; an alkoxycarbonyl group such as a methoxycarbonyl group and an ethoxycarbonyl group; an arylmethoxy carbonyl group such as a paramethoxybenzyloxy carbonyl group, and a para (or ortho)nitrobenzyloxy carbonyl group; an arylmethyl group such as a benzyl group and a triphenyl methyl group; an aroyl group such as a benzoyl group; and an aryl sulfonyl group such as a 2,4-dinitrobenzene sulfonyl group and an orthonitrobenzene sulfonyl group. The protecting group $P^1$ can be selected depending on, e.g., the properties of the compound having the amino group to be protected.

By deprotecting the protecting group $P^1$ for the terminal amino group of the compound (6) obtained, the compound (7) can be produced. Reagents and conditions can be selected depending on the protecting group.

The compound (9) can be produced by derivatizing the peptide carboxylic acid (8) having the N terminal protected with $P^2$ into an active ester, mixed acid anhydride, or the like and reacting it with the compound (7) obtained. The reaction conditions, reagents, base, and inert solvent used for forming a peptide bond between the peptide carboxylic acid (8) and the compound (7) can be suitably selected from those described for the synthesis of the compound (6). The protecting group $P^2$ can be suitably selected from those described for the protecting group of the compound (6), and the selection can be made based on, e.g., the properties of the compound having the amino group to be protected. As it is generally used for peptide synthesis, by repeating sequentially the reaction and deprotection of the amino acid or peptide constituting the peptide carboxylic acid (8) for elongation, the compound (9) can be also produced.

By deprotecting the protecting group $P^2$ for the amino group of the compound (9) obtained, the compound (10) can be produced. Reagents and conditions can be selected depending on the protecting group.

The compound (2) or (2b) can be produced by derivatizing the carboxylic acid (11) or (11b) into an active ester, mixed acid anhydride, acid halide, or the like and reacting it with the compound (10) obtained. The reaction conditions, reagents, base, and inert solvent used for forming a peptide bond between the carboxylic acid (11) or (11b) and the compound (10) can be suitably selected from those described for the synthesis of the compound (6).

The compound (9) can be also produced by the following method, for example.

The compound (13) can be produced by derivatizing the peptide carboxylic acid (8) having the N terminal protected with $P^2$ into an active ester, mixed acid anhydride, or the like and reacting it in the presence of a base with the amine compound (12) having the carboxy group protected with $P^3$. The reaction conditions, reagents, base, and inert solvent used for forming a peptide bond between the peptide carboxylic acid (8) and the compound (12) can be suitably selected from those described for the synthesis of the compound (6). The protecting group $P^2$ for the amino group of the compound (13) can be suitably selected from those described for the protecting group of the compound (6). As for the protecting group $P^3$ for a carboxy group, a protecting group commonly used as a protecting group for a carboxy group in organic synthetic chemistry, in particular, peptide synthesis can be used. Specifically, it can be suitably selected from those described for the protecting group of the compound (6), for example, esters with an alkyl group such as a methyl group, an ethyl group, or a tert-butyl, allyl esters, and benzyl esters. It is necessary in this case that the protecting group for an amino group and the protecting group for a carboxy group should be the protecting groups that can be removed by a different method or different conditions. For example, a representative example includes a combination in which $P^2$ is a tert-butyloxy carbonyl group and $P^3$ is a benzyl group. The protecting groups can be selected from the aforementioned ones depending on, e.g., the properties of the compounds having the amino group and the carboxy group to be protected. For removal of the protecting groups, reagents and conditions can be selected depending on the protecting group.

By deprotecting the protecting group $P^3$ for the carboxy group of the compound (13) obtained, the compound (14) can be produced. Reagents and conditions can be selected depending on the protecting group.

The compound (9) can be produced by derivatizing the compound (14) obtained into an active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and inert solvent used for the reaction can be suitably selected from those described for the synthesis of the compound (6).

The compound (2) or (2b) can be also produced by the following method, for example.

By deprotecting the protecting group $P^2$ for the amino group of the compound (13), the compound (15) can be produced. Reagents and conditions can be selected depending on the protecting group.

The compound (16) or (16b) can be produced by derivatizing the carboxylic acid derivative (11) or (11b) into an active ester, mixed acid anhydride, acid halide, or the like and reacting it in the presence of a base with the compound (15) obtained. The reaction conditions, reagents, base, and inert solvent used for forming an amide bond between the peptide carboxylic acid (11) or (11b) and the compound (15) can be suitably selected from those described for the synthesis of the compound (6).

By deprotecting the protecting group for the carboxy group of the compound (16) or (16b) obtained, the compound (17) or (17b) can be produced. The deprotection can be carried out similarly to the deprotection at the carboxy group for producing the compound (14).

The compound (2) or (2b) can be produced by derivatizing the compound (17) or (17b) into an active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and inert solvent used for the reaction can be suitably selected from those described for the synthesis of the compound (6).

5. Production Method 5

The compound represented by the formula (2) of an intermediate can be also produced by the following method.

[Formula 40]

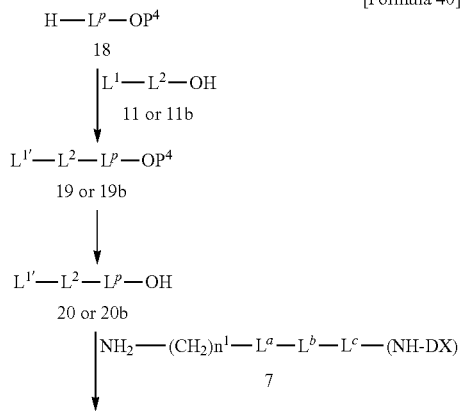

5-dione-N-yl)-O—C(=O)—$(CH_2)n^4$-C(=O)—, and $P^4$ represents a protecting group.

The compound (19) or (19b) can be produced by derivatizing the compound (11) or (11b) into an active ester, mixed acid anhydride, or the like and reacting it in the presence of a base with the peptide carboxylic acid (18) having the C terminal protected with $P^4$. The reaction conditions, reagents, base, and inert solvent used for forming a peptide bond between the peptide carboxylic acid (18) and the compound (11) can be suitably selected from those described for the synthesis of the compound (6). The protecting group $P^4$ for the carboxy group of the compound (18) can be suitably selected from those described for the protecting group of the compound (6).

By deprotecting the protecting group for the carboxy group of the compound (19) or (19b) obtained, the compound (20) or (20b) can be produced. The deprotection can be performed similar to the deprotection of the carboxy group for producing the compound (14).

The compound (2) can be produced by derivatizing the compound (20) or (20b) obtained into an active ester, mixed acid anhydride, or the like and reacting it with the compound (7). For the reaction, reaction reagents and conditions that are generally used for peptide synthesis can be also used, and the reaction conditions, reagents, base, and inert solvent used for the reaction can be suitably selected from those described for the synthesis of the compound (6).

6. Production Method 6

A compound as the production intermediate (2a) described in Production method 2 in which $L^{21}$ corresponds to $L^2$ having a structure in which the terminal is converted to a mercaptoalkanoyl group can be produced by the following method.

[Formula 41]

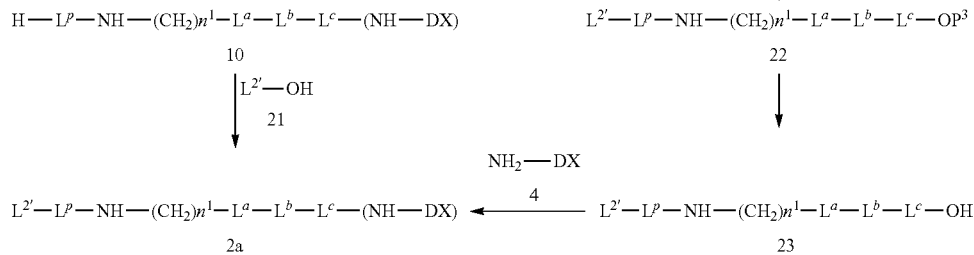

In the formula, $L^c$ is —C(=O)— and is connected to —(NH-DX) by forming an amide bond, $L^{11}$ corresponds to $L^1$ having a structure in which the terminal is converted to a maleimidyl group, a haloacetyl group, or (Pyrrolidine-2, The compound (2a) can be produced by derivatizing the carboxylic acid (21) having a terminal mercapto group into an active ester, mixed acid anhydride, or the like and reacting it with the compound (10). For the reaction, reaction reagents and conditions that are generally used for peptide synthesis can be also used, and the reaction conditions, reagents, base, and inert solvent used for the reaction can be suitably selected from those described for the synthesis of the compound (4).

Also, the compound (23) can be produced by derivatizing the compound (21) into an active ester, mixed acid anhydride, acid halide, or the like, reacting it with the compound (15), and deprotecting the protecting group for the carboxy group of the compound (22) obtained.

The compound (2a) can be produced by derivatizing the compound (23) into an active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and inert solvent used for the reaction can be suitably selected from those described for the synthesis of the compound (6).

7. Production Method 7

Hereinbelow, the method for producing the compound (10') having $n^1=1$, $L^a=O$, and $L^b=CR^2(R^3)$ in the production intermediate (10) described in Production method 4 is described in detail. The compound represented by the formula (10'), a salt or a solvate thereof can be produced by the following method, for example.

[Formula 42]

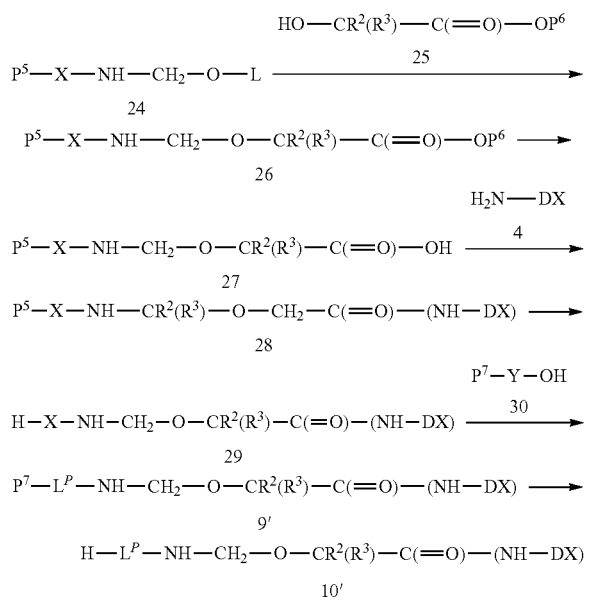

In the formula, $L^P$, $R^2$, and $R^3$ are as defined above, L represents an acetyl group or a hydrogen atom, or the like, X and Y each independently represent one amino acid residue or an oligopeptide consisting of 2 or 3 amino acids, $P^5$ and $P^7$ each represent a protecting group for an amino group, and $P^6$ represents a protecting group for a carboxy group.

A compound represented by the formula (24) can be produced by using or applying the method described in Japanese Patent Laid-Open No. 2002-60351 or the literature (J. Org. Chem., Vol. 51, page 3196, 1986), and by conducting removal of the protecting groups or modification of the functional groups, if necessary. Furthermore, it can be also obtained by treating an amino acid with the protected terminal amino group or an acid amide of an oligopeptide with the protected amino group with an aldehyde or a ketone.

By reacting the compound (24) with the compound (25) having a hydroxyl group at a temperature ranging from under cooling to room temperature in an inert solvent in the presence of an acid or a base, the compound (26) can be produced. Examples of the acid used include an inorganic acid such as hydrofluoric acid, hydrochloric acid, sulfuric acid, nitric acid, phosphoric acid, and boric acid; an organic acid such as acetic acid, citric acid, paratoluenesulfonic acid, and methanesulfonic acid; and a Lewis acid such as tetrafluoroborate, zinc chloride, tin chloride, aluminum chloride, and iron chloride. Paratoluenesulfonic acid is particularly preferable. As for the base used, any one of the already mentioned bases can be suitably selected and used. In particular, preferred examples thereof include an alkali metal alkoxide such as potassium tert-butoxide, an alkali metal hydroxide such as sodium hydroxide and potassium hydroxide; an alkali metal hydride such as sodium hydride and potassium hydride; an organometallic base represented by dialkylamino lithium such as lithium diisopropylamide; and an organometallic base of bissilylamine such as lithium bis(trimethylsilyl)amide. Examples of the solvent to be used for the reaction include an ether solvent such as tetrahydrofuran and 1,4-dioxane; and an aromatic hydrocarbon solvent such as benzene and toluene. Those solvents can be prepared as a mixture with water. Further, the protecting group for an amino group as exemplified by $P^5$ is not particularly limited provided it is a group commonly used for protection of an amino group. Representative examples include the protecting groups for an amino group that are described in Production method 4. However, in the present reaction, there may be cases in which the protecting group for an amino group as exemplified by $P^5$ is cleaved off. In such cases, a reaction needs to be performed with a suitable reagent for protecting an amino group as may be required.

The compound (27) can be produced by removing the protecting group $P^6$ of the compound (26). Herein, representative examples of the protecting group for a carboxy group as exemplified by $P^6$ are described in Production method 4, and it is desirable in this case that the protecting group $P^5$ for an amino group and protecting group $P^6$ for a carboxy group should be the protecting groups that can be removed by a different method or different conditions. For example, a representative example includes a combination in which $P^5$ is a 9-fluorenylmethyloxy carbonyl group and $P^6$ is a benzyl group. The protecting groups can be selected depending on, e.g., the properties of the compounds having the amino group and the carboxy group to be protected. For removal of the protecting groups, reagents and conditions can be selected depending on the protecting group.

The compound (29) can be produced by derivatizing the carboxylic acid (27) into an active ester, mixed acid anhydride, acid halide, or the like and reacting it with the compound (4) or a pharmacologically acceptable salt thereof in the presence of a base to produce the compound (28) followed by removing the protecting group $P^5$ of the compound (28) obtained. For the reaction between the compound (4) and the carboxylic acid (27) and the reaction for removing the protecting group $P^6$, the same reagents and reaction conditions as those described for Production method 4 can be used.

The compound (10') can be produced by reacting the compound (29) with an amino acid with the protected terminal amino group or the oligopeptide (30) with the protected amino group to produce the compound (9') and removing the protecting group $P^7$ of the compound (9') obtained. The protecting group for an amino group as exemplified by $P^7$ is not particularly limited provided it is generally used for protection of an amino group. Representative examples thereof include the protecting groups for an amino group that are described in Production method 4. For removing the protecting group, reagents and conditions can be selected depending on the protecting group. For the reaction between the compound (29) and the compound (30), reaction reagents and conditions that are commonly used for peptide synthesis can be employed. The compound (10') produced by the aforementioned method can be derivatized into the compound (1) of the present invention according to the production method described above.

8. Production Method 8

Hereinbelow, the method for producing the compound (2') or (2b') having $n^1=1$, $L^a=O$, and $L^b=CR^2(-R^3)$ in the production intermediate (2) described in Production method 4 is described in detail. The compound represented by the formula (2') or (2b'), a salt or a solvate thereof can be produced by the following method, for example.

tized into the compound (1) of the present invention according to the production method described above.

9. Production Method 9

Hereinbelow, the method for producing the compound (17') or (17b') having $n^1=1$, $L^a=O$, and $L^b=CR^2(R^3)$ in the production intermediate (17) described in Production method 4 is described in detail. The compound represented by the formula (17') or (17b'), a salt or a solvate thereof can be also produced by the following method, for example.

[Formula 44]

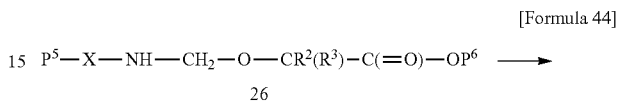

[Formula 43]

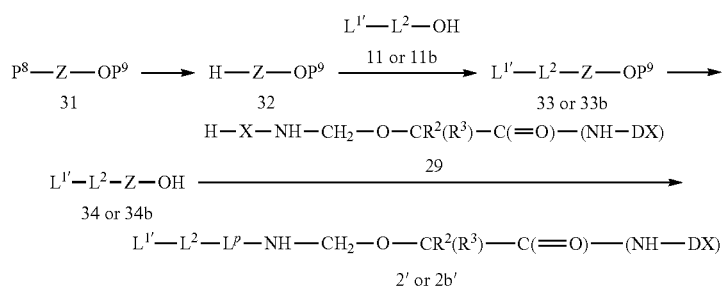

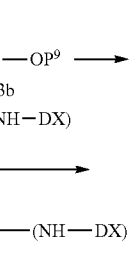

In the formula, $L^{11}$, If, $L^P$, $R^2$, and $R^3$ are as defined above, Z represents one amino acid residue or an oligopeptide consisting of 2 or 3 amino acids, $P^8$ represents a protecting group for an amino group, and $P^9$ represents a protecting group for a carboxy group.

The compound (33) or (33b) can be produced by removing the protecting group $P^8$ of the amino acid or oligopeptide (31) with the protected terminal amino group and carboxy group to produce the compound (32) and reacting the obtained amine form (32) with the compound (11) or (11b). The protecting group for an amino group as exemplified by $P^8$ is not particularly limited provided it is a group commonly used for protection of an amino group. Representative examples include the protecting groups for an amino group that are described in Production method 4. Further, for removing the protecting group $P^8$, reagents and conditions can be selected depending on the protecting group. For the reaction between the compound (32) and the carboxylic acid (11) or (11b), the same reagents and reaction conditions as those described for Production method 4 can be used.

The production intermediate (2') or (2b') was produced by removing the protecting group $P^9$ of the compound (33) or (33b) to produce the compound (34) or (34b) and reacting the obtained carboxylic acid (34) with the compound (29). The representative examples of the protecting group for a carboxy group as exemplified by $P^9$ are described in Production method 4. For the deprotection reaction thereof, the same reagents and reaction conditions as those described for Production method 4 can be used. For the reaction between the compound (29) and the carboxylic acid (34) or (34b), reaction reagents and conditions that are generally used for peptide synthesis can be employed. The compound (2') or (2b') produced by the aforementioned method can be deriva-

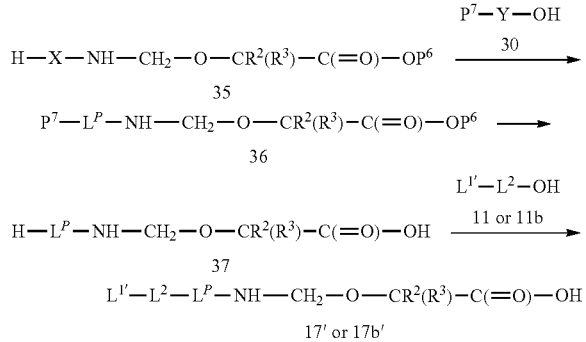

In the formula, $L^{11}$, $L^2$, $L^P$, $R^2$, $R^3$, X, Y, $P^5$, $P^6$, and $P^7$ are as defined above.

The compound (36) can be produced by deprotecting the protecting group $P^5$ for the amino group of the compound (26) with the protected terminal amino group and carboxy group to produce the compound (35) and reacting the obtained amine derivative (35) with the oligopeptide (30) with the protected terminal amino group or the protected amino group. The protecting group for an amino group as exemplified by $P^5$ is not particularly limited provided it is a group commonly used for protection of an amino group. Representative examples include the protecting groups for an amino group that are described in Production method 4. Further, for removing the protecting group $P^5$, reagents and conditions can be selected depending on the protecting group. Herein, although representative examples of the protecting group for a carboxy group as represented by $P^6$ and the protecting group for an amino group as represented by $P^7$ include the protecting groups for a carboxy group and an amino group that are described in Production method 4, it is desirable that the protecting group $P^6$ for a carboxy group and the protecting group $P^7$ for an amino group should be protecting groups that can be removed by the same method or the same conditions. For example, a representative example includes a combination in which $P^6$ is a benzyl ester group and $P^7$ is a benzyloxy carbonyl group.

The compound (37) can be produced by removing the protecting group $P^6$ for the carboxy group of the compound (36) and the protecting group $P^7$ for the amino group of the compound (36). The compound (37) can be also produced by sequentially removing the protecting group $P^6$ for the carboxy group and the protecting group $P^7$ for the amino group, and furthermore, the compound (37) can be produced simply by removing at once both of the protecting groups $P^6$ and $P^7$ that can be removed by the same method or the same conditions.

The compound (17') or (17b') can be produced by reacting the obtained compound (37) with the compound (11) or (11b). For the reaction between the compound (37) and the compound (11) or (11b), the same reagents and reaction conditions as those described for Production method 4 can be used.

10. Production Method 10

The compound represented by the formula (2) as an intermediate used in the previous production method, in which the linker has a structure represented by $-L^1-L^2-L^P-NH-(CH_2)n^1-L^a-L^b-L^c-$, and $L^P$ is a peptide residue having an N-terminal hydrophilic amino acid which is a hydrophilic amino acid other than glycine, or a pharmacologically acceptable salt thereof can be produced by the following method, for example.

[Formula 45]
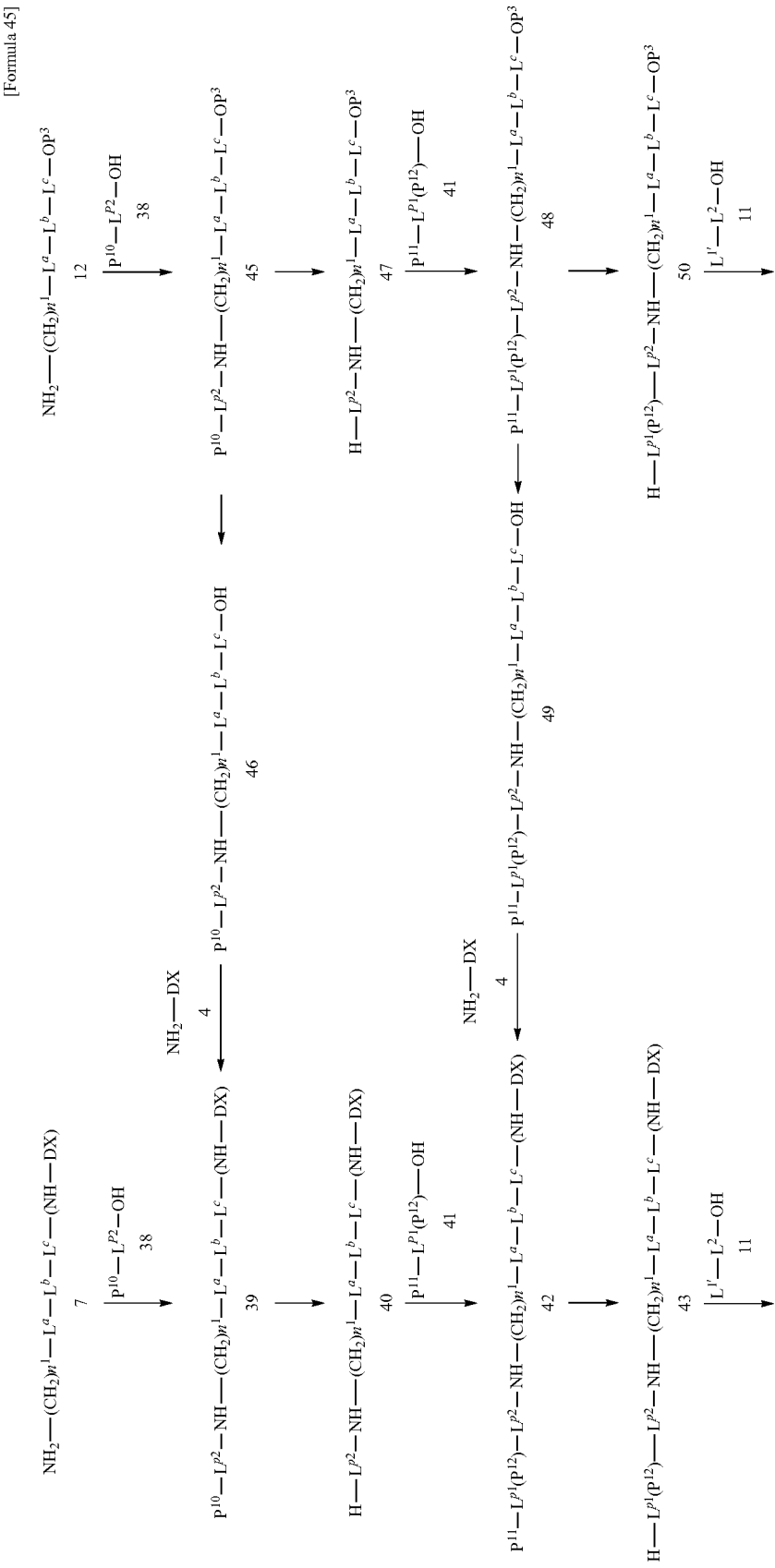

-continued
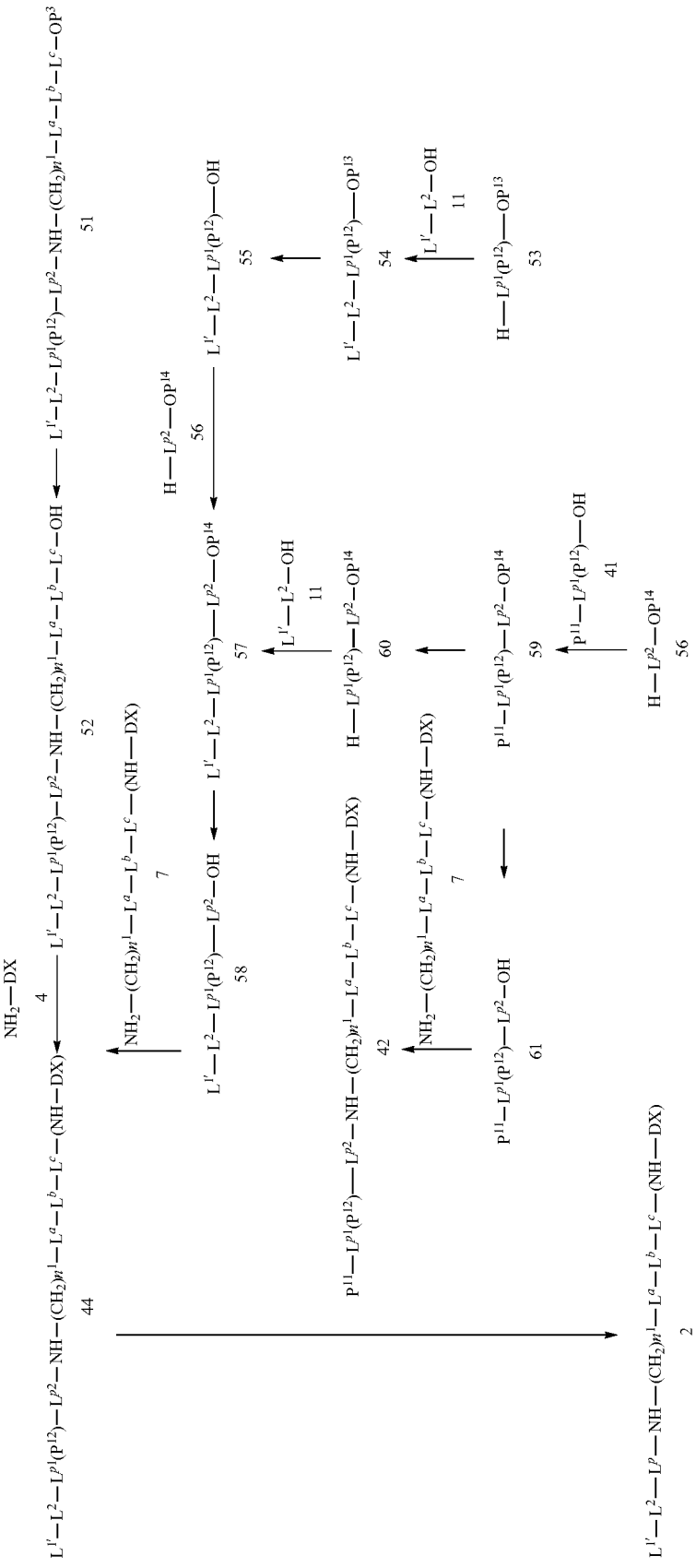

In the formula, $L^c$ represents a —C(=O)— group, $L^{11}$ corresponds to $L^1$ having a structure in which the terminal is converted to a maleimidyl group or a haloacetyl group, $L^P$ represents a structure consisting of $L^{P1}$-$L^{P2}$-, and $P^3$, $P^{10}$, $P^{11}$, $P^{12}$, $P^{13}$, and $P^{14}$ each represent a protecting group.

Since $L^P$ is formed by connecting $L^{P1}$ and $L^{P2}$, the N-terminal hydrophilic amino acid of $L^P$ is derived from $L^{P1}$. Therefore, $L^{P1}$ having an N-terminal hydrophilic amino acid can be adopted. It may be a plurality of hydrophilic amino acids. By adopting $L^{P2}$ having a hydrophilic amino acid, $L^P$ including a plurality of hydrophilic amino acids at the N terminal of $L^P$ or at the N terminal and other positions can be produced according to the position thereof.

The compound (39) can be produced by derivatizing the peptide or amino acid (38) having the N terminal protected with $P^{10}$ into an active ester, mixed acid anhydride, or the like and reacting it with the compound (7) obtained. The reaction conditions, reagents, base, and solvent used for forming an amide bond between the peptide or amino acid (38) and the compound (7) can be suitably selected from those described for the synthesis of the compound (6) unless the reaction is inhibited. The protecting group $P^{10}$ for an amino group can be suitably selected from those described for the protecting group of the compound (6), and the selection can be made based on, e.g., the properties of the compound. As it is generally used for peptide synthesis, by repeating sequentially the reaction and deprotection of the amino acid or peptide constituting the peptide or amino acid (38) for elongation, the compound (39) can be also produced.

By deprotecting the protecting group $P^{10}$ for the amino group of the compound (39) obtained, the compound (40) can be produced. Reagents and conditions can be selected depending on the protecting group.

The compound (42) can be produced by derivatizing the amino acid or peptide (41) having the N terminal protected with $P^{11}$ and the side chain carboxy group, hydroxyl group, or amino group protected with $P^{12}$ into an active ester, mixed acid anhydride, or the like and reacting it with the compound (40) obtained. The reaction conditions, reagents, base, and solvent used for forming a peptide bond between the amino acid or peptide (41) and the compound (40) can be suitably selected from those described for the synthesis of the compound (6). The protecting groups $P^{11}$ and $P^{12}$ can be suitably selected from those described for the protecting group for the amino group, the carboxy group, or the hydroxy group of the compound (6). However, it is necessary in this case that the protecting group $P^{11}$ for an amino group and protecting group $P^{12}$ for a side chain functional group should be the protecting groups that can be removed by a different method or different conditions. For example, a representative example includes a combination in which $P^{11}$ is a 9-fluorenylmethyloxy carbonyl group and $P^{12}$ is a tert-butyl group, etc. as the protecting group for a carboxy group, a methoxymethyl group, etc. as the protecting group for a hydroxyl group, or a tert-butyloxy carbonyl group, etc. as the protecting group for an amino group. The protecting group $P^{12}$ for a side chain functional group is preferably a protecting group that can be deprotected under acidic conditions, but it is not limited thereto, and the protecting group can be selected from the aforementioned ones depending on, e.g., the properties of the compound having the amino group, the carboxy group, or the hydroxyl group to be protected. For removal of the protecting groups, reagents and conditions can be selected depending on the protecting group. As it is generally used for peptide synthesis, by repeating sequentially the reaction and deprotection of the amino acid or peptide constituting the compound (42) for elongation, the compound (42) can be also produced.

By deprotecting the protecting group $P^{11}$ for the terminal amino group of the compound (42) obtained, the compound (43) can be produced. Reagents and conditions can be selected depending on the protecting group.

The compound (44) can be produced by derivatizing the carboxylic acid derivative (11) into an active ester, mixed acid anhydride, acid halide, or the like and reacting it with the compound (43) obtained. Herein, the carboxylic acid derivative (11) is a compound having a structure in which the linker terminal of $L^{11}$ has a maleimidyl group or a haloacetyl group.

The reaction conditions, reagents, base, and solvent used for forming a peptide bond between the carboxylic acid derivative (11) and the compound (43) can be suitably selected from those described for the synthesis of the compound (6).

By deprotecting the protecting group $P^{12}$ for the amino acid side chain carboxy group, hydroxyl group, or amino group of the peptide moiety of the compound (44) obtained, the compound (2) can be produced. Reagents and conditions can be selected depending on the protecting group.

The compound (39) can be also produced by the following method, for example.

The compound (45) can be produced by derivatizing the peptide or amino acid (38) having the N terminal protected with $P^{10}$ into an active ester, mixed acid anhydride, or the like and reacting it in the presence of a base with the amine compound (12) having the terminal carboxy group protected with $P^3$. The reaction conditions, reagents, base, and solvent used for forming a peptide bond between the peptide or amino acid (38) and the compound (12) can be suitably selected from those described for the synthesis of the compound (6). The protecting group $P^{10}$ for the amino group of the compound (45) can be suitably selected from those described for the protecting group of the compound (6). As for the protecting group $P^3$ for a carboxy group, a protecting group commonly used as a protecting group for a carboxy group in organic synthetic chemistry, in particular, peptide synthesis can be used. Specifically, it can be suitably selected from those described for the protecting group of the compound (6), for example, esters with an alkyl group such as a methyl group, an ethyl group, or a tert-butyl, allyl esters, and benzyl esters. It is necessary in this case that the protecting group $P^{10}$ for an amino group and protecting group $P^3$ for a carboxy group should be the protecting groups that can be removed by a different method or different conditions. For example, a representative example includes a combination in which $P^{10}$ is a tert-butyloxy carbonyl group and $P^3$ is a benzyl group. The protecting groups can be selected from the aforementioned ones depending on, e.g., the properties of the compounds having the amino group and the carboxy group to be protected. For removal of the protecting groups, reagents and conditions can be selected depending on the protecting group.

By deprotecting the protecting group $P^3$ for the carboxy group of the compound (45) obtained, the compound (46) can be produced. Reagents and conditions can be selected depending on the protecting group.

The compound (39) can be produced by derivatizing the compound (46) obtained into an active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

The compound (42) can be also produced by the following method, for example.

By deprotecting the protecting group $P^{10}$ for the amino group of the compound (45), the compound (47) can be produced. Reagents and conditions can be selected depending on the protecting group.

The compound (48) can be produced by derivatizing the amino acid or peptide (41) into an active ester, mixed acid anhydride, acid halide, or the like and reacting it in the presence of a base with the compound (47) obtained. The reaction conditions, reagents, base, and solvent used for forming an amide bond between the amino acid or peptide (41) and the compound (47) can be suitably selected from those described for the synthesis of the compound (6). Herein, it is necessary that the protecting groups $P^{11}$ and $P^{12}$ for the amino acid or peptide (41) and protecting group $P^3$ for the compound (47) should be the protecting groups that can be removed by a different method or different conditions. For example, a representative example includes a combination in which $P^{11}$ is a 9-fluorenylmethyloxy carbonyl group, $P^{12}$ is a tert-butyloxy carbonyl group, a tert-butyl group, or a methoxymethyl group, and $P^3$ is a benzyl group, etc. As mentioned above, the protecting group $P^{12}$ for a side chain functional group is preferably a protecting group that can be deprotected under acidic conditions, but it is not limited thereto, and the protecting group can be selected from the aforementioned ones depending on, e.g., the properties of the amino group, the carboxy group, or the hydroxyl group to be protected. For removal of the protecting groups, reagents and conditions can be selected depending on the protecting group.

By deprotecting the protecting group $P^3$ for the carboxy group of the compound (48) obtained, the compound (49) can be produced. Reagents and conditions can be selected depending on the protecting group.

The compound (42) can be produced by derivatizing the compound (49) into an active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

The compound (44) can be also produced by the following method, for example.

By deprotecting the protecting group $P^{11}$ for the amino group of the compound (48), the compound (50) can be produced. Reagents and conditions can be selected depending on the protecting group.

The compound (51) can be produced by derivatizing the carboxylic acid derivative (11) into an active ester, mixed acid anhydride, acid halide, or the like and reacting it in the presence of a base with the compound (50) obtained. The reaction conditions, reagents, base, and solvent used for forming an amide bond between the carboxylic acid derivative (11) and the compound (50) can be suitably selected from those described for the synthesis of the compound (6).

By deprotecting the protecting group $P^3$ for the carboxy group of the compound (51) obtained, the compound (52) can be produced. Reagents and conditions can be selected depending on the protecting group.

The compound (44) can be produced by derivatizing the compound (52) into an active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

The compound (44) can be also produced by the following method, for example.

The compound (54) can be produced by derivatizing the carboxylic acid derivative (11) into an active ester, mixed acid anhydride, acid halide, or the like and reacting it in the presence of a base with the amino acid or peptide (53) having the carboxy group protected with $P^{13}$ and the side chain carboxy group, hydroxyl group, or amino group protected with $P^{12}$. The reaction conditions, reagents, base, and solvent used for forming an amide bond between the carboxylic acid derivative (11) and the compound (53) can be suitably selected from those described for the synthesis of the compound (6). Herein, the protecting groups $P^{12}$ and $P^{13}$ for the compound (54) can be suitably selected from those described for the protecting group for the carboxy group, the hydroxyl group, or the amino group of the compound (6). However, it is necessary in this case that the protecting group $P^{13}$ for a carboxy group and protecting group $P^{12}$ for a side chain functional group should be the protecting groups that can be removed by a different method or different conditions. For example, a representative example includes a combination in which $P^{13}$ is a benzyl group and $P^{12}$ is a tert-butyl group, etc. as the protecting group for a carboxy group, a methoxymethyl group, etc. as the protecting group for a hydroxyl group, or a tert-butyloxy carbonyl group, etc. as the protecting group for an amino group. The protecting group $P^{12}$ for a side chain functional group is preferably a protecting group that can be deprotected under acidic conditions, but it is not limited thereto, and the protecting group can be selected from the aforementioned ones depending on, e.g., the properties of the compound having the amino group, the carboxy group, or the hydroxyl group to be protected. For removal of the protecting groups, reagents and conditions can be selected depending on the protecting group.

By deprotecting the protecting group $P^{13}$ for the carboxy group of the compound (54) obtained, the compound (55) can be produced. Reagents and conditions can be selected depending on the protecting group.

The compound (57) can be produced by derivatizing the compound (55) into an active ester, mixed acid anhydride, acid halide, or the like and reacting it in the presence of a base with the amino acid or peptide (56) having the carboxy group protected with $P^{14}$. For the reaction, reaction reagents and conditions that are generally used for peptide synthesis can be also used, and the reaction conditions, reagents, base, and solvent used for the reaction can be suitably selected from those described for the synthesis of the compound (6). Herein, the protecting groups $P^{12}$ and $P^{14}$ for the compound (57) can be suitably selected from those described for the protecting group for the carboxy group, the hydroxyl group, or the amino group of the compound (6). However, it is necessary in this case that the protecting group $P^{14}$ for a carboxy group and protecting group $P^{12}$ for a side chain functional group should be the protecting groups that can be removed by a different method or different conditions. For example, a representative example includes a combination in which $P^{14}$ is a benzyl group and $P^{12}$ is a tert-butyl group, etc. as the protecting group for a carboxy group, a methoxymethyl group, etc. as the protecting group for a hydroxyl group, or a tert-butyloxy carbonyl group, etc. as the protecting group for an amino group. The protecting group $P^{12}$ for a side chain functional group is preferably a protecting group that can be deprotected under acidic conditions, but it is not limited thereto, and the protecting group can be selected from the aforementioned ones depending on, e.g., the properties of the compound having the amino group, the carboxy group, or the hydroxyl group to be protected. For removal of the protecting groups, reagents and conditions can be selected depending on the protecting group. By repeating sequentially the reaction and deprotection of the amino acid or peptide constituting the compound (57) for elongation, the compound (57) can be also produced.

By deprotecting the protecting group $P^{14}$ for the carboxy group of the compound (57) obtained, the compound (58) can be produced. Reagents and conditions can be selected depending on the protecting group.

The compound (44) can be produced by derivatizing the compound (58) into an active ester, mixed acid anhydride, acid halide, or the like and reacting it with the compound (40) in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

The compound (57) can be also produced by the following method, for example.

The compound (59) can be produced by derivatizing the amino acid or peptide (56) into an active ester, mixed acid anhydride, acid halide, or the like and reacting it in the presence of a base with the amino acid or peptide (41) having the N terminal protected with $P^{11}$ and the side chain carboxy group, hydroxyl group, or amino group protected with $P^{12}$. The reaction conditions, reagents, base, and solvent used for forming a peptide bond between the amino acid or peptide (56) and the amino acid or peptide (41) can be suitably selected from those described for the synthesis of the compound (6). Herein, it is necessary that the protecting group $P^{14}$ for the carboxy group of the amino acid or peptide (56) and protecting groups $P^{11}$ and $P^{12}$ for the amino acid or peptide (41) should be, as mentioned above, the protecting groups that can be removed by a different method or different conditions. For example, a representative example includes a combination in which $P^{11}$ is a 9-fluorenylmethyloxy carbonyl group, $P^{12}$ is a tert-butyl group, etc. as the protecting group for a carboxy group, a methoxymethyl group, etc. as the protecting group for a hydroxyl group, or a tert-butyloxy carbonyl group, etc. as the protecting group for an amino group, and $P^7$ is a benzyl group. The protecting group $P^4$ for a side chain functional group is preferably a protecting group that can be deprotected under acidic conditions, but it is not limited thereto, and the protecting group can be selected from the aforementioned ones depending on, e.g., the properties of the compound having the amino group, the carboxy group, or the hydroxyl group to be protected. For removal of the protecting groups, reagents and conditions can be selected depending on the protecting group.

By deprotecting the protecting group $P^{11}$ for the N terminal of the peptide (59) obtained, the peptide (60) can be produced. Reagents and conditions can be selected depending on the protecting group.

The compound (57) can be produced by derivatizing the carboxylic acid derivative (11) into an active ester, mixed acid anhydride, acid halide, or the like and reacting it in the presence of a base with the peptide (60) obtained. The reaction conditions, reagents, base, and solvent used for forming an amide bond between the carboxylic acid derivative (11) and the peptide (60) can be suitably selected from those described for the synthesis of the compound (6).

The compound (42) can be also produced by the following method, for example.

By deprotecting the protecting group $P^{14}$ for the C terminal of the above peptide (59), the peptide (61) can be produced. Reagents and conditions can be selected depending on the protecting group.

The compound (42) can be produced by derivatizing the peptide (61) obtained into an active ester, mixed acid anhydride, acid halide, or the like and reacting it with the above compound (7) in the presence of a base. The reaction conditions, reagents, base, and solvent used for forming an amide bond between the peptide (61) and the compound (7) can be suitably selected from those described for the synthesis of the compound (6).

11. Production Method 11

The production intermediate represented by the formula (2) in which the linker has a structure represented by $-L^1-L^2-L^P-$, and $L^P$ is a peptide residue having an N-terminal hydrophilic amino acid which is a hydrophilic amino acid other than glycine can be also produced by the following method.

[Formula 46]

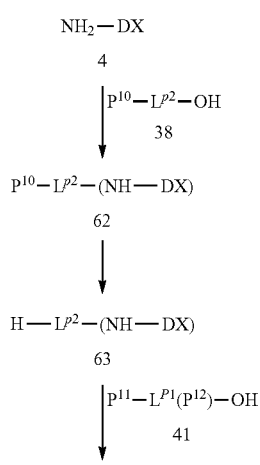

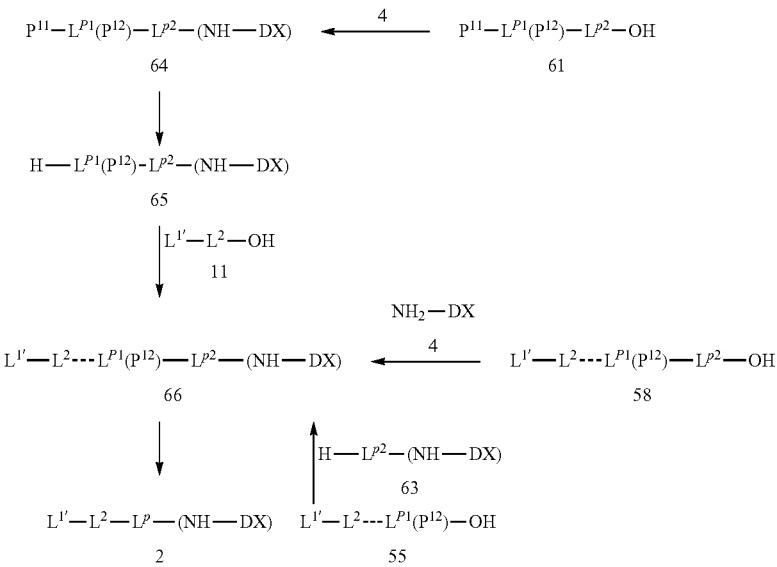

In the formula, $L^{11}$ corresponds to $L^1$ having a structure in which the terminal is converted to a maleimidyl group or a haloacetyl group, $L^P$ represents a structure consisting of $L^{P1}$-$L^{P2}$-, and $P^{10}$, $P^{11}$, $P^{12}$, and $P^{14}$ each represent a protecting group.

Since $L^P$ is formed by connecting $L^{P1}$ and $L^{P2}$, the N-terminal hydrophilic amino acid of $L^P$ is derived from $L^{P1}$. Therefore, $L^{P1}$ having an N-terminal hydrophilic amino acid can be adopted. It may be a plurality of hydrophilic amino acids. By adopting $L^{P2}$ having a hydrophilic amino acid, $L^P$ including a plurality of hydrophilic amino acids at the N terminal of $L^P$ or at the N terminal and other positions can be produced according to the position thereof.

The compound (62) can be produced by derivatizing the peptide or amino acid (38) having the N terminal protected with $P^{10}$ described in Production method 10 into an active ester, mixed acid anhydride, or the like and reacting it with the compound (4) or a salt thereof. The reaction conditions, reagents, base, and solvent used for forming a peptide bond between the peptide or amino acid (38) and the compound (4) can be suitably selected from those described for the synthesis of the compound (6) unless the reaction is inhibited. The protecting group $P^{10}$ can be suitably selected from those described for the protecting group of the compound (6), and the selection can be made based on, e.g., the properties of the compound having the amino group to be protected. As it is generally used for peptide synthesis, by repeating sequentially the reaction and deprotection of the amino acid or peptide constituting the peptide or amino acid (38) for elongation, the compound (62) can be also produced.

By deprotecting the protecting group $P^{10}$ for the amino group of the compound (62) obtained, the compound (63) can be produced. Reagents and conditions can be selected depending on the protecting group.

The compound (64) can be produced by derivatizing the amino acid or peptide (41) having the N terminal protected with $P^{11}$ and the side chain carboxy group, hydroxyl group, or amino group protected with $P^{12}$ described in Production method 10 into an active ester, mixed acid anhydride, or the like and reacting it with the compound (63) obtained. The reaction conditions, reagents, base, and solvent used for forming a peptide bond between the amino acid or peptide (41) and the compound (63) can be suitably selected from those described for the synthesis of the compound (6). The protecting groups $P^{11}$ and $P^{12}$ are as described in Production method 10. As it is generally used for peptide synthesis, by repeating sequentially the reaction and deprotection of the amino acid or peptide constituting the compound (64) for elongation, the compound (64) can be also produced.

By deprotecting the protecting group $P^{11}$ for the amino group of the compound (64) obtained, the compound (65) can be produced. Reagents and conditions can be selected depending on the protecting group.

The compound (66) can be produced by derivatizing the carboxylic acid derivative (11) into an active ester, mixed acid anhydride, acid halide, or the like and reacting it with the compound (65) obtained. The reaction conditions, reagents, base, and solvent used for forming a peptide bond between the carboxylic acid derivative (11) and the compound (65) can be suitably selected from those described for the synthesis of the compound (6).

By deprotecting the protecting group $P^{12}$ for the carboxy group, the hydroxyl group, or the amino group of the compound (66) obtained, the compound (2) can be produced. Reagents and conditions can be selected depending on the protecting group.

The compound (64) can be also produced by the following method, for example.

The compound (64) can be produced by derivatizing the peptide (61) described in Production method 10 into an active ester, mixed acid anhydride, acid halide, or the like and reacting it with the compound (4) or a salt thereof. The reaction conditions, reagents, base, and solvent used for forming a peptide bond between the peptide (61) and the compound (4) can be suitably selected from those described for the synthesis of the compound (6).

The compound (66) can be also produced by the following method, for example.

The compound (66) can be produced by derivatizing the compound (58) described in Production method 10 into an active ester, mixed acid anhydride, or the like and reacting it with the compound (4) in the presence of a base, or by derivatizing the amino acid or peptide (55) described in Production method 10 into an active ester, mixed acid anhydride, or the like and reacting it with the above compound (63) in the presence of a base. The reaction conditions, reagents, base, and solvent used for forming each peptide bond can be suitably selected from those described for the synthesis of the compound (6).

12. Production Method 12

The production intermediate represented by the formula (2) in which the linker has a structure of -$L^1$-$L^2$-$L^P$-NH—($CH_2$)$n^1$-$L^a$-$L^b$-$L^c$- or -$L^1$-$L^2$-$L^P$-, and $L^P$ is a peptide residue having an N-terminal hydrophilic amino acid which is a hydrophilic amino acid other than glycine can be also produced by the following method, for example.

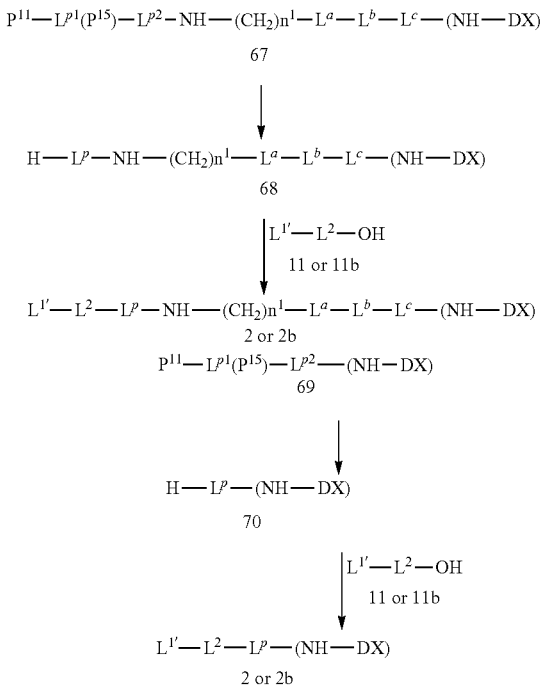

[Formula 47]

In the formula, $L^{11}$ corresponds to $L^1$ having a structure in which the terminal is converted to a maleimidyl group, a haloacetyl group, or (Pyrrolidine-2,5-dione-N-yl)-O—C(=O)—($CH_2$)$n^4$-C(=O)—, $L^P$ represents a structure consisting of $L^{p1}$-$L^{p2}$-, and $P^{11}$ and $P^{15}$ each represent a protecting group.

The production intermediate represented by the formula (2) has two forms, i.e., the linker has a structure represented by -$L^1$-$L^2$-$L^P$-NH—($CH_2$)$n^1$-$L^a$-$L^b$-$L^c$- and has a structure represented by -$L^1$-$L^2$-$L^P$-.

The compound (2) or (2b) in which the linker has a structure represented by -$L^1$-$L^2$-$L^P$-NH—($CH_2$)$n^1$-$L^a$-$L^b$-$L^c$-can be produced as follows.

The compound (67) can be synthesized in the same manner as in the compound (42) described in Production method 10. Unlike the compound (42), for the compound (67), it may not be necessary that the protecting group $P^{11}$ for an amino group and protecting group $P^{15}$ for a side chain functional group should be the protecting groups that can be removed by a different method or different conditions. The side chain functional group is a carboxy group or a hydroxyl group, and the protecting group $P^{11}$ for an amino group and the protecting group $P^{15}$ for a side chain carboxy group or hydroxyl group may be deprotected at the same time. For example, a representative example includes a combination in which $P^{11}$ is a tert-butyloxy carbonyl group and $P^{15}$ is a tert-butyl group or a trityl group, or $P^{11}$ is a benzyloxy carbonyl group and $P^{15}$ is a benzyl group, etc. The protecting groups can be suitably selected from those described for the protecting group of the compound (6), depending on, e.g., the properties of the compound having the amino group, the carboxy group, or the hydroxyl group to be protected. For removal of the protecting groups, reagents and conditions can be selected depending on the protecting group. The compound (67) can be synthesized in the same manner as Production method 10 by using a protected amino acid or peptide that satisfies the above properties.

By deprotecting, either sequentially or at the same time, the protecting groups $P^{11}$ and $P^{15}$ for the compound (67), the compound (68) can be produced. Reagents and conditions can be selected depending on the protecting group.

Although the hydrophilic side chain functional group of $L^P$ is not protected, the compound (2) or (2b) can be produced by reacting the compound (68) in the presence of a base with the compound (11) or (11b) derivatized into an active ester, mixed acid anhydride, or the like. The reaction conditions, reagents, base, and solvent used for forming each peptide bond can be suitably selected from those described for the synthesis of the compound (6).

The compound (2) or (2b) in which the linker has a structure represented by -$L^1$-$L^2$-$L^P$-can be produced as follows.

The compound (69) can be also synthesized in the same manner as in the compound (64) described in Production method 11. Unlike the compound (64), for the compound (69), it may not be necessary that the protecting group $P^{11}$ for an amino group and protecting group $P^{15}$ for a side chain functional group should be the protecting groups that can be removed by a different method or different conditions. The side chain functional group is a carboxy group or a hydroxyl group, and the protecting group $P^{11}$ for an amino group and the protecting group $P^{15}$ for a side chain carboxy group or hydroxyl group may be deprotected at the same time. For example, a representative example includes a combination in which $P^{11}$ is a tert-butyloxy carbonyl group and $P^{15}$ is a tert-butyl group or a trityl group, or $P^{11}$ is a benzyloxy carbonyl group and $P^{15}$ is a benzyl group, etc. The protecting groups can be suitably selected from those described for the protecting group of the compound (6), depending on, e.g., the properties of the compound having the amino group, the carboxy group, or the hydroxyl group to be protected. For removal of the protecting groups, reagents and conditions can be selected depending on the protecting group. The compound (69) can be synthesized in the same manner as Production method 11 by using a protected amino acid or peptide that satisfies the above properties.

By deprotecting, either sequentially or at the same time, the protecting groups $P^{11}$ and $P^{15}$ for the compound (69), the compound (70) can be produced. Reagents and conditions can be selected depending on the protecting group.

Although the Hydrophilic Side Chain Functional Group of $L^P$ is not protected, the compound (2) or (2b) can be produced by reacting the compound (70) in the presence of a base with the compound (11) or (11b) derivatized into an active ester, mixed acid anhydride, or the like. The reaction conditions, reagents, base, and solvent used for forming each peptide bond can be suitably selected from those described for the synthesis of the compound (6).

13. Production Method 13

The compound (64) shown in Production method 11, in which -$L^P$- in the linker has a structure consisting of -$L^{p1}$-Gly-Gly-Phe-Gly- (SEQ ID NO: 3) can be also produced by the following method.

[Formula 48]

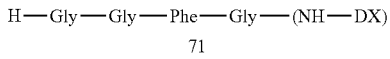
("Gly—Gly—Phe—Gly" disclosed as SEQ ID NO: 3)
H—Gly—Gly—Phe—Gly—(NH—DX)
71

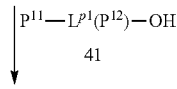
$P^{11}$—$L^{p1}(P^{12})$—OH
41

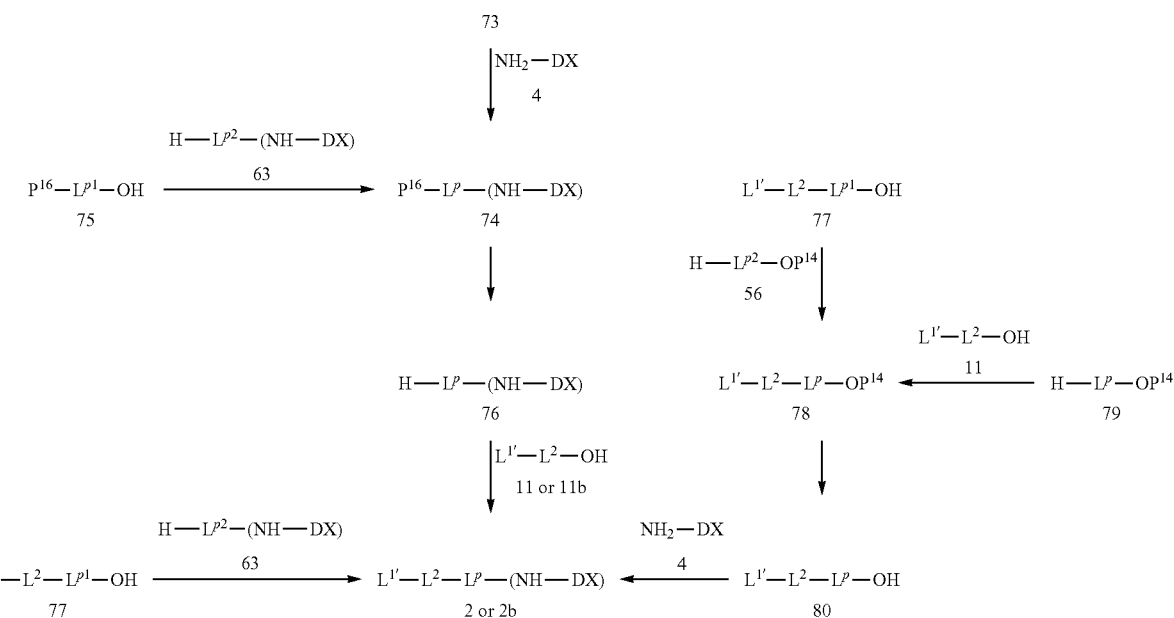

-continued $P^{11}$—$L^{p1}(P^{12})$—Gly—Gly—Phe—Gly—(NH—DX)
72

In the formula, $P^{11}$ and $P^{12}$ each represent a protecting group.

The compound (72) can be produced by derivatizing the amino acid or peptide (41) described in Production method 10 into an active ester, mixed acid anhydride, acid halide, or the like and reacting it in the presence of a base with glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (free form of a pharmaceutical compound described in International Publication No. WO 97/46260) (71) or a salt thereof. The reaction conditions, reagents, base, and solvent used for forming a peptide bond between the amino acid or peptide (41) and the compound (71) can be suitably selected from those described for the synthesis of the compound (6). The protecting group $P^{11}$ for the N terminal and the protecting group $P^{12}$ for a side chain functional group are as described above in Production method 10. The protecting group $P^{12}$ for a side chain functional group may be absent, and the compound (72) can be obtained by using the amino acid or peptide (41) protected only at its N terminal in the reaction.

14. Production Method 14

The compound represented by the formula (2) or (2b) in which the linker has a structure represented by -$L^1$-$L^2$-$L^P$-, or a pharmacologically acceptable salt thereof can be produced by the following method, for example.

[Formula 49]

In the formula, $L^{1'}$ corresponds to $L^1$ having a structure in which the terminal is converted to a maleimidyl group, a terminal haloacetyl group, or (Pyrrolidine-2,5-dione-N-yl)-O—C(=O)—(CH$_2$)n$^4$-C(=O)—, $L^P$ represents a structure consisting of $L^{p1}$-$L^{p2}$-, and $P^{14}$ and $P^{16}$ each represent a protecting group.

The peptide (73) is protected at its N terminal with $P^{16}$. As it is generally used for peptide synthesis, by repeating sequentially the condensation reaction and deprotection of the amino acid or peptide constituting the peptide (73), the peptide (73) can be synthesized.

The compound (74) can be produced by derivatizing the peptide (73) into an active ester, mixed acid anhydride, or the like and reacting it with the compound (4) or a salt thereof. The reaction conditions, reagents, base, and solvent used for forming a peptide bond between the peptide (73) and the compound (4) can be suitably selected from those described for the synthesis of the compound (6). The protecting group $P^{16}$ can be suitably selected from those described for the synthesis of the compound (6).

The compound (74) can be also produced by derivatizing the amino acid or peptide (75) having the N terminal protected with $P^{16}$ into an active ester, mixed acid anhydride, or the like and reacting it with the compound (63) described in Production method 11. The reaction conditions, reagents, base, and solvent used for forming a peptide bond between the amino acid or peptide (75) and the compound (63) can be suitably selected from those described for the synthesis of the compound (6). The protecting group $P^{16}$ can be suitably selected from those described for the synthesis of the compound (6).

By deprotecting the protecting group $P^{16}$ for the amino group of the compound (74) obtained, the compound (76) can be produced. Reagents and conditions can be selected depending on the protecting group.

The compound (2) or (2b) can be produced by derivatizing the carboxylic acid derivative (11) or (11b) into an active ester, mixed acid anhydride, acid halide, or the like and reacting it with the compound (76) obtained. The reaction conditions, reagents, base, and solvent used for forming an amide bond between the carboxylic acid derivative (11) or (11b) and the compound (76) can be suitably selected from those described for the synthesis of the compound (6).

The compound (2) can be also produced by the following method.

The compound (77) can be synthesized in the same manner as in the compound (55) described in Production method 10. The compound (78) can be produced by derivatizing the amino acid or peptide (56) described in Production method 10 into an active ester, mixed acid anhydride, acid halide, or the like and reacting it with the compound (77). Herein, the amino acid or peptide (56) is protected at its C terminal with $P^{14}$. The reaction conditions, reagents, base, and solvent used for forming an amide bond between the amino acid or peptide (56) and the compound (77) can be suitably selected from those described for the synthesis of the compound (6).

The compound (78) can be also produced by derivatizing the compound (11) into an active ester, mixed acid anhydride, or the like and reacting it with the peptide (79) having the C terminal protected with $P^{14}$. As it is generally used for peptide synthesis, by repeating sequentially the condensation reaction and deprotection of the amino acid or peptide constituting the peptide (79), the peptide (79) can be synthesized. The reaction conditions, reagents, base, and solvent used for forming a peptide bond between the peptide (79) and the compound (11) can be suitably selected from those described for the synthesis of the compound (6). The protecting group $P^{14}$ is preferably a protecting group that can be deprotected under acidic conditions, but it is not limited thereto, and can be suitably selected from those described for the synthesis of the compound (6).

By deprotecting the protecting group $P^{14}$ for the carboxy group of the compound (78) obtained, the compound (80) can be produced. Reagents and conditions can be selected depending on the protecting group.

The compound (2) can be produced by derivatizing the compound (80) into an active ester, mixed acid anhydride, or the like and reacting it with the compound (4) or a salt thereof. The reaction conditions, reagents, base, and solvent used for forming a peptide bond between the compound (80) and the compound (4) can be suitably selected from those described for the synthesis of the compound (6).

Additionally, the compound (2) can be also produced by the following method.

The compound (2) can be produced by derivatizing the compound (63) described in Production method 11 into an active ester, mixed acid anhydride, or the like and reacting it with the compound (77) in the presence of a base. The reaction conditions, reagents, base, and solvent used for forming a peptide bond between the compound (77) and the compound (63) can be suitably selected from those described for the synthesis of the compound (6).

15. Production Method 15

The production intermediate represented by the formula (2a) described in Production method 2, in which $L^{21}$ corresponds to $L^2$ having a structure in which the terminal is converted to a mercaptoalkanoyl group can be produced by the following method.

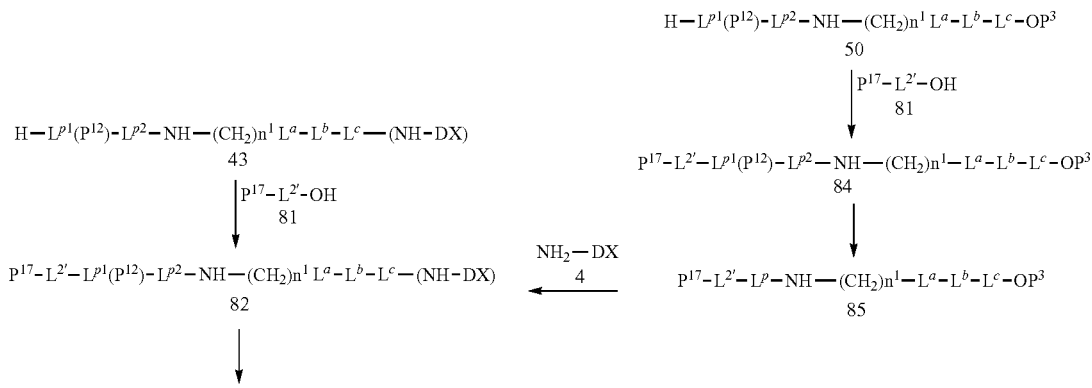

[Formula 50]

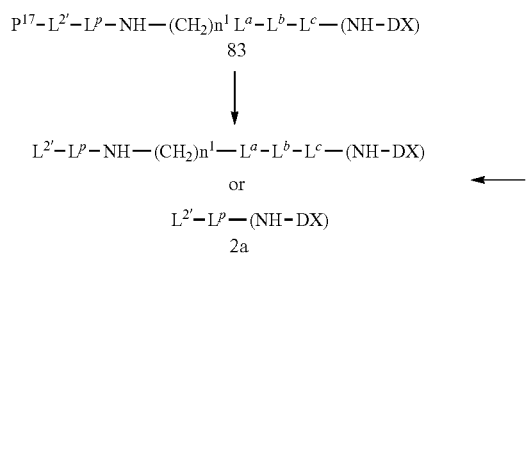

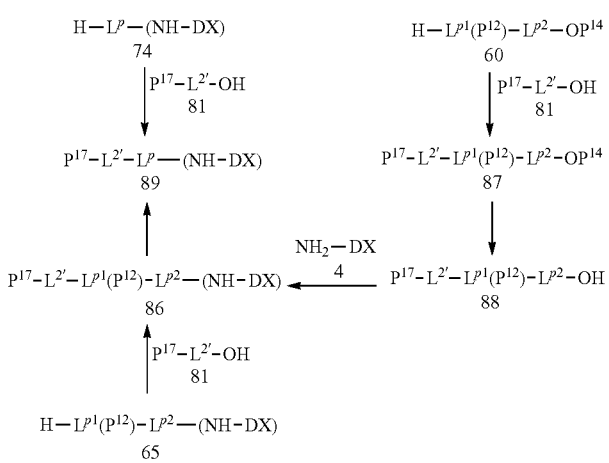

-continued

In the formula, $L^P$ represents a structure consisting of $L^{p1}$-$L^{p2}$, and $P^3$, $P^{12}$, $P^{14}$, and $P^{17}$ each represent a protecting group.

The production intermediate represented by the formula (2a) has two forms, i.e., the linker has a structure represented by -$L^1$-$L^2$-$L^P$-NH—(CH$_2$)n$^1$-$L^a$-$L^b$-$L^c$- and has a structure represented by -$L^1$-$L^2$-$L^P$-.

The compound (2a) in which the linker has a structure represented by -$L^1$-$L^2$-$L^P$-NH—(CH$_2$)n$^1$-$L^a$-$L^b$-$L^c$-can be produced as follows.

The compound (82) can be produced by derivatizing the carboxylic acid compound (81) having the terminal mercapto group protected with $P^{17}$ into an active ester, mixed acid anhydride, or the like and reacting it with the compound (43) described in Production method 10. For the reaction, reaction reagents and conditions that are generally used for peptide synthesis can be also used, and the reaction conditions, reagents, base, and solvent used for the reaction can be suitably selected from those described for the synthesis of the compound (6). As for the protecting group $P^{17}$ for a mercapto group, a protecting group commonly used as a protecting group for a mercapto group in organic synthetic chemistry can be used. Specifically, it can be suitably selected from, for example, sulfide groups such as a S-methyl sulfide group, a S-ethyl sulfide group, and a S-2-pyridyl sulfide group, ester groups such as an acetyl group, aryl methyl ether groups such as a benzyl group, a 9-fluorenylmethyl group, and a trityl group, ethyl ether groups such as a S-2-cyanoethyl group. In this case, the protecting group $P^{12}$ for the side chain amino group, carboxy group, or hydroxyl group of $L^{p1}$ is preferably a protecting group that can be deprotected under acidic conditions, but it is not limited thereto, and the protecting group can be selected from the aforementioned ones depending on, e.g., the properties of the compound having the amino group, the carboxy group, or the hydroxyl group to be protected. However, it is necessary that the protecting group $P^{17}$ for a mercapto group and protecting group $P^{12}$ for the side chain carboxy group, hydroxyl group, or amino group of $L^{p1}$ should be the protecting groups that can be removed by a different method or different conditions. For example, in the case of a carboxy group, a representative example includes a combination in which the protecting group $P^{12}$ is a tert-butyl group and the protecting group $P^{17}$ is a S-methyl sulfide group. The protecting group $P^{17}$ may not be present, and in this case, the mercapto group of the compound (82) is present in an unprotected state.

By deprotecting the protecting group $P^{12}$ for the side chain carboxy group, hydroxyl group, or amino group of $L^{p1}$ of the compound (82) obtained, the compound (83) can be produced. Reagents and conditions can be selected depending on the protecting group.

By deprotecting the protecting group $P^{17}$ for the mercapto group of the compound (83) obtained, the compound (2a) can be produced. Reagents and conditions can be selected depending on the protecting group.

The compound (82) can be also produced by the following method.

The compound (84) can be produced by derivatizing the above carboxylic acid compound (81) having the mercapto group protected with $P^{14}$ into an active ester, mixed acid anhydride, acid halide, or the like and reacting it with the compound (50) described in Production method 10. For the reaction, reaction reagents and conditions that are generally used for peptide synthesis can be also used, and the reaction conditions, reagents, base, and solvent used for the reaction can be suitably selected from those described for the synthesis of the compound (6). The protecting groups $P^{12}$ and $P^{17}$ are as described above. The protecting group $P^3$ for a carboxy group can be suitably selected from those described for the protecting group of the compound (6). However, it is necessary that the protecting group $P^{17}$ for a mercapto group and protecting group $P^{12}$ for a side chain functional group should be the protecting groups that can be removed by a different method or different conditions from those for the protecting group $P^3$ for a carboxy group. For example, a representative example includes a combination in which $P^{12}$ is a tert-butyl group as the protecting group for a carboxy group, $P^{17}$ is a S-methyl sulfide group, and $P^3$ is an allyl group. $P^{17}$ may not be present, and in this case, the mercapto group of the compound (84) is present in an unprotected state.

By deprotecting the protecting group $P^3$ for the carboxy group of the compound (84) obtained, the compound (85) can be produced. Reagents and conditions can be selected depending on the protecting group.

The compound (82) can be produced by derivatizing the compound (85) into an active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

The compound (2a) in which the linker has a structure represented by $-L^1-L^2-L^P-$, and $L^P$ is a peptide residue having an N-terminal hydrophilic amino acid which is a hydrophilic amino acid other than glycine can be produced as follows.

The compound (86) can be produced by derivatizing the above carboxylic acid compound (81) having the mercapto group protected with $P^{17}$ into an active ester, mixed acid anhydride, acid halide, or the like and reacting it with the compound (65) described in Production method 11. For the reaction, reaction reagents and conditions that are generally used for peptide synthesis can be also used, and the reaction conditions, reagents, base, and solvent used for the reaction can be suitably selected from those described for the synthesis of the compound (6). The protecting groups $P^{12}$ and $P^{17}$ are as described above.

The compound (86) can be also produced by the following method, for example.

The compound (87) can be produced by derivatizing the carboxylic acid compound (81) having the mercapto group protected with $P^{17}$ into an active ester, mixed acid anhydride, or the like and reacting it with the peptide (60) described in Production method 10. For the reaction, reaction reagents and conditions that are generally used for peptide synthesis can be also used, and the reaction conditions, reagents, base, and solvent used for the reaction can be suitably selected from those described for the synthesis of the compound (6). The protecting groups $P^{12}$, $P^{14}$, and $P^{17}$ are as described above, and can be suitably selected from those described for the protecting group of the compound (6). However, it is necessary that the protecting group $P^{17}$ for a mercapto group and protecting group $P^{12}$ for a side chain functional group should be the protecting groups that can be removed by a different method or different conditions from those for the protecting group $P^{14}$ for a carboxy group. For example, a representative example includes a combination in which $P^{12}$ is a tert-butyl group as the protecting group for a carboxy group, $P^{17}$ is a S-methyl sulfide group, and $P^3$ is an allyl group. $P^{17}$ may not be present, and in this case, the mercapto group of the compound (87) is present in an unprotected state.

By deprotecting the protecting group $P^{14}$ for the peptide carboxy group of the compound (87) obtained, the compound (88) can be produced. Reagents and conditions can be selected depending on the protecting group.

The compound (86) can be produced by derivatizing the compound (88) obtained into an active ester, mixed acid anhydride, acid halide, or the like and reacting it with the compound (4) or a salt thereof in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

By deprotecting the protecting group $P^4$ for the side chain of $L^{P1}$ of the compound (86) obtained, the compound (89) can be produced. Reagents and conditions can be selected depending on the protecting group.

By deprotecting the protecting group $P^{17}$ for the mercapto group of the compound (89) obtained, the compound (2a) can be produced. Reagents and conditions can be selected depending on the protecting group.

The compound (2a) in which the linker has a structure represented by $-L^1-L^2-L^P-$, and $L^P$ is a peptide residue that has an oligopeptide consisting of 2 or 3 or more glycine residues at the C terminal which is connected to the drug, and has a hydrophilic amino acid not other than glycine at the N terminal, can be produced as follows.

The compound (2a) can be produced by derivatizing the carboxylic acid compound (81) into an active ester, mixed acid anhydride, or the like and reacting it with the compound (76) described in Production method 14. Here, the mercapto group may not be protected with $P^{17}$. For the reaction, reaction reagents and conditions that are generally used for peptide synthesis can be also used, and the reaction conditions, reagents, base, and solvent used for the reaction can be suitably selected from those described for the synthesis of the compound (6).

16. Production Method 16

The production intermediate represented by the formula (2) in which $L^{1'}$ corresponds to $L^1$ having a structure in which the terminal is converted to (maleimid-N-yl)-CH[—(CH$_2$)n$^3$-COOH]—C(=O)— can be produced by the following method.

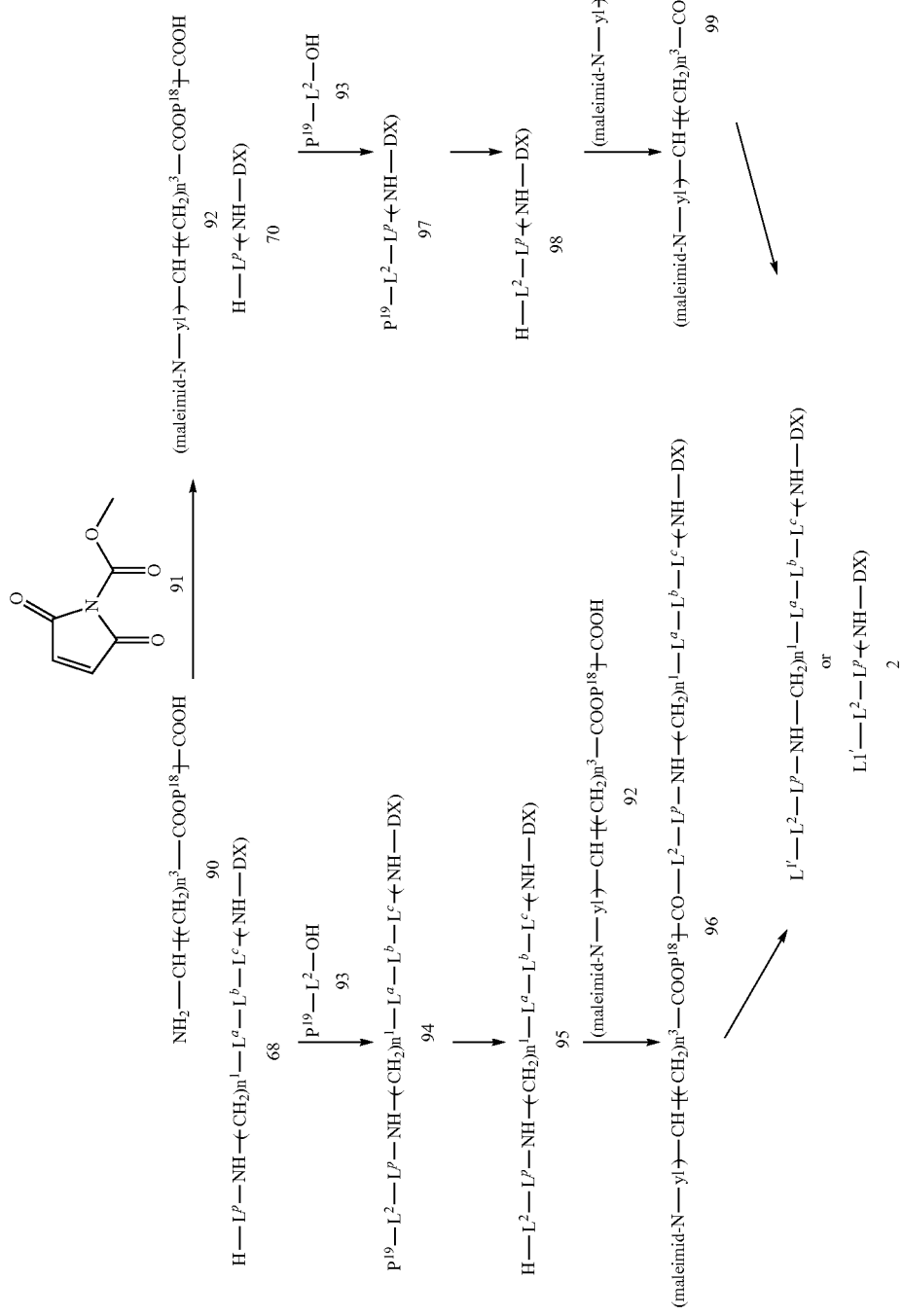

In the formula, $P^{18}$ and $P^{19}$ each represent a protecting group.

The production intermediate represented by the formula (2) has two forms, i.e., the linker has a structure represented by -$L^1$-$L^2$-$L^P$-NH—$(CH_2)n^1$-$L^a$-$L^b$-$L^c$- and has a structure represented by -$L^1$-$L^2$-$L^P$-.

The compound (2) in which the linker has a structure represented by -$L^1$-$L^2$-$L^P$-NH—$(CH_2)n^1$-$L^a$-$L^b$-$L^c$-can be produced as follows.

The compound (92) having the (maleimid-N-yl)- moiety can be produced by reacting the amino acid (90) having the side chain carboxy group protected with $P^{18}$ with N-methoxycarbonylmaleimide (91) at −40° C. to 100° C. in the presence of a base such as sodium bicarbonate in water. The maleimidyl compound can be synthesized from a compound having an amino group by a method known in the art (e.g., Keller, O.; Rudinger, J. Helv. Chem. Acta 1975, 58 (2), 531-541.) or a method equivalent thereto by using N-methoxycarbonylmaleimide. As for the protecting group $P^{18}$ for a carboxy group, a protecting group commonly used as a protecting group for a carboxy group in organic synthetic chemistry can be used, and is preferably a protecting group that can be deprotected under acidic conditions, but it is not limited thereto.

The compound (94) can be produced by derivatizing the compound (93) having the terminal amino group protected with $P^{19}$ into an active ester, mixed acid anhydride, or the like and reacting it in the presence of a base with the compound (68) described in Production method 12. The reaction conditions, reagents, base, and solvent used for forming an amide bond between the compound (93) and the compound (68) can be suitably selected from those described for the synthesis of the compound (6). The protecting group $P^{19}$ for the amino group of the compound (93) can be suitably selected from those described for the protecting group of the compound (6).

By deprotecting the protecting group $P^{19}$ for the amino group of the compound (94) obtained, the compound (95) can be produced. Reagents and conditions can be selected depending on the protecting group.

The compound (96) can be produced by derivatizing the above compound (92) into an active ester, mixed acid anhydride, or the like and reacting it in the presence of a base with the compound (95) obtained. The reaction conditions, reagents, base, and solvent used for forming an amide bond between the compound (92) and the compound (95) can be suitably selected from those described for the synthesis of the compound (6).

By deprotecting the protecting group $P^{18}$ for the carboxy group of the compound (96) obtained, the compound (2) can be produced. Reagents and conditions can be selected depending on the protecting group.

The compound (2) in which the linker has a structure represented by -$L^1$-$L^2$-$L^P$-can be produced as follows.

Similarly, the compound (97) can be produced by derivatizing the compound (93) having the terminal amino group protected with $P^{19}$ into an active ester, mixed acid anhydride, or the like and reacting it in the presence of a base with the compound (70) described in Production method 12. The reaction conditions, reagents, base, and solvent used for forming an amide bond between the compound (93) and the compound (70) can be suitably selected from those described for the synthesis of the compound (6). The protecting group $P^{19}$ is as described above.

By deprotecting the protecting group $P^{19}$ for the amino group of the compound (97) obtained, the compound (98) can be produced. Reagents and conditions can be selected depending on the protecting group.

The compound (99) can be produced by derivatizing the above compound (92) into an active ester, mixed acid anhydride, or the like and reacting it in the presence of a base with the compound (98) obtained. The reaction conditions, reagents, base, and solvent used for forming an amide bond between the compound (92) and the compound (98) can be suitably selected from those described for the synthesis of the compound (6).

By deprotecting the protecting group $P^{18}$ for the carboxy group of the compound (99) obtained, the compound (2) can be produced. Reagents and conditions can be selected depending on the protecting group.

17. Production Method 17

The production intermediate represented by the formula (2) in which $L^{1'}$ corresponds to $L^1$ having a structure in which the terminal is converted to a maleimidyl group or a haloacetyl group, and $L^2$ is —N[—$(CH_2CH_2$—O$)n^7$-$CH_2CH_2$—OH]—$CH_2$—C(=O)— can be produced by the following method.

[Formula 52]

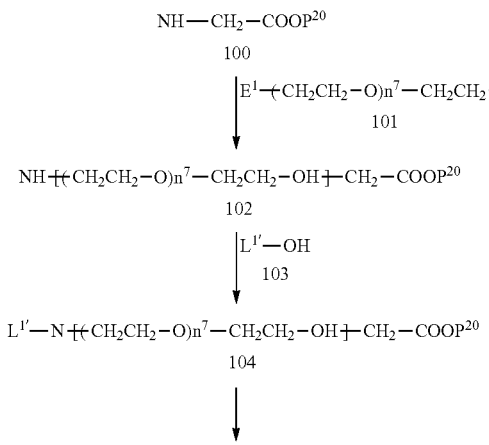

-continued

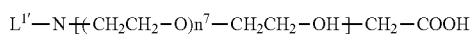

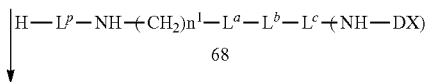

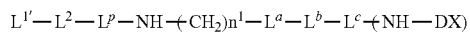  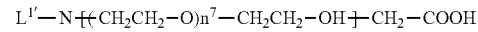

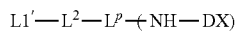  

In the formula, $P^{20}$ represents a protecting group, and $E^1$ represents a leaving group.

The production intermediate represented by the formula (2) has two forms, i.e., the linker has a structure represented by $-L^1-L^2-L^P-NH-(CH_2)n^1-L^a-L^b-L^c-$ and has a structure represented by $-L^1-L^2-L^P-$.

The compound (2) in which the linker has a structure represented by $-L^1-L^2-L^P-NH-(CH_2)n^1-L^a-L^b-L^c$-can be produced as follows.

The compound (102) can be produced by reacting the glycine derivative (100) having the C terminal protected with $P^{20}$ with the compound (101) in the presence of a base. The protecting group $P^{20}$ for a carboxy group is preferably a protecting group that can be deprotected under acidic conditions, but it is not limited thereto. Examples of the leaving group $E^1$ of the compound (101) can include sulfonic acid esters such as p-toluenesulfonate, methylsulfonate, and trifluoromethylsulfonate as well as halides such as iodide, bromide, and chloride. For the reaction, reaction conditions that are generally used for N-alkylation can be also used, and the base and solvent used for the reaction can be selected from those described for the synthesis of the compound (6).

The compound (104) can be produced by derivatizing the carboxylic acid derivative (103) into an active ester, mixed acid anhydride, acid halide, or the like and reacting it with the compound (102) obtained. The reaction conditions, reagents, base, and solvent used for forming a peptide bond between the carboxylic acid derivative (103) and the compound (102) can be suitably selected from those described for the synthesis of the compound (6).

By deprotecting the protecting group $P^{13}$ for the carboxy group of the compound (104) obtained, the compound (105) can be produced. Reagents and conditions can be selected depending on the protecting group.

The compound (2) can be produced by derivatizing the compound (105) obtained into an active ester, mixed acid anhydride, acid halide, or the like and reacting it with the compound (68) described in Production method 12. The reaction conditions, reagents, base, and solvent used for forming an amide bond between the carboxylic acid derivative (105) and the compound (68) can be suitably selected from those described for the synthesis of the compound (6).

The compound (2) in which the linker has a structure represented by $-L^1-L^2-L^P$-can be produced as follows.

Similarly, the compound (2) can be produced by derivatizing the compound (105) into an active ester, mixed acid anhydride, acid halide, or the like and reacting it with the compound (70) described in Production method 12. The reaction conditions, reagents, base, and solvent used for forming an amide bond between the carboxylic acid derivative (105) and the compound (70) can be suitably selected from those described for the synthesis of the compound (6).

18. Production Method 18

The compound (10) shown in Production method 4, in which $-L^a-L^b-L^c$-has a structure consisting of $-N(-Q-H)-(CH_2)n^8-CO-$ can be also produced by the following method.

[Formula 53]
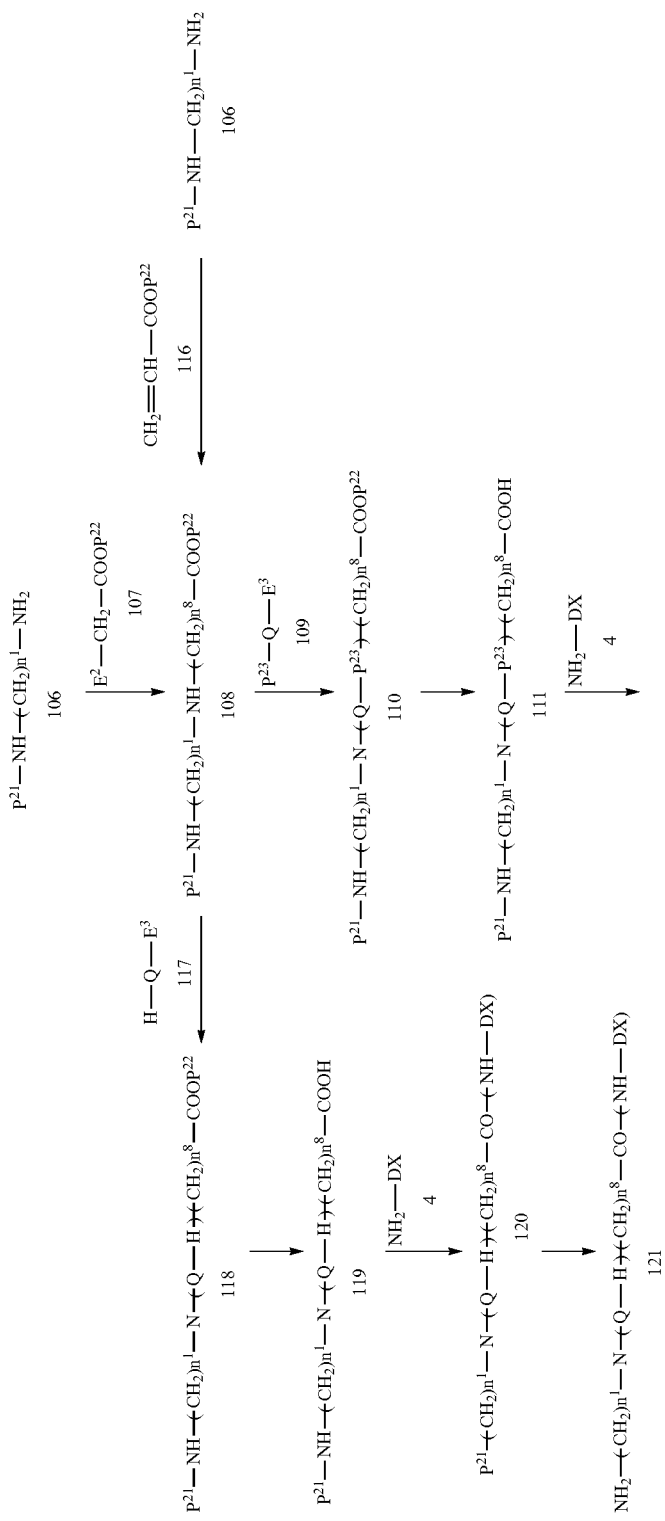

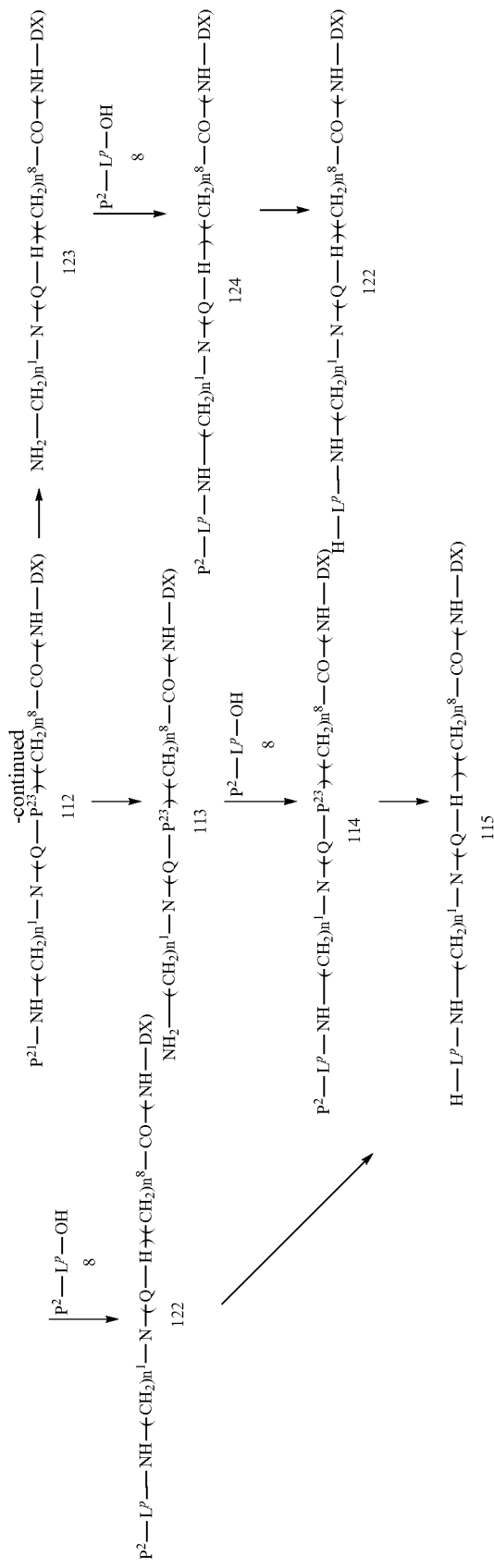

In the formula, -Q- represents a single bond, —$CH_2$—, —($CH_2$)—O—, or —($CH_2$)—COO—, $P^2$, $P^{21}$, $P^{22}$, and $P^{23}$ each represent a protecting group, and $E^2$ and $E^3$ each represent a leaving group.

The compound (108) can be produced by reacting the alkylenediamine (106) having the terminal amino group on one side protected with $P^{21}$ with the compound (107) in the presence of a base. The protecting group $P^{21}$ for an amino group is preferably a protecting group that can be deprotected under acidic conditions, but it is not limited thereto. As for the protecting group $P^{22}$ for a carboxy group, a representative example includes a benzyl group. The protecting groups can be selected depending on, e.g., the properties of the compounds to be protected. For removal of the protecting groups, reagents and conditions can be selected depending on the protecting group. Examples of the leaving group $E^2$ of the compound (107) and the leaving group $E^3$ of the compound (109) or the compound (117) can include halides such as iodide, bromide, and chloride as well as sulfonic acid esters such as p-toluenesulfonate, methylsulfonate, and trifluoromethylsulfonate. For the reaction, reaction conditions that are generally used for N-alkylation can be also used, and the base and solvent used for the reaction can be selected from those described for the synthesis of the compound (6).

The compound (110) can be produced by reacting the compound (108) obtained with the compound (109) in the presence of a base. The reaction conditions, reagents, base, and solvent used for forming an aminoalkyl between the compound (108) and the compound (109) can be suitably selected from those described for the synthesis of the compound (108). When the protecting group $P^{23}$ is a protecting group for an amino group, it is preferably a protecting group that can be deprotected under basic conditions, and the amino group may be protected with a protecting group which is generally used for organic compound synthesis. Specifically, it can be selected from those described for the synthesis of the compound (6).

By deprotecting the protecting group $P^{22}$ for the carboxy group of the compound (110) obtained, the compound (111) can be produced. Reagents and conditions can be selected depending on the protecting group.

The compound (112) can be produced by derivatizing the compound (111) obtained into an active ester, mixed acid anhydride, or the like and reacting it with the compound (4) or a salt thereof. The reaction conditions, reagents, base, and solvent used for forming a peptide bond between the carboxylic acid (111) and the compound (4) can be suitably selected from those described for the synthesis of the compound (6) unless the reaction is inhibited.

By deprotecting the protecting group $P^{21}$ for the amino group of the compound (112) obtained, the compound (113) can be produced. Reagents and conditions can be selected depending on the protecting group.

The compound (114) can be produced by derivatizing the compound (113) obtained into an active ester, mixed acid anhydride, or the like and reacting it with the compound (8) described in Production method 4 or a salt thereof. The reaction conditions, reagents, base, and solvent used for forming a peptide bond between the peptide or amino acid (8) and the compound (113) can be suitably selected from those described for the synthesis of the compound (6) unless the reaction is inhibited.

By deprotecting the protecting group $P^{23}$ for the compound (114) obtained, the compound (115) can be produced. Reagents and conditions can be selected depending on the protecting group.

The compound (108) can be also produced by the following method.

The compound (108) can be produced by reacting the alkylenediamine (106) having the terminal amino group on one side protected with $P^{21}$ with the compound (116) in the presence of a base. The protecting group $P^{21}$ for an amino group is preferably a protecting group that can be deprotected under acidic conditions, but it is not limited thereto. As for the protecting group $P^{22}$ for a carboxy group, a representative example includes a benzyl group. The protecting groups can be selected depending on, e.g., the properties of the compounds to be protected. For removal of the protecting groups, reagents and conditions can be selected depending on the protecting group. For the reaction, reaction conditions that are generally used for organic synthesis can be also used, and the base and solvent used for the reaction can be selected from those described for the synthesis of the compound (6).

The compound (115) can be also produced by the following method.

The compound (118) can be produced by reacting the compound (108) with the compound (117) in the presence of a base. The reaction conditions, reagents, base, and solvent used for forming an aminoalkyl between the compound (108) and the compound (117) can be suitably selected from those described for the synthesis of the compound (108).

By deprotecting the protecting group $P^{22}$ for the carboxy group of the compound (118) obtained, the compound (119) can be produced. Reagents and conditions can be selected depending on the protecting group.

The compound (120) can be produced by derivatizing the compound (119) obtained into an active ester, mixed acid anhydride, or the like and reacting it with the compound (4) or a salt thereof. The reaction conditions, reagents, base, and solvent used for forming a peptide bond between the carboxylic acid (119) and the compound (4) can be suitably selected from those described for the synthesis of the compound (6) unless the reaction is inhibited.

By deprotecting the protecting group $P^{21}$ for the amino group of the compound (120) obtained, the compound (121) can be produced. Reagents and conditions can be selected depending on the protecting group.

The compound (122) can be produced by derivatizing the compound (121) obtained into an active ester, mixed acid anhydride, or the like and reacting it with the compound (8) described in Production method 4 or a salt thereof. The reaction conditions, reagents, base, and solvent used for forming a peptide bond between the peptide or amino acid (8) and the compound (121) can be suitably selected from those described for the synthesis of the compound (6) unless the reaction is inhibited.

By deprotecting the protecting group $P^2$ for the compound (122) obtained, the compound (115) can be produced. Reagents and conditions can be selected depending on the protecting group.

The compound (122) can be also produced by the following method.

By deprotecting the protecting groups $P^{21}$ and $P^{23}$ for the amino groups of the compound (112), the compound (123) can be produced. Reagents and conditions can be selected depending on the protecting group.

The compound (124) can be produced by derivatizing the compound (123) obtained into an active ester, mixed acid anhydride, or the like and reacting it with the compound (8) described in Production method 4 or a salt thereof. The reaction conditions, reagents, base, and solvent used for forming a peptide bond between the peptide or amino acid (8) and the compound (123) can be suitably selected from those described for the synthesis of the compound (6) unless the reaction is inhibited.

By deprotecting the protecting group $P^2$ for the compound (124) obtained, the compound (122) can be produced. Reagents and conditions can be selected depending on the protecting group.

Any of the intermediate compounds of Production method 1 to Production method 18 may be in the form of a salt.

The antibody-drug conjugate of the present invention, when it is left in air or recrystallized or purified, may absorb moisture or have adsorption water or turn into a hydrate, and such compounds or salts containing water are also included in the present invention.

Compounds labeled with various radioactive or non-radioactive isotopes are also included in the present invention. One or more atoms constituting the antibody-drug conjugate of the present invention may contain an atomic isotope at a non-natural ratio. Examples of atomic isotopes include deuterium ($^2$H), tritium ($^3$H), iodine-125 ($^{125}$I), and carbon-13 ($^{13}$C). Further, the compound of the present invention may be radioactive-labeled with a radioactive isotope such as tritium ($^3$H), iodine-125 ($^{125}$I), or carbon-14 ($^{14}$C). The compound labeled with a radioactive isotope is useful as a therapeutic or prophylactic agent, a reagent for research such as an assay reagent and an agent for diagnosis such as an in vivo diagnostic imaging agent. Without being related to radioactivity, any isotope variant type of the antibody-drug conjugate of the present invention is within the scope of the present invention.

[Drugs]

The anti-HER2 antibody-drug conjugate of the present invention exhibits cytotoxic activity against cancer cells, and thus, it can be used as a drug, particularly as a therapeutic agent and/or prophylactic agent for cancer.

That is, the anti-HER2 antibody-drug conjugate of the present invention can be selectively used as a drug for chemotherapy, which is a main method for treating cancer, and as a result, can delay development of cancer cells, inhibit growth thereof, and further kill cancer cells. This can allow cancer patients to be free from symptoms caused by cancer or achieve improvement in QOL of cancer patients and attains a therapeutic effect by sustaining the lives of the cancer patients. Even if the anti-HER2 antibody-drug conjugate of the present invention does not accomplish killing cancer cells, it can achieve higher QOL of cancer patients while achieving longer-term survival, by inhibiting or controlling the growth of cancer cells.

In such drug therapy, it can be used as a drug alone and in addition, it can be used as a drug in combination with an additional therapy in adjuvant therapy and can be combined with surgical operation, radiotherapy, hormone therapy, or the like. Furthermore, it can also be used as a drug for drug therapy in neoadjuvant therapy.

In addition to the therapeutic use as described above, an effect of suppressing the growth of small metastatic cancer cells and further killing them can also be expected. Particularly, when the expression of HER2 is confirmed in primary cancer cells, inhibition of cancer metastasis or a prophylactic effect can be expected by administering the anti-HER2 antibody-drug conjugate of the present invention. For example, an effect of inhibiting and killing cancer cells in a body fluid in the course of metastasis or an effect of, for example, inhibiting and killing small cancer cells immediately after implantation in any tissue can be expected. Accordingly, inhibition of cancer metastasis or a prophylactic effect can be expected, particularly, after surgical removal of cancer.

The anti-HER2 antibody-drug conjugate of the present invention can be expected to exert a therapeutic effect by administration as systemic therapy to patients, and additionally, by local administration to cancer tissues.

Examples of the cancer type to which the anti-HER2 antibody-drug conjugate of the present invention is applied can include lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, or penis cancer. The treatment subject of the anti-HER2 antibody-drug conjugate of the present invention is a cancer cell expressing, in a cancer cell as a treatment subject, HER2 protein which the antibody within the antibody-drug conjugate can recognize. The term "cancer expressing HER2 protein" as used in the specification is a cancer containing cells having HER2 protein on their cell surface. The HER2 protein is overexpressed in various human tumors and can be evaluated using a method generally carried out in the art, such as immunohistochemical staining method (IHC) for evaluating the overexpression of the HER2 protein, or fluorescence in situ hybridization method (FISH) for evaluating amplification of the HER2 gene.

Further, the anti-HER2 antibody-drug conjugate of the present invention exhibits an antitumor effect by recognizing, through its anti-HER2 antibody, the HER2 protein expressed on the surface of cancer cells and internalizing in the cancer cells. Thus, the treatment subject of the anti-HER2 antibody-drug conjugate of the present invention is not limited to the "cancer expressing HER2 protein" and can also be, for example, leukemia, malignant lymphoma, plasmacytoma, myeloma, or sarcoma.

The anti-HER2 antibody-drug conjugate of the present invention can be preferably administered to a mammal, but it is more preferably administered to a human.

Substances used in a pharmaceutical composition containing the anti-HER2 antibody-drug conjugate of the present invention can be suitably selected and applied from formulation additives or the like that are generally used in the art, in view of the dosage or administration concentration.

The anti-HER2 antibody-drug conjugate of the present invention can be administered as a pharmaceutical composition containing at least one pharmaceutically suitable ingredient. For example, the pharmaceutical composition above typically contains at least one pharmaceutical carrier (for example, sterilized liquid). Herein, the liquid includes, for example, water and oil (petroleum oil and oil of animal origin, plant origin, or synthetic origin). The oil may be, for example, peanut oil, soybean oil, mineral oil, or sesame oil. Water is a more typical carrier when the pharmaceutical composition above is intravenously administered. Saline solution, an aqueous dextrose solution, and an aqueous glycerol solution can be also used as a liquid carrier, in particular, for an injection solution. A suitable pharmaceutical vehicle can be selected from ones known in the art. If desired, the composition above may also contain a trace amount of a moisturizing agent, an emulsifying agent, or a pH buffering agent. Examples of suitable pharmaceutical carrier are disclosed in "Remington's Pharmaceutical Sciences" by E. W. Martin. The formulations correspond to an administration mode.

Various delivery systems are known and they can be used for administering the anti-HER2 antibody-drug conjugate of the present invention. Examples of the administration route can include intradermal, intramuscular, intraperitoneal, intravenous, and subcutaneous routes, but not limited thereto. The administration can be made by injection or bolus injection, for example. According to a specific preferred embodiment, the administration of the antibody-drug conjugate is performed by injection. Parenteral administration is a preferred administration route.

According to a representative embodiment, the pharmaceutical composition is prescribed, as a pharmaceutical composition suitable for intravenous administration to human, according to the conventional procedures. The composition for intravenous administration is typically a solution in a sterile and isotonic aqueous buffer solution. If necessary, the drug may contain a solubilizing agent and local anesthetics to alleviate pain at injection site (for example, lignocaine). Generally, the ingredient above is provided individually as any one of lyophilized powder or an anhydrous concentrate contained in a container which is obtained by sealing in an ampoule or a sachet having an amount of the active agent or as a mixture in a unit dosage form. When the drug is to be administered by injection, it may be administered from an injection bottle containing water or saline of sterile pharmaceutical grade. When the drug is administered by injection, an ampoule of sterile water or saline for injection may be provided such that the aforementioned ingredients are admixed with each other before administration.

The pharmaceutical composition of the present invention may be a pharmaceutical composition containing only the anti-HER2 antibody-drug conjugate of the present invention or a pharmaceutical composition containing the anti-HER2 antibody-drug conjugate and at least one cancer treating agent other than the conjugate. The anti-HER2 antibody-drug conjugate of the present invention can be administered with other cancer treating agents. The anti-cancer effect may be enhanced accordingly. Other anti-cancer agents used for such purpose may be administered to an individual simultaneously with, separately from, or subsequently to the antibody-drug conjugate, and may be administered while varying the administration interval for each. Examples of cancer treating agents include 5-FU, pertuzumab, carboplatin, cisplatin, gemcitabine, capecitabine, irinotecan (CPT-11), paclitaxel, docetaxel, pemetrexed, sorafenib, vinblastin, vinorelbine, everolims, tanespimycin, bevacizumab, oxaliplatin, lapatinib, ado-trastuzumab emtansine (T-DM1), or drugs described in International Publication No. WO 2003/038043, LH-RH analogues (leuprorelin, goserelin, or the like), estramustine phosphate, estrogen antagonists (tamoxifen, raloxifene, or the like), and aromatase inhibitors (anastrozole, letrozole, exemestane, or the like), but are not limited as long as they are drugs having an antitumor activity.

The pharmaceutical composition can be formulated into a lyophilization formulation or a liquid formulation as a formulation having the desired composition and required purity. When formulated as a lyophilization formulation, it may be a formulation containing suitable formulation additives that are used in the art. Also for a liquid formulation, it can be formulated as a liquid formulation containing various formulation additives that are used in the art.

The composition and concentration of the pharmaceutical composition may vary depending on administration method. However, the anti-HER2 antibody-drug conjugate contained in the pharmaceutical composition of the present invention can exhibit a pharmaceutical effect even at a small dosage when the antibody-drug conjugate has a higher affinity for an antigen, that is, a higher affinity (=lower Kd value) in terms of the dissociation constant (that is, Kd value) for the antigen. Thus, for determining the dosage of the antibody-drug conjugate, the dosage can be determined in view of the situation relating to the affinity between the antibody-drug conjugate and antigen. When the antibody-drug conjugate of the present invention is administered to a human, for example, about 0.001 to 100 mg/kg can be administered once or administered several times with an interval of for 1 to 180 days.

EXAMPLES

The present invention is specifically described in view of the examples shown below. However, the present invention is not limited to these. Further, it is by no means interpreted in a limited way. Further, unless specifically described otherwise, the reagent, solvent, and starting material described in the specification can be easily obtained from a commercial supplier.

Reference Example 1 Preparation of Trastuzumab

Fourteen vials of 440 mg/vial Herceptin (Genentech, Inc.) were dissolved in 2 L of cation-exchange chromatography buffer A (25 mM citrate buffer, 30 mM NaCl, pH 5.0) and filtered through a 0.2 μm filter (Millipore Corp.: Stericup 0.22 μm, GVPVDF Membrane). The samples were applied to a cation-exchange chromatography column (SP Sepharose HP 240 ml, XK50 column), followed by elution under a NaCl concentration linear gradient from 30 mM to 500 mM using cation-exchange chromatography buffer B (25 mM citrate buffer, 500 mM NaCl, pH 5.0) to separate IgG monomer fractions. Monomer samples having a higher purity over 98% by size exclusion chromatography analysis were combined and concentrated with UF30K (Millipore Corp.: PELLICON XL Filter, BIOMAX 30K, PXB030A50), and the buffer was replaced with CBS buffer (10 mM citrate/140 mM NaCl, pH 6.0). The CBS buffer-replaced samples were filtered through a 0.2 μm filter (Sartorius AG: Minisart-Plus 0.2 μm, 17823K).

Reference Example 2 Production of Trastuzumab Emtansine T-DM1

SMCC derivatization of antibody: By using the Common procedure C-2 (PBS6.5/EDTA was used as a buffer solution), Common procedure A, and Common procedure B (as absorption coefficient at 280 nm, 1.37 mL·mg$^{-1}$ cm$^{-1}$ was used) described in Production method 1, replacement of buffer with PBS6.5/EDTA was conducted on the trastuzumab produced in Reference Example 1 to prepare a solution containing trastuzumab (160.0 mg) dissolved in PBS6.5/EDTA (7.60 mL) in a 15 mL polypropylene tube. Subsequently, SMCC (1.84 mg) DMSO solution (0.40 mL; which corresponds to about 5.1 equivalents per antibody molecule) was added at room temperature. The reaction mixture was adjusted to have an antibody concentration of 20 mg/mL, and the reaction was carried out at room temperature by using a tube rotator (MTR-103, manufactured by AS ONE Corporation) for 2 hours. This reaction solution was subjected to purification according to the Common procedure D-2 (PBS6.5/EDTA was used as a buffer solution) to yield 12 mL of a solution containing 154.9 mg of the SMCC-derivatized antibody.

Conjugation between antibody and drug linker: After adding PBS6.5/EDTA (2.56 mL) and $N^2$-deacetyl-$N^2$-(3-mercapto-1-oxopropyl)-maytansine (4.67 mg; DM1, Journal of Medicinal Chemistry, 2006, Vol. 49, No. 14, p. 4392) DMA (dimethylacetamide) solution (0.93 mL; which corresponds to about 5.8 equivalents per SMCC-derivatized antibody molecule) to the solution obtained above in the 50 mL polypropylene tube at room temperature, the reaction solution was adjusted to an antibody concentration of 10 mg/mL, and the reaction was carried out at room temperature by using a tube rotator for 16.5 hours.

Purification procedure: The above solution was subjected to purification using the Common procedure D-1 using a sodium phosphate buffer solution (10 mM, pH 6.5) containing sodium chloride (137 mM) to yield 35 mL of a solution containing the target Reference Example compound. Physicochemical characterization: By using the Common procedure E using UV absorbance at two wavelengths of 252 nm and 280 nm, the following characteristic values were obtained.

Antibody concentration: 4.14 mg/mL, antibody yield: 144.9 mg (91%), and average number of conjugated drug molecules (n) per antibody molecule: 3.0.

Example 1 Intermediate (1)

Process 1: tert-Butyl (4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl) carbamate 4-(tert-Butoxycarbonylamino)butanoic acid (0.237 g, 1.13 mmol) was dissolved in dichloromethane (10 mL), charged with N-hydroxysuccinimide (0.130 g, 1.13 mmol) and 1-ethyl-3-(3-dimethylaminopropyl)carbodiimide hydrochloride (0.216 g, 1.13 mmol), and stirred for 1 hour. The reaction solution was added dropwise to an N,N-dimethylformamide solution (10 mL) charged with methanesulfonic acid salt of exatecan (0.500 g, 0.94 mmol) and triethylamine (0.157 mL, 1.13 mmol), and stirred at room temperature for 1 day. The solvent was removed under reduced pressure and the residues obtained were purified by silica gel column chromatography [chloroform-chloroform:methanol=8:2 (v/v)] to yield the titled compound (0.595 g, quantitative).

$^1$H-NMR (400 MHz, DMSO-$d_6$) δ: 0.87 (3H, t, J=7.2 Hz), 1.31 (9H, s), 1.58 (1H, t, J=7.2 Hz), 1.66 (2H, t, J=7.2 Hz), 1.82-1.89 (2H, m), 2.12-2.21 (3H, m), 2.39 (3H, s), 2.92 (2H, t, J=6.5 Hz), 3.17 (2H, s), 5.16 (1H, d, J=18.8 Hz), 5.24 (1H, d, J=18.8 Hz), 5.42 (2H, s), 5.59-5.55 (1H, m), 6.53 (1H, s), 6.78 (1H, t, J=6.3 Hz), 7.30 (1H, s), 7.79 (1H, d, J=11.0 Hz), 8.40 (1H, d, J=8.6 Hz).

MS (APCI) m/z: 621 (M+H)$^+$.

[Formula 54]

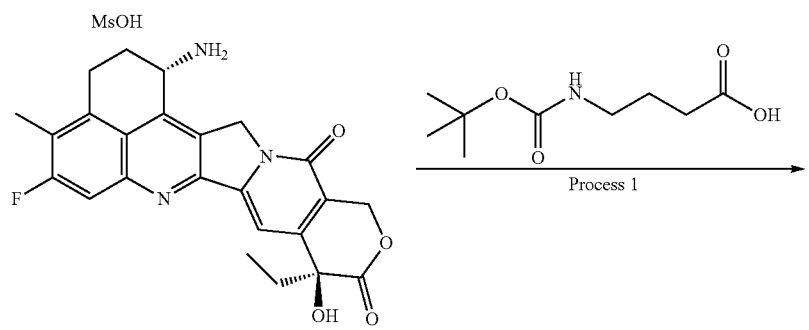

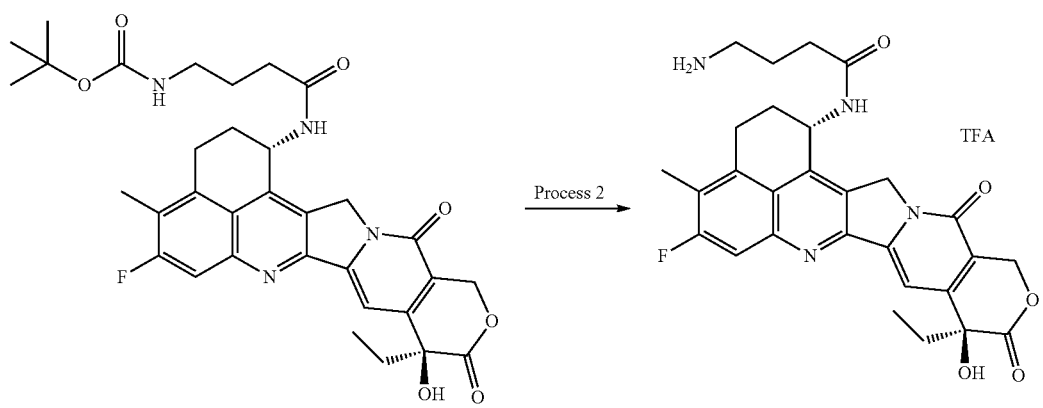

147

Process 2: 4-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]butanamide The compound (0.388 g, 0.61 mmol) obtained in Process 1 above was dissolved in dichloromethane (9 mL). After adding trifluoroacetic acid (9 mL), it was stirred for 4 hours. The solvent was removed under reduced pressure and the residues obtained were purified by silica gel column chromatography [chloroform -partitioned organic layer of chloroform:methanol:water=7:3:1 (v/v/v)] to yield trifluoroacetic acid salt of the titled compound (0.343 g, quantitative).

148

$^1$H-NMR (400 MHz, DMSO-$d_6$) δ: 0.87 (3H, t, J=7.2 Hz), 1.79-1.92 (4H, m), 2.10-2.17 (2H, m), 2.27 (2H, t, J=7.0 Hz), 2.40 (3H, s), 2.80-2.86 (2H, m), 3.15-3.20 (2H, m), 5.15 (1H, d, J=18.8 Hz), 5.26 (1H, d, J=18.8 Hz), 5.42 (2H, s), 5.54-5.61 (1H, m), 6.55 (1H, s), 7.32 (1H, s), 7.72 (3H, brs), 7.82 (1H, d, J=11.0 Hz), 8.54 (1H, d, J=8.6 Hz).

MS (APCI) m/z: 521 (M+H)$^+$.

Example 2 Antibody-Drug Conjugate (2)

[Formula 55]

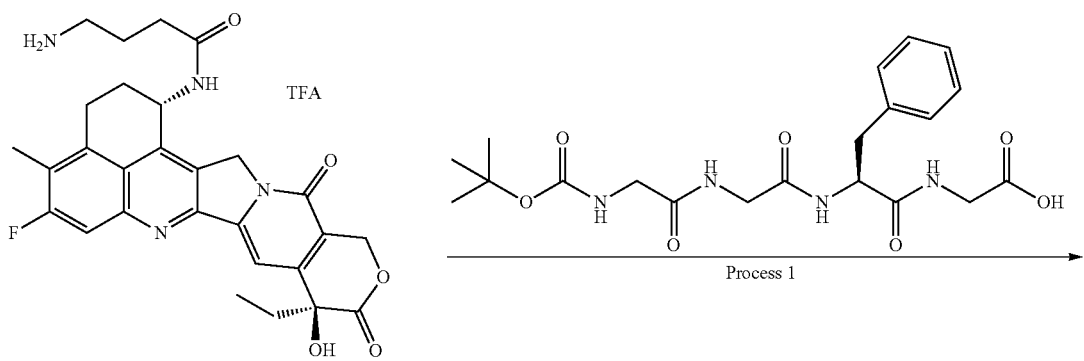

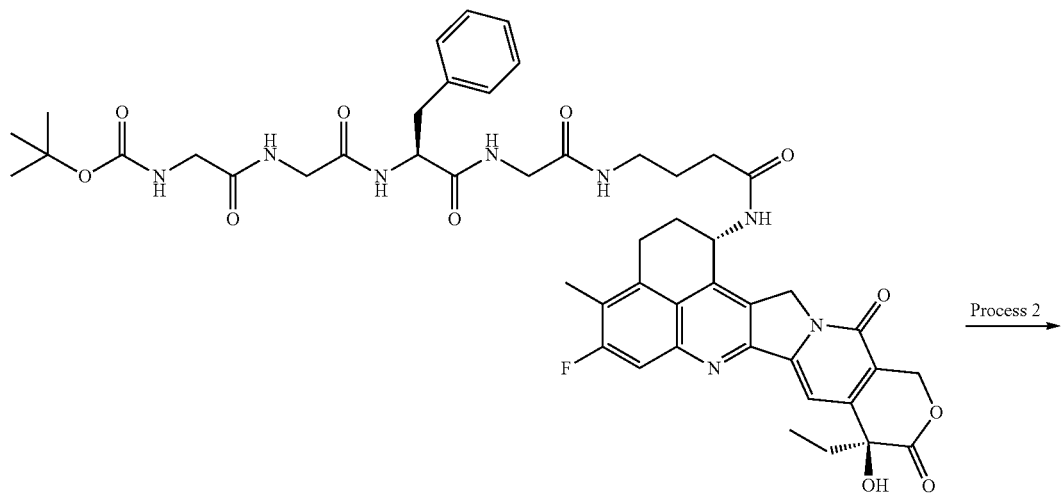

149 -continued 150
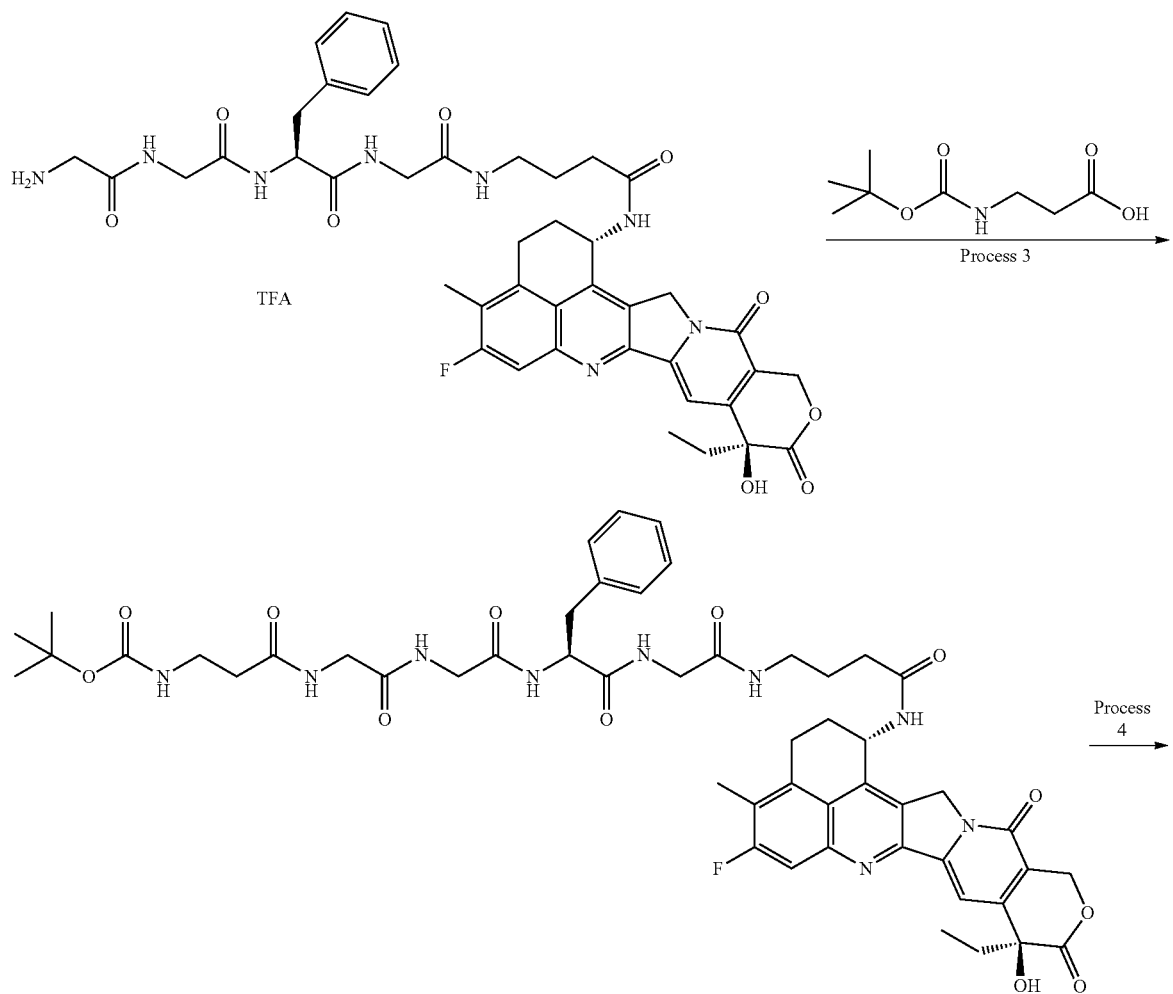
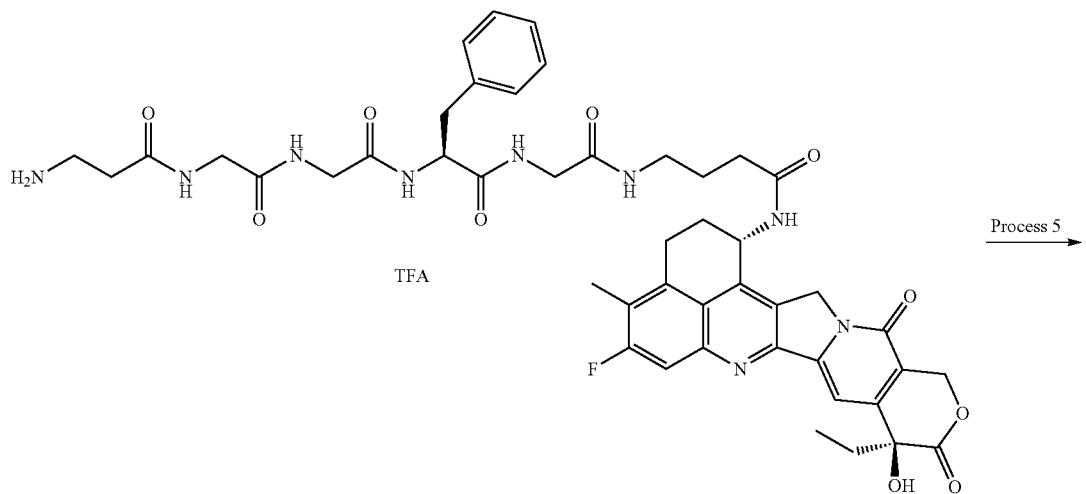

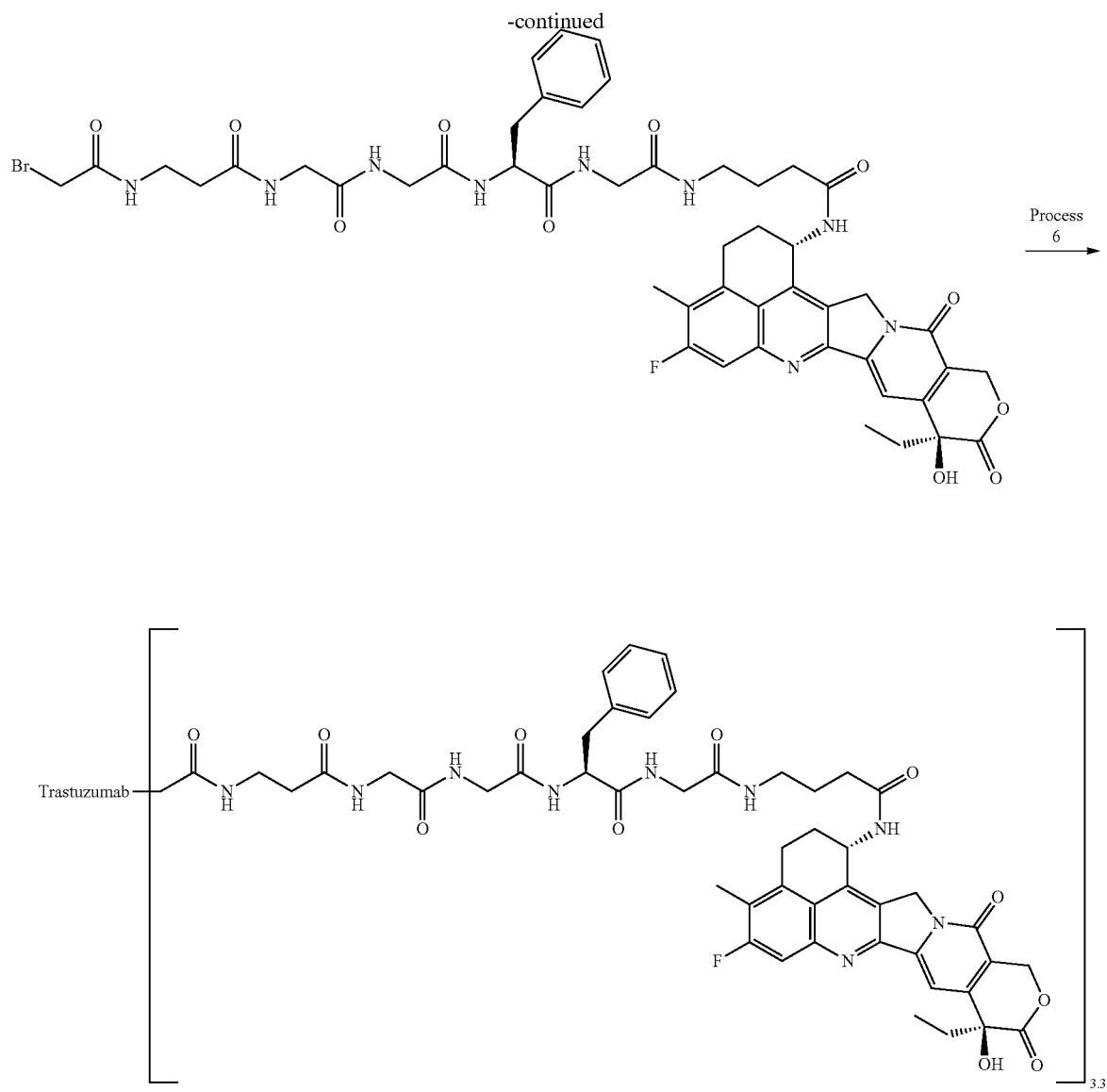

Process 1: N-(tert-Butoxycarbonyl)glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide N-(tert-Butoxycarbonyl)glycylglycyl-L-phenylalanylglycine (0.081 g, 0.19 mmol) was dissolved in dichloromethane (3 mL), charged with N-hydroxysuccinimide (0.021 g, 0.19 mmol) and 1-ethyl-3-(3-dimethylaminopropyl)carbodiimide hydrochloride (0.036 g, 0.19 mmol), and stirred for 3.5 hours. The reaction solution was added dropwise to an N,N-dimethylformamide solution (1.5 mL) charged with the compound (0.080 g, 0.15 mmol) obtained in Process 2 of Example 1, and stirred at room temperature for 4 hours. The solvent was removed under reduced pressure and the residues obtained were purified by silica gel column chromatography [chloroform-chloroform:methanol=8:2 (v/v)] to yield the titled compound (0.106 g, 73%).

$^1$H-NMR (400 MHz, DMSO-$d_6$) δ: 0.87 (3H, t, J=7.4 Hz), 1.36 (9H, s), 1.71 (2H, m), 1.86 (2H, t, J=7.8 Hz), 2.15-2.19 (4H, m), 2.40 (3H, s), 2.77 (1H, dd, J=12.7, 8.8 Hz), 3.02 (1H, dd, J=14.1, 4.7 Hz), 3.08-3.11 (2H, m), 3.16-3.19 (2H, m), 3.54 (2H, d, J=5.9 Hz), 3.57-3.77 (4H, m), 4.46-4.48 (1H, m), 5.16 (1H, d, J=19.2 Hz), 5.25 (1H, d, J=18.8 Hz), 5.42 (2H, s), 5.55-5.60 (1H, m), 6.53 (1H, s), 7.00 (1H, t, J=6.3 Hz), 7.17-7.26 (5H, m), 7.31 (1H, s), 7.71 (1H, t, J=5.7 Hz), 7.80 (1H, d, J=11.0 Hz), 7.92 (1H, t, J=5.7 Hz), 8.15 (1H, d, J=8.2 Hz), 8.27 (1H, t, J=5.5 Hz), 8.46 (1H, d, J=8.2 Hz).

MS (APCI) m/z: 939 (M+H)$^+$.

Process 2: Glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (1.97 g, 2.10 mmol) obtained in Process 1 above was dissolved in dichloromethane (7 mL). After adding trifluoroacetic acid (7 mL), it was stirred for 1 hour. The solvent was removed under reduced pressure, and the residues were charged with toluene for azeotropic distillation. The residues obtained were purified by silica gel column chromatography [chloroform -partitioned organic layer of chloroform:methanol:water=7:3:1 (v/v/v)] to yield trifluoroacetic acid salt of the titled compound (1.97 g, 99%).

$^1$H-NMR (400 MHz, DMSO-$d_6$) δ:0.87 (3H, t, J=7.4 Hz), 1.71-1.73 (2H, m), 1.82-1.90 (2H, m), 2.12-2.20 (4H, m), 2.40 (3H, s), 2.75 (1H, dd, J=13.7, 9.4 Hz), 3.03-3.09 (3H, m), 3.18-3.19 (2H, m), 3.58-3.60 (2H, m), 3.64 (1H, d, J=5.9 Hz), 3.69 (1H, d, J=5.9 Hz), 3.72 (1H, d, J=5.5 Hz), 3.87 (1H, dd, J=16.8, 5.9 Hz), 4.50-4.56 (1H, m), 5.16 (1H, d, J=19.2 Hz), 5.25 (1H, d, J=18.8 Hz), 5.42 (2H, s), 5.55-5.60 (1H, m), 7.17-7.27 (5H, m), 7.32 (1H, s), 7.78-7.81 (2H, m), 7.95-7.97 (3H, m), 8.33-8.35 (2H, m), 8.48-8.51 (2H, m).

MS (APCI) m/z: 839 (M+H)$^+$.

Process 3: N-(tert-Butoxycarbonyl)-β-alanylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (0.839 g, 1.00 mmol) obtained in Process 2 above was reacted in the same manner as Process 1 of Example 1 by using N-(tert-butoxycarbonyl)-β-alanine instead of 4-(tert-butoxycarbonylamino)butanoic acid, and the crude product obtained was used for the next process without purification.

Process 4: β-Alanylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The crude product obtained in Process 3 above was reacted in the same manner as Process 3 above to yield the titled compound as a pale yellow solid (0.610 g, 67%).

$^1$H-NMR (400 MHz, DMSO-$d_6$) δ: 0.87 (3H, t, J=7.4 Hz), 1.67-1.77 (2H, m), 1.79-1.92 (2H, m), 2.09-2.22 (4H, m), 2.40 (3H, s), 2.46-2.55 (2H, m), 2.82-2.73 (1H, m), 2.95-3.13 (5H, m), 3.14-3.21 (2H, m), 3.55-3.80 (6H, m), 4.44-4.52 (1H, m), 5.20 (2H, dd, J=35.0, 19.0 Hz), 5.42 (2H, s), 5.53-5.60 (1H, m), 6.54 (1H, s), 7.14-7.28 (5H, m), 7.31 (1H, s), 7.67 (2H, brs), 7.72-7.78 (1H, m), 7.80 (1H, d, J=11.0 Hz), 8.10-8.17 (2H, m), 8.29 (1H, t, J=5.9 Hz), 8.42 (1H, t, J=5.7 Hz), 8.47 (1H, d, J=8.6 Hz).

Process 5: N-(Bromoacetyl)-β-alanylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide To a dichloromethane (4.5 mL) solution of 2-bromoacetic acid (96.3 mg, 0.693 mmol), N-hydroxysuccinimide (79.7 mg, 0.693 mmol) and 1,3-diisopropylcarbodiimide (0.107 mL, 0.693 mmol) were added and stirred at room temperature. The reaction solution was added to an N,N-dimethylformamide (4.5 mL) solution of the compound (473 mg, 0.462 mmol) obtained in Process 4 above and triethylamine (0.154 mL, 1.11 mmol) at 0° C. and stirred at room temperature for 1 hour. The reaction solution was purified by silica gel column chromatography [elution solvent: chloroform-chloroform:methanol=85:15 (v/v)], and the solid obtained was washed with a chloroform:methanol:diethyl ether mixed solvent to yield the titled compound as a pale yellow solid (191 mg, 40%).

$^1$H-NMR (400 MHz, DMSO-$d_6$) δ: 0.87 (3H, t, J=7.4 Hz), 1.67-1.77 (2H, m), 1.79-1.92 (2H, m), 2.08-2.22 (4H, m), 2.33 (2H, t, J=7.0 Hz), 2.40 (3H, s), 2.74-2.83 (1H, m), 2.99-3.12 (3H, m), 3.14-3.21 (2H, m), 3.24-3.30 (2H, m), 3.56-3.77 (6H, m), 3.82 (2H, s), 4.41-4.51 (1H, m), 5.20 (2H, q, J=18.9 Hz), 5.42 (2H, s), 5.54-5.60 (1H, m), 6.54 (1H, s), 7.15-7.27 (5H, m), 7.31 (1H, s), 7.69-7.74 (1H, m), 7.80 (1H, d, J=10.9 Hz), 8.06 (1H, t, J=5.7 Hz), 8.13 (1H, d, J=7.8 Hz), 8.21-8.34 (3H, m), 8.46 (1H, d, J=8.6 Hz).

MS (ESI) m/z: 1030, 1032 (M+H)$^+$.

Process 6: Antibody-Drug Conjugate (2)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (1.25 mL) was placed in a 1.5 mL polypropylene tube and charged with an aqueous solution of 10 mM TCEP (0.019 mL; 2.3 equivalents per antibody molecule) and an aqueous solution of 1 M dipotassium hydrogenphosphate (0.0625 mL). After confirming that the solution had a pH of 7.4±0.1, the disulfide bond at the hinge part in the antibody was reduced by incubating at 37° C. for 1 hour.

Conjugation between antibody and drug linker: After adding DMSO (Sigma-Aldrich Co. LLC; 0.098 mL) and a DMSO solution containing 10 mM of the compound of Process 5 above (0.039 mL; 4.6 equivalents per antibody molecule) to the above solution at room temperature, it was stirred by using a tube rotator for conjugating the drug linker to the antibody at room temperature for 40 minutes. Next, an aqueous solution of 100 mM NAC (0.008 mL) was added thereto and stirred at room temperature to terminate the reaction of the drug linker for another 20 minutes.

Purification: The above solution was subjected to purification using the Common procedure D (ABS was used as a buffer solution) to yield 6 mL of a solution containing the compound of interest.

Physicochemical characterization: By using the Common procedure B and Common procedure E, the following characteristic values were obtained.

Antibody concentration: 1.41 mg/mL, antibody yield: 8.5 mg (68%), and average number of conjugated drug molecules (n) per antibody molecule: 3.3.

Example 3 Antibody-Drug Conjugate (3)

[Formula 56]

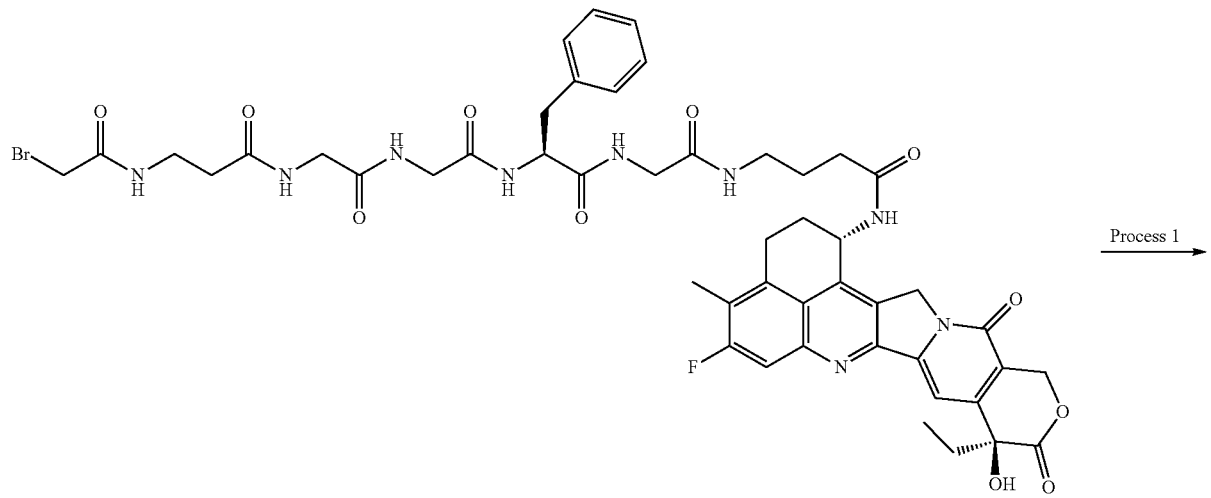

Process 1

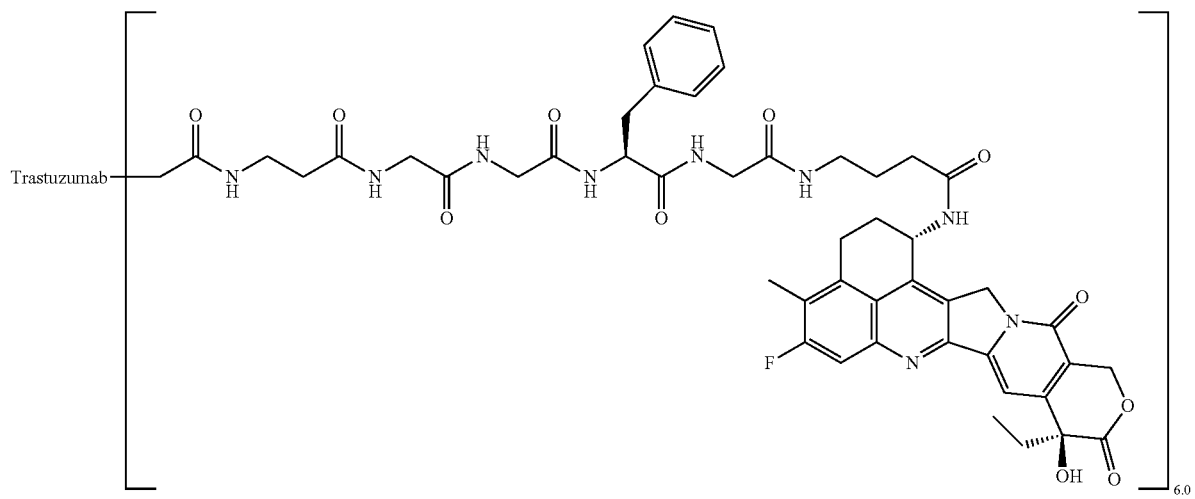

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (1.25 mL) was placed in a 1.5 mL polypropylene tube and charged with an aqueous solution of 10 mM TCEP (0.039 mL; 4.6 equivalents per antibody molecule) and an aqueous solution of 1 M dipotassium hydrogenphosphate (0.0625 mL). After confirming that the solution had a pH of 7.4±0.1, the disulfide bond at the hinge part in the antibody was reduced by incubating at 37° C. for 1 hour.

Conjugation between antibody and drug linker: After adding DMSO (0.065 mL) and a DMSO solution containing 10 mM of the compound of Process 5 of Example 2 (0.078 mL; 9.2 equivalents per antibody molecule) to the above solution at room temperature, it was stirred by using a tube rotator for conjugating the drug linker to the antibody at room temperature for 40 minutes. Next, an aqueous solution of 100 mM NAC (0.0155 mL) was added thereto and stirred at room temperature to terminate the reaction of the drug linker for another 20 minutes.

Purification: The above solution was subjected to purification using the Common procedure D (ABS was used as a buffer solution) to yield 6 mL of a solution containing the compound of interest.

Physicochemical characterization: By using the Common procedure B and Common procedure E, the following characteristic values were obtained.

Antibody concentration: 1.55 mg/mL, antibody yield: 9.3 mg (74%), and average number of conjugated drug molecules (n) per antibody molecule: 6.0.

Example 4 Intermediate (4)

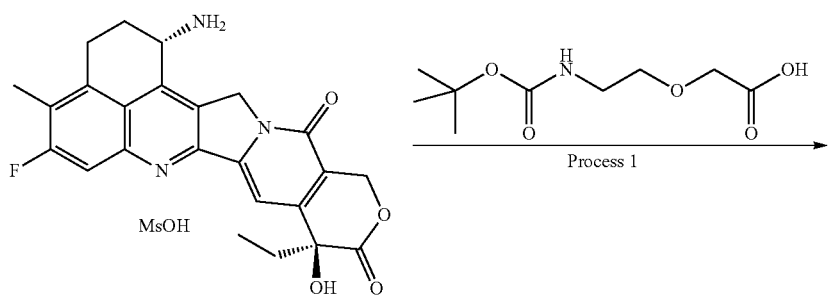

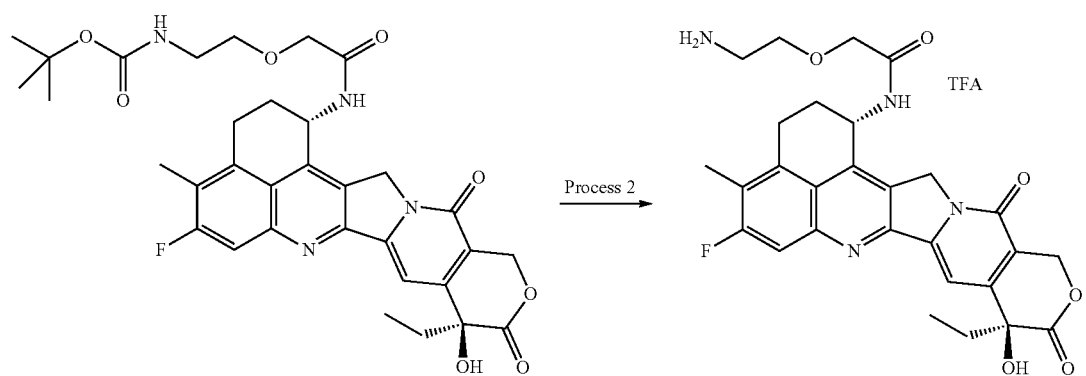

Process 1: tert-Butyl [2-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)ethyl]carbamate Methanesulfonic acid salt of exatecan (3.10 g, 5.47 mol) was reacted in the same manner as Process 1 of Example 1 by using {2-[(tert-butoxycarbonyl)amino]ethoxy}acetic acid (J. Med. Chem., 1992, Vol. 35, p. 2928; 1.55 g, 6.01 mmol) instead of 4-(tert-butoxycarbonylamino)butanoic acid to yield the titled compound as a pale yellow solid (2.56 g, 73%).

$^1$H-NMR (400 MHz, DMSO-$d_6$) δ: 0.87 (3H, t, J=7.3 Hz), 1.26 (9H, s), 1.81-1.91 (2H, m), 2.13-2.22 (2H, m), 2.40 (3H, s), 3.08-3.26 (4H, m), 3.43-3.53 (2H, m), 4.00 (1H, d, J=15.1 Hz), 4.05 (1H, d, J=15.1 Hz), 5.14 (1H, d, J=18.7 Hz), 5.22 (1H, d, J=18.7 Hz), 5.40 (1H, d, J=16.6 Hz), 5.44 (1H, d, J=16.6 Hz), 5.59-5.66 (1H, m), 6.53 (1H, s), 6.86 (1H, t, J=5.4 Hz), 7.31 (1H, s), 7.79 (1H, d, J=10.9 Hz), 8.49 (1H, d, J=9.1 Hz).

MS (APCI) m/z: 637 (M+H)$^+$.

Process 2: 2-(2-Aminoethoxy)-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]acetamide The compound (1.50 g, 2.36 mol) obtained in Process 1 above was reacted in the same manner as Process 2 of Example 1 to yield trifluoroacetic acid salt of the titled compound as a pale yellow solid (1.50 g, quantitative).

$^1$H-NMR (400 MHz, DMSO-$d_6$) δ: 0.87 (3H, t, J=7.5 Hz), 1.81-1.92 (2H, m), 2.15-2.23 (2H, m), 2.41 (3H, s), 3.05 (2H, t, J=5.1 Hz), 3.15-3.23 (2H, m), 3.71 (2H, t, J=5.1 Hz), 4.10 (2H, s), 5.19 (1H, d, J=18.7 Hz), 5.24 (1H, d, J=18.7 Hz), 5.43 (2H, s), 5.58-5.66 (1H, m), 6.55 (1H, s), 7.33 (1H, s), 7.73-7.84 (4H, m), 8.55 (1H, d, J=9.1 Hz).

MS (APCI) m/z: 537 (M+H)$^+$.

Example 5 Antibody-Drug Conjugate (5)
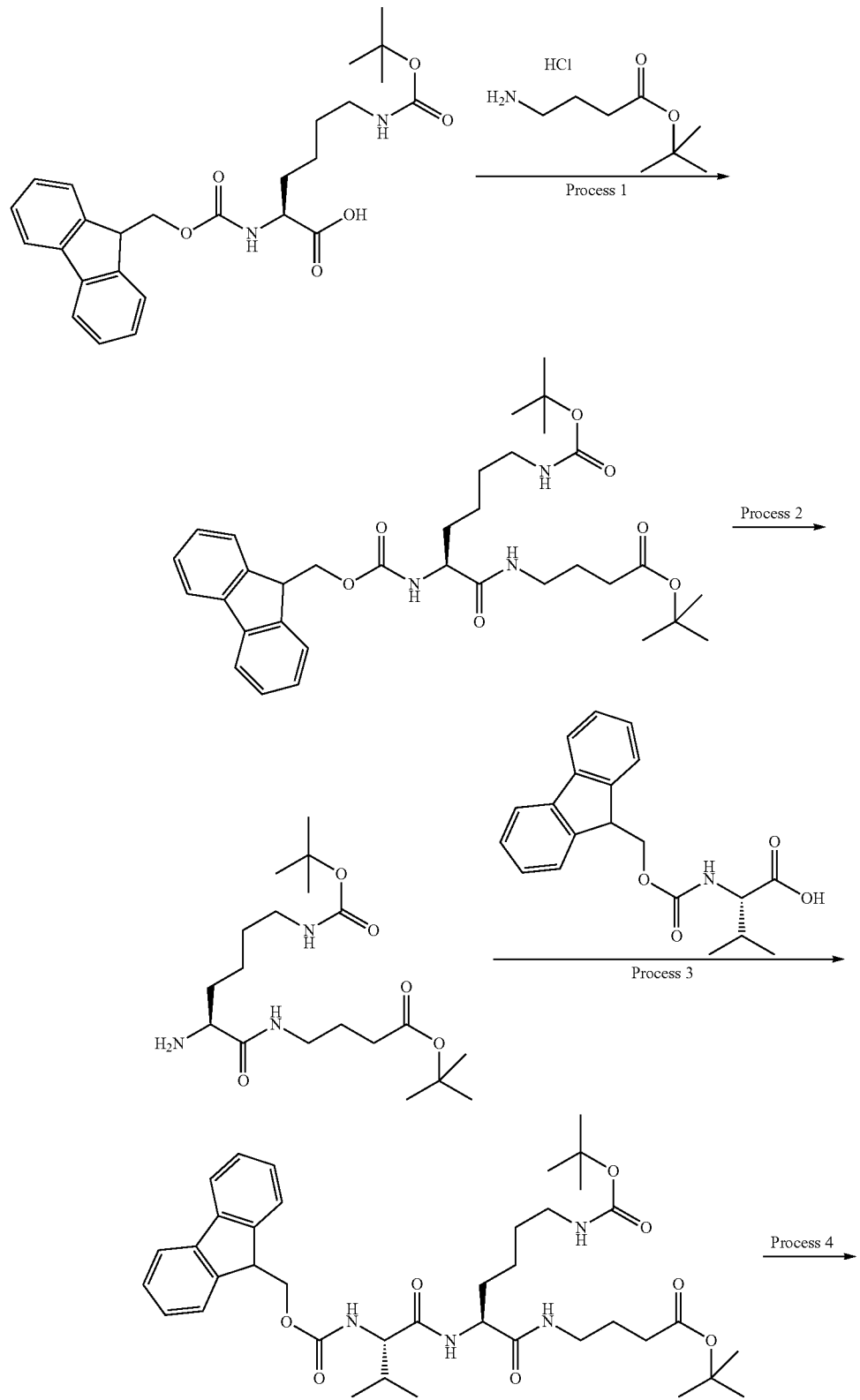
[Formula 58]

-continued
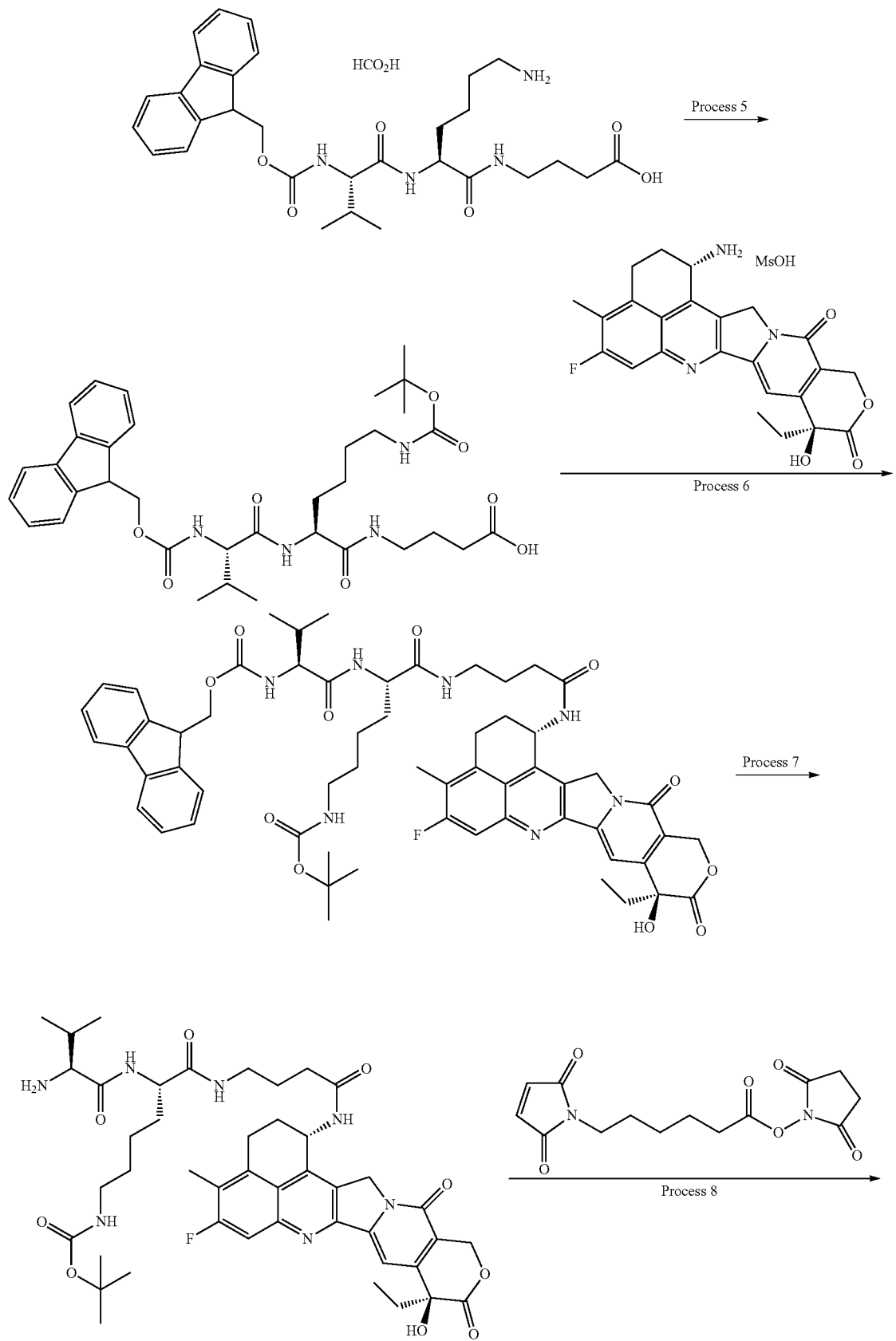

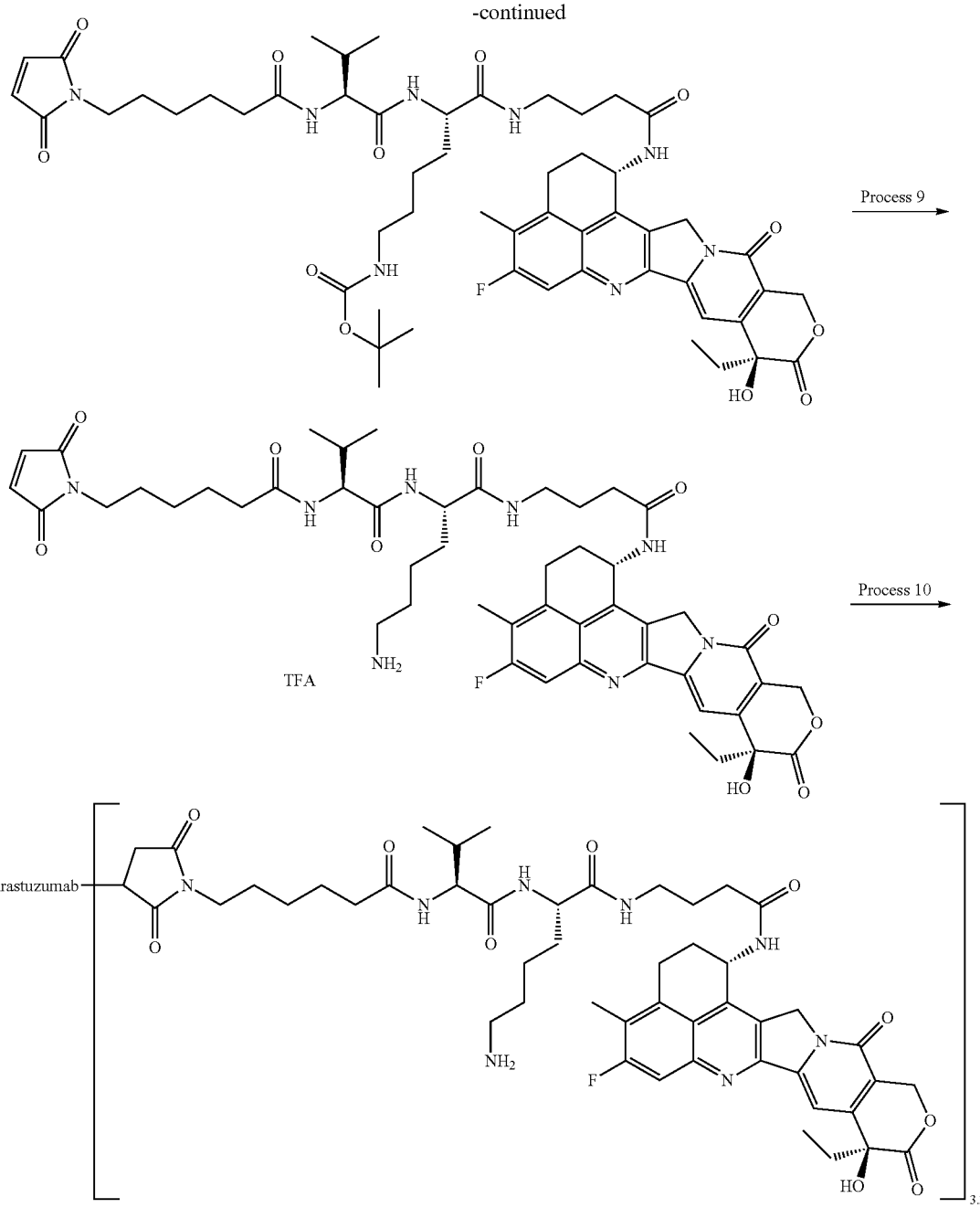

Process 1: tert-Butyl 4-({$N^6$-(tert-butoxycarbonyl)-$N^2$-[(9H-fluoren-9-ylmethoxy)carbonyl]-L-lysyl}amino)butanoate To an N,N-dimethylformamide (10.0 mL) solution of $N^\varepsilon$-(tert-butoxycarbonyl)-$N^\alpha$-[(9H-fluoren-9-ylmethoxy)carbonyl]-L-lysine (1.00 g, 2.14 mmol), N-hydroxysuccinimide (0.370 g, 3.20 mmol), and 4-aminobutanoic acid tert-butyl ester hydrochloride (0.830 g, 4.27 mmol), 1-ethyl-3-(3-dimethylaminopropyl)carbodiimide hydrochloride (0.610 g, 3.20 mmol) and N,N-diisopropylethylamine (0.410 mL, 2.35 mmol) were added and stirred at room temperature for 3 days. The reaction solution was diluted with ethyl acetate and washed with an aqueous solution of 10% citric acid, a saturated sodium hydrogen carbonate aqueous solution, and a saturated sodium chloride aqueous solution, and then the organic layer was dried over anhydrous magnesium sulfate. The solvent was removed under reduced pressure to yield the titled compound as a colorless solid (1.35 g, quantitative).

$^1$H-NMR (400 MHz, DMSO-$d_6$) δ: 1.14-1.42 (4H, m), 1.36 (9H, s), 1.37 (9H, s), 1.48-1.67 (4H, m), 2.18 (2H, t, J=7.6 Hz), 2.84-2.93 (2H, m), 2.99-3.11 (2H, m), 3.84-3.94 (1H, m), 4.18-4.30 (3H, m), 6.76 (1H, t, J=5.4 Hz), 7.33 (2H, t, J=7.3 Hz), 7.39-7.45 (3H, m), 7.73 (2H, dd, J=7.3, 2.7 Hz), 7.85-7.92 (3H, m).

Process 2: tert-Butyl 4-{[N⁶-(tert-butoxycarbonyl)-L-lysyl]amino}butanoate

To an N,N-dimethylformamide (8.00 mL) solution of the compound (1.35 g, 2.22 mmol) obtained in Process 1 above, piperidine (2.00 mL) was added and stirred at room temperature for 1.5 hours. The solvent was removed under reduced pressure to yield a mixture containing the titled compound. The mixture was used for the next reaction without further purification.

Process 3: N-[(9H-Fluoren-9-ylmethoxy)carbonyl]-L-valyl-N⁶-(tert-butoxycarbonyl)-N-(4-tert-butoxy-4-oxobutyl)-L-lysinamide To an N,N-dimethylformamide (30.0 mL) solution of the mixture (2.22 mmol) obtained in Process 2 above, N-[(9H-fluoren-9-ylmethoxy)carbonyl]-L-valine (1.13 g, 3.32 mmol), N-hydroxysuccinimide (0.310 g, 2.66 mmol), and 1-ethyl-3-(3-dimethylaminopropyl)carbodiimide hydrochloride (0.550 g, 2.88 mmol) were added and stirred at room temperature for 18 hours. The reaction solution was diluted with ethyl acetate and washed with a saturated sodium hydrogen carbonate aqueous solution and a saturated sodium chloride aqueous solution, and then the organic layer was dried over anhydrous magnesium sulfate. The solvent was removed under reduced pressure and the residues obtained were purified by silica gel column chromatography [chloroform-chloroform:methanol=9:1 (v/v)] to yield the titled compound as a colorless solid (0.363 g, 23%).

¹H-NMR (400 MHz, DMSO-d₆) δ: 0.84 (6H, t, J=6.0 Hz), 1.12-1.64 (8H, m), 1.34 (9H, s), 1.38 (9H, s), 1.90-2.04 (1H, m), 2.17 (2H, t, J=7.3 Hz), 2.79-2.90 (2H, m), 2.99-3.09 (2H, m), 3.83-3.91 (1H, m), 4.08-4.44 (4H, m), 6.71 (1H, t, J=5.4 Hz), 7.32 (2H, t, J=7.3 Hz), 7.42 (3H, t, J=7.3 Hz), 7.74 (2H, t, J=7.0 Hz), 7.85-7.91 (4H, m).

MS (ESI) m/z: 709 (M+H)⁺.

Process 4: N-[(9H-Fluoren-9-ylmethoxy)carbonyl]-L-valyl-N-(3-carboxypropyl)-L-lysinamide To the compound (0.363 mg, 0.512 mmol) obtained in Process 3 above, formic acid (10.0 mL) was added and stirred at room temperature for 4 hours. The solvent was removed under reduced pressure to yield formic acid salt of the titled compound. The compound was used for the next reaction without further purification.

Process 5: N-[(9H-Fluoren-9-ylmethoxy)carbonyl]-L-valyl-N⁶-(tert-butoxycarbonyl)-N-(3-carboxypropyl)-L-lysinamide To a 1,4-dioxane (5.00 mL) suspension of the compound (0.512 mmol) obtained in Process 4 above, a saturated sodium hydrogen carbonate aqueous solution (20.0 mL) and di-tert-butyl dicarbonate (0.178 mL, 0.769 mmol) were added and stirred at room temperature for 3 hours. The reaction solution was diluted with ethyl acetate and washed with an aqueous solution of 10% citric acid and a saturated sodium chloride aqueous solution, and then the organic layer was dried over anhydrous magnesium sulfate. The solvent was removed under reduced pressure to yield the titled compound as a colorless solid (0.295 g, 88%).

¹H-NMR (400 MHz, DMSO-d₆) δ: 0.84 (6H, t, J=6.7 Hz), 1.13-1.39 (4H, m), 1.35 (9H, s), 1.48-1.62 (4H, m), 1.91-2.04 (1H, m), 2.20 (2H, t, J=7.3 Hz), 2.80-2.89 (2H, m), 2.99-3.11 (2H, m), 3.87 (1H, dd, J=8.5, 6.7 Hz), 4.06-4.35 (4H, m), 6.71 (1H, t, J=6.0 Hz), 7.32 (2H, t, J=7.6 Hz), 7.39-7.46 (3H, m), 7.74 (2H, t, J=7.6 Hz), 7.83-7.94 (4H, m).

MS (ESI) m/z: 653 (M+H)⁺

Process 6: N-[(9H-Fluoren-9-ylmethoxy)carbonyl]-L-valyl-N⁶-(tert-butoxycarbonyl)-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-lysinamide Methanesulfonic acid salt of exatecan (0.240 g, 0.452 mmol) was reacted in the same manner as Process 1 of Example 1 by using the compound (0.295 g, 0.452 mmol) obtained in Process 5 above instead of 4-(tert-butoxycarbonylamino)butanoic acid to yield the titled compound as a pale orange solid (0.208 g, 43%).

MS(ESI) m/z: 1071 (M+H)⁺.

Process 7: L-Valyl-N⁶-(tert-butoxycarbonyl)-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-lysinamide The compound (0.208 g, 0.194 mmol) obtained in Process 6 above was reacted in the same manner as Process 2 above to yield a mixture containing the titled compound. The mixture was used for the next reaction without further purification.

Process 8: N-[6-(2,5-Dioxo-2,5-dihydro-1H-pyrrol-1-yl)hexanoyl]-L-valyl-N⁶-(tert-butoxycarbonyl)-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-lysinamide To an N,N-dimethylformamide (110 mL) solution of the mixture (0.194 mmol) obtained in Process 7 above, N-succinimidyl 6-maleimidohexanoate (84.5 mg, 0.271 mmol) was added and stirred at room temperature for 17 hours. The solvent was removed under reduced pressure and the residues obtained were purified by silica gel column chromatography [chloroform-chloroform:methanol=9:1 (v/v)] to yield the titled compound as a pale yellow solid (0.133 g, 56%).

¹H-NMR (400 MHz, DMSO-d₆) δ: 0.77 (6H, t, J=5.7 Hz), 0.87 (3H, t, J=7.3 Hz), 1.14-1.71 (10H, m), 1.35 (9H, s), 1.77-1.95 (3H, m), 2.02-2.23 (7H, m), 2.40 (3H, s), 2.84 (3H, q, J=6.4 Hz), 3.05 (2H, d, J=6.7 Hz), 3.17 (2H, s), 3.26-3.39 (3H, m), 4.01-4.16 (2H, m), 5.15 (1H, d, J=18.7 Hz), 5.24 (1H, d, J=18.7 Hz), 5.36-5.48 (2H, m), 5.51-5.60 (1H, m), 6.52 (1H, s), 6.72 (1H, t, J=6.0 Hz), 6.99 (2H, s), 7.31 (1H, s), 7.71-7.85 (5H, m), 8.41 (1H, d, J=9.1 Hz).

MS (ESI) m/z: 1041 (M+H)⁺.

Process 9: N-[6-(2,5-Dioxo-2,5-dihydro-1H-pyrrol-1-yl)hexanoyl]-L-valyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-lysinamide To a dichloromethane (10.0 mL) solution of the compound (0.110 mg, 0.106 mmol) obtained in Process 8 above, trifluoroacetic acid (4.00 mL) was added and stirred at room temperature for 5 hours. The solvent was removed under reduced pressure to yield trifluoroacetic acid salt of the titled compound as a pale yellow solid (70.0 mg, 64%).

$^1$H-NMR (400 MHz, DMSO-$d_6$) δ: 0.76-0.81 (6H, m), 0.87 (3H, t, J=7.3 Hz), 1.12-1.31 (4H, m), 1.39-1.56 (8H, m), 1.57-1.74 (3H, m), 1.79-1.96 (3H, m), 2.06-2.18 (7H, m), 2.40 (3H, s), 2.70-2.80 (2H, m), 3.01-3.10 (2H, m), 3.13-3.22 (2H, m), 4.04 (1H, t, J=7.6 Hz), 4.10-4.20 (1H, m), 5.15 (1H, d, J=18.7 Hz), 5.24 (1H, d, J=18.7 Hz), 5.36-5.47 (2H, m), 5.52-5.60 (1H, m), 6.53 (1H, s), 7.00 (2H, s), 7.32 (1H, s), 7.61 (3H, brs), 7.75-7.88 (4H, m), 8.43 (1H, d, J=8.5 Hz).

MS (ESI) m/z: 941 (M+H)$^+$.

Process 10: Antibody-Drug Conjugate (5)

By using the trastuzumab produced in Reference Example 1 and the compound obtained in Process 9 above, the titled antibody-drug conjugate was obtained in the same manner as Process 6 of Example 2. The solution was further concentrated by the Common procedure A. After that, by using the Common procedure B and Common procedure E, the following characteristic values were obtained.

Antibody concentration: 10.64 mg/mL, antibody yield: 7.4 mg (59%), and average number of conjugated drug molecules (n) per antibody molecule: 3.3.

Example 6 Antibody-Drug Conjugate (6)

Process 1: Antibody-Drug Conjugate (6)

By using the trastuzumab produced in Reference Example 1 and the compound obtained in Process 9 of Example 5, the titled antibody-drug conjugate was obtained in the same manner as Process 1 of Example 2. The solution was further concentrated by the Common procedure A. After that, by using the Common procedure B and Common procedure E, the following characteristic values were obtained.

Antibody concentration: 10.41 mg/mL, antibody yield: 7.3 mg (58%), and average number of conjugated drug molecules (n) per antibody molecule: 5.9.

Example 7 Intermediate (7)

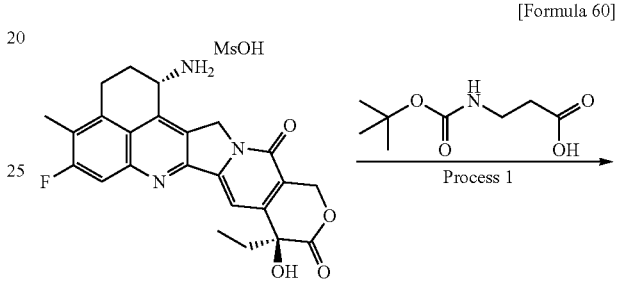

[Formula 60]

[Formula 59]

-continued

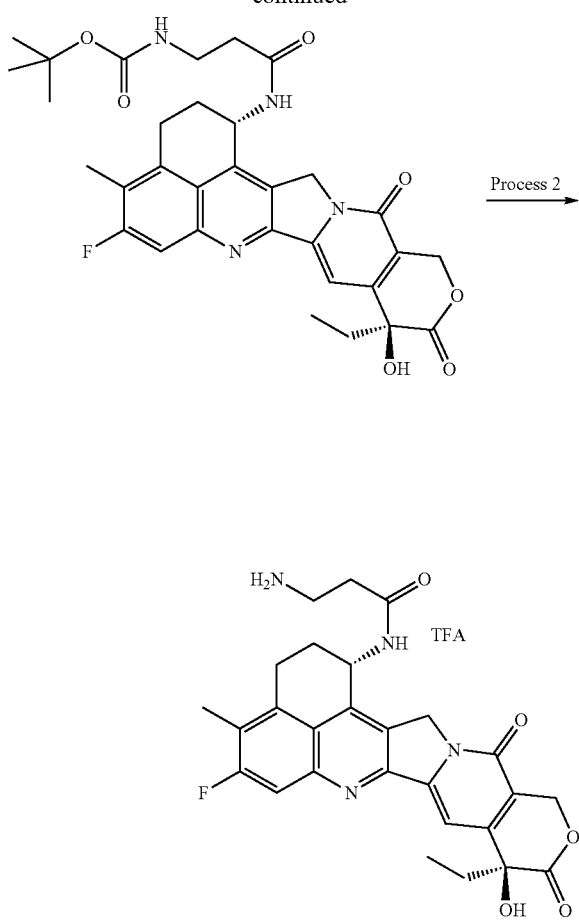

Process 1: tert-Butyl (3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl) carbamate Methanesulfonic acid salt of exatecan (500 mg, 0.941 mmol) was reacted in the same manner as Process 1 of Example 1 by using N-(tert-butoxycarbonyl)-β-alanine instead of 4-(tert-butoxycarbonylamino)butanoic acid to yield the titled compound as a yellow-brown solid (616 mg, quantitative).

$^1$H-NMR (400 MHz, DMSO-d$_6$) δ: 0.87 (3H, t, J=7.2 Hz), 1.29 (9H, s), 1.86 (2H, dt, J=15.1, 7.3 Hz), 2.04-2.22 (2H, m), 2.31 (2H, t, J=6.8 Hz), 2.40 (3H, s), 3.10-3.26 (4H, m), 5.15 (1H, d, J=18.8 Hz), 5.26 (1H, d, J=19.2 Hz), 5.42 (2H, dd, J=18.8, 16.4 Hz), 5.57 (1H, dt, J=8.5, 4.2 Hz), 6.53 (1H, s), 6.78 (1H, t, J=5.5 Hz), 7.30 (1H, s), 7.80 (1H, d, J=11.0 Hz), 8.46 (1H, d, J=8.6 Hz).

MS (ESI) m/z: 607 (M+H)$^+$.

Process 2: N-[(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound obtained in Process 1 above was reacted in the same manner as Process 2 of Example 1 to yield trifluoroacetic acid salt of the titled compound as a yellow solid (499 mg, 86%).

$^1$H-NMR (400 MHz, DMSO-d$_6$) δ: 0.87 (3H, t, J=7.2 Hz), 1.86 (2H, dquin, J=14.6, 7.2, 7.2, 7.2, 7.2 Hz), 2.06-2.27 (1H, m), 2.41 (3H, s), 2.46-2.57 (2H, m), 3.08 (2H, t, J=6.8 Hz), 3.14-3.24 (2H, m), 5.22 (1H, d, J=18.8 Hz), 5.29 (1H, d, J=18.8 Hz), 5.43 (2H, s), 5.58 (1H, dt, J=8.5, 4.5 Hz), 6.55 (1H, s), 7.32 (1H, s), 7.74 (3H, brs), 7.82 (1H, d, J=11.0 Hz), 8.67 (1H, d, J=8.6 Hz).

MS (ESI) m/z: 507 (M+H)$^+$.

Example 8 Intermediate (8)

[Formula 61]

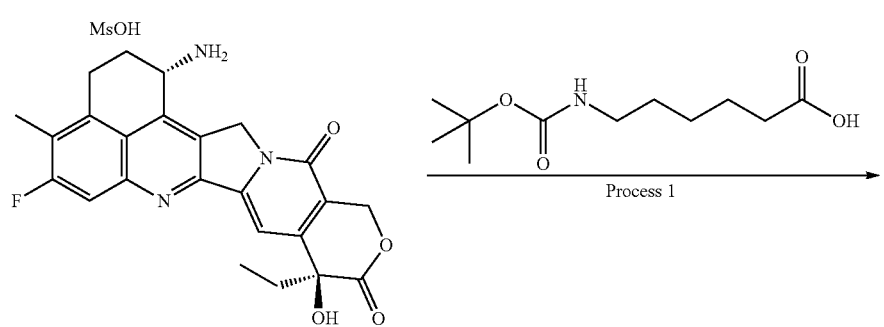

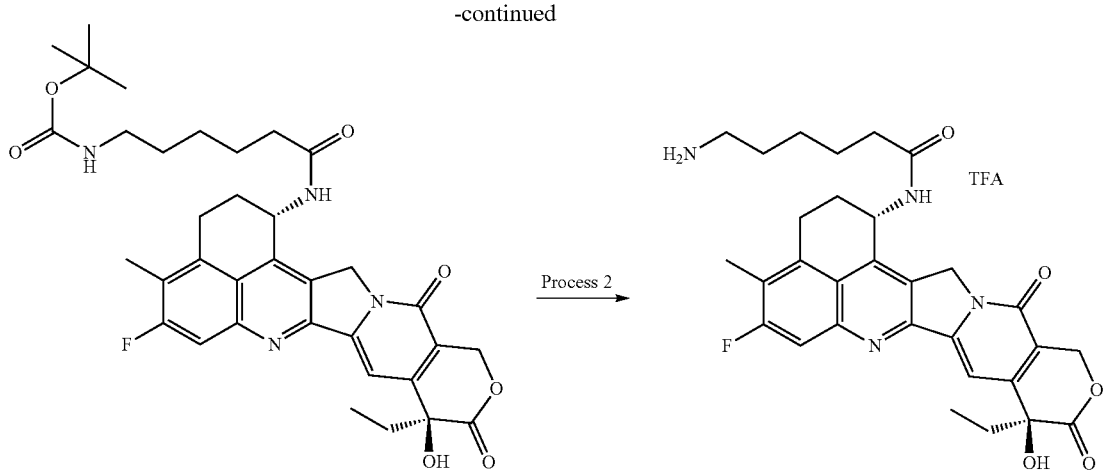

Process 1: tert-Butyl (6-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-6-oxohexyl)carbamate Methanesulfonic acid salt of exatecan (0.500 g, 0.882 mmol) was reacted in the same manner as Process 1 of Example 1 by using 6-(tert-butoxycarbonylamino)hexanoic acid instead of 4-(tert-butoxycarbonylamino)butanoic acid to yield the titled compound (0.620 g, quantitative).

$^1$H-NMR (DMSO-$d_6$) δ: 0.83 (3H, t, J=7.8 Hz), 1.14-1.28 (2H, m), 1.31 (9H, s), 1.47-1.61 (2H, m), 1.75-1.89 (2H, m), 2.04-2.17 (4H, m), 2.35 (3H, s), 2.81-2.88 (2H, m), 3.09-3.16 (2H, m), 5.10 (1H, d, J=19.4 Hz), 5.16 (1H, d, J=19.4 Hz), 5.39 (2H, s), 5.48-5.55 (1H, m), 6.50 (1H, s), 6.73-6.78 (1H, m), 7.26 (1H, s), 7.74 (1H, d, J=10.9 Hz), 8.39 (1H, d, J=9.0 Hz).

Process 2: 6-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]hexanamide The compound (0.397 g, 0.611 mmol) obtained in Process 1 above was reacted in the same manner as Process 2 of Example 1 to yield trifluoroacetic acid salt of the titled compound (0.342 g, 84%).

$^1$H-NMR (DMSO-$d_6$) δ: 0.88 (3H, t, J=7.2 Hz), 1.31-1.41 (2H, m), 1.52-1.70 (4H, m), 1.80-1.94 (2H, m), 2.05-2.18 (2H, m), 2.21 (2H, t, J=7.4 Hz), 2.40 (3H, s), 2.81 (2H, t, J=7.4 Hz), 3.10-3.25 (2H, m), 3.33 (2H, brs), 5.18 (1H, d, J=19.8 Hz), 5.22 (1H, d, J=19.8 Hz), 5.41 (2H, d, J=16.6 Hz), 5.45 (2H, d, J=16.6 Hz), 5.53-5.60 (1H, m), 6.55 (1H, s), 7.32 (1H, s), 7.80 (1H, d, J=10.9 Hz), 8.49 (1H, d, J=9.2 Hz).

Example 9 Intermediate (9)

[Formula 62]

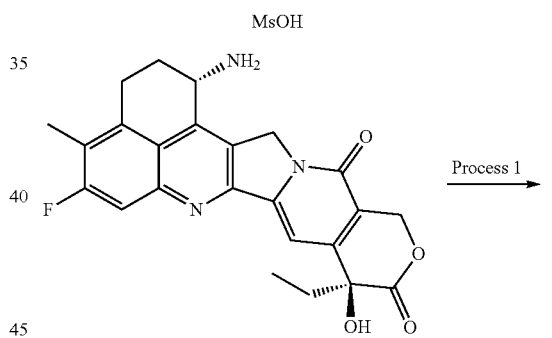

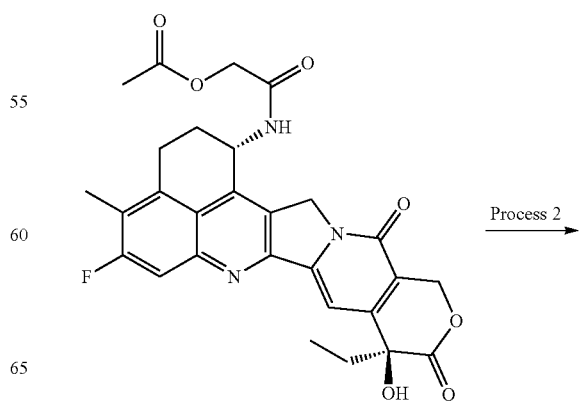

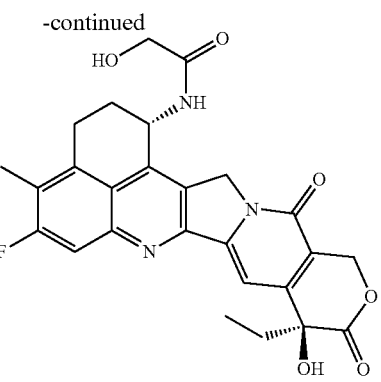

Process 1: 2-{[(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethylacetate Under ice cooling, to an N,N-dimethylformamide (20.0 mL) suspension of methanesulfonic acid salt of exatecan (0.500 g, 0.941 mmol), N,N-diisopropylethylamine (0.492 mL, 2.82 mmol) and acetoxyacetyl chloride (0.121 mL, 1.13 mmol) were added and stirred at room temperature for 1 hour. The solvent was removed under reduced pressure and the residues obtained were purified by silica gel column chromatography [chloroform-partitioned organic layer of chloroform:methanol:water=7:3:1 (v/v/v)] to yield the titled compound as a pale yellow solid (0.505 g, quantitative).

$^1$H-NMR (400 MHz, DMSO-$d_6$) δ: 0.87 (3H, t, J=7.4 Hz), 1.81-1.92 (2H, m), 2.08 (3H, s), 2.08-2.22 (2H, m), 2.41 (3H, s), 3.14-3.21 (2H, m), 4.51 (2H, dd, J=19.4, 14.7 Hz), 5.22 (2H, dd, J=40.1, 19.0 Hz), 5.43 (2H, s), 5.56-5.61 (1H, m), 6.53 (1H, s), 7.31 (1H, s), 7.81 (1H, d, J=11.0 Hz), 8.67 (1H, d, J=8.6 Hz).

MS (ESI) m/z: 536 (M+H)$^+$.

Process 2: N-[(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-2-hydroxyacetamide To a methanol (50.0 mL) suspension of the compound (0.504 g, 0.941 mmol) obtained in Process 1 above, tetrahydrofuran (20.0 mL) and a 1 N sodium hydroxide aqueous solution (4.00 mL, 4.00 mmol) were added and stirred at room temperature for 1 hour. The reaction was terminated by the addition of 1 N hydrochloric acid (5.00 mL, 5.00 mmol), and the solvent was removed under reduced pressure. The residues obtained were purified by silica gel column chromatography [chloroform-partitioned organic layer of chloroform:methanol:water=7:3:1 (v/v/v)] to yield the titled compound as a pale yellow solid (0.412 g, 89%).

$^1$H-NMR (400 MHz, DMSO-$d_6$) δ: 0.87 (3H, t, J=7.3 Hz), 1.78-1.95 (2H, m), 2.09-2.28 (2H, m), 2.39 (3H, s), 3.07-3.27 (2H, m), 3.96 (2H, d, J=6.0 Hz), 5.11-5.26 (2H, m), 5.42 (2H, s), 5.46-5.54 (1H, m), 5.55-5.63 (1H, m), 6.52 (1H, s), 7.30 (1H, s), 7.78 (1H, d, J=10.9 Hz), 8.41 (1H, d, J=9.1 Hz).

MS (ESI) m/z: 494 (M+H)$^+$.

Example 10 (Alternative Method for Synthesizing Compound of Example 9)

[Formula 63]

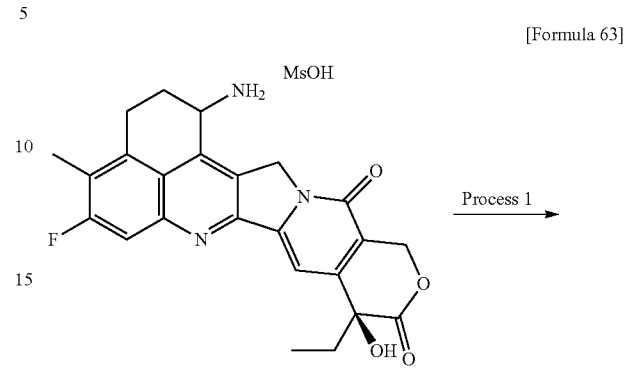

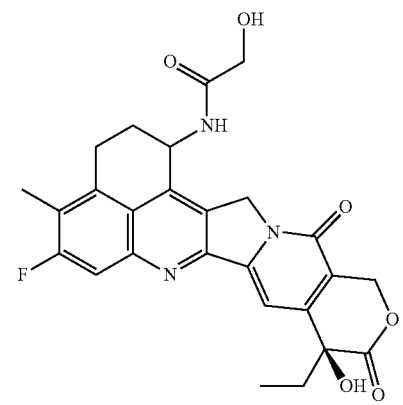

Process 1: N-[(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-2-hydroxyacetamide Glycolic acid (0.0201 g, 0.27 mmol) was dissolved in N,N-dimethylformamide (1.0 mL), charged with N-hydroxysuccinimide (0.0302 g, 0.27 mmol) and 1-(3-dimethylaminopropyl)-3-ethylcarbodiimide hydrochloride (0.0508 g, 0.27 mmol), and stirred for 1 hour. The reaction solution was added to an N,N-dimethylformamide (1.0 mL) suspension of methanesulfonic acid salt of exatecan (0.1 g, 0.176 mmol) and triethylamine (0.025 mL, 0.18 mmol), and stirred at room temperature for 24 hours. The solvent was removed under reduced pressure and the residues obtained were purified by silica gel column chromatography [chloroform-chloroform:methanol=10:1 (v/v)] to yield the titled compound as a pale yellow solid (0.080 g, 92%). The instrumental data of the compound was the same as that of Process 2 of Example 9.

Example 11 Antibody-Drug Conjugate (11)
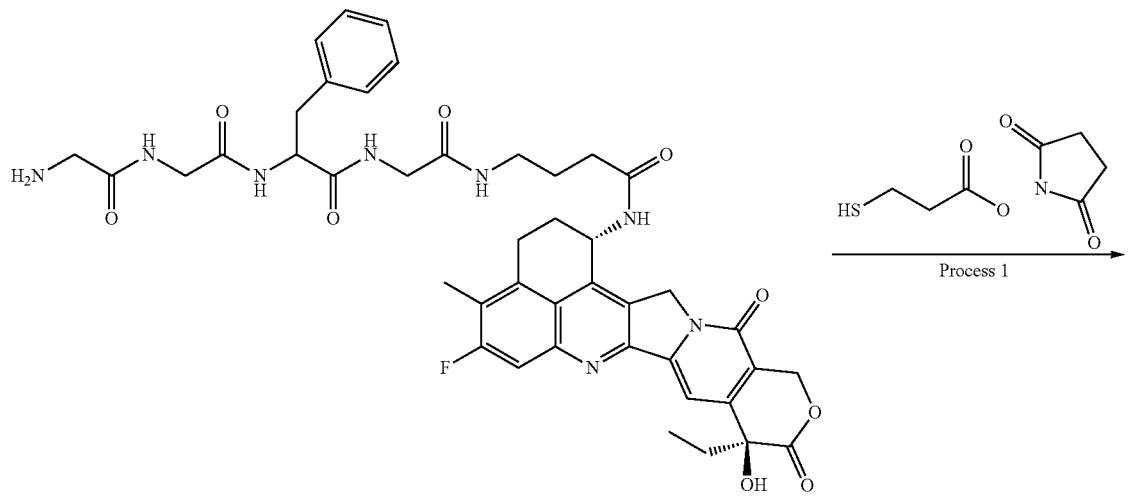
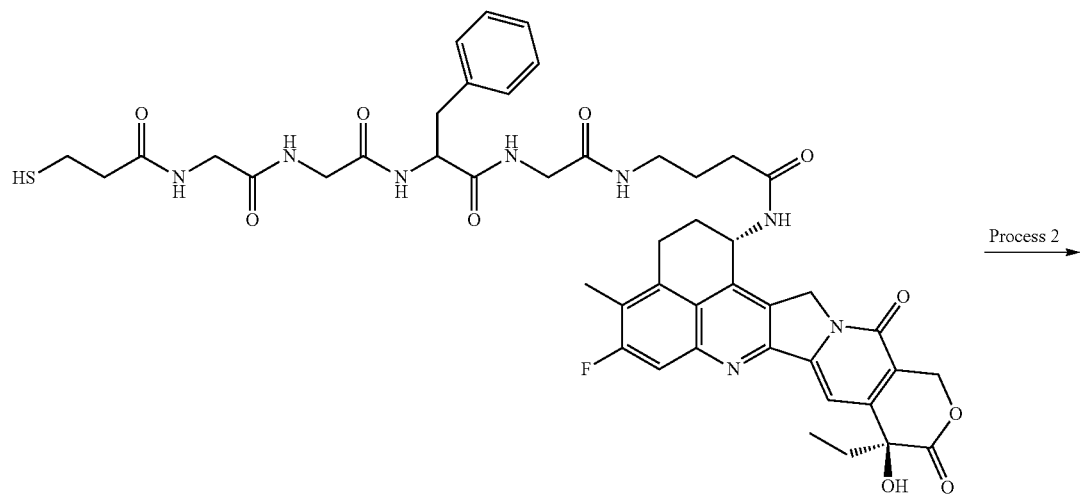
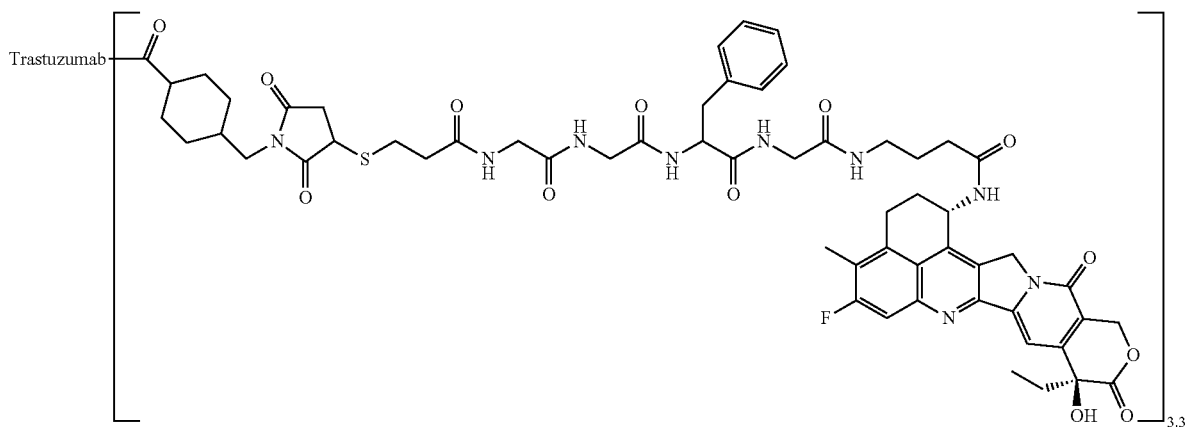

Process 1: N-(3-Sulfanylpropanoyl)glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (84.0 mg, 0.100 mmol) obtained in Process 2 of Example 2 was reacted in the same manner as Process 8 of Example 5 by using N-succinimidyl 3-mercaptopropionate instead of N-succinimidyl 6-maleimidohexanoate to yield the titled compound as a pale yellow solid (61.2 mg, 66%).

$^1$H-NMR (DMSO-$d_6$) δ: 0.87 (3H, t, J=7.4 Hz), 1.77-1.66 (2H, m), 1.79-1.92 (2H, m), 2.07-2.24 (4H, m), 2.31-2.47 (3H, m), 2.40 (3H, s), 2.59-2.69 (2H, m), 2.78 (1H, dd, J=13.7, 9.8 Hz), 2.98-3.13 (3H, m), 3.14-3.23 (2H, m), 3.54-3.79 (6H, m), 4.40-4.50 (1H, m), 5.20 (2H, dd, J=36.8, 19.2 Hz), 5.36-5.47 (2H, m), 5.52-5.63 (1H, m), 6.54 (1H, s), 7.14-7.28 (5H, m), 7.31 (1H, s), 7.68-7.74 (1H, m), 7.80 (1H, d, J=10.9 Hz), 8.03-8.09 (1H, m), 8.13 (1H, d, J=7.8 Hz), 8.19-8.29 (2H, m), 8.46 (1H, d, J=8.6 Hz).

MS (ESI) m/z: 927 (M+H)$^+$.

Process 2: Antibody-Drug Conjugate (11)

SMCC derivatization of antibody: The trastuzumab produced in Reference Example 1 was prepared to have an antibody concentration of 20 mg/mL by replacing the medium with PBS6.5/EDTA by using the Common procedure C-2 and Common procedure B (as absorption coefficient at 280 nm, 1.37 mLmg$^{-1}$ cm$^{-1}$ was used). The solution (0.5 mL) was placed in a 1.5 mL tube, charged with a DMSO solution (0.0125 mL; which corresponds to about 5.1 equivalents per antibody molecule) containing 27.6 mM of succinimidyl 4-(N-maleimidomethyl)cyclohexane-1-carboxylate (SMCC, Thermo Fisher Scientific Inc.) and DMSO (0.0125 mL) at room temperature, and reacted at room temperature for 2 hours. This reaction solution was subjected to purification according to the Common procedure D-2 to yield 1.2 mL of a solution containing about 10 mg of the SMCC-derivatized antibody.

Conjugation between antibody and drug linker: After adding DMSO (0.09 mL) and a DMSO solution containing 10 mM of the compound obtained in Process 1 above (0.03 mL; which corresponds to about 5.8 equivalents per antibody molecule) to the above solution at room temperature, it was stirred by using a tube rotator (MTR-103, manufactured by AS ONE Corporation) for conjugating the drug linker to the antibody at room temperature for 16 hours.

Purification: The above solution was subjected to purification using the Common procedure D (ABS was used as a buffer solution) to yield 6 mL of a solution containing the compound of interest.

Physicochemical characterization: By using the Common procedure B and Common procedure E, the following characteristic values were obtained.

Antibody concentration: 1.20 mg/mL, antibody yield: 7.2 mg (72%), and average number of conjugated drug molecules (n) per antibody molecule: 3.3.

Example 12 Antibody-Drug Conjugate (12)

[Formula 65]

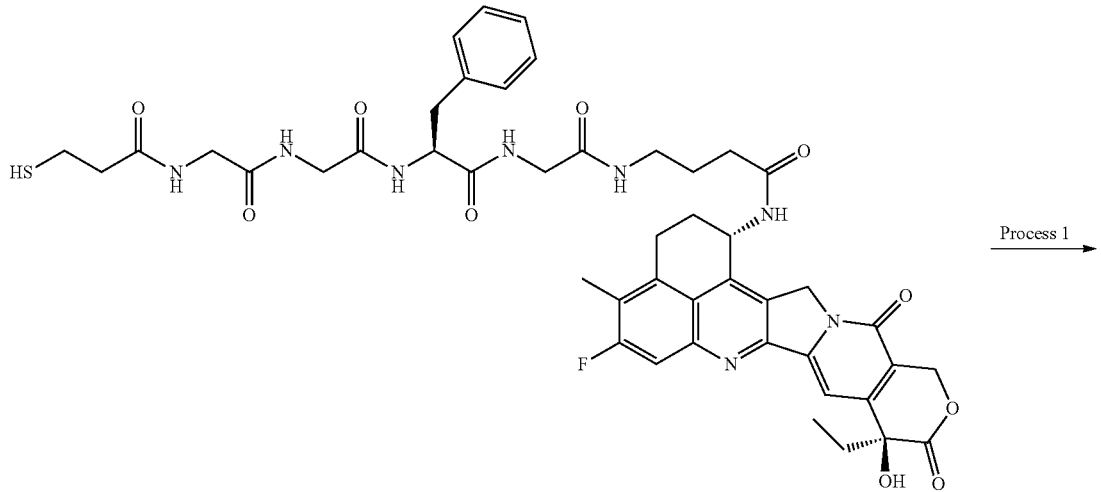

Process 1

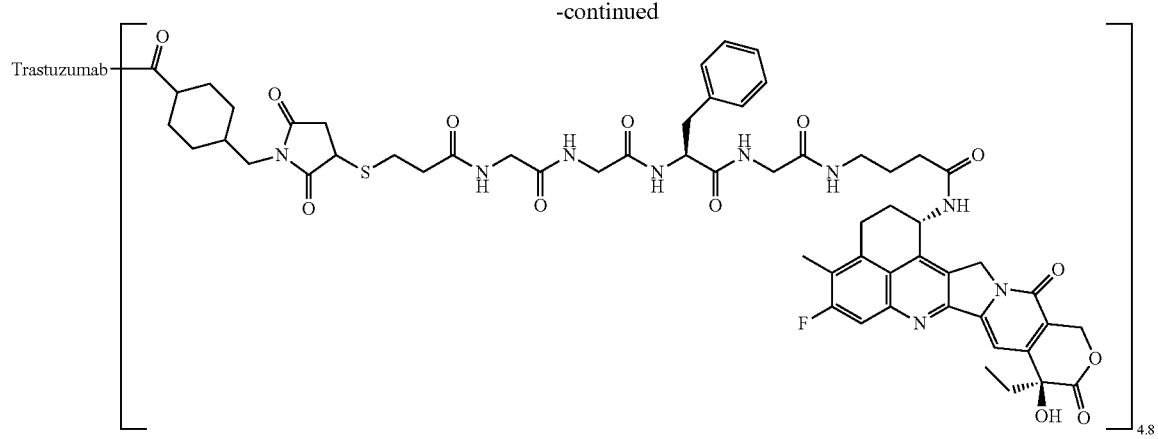

Process 1: Antibody-Drug Conjugate (12)

SMCC derivatization of antibody: The trastuzumab produced in Reference Example 1 was prepared to have an antibody concentration of 20 mg/mL by replacing the medium with PBS6.5/EDTA by using the Common procedure C-2 and Common procedure B (as absorption coefficient at 280 nm, 1.37 mLmg$^{-1}$ cm$^{-1}$ was used). The solution (0.5 mL) was placed in a 1.5 mL tube, charged with a DMSO solution (0.025 mL; which corresponds to about 10 equivalents per antibody molecule) containing 27.6 mM of succinimidyl 4-(N-maleimidomethyl)cyclohexane-1-carboxylate (SMCC, Thermo Fisher Scientific Inc.) at room temperature, and reacted at room temperature for 2 hours. This reaction solution was subjected to purification according to the Common procedure D-2 to yield 1.2 mL of a solution containing about 10 mg of the SMCC-derivatized antibody.

Conjugation between antibody and drug linker: After adding DMSO (0.06 mL) and a DMSO solution containing 10 mM of the compound obtained in Process 1 of Example 11 (0.06 mL; which corresponds to about 11.6 equivalents per antibody molecule) to the above solution at room temperature, it was stirred by using a tube rotator (MTR-103, manufactured by AS ONE Corporation) for conjugating the drug linker to the antibody at room temperature for 16 hours.

Purification: The above solution was subjected to purification using the Common procedure D (ABS was used as a buffer solution) to yield 6 mL of a solution containing the compound of interest. The solution was further concentrated by the Common procedure A. After that, by using the Common procedure B and Common procedure E, the following characteristic values were obtained.

Antibody concentration: 2.36 mg/mL, antibody yield: 2.8 mg (28%), and average number of conjugated drug molecules (n) per antibody molecule: 4.8.

Example 13 Antibody-Drug Conjugate (13)

[Formula 66]

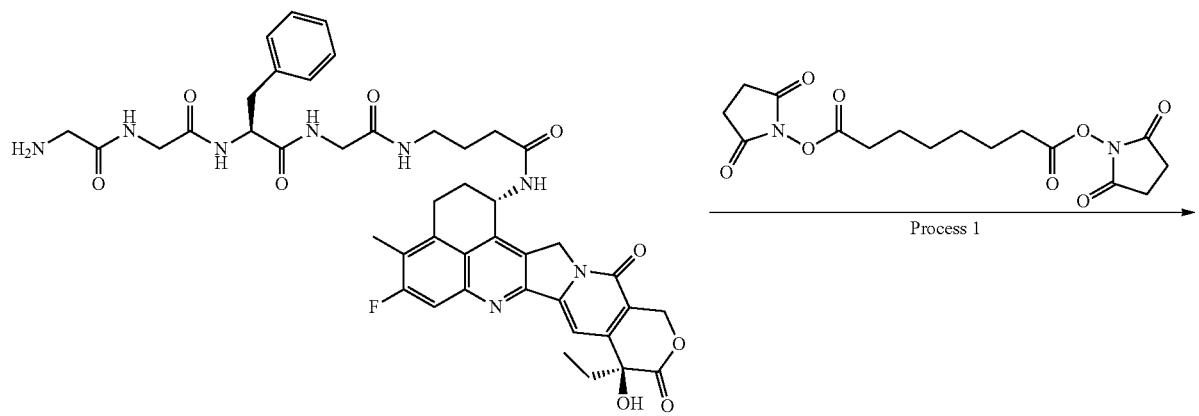

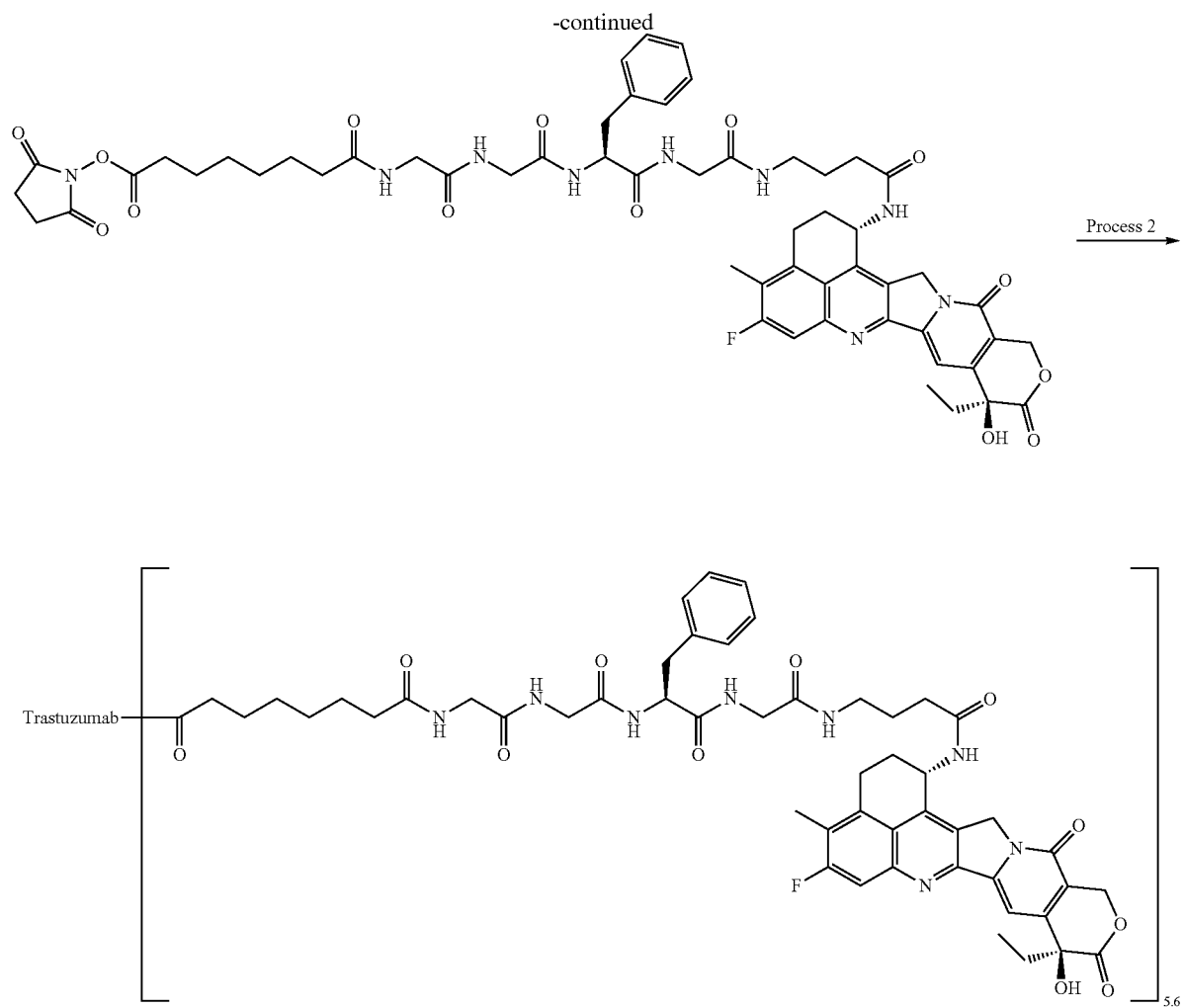

Process 1: N-{8-[(2,5-Dioxopyrrolidin-1-yl)oxy]-8-oxoocatnoyl}glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (84.0 mg, 0.100 mmol) obtained in Process 2 of Example 2 was reacted in the same manner as Process 8 of Example 5 by using suberic acid di(N-succinimidyl) instead of N-succinimidyl 6-maleimidohexanoate to yield the titled compound as a pale yellow solid (77.1 mg, 71%).

$^1$H-NMR (DMSO-d$_6$) δ: 0.87 (3H, t, J=7.2 Hz), 1.21-1.38 (4H, m), 1.43-1.50 (2H, m), 1.55-1.63 (2H, m), 1.68-1.76 (2H, m), 1.80-1.91 (2H, m), 2.07-2.22 (6H, m), 2.40 (3H, s), 2.60-2.67 (2H, m), 2.76-2.84 (5H, m), 2.97-3.22 (5H, m), 3.56-3.76 (6H, m), 4.40-4.50 (1H, m), 5.20 (2H, q, J=18.8 Hz), 5.37-5.48 (2H, m), 5.53-5.62 (1H, m), 6.54 (1H, s), 7.15-7.28 (5H, m), 7.31 (1H, s), 7.71 (1H, t, J=5.5 Hz), 7.80 (1H, d, J=10.9 Hz), 8.04 (1H, t, J=5.9 Hz), 8.09 (1H, t, J=5.9 Hz), 8.14 (1H, d, J=7.8 Hz), 8.26 (1H, t, J=5.9 Hz), 8.47 (1H, d, J=8.6 Hz).

MS (ESI) m/z: 1092 (M+H)$^+$.

Process 2: Antibody-Drug Conjugate (13)

Conjugation between antibody and drug linker: The trastuzumab produced in Reference Example 1 was prepared to have an antibody concentration of 20 mg/mL by replacing the medium with PBS6.5/EDTA by using the Common procedure C-2 and Common procedure B (as absorption coefficient at 280 nm, 1.37 mLmg$^{-1}$ cm$^{-1}$ was used). The solution (0.33 mL) was placed in a 1.5 mL tube, charged with a DMSO solution (0.04 mL; which corresponds to about 9 equivalents per antibody molecule) containing 10 mM of the compound obtained in Process 1 above at room temperature, and stirred by using a tube rotator (MTR-103, manufactured by AS ONE Corporation) for conjugating the drug linker to the antibody at room temperature for 16 hours.

Purification: The above solution was subjected to purification using the Common procedure D (ABS was used as a buffer solution) to yield 3.5 mL of a solution containing the titled antibody-drug conjugate.

Physicochemical characterization: By using the Common procedure B and Common procedure E, the following characteristic values were obtained.

Antibody concentration: 1.20 mg/mL, antibody yield: 4.2 mg (63%), and average number of conjugated drug molecules (n) per antibody molecule: 5.6.

Example 14 Antibody-Drug Conjugate (14)

[Formula 67]

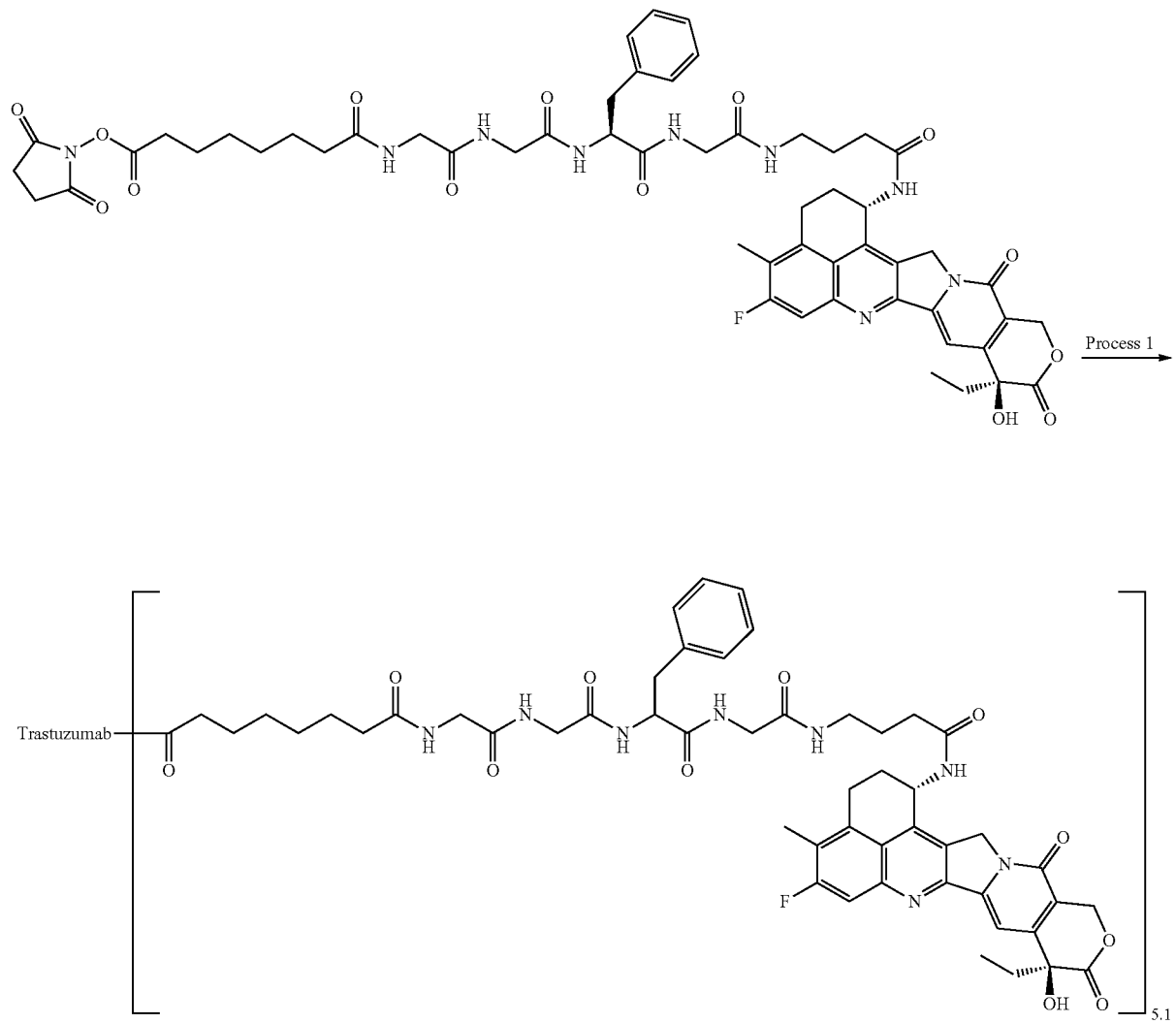

Process 1: Antibody-Drug Conjugate (14)

Conjugation between antibody and drug linker: The trastuzumab produced in Reference Example 1 was prepared to have an antibody concentration of 20 mg/mL by replacing the medium with PBS6.5/EDTA by using the Common procedure C-2 and Common procedure B (as absorption coefficient at 280 nm, 1.37 mLmg$^{-1}$ cm$^{-1}$ was used). The solution (0.33 mL) was placed in a 1.5 mL tube and then charged with an aqueous solution of 1 M dipotassium hydrogenphosphate (Nacalai Tesque, Inc.) to adjust the pH to 7.2. After adding a DMSO solution containing 10 mM of the compound obtained in Process 1 of Example 14 (0.04 mL; which corresponds to about 9 equivalents per antibody molecule) to the above solution at room temperature, it was stirred by using a tube rotator (MTR-103, manufactured by AS ONE Corporation) for conjugating the drug linker to the antibody at room temperature for 16 hours.

Purification: The above solution was subjected to purification using the Common procedure D (ABS was used as a buffer solution) to yield 3.5 mL of a solution containing the compound of interest.

Physicochemical characterization: By using the Common procedure B and Common procedure E, the following characteristic values were obtained.

Antibody concentration: 1.09 mg/mL, antibody yield: 3.8 mg (57%), and average number of conjugated drug molecules (n) per antibody molecule: 5.1.

Example 15 Antibody-Drug Conjugate (15)
[Formula 68]
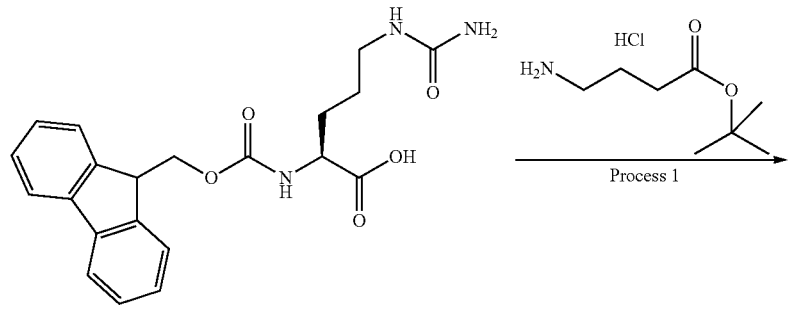
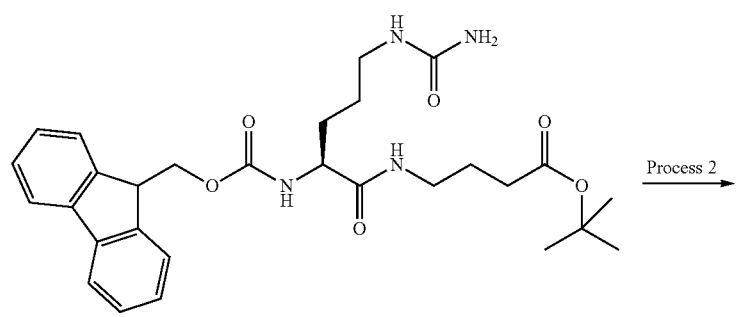
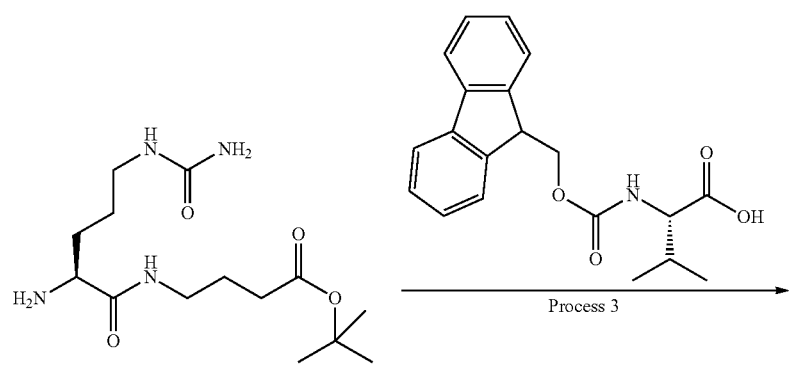
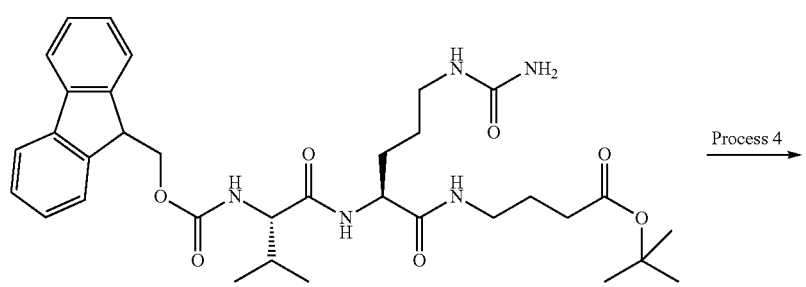

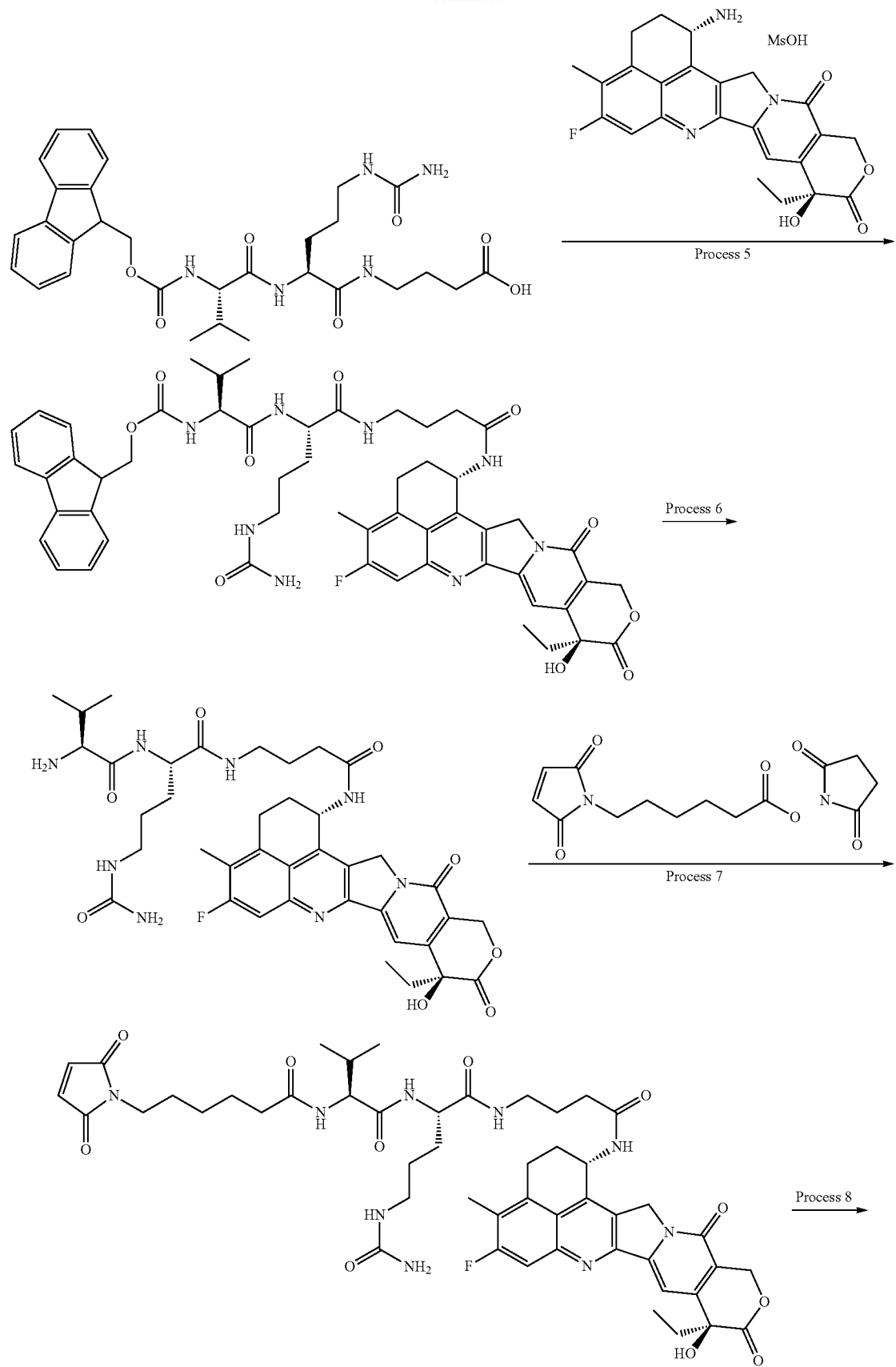

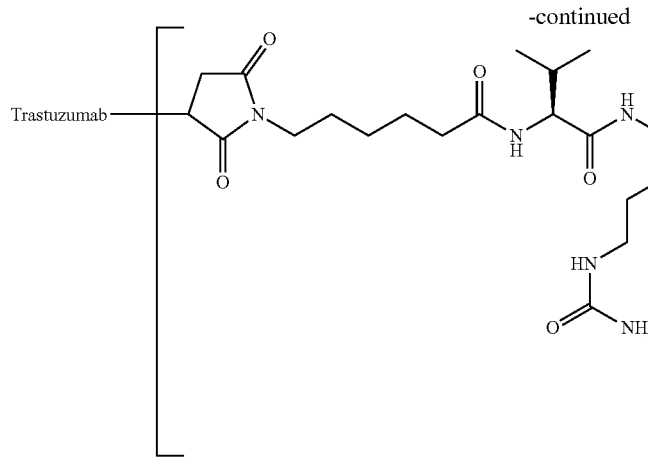
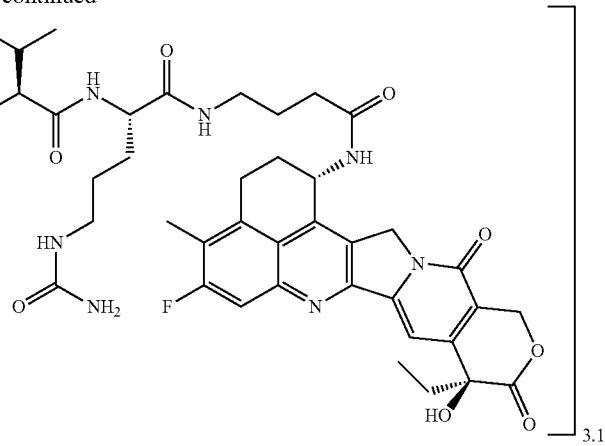

Process 1: 4-({N⁵-Carbamoyl-N²-[(9H-fluoren-9-ylmethoxy)carbonyl]-L-ornithyl}amino)butanoic acid tert-butyl ester To an N,N-dimethylformamide (40.0 mL) solution of N-α-(9-fluorenylmethoxycarbonyl)-L-citrulline (2.00 g, 5.03 mmol), N-hydroxysuccinimide (0.869 g, 7.55 mmol), and 4-aminobutanoic acid tert-butyl ester hydrochloride (1.48 g, 7.55 mmol), 1-ethyl-3-(3-dimethylaminopropyl)carbodiimide hydrochloride (1.45 g, 7.55 mmol) and N,N-diisopropylethylamine (0.877 mL, 5.03 mmol) were added and stirred at room temperature for 3 days. The reaction solution was poured to water and stirred, and then the deposited insolubles were collected by filtration to yield the titled compound as a colorless solid (2.70 g, 99%).

¹H-NMR (400 MHz, DMSO-d₆) δ: 1.36 (9H, s), 1.44 (6H, tt, J=44.0, 13.2 Hz), 2.17 (2H, t, J=7.4 Hz), 2.89-3.07 (4H, m), 3.85-3.95 (1H, m), 4.15-4.26 (3H, m), 5.37 (2H, brs), 5.93 (1H, t, J=5.9 Hz), 7.31 (2H, td, J=7.4, 1.2 Hz), 7.40 (2H, t, J=7.4 Hz), 7.47 (1H, d, J=8.2 Hz), 7.72 (2H, dd, J=7.4, 2.7 Hz), 7.87-7.89 (3H, m).

Process 2: tert-Butyl 4-[(N⁵-carbamoyl-L-ornithyl)amino]butanoate

To an N,N-dimethylformamide (20.0 mL) solution of the compound (1.70 g, 3.16 mmol) obtained in Process 1 above, piperidine (1.56 mL, 15.8 mmol) was added and stirred at room temperature for 1 hour. The solvent was removed under reduced pressure to yield the titled compound. The compound was used for the next reaction without further purification.

Process 3: N-[(9H-Fluoren-9-ylmethoxy)carbonyl]-L-valyl-N-(4-tert-butoxy-4-oxobutyl)-N⁵-carbamoyl-L-ornithinamide To an N,N-dimethylformamide (40.0 mL) solution of the compound (3.16 mmol) obtained in Process 2 above, N-[(9H-fluoren-9-ylmethoxy)carbonyl]-L-valine (1.07 g, 3.16 mmol), N-hydroxysuccinimide (0.363 g, 3.16 mmol), and 1-ethyl-3-(3-dimethylaminopropyl)carbodiimide hydrochloride (0.908 g, 4.73 mmol) were added and stirred at room temperature for 11 days. The reaction solution was diluted with ethyl acetate and washed with a saturated sodium hydrogen carbonate aqueous solution and a saturated sodium chloride aqueous solution, and then the organic layer was dried over anhydrous magnesium sulfate. The solvent was removed under reduced pressure and the residues obtained were purified by silica gel column chromatography [chloroform/(chloroform:methanol=9:1 (v/v))=100/0-0/100] to yield the titled compound as a pale yellow solid (0.280 g, 14%).

¹H-NMR (400 MHz, DMSO-d₆) δ: 0.82 (6H, t, J=6.6 Hz), 1.36 (9H, s), 1.25-1.64 (4H, m), 1.86-2.06 (1H, m), 2.16 (3H, t, J=7.4 Hz), 2.80-3.07 (4H, m), 3.86 (1H, dd, J=8.8, 6.8 Hz), 4.06-4.37 (5H, m), 5.35 (2H, brs), 5.90 (1H, t, J=5.5 Hz), 7.31 (2H, t, J=7.4 Hz), 7.37-7.44 (3H, m), 7.72 (2H, t, J=6.6 Hz), 7.84-7.94 (4H, m).

Process 4: N-[(9H-Fluoren-9-ylmethoxy)carbonyl]-L-valyl-N⁵-carbamoyl-N-(3-carboxypropyl)-L-ornithinamide To a dichloromethane (10.0 mL) solution of the compound (0.280 g, 0.439 mmol) obtained in Process 3 above, trifluoroacetic acid (10.0 mL) was added and stirred at room temperature for 3 days. The solvent was removed under reduced pressure to yield the titled compound as a pale yellow solid (0.212 g, 83%).

¹H-NMR (400 MHz, DMSO-d₆) δ: 0.82 (6H, t, J=6.8 Hz), 1.17-1.69 (4H, m), 1.87-2.01 (1H, m), 2.15-2.32 (3H, m), 2.83-3.09 (4H, m), 3.87 (1H, dd, J=8.8, 6.8 Hz), 4.08-4.37 (5H, m), 5.35 (2H, brs), 5.91 (1H, brs), 7.31 (2H, t, J=7.4 Hz), 7.36-7.44 (3H, m), 7.72 (2H, t, J=6.8 Hz), 7.85-7.94 (4H, m), 12.04 (1H, brs).

Process 5: N-[(9H-Fluoren-9-ylmethoxy)carbonyl]-L-valyl-N⁵-carbamoyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-ornithinamide To an N,N-dimethylformamide (10.0 mL) solution of the compound (0.212 g, 0.364 mmol) obtained in Process 4 above, N-hydroxysuccinimide (42.0 mg, 0.364 mmol), and methanesulfonic acid salt of exatecan (0.194 g, 0.364 mmol), 1-ethyl-3-(3-dimethylaminopropyl)carbodiimide hydrochloride (0.145 g, 0.547 mmol) and N,N-diisopropylethylamine (63.5 μL, 0.364 mmol) were added and stirred at room temperature for 1 day. The solvent was removed under reduced pressure and the residues obtained were purified by silica gel column chromatography [chloroform/

(chloroform:methanol=9:1 (v/v))=100/0-0/100] to yield the titled compound as a pale yellow solid (0.169 g, 46%).
MS(ES+APCI) m/z: 999 (M+H)+.

Process 6: L-Valyl-$N^5$-carbamoyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-ornithinamide The compound (0.169 g, 0.169 mmol) obtained in Process 5 above was reacted in the same manner as Process 2 above to yield the titled compound. The compound was used for the next reaction without further purification.

Process 7: N-[6-(2,5-Dioxo-2,5-dihydro-1H-pyrrol-1-yl) hexanoyl]-L-valyl -$N^5$-carbamoyl-N-(4-{[(1S, 9S)-9-ethyl -5-fluoro-9-hydroxy-4-methyl-10,13-dioxo-2,3,9,10,13,15-hexahydro-1H,12H-benzo[de] pyrano[3',4':6,7]indolizino[1,2-b]quinolin-1-yl] amino}-4-oxobutyl)-L-ornithinamide To an N,N-dimethylformamide (10.0 mL) solution of the compound (0.131 g, 0.169 mmol) obtained in Process 6 above, N-succinimidyl 6-maleimidohexanoate (78.2 mg, 0.254 mmol) was added and stirred at room temperature for 18 hours. The solvent was removed under reduced pressure and the residues obtained were purified by silica gel column chromatography [chloroform/(chloroform:methanol=9:1 (v/v))=100/0-0/100] to yield the titled compound as a pale orange solid (52.0 mg, 40%).

$^1$H-NMR (400 MHz, DMSO-$d_6$) δ: 0.74 (6H, t, J=6.6 Hz), 0.85 (4H, t, J=7.2 Hz), 1.10-1.19 (1H, m), 1.19-1.36 (1H, m), 1.38-1.50 (4H, m), 1.50-1.62 (1H, m), 1.62-1.73 (2H, m), 1.77-1.94 (4H, m), 2.03-2.19 (6H, m), 2.38 (3H, s), 2.56 (1H, s), 2.82-2.95 (2H, m), 2.98-3.08 (2H, m), 3.09-3.21 (2H, m), 3.32 (2H, q, J=8.2 Hz), 4.02-4.16 (2H, m), 5.18 (2H, q, J=17.0 Hz), 5.34 (2H, s), 5.41 (2H, s), 5.50-5.58 (1H, m), 5.89 (1H, t, J=6.3 Hz), 6.52 (1H, s), 6.98 (2H, s), 7.29 (1H, s), 7.73-7.88 (4H, m), 8.42 (1H, d, J=8.6 Hz).
MS (ES+APCI) m/z: 970 (M+H)+.

Process 8: Antibody-Drug Conjugate (15)

By using the trastuzumab produced in Reference Example 1 and the compound obtained in Process 7 above, the titled antibody-drug conjugate was obtained in the same manner as Process 6 of Example 2.
Antibody concentration: 1.62 mg/mL, antibody yield: 9.7 mg (78%), and average number of conjugated drug molecules (n) per antibody molecule: 3.1.

Example 16 Antibody-Drug Conjugate (16)

[Formula 69]

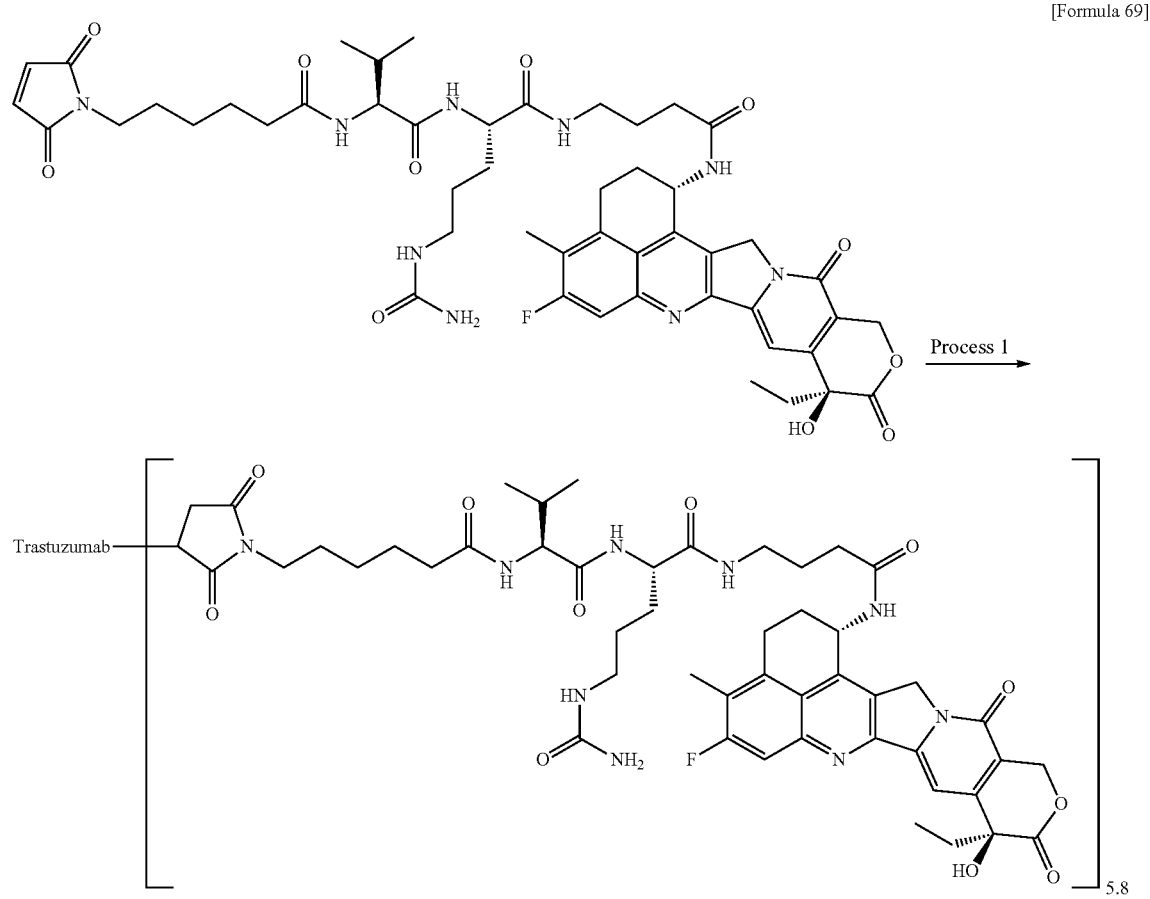

Process 1: Antibody-Drug Conjugate (16)

By using the trastuzumab produced in Reference Example 1 and the compound obtained in Process 7 of Example 15, the titled antibody-drug conjugate was obtained in the same manner as Process 1 of Example 3.
Antibody concentration: 1.47 mg/mL, antibody yield: 8.8 mg (70%), and average number of conjugated drug molecules (n) per antibody molecule: 5.8.

Example 17 Intermediate (17)

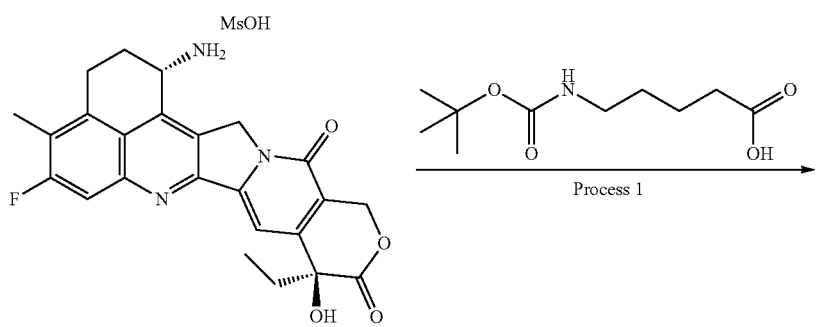

[Formula 70]

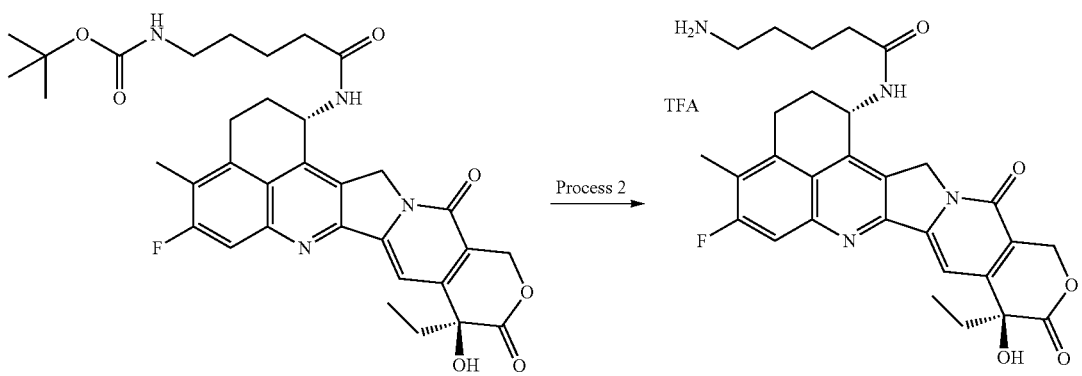

Process 1: tert-Butyl (5-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-5-oxopentyl) carbamate Methanesulfonic acid salt of exatecan (500 mg, 0.941 mmol) was reacted in the same manner as Process 1 of Example 1 by using 5-(tert-butoxycarbonylamino)valeric acid instead of 4-(tert-butoxycarbonylamino)butanoic acid to yield the titled compound as a yellow-brown solid (571 mg, 96%). The compound was used for the next reaction without further purification.
MS(ESI) m/z: 635 (M+H)$^+$.

Process 2: 5-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]pentanamide The compound (558 mg, 0.879 mmol) obtained in Process 1 above was reacted in the same manner as Process 2 of Example 1 to yield trifluoroacetic acid salt of the titled compound as a yellow solid (363 mg, 64%).
$^1$H-NMR (400 MHz, DMSO-d$_6$) δ: 0.88 (3H, t, J=7.4 Hz), 1.52-1.71 (4H, m), 1.87 (2H, tt, J=14.4, 6.9 Hz), 2.07-2.18 (2H, m), 2.22 (2H, t, J=7.0 Hz), 2.40 (3H, s), 2.76-2.88 (2H, m), 3.13-3.22 (2H, m), 5.18 (1H, d, J=18.8 Hz), 5.24 (1H, d, J=18.8 Hz), 5.43 (2H, s), 5.53-5.61 (1H, m), 6.55 (1H, s), 7.33 (1H, s), 7.65 (3H, br.s.), 7.81 (1H, d, J=11.3 Hz), 8.49 (1H, d, J=8.6 Hz).
MS (ESI) m/z: 535 (M+H)$^+$.

Example 18 Intermediate (18)

[Formula 71]

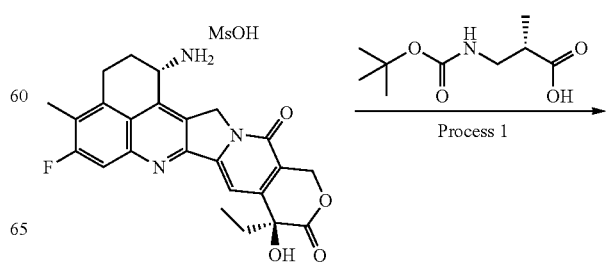

-continued

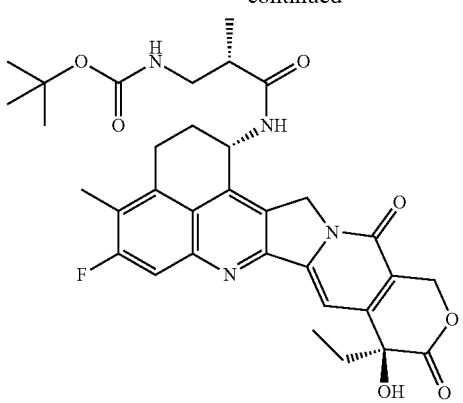

Process 2 →

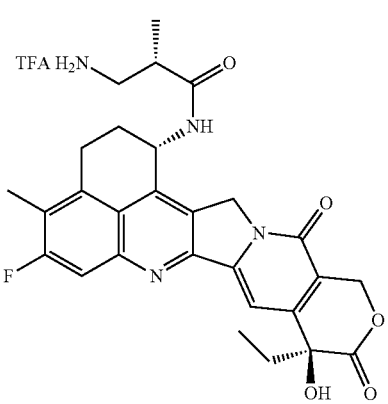

Process 1: tert-Butyl [(2S)-3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-methyl-3-oxopropyl]carbamate Methanesulfonic acid salt of exatecan (300 mg, 0.564 mmol) was reacted in the same manner as Process 1 of Example 1 by using (2S)-3-[(tert-butoxycarbonyl)amino]-2-methylpropionic acid instead of 4-(tert-butoxycarbonylamino)butanoic acid and 3H-1,2,3-triazplo[4,5-b]pyridin-3-ol instead of N-hydroxysuccinimide to yield the titled compound as a pale white solid (376 mg, quantitative). The compound was used for the next reaction without further purification.

$^1$H-NMR (400 MHz, DMSO-$d_6$) δ: 0.87 (3H, t, J=7.2 Hz), 1.01 (3H, d, J=6.6 Hz), 1.16 (9H, s), 1.84 (2H, tt, J=13.8, 7.3 Hz), 2.02-2.21 (2H, m), 2.40 (3H, s), 2.44-2.55 (1H, m), 2.84-2.94 (1H, m), 3.07-3.23 (3H, m), 5.10 (1H, d, J=18.8 Hz), 5.31 (1H, d, J=18.8 Hz), 5.39 (1H, d, J=16.4 Hz), 5.45 (1H, d, J=16.4 Hz), 5.53-5.63 (1H, m), 6.54 (1H, s), 6.70 (1H, t, J=5.5 Hz), 7.30 (1H, s), 7.81 (1H, d, J=10.9 Hz), 8.43 (1H, d, J=9.0 Hz).

Process 2: (2S)-3-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-2-methylpropanamide The compound obtained in Process 1 above was reacted in the same manner as Process 2 of Example 1 to yield trifluoroacetic acid salt of the titled compound (339 mg, 95%, 2 steps).

$^1$H-NMR (400 MHz, DMSO-$d_6$) δ: 0.87 (3H, t, J=7.2 Hz), 1.17 (3H, d, J=7.0 Hz), 1.86 (2H, tt, J=14.4, 7.3 Hz), 2.05-2.15 (1H, m), 2.15-2.24 (1H, m), 2.42 (3H, s), 2.63 (1H, q, J=6.3 Hz), 2.82-2.91 (1H, m), 3.03-3.12 (1H, m), 3.14-3.23 (2H, m), 5.27 (1H, d, J=19.2 Hz), 5.33 (1H, d, J=18.8 Hz), 5.44 (2H, s), 5.50-5.58 (1H, m), 6.57 (1H, s), 7.33 (1H, s), 7.75 (3H, br.s.), 7.83 (1H, d, J=10.9 Hz), 8.62 (1H, d, J=8.2 Hz).

MS (ESI) m/z: 521 (M+H)$^+$.

Example 19 Antibody-Drug Conjugate (19)

[Formula 72]

197  198
-continued
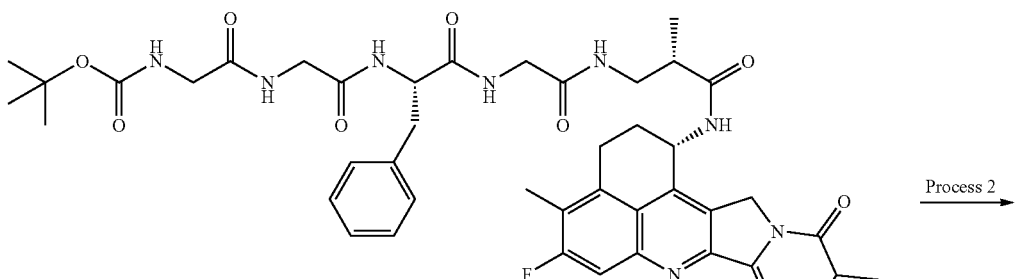
Process 2 →
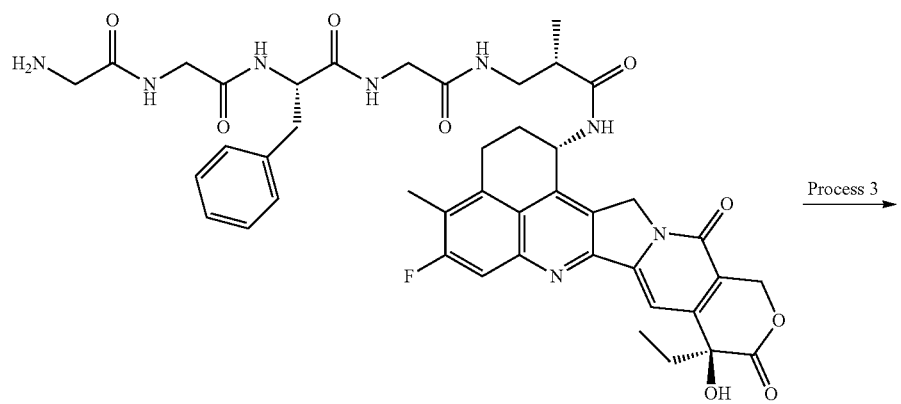
Process 3 →
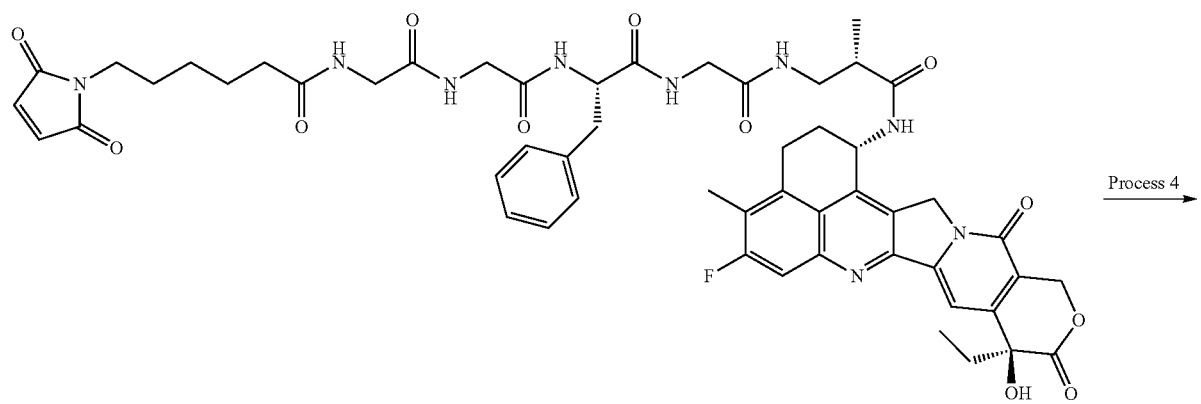
Process 4 →
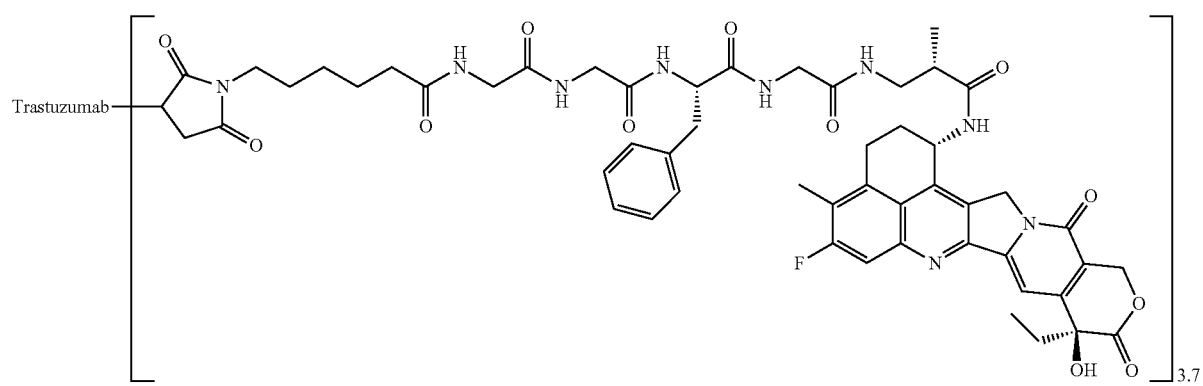

Process 1: N-(tert-Butoxycarbonyl)glycylglycyl-L-phenylalanyl-N-[(2S)-3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-methyl-3-oxopropyl]glycinamide The compound (308 mg, 0.485 mmol) obtained in Process 2 of Example 18 was reacted in the same manner as Process 1 of Example 2 to yield the titled compound (422 mg, 93%). The compound was used for the next reaction without further purification.

Process 2: Glycylglycyl-L-phenylalanyl-N-[(2S)-3-{[(1S,9S)-9-ethyl-5-fluoro-9-hydroxy-4-methyl-10,13-dioxo-2,3,9,10,13,15-hexahydro-1H,12H-yl]amino}-2-methyl-3-oxopropyl]glycinamide The compound obtained in Process 1 above was reacted in the same manner as Process 2 of Example 2 to yield trifluoroacetic acid salt of the titled compound (419 mg, 91%, 2 steps).

$^1$H-NMR (400 MHz, DMSO-$d_6$) δ: 0.86 (3H, t, J=7.4 Hz), 1.06 (3H, d, J=7.0 Hz), 1.78-1.90 (2H, m), 2.05-2.19 (2H, m), 2.40 (3H, s), 2.57 (1H, t, J=6.6 Hz), 2.73 (1H, dd, J=13.7, 10.2 Hz), 3.01 (1H, dd, J=14.5, 4.7 Hz), 3.10-3.22 (2H, m), 3.21-3.46 (2H, m), 3.57 (2H, br.s.), 3.61-3.75 (3H, m), 3.87 (1H, dd, J=16.8, 5.9 Hz), 4.47-4.58 (1H, m), 5.18 (1H, d, J=18.8 Hz), 5.28 (1H, d, J=19.2 Hz), 5.39 (1H, d, J=16.0 Hz), 5.45 (1H, d, J=16.0 Hz), 5.50-5.58 (1H, m), 6.55 (1H, s), 7.13-7.28 (5H, m), 7.33 (1H, s), 7.81 (2H, d, J=10.6 Hz), 7.96 (3H, br.s.), 8.27-8.36 (2H, m), 8.48 (1H, t, J=5.3 Hz), 8.53 (1H, d, J=8.2 Hz).
MS (ESI) m/z: 839 (M+H)$^+$.

Process 3: N-[6-(2,5-Dioxo-2,5-dihydro-1H-pyrrol-1-yl)hexanoyl]glycylglycyl-L-phenylalanyl-N-[(2S)-3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-methyl-3-oxopropyl]glycinamide The compound (100 mg, 0.105 mmol) obtained in Process 2 above was reacted in the same manner as Process 8 of Example 5 to yield the titled compound as a pale yellow solid (27.0 mg, 25%).

$^1$H-NMR (400 MHz, DMSO-$d_6$) δ: 0.86 (3H, t, J=7.2 Hz), 1.05 (3H, d, J=6.3 Hz), 1.11-1.26 (3H, m), 1.44 (4H, quin, J=7.4 Hz), 1.77-1.90 (2H, m), 2.01-2.18 (4H, m), 2.39 (3H, s), 2.76 (1H, dd, J=14.1, 8.6 Hz), 2.99 (1H, dd, J=14.3, 4.5 Hz), 3.10-3.22 (3H, m), 3.22-3.38 (3H, m), 3.39-3.82 (6H, m), 4.38-4.47 (1H, m), 5.18 (1H, d, J=18.8 Hz), 5.28 (1H, d, J=18.8 Hz), 5.41 (2H, d, J=6.6 Hz), 5.49-5.60 (1H, m), 6.53 (1H, s), 6.99 (2H, s), 7.11-7.29 (5H, m), 7.32 (1H, s), 7.73 (1H, t, J=5.5 Hz), 7.80 (1H, d, J=11.3 Hz), 7.99 (1H, t, J=5.7 Hz), 8.06 (1H, t, J=5.3 Hz), 8.13 (1H, d, J=8.6 Hz), 8.25 (1H, t, J=6.3 Hz), 8.52 (1H, d, J=8.6 Hz).
MS (ESI) m/z: 1032 (M+H)$^+$.

Process 4: Antibody-Drug Conjugate (19)

By using the trastuzumab produced in Reference Example 1 and the compound obtained in Process 3 above, the titled antibody-drug conjugate was obtained in the same manner as Process 6 of Example 2.
Antibody concentration: 1.59 mg/mL, antibody yield: 9.5 mg (76%), and average number of conjugated drug molecules (n) per antibody molecule: 3.7.

Example 20 Antibody-Drug Conjugate (20)

[Formula 73]

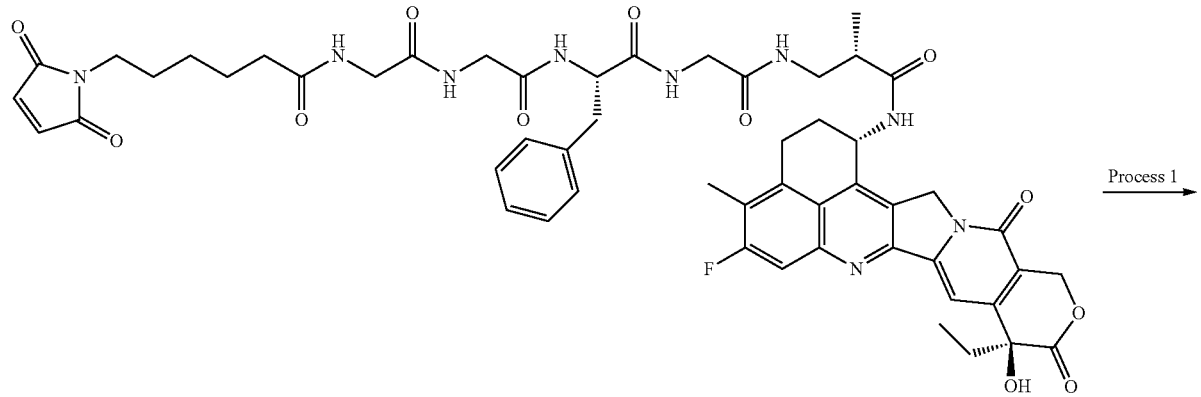

Process 1

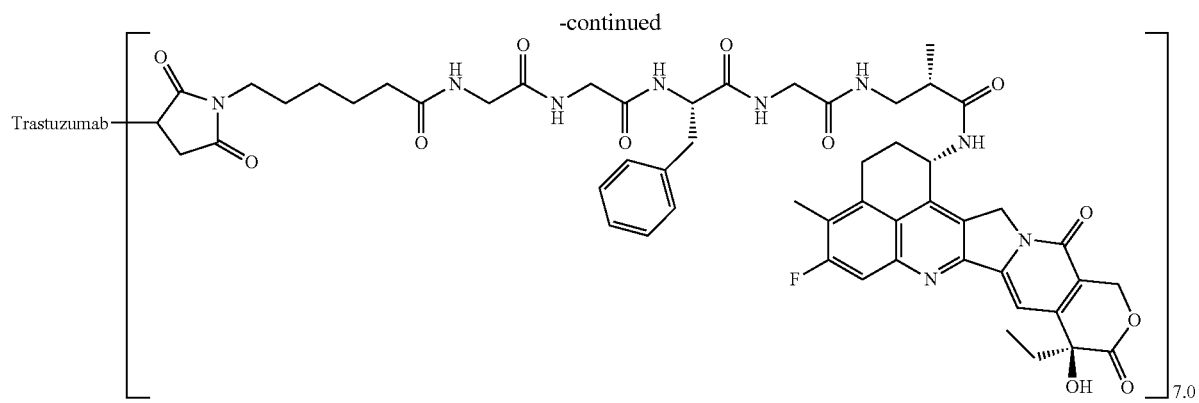

Process 1: Antibody-Drug Conjugate (20)

By using the trastuzumab produced in Reference Example 1 and the compound obtained in Process 3 of Example 19, the titled antibody-drug conjugate was obtained in the same manner as Process 1 of Example 3.

Antibody concentration: 1.62 mg/mL, antibody yield: 9.7 mg (78%), and average number of conjugated drug molecules (n) per antibody molecule: 7.0.

Example 21 Intermediate (21)

[Formula 74]

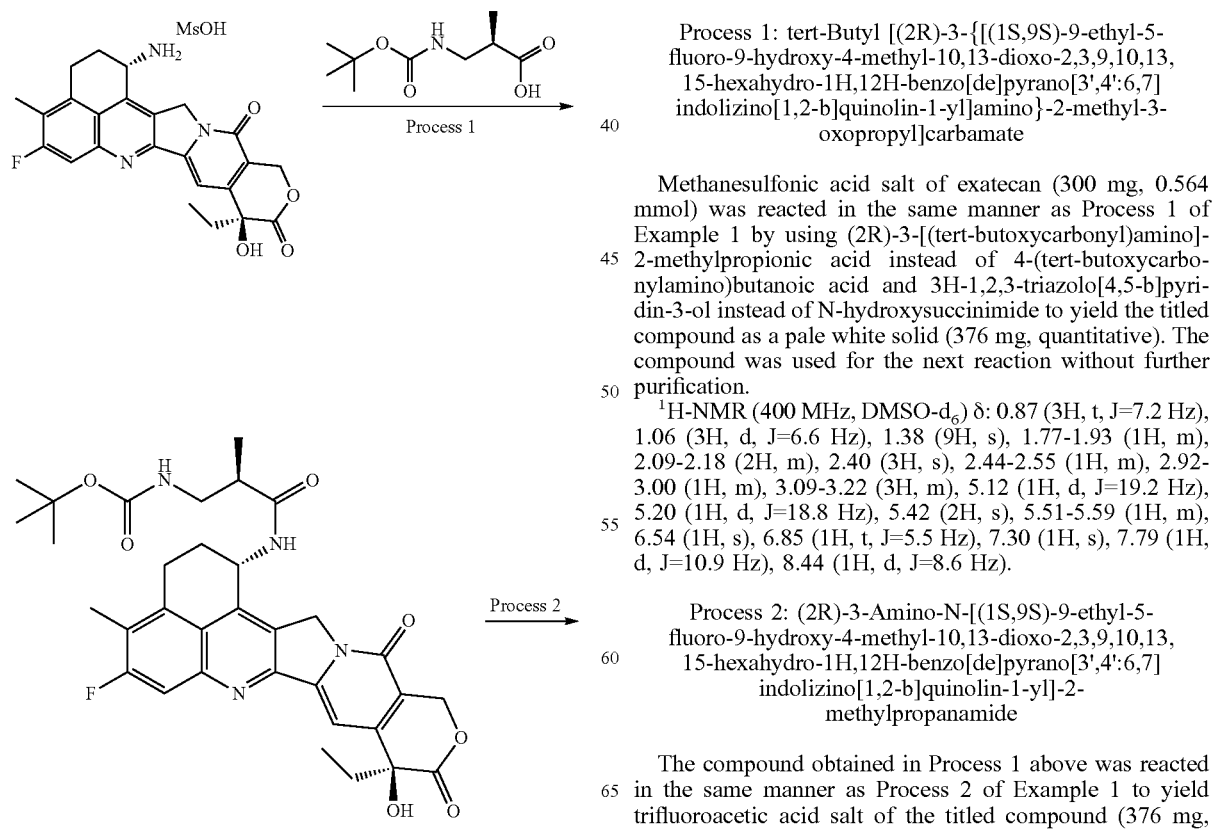

Process 1: tert-Butyl [(2R)-3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-methyl-3-oxopropyl]carbamate Methanesulfonic acid salt of exatecan (300 mg, 0.564 mmol) was reacted in the same manner as Process 1 of Example 1 by using (2R)-3-[(tert-butoxycarbonyl)amino]-2-methylpropionic acid instead of 4-(tert-butoxycarbonylamino)butanoic acid and 3H-1,2,3-triazolo[4,5-b]pyridin-3-ol instead of N-hydroxysuccinimide to yield the titled compound as a pale white solid (376 mg, quantitative). The compound was used for the next reaction without further purification.

$^1$H-NMR (400 MHz, DMSO-$d_6$) δ: 0.87 (3H, t, J=7.2 Hz), 1.06 (3H, d, J=6.6 Hz), 1.38 (9H, s), 1.77-1.93 (1H, m), 2.09-2.18 (2H, m), 2.40 (3H, s), 2.44-2.55 (1H, m), 2.92-3.00 (1H, m), 3.09-3.22 (3H, m), 5.12 (1H, d, J=19.2 Hz), 5.20 (1H, d, J=18.8 Hz), 5.42 (2H, s), 5.51-5.59 (1H, m), 6.54 (1H, s), 6.85 (1H, t, J=5.5 Hz), 7.30 (1H, s), 7.79 (1H, d, J=10.9 Hz), 8.44 (1H, d, J=8.6 Hz).

Process 2: (2R)-3-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-2-methylpropanamide The compound obtained in Process 1 above was reacted in the same manner as Process 2 of Example 1 to yield trifluoroacetic acid salt of the titled compound (376 mg, 92%, 2 steps).

¹H-NMR (400 MHz, DMSO-d₆) δ: 0.88 (3H, t, J=7.4 Hz), 1.16 (3H, d, J=7.0 Hz), 1.86 (2H, tt, J=13.7, 6.8 Hz), 2.12-2.24 (2H, m), 2.41 (3H, s), 2.67 (1H, q, J=5.9 Hz), 2.82-2.93 (1H, m), 3.03-3.12 (1H, m), 3.13-3.22 (2H, m), 5.10 (1H, d, J=18.8 Hz), 5.24 (1H, d, J=18.8 Hz), 5.42 (2H, s), 5.58 (1H, dt, J=8.9, 4.7 Hz), 6.55 (1H, s), 7.31 (1H, s), 7.79 (3H, br.s.), 7.82 (1H, d, J=11.3 Hz), 8.73 (1H, d, J=8.6 Hz).
MS (ESI) m/z: 521 (M+H)⁺.
Example 22 Antibody-Drug Conjugate (22)
[Formula 75]
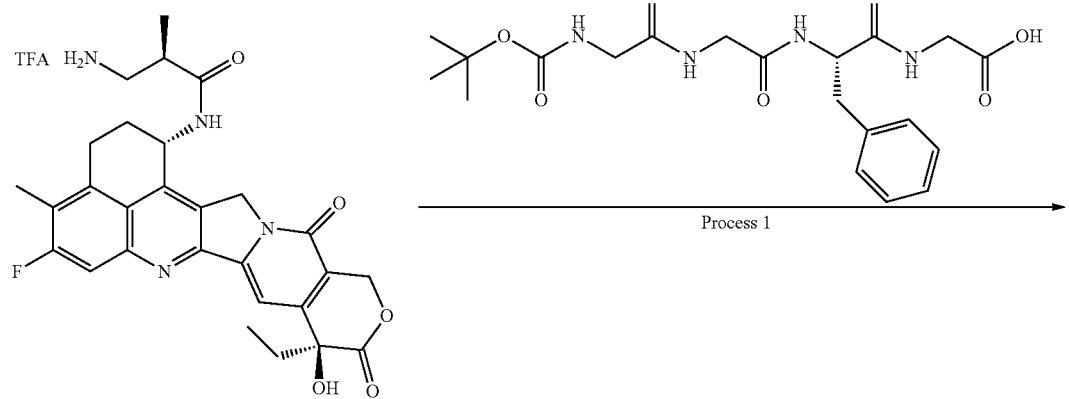
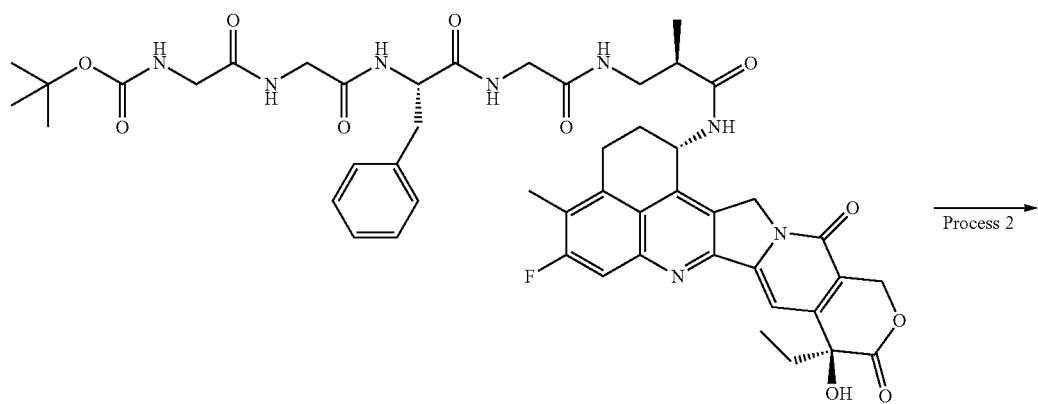
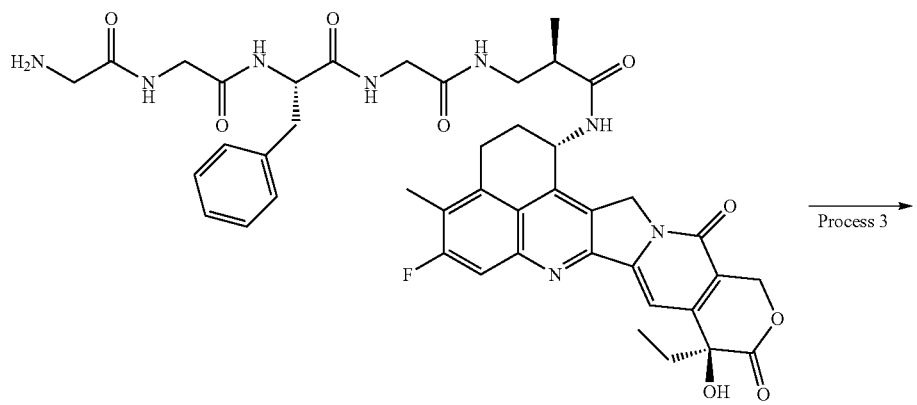

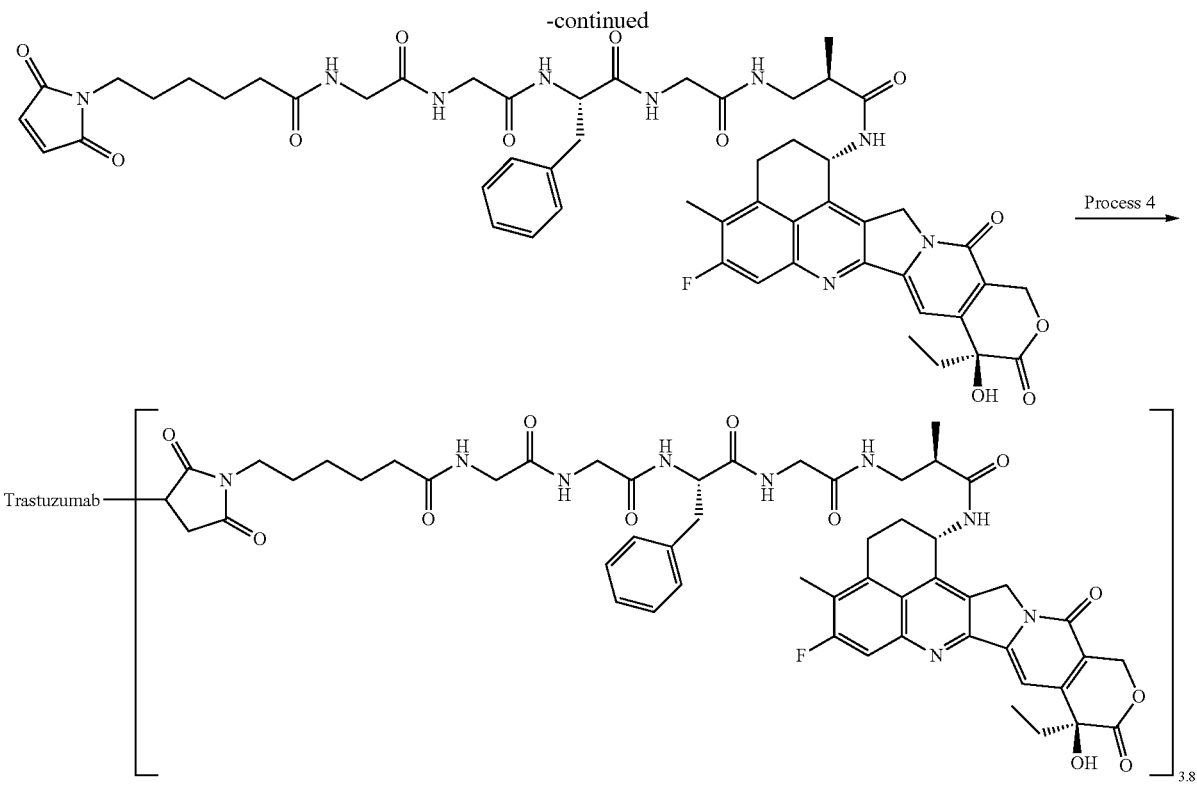

Process 1: N-(tert-Butoxycarbonyl)glycylglycyl-L-phenylalanyl-N-[(2R)-3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-methyl-3-oxopropyl]glycinamide The compound (296 mg, 0.466 mmol) obtained in Process 2 of Example 21 was reacted in the same manner as Process 1 of Example 2 to yield the titled compound (398 mg, 91%). The compound was used for the next reaction without further purification.

Process 2: Glycylglycyl-L-phenylalanyl-N-[(2R)-3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-methyl-3-oxopropyl]glycinamide The compound obtained in Process 1 above was reacted in the same manner as Process 2 of Example 2 to yield trifluoroacetic acid salt of the titled compound (398 mg, 92%, 2 steps).

$^1$H-NMR (400 MHz, DMSO-$d_6$) δ: 0.87 (3H, t, J=7.2 Hz), 1.09 (3H, d, J=6.6 Hz), 1.79-1.92 (2H, m), 2.11-2.20 (2H, m), 2.40 (3H, s), 2.52-2.59 (1H, m), 2.76 (1H, dd, J=13.7, 10.2 Hz), 3.05 (1H, dd, J=13.9, 4.1 Hz), 3.12-3.19 (2H, m), 3.21 (2H, t, J=6.5 Hz), 3.58 (2H, br.s.), 3.64-3.79 (3H, m), 3.87 (1H, dd, J=16.6, 5.7 Hz), 4.51-4.61 (1H, m), 5.13 (1H, d, J=19.2 Hz), 5.19 (1H, d, J=18.8 Hz), 5.42 (2H, s), 5.52-5.60 (1H, m), 6.54 (1H, s), 7.15-7.29 (5H, m), 7.31 (1H, s), 7.80 (1H, d, J=11.3 Hz), 7.91 (1H, t, J=6.3 Hz), 7.96 (3H, br.s.), 8.31-8.38 (2H, m), 8.49 (1H, t, J=5.5 Hz), 8.56 (1H, d, J=8.6 Hz).

MS (ESI) m/z: 839 (M+H)$^+$.

Process 3: N-[6-(2,5-Dioxo-2,5-dihydro-1H-pyrrol-1-yl)hexanoyl]glycylglycyl-L-phenylalanyl-N-[(2R)-3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-methyl-3-oxopropyl]glycinamide The compound (100 mg, 0.105 mmol) obtained in Process 2 above was reacted in the same manner as Process 8 of Example 5 to yield the titled compound as a pale yellow solid (27.0 mg, 25%).

$^1$H-NMR (400 MHz, DMSO-$d_6$) δ: 0.87 (3H, t, J=7.0 Hz), 1.09 (3H, d, J=7.0 Hz), 1.13-1.26 (3H, m), 1.37-1.51 (4H, m), 1.77-1.92 (2H, m), 2.08 (2H, t, J=7.4 Hz), 2.11-2.20 (2H, m), 2.39 (3H, s), 2.79 (1H, dd, J=13.7, 9.8 Hz), 3.04 (1H, dd, J=13.7, 3.9 Hz), 3.10-3.25 (4H, m), 3.28-3.38 (2H, m), 3.50-3.80 (6H, m), 4.42-4.54 (1H, m), 5.14 (1H, d, J=19.6 Hz), 5.19 (1H, d, J=19.2 Hz), 5.42 (2H, s), 5.51-5.61 (1H, m), 6.53 (1H, s), 6.99 (2H, s), 7.13-7.28 (5H, m), 7.30 (1H, s), 7.79 (1H, d, J=10.9 Hz), 7.84 (1H, t, J=5.9 Hz), 8.01 (1H, t, J=5.7 Hz), 8.07 (1H, t, J=5.3 Hz), 8.14 (1H, d, J=7.8 Hz), 8.25 (1H, d, J=10.9 Hz), 8.54 (1H, d, J=9.0 Hz).

MS (ESI) m/z: 1032 (M+H)$^+$.

Process 4: Antibody-Drug Conjugate (22)

By using the trastuzumab produced in Reference Example 1 and the compound obtained in Process 3 above, the titled antibody-drug conjugate was obtained in the same manner as Process 6 of Example 2.
Antibody concentration: 1.59 mg/mL, antibody yield: 9.5 mg (76%), and average number of conjugated drug molecules (n) per antibody molecule: 3.8.

Example 23 Antibody-Drug Conjugate (23)

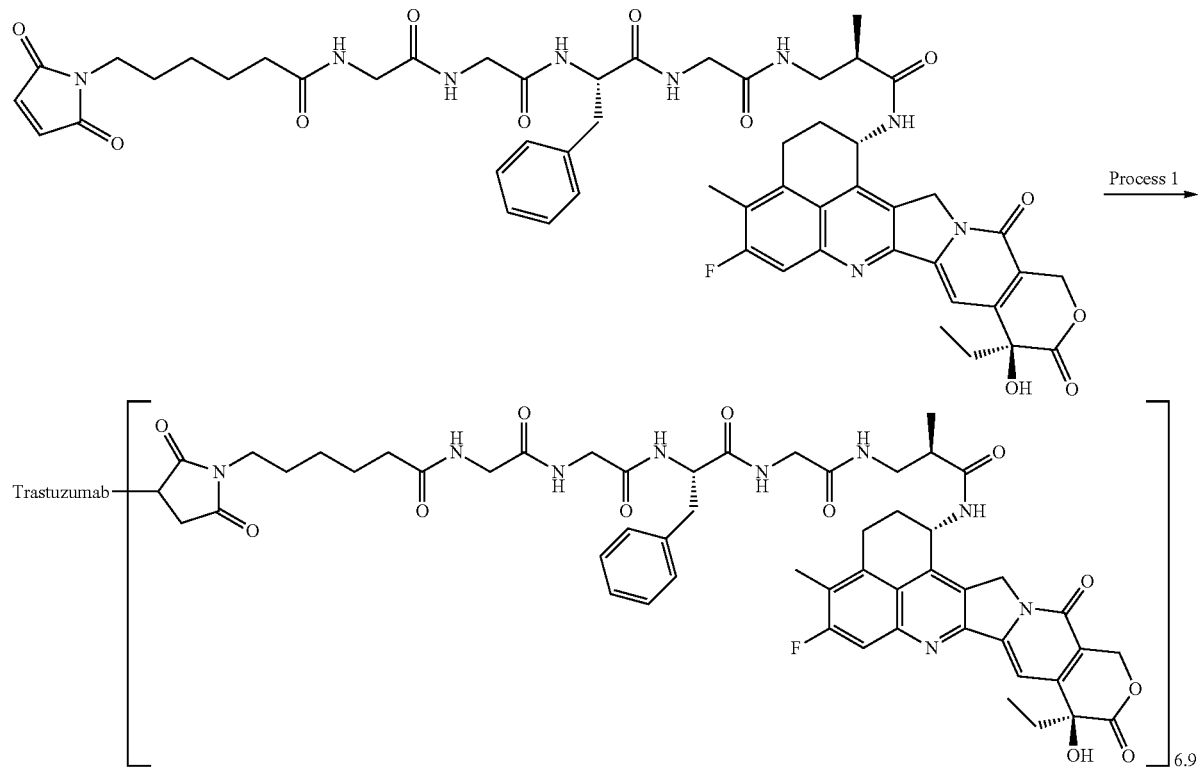

[Formula 76]

Process 1: Antibody-Drug Conjugate (23)

By using the trastuzumab produced in Reference Example 1 and the compound obtained in Process 3 of Example 22, the titled antibody-drug conjugate was obtained in the same manner as Process 1 of Example 3.
Antibody concentration: 1.59 mg/mL, antibody yield: 9.5 mg (76%), and average number of conjugated drug molecules (n) per antibody molecule: 6.9.

Example 24 Intermediate (24)

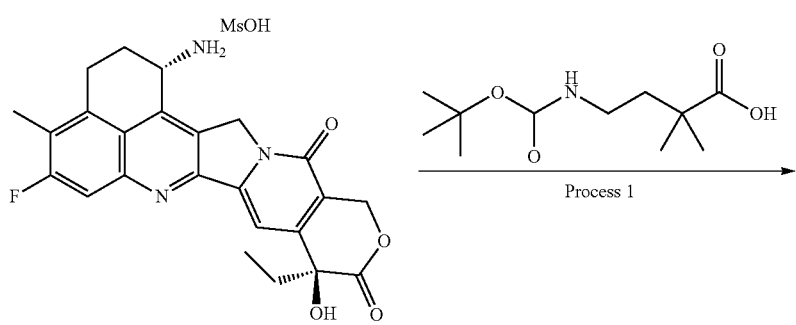

[Formula 77]

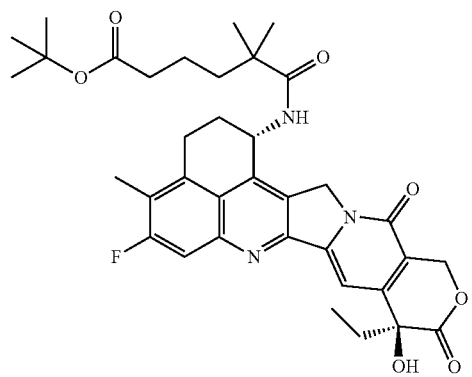 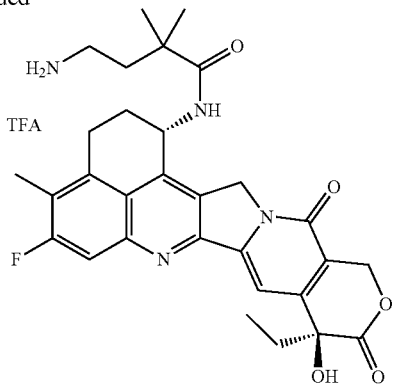

Process 1: tert-Butyl (4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3,3-dimethyl-4-oxobutyl)carbamate Methanesulfonic acid salt of exatecan (300 mg, 0.564 mmol) was reacted in the same manner as Process 1 of Example 1 by using 4-[(tert-butoxycarbonyl)amino]-2,2-dimethylbutanoic acid instead of 4-(tert-butoxycarbonylamino)butanoic acid and 3H-1,2,3-triazolo[4,5-b]pyridin-3-ol instead of N-hydroxysuccinimide to yield the titled compound. The compound was used for the next reaction without further purification.

Process 2: 4-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-2,2-dimethylbutanamide trifluoroacetic acid salt The compound obtained in Process 1 above was reacted in the same manner as Process 2 of Example 1 to yield the titled compound (358 mg, 96%, 2 steps).

$^1$H-NMR (400 MHz, DMSO-$d_6$) δ: 0.88 (3H, t, J=7.4 Hz), 1.21 (3H, s), 1.24 (3H, s), 1.74-1.93 (4H, m), 2.13 (2H, q, J=6.6 Hz), 2.41 (3H, d, J=1.6 Hz), 2.79-2.90 (1H, m), 3.09-3.25 (2H, m), 5.10 (1H, d, J=18.4 Hz), 5.19 (1H, d, J=18.4 Hz), 5.42 (2H, s), 5.55-5.63 (1H, m), 6.56 (1H, s), 7.33 (1H, s), 7.71 (3H, brs), 7.81 (1H, d, J=10.9 Hz), 8.20 (1H, d, J=8.2 Hz).

MS (ESI) m/z: 549 (M+H)$^+$.

Example 25 Antibody-Drug Conjugate (25)

[Formula 78]

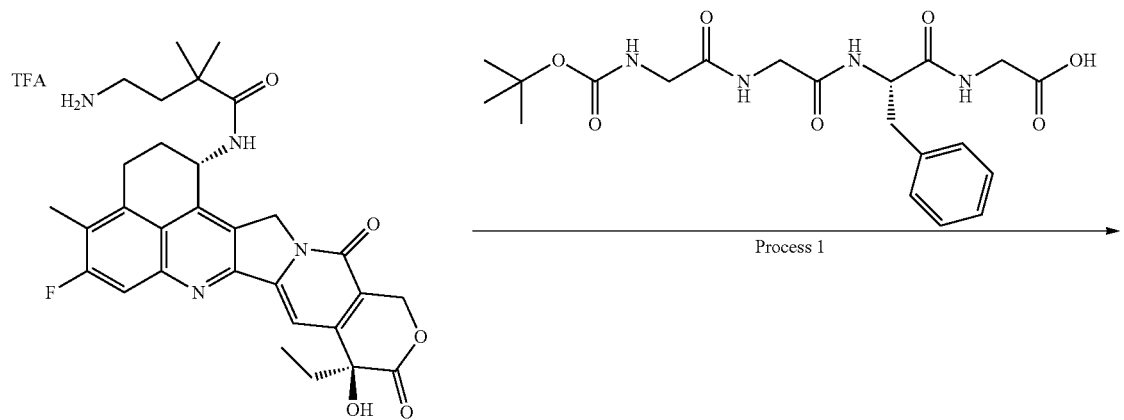

211
212
-continued
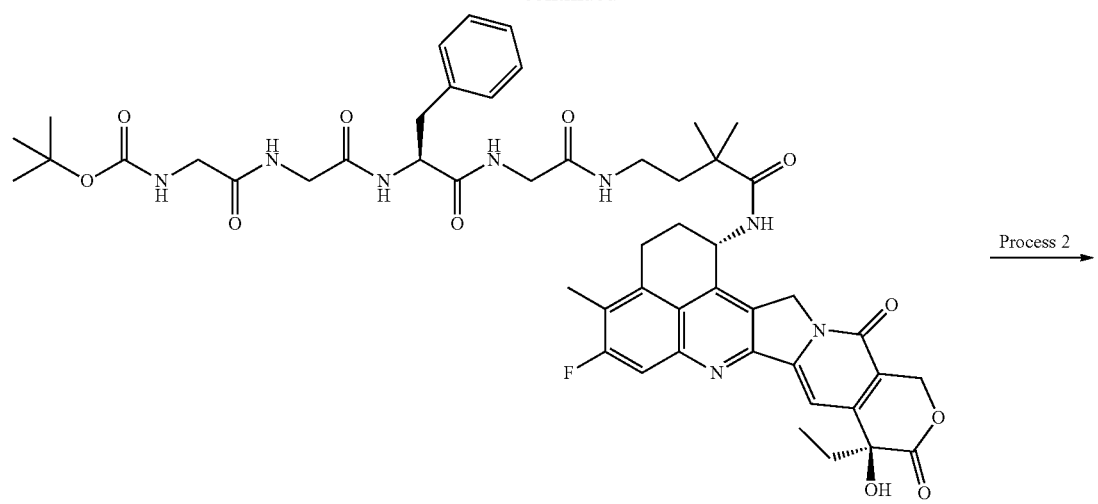
Process 2 →
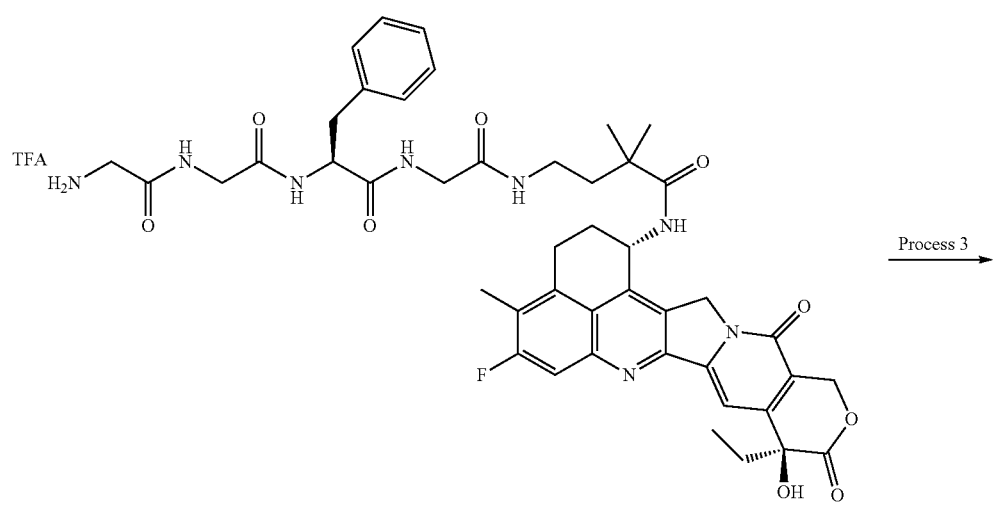
Process 3 →
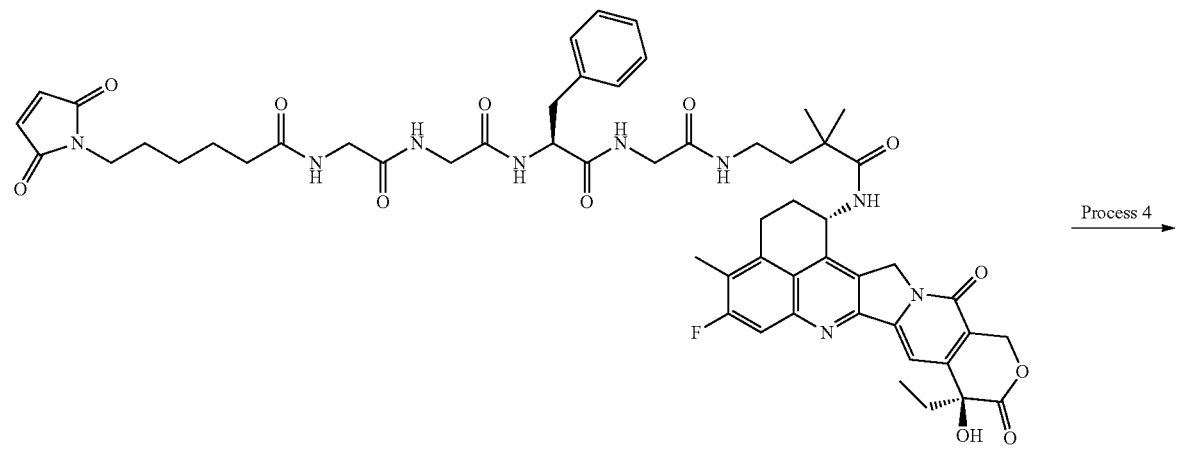
Process 4 →

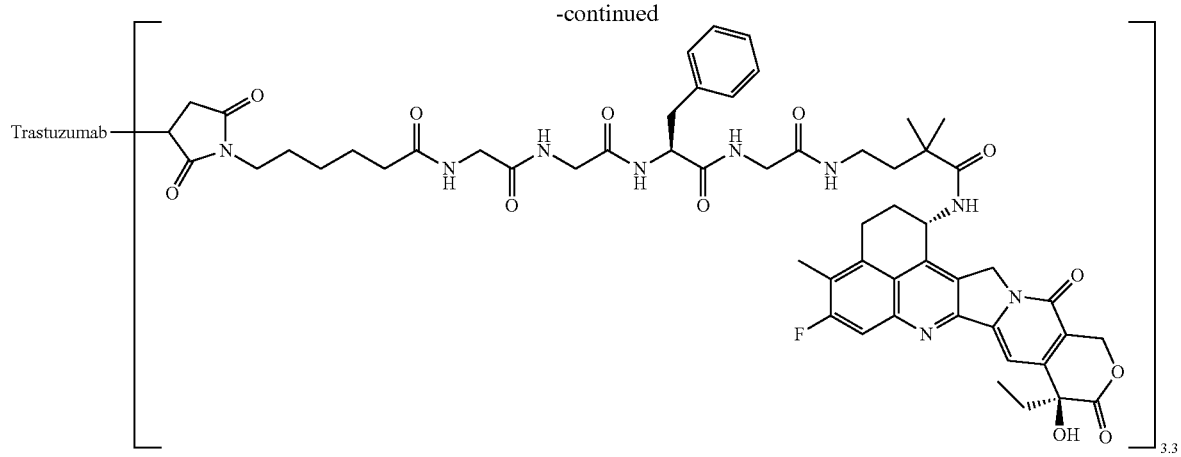

Process 1: N-(tert-Butoxycarbonyl)glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3,3-dimethyl-4-oxobutyl)glycinamide The compound (358 mg, 0.540 mmol) obtained in Process 2 of Example 24 was reacted in the same manner as Process 1 of Example 2 to yield the titled compound. The compound was used for the next reaction without further purification.

Process 2: Glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3,3-dimethyl-4-oxobutyl)glycinamide trifluoroacetic acid salt The compound obtained in Process 1 above was reacted in the same manner as Process 2 of Example 2 to yield the titled compound (576 mg, quantitative, 2 steps).

$^1$H-NMR (400 MHz, DMSO-$d_6$) δ: 0.88 (3H, t, J=7.4 Hz), 1.20 (3H, s), 1.21 (3H, s), 1.64-1.71 (2H, m), 1.80-1.92 (2H, m), 2.09-2.18 (2H, m), 2.39 (3H, d, J=1.2 Hz), 2.76 (1H, dd, J=14.1, 9.8 Hz), 3.05 (2H, dd, J=14.1, 4.3 Hz), 3.09-3.24 (2H, m), 3.54-3.60 (2H, m), 3.63-3.75 (3H, m), 3.82-3.91 (2H, m), 4.52-4.61 (1H, m), 5.12 (1H, d, J=18.4 Hz), 5.18 (1H, d, J=18.4 Hz), 5.42 (2H, s), 5.55-5.63 (1H, m), 6.55 (1H, s), 7.15-7.30 (5H, m), 7.32 (1H, s), 7.77-7.84 (2H, m), 7.97 (3H, d, J=7.0 Hz), 8.16 (1H, d, J=8.2 Hz), 8.29-8.37 (2H, m), 8.50 (1H, t, J=5.5 Hz).

MS (ESI) m/z: 867 (M+H)$^+$.

Process 3: N-[6-(2,5-Dioxo-2,5-dihydro-1H-pyrrol-1-yl)hexanoyl]glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3,3-dimethyl-4-oxobutyl)glycinamide The compound (100 mg, 0.102 mmol) obtained in Process 2 above was reacted in the same manner as Process 8 of Example 5 to yield the titled compound as a solid (24 mg, 22%).

$^1$H-NMR (400 MHz, DMSO-$d_6$) δ: 0.87 (3H, t, J=7.2 Hz), 1.13-1.25 (2H, m), 1.20 (3H, s), 1.21 (3H, s), 1.39-1.52 (4H, m), 1.62-1.72 (2H, m), 1.86 (2H, dt, J=14.2, 6.8 Hz), 2.09 (2H, t, J=7.4 Hz), 2.10-2.18 (2H, m), 2.39 (3H, s), 2.79 (1H, dd, J=13.7, 9.4 Hz), 2.98-3.08 (2H, m), 3.08-3.22 (3H, m), 3.29-3.39 (2H, m), 3.53-3.79 (6H, m), 4.41-4.52 (1H, m), 5.11 (1H, d, J=18.8 Hz), 5.18 (1H, d, J=18.4 Hz), 5.42 (2H, s), 5.53-5.64 (1H, m), 6.54 (1H, s), 6.99 (2H, s), 7.14-7.29 (5H, m), 7.31 (1H, s), 7.71 (1H, t, J=5.5 Hz), 7.79 (1H, d, J=10.9 Hz), 8.03 (1H, t, J=5.9 Hz), 8.06-8.19 (3H, m), 8.24 (1H, t, J=6.1 Hz).

MS (ESI) m/z: 1060 (M+H)$^+$.

Process 4: Antibody-Drug Conjugate (25)

By using the trastuzumab produced in Reference Example 1 and the compound obtained in Process 3 above, the titled antibody-drug conjugate was obtained in the same manner as Process 6 of Example 2. By using the Common procedure B and Common procedure E, the following characteristic values were obtained.

Antibody concentration: 1.44 mg/mL, antibody yield: 8.6 mg (69%), and average number of conjugated drug molecules (n) per antibody molecule: 3.3.

Example 26 Antibody-Drug Conjugate (26)

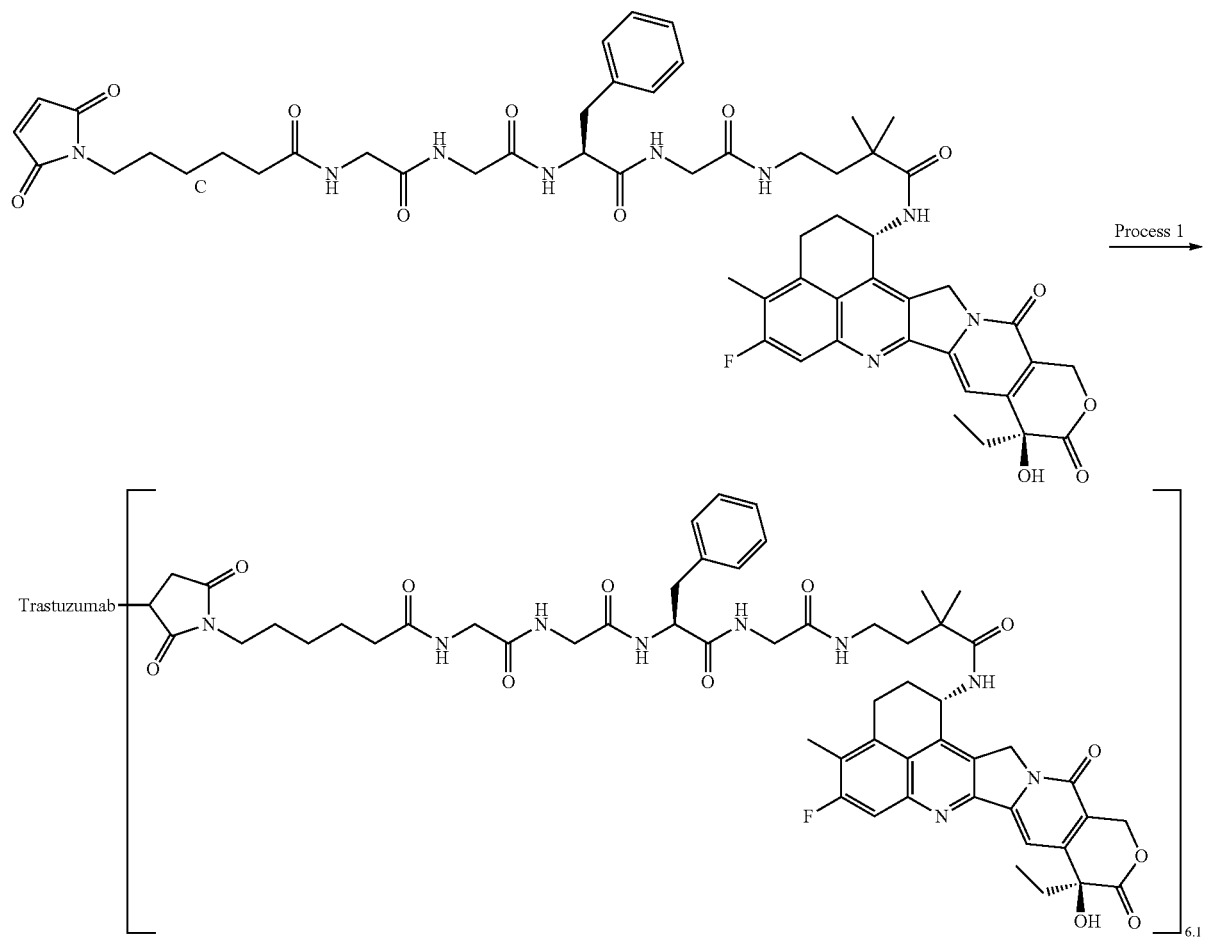

Process 1: Antibody-Drug Conjugate (26)

By using the trastuzumab produced in Reference Example 1 and the compound obtained in Process 3 of Example 25, the titled antibody-drug conjugate was obtained in the same manner as Process 1 of Example 3. The solution was further concentrated by the Common procedure A. After that, by using the Common procedure B and Common procedure E, the following characteristic values were obtained.

Antibody concentration: 1.38 mg/mL, antibody yield: 8.3 mg (66%), and average number of conjugated drug molecules (n) per antibody molecule: 6.1.

Example 27 Antibody-Drug Conjugate (27)

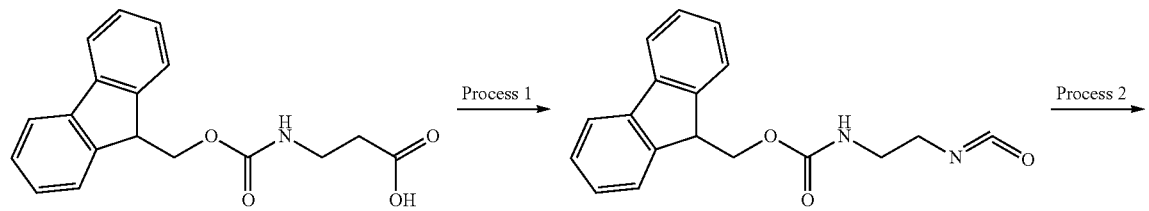

-continued
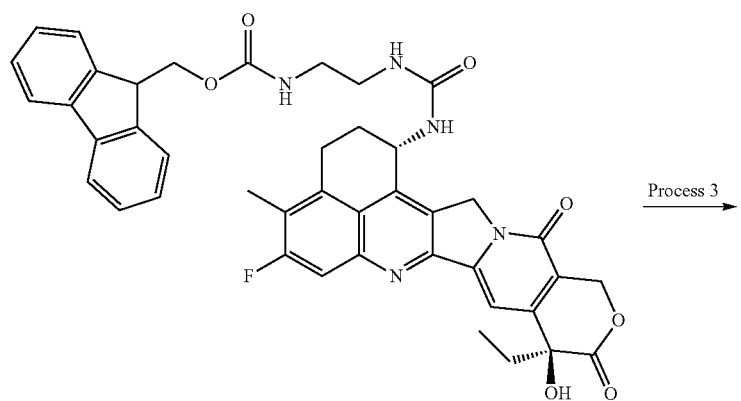
Process 3
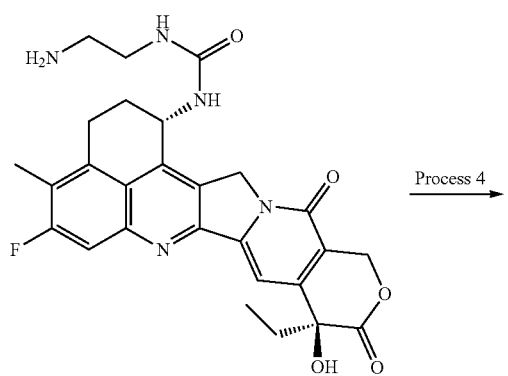
Process 4
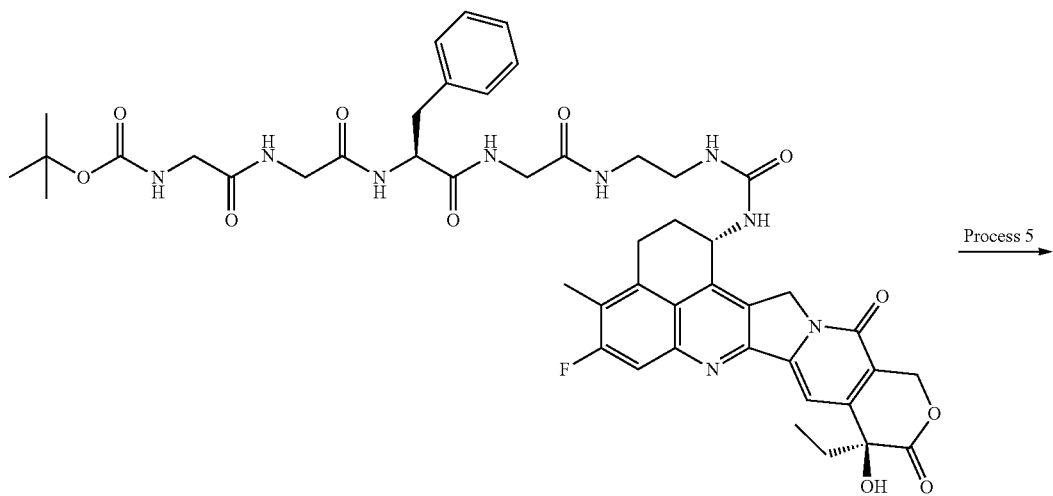
Process 5

-continued

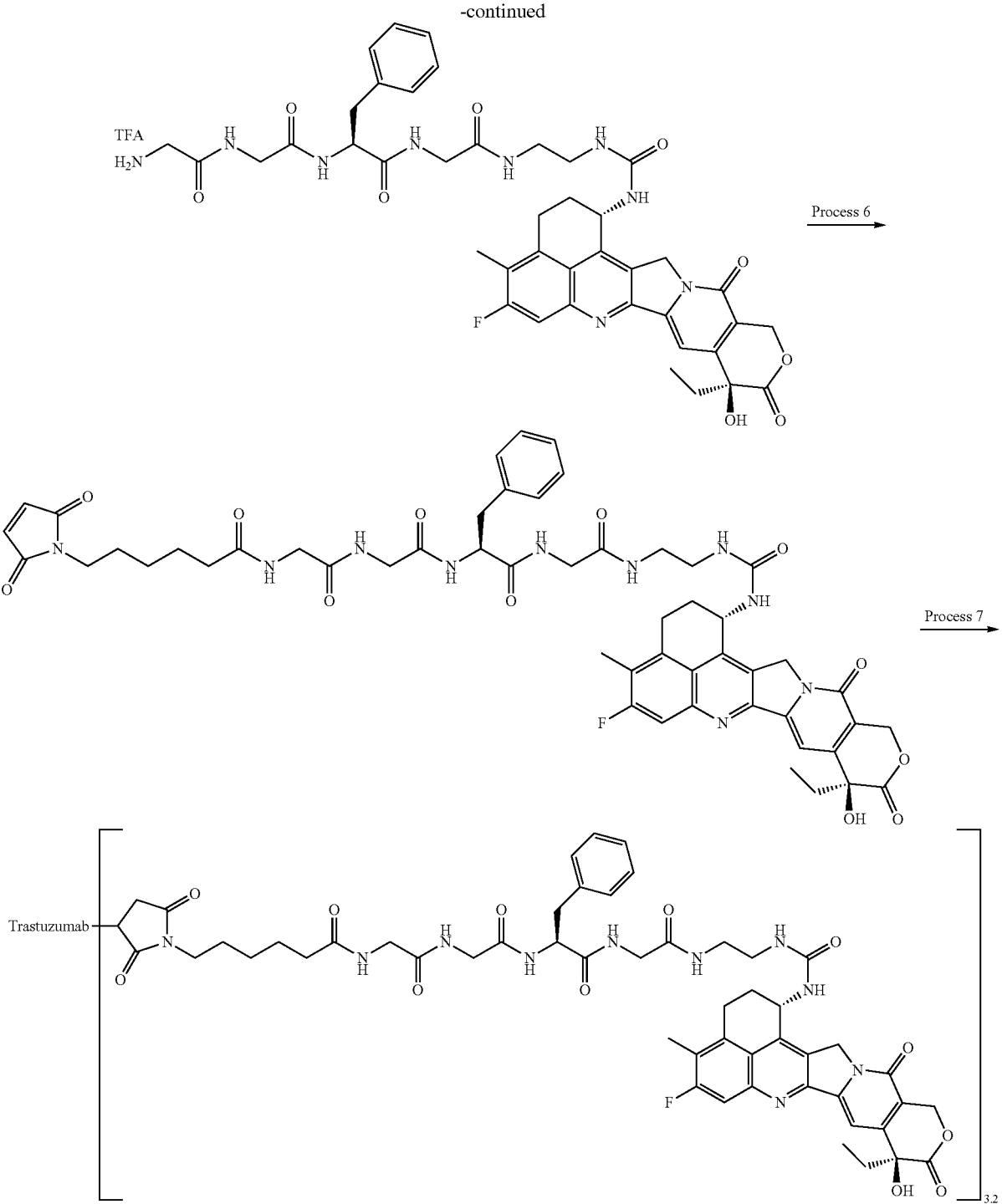

Process 1:
9H-Fluoren-9-ylmethyl(2-isocyanateethyl)carbamate

After cooling a tetrahydrofuran (30 mL) solution of N-[(9H-fluoren-9-ylmethoxy)carbonyl]-β-alanine (3.1 g, 10 mmol) to −15° C. under a nitrogen atmosphere, N-methylmorpholine (1.2 mL, 11 mmol) and ethyl chloroformate (1.1 mL, 11 mmol) were added dropwise in this order and stirred at −15° C. for 10 minutes. A sodium azide (0.98 g, 15 mmol) aqueous solution (2 mL) was added dropwise to this solution at −15° C. and stirred at −15° C. for 1 hour. The reaction solution was charged with a 5% sodium carbonate aqueous solution and then extracted with methylene chloride. The organic layer was washed with 10% citric acid and subsequently water and dried over anhydrous sodium sulfate, and then the solvent was removed under reduced pressure. The residues (colorless solid) obtained were dissolved in toluene (50 mL) and stirred at 65° C. for 1 hour. The solvent was removed under reduced pressure and the residues (colorless solid) obtained were used for the next reaction without purification.

¹H-NMR (400 MHz, CDCl₃) δ: 3.30-3.38 (2H, m), 3.41-3.47 (2H, m), 4.21 (1H, t, J=6.6 Hz), 4.42 (2H, d, J=7.0 Hz), 5.03 (1H, brs), 7.31 (2H, t, J=7.4 Hz), 7.39 (2H, t, J=7.4 Hz), 7.57 (2H, d, J=7.4 Hz), 7.75 (2H, d, J=7.4 Hz).

Process 2: 9H-Fluoren-9-ylmethyl[2-({[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamoyl}amino)ethyl]carbamate To an N,N-dimethylformamide (10 mL) solution of the compound (0.36 g, 1.2 mmol) obtained in Process 1 above, methanesulfonic acid salt of exatecan (0.55 g, 0.97 mmol) and N,N-diisopropylethylamine (0.33 mL, 1.9 mmol) were added, stirred at 50° C. for 1 hour, then charged with a 10% potassium bisulfate aqueous solution, and then extracted with ethyl acetate. The organic layer was washed with water and dried over anhydrous sodium sulfate, and then the solvent was removed under reduced pressure and the residues obtained were purified by silica gel column chromatography [chloroform-chloroform:methanol=10:1 (v/v)] to yield the titled compound as a pale yellow solid (0.79 g, quantitative).

¹H-NMR (400 MHz, DMSO-d₆) δ: 0.82 (2H, t, J=7.2 Hz), 1.73-1.86 (2H, m), 2.00-2.20 (2H, m), 2.35 (3H, s), 3.00-3.16 (5H, m), 3.17-3.27 (1H, m), 4.11-4.27 (3H, m), 5.08 (1H, d, J=19.2 Hz), 5.26-5.38 (4H, m), 5.97-6.03 (1H, m), 6.51 (1H, s), 6.67 (1H, d, J=9.0 Hz), 7.24-7.30 (2H, m), 7.32-7.39 (3H, m), 7.62 (2H, t, J=7.4 Hz), 7.72-7.82 (3H, m).

MS (APCI) m/z: 744 (M+H)⁺.

Process 3: 1-(2-Aminoethyl)-3-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]urea The compound (0.744 g, 1.00 mmol) obtained in Process 2 above was reacted in the same manner as Process 2 of Example 15 to yield the titled compound as a pale yellow solid (0.452 g, 87%).

¹H-NMR (400 MHz, DMSO-d₆) δ: 0.65 (3H, t, J=7.2 Hz), 1.50-2.35 (3H, m), 2.23 (3H, s), 2.84-3.07 (4H, m), 3.11-3.22 (1H, m), 3.42-3.76 (3H, m), 4.40-4.46 (1H, m), 4.53-4.73 (2H, m), 4.81 (1H, d, J=19.9 Hz), 5.24-5.35 (1H, m), 6.12 (1H, s), 6.39-6.47 (1H, m), 6.56 (1H, d, J=9.8 Hz), 7.38 (1H, d, J=10.6 Hz), 7.71 (1H, s), 8.17 (1H, s).

Process 4: N-(tert-Butoxycarbonyl)glycylglycyl-L-phenylalanyl-N-[2-({[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamoyl}amino)ethyl]glycinamide The compound (0.452 g, 0.867 mmol) obtained in Process 3 above was reacted in the same manner as Process 1 of Example 2 to yield the titled compound as a pale yellow solid (0.510 g, 63%).

¹H-NMR (400 MHz, DMSO-d₆) δ: 0.87 (3H, t, J=7.2 Hz), 1.35 (9H, s), 1.77-1.94 (2H, m), 2.08-2.24 (2H, m), 2.39 (3H, s), 2.71-2.82 (1H, m), 2.98-3.80 (13H, m), 4.40-4.55 (1H, m), 5.16-5.49 (5H, m), 6.06-6.11 (1H, m), 6.53 (1H, s), 6.77 (1H, d, J=8.6 Hz), 6.96-7.03 (1H, m), 7.14-7.27 (5H, m), 7.32 (1H, s), 7.78 (1H, d, J=11.0 Hz), 7.83-7.95 (2H, m), 8.15 (1H, s), 8.29 (1H, s).

Process 5: Glycylglycyl-L-phenylalanyl-N-[2-({[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamoyl}amino)ethyl]glycinamide The compound (0.510 g, 0.543 mmol) obtained in Process 4 above was reacted in the same manner as Process 2 of Example 2 to yield the titled compound (0.351 g, 77%) as a pale yellow solid.

¹H-NMR (400 MHz, DMSO-d₆) δ: 0.87 (3H, t, J=7.2 Hz), 1.79-1.92 (2H, m), 2.04-2.24 (2H, m), 2.39 (3H, s), 2.76 (1H, dd, J=13.7, 9.8 Hz), 3.03-3.18 (7H, m), 3.58 (2H, brs), 3.62-3.91 (4H, m), 4.50-4.58 (1H, m), 5.17-5.49 (5H, m), 6.08-6.15 (1H, m), 6.54 (1H, s), 6.79 (1H, d, J=9.0 Hz), 7.13-7.30 (5H, m), 7.32 (1H, s), 7.79 (1H, d, J=10.9 Hz), 7.91-8.03 (3H, m), 8.34 (2H, d, J=7.4 Hz), 8.49 (1H, t, J=5.7 Hz).

Process 6: N-[6-(2,5-Dioxo-2,5-dihydro-1H-pyrrol-1-yl)hexanoyl]glycylglycyl-L-phenylalanyl-N-[2-({[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamoyl}amino)ethyl]glycinamide The compound (84.0 mg, 0.100 mmol) obtained in Process 5 above was reacted in the same manner as Process 8 of Example 5 to yield the titled compound as a pale yellow solid (75.6 mg, 73%).

¹H-NMR (400 MHz, DMSO-d₆) δ: 0.87 (3H, t, J=7.2 Hz), 1.12-1.22 (2H, m), 1.40-1.51 (4H, m), 1.79-1.93 (2H, m), 2.03-2.22 (4H, m), 2.38 (3H, s), 2.47-3.38 (11H, m), 3.54-3.76 (6H, m), 4.42-4.52 (1H, m), 5.14-5.49 (5H, m), 6.07-6.12 (1H, m), 6.53 (1H, s), 6.77 (1H, d, J=9.0 Hz), 6.99 (1H, s), 7.19 (5H, dd, J=22.1, 6.5 Hz), 7.31 (1H, s), 7.78 (1H, d, J=10.6 Hz), 7.84-7.88 (1H, m), 7.99-8.10 (2H, m), 8.14 (1H, d, J=7.8 Hz), 8.23-8.29 (1H, m).

MS (ESI) m/z: 1033 (M+H)⁺.

Process 7: Antibody-Drug Conjugate (15)

By using the trastuzumab produced in Reference Example 1 and the compound obtained in Process 6 above, the titled antibody-drug conjugate was obtained in the same manner as Process 6 of Example 2.

Antibody concentration: 1.65 mg/mL, antibody yield: 9.9 mg (79%), and average number of conjugated drug molecules (n) per antibody molecule: 3.2.

Example 28 Antibody-Drug Conjugate (28)

[Formula 81]

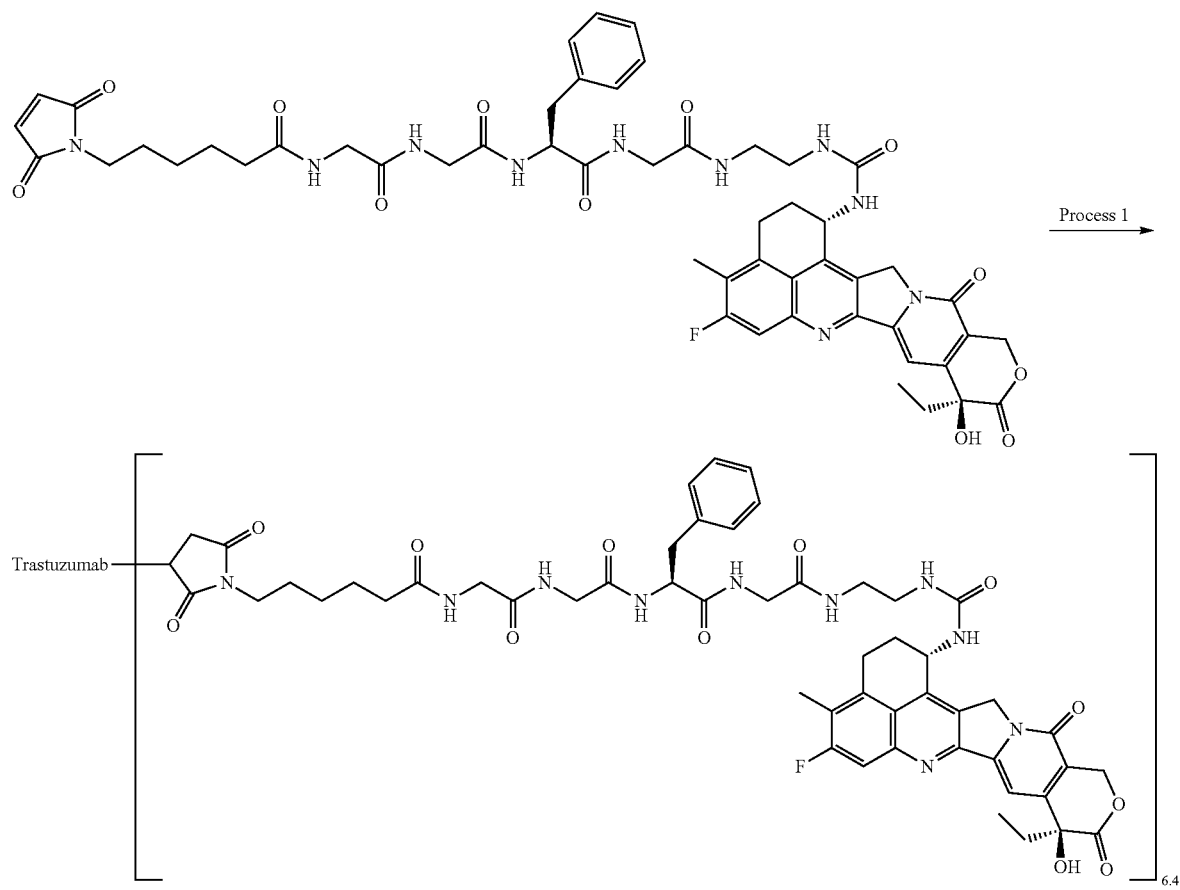

Process 1: Antibody-Drug Conjugate (28)

By using the trastuzumab produced in Reference Example 1 and the compound obtained in Process 6 of Example 27, the titled antibody-drug conjugate was obtained in the same manner as Process 1 of Example 3.

Antibody concentration: 1.83 mg/mL, antibody yield: 11.0 mg (88%), and average number of conjugated drug molecules (n) per antibody molecule: 6.4.

Example 29 Antibody-Drug Conjugate (29)

[Formula 82]

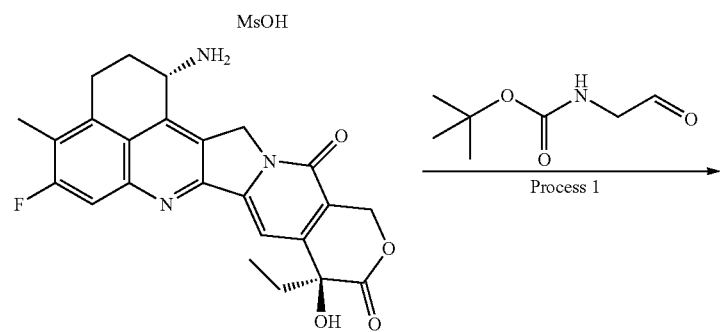

225 226
-continued
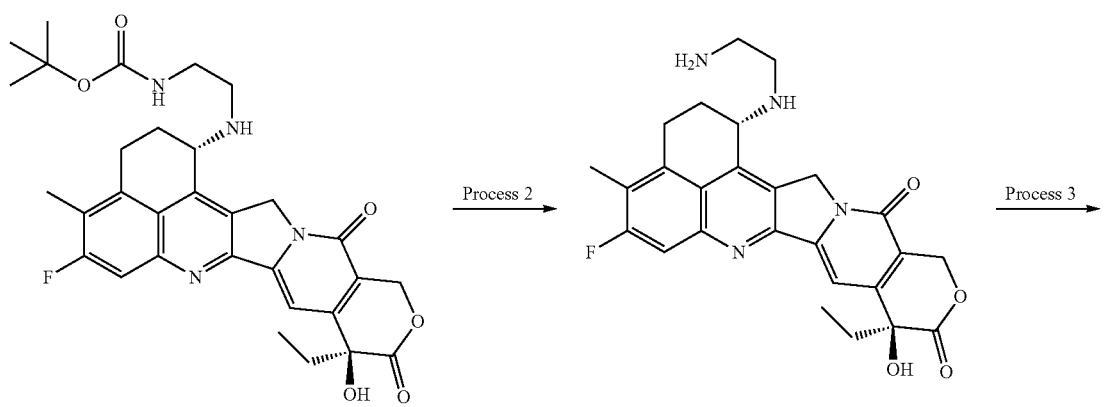
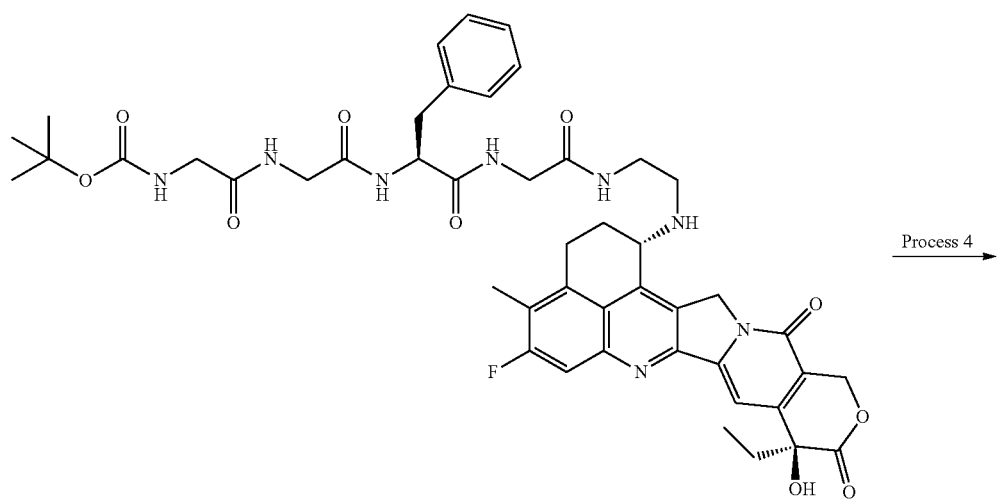
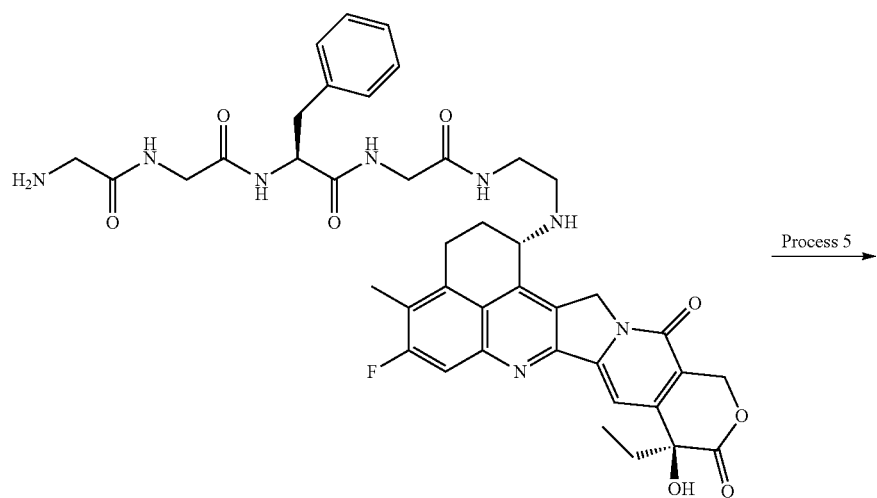

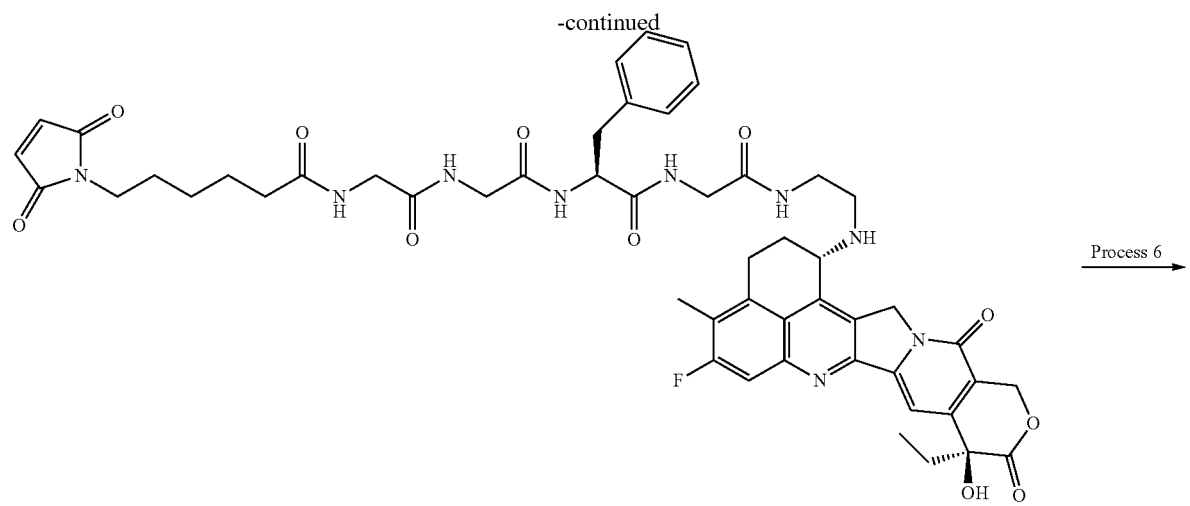

Process 6 →

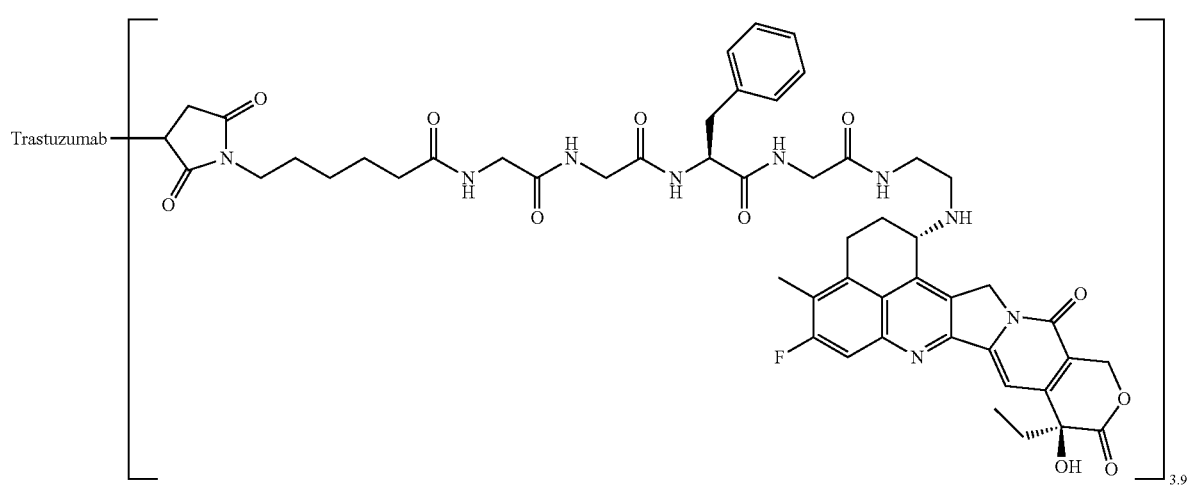

Process 1: tert-Butyl (2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}ethyl)carbamate Methanesulfonic acid salt of exatecan (0.541 g, 1.00 mmol) was dissolved in N,N-dimethylformamide (0.5 mL) and charged with chloroform (100 mL), methanol (100 mL), tert-butyl N-(2-oxoethyl)carbamate (0.238 g, 1.5 mmol), and acetic acid (0.086 mL, 1.5 mmol). This solution was charged with sodium triacetoxyborohydride (316 mg, 1.5 mmol) and stirred at room temperature for 12 hours. The reaction solution was charged with water and then extracted with chloroform. The organic layer was dried over anhydrous sodium sulfate, and then the solvent was removed under reduced pressure and the residues obtained were purified by silica gel column chromatography [chloroform-chloroform:methanol=10:1 (v/v)] to yield the titled compound as a pale yellow solid (0.20 g, 34%).

$^1$H-NMR (400 MHz, DMSO-$d_6$) δ: 0.96 (4H, t, J=7.3 Hz), 1.44 (9H, s), 1.88-2.03 (2H, m), 2.04-2.14 (1H, m), 2.23-2.37 (1H, m), 2.47 (3H, s), 2.73-2.82 (1H, m), 2.86-2.94 (1H, m), 3.08-3.17 (3H, m), 3.25-3.34 (1H, m), 4.31-4.36 (1H, m), 5.48 (2H, s), 5.52 (2H, s), 6.62 (1H, s), 6.85-6.90 (1H, m), 7.40 (1H, s), 7.84 (1H, d, J=10.7 Hz).

MS (APCI) m/z: 579 (M+H)$^+$.

Process 2: ((1S,9S)-1-[(2-Aminoethyl)amino]-9-ethyl-5-fluoro-9-hydroxy-4-methyl-1,2,3,9,12,15-hexahydro-10H,13H-benzo[de]pyrano[3',4':6,7]indolizino[1,2-b]quinoline-10,13-dione The compound (0.174 g, 0.300 mmol) obtained in Process 1 above was reacted in the same manner as Process 2 of Example 1, and the crude product obtained was used for the next reaction without purification.

Process 3: N-(tert-Butoxycarbonyl)glycylglycyl-L-phenylalanyl-N-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}ethyl)glycinamide The crude product obtained in Process 2 above was reacted in the same manner as Process 1 of Example 2, and the crude product obtained was used for the next reaction without purification.

Process 4: Glycylglycyl-L-phenylalanyl-N-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}ethyl)glycinamide The crude product obtained in Process 3 above was reacted in the same manner as Process 2 of Example 2, and the crude product obtained was used for the next reaction without purification.

Process 5: N-[6-(2,5-Dioxo-2,5-dihydro-1H-pyrrol-1-yl)hexanoyl]glycylglycyl-L-phenylalanyl-N-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}ethyl)glycinamide The crude product obtained in Process 4 above was reacted in the same manner as Process 8 of Example 5 to yield the titled compound as a pale yellow solid (42.2 mg, 14%, 4 steps).

$^1$H-NMR (400 MHz, DMSO-$d_6$) δ: 0.86 (3H, t, J=7.2 Hz), 1.11-1.20 (2H, m), 1.38-1.50 (4H, m), 1.79-1.92 (2H, m), 2.02-2.25 (5H, m), 2.38 (3H, s), 2.69-3.39 (10H, m), 3.53-3.77 (6H, m), 4.21-4.31 (1H, m), 4.42-4.51 (1H, m), 5.31-5.55 (4H, m), 6.54 (1H, s), 6.99 (2H, s), 7.12-7.28 (5H, m), 7.32 (1H, s), 7.65-7.71 (1H, m), 7.75 (1H, d, J=10.9 Hz), 7.98-8.10 (2H, m), 8.16 (1H, d, J=7.4 Hz), 8.39 (1H, t, J=6.1 Hz).

MS (ESI) m/z: 990 (M+H)$^+$.

Process 6: Antibody-Drug Conjugate (29)

By using the trastuzumab produced in Reference Example 1 and the compound obtained in Process 5 above, the titled antibody-drug conjugate was obtained in the same manner as Process 6 of Example 2.
Antibody concentration: 1.75 mg/mL, antibody yield: 10.5 mg (84%), and average number of conjugated drug molecules (n) per antibody molecule: 3.9.

Example 30 Antibody-Drug Conjugate (30)

[Formula 83]

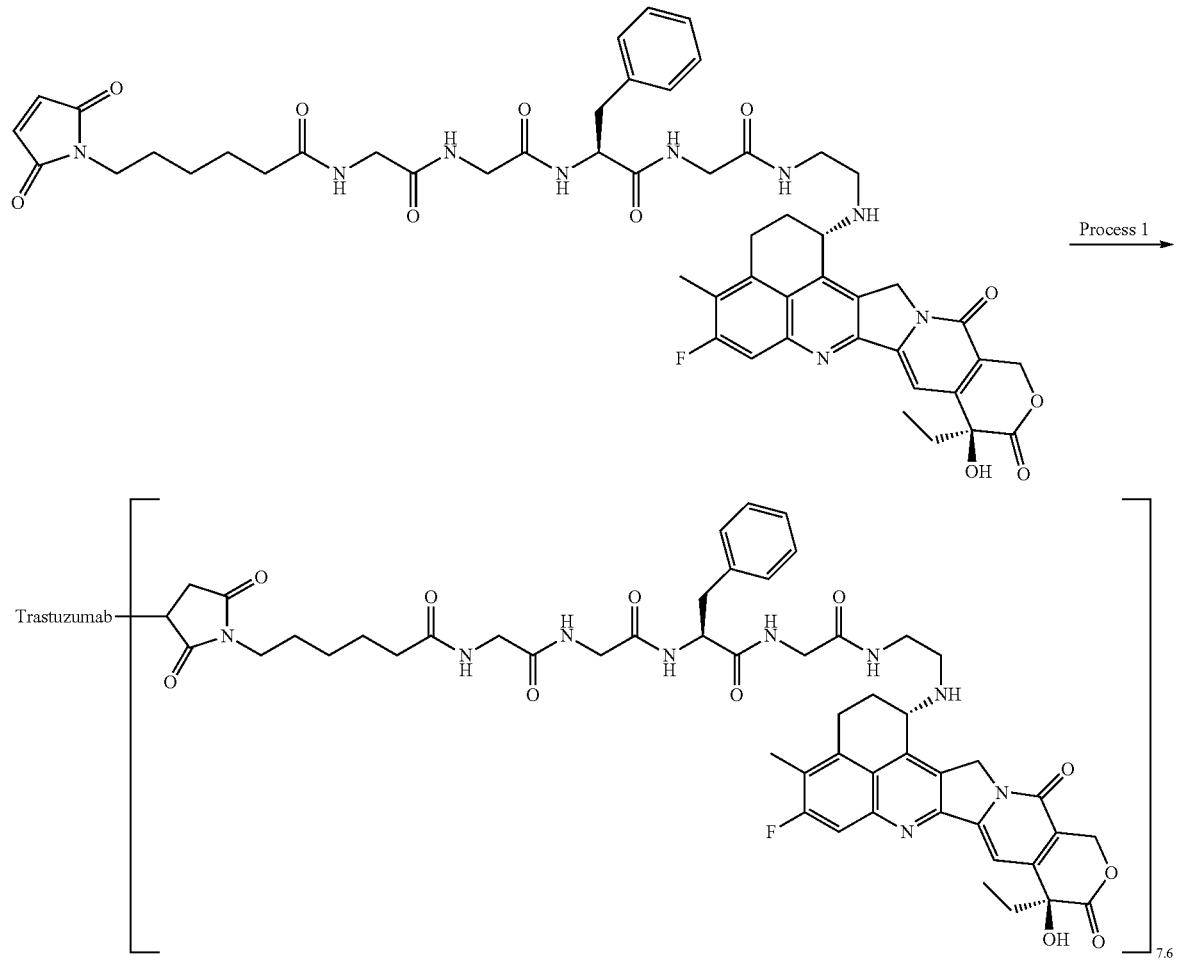

231

Process 1: Antibody-Drug Conjugate (30)

By using the trastuzumab produced in Reference Example 1 and the compound obtained in Process 5 of Example 29, the titled antibody-drug conjugate was obtained in the same manner as Process 1 of Example 3.

232

Antibody concentration: 1.70 mg/mL, antibody yield: 10.2 mg (82%), and average number of conjugated drug molecules (n) per antibody molecule: 7.6.

Example 31 Antibody-Drug Conjugate (31)

[Formula 84]

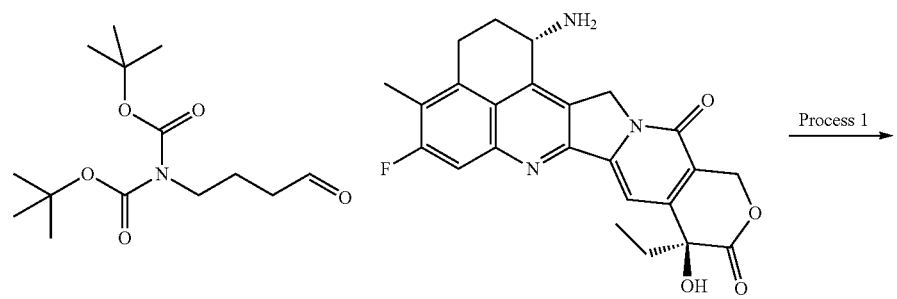

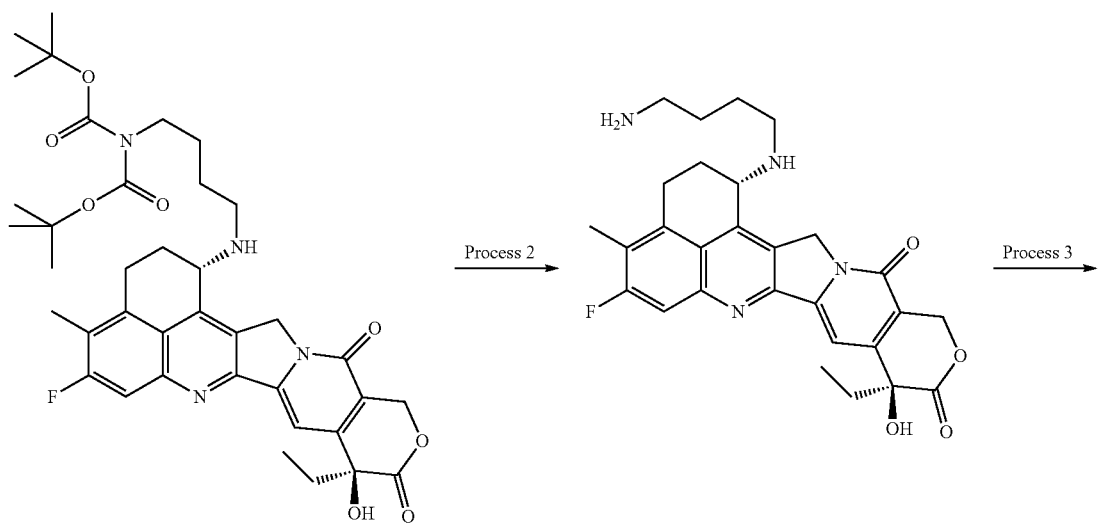

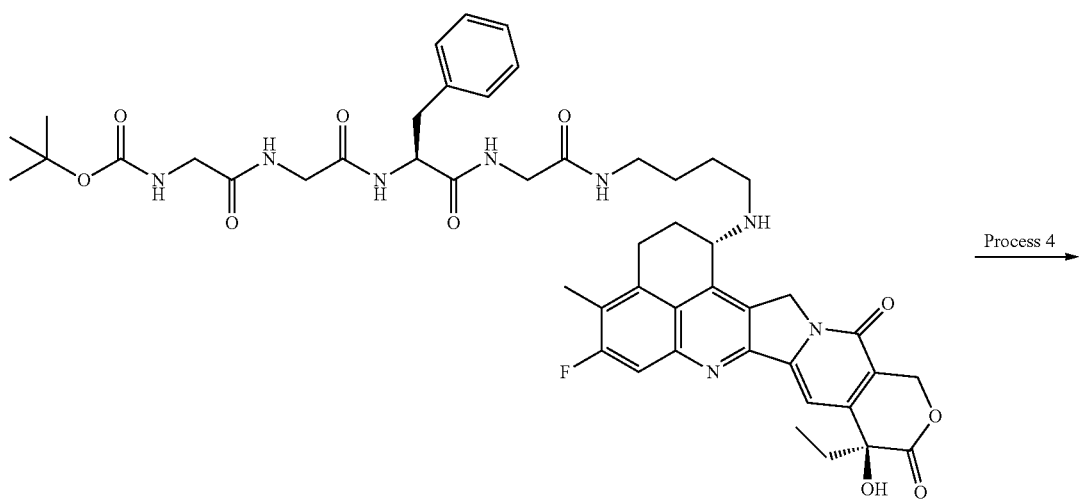

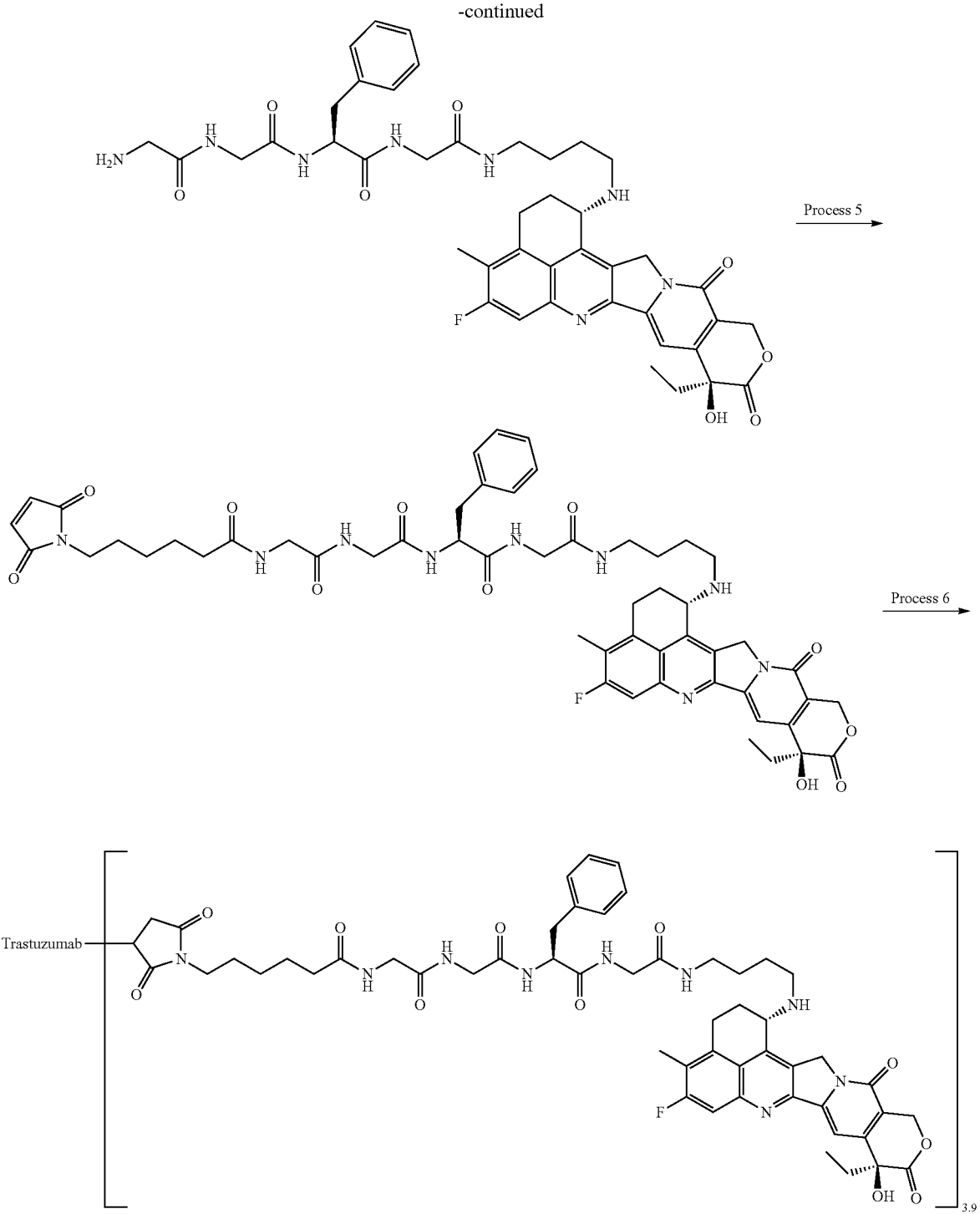

Process 1: Di-tert-butyl (4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}butyl)imidodicarbonate Methanesulfonic acid salt of exatecan (2.13 g, 4.00 mmol) was reacted in the same manner as Process 1 of Example 29 by using di-tert-butyl (4-oxobutyl)imidodicarbonate instead of tert-butyl N-(2-oxoethyl)carbamate to yield the titled compound as a pale yellow solid (1.73 g, 61%).

$^1$H-NMR (400 MHz, DMSO-$d_6$) δ: 0.87 (4H, t, J=7.2 Hz), 1.39 (18H, s), 1.60-1.34 (4H, m), 1.80-1.93 (2H, m), 1.96-2.05 (1H, m), 2.19-2.30 (1H, m), 2.37 (3H, s), 2.61-2.71 (1H, m), 2.73-2.83 (1H, m), 2.96-3.06 (1H, m), 3.17-3.26 (1H, m), 3.42-3.51 (2H, m), 4.19-4.25 (1H, m), 5.29-5.46 (4H, m), 6.52 (1H, s), 7.30 (1H, s), 7.74 (1H, d, J=11.3 Hz).

235

Process 2: (1S,9S)-1-[(4-Aminobutyl)amino]-9-ethyl-5-fluoro-9-hydroxy-4-methyl-1,2,3,9,12,15-hexahydro-10H,13H-benzo[de]pyrano[3',4':6,7]indolizino[1,2-b]quinoline-10,13-dione The compound (0.283 g, 0.400 mmol) obtained in Process 1 above was reacted in the same manner as Process 2 of Example 1, and the crude product obtained was used for the next process without purification.

Process 3: N-(tert-Butoxycarbonyl)glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}butyl)glycinamide The crude product obtained in Process 2 above was reacted in the same manner as Process 1 of Example 2, and the crude product obtained was used for the next reaction without purification.

Process 4: Glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}butyl)glycinamide The crude product obtained in Process 3 above was reacted in the same manner as Process 2 of Example 2, and the crude product obtained was used for the next reaction without purification.

236

Process 5: N-[6-(2,5-Dioxo-2,5-dihydro-1H-pyrrol-1-yl)hexanoyl]glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}butyl)glycinamide The crude product obtained in Process 4 above was reacted in the same manner as Process 8 of Example 5 to yield the titled compound as a pale yellow solid (53.7 g, 13%, 4 steps).

$^1$H-NMR (400 MHz, DMSO-$d_6$) δ: 0.87 (3H, t, J=6.6 Hz), 1.14-1.28 (2H, m), 1.40-1.56 (8H, m), 1.81-1.92 (2H, m), 1.97-2.28 (5H, m), 2.37 (3H, s), 2.46-3.42 (10H, m), 3.51-3.80 (6H, m), 4.19-4.26 (1H, m), 4.41-4.50 (1H, m), 5.29-5.48 (4H, m), 6.54 (1H, s), 6.99 (2H, s), 7.09-7.28 (5H, m), 7.31 (1H, s), 7.61-7.69 (1H, m), 7.74 (1H, d, J=11.3 Hz), 7.99-8.17 (3H, m), 8.24 (1H, s).

MS (ESI) m/z: 1018 (M+H)$^+$.

Process 6: Antibody-Drug Conjugate (31)

By using the trastuzumab produced in Reference Example 1 and the compound obtained in Process 5 above, the titled antibody-drug conjugate was obtained in the same manner as Process 6 of Example 2.

Antibody concentration: 1.81 mg/mL, antibody yield: 10.9 mg (87%), and average number of conjugated drug molecules (n) per antibody molecule: 3.9.

Example 32 Antibody-Drug Conjugate (32)

[Formula 85]

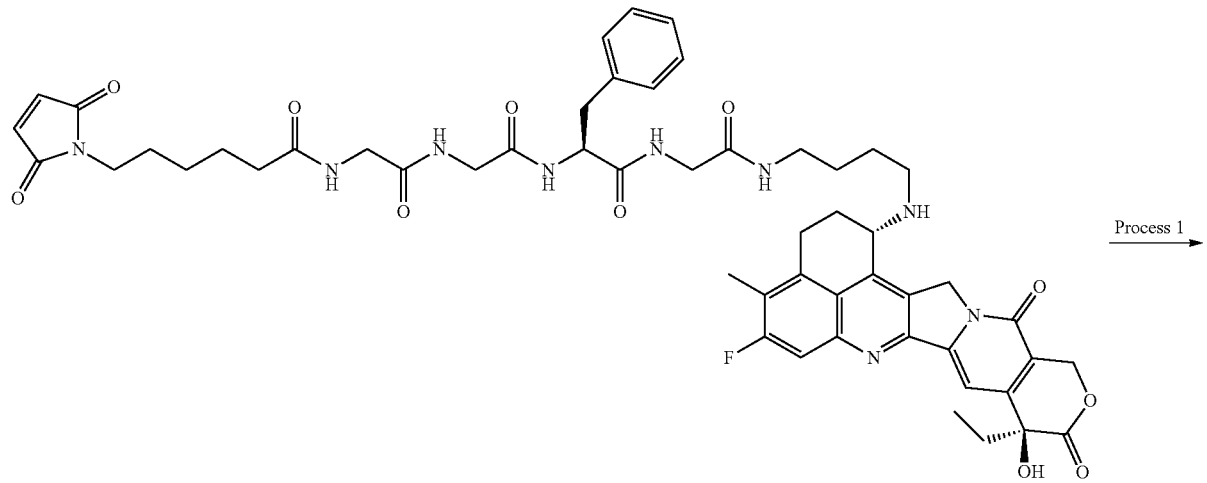

Process 1

-continued

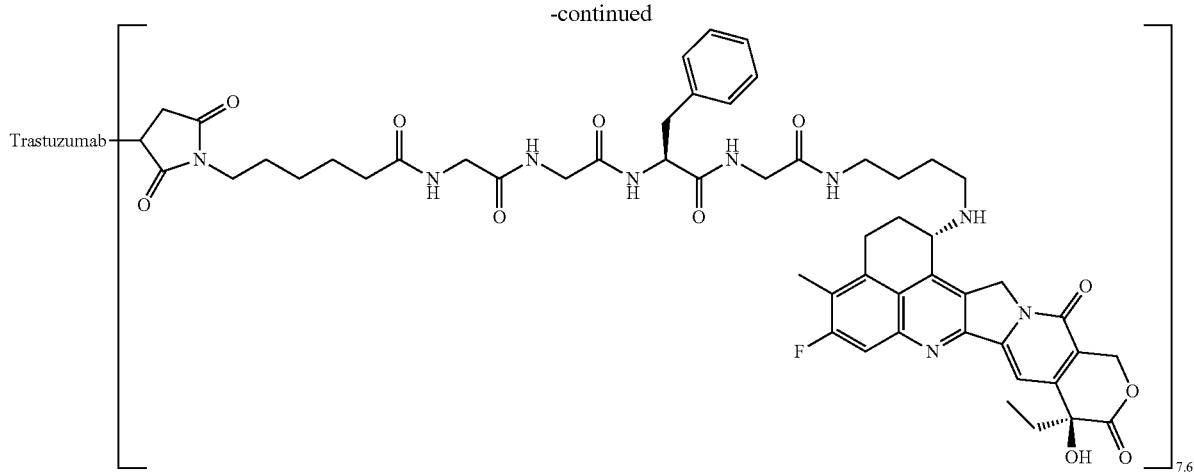

Process 1: Antibody-Drug Conjugate (32) By using the trastuzumab produced in Reference Example 1 and the compound obtained in Process 5 of Example 31, the titled antibody-drug conjugate was obtained in the same manner as Process 1 of Example 3.

Antibody concentration: 1.77 mg/mL, antibody yield: 10.6 mg (85%), and average number of conjugated drug molecules (n) per antibody molecule: 7.6.

Example 33 Intermediate (33)

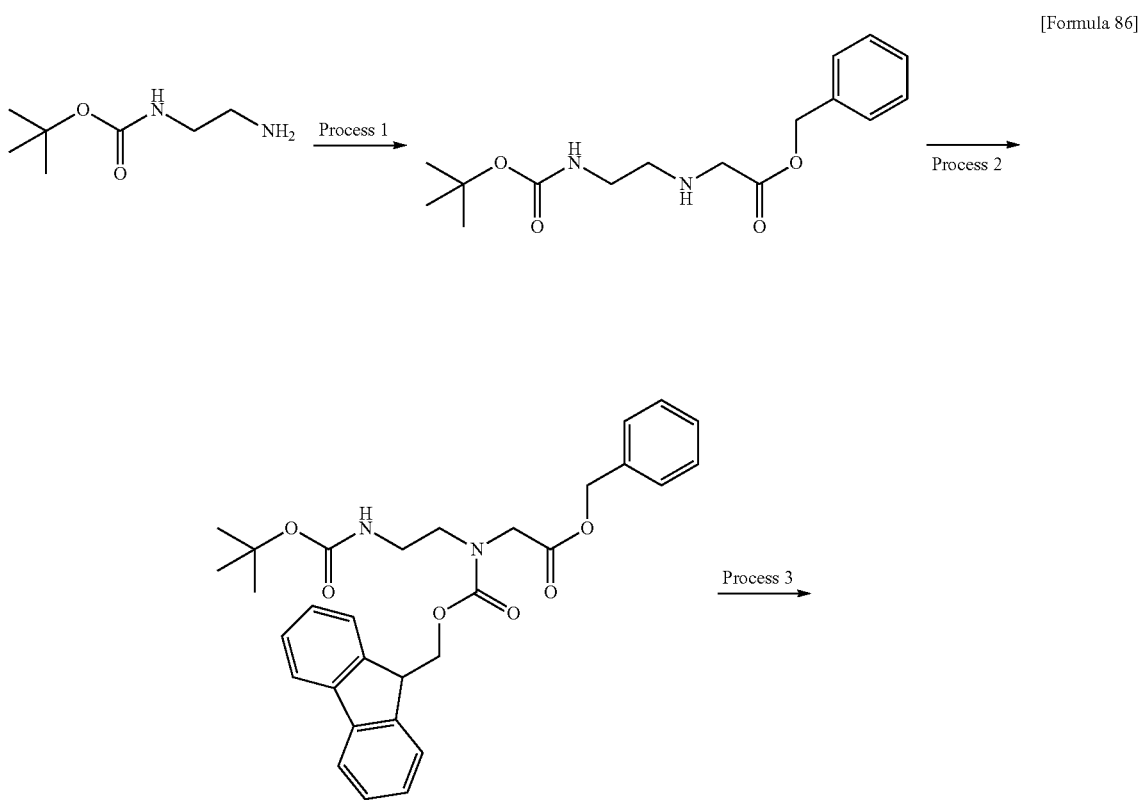

[Formula 86]

-continued
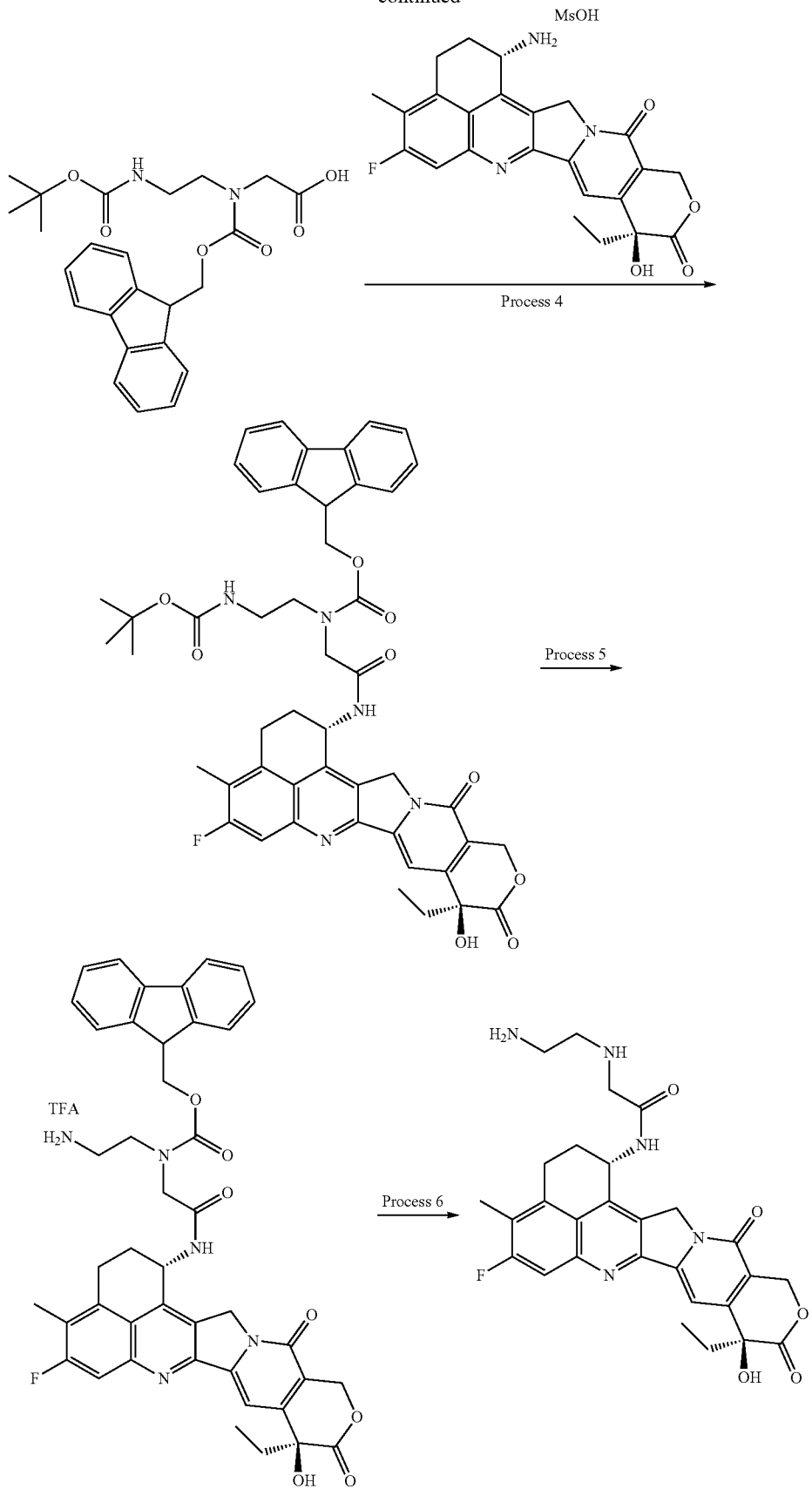

Process 1: Benzyl N-{2-[(tert-butoxycarbonyl)amino]ethyl}glycinate tert-Butyl N-(2-aminoethyl)carbamate (3.00 g, 18.7 mmol) was dissolved in acetonitrile (10.0 mL), charged with potassium carbonate (2.59 g, 18.7 mmol) and benzyl 2-bromoacetate (1.46 mL, 9.36 mmol), and stirred at room temperature for 1 day. The reaction solution was filtered, and the solvent in the filtrate obtained was removed under reduced pressure. The residues obtained were purified by silica gel column chromatography [chloroform-chloroform:methanol=8:2 (v/v)] to yield the titled compound as a colorless oily substance (1.71 g, 59%).

$^1$H-NMR (400 MHz, CDCl$_3$) δ: 1.44 (9H, s), 2.72 (2H, t, J=5.7 Hz), 3.19 (2H, q, J=5.7 Hz), 3.43 (2H, s), 4.68 (1H, s), 5.16 (2H, s), 7.34-7.36 (6H, m).

MS (APCI) m/z: 309 (M+H)$^+$.

Process 2: Benzyl N-{2-[(tert-butoxycarbonyl)amino]ethyl}-N-[(9H-fluoren-9-ylmethoxy)carbonyl]glycinate The compound (0.370 g, 1.19 mmol) obtained in Process 1 above was dissolved in 1,4-dioxane (5.00 mL). After adding diisopropylethylamine (2.00 mL, 11.9 mmol) and 9-fluorenylmethyl chloroformate (1.23 g, 4.76 mmol), it was stirred at room temperature for 3 hours. The solvent was removed under reduced pressure and the residues obtained were purified by silica gel column chromatography [hexane-hexane/ethyl acetate=1:1 (v/v)] to yield the titled compound as a colorless oily substance (0.479 g, 76%).

$^1$H-NMR (400 MHz, CDCl$_3$) δ: 1.40-1.43 (9H, m), 2.99-3.25 (2H, m), 3.34-3.40 (2H, m), 3.95-4.01 (2H, m), 4.08-4.24 (1H, m), 4.38 (1H, d, J=6.6 Hz), 4.52 (1H, d, J=6.3 Hz), 5.10-5.16 (2H, m), 7.24-7.41 (9H, m), 7.50 (1H, d, J=7.4 Hz), 7.56 (1H, d, J=7.4 Hz), 7.73 (1H, d, J=7.4 Hz), 7.76 (1H, d, J=7.4 Hz).

Process 3: N-{2-[(tert-Butoxycarbonyl)amino]ethyl}-N-[(9H-fluoren-9-ylmethoxy)carbonyl]glycine The compound (461 mg, 0.868 mmol) obtained in Process 2 above was dissolved in methanol (5.00 mL). After adding a catalytic amount of palladium on carbon catalyst, it was stirred under a hydrogen atmosphere for 1 hour. After filtration through a celite layer, the solvent in the filtrate was removed under reduced pressure. The residues obtained were purified by silica gel column chromatography [chloroform-partitioned organic layer of chloroform:methanol:water=7:3:1 (v/v/v)] to yield the titled compound as a colorless oily substance (236 mg, 62%).

$^1$H-NMR (400 MHz, CDCl$_3$) δ: 1.36 (9H, s), 3.00-3.02 (1H, m), 3.24-3.27 (2H, m), 3.41-3.43 (1H, m), 3.67-3.69 (1H, m), 3.90-3.95 (2H, m), 4.17-4.20 (1H, m), 4.34-4.43 (2H, m), 7.29-7.33 (4H, m), 7.52-7.54 (2H, m), 7.71 (2H, d, J=7.0 Hz).

MS (APCI) m/z: 439 (M−H)$^−$.

Process 4: 9H-Fluoren-9-ylmethyl{2-[(tert-butoxycarbonyl)amino]ethyl} (2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)carbamate Methanesulfonic acid salt of exatecan (230 mg, 0.435 mmol) was reacted in the same manner as Process 1 of Example 1 by using the compound (228 mg, 0.519 mmol) obtained in Process 3 above instead of 4-(tert-butoxycarbonylamino)butanoic acid to yield the titled compound as a yellow solid (336 mg, 90%).

$^1$H-NMR (400 MHz, CD$_3$OD) δ: 0.89-0.97 (3H, m), 1.35-1.40 (9H, m), 1.77-1.79 (2H, m), 2.16-2.23 (2H, m), 2.29 (3H, s), 2.62 (1H, s), 3.12-3.22 (4H, m), 3.36-3.52 (1H, m), 3.88-4.17 (3H, m), 4.32-4.36 (2H, m), 4.67-4.81 (2H, m), 5.03-5.38 (2H, m), 5.59 (1H, dd, J=20.1, 15.1 Hz), 6.69 (1H, t, J=7.6 Hz), 7.03 (1H, dt, J=28.0, 7.5 Hz), 7.16-7.57 (6H, m), 7.69 (1H, d, J=7.4 Hz), 7.96 (1H, s).

MS (APCI) m/z: 858 (M+H)$^+$.

Process 5: 9H-Fluoren-9-ylmethyl (2-aminoethyl) (2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)carbamate The compound (347 mg, 0.404 mmol) obtained in Process 4 above was reacted in the same manner as Process 2 of Example 1 to yield trifluoroacetic acid salt of the titled compound as a yellow solid (307 mg, quantitative).

$^1$H-NMR (400 MHz, CDCl$_3$) δ: 1.05 (3H, t, J=7.4 Hz), 1.85-1.92 (2H, m), 2.29-2.32 (2H, m), 2.45 (3H, s), 2.82-2.84 (1H, m), 3.25-3.28 (2H, m), 3.58-3.65 (1H, m), 3.98-4.12 (3H, m), 4.30-4.33 (2H, m), 4.55-4.62 (2H, m), 4.89-5.41 (4H, m), 5.60-5.72 (1H, m), 6.83 (1H, t, J=7.4 Hz), 7.12-7.19 (1H, m), 7.30-7.65 (7H, m), 7.81 (1H, d, J=7.4 Hz).

MS (APCI) m/z: 758 (M+H)$^+$.

Process 6: N$^2$-(2-Aminoethyl)-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (191 mg, 0.253 mmol) obtained in Process 5 above was reacted in the same manner as Process 6 of Example 15 to yield the titled compound as a pale yellow solid (97.7 mg, 72%).

$^1$H-NMR (DMSO-d$_6$) δ: 0.87 (3H, t, J=7.2 Hz), 1.84-1.87 (2H, m), 2.16-2.17 (2H, m), 2.38 (3H, s), 2.76 (2H, t, J=5.5 Hz), 2.86-2.87 (2H, m), 3.00-3.02 (2H, m), 3.17-3.18 (2H, m), 3.26-3.28 (2H, m), 3.35 (2H, br.s), 5.19 (2H, s), 5.42 (2H, s), 5.58-5.60 (1H, m), 7.31 (1H, s), 7.78 (1H, d, J=11.0 Hz), 8.57 (1H, d, J=9.0 Hz).

MS (APCI) m/z: 758 (M+H)$^+$.

Example 34 Antibody-Drug Conjugate (34)
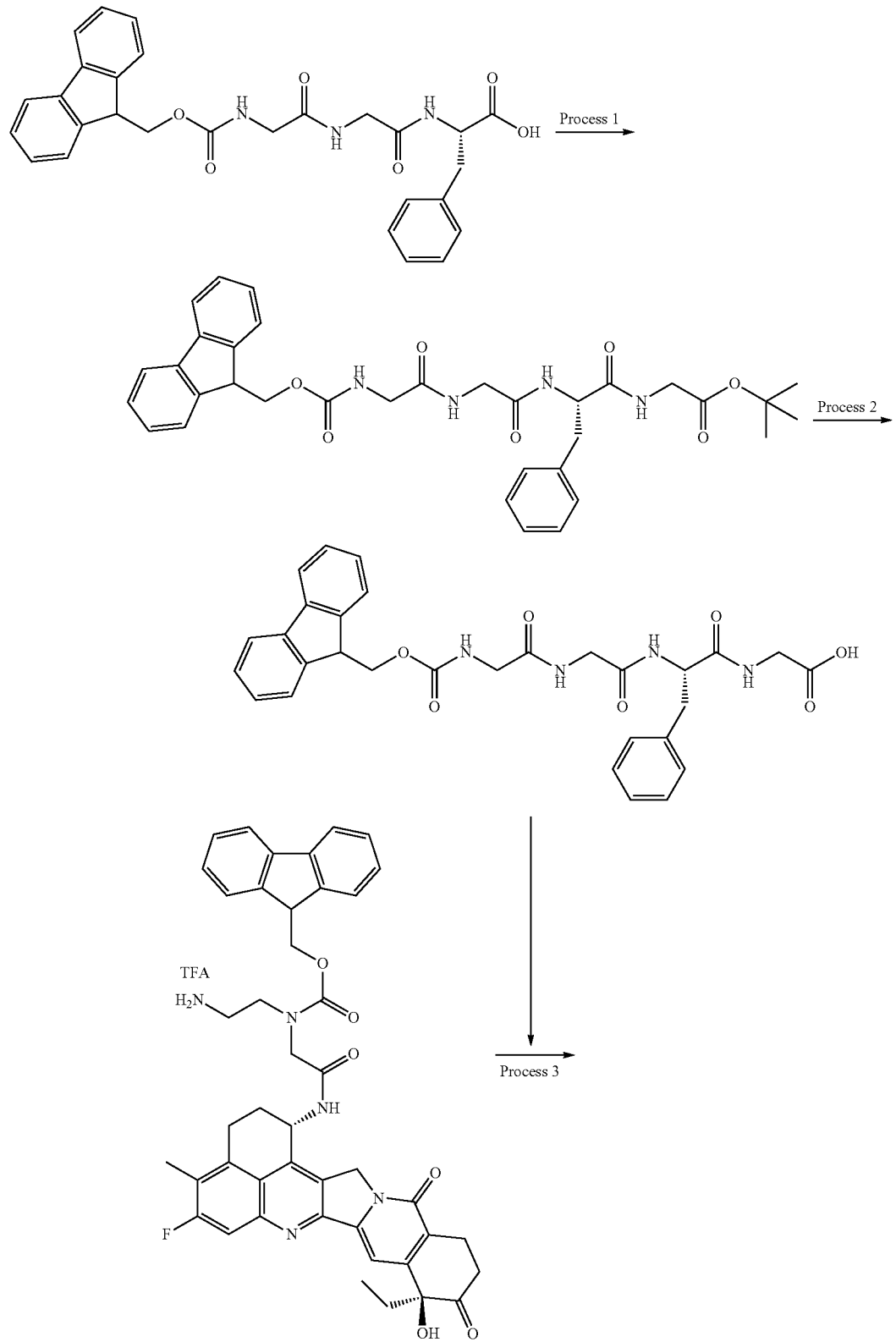

245
246
-continued
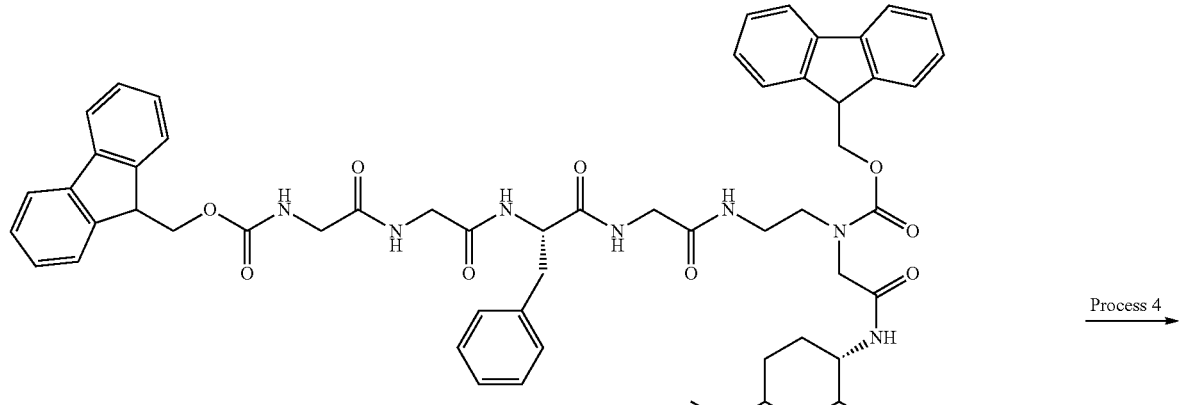
Process 4 →
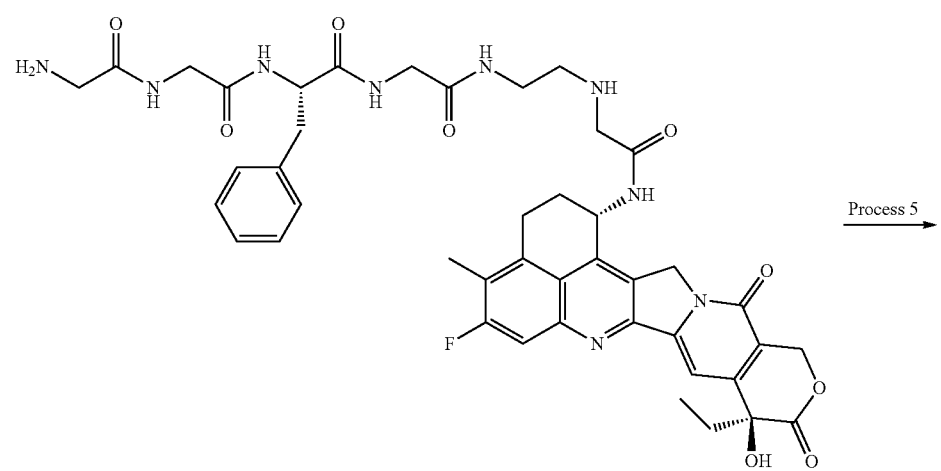
Process 5 →
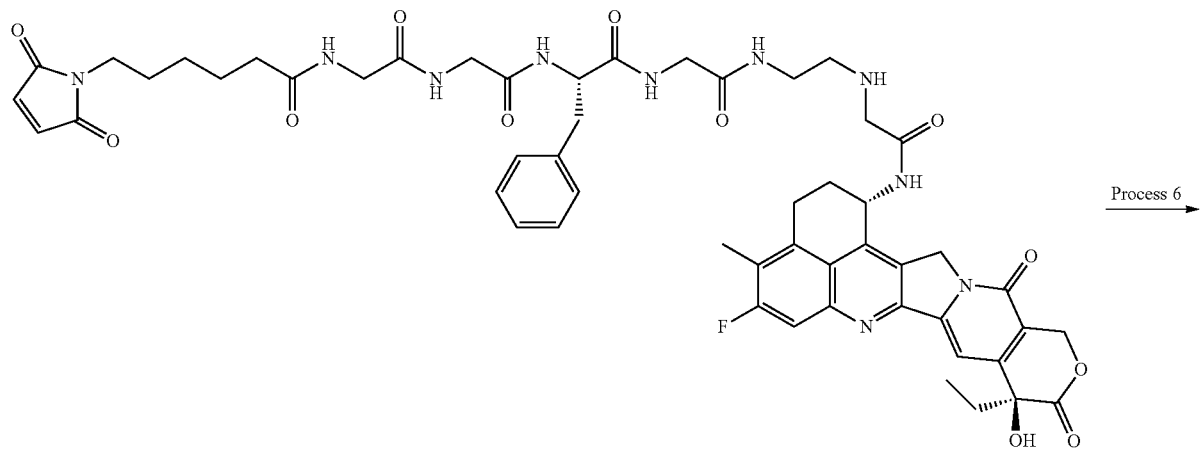
Process 6 →

-continued

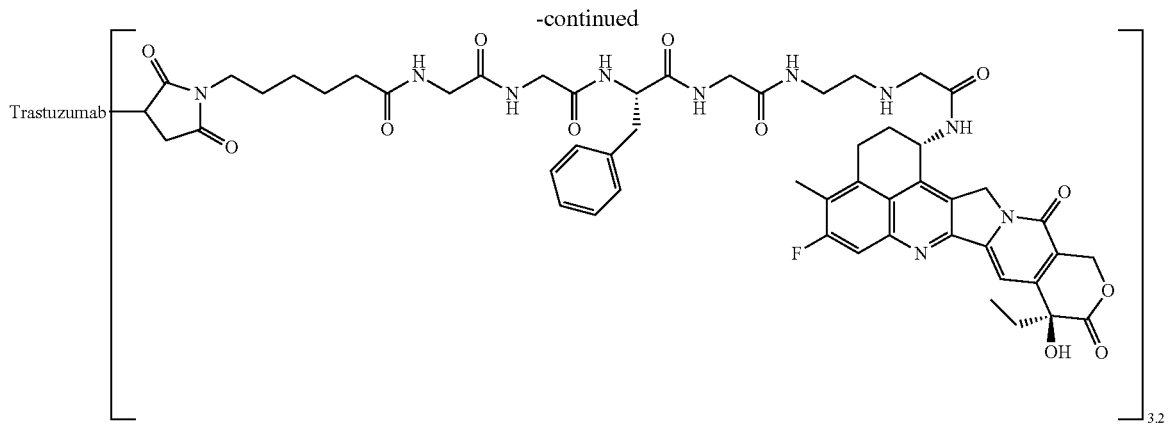

Process 1: tert-Butyl N-[(9H-fluoren-9-ylmethoxy)carbonyl]glycylglycyl-L-phenylalanylglycinate To a dichloromethane (50.0 mL) solution of N-[(9H-fluoren-9-ylmethoxy)carbonyl]glycylglycyl-L-phenylalanine (Japanese Patent Laid-Open No. 2002-60351; 5.43 g, 10.8 mmol), 1-hydroxybenzotriazole (2.93 g, 21.7 mmol), glycine tert-butyl ester hydrochloride (2.72 g, 16.2 mmol), and triethylamine (3.02 mL, 21.7 mmol), l-ethyl-3-(3-dimethylaminopropyl)carbodiimide hydrochloride (4.15 g, 21.7 mmol) was added and stirred at room temperature for 20 hours. After adding an aqueous solution of 10% citric acid (100 mL), it was extracted with chloroform (100 mL) 3 times, and the organic layer was dried over anhydrous sodium sulfate. After removing the solvent under reduced pressure, the residues obtained were purified by silica gel column chromatography [chloroform-chloroform:methanol=8:2 (v/v)] to yield the titled compound as a colorless solid (6.02 g, quantitative).

$^1$H-NMR (DMSO-$d_6$) δ: 1.40 (9H, s), 2.76 (1H, dd, J=13.7, 10.6 Hz), 3.05 (1H, dd, J=13.7, 3.9 Hz), 3.55-3.80 (6H, m), 4.21-4.31 (3H, m), 4.52 (1H, td, J=9.3, 3.4 Hz), 7.19-7.26 (5H, m), 7.32 (2H, t, J=7.4 Hz), 7.42 (2H, t, J=7.4 Hz), 7.60 (1H, t, J=5.9 Hz), 7.71 (2H, d, J=7.0 Hz), 7.89 (2H, d, J=7.8 Hz), 8.00 (1H, t, J=5.3 Hz), 8.14 (1H, d, J=8.2 Hz), 8.39 (1H, t, J=5.7 Hz).

MS (APCI) m/z: 615 (M+H)$^+$.

Process 2: N-[(9H-Fluoren-9-ylmethoxy)carbonyl]glycylglycyl-L-phenylalanylglycine The compound (5.00 g, 8.13 mmol) obtained in Process 1 above was reacted in the same manner as Process 2 of Example 2 to yield the titled compound (4.47 g, 98%).

$^1$H-NMR (DMSO-$d_6$) δ: 2.76 (1H, dd, J=13.7, 10.2 Hz), 3.05 (1H, dd, J=13.7, 3.9 Hz), 3.55-3.79 (7H, m), 4.21-4.30 (3H, m), 4.54 (1H, td, J=9.0, 3.7 Hz), 7.16-7.25 (5H, m), 7.33 (2H, t, J=7.4 Hz), 7.42 (2H, t, J=7.4 Hz), 7.59 (1H, t, J=5.7 Hz), 7.71 (2H, d, J=7.4 Hz), 7.89 (2H, d, J=7.4 Hz), 8.00 (1H, t, J=5.3 Hz), 8.13 (1H, d, J=8.6 Hz), 8.38 (1H, t, J=5.7 Hz).

MS (APCI) m/z: 559 (M+H)$^+$.

Process 3: N-[(9H-Fluoren-9-ylmethoxy)carbonyl]glycylglycyl-L-phenylalanyl-N-(2-{(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl) [(9H-fluoren-9-ylmethoxy)carbonyl]amino}ethyl)glycinamide The compound (200 mg, 0.264 mmol) obtained in Process 5 of Example 33 was reacted in the same manner as Process 1 of Example 2 by using the compound (177 mg, 0.317 mmol) obtained in Process 2 above instead of N-(tert-butoxycarbonyl)glycylglycyl-L-phenylalanylglycine to yield the titled compound as a pale yellow solid (297 mg, 87%).

$^1$H-NMR (400 MHz, DMSO-$d_6$) δ: 0.80-0.86 (3H, m), 1.75-1.82 (2H, m), 2.10-2.12 (2H, m), 2.35-2.38 (4H, m), 2.75-2.81 (2H, m), 3.00-3.17 (7H, m), 3.58-3.86 (8H, m), 4.18-4.28 (4H, m), 4.47-4.49 (1H, m), 5.14-5.23 (2H, m), 5.33-5.38 (2H, m), 5.56-5.58 (1H, m), 6.52-6.53 (1H, m), 7.17-7.43 (17H, m), 7.59-7.62 (2H, m), 7.69-7.71 (2H, m), 7.80-7.90 (4H, m), 8.01-8.03 (1H, m), 8.14-8.16 (1H, m), 8.29-8.32 (1H, m), 8.50-8.54 (1H, m).

MS (APCI) m/z: 1298 (M+H)$^+$.

Process 4: Glycylglycyl-L-phenylalanyl-N-{2-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)amino]ethyl}glycinamide The compound (297 mg, 0.229 mmol) obtained in Process 3 above was reacted in the same manner as Process 2 of Example 5 to yield the titled compound (95.6 mg, 49%) as a pale yellow solid.

$^1$H-NMR (400 MHz, DMSO-$d_6$) δ: 0.86 (3H, t, J=7.2 Hz), 1.82-1.89 (2H, m), 2.15-2.17 (2H, m), 2.29-2.31 (1H, m), 2.38 (3H, s), 2.60 (2H, t, J=6.1 Hz), 2.76 (1H, dd, J=15.1, 11.1 Hz), 3.00 (1H, dd, J=14.1, 4.3 Hz), 3.15-3.18 (5H, m), 3.27-3.46 (3H, m), 3.55-3.80 (6H, m), 4.46 (1H, dd, J=8.2, 4.3 Hz), 5.20 (2H, s), 5.43 (2H, s), 5.58 (1H, d, J=7.8 Hz), 6.54 (1H, s), 7.19-7.24 (5H, m), 7.31 (1H, s), 7.74-7.78 (2H, m), 8.23-8.31 (3H, m), 8.51 (1H, d, J=8.6 Hz).

MS (APCI) m/z: 854 (M+H)$^+$.

249

Process 5: N-[6-(2,5-Dioxo-2,5-dihydro-1H-pyrrol-1-yl)hexanoyl]glycylglycyl-L-phenylalanyl-N-{2-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)amino]ethyl}glycinamide The compound (90.0 mg, 0.105 mmol) obtained in Process 4 above was reacted in the same manner as Process 6 of Example 15 to yield the titled compound as a pale yellow solid (60.1 mg, 55%).

$^1$H-NMR (400 MHz, DMSO-d$_6$) δ: 0.81 (3H, t, J=7.2 Hz), 1.13-1.14 (2H, m), 1.39-1.40 (4H, m), 1.78-1.82 (2H, m), 2.03 (2H, t, J=7.2 Hz), 2.09-2.12 (2H, m), 2.31 (3H, s), 2.57-2.59 (2H, m), 2.72-2.75 (1H, m), 2.92-2.96 (1H, m), 3.08-3.30 (8H, m), 3.57-3.65 (6H, m), 4.38-4.39 (1H, m), 5.12 (2H, s), 5.36 (2H, s), 5.51-5.53 (1H, m), 6.48 (1H, s), 6.93 (2H, s), 7.13-7.18 (5H, m), 7.24 (1H, s), 7.62 (1H, t, J=5.9 Hz), 7.71 (1H, d, J=10.9 Hz), 7.89 (1H, s), 7.97 (1H, t, J=5.5 Hz), 8.04 (1H, t, J=5.7 Hz), 8.08 (1H, d, J=7.8 Hz), 8.19 (1H, t, J=5.5 Hz), 8.43 (1H, d, J=9.0 Hz).

MS (APCI) m/z: 1047 (M+H)$^+$.

250

Process 6: Antibody-Drug Conjugate (34)

By using the trastuzumab produced in Reference Example 1 and the compound obtained in Process 5 above, the titled antibody-drug conjugate was obtained in the same manner as Process 6 of Example 2.

Antibody concentration: 1.51 mg/mL, antibody yield: 9.1 mg (73%), and average number of conjugated drug molecules (n) per antibody molecule: 3.2.

Example 35 Antibody-Drug Conjugate (35)

[Formula 88]

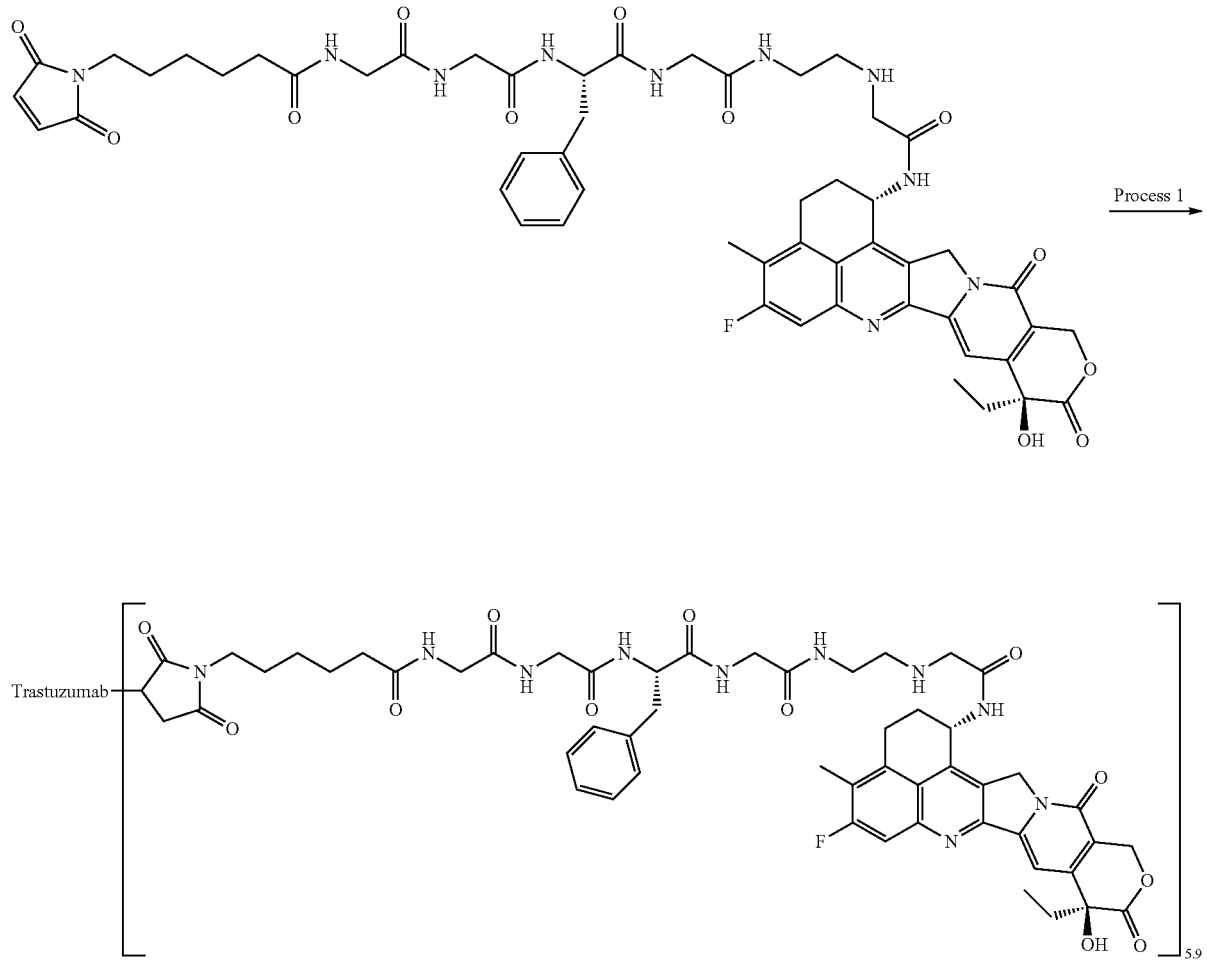

Process 1: Antibody-Drug Conjugate (35)

By using the trastuzumab produced in Reference Example 1 and the compound obtained in Process 5 of Example 34 above, the titled antibody-drug conjugate was obtained in the same manner as Process 1 of Example 3.

Antibody concentration: 1.58 mg/mL, antibody yield: 9.5 mg (76%), and average number of conjugated drug molecules (n) per antibody molecule: 5.9.

251
Example 36 Intermediate (36)

[Formula 89]

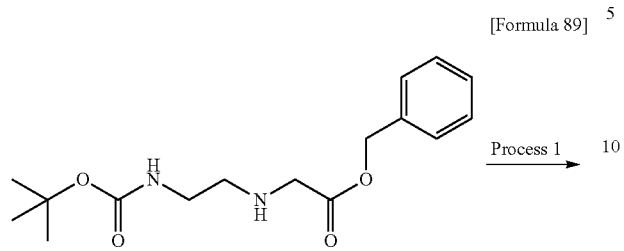

Process 1 →

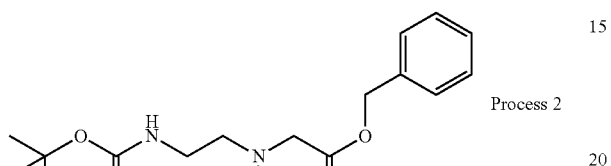

Process 2 →

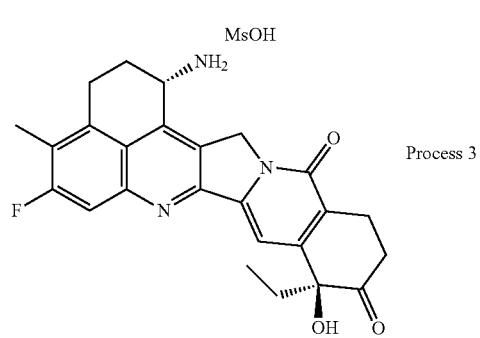

Process 3 →

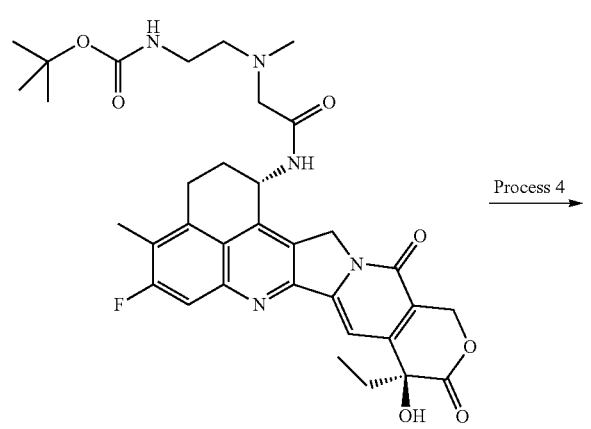

Process 4 →

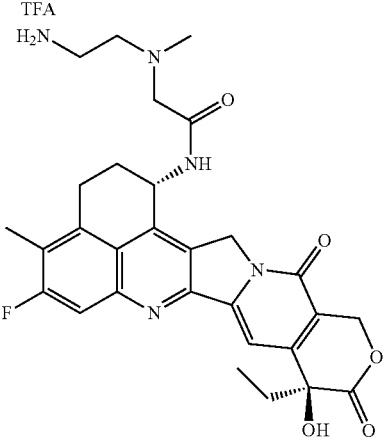

Process 1: Benzyl N-{2-[(tert-butoxycarbonyl)amino]ethyl}-N-methylglycinate

The compound (335 mg, 1.09 mmol) obtained in Process 1 of Example 33 was dissolved in dichloromethane (5.00 mL). After adding diisopropylethylamine (0.379 mL, 2.18 mmol) and iodomethane (0.102 mL, 1.63 mmol), it was stirred at room temperature for 1 day. The solvent was removed under reduced pressure and the residues obtained were purified by silica gel column chromatography [chloroform:methanol=9:1 (v/v)] to yield the titled compound as a colorless oily substance (319 mg, 91%).

$^1$H-NMR (400 MHz, CDCl$_3$) δ: 1.44 (9H, s), 2.37 (3H, s), 2.63 (2H, t, J=5.9 Hz), 3.19 (2H, q, J=5.3 Hz), 3.32 (2H, s), 5.15 (2H, s), 7.31-7.33 (5H, m).
MS (APCI) m/z: 323 (M+H)$^+$.

Process 2: N-{2-[(tert-Butoxycarbonyl)amino]ethyl}-N-methylglycine

The compound (319 mg, 0.990 mmol) obtained in Process 1 above was reacted in the same manner as Process 3 of Example 33 to yield the titled compound as a colorless oily substance (203 mg, 88%).

$^1$H-NMR (400 MHz, CDCl$_3$) δ: 1.42 (9H, s), 2.91 (3H, br.s), 3.28 (2H, br.s), 3.51 (2H, br.s), 3.70 (2H, br.s).
MS (APCI) m/z: 233 (M+H)$^+$.

Process 3: tert-Butyl {2-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)(methyl)amino]ethyl}carbamate Methanesulfonic acid salt of exatecan (385 mg, 0.724 mmol) was reacted in the same manner as Process 1 of Example 1 by using the compound (202 mg, 0.869 mmol) obtained in Process 2 above instead of 4-(tert-butoxycarbonylamino)butanoic acid to yield the titled compound as a yellow solid (332 mg, 71%).

$^1$H-NMR (400 MHz, DMSO-d$_6$) δ: 0.88 (3H, t, J=7.8 Hz), 1.37 (9H, s), 1.83-1.90 (2H, m), 2.11-2.14 (2H, m), 2.33 (3H, s), 2.39 (3H, s), 2.92-3.59 (8H, m), 4.26 (1H, s), 5.21 (1H, s), 5.27 (1H, s), 5.38 (2H, s), 5.55 (1H, s), 6.53 (1H, s), 7.30 (1H, s), 7.76 (1H, d, J=10.9 Hz), 8.57 (1H, d, J=9.0 Hz).
MS (APCI) m/z: 650 (M+H)$^+$.

Process 4: N²-(2-Aminoethyl)-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-N²-methylglycinamide The compound (340 mg, 0.523 mmol) obtained in Process 3 above was reacted in the same manner as Process 2 of Example 1 to yield trifluoroacetic acid salt of the titled compound as a yellow solid (289 mg, quantitative).

¹H-NMR (400 MHz, DMSO-$d_6$) δ: 0.87 (3H, t, J=7.4 Hz), 1.86 (2H, tt, J=21.1, 7.1 Hz), 2.16-2.24 (2H, m), 2.40 (3H, s), 2.59 (2H, br.s), 3.08 (3H, br.s), 3.17-3.19 (2H, m), 3.70 (4H, br.s), 5.21 (1H, d, J=18.8 Hz), 5.27 (1H, d, J=19.2 Hz), 5.42 (2H, s), 5.60-5.64 (1H, m), 6.57 (1H, br.s), 7.32 (1H, s), 7.81 (1H, d, J=11.0 Hz), 7.95 (3H, br.s), 8.88 (1H, br.s).
MS (APCI) m/z: 550 (M+H)⁺.

Example 37 Antibody-Drug Conjugate (37)

[Formula 90]

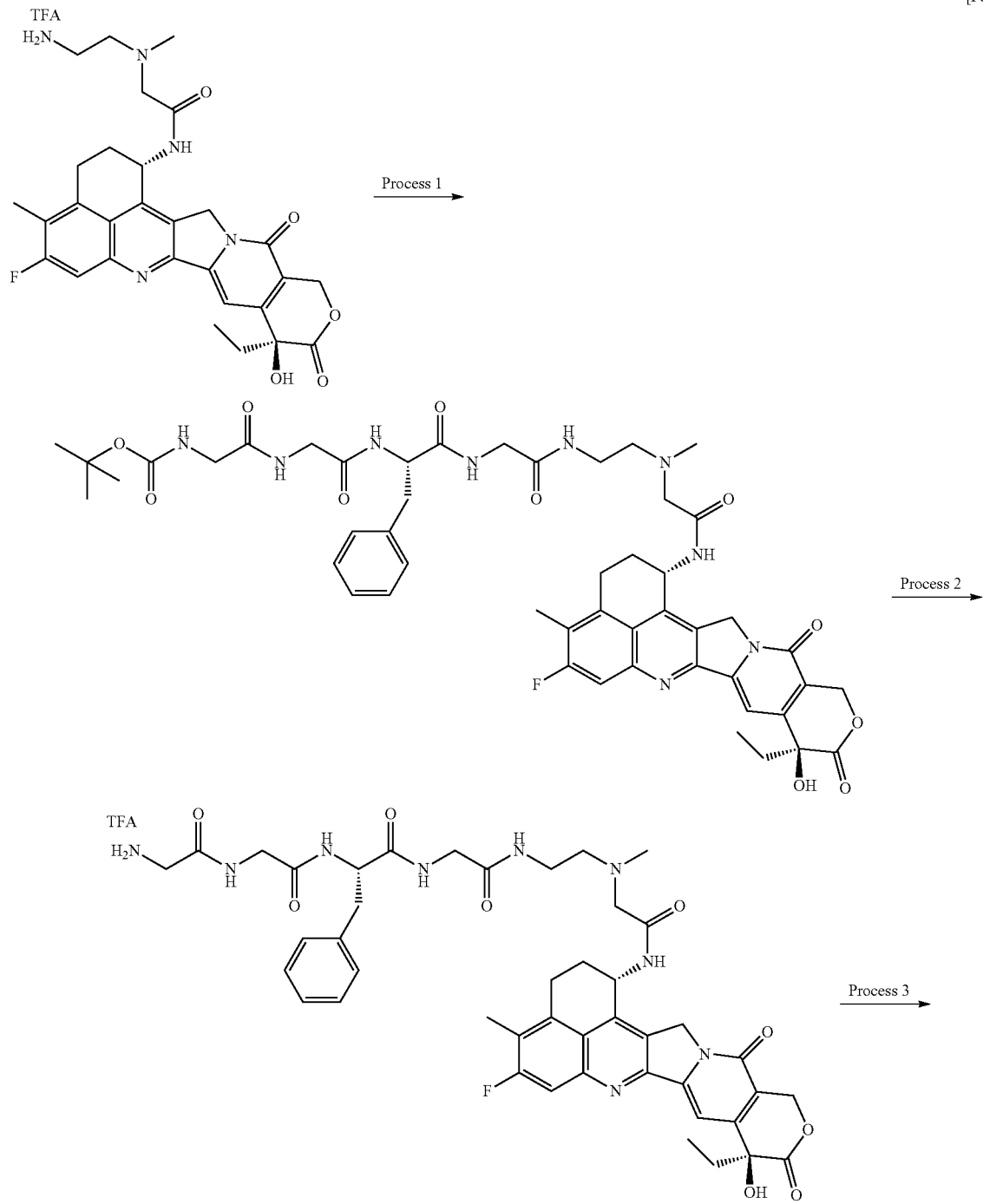

-continued

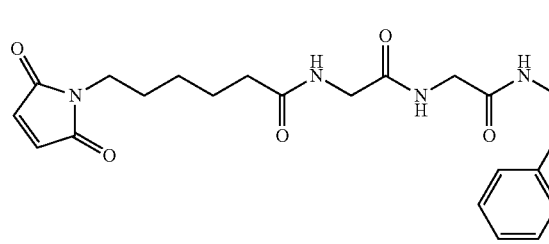
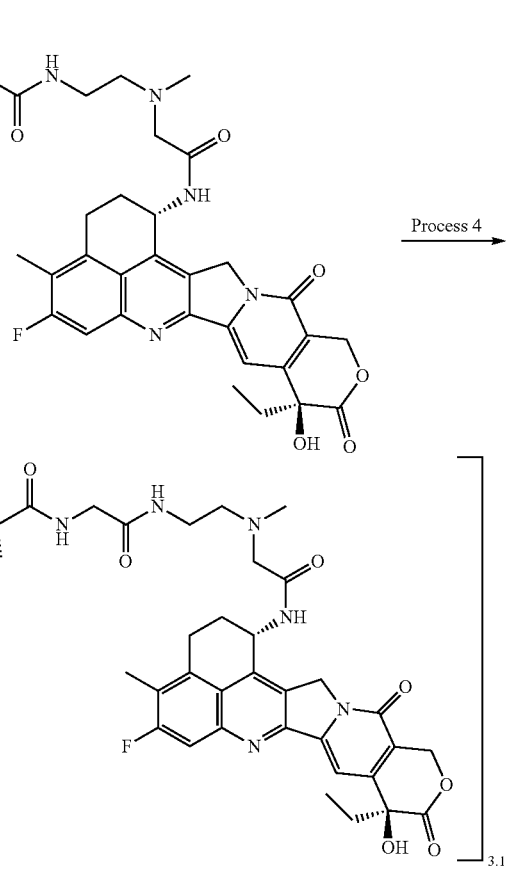
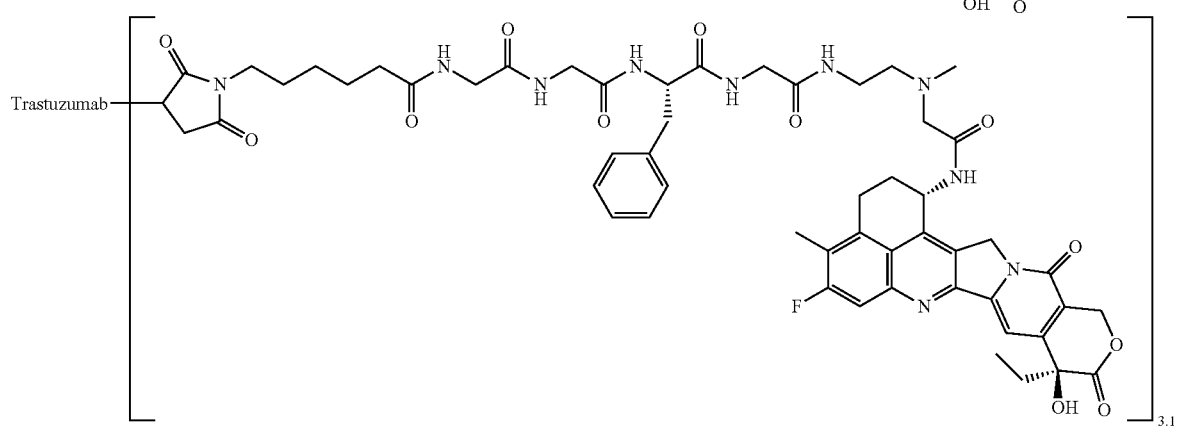

Process 1: N-(tert-Butoxycarbonyl)glycylglycyl-L-phenylalanyl-N-{2-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)(methyl)amino]ethyl}glycinamide The compound (200 mg, 0.364 mmol) obtained in Process 4 of Example 36 was reacted in the same manner as Process 1 of Example 2 to yield the titled compound as a pale yellow solid (140 mg, 40%).

$^1$H-NMR (400 MHz, DMSO-$d_6$) δ: 0.86 (3H, t, J=7.2 Hz), 1.36 (9H, s), 1.81-1.84 (2H, m), 2.15-2.18 (2H, m), 2.28 (3H, s), 2.37 (3H, s), 2.90-3.22 (7H, m), 3.40-3.86 (9H, m), 4.37-4.38 (1H, m), 5.20 (2H, s), 5.42 (2H, s), 5.56-5.59 (1H, m), 6.53 (1H, s), 7.01 (1H, t, J=6.1 Hz), 7.17-7.25 (5H, m), 7.30 (1H, s), 7.62 (1H, t, J=5.7 Hz), 7.78 (1H, d, J=10.9 Hz), 7.92 (1H, t, J=5.5 Hz), 8.15-8.24 (2H, m), 8.45 (1H, d, J=9.0 Hz).

MS (APCI) m/z: 968 (M+H)$^+$.

Process 2: Glycylglycyl-L-phenylalanyl-N-{2-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)(methyl)amino]ethyl}glycinamide The compound (140 mg, 0.145 mol) obtained in Process 1 above was reacted in the same manner as Process 2 of Example 2 to yield the titled compound as a pale yellow solid (113 mg, 90%).

$^1$H-NMR (400 MHz, DMSO-$d_6$) δ: 0.86 (3H, t, J=7.2 Hz), 1.85-1.88 (2H, m), 2.20-2.29 (2H, m), 2.42 (3H, s), 2.75-2.77 (2H, m), 2.89 (3H, s), 3.01-3.04 (2H, m), 3.34-3.45 (4H, m), 3.56-3.57 (4H, m), 3.64-3.72 (4H, m), 3.85 (2H, dd, J=14.3, 5.7 Hz), 4.54-4.59 (1H, m), 5.24 (1H, d, J=18.0 Hz), 5.34 (1H, d, J=20.3 Hz), 5.43 (2H, s), 5.62-5.68 (1H, m), 6.58 (1H, s), 7.19-7.27 (5H, m), 7.33 (1H, s), 7.84 (1H, d, J=10.9 Hz), 7.98 (3H, br.s), 8.33 (1H, d, J=8.2 Hz), 8.41 (1H, s), 8.50 (1H, t, J=5.3 Hz).

MS (APCI) m/z: 868 (M+H)$^+$.

Process 3: N-[6-(2,5-Dioxo-2,5-dihydro-1H-pyrrol-1-yl)hexanoyl]glycylglycyl-L-phenylalanyl-N-{2-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)(methyl)amino]ethyl}glycinamide The compound (110 mg, 0.126 mmol) obtained in Process 2 above was reacted in the same manner as Process 8 of Example 5 to yield the titled compound as a pale yellow solid (41.1 mg, 31%).

$^1$H-NMR (400 MHz, DMSO-$d_6$) δ: 0.86 (3H, s), 1.17-1.19 (2H, m), 1.44-1.47 (6H, m), 1.83-1.85 (2H, m), 2.08-2.16 (3H, m), 2.27-2.30 (2H, m), 2.38 (3H, s), 2.59 (3H, s), 2.78-2.80 (2H, m), 2.91 (2H, s), 3.17 (4H, s), 3.55 (7H, t, J=40.5 Hz), 4.37-4.40 (1H, m), 5.21 (2H, s), 5.42 (2H, s), 5.56-5.59 (1H, m), 6.52 (1H, s), 6.99 (2H, s), 7.17-7.21 (5H, m), 7.31 (1H, s), 7.61 (1H, s), 7.78 (1H, d, J=9.8 Hz), 8.01-8.08 (2H, m), 8.20 (1H, s), 8.32 (1H, s), 8.45 (1H, s).

MS (APCI) m/z: 1061 (M+H)$^+$.

Process 4: Antibody-Drug Conjugate (37)

By using the trastuzumab produced in Reference Example 1 and the compound obtained in Process 3 above, the titled antibody-drug conjugate was obtained in the same manner as Process 6 of Example 2.
Antibody concentration: 1.46 mg/mL, antibody yield: 8.8 mg (60%), and average number of conjugated drug molecules (n) per antibody molecule: 3.1.

Example 38 Antibody-Drug Conjugate (38)

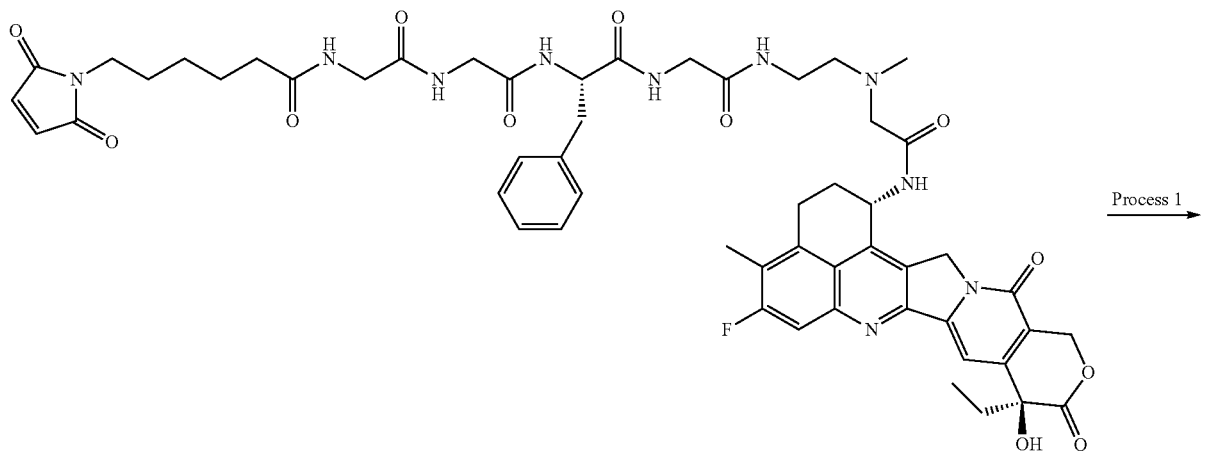

Process 1: Antibody-Drug Conjugate (38)

By using the trastuzumab produced in Reference Example 1 and the compound obtained in Process 3 of Example 37, the titled antibody-drug conjugate was obtained in the same manner as Process 1 of Example 3.

Antibody concentration: 1.44 mg/mL, antibody yield: 8.6 mg (69%), and average number of conjugated drug molecules (n) per antibody molecule: 6.1.

Example 39 Intermediate (39)

[Formula 92]

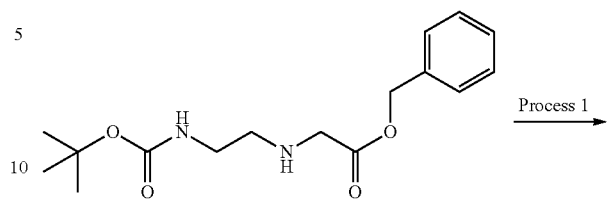

Process 1

[Formula 91]

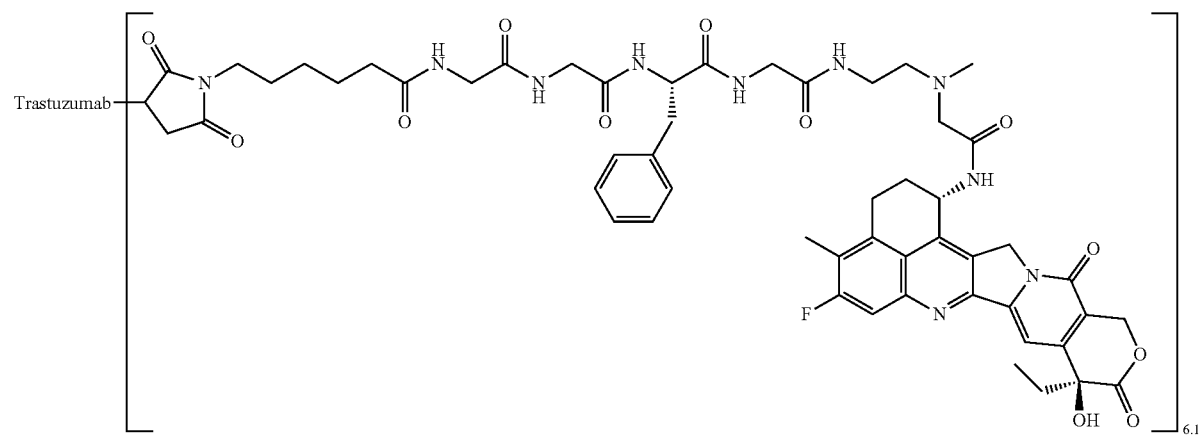

Process 1

-continued

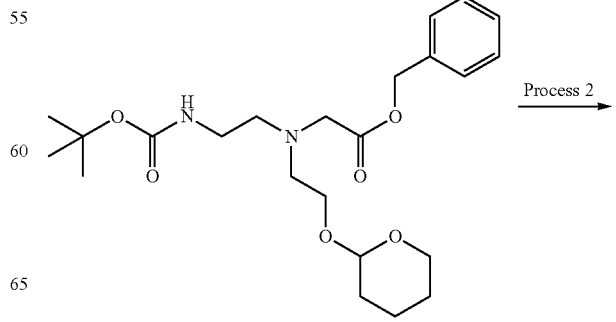

Process 2

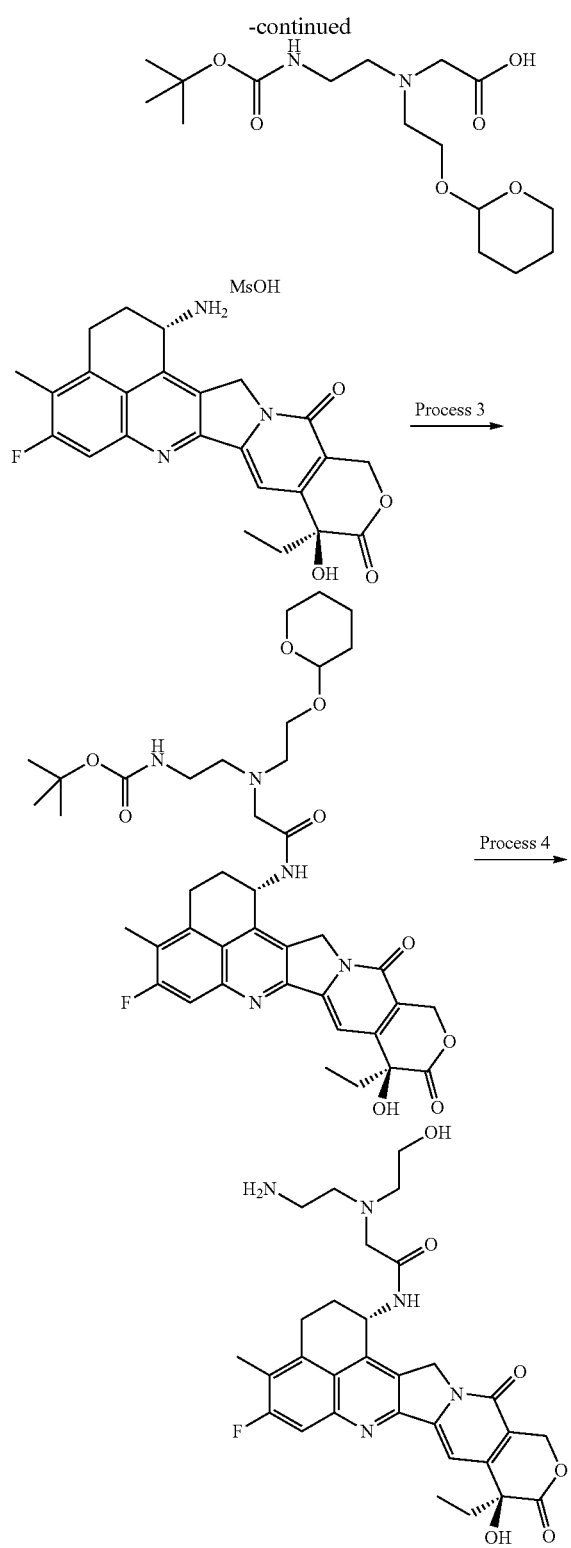

Process 1: Benzyl N-{2-[(tert-butoxycarbonyl)amino]ethyl}-N-[2-(tetrahydro-2H-pyran-2-yloxy)ethyl]glycinate The compound (299 mg, 0.970 mmol) obtained in Process 1 of Example 33 was dissolved in dimethylformamide (5.00 mL). After adding potassium carbonate (268 mg, 1.94 mmol) and 2-(2-bromoethoxy)tetrahydropyran (0.232 mL, 1.45 mmol), it was stirred at 60° C. for 3 days. The reaction solution was filtered, and the solvent in the filtrate obtained was removed under reduced pressure. The residues obtained were purified by silica gel column chromatography [hexane:ethyl acetate=9:1 (v/v)-hexane:ethyl acetate=1:1 (v/v)] to yield the titled compound as a colorless oily substance (121 mg, 29%).

$^1$H-NMR (400 MHz, CDCl$_3$) δ: 1.44 (9H, s), 1.47-1.81 (6H, m), 2.80-2.83 (2H, m), 2.89 (2H, t, J=5.5 Hz), 3.17 (2H, s), 3.46 (2H, dq, J=18.5, 4.4 Hz), 3.52 (2H, s), 3.76-3.86 (2H, m), 4.58 (1H, t, J=3.5 Hz), 5.14 (2H, s), 5.47 (1H, br.s), 7.31-7.35 (5H, m).

MS (APCI) m/z: 437 (M+H)$^+$.

Process 2: N-{2-[(tert-Butoxycarbonyl)amino]ethyl}-N-[2-(tetrahydro-2H-pyran-2-yloxy)ethyl]glycine The compound (823 mg, 1.89 mmol) obtained in Process 1 above was reacted in the same manner as Process 3 of Example 33 to yield the titled compound as a colorless oily substance (616 mg, 94%).

$^1$H-NMR (400 MHz, CDCl$_3$) δ: 1.43 (9H, s), 1.54-1.81 (6H, m), 3.28-3.67 (8H, m), 3.74-4.00 (4H, m), 4.62 (1H, s), 6.35 (1H, s), 9.76 (1H, s).

MS (APCI) m/z: 347 (M+H)$^+$.

Process 3: tert-Butyl (2-{(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)[2-(tetrahydro-2H-pyran-2-yloxy)ethyl]amino}ethyl)carbamate Methanesulfonic acid salt of exatecan (780 mg, 1.47 mmol) was reacted in the same manner as Process 1 of Example 1 by using the compound (610 mg, 1.76 mmol) obtained in Process 2 above instead of 4-(tert-butoxycarbonylamino)butanoic acid to yield the titled compound as a yellow solid (874 mg, 78%).

$^1$H-NMR (400 MHz, DMSO-d$_6$) δ: 0.87 (3H, s), 1.29-1.59 (15H, m), 1.84-1.87 (2H, m), 2.16-2.18 (2H, m), 2.40 (3H, s), 2.62-2.97 (6H, m), 3.48-3.81 (8H, m), 4.34-4.56 (1H, m), 5.20 (2H, s), 5.42 (2H, s), 5.60 (1H, s), 6.55 (1H, s), 6.69 (1H, s), 7.31 (1H, s), 7.80 (1H, d, J=10.6 Hz), 8.32 (1H, s).

MS (APCI) m/z: 764 (M+H)$^+$.

Process 4: N$^2$-(2-Aminoethyl)-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-N$^2$-(2-hydroxyethyl)glycinamide The compound (707 mg, 0.926 mmol) obtained in Process 3 above was reacted in the same manner as Process 2 of Example 1 to yield trifluoroacetic acid salt of the titled compound as a yellow solid (524 mg, 98%).

$^1$H-NMR (400 MHz, DMSO-d$_6$) δ: 0.87 (3H, t, J=7.2 Hz), 1.81-1.91 (2H, m), 2.17-2.18 (2H, m), 2.39 (3H, s), 2.75-3.00 (6H, m), 3.34-4.02 (6H, m), 5.23 (2H, s), 5.42 (2H, s), 5.57-5.59 (1H, m), 6.56 (1H, s), 7.31 (1H, s), 7.70-7.84 (4H, m), 8.69-8.77 (1H, m).

MS (APCI) m/z: 580 (M+H)$^+$.

Example 40 Antibody-Drug Conjugate (40)
[Formula 93]
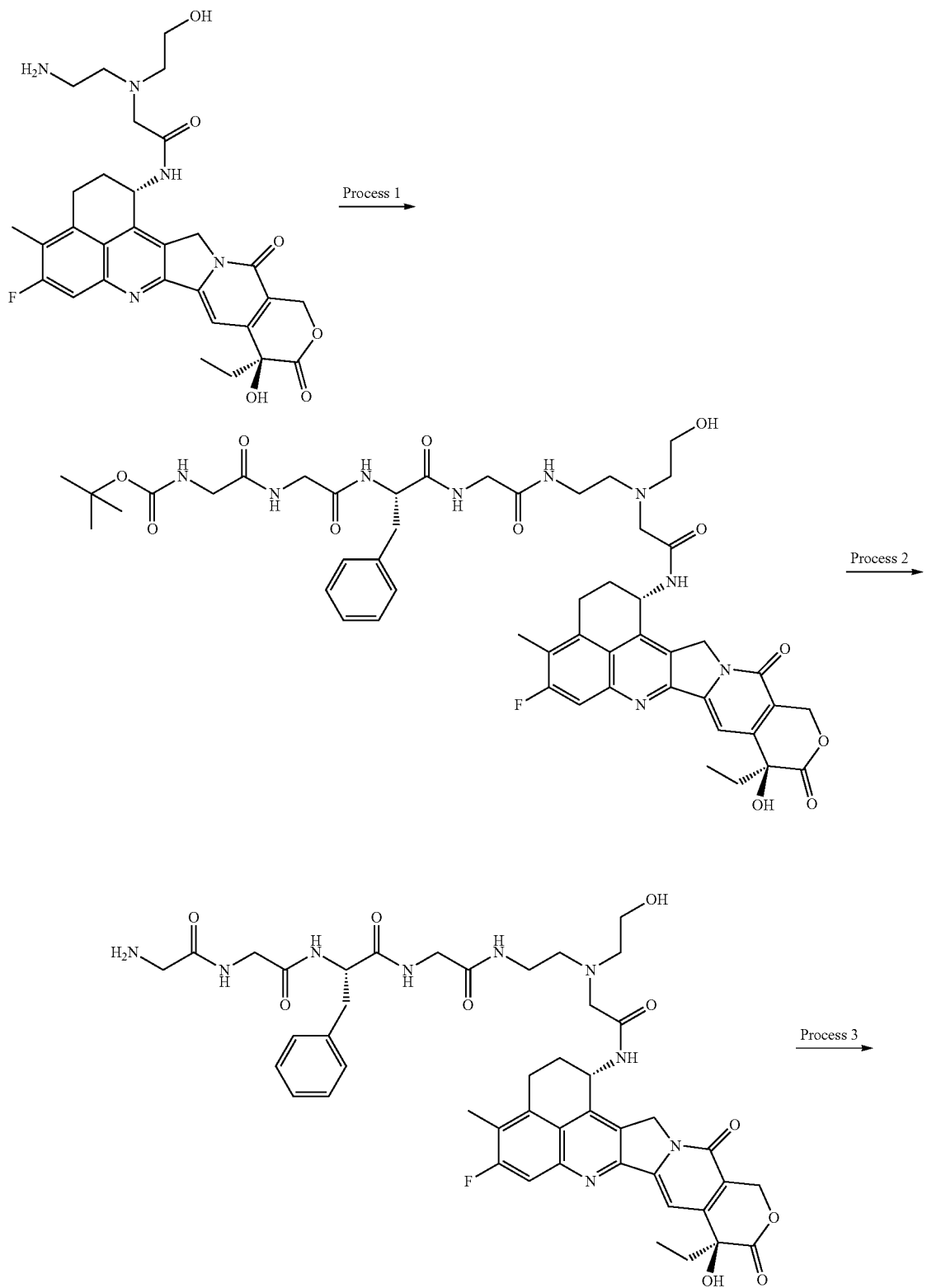

-continued

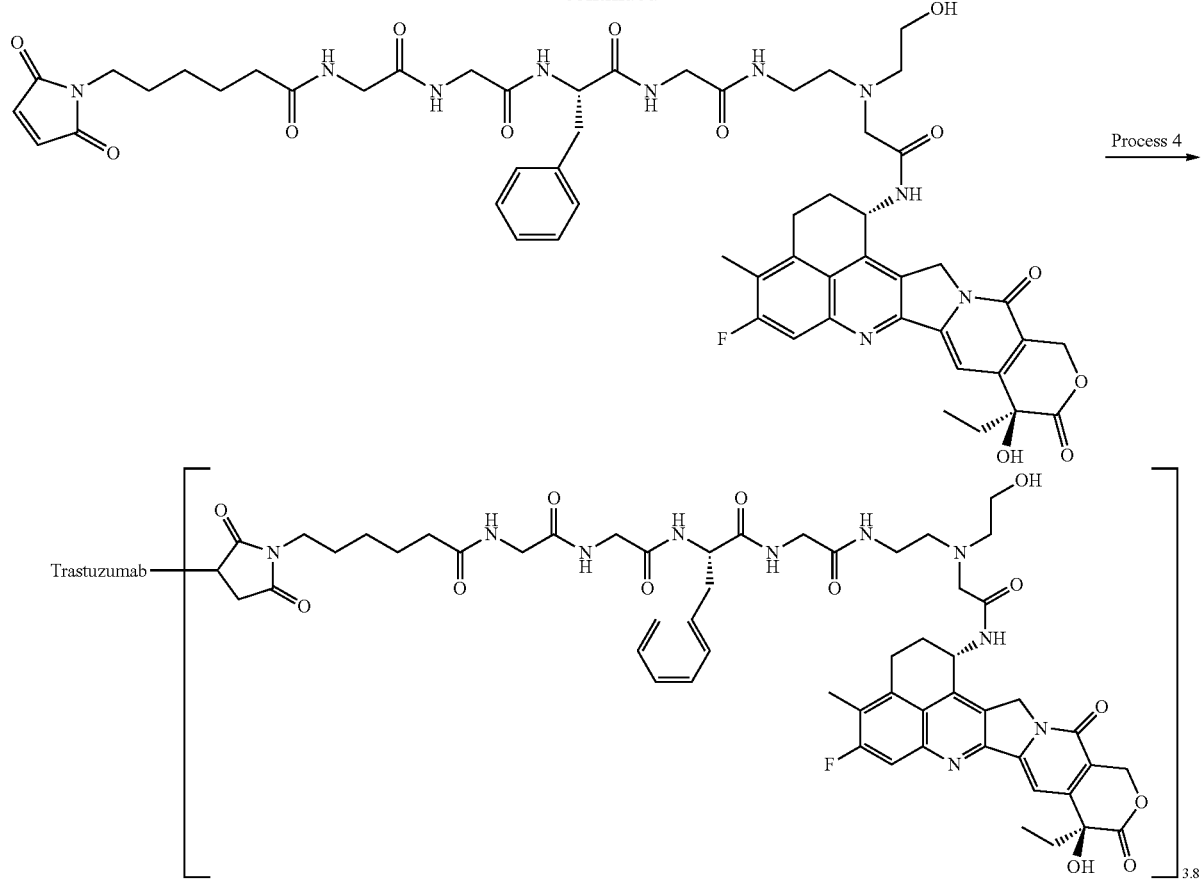

Process 4 →

Process 1: N-(tert-Butoxycarbonyl)glycylglycyl-L-phenylalanyl-N-{2-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)(2-hydroxyethyl)amino]ethyl}glycinamide The compound (200 mg, 0.345 mmol) obtained in Process 4 of Example 39 was reacted in the same manner as Process 1 of Example 2 to yield the titled compound as a yellow solid (198 mg, 57%).

$^1$H-NMR (400 MHz, DMSO-$d_6$) δ: 0.87 (3H, t, J=7.0 Hz), 1.38 (9H, s), 1.84-1.87 (2H, m), 2.12-2.14 (2H, m), 2.33-2.38 (2H, m), 2.40 (3H, s), 3.16-3.17 (8H, m), 3.54-3.60 (3H, m), 3.62-3.65 (2H, m), 3.73-3.78 (2H, m), 3.86 (2H, d, J=5.9 Hz), 4.10-4.12 (1H, m), 4.52-4.55 (2H, m), 5.22 (2H, s), 5.43 (2H, s), 5.57-5.59 (1H, m), 6.54 (1H, s), 7.01 (1H, s), 7.18-7.26 (5H, m), 7.31 (1H, s), 7.89-7.92 (2H, m), 8.17-8.19 (2H, m), 8.49-8.51 (2H, m).
MS (APCI) m/z: 998 (M+H)$^+$.

Process 2: Glycylglycyl-L-phenylalanyl-N-{2-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)(2-hydroxyethyl)amino]ethyl}glycinamide The compound (198 mg, 0.198 mmol) obtained in Process 1 above was reacted in the same manner as Process 2 of Example 2 to yield trifluoroacetic acid salt of the titled compound as a yellow solid (59.5 mg, 34%).

$^1$H-NMR (400 MHz, DMSO-$d_6$) δ: 0.87 (3H, t, J=7.2 Hz), 1.85-1.86 (2H, m), 2.16-2.33 (2H, m), 2.40 (3H, s), 2.80-2.94 (8H, m), 3.34-4.11 (10H, m), 4.53-4.56 (2H, m), 5.26-5.28 (2H, m), 5.43 (2H, s), 5.59-5.61 (1H, m), 6.57 (1H, s), 7.21-7.24 (5H, m), 7.33 (1H, s), 7.82 (1H, d, J=10.9 Hz), 7.99 (4H, br.s), 8.33-8.36 (2H, m), 8.49-8.51 (2H, m).
MS (APCI) m/z: 898 (M+H)$^+$.

Process 3: N-[6-(2,5-Dioxo-2,5-dihydro-1H-pyrrol-1-yl)hexanoyl]glycylglycyl-L-phenylalanyl-N-{2-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)(2-hydroxyethyl)amino]ethyl}glycinamide The compound (100 mg, 0.111 mmol) obtained in Process 2 above was reacted in the same manner as Process 8 of Example 5 to yield the titled compound as a yellow solid (33.0 mg, 27%).

$^1$H-NMR (400 MHz, DMSO-$d_6$) δ: 0.87 (3H, t, J=7.4 Hz), 1.16-1.19 (2H, m), 1.45-1.48 (4H, m), 1.83-1.85 (2H, m), 2.09-2.17 (4H, m), 2.36 (3H, s), 2.70-2.96 (2H, m), 3.14-3.76 (2 OH, m), 4.39-4.41 (1H, m), 4.47-4.50 (1H, m), 5.14 (1H, d, J=19.2 Hz), 5.24 (1H, d, J=18.8 Hz), 5.42 (2H, s), 5.57-5.58 (1H, m), 6.53 (1H, s), 6.99 (2H, s), 7.19-7.23 (5H, m), 7.30 (1H, s), 7.58 (1H, s), 7.75 (1H, d, J=10.9 Hz), 8.01-8.03 (1H, m), 8.10-8.12 (2H, m), 8.21-8.23 (1H, m), 8.49 (1H, d, J=8.6 Hz).
MS (APCI) m/z: 1091 (M+H)$^+$.

Process 4: Antibody-Drug Conjugate (40)

By using the trastuzumab produced in Reference Example 1 and the compound obtained in Process 3 above, the titled antibody-drug conjugate was obtained in the same manner as Process 6 of Example 2.

Antibody concentration: 1.54 mg/mL, antibody yield: 9.2 mg (74%), and average number of conjugated drug molecules (n) per antibody molecule: 3.8.

Example 41 Antibody-Drug Conjugate (41)

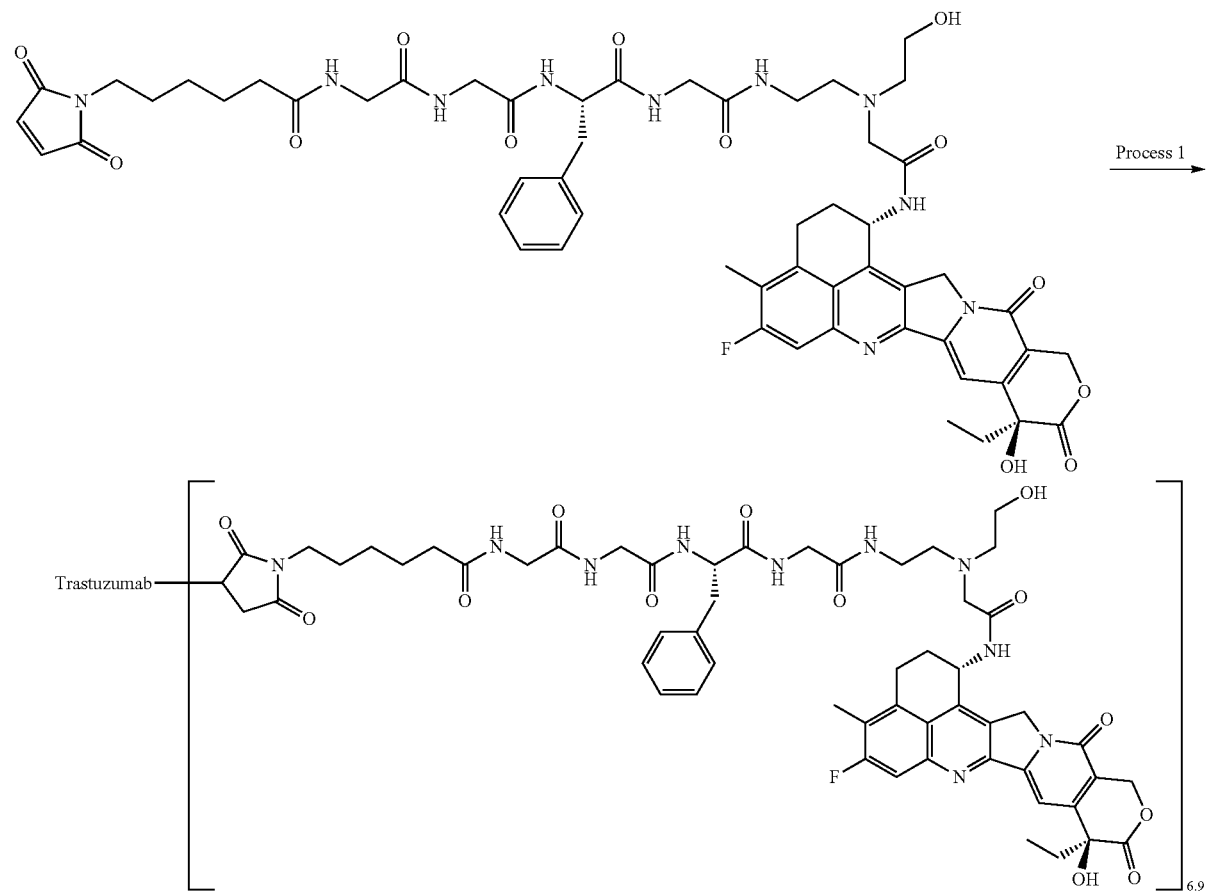

Process 1: Antibody-Drug Conjugate (41) By using the trastuzumab produced in Reference Example 1 and the compound obtained in Process 3 of Example 40, the titled antibody-drug conjugate was obtained in the same manner as Process 1 of Example 3.

Antibody concentration: 1.54 mg/mL, antibody yield: 9.2 mg (74%), and average number of conjugated drug molecules (n) per antibody molecule: 6.9.

Example 42 Intermediate (42)

[Formula 95]

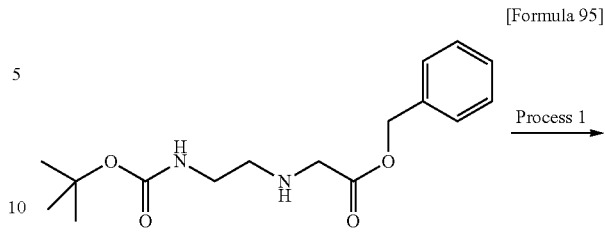

-continued

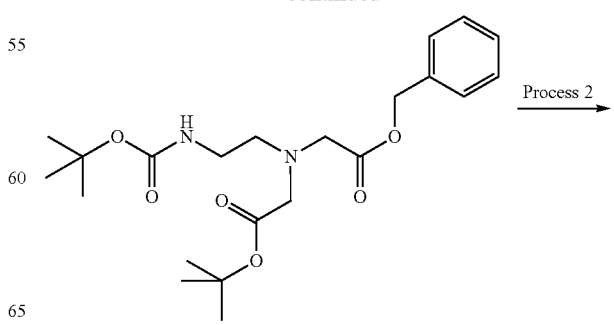

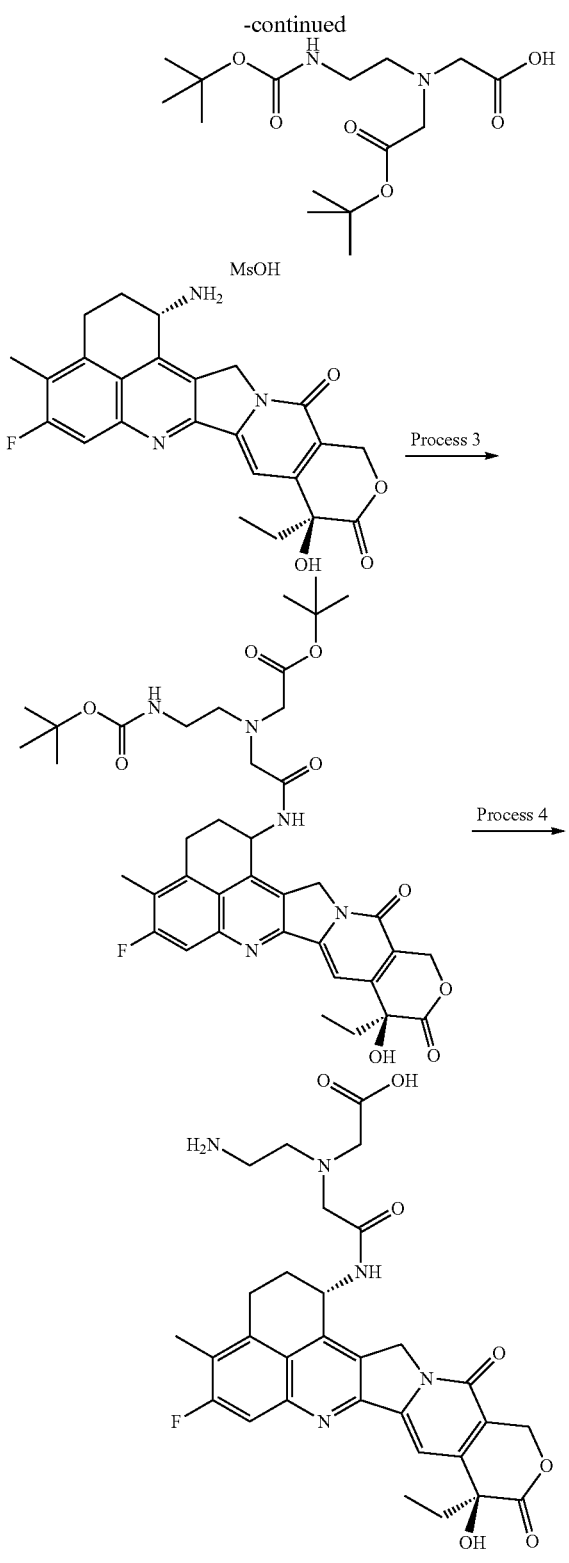

Process 1: Benzyl tert-butyl 2,2'-({2-[(tert-butoxy-carbonyl)amino]ethyl}imino)diacetate The compound (0.753 g, 2.44 mmol) obtained in Process 1 of Example 33 was dissolved in dichloromethane (10.0 mL). After adding N,N-diisopropylethylamine (0.851 mL, 4.89 mmol) and tert-butyl 2-bromoacetate (0.541 mL, 3.66 mmol), it was stirred for 1 day. The solvent was removed under reduced pressure and the residues obtained were purified by silica gel column chromatography [hexane:ethyl acetate=90:10-0:100 (v/v)] to yield the titled compound as a colorless oily substance (0.614 g, 60%).

$^1$H-NMR (400 MHz, CDCl$_3$) δ: 1.44 (9H, s), 1.45 (9H, s), 2.84 (2H, t, J=5.7 Hz), 3.15 (2H, q, J=5.3 Hz), 3.42 (2H, s), 3.58 (2H, s), 5.13 (2H, d, J=4.7 Hz), 5.62 (1H, s), 7.30-7.38 (5H, m).

MS (APCI) m/z: 423 (M+H)$^+$.

Process 2: [{2-[(tert-Butoxycarbonyl)amino]ethyl} (2-tert-butoxy-2-oxoethyl)amino]acetic acid The compound (0.614 g, 1.45 mmol) obtained in Process 1 above was reacted in the same manner as Process 3 of Example 33 to yield the titled compound as a colorless oily substance (0.469 g, 97%).

$^1$H-NMR (400 MHz, CDCl$_3$) δ: 1.44 (9H, s), 1.47 (9H, s), 2.95 (2H, s), 3.24 (2H, s), 3.57 (4H, s), 5.79 (1H, s), 10.68 (1H, brs).

MS (APCI) m/z: 333 (M+H)$^+$.

Process 3: tert-Butyl [{2-[(tert-butoxycarbonyl) amino]ethyl}(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino [1,2-b]quinolin-1-yl]amino}-2-oxoethyl)amino] acetate Methanesulfonic acid salt of exatecan (620 mg, 1.17 mmol) was reacted in the same manner as Process 1 of Example 1 by using the compound (465 mg, 1.40 mmol) obtained in Process 2 above instead of 4-(tert-butoxycarbonylamino)butanoic acid to yield the titled compound as a yellow solid (666 mg, 76%).

$^1$H-NMR (400 MHz, CD$_3$OD) δ: 1.01 (3H, t, J=7.0 Hz), 1.14 (9H, s), 1.37 (9H, s), 1.94 (2H, q, J=6.9 Hz), 2.24-2.26 (1H, m), 2.35 (3H, s), 2.45-2.48 (1H, m), 2.75-2.86 (2H, m), 3.16-3.21 (3H, m), 3.34-3.46 (3H, m), 3.52 (1H, d, J=17.2 Hz), 3.62 (1H, d, J=17.6 Hz), 4.66 (1H, d, J=18.8 Hz), 5.20 (1H, d, J=18.8 Hz), 5.32 (1H, d, J=16.0 Hz), 5.56 (1H, d, J=16.0 Hz), 5.70-5.76 (1H, m), 6.51-6.57 (1H, m), 7.44 (1H, d, J=10.6 Hz), 7.50 (1H, s), 8.04 (2H, brs).

MS (APCI) m/z: 750 (M+H)$^+$.

Process 4: [(2-Aminoethyl)(2-{[(1S,9S)-9-ethyl-5-fluoro-9-hydroxy-4-methyl-10,13-dioxo-2,3,9,10,13, 15-hexahydro-1H,12H-benzo[de]pyrano[3',4':6,7] indolizino[1,2-b]quinolin-1-yl]amino}-2-oxoethyl) amino]acetic acid The compound (587 mg, 0.783 mmol) obtained in Process 3 above was reacted in the same manner as Process 2 of Example 1 to yield the titled compound as a yellow solid (477 mg, quantitative).

$^1$H-NMR (400 MHz, CD$_3$OD) δ: 0.96 (3H, t, J=7.2 Hz), 1.90 (2H, q, J=7.0 Hz), 2.07-2.09 (1H, m), 2.28 (3H, s), 2.38-2.40 (1H, m), 3.02-3.23 (6H, m), 3.56-3.67 (4H, m), 4.71 (1H, d, J=18.4 Hz), 5.02 (1H, d, J=18.4 Hz), 5.28 (1H, d, J=16.0 Hz), 5.49 (1H, d, J=16.4 Hz), 5.63-5.65 (1H, m), 7.32 (1H, d, J=10.6 Hz), 7.44 (1H, s).

MS (APCI) m/z: 594 (M+H)$^+$.

Example 43 Antibody-Drug Conjugate (43)
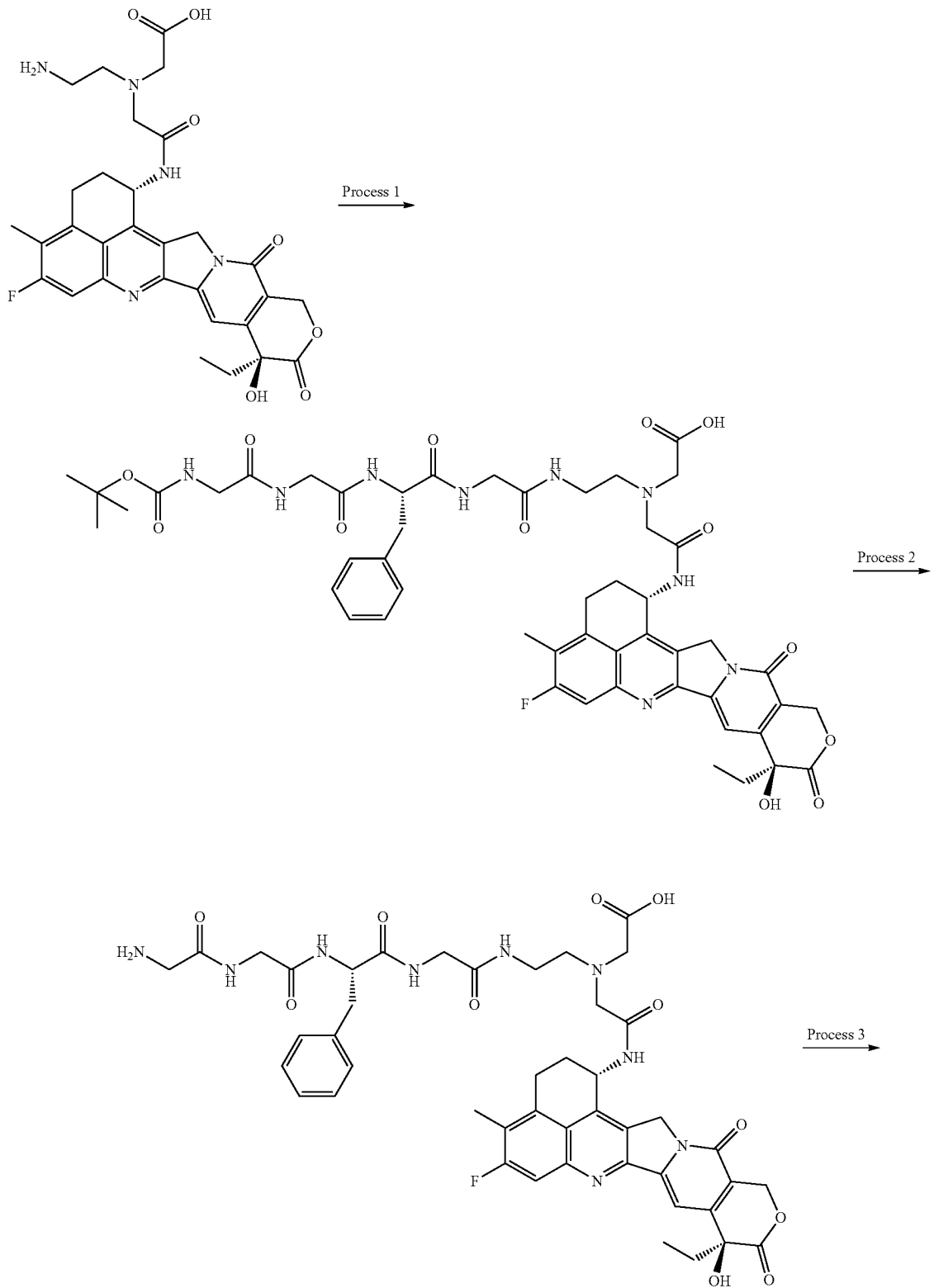
[Formula 96]

-continued

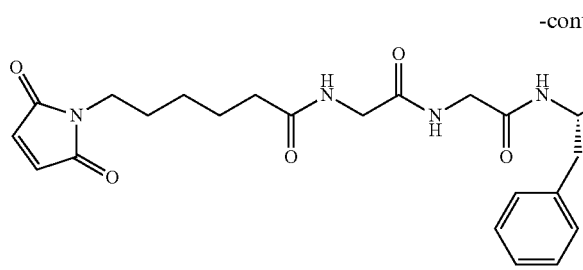

Process 4 →

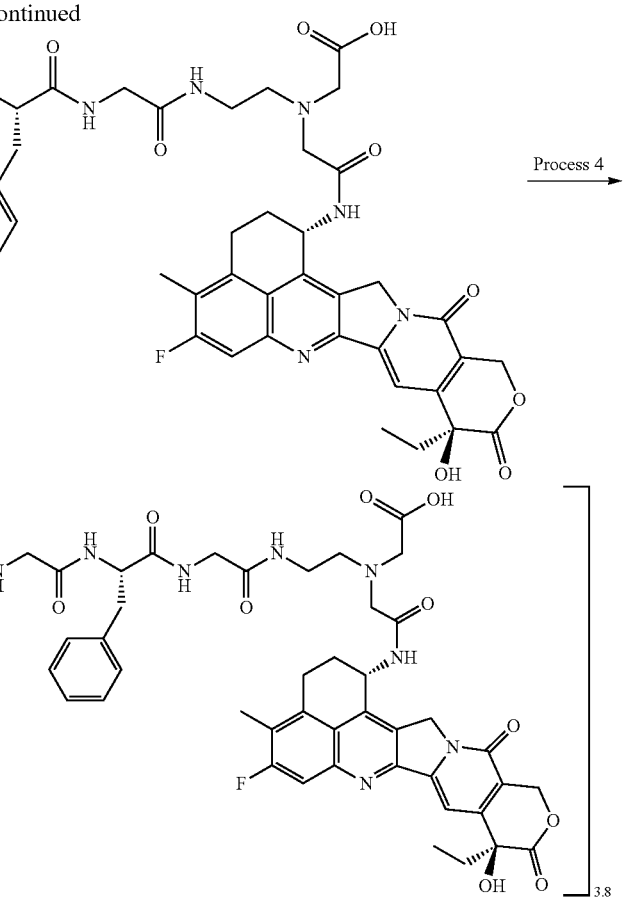

Process 1: N-(tert-Butoxycarbonyl)glycylglycyl-L-phenylalanyl-N-{2-[(carboxymethyl) (2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)amino]ethyl}glycinamide The compound (300 mg, 0.505 mmol) obtained in Process 4 of Example 42 was reacted in the same manner as Process 1 of Example 2 to yield the titled compound as a pale yellow solid (316 mg, 62%).
$^1$H-NMR (400 MHz, DMSO-$d_6$) δ: 0.86 (3H, t, J=6.8 Hz), 1.36 (9H, s), 1.81-1.83 (2H, m), 2.14-2.20 (2H, m), 2.37 (3H, s), 2.86-3.46 (18H, m), 4.38-4.41 (1H, m), 5.14 (1H, d, J=19.6 Hz), 5.22 (1H, d, J=18.8 Hz), 5.41 (2H, s), 5.56-5.58 (1H, m), 6.53 (1H, s), 7.06-7.20 (5H, m), 7.75 (1H, d, J=10.6 Hz), 7.90-7.92 (2H, m), 8.09 (1H, s), 8.18 (2H, s), 8.34-8.40 (2H, m), 8.73 (1H, s).
MS (APCI) m/z: 1012 (M+H)$^+$.

Process 2: Glycylglycyl-L-phenylalanyl-N-{2-[(carboxymethyl) (2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)amino]ethyl}glycinamide The compound (316 mg, 0.312 mmol) obtained in Process 1 above was reacted in the same manner as Process 2 of Example 2 to yield the titled compound as a pale yellow solid (285 mg, quantitative).
$^1$H-NMR (400 MHz, DMSO-$d_6$) δ: 0.86 (3H, t, J=7.2 Hz), 1.85-1.86 (2H, m), 2.21-2.24 (2H, m), 2.40 (3H, s), 2.69-2.75 (2H, m), 3.01-3.03 (3H, m), 3.17-3.19 (3H, m), 3.28-3.30 (1H, m), 3.56-3.89 (9H, m), 3.96 (1H, s), 4.55 (1H, td, J=8.8, 4.7 Hz), 5.23 (1H, d, J=19.6 Hz), 5.30 (1H, d, J=21.5 Hz), 5.43 (2H, s), 5.58-5.63 (1H, m), 7.16-7.26 (6H, m), 7.33 (1H, s), 7.82 (1H, d, J=10.0 Hz), 7.97 (3H, brs), 8.31 (1H, d, J=7.0 Hz), 8.37 (1H, t, J=5.5 Hz), 8.49 (1H, t, J=5.7 Hz), 8.80 (1H, s).
MS (APCI) m/z: 912 (M+H)$^+$.

Process 3: N-[6-(2,5-Dioxo-2,5-dihydro-1H-pyrrol-1-yl)hexanoyl]glycylglycyl-L-phenylalanyl-N-{2-[(carboxymethyl) (2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)amino]ethyl}glycinamide The compound (100 mg, 0.110 mmol) obtained in Process 2 above was reacted in the same manner as Process 8 of Example 5 to yield the titled compound as a pale yellow solid (79.6 mg, 66%).
$^1$H-NMR (400 MHz, DMSO-$d_6$) δ: 0.86 (3H, t, J=7.2 Hz), 1.12-1.18 (2H, m), 1.44-1.46 (4H, m), 1.81-1.83 (2H, m), 2.08-2.11 (2H, m), 2.23-2.29 (2H, m), 2.38 (3H, s), 2.65-2.74 (5H, m), 3.11-3.72 (15H, m), 4.36 (1H, td, J=8.2, 3.4 Hz), 5.14 (1H, d, J=18.8 Hz), 5.23 (1H, d, J=18.8 Hz), 5.38-5.42 (2H, m), 5.55-5.58 (1H, m), 6.50 (1H, s), 6.99 (2H, s), 7.15-7.22 (6H, m), 7.74 (1H, d, J=10.9 Hz), 8.06-8.23 (5H, m), 8.49 (1H, brs), 8.81 (1H, b).
MS (APCI) m/z: 1105 (M+H)$^+$.

Process 4: Antibody-Drug Conjugate (43)

By using the trastuzumab produced in Reference Example 1 and the compound obtained in Process 3 above, the titled antibody-drug conjugate was obtained in the same manner as Process 6 of Example 2.

Antibody concentration: 1.58 mg/mL, antibody yield: 9.5 mg (76%), and average number of conjugated drug molecules (n) per antibody molecule: 3.8.

Example 44 Antibody-Drug Conjugate (44)

[Formula 97]

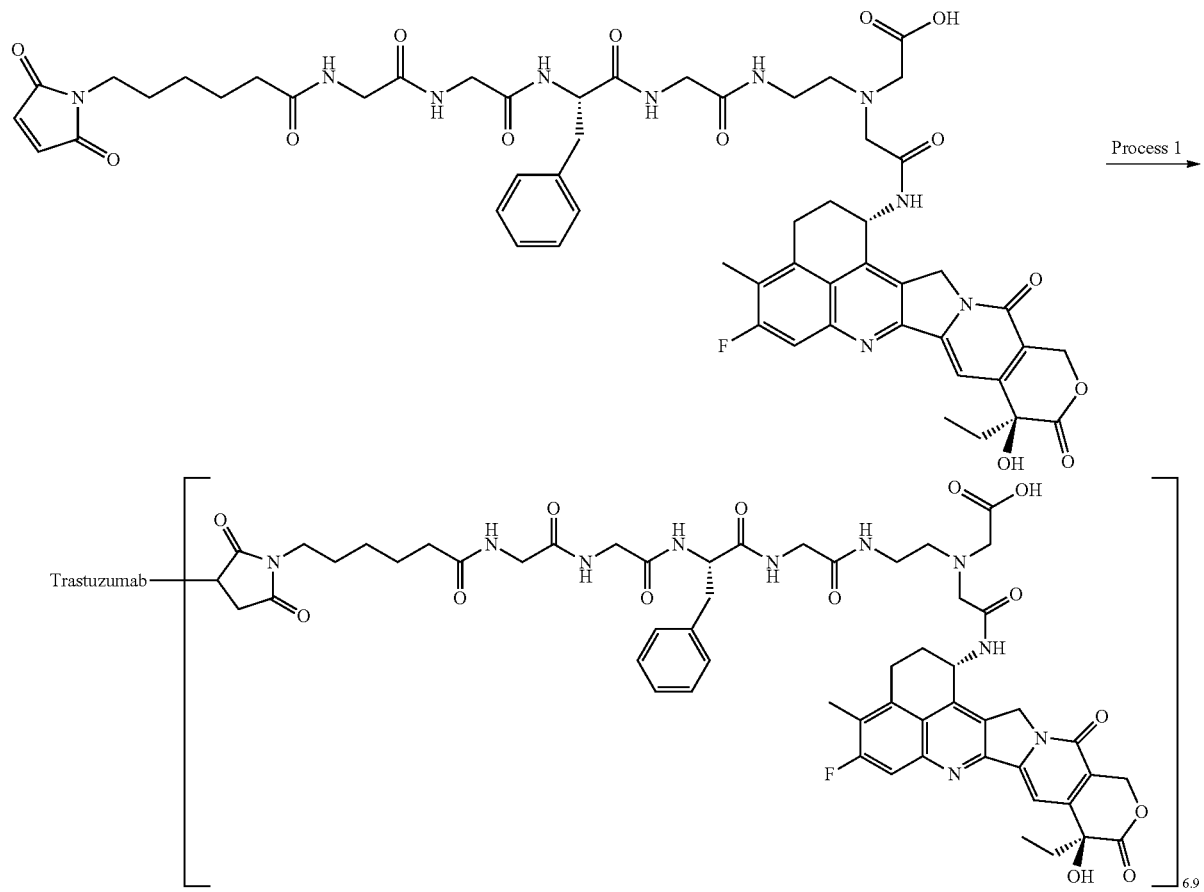

Process 1: Antibody-Drug Conjugate (44)

By using the trastuzumab produced in Reference Example 1 and the compound obtained in Process 3 of Example 43, the titled antibody-drug conjugate was obtained in the same manner as Process 1 of Example 3.

Antibody concentration: 1.68 mg/mL, antibody yield: 10.1 mg (81%), and average number of conjugated drug molecules (n) per antibody molecule: 6.9.

Example 45 Intermediate (45)

[Formula 98]

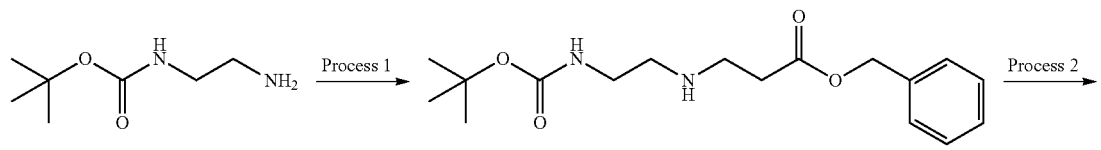

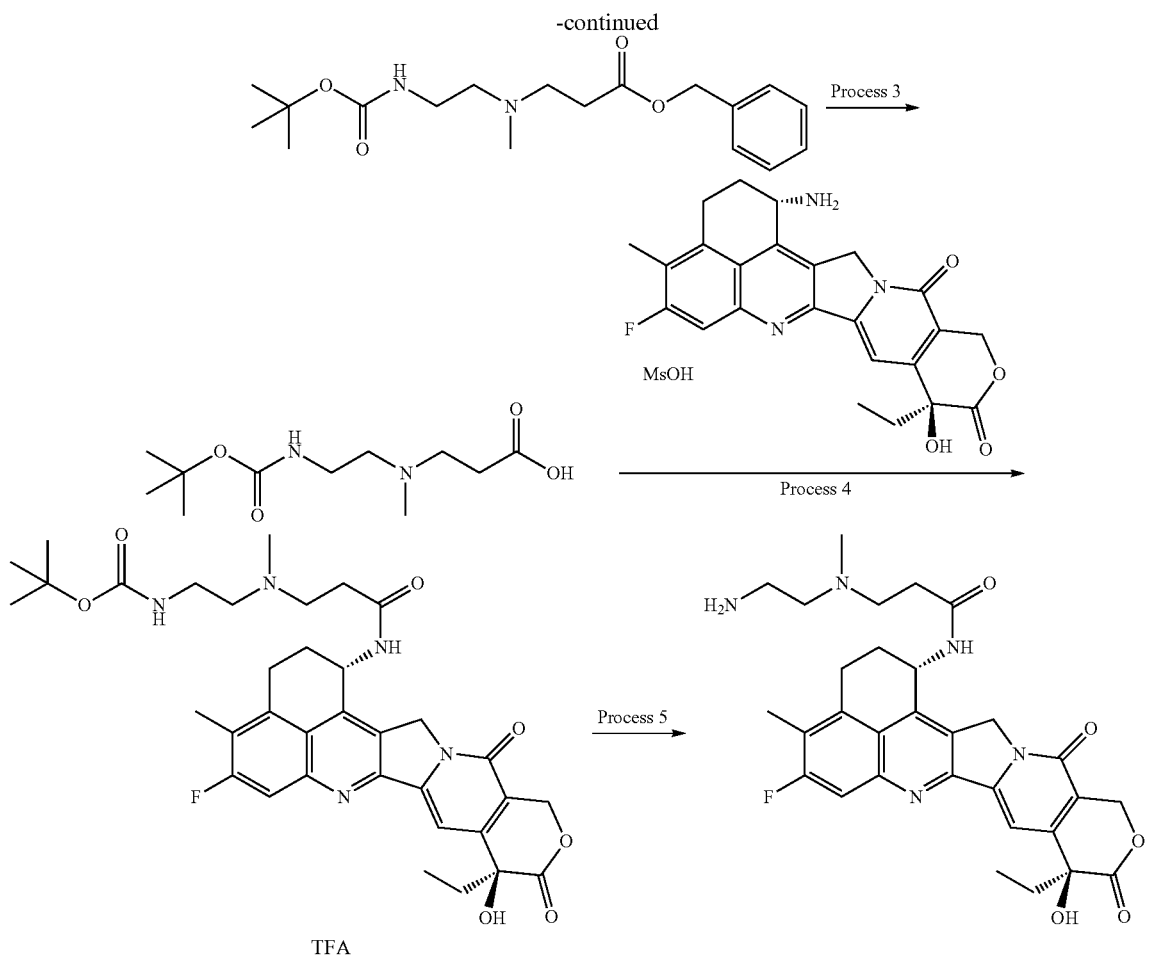

Process 1: Benzyl N-{2-[(tert-butoxycarbonyl)amino]ethyl}-β-alaninate tert-Butyl N-(2-aminoethyl)carbamate (3.00 g, 18.7 mmol) was dissolved in pyridine (10.0 mL), charged with potassium carbonate (2.59 g, 18.7 mmol) and benzyl acrylate (1.43 mL, 9.36 mmol), and stirred at room temperature for 1 day. The solvent in the reaction solution was removed under reduced pressure. The residues obtained were purified by silica gel column chromatography [chloroform-chloroform:methanol=8:2 (v/v)] to yield the titled compound as a colorless oily substance (1.58 g, 52%).

$^1$H-NMR (400 MHz, CDCl$_3$) δ: 1.44 (9H, s), 2.54 (2H, t, J=6.5 Hz), 2.71 (2H, t, J=5.9 Hz), 2.89 (2H, t, J=6.5 Hz), 3.19 (2H, q, J=5.5 Hz), 5.00 (1H, brs), 5.13 (2H, s), 7.32-7.37 (6H, m).
MS (APCI) m/z: 323 (M+H)$^+$.

Process 2: Benzyl N-{2-[(tert-butoxycarbonyl)amino]ethyl}-N-methyl-β-alaninate

The compound (490 mg, 1.52 mmol) obtained in Process 1 above was reacted in the same manner as Process 1 of Example 36 to yield the titled compound as a colorless oily substance (327 mg, 64%).

$^1$H-NMR (400 MHz, CDCl$_3$) δ: 1.43 (9H, s), 2.20 (3H, s), 2.45 (2H, t, J=5.9 Hz), 2.50 (2H, t, J=6.8 Hz), 2.70 (2H, t, J=7.0 Hz), 3.18 (2H, q, J=5.5 Hz), 5.13 (2H, s), 7.32-7.34 (5H, m).
MS (APCI) m/z: 337 (M+H)$^+$.

Process 3: N-{2-[(tert-butoxycarbonyl)amino]ethyl}-N-methyl-β-alanine

The compound (327 mg, 0.971 mmol) obtained in Process 2 above was reacted in the same manner as Process 3 of Example 33 to yield the titled compound as a colorless oily substance (236 mg, 99%).

$^1$H-NMR (400 MHz, CDCl$_3$) δ: 1.43 (9H, s), 2.61-2.64 (2H, m), 2.75 (3H, s), 3.08-3.11 (2H, m), 3.20-3.23 (2H, m), 3.47-3.50 (2H, m), 6.43 (1H, br.s), 11.09 (1H, br.s).
MS (APCI) m/z: 247 (M+H)$^+$.

Process 4: tert-Butyl {2-[(3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)(methyl)amino]ethyl}carbamate Methanesulfonic acid salt of exatecan (410 mg, 0.771 mmol) was reacted in the same manner as Process 1 of Example 1 by using the compound (228 mg, 0.926 mmol) obtained in Process 3 above instead of 4-(tert-butoxycarbonylamino)butanoic acid to yield the titled compound as a yellow solid (122 mg, 24%).

$^1$H-NMR (400 MHz, DMSO-d$_6$) δ: 0.87 (3H, t, J=7.4 Hz), 1.31 (9H, s), 1.82-1.90 (2H, m), 2.14-2.16 (4H, m), 2.30-

2.32 (2H, m), 2.41 (3H, s), 2.59 (3H, s), 2.59-2.64 (2H, m), 2.91-2.93 (2H, m), 3.16-3.17 (2H, m), 5.23 (2H, s), 5.43 (2H, s), 5.54-5.56 (1H, m), 6.42-6.63 (1H, m), 6.54 (1H, s), 7.31 (1H, s), 7.80 (1H, d, J=10.9 Hz), 8.54 (1H, d, J=7.8 Hz).
MS (APCI) m/z: 664 (M+H)⁺.

Process 5: N³-(2-Aminoethyl)-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-N³-methyl-β-alaninamide The compound (389 mg, 0.585 mmol) obtained in Process 4 above was reacted in the same manner as Process 2 of Example 1 to yield trifluoroacetic acid salt of the titled compound as a yellow solid (304 mg, 92%).
¹H-NMR (400 MHz, DMSO-d₆) δ: 0.87 (3H, br.s), 1.85-1.88 (2H, m), 2.16-2.19 (2H, m), 2.40 (3H, s), 2.67 (3H, s), 2.77-2.79 (2H, m), 3.25-3.37 (8H, m), 5.24-5.29 (2H, m), 5.43 (2H, s), 5.58-5.60 (1H, m), 6.56 (1H, s), 7.32 (1H, s), 7.80 (1H, d, J=10.2 Hz), 8.17 (3H, br.s), 8.81 (1H, s).
MS (APCI) m/z: 564 (M+H)⁺.

Example 46 Antibody-Drug Conjugate (46)

[Formula 99]

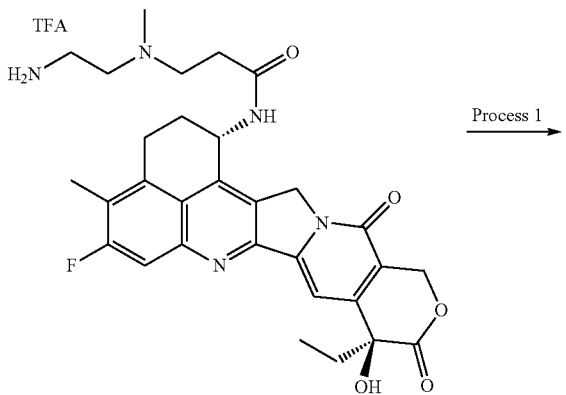

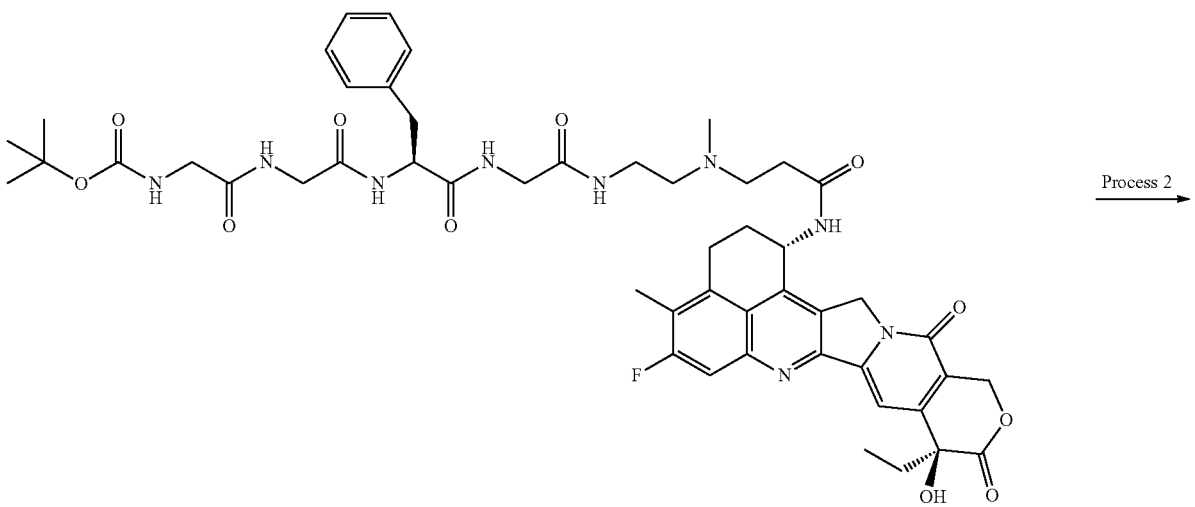

-continued
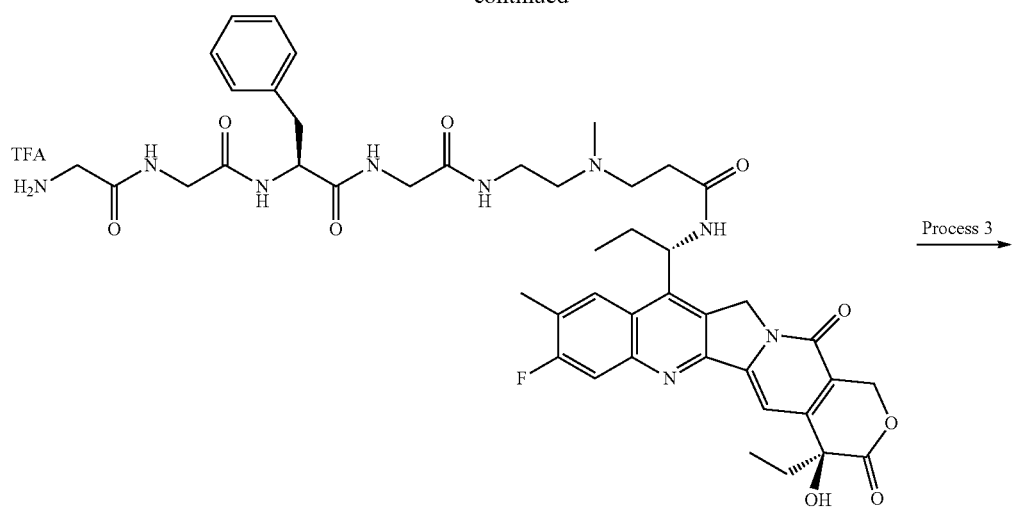
Process 3 →
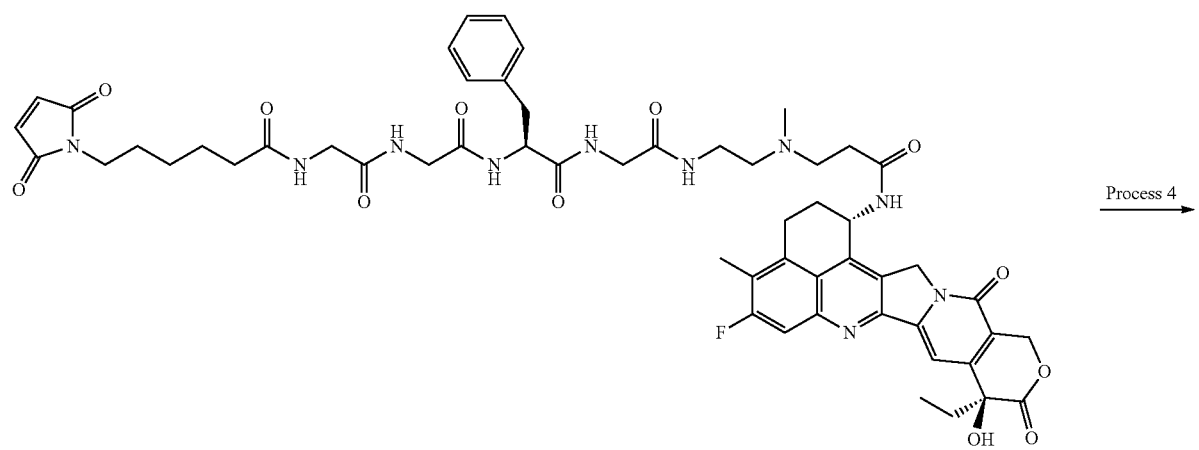
Process 4 →
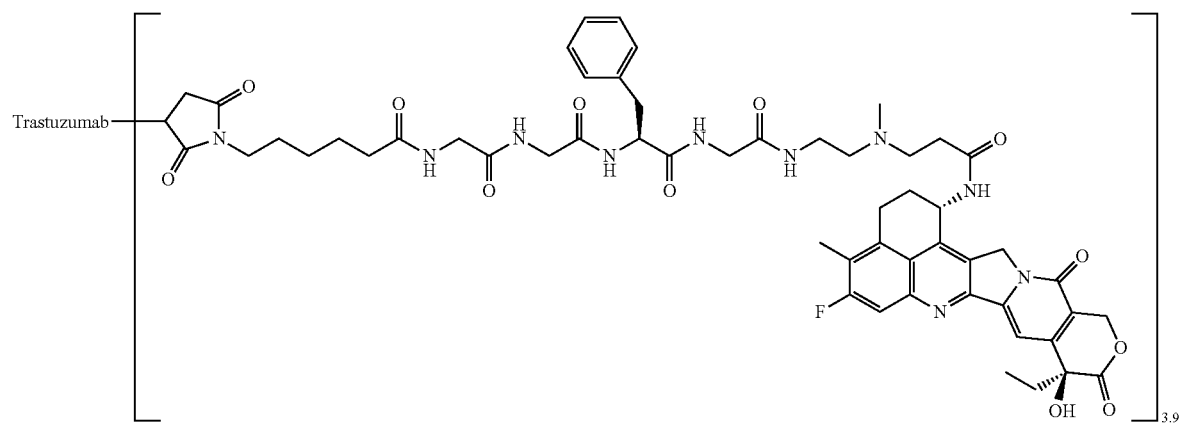

281

Process 1: N-(tert-Butoxycarbonyl)glycylglycyl-L-phenylalanyl-N-{2-[(3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)(methyl)amino]ethyl}glycinamide The compound (200 mg, 0.355 mmol) obtained in Process 5 of Example 45 was reacted in the same manner as Process 1 of Example 2 to yield the titled compound as a pale yellow solid (165 mg, 47%).

$^1$H-NMR (400 MHz, DMSO-$d_6$) δ: 0.86 (3H, t, J=7.2 Hz), 1.37 (9H, s), 1.85 (2H, td, J=14.9, 7.2 Hz), 2.14-2.16 (2H, m), 2.15 (3H, s), 2.32-2.37 (4H, m), 2.39 (3H, s), 2.65-2.67 (2H, m), 2.76 (1H, dd, J=13.5, 9.6 Hz), 3.01 (1H, dd, J=13.7, 4.3 Hz), 3.10 (2H, q, J=6.4 Hz), 3.16-3.17 (2H, m), 3.53-3.77 (6H, m), 4.45-4.50 (1H, m), 5.22 (2H, s), 5.43 (2H, s), 5.53-5.57 (1H, m), 6.54 (1H, s), 7.01 (1H, t, J=5.9 Hz), 7.14-7.26 (5H, m), 7.30 (1H, s), 7.60 (1H, t, J=5.5 Hz), 7.79 (1H, d, J=10.9 Hz), 7.93 (1H, t, J=5.5 Hz), 8.16 (1H, d, J=8.2 Hz), 8.29 (1H, t, J=5.7 Hz), 8.55 (1H, d, J=8.6 Hz).

MS (APCI) m/z: 982 (M+H)$^+$.

Process 2: Glycylglycyl-L-phenylalanyl-N-{2-[(3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)(methyl)amino]ethyl}glycinamide The compound (165 mg, 0.168 mmol) obtained in Process 1 above was reacted in the same manner as Process 2 of Example 2 to yield the titled compound as a pale yellow solid (148 mg, quantitative).

$^1$H-NMR (400 MHz, DMSO-$d_6$) δ: 0.87 (3H, t, J=7.2 Hz), 1.81-1.92 (2H, m), 2.13-2.19 (2H, m), 2.41 (3H, s), 2.66 (2H, dd, J=8.6, 5.1 Hz), 2.74 (1H, dd, J=13.9, 10.0 Hz), 2.82 (3H, s), 3.03 (1H, dd, J=13.9, 4.5 Hz), 3.45-3.48 (9H, m), 3.57 (2H, d, J=5.1 Hz), 3.67-3.76 (2H, m), 3.86 (1H, dd, J=16.8, 5.9 Hz), 4.57 (1H, td, J=9.1, 4.0 Hz), 5.20 (1H, d, J=18.8 Hz), 5.28 (1H, d, J=19.2 Hz), 5.44 (2H, s), 5.57-5.61 (1H, m), 6.58 (1H, s), 7.11-7.25 (5H, m), 7.33 (1H, s), 7.84 (1H, d, J=10.9 Hz), 7.98 (3H, s), 8.13 (1H, s), 8.34 (1H, d, J=7.8 Hz), 8.43 (1H, t, J=5.9 Hz), 8.49 (1H, t, J=5.3 Hz), 8.79 (1H, d, J=8.6 Hz).

MS (APCI) m/z: 882 (M+H)$^+$.

Process 3: N-[6-(2,5-Dioxo-2,5-dihydro-1H-pyrrol-1-yl)hexanoyl]glycylglycyl-L-phenylalanyl-N-{2-[(3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)(methyl)amino]ethyl}glycinamide The compound (100 mg, 0.113 mmol) obtained in Process 2 above was reacted in the same manner as Process 8 of Example 5 to yield the titled compound as a pale yellow solid (43.4 mg, 36%).

$^1$H-NMR (400 MHz, DMSO-$d_6$) δ: 0.86 (3H, t, J=7.2 Hz), 1.14-1.22 (4H, m), 1.44-1.48 (4H, m), 1.80-1.91 (2H, m), 2.09-2.13 (3H, m), 2.10 (2H, t, J=7.4 Hz), 2.38-2.40 (6H, m), 2.79 (2H, dd, J=13.7, 9.8 Hz), 3.02 (1H, dd, J=13.7, 4.3 Hz), 3.09 (1H, q, J=7.3 Hz), 3.15-3.18 (4H, m), 3.35-3.77 (9H, m), 4.46 (1H, td, J=8.7, 4.2 Hz), 5.21 (2H, s), 5.42 (2H, s), 5.53-5.58 (1H, m), 6.54 (1H, s), 6.99 (2H, s), 7.14-7.25 (5H, m), 7.30 (1H, s), 7.68 (1H, br.s), 7.79 (1H, d, J=10.4 Hz), 8.03 (1H, t, J=5.7 Hz), 8.09 (1H, t, J=5.7 Hz), 8.13 (1H, d, J=7.8 Hz), 8.27 (1H, t, J=5.3 Hz), 8.59 (1H, d, J=5.5 Hz).

MS (APCI) m/z: 1075 (M+H)$^+$.

Process 4: Antibody-Drug Conjugate (46)

By using the trastuzumab produced in Reference Example 1 and the compound obtained in Process 3 above, the titled antibody-drug conjugate was obtained in the same manner as Process 6 of Example 2.

Antibody concentration: 1.57 mg/mL, antibody yield: 9.4 mg (75%), and average number of conjugated drug molecules (n) per antibody molecule: 3.9.

Example 47 Antibody-Drug Conjugate (47)

[Formula 100]

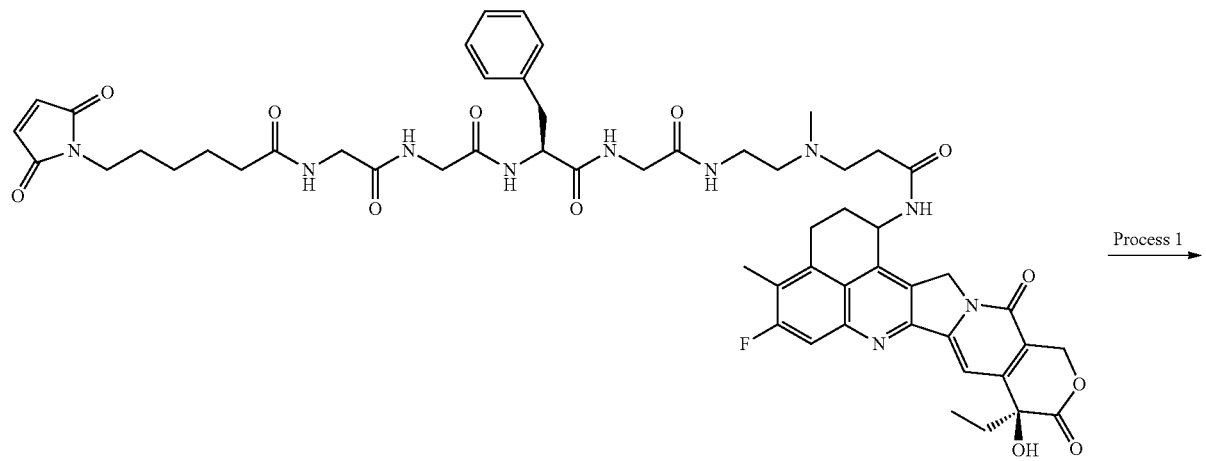

Process 1 →

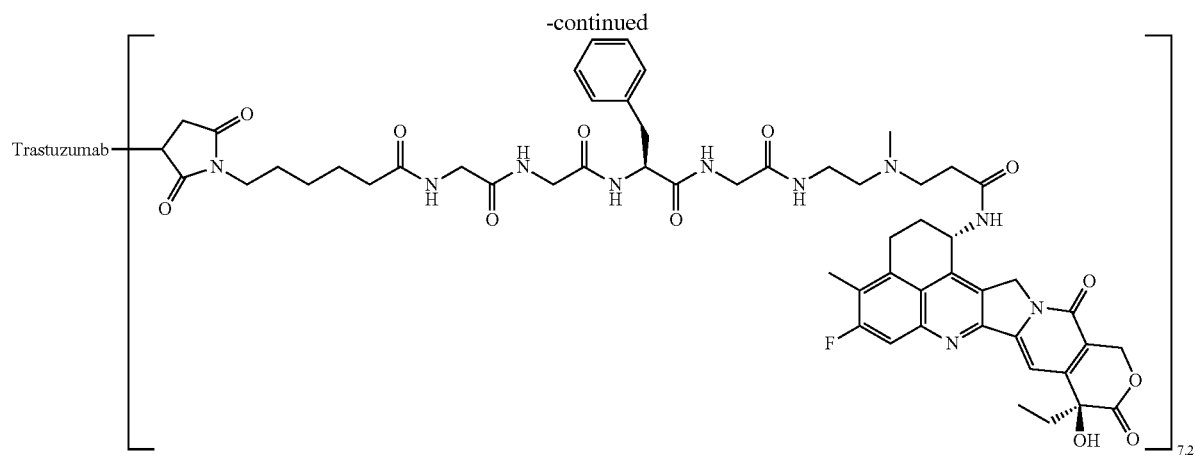

-continued

Process 1: Antibody-Drug Conjugate (47)

By using the trastuzumab produced in Reference Example 1 and the compound obtained in Process 3 of Example 46, the titled antibody-drug conjugate was obtained in the same manner as Process 1 of Example 3.
Antibody concentration: 1.61 mg/mL, antibody yield: 9.7 mg (78%), and average number of conjugated drug molecules (n) per antibody molecule: 7.2.

Example 48 Intermediate (48)

[Formula 101]

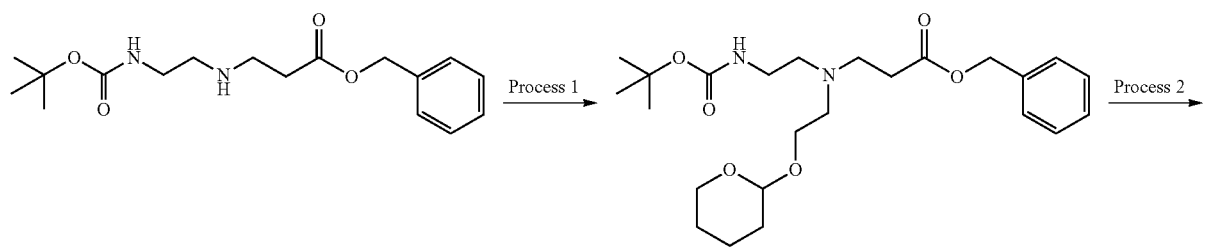

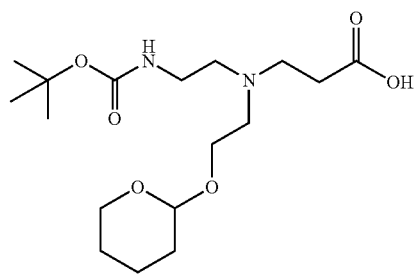

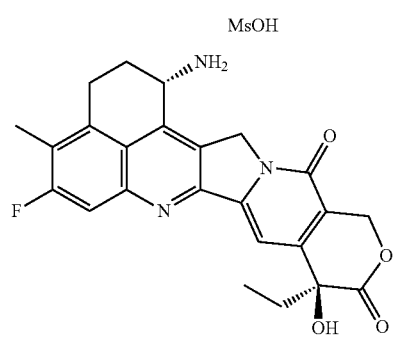

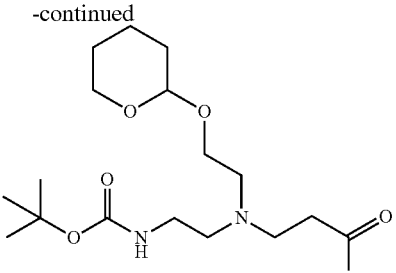

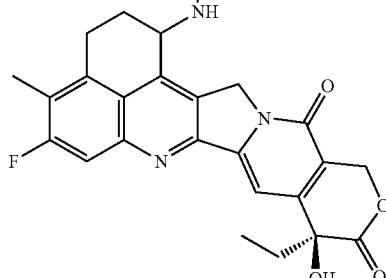

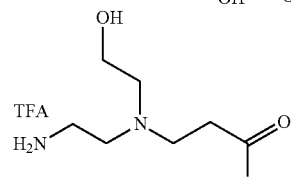

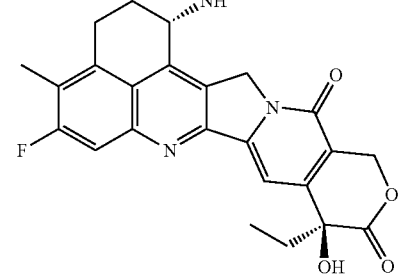

Process 1: Benzyl N-{2-[(tert-butoxycarbonyl)amino]ethyl}-N-[2-(tetrahydro-2H-pyran-2-yloxy)ethyl]-β-alaninate The compound (387 mg, 1.20 mmol) obtained in Process 1 of Example 45 was reacted in the same manner as Process 1 of Example 39 to yield the titled compound as a colorless oily substance (251 mg, 46%).

$^1$H-NMR (400 MHz, CDCl$_3$) δ: 1.43 (9H, s), 1.48-1.82 (6H, m), 2.51 (2H, t, J=7.0 Hz), 2.60 (2H, t, J=5.7 Hz), 2.66-2.69 (2H, m), 2.88 (2H, dd, J=10.8, 4.1 Hz), 3.17 (2H, t, J=4.5 Hz), 3.41 (1H, dt, J=11.5, 5.2 Hz), 3.50 (1H, dq, J=12.9, 2.9 Hz), 3.73-3.78 (1H, m), 3.81-3.87 (1H, m), 4.57 (1H, t, J=3.5 Hz), 5.13 (2H, s), 5.30 (1H, d, J=4.3 Hz), 7.29-7.37 (5H, m).

MS (APCI) m/z: 451 (M+H)$^+$.

Process 2: N-{2-[(tert-Butoxycarbonyl)amino]ethyl}-N-[2-(tetrahydro-2H-pyran-2-yloxy)ethyl]-β-alanine The compound (436 mg, 0.968 mmol) obtained in Process 1 above was reacted in the same manner as Process 3 of Example 33 to yield the titled compound as a colorless oily substance (337 mg, 97%).

$^1$H-NMR (400 MHz, CDCl$_3$) δ: 1.43 (9H, s), 1.57-1.77 (6H, m), 2.71-2.72 (2H, m), 3.21-3.23 (2H, m), 3.32-3.35 (4H, m), 3.50-3.53 (3H, m), 3.72-3.77 (1H, m), 3.83 (1H, dt, J=13.0, 4.5 Hz), 4.04 (1H, dt, J=11.3, 4.4 Hz), 4.62 (1H, s), 6.21 (1H, s), 9.04 (1H, br.s).

MS (APCI) m/z: 361 (M+H)$^+$.

Process 3: tert-Butyl (2-{(3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)[2-(tetrahydro-2H-pyran-2-yloxy)ethyl]amino}ethyl)carbamate Methanesulfonic acid salt of exatecan (410 mg, 0.771 mmol) was reacted in the same manner as Process 1 of Example 1 by using the compound (334 mg, 0.926 mmol) obtained in Process 2 above instead of 4-(tert-butoxycarbonylamino)butanoic acid to yield the titled compound as a yellow solid (366 mg, 61%).

$^1$H-NMR (400 MHz, DMSO-d$_6$) δ: 0.87 (3H, t, J=7.0 Hz), 1.33-1.40 (6H, m), 1.33 (9H, s), 1.85-1.87 (2H, m), 2.12-2.14 (2H, m), 2.28-2.34 (2H, m), 2.40 (3H, s), 2.79-3.08 (12H, m), 3.57-3.66 (2H, m), 4.43-4.45 (1H, m), 5.18 (1H, d, J=18.2 Hz), 5.25 (1H, d, J=18.4 Hz), 5.42 (2H, s), 5.55-5.58 (1H, m), 6.49-6.52 (1H, m), 6.54 (1H, s), 7.30 (1H, m), 7.80 (1H, d, J=11.3 Hz), 8.50 (1H, d, J=8.2 Hz).

MS (APCI) m/z: 778 (M+H)$^+$.

287

Process 4: N³-(2-Aminoethyl)-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-N³-(2-hydroxyethyl)-β-alaninamide

The compound (356 mg, 0.458 mmol) obtained in Process 3 above was reacted in the same manner as Process 2 of Example 1 to yield trifluoroacetic acid salt of the titled compound as a yellow solid (270 mg, 99%).

288

¹H-NMR (400 MHz, DMSO-d₆) δ: 0.87 (3H, t, J=7.2 Hz), 1.81-1.92 (2H, m), 2.15-2.17 (2H, m), 2.40 (3H, s), 2.58-2.61 (2H, m), 2.92-3.60 (12H, m), 5.20 (1H, d, J=18.8 Hz), 5.26 (1H, d, J=19.2 Hz), 5.43 (2H, s), 5.59-5.60 (1H, m), 6.55 (1H, s), 7.32 (1H, s), 7.79-7.82 (2H, m), 8.03 (3H, br.s), 8.77-8.79 (1H, m).

MS (APCI) m/z: 594 (M+H)⁺.

Example 49 Antibody-Drug Conjugate (49)

[Formula 102]

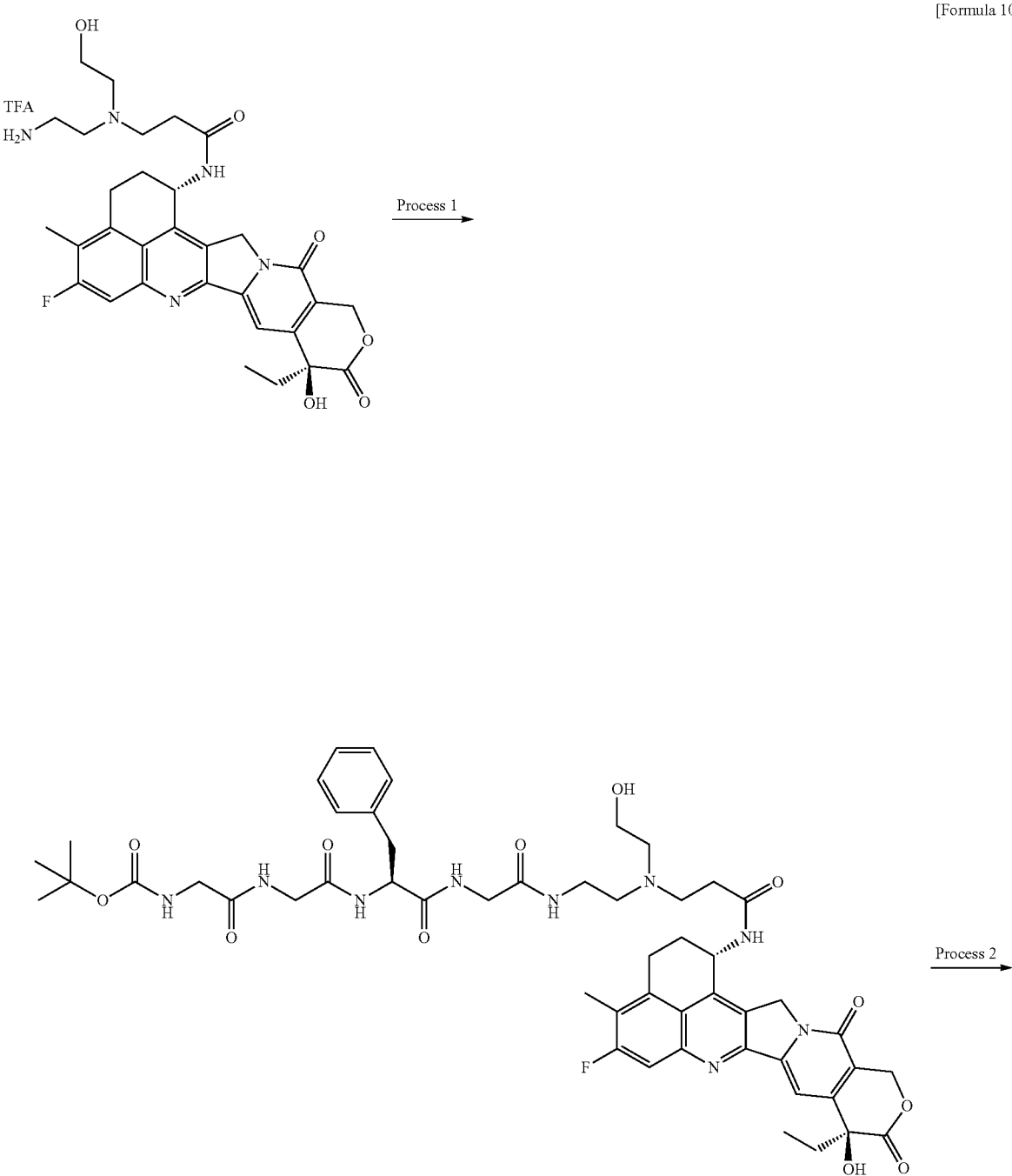

-continued
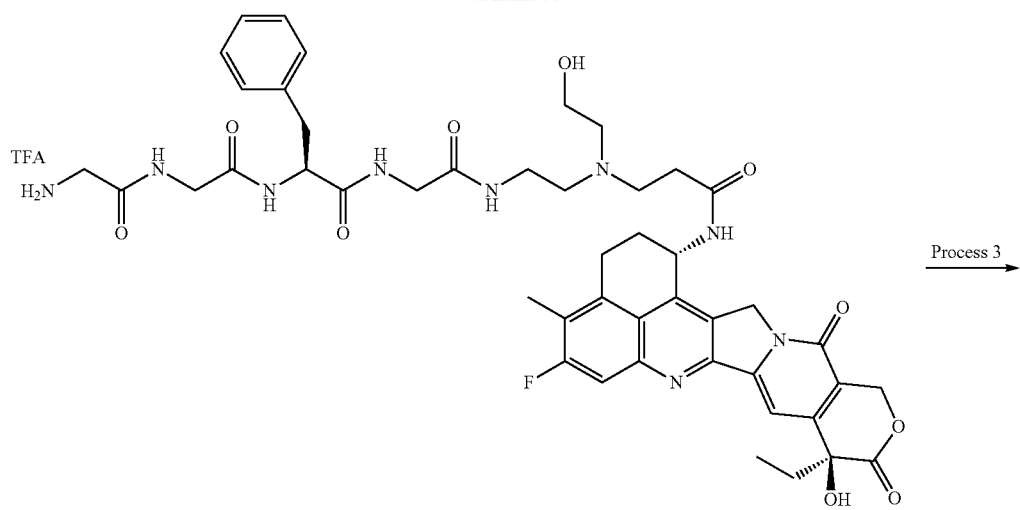
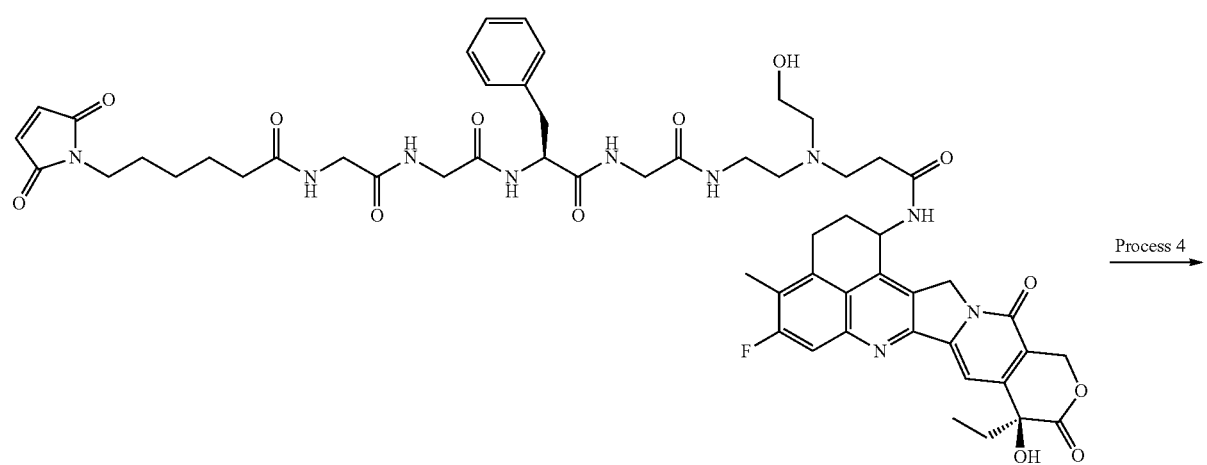
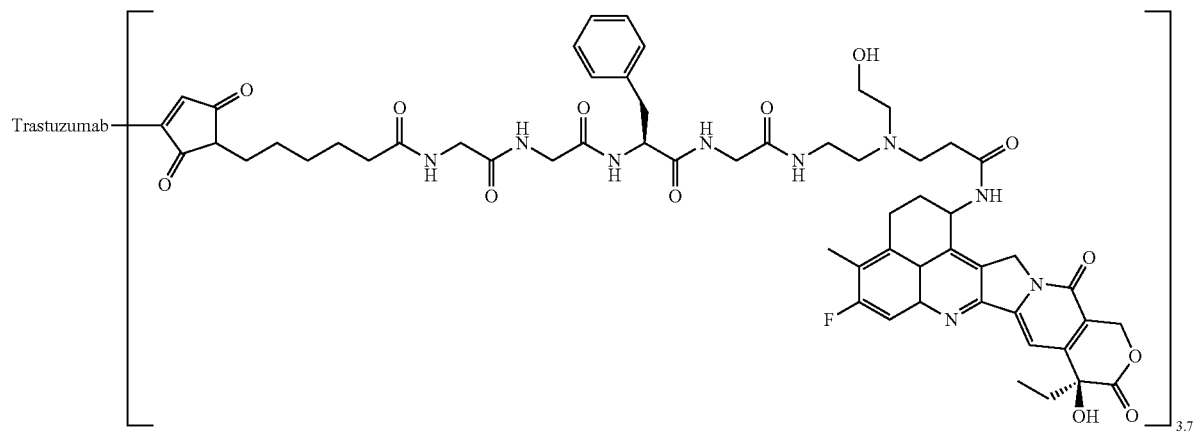

Process 1: N-(tert-Butoxycarbonyl)glycylglycyl-L-phenylalanyl-N-{2-[(3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)(2-hydroxyethyl)amino]ethyl}glycinamide The compound (200 mg, 0.337 mmol) obtained in Process 4 of Example 48 was reacted in the same manner as Process 1 of Example 2 to yield the titled compound as a yellow solid (270 mg, 79%).

$^1$H-NMR (400 MHz, DMSO-$d_6$) δ: 0.86 (3H, t, J=7.0 Hz), 1.36 (9H, s), 1.83-1.85 (2H, m), 2.16-2.18 (2H, m), 2.38 (3H, s), 2.59 (4H, s), 3.02-3.94 (18H, m), 4.43-4.47 (2H, m), 5.19 (1H, d, J=19.2 Hz), 5.26 (1H, d, J=19.2 Hz), 5.43 (2H, s), 5.58 (1H, s), 6.54 (1H, d, J=5.1 Hz), 7.00 (1H, s), 7.21-7.23 (5H, m), 7.31 (1H, s), 7.80 (1H, t, J=11.3 Hz), 7.92-7.95 (2H, m), 8.12-8.14 (1H, m), 8.23-8.26 (1H, m), 8.49 (1H, d, J=8.2 Hz).

Process 2: Glycylglycyl-L-phenylalanyl-N-{2-[(3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)(2-hydroxyethyl)amino]ethyl}glycinamide trifluoroacetic acid salt The compound (270 mg, 0.267 mmol) obtained in Process 1 above was reacted in the same manner as Process 2 of Example 2 to yield the titled compound as a yellow solid (103 mg, 42%).

$^1$H-NMR (400 MHz, DMSO-$d_6$) δ: 0.87 (3H, t, J=7.2 Hz), 1.85-1.88 (2H, m), 2.17-2.20 (2H, m), 2.41 (3H, s), 2.66-3.04 (8H, m), 3.31-4.11 (12H, m), 4.57-4.59 (2H, m), 5.21 (1H, d, J=18.4 Hz), 5.28 (1H, d, J=18.4 Hz), 5.43-5.45 (2H, m), 5.58-5.61 (1H, m), 6.58 (1H, s), 7.21-7.23 (5H, m), 7.34 (1H, s), 7.84 (1H, d, J=10.9 Hz), 7.96 (4H, br.s), 8.31-8.33 (2H, m), 8.47-8.49 (2H, m).

MS (APCI) m/z: 912 (M+H)$^+$.

Process 3: N-[6-(2,5-Dioxo-2,5-dihydro-1H-pyrrol-1-yl)hexanoyl]glycylglycyl-L-phenylalanyl-N-{2-[(3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)(2-hydroxyethyl)amino]ethyl}glycinamide The compound (100 mg, 0.110 mmol) obtained in Process 2 above was reacted in the same manner as Process 8 of Example 5 to yield the titled compound as a yellow solid (38.4 mg, 32%).

$^1$H-NMR (400 MHz, DMSO-$d_6$) δ: 0.87 (3H, t, J=7.0 Hz), 1.15-1.22 (2H, m), 1.45-1.48 (4H, m), 1.82-1.89 (2H, m), 2.09-2.11 (4H, m), 2.30-2.33 (1H, m), 2.38 (3H, s), 2.59 (1H, s), 2.77-2.79 (2H, m), 3.03-3.72 (18H, m), 4.35-4.37 (1H, m), 4.46-4.49 (1H, m), 5.19 (2H, s), 5.42 (2H, s), 5.55-5.56 (1H, m), 6.53 (1H, s), 6.99 (2H, s), 7.16-7.25 (5H, m), 7.30 (1H, s), 7.61 (1H, s), 7.78 (1H, d, J=10.9 Hz), 8.02 (1H, t, J=5.5 Hz), 8.08-8.11 (2H, m), 8.25 (1H, t, J=5.5 Hz), 8.55 (1H, d, J=8.6 Hz).

MS (APCI) m/z: 1105 (M+H)$^+$.

Process 4: Antibody-Drug Conjugate (49)

By using the trastuzumab produced in Reference Example 1 and the compound obtained in Process 3 above, the titled antibody-drug conjugate was obtained in the same manner as Process 6 of Example 2.

Antibody concentration: 1.57 mg/mL, antibody yield: 9.4 mg (75%), and average number of conjugated drug molecules (n) per antibody molecule: 3.7.

Example 50 Antibody-Drug Conjugate (50)

[Formula 103]

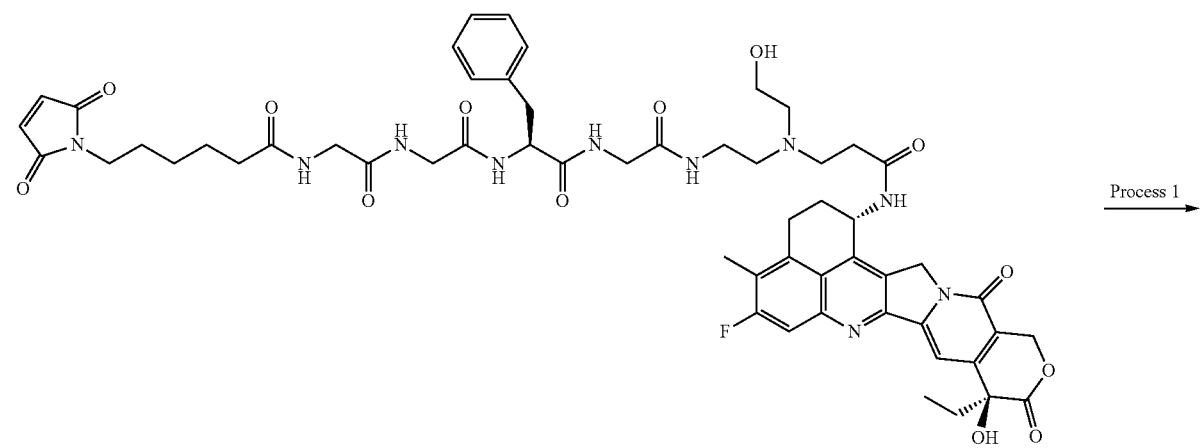

Process 1

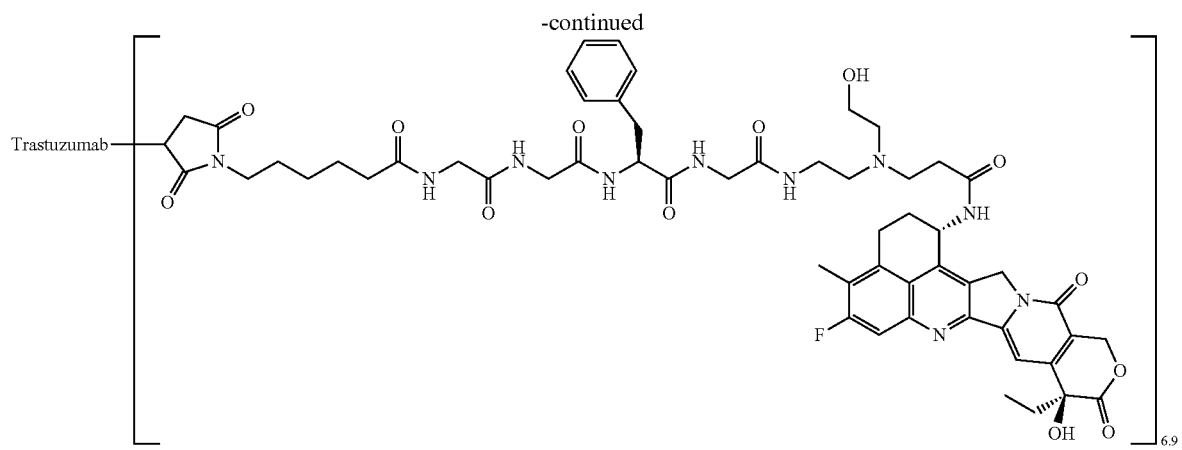

Process 1: Antibody-Drug Conjugate (50) By using the trastuzumab produced in Reference Example 1 and the compound obtained in Process 3 of Example 49, the titled antibody-drug conjugate was obtained in the same manner as Process 1 of Example 3.

Antibody concentration: 1.61 mg/mL, antibody yield: 9.7 mg (78%), and average number of conjugated drug molecules (n) per antibody molecule: 6.9.

Example 51 Intermediate (51)

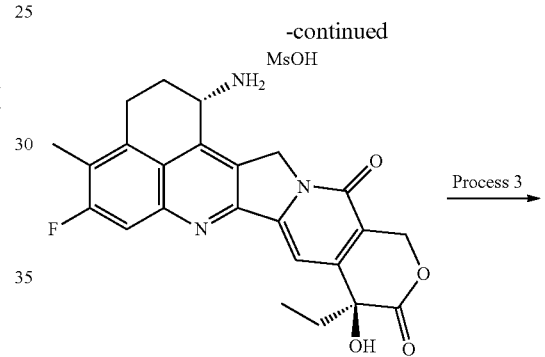

[Formula 104]

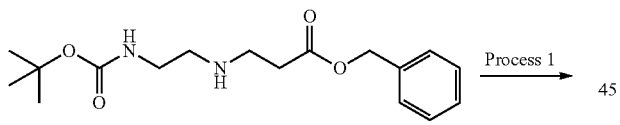

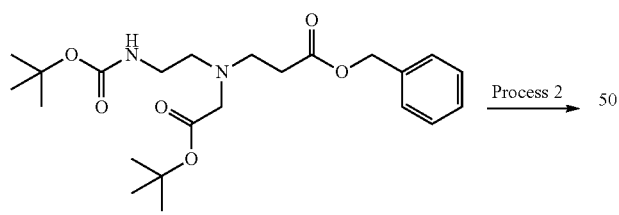

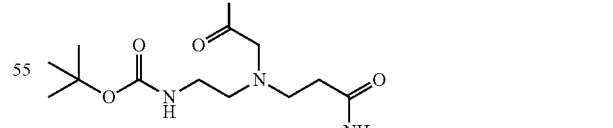

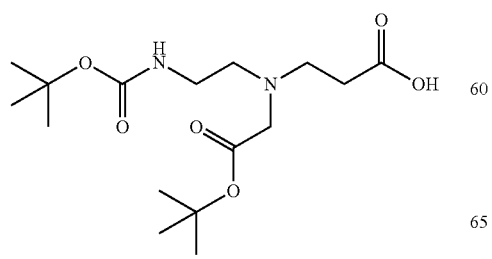

-continued

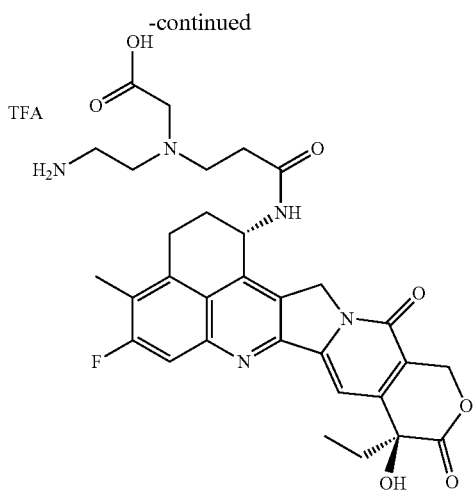

Process 1: Benzyl N-{2-[(tert-butoxycarbonyl)amino]ethyl}-N-(2-tert-butoxy-2-oxoethyl)-β-alaninate The compound (0.926 mg, 2.87 mmol) obtained in Process 1 of Example 45 was reacted in the same manner as Process 1 of Example 42 to yield the titled compound as a colorless oily substance (1.10 g, 88%).

¹H-NMR (400 MHz, CDCl₃) δ: 1.43 (9H, s), 1.45 (9H, s), 2.49 (2H, t, J=6.8 Hz), 2.72 (2H, t, J=5.7 Hz), 2.98 (2H, t, J=6.8 Hz), 3.14 (2H, q, J=5.6 Hz), 3.22 (2H, s), 5.13 (2H, s), 5.30 (1H, brs), 7.30-7.34 (5H, m).

MS (APCI) m/z: 437 (M+H)⁺.

Process 2: N-{2-[(tert-Butoxycarbonyl)amino]ethyl}-N-(2-tert-butoxy-2-oxoethyl)-β-alanine The compound (1.25 g, 2.87 mmol) obtained in Process 1 above was reacted in the same manner as Process 3 of Example 33 to yield the titled compound as a colorless oily substance (0.850 g, 83%).

¹H-NMR (400 MHz, CDCl₃) δ: 1.43 (9H, s), 1.47 (9H, s), 2.50 (2H, t, J=6.3 Hz), 2.82-2.85 (2H, m), 3.02 (2H, t, J=6.5 Hz), 3.22-3.25 (2H, m), 3.39 (2H, s), 5.62 (1H, brs), 10.36 (1H, brs).

MS (APCI) m/z: 347 (M+H)⁺.

Process 3: tert-Butyl N-{2-[(tert-butoxycarbonyl)amino]ethyl}-N-(3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)glycinate Methanesulfonic acid salt of exatecan (1.00 g, 1.88 mmol) was reacted in the same manner as Process 1 of Example 1 by using the compound (0.782 g, 2.26 mmol) obtained in Process 2 above instead of 4-(tert-butoxycarbonylamino)butanoic acid to yield the titled compound as a yellow solid (1.43 g, quantitative).

¹H-NMR (400 MHz, CD₃OD) δ: 0.95 (3H, t, J=7.4 Hz), 1.20 (9H, s), 1.33 (9H, s), 1.87 (2H, q, J=7.3 Hz), 2.24-2.28 (1H, m), 2.29 (3H, s), 2.35-2.48 (3H, m), 2.57-2.65 (2H, m), 2.89-2.92 (2H, m), 3.06-3.28 (6H, m), 3.66-3.67 (1H, m), 4.76 (1H, d, J=19.2 Hz), 5.13 (1H, d, J=18.8 Hz), 5.25 (1H, d, J=16.0 Hz), 5.49 (1H, d, J=16.0 Hz), 5.62 (1H, t, J=5.7 Hz), 7.37 (1H, d, J=10.6 Hz), 7.43 (1H, s), 7.97 (2H, s).

MS (APCI) m/z: 764 (M+H)⁺.

Process 4: N-(2-Aminoethyl)-N-(3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)glycine The compound (1.43 g, 1.87 mmol) obtained in Process 3 above was reacted in the same manner as Process 2 of Example 1 to yield trifluoroacetic acid salt of the titled compound as a yellow solid (1.06 g, 93%).

¹H-NMR (400 MHz, CD₃OD) δ: 0.96 (3H, t, J=6.3 Hz), 1.90 (2H, d, J=6.3 Hz), 2.22-2.27 (1H, m), 2.29 (3H, s), 2.42-2.54 (2H, m]), 2.95-3.08 (6H, m), 3.33-3.35 (3H, m), 3.66-3.69 (2H, m), 4.04-4.07 (1H, m), 4.84 (1H, d, J=18.4 Hz), 5.10 (1H, d, J=18.4 Hz), 5.25 (1H, d, J=16.0 Hz), 5.45 (1H, d, J=16.0 Hz), 5.76-5.79 (1H, m), 7.09 (1H, d, J=10.6 Hz), 7.33 (1H, s).

MS (APCI) m/z: 608 (M+H)⁺.

Example 52 Antibody-Drug Conjugate (52)

[Formula 105]

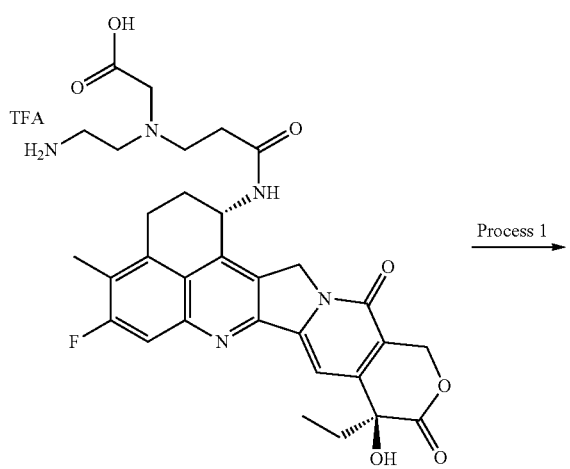

Process 1 →

-continued
297
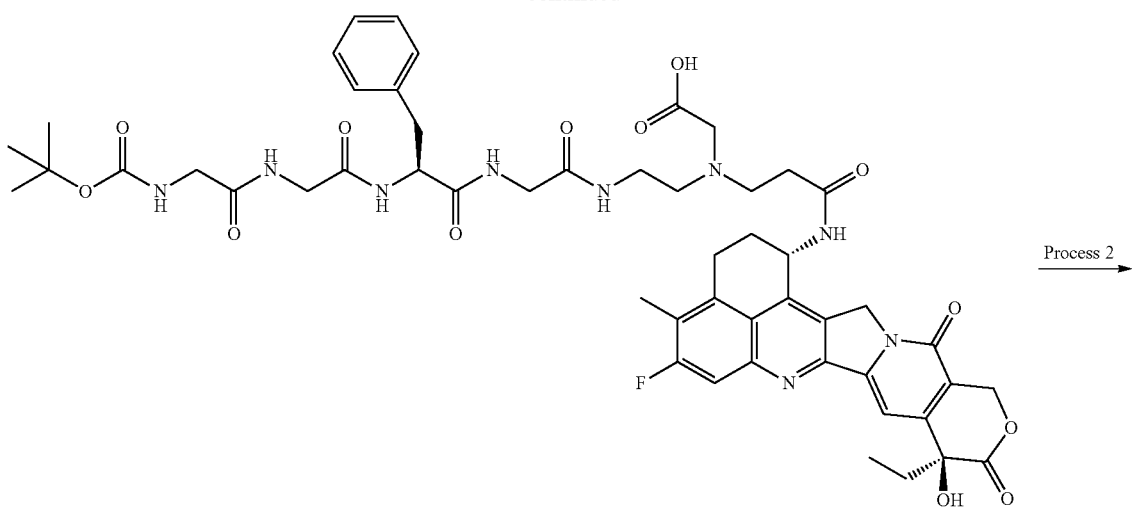
Process 2 →
298
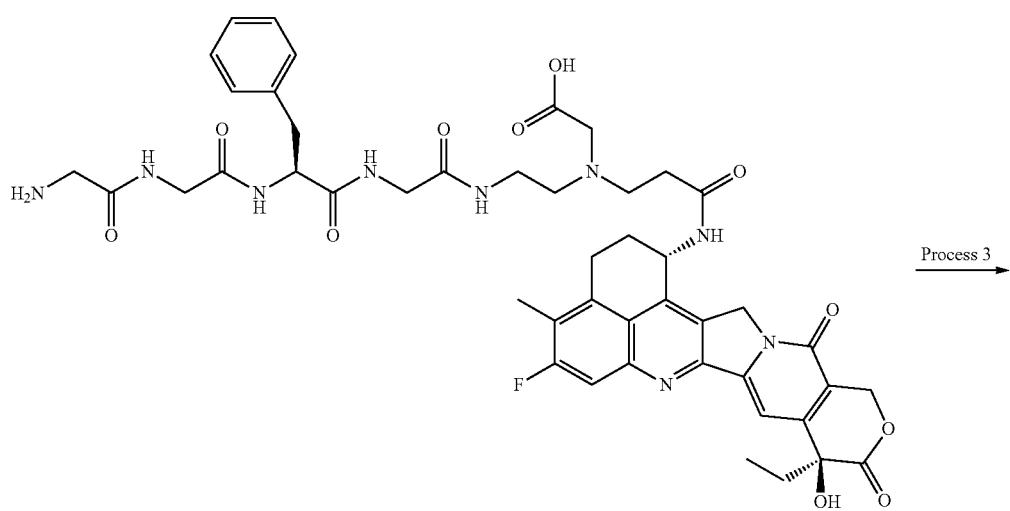
Process 3 →
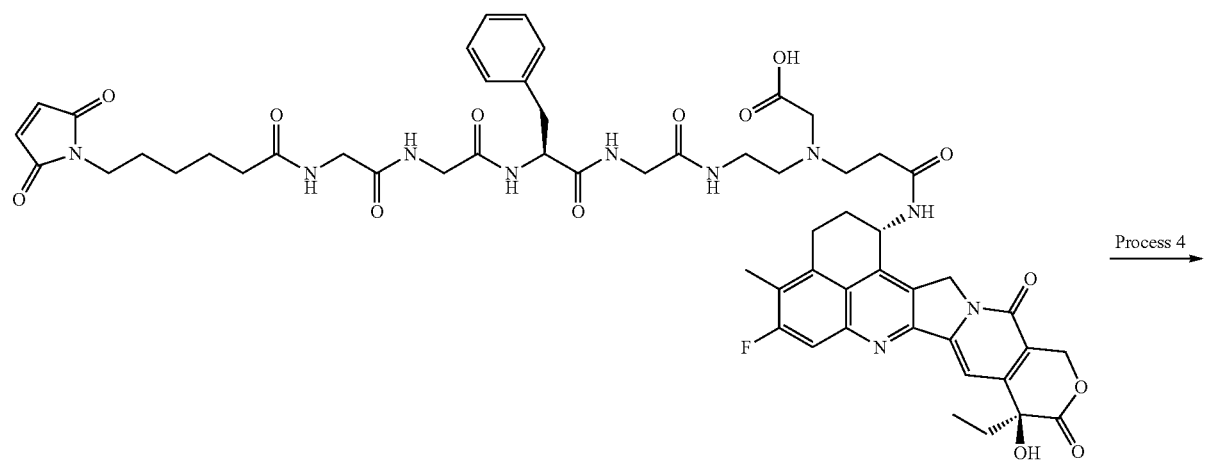
Process 4 →

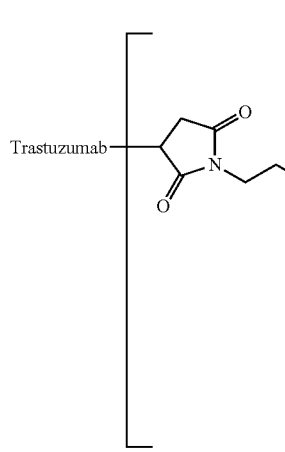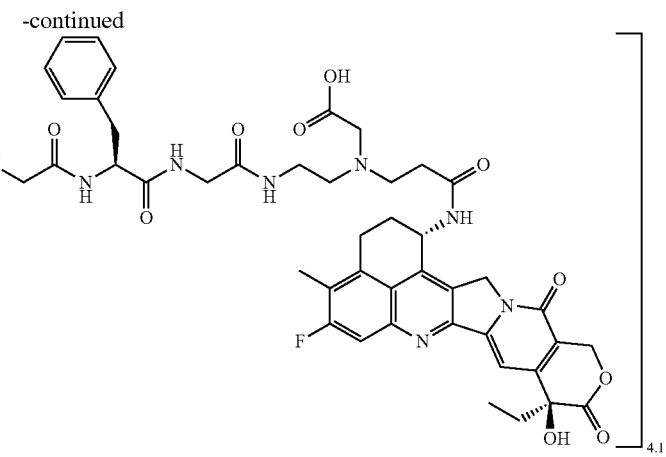

Process 1: N-(tert-Butoxycarbonyl)glycylglycyl-L-phenylalanyl-N-{2-[(carboxymethyl) (3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)amino]ethyl}glycinamide Trifluoroacetic acid salt of the compound (300 mg, 0.494 mmol) obtained in Process 4 of Example 51 was reacted in the same manner as Process 1 of Example 2 to yield the titled compound as a pale yellow solid (221 mg, 44%).

$^1$H-NMR (400 MHz, DMSO-$d_6$) δ: 0.86 (3H, t, J=7.2 Hz), 1.36 (9H, s), 1.83-1.85 (2H, m), 2.12-2.14 (2H, m), 2.33 (3H, s), 2.37-2.39 (1H, m), 2.43-2.45 (1H, m), 2.64-3.73 (18H, m), 4.48-4.51 (1H, m), 5.20 (2H, s), 5.42 (2H, s), 5.53-5.56 (1H, m), 6.54 (1H, s), 7.01-7.29 (5H, m), 7.79 (1H, d, J=10.6 Hz), 7.91 (1H, s), 8.09-8.14 (2H, m), 8.26-8.31 (4H, m), 8.63 (1H, s).

MS (APCI) m/z: 1026 (M+H)$^+$.

Process 2: Glycylglycyl-L-phenylalanyl-N-{2-[(carboxymethyl) (3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)amino]ethyl}glycinamide The compound (221 mg, 0.216 mmol) obtained in Process 1 above was reacted in the same manner as Process 2 of Example 2 to yield the titled compound as a pale yellow solid (196 mg, 98%).

$^1$H-NMR (400 MHz, DMSO-$d_6$) δ: 0.87 (3H, t, J=7.2 Hz), 1.85-1.87 (2H, m), 2.17-2.19 (2H, m), 2.41 (3H, s), 2.67-2.77 (2H, m), 2.99-3.05 (3H, m), 3.32-3.35 (3H, m), 3.56-3.96 (13H, m), 4.54-4.56 (1H, m), 5.21 (1H, d, J=19.0 Hz), 5.27 (1H, d, J=19.0 Hz), 5.43 (2H, s), 5.58-5.59 (1H, m), 6.57 (1H, s), 7.18-7.24 (5H, m), 7.33 (1H, s), 7.83 (1H, d, J=10.9 Hz), 7.98 (3H, br.s), 8.33 (1H, d, J=8.2 Hz), 8.39 (1H, s), 8.50 (1H, s), 8.71 (1H, s).

MS (APCI) m/z: 926 (M+H)$^+$.

Process 3: N-[6-(2,5-Dioxo-2,5-dihydro-1H-pyrrol-1-yl)hexanoyl]glycylglycyl-L-phenylalanyl-N-{2-[(carboxymethyl) (3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)amino]ethyl}glycinamide The compound (100 mg, 0.108 mmol) obtained in Process 2 above was reacted in the same manner as Process 8 of Example 5 to yield the titled compound as a pale yellow solid (79.2 mg, 66%).

$^1$H-NMR (400 MHz, DMSO-$d_6$) δ: 0.87 (3H, t, J=7.4 Hz), 1.12-1.18 (2H, m), 1.44-1.48 (4H, m), 1.80-1.91 (2H, m), 2.09-2.15 (2H, m), 2.09 (2H, t, J=7.6 Hz), 2.33 (2H, t, J=6.8 Hz), 2.39 (3H, s), 2.65 (2H, t, J=6.8 Hz), 2.78 (2H, dd, J=13.7, 9.8 Hz), 2.91 (2H, t, J=6.6 Hz), 3.00-3.76 (14H, m), 4.47 (1H, td, J=8.8, 4.3 Hz), 5.22 (2H, s), 5.43 (2H, s), 5.54-5.58 (1H, m), 6.52 (1H, s), 6.99 (2H, s), 7.13-7.25 (6H, m), 7.30 (1H, s), 7.71 (1H, s), 7.79 (1H, d, J=10.9 Hz), 8.09-8.13 (2H, m), 8.21-8.23 (2H, m), 8.57 (1H, d, J=8.6 Hz).

MS (APCI) m/z: 1119 (M+H)$^+$.

Process 4: Antibody-Drug Conjugate (52)

By using the trastuzumab produced in Reference Example 1 and the compound obtained in Process 3 above, the titled antibody-drug conjugate was obtained in the same manner as Process 6 of Example 2.

Antibody concentration: 1.56 mg/mL, antibody yield: 9.4 mg (75%), and average number of conjugated drug molecules (n) per antibody molecule: 4.1.

Example 53 Antibody-Drug Conjugate (53)

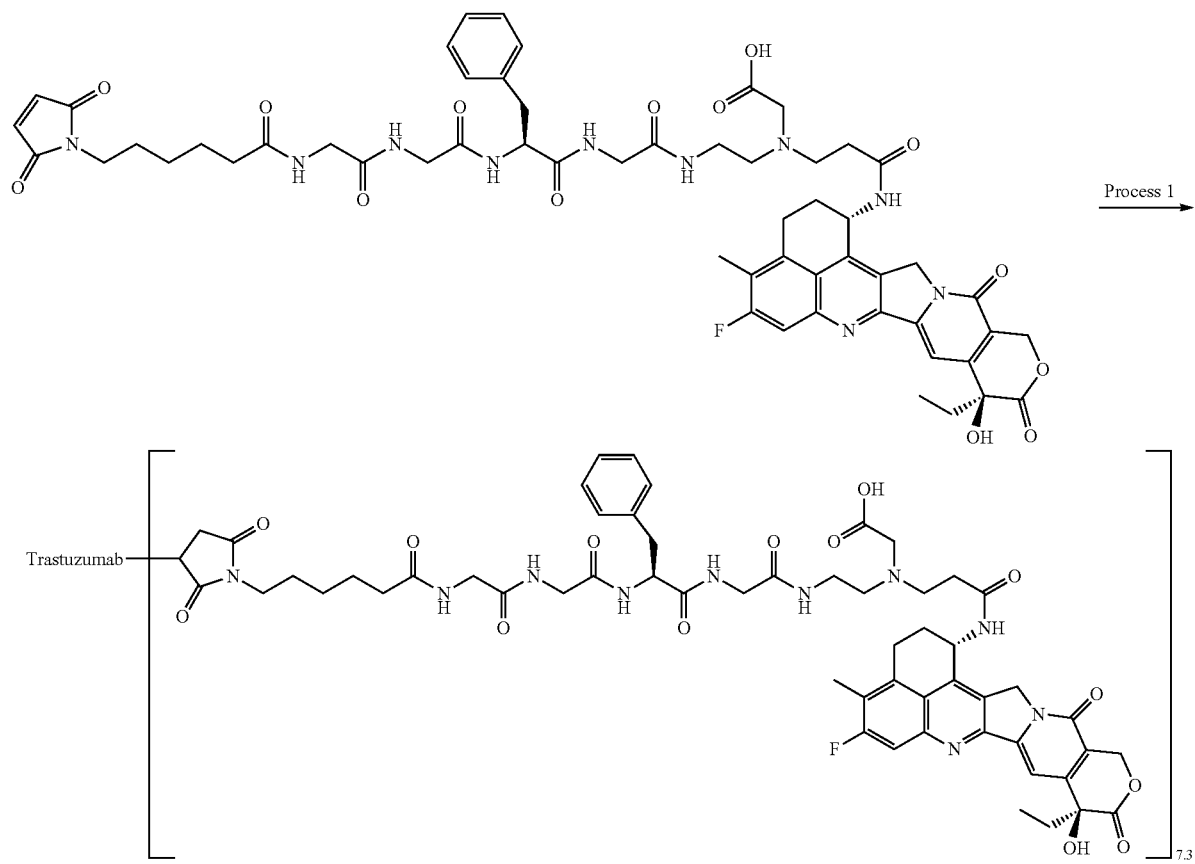

Process 1: Antibody-Drug Conjugate (53)

By using the trastuzumab produced in Reference Example 1 and the compound obtained in Process 3 of Example 52, the titled antibody-drug conjugate was obtained in the same manner as Process 1 of Example 3.

Antibody concentration: 1.61 mg/mL, antibody yield: 9.7 mg (78%), and average number of conjugated drug molecules (n) per antibody molecule: 7.3.

Example 54 Antibody-Drug Conjugate (54)

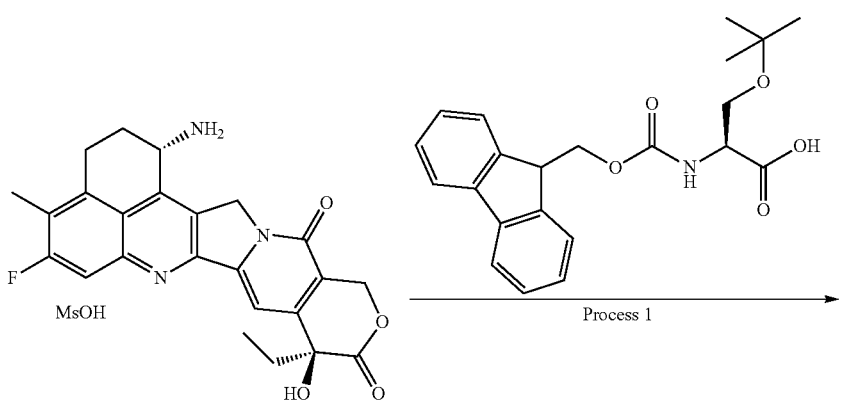

303
304
-continued
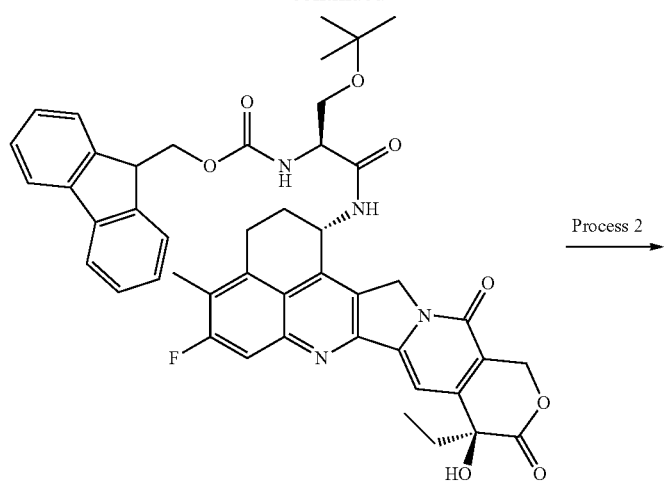
Process 2
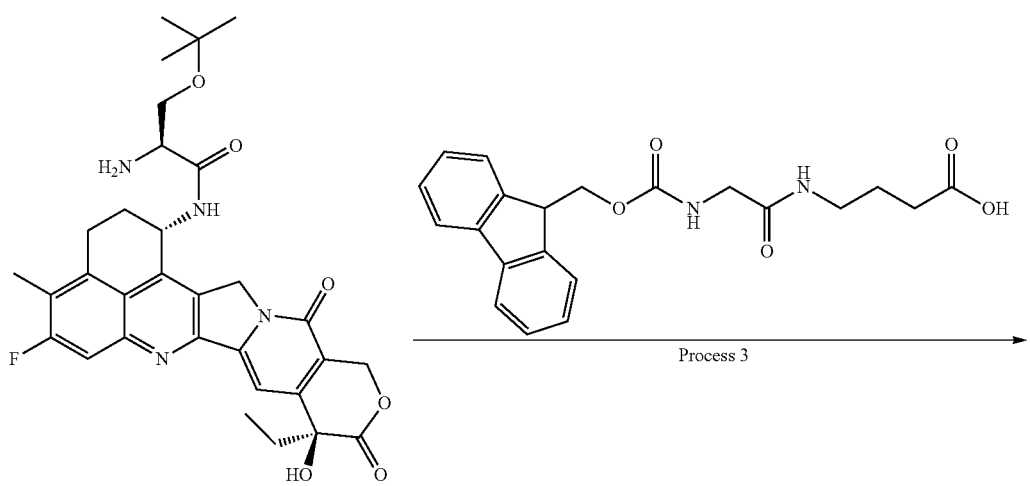
Process 3
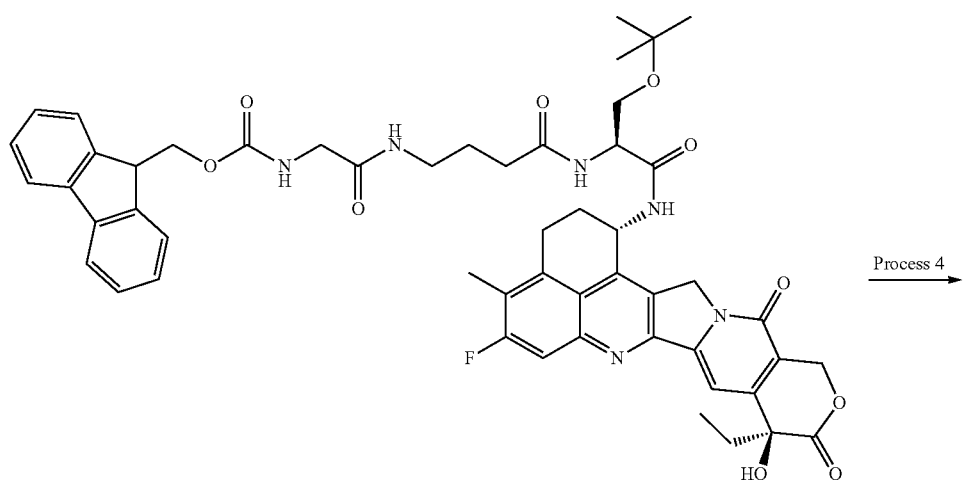
Process 4

305 306
-continued
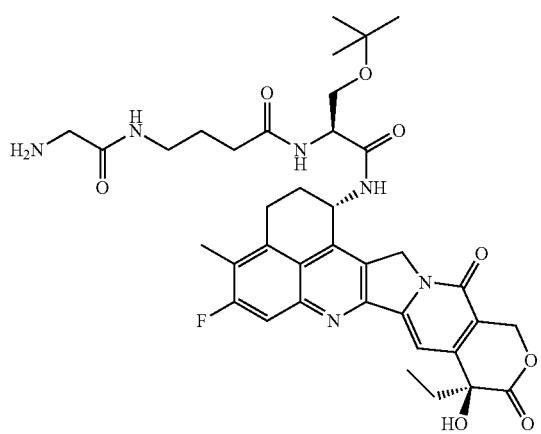
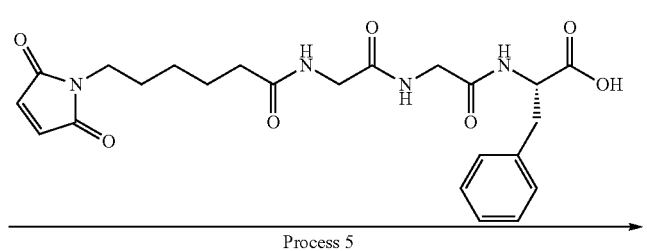
Process 5
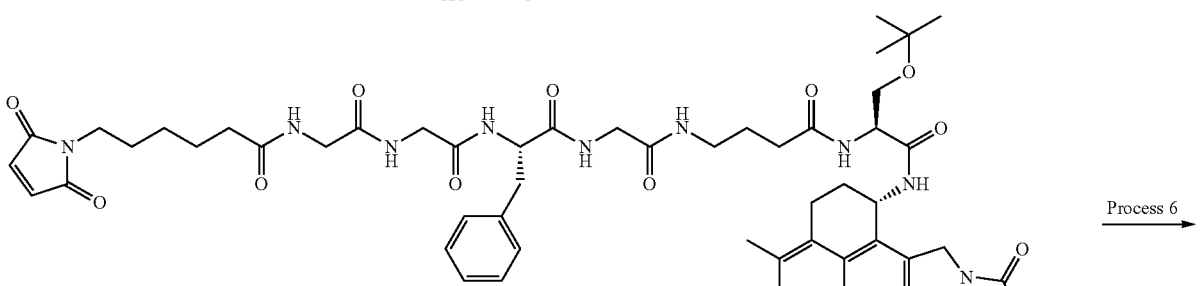
Process 6
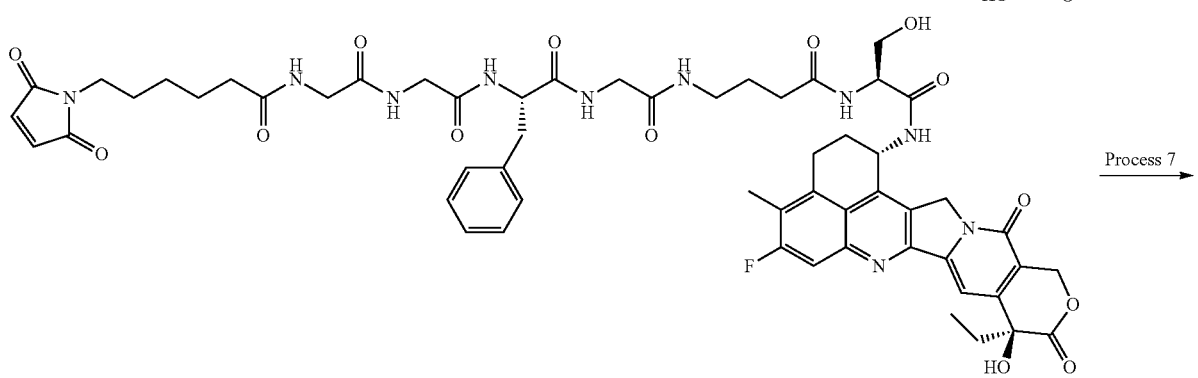
Process 7
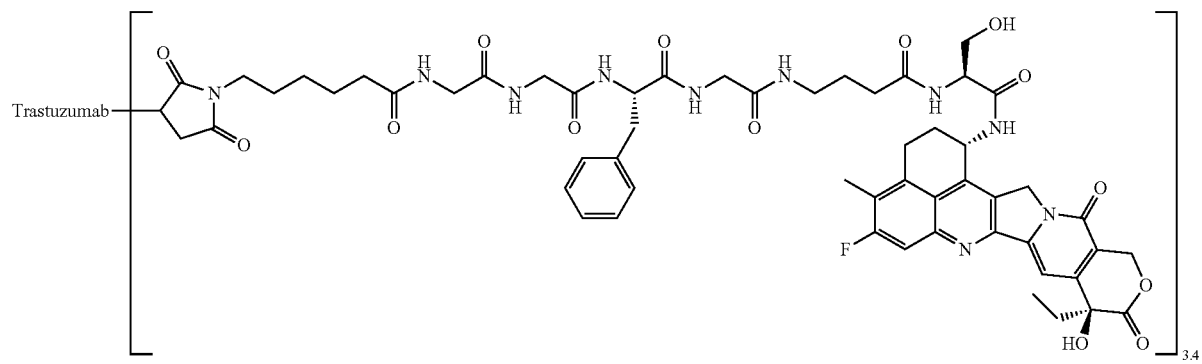

Process 1: 9H-Fluoren-9-ylmethyl[(2S)-3-tert-butoxy-1-{[(1S,9S)-9-ethyl-5-fluoro-9-hydroxy-4-methyl-10,13-dioxo-2,3,9,10,13,15-hexahydro-1H,12H-yl]amino}-1-oxopropan-2-yl]carbamate Methanesulfonic acid salt of exatecan was reacted in the same manner as Process 1 of Example 1 by using 0-tert-butyl-N-[(9H-fluoren-9-ylmethoxy)carbonyl]-L-serine instead of 4-(tert-butoxycarbonylamino)butanoic acid to yield the titled compound. The compound was used for the next reaction without further purification.
MS(ES+APCI) m/z: 801 (M+H)$^+$.

Process 2: O-tert-Butyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-serinamide The compound (1.10 g, 1.37 mmol) obtained in Process 1 above was reacted in the same manner as Process 6 of Example 15 to yield the titled compound. The compound was used for the next reaction without further purification.

Process 3: 9H-Fluoren-9-ylmethyl{2-[(4-{[(2S)-3-tert-butoxy-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1-ooxopropan-2-yl]amino}-4-oxobutyl)amino]-2-oxoethyl}carbamate The compound (0.460 mmol) obtained in Process 2 above was reacted in the same manner as Process 1 of Example 2 by using 4-({N-[(9H-fluoren-9-ylmethoxy)carbonyl]glycyl}amino)butanoic acid instead of N-(tert-butoxycarbonyl)glycylglycyl-L-phenylalanylglycine to yield the titled compound as a pale yellow solid (0.106 g, 24%, 3 steps).
MS(ES+APCI) m/z: 943 (M+H)$^+$.

Process 4: N-[(2S)-3-tert-Butoxy-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1-oxopropan-2-yl]-4-(glycylamino)butanamide The compound (0.106 g, 0.112 mmol) obtained in Process 3 above was reacted in the same manner as Process 6 of Example 15 to yield the titled compound. The compound was used for the next reaction without further purification.

Process 5: N-[6-(2,5-Dioxo-2,5-dihydro-1H-pyrrol-1-yl)hexanoyl]glycylglycyl-L-phenylalanyl-N-(4-{[(2S)-3-tert-butoxy-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1-oxopropan-2-yl]amino}-4-oxobutyl)glycinamide The compound (0.112 mmol) obtained in Process 4 above was reacted in the same manner as Process 1 of Example 2 by using N-[6-(2,5-dioxo-2,5-dihydro-1H-pyrrol-1-yl)hexanoyl]glycylglycyl-L-phenylalanine instead of N-(tert-butoxycarbonyl)glycylglycyl-L-phenylalanylglycine to yield the titled compound as an orange solid (63.0 mg, 48%).
MS(ES+APCI) m/z: 1175 (M+H)$^+$.

Process 6: N-[6-(2,5-Dioxo-2,5-dihydro-1H-pyrrol-1-yl)hexanoyl]glycylglycyl-L-phenylalanyl-N-(4-{[(2S)-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-hydroxy-1-oxopropan-2-yl]amino}-4-oxobutyl)glycinamide The compound (63.0 mg, 53.6 µmol) obtained in Process 5 above was reacted in the same manner as Process 8 of Example 5 to yield the titled compound as a yellow solid (20.0 mg, 33%).
$^1$H-NMR (400 MHz, DMSO-d$_6$) δ: 0.84 (3H, t, J=7.2 Hz), 1.09-1.20 (2H, m), 1.28-1.60 (6H, m), 1.74-1.91 (2H, m), 2.01-2.20 (6H, m), 2.37 (3H, s), 2.69-2.84 (1H, m), 2.88-3.05 (3H, m), 3.07-3.18 (2H, m), 3.21-3.40 (3H, m), 3.46-3.78 (8H, m), 4.17-4.35 (1H, m), 4.36-4.48 (1H, m), 5.07-5.27 (2H, m), 5.40 (2H, s), 5.47-5.59 (1H, m), 6.50 (1H, brs), 6.96 (2H, s), 7.10-7.29 (6H, m), 7.58 (1H, t, J=4.7 Hz), 7.77 (1H, d, J=11.3 Hz), 7.87 (1H, t, J=7.4 Hz), 7.96-8.13 (3H, m), 8.21 (1H, t, J=5.9 Hz), 8.52 (1H, d, J=8.2 Hz).
MS (ES+APCI) m/z: 1119 (M+H)$^+$.

Process 7: Antibody-Drug Conjugate (54)

By using the trastuzumab produced in Reference Example 1 and the compound obtained in Process 6 above, the titled antibody-drug conjugate was obtained in the same manner as Process 6 of Example 2.
Antibody concentration: 1.46 mg/mL, antibody yield: 8.8 mg (88%), and average number of conjugated drug molecules (n) per antibody molecule: 3.4.

Example 55 Antibody-Drug Conjugate (55)

[Formula 108]

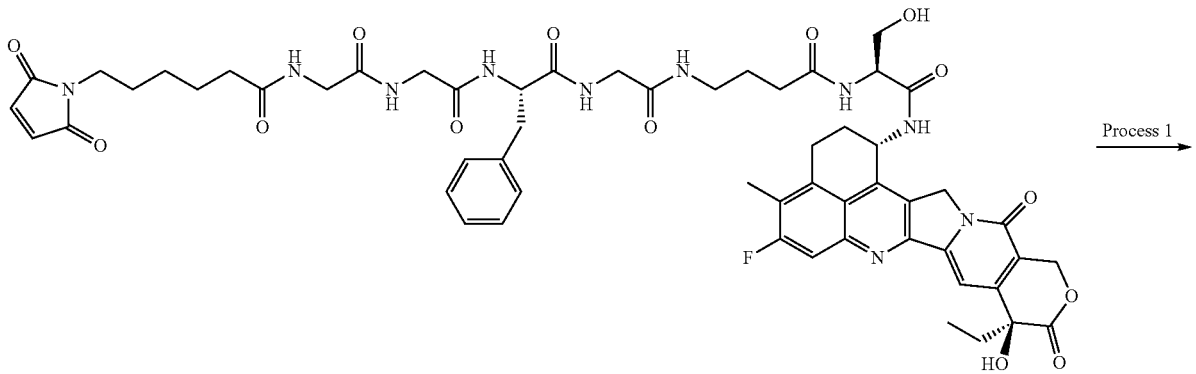

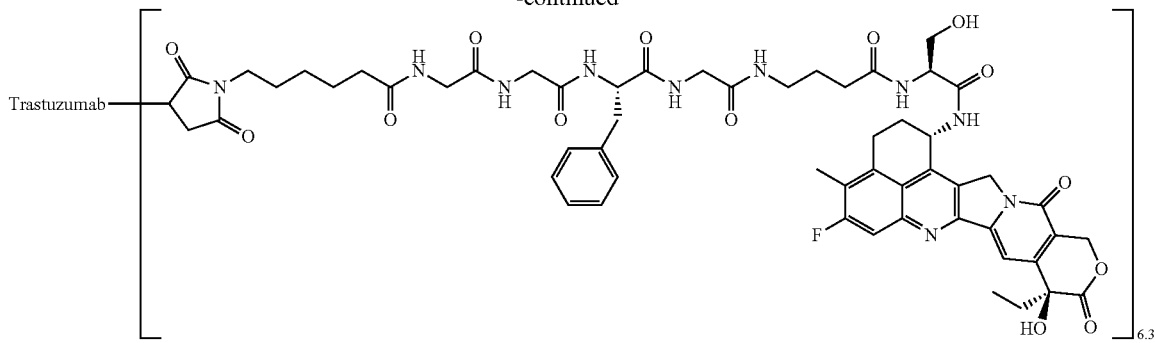

Process 1: Antibody-Drug Conjugate (55)

By using the trastuzumab produced in Reference Example 1 and the compound obtained in Process 6 of Example 54, the titled antibody-drug conjugate was obtained in the same manner as Process 1 of Example 3.
Antibody concentration: 1.35 mg/mL, antibody yield: 7.2 mg (72%), and average number of conjugated drug molecules (n) per antibody molecule: 6.3.

Example 56 Antibody-Drug Conjugate (56)

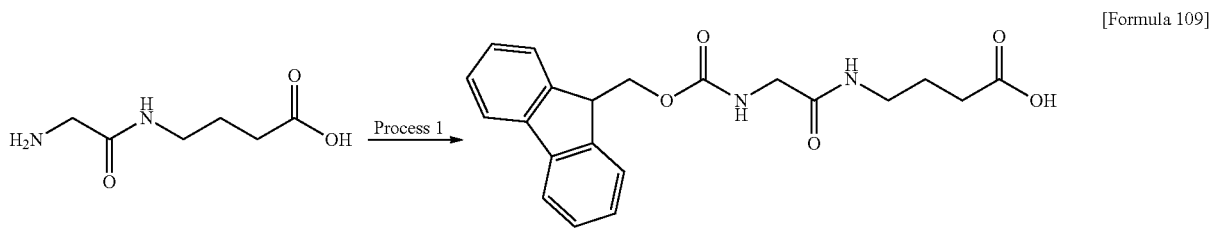

[Formula 109]

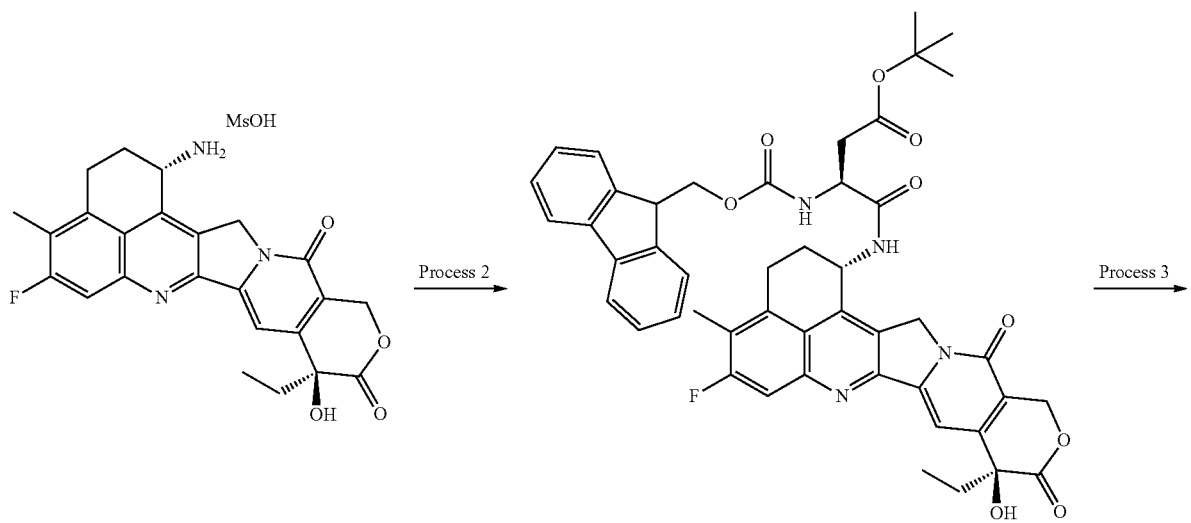

311
312
-continued
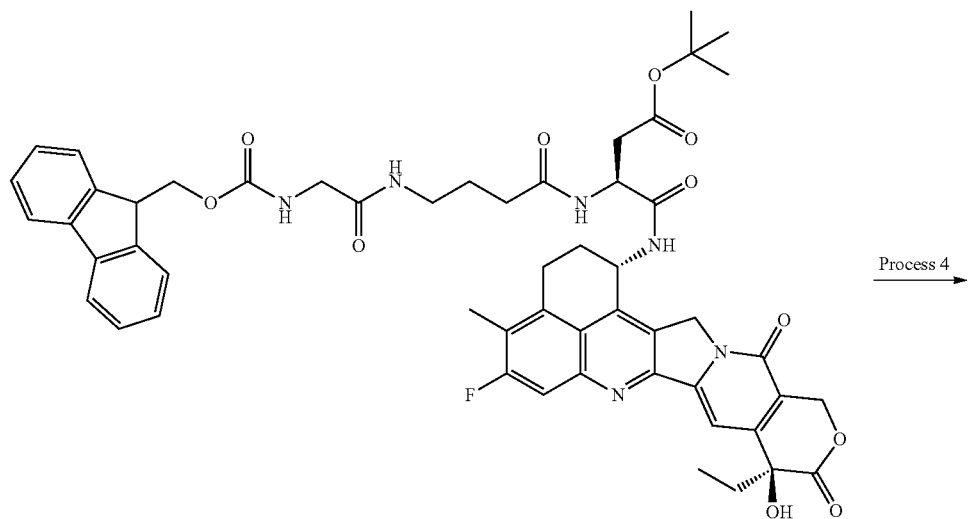
Process 4
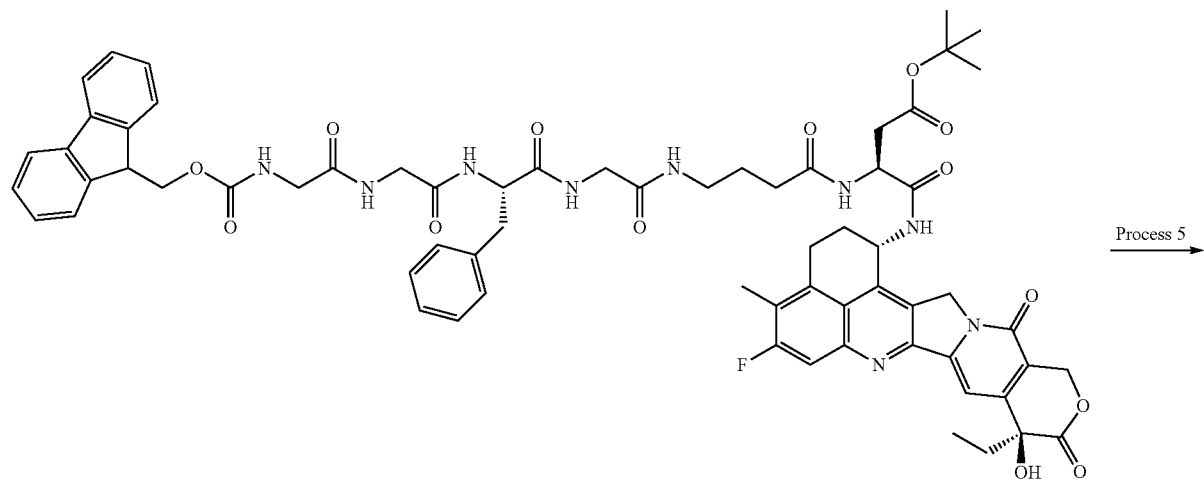
Process 5
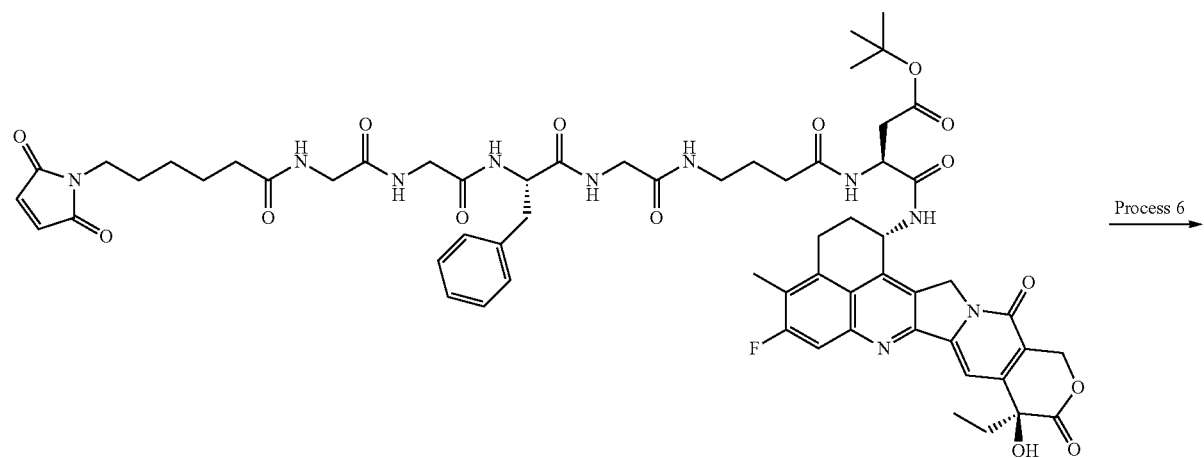
Process 6

-continued

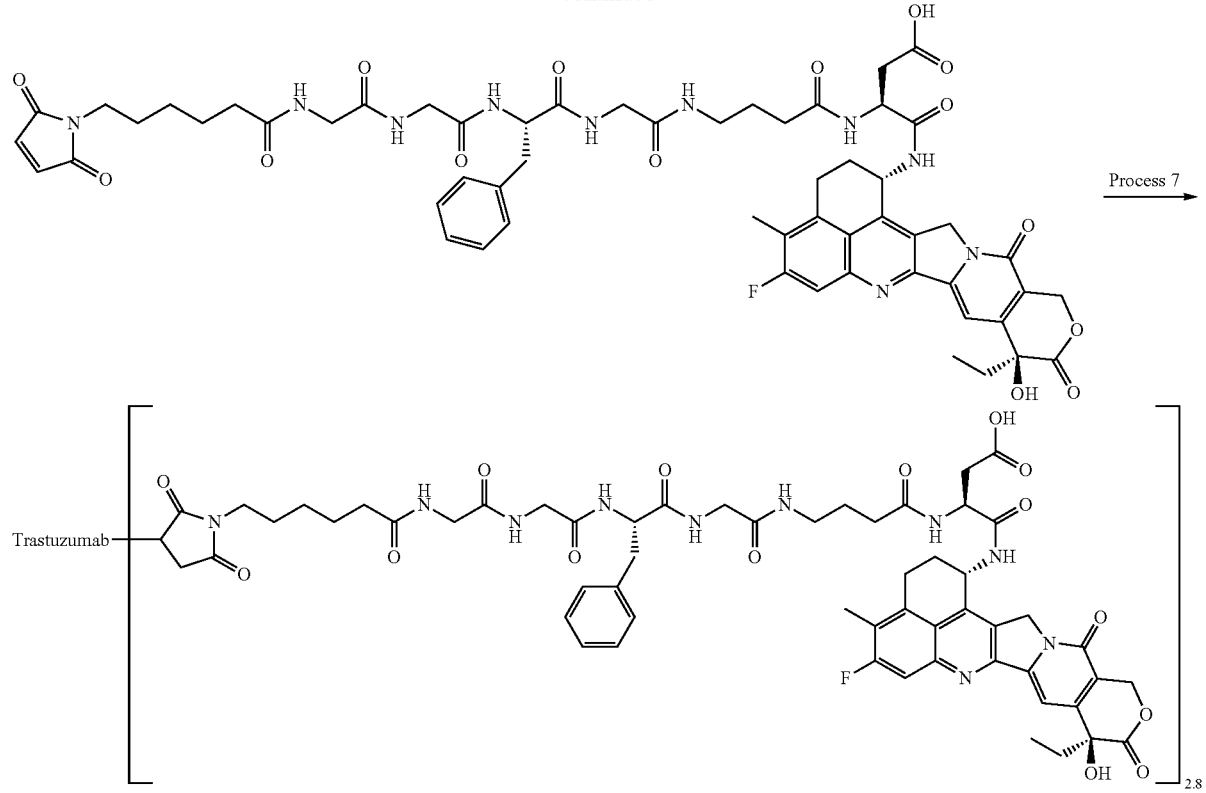

Process 7 →

Process 1: 4-[[2-(9H-Fluoren-9-ylmethoxycarbonylamino)acetyl]amino]butanoic acid 4-[(2-Aminoacetyl)amino]butanoic acid (0.500 g, 3.12 mmol) was dissolved in a saturated sodium bicarbonate aqueous solution (20.0 mL). N-(Fluorenylmethyloxycarbonyloxy)succinimide (1.58 g, 4.68 mmol) dissolved in 1,4-dioxane (10.0 mL) was added dropwise and stirred for 3 days. After washing with diethyl ether, the aqueous layer was rendered acidic with 5 N hydrochloric acid, and the deposited precipitates were collected by suction filtration to yield the titled compound as a pale yellow solid (1.19 g, 99%).

$^1$H-NMR (400 MHz, DMSO-$d_6$) δ: 1.61-1.62 (2H, m), 2.21 (2H, t, J=7.4 Hz), 3.07 (2H, q, J=6.5 Hz), 3.57 (2H, t, J=2.9 Hz), 4.21-4.29 (3H, m), 7.33 (2H, t, J=7.4 Hz), 7.42 (2H, t, J=7.4 Hz), 7.51 (1H, t, J=6.1 Hz), 7.70 (2H, t, J=10.4 Hz), 7.86 (1H, t, J=5.5 Hz), 7.90 (3H, d, J=7.4 Hz).

Process 2: tert-Butyl N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-N²-[(9H-fluoren-9-ylmethoxy)carbonyl]-L-α-asparaginate Methanesulfonic acid salt of exatecan (1.00 g, 1.88 mmol) was reacted in the same manner as Process 1 of Example 1 by using N-α-(9-fluorenylmethoxycarbonyl)-L-aspartic acid β-t-butyl ester (0.930 mg, 2.26 mmol) instead of 4-(tert-butoxycarbonylamino)butanoic acid to yield the titled compound as a pale yellow solid (0.890 mg, 57%).

$^1$H-NMR (400 MHz, CDCl$_3$) δ: 1.01 (3H, t,), 1.35 (9H, s), 1.83 (2H, brs), 2.13-2.26 (2H, m), 2.32 (3H, s), 2.67-2.69 (1H, m), 2.92-3.02 (4H, m), 3.46 (1H, s), 4.09 (1H, s), 4.33 (2H, s), 4.57 (1H, s), 4.99-5.18 (2H, m), 5.53-5.56 (1H, m), 6.28 (1H, s), 7.16-7.67 (11H, m), 7.99 (1H, s).

MS (APCI) m/z: 829 (M+H)$^+$.

Process 3: tert-Butyl N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-N²-[4-({N-[(9H-fluoren-9-ylmethoxy)carbonyl]glycyl}amino)butanoyl]-L-α-asparaginate The compound (0.500 g, 0.604 mmol) obtained in Process 2 above was dissolved in N,N-dimethylformamide (3.00 mL), charged with piperidine (0.598 mL, 6.04 mmol), and stirred for 1 hour. The solvent was removed by dryness under reduced pressure and the residues obtained were dissolved in N,N-dimethylformamide (10.0 mL). A reaction solution obtained by dissolving the compound (0.277 mg, 0.724 mmol) obtained in Process 1 above, 1-(3-dimethylaminopropyl)-3-ethylcarbodiimide hydrochloride (0.139 mg, 0.724 mmol), and N-hydroxysuccinimide (0.0834 mg, 0.724 mmol) in dichloromethane (5.00 mL) and stirring it for 2 hours was added dropwise to the solution obtained above, and stirred for 15.5 hours. After adding a 10% citric acid aqueous solution (20.0 mL), it was extracted with chloroform (20.0 mL, 3 times), and the organic layer was washed with a saturated sodium chloride aqueous solution, then dried over anhydrous sodium sulfate, and filtered. The solvent in the filtrate was removed under reduced pressure and the residues obtained were purified by silica gel column chromatography [chloroform-chloroform:methanol=8:2 (v/v)] to yield the titled compound as a pale yellow solid (0.333 g, 57%).

$^1$H-NMR (400 MHz, DMSO-d$_6$) δ: 0.86 (3H, brs), 1.26 (9H, s), 1.57-1.59 (2H, m), 1.84-1.87 (2H, m), 2.14-2.23 (4H, m), 2.37 (3H, s), 2.67-2.71 (1H, m), 3.04-3.40 (5H, m), 3.54-3.57 (2H, m), 4.13-4.25 (3H, m), 4.58-4.60 (1H, m), 5.08-5.24 (2H, m), 5.41-5.53 (3H, m), 6.53 (1H, s), 7.31-7.46 (6H, m), 7.70-7.89 (6H, m), 8.16-8.24 (1H, m), 8.59-8.61 (1H, m).

MS (APCI) m/z: 971 (M+H)$^+$.

Process 4: tert-Butyl (11S,22S)-11-benzyl-22-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamoyl}-1-(9H-fluoren-9-yl)-3,6,9,12,15,20-hexaoxo-2-oxa-4,7,10,13,16,21-hexaazatetracosanoate The compound (413 mg, 0.418 mmol) obtained in Process 3 above was reacted in the same manner as Process 3 above by using (2S)-2-[[2-[[2-(9H-fluoren-9-ylmethoxycarbonylamino)acetyl]amino]acetyl]amino]-3-phenyl-propanoic acid instead of the compound obtained in Process 1 above to yield the titled compound as a yellow solid (122.6 mg, 32%).

$^1$H-NMR (400 MHz, CD$_3$OD) δ: 0.90 (3H, t, J=6.8 Hz), 1.29 (9H, s), 1.40-1.46 (2H, m), 1.66-1.78 (2H, m), 2.20-2.28 (4H, m), 2.25 (3H, s), 2.67 (1H, t, J=8.8 Hz), 2.79-3.18 (6H, m), 3.42-3.47 (1H, m), 3.59-3.91 (6H, m), 4.03 (1H, t, J=6.7 Hz), 4.18-4.21 (1H, m), 4.34-4.41 (2H, m), 4.70 (1H, t, J=6.5 Hz), 5.17 (2H, t, J=18.2 Hz), 5.41-5.45 (3H, m), 7.15-7.25 (9H, m), 7.34-7.41 (2H, m), 7.50 (2H, d, J=7.4 Hz), 7.60-7.63 (2H, m).

MS (APCI) m/z: 1232 (M+H)$^+$.

Process 5: tert-Butyl (3S,14S)-14-benzyl-27-(2,5-dioxo-2,5-dihydro-1H-pyrrol-1-yl)-3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamoyl}-5,10,13,16,19,22-hexaoxo-4,9,12,15,18,21-hexaazaheptacosanoate The compound (100 mg, 81.1 μmol) obtained in Process 4 above was dissolved in N,N-dimethylformamide (3.00 mL), charged with piperidine (9.64 μL, 97.4 μmol), and stirred for 1 hour. The solvent was removed by dryness under reduced pressure and the residues obtained were dissolved in N,N-dimethylformamide (5.00 mL). After adding N-succinimidyl 6-maleimidohexanoate (30.0 mg, 97.4 μmol), it was stirred for 2 days. After adding a 10% citric acid aqueous solution (20.0 mL), it was extracted with chloroform (20.0 mL, 3 times), and the organic layer was washed with a saturated sodium chloride aqueous solution, then dried over anhydrous sodium sulfate, and filtered. The solvent in the filtrate was removed under reduced pressure and the residues obtained were purified by silica gel column chromatography [chloroform:methanol=10:1 (v/v)] to yield the titled compound as a pale yellow solid (15.5 mg, 16%).

$^1$H-NMR (400 MHz, CD$_3$OD) δ: 0.98 (3H, t, J=7.3 Hz), 1.21-1.30 (2H, m), 1.33 (9H, s), 1.44-1.79 (6H, m), 1.93-1.94 (1H, m), 2.16-2.48 (6H, m), 2.40 (3H, s), 2.70-2.81 (1H, m), 2.95-3.00 (2H, m), 3.13-3.21 (3H, m), 3.39-3.51 (4H, m), 3.75-3.93 (6H, m), 4.39-4.44 (1H, m), 4.61 (2H, s), 5.07-5.16 (1H, m), 5.35 (2H, dd, J=17.3, 5.1 Hz), 5.55-5.60 (2H, m), 6.76 (2H, s), 7.20-7.26 (5H, m), 7.56-7.58 (2H, m).

MS (APCI) m/z: 1203 (M+H)$^+$.

Process 6: (3S,14S)-14-Benzyl-27-(2,5-dioxo-2,5-dihydro-1H-pyrrol-1-yl)-3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamoyl}-5,10,13,16,19,22-hexaoxo-4,9,12,15,18,21-hexaazaheptacosanoic acid The compound (15.5 mg, 12.9 μmol) obtained in Process 5 above was reacted in the same manner as Process 2 of Example 1 to yield the titled compound as a pale yellow solid (5.50 mg, 37%).

$^1$H-NMR (400 MHz, CD$_3$OD) δ: 0.99 (3H, t, J=7.4 Hz), 1.22-1.30 (2H, m), 1.49-1.79 (6H, m), 1.94 (1H, t, J=7.8 Hz), 2.20-2.22 (4H, m), 2.30-2.40 (2H, m), 2.39 (3H, s), 2.72-2.77 (2H, m), 2.87-3.26 (6H, m), 3.43-3.51 (2H, m), 3.59-3.69 (2H, m), 3.77-3.87 (4H, m), 4.38-4.45 (1H, m), 4.69 (2H, q, J=6.7 Hz), 5.15 (1H, t, J=18.0 Hz), 5.32-5.38 (2H, m), 5.51-5.60 (2H, m), 6.76 (2H, s), 7.19-7.23 (5H, m), 7.53-7.55 (2H, m).

MS (APCI) m/z: 1147 (M+H)$^+$.

Process 7: Antibody-Drug Conjugate (56)

By using the trastuzumab produced in Reference Example 1 and the compound obtained in Process 6 above, the titled antibody-drug conjugate was obtained in the same manner as Process 6 of Example 2.

Antibody concentration: 1.60 mg/mL, antibody yield: 9.6 mg (77%), and average number of conjugated drug molecules (n) per antibody molecule: 2.8.

Example 57 Antibody-Drug Conjugate (57)

[Formula 110]

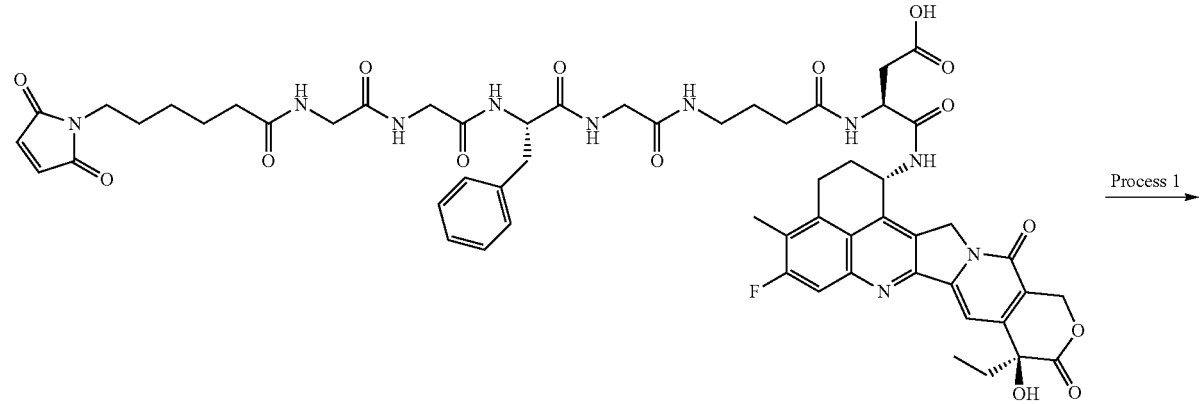

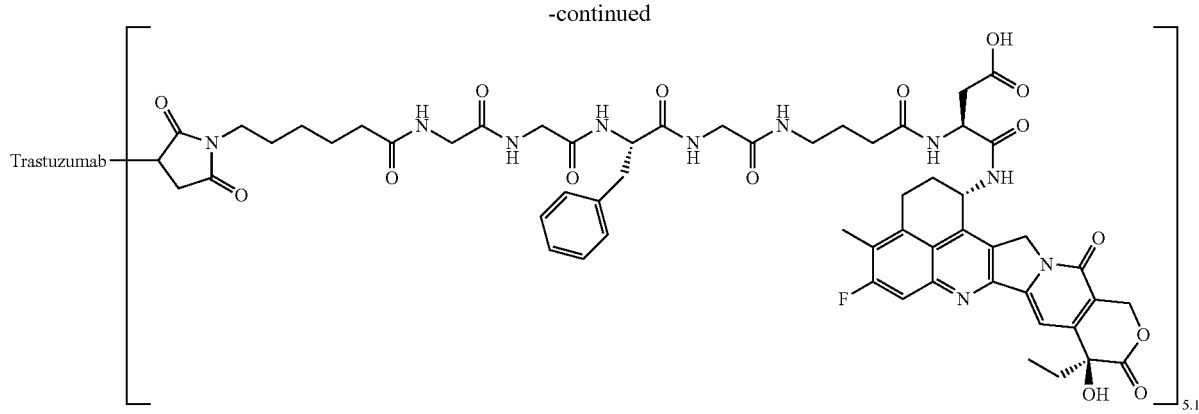

Process 1: Antibody-Drug Conjugate (57)

By using the trastuzumab produced in Reference Example 1 and the compound obtained in Process 6 of Example 56, the titled antibody-drug conjugate was obtained in the same manner as Process 1 of Example 3.
Antibody concentration: 1.53 mg/mL, antibody yield: 9.2 mg (74%), and average number of conjugated drug molecules (n) per antibody molecule: 5.1.

Example 58 Antibody-Drug Conjugate (58)

[Formula 111]

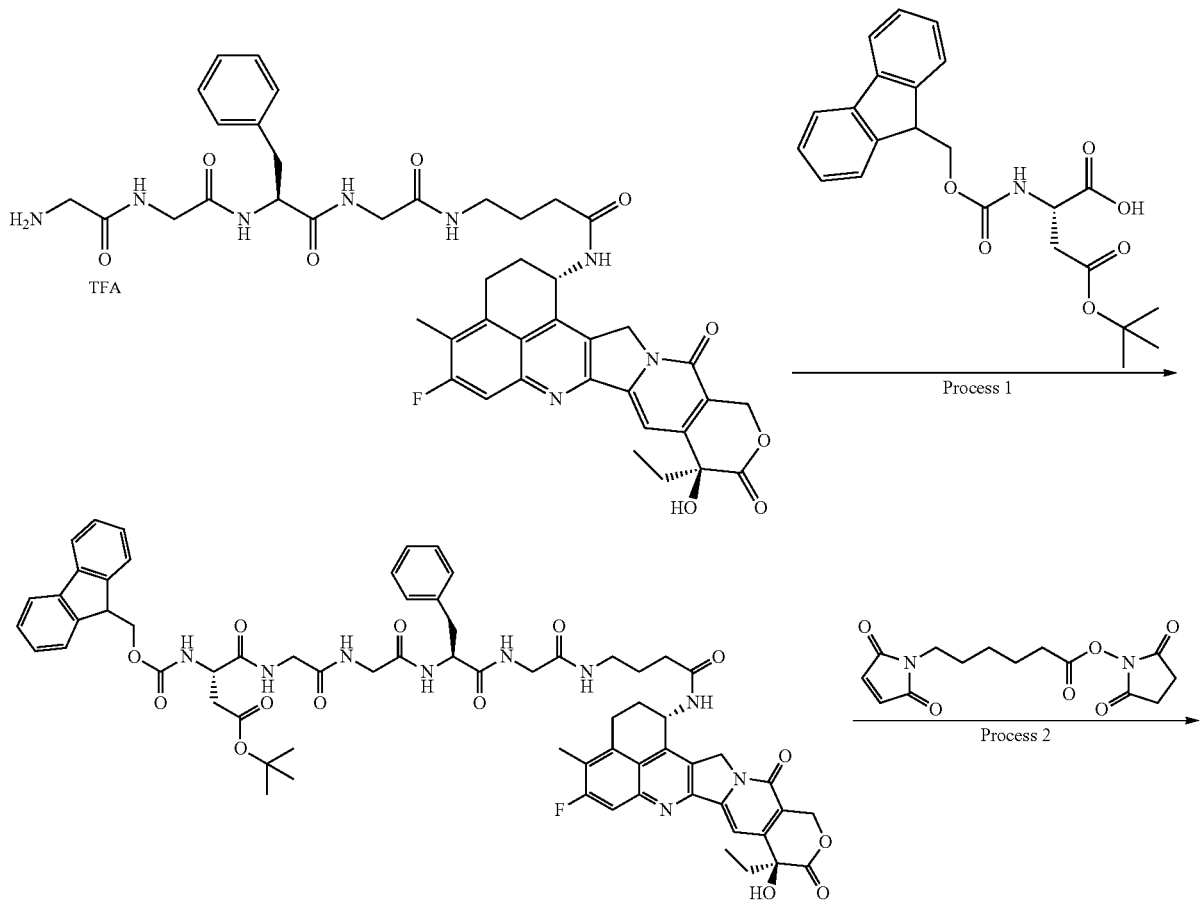

319  320
-continued
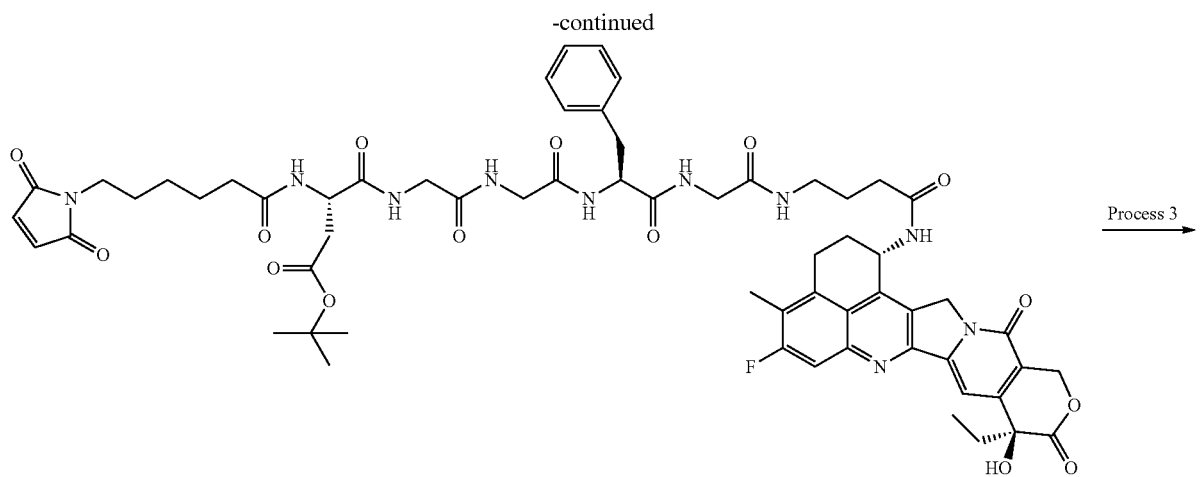
Process 3 →
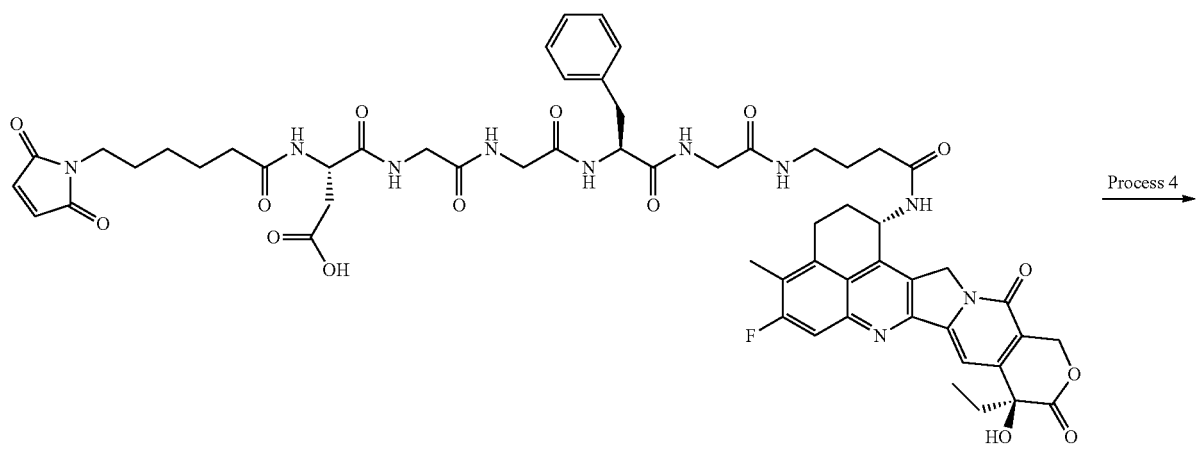
Process 4 →
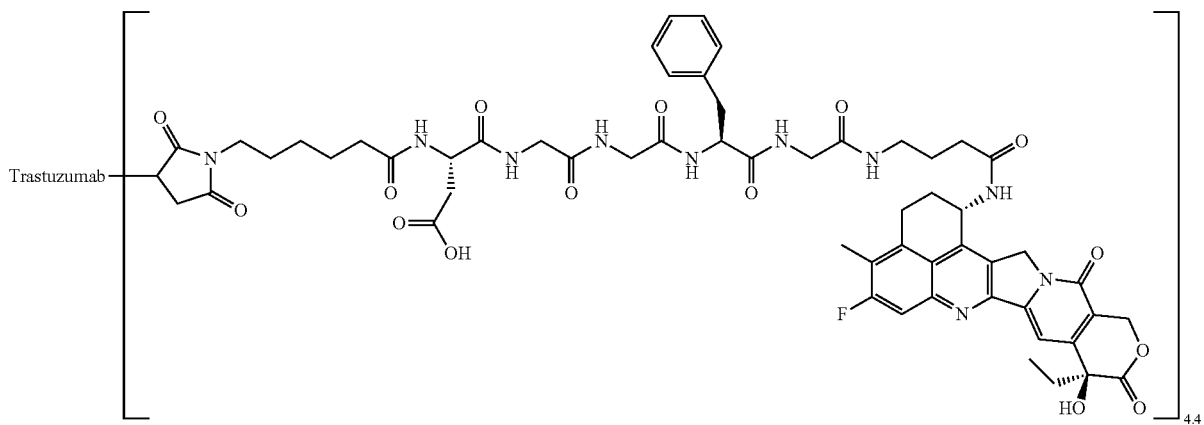

Process 1: tert-Butyl (3S,12S)-12-benzyl-21-{[(1S, 9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-{[(9H-fluoren-9-ylmethoxy)carbonyl]amino}-4,7,10,13,16,21-hexaoxo-5,8,11,14,17-pentaazaheneicosan-1-oate (2S)-4-tert-Butoxy-2-{[(9H-fluoren-9-ylmethoxy)carbonyl]amino}-4-oxobutanoic acid (0.625 g, 1.52 mmol) was dissolved in dichloromethane (10.0 mL), charged with N-hydroxysuccinimide (0.175 g, 1.52 mol) and 1-(3-dimethylaminopropyl)-3-ethylcarbodiimide hydrochloride (0.291 g, 1.52 mmol), and stirred for 1 hour. The reaction solution was added dropwise to an N, N-dimethylformamide solution (10.0 mL) charged with the compound (1.00 g, 1.01 mmol) obtained in Process 2 of Example 2, and stirred at room temperature for 20 hours. The solvent was removed under reduced pressure and the residues obtained were purified by silica gel column chromatography [chloroform-chloroform:methanol=8:2 (v/v)] to yield the titled compound as a pale yellow solid (0.873 g, 70%).

$^1$H-NMR (400 MHz, DMSO-$d_6$): 0.88 (3H, t, J=7.4 Hz), 1.37 (9H, s), 1.68-1.78 (2H, m), 1.81-1.93 (2H, m), 2.10-2.23 (4H, m), 2.41 (3H, s), 2.68-2.85 (3H, m), 2.99-3.22 (5H, m), 3.58-3.81 (6H, m), 4.19-4.36 (3H, m), 4.38-4.52 (2H, m), 5.17 (1H, d, J=19.2 Hz), 5.25 (1H, d, J=19.2 Hz), 5.43 (2H, s), 5.54-5.62 (1H, m), 6.55 (1H, s), 7.15-7.34 (8H, m), 7.41 (2H, t, J=7.2 Hz), 7.66-7.75 (4H, m), 7.81 (1H, d, J=11.0 Hz), 7.88 (2H, d, J=7.4 Hz), 8.01-8.06 (1H, m), 8.14 (1H, d, J=8.2 Hz), 8.17-8.22 (1H, m), 8.25-8.30 (1H, m), 8.47 (1H, d, J=8.6 Hz). MS (APCI) m/z: 1232 (M+H)$^+$.

Process 2: tert-Butyl (3S,12S)-12-benzyl-3-{[6-(2,5-dioxo-2,5-dihydro-1H-pyrrol-1-yl)hexanoyl]amino}-21-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,16,21-hexaoxo-5,8,11,14,17-pentaazaheneicosan-1-oate The compound (0.800 g, 0.649 mmol) obtained in Process 1 above was dissolved in N,N-dimethylformamide (3.00 mL), charged with piperidine (0.643 mL, 6.49 mmol), and stirred for 1 hour. The solvent was removed by dryness under reduced pressure and the residues obtained were dissolved in N,N-dimethylformamide (10 mL). After adding N-succinimidyl 6-maleimidohexanoate (0.300 g, 0.974 mmol), it was stirred for 20 hours. The solvent was removed under reduced pressure and the residues obtained were purified by silica gel column chromatography [[chloroform-chloroform:methanol=8:2 (v/v)] to yield the titled compound as a pale yellow solid (0.224 g, 29%).

$^1$H-NMR (400 MHz, DMSO-$d_6$) δ: 0.87 (3H, t, J=7.6 Hz), 1.15-1.22 (2H, m), 1.35 (9H, s), 1.44-1.47 (4H, m), 1.71-1.73 (2H, m), 1.80-1.91 (2H, m), 2.08 (2H, t, J=7.6 Hz), 2.13-2.20 (4H, m), 2.40 (3H, s), 2.67 (1H, dt, J=11.1, 4.8 Hz), 2.78 (1H, dd, J=13.6, 9.4 Hz), 2.99-3.17 (6H, m), 3.31-3.36 (2H, m), 3.57-3.76 (6H, m), 4.45-4.47 (1H, m), 4.57-4.60 (1H, m), 5.16 (1H, d, J=18.7 Hz), 5.25 (1H, d, J=18.7 Hz), 5.42 (2H, s), 5.55-5.60 (1H, m), 6.53 (1H, s), 6.99 (2H, s), 7.15-7.27 (5H, m), 7.31 (1H, s), 7.70 (1H, t, J=5.4 Hz), 7.80 (1H, d, J=10.9 Hz), 7.99 (1H, t, J=5.7 Hz), 8.09-8.12 (3H, m), 8.25 (1H, t, J=6.0 Hz), 8.45 (1H, d, J=9.1 Hz).

MS (APCI) m/z: 1203 (M+H)$^+$.

Process 3: N-[6-(2,5-Dioxo-2,5-dihydro-1H-pyrrol-1-yl)hexanoyl]-L-α-aspartylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (0.224 g, 0.186 mmol) obtained in Process 2 above was reacted in the same manner as Process 2 of Example 1 to yield the titled compound as a pale yellow solid (21.2 mg, 10%).

$^1$H-NMR (400 MHz, DMSO-$d_6$) δ: 0.87 (3H, t, J=7.2 Hz), 1.13-1.21 (2H, m), 1.42-1.45 (6H, m), 1.70-1.72 (2H, m), 1.85-1.88 (2H, m), 2.06-2.20 (6H, m), 2.39 (3H, s), 2.63-2.67 (1H, m), 2.78-2.81 (1H, m), 3.04-3.12 (6H, m), 3.63-3.70 (6H, m), 4.46-4.52 (2H, m), 5.16 (1H, d, J=19.2 Hz), 5.25 (1H, d, J=18.8 Hz), 5.42 (2H, s), 5.55-5.58 (1H, m), 6.53 (1H, s), 6.99 (2H, s), 7.18-7.23 (6H, m), 7.30 (1H, s), 7.71 (1H, t, J=5.5 Hz), 7.79 (1H, d, J=10.9 Hz), 7.99-8.02 (1H, m), 8.10-8.11 (3H, m), 8.27-8.30 (1H, m), 8.47-8.50 (1H, m).

MS (APCI) m/z: 1147 (M+H)$^+$.

Process 8: Antibody-Drug Conjugate (58)

Reduction of the antibody: The trastuzumab produced in Reference Example 1 was prepared to have an antibody concentration of 10 mg/mL with PBS6.0/EDTA by using the Common procedure B (as absorption coefficient at 280 nm, 1.37 mLmg$^{-1}$ cm$^{-1}$ was used) and Common procedure C-1. The solution (1 mL) was placed in a 1.5 mL tube and charged with an aqueous solution of 10 mM tris(2-carboxyethyl)phosphine hydrochloride (TCEP, Tokyo Chemical Industry Co., Ltd.) (0.032 mL) and an aqueous solution of 1 M dipotassium hydrogenphosphate (Nacalai Tesque, Inc.; 0.100 mL) to prepare a reaction solution in which the molar ratio of TCEP to the antibody was 4.6. After confirming that the solution had a pH of 7.4±0.1, the disulfide bond at the hinge part in the antibody was reduced by incubating at 37° C. for 1 hour.

Conjugation between antibody and drug linker: After adding a DMSO solution containing 10 mM of the compound obtained in Process 3 above (0.062 mL) to the above solution at room temperature to prepare a reaction solution in which the molar ratio of the drug linker to the antibody was 9.2, it was stirred by using a tube rotator (MTR-103, manufactured by AS ONE Corporation) for conjugating the drug linker to the antibody at room temperature for 40 minutes. Next, an aqueous solution (0.0062 mL) of 100 mM N-acetylcysteine (NAC) was added thereto to prepare a reaction solution in which the molar ratio of NAC to the antibody was 18.4, and it was stirred at room temperature to terminate the reaction of the drug linker for another 20 minutes.

Purification: The above solution was subjected to purification using the Common procedure D-1 (PBS6.0 was used as buffer solution) to yield 6 mL of a solution containing the compound of interest.

Antibody concentration: 1.22 mg/mL, antibody yield: 7.3 mg (73%), and average number of conjugated drug molecules (n) per antibody molecule: 4.4.

Example 59 Antibody-Drug Conjugate (59)

[Formula 112]

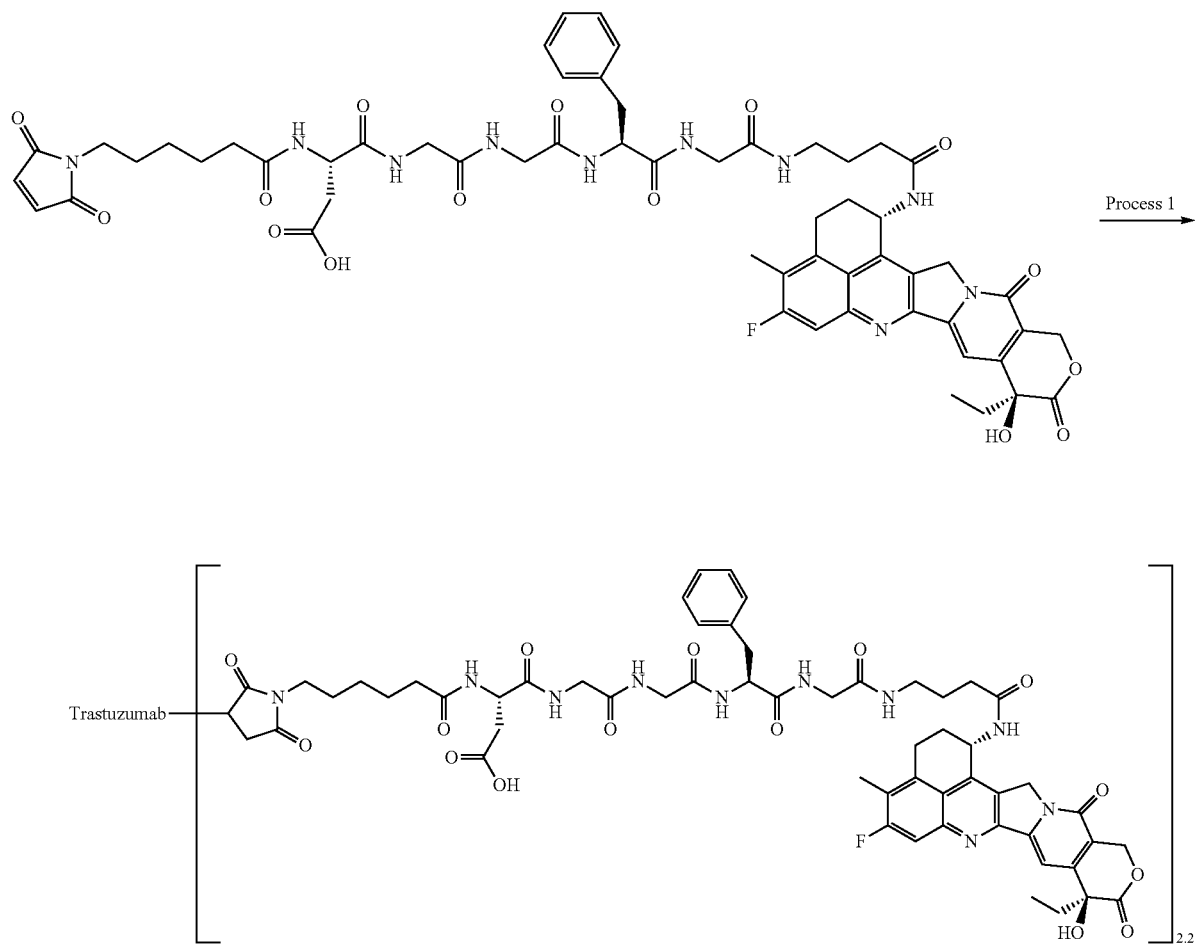

Process 1: Antibody-Drug Conjugate (59)

Reduction of the antibody: The trastuzumab produced in Reference Example 1 was prepared to have an antibody concentration of 10 mg/mL with PBS6.0/EDTA by using the Common procedure B (as absorption coefficient at 280 nm, 1.37 mLmg$^{-1}$ cm$^{-1}$ was used) and Common procedure C-1. The solution (1 mL) was placed in a 1.5 mL tube and charged with an aqueous solution of 10 mM TCEP (0.016 mL) and an aqueous solution of 1 M dipotassium hydrogenphosphate (0.050 mL) to prepare a reaction solution in which the molar ratio of TCEP to the antibody was 2.3. After confirming that the solution had a pH of 7.4±0.1, the disulfide bond at the hinge part in the antibody was reduced by incubating at 37° C. for 1 hour.

Conjugation between antibody and drug linker: After adding a DMSO solution containing 10 mM of the compound obtained in Process 3 of Example 58 (0.031 mL) to the above solution at room temperature to prepare a reaction solution in which the molar ratio of the drug linker to the antibody was 4.6, it was stirred by using a tube rotator for conjugating the drug linker to the antibody at room temperature for 40 minutes. Next, an aqueous solution (0.0062 mL) of 100 mM NAC was added thereto to prepare a reaction solution in which the molar ratio of NAC to the antibody was 9.2, and it was stirred at room temperature to terminate the reaction of the drug linker for another 20 minutes.

Purification: The above solution was subjected to purification using the Common procedure D-1 (PBS6.0 was used as buffer solution) to yield 6 mL of a solution containing the compound of interest. Two batches of this sample were prepared to yield 12 mL in total, 8 mL of which was concentrated to yield 2.5 mL of a solution containing the compound of interest. By using the Common procedure B, Common procedure E, and Common procedure F, the following characteristic values were obtained.

Antibody concentration: 3.82 mg/mL, antibody yield: 9.6 mg (72%), and average number of conjugated drug molecules (n) per antibody molecule: 2.2.

Example 60 Antibody-Drug Conjugate (60)

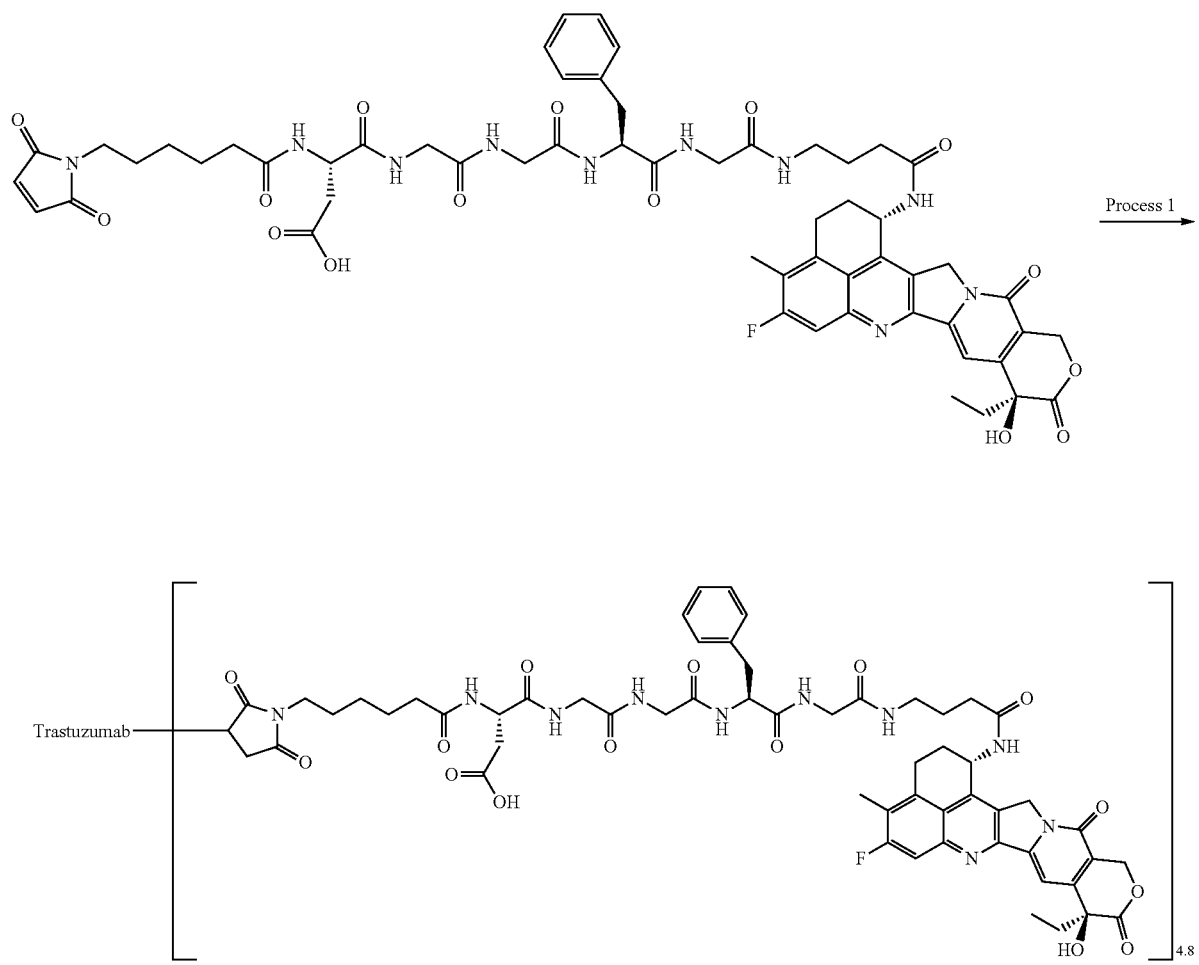

Process 1: Antibody-Drug Conjugate (60) A solution containing the compound of interest was obtained in the same manner as Process 4 of Example 58 except that the amount of the antibody used as a raw material was changed to 80 mg (i.e., 8 mL of a solution having an antibody concentration of 10 mg/mL with PBS6.0/EDTA as a medium) and the reaction vessel was changed to a 50 mL polypropylene tube. By using a centrifugal ultrafiltration filter (Amicon Ultra-4, molecular weight cutoff: 50 k), concentration was performed to yield 13 mL of a solution containing the compound of interest. The following characteristic values were obtained.

Antibody concentration: 4.16 mg/mL, antibody yield: 54 mg (68%), and average number of conjugated drug molecules (n) per antibody molecule: 4.8.

Example 61 Antibody-Drug Conjugate (61)

[Formula 114]

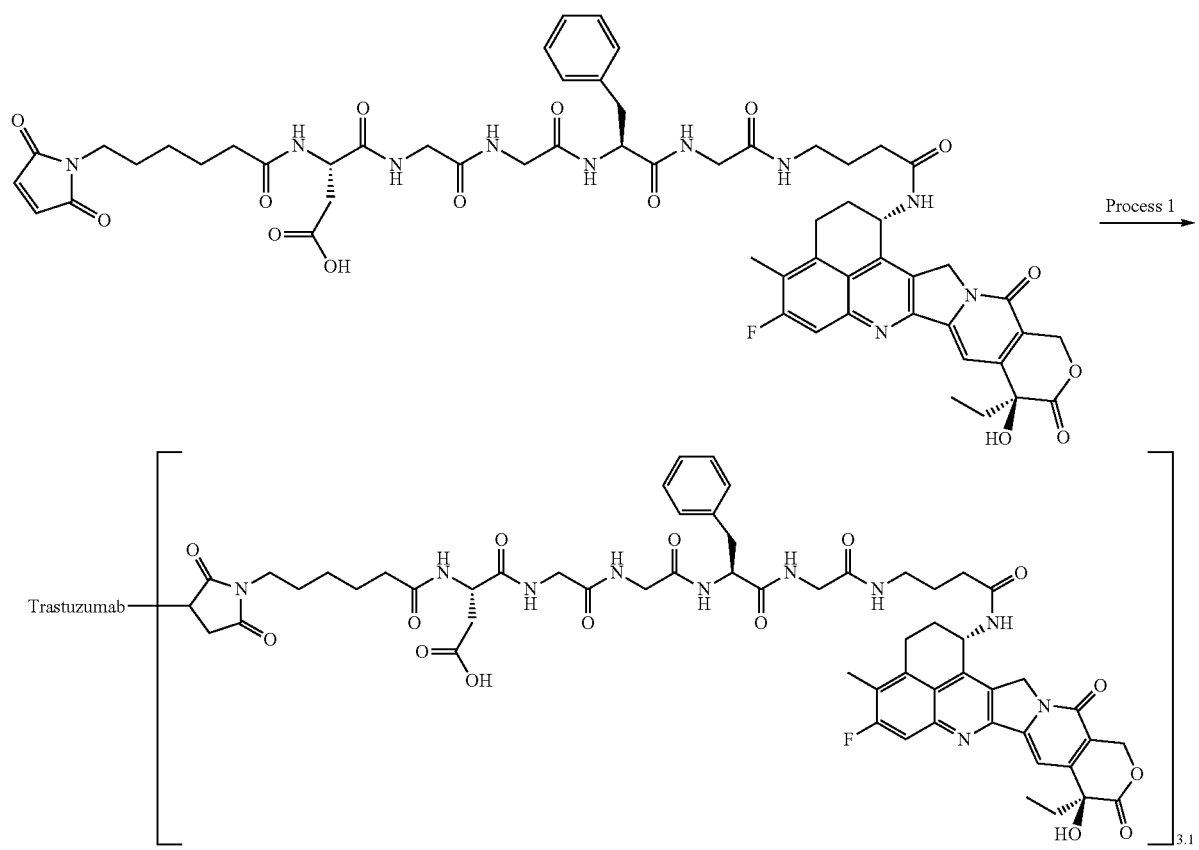

Process 1: Antibody-Drug Conjugate (61)

A solution containing the compound of interest was obtained in the same manner as Process 1 of Example 59 except that the amount of the antibody used as a raw material was changed to 80 mg (i.e., 8 mL of a solution having an antibody concentration of 10 mg/mL with PBS6.0/EDTA as a medium) and the reaction vessel was changed to a 50 mL polypropylene tube. By using a centrifugal ultrafiltration filter (Amicon Ultra-4, molecular weight cutoff: 50 k), concentration was performed to yield 17 mL of a solution containing the compound of interest. The following characteristic values were obtained.

Antibody concentration: 3.79 mg/mL, antibody yield: 64 mg (80%), and average number of conjugated drug molecules (n) per antibody molecule: 3.1.

Example 62 Antibody-Drug Conjugate (62)

[Formula 115]

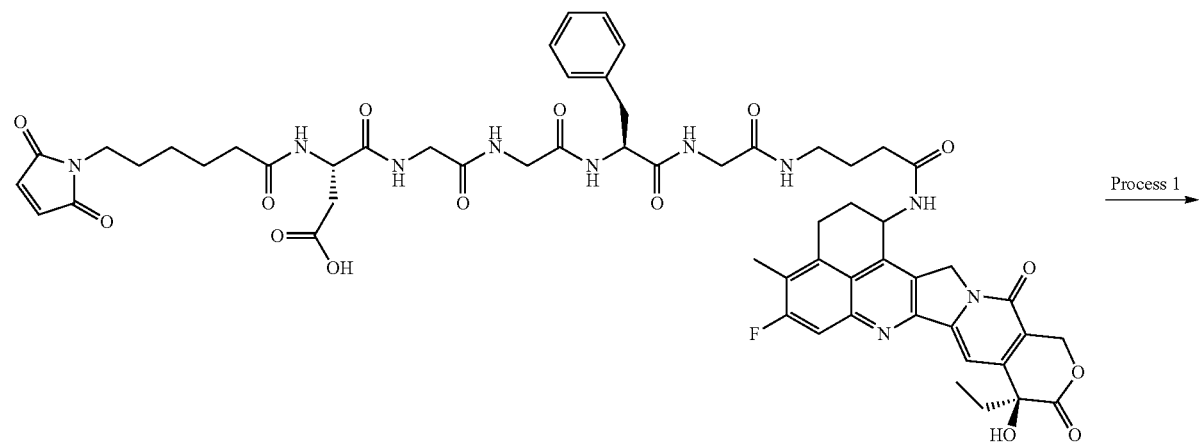

-continued

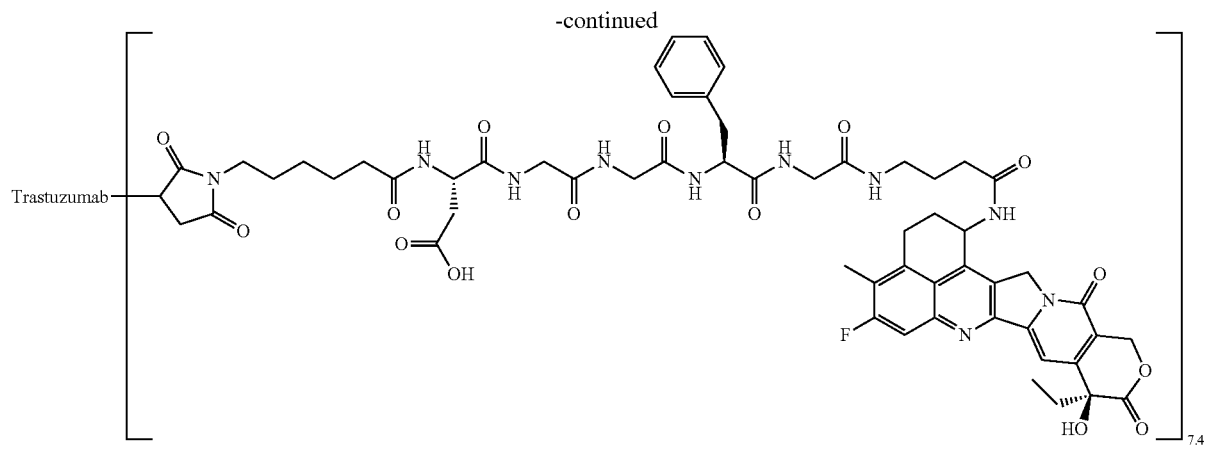

Process 1: Antibody-Drug Conjugate (62)

Reduction of the antibody: The trastuzumab produced in Reference Example 1 was prepared to have an antibody concentration of 10 mg/mL with PBS6.0/EDTA by using the Common procedure B (as absorption coefficient at 280 nm, 1.37 mLmg$^{-1}$ cm$^{-1}$ was used) and Common procedure C-1. The solution (5.0 mL) was collected into a 15 mL tube and charged with an aqueous solution of 30 mM TCEP (0.0777 mL; 6.9 equivalents per antibody molecule) and an aqueous solution of 1 M dipotassium hydrogenphosphate (0.250 mL). After confirming that the solution had a pH of 7.4±0.1, the disulfide bond at the hinge part in the antibody was reduced by incubating at 37° C. for 1 hour.

Conjugation between antibody and drug linker: After incubating the above solution for 10 minutes at 22° C., a DMSO solution (0.1555 mL; 13.8 equivalents per antibody molecule) containing 30 mM of the compound obtained in Process 3 of Example 58 was added thereto and incubated for conjugating the drug linker to the antibody at 22° C. for 40 minutes. Next, an aqueous solution (0.0933 mL; 27.6 equivalents per antibody molecule) of 100 mM NAC was added thereto and incubated at 22° C. to terminate the reaction of the drug linker for another 20 minutes.

Purification: The above solution was subjected to purification using the Common procedure D-1 (ABS was used as buffer solution) to yield a solution containing the compound of interest.

Physicochemical characterization: By using the Common procedure B, Common procedure E, and Common procedure F, the following characteristic values were obtained.

Antibody concentration: 3.35 mg/mL, antibody yield: 29.5 mg (59%), and average number of conjugated drug molecules (n) per antibody molecule: 7.4.

Example 63 Antibody-Drug Conjugate (63)

[Formula 116]

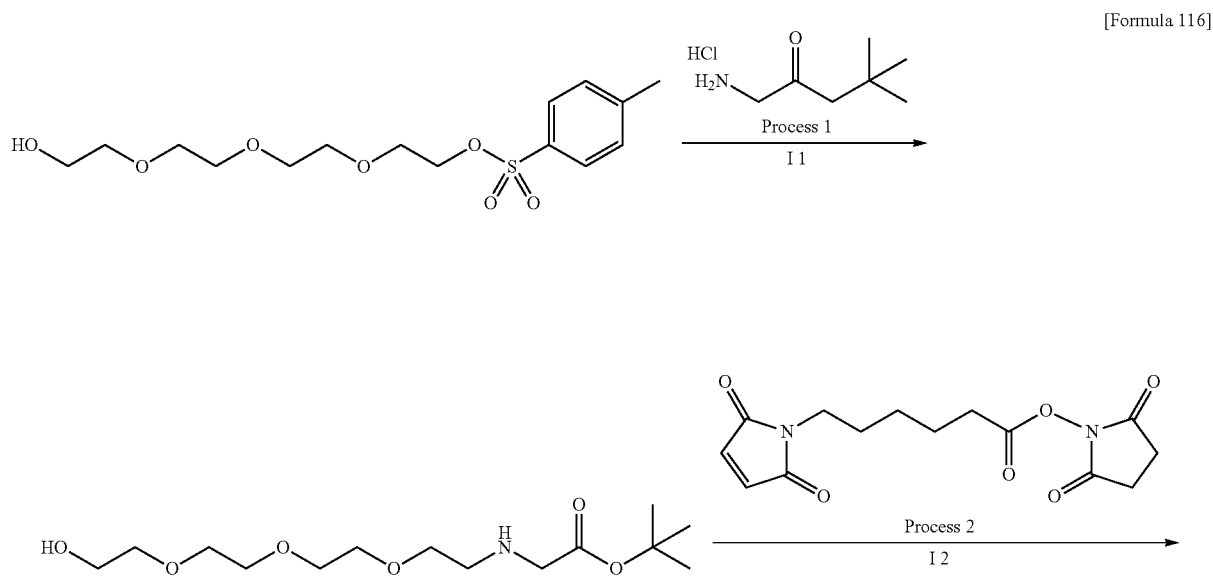

331
-continued
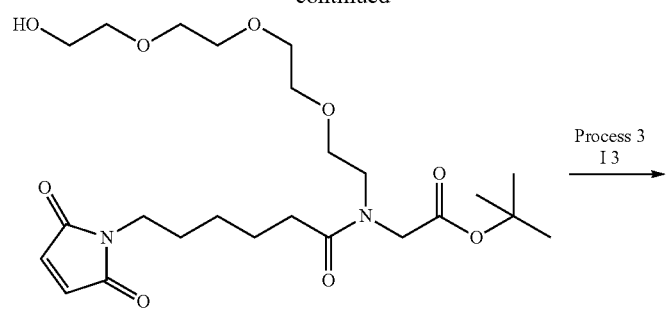
Process 3
I 3 →
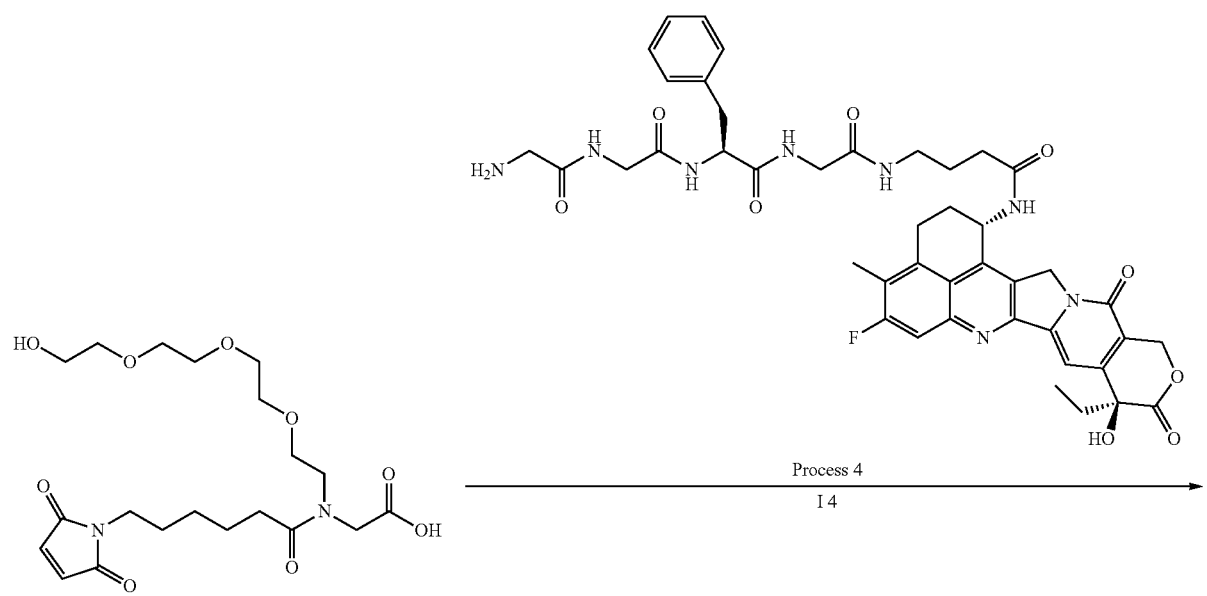
Process 4
I 4 →
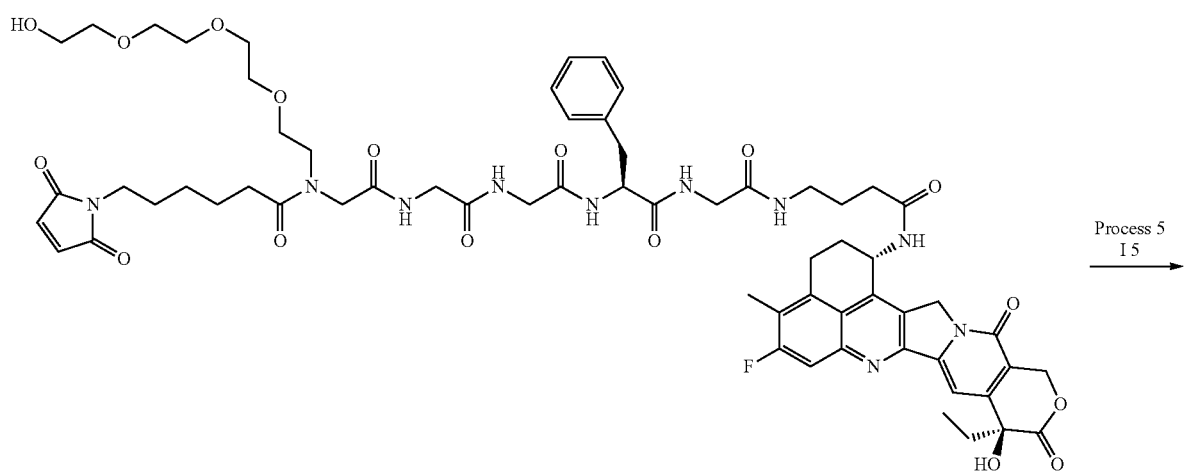
Process 5
I 5 →

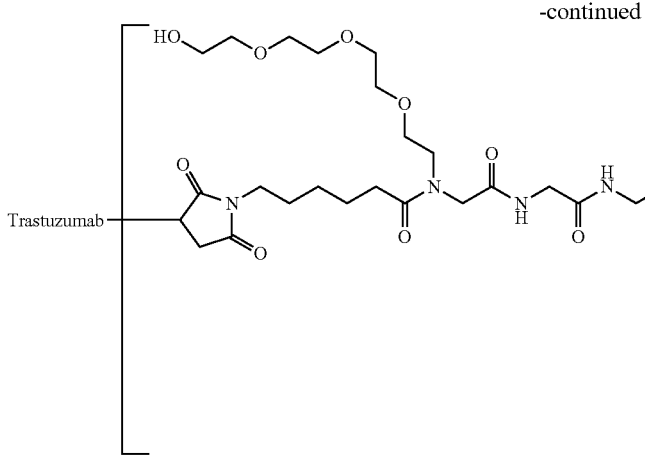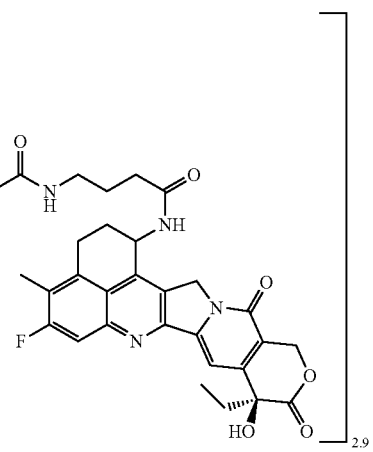

Process 1: tert-Butyl N-(2-{2-[2-(2-hydroxyethoxy)ethoxy]ethoxy}ethyl)glycinate To an N,N-dimethylformamide (50.0 mL) solution of 2-{2-[2-(2-hydroxyethoxy)ethoxy]ethoxy}ethyl 4-methylbenzenesulfonate (Bioorg. Med. Chem. Lett., 2011, Vol. 21, p. 550; 1.75 g, 5.00 mmol) and glycine tert-butyl ester hydrochloride (1.26 g, 7.52 mmol), N,N-diisopropylethylamine (1.94 g, 15.0 mmol) was added and stirred at 60° C. for 10 hours. The reaction solution was charged with chloroform. The organic layer was washed with 1 N hydrochloric acid and the organic layer obtained was dried over sodium sulfate and filtered. The solvent was removed under reduced pressure and the residues obtained were purified by silica gel column chromatography [chloroform-chloroform:methanol=8:1 (v/v)] to yield the titled compound as a colorless oily substance (426 mg, 28%).

$^1$H-NMR (400 MHz, CDCl$_3$) δ: 1.47 (9H, s), 2.80 (2H, t, J=5.3 Hz), 3.32 (2H, s), 3.76-3.54 (17H, m).

Process 2: tert-Butyl N-[6-(2,5-dioxo-2,5-dihydro-1H-pyrrol-1-yl)hexanoyl]-N-(2-{2-[2-(2-hydroxyethoxy)ethoxy]ethoxy}ethyl)glycinate The compound (426 mg, 1.39 mmol) obtained in Process 1 above was reacted in the same manner as Process 8 of Example 5 to yield the titled compound as a colorless oily substance (489 mg, 70%).

$^1$H-NMR (400 MHz, CDCl$_3$) δ: 1.28-1.36 (2H, m), 1.45 (9H, s), 1.57-1.71 (4H, m), 2.39 (2H, t, J=7.3 Hz), 3.48-3.76 (3H, m), 4.02 (2H, s), 6.68 (2H, s).

Process 3: N-[6-(2,5-Dioxo-2,5-dihydro-1H-pyrrol-1-yl)hexanoyl]-N-(2-{2-[2-(2-hydroxyethoxy)ethoxy]ethoxy}ethyl)glycine The compound (489 mg, 0.977 mmol) obtained in Process 2 above was reacted in the same manner as Process 2 of Example 1 to yield the titled compound as a colorless solid (211 mg, 49%).

$^1$H-NMR (400 MHz, CDCl$_3$) δ: 1.38-1.28 (2H, m), 1.73-1.55 (4H, m), 2.28 (2H, t, J=7.0 Hz), 3.50-3.79 (18H, m), 4.12 (2H, s), 6.68 (2H, s).

Process 4: N-[6-(2,5-Dioxo-2,5-dihydro-1H-pyrrol-1-yl)hexanoyl]-N-(2-{2-[2-(2-hydroxyethoxy)ethoxy]ethoxy}ethyl)glycylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3′,4′:6,7]indolizino[1,2-b]quinolin-1-yl]amino}-4-oxobutyl)glycinamide The compound (48.9 mg, 0.110 mmol) obtained in Process 3 above was reacted in the same manner as Process 1 of Example 1 by using the compound (84.0 mg, 0.100 mmol) obtained in Process 2 of Example 2 instead of methanesulfonic acid salt of exatecan to yield the titled compound as a pale yellow solid (54.0 mg, 43%).

$^1$H-NMR (400 MHz, DMSO-d$_6$) δ: 0.87 (3H, t, J=7.2 Hz), 1.14-1.26 (2H, m), 1.39-1.51 (4H, m), 1.68-1.76 (2H, m), 1.81-1.91 (2H, m), 2.08-2.23 (4H, m), 2.40 (3H, s), 2.73-2.84 (1H, m), 2.98-3.21 (5H, m), 3.25-3.79 (26H, m), 3.93 (2H, s), 4.43-4.49 (1H, m), 4.54-4.61 (1H, m), 5.21 (2H, q, J=18.6 Hz), 5.42 (2H, s), 5.54-5.60 (1H, m), 6.53 (1H, s), 7.00 (2H, s), 7.14-7.27 (5H, m), 7.31 (1H, s), 7.68-7.74 (1H, m), 7.80 (1H, d, J=11.0 Hz), 8.02-8.32 (4H, m), 8.46 (1H, d, J=8.6 Hz).

MS (ESI) m/z: 1265 (M+H)$^+$.

Process 5: Antibody-Drug Conjugate (63)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.37 mLmg$^{-1}$ cm$^{-1}$ was used). The solution (1.25 mL) was placed in a 1.5 mL polypropylene tube and charged with an aqueous solution of 10 mM TCEP (0.019 mL; 2.3 equivalents per antibody molecule) and an aqueous solution of 1 M dipotassium hydrogenphosphate (0.0625 mL). After confirming that the solution had a pH of 7.4±0.1, the disulfide bond at the hinge part in the antibody was reduced by incubating at 37° C. for 1 hour.

Conjugation between antibody and drug linker: After adding DMSO (Sigma-Aldrich Co. LLC; 0.109 mL) and a DMSO solution containing 10 mM of the compound obtained in Process 4 above (0.039 mL; 4.6 equivalents per antibody molecule) to the above solution at room temperature, it was stirred by using a tube rotator for conjugating the drug linker to the antibody at room temperature for 40 minutes. Next, an aqueous solution (0.008 mL) of 100 mM NAC was added thereto and stirred at room temperature to terminate the reaction of the drug linker for another 20 minutes.
Purification: The above solution was subjected to purification using the Common procedure D-1 (ABS was used as buffer solution) to yield 6 mL of a solution containing the compound of interest.
Physicochemical characterization: By using the Common procedure B and Common procedure E, the following characteristic values were obtained.
Antibody concentration: 1.76 mg/mL, antibody yield: 10.6 mg (84%), and average number of conjugated drug molecules (n) per antibody molecule: 2.9.

Example 64 Antibody-Drug Conjugate (64)

aqueous solution of 10 mM TCEP (0.039 mL; 4.6 equivalents per antibody molecule) and an aqueous solution of 1 M dipotassium hydrogenphosphate (0.0625 mL). After confirming that the solution had a pH of 7.4±0.1, the disulfide bond at the hinge part in the antibody was reduced by incubating at 37° C. for 1 hour.

Conjugation between antibody and drug linker: After adding DMSO (Sigma-Aldrich Co. LLC; 0.072 mL) and a DMSO solution containing 10 mM of the compound obtained in Process 4 of Example 63 (0.078 mL; 9.2 equivalents per antibody molecule) to the above solution at room temperature, it was stirred by using a tube rotator for conjugating the drug linker to the antibody at room temperature for 40 minutes. Next, an aqueous solution (0.0155 mL) of 100 mM

[Formula 117]

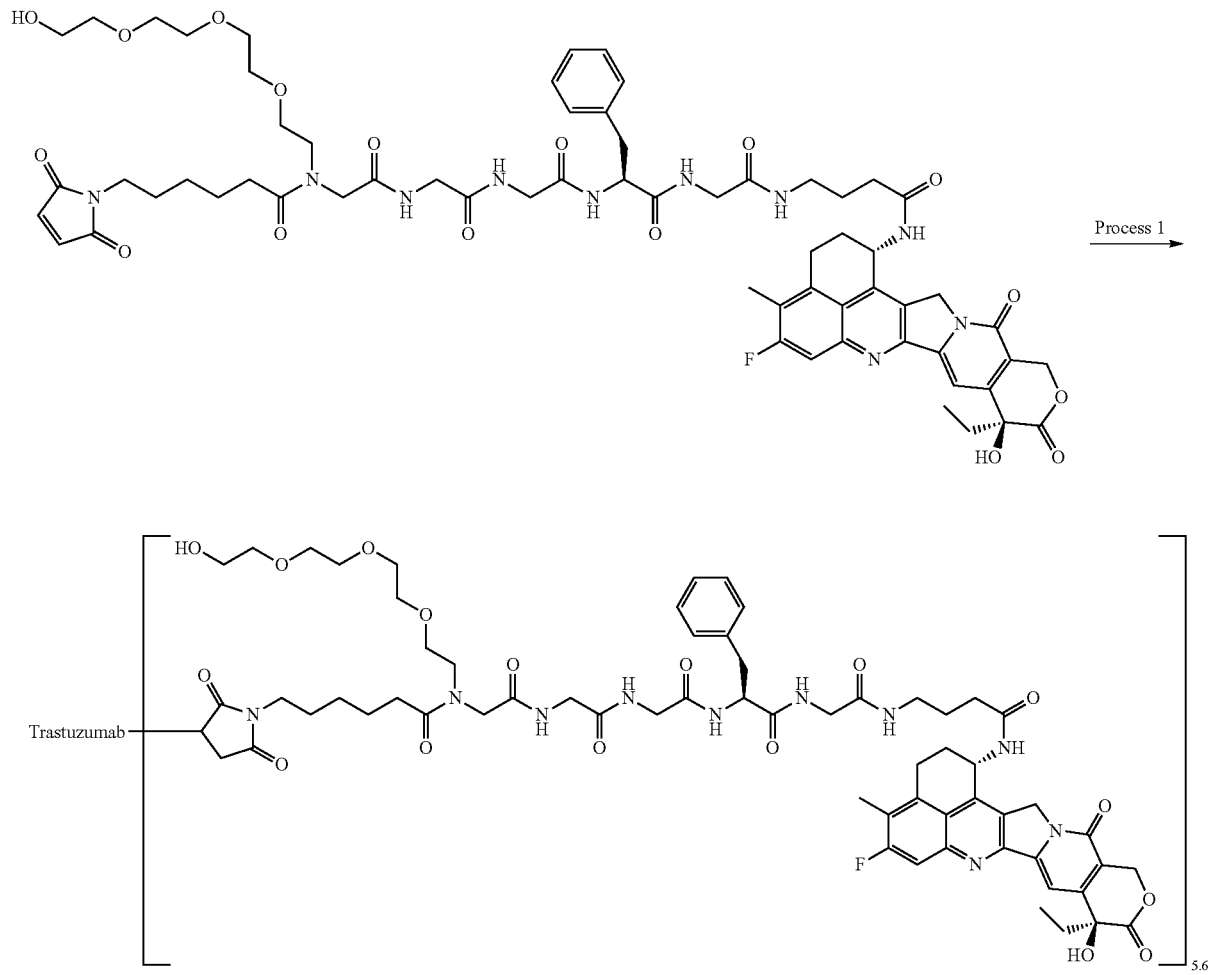

Process 1: Antibody-Drug Conjugate (64)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.37 mLmg$^{-1}$ cm$^{-1}$ was used). The solution (1.25 mL) was placed in a 1.5 mL polypropylene tube and charged with an NAC was added thereto and stirred at room temperature to terminate the reaction of the drug linker for another 20 minutes.
Purification: The above solution was subjected to purification using the Common procedure D-1 (ABS was used as buffer solution) to yield 6 mL of a solution containing the Example compound of interest.
Physicochemical characterization: By using the Common procedure B and Common procedure E, the following characteristic values were obtained.

Antibody concentration: 1.74 mg/mL, antibody yield: 10.4 mg (83%), and average number of conjugated drug molecules (n) per antibody molecule: 5.6.
Example 65 Antibody-Drug Conjugate (65)
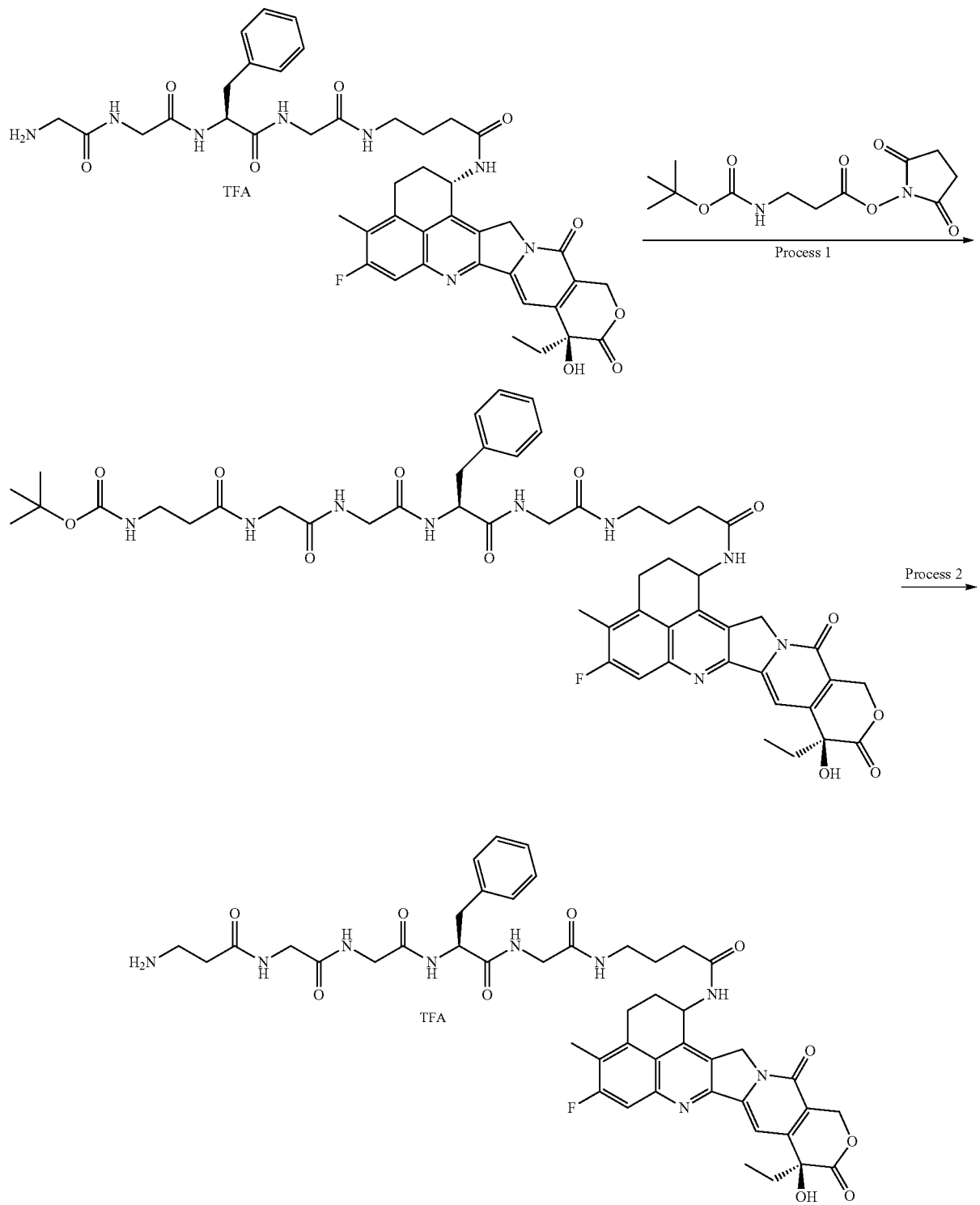

339
340
-continued
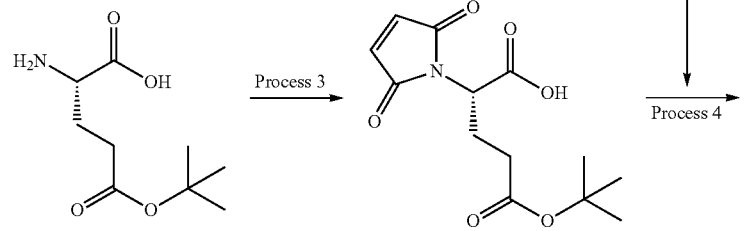
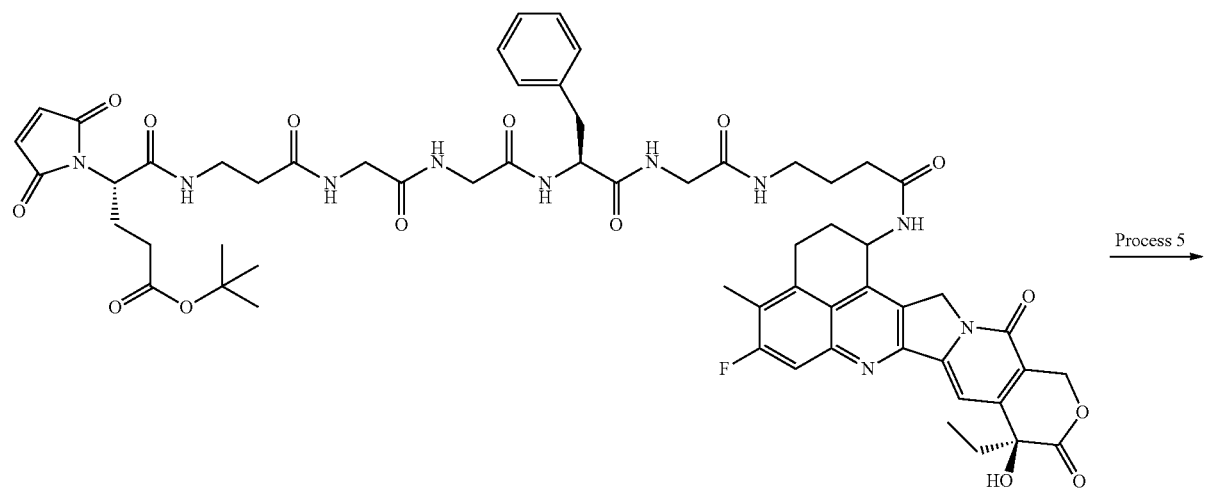
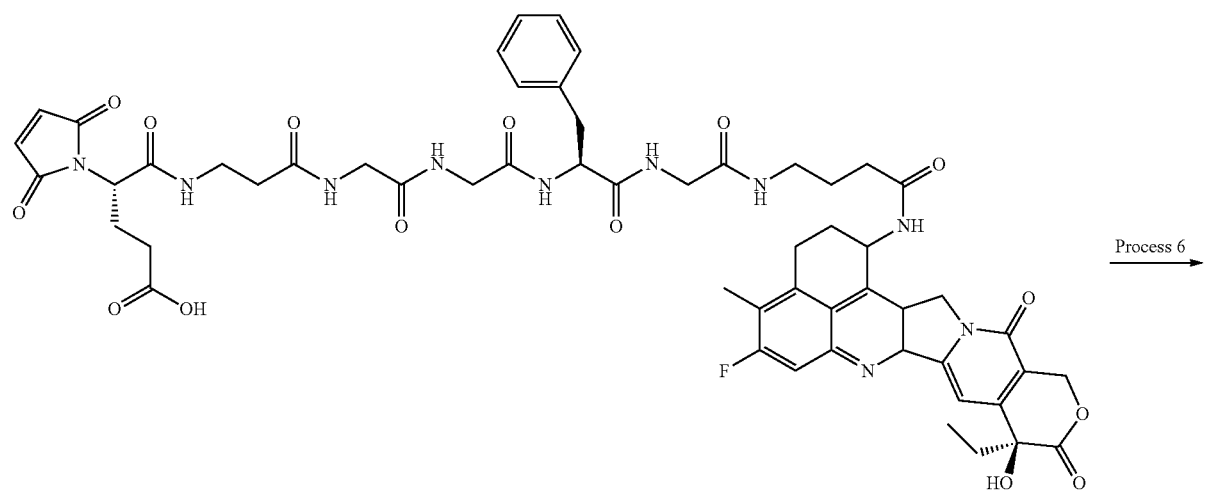

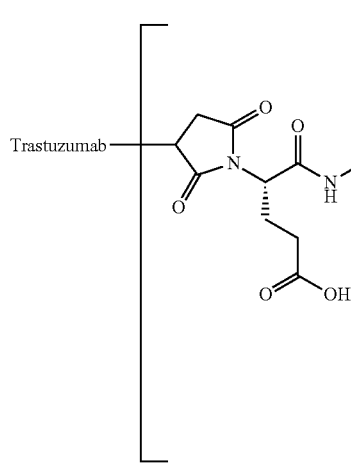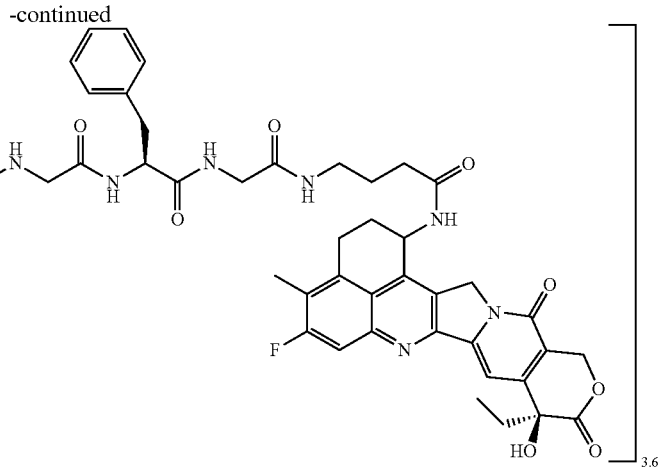

Process 1: N-(tert-Butoxycarbonyl)-β-alanylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (0.839 g, 1.00 mmol) obtained in Process 2 of Example 2 was reacted in the same manner as Process 8 of Example 5 by using N-(tert-butoxycarbonyl)-β-alanine instead of N-succinimidyl 6-maleimidohexanoate, and the crude product obtained was used for the next process without purification.

Process 2: β-Alanylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The crude product obtained in Process 1 above was reacted in the same manner as Process 2 of Example 1 to yield the titled compound as a pale yellow solid (0.610 g, 67%, 2 steps).

$^1$H-NMR (400 MHz, DMSO-$d_6$) δ: 0.87 (3H, t, J=7.4 Hz), 1.67-1.77 (2H, m), 1.79-1.92 (2H, m), 2.09-2.22 (4H, m), 2.40 (3H, s), 2.46-2.55 (2H, m), 2.82-2.73 (1H, m), 2.95-3.13 (5H, m), 3.14-3.21 (2H, m), 3.55-3.80 (6H, m), 4.44-4.52 (1H, m), 5.20 (2H, dd, J=35.0, 19.0 Hz), 5.42 (2H, s), 5.53-5.60 (1H, m), 6.54 (1H, s), 7.14-7.28 (5H, m), 7.31 (1H, s), 7.67 (2H, brs), 7.72-7.78 (1H, m), 7.80 (1H, d, J=11.0 Hz), 8.10-8.17 (2H, m), 8.29 (1H, t, J=5.9 Hz), 8.42 (1H, t, J=5.7 Hz), 8.47 (1H, d, J=8.6 Hz).

Process 3: (2S)-5-tert-Butoxy-2-(2,5-dioxo-2,5-dihydro-1H-pyrrol-1-yl)-5-oxopentanoic acid L-Glutamic acid 5-tert-butyl (1.02 g, 5.00 mmol) was dissolved in a saturated sodium hydrogen carbonate aqueous solution (20.0 mL), charged with N-methoxycarbonylmaleimide (0.775 g, 5.00 mmol) at 0° C., stirred at 0° C. for 30 minutes, and then stirred at room temperature for 1 hour. The reaction solution was rendered acidic by the addition of 5 N hydrochloric acid at 0° C. and then extracted with ethyl acetate. The organic layer obtained was dried over sodium sulfate and filtered. The solvent was removed under reduced pressure to yield a crude product. The crude product obtained was used for the next process without purification.

Process 4: N-[(2S)-5-tert-Butoxy-2-(2,5-dioxo-2,5-dihydro-1H-pyrrol-1-yl)-5-oxopentanoyl]-β-alanylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The crude product (85.0 mg, 0.300 mmol) obtained in Process 3 above was reacted in the same manner as Process 1 of Example 1 by using the compound (182 mg, 0.200 mmol) obtained in Process 2 above instead of methanesulfonic acid salt of exatecan to yield the titled compound as a pale yellow solid (102 mg, 43%).

$^1$H-NMR (400 MHz, DMSO-$d_6$) δ: 0.87 (3H, t, J=7.2 Hz), 1.35 (9H, s), 1.67-1.76 (2H, m), 1.81-1.90 (2H, m), 2.35-2.05 (10H, m), 2.40 (3H, s), 2.75-2.83 (1H, m), 2.99-3.13 (3H, m), 3.14-3.26 (4H, m), 3.55-3.76 (6H, m), 4.36-4.50 (2H, m), 5.21 (2H, q, J=18.9 Hz), 5.42 (2H, s), 5.54-5.61 (1H, m), 6.53 (1H, s), 7.03 (2H, s), 7.17-7.26 (5H, m), 7.31 (1H, s), 7.68-7.73 (1H, m), 7.80 (1H, d, J=10.6 Hz), 8.00-8.05 (2H, m), 8.12 (1H, d, J=7.8 Hz), 8.16-8.20 (1H, m), 8.23-8.28 (1H, m), 8.46 (1H, d, J=8.6 Hz).

Process 5: N-[(2S)-4-Carboxy-2-(2,5-dioxo-2,5-dihydro-1H-pyrrol-1-yl)butanoyl]-β-alanylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (102 mg, 86.8 μmol) obtained in Process 4 above was reacted in the same manner as Process 2 of Example 1 to yield the titled compound as a pale yellow solid (76.0 mg, 78%).

$^1$H-NMR (400 MHz, DMSO-$d_6$) δ: 0.87 (3H, t, J=7.4 Hz), 1.68-1.75 (2H, m), 1.84-1.91 (2H, m), 2.35-2.05 (10H, m), 2.40 (3H, s), 2.74-2.83 (1H, m), 2.99-3.12 (3H, m), 3.14-3.26 (4H, m), 3.55-3.77 (6H, m), 4.41-4.49 (2H, m), 5.21 (2H, dd, J=38.7, 18.8 Hz), 5.42 (2H, s), 5.54-5.61 (1H, m), 6.54 (1H, s), 7.03 (2H, s), 7.15-7.27 (5H, m), 7.31 (1H, s), 7.69-7.74 (1H, m), 7.80 (1H, d, J=10.9 Hz), 8.01-8.07 (2H, m), 8.12 (1H, d, J=8.2 Hz), 8.19 (1H, t, J=5.5 Hz), 8.27 (1H, t, J=6.3 Hz), 8.47 (1H, d, J=8.6 Hz), 12.12 (1H, s).

MS (ESI) m/z: 1119 (M+H)$^+$.

Process 6: Antibody-Drug Conjugate (65)

By using the trastuzumab produced in Reference Example 1 and the compound obtained in Process 5 above, the titled antibody-drug conjugate was obtained in the same manner as Process 6 of Example 2.
Antibody concentration: 1.39 mg/mL, antibody yield: 8.3 mg (66%), and average number of conjugated drug molecules (n) per antibody molecule: 3.6.

Example 66 Antibody-Drug Conjugate (66)

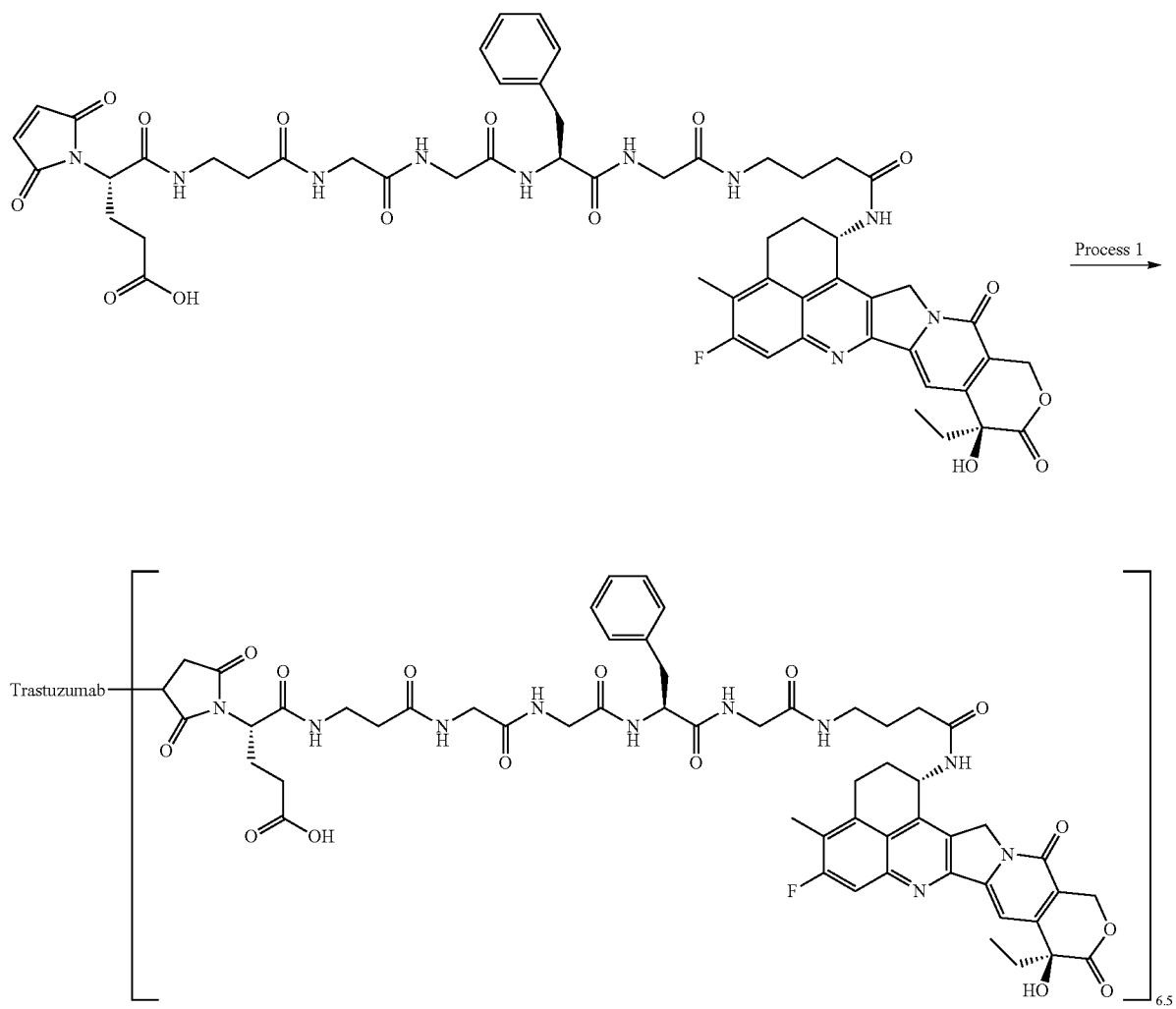

Process 1: Antibody-Drug Conjugate (66) By using the trastuzumab produced in Reference Example 1 and the compound obtained in Process 5 of Example 65, the titled antibody-drug conjugate was obtained in the same manner as Process 1 of Example 3.

Antibody concentration: 1.45 mg/mL, antibody yield: 8.7 mg (70%), and average number of conjugated drug molecules (n) per antibody molecule: 6.5.

Example 67 Antibody-Drug Conjugate (67)
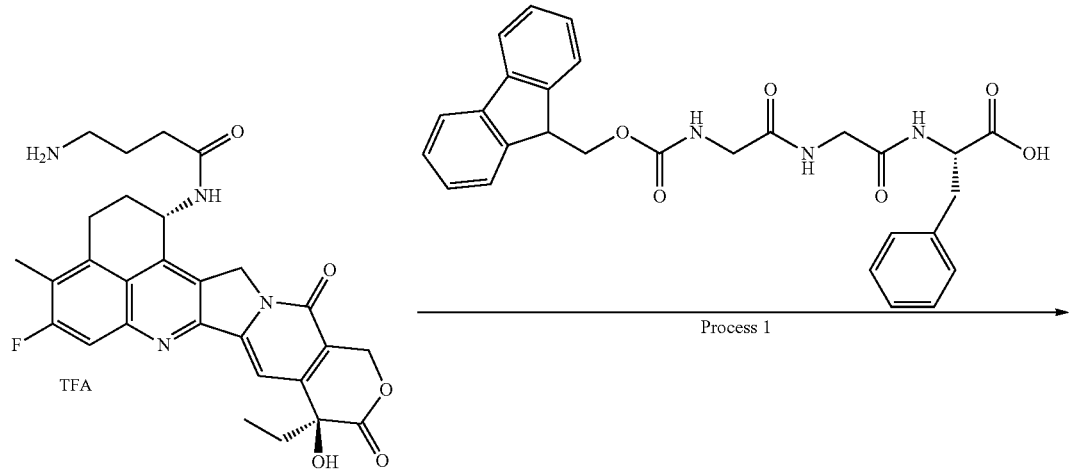
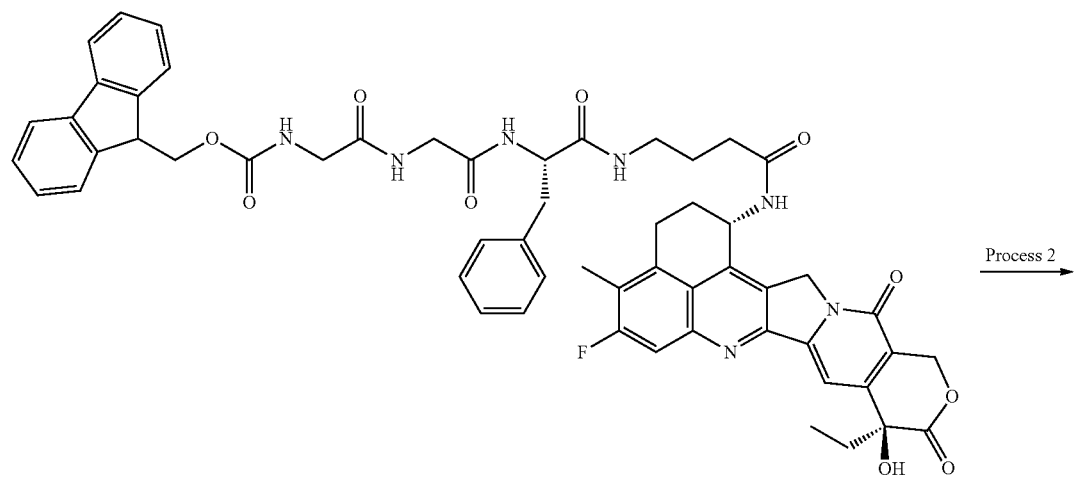
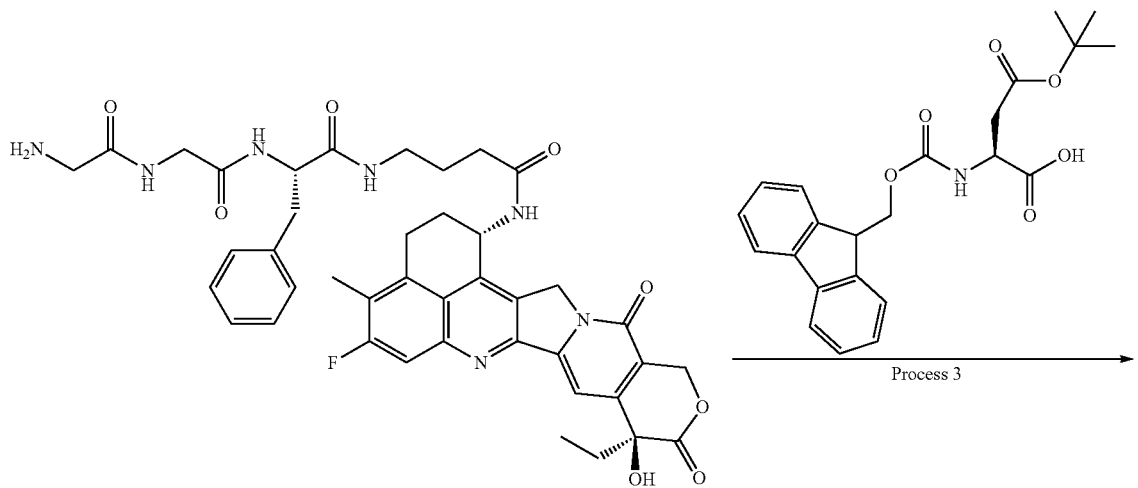

347
348
-continued
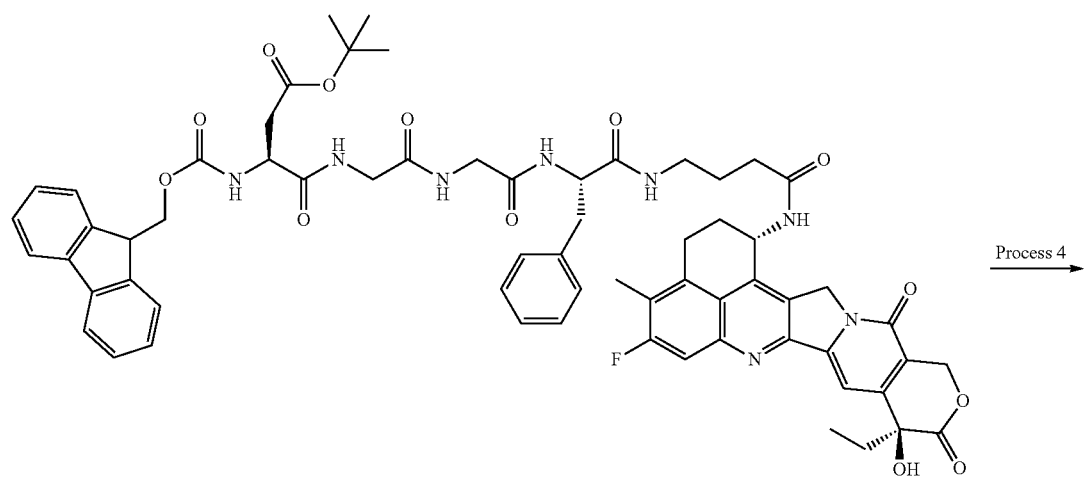
Process 4 →
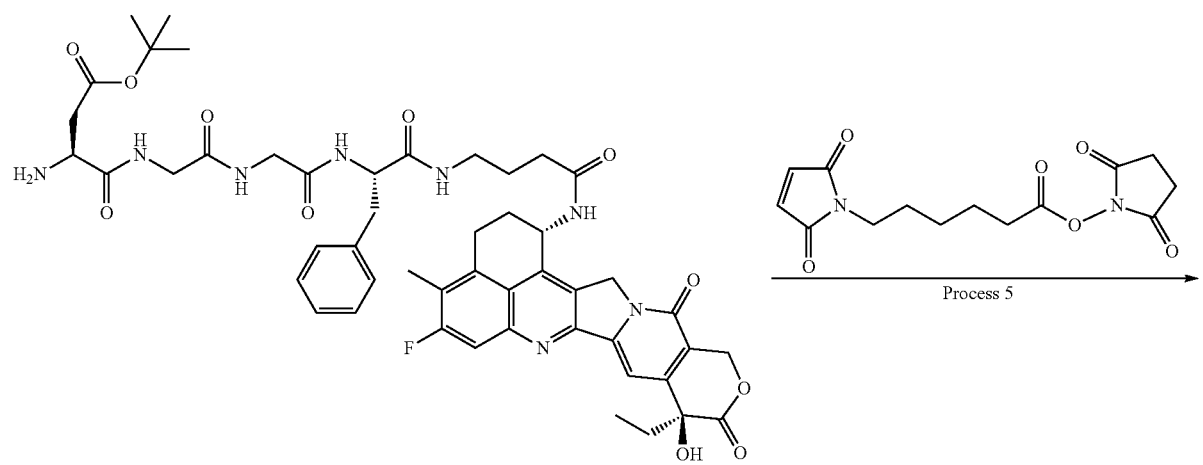
Process 5 →
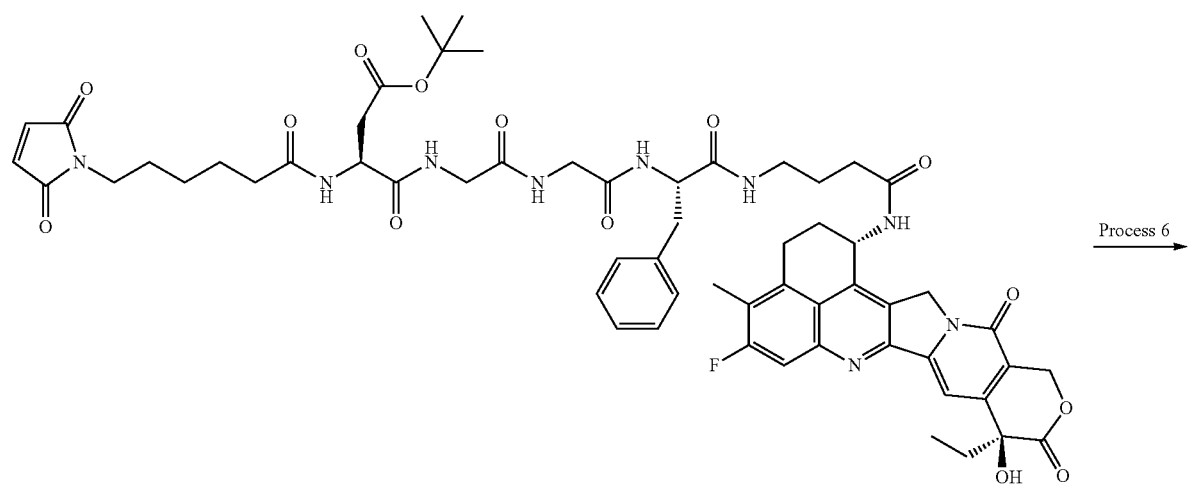
Process 6 →

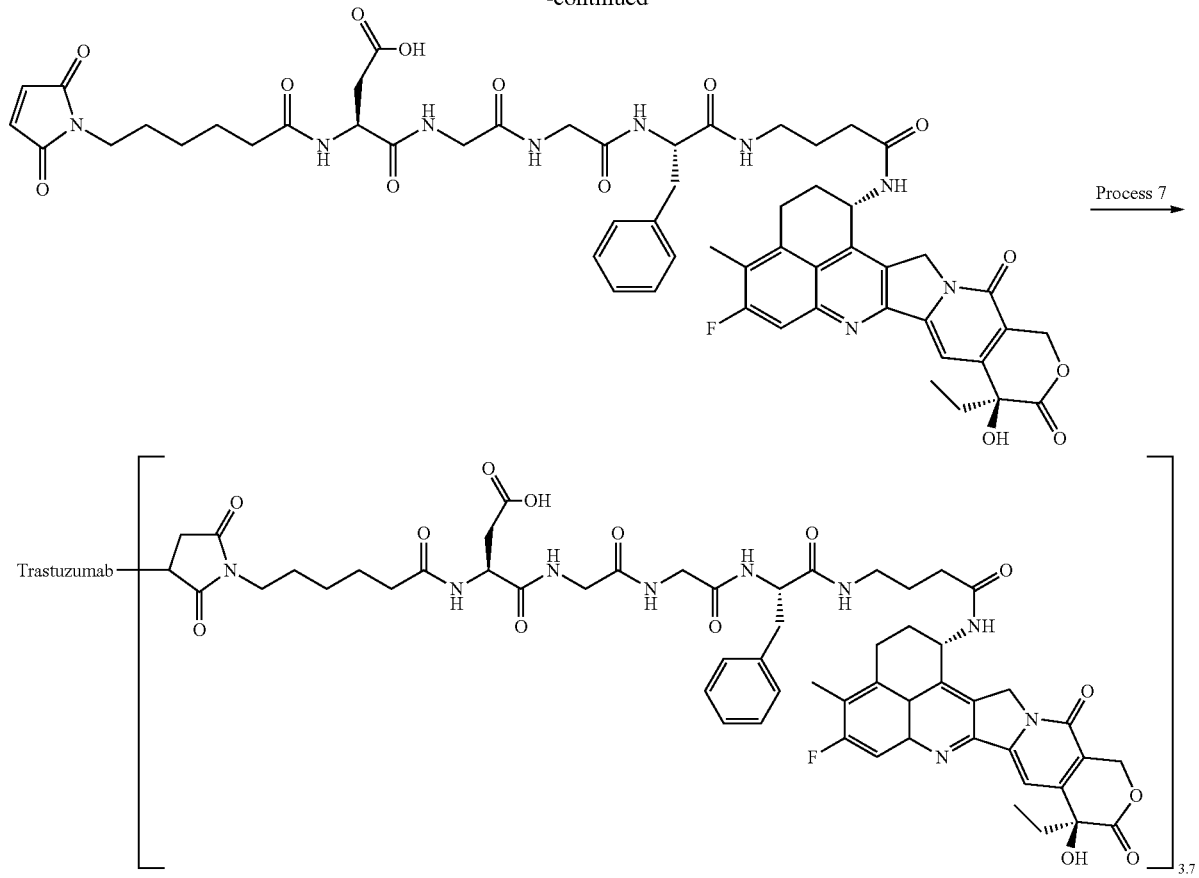

Process 1: N-[(9H-Fluoren-9-ylmethoxy)carbonyl]glycylglycyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-phenylalaninamide The compound (300 mg, 0.473 mmol) obtained in Process 2 of Example 1 was reacted in the same manner as Process 1 of Example 1 by using N-[(9H-fluoren-9-ylmethoxy)carbonyl]glycylglycyl-L-phenylalanine (Japanese Patent Laid-Open No. 2002-60351; 346 mg, 0.691 mmol) instead of 4-(tert-butoxycarbonylamino)butanoic acid to yield the titled compound as a pale yellow solid (230 mg, 40%).

$^1$H-NMR (400 MHz, DMSO-d$_6$) δ: 0.85 (3H, t, J=7.2 Hz), 1.67-1.68 (2H, m), 1.81-1.84 (2H, m), 2.13 (4H, t, J=6.8 Hz), 2.39 (3H, s), 2.76 (1H, t, J=11.4 Hz), 2.96-3.08 (4H, m), 3.16-3.17 (2H, m), 3.59-3.74 (4H, m), 4.22-4.28 (2H, m), 4.39-4.42 (1H, m), 5.16-5.22 (2H, m), 5.36-5.41 (2H, m), 5.56-5.59 (1H, m), 6.52 (1H, s), 7.14-7.20 (5H, m), 7.29-7.31 (3H, m), 7.38-7.41 (2H, m), 7.61 (1H, t, J=6.0 Hz), 7.69 (2H, d, J=7.4 Hz), 7.79 (1H, d, J=11.0 Hz), 7.87 (2H, d, J=7.8 Hz), 7.95 (1H, s), 8.07 (2H, t, J=4.3 Hz), 8.42 (1H, d, J=8.6 Hz).

MS (APCI) m/z: 1004 (M+H)$^+$.

Process 2: Glycylglycyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-phenylalaninamide To an N,N-dimethylformamide (1.00 mL) solution of the compound (226 mg, 0.225 mmol) obtained in Process 1 above, piperidine (0.223 mL, 2.25 mmol) was added and stirred at room temperature for 5 hours. The solvent was removed under reduced pressure to yield a mixture containing the titled compound. The mixture was used for the next reaction without further purification.

Process 3: tert-Butyl (3S,12S)-12-benzyl-18-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-{[(9H-fluoren-9-ylmethoxy)carbonyl]amino}-4,7,10,13,18-pentaoxo-5,8,11,14-tetraazaoctadecan-1-oate The compound (0.225 mmol) obtained in Process 2 above was reacted in the same manner as Process 1 of Example 1 by using N-[(9H-fluoren-9-ylmethoxy)carbonyl]-L-aspartic acid 4-tert-butyl (104 mg, 0.337 mmol) instead of 4-(tert-butoxycarbonylamino)butanoic acid to yield the titled compound as a pale yellow solid (114 mg, 43%).

$^1$H-NMR (400 MHz, DMSO-d$_6$) δ: 0.86 (3H, t, J=7.2 Hz), 1.35 (9H, s), 1.66-1.69 (2H, m), 1.84-1.85 (2H, m), 2.11-2.13 (4H, m), 2.39 (3H, s), 2.43-2.45 (1H, m), 2.68-2.79

(2H, m), 2.94-3.16 (5H, m), 3.66 (5H, tt, J=30.5, 10.0 Hz), 4.23-4.30 (3H, m), 4.39-4.41 (1H, m), 5.15 (1H, d, J=19.2 Hz), 5.21 (1H, d, J=18.8 Hz), 5.37 (1H, d, J=17.2 Hz), 5.42 (1H, d, J=16.0 Hz), 5.53-5.57 (1H, m), 6.54 (1H, s), 7.15-7.22 (5H, m), 7.26-7.34 (3H, m), 7.38-7.40 (2H, m), 7.68-7.70 (2H, m), 7.79 (1H, d, J=10.9 Hz), 7.86-7.87 (2H, m), 7.88-7.90 (1H, m), 7.96 (1H, t, J=6.3 Hz), 8.03-8.07 (2H, m), 8.20 (1H, t, J=5.5 Hz), 8.43 (1H, d, J=8.6 Hz).

MS (APCI) m/z: 1175 (M+H)$^+$.

Process 4: tert-Butyl (3S,12S)-3-amino-12-benzyl-18-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,18-pentaoxo-5,8,11,14-tetraazaoctadecan-1-oate The compound (110 mg, 0.0936 mmol) obtained in Process 3 above was reacted in the same manner as Process 2 above to yield a mixture containing the titled compound. The mixture was used for the next reaction without further purification.

Process 5: tert-Butyl (3S,12S)-12-benzyl-3-{[6-(2,5-dioxo-2,5-dihydro-1H-pyrrol-1-yl)hexanoyl]amino}-18-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,18-pentaoxo-5,8,11,14-tetraazaoctadecan-1-oate The compound (0.0936 mmol) obtained in Process 4 above was reacted in the same manner as Process 8 of Example 5 to yield the titled compound as a pale yellow solid (40.2 mg, 38%).

$^1$H-NMR (400 MHz, DMSO-d$_6$) δ: 0.86 (3H, t, J=7.4 Hz), 1.17-1.19 (2H, m), 1.35 (9H, s), 1.44-1.47 (4H, m), 1.66-1.67 (2H, m), 1.81-1.88 (2H, m), 2.06-2.13 (6H, m), 2.39-2.41 (1H, m), 2.40 (3H, s), 2.67 (1H, dd, J=16.0, 5.5 Hz), 2.76 (1H, dd, J=13.3, 9.0 Hz), 2.96 (1H, dd, J=13.5, 4.9 Hz), 3.04 (2H, td, J=13.4, 6.6 Hz), 3.18 (2H, s), 3.36 (2H, d, J=7.0 Hz), 3.58 (1H, dd, J=16.8, 5.5 Hz), 3.70 (3H, dt, J=21.5, 7.2 Hz), 4.38-4.41 (1H, m), 4.57-4.59 (1H, m), 5.16 (1H, d, J=18.8 Hz), 5.24 (1H, d, J=19.2 Hz), 5.38 (1H, d, J=16.4 Hz), 5.43 (1H, d, J=16.0 Hz), 5.57-5.58 (1H, m), 6.54 (1H, s), 6.99 (2H, s), 7.13-7.25 (5H, m), 7.31 (1H, s), 7.80 (1H, d, J=10.9 Hz), 7.94-8.04 (3H, m), 8.13-8.16 (2H, m), 8.43 (1H, d, J=8.6 Hz).

MS (APCI) m/z: 1146 (M+H)$^+$.

Process 6: N-[6-(2,5-Dioxo-2,5-dihydro-1H-pyrrol-1-yl)hexanoyl]-L-α-aspartylglycylglycyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-phenylalaninamide The compound (40.0 mg, 0.0349 mmol) obtained in Process 5 above was reacted in the same manner as Process 2 of Example 1 to yield the titled compound as a pale yellow solid (33.6 g, 88%).

$^1$H-NMR (400 MHz, DMSO-d$_6$) δ: 0.87 (3H, q, J=7.2 Hz), 1.14-1.20 (2H, m), 1.46 (4H, td, J=14.8, 7.3 Hz), 1.67 (2H, td, J=12.9, 6.3 Hz), 1.84 (2H, dq, J=25.5, 7.2 Hz), 2.11 (6H, dt, J=23.4, 7.3 Hz), 2.39 (3H, s), 2.45-2.47 (1H, m), 2.69 (1H, dd, J=16.5, 5.5 Hz), 2.76 (1H, dd, J=13.7, 9.3 Hz), 2.94-3.01 (1H, m), 3.05 (2H, dq, J=25.1, 6.4 Hz), 3.17-3.19 (1H, m), 3.34-3.46 (4H, m), 3.59 (1H, dd, J=16.6, 5.6 Hz), 3.69 (2H, dt, J=20.1, 6.8 Hz), 4.37-4.41 (1H, m), 4.55 (1H, dd, J=13.5, 7.7 Hz), 5.16 (1H, d, J=19.0 Hz), 5.22 (1H, d, J=18.6 Hz), 5.38 (1H, d, J=16.4 Hz), 5.43 (1H, d, J=16.4 Hz), 5.55-5.59 (1H, m), 6.54 (1H, s), 6.99 (2H, s), 7.19 (5H, dq, J=31.6, 7.9 Hz), 7.31 (1H, s), 7.79 (1H, d, J=11.0 Hz), 7.99 (3H, ddd, J=25.1, 14.2, 6.2 Hz), 8.11 (1H, t, J=5.5 Hz), 8.17 (1H, d, J=7.6 Hz), 8.44 (1H, d, J=8.5 Hz), 12.32 (1H, s).

MS (APCI) m/z: 1090 (M+H)$^+$.

Process 7: Antibody-Drug Conjugate (67)

By using the trastuzumab produced in Reference Example 1 and the compound obtained in Process 6 above, the titled antibody-drug conjugate was obtained in the same manner as Process 6 of Example 2. After that, the solution was concentrated by the Common procedure A.

Antibody concentration: 17.6 mg/mL, antibody yield: 8.8 mg (70%), and average number of conjugated drug molecules (n) per antibody molecule: 3.7.

Example 68 Antibody-Drug Conjugate (68)

[Formula 121]

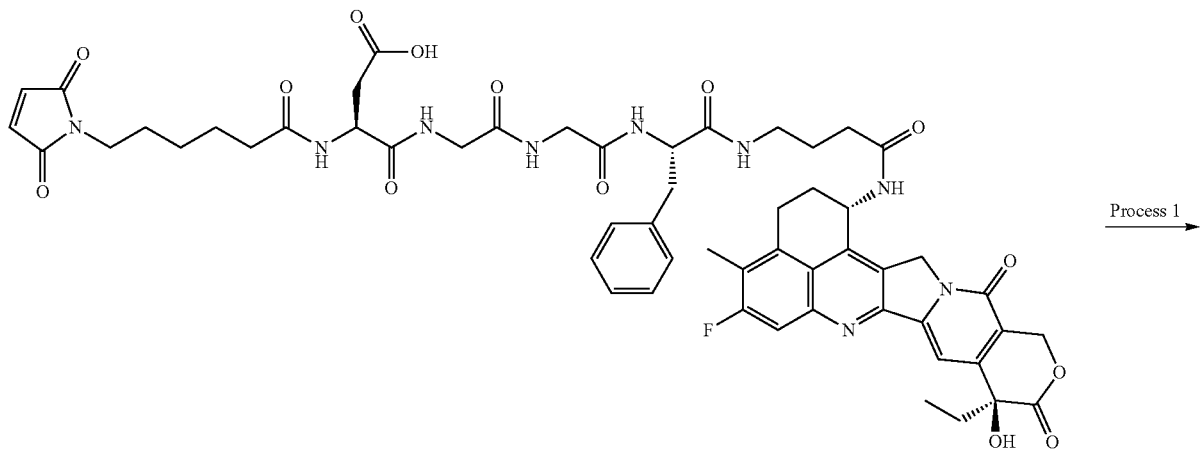

Process 1 →

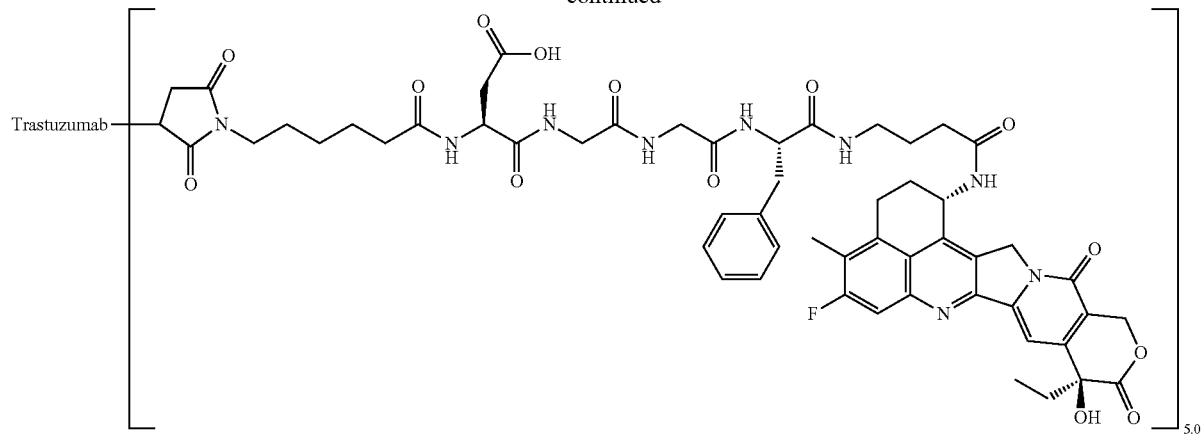

Process 1: Antibody-Drug Conjugate (68)

By using the trastuzumab produced in Reference Example 1 and the compound obtained in Process 6 of Example 67, the titled antibody-drug conjugate was obtained in the same manner as Process 1 of Example 3. After that, the solution was concentrated by the Common procedure A.
Antibody concentration: 13.3 mg/mL, antibody yield: 9.3 mg (74%), and average number of conjugated drug molecules (n) per antibody molecule: 5.0.

Example 69 Antibody-Drug Conjugate (69)

[Formula 122]

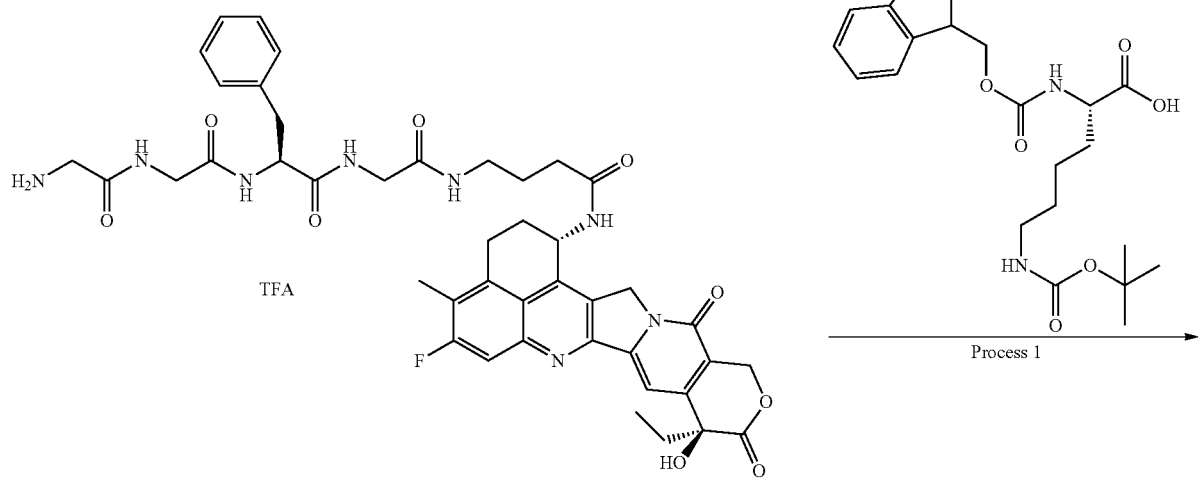

-continued
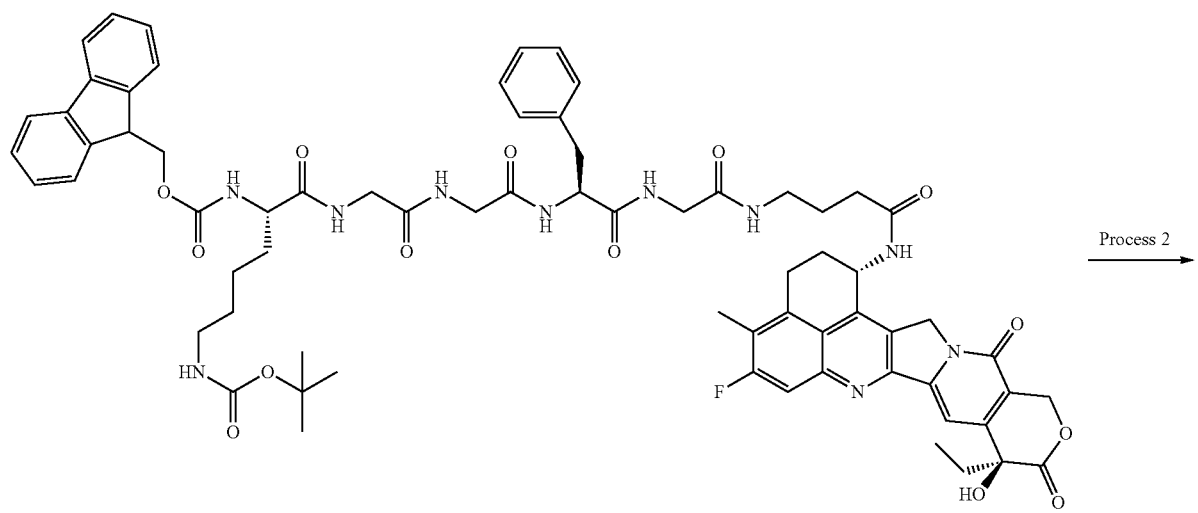
Process 2
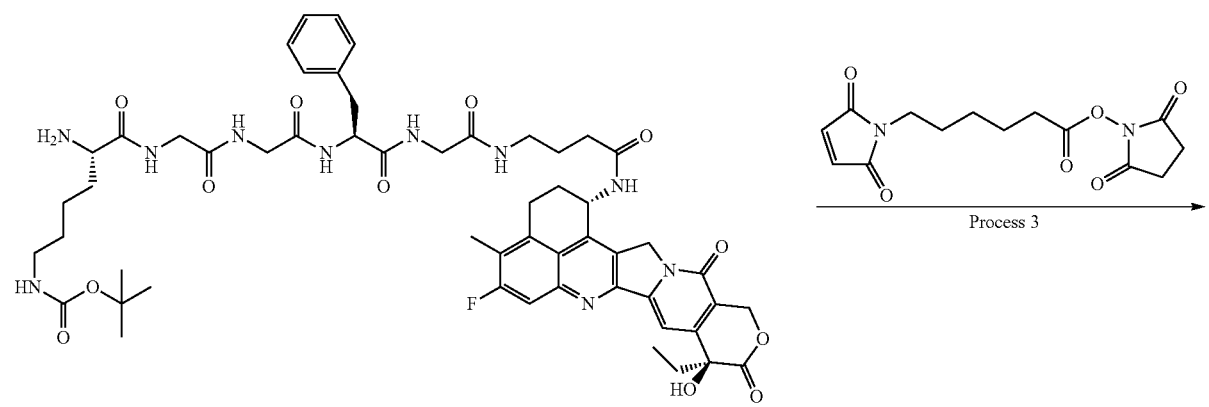
Process 3
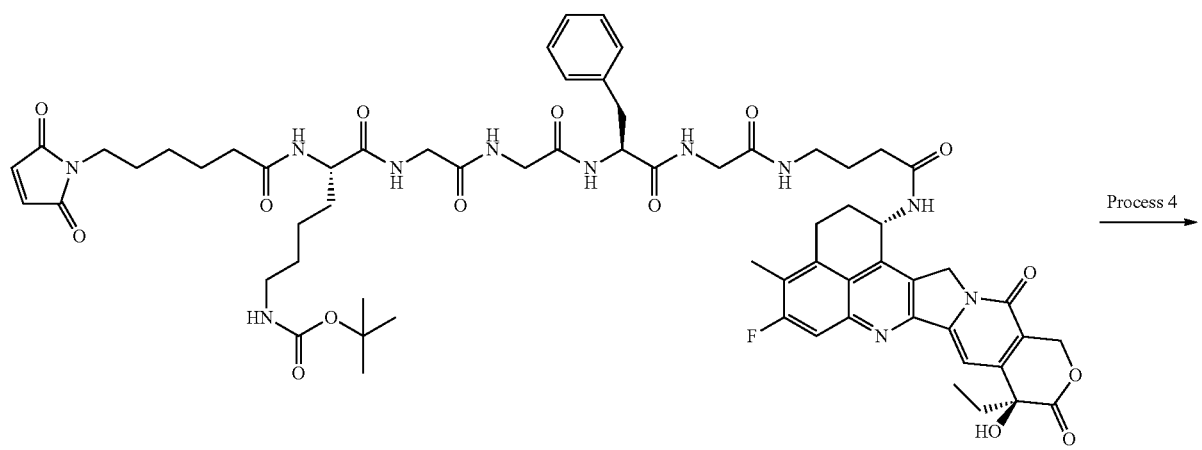
Process 4

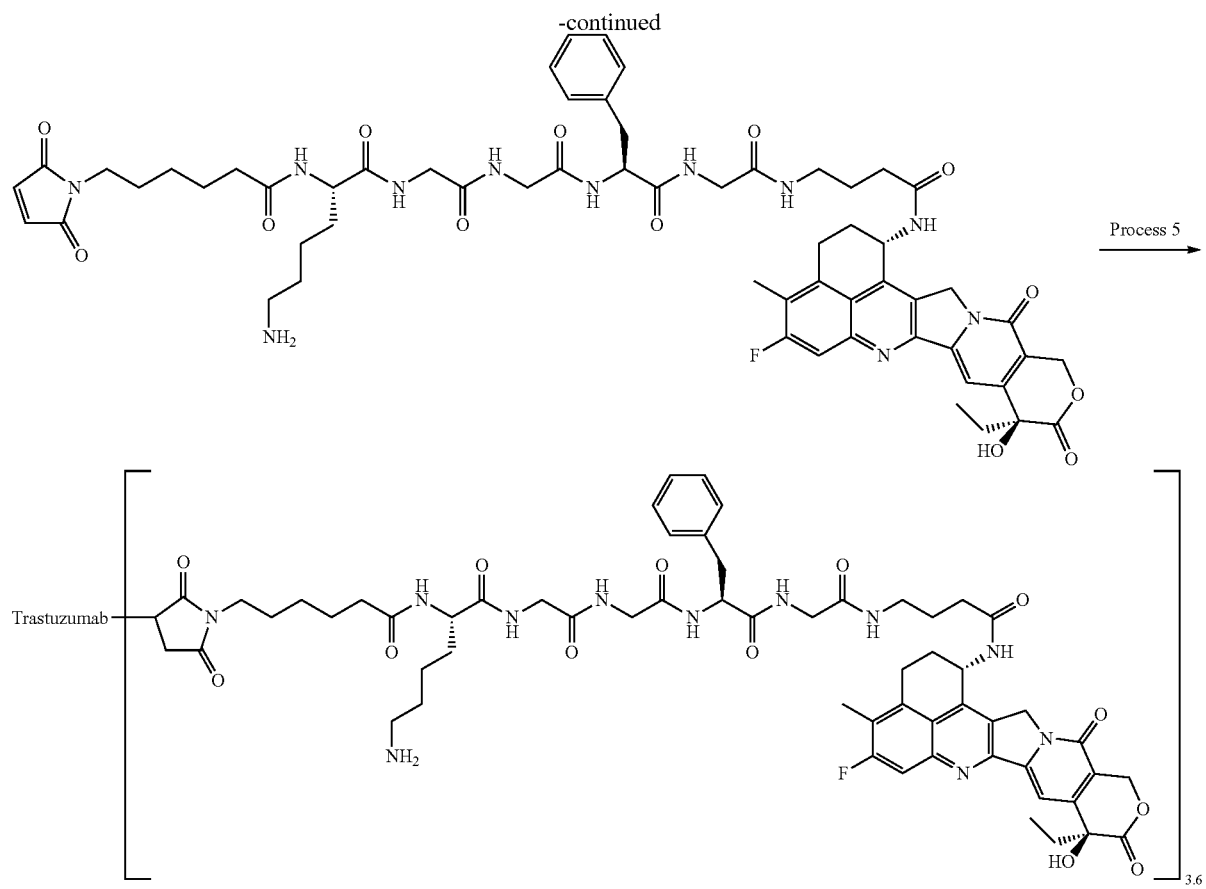

Process 1: N⁶-(tert-Butoxycarbonyl)-N²-[(9H-fluoren-9-ylmethoxy)carbonyl]-L-lysylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-yl]amino}-4-oxobutyl)glycinamide The compound (167 mg, 0.176 mmol) obtained in Process 2 of Example 2 was reacted in the same manner as Process 1 of Example 1 by using N^ε-(tert-butoxycarbonyl)-N^α-[(9H-fluoren-9-ylmethoxy)carbonyl]-L-lysine (103 mg, 0.22 mmol) instead of 4-(tert-butoxycarbonylamino)butanoic acid, and the crude product obtained was used for the next process without purification.

Process 2: N⁶-(tert-Butoxycarbonyl)-L-lysylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide To an N,N-dimethylformamide (4.00 mL) solution of the crude product obtained in Process 1 above, piperidine (0.400 mL) was added and stirred at room temperature for 2 hours. The solvent was removed under reduced pressure and the residues obtained were purified by silica gel column chromatography [chloroform-partitioned organic layer of chloroform:methanol:water=7:3:1 (v/v/v)] to yield the titled compound as a pale yellow solid (113 mg, 60%).

¹H-NMR (400 MHz, DMSO-$d_6$) δ: 0.87 (3H, t, J=7.4 Hz), 1.18-1.49 (5H, m), 1.36 (9H, s), 1.51-1.60 (1H, m), 1.67-1.76 (2H, m), 1.80-1.91 (2H, m), 2.09-2.20 (4H, m), 2.39 (3H, s), 2.76-2.89 (3H, m), 2.99-3.22 (6H, m), 3.58-3.77 (6H, m), 4.43-4.49 (1H, m), 5.20 (2H, q, J=18.5 Hz), 5.42 (2H, s), 5.55-5.60 (1H, m), 6.54 (1H, s), 6.76 (1H, t, J=5.5 Hz), 7.15-7.26 (5H, m), 7.31 (1H, s), 7.69-7.74 (1H, m), 7.80 (1H, d, J=10.9 Hz), 8.08 (1H, t, J=5.7 Hz), 8.14 (1H, d, J=7.8 Hz), 8.22-8.30 (2H, m), 8.47 (1H, d, J=8.6 Hz).

Process 3: N⁶-(tert-Butoxycarbonyl)-N²-[6-(2,5-dioxo-2,5-dihydro-1H-pyrrol-1-yl) hexanoyl]-L-lysylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (113 mg, 0.106 mmol) obtained in Process 2 above was reacted in the same manner as Process 8 of Example 5 to yield the titled compound as a pale yellow solid (102 mg, 61%).

¹H-NMR (400 MHz, DMSO-$d_6$) δ: 0.87 (3H, t, J=7.2 Hz), 1.11-1.53 (11H, m), 1.35 (9H, s), 1.56-1.65 (1H, m), 1.68-1.76 (2H, m), 1.81-1.92 (2H, m), 2.06-2.20 (6H, m), 2.40 (3H, s), 2.74-2.90 (3H, m), 2.96-3.39 (7H, m), 3.57-3.74 (6H, m), 4.14-4.21 (1H, m), 4.42-4.49 (1H, m), 5.20 (2H, q, J=18.9 Hz), 5.42 (2H, s), 5.55-5.60 (1H, m), 6.54 (1H, s), 6.72-6.78 (1H, m), 7.00 (2H, s), 7.15-7.26 (5H, m), 7.31 (1H, s), 7.69-7.72 (1H, m), 7.80 (1H, d, J=10.9 Hz), 7.93

(1H, d, J=7.4 Hz), 7.99-8.04 (1H, m), 8.10-8.18 (2H, m), 8.26 (1H, t, J=6.1 Hz), 8.46 (1H, d, J=8.2 Hz).

Process 4: N²-[6-(2,5-Dioxo-2,5-dihydro-1H-pyrrol-1-yl)hexanoyl]-L-lysylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide To a dichloromethane (4.00 mL) solution of the compound (102 mg, 80.9 μmol) obtained in Process 3 above, trifluoroacetic acid (1.00 mL) was added and stirred at room temperature for 2 hours. The solvent was removed under reduced pressure and the residues obtained were purified by silica gel column chromatography [chloroform-partitioned organic layer of chloroform:methanol:water=7:3:1 (v/v/v)] to yield the titled compound as a pale yellow solid (57.0 mg, 61%).

¹H-NMR (400 MHz, DMSO-d₆) δ: 0.87 (3H, t, J=7.2 Hz), 1.12-1.35 (4H, m), 1.41-1.55 (7H, m), 1.61-1.77 (3H, m), 1.80-1.91 (2H, m), 2.07-2.22 (6H, m), 2.40 (3H, s), 2.84-2.71 (3H, m), 2.97-3.40 (7H, m), 3.59-3.76 (6H, m), 4.20-4.25 (1H, m), 4.45-4.50 (1H, m), 5.20 (2H, q, J=18.5 Hz), 5.42 (2H, s), 5.54-5.60 (1H, m), 6.55 (1H, s), 7.01 (2H, s), 7.15-7.26 (5H, m), 7.31 (1H, s), 7.74 (1H, t, J=5.7 Hz), 7.81 (1H, d, J=10.9 Hz), 7.97 (1H, d, J=7.8 Hz), 8.05 (1H, t, J=6.1 Hz), 8.13-8.18 (2H, m), 8.28 (1H, t, J=5.7 Hz), 8.47 (1H, d, J=8.6 Hz).

MS (ESI) m/z: 1160 (M+H)⁺.

Process 5: Antibody-Drug Conjugate (69)

By using the trastuzumab produced in Reference Example 1 and the compound obtained in Process 4 above, the titled antibody-drug conjugate was obtained in the same manner as Process 6 of Example 2. After that, the solution was concentrated by the Common procedure A.

Antibody concentration: 20.6 mg/mL, antibody yield: 8.3 mg (66%), and average number of conjugated drug molecules (n) per antibody molecule: 3.6.

Example 70 Antibody-Drug Conjugate (70)

[Formula 123]

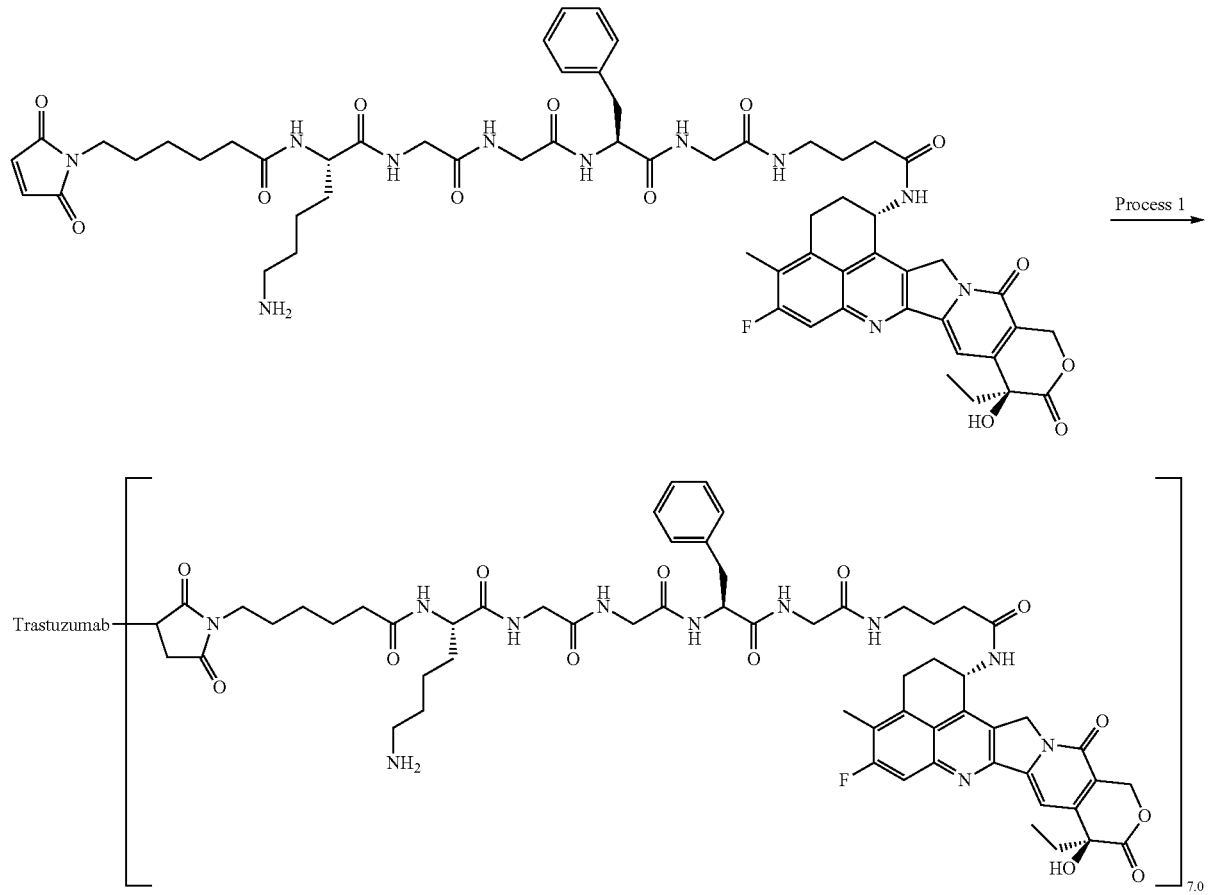

Process 1: Antibody-Drug Conjugate (70) By using the trastuzumab produced in Reference Example 1 and the compound obtained in Process 4 of Example 69, the titled antibody-drug conjugate was obtained in the same manner as Process 1 of Example 3. After that, the solution was concentrated by the Common procedure A.

Antibody concentration: 23.5 mg/mL, antibody yield: 9.4 mg (75%), and average number of conjugated drug molecules (n) per antibody molecule: 7.0.

Example 71 Antibody-Drug Conjugate (71)
[Formula 124]
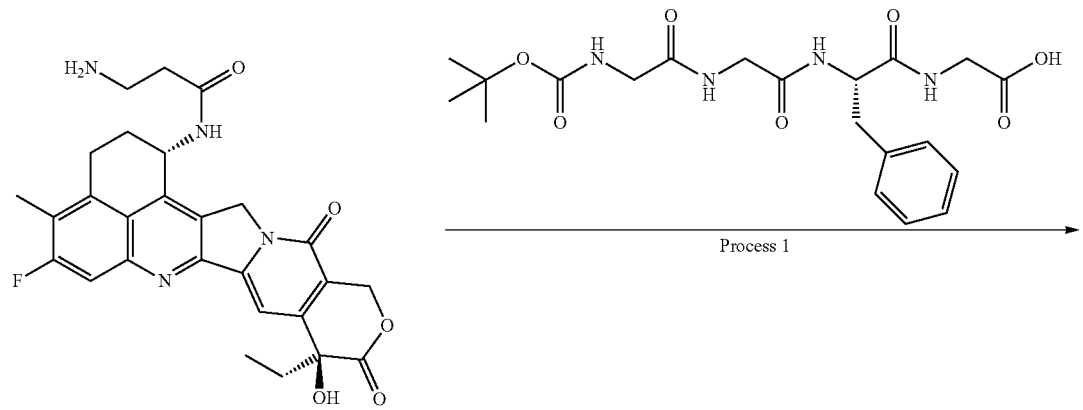
Process 1
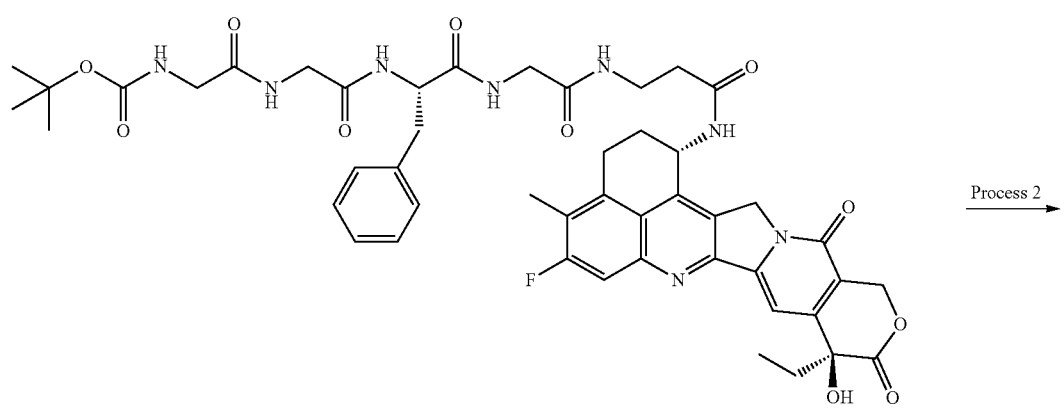
Process 2
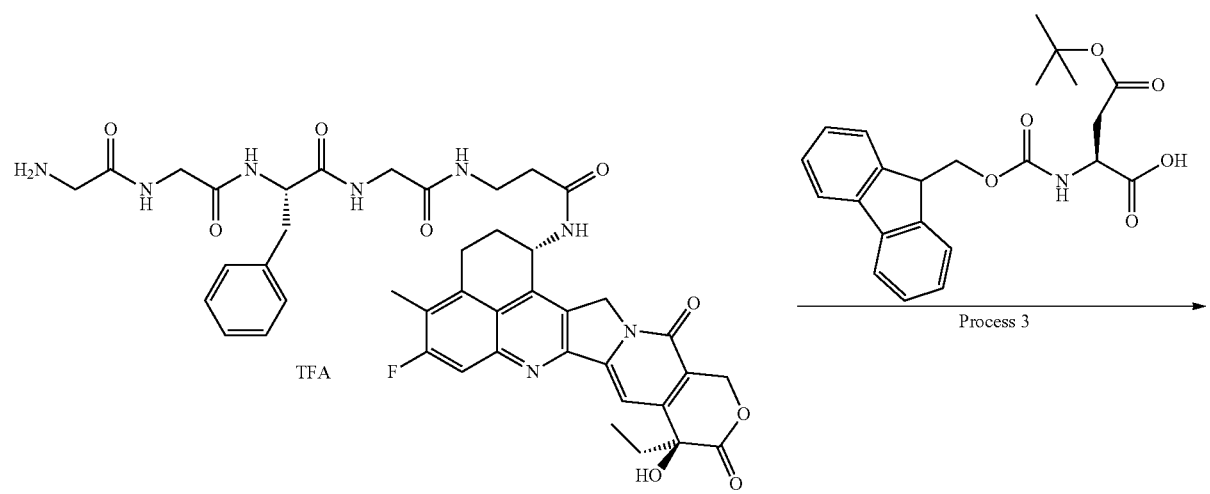
Process 3

363 364
-continued
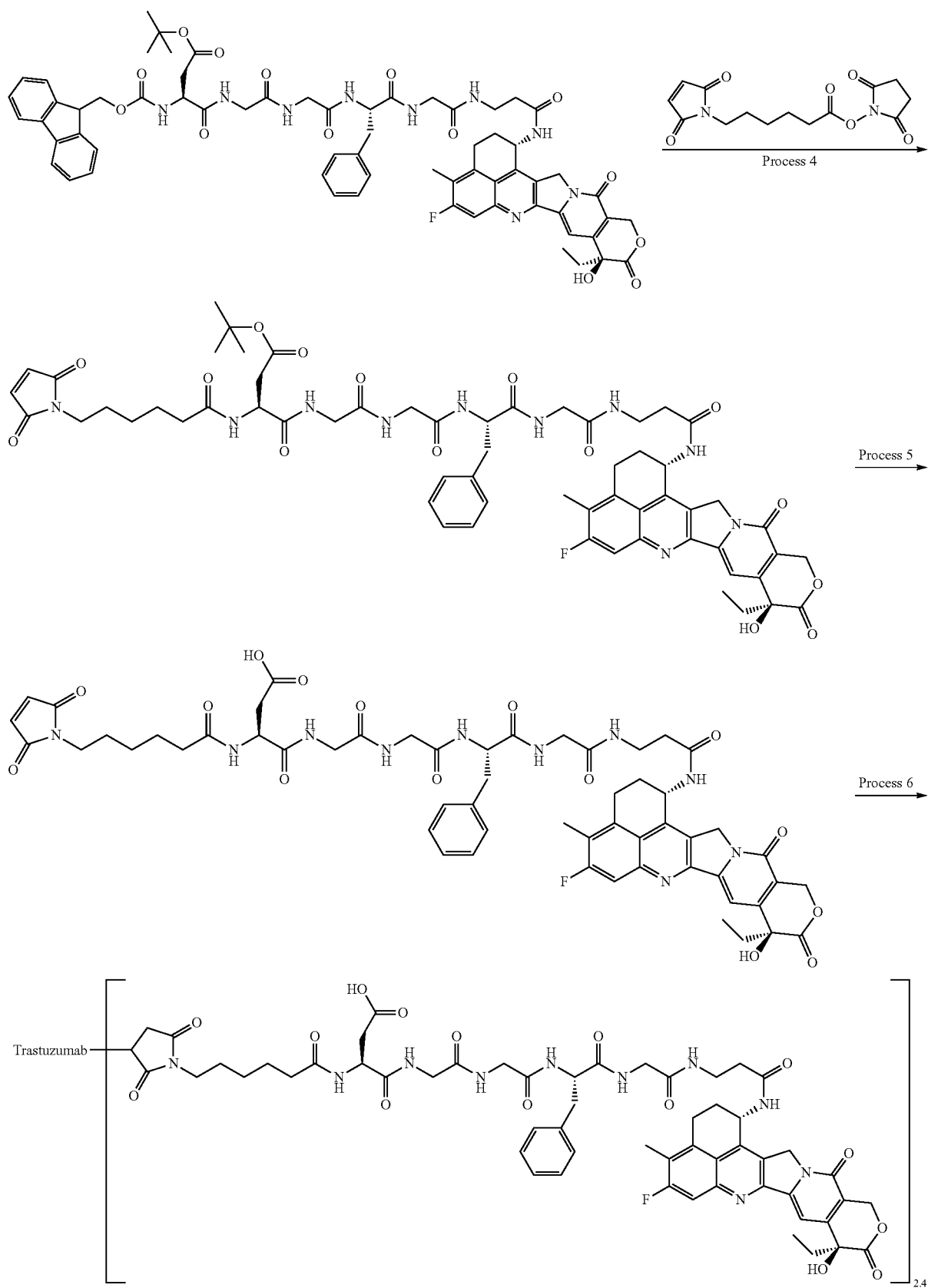

Process 1: N-(tert-Butoxycarbonyl)glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (484 mg, 0.780 mmol) obtained in Process 2 of Example 7 was reacted in the same manner as Process 1 of Example 2 to yield the titled compound as a pale yellow solid (626 mg, 87%).

$^1$H-NMR (400 MHz, DMSO-d$_6$) δ: 0.87 (3H, t, J=7.4 Hz), 1.27-1.42 (9H, m), 1.77-1.93 (2H, m), 2.06-2.22 (2H, m), 2.36 (2H, t, J=7.2 Hz), 2.40 (3H, d, J=1.6 Hz), 2.44-2.54 (2H, m), 2.76 (1H, dd, J=14.5, 10.2 Hz), 3.02 (1H, dd, J=13.9, 4.5 Hz), 3.12-3.22 (2H, m), 3.52 (6H, d, J=6.3 Hz), 4.42-4.54 (1H, m), 5.19 (1H, d, J=19.2 Hz), 5.26 (1H, d, J=18.4 Hz), 5.42 (1H, dd, J=18.4, 16.4 Hz), 5.57 (1H, dt, J=8.7, 4.4 Hz), 6.53 (1H, s), 6.98 (1H, t, J=5.9 Hz), 7.14-7.28 (5H, m), 7.31 (1H, s), 7.77-7.84 (1H, m), 7.91 (1H, t, J=5.5 Hz), 8.16 (1H, d, J=7.8 Hz), 8.27 (1H, t, J=5.1 Hz), 8.52 (1H, d, J=9.0 Hz).

Process 2: Glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide trifluoroacetic acid salt The compound (624 mg, 0.675 mmol) obtained in Process 1 above was reacted in the same manner as Process 2 of Example 2 to yield the titled compound as a yellow solid (626 mg, 92%).

$^1$H-NMR (400 MHz, DMSO-d$_6$) δ: 0.87 (3H, t, J=7.4 Hz), 1.86 (2H, tt, J=14.5, 7.2 Hz), 2.07-2.22 (2H, m), 2.36 (2H, t, J=7.2 Hz), 2.40 (3H, s), 2.44-2.54 (2H, m), 2.75 (1H, dd, J=13.7, 9.8 Hz), 3.04 (1H, dd, J=13.7, 4.3 Hz), 3.12-3.22 (2H, m), 3.58 (2H, d, J=4.7 Hz), 3.69 (3H, td, J=11.2, 5.7 Hz), 3.87 (1H, dd, J=17.0, 5.7 Hz), 4.54 (1H, m, J=17.8, 4.5 Hz), 5.19 (1H, d, J=19.2 Hz), 5.26 (1H, d, J=18.8 Hz), 5.43 (2H, s), 5.51-5.60 (1H, m), 6.55 (1H, s), 7.14-7.29 (5H, m), 7.32 (1H, s), 7.81 (1H, d, J=10.9 Hz), 7.88 (1H, t, J=5.7 Hz), 7.97 (3H, brs), 8.29-8.38 (2H, m), 8.50 (1H, t, J=5.7 Hz), 8.55 (1H, d, J=8.6 Hz).

MS (ESI) m/z: 825 (M+H)$^+$.

Process 3: tert-Butyl (9S,18S)-9-benzyl-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-18-{[(9H-fluoren-9-ylmethoxy)carbonyl]amino}-1,5,8,11,14,17-hexaoxo-4,7,10,13,16-pentaazaicosan-20-oate The compound (150 mg, 0.182 mmol) obtained in Process 2 above was reacted in the same manner as Process 1 of Example 2 by using (2S)-4-tert-butoxy-2-{[(9H-fluoren-9-ylmethoxy)carbonyl]amino}-4-oxobutanoic acid (90.0 mg, 0.219 mmol) instead of N-(tert-butoxycarbonyl)glycylglycyl-L-phenylalanylglycine to yield the titled compound as a pale yellow solid (84.0 mg, 38%).

$^1$H-NMR (400 MHz, DMSO-d$_6$) δ: 0.82-0.91 (3H, m), 1.35 (9H, s), 1.85 (2H, tt, J=14.0, 7.3 Hz), 2.06-2.21 (2H, m), 2.39 (3H, s), 2.31-2.53 (5H, m), 2.64-2.73 (1H, m), 2.78 (1H, dd, J=13.7, 9.8 Hz), 3.02 (1H, dd, J=13.9, 4.5 Hz), 3.11-3.20 (2H, m), 3.55-3.80 (6H, m), 4.17-4.35 (3H, m), 4.35-4.43 (1H, m), 4.44-4.51 (1H, m), 5.18 (1H, d, J=19.2 Hz), 5.24 (1H, d, J=19.2 Hz), 5.41 (2H, dd, J=18.8, 16.4 Hz), 5.51-5.60 (1H, m), 6.53 (1H, s), 7.13-7.20 (1H, m), 7.20-7.27 (4H, m), 7.27-7.34 (3H, m), 7.39 (2H, t, J=7.2 Hz), 7.65-7.73 (3H, m), 7.79 (2H, d, J=10.6 Hz), 7.87 (2H, d, J=7.4 Hz), 8.00 (1H, t, J=6.1 Hz), 8.08-8.20 (2H, m), 8.22-8.31 (1H, m), 8.52 (1H, d, J=8.2 Hz).

MS (ESI) m/z: 1218 (M+H)$^+$.

Process 4: tert-Butyl (9S,18S)-9-benzyl-18-{[6-(2,5-dioxo-2,5-dihydro-1H-pyrrol-1-yl)hexanoyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,5,8,11,14,17-hexaoxo-4,7,10,13,16-pentaazaicosan-20-oate The compound (81.0 mg, 0.0665 mmol) obtained in Process 3 above was reacted in the same manner as Process 2 of Example 58 to yield the titled compound (56.0 mg, 71%).

MS(ESI) m/z: 1189.5 (M+H)$^+$.

Process 5: N-[6-(2,5-Dioxo-2,5-dihydro-1H-pyrrol-1-yl)hexanoyl]-L-α-aspartylglycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (52.0 mg, 0.0437 mmol) obtained in Process 2 above was reacted in the same manner as Process 2 of Example 1 to yield the titled compound as a pale yellow solid (35.0 mg, 71%).

$^1$H-NMR (400 MHz, DMSO-d$_6$) δ: 0.87 (3H, t, J=7.4 Hz), 1.12-1.22 (2H, m), 1.39-1.51 (4H, m), 1.78-1.92 (2H, m), 2.04-2.19 (2H, m), 2.08 (2H, t, J=7.2 Hz), 2.40 (3H, s), 2.31-2.46 (6H, m), 2.61-2.72 (1H, m), 2.73-2.85 (1H, m), 3.02 (1H, dd, J=14.1, 4.7 Hz), 3.17 (2H, m, J=5.5 Hz), 3.26-3.43 (2H, m), 3.55-3.77 (6H, m), 4.42-4.50 (1H, m), 4.51-4.58 (1H, m), 5.19 (1H, d, J=18.4 Hz), 5.26 (1H, d, J=18.4 Hz), 5.42 (2H, brs), 5.52-5.60 (1H, m), 6.53 (1H, s), 6.99 (2H, s), 7.12-7.27 (5H, m), 7.31 (1H, s), 7.80 (2H, d, J=10.9 Hz), 7.93-8.02 (1H, m), 8.03-8.17 (3H, m), 8.22-8.31 (1H, m), 8.53 (1H, d, J=8.6 Hz).

MS (ESI) m/z: 1133 (M+H)$^+$.

Process 6: Antibody-Drug Conjugate (71)

By using the trastuzumab produced in Reference Example 1 and the compound obtained in Process 3 above, the titled antibody-drug conjugate was obtained in the same manner as Process 6 of Example 2.

Antibody concentration: 1.18 mg/mL, antibody yield: 7.08 mg (71%), and average number of conjugated drug molecules (n) per antibody molecule: 2.4.

Example 72 Antibody-Drug Conjugate (72)

[Formula 125]

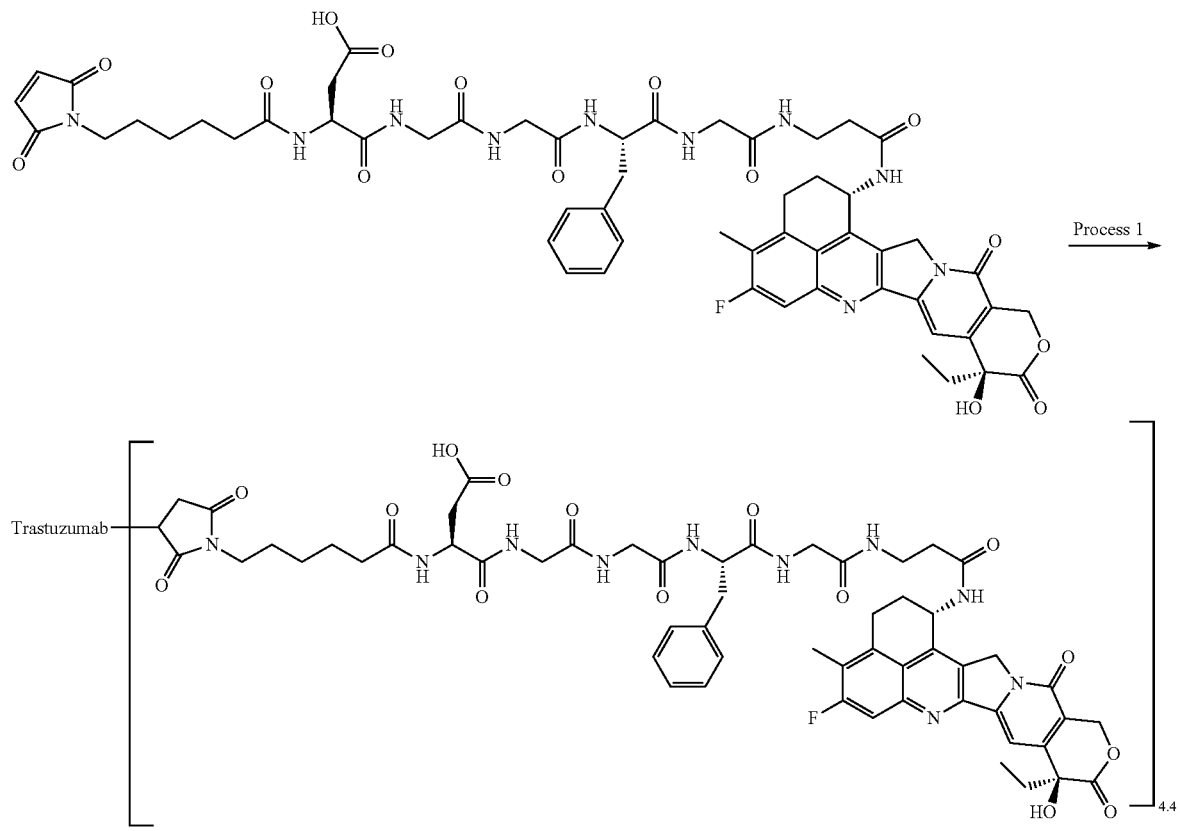

Process 1: Antibody-Drug Conjugate (72)

By using the trastuzumab produced in Reference Example 1 and the compound obtained in Process 5 of Example 71, the titled antibody-drug conjugate was obtained in the same manner as Process 1 of Example 3.

Antibody concentration: 1.04 mg/mL, antibody yield: 6.24 mg (62%), and average number of conjugated drug molecules (n) per antibody molecule: 4.4.

Example 73 Antibody-Drug Conjugate (73)

[Formula 126]

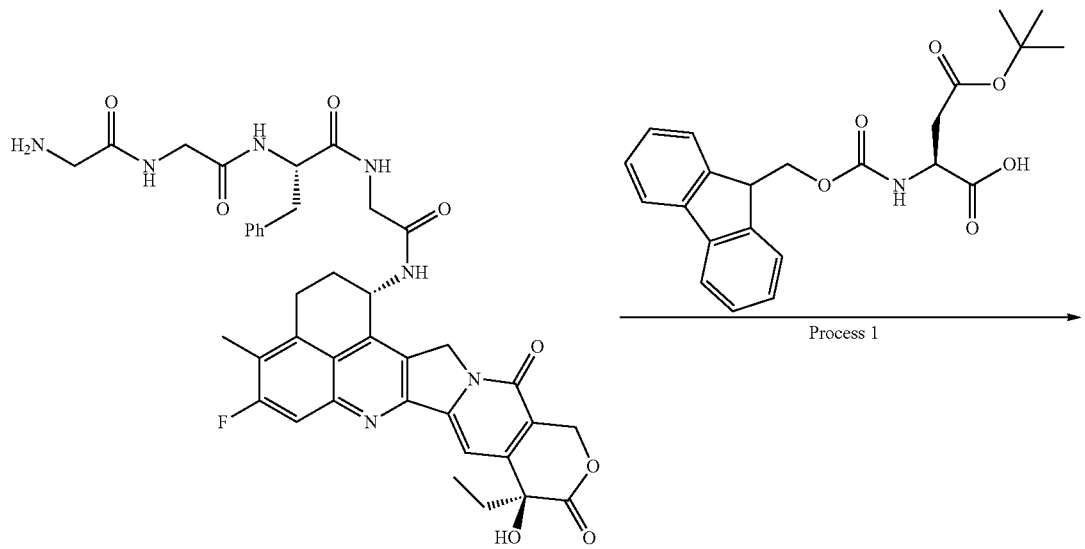

-continued
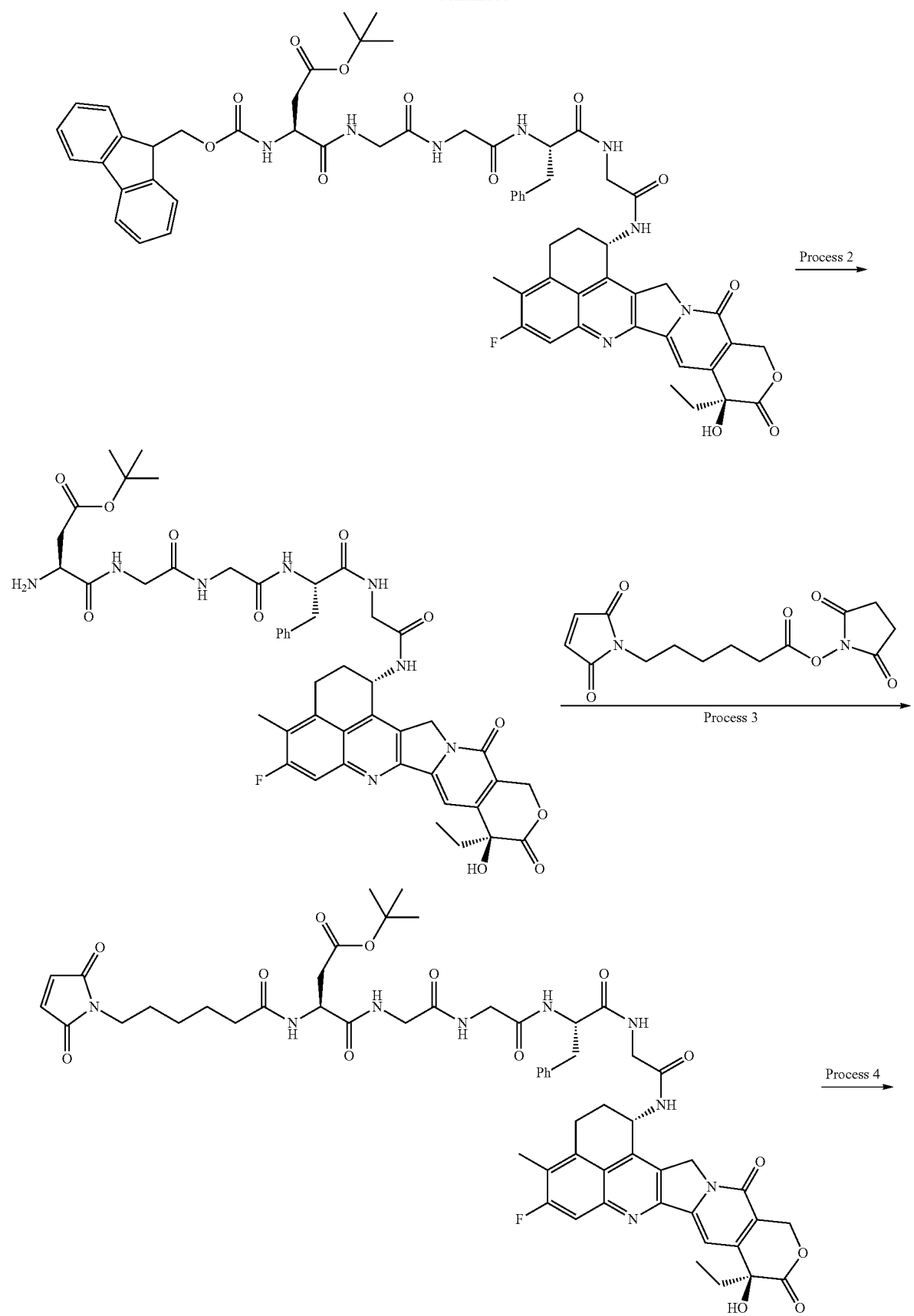

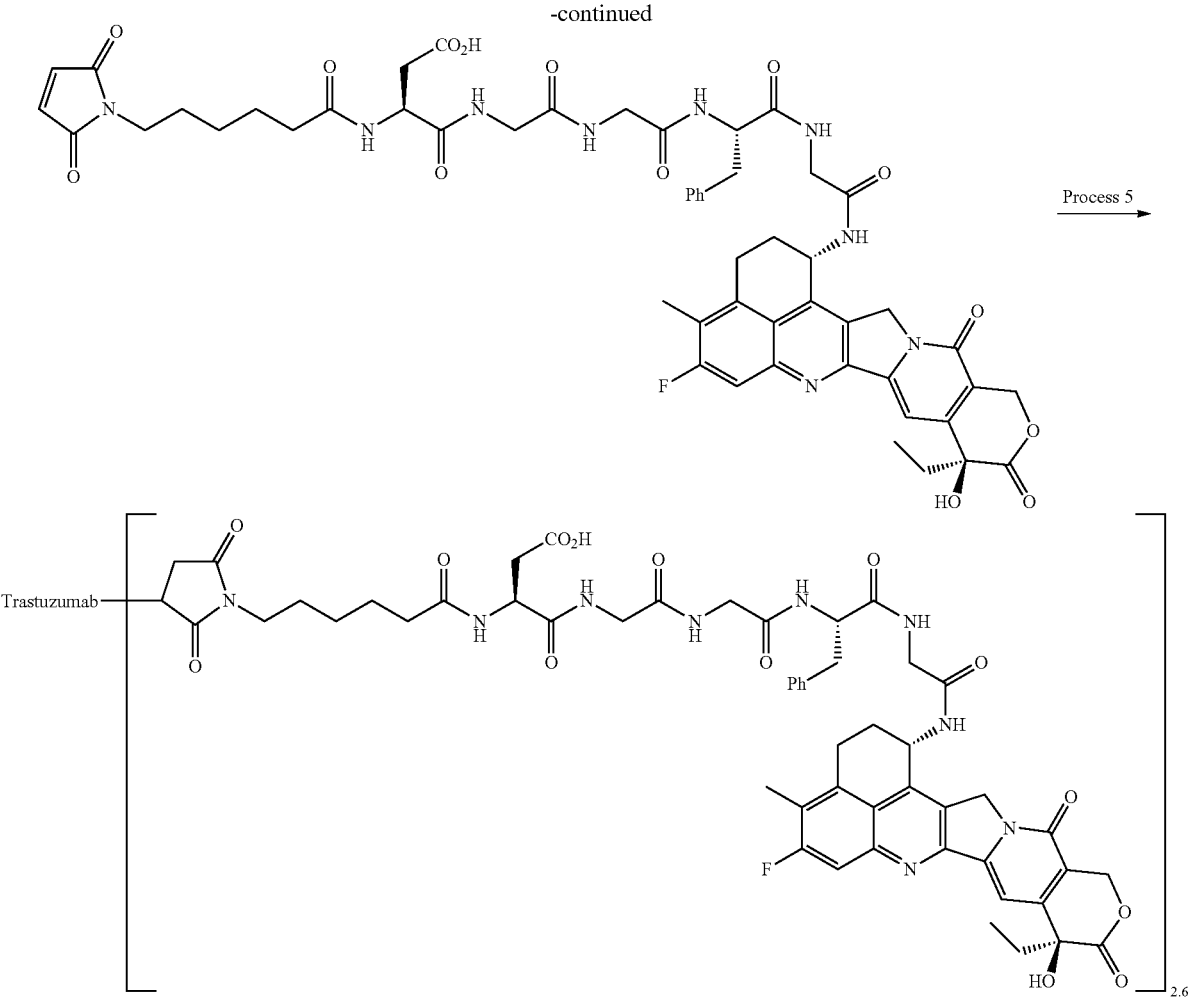

Process 1: tert-Butyl (5S,14S)-5-benzyl-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-14-{[(9H-fluoren-9-ylmethoxy)carbonyl]amino}-1,4,7,10,13-pentaoxo-3,6,9,12-tetraazahexadecan-16-oate Under ice cooling, to an N,N-dimethylformamide (10.0 mL) solution of a free form of glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (International Publication No. WO 97/46260; 0.250 g, 0.332 mmol), N-hydroxysuccinimide (57.2 mg, 0.497 mmol), and N-[(9H-fluoren-9-ylmethoxy)carbonyl]-L-aspartic acid 4-tert-butyl (0.205 g, 0.497 mmol), N,N-dicyclohexylcarbodiimide (0.123 g, 0.497 mmol) was added and stirred at room temperature for 2 days. The solvent was removed under reduced pressure and the residues obtained were purified by silica gel column chromatography [chloroform-chloroform:methanol=9:1 (v/v)] to yield the titled compound as a pale yellow solid (0.278 g, 73%).

$^1$H-NMR (400 MHz, DMSO-$d_6$) δ: 0.86 (3H, t, J=7.1 Hz), 1.35 (9H, s), 1.79-1.90 (2H, m), 2.03-2.25 (2H, m), 2.40 (3H, s), 2.40-2.51 (2H, m), 2.64-2.82 (2H, m), 2.98 (1H, dd, J=13.7, 4.6 Hz), 3.16 (2H, brs), 3.55 (1H, dd, J=16.7, 5.7 Hz), 3.63-3.80 (4H, m), 4.16-4.34 (3H, m), 4.36-4.50 (2H, m), 5.23 (2H, s), 5.37 (1H, d, J=16.5 Hz), 5.43 (1H, d, J=16.5 Hz), 5.51-5.62 (1H, m), 6.52 (1H, s), 7.10-7.25 (5H, m), 7.26-7.33 (3H, m), 7.39 (2H, t, J=7.3 Hz), 7.65-7.72 (3H, m), 7.80 (1H, d, J=11.0 Hz), 7.86 (2H, d, J=7.3 Hz), 7.98 (1H, t, J=5.5 Hz), 8.07 (1H, d, J=7.8 Hz), 8.15 (1H, t, J=5.5 Hz), 8.31 (1H, t, J=5.5 Hz), 8.41 (1H, d, J=8.7 Hz). MS (ESI) m/z: 1147 (M+H)$^+$.

Process 2: tert-Butyl (5S,14S)-14-amino-5-benzyl-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,4,7,10,13-pentaoxo-3,6,9,12-tetraazahexadecan-16-oate To an N,N-dimethylformamide (2.00 mL) solution of the compound (0.279 g, 0.242 mmol) obtained in Process 1 above, piperidine (0.240 mL, 2.42 mmol) was added and stirred at room temperature for 1 hour. The solvent was removed under reduced pressure and the residues obtained were purified by silica gel column chromatography [chloroform-chloroform:methanol=2:1 (v/v)] to yield the titled compound as a pale yellow solid (0.265 g, quantitative).

$^1$H-NMR (400 MHz, DMSO-$d_6$) δ: 0.88 (3H, t, J=7.2 Hz), 1.39 (9H, s), 1.81-1.94 (1H, m), 2.07-2.28 (2H, m), 2.37 (1H, dd, J=15.8, 8.0 Hz), 2.43 (3H, s), 2.60 (1H, dd, J=15.8, 4.9 Hz), 2.75-2.82 (1H, m), 3.00 (1H, dd, J=13.9, 4.5 Hz), 3.16-3.25 (2H, m), 3.50-3.61 (2H, m), 3.65-3.81 (5H, m), 4.40-4.51 (1H, m), 5.27 (2H, dd, J=24.1, 19.0 Hz), 5.43 (2H, dd, J=21.3, 16.2 Hz), 5.56-5.65 (1H, m), 6.55 (1H, s), 7.15-7.28 (5H, m), 7.33 (1H, s), 7.83 (1H, d, J=11.0 Hz), 8.04 (1H, t, J=5.7 Hz), 8.09 (1H, d, J=8.2 Hz), 8.26-8.39 (2H, m), 8.44 (1H, d, J=8.2 Hz).

Process 3: tert-Butyl (5S,14S)-5-benzyl-14-{[6-(2,5-dioxo-2,5-dihydro-1H-pyrrol-1-yl)hexanoyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,4,7,10,13-pentaoxo-3,6,9,12-tetraazahexadecan-16-oate To an N,N-dimethylformamide (2.00 mL) solution of the compound (0.100 g, 0.108 mmol) obtained in Process 2 above, N-succinimidyl 6-maleimidohexanoate (40.0 mg, 0.130 mmol) was added and stirred at room temperature for 2 days. The solvent was removed under reduced pressure and the residues obtained were purified by silica gel column chromatography [chloroform-chloroform:methanol=9:1 (v/v)] to yield the titled compound as a pale yellow solid (80.0 mg, 66%).

$^1$H-NMR (400 MHz, DMSO-$d_6$) δ: 0.88 (3H, t, J=7.2 Hz), 1.13-1.23 (2H, m), 1.37 (9H, s), 1.42-1.54 (4H, m), 1.80-1.96 (2H, m), 2.08-2.25 (4H, m), 2.35-3.76 (15H, m), 2.43 (3H, s), 4.39-4.49 (1H, m), 4.55-4.67 (1H, m), 5.21-5.34 (2H, m), 5.43 (2H, dd, J=21.1, 16.4 Hz), 5.56-5.64 (1H, m), 6.55 (1H, s), 7.01 (2H, d, J=0.8 Hz), 7.16-7.26 (5H, m), 7.33 (1H, s), 7.83 (1H, d, J=11.3 Hz), 8.04-8.18 (3H, m), 8.30-8.37 (1H, m), 8.43 (1H, d, J=8.6 Hz).

MS (ESI) m/z: 1118 (M+H)$^+$.

Process 4: N-[6-(2,5-Dioxo-2,5-dihydro-1H-pyrrol-1-yl)hexanoyl]-L-α-aspartylglycylglycyl-L-phenyl-alanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide Under ice cooling, to the compound (70.0 mg, 62.6 μmol) obtained in Process 3 above, trifluoroacetic acid (4.00 mL) was added and stirred at room temperature for 1 hour. The solvent was removed under reduced pressure to yield the titled compound as a pale yellow solid (55.0 mg, 83%).

$^1$H-NMR (400 MHz, DMSO-$d_6$) δ: 0.88 (3H, t, J=7.4 Hz), 1.14-1.24 (2H, m), 1.41-1.53 (4H, m), 1.79-1.95 (2H, m), 2.08-2.28 (4H, m), 2.37-2.60 (2H, m), 2.42 (3H, s), 2.63-2.82 (2H, m), 2.99 (1H, dd, J=14.1, 5.1 Hz), 3.12-3.25 (2H, m), 3.29-3.44 (1H, m), 3.52-3.80 (6H, m), 4.38-4.48 (1H, m), 4.56 (1H, dd, J=13.7, 7.4 Hz), 5.27 (2H, dd, J=24.3, 18.8 Hz), 5.43 (2H, dd, J=21.5, 16.4 Hz), 5.57-5.62 (1H, m), 6.55 (1H, s), 7.01 (2H, s), 7.15-7.26 (5H, m), 7.33 (1H, s), 7.82 (1H, d, J=11.0 Hz), 7.98 (1H, brs), 8.08 (1H, d, J=6.7 Hz), 8.15 (1H, d, J=7.8 Hz), 8.34 (1H, brs), 8.44 (1H, d, J=8.6 Hz), 12.26 (1H, brs). MS (ESI) m/z: 1062 (M+H)$^+$.

Process 5: Antibody-Drug Conjugate (73)

Reduction of the antibody: The trastuzumab produced in Reference Example 1 was prepared to have an antibody concentration of 10 mg/mL with PBS6.0/EDTA by using the Common procedure B (as absorption coefficient at 280 nm, 1.37 mLmg$^{-1}$ cm$^{-1}$ was used) and Common procedure C-1. The solution (3.0 mL) was collected into a 15 mL tube and charged with an aqueous solution of 30 mM TCEP (0.0467 mL; 6.9 equivalents per antibody molecule) and an aqueous solution of 1 M dipotassium hydrogenphosphate (0.150 mL). After confirming that the solution had a pH of 7.4±0.1, the disulfide bond at the hinge part in the antibody was reduced by incubating at 37° C. for 1 hour.

Conjugation between antibody and drug linker: After incubating the above solution for 10 minutes at 22° C., a DMSO solution (0.0933 mL; 13.8 equivalents per antibody molecule) containing 30 mM of the compound obtained in Process 4 above was added thereto and incubated for conjugating the drug linker to the antibody at 22° C. for 40 minutes. Next, an aqueous solution (0.0560 mL; 27.6 equivalents per antibody molecule) of 100 mM NAC was added thereto and incubated at 22° C. to terminate the reaction of the drug linker for another 20 minutes.

Purification: The above solution was subjected to purification using the Common procedure D-1 (PBS6.0 was used as buffer solution) to yield a solution containing the Example compound of interest.

Physicochemical characterization: By using the Common procedure B, Common procedure E, and Common procedure F, the following characteristic values were obtained.

Antibody concentration: 3.24 mg/mL, antibody yield: 19.4 mg (65%), and average number of conjugated drug molecules (n) per antibody molecule: 2.6.

Example 74 Antibody-Drug Conjugate (74)

[Formula 127]

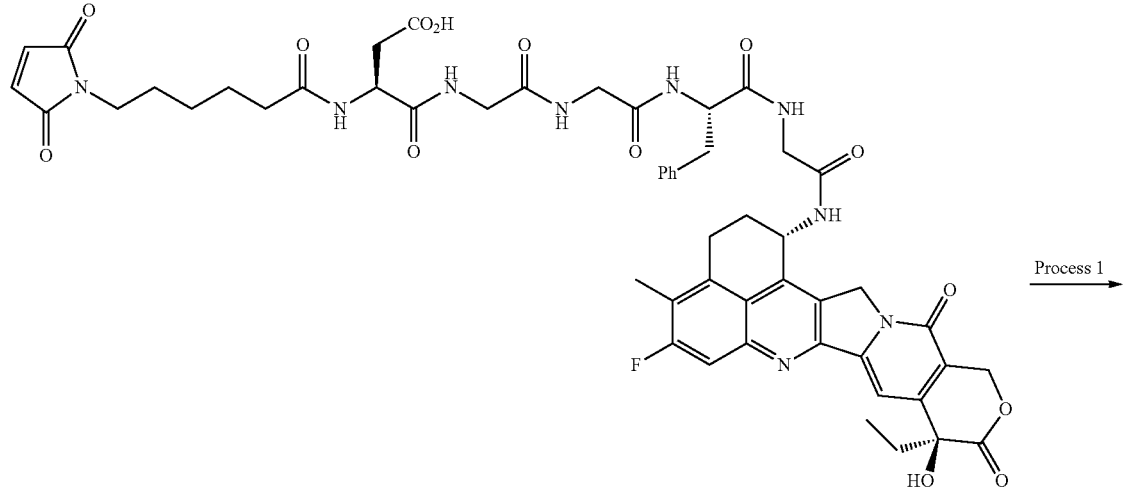

-continued

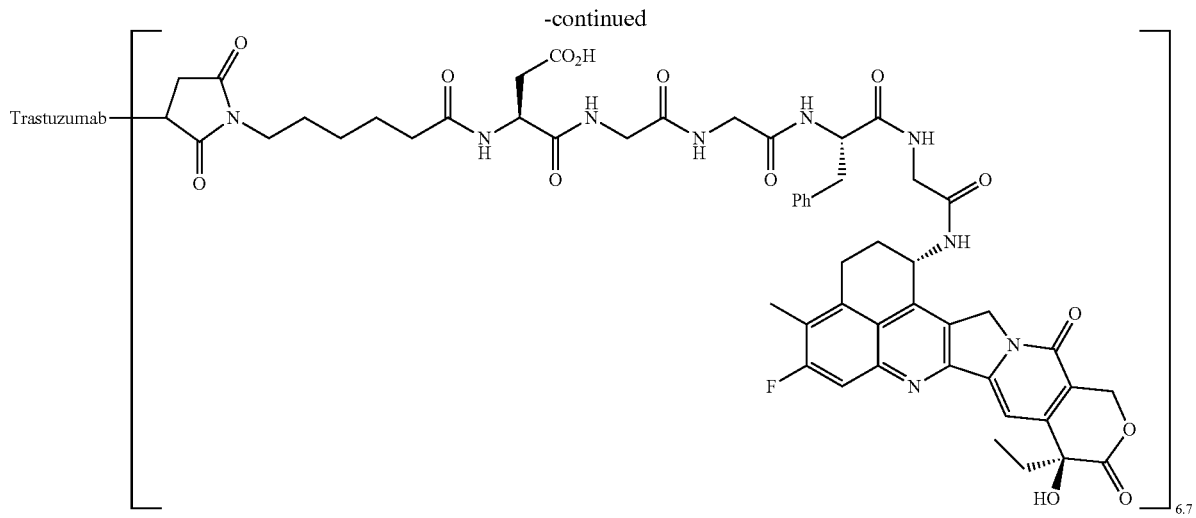

Process 1: Antibody-Drug Conjugate (74)

Reduction of the antibody: The trastuzumab produced in Reference Example 1 was prepared to have an antibody concentration of 10 mg/mL with PBS6.0/EDTA by using the Common procedure B (as absorption coefficient at 280 nm, 1.37 mLmg$^{-1}$ cm$^{-1}$ was used) and Common procedure C-1. The solution (8 mL) was placed in a 50 mL tube and charged with an aqueous solution of 10 mM TCEP (0.124 mL) and an aqueous solution of 1 M dipotassium hydrogenphosphate (0.400 mL) to prepare a reaction solution in which the molar ratio of TCEP to the antibody was 4.6. After confirming that the solution had a pH of 7.4±0.1, the disulfide bond at the hinge part in the antibody was reduced by incubating at 37° C. for 1 hour.

Conjugation between antibody and drug linker: After adding a DMSO solution containing 10 mM of the compound obtained in Process 4 of Example 73 (0.249 mL; 9.2 equivalents per antibody molecule) to the above solution at room temperature, it was stirred by using a tube rotator for conjugating the drug linker to the antibody at room temperature for 40 minutes. Next, an aqueous solution (0.050 mL) of 100 mM NAC was added thereto to prepare a reaction solution in which the molar ratio of NAC to the antibody was 18.4, and it was stirred at room temperature to terminate the reaction of the drug linker for another 20 minutes.

Purification: The above solution was subjected to purification using the Common procedure D-1 (PBS6.0 was used as buffer solution) to yield 6 mL of a solution containing the compound of interest. By using a centrifugal ultrafiltration filter (Amicon Ultra-4, molecular weight cutoff: 50 k), concentration was performed to yield 13 mL of a solution containing the compound of interest. The following characteristic values were obtained.

Antibody concentration: 3.69 mg/mL, antibody yield: 48 mg (60%), and average number of conjugated drug molecules (n) per antibody molecule: 6.7.

Example 75 Antibody-Drug Conjugate (75)

[Formula 128]

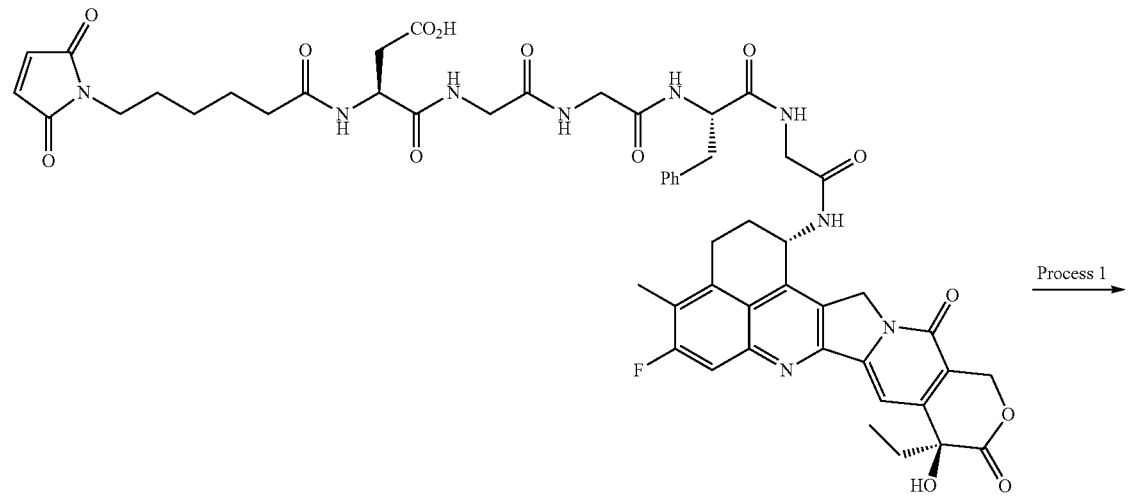

Process 1

-continued

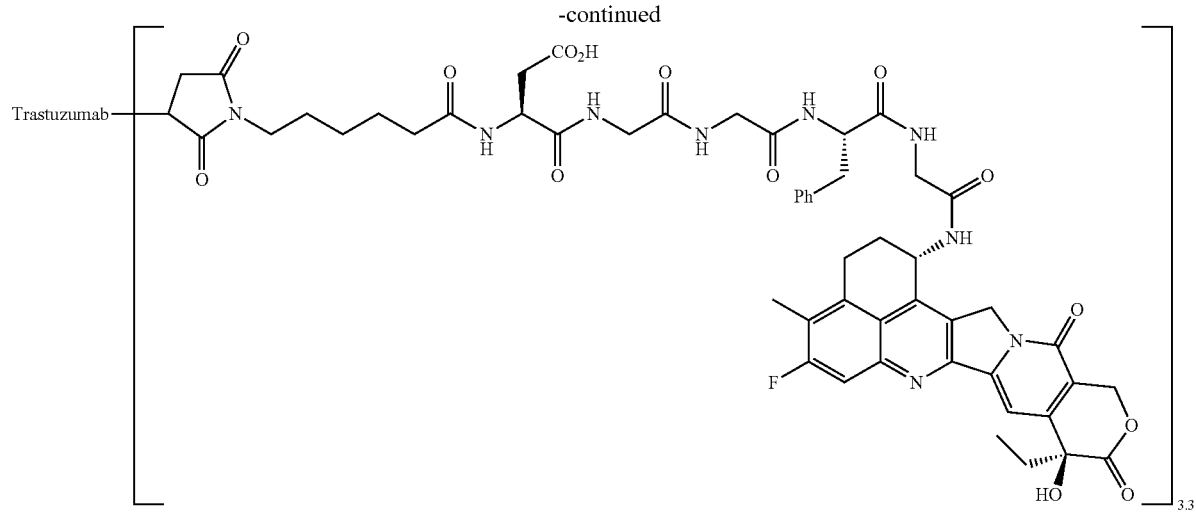

Process 1: Antibody-Drug Conjugate (75)

The amount of the aqueous solution of 10 mM TCEP added was adjusted such that the molar ratio of TCEP to the antibody at the antibody reduction was 2.3. And the amount of the 10 mM drug linker solution added was adjusted such that the molar ratio of the drug linker to the antibody at the drug linker conjugation was 4.6. Then the amount of the aqueous solution of 100 mM NAC added was adjusted such that the molar ratio of NAC to the antibody at the termination of the reaction was 9.2. By the same procedures as Process 1 of Example 74, 17 mL of a solution containing the compound of interest was obtained, and the following characteristic values were obtained.

Antibody concentration: 3.66 mg/mL, antibody yield: 62 mg (78%), and average number of conjugated drug molecules (n) per antibody molecule: 3.3.

Example 76 Antibody-Drug Conjugate (76)

[Formula 129]

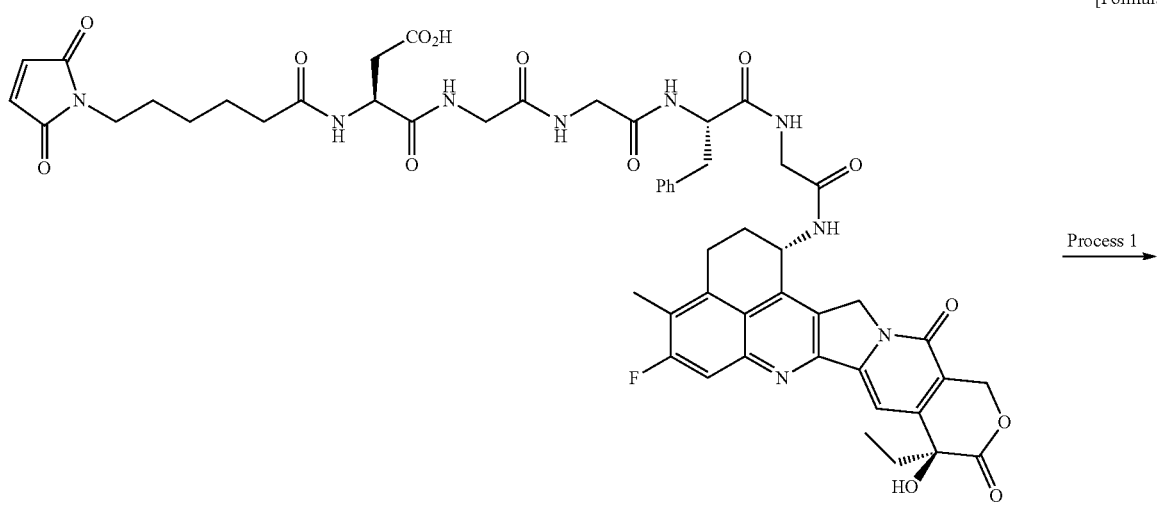

Process 1

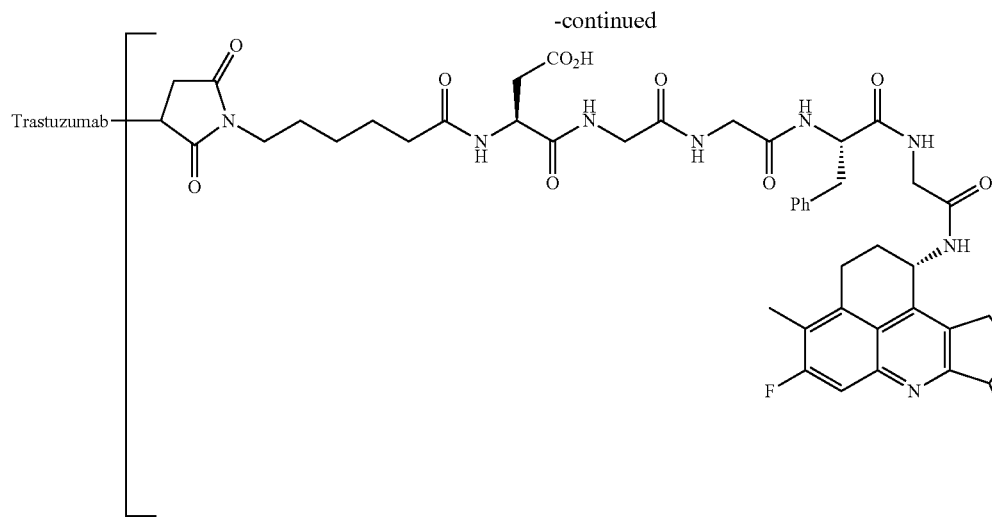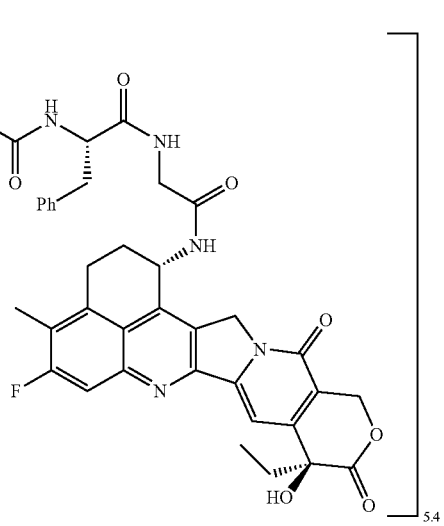

Process 1: Antibody-Drug Conjugate (76)

Reduction of the antibody: The trastuzumab produced in Reference Example 1 was prepared to have an antibody concentration of 10 mg/mL with PBS6.0/EDTA by using the Common procedure B (as absorption coefficient at 280 nm, 1.37 mLmg$^{-1}$cm$^{-1}$ was used) and Common procedure C-1. The solution (5.0 mL) was collected into a 15 mL tube and charged with an aqueous solution of 30 mM TCEP (0.0777 mL; 6.9 equivalents per antibody molecule) and an aqueous solution of 1 M dipotassium hydrogenphosphate (0.250 mL). After confirming that the solution had a pH of 7.4±0.1, the disulfide bond at the hinge part in the antibody was reduced by incubating at 37° C. for 1 hour.

Conjugation between antibody and drug linker: After incubating the above solution for 10 minutes at 22° C., a DMSO solution (0.1555 mL; 13.8 equivalents per antibody molecule) containing 30 mM of the compound obtained in Process 4 of Example 73 was added thereto and incubated for conjugating the drug linker to the antibody at 22° C. for 40 minutes. Next, an aqueous solution (0.0933 mL; 27.6 equivalents per antibody molecule) of 100 mM NAC was added thereto and incubated at 22° C. to terminate the reaction of the drug linker for another 20 minutes.

Purification: The above solution was subjected to purification using the Common procedure D-1 (ABS was used as buffer solution) to yield a solution containing the compound of interest.

Physicochemical characterization: By using the Common procedure B, Common procedure E, and Common procedure F, the following characteristic values were obtained.

Antibody concentration: 3.91 mg/mL, antibody yield: 27.4 mg (55%), and average number of conjugated drug molecules (n) per antibody molecule: 5.4.

Example 77 Antibody-Drug Conjugate (77)

[Formula 130]

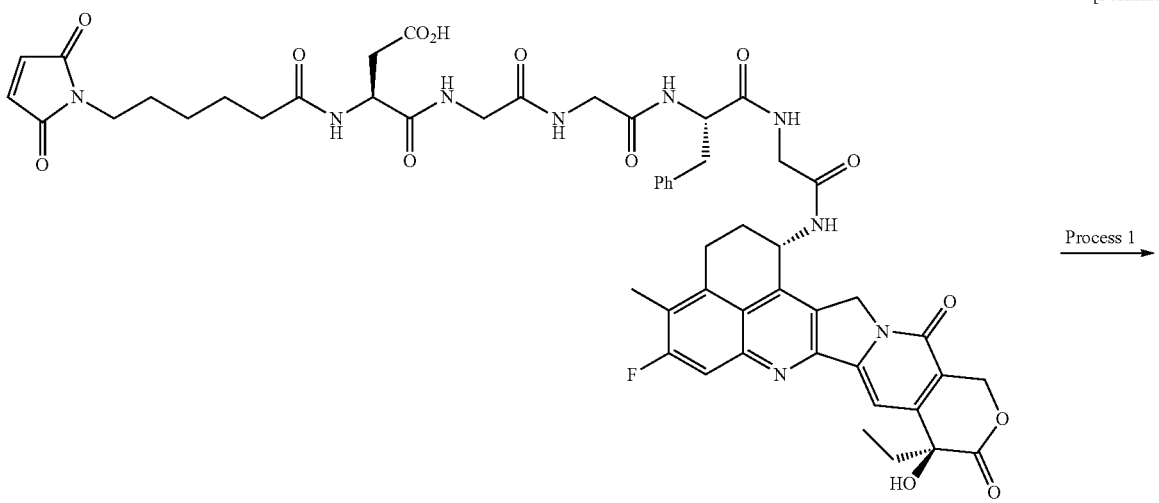

Process 1

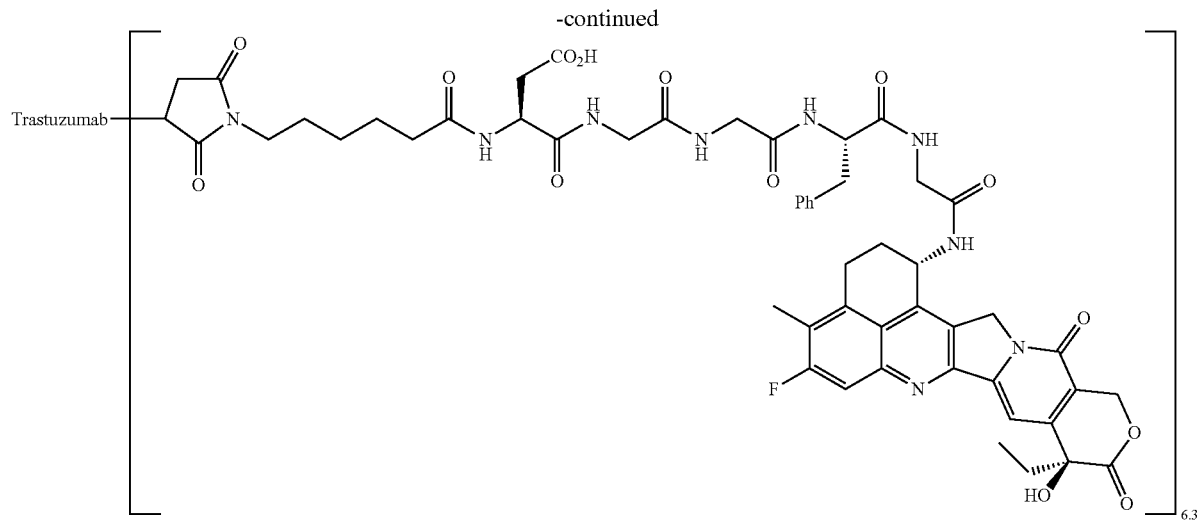

The compound obtained in Process 4 of Example 73 was used as the drug linker. The amount of the aqueous solution of 10 mM TCEP added was adjusted such that the molar ratio of TCEP to the antibody at the antibody reduction was 4.6. And the amount of the 10 mM drug linker solution added was adjusted such that the molar ratio of the drug linker to the antibody at the drug linker conjugation was 9.2. Then the amount of the aqueous solution of 100 mM NAC added was adjusted such that the molar ratio of NAC to the antibody at the termination of the reaction was 18.4. By the same procedures as Process 1 of Example 3, 6 mL of a solution containing the compound of interest was obtained, and the following characteristic values were obtained.
Antibody concentration: 1.50 mg/mL, antibody yield: 8.55 mg (68%), and average number of conjugated drug molecules (n) per antibody molecule: 6.3.

Example 78 Antibody-Drug Conjugate (78)

[Formula 131]

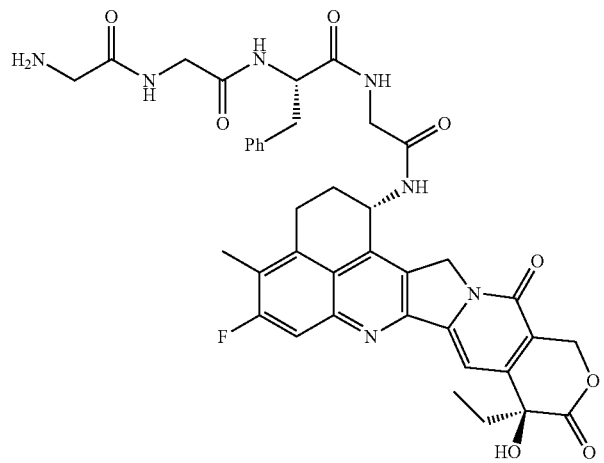 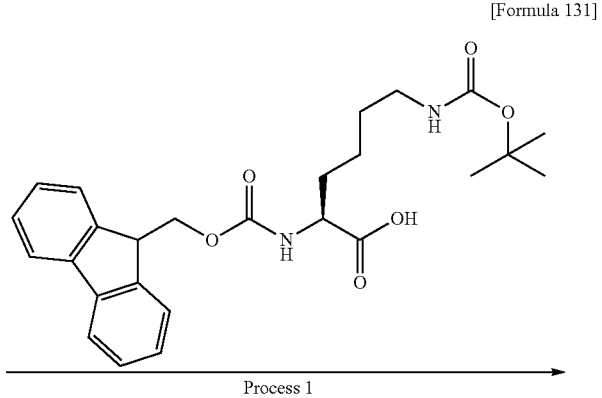

Process 1

383
384
-continued
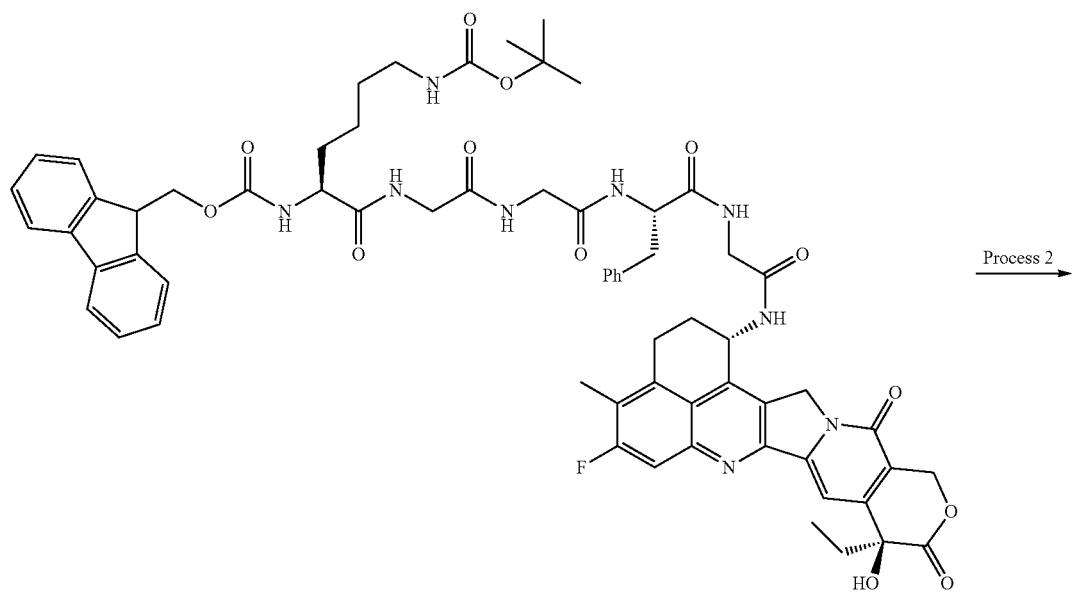
Process 2
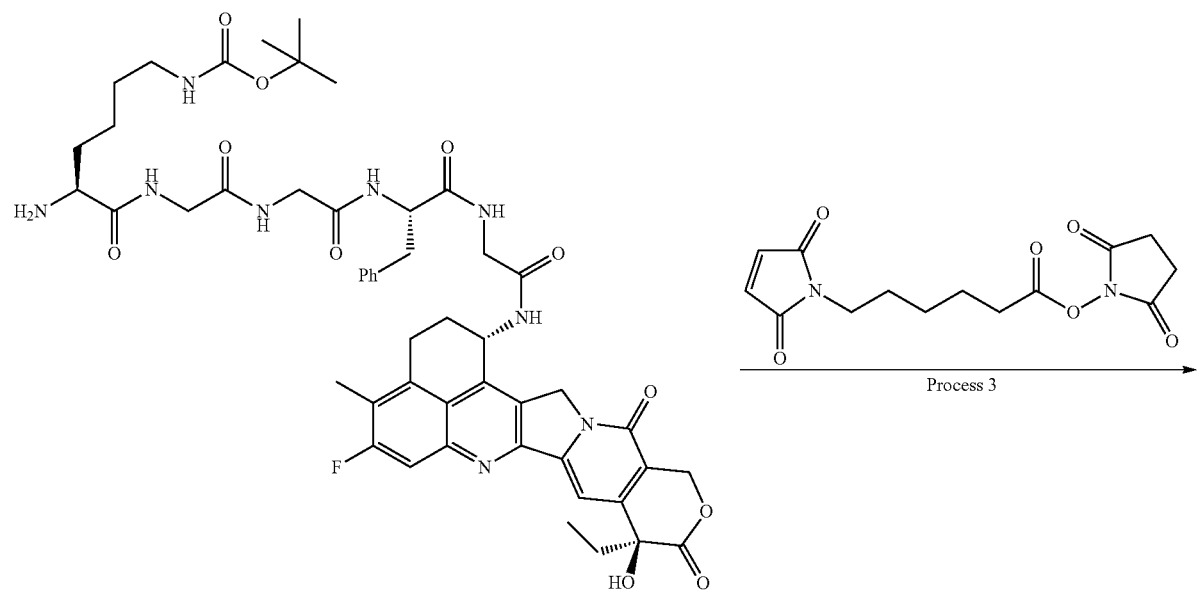
Process 3

-continued
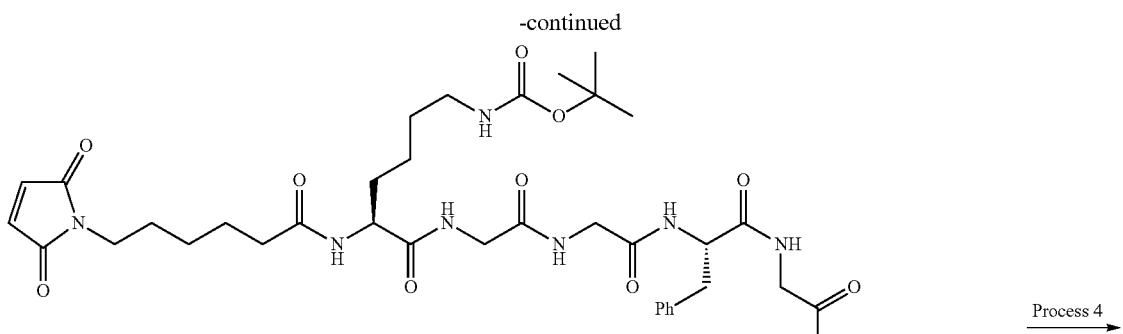
Process 4 →
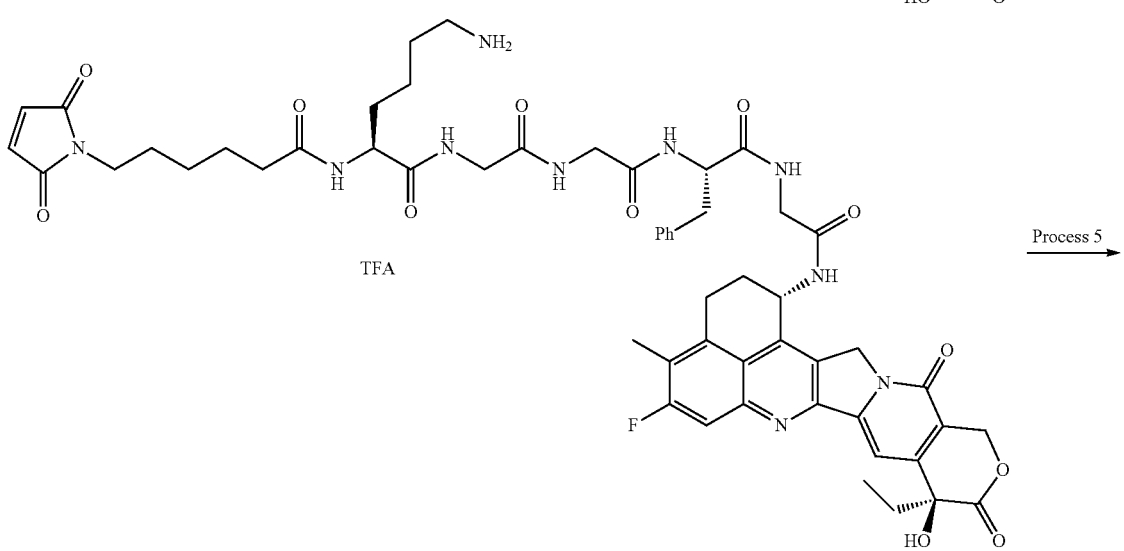
TFA
Process 5 →
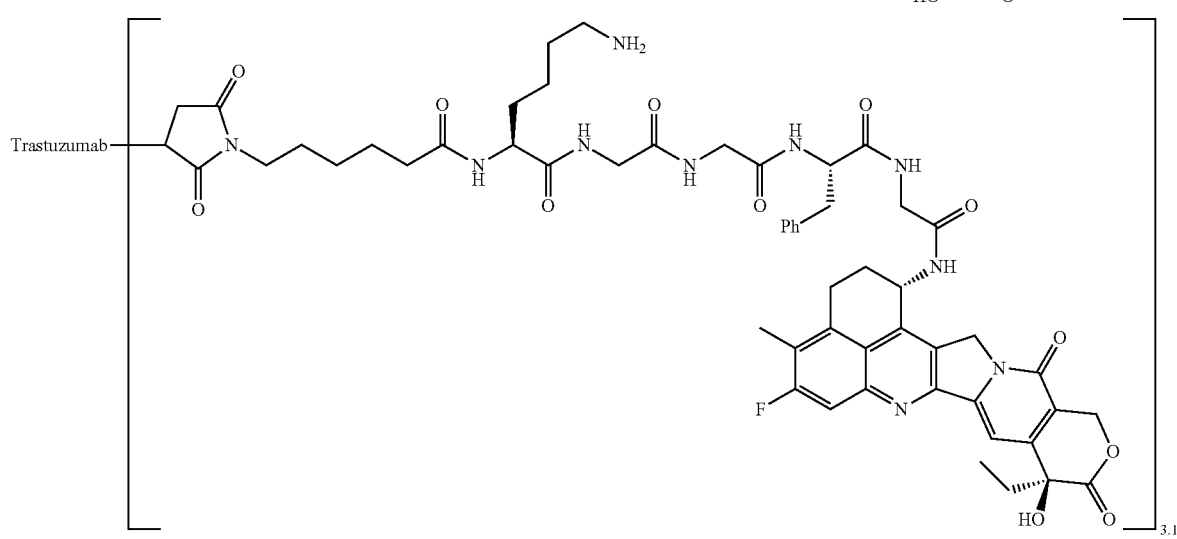

Process 1: N⁶-(tert-Butoxycarbonyl)-N²-[(9H-fluoren-9-ylmethoxy)carbonyl]-L-lysylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide A free form of glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (International Publication No. WO 97/46260; 0.300 g, 0.397 mmol) was reacted in the same manner as Process 1 of Example 73 by using N$^\varepsilon$-(tert-butoxycarbonyl)-N$^\alpha$-[(9H-fluoren-9-ylmethoxy)carbonyl]-L-lysine instead of N-[(9H-fluoren-9-ylmethoxy)carbonyl]-L-aspartic acid 4-tert-butyl to yield the titled compound as a yellow solid (0.471 g, 98%).

MS(ESI) m/z: 1204 (M+H)⁺.

Process 2: N⁶-(tert-Butoxycarbonyl)-L-lysylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.417 g, 0.391 mmol) obtained in Process 1 above was reacted in the same manner as Process 2 of Example 73 to yield the titled compound as a pale yellow solid (0.272 g, 71%).

MS(ESI) m/z: 1062 (M+H)⁺.

Process 3: N⁶-(tert-Butoxycarbonyl)-N²-[6-(2,5-dioxo-2,5-dihydro-1H-pyrrol-1-yl)hexanoyl]-L-lysylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.210 g, 0.213 mmol) obtained in Process 2 above was reacted in the same manner as Process 3 of Example 73 to yield the titled compound as a pale yellow solid (63.0 mg, 21%).

MS(ESI) m/z: 1175 (M+H)⁺.

Process 4: N²-[6-(2,5-Dioxo-2,5-dihydro-1H-pyrrol-1-yl)hexanoyl]-L-lysylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide Under ice cooling, to the compound (63.0 mg, 53.6 μmol) obtained in Process 3 above, trifluoroacetic acid (2.00 mL) was added and stirred at room temperature for 1 hour. The solvent was removed under reduced pressure to yield trifluoroacetic acid salt of the titled compound as a yellow solid (50.0 mg, 78%).

¹H-NMR (400 MHz, DMSO-d₆) δ: 0.89 (3H, t, J=7.2 Hz), 1.13-1.39 (4H, m), 1.43-1.58 (7H, m), 1.61-1.73 (1H, m), 1.80-1.94 (2H, m), 2.07-2.28 (4H, m), 2.43 (3H, s), 2.72-2.84 (4H, m), 3.00 (1H, dd, J=13.7, 3.9 Hz), 3.20 (2H, brs), 3.55-3.80 (6H, m), 4.20-4.30 (1H, m), 4.42-4.52 (1H, m), 5.27 (2H, dd, J=23.7, 19.8 Hz), 5.43 (2H, dd, J=21.9, 16.4 Hz), 5.55-5.65 (1H, m), 6.56 (1H, s), 7.02 (2H, s), 7.15-7.27 (5H, m), 7.34 (1H, s), 7.64 (3H, brs), 7.83 (1H, d, J=10.6 Hz), 7.98-8.04 (2H, m), 8.09-8.20 (2H, m), 8.37 (1H, t, J=5.5 Hz), 8.47 (1H, d, J=8.6 Hz).

MS (ESI) m/z: 1075 (M+H)⁺.

Process 5: Antibody-Drug Conjugate (78)

Reduction of the antibody: The trastuzumab produced in Reference Example 1 was prepared to have an antibody concentration of 10 mg/mL with PBS6.0/EDTA by using the Common procedure B (as absorption coefficient at 280 nm, 1.37 mLmg⁻¹ cm⁻¹ was used) and Common procedure C-1. The solution (1 mL) was placed in a 1.5 mL tube and charged with an aqueous solution of 10 mM TCEP (0.024 mL) and an aqueous solution of 1 M dipotassium hydrogenphosphate (0.050 mL) to prepare a reaction solution in which the molar ratio of TCEP to the antibody was 3.5. After confirming that the solution had a pH of 7.4±0.1, the disulfide bond at the hinge part in the antibody was reduced by incubating at 37° C. for 1 hour.

Conjugation between antibody and drug linker: After adding a DMSO solution containing 10 mM of the compound obtained in Process 4 above (0.047 mL) to the above solution at room temperature to prepare a reaction solution in which the molar ratio of the compound obtained in Process 4 above to the antibody was 6.9, it was stirred by using a tube rotator for conjugating the drug linker to the antibody at room temperature for 40 minutes. Next, an aqueous solution (0.0093 mL) of 100 mM NAC was added thereto to prepare a reaction solution in which the molar ratio of NAC to the antibody was 13.8, and it was stirred at room temperature to terminate the reaction of the drug linker for another 20 minutes.

Purification: The above solution was subjected to purification using the Common procedure D-1 (PBS6.0 was used as buffer solution) to yield 6 mL of a solution containing the compound of interest.

Physicochemical characterization: By using the Common procedure B, Common procedure E and Common procedure F, the following characteristic values were obtained.

Antibody concentration: 1.26 mg/mL, antibody yield: 7.6 mg (76%), and average number of conjugated drug molecules (n) per antibody molecule: 3.1.

Example 79 Antibody-Drug Conjugate (79)

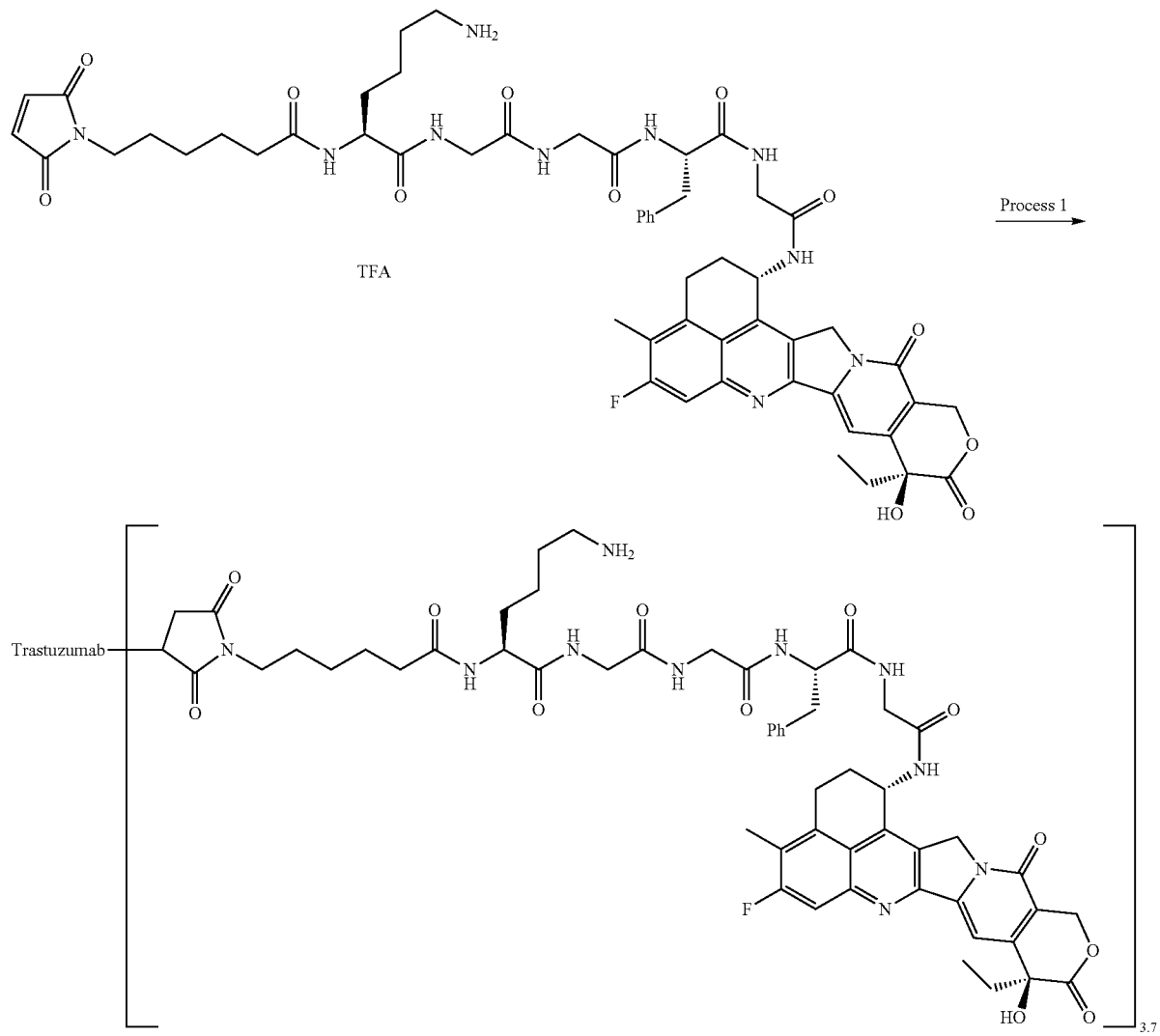

[Formula 132]

Process 1: Antibody-Drug Conjugate (79)

The amount of the aqueous solution of 10 mM TCEP added was adjusted such that the molar ratio of TCEP to the antibody at the antibody reduction was 4.6. And the amount of the 10 mM drug linker solution added was adjusted such that the molar ratio of the drug linker to the antibody at the drug linker conjugation was 9.2. Then the amount of the aqueous solution of 100 mM NAC added was adjusted such that the molar ratio of NAC to the antibody at the termination of the reaction was 18.4. By the same procedures as Process 5 of Example 78, 6 mL of a solution containing the compound of interest was obtained, and the following characteristic values were obtained.

Antibody concentration: 1.19 mg/mL, antibody yield: 7.1 mg (71%), and average number of conjugated drug molecules (n) per antibody molecule: 3.7.

Example 80 Intermediate (80)

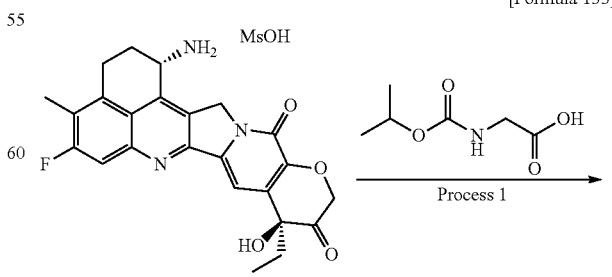

[Formula 133]

391
-continued

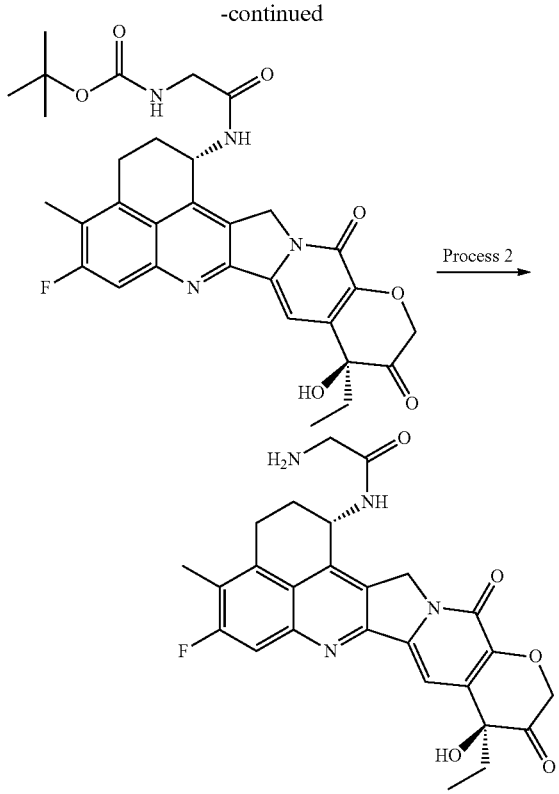

Process 1: tert-Butyl (2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)carbamate To a dichloromethane (3.00 mL) solution of N-(tert-butoxycarbonyl)-glycine (0.395 g, 2.26 mmol), N-hydroxysuccinimide (0.260 g, 2.26 mmol) and 1-ethyl-3-(3-dimethylaminopropyl)carbodiimide hydrochloride (0.433 mg, 2.26 mmol) were added and stirred at room temperature for 1 hour. This solution was added to a solution consisting of methanesulfonic acid salt of exatecan (1.00 g, 1.88 mmol), triethylamine (0.315 mL, 2.26 mmol), and N,N-dimethylformamide (3.00 mL) and stirred at room temperature for 16.5 hours. The reaction solution was diluted with chloroform and washed with a 10% citric acid solution, and then the organic layer was dried over anhydrous sodium sulfate. The solvent was removed under reduced pressure and the residues obtained were purified by silica gel column chromatography [chloroform -chloroform:methanol=9:1 (v/v)] to yield the titled compound as a yellow solid (1.16 g, 99%).

$^1$H-NMR (400 MHz, DMSO-$d_6$) δ: 0.86 (3H, t, J=7.2 Hz), 1.30 (9H, s), 1.81-1.89 (2H, m), 2.09-2.21 (2H, m), 2.38 (3H, s), 3.15-3.17 (2H, m), 3.55-3.56 (2H, m), 5.15 (1H, d, J=18.8 Hz), 5.23 (1H, d, J=19.2 Hz), 5.41 (2H, s), 5.55-5.56 (1H, m), 6.53 (1H, s), 6.95 (1H, t, J=5.5 Hz), 7.28 (1H, s), 7.77 (1H, d, J=11.0 Hz), 8.39 (1H, d, J=8.6 Hz).

MS (APCI) m/z: 593 (M+H)$^+$.

Process 2: N-[(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.513 g, 1.01 mmol) obtained in Process 1 above was reacted in the same manner as Process 4 of Example 69 to yield the titled compound as a yellow solid (0.463 g, 93%).

$^1$H-NMR (400 MHz, CD$_3$OD) δ: 0.96 (3H, t, J=7.0 Hz), 1.89-1.91 (2H, m), 2.14-2.16 (1H, m), 2.30 (3H, s), 2.40-2.42 (1H, m), 3.15-3.21 (2H, m), 3.79-3.86 (2H, m), 4.63-4.67 (1H, m), 5.00-5.05 (1H, m), 5.23 (1H, d, J=16.0 Hz), 5.48 (1H, d, J=16.0 Hz), 5.62-5.64 (1H, m), 7.40-7.45 (2H, m).

MS (APCI) m/z: 493 (M+H)$^+$.

Example 81 Antibody-Drug Conjugate (81)

[Formula 134]

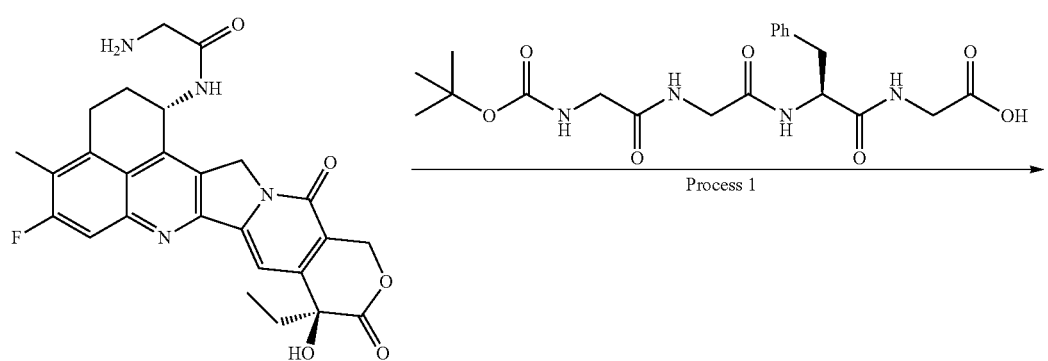

-continued
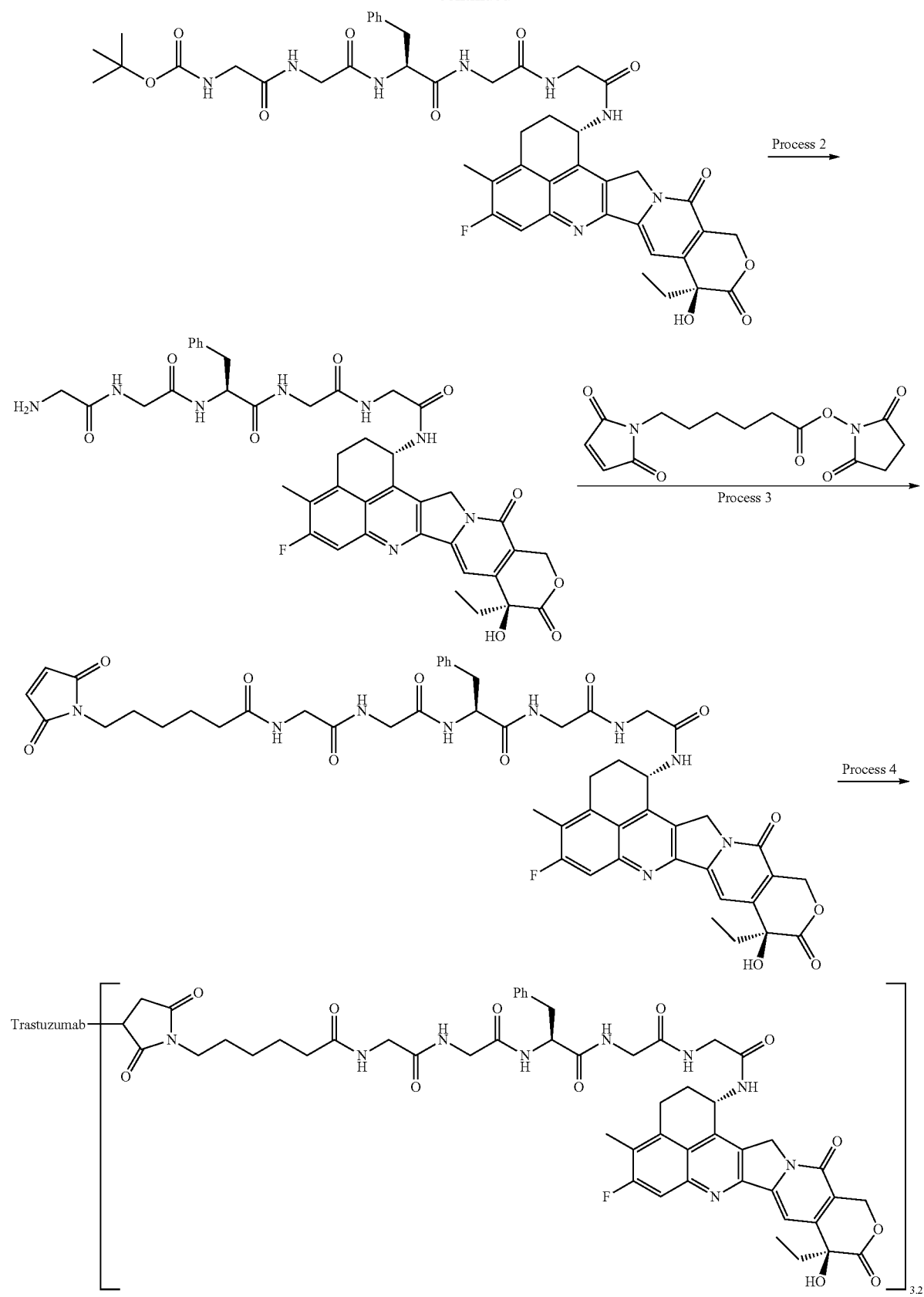

Process 1: N-(tert-Butoxycarbonyl)glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide N-(tert-Butoxycarbonyl)-glycylglycyl-L-phenylalanylglycine (0.292 mg, 0.669 mmol) was dissolved in dichloromethane (5.00 mL), charged with N-hydroxysuccinimide (77.0 mg, 0.669 mmol) and N,N-dicyclohexylcarbodiimide (128 mg, 0.669 mmol), and stirred for 1 hour and 20 minutes. The reaction solution was added dropwise to an N,N-dimethylformamide solution (5.00 mL) of the compound (0.275 g, 0.558 mmol) of Process 2 of Example 80 and stirred at room temperature for 1 day. After adding an aqueous solution of 10% citric acid (20.0 mL), it was extracted with chloroform (20 mL) 3 times. The solvent in the organic layer obtained was removed under reduced pressure and the residues obtained were purified by silica gel column chromatography [chloroform-chloroform:methanol=8:2 (v/v)] to yield the titled compound as a pale yellow solid (0.430 g, 85%).

$^1$H-NMR (400 MHz, CD$_3$OD) δ: 0.94 (3H, t, J=7.2 Hz), 1.43 (9H, s), 1.83-1.85 (2H, m), 2.20-2.22 (1H, m), 2.29 (3H, s), 2.36-2.39 (2H, m), 2.50-2.53 (1H, m), 2.67 (1H, s), 3.08-3.11 (1H, m), 3.18-3.21 (1H, m), 3.63-3.67 (4H, m), 3.78-3.82 (1H, m), 3.99 (2H, dd, J=23.5, 16.8 Hz), 4.16 (1H, s), 4.58 (1H, d, J=18.8 Hz), 5.15 (1H, d, J=19.2 Hz), 5.25 (1H, d, J=16.4 Hz), 5.52 (1H, d, J=16.4 Hz), 5.59-5.61 (1H, m), 6.89 (2H, d, J=6.7 Hz), 7.15-7.17 (3H, m), 7.28 (1H, d, J=10.6 Hz), 7.41 (1H, s).

MS (APCI) m/z: 911 (M+H)$^+$.

Process 2: Glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.227 g, 0.249 mmol) obtained in Process 1 above was dissolved in dichloromethane (1.00 mL). After adding trifluoroacetic acid (3.00 mL), it was stirred for 1 hour. The solvent was removed under reduced pressure and the residues obtained were purified by silica gel column chromatography [chloroform -partitioned organic layer of chloroform:methanol:water=7:3:1 (v/v/v)] to yield the titled compound as a pale yellow solid (0.200 g, 99%).

$^1$H-NMR (400 MHz, CD$_3$OD) δ: 0.93 (3H, t, J=7.4 Hz), 1.85 (2H, q, J=7.3 Hz), 2.24-2.45 (5H, m), 2.32 (3H, s), 2.56 (1H, dd, J=13.7, 5.5 Hz), 3.09-3.25 (2H, m), 3.66-3.76 (6H, m), 4.18-4.24 (1H, m), 4.76 (1H, d, J=19.2 Hz), 5.18 (1H, d, J=18.8 Hz), 5.30 (1H, t, J=18.4 Hz), 5.52 (1H, d, J=16.0 Hz), 5.63 (1H, t, J=5.9 Hz), 6.93 (2H, d, J=6.6 Hz), 7.17 (3H, q, J=7.3 Hz), 7.30 (1H, d, J=10.9 Hz), 7.42 (1H, s).

MS (APCI) m/z: 811 (M+H)$^+$.

Process 3: N-[6-(2,5-Dioxo-2,5-dihydro-1H-pyrrol-1-yl)hexanoyl]glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.125 g, 0.154 mmol) obtained in Process 2 above was reacted in the same manner as Process 3 of Example 73 to yield the titled compound as a pale yellow solid (0.0775 g, 50%).

$^1$H-NMR (400 MHz, DMSO-d$_6$) δ: 0.86 (3H, t, J=7.2 Hz), 1.18-1.19 (2H, m), 1.45-1.48 (4H, m), 1.83-1.85 (2H, m), 2.12-2.17 (4H, m), 2.39 (3H, s), 2.68 (1H, dd, J=24.4, 14.7 Hz), 2.83-2.87 (1H, m), 3.17-3.78 (12H, m), 4.42-4.45 (1H, m), 5.23 (2H, s), 5.41 (2H, s), 5.58-5.60 (1H, m), 6.53 (1H, s), 6.99 (2H, s), 7.15-7.29 (6H, m), 7.76 (1H, d, J=10.9 Hz), 7.97-8.00 (1H, m), 8.09-8.12 (3H, m), 8.25-8.28 (1H, m), 8.44 (1H, d, J=8.2 Hz).

MS (APCI) m/z: 1004 (M+H)$^+$.

Process 4: Antibody-Drug Conjugate (81)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.37 mLmg$^{-1}$ cm$^{-1}$ was used). The solution (0.5 mL) was placed in a 1.5 mL tube and charged with an aqueous solution of 10 mM TCEP (0.0078 mL; 2.3 equivalents per antibody molecule) and an aqueous solution of 1 M dipotassium hydrogenphosphate (0.025 mL). After confirming that the solution had a pH of 7.4±0.1, the disulfide bond at the hinge part in the antibody was reduced by incubating at 37° C. for 1 hour.

Conjugation between antibody and drug linker: After adding DMSO (Sigma-Aldrich Co., LLC; 0.039 mL) and a DMSO solution containing 10 mM of the compound obtained in Process 3 above (0.0155 mL; 4.6 equivalents per antibody molecule) to the above solution at room temperature, it was stirred by using a tube rotator for conjugating the drug linker to the antibody at room temperature for 40 minutes. Next, an aqueous solution (0.003 mL) of 100 mM NAC was added thereto and stirred at room temperature to terminate the reaction of the drug linker for another 20 minutes.

Purification: The above solution was subjected to purification using the Common procedure D-1 (ABS was used as a buffer solution) to yield 3 mL of a solution containing the compound of interest. The solution was further concentrated by the Common procedure A. After that, by using the Common procedure B and Common procedure E, the following characteristic values were obtained.

Antibody concentration: 8.31 mg/mL, antibody yield: 3.3 mg (83%), and average number of conjugated drug molecules (n) per antibody molecule: 3.2.

Example 82 Antibody-Drug Conjugate (82)

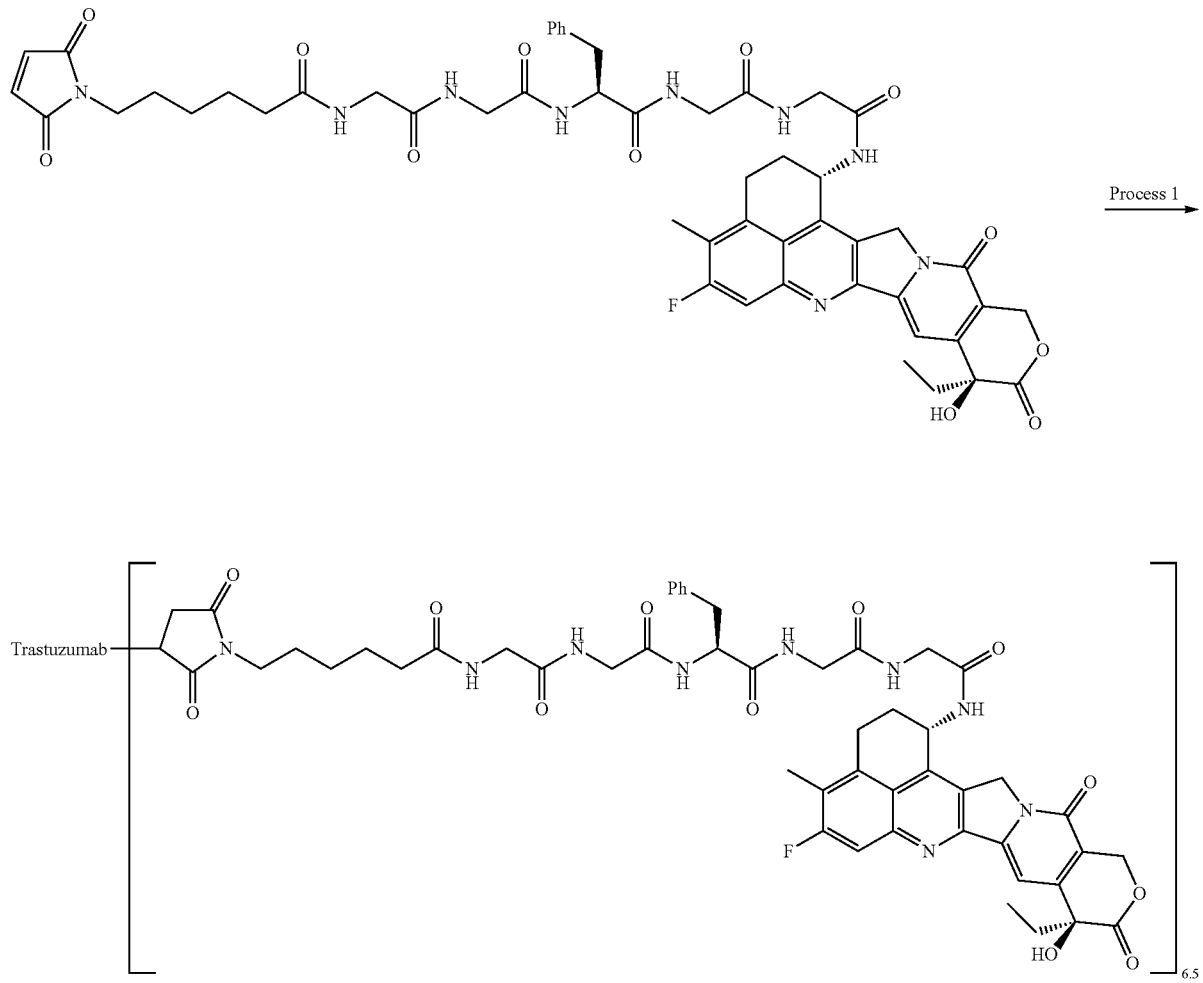

[Formula 135]

Process 1

Process 1: Antibody-Drug Conjugate (82)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.37 mLmg$^{-1}$ cm$^{-1}$ was used). The solution (0.5 mL) was placed in a 1.5 mL tube and charged with an aqueous solution of 10 mM TCEP (0.0155 mL; 4.6 equivalents per antibody molecule) and an aqueous solution of 1 M dipotassium hydrogenphosphate (0.025 mL). After confirming that the solution had a pH of 7.4±0.1, the disulfide bond at the hinge part in the antibody was reduced by incubating at 37° C. for 1 hour.

Conjugation between antibody and drug linker: After adding DMSO (Sigma-Aldrich Co., LLC; 0.029 mL) and a DMSO solution containing 10 mM of the compound obtained in Process 3 of Example 81 (0.031 mL; 9.2 equivalents per antibody molecule) to the above solution at room temperature, it was stirred by using a tube rotator for conjugating the drug linker to the antibody at room temperature for 40 minutes. Next, an aqueous solution (0.006 mL) of 100 mM NAC was added thereto and stirred at room temperature to terminate the reaction of the drug linker for another 20 minutes.

Purification: The above solution was subjected to purification using the Common procedure D-1 (ABS was used as a buffer solution) to yield 3 mL of a solution containing the compound of interest. The solution was further concentrated by the Common procedure A. After that, by using the Common procedure B and Common procedure E, the following characteristic values were obtained.

Antibody concentration: 9.62 mg/mL, antibody yield: 3.8 mg (76%), and average number of conjugated drug molecules (n) per antibody molecule: 6.5.

Example 83 Antibody-Drug Conjugate (83)

[Formula 136]

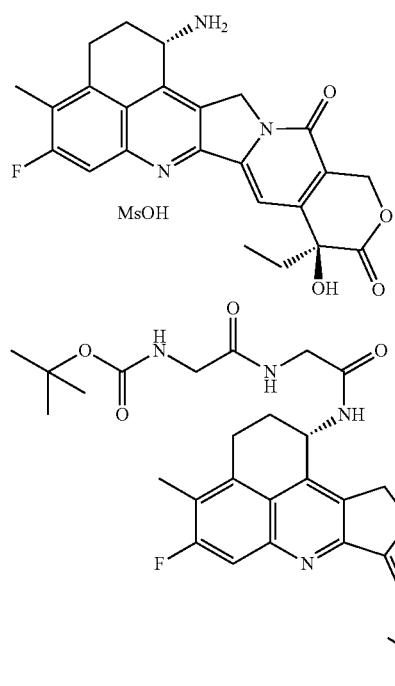

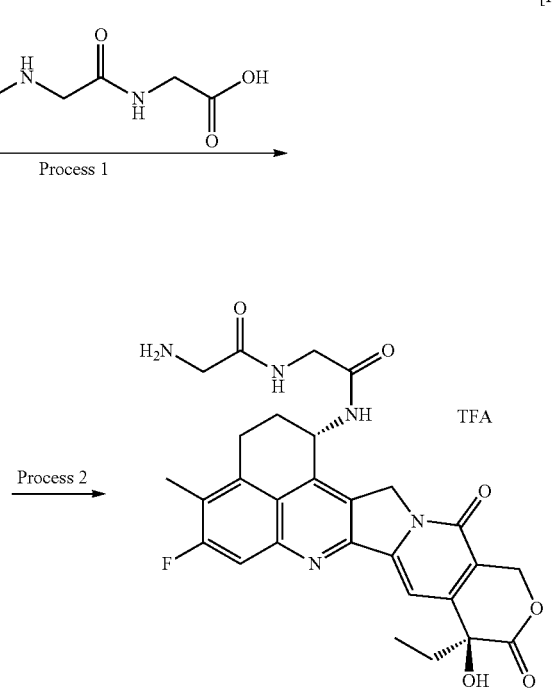

Process 1: N-(tert-Butoxycarbonyl)glycyl-N-[(1S, 9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide Methanesulfonic acid salt of exatecan (0.800 g, 1.51 mmol) was reacted in the same manner as Process 1 of Example 1 by using N-(tert-butoxycarbonyl)-glycylglycine (0.419 g, 1.81 mmol) instead of 4-(tert-butoxycarbonylamino)butanoic acid to yield the titled compound as a yellow solid (0.965 g, 99%).

$^1$H-NMR (400 MHz, DMSO-d$_6$) δ: 0.87 (3H, t, J=7.4 Hz), 1.23 (9H, s), 1.82-1.89 (2H, m), 2.11-2.19 (2H, m), 2.40 (3H, s), 3.16-3.17 (2H, m), 3.52 (2H, ddd, J=21.3, 15.5, 4.7 Hz), 3.77 (2H, ddd, J=24.3, 16.8, 5.9 Hz), 5.23 (2H, s), 5.43 (2H, s), 5.56-5.60 (1H, m), 6.53 (1H, s), 7.04 (1H, t, J=5.9 Hz), 7.31 (1H, s), 7.80 (1H, d, J=11.0 Hz), 8.12 (1H, t, J=5.5 Hz), 8.31 (1H, d, J=8.6 Hz).

MS (APCI) m/z: 650 (M+H)$^+$.

Process 2: Glycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.884 g, 1.36 mmol) obtained in Process 1 above was reacted in the same manner as Process 2 of Example 1 to yield trifluoroacetic acid salt of the titled compound as a yellow solid (0.787 g, quantitative).

$^1$H-NMR (400 MHz, DMSO-d$_6$) δ: 0.87 (3H, t, J=7.2 Hz), 1.82-1.89 (2H, m), 2.11-2.18 (2H, m), 2.41 (3H, s), 3.17-3.18 (2H, m), 3.63 (2H, s), 3.88 (2H, d, J=5.5 Hz), 5.19 (1H, d, J=18.8 Hz), 5.25 (1H, d, J=19.2 Hz), 5.42 (2H, s), 5.56-5.61 (1H, m), 6.56 (1H, s), 7.32 (1H, s), 7.81 (1H, d, J=11.0 Hz), 8.01 (3H, brs), 8.65 (1H, d, J=8.6 Hz), 8.72 (1H, t, J=5.5 Hz).

MS (APCI) m/z: 550 (M+H)$^+$.

Example 84 Antibody-Drug Conjugate (84)

[Formula 137]

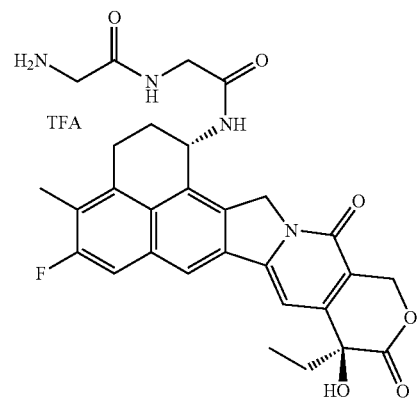

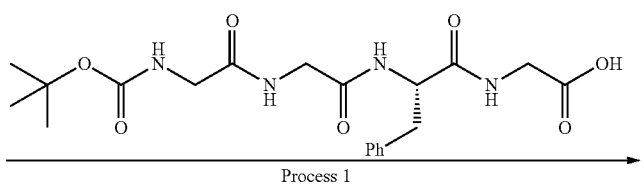

-continued

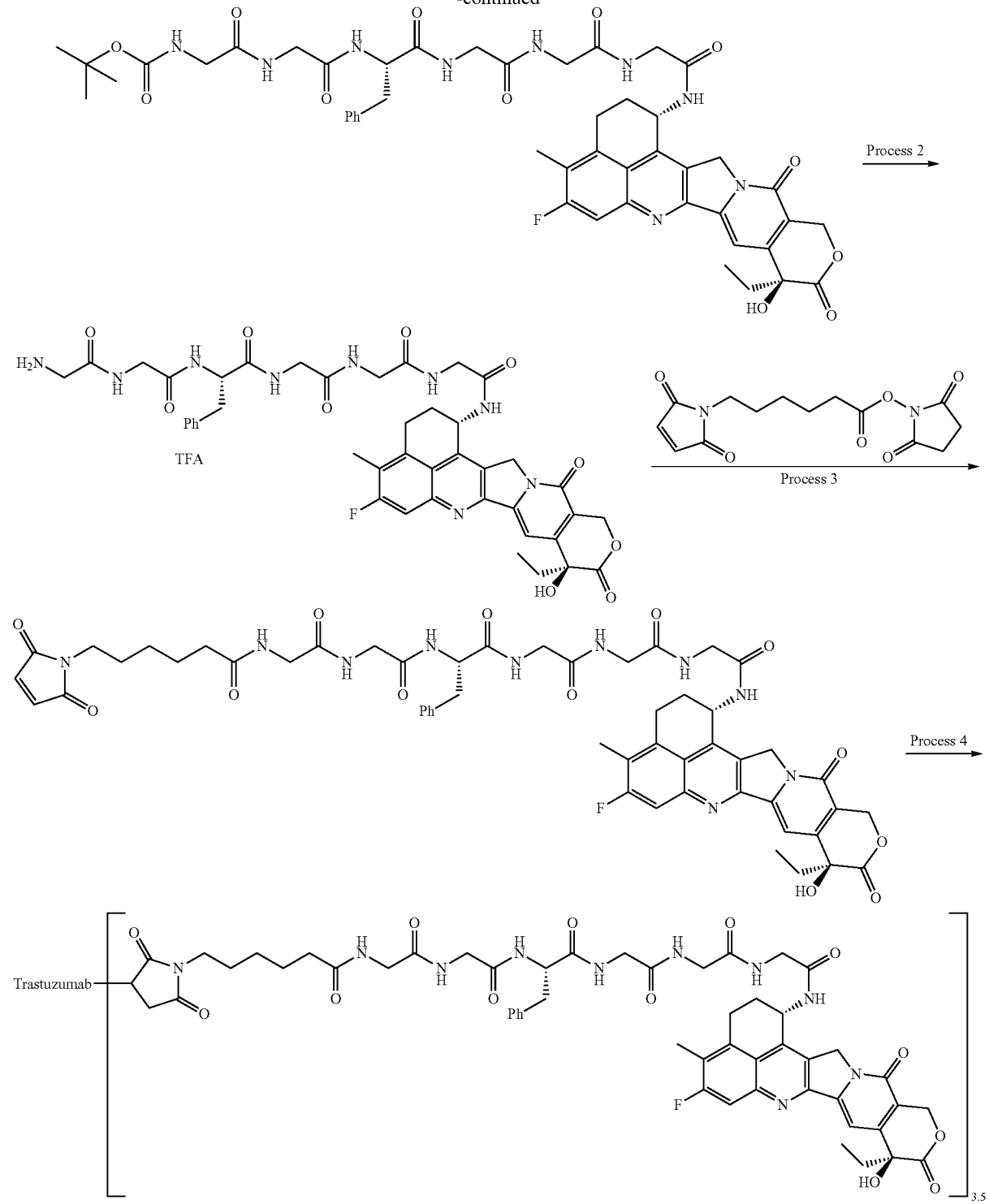

Process 1: N-(tert-Butoxycarbonyl)glycylglycylphenylalanylglycylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide Trifluoroacetic acid salt of the compound (0.400 g, 0.728 mmol) obtained in Process 2 of Example 83 was reacted in the same manner as Process 1 of Example 1 by using N-(tert-butoxycarbonyl)-glycylglycyl-L-phenylalanylglycine (0.381 mg, 0.873 mmol) instead of 4-(tert-butoxycarbonylamino)butanoic acid to yield the titled compound as a pale yellow solid (0.545 g, 77%).

$^1$H-NMR (400 MHz, DMSO-$d_6$) δ: 0.87 (3H, t, J=7.2 Hz), 1.37 (9H, s), 1.80-1.90 (2H, m), 2.09-2.11 (1H, m), 2.18-2.21 (1H, m), 2.40 (3H, s), 2.72-2.77 (1H, m), 3.01 (1H, dd,

J=13.7, 4.3 Hz), 3.16-3.17 (2H, m), 3.52-3.83 (10H, m), 4.48-4.51 (1H, m), 5.21 (1H, d, J=19.2 Hz), 5.26 (1H, d, J=18.8 Hz), 5.43 (2H, s), 5.55-5.59 (1H, m), 6.53 (1H, s), 6.99 (1H, t, J=5.9 Hz), 7.18-7.24 (5H, m), 7.31 (1H, s), 7.80 (1H, d, J=11.0 Hz), 7.90 (1H, t, J=5.3 Hz), 8.02 (1H, t, J=5.5 Hz), 8.15-8.19 (2H, m), 8.30 (1H, t, J=5.5 Hz), 8.43 (1H, d, J=8.6 Hz).

MS (APCI) m/z: 968 (M+H)$^+$.

Process 2: Glycylglycylphenylalanylglycylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide trifluoroacetic acid salt The compound (0.429 g, 0.443 mmol) obtained in Process 1 above was reacted in the same manner as Process 2 of Example 1 to yield the titled compound as a yellow solid (0.385 g, quantitative).

$^1$H-NMR (400 MHz, DMSO-d$_6$) δ: 0.87 (3H, t, J=7.4 Hz), 1.82-1.89 (2H, m), 2.11-2.19 (2H, m), 2.40 (3H, s), 2.74 (1H, dd, J=13.7, 9.8 Hz), 3.03 (1H, dd, J=13.7, 4.3 Hz), 3.16-3.18 (2H, m), 3.57-3.58 (2H, m), 3.67-3.76 (7H, m), 3.82-3.90 (1H, m), 4.53-4.56 (1H, m), 5.23 (2H, s), 5.43 (2H, s), 5.55-5.59 (1H, m), 6.55 (1H, s), 7.17-7.19 (1H, m), 7.22-7.29 (4H, m), 7.31 (1H, s), 7.80 (1H, d, J=10.9 Hz), 8.00 (3H, brs), 8.07 (1H, t, J=5.7 Hz), 8.22 (1H, t, J=5.7 Hz), 8.36 (2H, dd, J=10.9, 7.0 Hz), 8.47-8.52 (2H, m).

MS (APCI) m/z: 868 (M+H)$^+$.

Process 3: N-[6-(2,5-Dioxo-2,5-dihydro-1H-pyrrol-1-yl)hexanoyl]glycylglycylphenylalanylglycylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.278 g, 0.320 mmol) obtained in Process 2 above was reacted in the same manner as Process 3 of Example 73 to yield the titled compound as a pale yellow solid (0.166 g, 49%).

$^1$H-NMR (400 MHz, DMSO-d$_6$) δ: 0.87 (3H, t, J=7.2 Hz), 1.14-1.22 (2H, m), 1.44-1.49 (4H, m), 1.80-1.90 (2H, m), 2.06-2.13 (3H, m), 2.20 (1H, d, J=14.1 Hz), 2.40 (3H, s), 2.77 (1H, dd, J=13.3, 8.7 Hz), 3.01 (1H, dd, J=13.3, 4.3 Hz), 3.17 (2H, t, J=6.7 Hz), 3.35-3.38 (2H, m), 3.56-3.84 (10H, m), 4.48 (1H, dd, J=13.1, 9.2 Hz), 5.23 (2H, s), 5.43 (2H, s), 5.55-5.59 (1H, m), 6.53 (1H, s), 6.99 (2H, s), 7.20-7.24 (5H, m), 7.31 (1H, s), 7.80 (1H, d, J=11.0 Hz), 8.00 (2H, q, J=5.5 Hz), 8.06 (1H, t, J=5.9 Hz), 8.13 (1H, d, J=8.2 Hz), 8.18 (1H, t, J=5.7 Hz), 8.28 (1H, t, J=5.7 Hz), 8.43 (1H, d, J=8.6 Hz).

MS (APCI) m/z: 1061 (M+H)$^+$.

Process 4: Antibody-Drug Conjugate (84)

By using the trastuzumab produced in Reference Example 1 and the compound obtained in Process 3 above, the compound of interest was obtained in the same manner as Process 6 of Example 2.
Antibody concentration: 1.53 mg/mL, antibody yield: 9.2 mg (74%), and average number of conjugated drug molecules (n) per antibody molecule: 3.5.

Example 85 Antibody-Drug Conjugate (85)

[Formula 138]

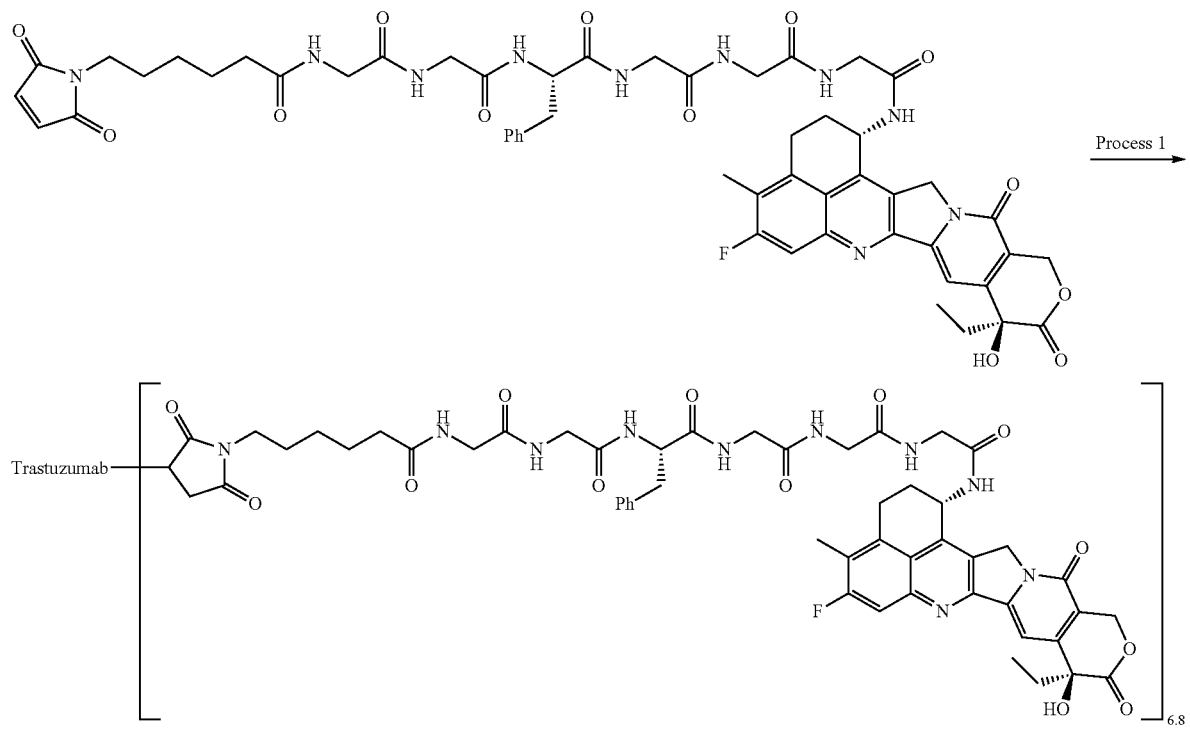

Process 1: Antibody-Drug Conjugate (85)

By using the trastuzumab produced in Reference Example 1 and the compound obtained in Process 3 of Example 84, the compound of interest was obtained in the same manner as Process 1 of Example 3.

Antibody concentration: 1.51 mg/mL, antibody yield: 9.1 mg (73%), and average number of conjugated drug molecules (n) per antibody molecule: 6.8.

Example 86 Antibody-Drug Conjugate (86)

[Formula 139]

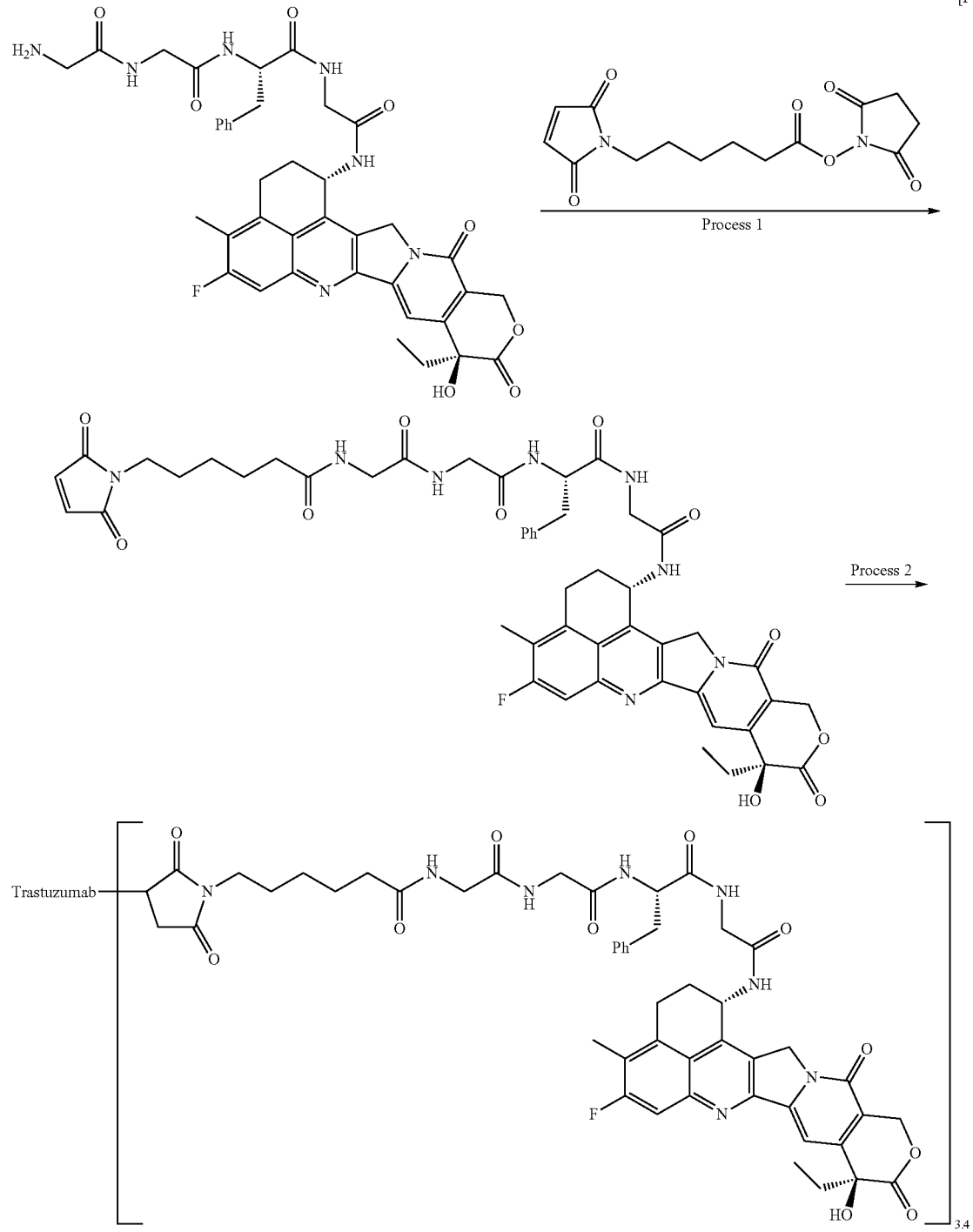

Process 1: N-[6-(2,5-Dioxo-2,5-dihydro-1H-pyrrol-1-yl)hexanoyl]glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] glycinamide A free form of glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (International Publication No. WO 97/46260; 0.150 g, 0.200 mol) was reacted in the same manner as Process 3 of Example 73 to yield the titled compound as a pale yellow solid (70.0 mg, 37%).

$^1$H-NMR (400 MHz, DMSO-$d_6$) δ: 0.87 (3H, t, J=7.4 Hz), 1.15-1.21 (2H, m), 1.41-1.50 (4H, m), 1.80-1.90 (2H, m), 2.07-2.12 (4H, m), 2.17-2.23 (1H, m), 2.35-2.40 (1H, m), 2.41 (3H, s), 2.73-2.81 (1H, m), 2.98 (1H, dd, J=13.7, 4.6 Hz), 3.15-3.20 (2H, m), 3.53 (1H, dd, J=16.6, 5.7 Hz), 3.62-3.77 (5H, m), 4.39-4.45 (1H, m), 5.22 (1H, d, J=18.9 Hz), 5.27 (1H, d, J=18.9 Hz), 5.39 (1H, d, J=16.0 Hz), 5.44 (1H, d, J=16.0 Hz), 5.55-5.60 (1H, m), 6.53 (1H, s), 6.98 (2H, s), 7.13-7.24 (5H, m), 7.32 (1H, s), 7.81 (1H, d, J=10.3 Hz), 7.95-8.00 (1H, m), 8.05-8.09 (2H, m), 8.28-8.31 (1H, m), 8.41 (1H, d, J=8.6 Hz).

MS (APCI) m/z: 947 (M+H)$^+$.

Process 2: Antibody-Drug Conjugate (86)

The trastuzumab produced in Reference Example 1 was prepared to have an antibody concentration of 10 mg/mL with PBS6.0/EDTA by using the Common procedure B (as absorption coefficient at 280 nm, 1.37 mLmg$^{-1}$ cm$^{-1}$ was used) and Common procedure C-1. The solution (5.0 mL) was collected into a 15 mL tube and charged with an aqueous solution of 10 mM TCEP (0.155 mL; 4.6 equivalents per antibody molecule) and an aqueous solution of 1 M dipotassium hydrogenphosphate (0.250 mL). After confirming that the solution had a pH of 7.4±0.1, the disulfide bond at the hinge part in the antibody was reduced by incubating at 37° C. for 1 hour.

Conjugation between antibody and drug linker: After incubating the above solution for 10 minutes at 22° C., a DMSO solution (0.311 mL; 9.2 equivalents per antibody molecule) containing 10 mM of the compound obtained in Process 1 above was added thereto and incubated for conjugating the drug linker to the antibody at 22° C. for 40 minutes. Next, an aqueous solution (0.0622 mL; 18.4 equivalents per antibody molecule) of 100 mM NAC was added thereto and incubated at 22° C. to terminate the reaction of the drug linker for another 20 minutes.

Purification: The above solution was subjected to purification using the Common procedure D-1 (PBS7.4 was used as buffer solution) to yield a solution containing the Example compound of interest.

Physicochemical characterization: By using the Common procedure B, Common procedure E, and Common procedure F, the following characteristic values were obtained.

Antibody concentration: 3.04 mg/mL, antibody yield: 32.5 mg (65%), and average number of conjugated drug molecules (n) per antibody molecule: 3.4.

Example 87 Antibody-Drug Conjugate (87)

[Formula 140]

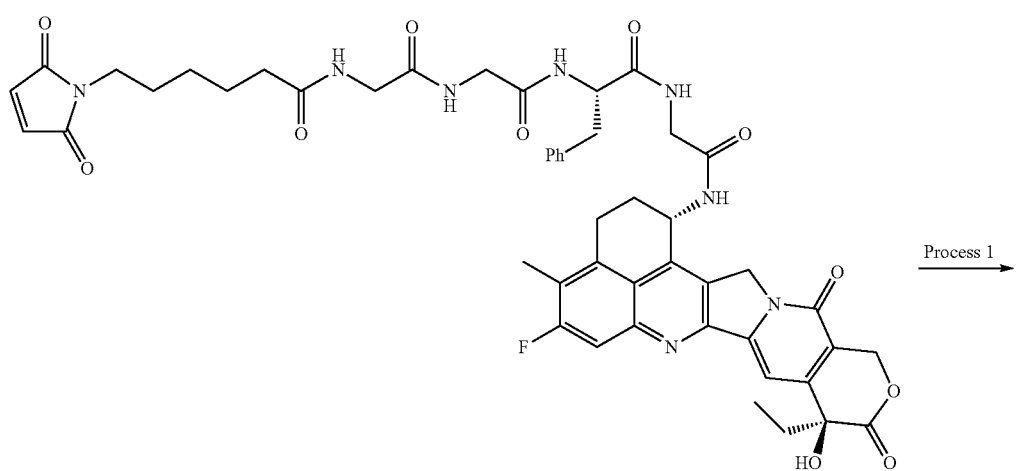

Process 1

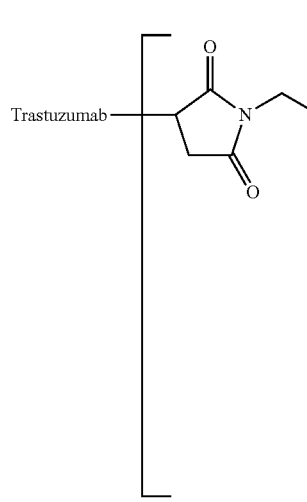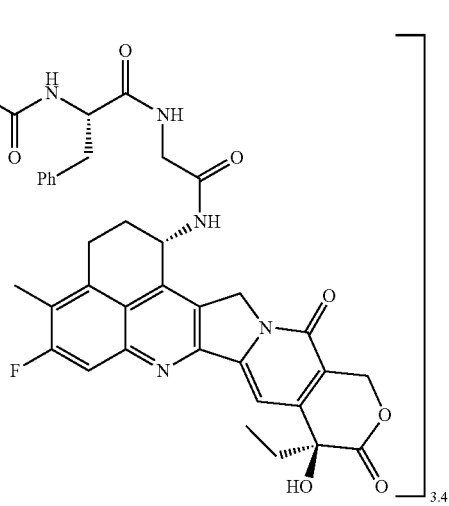

Process 1: Antibody-Drug Conjugate (87)

Reduction of the antibody: The trastuzumab produced in Reference Example 1 was prepared to have an antibody concentration of 10 mg/mL with PBS6.0/EDTA by using the Common procedure B (as absorption coefficient at 280 nm, 1.37 mLmg$^{-1}$ cm$^{-1}$ was used) and Common procedure C-1. The solution (9.0 mL) was collected into a 50 mL tube and charged with an aqueous solution of 10 mM TCEP (0.280 mL; 4.6 equivalents per antibody molecule) and an aqueous solution of 1 M dipotassium hydrogenphosphate (0.450 mL). After confirming that the solution had a pH of 7.4±0.1, the disulfide bond at the hinge part in the antibody was reduced by incubating at 37° C. for 1 hour.

Conjugation between antibody and drug linker: After incubating the above solution for 10 minutes at 22° C., a DMSO solution (0.559 mL; 9.2 equivalents per antibody molecule) containing 10 mM of the compound obtained in Process 1 of Example 31 was added thereto and incubated for conjugating the drug linker to the antibody at 22° C. for 40 minutes. Next, an aqueous solution (0.112 mL; 18.4 equivalents per antibody molecule) of 100 mM NAC was added thereto and incubated at 22° C. to terminate the reaction of the drug linker for another 20 minutes.

Purification: The above solution was subjected to purification using the Common procedure D-1 (PBS7.4 was used as buffer solution) to yield a solution containing the Example compound of interest.

Physicochemical characterization: By using the Common procedure B, Common procedure E, and Common procedure F, the following characteristic values were obtained.

Antibody concentration: 3.45 mg/mL, antibody yield: 49.7 mg (55%), and average number of conjugated drug molecules (n) per antibody molecule: 3.4.

Example 88 Antibody-Drug Conjugate (88)

[Formula 141]

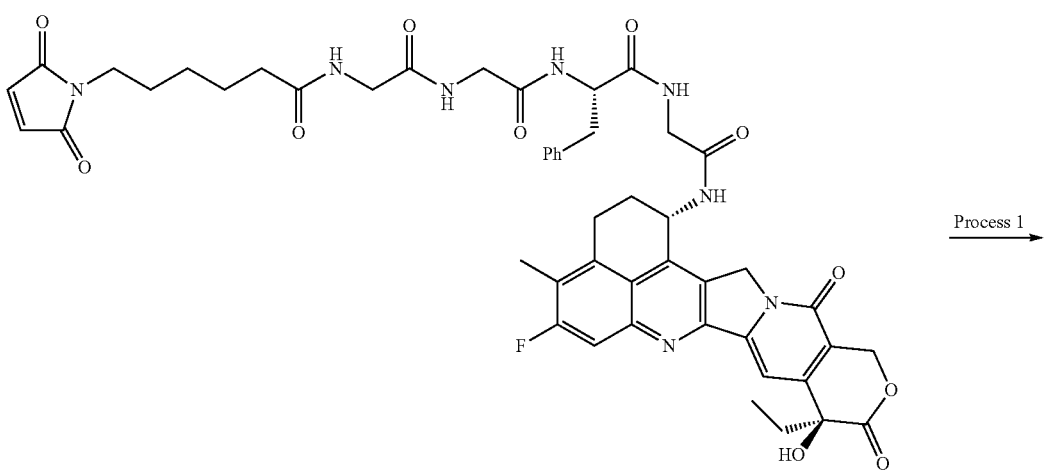

Process 1

411

-continued

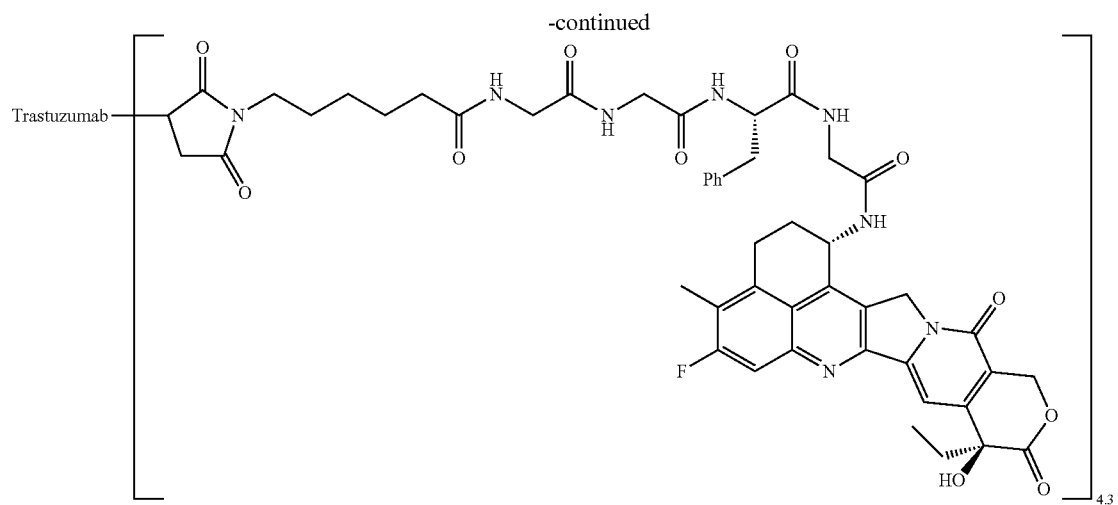

Process 1: Antibody-Drug Conjugate (88)

The compound obtained in Process 1 of Example 86 was used as the drug linker. The amount of the aqueous solution of 10 mM TCEP added was adjusted such that the molar ratio of TCEP to the antibody at the antibody reduction was 4.6. And the amount of the 10 mM drug linker solution added was adjusted such that the molar ratio of the drug linker to the antibody at the drug linker conjugation was 9.2. Then the amount of the aqueous solution of 100 mM NAC added was adjusted such that the molar ratio of NAC to the antibody at the termination of the reaction was 18.4. By the same procedures as Process 1 of Example 3, 6 mL of a solution containing the compound of interest was obtained, and the following characteristic values were obtained. Antibody concentration: 1.50 mg/mL, antibody yield: 8.55 mg (68%), and average number of conjugated drug molecules (n) per antibody molecule: 4.3.

Example 89 Antibody-Drug Conjugate (89)

[Formula 142]

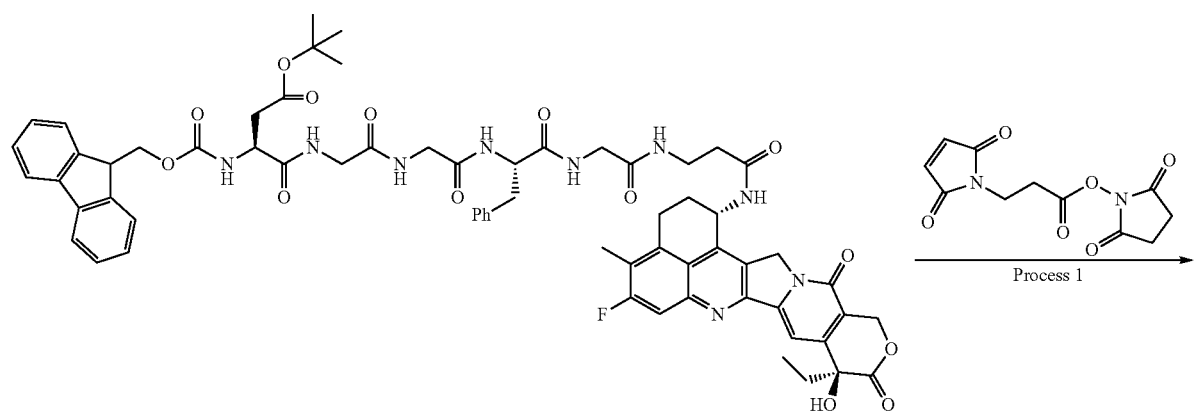

-continued
413
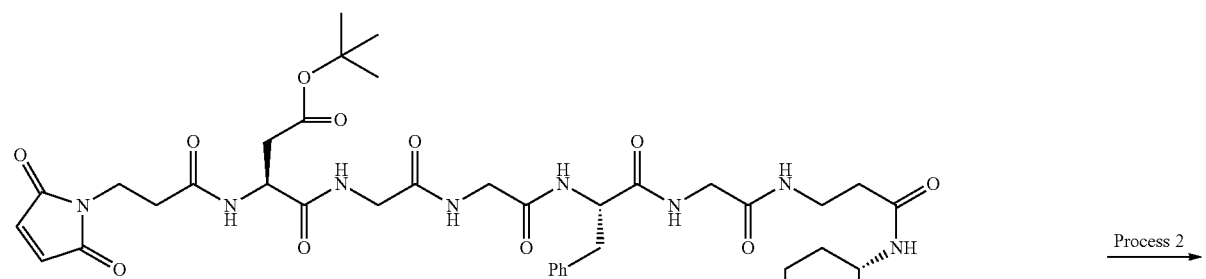
Process 2 →
414
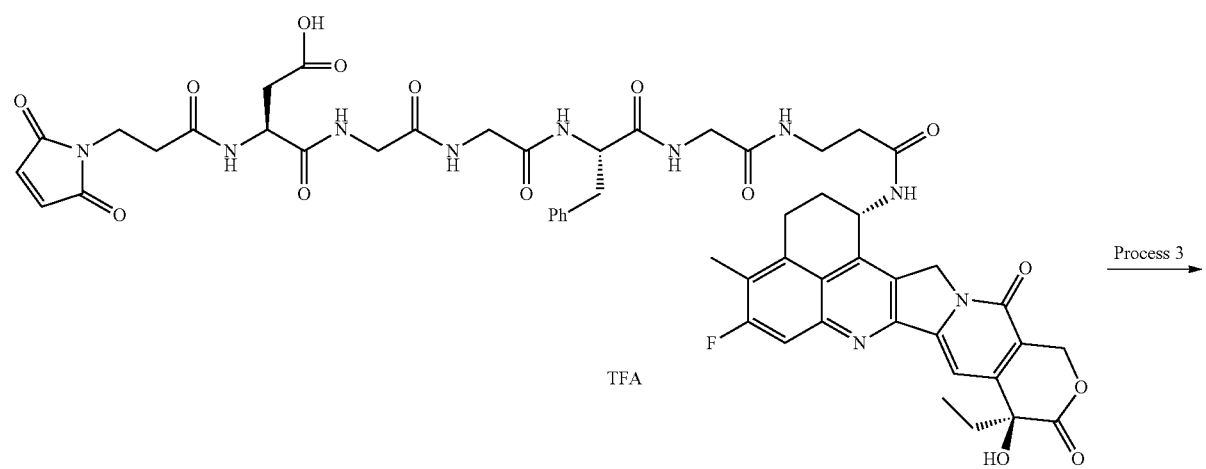
TFA
Process 3 →
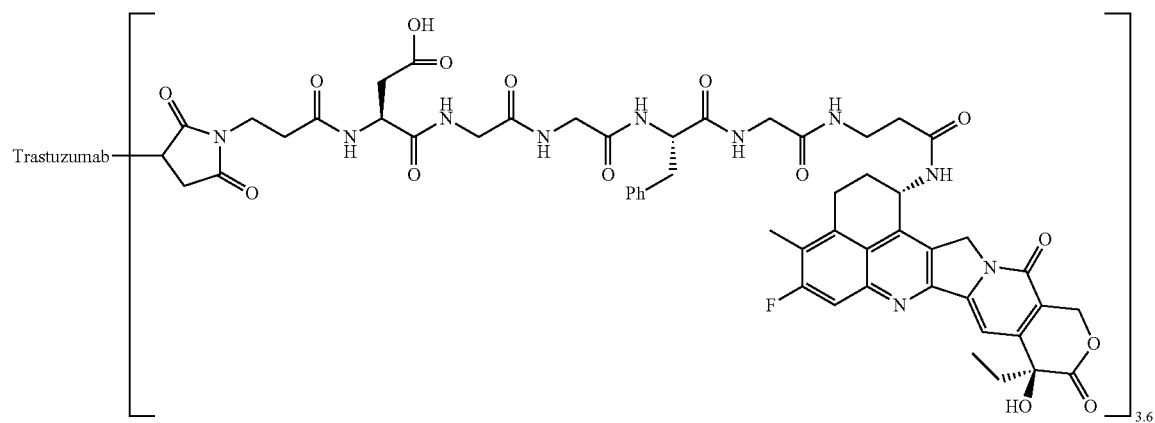

Process 1: tert-Butyl (9S,18S)-9-benzyl-18-{[3-(2,5-dioxo-2,5-dihydro-1H-pyrrol-1-yl)propanoyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,5,8,11,14,17-hexaoxo-4,7,10,13,16-pentaazaicosane-20-oate The compound (76 mg, 0.076 mmol) obtained in Process 2 of Example 71 was reacted in the same manner as Process 2 of Example 58 by using N-succinimidyl 3-maleimidopropionate instead of N-succinimidyl 6-maleimidohexanoate to yield the titled compound as a pale yellow solid (73 mg, 83%).

MS(ESI) m/z: 1147 (M+H)$^+$.

Process 2: N-[3-(2,5-Dioxo-2,5-dihydro-1H-pyrrol-1-yl)propanoyl]-L-α-aspartylglycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (69 mg, 0.060 mmol) obtained in Process 1 above was reacted in the same manner as Process 2 of Example 1 to yield trifluoroacetic acid salt of the titled compound as a yellow solid (32 mg, 44%).

$^1$H-NMR (400 MHz, DMSO-d$_6$) δ: 0.87 (3H, t, J=7.6 Hz), 1.85 (2H, m, J=14.1 Hz), 2.06-2.20 (2H, m), 2.40 (3H, s), 2.31-2.57 (7H, m), 2.61-2.71 (1H, m), 2.73-2.83 (1H, m), 2.98-3.06 (1H, m), 3.12-3.22 (2H, m), 3.29-3.40 (2H, m), 3.54-3.79 (6H, m), 3.80-4.41 (3H, m), 4.43-4.57 (2H, m), 5.19 (1H, d, J=19.6 Hz), 5.26 (1H, d, J=19.2 Hz), 5.42 (2H, brs), 5.52-5.60 (1H, m), 6.98 (2H, s), 7.14-7.28 (5H, m), 7.31 (1H, s), 7.77-7.84 (2H, m), 7.90-7.97 (1H, m), 8.07-8.14 (2H, m), 8.23-8.30 (1H, m), 8.35 (1H, d, J=7.0 Hz), 8.53 (1H, d, J=8.6 Hz).

MS (ESI) m/z: 1091 (M+H)$^+$.

Process 3: Antibody-Drug Conjugate (89)

By using the trastuzumab produced in Reference Example 1 and the compound obtained in Process 2 above, the compound of interest was obtained in the same manner as Process 6 of Example 2.

Antibody concentration: 1.67 mg/mL, antibody yield: 10.0 mg (80%), and average number of conjugated drug molecules (n) per antibody molecule: 3.6.

Example 90 Antibody-Drug Conjugate (90)

[Formula 143]

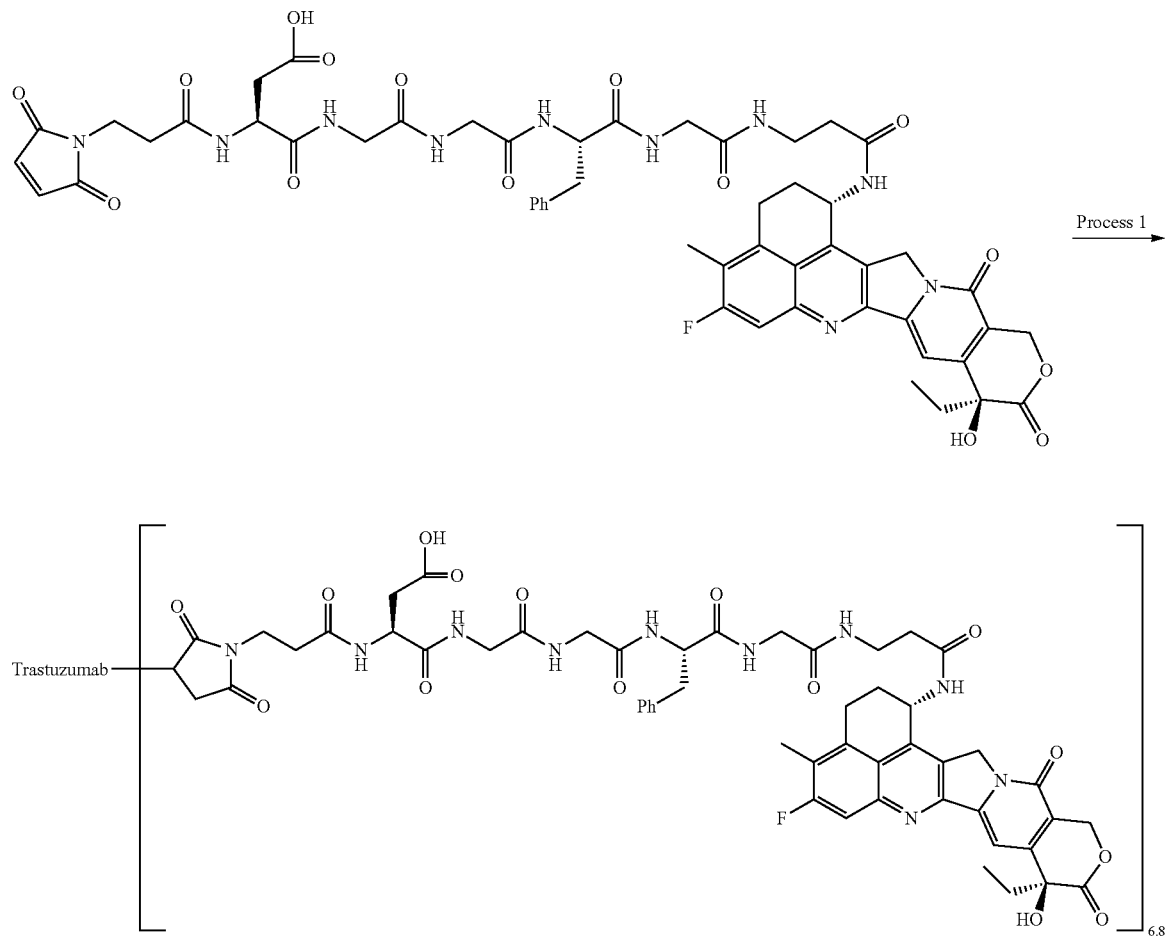

Process 1: Antibody-Drug Conjugate (90)

By using the trastuzumab produced in Reference Example 1 and the compound obtained in Process 2 of Example 89, the compound of interest was obtained in the same manner as Process 1 of Example 3.

Antibody concentration: 1.64 mg/mL, antibody yield: 9.8 mg (78%), and average number of conjugated drug molecules (n) per antibody molecule: 6.8.

Example 91 Antibody-Drug Conjugate (91)

[Formula 144]

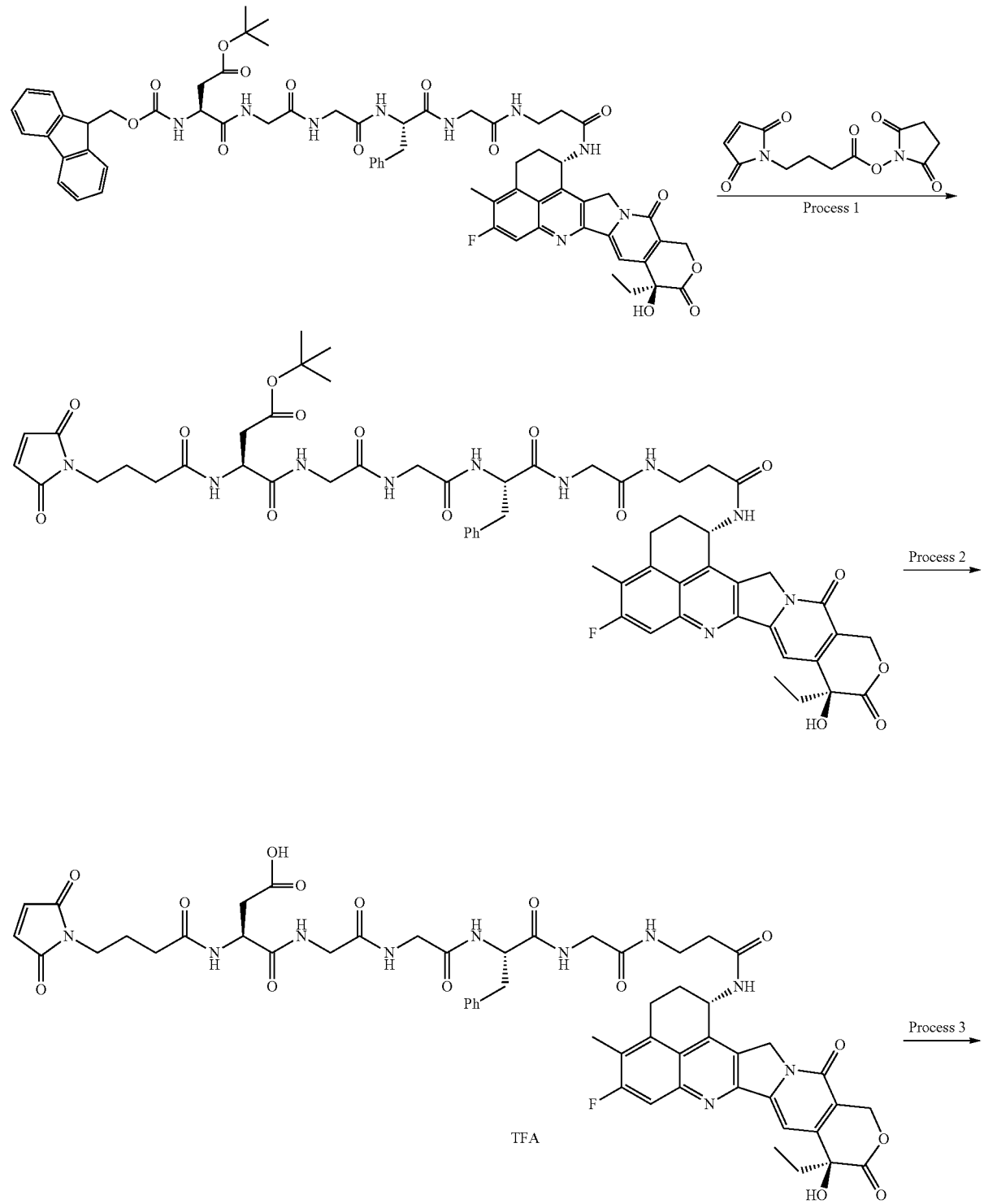

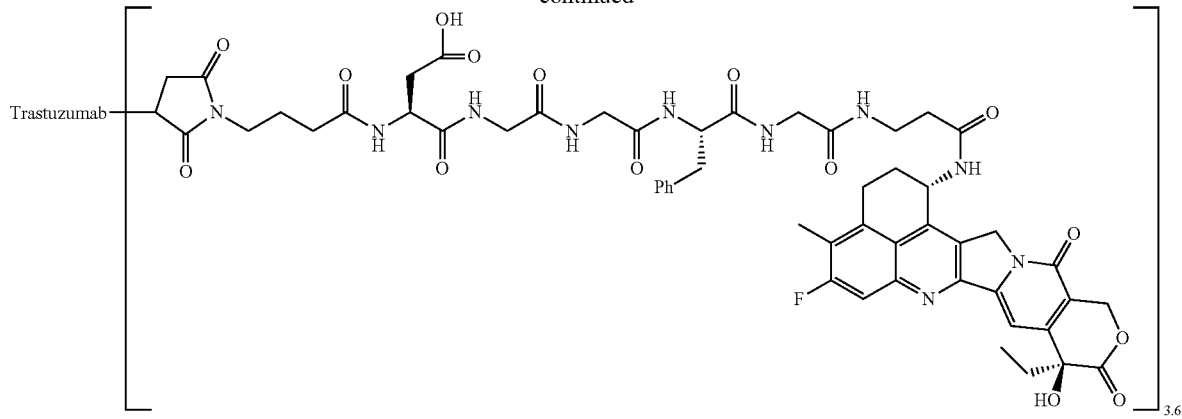

Process 1: tert-Butyl (9S,18S)-9-benzyl-18-{[4-(2,5-dioxo-2,5-dihydro-1H-pyrrol-1-yl)butanoyl]amino}-1-{[(1S,9S)-9-ethyl-5-fluoro-9-hydroxy-4-methyl-10,13-dioxo-2,3,9,10,13,15-hexahydro-1H,12H-yl]amino}-1,5,8,11,14,17-hexaoxo-4,7,10,13,16-pentaazaicosane-20-oate The compound (75 mg, 0.075 mmol) obtained in Process 2 of Example 71 was reacted in the same manner as Process 2 of Example 58 by using N-succinimidyl 4-maleimidobutanoate instead of N-succinimidyl 6-maleimidohexanoate to yield the titled compound as a pale yellow solid (72 mg, 82%).
MS(ESI) m/z: 1161 (M+H)$^+$.

Process 2: N-[4-(2,5-Dioxo-2,5-dihydro-1H-pyrrol-1-yl)butanoyl]-L-α-aspartylglycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alanylamide The compound (69 mg, 0.059 mmol) obtained in Process 1 above was reacted in the same manner as Process 2 of Example 1 to yield trifluoroacetic acid salt of the titled compound as a yellow solid (24 mg, 34%).
$^1$H-NMR (400 MHz, DMSO-d$_6$) δ: 0.86 (3H, t, J=7.4 Hz), 1.63-1.74 (2H, m), 1.78-1.91 (2H, m), 2.05-2.21 (4H, m), 2.30-2.56 (3H, m), 2.40 (3H, s), 2.61-2.72 (1H, m), 2.73-2.83 (1H, m), 2.97-3.07 (1H, m), 3.12-3.23 (2H, m), 3.29-3.43 (4H, m), 3.53-3.79 (6H, m), 3.80-4.58 (3H, m), 4.43-4.57 (2H, m), 5.19 (1H, d, J=19.2 Hz), 5.26 (1H, d, J=18.8 Hz), 5.42 (2H, s), 5.51-5.61 (1H, m), 7.00 (2H, s), 7.12-7.29 (5H, m), 7.31 (1H, s), 7.76-7.84 (2H, m), 7.94 (1H, t, J=5.9 Hz), 8.05-8.14 (2H, m), 8.19 (1H, d, J=7.0 Hz), 8.26 (1H, t, J=5.7 Hz), 8.52 (1H, d, J=9.0 Hz).
MS (ESI) m/z: 1105 (M+H)$^+$.

Process 3: Antibody-Drug Conjugate (91)

By using the trastuzumab produced in Reference Example 1 and the compound obtained in Process 2 above, the compound of interest was obtained in the same manner as Process 6 of Example 2.
Antibody concentration: 1.51 mg/mL, antibody yield: 9.7 mg (78%), and average number of conjugated drug molecules (n) per antibody molecule: 3.6.

Example 92 Antibody-Drug Conjugate (92)

[Formula 145]

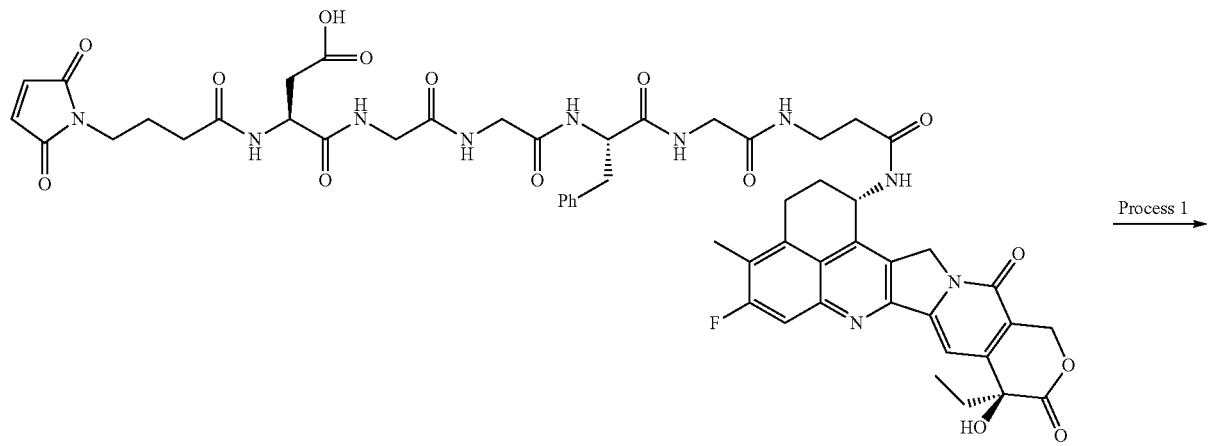

Process 1 →

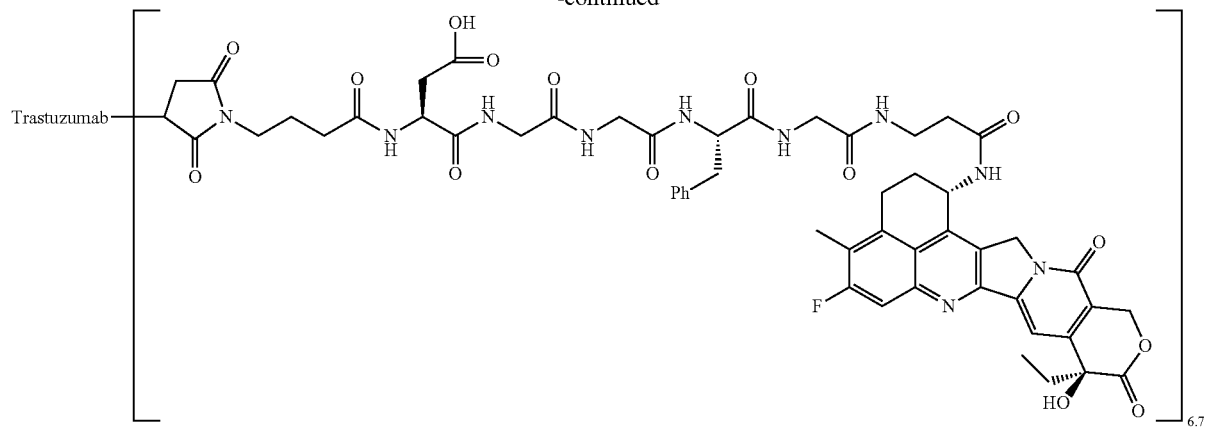

Process 1: Antibody-Drug Conjugate (92)

By using the trastuzumab produced in Reference Example 1 and the compound obtained in Process 2 of Example 91, the compound of interest was obtained in the same manner as Process 1 of Example 3.
Antibody concentration: 1.66 mg/mL, antibody yield: 10.0 mg (80%), and average number of conjugated drug molecules (n) per antibody molecule: 6.7.

Example 93 Antibody-Drug Conjugate (93)

[Formula 146]

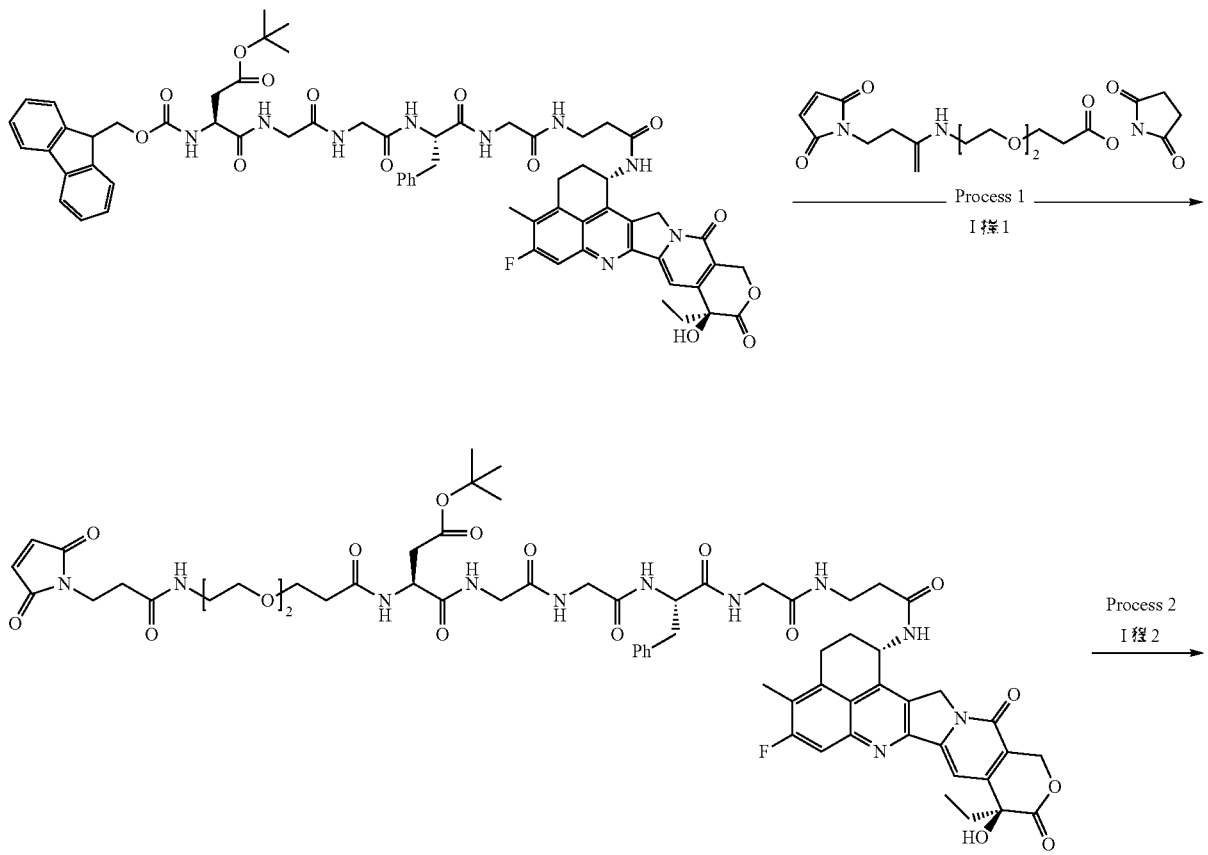

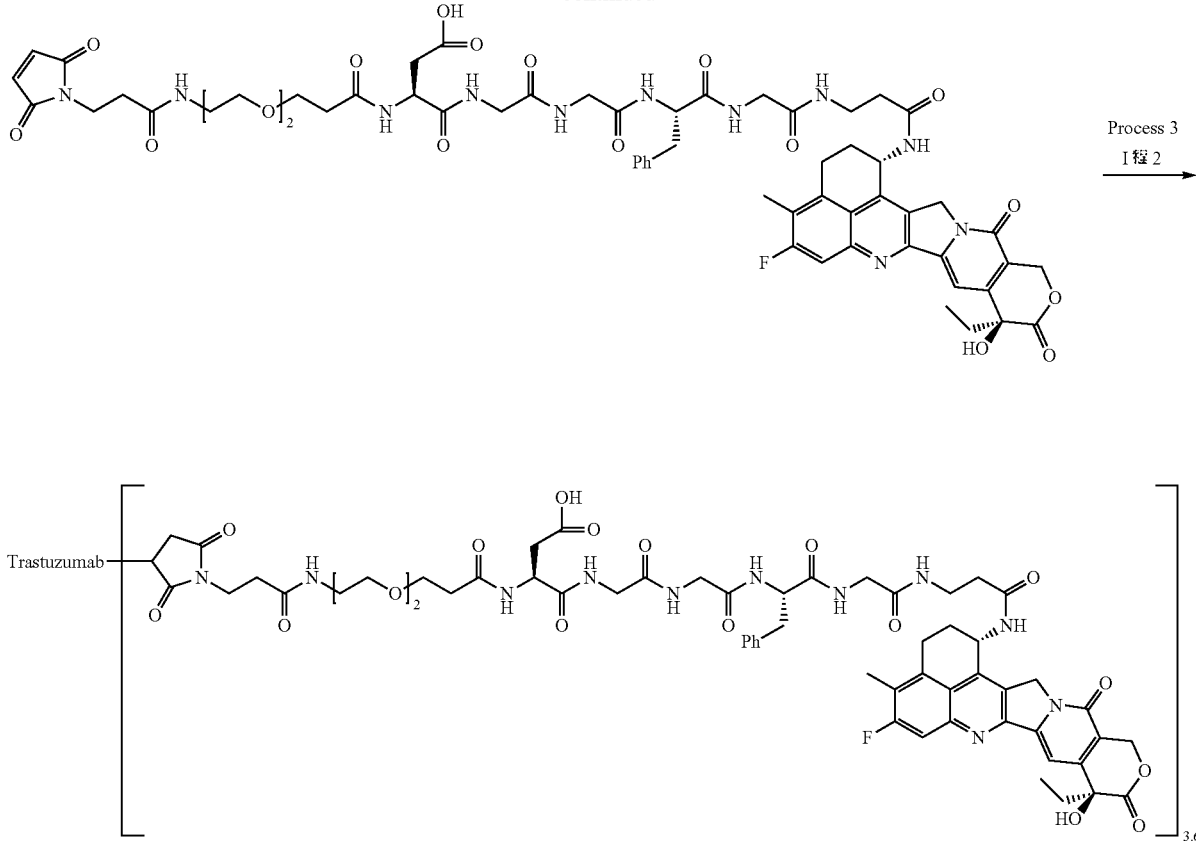

Process 1: tert-Butyl (9S,18S)-9-benzyl-18-({3-[2-(2-{[3-(2,5-dioxo-2,5-dihydro-1H-pyrrol-1-yl)propanoyl]amino}ethoxy)ethoxy]propanoyl}amino)-1-{[(1S,9S)-9-ethyl-5-fluoro-9-hydroxy-4-methyl-10, 13-dioxo-2,3,9,10,13,15-hexahydro-1H,12H-benzo[de]pyrano[3',4':6,7]indolizino[1,2-b]quinolin-1-yl]amino}-1,5,8,11,14,17-hexaoxo-4,7,10,13,16-pentaazaicosane-20-oate The compound (80 mg, 0.080 mmol) obtained in Process 2 of Example 71 was reacted in the same manner as Process 2 of Example 58 by using N-succinimidyl 3-(2-(2-(3-maleimidopropanamide)ethoxy)ethoxy)propanoate instead of N-succinimidyl 6-maleimidohexanoate to yield the titled compound as a pale yellow solid (87 mg, 83%).
MS(ESI) m/z: 1307 (M+H)$^+$.

Process 2: N-{3-[2-(2-{[3-(2,5-Dioxo-2,5-dihydro-1H-pyrrol-1-yl)propanoyl]amino}ethoxy)ethoxy]propanoyl}-L-α-aspartylglycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alanylamide The compound (82 mg, 0.063 mmol) obtained in Process 1 above was reacted in the same manner as Process 2 of Example 1 to yield trifluoroacetic acid salt of the titled compound as a yellow solid (30 mg, 35%).

$^1$H-NMR (400 MHz, DMSO-d$_6$) δ: 0.86 (3H, t, J=7.0 Hz), 1.85 (2H, dt, J=14.6, 7.4 Hz), 2.07-2.22 (2H, m), 2.40 (3H, s), 2.29-2.58 (7H, m), 2.63-2.72 (1H, m), 2.78 (1H, dd, J=13.7, 10.6 Hz), 3.02 (1H, dd, J=13.9, 4.1 Hz), 3.09-3.21 (4H, m), 3.30-3.39 (4H, m), 3.45 (4H, s), 3.54-3.78 (10H, m), 3.78-4.53 (3H, m), 4.43-4.52 (1H, m), 4.52-4.59 (1H, m), 5.19 (1H, d, J=18.8 Hz), 5.26 (1H, d, J=19.2 Hz), 5.43 (2H, s), 5.52-5.61 (1H, m), 7.00 (2H, s), 7.13-7.28 (5H, m), 7.31 (1H, s), 7.77-7.85 (2H, m), 7.94 (1H, t, J=5.7 Hz), 8.02 (1H, t, J=6.3 Hz), 8.05-8.14 (2H, m), 8.22-8.30 (2H, m), 8.53 (1H, d, J=9.0 Hz).
MS (ESI) m/z: 1250 (M+H)$^+$.

Process 3: Antibody-Drug Conjugate (93)

By using the trastuzumab produced in Reference Example 1 and the compound obtained in Process 2 above, the compound of interest was obtained in the same manner as Process 6 of Example 2.

Antibody concentration: 1.70 mg/mL, antibody yield: 10.2 mg (82%), and average number of conjugated drug molecules (n) per antibody molecule: 3.6.

Example 94 Antibody-Drug Conjugate (94)

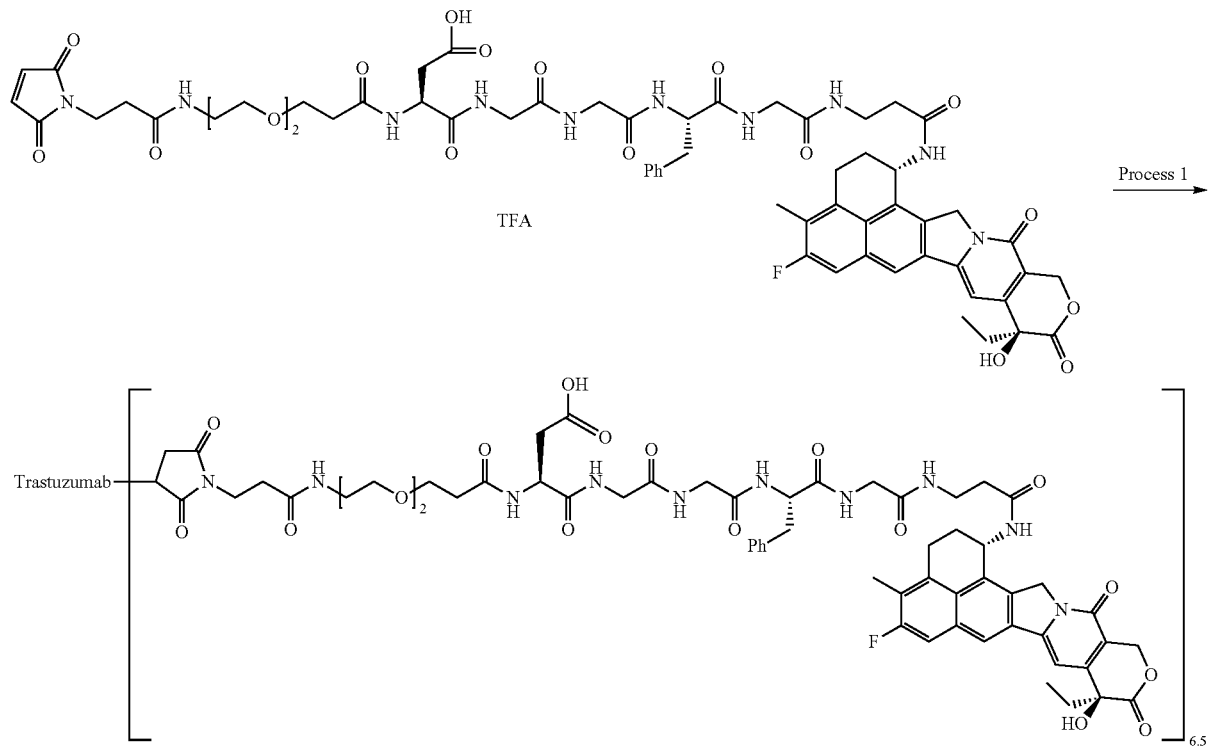

Process 1: Antibody-Drug Conjugate (94)

By using the trastuzumab produces in Reference Example 1 and the compound obtained in Process 2 of Example 93, the compound of interest was obtained in the same manner as Process 1 of Example 3.
Antibody concentration: 1.65 mg/mL, antibody yield: 9.9 mg (79%), and average number of conjugated drug molecules (n) per antibody molecule: 6.5.

Example 95 Antibody-Drug Conjugate (95)

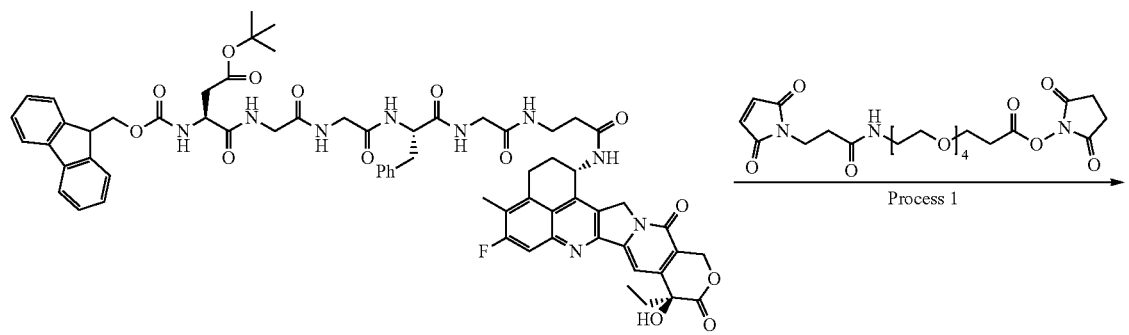

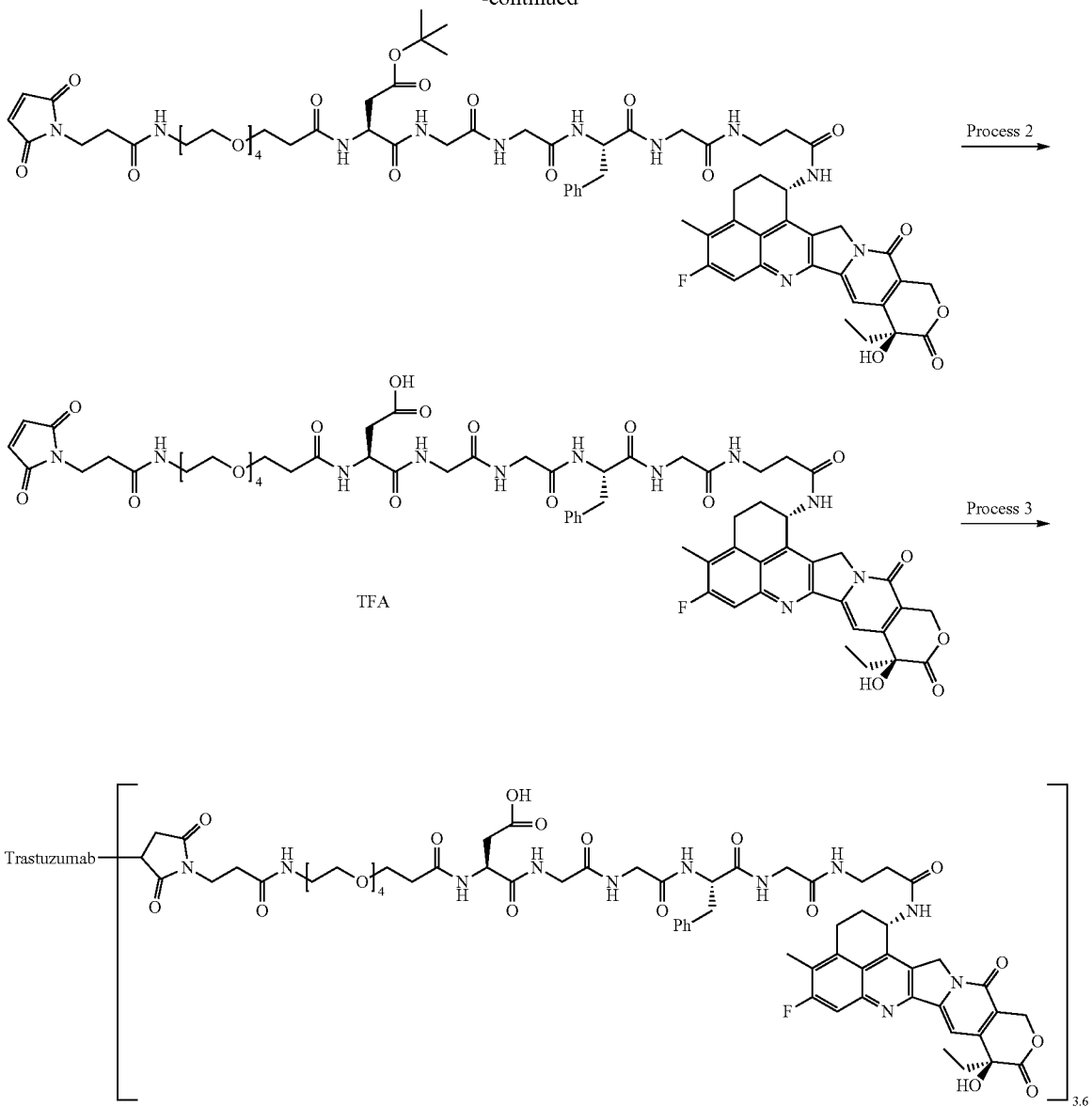

Process 1: tert-Butyl (21S)-21-{[(7S)-7-benzyl-15-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2,5,8,11,15-pentaoxo-3,6,9,12-tetraazapentadec-1-yl]carbamoyl}-1-(2,5-dioxo-2,5-dihydro-1H-pyrrol-1-yl)-3,19-dioxo-7,10,13,16-tetraoxa-4,20-diazatricosan-23-oate The compound (80 mg, 0.080 mmol) obtained in Process 2 of Example 71 was reacted in the same manner as Process 2 of Example 58 by using N-succinimidyl 1-maleimido-3-oxo-7,10,13,16-tetraoxa-4-azanonadecan-19-oate instead of N-succinimidyl 6-maleimidohexanoate to yield the titled compound as a pale yellow solid (91 mg, 81%).

MS(ESI) m/z: 1395 (M+H)⁺.

Process 2: N-[19-(2,5-Dioxo-2,5-dihydro-1H-pyrrol-1-yl)-17-oxo-4,7,10,13-tetraoxa-16-azanonadecan-1-oyl]-L-α-aspartylglycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alanylamide The compound (86 mg, 0.062 mmol) obtained in Process 1 above was reacted in the same manner as Process 2 of Example 1 to yield trifluoroacetic acid salt of the titled compound as a yellow solid (30 mg, 34%).

¹HNMR (400 MHz, DMSO-d₆) δ: 0.86 (3H, t, J=7.4 Hz), 1.85 (2H, dt, J=14.5, 7.2 Hz), 2.05-2.22 (2H, m), 2.28-2.59 (7H, m), 2.40 (3H, s), 2.64-2.72 (1H, m), 2.73-2.82 (1H, m), 3.02 (1H, dd, J=13.5, 4.5 Hz), 3.09-3.21 (4H, m), 3.35 (4H, t, J=6.3 Hz), 3.48 (1H, d, J=8.2 Hz), 3.53-3.78 (11H, m), 3.98-4.89 (3H, m), 4.43-4.51 (1H, m), 4.52-4.59 (1H, m), 5.19 (1H, d, J=19.6 Hz), 5.26 (1H, d, J=18.8 Hz), 5.42 (2H, s), 5.52-5.61 (1H, m), 7.00 (2H, s), 7.13-7.29 (5H, m), 7.31 (1H, s), 7.77-7.85 (2H, m), 7.94 (1H, t, J=5.1 Hz), 8.02 (1H, t, J=5.7 Hz), 8.05-8.14 (2H, m), 8.22-8.31 (2H, m), 8.53 (1H, d, J=9.4 Hz). MS (ESI) m/z: 1339 (M+H)+.

Process 3: Antibody-Drug Conjugate (95)

By using the trastuzumab produced in Reference Example 1 and the compound obtained in Process 2 above, the compound of interest was obtained in the same manner as Process 6 of Example 2.
Antibody concentration: 1.68 mg/mL, antibody yield: 10.1 mg (81%), and average number of conjugated drug molecules (n) per antibody molecule: 3.6.

Example 96 Antibody-Drug Conjugate (96)

[Formula 149]

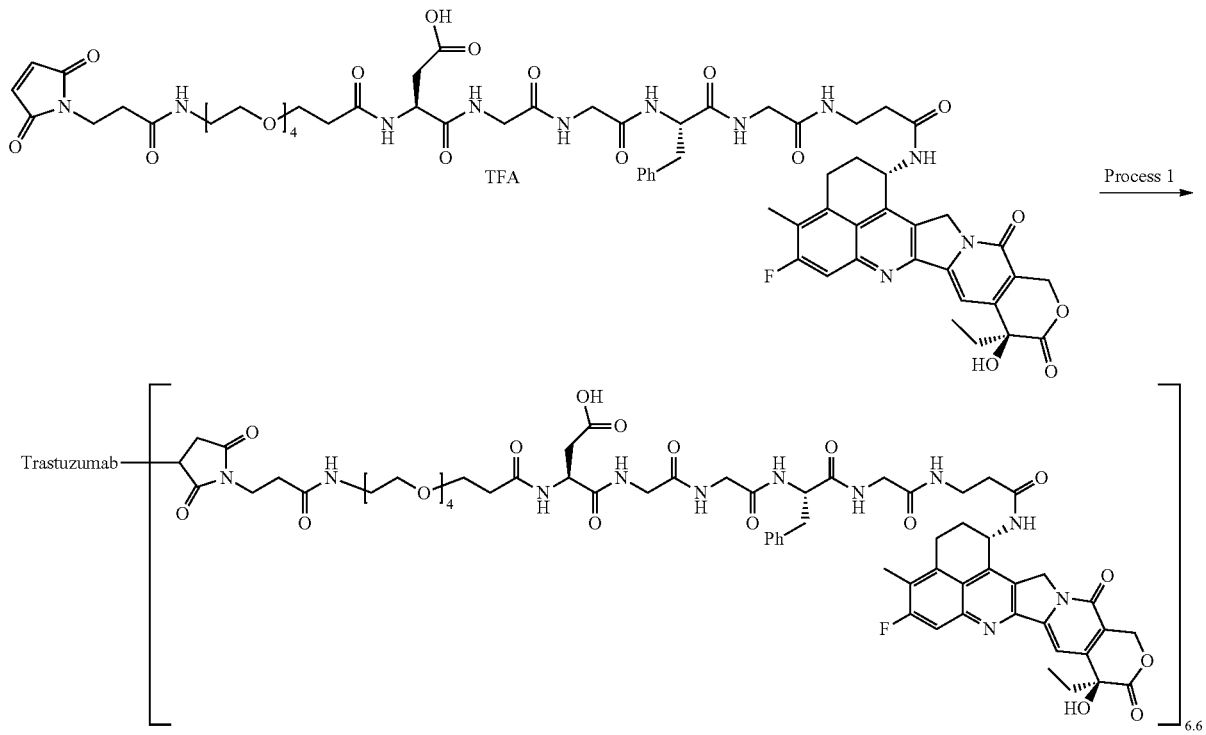

Process 1: Antibody-Drug Conjugate (96)

By using the trastuzumab produced in Reference Example 1 and the compound obtained in Process 2 of Example 95, the compound of interest was obtained in the same manner as Process 1 of Example 3.
Antibody concentration: 1.67 mg/mL, antibody yield: 10.0 mg (80%), and average number of conjugated drug molecules (n) per antibody molecule: 6.6.

Example 97 Antibody-Drug Conjugate (97)

[Formula 150]

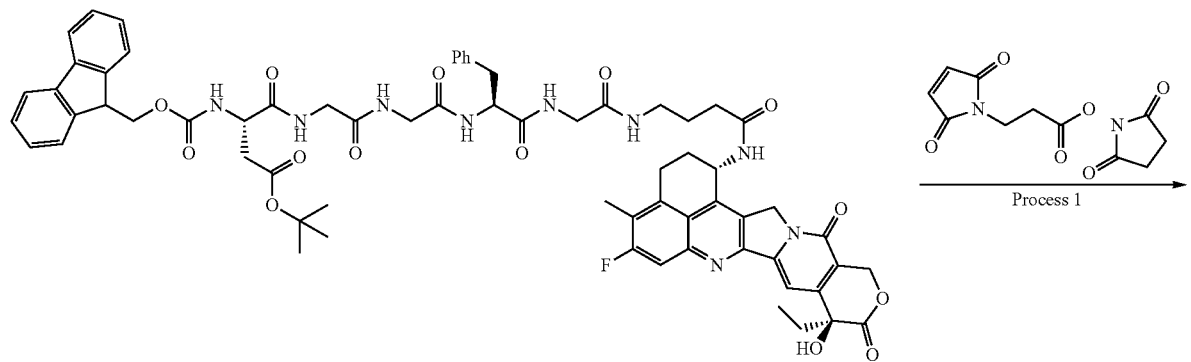

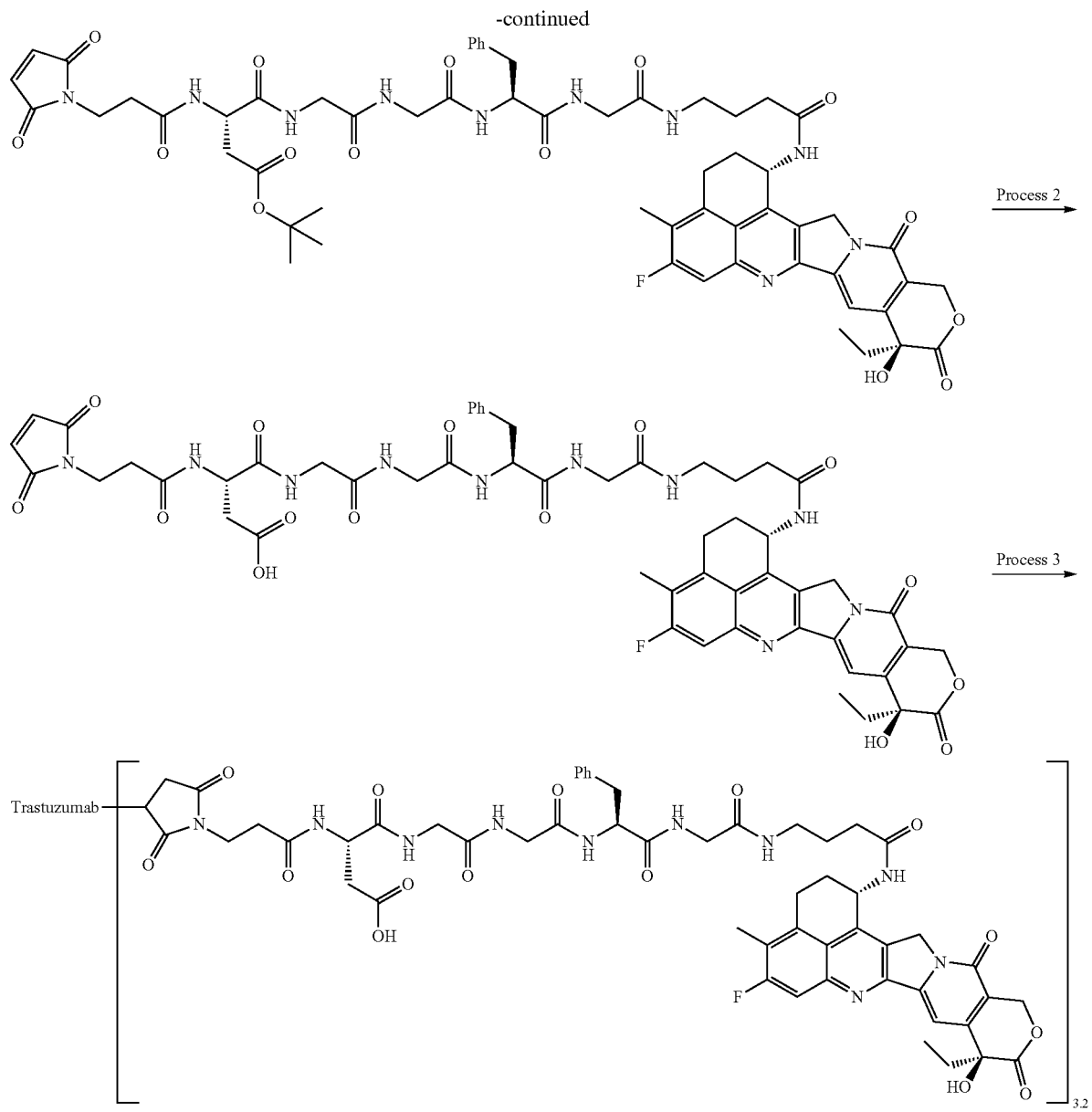

Process 1: tert-Butyl (3S,12S)-12-benzyl-3-{[3-(2,5-dioxo-2,5-dihydro-1H-pyrrol-1-yl)propanoyl]amino}-21-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,16,21-hexaoxo-5,8,11,14,17-pentaazaheneicosan-1-oate The compound (90 mg, 0.089 mmol) obtained in Process 1 of Example 58 was reacted in the same manner as Process 2 of Example 58 by using N-succinimidyl 3-maleimidopropionate instead of N-succinimidyl 6-maleimidohexanoate to yield the titled compound as a pale yellow solid (67 mg, 65%).

$^1$H-NMR (400 MHz, DMSO-$d_6$) δ: 0.87 (3H, t, J=7.4 Hz), 1.35 (9H, s), 1.66-1.77 (2H, m), 1.79-1.92 (2H, m), 2.08-2.22 (4H, m), 2.31-2.46 (3H, m), 2.40 (3H, s), 2.65 (1H, dd, J=15.8, 5.7 Hz), 2.78 (1H, dd, J=13.7, 9.8 Hz), 2.97-3.04 (1H, m), 3.05-3.12 (2H, m), 3.14-3.21 (2H, m), 3.54-3.80 (8H, m), 4.42-4.50 (1H, m), 4.54-4.62 (1H, m), 5.16 (1H, d, J=18.8 Hz), 5.25 (1H, d, J=18.8 Hz), 5.42 (2H, s), 5.54-5.62 (1H, m), 6.53 (1H, s), 6.99 (2H, s), 7.14-7.29 (5H, m), 7.31 (1H, s), 7.71 (1H, t, J=5.5 Hz), 7.80 (1H, d, J=10.9 Hz), 7.97 (1H, t, J=5.9 Hz), 8.10 (1H, d, J=8.2 Hz), 8.15 (1H, t, J=5.9 Hz), 8.26 (1H, t, J=4.7 Hz), 8.34 (1H, d, J=8.2 Hz), 8.46 (1H, d, J=8.6 Hz).

MS (ESI) m/z: 1161 (M+H)$^+$.

Process 2: N-[3-(2,5-Dioxo-2,5-dihydro-1H-pyrrol-1-yl)propanoyl]-L-α-aspartylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (67 mg, 0.058 mmol) obtained in Process 1 above was reacted in the same manner as Process 2 of Example 1 to yield the titled compound as a yellow solid (50 mg, 78%).

¹H-NMR (400 MHz, DMSO-d₆) δ: 0.87 (3H, t, J=7.2 Hz), 1.71 (2H, dt, J=14.6, 7.4 Hz), 1.86 (2H, dt, J=15.0, 7.2 Hz), 2.08-2.22 (4H, m), 2.31-2.55 (3H, m), 2.39 (3H, brs), 2.67 (1H, dd, J=16.2, 6.1 Hz), 2.78 (1H, dd, J=13.9, 9.2 Hz), 3.01 (1H, dd, J=12.7, 4.5 Hz), 3.04-3.12 (2H, m), 3.13-3.21 (2H, m), 3.30-3.51 (2H, m), 3.53-3.79 (6H, m), 4.42-4.50 (1H, m), 4.54 (1H, dd, J=13.7, 7.4 Hz), 5.16 (1H, d, J=19.2 Hz), 5.25 (1H, d, J=18.8 Hz), 5.42 (2H, s), 5.53-5.61 (1H, m), 6.53 (1H, brs), 6.98 (2H, s), 7.12-7.27 (5H, m), 7.31 (1H, s), 7.71 (1H, t, J=5.5 Hz), 7.80 (1H, d, J=10.9 Hz), 7.95 (1H, t, J=5.9 Hz), 8.05-8.15 (2H, m), 8.26 (1H, t, J=6.1 Hz), 8.35 (1H, d, J=7.8 Hz), 8.46 (1H, d, J=8.6 Hz), 12.30 (1H, brs).

MS (ESI) m/z: 1105 (M+H)⁺.

Process 3: Antibody-Drug Conjugate (97)

Reduction of the antibody: The trastuzumab produced in Reference Example 1 was prepared to have an antibody concentration of 10 mg/mL with PBS6.0/EDTA by using the Common procedure B (as absorption coefficient at 280 nm, 1.37 mLmg⁻¹ cm⁻¹ was used) and Common procedure C-1. The solution (1 mL) was placed in a 1.5 mL tube and charged with an aqueous solution of 10 mM TCEP (0.016 mL) and an aqueous solution of 1 M dipotassium hydrogenphosphate (0.050 mL) to prepare a reaction solution in which the molar ratio of TCEP to the antibody was 2.3. After confirming that the solution had a pH of 7.4±0.1, the disulfide bond at the hinge part in the antibody was reduced by incubating at 37° C. for 1 hour.

Conjugation between antibody and drug linker: After adding a DMSO solution containing 10 mM of the compound obtained in Process 2 above (0.031 mL) to the above solution at room temperature to prepare a reaction solution in which the molar ratio of the compound obtained in Process 2 above to the antibody was 4.6, it was stirred by using a tube rotator for conjugating the drug linker to the antibody at room temperature for 40 minutes. Next, an aqueous solution (0.0062 mL) of 100 mM NAC was added thereto to prepare a reaction solution in which the molar ratio of NAC to the antibody was 9.2, and it was stirred at room temperature to terminate the reaction of the drug linker for another 20 minutes.

Purification: The above solution was subjected to purification using the Common procedure D-1 (PBS6.0 was used as buffer solution) to yield 6 mL of a solution containing the compound of interest.

Physicochemical characterization: By using the Common procedure B, Common procedure E, and Common procedure F, the following characteristic values were obtained.

Antibody concentration: 1.37 mg/mL, antibody yield: 8.2 mg (82%), and average number of conjugated drug molecules (n) per antibody molecule: 3.2.

Example 98 Antibody-Drug Conjugate (98)

[Formula 151]

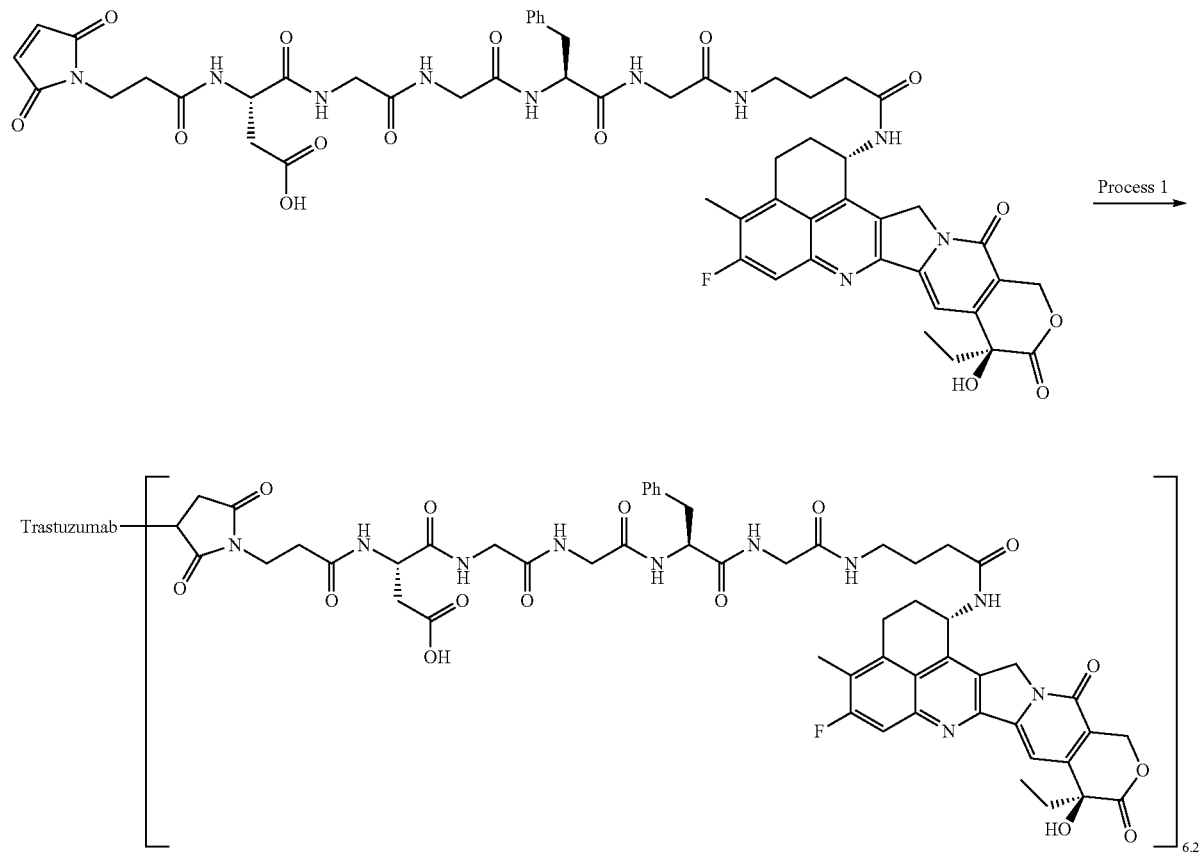

Process 1: Antibody-Drug Conjugate (98)

The amount of the aqueous solution of 10 mM TCEP added was adjusted such that the molar ratio of TCEP to the antibody at the antibody reduction was 4.6. And the amount of the 10 mM drug linker solution added was adjusted such that the molar ratio of the drug linker to the antibody at the drug linker conjugation was 9.2. Then the amount of the aqueous solution of 100 mM NAC added was adjusted such that the molar ratio of NAC to the antibody at the termination of the reaction was 18.4. By the same procedures as Process 3 of Example 97, 6 mL of a solution containing the compound of interest was obtained, and the following characteristic values were obtained.

Antibody concentration: 1.25 mg/mL, antibody yield: 7.5 mg (75%), and average number of conjugated drug molecules (n) per antibody molecule: 6.2.

Example 99 Antibody-Drug Conjugate (99)

[Formula 152]

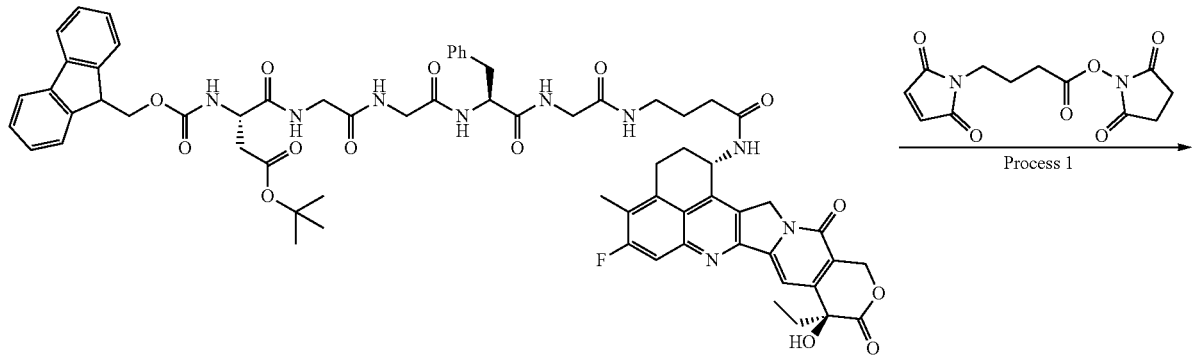

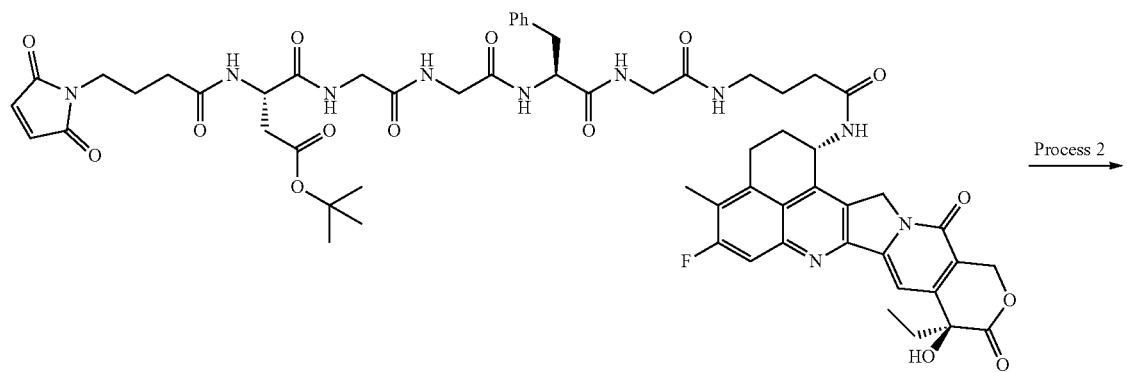

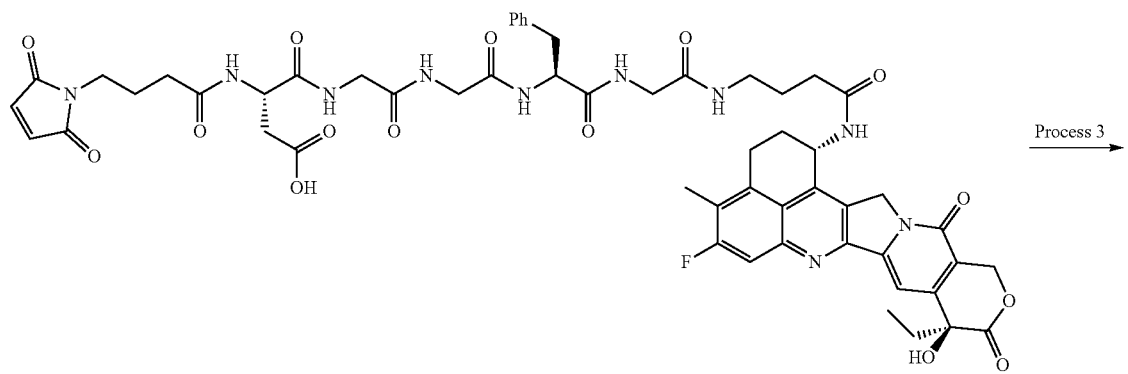

-continued

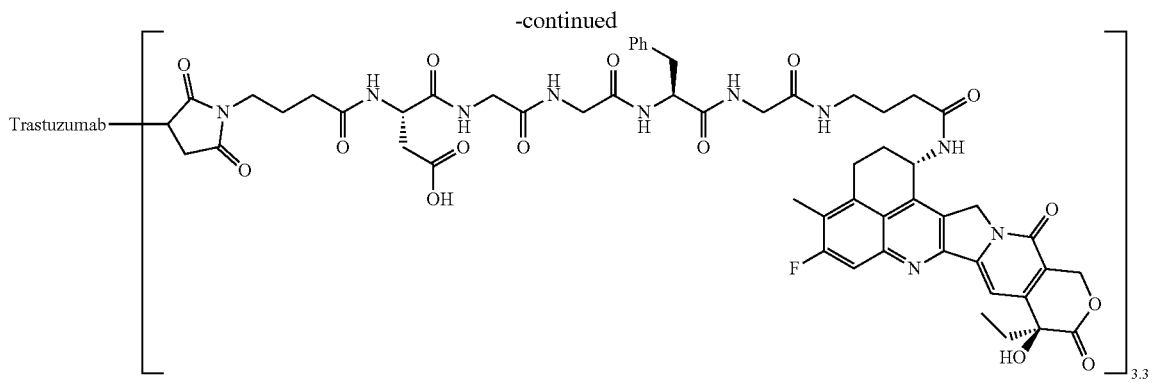

Process 1: tert-Butyl (3S,12S)-12-benzyl-3-{[4-(2,5-dioxo-2,5-dihydro-1H-pyrrol-1-yl)butanoyl]amino}-21-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,16,21-hexaoxo-5,8,11,14,17-pentaazaheneicosan-1-oate The compound (90 mg, 0.089 mmol) obtained in Process 1 of Example 58 was reacted in the same manner as Process 2 of Example 58 by using N-succinimidyl 4-maleimidobutanoate instead of N-succinimidyl 6-maleimidohexanoate to yield the titled compound as a pale yellow solid (88 mg, 84%).

$^1$H-NMR (400 MHz, DMSO-$d_6$) δ: 0.87 (3H, t, J=7.4 Hz), 1.34 (9H, s), 1.64-1.76 (4H, m), 1.86 (2H, tt, J=14.8, 7.1 Hz), 2.05-2.22 (6H, m), 2.35-2.55 (1H, m), 2.39 (3H, s), 2.67 (1H, dd, J=16.0, 5.9 Hz), 2.78 (1H, dd, J=13.9, 9.2 Hz), 3.01 (1H, dd, J=13.9, 4.5 Hz), 3.05-3.12 (2H, m), 3.14-3.21 (2H, m), 3.39 (2H, t, J=7.0 Hz), 3.53-3.79 (6H, m), 4.42-4.50 (1H, m), 4.53-4.62 (1H, m), 5.16 (1H, d, J=19.2 Hz), 5.25 (1H, d, J=18.8 Hz), 5.42 (2H, s), 5.54-5.61 (1H, m), 6.53 (1H, s), 7.00 (2H, s), 7.13-7.29 (5H, m), 7.31 (1H, s), 7.68-7.73 (1H, m), 7.80 (1H, d, J=10.9 Hz), 7.97 (1H, t, J=5.9 Hz), 8.07-8.15 (2H, m), 8.18 (1H, d, J=7.8 Hz), 8.25 (1H, t, J=6.1 Hz), 8.46 (1H, d, J=9.0 Hz).

MS (ESI) m/z: 1175 (M+H)$^+$.

Process 2: N-[4-(2,5-Dioxo-2,5-dihydro-1H-pyrrol-1-yl)butanoyl]-L-α-aspartylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (88 mg, 0.075 mmol) obtained in Process 1 above was reacted in the same manner as Process 2 of Example 1 to yield the titled compound as a pale yellow solid (72 mg, 86%).

$^1$HNMR (400 MHz, DMSO-$d_6$) δ: 0.87 (3H, t, J=7.4 Hz), 1.62-1.77 (4H, m), 1.86 (2H, dt, J=15.4, 7.5 Hz), 2.04-2.24 (6H, m), 2.39 (3H, s), 2.30-2.53 (2H, m), 2.75-2.87 (1H, m), 3.01 (1H, dd, J=13.7, 4.7 Hz), 3.04-3.12 (2H, m), 3.13-3.20 (2H, m), 3.38 (2H, t, J=7.0 Hz), 3.52-3.77 (6H, m), 4.31-4.46 (1H, m), 4.46-4.56 (1H, m), 5.16 (1H, d, J=18.8 Hz), 5.25 (1H, d, J=19.2 Hz), 5.42 (2H, s), 5.53-5.61 (1H, m), 6.53 (1H, s), 7.00 (2H, s), 7.12-7.28 (5H, m), 7.31 (1H, s), 7.79 (1H, d, J=11.3 Hz), 7.67-7.84 (1H, m), 7.95-8.22 (4H, m), 8.25-8.43 (1H, m), 8.42-8.61 (1H, m), 12.30 (1H, brs). MS (ESI) m/z: 1119 (M+H)$^+$.

Process 3: Antibody-Drug Conjugate (99)

The compound obtained in Process 2 above was used as the drug linker. By the same procedures as Process 6 of Example 2, 6 mL of a solution containing the compound of interest was obtained, and the following characteristic values were obtained.

Antibody concentration: 1.32 mg/mL, antibody yield: 7.9 mg (79%), and average number of conjugated drug molecules (n) per antibody molecule: 3.3.

Example 100 Antibody-Drug Conjugate (100)

[Formula 153]

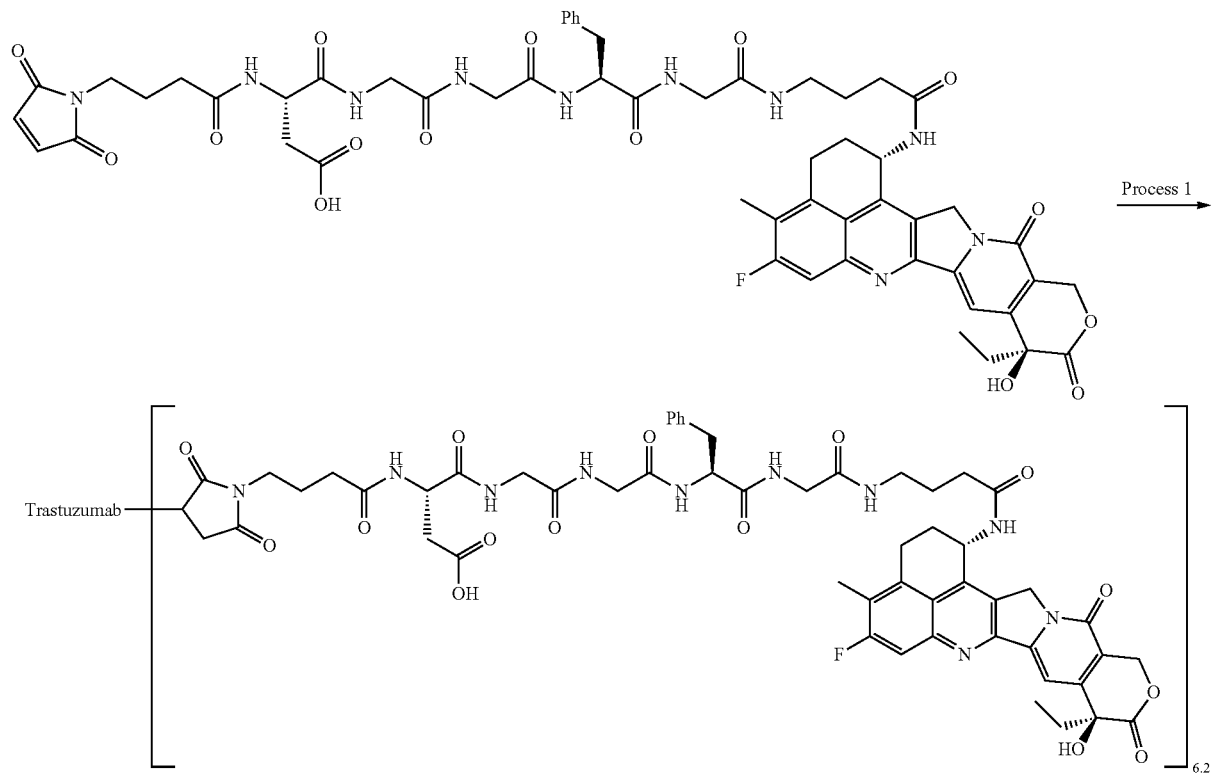

Process 1: Antibody-Drug Conjugate (100)

The amount of the aqueous solution of 10 mM TCEP added was adjusted such that the molar ratio of TCEP to the antibody at the antibody reduction was 4.6. The compound obtained in Process 2 of Example 99 was used as the drug linker. And the amount of the 10 mM drug linker solution added was adjusted such that the molar ratio of the drug linker to the antibody at the drug linker conjugation was 9.2. Then the amount of the aqueous solution of 100 mM NAC added was adjusted such that the molar ratio of NAC to the antibody at the termination of the reaction was 18.4. By the same procedures as Process 3 of Example 99, 6 mL of a solution containing the compound of interest was obtained, and the following characteristic values were obtained.

Antibody concentration: 1.17 mg/mL, antibody yield: 7.0 mg (70%), and average number of conjugated drug molecules (n) per antibody molecule: 6.2.

Example 101 Antibody-Drug Conjugate (101)

[Formula 154]

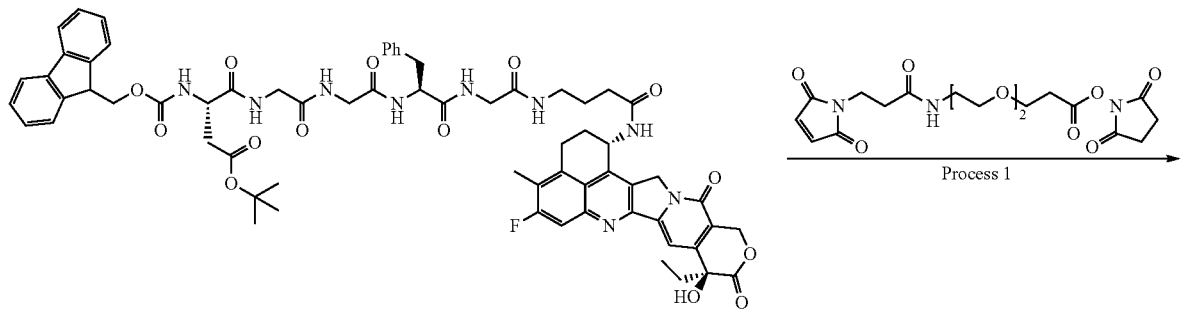

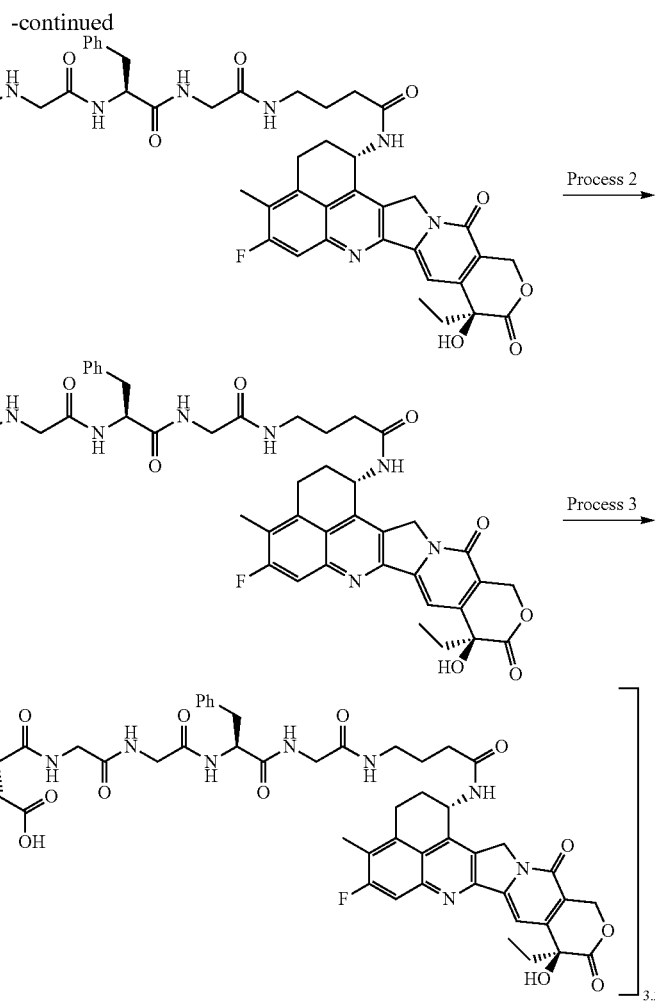

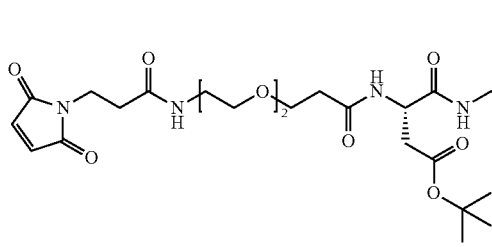

Process 1: tert-Butyl (3S,12S)-12-benzyl-3-({3-[2-(2-{[3-(2,5-dioxo-2,5-dihydro-1H-pyrrol-1-yl)propanoyl]amino}ethoxy)ethoxy]propanoyl}amino)-21-{[(1S,9S)-9-ethyl-5-fluoro-9-hydroxy-4-methyl-10,13-dioxo-2,3,9,10,13,15-hexahydro-1H, 12H-benzo[de]pyrano[3',4':6,7]indolizino[1,2-b]quinolin-1-yl]amino}-4,7,10,13,16,21-hexaoxo-5,8,11,14,17-pentaazaheneicosan-1-oate The compound (107 mg, 0.106 mmol) obtained in Process 1 of Example 58 was reacted in the same manner as Process 2 of Example 58 by using N-succinimidyl 3-(2-(2-(3-maleimidopropanamide)ethoxy)ethoxy)propanoate instead of N-succinimidyl 6-maleimidohexanoate to yield the titled compound as a pale yellow solid (107 mg, 76%).
MS(ESI) m/z: 1321 (M+H)+.

Process 2: N-{3-[2-(2-{[3-(2,5-Dioxo-2,5-dihydro-1H-pyrrol-1-yl)propanoyl]amino}ethoxy)ethoxy]propanoyl}-L-α-aspartylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H, 12H-benzo[de]pyrano[3',4':6,7]indolizino[1,2-b]quinolin-1-yl]amino}-4-oxobutyl)glycinamide The compound (107 mg, 0.081 mmol) obtained in Process 1 above was reacted in the same manner as Process 2 of Example 1 to yield the titled compound as a pale yellow solid (91 mg, 89%).

$^1$HNMR (400 MHz, DMSO-$d_6$) δ: 0.87 (3H, t, J=7.2 Hz), 1.71 (2H, t, J=7.0 Hz), 1.79-1.93 (2H, m), 2.07-2.22 (4H, m), 2.32 (2H, t, J=7.2 Hz), 2.35-2.41 (2H, m), 2.39 (3H, s), 2.75-2.86 (1H, m), 3.01 (1H, dd, J=13.9, 4.5 Hz), 3.05-3.21 (6H, m), 3.29-3.37 (6H, m), 3.45 (4H, s), 3.52-3.78 (8H, m), 4.38-4.47 (1H, m), 4.48-4.60 (1H, m), 5.16 (1H, d, J=18.8 Hz), 5.25 (1H, d, J=19.2 Hz), 5.42 (2H, s), 5.53-5.61 (1H, m), 6.53 (1H, s), 7.00 (2H, s), 7.12-7.27 (5H, m), 7.31 (1H, s), 7.73 (1H, t, J=5.7 Hz), 7.79 (1H, d, J=11.3 Hz), 8.03 (2H, t, J=5.7 Hz), 8.07-8.26 (3H, m), 8.26-8.42 (1H, m), 8.45-8.55 (1H, m), 12.32 (1H, brs). MS (ESI) m/z: 1264 (M+H)+.

Process 3: Antibody-Drug Conjugate (101)

The compound obtained in Process 2 above was used as the drug linker. By the same procedures as Process 6 of Example 2, 6 mL of a solution containing the compound of interest was obtained, and the following characteristic values were obtained.

Antibody concentration: 1.40 mg/mL, antibody yield: 8.4 mg (84%), and average number of conjugated drug molecules (n) per antibody molecule: 3.2.

Example 102 Antibody-Drug Conjugate (102)

[Formula 155]

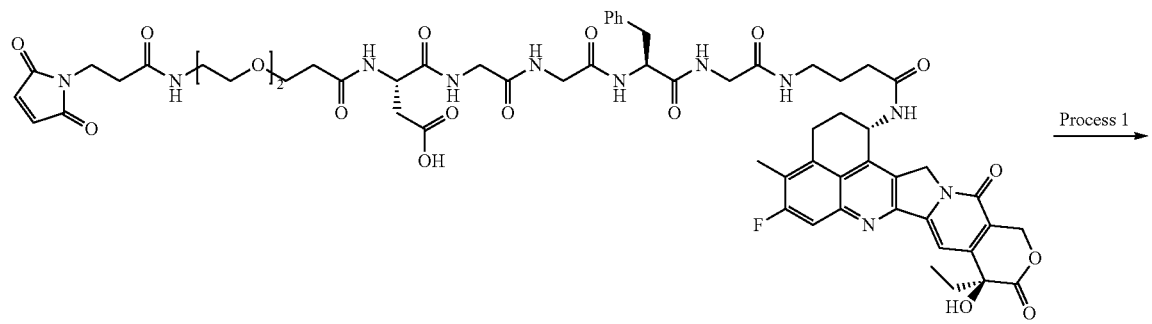

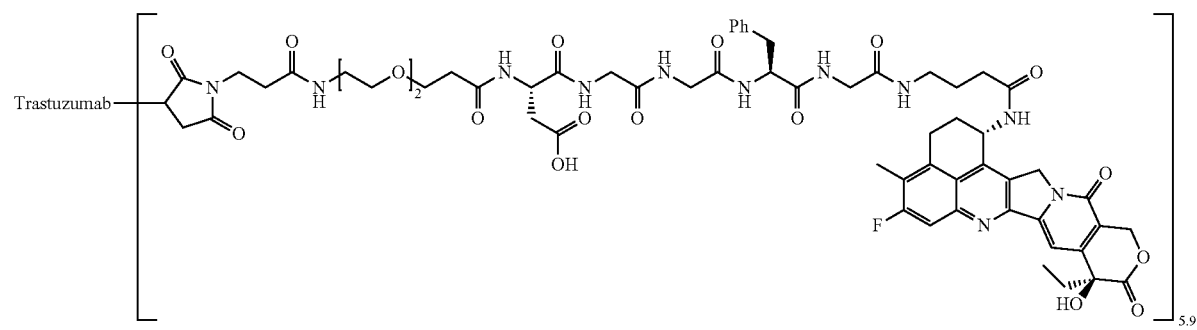

Process 1: Antibody-Drug Conjugate (102)

The compound obtained in Process 2 of Example 101 was used as the drug linker. The amount of the aqueous solution of 10 mM TCEP added was adjusted such that the molar ratio of TCEP to the antibody at the antibody reduction was 4.6. And the amount of the 10 mM drug linker solution added was adjusted such that the molar ratio of the drug linker to the antibody at the drug linker conjugation was 9.2. Then the amount of the aqueous solution of 100 mM NAC added was adjusted such that the molar ratio of NAC to the antibody at the termination of the reaction was 18.4. By the same procedures as Process 3 of Example 101, 6 mL of a solution containing the compound of interest was obtained, and the following characteristic values were obtained.
Antibody concentration: 1.22 mg/mL, antibody yield: 7.3 mg (73%), and average number of conjugated drug molecules (n) per antibody molecule: 5.9.

Example 103 Antibody-Drug Conjugate (103) on

[Formula 156]

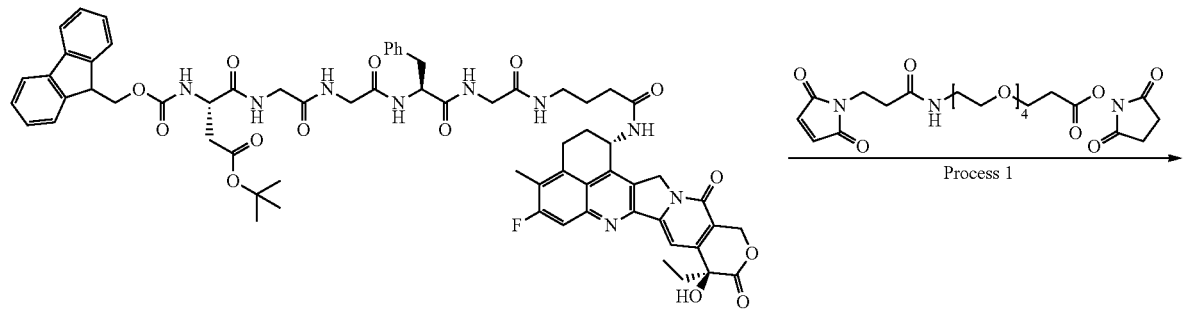

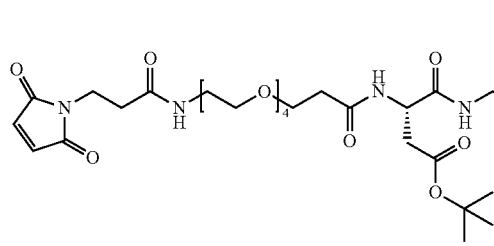
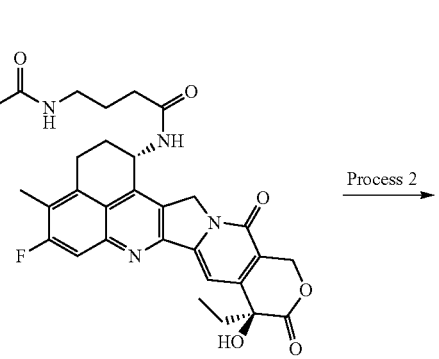
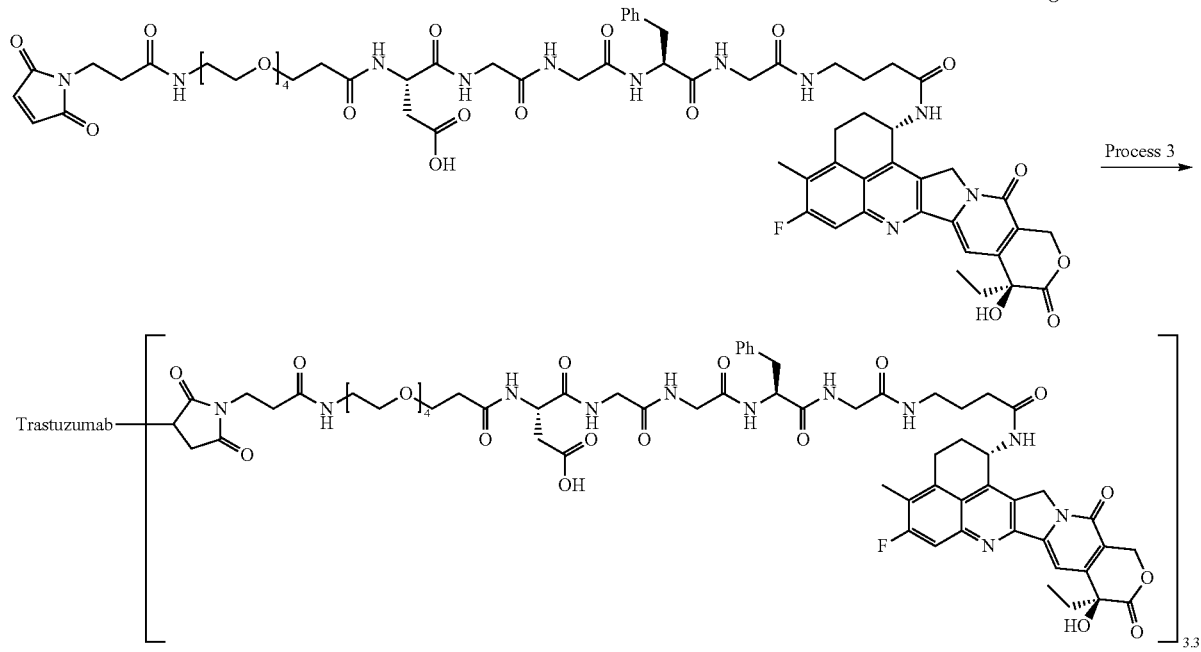

Process 1: tert-Butyl (21S)-21-{[(7S)-7-benzyl-16-{[(1S,9S)-9-ethyl-5-fluoro-9-hydroxy-4-methyl-10,13-dioxo-2,3,9,10,13,15-hexahydro-1H,12H-yl]amino}-2,5,8,11,16-pentaoxo-3,6,9,12-tetraazahexadec-1-yl]carbamoyl}-1-(2,5-dioxo-2,5-dihydro-1H-pyrrol-1-yl)-3,19-dioxo-7,10,13,16-tetraoxa-4,20-diazatriocsan-23-oate The compound (107 mg, 0.106 mmol) obtained in Process 1 of Example 58 was reacted in the same manner as Process 2 of Example 58 by using N-succinimidyl 1-maleimido-3-oxo-7,10,13,16-tetraoxa-4-azanonadecan-19-oate instead of N-succinimidyl 6-maleimidohexanoate to yield the titled compound as a pale yellow solid (157 mg, quantitative).

Process 2: N-[19-(2,5-Dioxo-2,5-dihydro-1H-pyrrol-1-yl)-17-oxo-4,7,10,13-tetraoxa-16-azanonadecan-1-oyl]-L-α-aspartylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (156 g, 0.111 mmol) obtained in Process 1 above was reacted in the same manner as Process 2 of Example 1 to yield the titled compound as a pale yellow solid (83 mg, 55%).

$^1$H-NMR (400 MHz, DMSO-d$_6$) δ: 0.87 (3H, t, J=7.4 Hz), 1.72 (2H, t, J=7.4 Hz), 1.79-1.93 (2H, m), 2.05-2.23 (4H, m), 2.32 (2H, t, J=7.4 Hz), 2.39 (3H, s), 2.35-2.42 (2H, m), 2.76-2.87 (1H, m), 3.01 (1H, dd, J=13.5, 4.5 Hz), 3.05-3.21 (6H, m), 3.29-3.38 (4H, m), 3.48 (12H, d, J=8.2 Hz), 3.54-3.79 (10H, m), 4.38-4.47 (1H, m), 4.48-4.59 (1H, m), 5.16 (1H, d, J=18.8 Hz), 5.25 (1H, d, J=19.2 Hz), 5.42 (2H, s), 5.53-5.62 (1H, m), 6.53 (1H, s), 7.00 (2H, s), 7.13-7.29 (5H, m), 7.31 (1H, s), 7.70-7.77 (1H, m), 7.79 (1H, d, J=10.9 Hz), 8.03 (2H, t, J=5.5 Hz), 8.07-8.28 (3H, m), 8.29-8.45 (1H, m), 8.46-8.57 (1H, m), 12.33 (1H, brs).

MS (ESI) m/z: 1353 (M+H)$^+$.

Process 3: Antibody-Drug Conjugate (103)

The compound obtained in Process 2 above was used as the drug linker. By the same procedures as Process 6 of Example 2, 6 mL of a solution containing the compound of interest was obtained, and the following characteristic values were obtained.

Antibody concentration: 1.27 mg/mL, antibody yield: 7.6 mg (76%), and average number of conjugated drug molecules (n) per antibody molecule: 3.3.

Example 104 Antibody-Drug Conjugate (104)

[Formula 157]

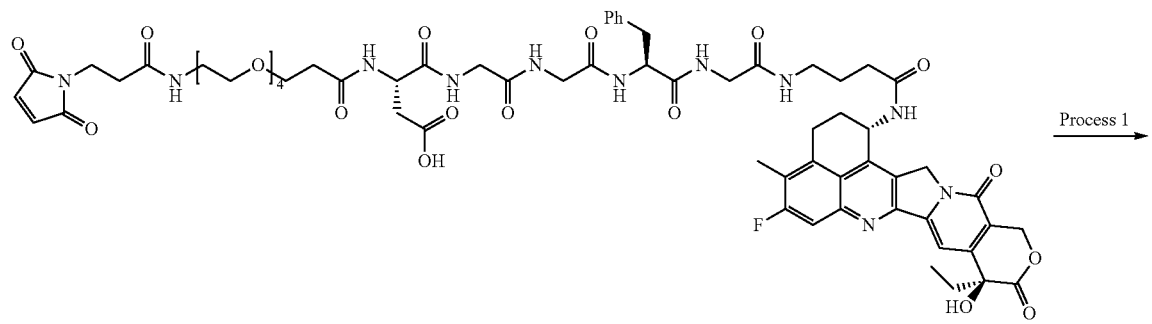

Process 1

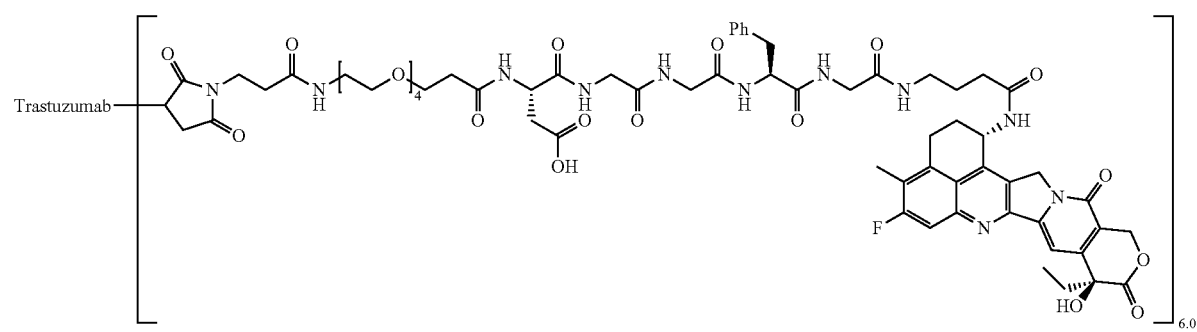

Process 1: Antibody-Drug Conjugate (104)

The compound obtained in Process 2 of Example 103 was used as the drug linker. The amount of the aqueous solution of 10 mM TCEP added was adjusted such that the molar ratio of TCEP to the antibody at the antibody reduction was 4.6. And the amount of the 10 mM drug linker solution added was adjusted such that the molar ratio of the drug linker to the antibody at the drug linker conjugation was 9.2. Then the amount of the aqueous solution of 100 mM NAC added was adjusted such that the molar ratio of NAC to the antibody at the termination of the reaction was 18.4. By the same procedures as Process 3 of Example 103, 6 mL of a solution containing the compound of interest was obtained, and the following characteristic values were obtained.
Antibody concentration: 1.21 mg/mL, antibody yield: 7.3 mg (73%), and average number of conjugated drug molecules (n) per antibody molecule: 6.0.

Example 105 Antibody-Drug Conjugate (105)

[Formula 158]

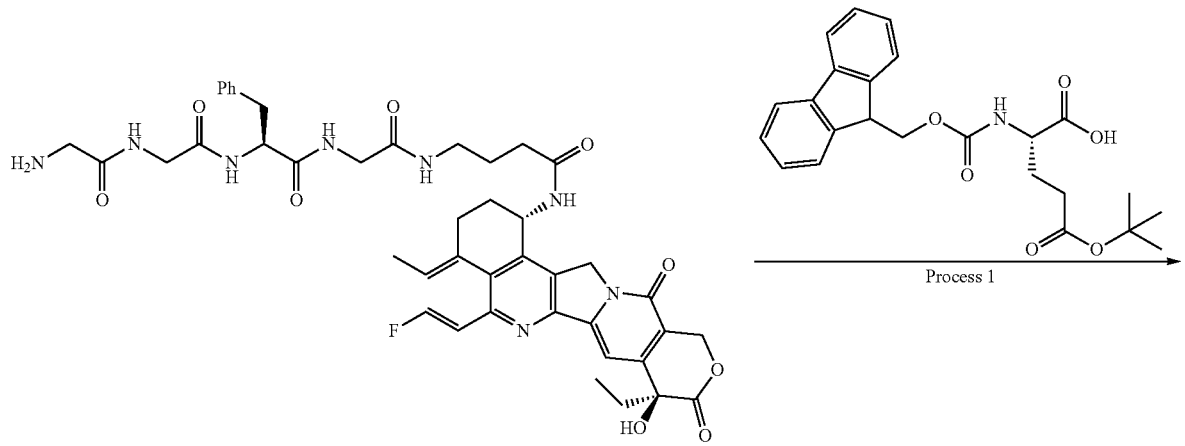

Process 1

449
450
-continued
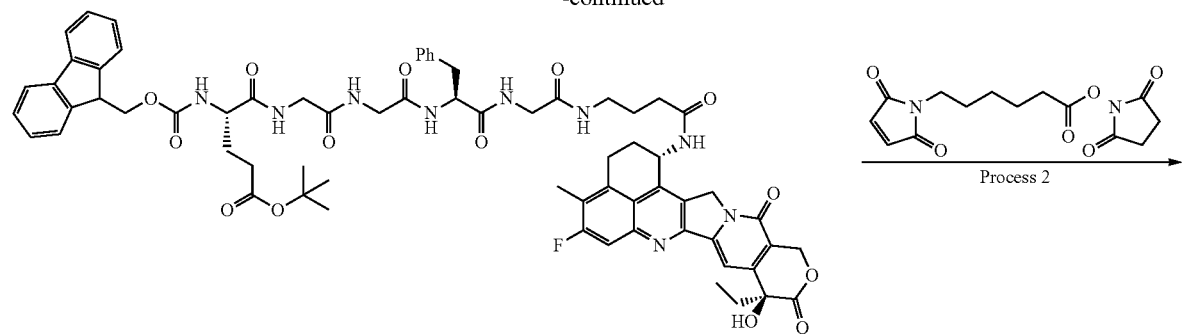
Process 2 →
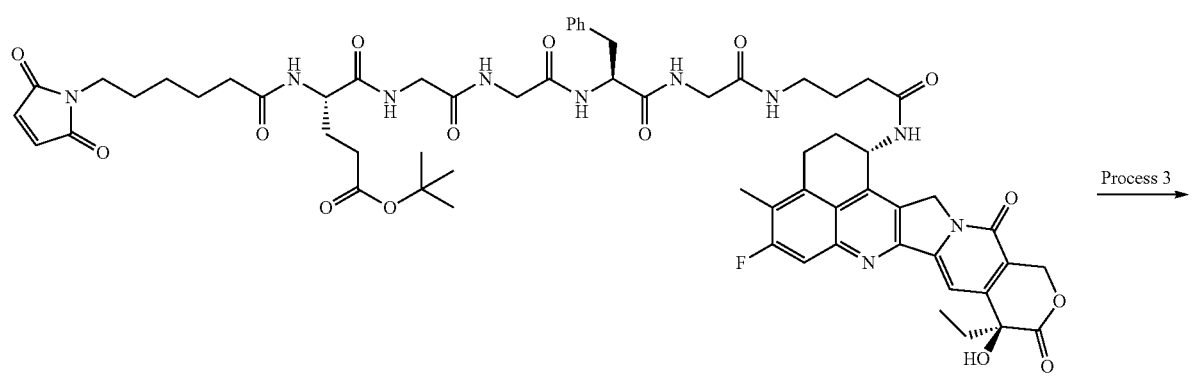
Process 3 →
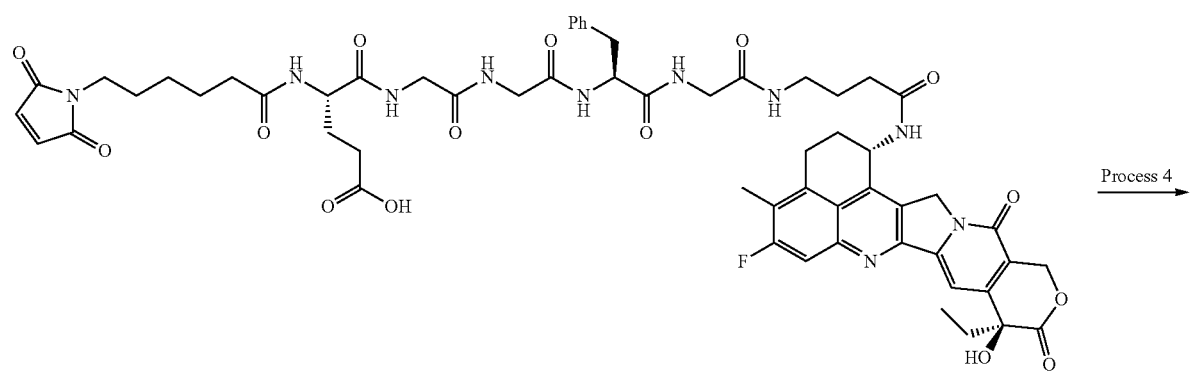
Process 4 →
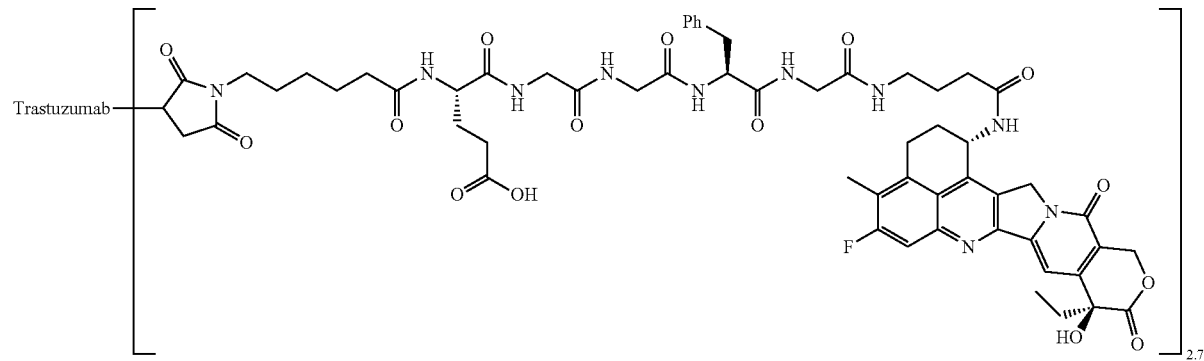

451

Process 1: tert-Butyl (10S,19S)-10-benzyl-1-{[(1S, 9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-19-{[(9H-fluoren-9-ylmethoxy)carbonyl]amino}-1,6,9,12,15,18-hexaoxo-5,8,11,14,17-pentaazadocosan-22-oate

The compound (150 mg, 0.179 mmol) obtained in Process 2 of Example 2 was reacted in the same manner as Process 1 of Example 58 by using (2S)-5-tert-butoxy-2-{[(9H-fluoren-9-ylmethoxy)carbonyl]amino}-5-oxopentanoic acid instead of (2S)-4-tert-butoxy-2-{[(9H-fluoren-9-ylmethoxy)carbonyl]amino}-4-oxobutanoic acid to yield the titled compound as a pale yellow solid (176 mg, 79%).

MS(ESI) m/z: 1247 (M+H)$^+$.

Process 2: tert-Butyl (10S,19S)-10-benzyl-19-{[6-(2,5-dioxo-2,5-dihydro-1H-pyrrol-1-yl)hexanoyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,6,9,12,15,18-hexaoxo-5,8,11,14,17-pentaazadocosan-22-oate

The compound (165 mg, 0.132 mmol) obtained in Process 1 above was reacted in the same manner as Process 2 of Example 58 to yield the titled compound as a white solid (125 mg, 78%).

MS(ESI) m/z: 1218 (M+H)$^+$.

Process 3: N-[6-(2,5-Dioxo-2,5-dihydro-1H-pyrrol-1-yl)hexanoyl]-L-α-glutamylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide

The compound (125 mg, 0.103 mmol) obtained in Process 2 above was reacted in the same manner as Process 2 of Example 1 to yield the titled compound as a pale yellow solid (102 mg, 85%).

$^1$H-NMR (400 MHz, DMSO-d$_6$) δ: 0.87 (3H, t, J=7.2 Hz), 1.16 (2H, m, J=14.5 Hz), 1.46 (4H, quin, J=7.3 Hz), 1.72 (3H, dt, J=14.2, 7.2 Hz), 1.78-1.94 (3H, m), 2.01-2.27 (8H, m), 2.39 (3H, s), 2.79 (1H, dd, J=13.7, 9.4 Hz), 3.02 (1H, dd, J=13.3, 4.7 Hz), 3.05-3.12 (2H, m), 3.17 (2H, d, J=5.1 Hz), 3.28-3.40 (2H, m), 3.50-3.83 (6H, m), 4.18-4.27 (1H, m), 4.40-4.50 (1H, m), 5.16 (1H, d, J=19.6 Hz), 5.25 (1H, d, J=19.2 Hz), 5.42 (2H, s), 5.51-5.62 (1H, m), 6.53 (1H, s), 6.99 (2H, s), 7.12-7.29 (5H, m), 7.31 (1H, s), 7.71 (1H, t, J=5.5 Hz), 7.79 (1H, d, J=10.9 Hz), 8.01 (1H, d, J=7.4 Hz), 8.05-8.21 (3H, m), 8.32 (1H, s), 8.47 (1H, d, J=8.6 Hz), 12.08 (1H, brs).

MS (ESI) m/z: 1161 (M+H)$^+$.

Process 4: Antibody-Drug Conjugate (105)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.37 mLmg$^{-1}$ cm$^{-1}$ was used). The solution (1.25 mL) was placed in a 1.5 mL polypropylene tube and charged with an aqueous solution of 10 mM TCEP (0.019 mL; 2.3 equivalents per antibody molecule) and an aqueous solution of 1 M dipotassium hydrogenphosphate (0.0625 mL). After confirming that the solution had a pH of 7.4±0.1, the disulfide bond at the hinge part in the antibody was reduced by incubating at 37° C. for 1 hour.

Conjugation between antibody and drug linker: After adding DMSO (Sigma-Aldrich Co. LLC; 0.109 mL) and a DMSO solution containing 10 mM of the compound obtained in Process 3 above (0.039 mL; 4.6 equivalents per antibody molecule) to the above solution at room temperature, it was stirred by using a tube rotator for conjugating the drug linker to the antibody at room temperature for 40 minutes. Next, an aqueous solution (0.008 mL) of 100 mM NAC was added thereto and stirred at room temperature to terminate the reaction of the drug linker for another 20 minutes.

Purification: The above solution was subjected to purification using the Common procedure D-1 (ABS was used as buffer solution) to yield 6 mL of a solution containing the compound of interest.

Physicochemical characterization: By using the Common procedure B and Common procedure E, the following characteristic values were obtained.

Antibody concentration: 1.71 mg/mL, antibody yield: 10.3 mg (82%), and average number of conjugated drug molecules (n) per antibody molecule: 2.7.

Example 106 Antibody-Drug Conjugate (106)

[Formula 159]

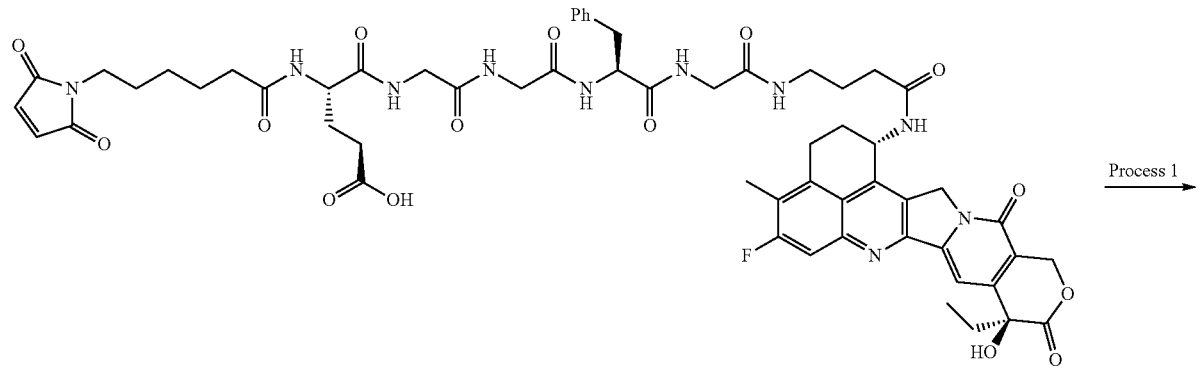

Process 1 →

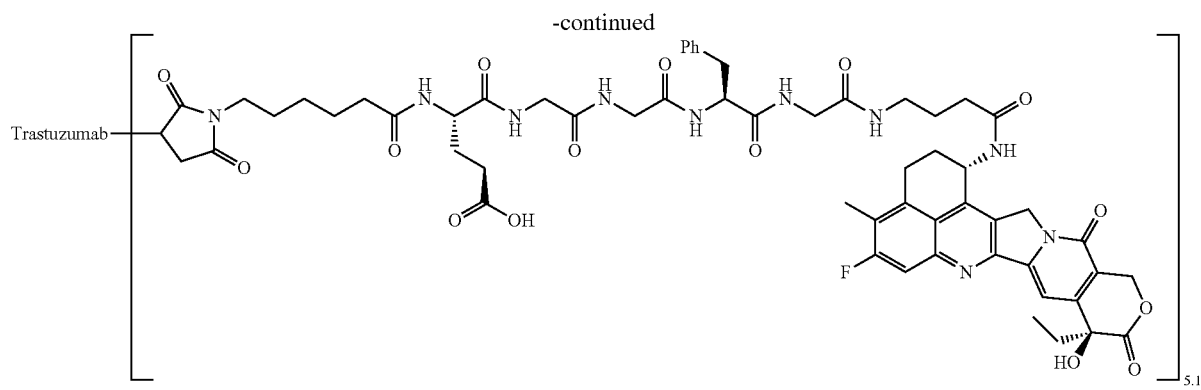

Process 1: Antibody-Drug Conjugate (106)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.37 mLmg$^{-1}$ cm$^{-1}$ was used). The solution (1.25 mL) was placed in a 1.5 mL polypropylene tube and charged with an aqueous solution of 10 mM TCEP (0.039 mL; 4.6 equivalents per antibody molecule) and an aqueous solution of 1 M dipotassium hydrogenphosphate (0.0625 mL). After confirming that the solution had a pH of 7.4±0.1, the disulfide bond at the hinge part in the antibody was reduced by incubating at 37° C. for 1 hour.

Conjugation between antibody and drug linker: After adding dimethyl sulfoxide (0.072 mL) and a DMSO solution containing 10 mM of the compound obtained in Process 3 of Example 105 (0.078 mL; 9.2 equivalents per antibody molecule) to the above solution at room temperature, it was stirred by using a tube rotator for conjugating the drug linker to the antibody at room temperature for 40 minutes. Next, an aqueous solution (0.0155 mL) of 100 mM NAC was added thereto and stirred at room temperature to terminate the reaction of the drug linker for another 20 minutes.

Purification: The above solution was subjected to purification using the Common procedure D-1 (ABS was used as buffer solution) to yield 6 mL of a solution containing the compound of interest.

Physicochemical characterization: By using the Common procedure B and Common procedure E, the following characteristic values were obtained.

Antibody concentration: 1.46 mg/mL, antibody yield: 8.8 mg (70%), and average number of conjugated drug molecules (n) per antibody molecule: 5.1.

Example 107 Antibody-Drug Conjugate (107)

[Formula 160]

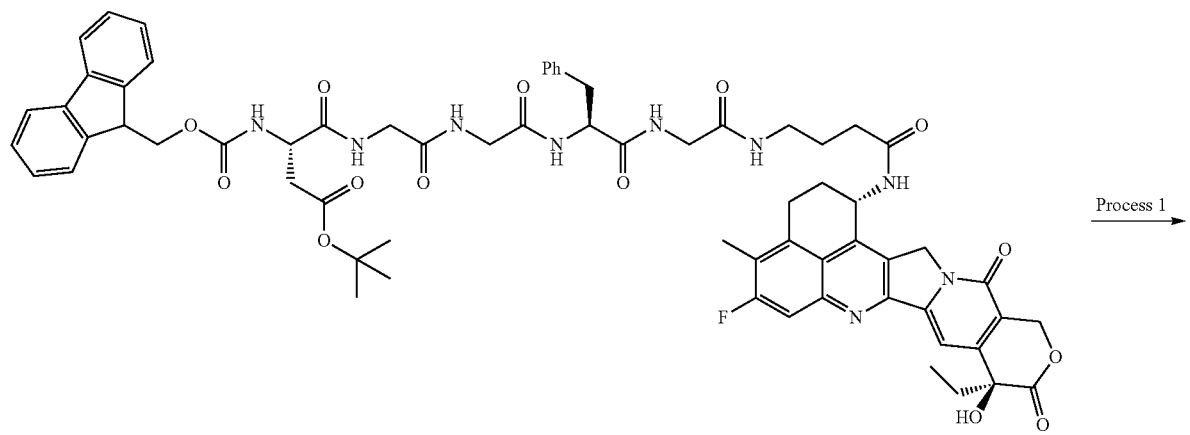

Process 1

455 456
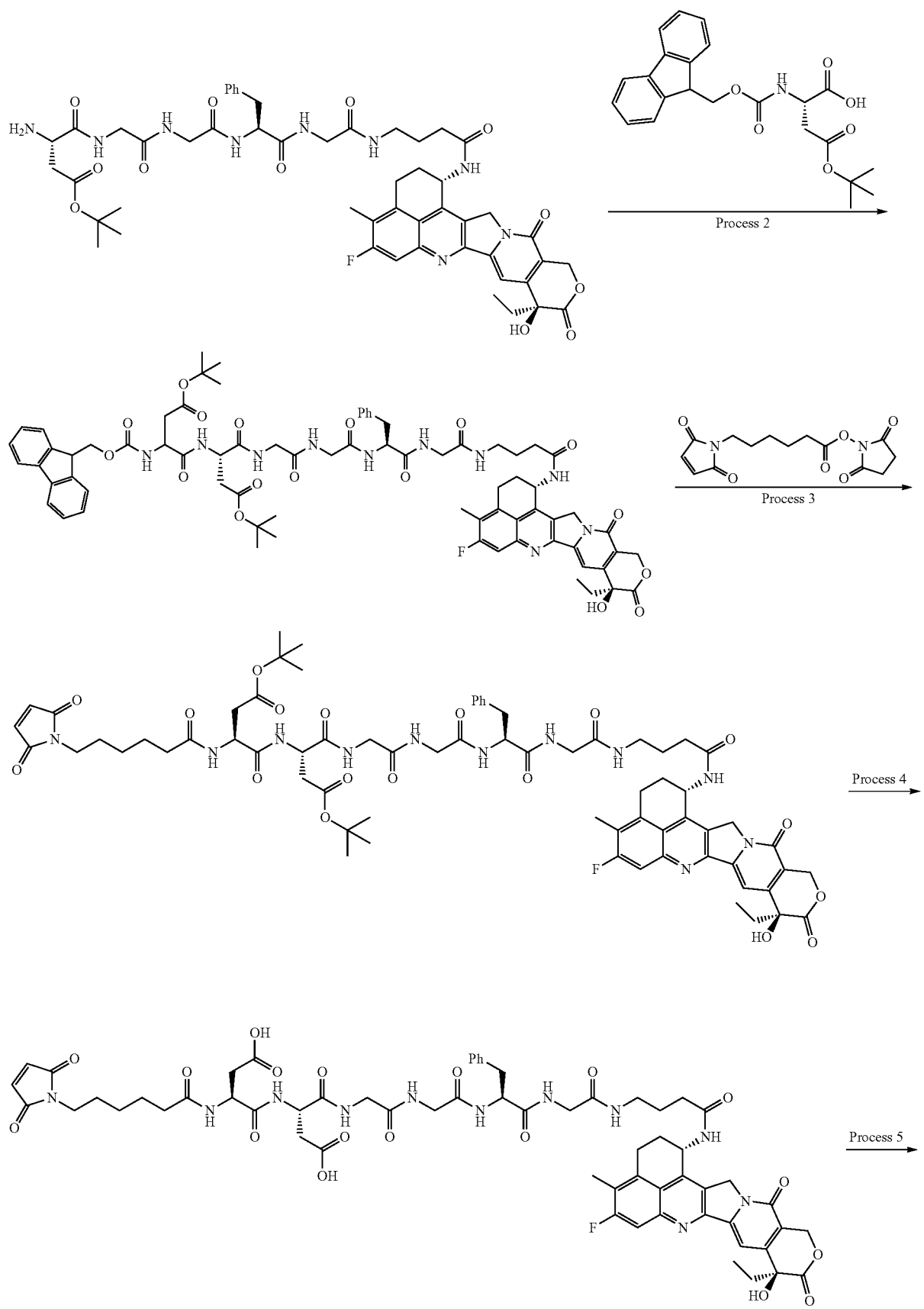

-continued

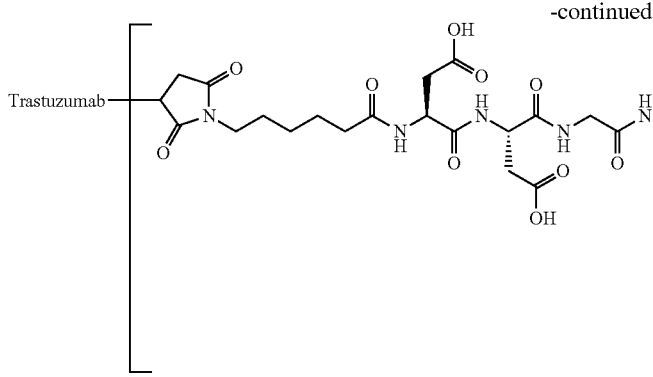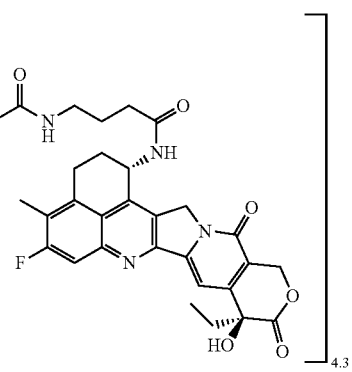

Process 1: tert-Butyl (3S,12S)-3-amino-12-benzyl-21-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,16,21-hexaoxo-5,8,11,14,17-pentaazaheneicosan-1-oate To an N,N-dimethylformamide (2.5 mL) solution of the compound (300 mg, 0.243 mmol) obtained in Process 1 of Example 58, piperidine (0.245 mL, 2.43 mmol) was added and stirred at room temperature for 1.5 hours. The solvent was removed under reduced pressure and the residues obtained were purified by silica gel column chromatography [chloroform-partitioned organic layer of chloroform:methanol:water=7:3:1 (v/v/v)] to yield the titled compound as a pale yellow solid (210 mg, 85%).

$^1$H-NMR (500 MHz, DMSO-$d_6$) δ: 0.90 (3H, t, J=6.8 Hz), 1.40 (9H, s), 1.70-1.77 (2H, m), 1.83-1.92 (2H, m), 2.12-2.23 (4H, m), 2.32-2.39 (1H, m), 2.42 (3H, s), 2.55-2.62 (1H, m), 2.78-2.85 (1H, m), 3.00-3.07 (1H, m), 3.07-3.13 (2H, m), 3.17-3.21 (2H, m), 3.50-3.80 (7H, m), 4.45-4.51 (1H, m), 5.19 (1H, d, J=17.3 Hz), 5.28 (1H, d, J=17.3 Hz), 5.43-5.47 (2H, m), 5.57-5.63 (1H, m), 6.56 (1H, s), 7.18-7.28 (5H, m), 7.34 (1H, s), 7.70-7.74 (1H, m), 7.83 (1H, d, J=10.7 Hz), 8.05-8.15 (3H, m), 8.28-8.30 (3H, m), 8.49 (1H, d, J=9.3 Hz).

Process 2: tert-Butyl (3S,6S,15S)-15-benzyl-6-(2-tert-butoxy-2-oxoethyl)-24-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-{[(9H-fluoren-9-ylmethoxy)carbonyl]amino}-4,7,10,13,16,19,24-heptaoxo-5,8,11,14,17,20-hezxaaztetracosan-1-oate The compound (105 mg, 0.104 mmol) obtained in Process 1 above was reacted in the same manner as Process 1 of Example 58 to yield the titled compound (105 mg, 72%).

$^1$H-NMR (400 MHz, DMSO-$d_6$) δ: 0.86 (3H, t, J=7.4 Hz), 1.33 (9H, s), 1.36 (9H, s), 1.65-1.76 (2H, m), 1.78-1.92 (2H, m), 2.06-2.22 (4H, m), 2.39 (3H, s), 2.41-2.53 (2H, m), 2.64-2.74 (2H, m), 2.78 (1H, dd, J=13.3, 9.8 Hz), 3.01 (1H, dd, J=13.7, 4.7 Hz), 3.08 (2H, dt, J=12.2, 6.2 Hz), 3.13-3.21 (2H, m), 3.54-3.80 (6H, m), 4.16-4.33 (3H, m), 4.34-4.43 (1H, m), 4.43-4.51 (1H, m), 4.54-4.63 (1H, m), 5.15 (1H, d, J=19.2 Hz), 5.23 (1H, d, J=18.8 Hz), 5.42 (2H, br.s.), 5.52-5.60 (1H, m), 6.54 (1H, s), 7.13-7.19 (1H, m), 7.20-7.27 (4H, m), 7.27-7.34 (3H, m), 7.40 (2H, t, J=7.6 Hz), 7.65-7.74 (4H, m), 7.80 (1H, d, J=10.9 Hz), 7.87 (2H, d, J=7.8 Hz), 7.98 (1H, t, J=5.9 Hz), 8.05-8.09 (1H, m), 8.12 (1H, d, J=7.8 Hz), 8.23-8.31 (2H, m), 8.46 (1H, d, J=9.0 Hz).

Process 3: tert-Butyl (3S,6S,15S)-15-benzyl-6-(2-tert-butoxy-2-oxoethyl)-3-{[6-(2,5-dioxo-2,5-dihydro-1H-pyrrol-1-yl)hexanoyl]amino}-24-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,16,19,24-heptaoxo-5,8,11,14,17,20-hezxaaztetracosan-1-oate The compound (99 mg, 0.071 mmol) obtained in Process 2 above was reacted in the same manner as Process 2 of Example 58 to yield the titled compound as a light brown-white solid (83 mg, 86%).

MS(ESI) m/z: 1375 (M+H)$^+$.

Process 4: N-[6-(2,5-Dioxo-2,5-dihydro-1H-pyrrol-1-yl)hexanoyl]-L-α-aspartyl-L-α-aspartylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (80 mg, 0.058 mmol) obtained in Process 3 above was reacted in the same manner as Process 2 of Example 1 to yield the titled compound as a pale yellow solid (30 mg, 41%).

$^1$HNMR (400 MHz, DMSO-$d_6$) δ: 0.87 (3H, t, J=7.2 Hz), 1.10-1.22 (2H, m), 1.45 (4H, t, J=7.0 Hz), 1.71 (2H, m, J=7.4 Hz), 1.78-1.93 (2H, m), 2.06 (2H, t, J=7.4 Hz), 2.10-2.23 (4H, m), 2.31-2.57 (2H, m), 2.40 (3H, s), 2.61-2.85 (3H, m), 3.01 (1H, dd, J=13.9, 3.7 Hz), 3.05-3.12 (2H, m), 3.17 (2H, brs), 3.28-3.41 (2H, m), 3.46-3.85 (6H, m), 4.41-4.50 (1H, m), 4.50-4.60 (2H, m), 5.16 (1H, d, J=19.6 Hz), 5.25 (1H, d, J=18.8 Hz), 5.42 (2H, s), 5.52-5.62 (1H, m), 6.54 (1H, s), 7.00 (2H, s), 7.12-7.28 (5H, m), 7.31 (1H, s), 7.72 (1H, brs), 7.80 (1H, d, J=11.3 Hz), 7.94 (1H, brs), 8.00 (1H, brs), 8.10 (1H, d, J=7.8 Hz), 8.15 (1H, d, J=7.0 Hz), 8.19 (1H, d, J=7.4 Hz), 8.28 (1H, brs), 8.46 (1H, d, J=8.2 Hz), 12.34 (2H, brs). MS (ESI) m/z: 1262 (M+H)$^+$.

Process 5: Antibody-Drug Conjugate (107)

By using the trastuzumab produced in Reference Example 1 and the compound obtained in Process 4 above, the compound of interest was obtained in the same manner as Process 6 of Example 2.

Antibody concentration: 1.74 mg/mL, antibody yield: 10.4 mg (83%), and average number of conjugated drug molecules (n) per antibody molecule: 4.3.

Example 108 Antibody-Drug Conjugate (108)

[Formula 161]

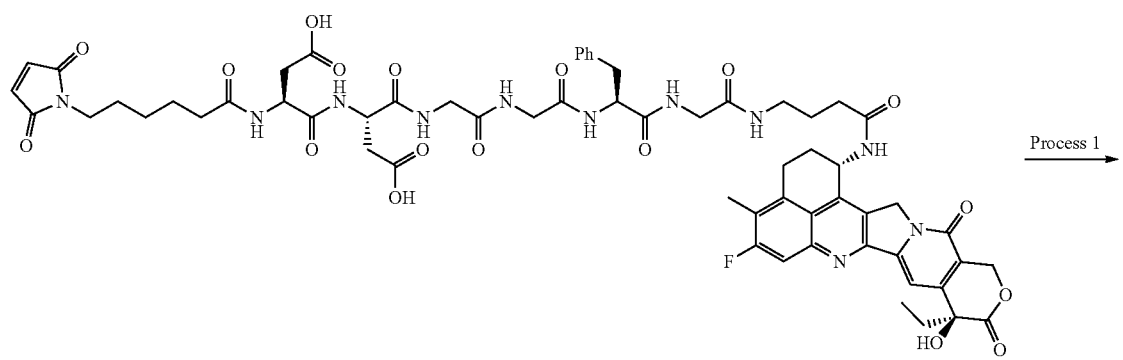

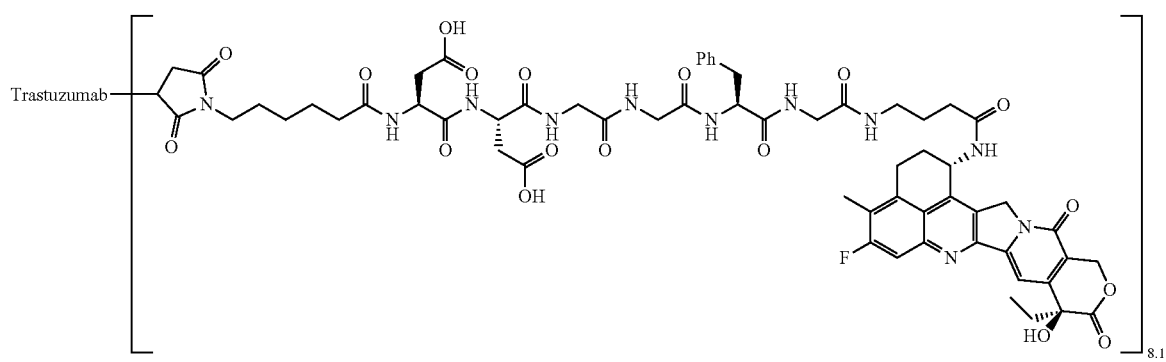

Process 1: Antibody-Drug Conjugate (108)

By using the trastuzumab produced in Reference Example 1 and the compound obtained in Process 4 of Example 107, the compound of interest was obtained in the same manner as Process 1 of Example 3.
Antibody concentration: 2.0 mg/mL, antibody yield: 12 mg (96%), and average number of conjugated drug molecules (n) per antibody molecule: 8.1.

Example 109 Antibody-Drug Conjugate (109)

[Formula 162]

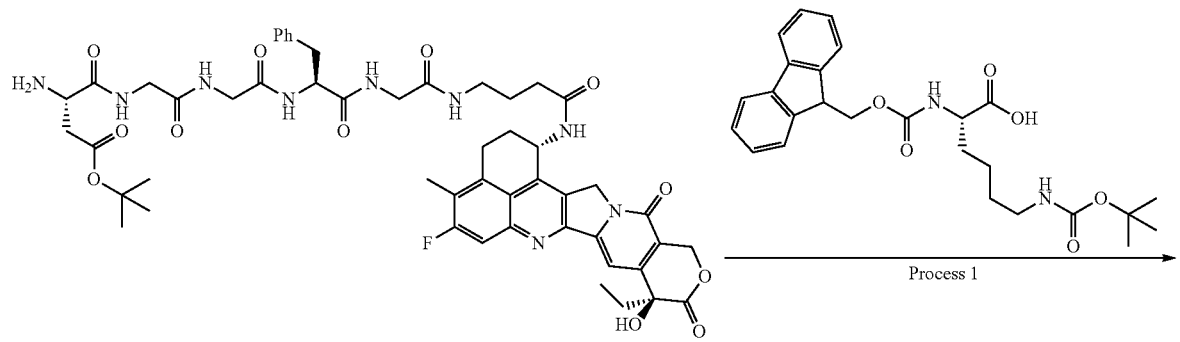

461 462
-continued
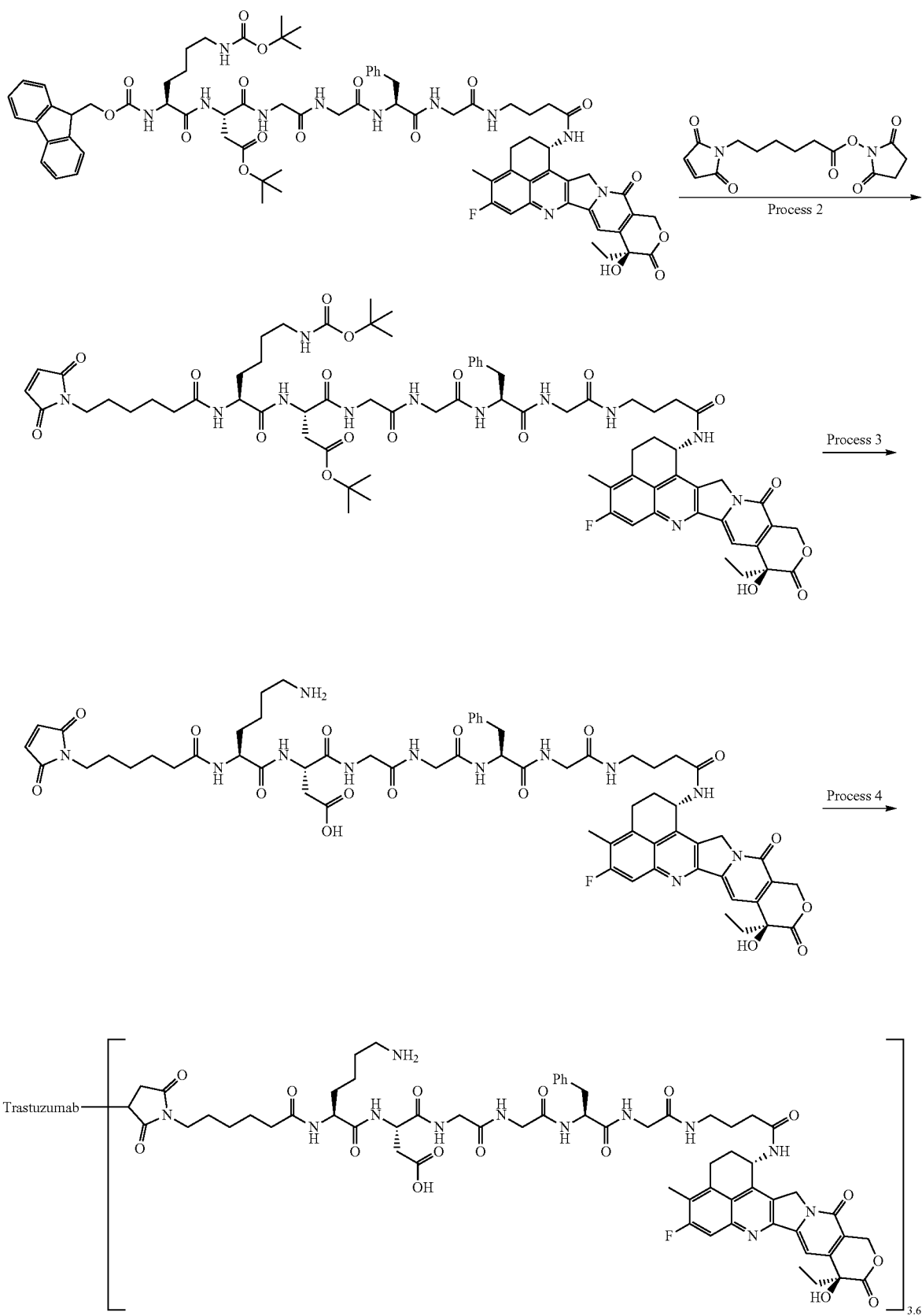

463

Process 1: tert-Butyl (3S,12S)-12-benzyl-3-{[(2S)-6-[(tert-butoxycarbonyl)amino]-2-{[(9H-fluoren-9-ylmethoxy)carbonyl]amino}hexanoyl]amino}-21-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,16,21-hexaoxo-5,8,11,14,17-pentaazaheneicosan-1-oate

The compound (105 mg, 0.104 mmol) obtained in Process 1 of Example 105 was reacted in the same manner as Process 1 of Example 58 by using $N^6$-(tert-butoxycarbonyl)-$N^2$-[(9H-fluoren-9-ylmethoxy)carbonyl]-L-lysine instead of (2S)-4-tert-butoxy-2-{[(9H-fluoren-9-ylmethoxy)carbonyl]amino}-4-oxobutanoic acid to yield the titled compound (105 mg, 69%).

$^1$H-NMR (400 MHz, DMSO-$d_6$) δ: 0.86 (3H, t, J=7.4 Hz), 1.30-1.34 (9H, m), 1.34-1.40 (9H, m), 1.44-1.54 (2H, m), 1.55-1.65 (2H, m), 1.66-1.77 (2H, m), 1.79-1.91 (2H, m), 2.06-2.22 (4H, m), 2.39 (3H, s), 2.43-2.55 (2H, m), 2.65-2.91 (5H, m), 3.01 (1H, dd, J=14.1, 4.7 Hz), 3.05-3.12 (2H, m), 3.13-3.21 (2H, m), 3.54-3.81 (6H, m), 3.89-4.01 (1H, m), 4.15-4.30 (3H, m), 4.42-4.51 (1H, m), 4.53-4.62 (1H, m), 5.17 (1H, d, J=19.9 Hz), 5.23 (1H, d, J=19.2 Hz), 5.42 (2H, s), 5.52-5.60 (1H, m), 6.54 (1H, s), 6.73-6.81 (1H, m), 7.12-7.27 (5H, m), 7.27-7.35 (3H, m), 7.36-7.44 (2H, m), 7.54 (1H, d, J=7.8 Hz), 7.66-7.75 (3H, m), 7.80 (1H, d, J=11.3 Hz), 7.87 (2H, d, J=7.8 Hz), 7.95-8.01 (1H, m), 8.01-8.06 (1H, m), 8.11 (1H, d, J=7.0 Hz), 8.21-8.31 (2H, m), 8.46 (1H, d, J=9.0 Hz).

Process 2: tert-Butyl (3S,12S)-12-benzyl-3-{[(2S)-6-[(tert-butoxycarbonyl)amino]-2-{[6-(2,5-dioxo-2,5-dihydro-1H-pyrrol-1-yl)hexanoyl]amino}hexanoyl]amino}-21-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,16,21-hexaoxo-5,8,11,14,17-pentaazaheneicosan-1-oate

The compound (101 mg, 0.069 mmol) obtained in Process 1 above was reacted in the same manner as Process 2 of Example 58 to yield the titled compound as a light brown-white solid (87 mg, 88%).

MS(ESI) m/z: 1432 (M+H)$^+$.

Process 3: $N^2$-[6-(2,5-Dioxo-2,5-dihydro-1H-pyrrol-1-yl)hexanoyl]-L-lysyl-L-α-aspartylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide

The compound (84 mg, 0.059 mmol) obtained in Process 2 above was reacted in the same manner as Process 2 of Example 1 to yield the titled compound as a light brown-white solid (28 mg, 37%).

$^1$HNMR (400 MHz, DMSO-$d_6$) δ: 0.87 (3H, t, J=7.0 Hz), 1.17 (2H, dt, J=13.7, 7.0 Hz), 1.21-1.34 (2H, m), 1.37-1.56 (6H, m), 1.57-1.77 (3H, m), 1.78-1.92 (2H, m), 1.99-2.25 (6H, m), 2.31-2.58 (3H, m), 2.40 (3H, s), 2.64-2.86 (3H, m), 3.02 (1H, dd, J=13.3, 4.3 Hz), 3.05-3.13 (2H, m), 3.13-3.22 (2H, m), 3.26-3.39 (2H, m), 3.39-3.81 (6H, m), 4.14-4.27 (1H, m), 4.40-4.58 (2H, m), 5.16 (1H, d, J=19.6 Hz), 5.25 (1H, d, J=19.9 Hz), 5.43 (2H, s), 5.51-5.63 (1H, m), 6.55 (1H, s), 7.01 (2H, s), 7.23 (5H, s), 7.31 (1H, s), 7.65 (2H, brs), 7.76 (1H, brs), 7.80 (1H, d, J=10.6 Hz), 7.94-8.09 (3H, m), 8.13 (1H, d, J=7.8 Hz), 8.23 (1H, d, J=7.4 Hz), 8.31-8.39 (1H, m), 8.49 (1H, d, J=7.8 Hz), 12.18-12.56 (1H, m). MS (ESI) m/z: 1276 (M+H)$^+$.

Process 4: Antibody-Drug Conjugate (109)

By using the trastuzumab produced in Reference Example 1 and the compound obtained in Process 3 above, the compound of interest was obtained in the same manner as Process 6 of Example 2.

Antibody concentration: 1.76 mg/mL, antibody yield: 10.6 mg (85%), and average number of conjugated drug molecules (n) per antibody molecule: 3.6.

Example 110 Antibody-Drug Conjugate (110)

[Formula 163]

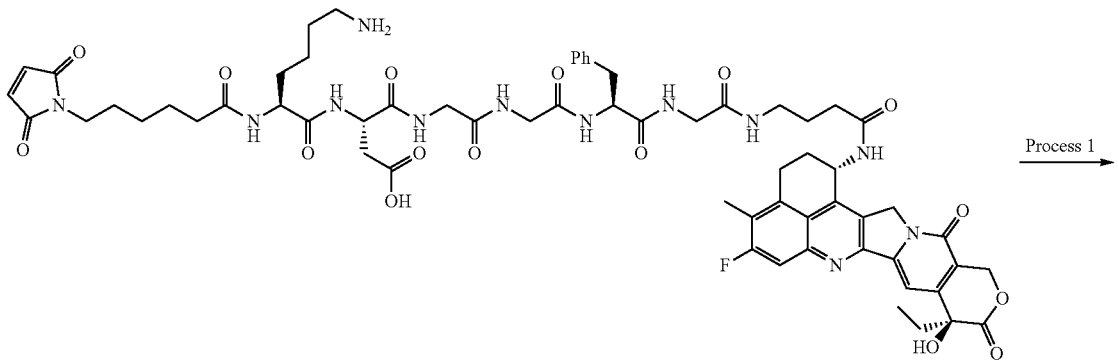

Process 1

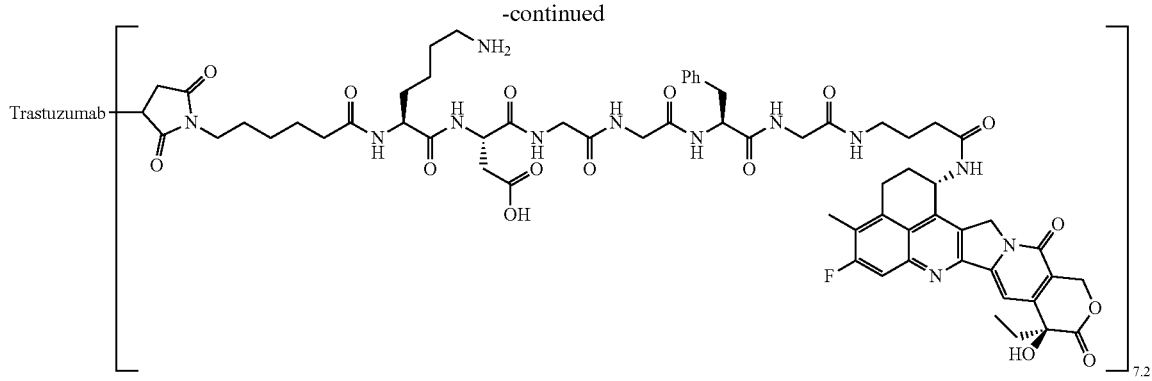

Process 1: Antibody-Drug Conjugate (110)

By using the trastuzumab produced in Reference Example 1 and the compound obtained in Process 3 of Example 109, the Example compound of interest was obtained in the same manner as Process 1 of Example 3.

Antibody concentration: 1.81 mg/mL, antibody yield: 10.8 mg (86%), and average number of conjugated drug molecules (n) per antibody molecule: 7.2.

Example 111 Antibody-Drug Conjugate (111)

[Formula 164]

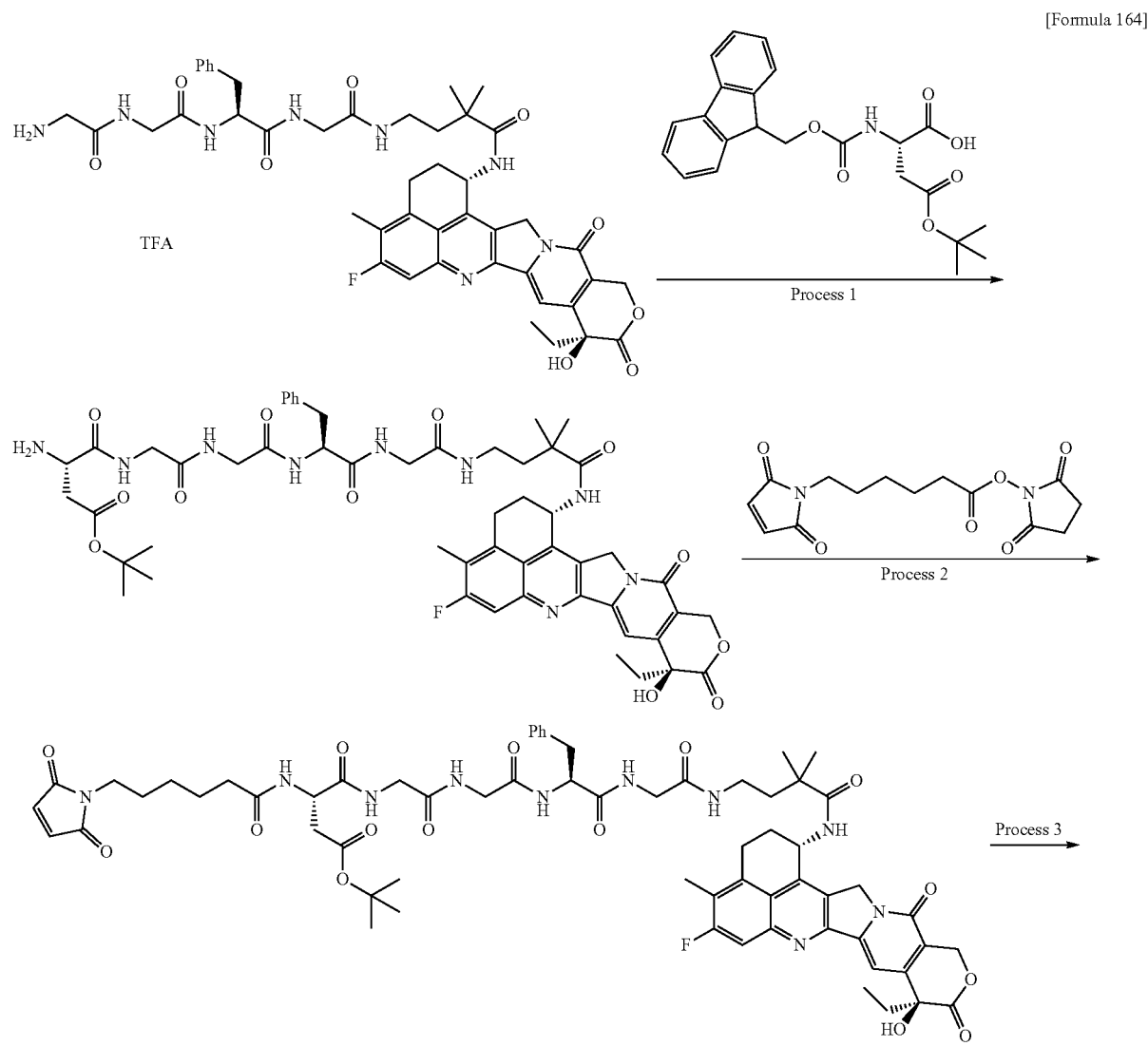

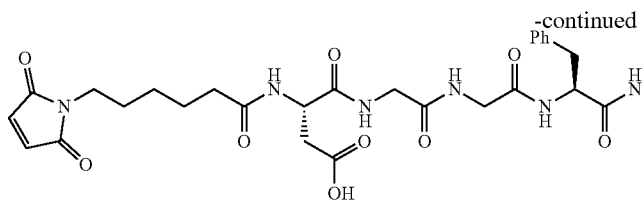
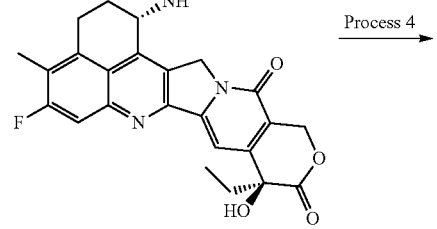

-continued

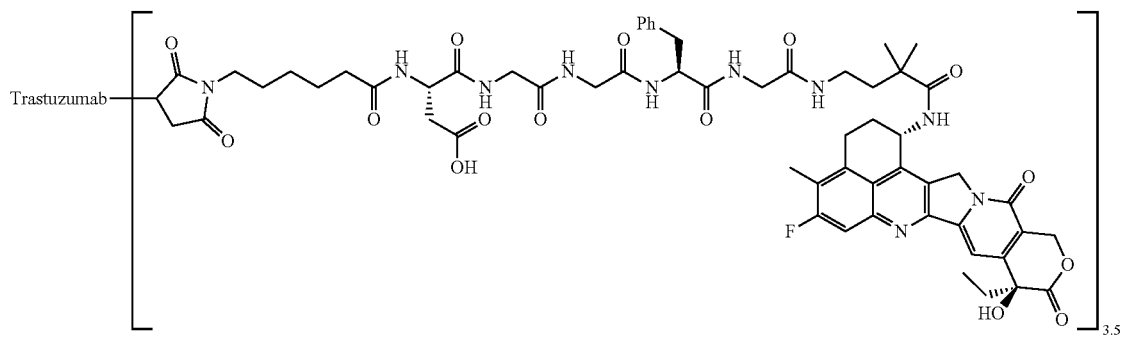

Process 1: tert-Butyl (3S,12S)-3-amino-12-benzyl-21-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-20,20-dimethyl-4,7,10,13,16,21-hexaoxo-5,8,11,14,17-pentaazaheneicosan-1-oate To a dichloromethane (2.5 mL) mixed solution of (2S)-4-tert-butoxy-2-{[(9H-fluoren-9-ylmethoxy)carbonyl]amino}-4-oxobutanoic acid (114 mg, 0.277 mmol), N-hydroxysuccinimide (31.9 mg, 0.277 mmol) and 1-(3-dimethylaminopropyl)-3-ethylcarbodiimide hydrochloride (66.3 mg, 0.346 mmol) were added and stirred at room temperature for 1 hour. The reaction solution was added dropwise to an N,N-dimethylformamide (2.0 mL) solution of the compound (200 mg, 0.231 mmol) obtained in Process 2 of Example 25, charged with triethylamine (0.0643 mL, 0.461 mmol), and stirred at room temperature for 23 hours. The reaction mixture was charged with an aqueous solution of 10% citric acid and extracted with chloroform. The organic phase obtained was washed with water-saturated sodium chloride aqueous solution (1:1) and a saturated sodium chloride aqueous solution in this order and dried over anhydrous sodium sulfate. After filtration, the solvent was removed under reduced pressure and the residues obtained were purified by silica gel column chromatography [dichloromethane -dichloromethane/methanol=9/1 (v/v)]. The compound obtained was dissolved in N,N-dimethylformamide (2.00 mL), charged with piperidine (0.140 mL, 1.42 mmol), and stirred for 1 hour. The solvent was removed under reduced pressure and the residues obtained were purified by silica gel column chromatography [chloroform -partitioned organic layer of chloroform:methanol:water=7:3:1 (v/v/v)] to yield the titled compound as a pale yellow solid (104 mg, 49%).

$^1$HNMR (500 MHz, DMSO-$d_6$) δ: 0.87 (3H, t, J=7.6 Hz), 1.20 (3H, s), 1.21 (3H, s), 1.37 (9H, s), 1.62-1.73 (2H, m), 1.81-1.91 (2H, m), 2.10-2.18 (2H, m), 2.34 (1H, dd, J=15.6, 7.8 Hz), 2.39 (3H, s), 2.57 (1H, dd, J=16.1, 4.9 Hz), 2.80 (1H, dd, J=13.9, 9.5 Hz), 2.99-3.07 (2H, m), 3.08-3.23 (3H, m), 3.27-3.37 (2H, m), 3.50 (1H, dd, J=7.3, 4.9 Hz), 3.56-3.78 (6H, m), 4.44-4.51 (1H, m), 5.12 (1H, d, J=18.6 Hz), 5.18 (1H, d, J=18.6 Hz), 5.42 (2H, s), 5.56-5.62 (1H, m), 6.52 (1H, s), 7.15-7.20 (1H, m), 7.21-7.27 (4H, m), 7.31 (1H, s), 7.70 (1H, t, J=5.6 Hz), 7.79 (1H, d, J=10.7 Hz), 8.05 (1H, t, J=5.6 Hz), 8.08 (1H, d, J=7.8 Hz), 8.14 (1H, d, J=8.8 Hz), 8.23 (1H, t, J=6.1 Hz), 8.28 (1H, brs). MS (ESI) m/z: 1038 (M+H)$^+$.

Process 2: tert-Butyl (3S,12S)-12-benzyl-3-{[6-(2,5-dioxo-2,5-dihydro-1H-pyrrol-1-yl)hexanoyl]amino}-21-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-20,20-dimethyl-4,7,10,13,16,21-hexaoxo-5,8,11,14,17-pentaazaheneicosan-1-oate The compound (104 mg, 0.100 mmol) obtained in Process 1 above was dissolved in N,N-dimethylformamide (1.00 mL), charged with N-succinimidyl 6-maleimidohexanoate (61.8 mg, 0.200 mmol), and stirred at room temperature for 17 hours. The solvent was removed under reduced pressure and the residues obtained were purified by silica gel column chromatography [dichloromethane-dichloromethane/methanol=17/3 (v/v)] to yield the titled compound as a light brown-white solid (114 mg, 92%).

MS(ESI) m/z: 1232 (M+H)$^+$.

Process 3: N-[6-(2,5-Dioxo-2,5-dihydro-1H-pyrrol-1-yl)hexanoyl]-L-α-aspartylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3,3-dimethyl-4-oxobutyl) glycinamide The compound (111 mg, 0.0901 mmol) obtained in Process 2 above was reacted in the same manner as Process 2 of Example 1 to yield the titled compound as a yellow solid (83.0 mg, 78%).

Process 4: Antibody-Drug Conjugate (111)

By using the trastuzumab produced in Reference Example 1 and the compound obtained in Process 3 above, the compound of interest was obtained in the same manner as Process 6 of Example 2.

Antibody concentration: 1.69 mg/mL, antibody yield: 10.1 mg (81%), and average number of conjugated drug molecules (n) per antibody molecule: 3.5.

Example 112 Antibody-Drug Conjugate (112)

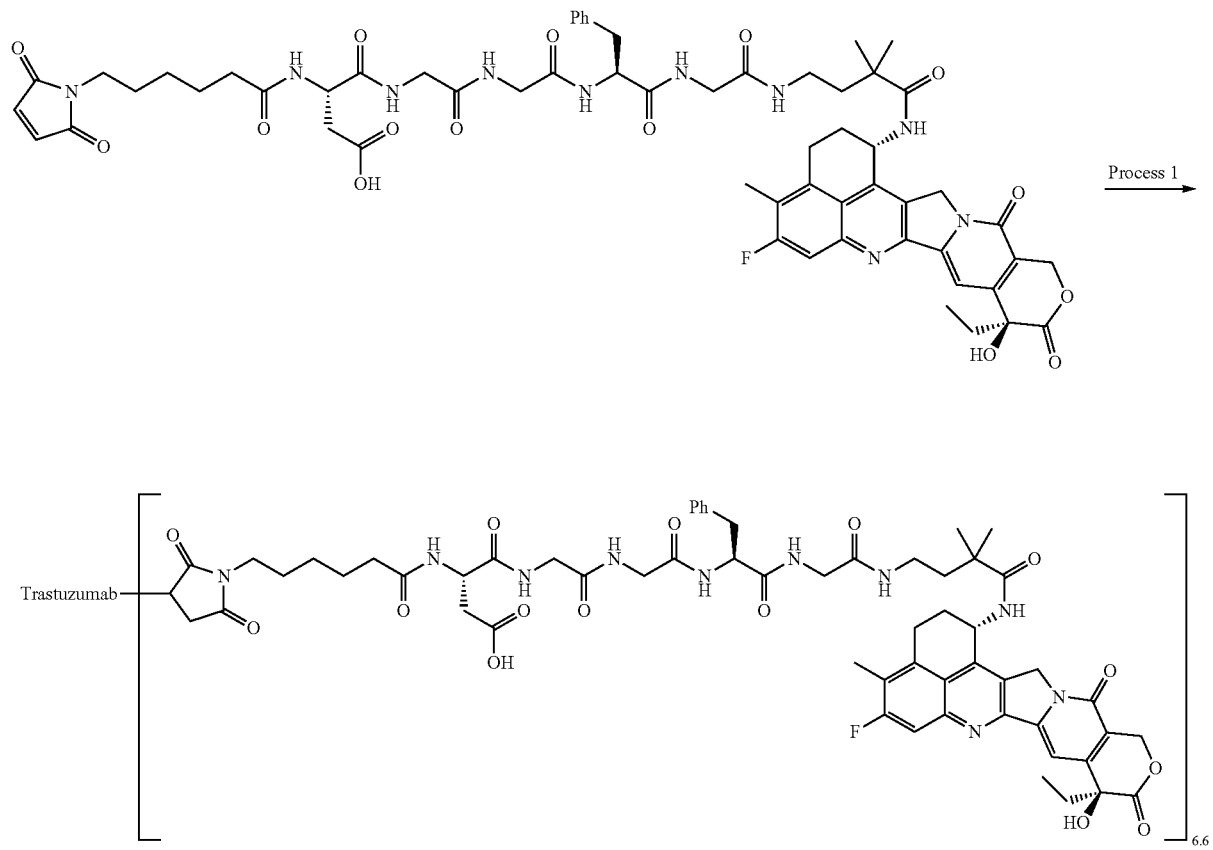

[Formula 165]

$^1$HNMR (400 MHz, DMSO-$d_6$) δ: 0.87 (3H, t, J=7.2 Hz), 1.12-1.25 (2H, m), 1.20 (3H, s), 1.21 (3H, s), 1.39-1.52 (4H, m), 1.63-1.72 (2H, m), 1.86 (2H, m, J=7.4 Hz), 2.08 (2H, t, J=7.4 Hz), 2.11-2.19 (2H, m), 2.39 (3H, s), 2.42-2.54 (1H, m), 2.68 (1H, dd, J=16.0, 5.5 Hz), 2.79 (1H, dd, J=13.5, 9.6 Hz), 2.96-3.08 (2H, m), 3.08-3.25 (3H, m), 3.35 (2H, t, J=7.0 Hz), 3.53-3.78 (6H, m), 4.43-4.52 (1H, m), 4.52-4.60 (1H, m), 5.11 (1H, d, J=19.2 Hz), 5.18 (1H, d, J=18.8 Hz), 5.42 (2H, s), 5.54-5.64 (1H, m), 6.54 (1H, brs), 6.99 (2H, s), 7.14-7.29 (5H, m), 7.31 (1H, s), 7.72 (1H, t, J=5.3 Hz), 7.79 (1H, d, J=10.9 Hz), 7.98 (1H, t, J=5.7 Hz), 8.05-8.12 (2H, m), 8.15 (2H, d, J=7.0 Hz), 8.25 (1H, t, J=5.5 Hz), 12.29 (1H, brs). MS (ESI) m/z: 1175 (M+H)$^+$.

Process 1: Antibody-Drug Conjugate (112)

By using the trastuzumab produced in Reference Example 1 and the compound obtained in Process 3 of Example 111, the compound of interest was obtained in the same manner as Process 1 of Example 3.

Antibody concentration: 1.84 mg/mL, antibody yield: 11.0 mg (88%), and average number of conjugated drug molecules (n) per antibody molecule: 6.6.

Example 113 Antibody-Drug Conjugate (113)
[Formula 166]
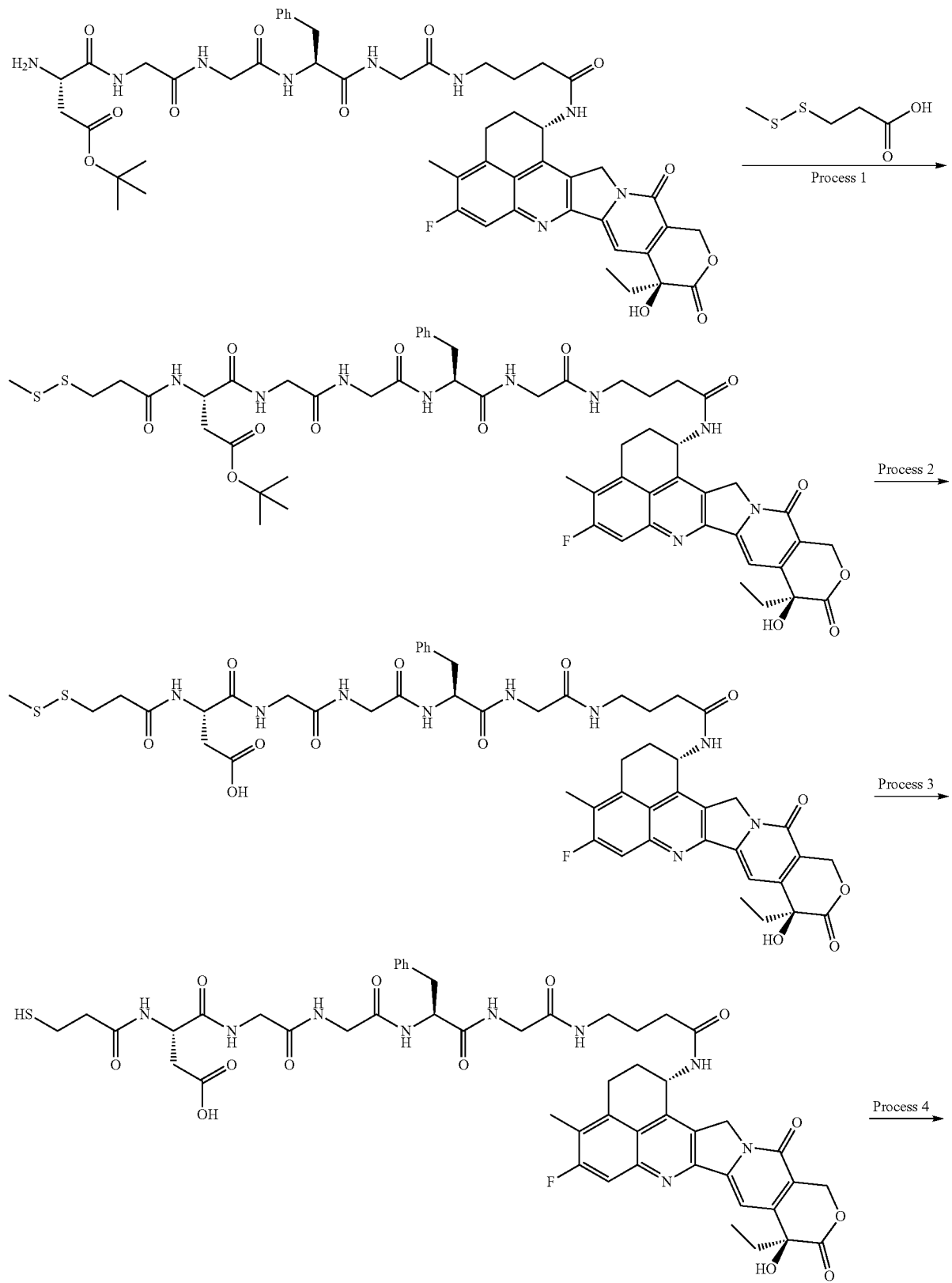

-continued

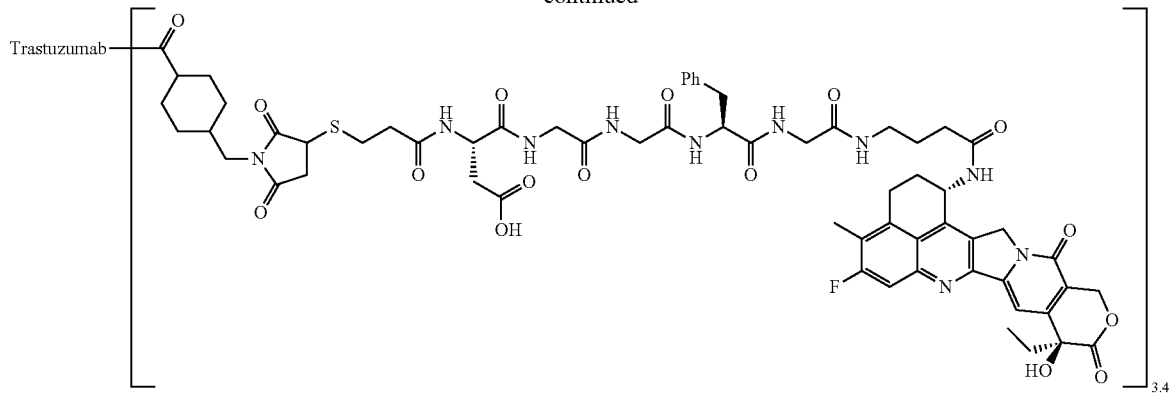

Process 1: tert-Butyl (3S,12S)-12-benzyl-21-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-{[3-(methyldisulfanyl)propanoyl]amino}-4,7,10,13,16,21-hexaoxo-5,8,11,14,17-pentaazaheneicosan-1-oate The compound (202 mg, 0.200 mmol) obtained in Process 1 of Example 107 was reacted in the same manner as Process 1 of Example 58 by using 4-(methyldithio)propanoic acid (36.5 mg, 0.240 mmol) instead of (2S)-4-tert-butoxy-2-{[(9H-fluoren-9-ylmethoxy)carbonyl]amino}-4-oxobutanoic acid to yield the titled compound as a pale yellow solid (153 mg, 67%).

$^1$H-NMR (400 MHz, DMSO-d$_6$) δ: 0.87 (3H, t, J=7.2 Hz), 1.36 (9H, s), 1.67-1.76 (2H, m), 1.79-1.92 (2H, m), 2.08-2.23 (4H, m), 2.36-2.57 (6H, m), 2.39 (3H, s), 2.69 (1H, dd, J=16.0, 5.5 Hz), 2.78 (1H, dd, J=13.3, 9.8 Hz), 2.88 (2H, t, J=7.2 Hz), 2.97-3.13 (3H, m), 3.14-3.21 (2H, m), 3.55-3.79 (6H, m), 4.42-4.51 (1H, m), 4.56-4.65 (1H, m), 5.20 (2H, q, J=18.5 Hz), 5.37-5.48 (2H, m), 5.52-5.62 (1H, m), 6.54 (1H, s), 7.13-7.28 (5H, m), 7.31 (1H, s), 7.68-7.74 (1H, m), 7.80 (1H, d, J=10.9 Hz), 7.95-8.01 (1H, m), 8.11 (1H, d, J=8.2 Hz), 8.14-8.20 (1H, m), 8.23-8.30 (1H, m), 8.34 (1H, d, J=8.2 Hz), 8.46 (1H, d, J=8.6 Hz).

Process 2: N-[3-(Methyldisulfanyl)propanoyl]-L-α-aspartylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (153 mg, 0.134 mmol) obtained in Process 1 above was reacted in the same manner as Process 2 of Example 1 to yield the titled compound as a pale yellow solid (103 mg, 71%).

$^1$H-NMR (400 MHz, DMSO-d$_6$) δ: 0.87 (3H, t, J=7.2 Hz), 1.67-1.77 (2H, m), 1.81-1.91 (2H, m), 2.09-2.21 (4H, m), 2.39 (3H, s), 2.58-2.35 (6H, m), 2.65-2.84 (2H, m), 2.88 (2H, t, J=7.2 Hz), 2.97-3.21 (5H, m), 3.58-3.76 (6H, m), 4.42-4.50 (1H, m), 4.53-4.62 (1H, m), 5.21 (2H, q, J=18.6 Hz), 5.42 (2H, s), 5.53-5.62 (1H, m), 6.53 (1H, s), 7.14-7.27 (5H, m), 7.31 (1H, s), 7.68-7.74 (1H, m), 7.80 (1H, d, J=11.0 Hz), 7.93-7.99 (1H, m), 8.07-8.17 (2H, m), 8.23-8.29 (1H, m), 8.35 (1H, d, J=7.8 Hz), 8.46 (1H, d, J=8.2 Hz), 12.33 (1H, brs).

Process 3: N-(3-Sulfanylpropanoyl)-L-α-aspartylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (103 mg, 0.0947 mmol) obtained in Process 2 above was dissolved in methanol (1.00 mL), ethyl acetate (0.500 mL), and a 0.05 N potassium phosphate buffer (0.500 mL), charged with tris(2-carboxyethyl)phosphine hydrochloride (81.4 mg, 0.284 mmol), and stirred at room temperature for 3 hours. The reaction solution was charged with water and extracted with chloroform. The organic layer obtained was dried over sodium sulfate and filtered. The solvent was removed under reduced pressure and the residues obtained were purified by silica gel column chromatography [chloroform-partitioned organic layer of chloroform:methanol:water=7:3:1 (v/v/v)] to yield the titled compound as a pale yellow solid (24.0 mg, 24%).

$^1$H-NMR (400 MHz, DMSO-d$_6$) δ: 0.87 (3H, t, J=7.4 Hz), 1.66-1.76 (2H, m), 1.80-1.91 (2H, m), 2.08-2.22 (4H, m), 2.37-2.69 (9H, m), 2.75-2.85 (1H, m), 2.99-3.17 (5H, m), 3.53-3.78 (6H, m), 4.39-4.49 (1H, m), 4.51-4.60 (1H, m), 5.20 (2H, q, J=18.6 Hz), 5.42 (2H, s), 5.53-5.61 (1H, m), 6.53 (1H, s), 7.14-7.27 (5H, m), 7.31 (1H, s), 7.69-7.75 (1H, m), 7.80 (1H, d, J=10.9 Hz), 7.92-8.21 (4H, m), 8.23-8.38 (2H, m), 8.45-8.52 (1H, m), 12.32 (1H, s).

MS (ESI) m/z: 1042 (M+H)$^+$.

Process 4: Antibody-Drug Conjugate (113)

SMCC derivatization of antibody: The trastuzumab produced in Reference Example 1 was prepared to have an antibody concentration of 20 mg/mL by replacing the medium with PBS6.5/EDTA by using the Common procedure C-2 and Common procedure B (as absorption coefficient at 280 nm, 1.37 mLmg$^{-1}$ cm$^{-1}$ was used). The solution (0.5 mL) was placed in a 1.5 mL tube, charged with a dimethyl sulfoxide solution (0.0125 mL; which corresponds to about 5.1 equivalents per antibody molecule) containing 27.6 mM of succinimidyl 4-(N-maleimidomethyl)cyclohexane-1-carboxylate (SMCC, Thermo Fisher Scientific Inc.) and dimethyl sulfoxide (0.0125 mL) at room temperature, and reacted at room temperature for 2 hours. This reaction solution was subjected to purification according to the Common procedure D-2 to yield 1.2 mL of a solution containing about 10 mg of the SMCC-derivatized antibody.

Conjugation between antibody and drug linker: After adding dimethyl sulfoxide (0.09 mL) and a dimethyl sulfoxide solution containing 10 mM of the compound obtained in Process 3 above (0.03 mL; which corresponds to about 5.8 equivalents per antibody molecule) to the above solution at room temperature, it was stirred by using a tube rotator for conjugating the drug linker to the antibody at room temperature for 16 hours.

Purification: The above solution was subjected to purification using the Common procedure D-1 (ABS was used as a buffer solution) to yield 6 mL of a solution containing the compound of interest.

Physicochemical characterization: By using the Common procedure B and Common procedure E, the following characteristic values were obtained.

Antibody concentration: 1.19 mg/mL, antibody yield: 7.1 mg (71%), and average number of conjugated drug molecules (n) per antibody molecule: 3.4.

Example 114 Antibody-Drug Conjugate (114)

(0.5 mL) was placed in a 1.5 mL tube, charged with a dimethyl sulfoxide solution (0.025 mL; which corresponds to about 10 equivalents per antibody molecule) containing 27.6 mM of SMCC at room temperature, and reacted at room temperature for 2 hours. This reaction solution was subjected to purification according to the Common procedure D-2 to yield 1.2 mL of a solution containing about 10 mg of the SMCC-derivatized antibody.

Conjugation between antibody and drug linker: After adding dimethyl sulfoxide (0.06 mL) and a dimethyl sulfoxide solution containing 10 mM of the compound obtained in Process 3 of Example 113 (0.06 mL; which corresponds to about 11.6 equivalents per antibody molecule) to the above solution at room temperature, it was stirred by using a tube rotator for conjugating the drug linker to the antibody at room temperature for 16 hours.

Purification: The above solution was subjected to purification using the Common procedure D (ABS was used as a

[Formula 167]

Process 1: Antibody-Drug Conjugate (114)

SMCC derivatization of antibody: The trastuzumab produced in Reference Example 1 was prepared to have an antibody concentration of 20 mg/mL by replacing the medium with PBS6.5/EDTA by using the Common procedure C-2 and Common procedure B (as absorption coefficient at 280 nm, 1.37 mLmg$^{-1}$ cm$^{-1}$ was used). The solution buffer solution) to yield 6 mL of a solution containing the compound of interest. The solution was further concentrated by the Common procedure A. After that, by using the Common procedure B and Common procedure E, the following characteristic values were obtained.

Antibody concentration: 1.96 mg/mL, antibody yield: 2.4 mg (24%), and average number of conjugated drug molecules (n) per antibody molecule: 5.0.

Example 115 Antibody-Drug Conjugate (115)
[Formula 168]
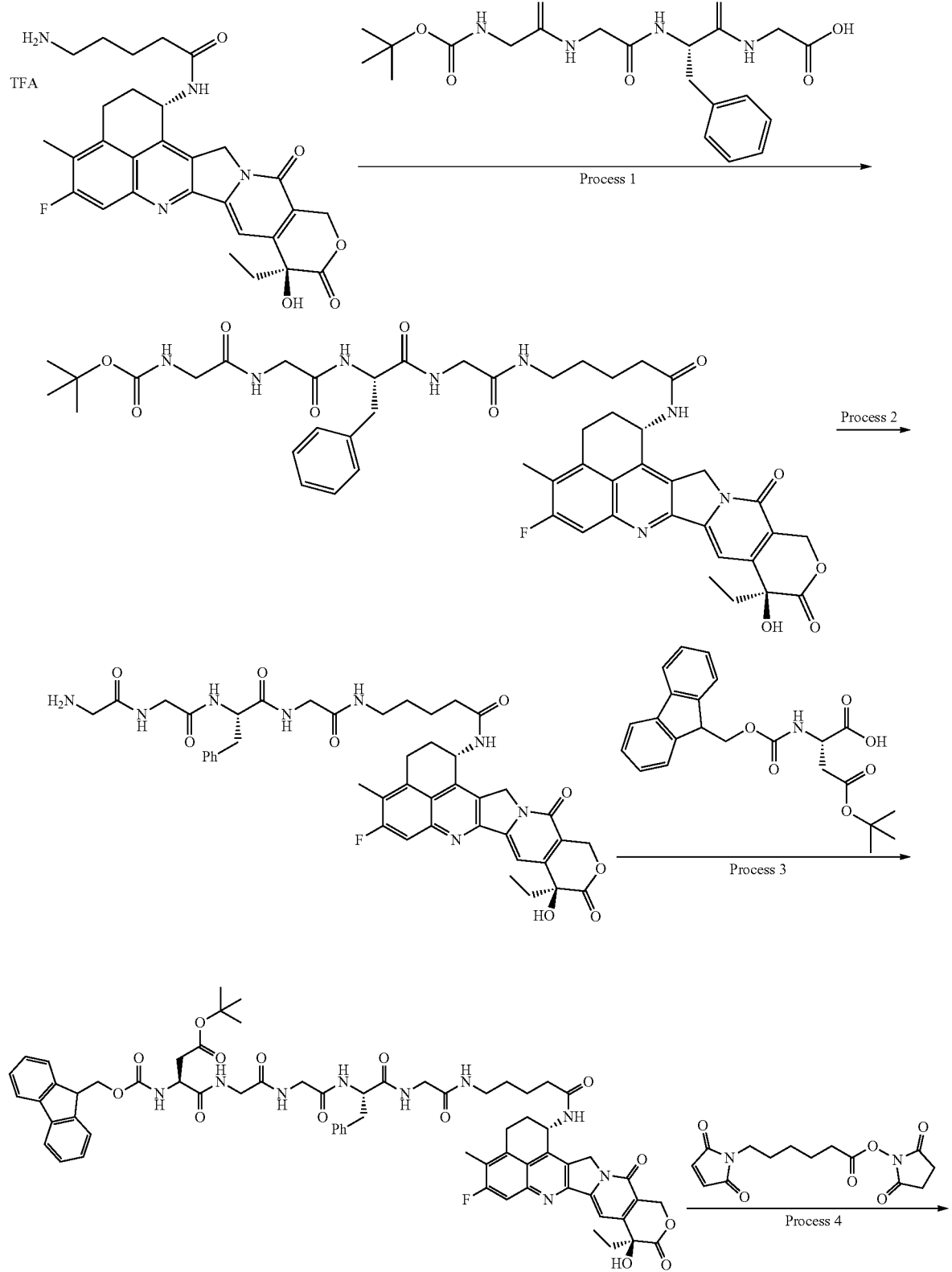

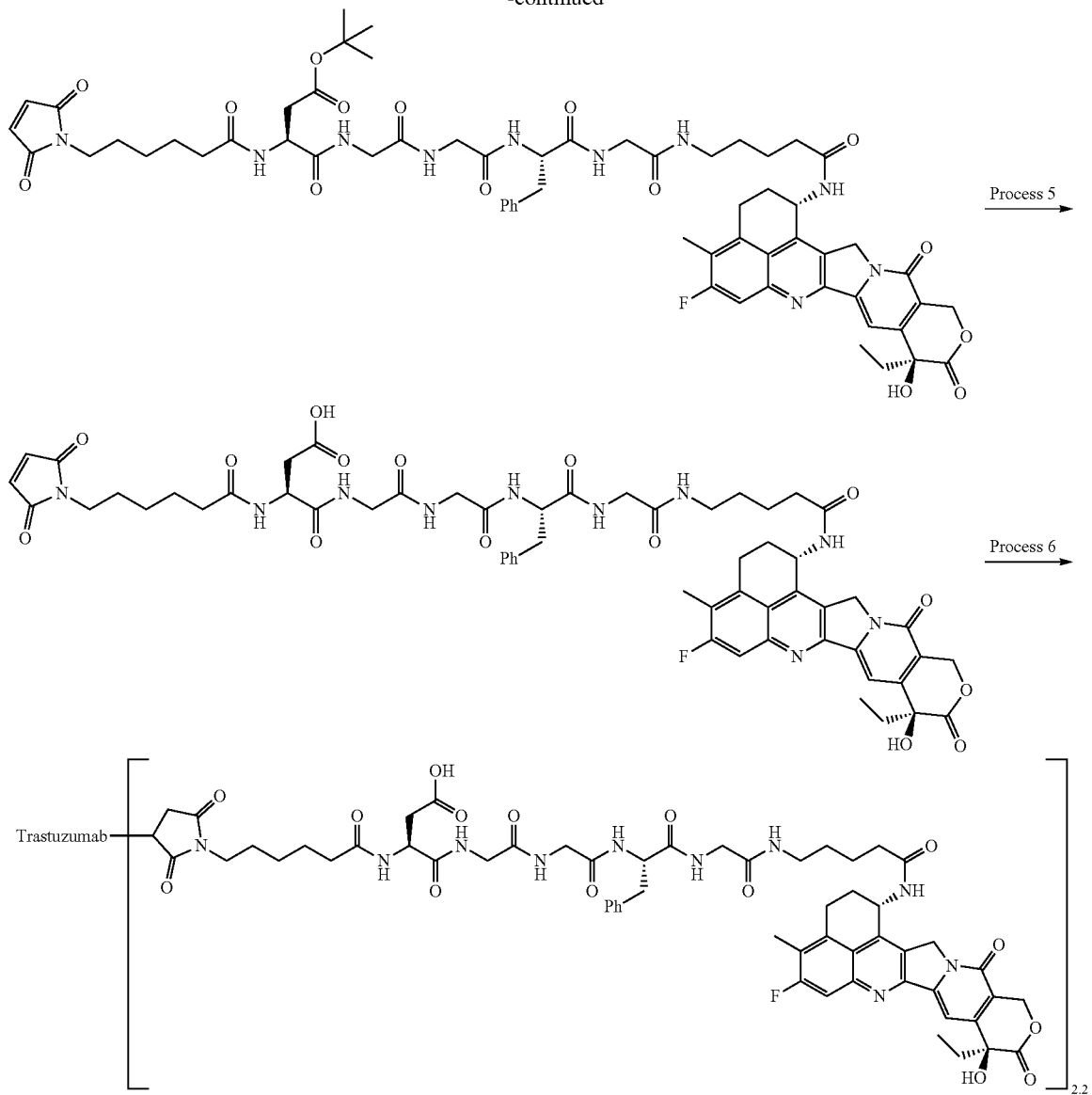

Process 1: N-(tert-Butoxycarbonyl)glycylglycyl-L-phenylalanyl-N-(5-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-5-oxopentyl)glycinamide The compound (348 mg, 0.537 mmol) obtained in Process 2 of Example 17 was reacted in the same manner as Process 1 of Example 2 to yield the titled compound as a pale yellow solid (429 mg, 84%). The compound was used for the next reaction without further purification.

Process 2: Glycylglycyl-L-phenylalanyl-N-(5-{[(1S,9S)-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl]amino}-5-oxopentyl)glycinamide The compound (427 mg, 0.448 mmol) obtained in Process 1 above was reacted in the same manner as Process 2 of Example 2 to yield trifluoroacetic acid salt of the titled compound as a yellow solid (430 mg, 99%).

$^1$H-NMR (400 MHz, DMSO-$d_6$) δ: 0.87 (3H, t, J=7.2 Hz), 1.38-1.49 (2H, m), 1.54-1.66 (2H, m), 1.86 (2H, tt, J=14.5, 7.0 Hz), 2.08-2.16 (2H, m), 2.19 (2H, t, J=7.2 Hz), 2.40 (3H, s), 2.76 (1H, dd, J=13.9, 10.0 Hz), 3.00-3.12 (3H, m), 3.14-3.21 (2H, m), 3.57 (2H, d, J=4.7 Hz), 3.60-3.75 (3H, m), 3.87 (1H, dd, J=16.8, 5.9 Hz), 4.55 (1H, td, J=9.0, 4.7 Hz), 5.16 (1H, d, J=18.8 Hz), 5.23 (1H, d, J=18.4 Hz), 5.44 (2H, s), 5.53-5.60 (1H, m), 6.55 (1H, s), 7.14-7.29 (5H, m), 7.32 (1H, s), 7.74 (1H, t, J=5.5 Hz), 7.81 (1H, d, J=10.9 Hz), 7.96 (3H, br.s.), 8.30-8.37 (1H, m), 8.44-8.53 (2H, m).

MS (ESI) m/z: 853 (M+H)$^+$.

Process 3: tert-Butyl (3S,12S)-12-benzyl-22-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-{[(9H-fluoren-9-ylmethoxy)carbonyl]amino}-4,7,10,13,16,22-hexaoxo-5,8,11,14,17-pentaazadocosan-1-oate The compound (140 mg, 0.164 mmol) obtained in Process 2 above was reacted in the same manner as Process 1 of Example 58 to yield the titled compound as a pale yellow solid (140 mg, 68%).
$^1$H-NMR (400 MHz, DMSO-$d_6$) δ: 0.86 (3H, t, J=7.2 Hz), 1.31-1.37 (9H, m), 1.39-1.47 (2H, m), 1.53-1.64 (2H, m), 1.85 (2H, tt, J=14.2, 7.1 Hz), 2.07-2.15 (2H, m), 2.18 (2H, t, J=7.2 Hz), 2.39 (3H, s), 2.40-2.54 (1H, m), 2.70 (1H, dd, J=16.8, 5.5 Hz), 2.79 (1H, dd, J=13.9, 9.6 Hz), 2.99-3.10 (3H, m), 3.12-3.20 (2H, m), 3.56-3.79 (6H, m), 4.17-4.35 (3H, m), 4.35-4.43 (1H, m), 4.44-4.52 (1H, m), 5.15 (1H, d, J=19.2 Hz), 5.21 (1H, d, J=19.2 Hz), 5.42 (2H, s), 5.51-5.60 (1H, m), 6.54 (1H, s), 7.12-7.19 (1H, m), 7.20-7.27 (4H, m), 7.27-7.34 (3H, m), 7.40 (2H, t, J=7.4 Hz), 7.62-7.73 (4H, m), 7.80 (1H, d, J=11.3 Hz), 7.87 (2H, d, J=7.4 Hz), 8.02 (1H, t, J=5.7 Hz), 8.11 (1H, d, J=7.8 Hz), 8.17 (1H, t, J=5.3 Hz), 8.25 (1H, t, J=5.7 Hz), 8.44 (1H, d, J=9.0 Hz).
MS (ESI) m/z: 1247 (M+H)$^+$.

Process 4: tert-Butyl (3S,12S)-12-benzyl-3-{[6-(2,5-dioxo-2,5-dihydro-1H-pyrrol-1-yl)hexanoyl]amino}-22-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,16,22-hexaoxo-5,8,11,14,17-pentaazadocosan-1-oate The compound (137 mg, 0.110 mmol) obtained in Process 3 above was reacted in the same manner as Process 2 of Example 58 to yield the titled compound (103 mg, 77%).
MS(ESI) m/z: 1218 (M+H)$^+$.

Process 5: N-[6-(2,5-Dioxo-2,5-dihydro-1H-pyrrol-1-yl)hexanoyl]-L-α-aspartylglycylglycyl-L-phenylalanyl-N-(5-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-5-oxopentyl)glycinamide The compound (88 mg, 0.072 mmol) obtained in Process 4 above was reacted in the same manner as Process 2 of Example 1 to yield the titled compound as a pale yellow solid (51 mg, 61%).

$^1$HNMR (400 MHz, DMSO-$d_6$) δ: 0.87 (3H, t, J=7.2 Hz), 1.12-1.22 (2H, m), 1.38-1.51 (6H, m), 1.54-1.64 (2H, m), 1.80-1.92 (2H, m), 2.03-2.15 (4H, m), 2.19 (2H, t, J=7.0 Hz), 2.31-2.56 (2H, m), 2.40 (3H, s), 2.60-2.71 (1H, m), 2.75-2.86 (1H, m), 2.98-3.10 (3H, m), 3.17 (2H, d, J=5.1 Hz), 3.26-3.40 (2H, m), 3.54-3.78 (6H, m), 4.39-4.49 (1H, m), 4.50-4.59 (1H, m), 5.16 (1H, d, J=19.6 Hz), 5.23 (1H, d, J=19.6 Hz), 5.43 (2H, s), 5.52-5.60 (1H, m), 6.53 (1H, s), 6.99 (2H, s), 7.14-7.28 (5H, m), 7.31 (1H, s), 7.62-7.72 (1H, m), 7.80 (1H, d, J=11.3 Hz), 7.95-8.19 (4H, m), 8.24-8.36 (1H, m), 8.45 (1H, d, J=9.0 Hz). MS (ESI) m/z: 1161 (M+H)$^+$.

Process 4: Antibody-Drug Conjugate (115)

Reduction of the antibody: The trastuzumab produced in Reference Example 1 was prepared to have an antibody concentration of 10 mg/mL with PBS6.0/EDTA by using the Common procedure B (as absorption coefficient at 280 nm, 1.37 mLmg$^{-1}$ cm$^{-1}$ was used) and Common procedure C-1. The solution (1.0 mL) was collected into a 2 mL tube and charged with an aqueous solution of 10 mM TCEP (0.0155 mL; 2.3 equivalents per antibody molecule) and an aqueous solution of 1 M dipotassium hydrogenphosphate (0.050 mL). After confirming that the solution had a pH of 7.4±0.1, the disulfide bond at the hinge part in the antibody was reduced by incubating at 37° C. for 1 hour.

Conjugation between antibody and drug linker: After incubating the above solution for 10 minutes at 22° C., a DMSO solution (0.0311 mL; 4.6 equivalents per antibody molecule) containing 10 mM of the compound obtained in Process 3 above was added thereto and incubated for conjugating the drug linker to the antibody at 22° C. for 40 minutes. Next, an aqueous solution (0.00622 mL; 9.2 equivalents per antibody molecule) of 100 mM NAC was added thereto and incubated at 22° C. to terminate the reaction of the drug linker for another 20 minutes.

Purification: The above solution was subjected to purification using the Common procedure D-1 (PBS6.0 was used as buffer solution) to yield 6 mL of a solution containing the compound of interest.

Physicochemical characterization: By using the Common procedure B, Common procedure E, and Common procedure F, the following characteristic values were obtained. Antibody concentration: 0.99 mg/mL, antibody yield: 5.94 mg (59%), and average number of conjugated drug molecules (n) per antibody molecule: 2.2.

Example 116 Antibody-Drug Conjugate (116)

[Formula 169]

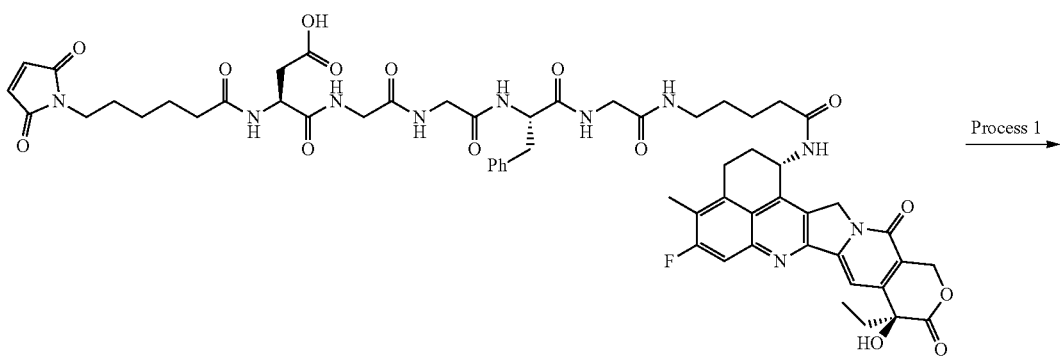

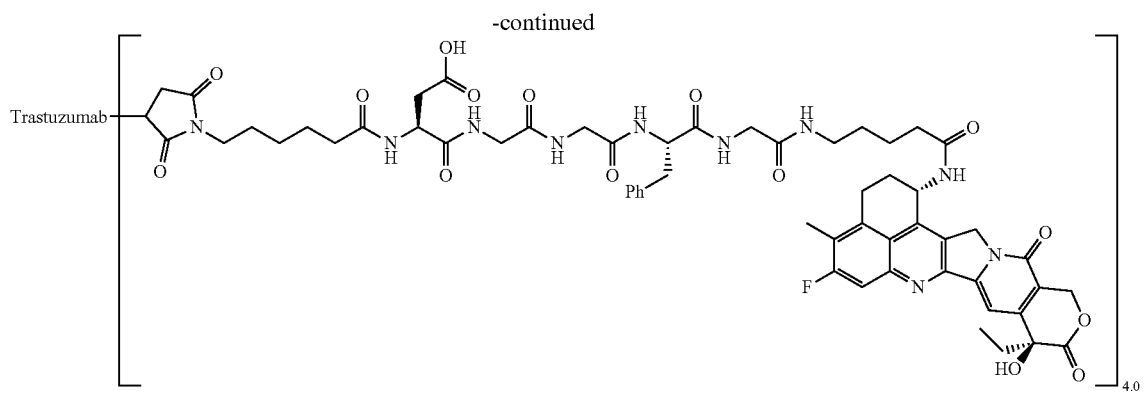

Process 1: Antibody-Drug Conjugate (116)

Reduction of the antibody: The trastuzumab produced in Reference Example 1 was prepared to have an antibody concentration of 10 mg/mL with PBS6.0/EDTA by using the Common procedure B (as absorption coefficient at 280 nm, 1.37 mLmg$^{-1}$ cm$^{-1}$ was used) and Common procedure C-1. The solution (1.0 mL) was collected into a 2 mL tube and charged with an aqueous solution of 10 mM TCEP (0.0311 mL; 4.6 equivalents per antibody molecule) and an aqueous solution of 1 M dipotassium hydrogenphosphate (0.050 mL). After confirming that the solution had a pH of 7.4±0.1, the disulfide bond at the hinge part in the antibody was reduced by incubating at 37° C. for 1 hour.

Conjugation between antibody and drug linker: After incubating the above solution for 10 minutes at 22° C., a DMSO solution (0.0622 mL; 9.2 equivalents per antibody molecule) containing 10 mM of the compound obtained in Process 3 of Example 115 was added thereto and incubated for conjugating the drug linker to the antibody at 22° C. for 40 minutes. Next, an aqueous solution (0.0124 mL; 18.4 equivalents per antibody molecule) of 100 mM NAC was added thereto and incubated at 22° C. to terminate the reaction of the drug linker for another 20 minutes.

Purification: The above solution was subjected to purification using the Common procedure D-1 (PBS6.0 was used as buffer solution) to yield 6 mL of a solution containing the compound of interest.

Physicochemical characterization: By using the Common procedure B, Common procedure E, and Common procedure F, the following characteristic values were obtained. Antibody concentration: 0.95 mg/mL, antibody yield: 5.70 mg (57%), and average number of conjugated drug molecules (n) per antibody molecule: 4.0.

Example 117 Antibody-Drug Conjugate (117)

[Formula 170]

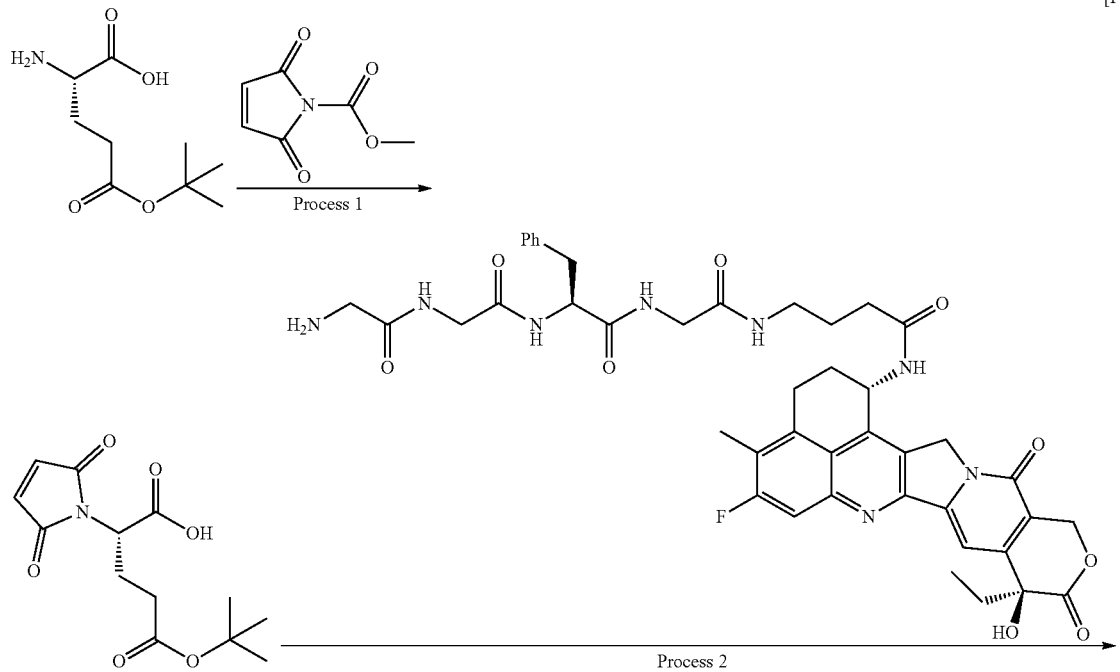

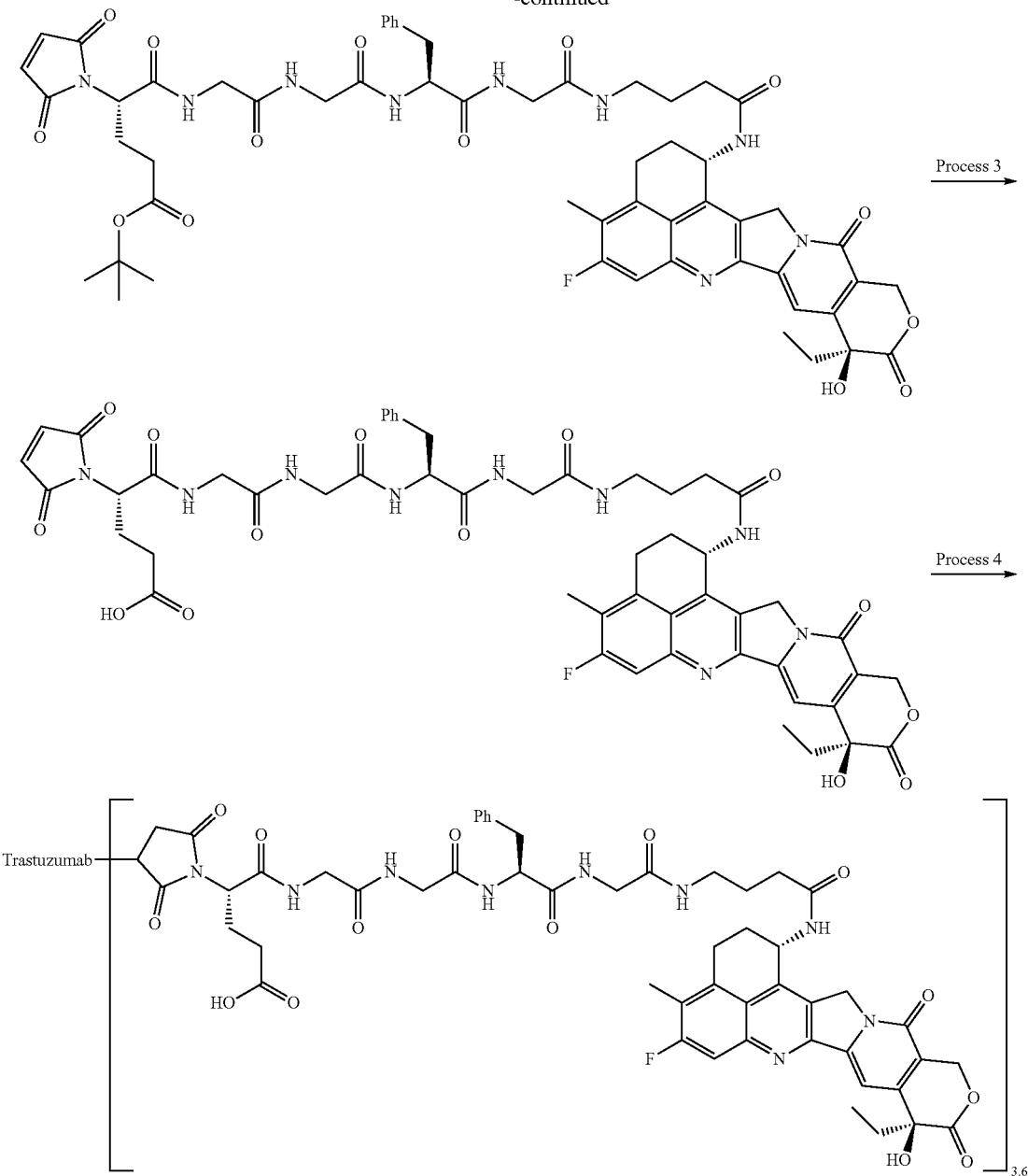

Process 1: (2S)-5-tert-Butoxy-2-(2,5-dioxo-2,5-dihydro-1H-pyrrol-1-yl)-5-oxopentanoic acid L-Glutamic acid 5-tert-butyl (1.02 g, 5.00 mmol) was dissolved in a saturated sodium hydrogen carbonate aqueous solution (20.0 mL), charged with N-methoxycarbonylmaleimide (0.775 g, 5.00 mmol) at 0° C., stirred at 0° C. for 30 minutes, and then stirred at room temperature for 1 hour. The reaction solution was rendered acidic by the addition of 5 N hydrochloric acid at 0° C. and then extracted with ethyl acetate. The organic layer obtained was dried over sodium sulfate and filtered. The solvent was removed under reduced pressure to yield a crude product. The crude product obtained was used for the next reaction without purification.

Process 2: N-[(2S)-5-tert-Butoxy-2-(2,5-dioxo-2,5-dihydro-1H-pyrrol-1-yl)-5-oxopentanoyl]glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (85.0 mg, 0.300 mmol) obtained in Process 1 above was reacted in the same manner as Process 1 of Example 1 by using the compound (168 mg, 0.200 mmol) obtained in Process 2 of Example 2 instead of methanesulfonic acid salt of exatecan to yield the titled compound as a pale yellow solid (113 mg, 51%).

$^1$H-NMR (400 MHz, DMSO-d$_6$) δ: 0.87 (3H, t, J=7.2 Hz), 1.35 (9H, s), 1.67-1.76 (2H, m), 1.79-1.93 (2H, m), 2.03-

2.29 (8H, m), 2.40 (3H, s), 2.74-2.82 (1H, m), 2.97-3.13 (3H, m), 3.14-3.22 (2H, m), 3.50-3.80 (6H, m), 4.41-4.49 (1H, m), 4.50-4.57 (1H, m), 5.20 (2H, q, J=18.6 Hz), 5.42 (2H, s), 5.54-5.61 (1H, m), 6.53 (1H, s), 7.04 (2H, s), 7.14-7.27 (5H, m), 7.31 (1H, s), 7.66-7.72 (1H, m), 7.80 (1H, d, J=11.0 Hz), 7.98-8.03 (1H, m), 8.11 (1H, d, J=7.8 Hz), 8.22-8.27 (1H, m), 8.31-8.37 (1H, m), 8.45 (1H, d, J=8.6 Hz).

Process 3: N-[(2S)-4-Carboxy-2-(2,5-dioxo-2,5-dihydro-1H-pyrrol-1-yl)butanoyl]glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (113 mg, 0.102 mmol) obtained in Process 2 above was reacted in the same manner as Process 2 of Example 1 to yield the titled compound as a pale yellow solid (81.0 mg, 76%).

$^1$H-NMR (400 MHz, DMSO-$d_6$) δ: 0.87 (3H, t, J=7.2 Hz), 1.67-1.75 (2H, m), 1.80-1.91 (2H, m), 2.07-2.35 (8H, m), 2.39 (3H, s), 2.77 (1H, dd, J=13.7, 9.8 Hz), 2.96-3.13 (3H, m), 3.13-3.22 (2H, m), 3.38-3.80 (6H, m), 4.42-4.50 (1H, m), 4.53-4.60 (1H, m), 5.20 (2H, q, J=18.6 Hz), 5.42 (2H, s), 5.54-5.60 (1H, m), 6.54 (1H, brs), 7.04 (2H, s), 7.17-7.26 (5H, m), 7.31 (1H, s), 7.70 (1H, t, J=5.3 Hz), 7.80 (1H, d, J=10.9 Hz), 8.01 (1H, t, J=5.5 Hz), 8.12 (1H, d, J=8.2 Hz), 8.26 (1H, t, J=5.9 Hz), 8.32-8.38 (1H, m), 8.46 (1H, d, J=8.6 Hz).

MS (ESI) m/z: 1048 (M+H)$^+$.

Process 4: Antibody-Drug Conjugate (117)

By using the trastuzumab produced in Reference Example 1 and the compound obtained in Process 3 above, the compound of interest was obtained in the same manner as Process 6 of Example 2.

Antibody concentration: 1.38 mg/mL, antibody yield: 8.3 mg (66%), and average number of conjugated drug molecules (n) per antibody molecule: 3.6.

Example 118 Antibody-Drug Conjugate (118)

[Formula 171]

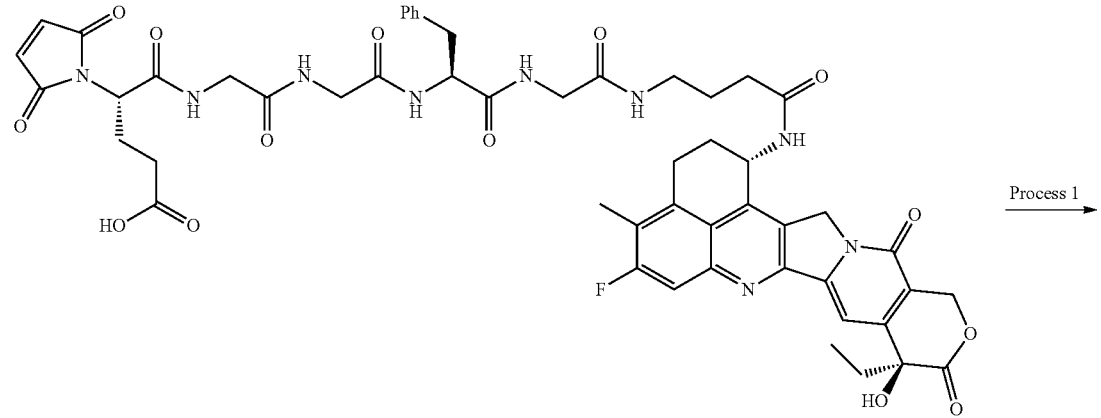

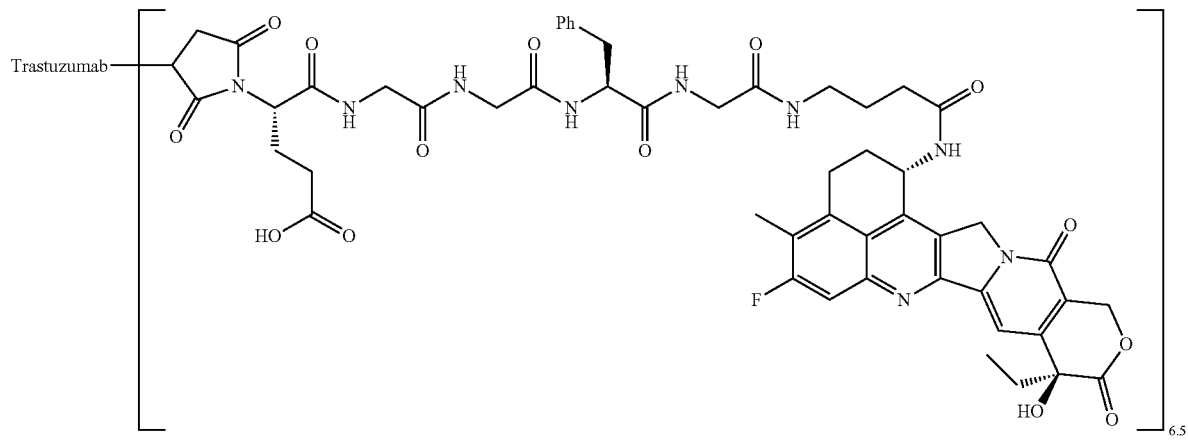

Process 1: Antibody-Drug Conjugate (118)

By using the trastuzumab produced in Reference Example 1 and the compound obtained in Process 3 of Example 117, the compound of interest was obtained in the same manner as Process 1 of Example 3.

Antibody concentration: 1.52 mg/mL, antibody yield: 9.1 mg (73%), and average number of conjugated drug molecules (n) per antibody molecule: 6.5.

Example 119 Antibody-Drug Conjugate (119)

[Formula 172]

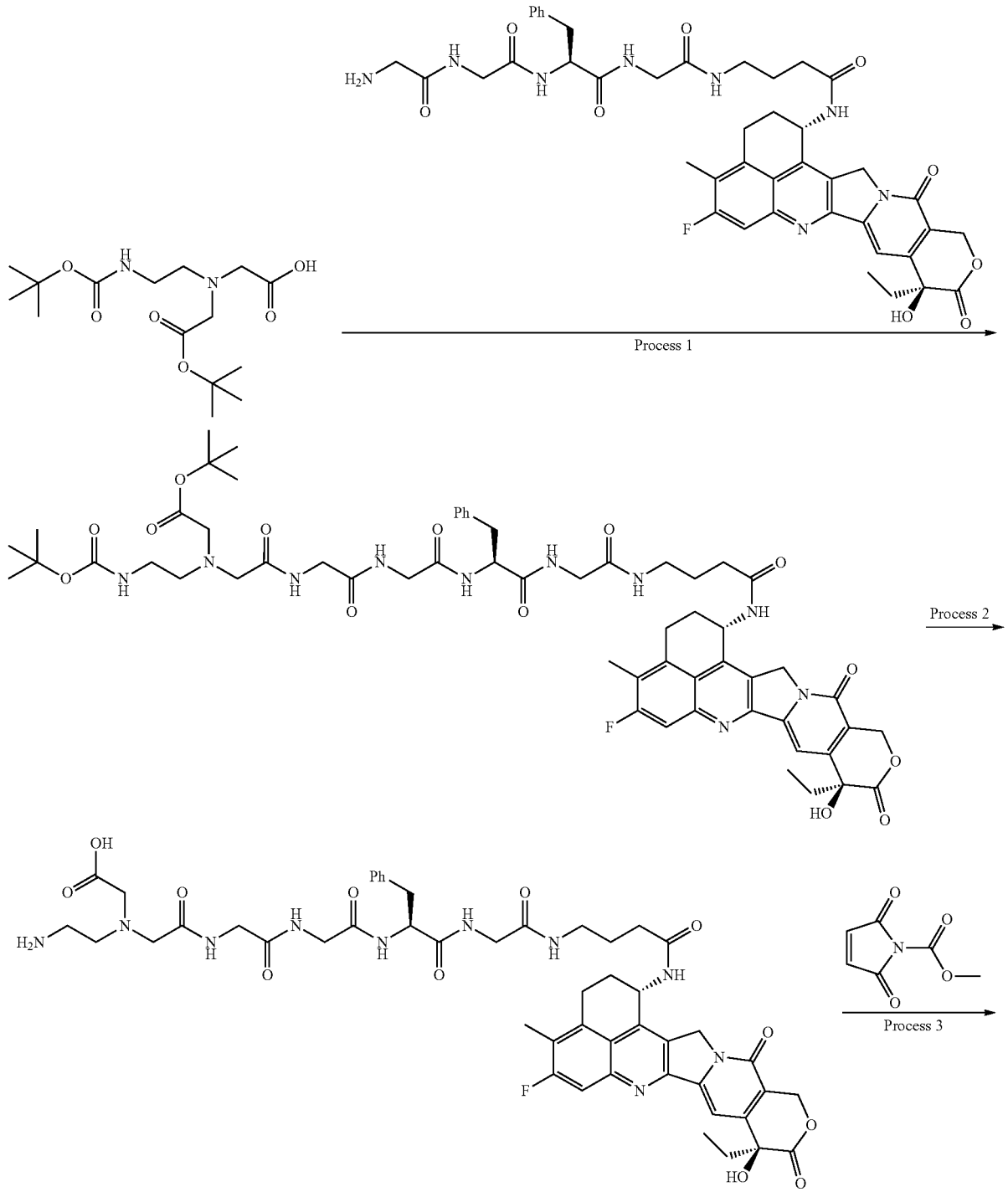

-continued

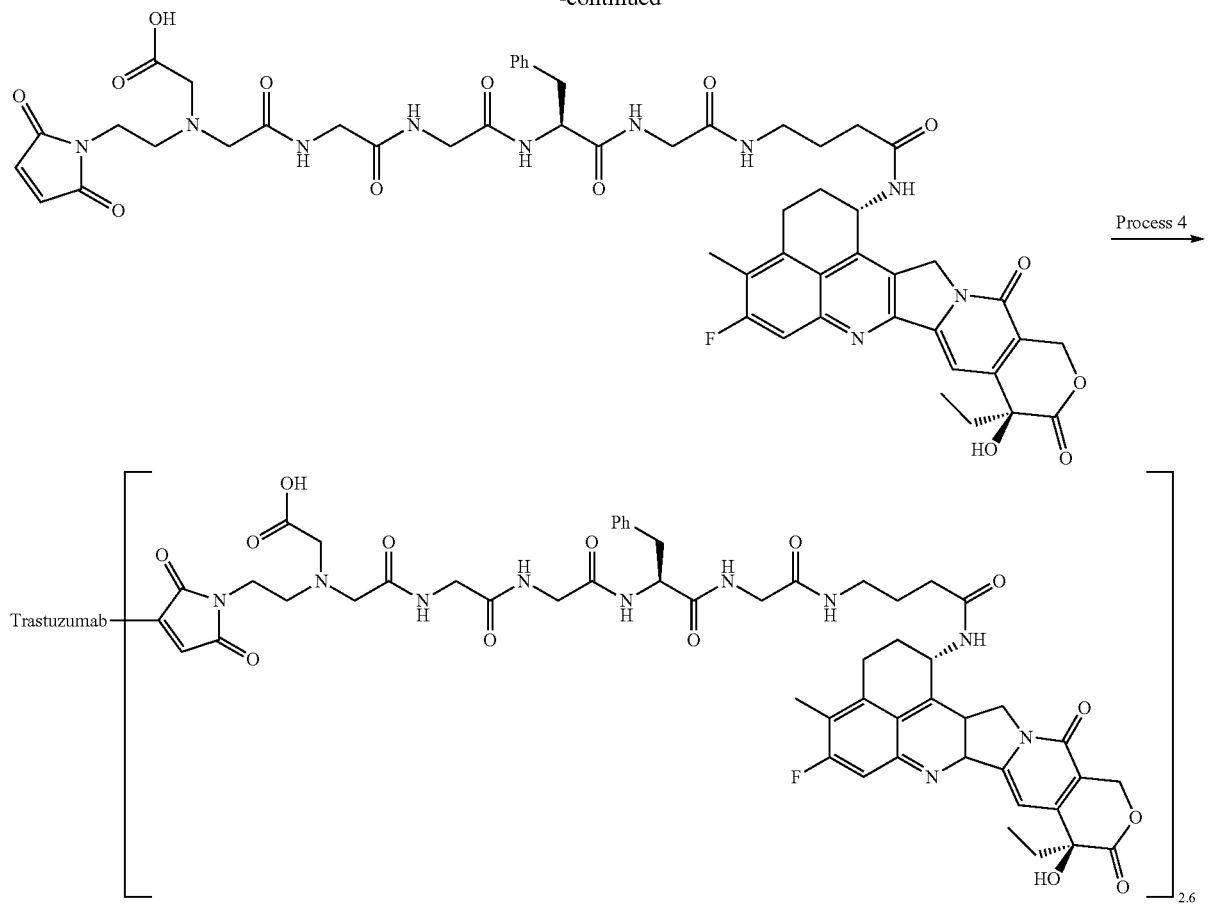

Process 1: N-{2-[(tert-Butoxycarbonyl)amino]ethyl}-N-(2-tert-butoxy-2-oxoethyl)glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (0.250 g, 0.300 mmol) obtained in Process 2 of Example 40 was used instead of (2S)-4-tert-butoxy-2-{[(9H-fluoren-9-ylmethoxy)carbonyl]amino}-4-oxobutanoic acid and reacted in the same manner as Process 1 of Example 58 to yield the titled compound as a pale yellow solid (59.9 mg, 17%).

$^1$H-NMR (400 MHz, DMSO-$d_6$) δ: 0.87 (3H, t, J=7.2 Hz), 1.35 (9H, s), 1.40 (9H, s), 1.68-1.75 (2H, m), 1.80-1.91 (2H, m), 2.16-2.31 (4H, m), 2.40 (3H, s), 2.80 (1H, d, J=7.0 Hz), 2.95-2.98 (3H, m), 3.19-3.24 (6H, m), 3.40 (4H, s), 3.62-3.72 (6H, m), 4.44-4.48 (1H, m), 5.16 (1H, d, J=19.2 Hz), 5.25 (1H, d, J=19.2 Hz), 5.42 (2H, s), 5.56-5.59 (1H, m), 6.54 (1H, s), 6.79 (1H, t, J=6.8 Hz), 7.20-7.22 (5H, m), 7.31 (1H, s), 7.72 (1H, t, J=6.5 Hz), 7.80 (1H, d, J=10.6 Hz), 8.09 (2H, t, J=5.7 Hz), 8.15 (1H, d, J=7.8 Hz), 8.27 (1H, t, J=5.7 Hz), 8.47 (1H, d, J=7.4 Hz).

MS (APCI) m/z: 1153 (M+H)$^+$.

Process 2: N-(2-Aminoethyl)-N-(carboxymethyl)glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (50.6 mg, 43.8 μmol) obtained in Process 1 above was reacted in the same manner as Process 2 of Example 1 to yield the titled compound as a pale yellow solid (29.5 mg, 67%).

$^1$H-NMR (400 MHz, DMSO-$d_6$) δ: 0.87 (3H, t, J=7.6 Hz), 1.71-1.74 (2H, m), 1.85-1.87 (2H, m), 2.10-2.20 (4H, m), 2.39 (3H, s), 2.66-2.68 (1H, m), 2.77-2.80 (7H, m), 3.15-3.18 (4H, m), 3.50 (2H, s), 3.60 (4H, s), 3.74-3.76 (2H, m), 4.37-4.39 (1H, m), 5.17 (1H, d, J=19.2 Hz), 5.25 (1H, d, J=19.2 Hz), 5.42 (2H, s), 5.57-5.59 (1H, m), 6.55 (1H, s), 7.23-7.24 (6H, m), 7.31 (1H, s), 7.76-7.80 (4H, m), 8.10-8.13 (2H, m), 8.39-8.41 (1H, m), 8.57-8.60 (2H, m).

MS (APCI) m/z: 997 (M+H)$^+$.

Process 3: N-(Carboxymethyl)-N-[2-(2,5-dioxo-2,5-dihydro-1H-pyrrol-1-yl)ethyl]glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide Under ice cooling, the compound (76.0 mg, 76.2 μmol) obtained in Process 2 above was dissolved in a saturated sodium hydrogen carbonate aqueous solution (2.00 mL) and stirred for 30 minutes. Under ice cooling, after adding methyl 2,5-dioxopyrrole-1-carboxylate (13.0 mg, 83.9 µmol), it was stirred for 20 minutes. It was further stirred at room temperature for 2 hours. After adding an aqueous solution of 10% citric acid, it was stirred overnight. The reaction solution was extracted with chloroform and the organic layer obtained was dried over sodium sulfate and filtered. The solvent in the filtrate was removed under reduced pressure. The residues obtained were purified by silica gel column chromatography [chloroform-partitioned organic layer of chloroform:methanol:water=7:3:1 (v/v/v)] to yield the titled compound as a pale yellow solid (18.1 mg, 22%).

Process 4: Antibody-Drug Conjugate (119)

By using the trastuzumab produced in Reference Example 1 and the compound obtained in Process 3 above, the compound of interest was obtained in the same manner as Process 6 of Example 2. The solution was further concentrated by the Common procedure A. After that, by using the Common procedure B and Common procedure E, the following characteristic values were obtained.
Antibody concentration: 10.02 mg/mL, antibody yield: 7.0 mg (56%), and average number of conjugated drug molecules (n) per antibody molecule: 2.6.

Example 120 Antibody-Drug Conjugate (120)

[Formula 173]

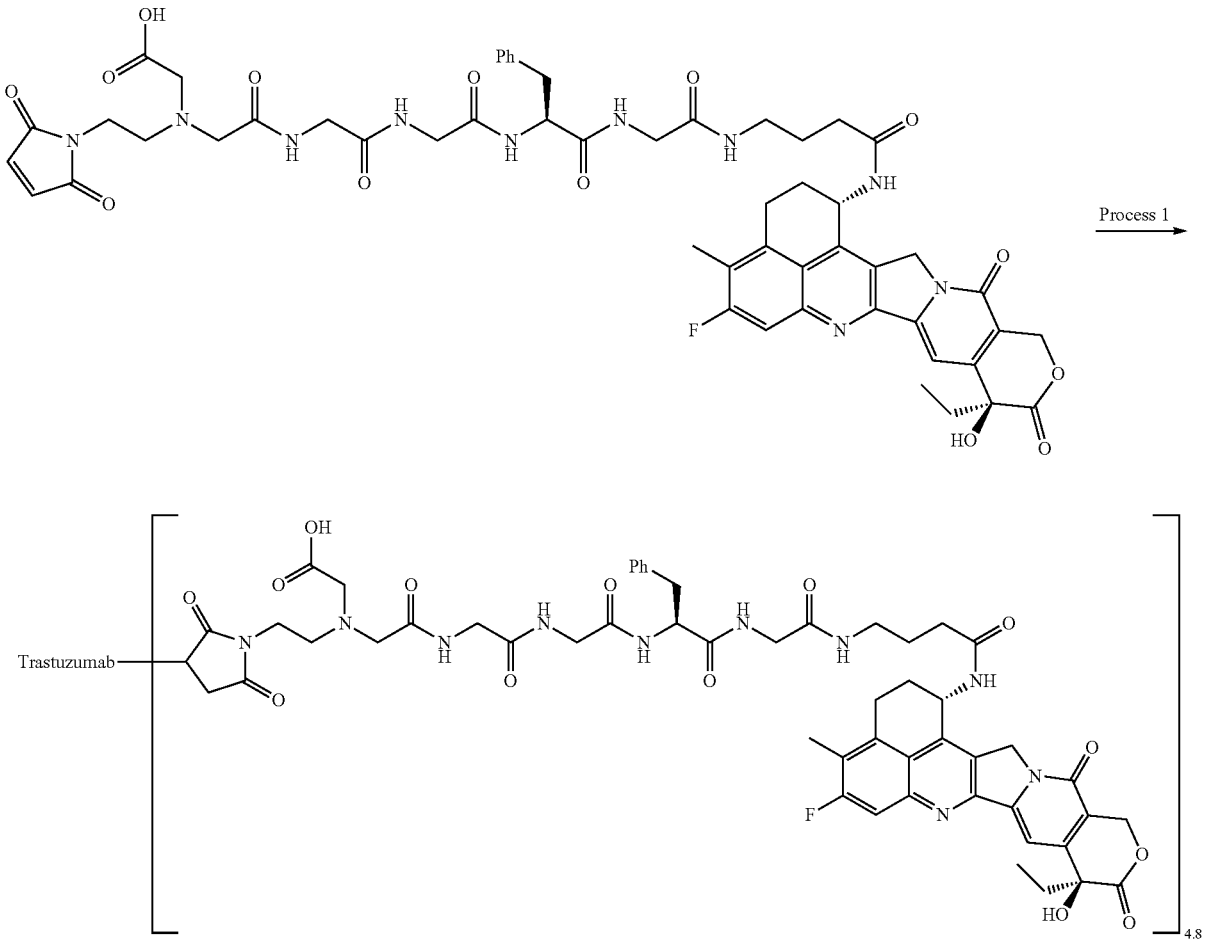

Process 1: Antibody-Drug Conjugate (120)

By using the trastuzumab produced in Reference Example 1 and the compound obtained in Process 3 of Example 119, the compound of interest was obtained in the same manner as Process 1 of Example 3. The solution was further concentrated by the Common procedure A. After that, by using the Common procedure B and Common procedure E, the following characteristic values were obtained.
Antibody concentration: 10.36 mg/mL, antibody yield: 7.3 mg (58%), and average number of conjugated drug molecules (n) per antibody molecule: 4.8.

$^1$H-NMR (400 MHz, DMSO-$d_6$) δ: 0.87 (3H, t, J=8.5 Hz), 1.71-1.73 (2H, m), 1.84-1.87 (2H, m), 2.12-2.19 (4H, m), 2.36 (3H, s), 2.65-2.68 (1H, m), 2.89-3.15 (9H, m), 3.48-3.66 (10H, m), 4.35-4.37 (1H, m), 5.16 (1H, d, J=18.4 Hz), 5.24 (1H, d, J=18.8 Hz), 5.42 (2H, s), 5.55-5.58 (1H, m), 6.53 (1H, s), 6.95 (2H, s), 7.19-7.21 (6H, m), 7.30 (1H, s), 7.77-7.80 (2H, m), 8.19 (1H, s), 8.32 (1H, s), 8.49 (1H, s), 8.62 (2H, s).

MS (APCI) m/z: 1077 (M+H)$^+$.

Example 121 Antibody-Drug Conjugate (121)

[Formula 174]
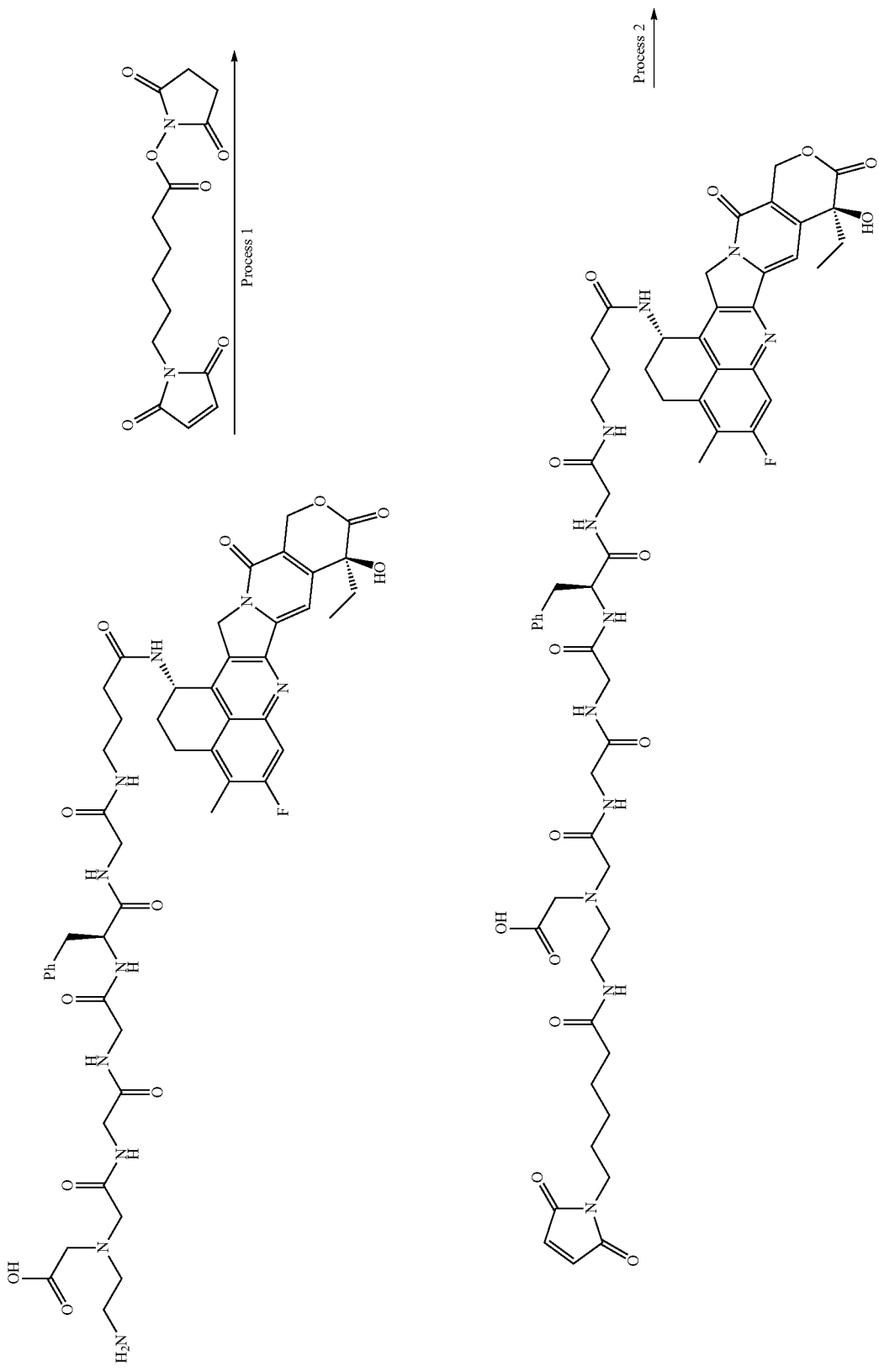

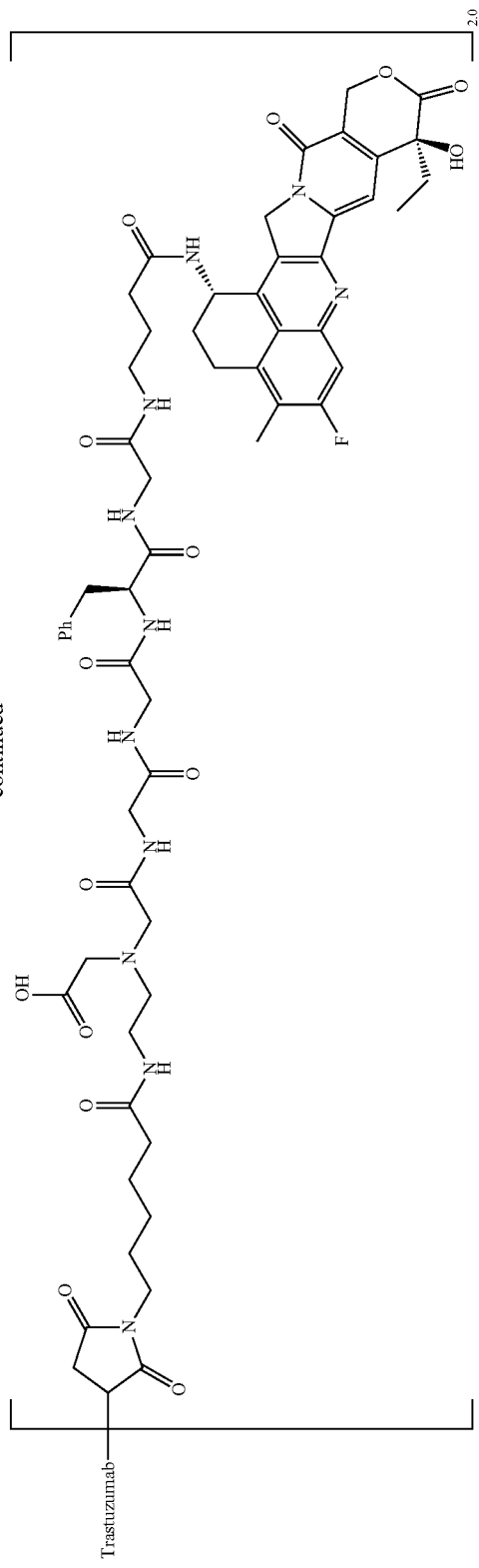

Process 1: N-(Carboxymethyl)-N-(2-{[6-(2,5-dioxo-2,5-dihydro-1H-pyrrol-1-yl) hexanoyl]amino}ethyl) glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl) glycinamide The compound (25.8 mg, 25.9 μmol) obtained in Process 2 of Example 119 was dissolved in N,N-dimethylformamide (1.50 mL). After adding N-succinimidyl 6-maleimidohexanoate (12.0 mg, 38.9 μmol), it was stirred for 1 day. The solvent was removed under reduced pressure and the residues obtained were purified by silica gel column chromatography [chloroform -partitioned organic layer of chloroform:methanol:water=7:3:1 (v/v/v)] to yield the titled compound as a pale yellow solid (6.07 mg, 20%).

$^1$H-NMR (400 MHz, DMSO-$d_6$) δ: 0.87 (3H, t, J=6.7 Hz), 1.18 (4H, dd, J=25.4, 19.2 Hz), 1.41-1.43 (4H, m), 1.73 (2H, d, J=4.3 Hz), 1.82-1.90 (2H, m), 1.98 (2H, s), 2.12-2.19 (4H, m), 2.38 (3H, s), 3.08-3.15 (10H, m), 3.39-3.41 (4H, m), 3.60-3.71 (8H, m), 4.32-4.35 (1H, m), 5.16 (1H, d, J=19.2 Hz), 5.25 (1H, d, J=18.0 Hz), 5.42 (2H, s), 5.57 (1H, s), 6.53 (1H, s), 6.99 (2H, s), 7.20-7.22 (5H, m), 7.30 (1H, s), 7.72-7.81 (3H, m), 8.26-8.32 (2H, m), 8.59-8.62 (2H, m).

MS (APCI) m/z: 1190 (M+H)$^+$.

Process 2: Antibody-Drug Conjugate (121)

By using the trastuzumab produced in Reference Example 1 and the compound obtained in Process 1 above, the compound of interest was obtained in the same manner as Process 6 of Example 2.

Antibody concentration: 1.40 mg/mL, antibody yield: 8.4 mg (67%), and average number of conjugated drug molecules (n) per antibody molecule: 2.0.

Example 122 Antibody-Drug Conjugate (122)

[Formula 175]
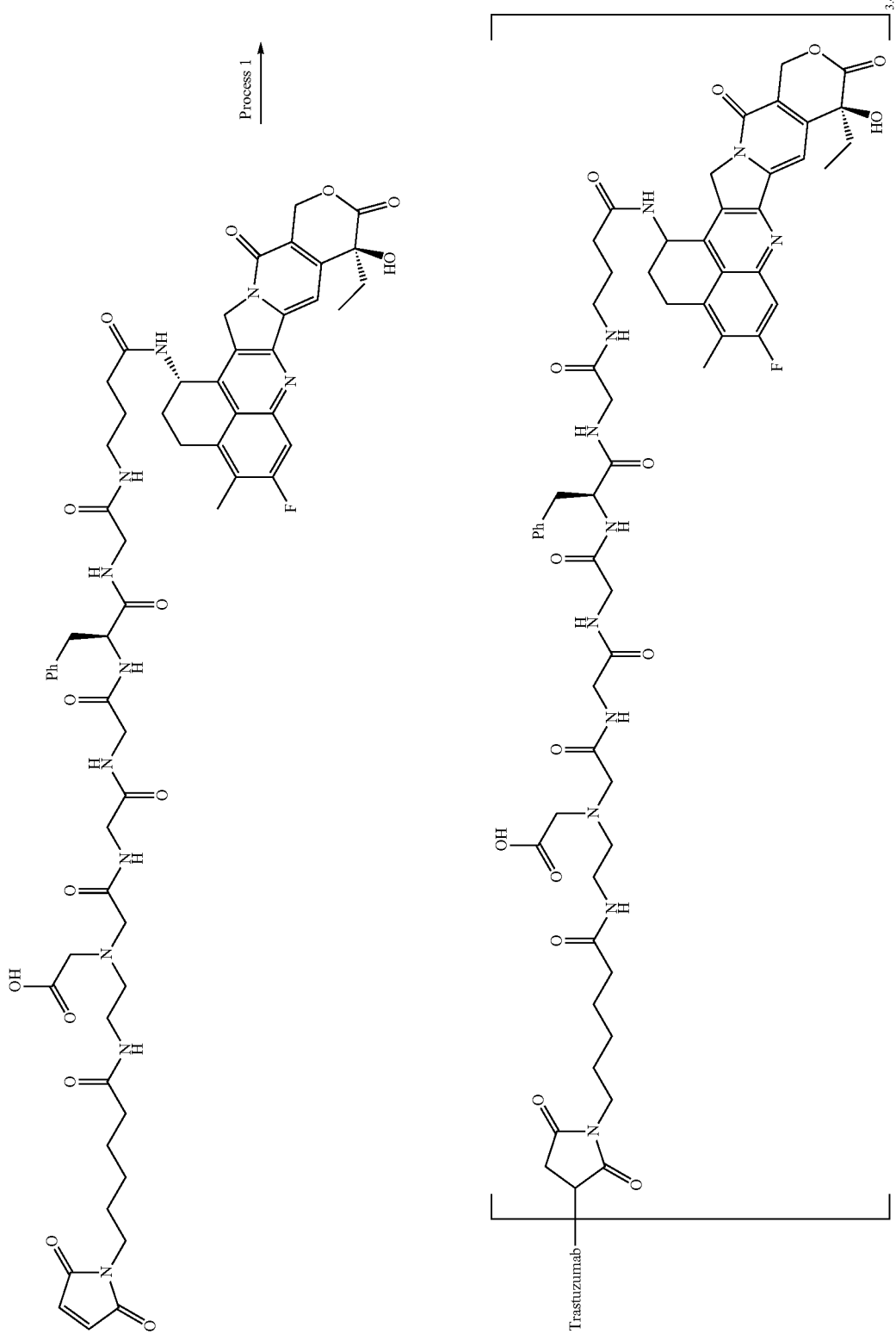

Process 1: Antibody-Drug Conjugate (122)

By using the trastuzumab produced in Reference Example 1 and the compound obtained in Process 1 of Example 121, the compound of interest was obtained in the same manner as Process 1 of Example 3.

Antibody concentration: 1.49 mg/mL, antibody yield: 8.9 mg (71%), and average number of conjugated drug molecules (n) per antibody molecule: 3.4.

Example 123 Antibody-Drug Conjugate (123)

[Formula 176]

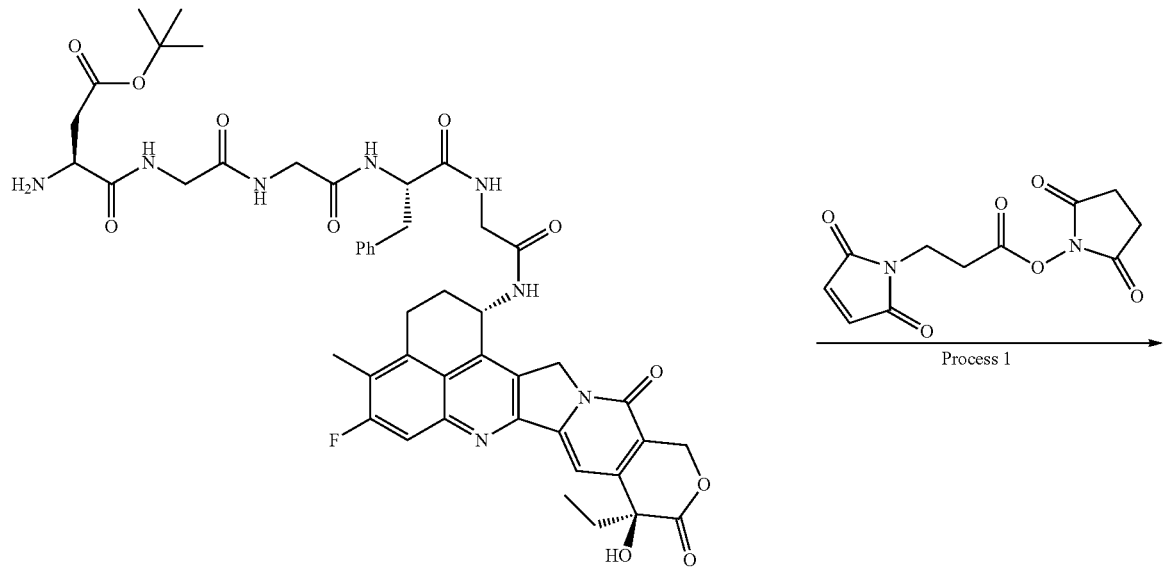

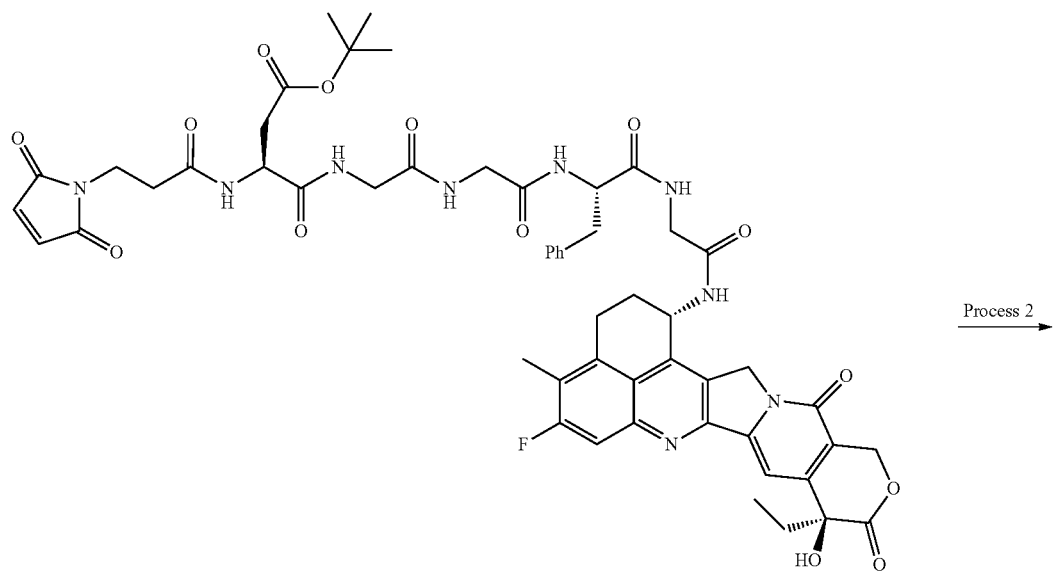

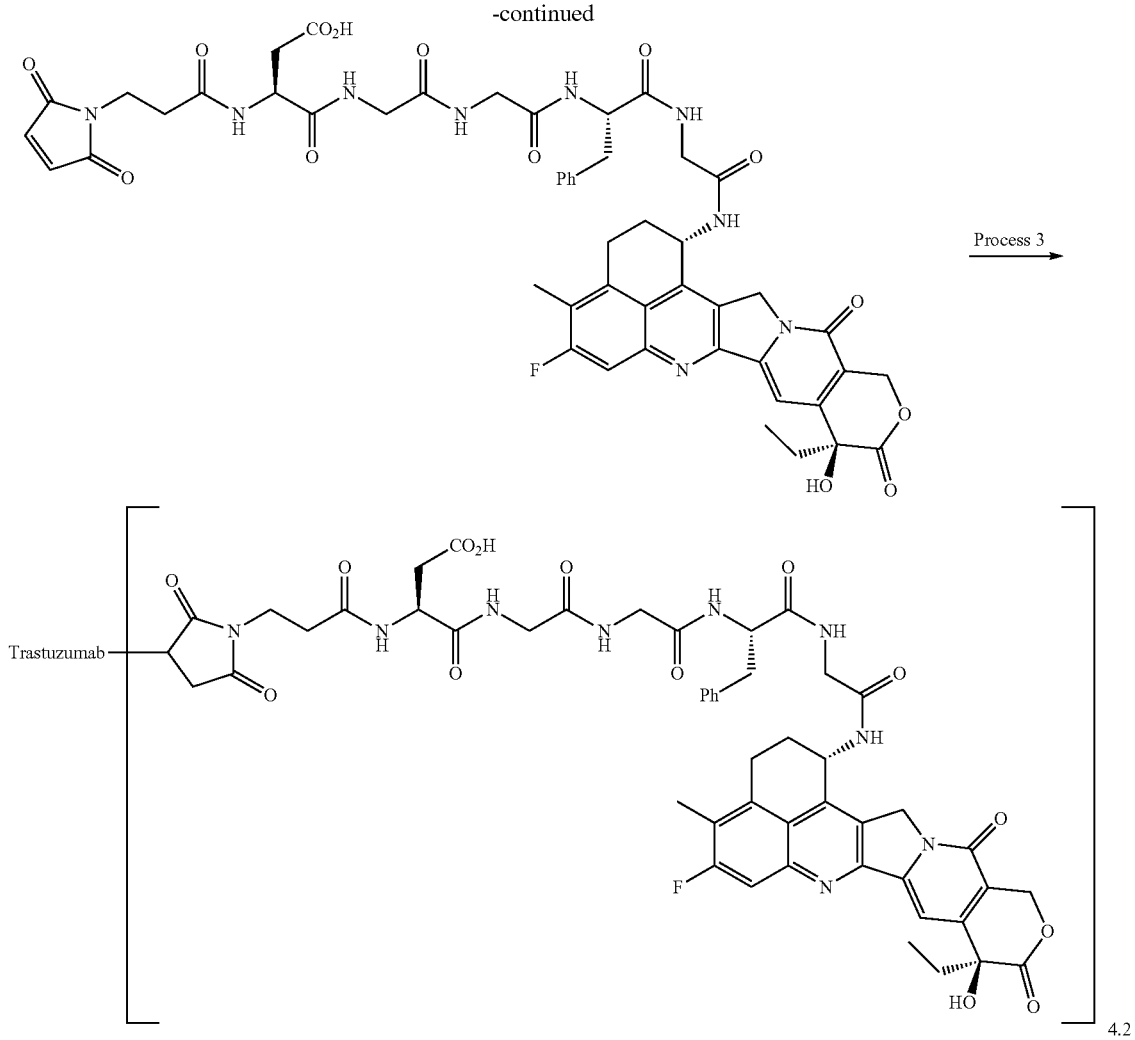

Process 1: tert-Butyl (5S,14S)-5-benzyl-14-{[3-(2,5-dioxo-2,5-dihydro-1H-pyrrol-1-yl)propanoyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,4,7,10,13-pentaoxo-3,6,9,12-tetraazahexadecan-16-oate The compound (0.185 g, 0.200 mmol) obtained in Process 2 of Example 73 was reacted in the same manner as Process 3 of Example 73 by using N-succinimidyl 3-maleimidopropionate instead of N-succinimidyl 6-maleimidohexanoate to yield the titled compound as a pale yellow solid (0.152 g, 71%).

$^1$H-NMR (400 MHz, DMSO-$d_6$) δ: 0.86 (3H, t, J=7.2 Hz), 1.35 (9H, s), 1.78-1.93 (2H, m), 2.04-2.46 (5H, m), 2.41 (3H, s), 2.61-2.69 (1H, m), 2.72-2.81 (1H, m), 2.93-3.02 (1H, m), 3.13-3.22 (2H, m), 3.49-3.80 (8H, m), 4.38-4.49 (1H, m), 4.53-4.62 (1H, m), 5.25 (2H, dd, J=25.0, 19.2 Hz), 5.41 (2H, dd, J=21.1, 16.4 Hz), 5.54-5.62 (1H, m), 6.54 (1H, s), 6.98 (2H, s), 7.12-7.26 (5H, m), 7.31 (1H, s), 7.81 (1H, d, J=10.9 Hz), 7.93 (1H, t, J=5.7 Hz), 8.06 (1H, d, J=7.8 Hz), 8.13 (1H, t, J=5.9 Hz), 8.29-8.39 (2H, m), 8.42 (1H, d, J=8.2 Hz).

Process 2: N-[3-(2,5-Dioxo-2,5-dihydro-1H-pyrrol-1-yl)propanoyl]-L-α-aspartylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.152 g, 0.141 mmol) obtained in Process 1 above was reacted in the same manner as Process 2 of Example 1 to yield the titled compound as a pale yellow solid (0.112 g, 78%).

$^1$H-NMR (400 MHz, DMSO-$d_6$) δ: 0.86 (3H, t, J=7.2 Hz), 1.81-1.89 (2H, m), 2.56-2.03 (6H, m), 2.41 (3H, s), 2.77 (1H, dd, J=13.5, 9.6 Hz), 2.94-3.02 (1H, m), 3.12-3.24 (2H, m), 3.48-3.80 (8H, m), 4.35-4.47 (1H, m), 4.47-4.57 (1H, m), 5.25 (2H, dd, J=25.2, 19.4 Hz), 5.41 (2H, dd, J=20.5, 16.2 Hz), 5.53-5.62 (1H, m), 6.54 (1H, s), 6.99 (2H, s), 7.12-7.27 (5H, m), 7.31 (1H, s), 7.81 (1H, d, J=11.3 Hz), 7.89-8.00 (1H, m), 8.03-8.17 (2H, m), 8.27-8.54 (3H, m), 12.31 (1H, s).

MS (ESI) m/z: 1020 (M+H)$^+$.

Process 3: Antibody-Drug Conjugate (123)

By using the trastuzumab produced in Reference Example 1 and the compound obtained in Process 2 above, the compound of interest was obtained in the same manner as Process 6 of Example 2.
Antibody concentration: 1.83 mg/mL, antibody yield: 11.0 mg (88%), and average number of conjugated drug molecules (n) per antibody molecule: 4.2.

Example 124 Antibody-Drug Conjugate (124)

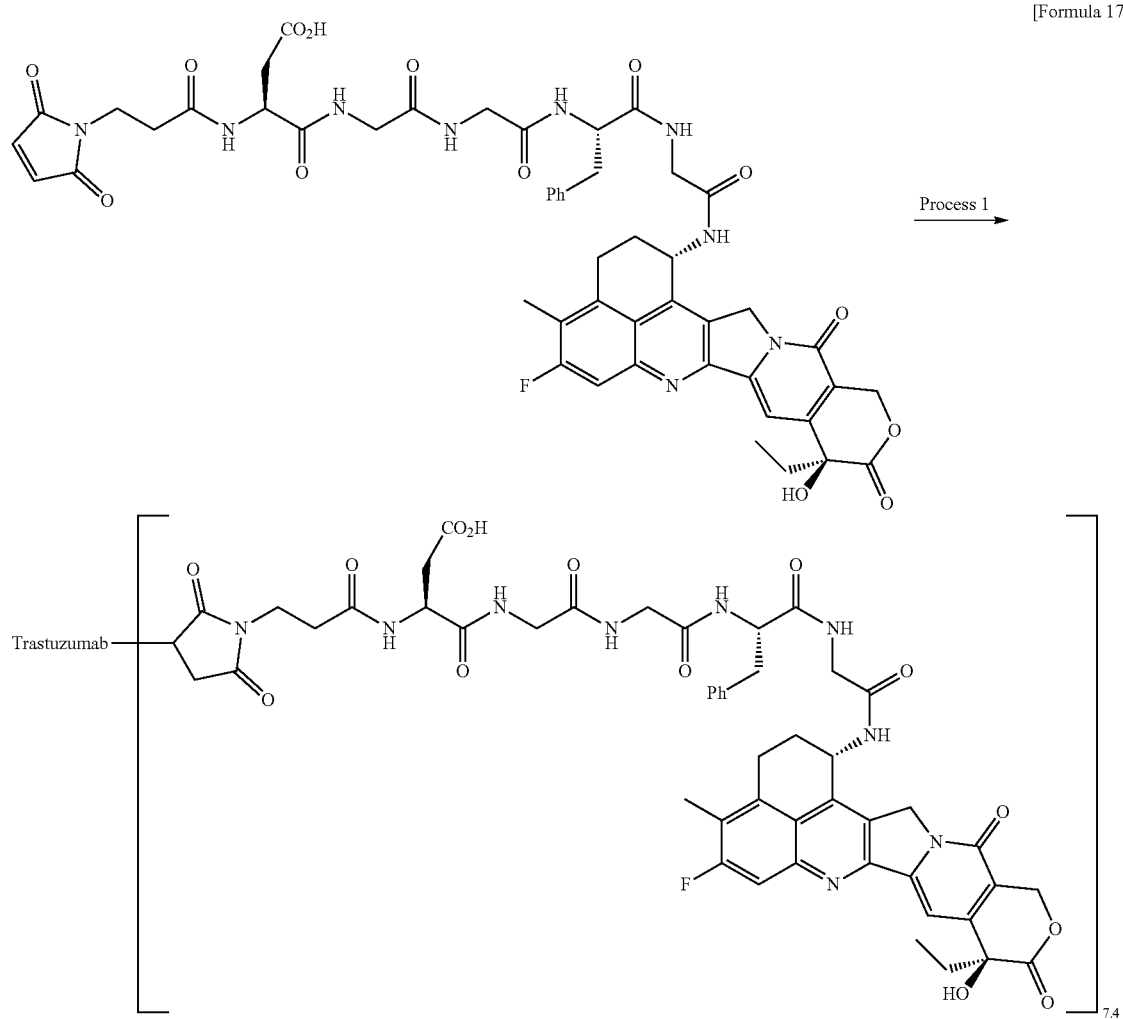

[Formula 177]

Process 1: Antibody-Drug Conjugate (124)

By using the trastuzumab produced in Reference Example 1 and the compound obtained in Process 2 of Example 123, the compound of interest was obtained in the same manner as Process 1 of Example 3.

Antibody concentration: 1.91 mg/mL, antibody yield: 11.5 mg (92%), and average number of conjugated drug molecules (n) per antibody molecule: 7.4.

Example 125 Antibody-Drug Conjugate (125)
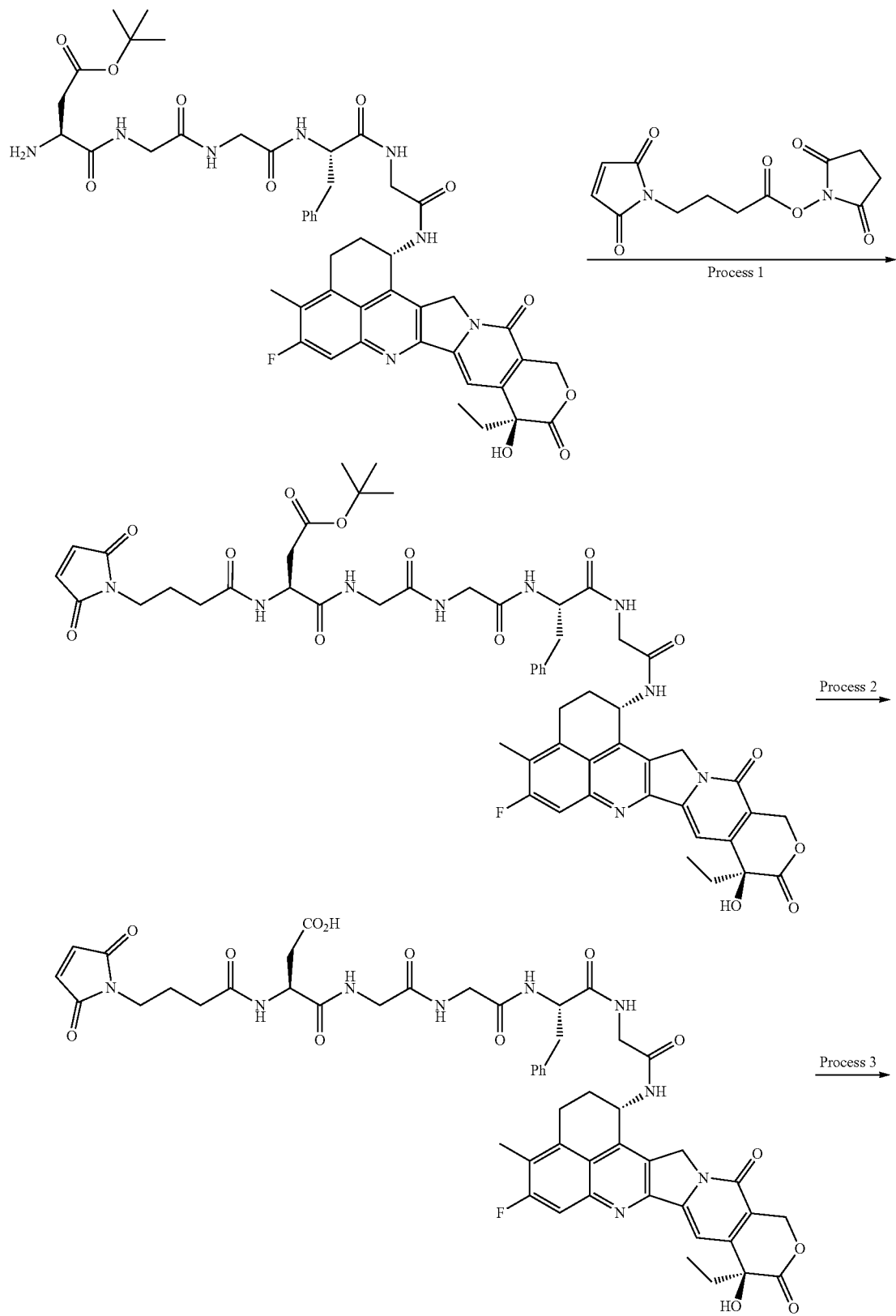
[Formula 178]

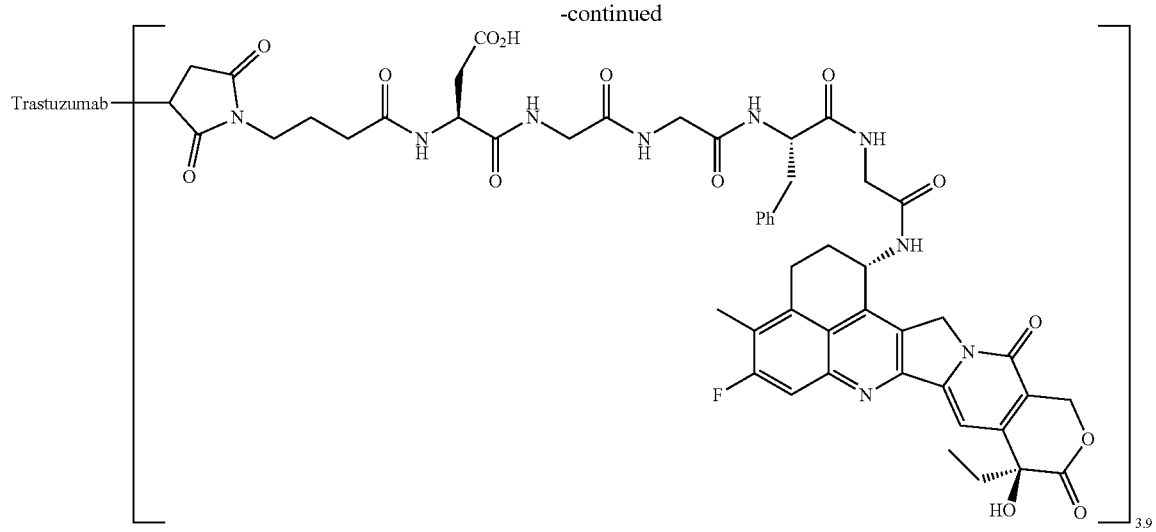

Process 1: tert-Butyl (5S,14S)-5-benzyl-14-{[4-(2,5-dioxo-2,5-dihydro-1H-pyrrol-1-yl)butanoyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,4,7,10,13-pentaoxo-3,6,9,12-tetraazahexadecan-16-oate The compound (0.185 g, 0.200 mmol) obtained in Process 2 of Example 73 was reacted in the same manner as Process 3 of Example 73 by using N-succinimidyl 4-maleimidobutanoate instead of N-succinimidyl 6-maleimidohexanoate to yield the titled compound as a pale yellow solid (0.166 g, 76%).

$^1$H-NMR (400 MHz, DMSO-$d_6$) δ: 0.86 (3H, t, J=7.2 Hz), 1.34 (9H, s), 1.64-1.74 (2H, m), 1.78-1.92 (2H, m), 2.03-2.45 (5H, m), 2.41 (3H, s), 2.63-2.71 (1H, m), 2.72-2.82 (1H, m), 2.93-3.02 (1H, m), 3.13-3.23 (2H, m), 3.42-3.36 (2H, m), 3.53 (1H, dd, J=16.8, 5.9 Hz), 3.61-3.77 (5H, m), 4.38-4.47 (1H, m), 4.53-4.61 (1H, m), 5.25 (2H, dd, J=25.6, 19.0 Hz), 5.41 (2H, dd, J=21.5, 16.4 Hz), 5.53-5.63 (1H, m), 6.54 (1H, s), 7.00 (2H, s), 7.12-7.27 (5H, m), 7.31 (1H, s), 7.81 (1H, d, J=10.9 Hz), 7.93 (1H, t, J=5.7 Hz), 8.06 (1H, d, J=8.2 Hz), 8.11 (1H, t, J=5.9 Hz), 8.18 (1H, d, J=8.2 Hz), 8.29-8.35 (1H, m), 8.42 (1H, d, J=8.6 Hz).

Process 2: N-[4-(2,5-Dioxo-2,5-dihydro-1H-pyrrol-1-yl)butanoyl]-L-α-aspartylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.166 g, 0.152 mmol) obtained in Process 1 above was reacted in the same manner as Process 2 of Example 1 to yield the titled compound as a pale yellow solid (0.100 g, 63%).

$^1$H-NMR (400 MHz, DMSO-$d_6$) δ: 0.86 (3H, t, J=7.2 Hz), 1.64-1.75 (2H, m), 1.79-1.92 (2H, m), 2.04-2.51 (5H, m), 2.41 (3H, s), 2.62-2.82 (2H, m), 2.97 (1H, dd, J=13.3, 4.7 Hz), 3.13-3.22 (2H, m), 3.38 (2H, t, J=6.8 Hz), 3.51-3.74 (6H, m), 4.38-4.47 (1H, m), 4.49-4.58 (1H, m), 5.25 (2H, dd, J=25.4, 19.2 Hz), 5.41 (2H, dd, J=20.5, 16.6 Hz), 5.53-5.63 (1H, m), 6.54 (1H, brs), 7.00 (2H, s), 7.11-7.27 (5H, m), 7.31 (1H, s), 7.81 (1H, d, J=10.9 Hz), 7.92 (1H, t, J=5.7 Hz), 8.03-8.12 (2H, m), 8.20 (1H, d, J=7.4 Hz), 8.32 (1H, t, J=5.7 Hz), 8.42 (1H, d, J=8.2 Hz).

MS (ESI) m/z: 1034 (M+H)$^+$.

Process 3: Antibody-Drug Conjugate (125)

By using the trastuzumab produced in Reference Example 1 and the compound obtained in Process 2 above, the compound of interest was obtained in the same manner as Process 6 of Example 2.

Antibody concentration: 1.81 mg/mL, antibody yield: 10.9 mg (87%), and average number of conjugated drug molecules (n) per antibody molecule: 3.9.

Example 126 Antibody-Drug Conjugate (126)

[Formula 179]

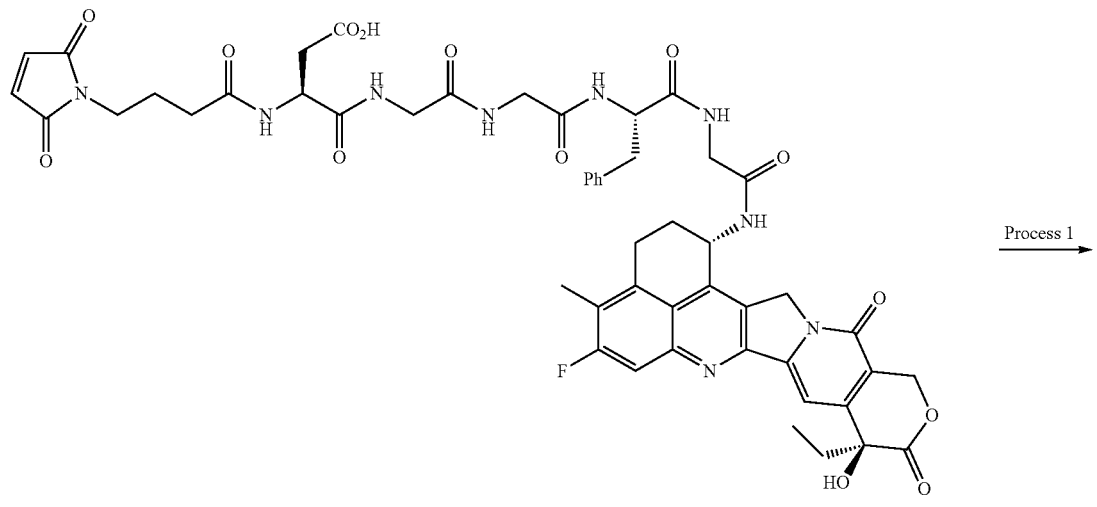

Process 1

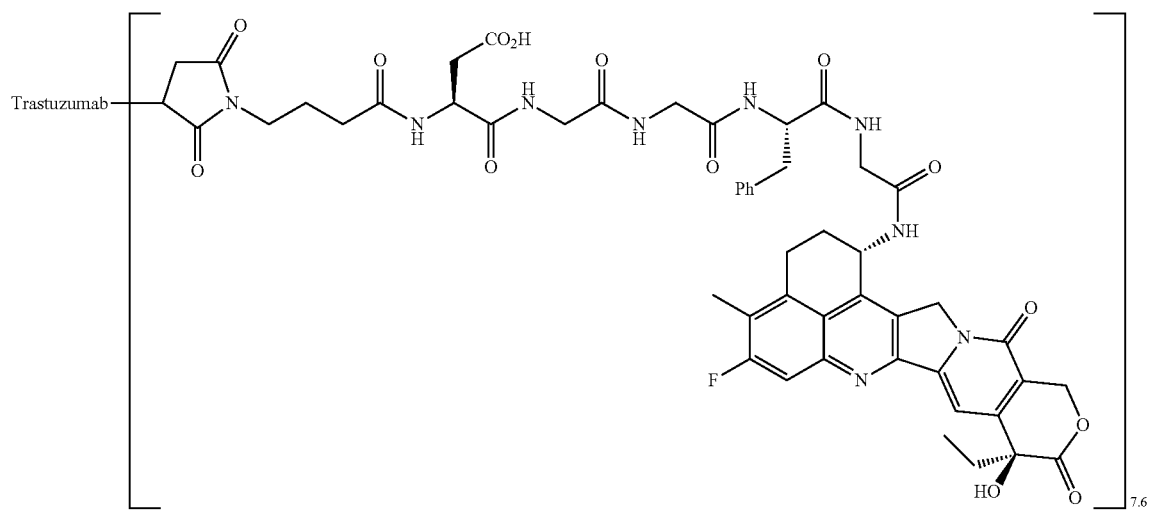

Process 1: Antibody-Drug Conjugate (126)

By using the trastuzumab produced in Reference Example 1 and the compound obtained in Process 2 of Example 125, the compound of interest was obtained in the same manner as Process 1 of Example 3.

Antibody concentration: 2.11 mg/mL, antibody yield: 12.0 mg (96%), and average number of conjugated drug molecules (n) per antibody molecule: 7.6.

Example 127 Antibody-Drug Conjugate (127)
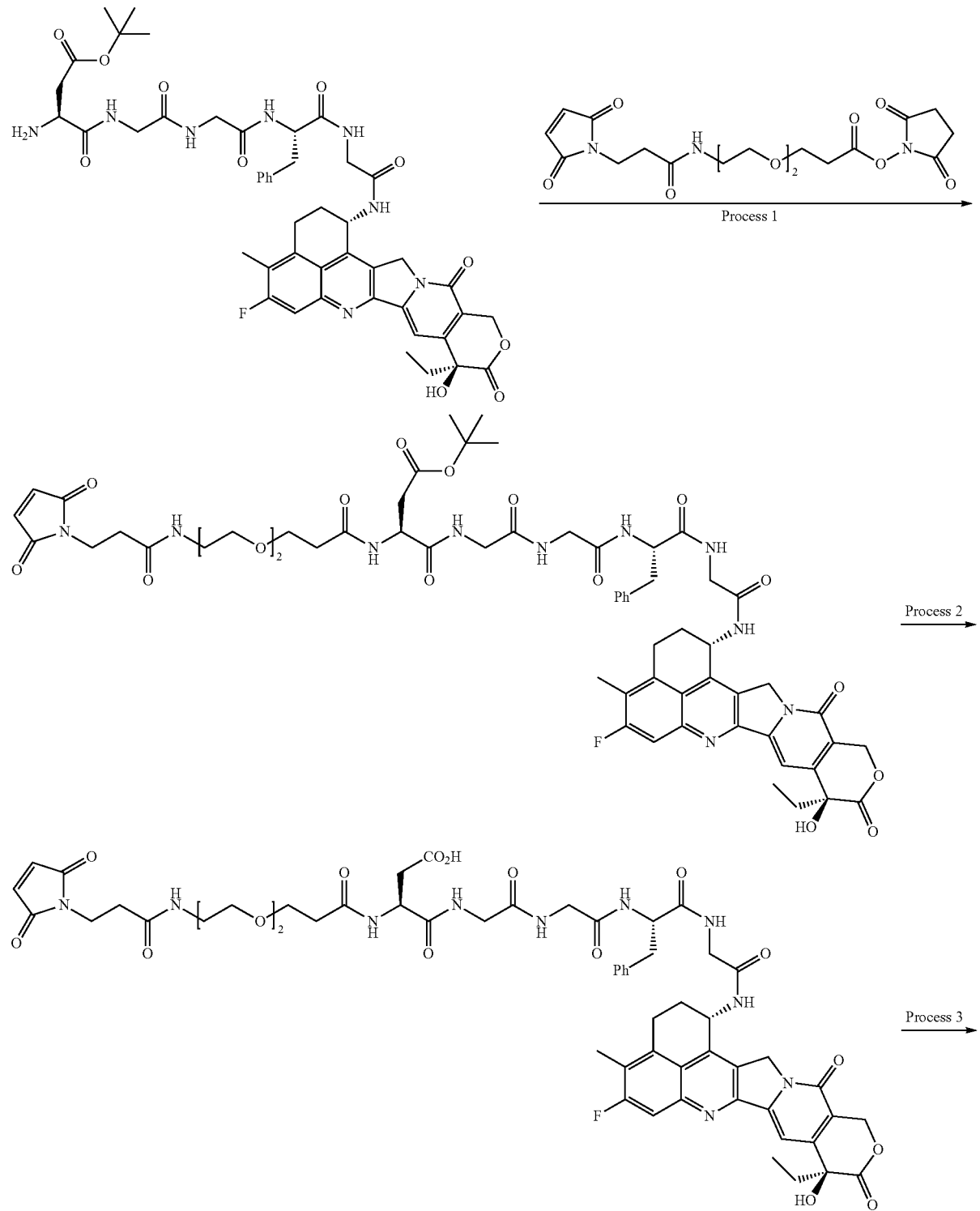
[Formula 180]

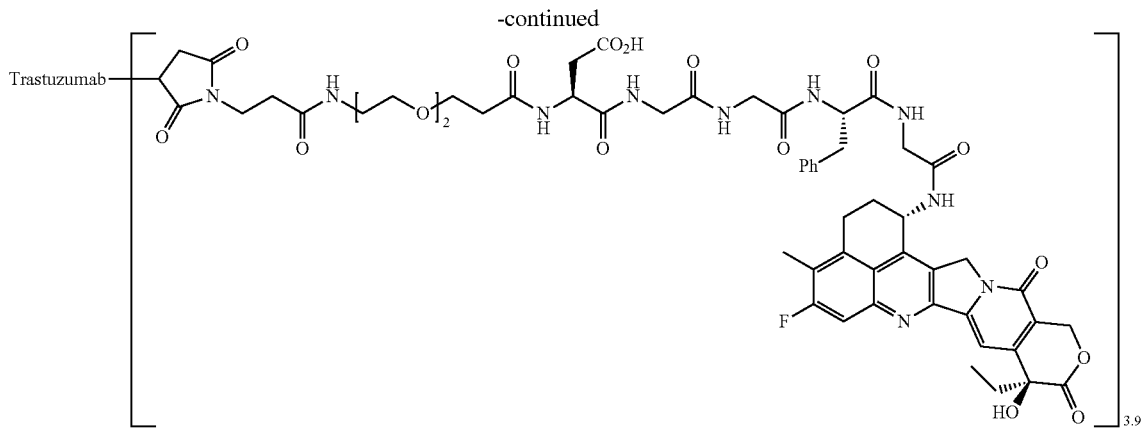

Process 1: tert-Butyl (15S)-1-(2,5-dioxo-2,5-dihydro-1H-pyrrol-1-yl)-15-[(2-{[2-({(2S)-1-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)amino]-1-oxo-3-phenylpropan-2-yl}amino)-2-oxoethyl]amino}-2-oxoethyl)carbamoyl]-3,13-dioxo-7,10-dioxa-4,14-diazaheptadecan-17-oate The compound (0.185 g, 0.200 mmol) obtained in Process 2 of Example 73 was reacted in the same manner as Process 3 of Example 73 by using N-succinimidyl 3-(2-(2-(3-maleimidopropanamide)ethoxy)ethoxy)propanoate instead of N-succinimidyl 6-maleimidohexanoate to yield the titled compound as a pale yellow solid (0.157 g, 64%).

$^1$H-NMR (400 MHz, DMSO-$d_6$) δ: 0.86 (3H, t, J=7.4 Hz), 1.35 (9H, s), 1.79-1.94 (2H, m), 2.05-2.26 (2H, m), 2.28-2.47 (8H, m), 2.63-2.71 (1H, m), 2.72-2.82 (1H, m), 2.93-3.03 (1H, m), 3.08-3.24 (4H, m), 3.28-3.49 (6H, m), 3.50-3.62 (5H, m), 3.63-3.77 (5H, m), 4.39-4.48 (1H, m), 4.55-4.65 (1H, m), 5.25 (2H, dd, J=25.6, 19.0 Hz), 5.41 (2H, dd, J=21.5, 16.4 Hz), 5.54-5.63 (1H, m), 6.54 (1H, s), 7.00 (2H, s), 7.13-7.26 (5H, m), 7.31 (1H, s), 7.81 (1H, d, J=10.9 Hz), 7.91-7.98 (1H, m), 7.99-8.04 (1H, m), 8.04-8.14 (2H, m), 8.24 (1H, d, J=8.2 Hz), 8.30-8.36 (1H, m), 8.42 (1H, d, J=9.0 Hz).

Process 2: N-{3-[2-(2-{[3-(2,5-Dioxo-2,5-dihydro-1H-pyrrol-1-yl)propanoyl]amino}ethoxy)ethoxy]propanoyl}-L-α-aspartylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.157 g, 0.127 mmol) obtained in Process 1 above was reacted in the same manner as Process 2 of Example 1 to yield the titled compound as a pale yellow solid (0.120 g, 80%).

$^1$H-NMR (400 MHz, DMSO-$d_6$) δ: 0.86 (3H, t, J=7.4 Hz), 1.79-1.92 (2H, m), 2.05-2.27 (2H, m), 2.28-2.45 (8H, m), 2.64-2.81 (2H, m), 2.92-3.02 (1H, m), 3.08-3.23 (4H, m), 3.30-3.78 (16H, m), 4.39-4.47 (1H, m), 4.52-4.61 (1H, m), 5.25 (2H, dd, J=26.4, 19.4 Hz), 5.41 (2H, dd, J=20.3, 16.4 Hz), 5.54-5.62 (1H, m), 6.55 (1H, brs), 7.00 (2H, s), 7.13-7.25 (5H, m), 7.31 (1H, s), 7.81 (1H, d, J=10.9 Hz), 7.89-7.97 (1H, m), 7.99-8.12 (3H, m), 8.26 (1H, d, J=7.8 Hz), 8.30-8.36 (1H, m), 8.43 (1H, d, J=8.6 Hz), 12.32 (1H, brs).

MS (ESI) m/z: 1179 (M+H)$^+$.

Process 3: Antibody-Drug Conjugate (127)

By using the trastuzumab produced in Reference Example 1 and the compound obtained in Process 2 above, the compound of interest was obtained in the same manner as Process 6 of Example 2.

Antibody concentration: 1.77 mg/mL, antibody yield: 10.6 mg (85%), and average number of conjugated drug molecules (n) per antibody molecule: 3.9.

Example 128 Antibody-Drug Conjugate (128)

[Formula 181]

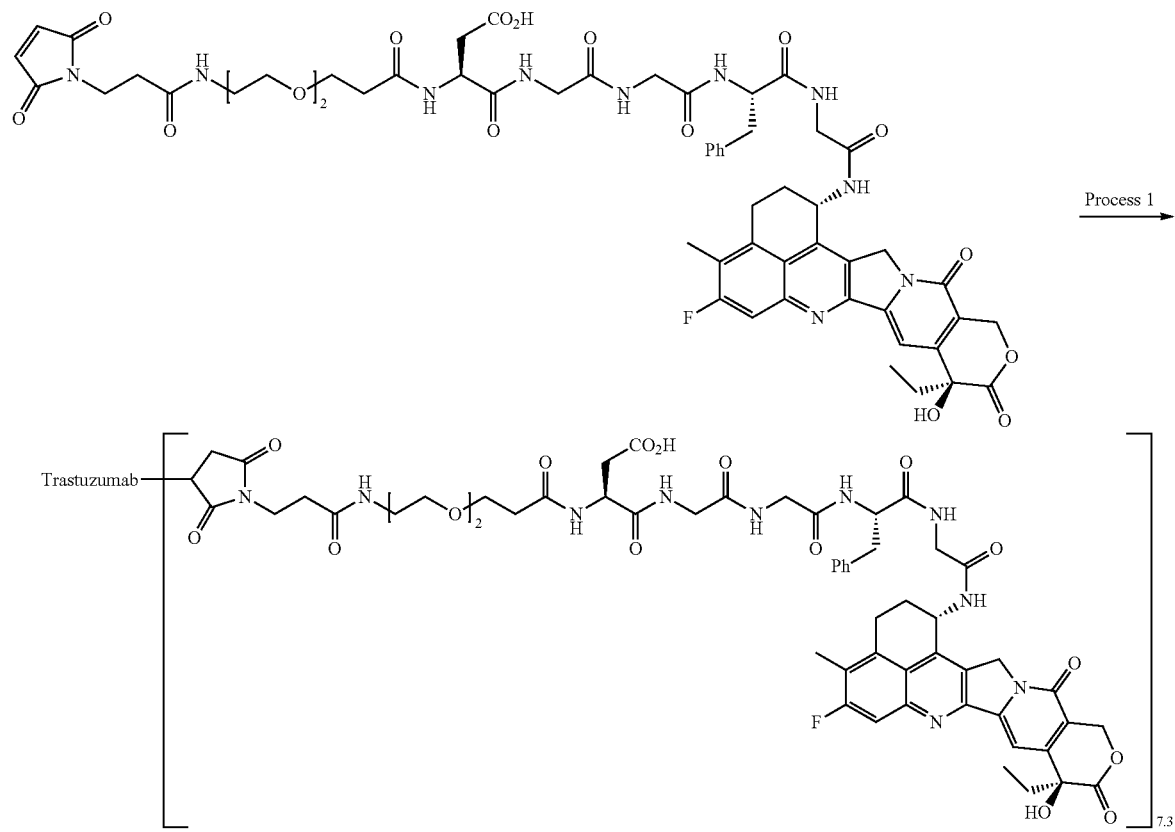

Process 1: Antibody-Drug Conjugate (128)

By using the trastuzumab produced in Reference Example 1 and the compound obtained in Process 2 of Example 127, the compound of interest was obtained in the same manner as Process 1 of Example 3.

Antibody concentration: 1.98 mg/mL, antibody yield: 11.9 mg (95%), and average number of conjugated drug molecules (n) per antibody molecule: 7.3.

Example 129 Antibody-Drug Conjugate (129)

[Formula 182]

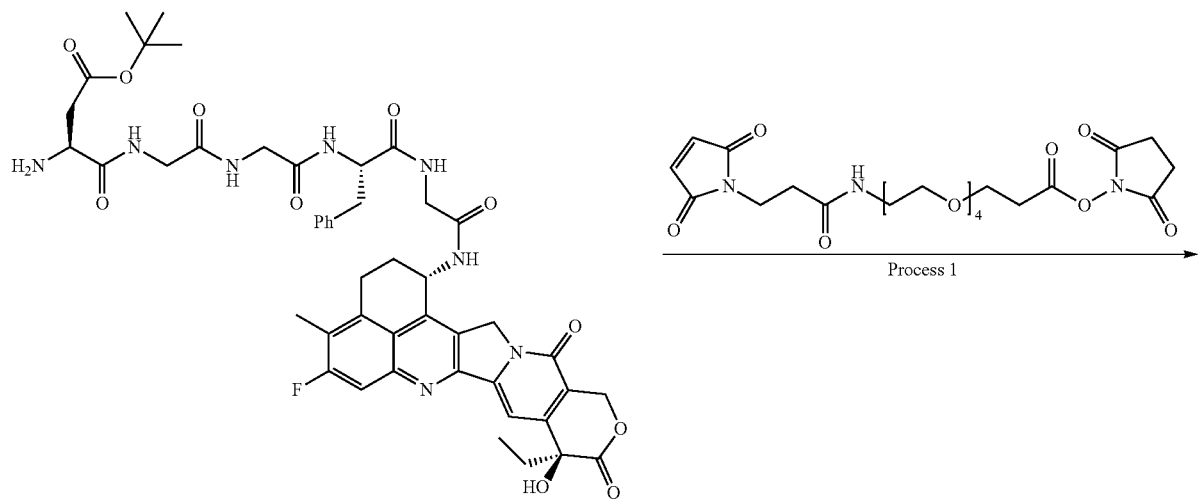

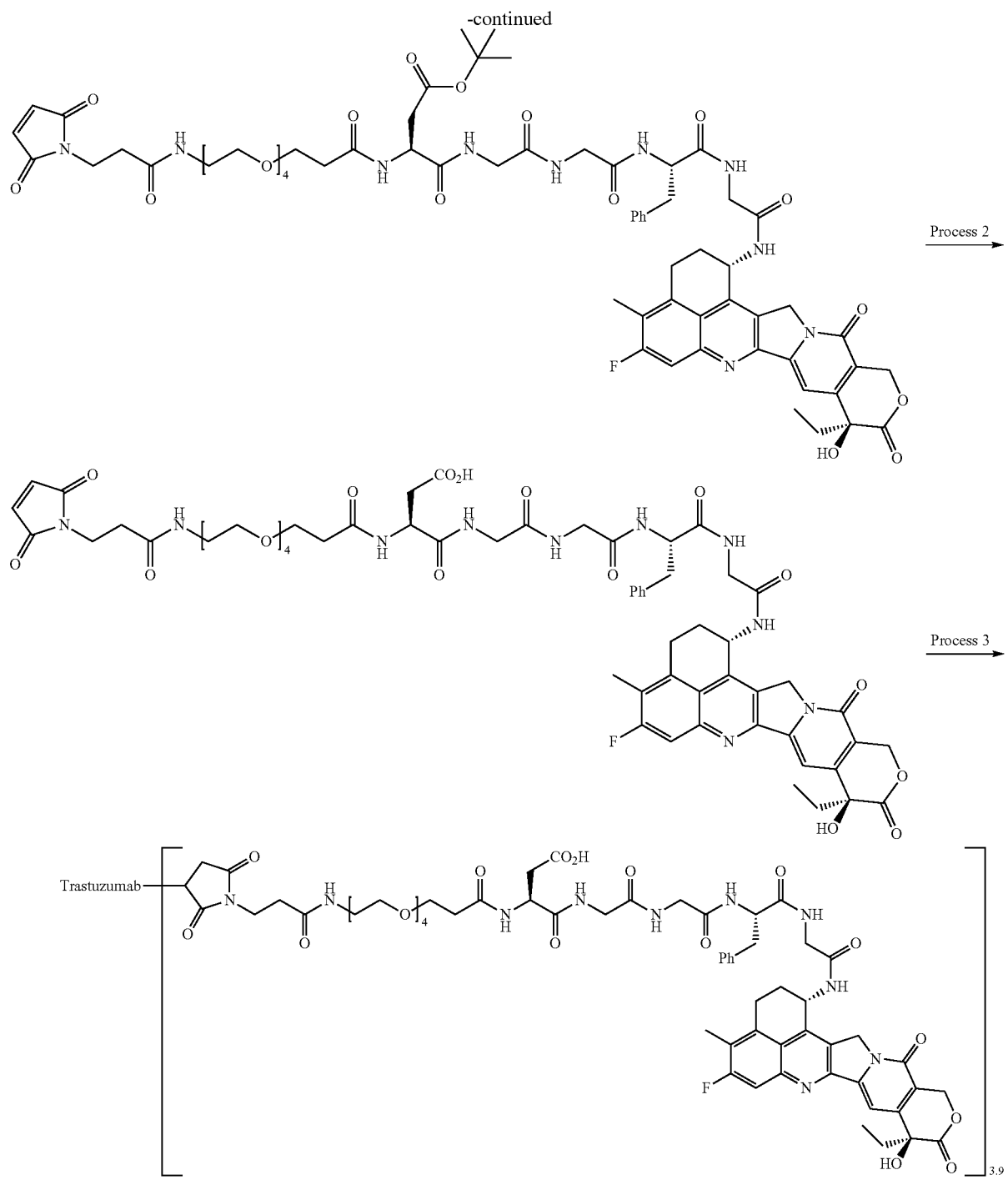

Process 1: tert-Butyl (21S)-1-(2,5-dioxo-2,5-dihydro-1H-pyrrol-1-yl)-21-[(2-{[2-({(2S)-1-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl)amino]-1-oxo-3-phenylpropan-2-yl}amino)-2-oxoethyl]amino}-2-oxoethyl)carbamoyl]-3,19-dioxo-7,10,13,16-tetraoxa-4,20-diazatricosan-23-oate The compound (0.185 g, 0.200 mmol) obtained in Process 2 of Example 73 was reacted in the same manner as Process 3 of Example 73 by using N-succinimidyl 1-maleimido-3-oxo-7,10,13,16-tetraoxa-4-aza-19-nonadecanoate instead of N-succinimidyl 6-maleimidohexanoate to yield the titled compound as a pale yellow solid (0.161 g, 61%).

$^1$H-NMR (400 MHz, DMSO-$d_6$) δ: 0.86 (3H, t, J=7.4 Hz), 1.35 (9H, s), 1.79-1.91 (2H, m), 2.06-2.26 (2H, m), 2.28-2.46 (8H, m), 2.63-2.71 (1H, m), 2.72-2.82 (1H, m), 2.93-3.03 (1H, m), 3.10-3.22 (4H, m), 3.28-3.53 (14H, m), 3.54-3.62 (5H, m), 3.63-3.78 (5H, m), 4.39-4.47 (1H, m), 4.55-4.65 (1H, m), 5.25 (2H, dd, J=25.4, 19.2 Hz), 5.41 (2H, dd, J=21.1, 16.4 Hz), 5.55-5.62 (1H, m), 6.54 (1H, s), 7.00

(2H, s), 7.16-7.25 (5H, m), 7.31 (1H, s), 7.81 (1H, d, J=10.9 Hz), 7.91-7.98 (1H, m), 8.00-8.15 (3H, m), 8.24 (1H, d, J=7.8 Hz), 8.30-8.36 (1H, m), 8.42 (1H, d, J=8.6 Hz).

Process 2: N-[19-(2,5-Dioxo-2,5-dihydro-1H-pyrrol-1-yl)-17-oxo-4,7,10,13-tetraoxa-16-azanonadecan-1-oyl]-L-α-aspartylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.161 g, 0.122 mmol) obtained in Process 1 above was reacted in the same manner as Process 4 of Example 73 to yield the titled compound as a pale yellow solid (0.133 g, 86%).
$^1$H-NMR (400 MHz, DMSO-$d_6$) δ: 0.86 (3H, t, J=7.4 Hz), 1.78-1.92 (2H, m), 2.03-2.25 (2H, m), 2.28-2.44 (8H, m), 2.65-2.82 (2H, m), 2.94-3.01 (1H, m), 3.10-3.22 (4H, m), 3.35 (2H, t, J=5.7 Hz), 3.42-3.80 (22H, m), 4.39-4.47 (1H, m), 4.52-4.60 (1H, m), 5.25 (2H, dd, J=26.2, 18.8 Hz), 5.41 (2H, dd, J=20.3, 16.4 Hz), 5.55-5.62 (1H, m), 6.55 (1H, brs), 7.00 (2H, s), 7.13-7.26 (5H, m), 7.31 (1H, s), 7.81 (1H, d, J=10.9 Hz), 7.90-7.96 (1H, m), 8.00-8.10 (3H, m), 8.27 (1H, d, J=7.8 Hz), 8.30-8.36 (1H, m), 8.43 (1H, d, J=9.0 Hz).
MS (ESI) m/z: 1267 (M+H)$^+$.

Process 3: Antibody-Drug Conjugate (129)

By using the trastuzumab produced in Reference Example 1 and the compound obtained in Process 2 above, the compound of interest was obtained in the same manner as Process 6 of Example 2.
Antibody concentration: 1.80 mg/mL, antibody yield: 10.8 mg (86%), and average number of conjugated drug molecules (n) per antibody molecule: 3.9.

Example 130 Antibody-Drug Conjugate (130)

[Formula 183]

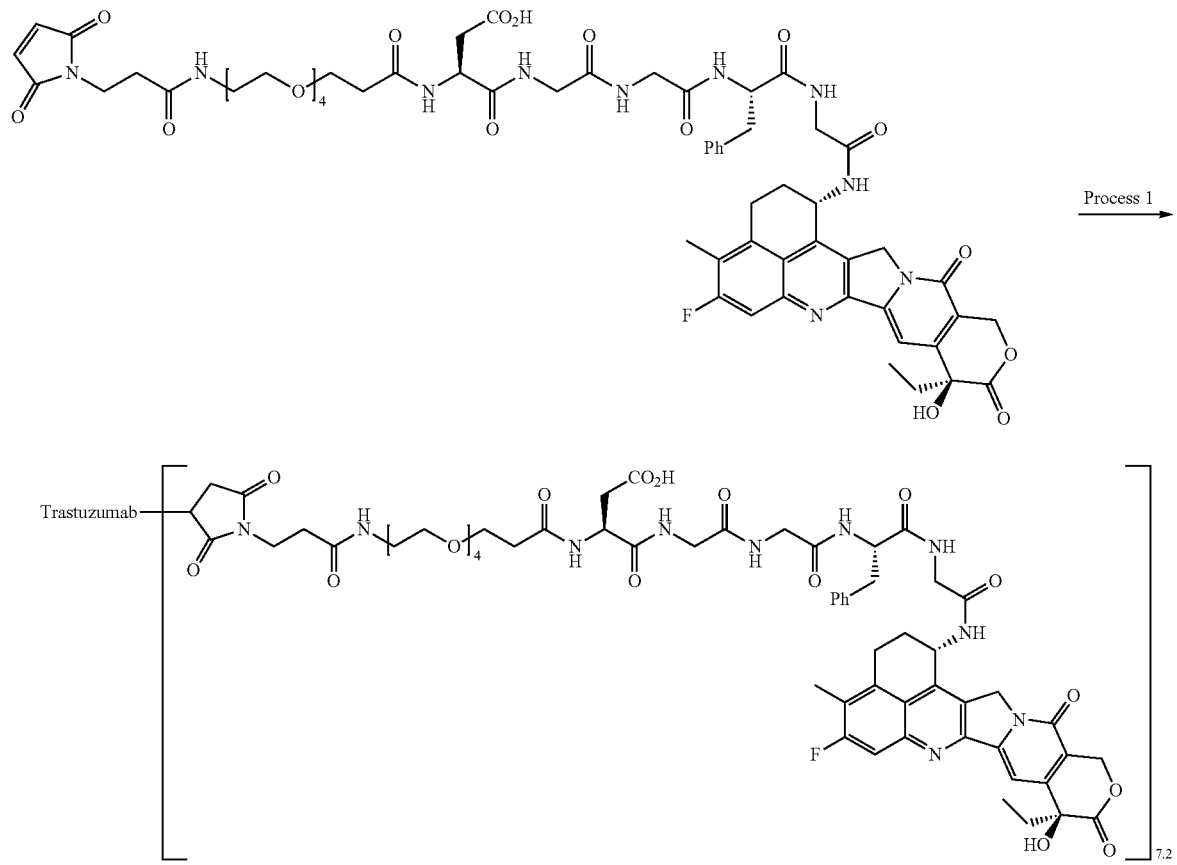

Process 1: Antibody-Drug Conjugate (130)

By using the trastuzumab produced in Reference Example 1 and the compound obtained in Process 2 of Example 129, the compound of interest was obtained in the same manner as Process 1 of Example 3.
Antibody concentration: 1.88 mg/mL, antibody yield: 11.3 mg (90%), and average number of conjugated drug molecules (n) per antibody molecule: 7.2.

Example 131 Antibody-Drug Conjugate (131)
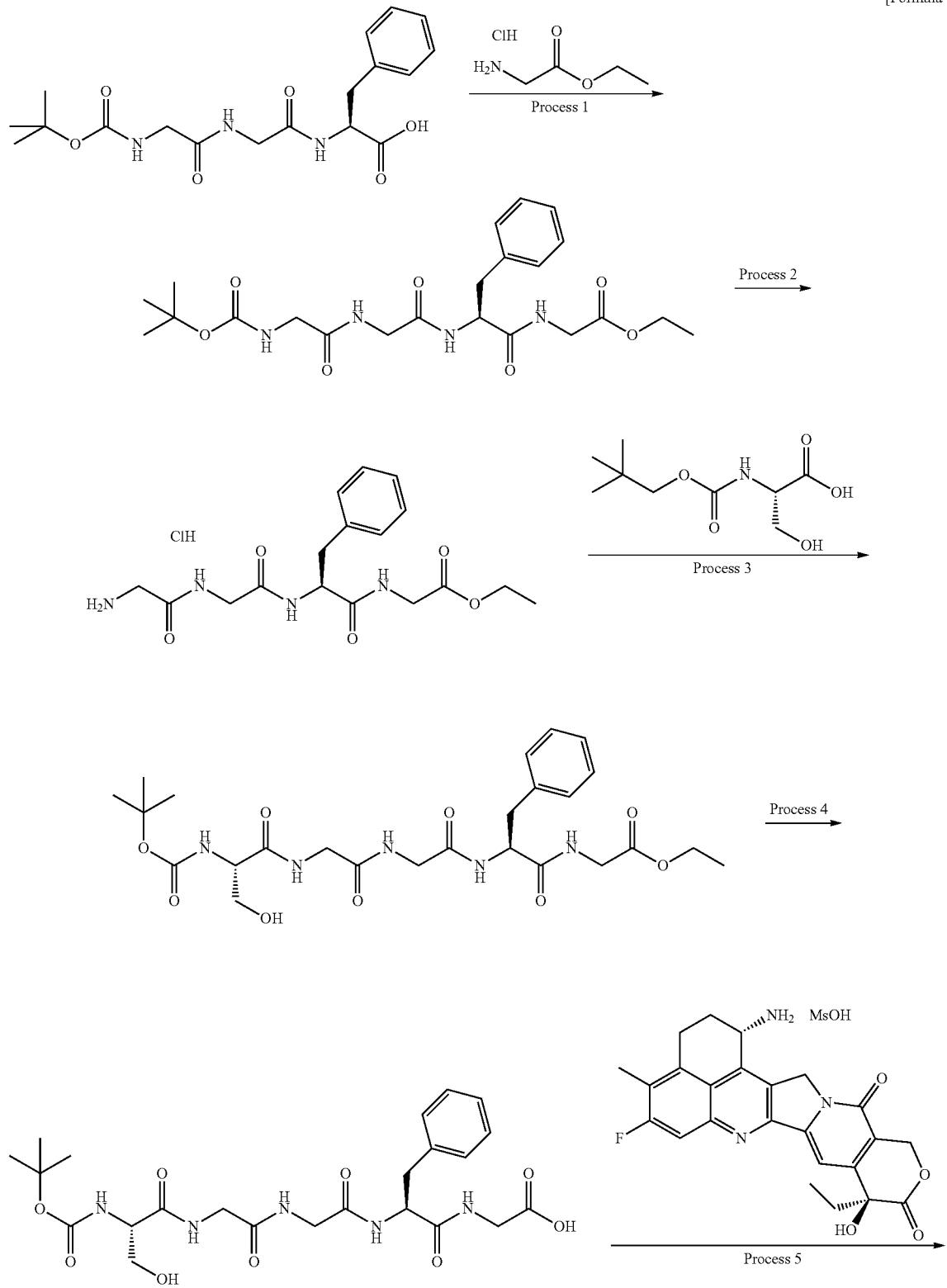
[Formula 184]

529                                                530
-continued
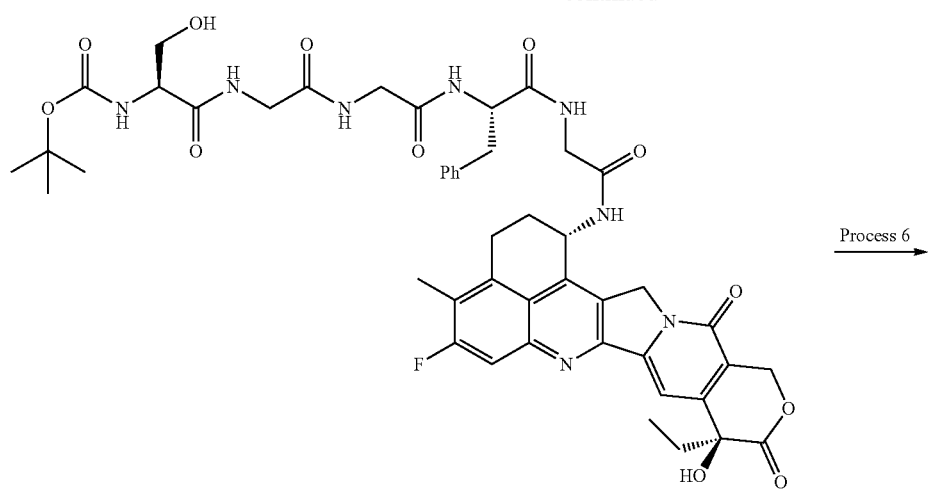
Process 6 →
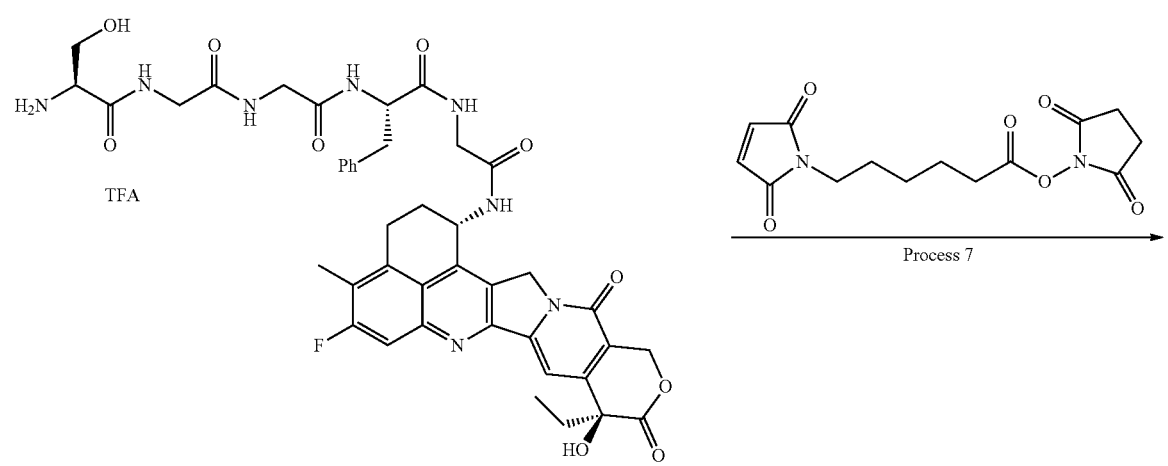
Process 7 →
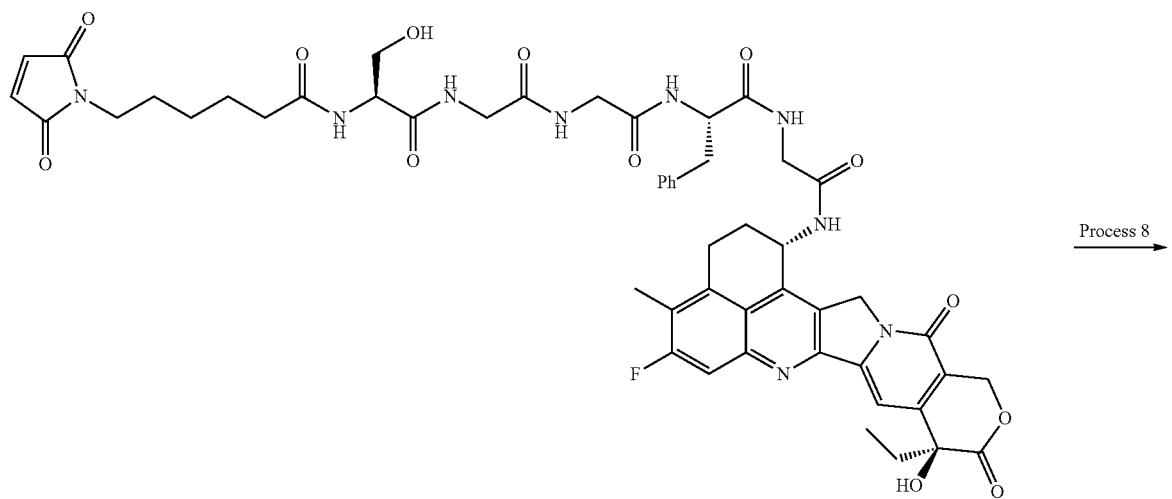
Process 8 →

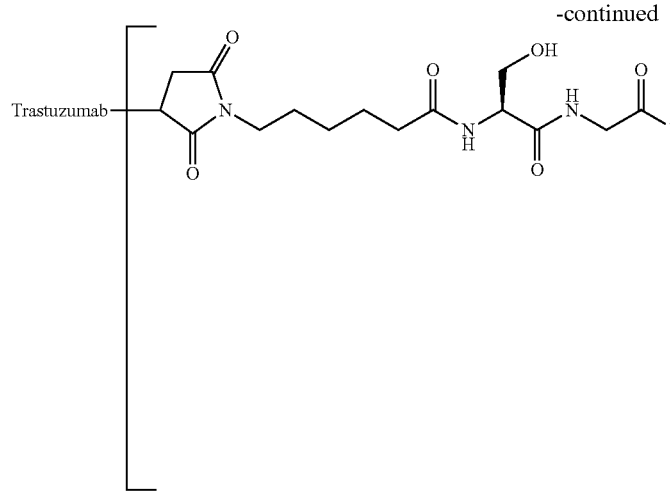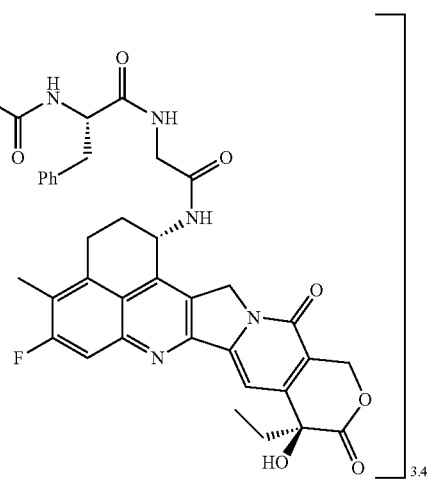

Process 1: Ethyl N-(tert-butoxycarbonyl)glycylglycyl-L-phenylalanylglycinate

To a dichloromethane (40.0 mL) solution of N-(tert-butoxycarbonyl)glycylglycyl-L-phenylalanine (Japanese Patent Laid-Open No. 2002-60351; 5.90 g, 15.6 mmol), 1-hydroxybenzotriazole (2.62 g, 17.1 mmol), glycine ethyl ester hydrochloride (2.62 g, 17.1 mmol), and diisopropylethylamine (5.42 mL, 31.1 mmol), 1-ethyl-3-(3-dimethylaminopropyl)carbodiimide hydrochloride (3.58 g, 18.68 mmol) was added and stirred at room temperature for 2 hours. The reaction solution was diluted with dichloromethane, then washed with 1 N hydrochloric acid, water, and a saturated sodium chloride aqueous solution, and dried over anhydrous sodium sulfate. After removing the solvent, the residues obtained were purified by silica gel column chromatography [chloroform -chloroform:methanol=9:1 (v/v)] to yield the titled compound as a colorless solid (5.86 g, 82%).
$^1$H-NMR (400 MHz, DMSO-$d_6$) δ: 1.20 (3H, q, J=7.3 Hz), 1.38 (9H, s), 2.75 (1H, dd, J=13.9, 9.7 Hz), 3.05 (1H, dd, J=13.9, 4.2 Hz), 3.51-3.61 (3H, m), 3.75 (1H, dd, J=16.9, 6.0 Hz), 3.81-3.86 (2H, m), 4.10 (2H, q, J=7.3 Hz), 4.53 (1H, td, J=9.4, 4.0 Hz), 6.96-7.02 (1H, m), 7.16-7.21 (1H, m), 7.23-7.28 (4H, m), 7.88 (1H, t, J=5.4 Hz), 8.15 (1H, d, J=9.1 Hz), 8.47 (1H, t, J=5.7 Hz).
MS (ESI) m/z: 465 (M+H)$^+$.

Process 2: Ethyl glycylglycyl-L-phenylalanylglycinate

To a dioxane (40.0 mL) solution of the compound (5.80 g, 12.5 mmol) obtained in Process 1 above, a 4 N hydrogen chloride dioxane solution (15.0 mL) was added and left overnight at room temperature. The solvent was removed under reduced pressure and the residues obtained were charged with ethyl acetate. The deposits were collected by filtration to yield hydrochloric acid salt of the titled compound as a colorless solid (5.74 g, quantitative).
$^1$H-NMR (400 MHz, DMSO-$d_6$) δ: 1.20 (3H, t, J=7.5 Hz), 2.76 (1H, dd, J=13.9, 10.3 Hz), 3.05 (1H, dd, J=13.9, 4.2 Hz), 3.53-3.57 (2H, m), 3.63-3.72 (1H, m), 3.82-3.90 (3H, m), 4.10 (2H, q, J=7.5 Hz), 4.53-4.60 (1H, m), 7.12-7.22 (2H, m), 7.23-7.29 (5H, m), 8.06 (1H, brs), 8.36 (1H, d, J=8.8 Hz), 8.55 (2H, td, J=11.3, 5.6 Hz).
MS (ESI) m/z: 365 (M+H)$^+$.

Process 3: Ethyl N-(tert-butoxycarbonyl)-L-serylglycylglycyl-L-phenylalanyl glycinate To an N,N-dimethylformamide (10.0 mL) solution of the compound (0.940 g, 2.34 mmol) obtained in Process 2 above, 4-dimethylaminopyridine (0.572 g, 4.69 mmol), N-(tert-butoxycarbonyl)-L-serine (0.625 g, 3.05 mmol), and 1-ethyl-3-(3-dimethylaminopropyl)carbodiimide hydrochloride (0.584 g, 3.05 mmol) were added and stirred at room temperature for 2 hours. The reaction solution was diluted with chloroform, then washed with 1 N hydrochloric acid and a 0.1 N phosphate buffer (pH 7.4) in this order, and dried over anhydrous sodium sulfate. After removing the solvent, the residues obtained were purified by silica gel column chromatography [chloroform-chloroform:methanol=9:1 (v/v)] to yield the titled compound (0.750 g, 58%).
$^1$H-NMR (400 MHz, DMSO-$d_6$) δ: 1.16 (3H, t, J=7.1 Hz), 1.35 (9H, s), 2.74 (1H, dd, J=13.7, 10.0 Hz), 3.01 (1H, dd, J=13.7, 4.4 Hz), 3.50-3.59 (3H, m), 3.64-3.74 (3H, m), 3.81 (2H, ddd, J=22.5, 16.6, 5.4 Hz), 3.96 (1H, q, J=6.2 Hz), 4.07 (2H, q, J=7.2 Hz), 4.50 (1H, td, J=9.2, 3.7 Hz), 4.85 (1H, t, J=5.9 Hz), 6.70 (1H, d, J=7.3 Hz), 7.13-7.18 (1H, m), 7.20-7.25 (5H, m), 7.96 (1H, t, J=5.4 Hz), 8.07-8.12 (1H, m), 8.44 (1H, t, J=5.9 Hz).
MS (ESI) m/z: 552 (M+H)$^+$.

Process 4: N-(tert-Butoxycarbonyl)-L-serylglycylglycyl-L-phenylalanylglycine

Under ice cooling, to a dioxane (5.00 mL) solution of the compound (0.155 g, 0.280 mmol) obtained in Process 3 above, a 1 N sodium hydroxide aqueous solution (0.310 mL, 0.310 mmol) was added and stirred for 10 minutes. 1 N hydrochloric acid (0.310 mL, 0.310 mmol) was added for neutralization, and then the solvent was removed to yield the titled compound as a colorless solid (0.147 g, quantitative).

$^1$H-NMR (400 MHz, DMSO-$d_6$) δ: 1.35 (9H, s), 2.73 (1H, dd, J=13.7, 9.8 Hz), 3.01 (1H, dd, J=13.7, 4.1 Hz), 3.51-3.59 (4H, m), 3.67-3.71 (2H, m), 3.72-3.76 (2H, m), 3.96 (1H, dd, J=12.9, 5.6 Hz), 4.50 (1H, td, J=9.3, 3.6 Hz), 6.71 (1H, d, J=7.8 Hz), 7.13-7.18 (1H, m), 7.20-7.24 (5H, m), 7.96 (1H, t, J=5.9 Hz), 8.06-8.13 (2H, m), 8.35 (1H, t, J=5.9 Hz), 12.56 (1H, s).

Process 5: N-(tert-Butoxycarbonyl)-L-serylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide To an N,N-dimethylformamide (1.00 mL) solution of the compound (0.147 g, 0.280 mmol) obtained in Process 4 above, N-hydroxysuccinimide (32.4 mg, 0.280 mmol) and 1-ethyl-3-(3-dimethylaminopropyl)carbodiimide hydrochloride (54 mg, 0.28 mmol) were added and stirred at room temperature for 30 minutes. This solution was added to a solution consisting of methanesulfonic acid salt of exatecan (0.145 mg, 0.260 mmol), N,N-diisopropylethylamine (89.3 μL, 0.510 mmol), and N,N-dimethylformamide (0.200 mL) and stirred at room temperature for 1 hour. The solvent in the reaction solution was removed under reduced pressure and the residues obtained were purified by silica gel column chromatography [chloroform-chloroform:methanol=9:1 (v/v)] to yield the titled compound (197 mg, 82%).

$^1$H-NMR (400 MHz, DMSO-$d_6$) δ: 0.84 (3H, t, J=7.6 Hz), 1.33 (9H, s), 1.83 (2H, dq, J=25.4, 7.2 Hz), 2.03-2.13 (1H, m), 2.14-2.21 (1H, m), 2.38 (3H, s), 2.50-2.52 (2H, m), 2.74 (1H, dd, J=13.7, 9.3 Hz), 2.95 (1H, dd, J=13.7, 4.6 Hz), 3.12-3.18 (2H, m), 3.49-3.56 (3H, m), 3.62-3.76 (5H, m), 3.93-3.99 (1H, m), 4.37-4.43 (1H, m), 4.84-4.91 (1H, m), 5.20 (1H, d, J=18.8 Hz), 5.25 (1H, d, J=18.8 Hz), 5.36 (1H, d, J=16.1 Hz), 5.41 (1H, d, J=16.1 Hz), 5.53-5.58 (1H, m), 6.51 (1H, s), 6.71 (1H, d, J=7.8 Hz), 7.11-7.23 (5H, m), 7.29 (1H, s), 7.78 (1H, d, J=10.7 Hz), 7.96 (1H, t, J=5.9 Hz), 8.05 (1H, d, J=7.3 Hz), 8.11 (1H, d, J=5.4 Hz), 8.28-8.33 (1H, m), 8.40 (1H, d, J=8.3 Hz).

MS (ESI) m/z: 941 (M+H)$^+$.

Process 6: L-Serylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.190 g, 0.200 mmol) obtained in Process 5 above was dissolved in trifluoroacetic acid and left at room temperature for 1 hour. The solvent in the reaction solution was removed under reduced pressure and the residues obtained were charged with diethyl ether and stirred. Then, the solid obtained was collected by filtration to yield trifluoroacetic acid salt of the titled compound (175 mg, 91%).

$^1$H-NMR (400 MHz, DMSO-$d_6$) δ: 0.90 (3H, t, J=7.3 Hz), 1.81-1.95 (2H, m), 2.11-2.19 (1H, m), 2.19-2.26 (1H, m), 2.44 (3H, s), 2.79 (1H, dd, J=14.3, 10.0 Hz), 3.00 (1H, dd, J=14.3, 4.4 Hz), 3.18-3.24 (2H, m), 3.65 (1H, dd, J=16.6, 5.4 Hz), 3.69-3.83 (6H, m), 3.87 (1H, dd, J=16.6, 5.4 Hz), 3.90-3.95 (1H, m), 4.52 (1H, td, J=8.8, 4.2 Hz), 5.25 (1H, d, J=19.0 Hz), 5.30 (1H, d, J=19.0 Hz), 5.42 (1H, d, J=16.1 Hz), 5.47 (1H, d, J=16.1 Hz), 5.51 (1H, t, J=5.1 Hz), 5.58-5.63 (1H, m), 6.58 (1H, s), 7.17-7.29 (6H, m), 7.35 (1H, s), 7.85 (1H, d, J=10.7 Hz), 8.09-8.18 (3H, m), 8.43 (1H, t, J=5.6 Hz), 8.52 (1H, d, J=8.8 Hz), 8.70 (1H, t, J=5.6 Hz).

MS (ESI) m/z: 841 (M+H)$^+$.

Process 7: N-[6-(2,5-Dioxo-2,5-dihydro-1H-pyrrol-1-yl)hexanoyl]-L-serylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide To an N,N-dimethylformamide (2.00 mL) solution of the compound (90.0 mg, 94.3 μmol) obtained in Process 6 above, N-succinimidyl 6-maleimidohexanoate (32.0 mg, 0.100 μmol) and N,N-diisopropylethylamine (17.4 μL, 0.100 μmol) were added and stirred at room temperature for 1 hour. The solvent in the reaction solution was removed under reduced pressure and the residues obtained were purified by silica gel column chromatography [chloroform-chloroform:methanol=9:1 (v/v)] to yield the titled compound as a pale yellow solid (50 mg, 51%).

$^1$H-NMR (400 MHz, DMSO-$d_6$) δ: 0.87 (3H, t, J=7.3 Hz), 1.12-1.25 (2H, m), 1.41-1.51 (4H, m), 1.79-1.92 (2H, m), 2.09-2.15 (3H, m), 2.17-2.24 (1H, m), 2.41 (3H, s), 2.77 (1H, dd, J=13.9, 9.7 Hz), 2.98 (1H, dd, J=13.9, 4.5 Hz), 3.14-3.21 (2H, m), 3.35-3.38 (2H, m), 3.50-3.60 (3H, m), 3.63-3.76 (5H, m), 4.26 (1H, q, J=6.2 Hz), 4.43 (1H, td, J=8.5, 4.8 Hz), 4.94 (1H, t, J=5.4 Hz), 5.21 (1H, d, J=19.3 Hz), 5.27 (1H, d, J=19.3 Hz), 5.38 (1H, d, J=16.3 Hz), 5.44 (1H, d, J=16.3 Hz), 5.54-5.60 (1H, m), 6.53 (1H, s), 6.99 (2H, s), 7.13-7.25 (5H, m), 7.31 (1H, s), 7.80 (1H, d, J=11.5 Hz), 7.89 (1H, d, J=7.9 Hz), 7.99 (1H, t, J=5.7 Hz), 8.06 (1H, d, J=7.9 Hz), 8.15 (1H, t, J=5.4 Hz), 8.29-8.34 (1H, m), 8.41 (1H, d, J=8.5 Hz).

MS (ESI) m/z: 1034 (M+H)$^+$.

Process 8: Antibody-Drug Conjugate (131)

By using the trastuzumab produced in Reference Example 1 and the compound obtained in Process 7 above, the compound of interest was obtained in the same manner as Process 6 of Example 2.

Antibody concentration: 1.79 mg/mL, antibody yield: 5.4 mg (43%), and average number of conjugated drug molecules (n) per antibody molecule: 3.4.

Example 132 Antibody-Drug Conjugate (132)

[Formula 185]

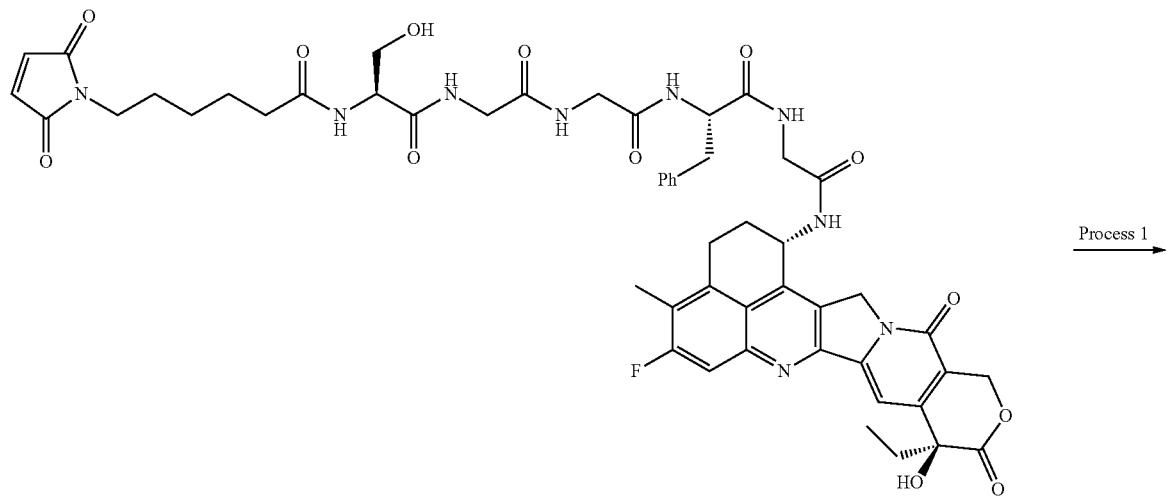

Process 1 →

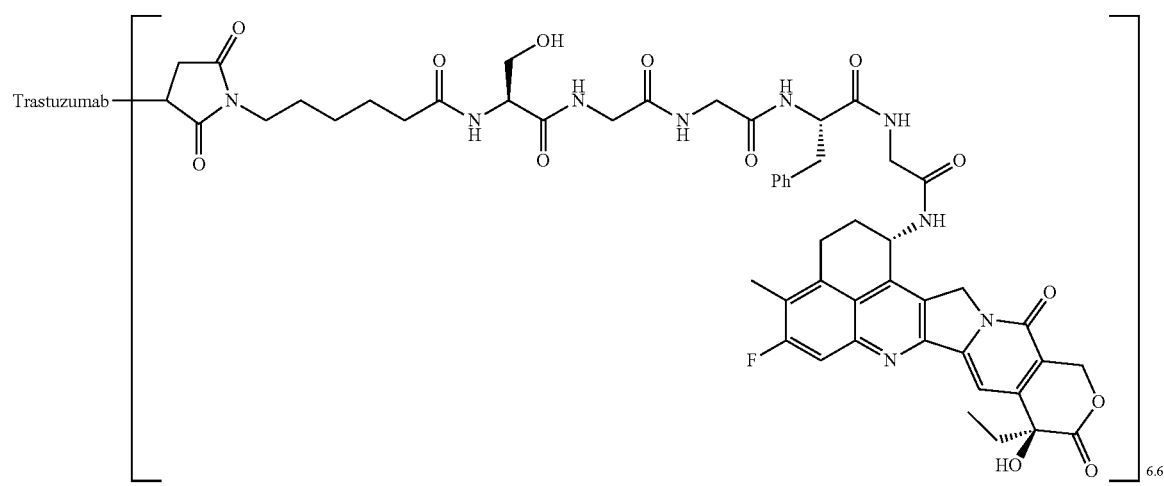

Process 1: Antibody-Drug Conjugate (132)

By using the trastuzumab produced in Reference Example 1 and the compound obtained in Process 7 of Example 131, the compound of interest was obtained in the same manner as Process 1 of Example 3.

Antibody concentration: 1.86 mg/mL, antibody yield: 10.7 mg (86%), and average number of conjugated drug molecules (n) per antibody molecule: 6.6.

Example 133 Antibody-Drug Conjugate (133)
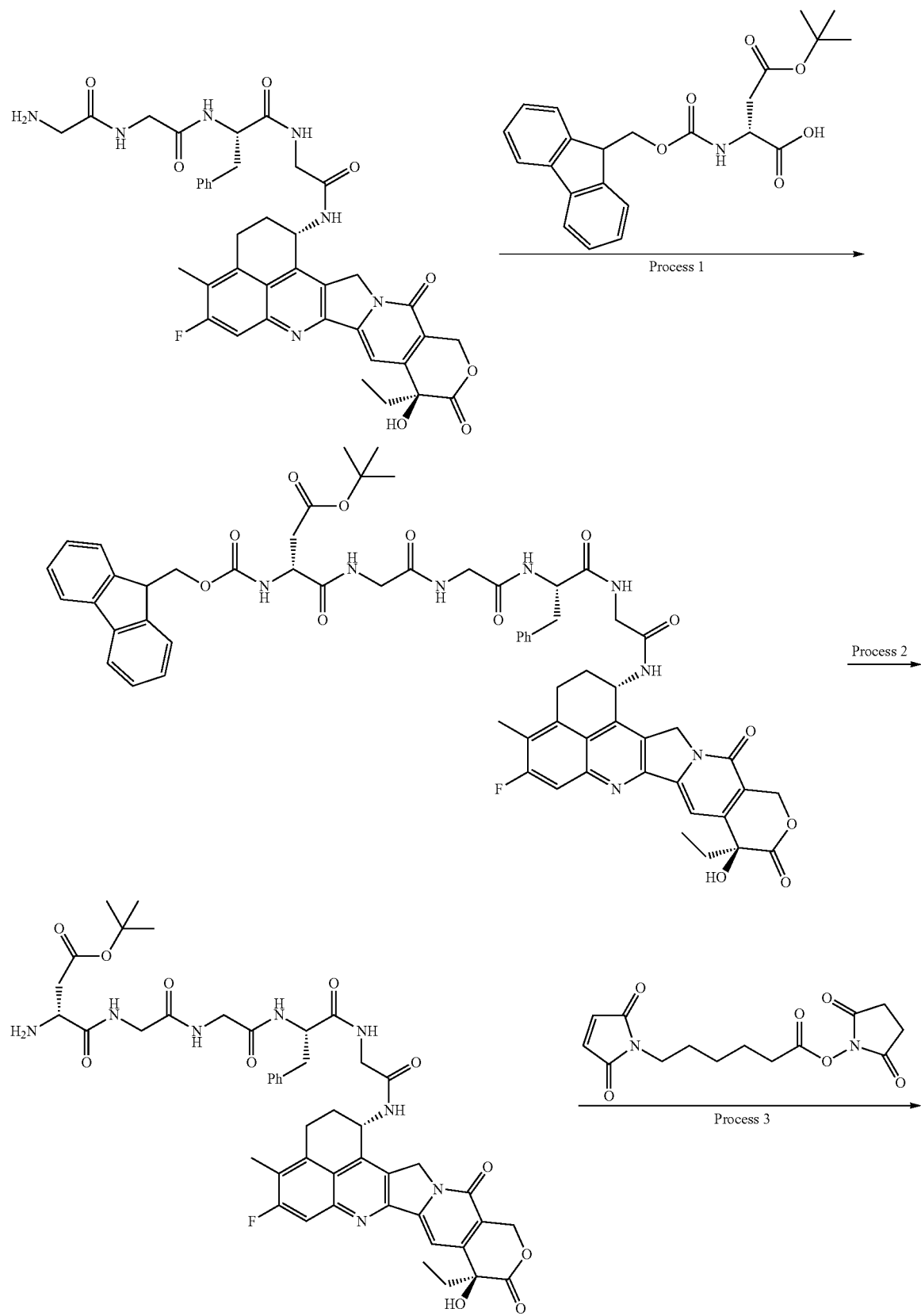
[Formula 186]

-continued
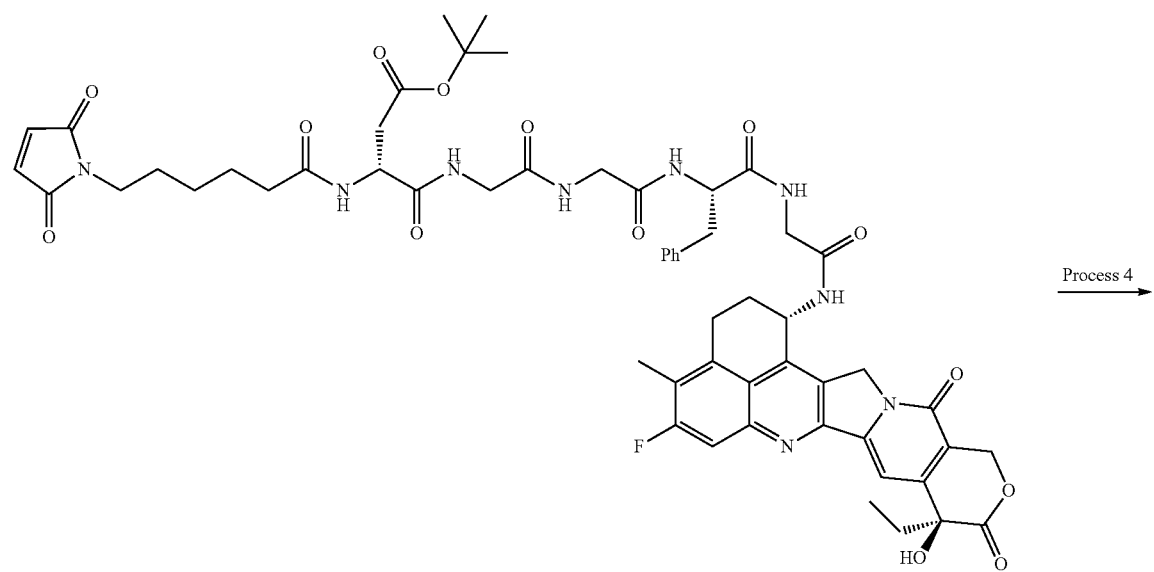
Process 4 →
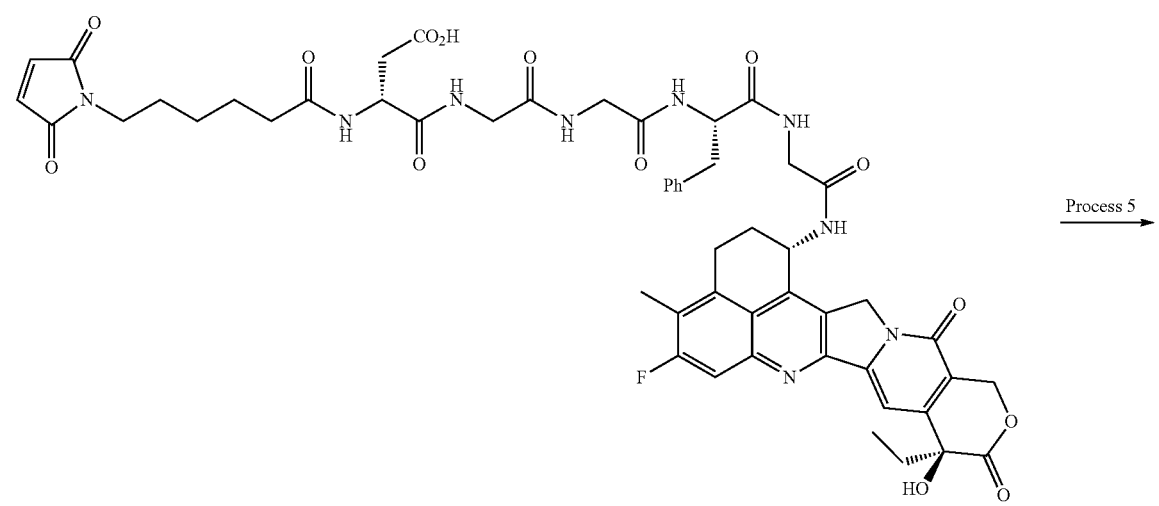
Process 5 →
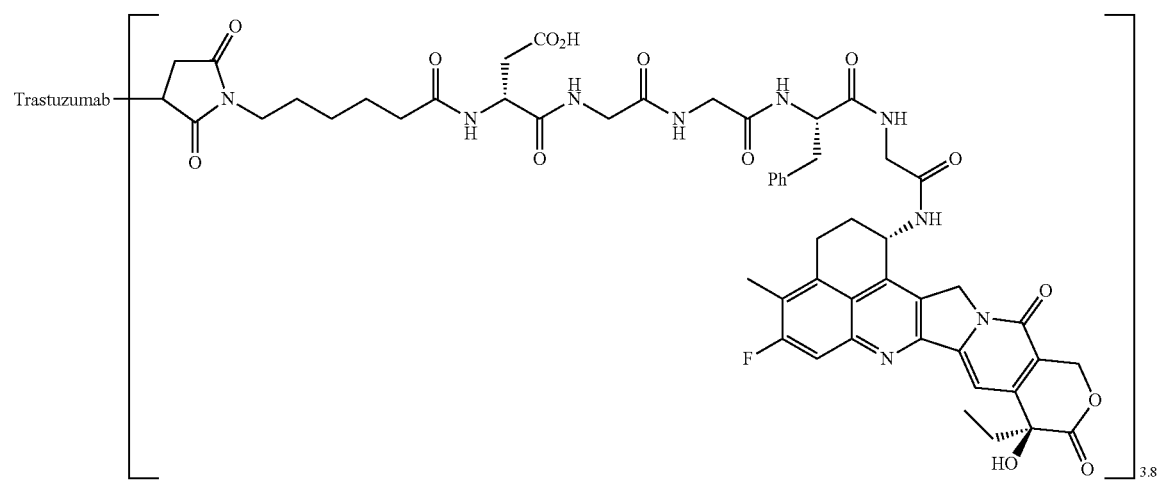

Process 1: tert-Butyl (5S,14R)-5-benzyl-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-14-{[(9H-fluoren-9-ylmethoxy)carbonyl]amino}-1,4,7,10,13-pentaoxo-3,6,9,12-tetraazahexadecan-16-oate To an N,N-dimethylformamide (1.00 mL) solution of N-hydroxysuccinimide (28.5 mg, 0.250 mmol) and N-[(9H-fluoren-9-ylmethoxy)carbonyl]-D-aspartic acid 4-tert-butyl (0.101 g, 0.250 mmol), 1-ethyl-3-(3-dimethylaminopropyl)carbodiimide hydrochloride (47.4 mg, 0.250 mmol) was added and stirred at room temperature for 30 minutes. This solution was added to a solution consisting of a free form of glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (International Publication No. WO 97/46260; 0.195 g, 0.225 mmol), N,N-diisopropylethylamine (78.4 μL, 0.450 mmol), and N,N-dimethylformamide (1.00 mL) and stirred at room temperature for 1 hour. The reaction solution was diluted with chloroform and washed with a 10% citric acid solution, and then the organic layer was dried over sodium sulfate. The solvent was removed under reduced pressure and the residues obtained were purified by silica gel column chromatography [chloroform-chloroform:methanol=9:1 (v/v)] to yield the titled compound (0.187 mg, 72%).

$^1$H-NMR (400 MHz, DMSO-$d_6$) δ: 0.86 (3H, t, J=6.7 Hz), 1.37 (9H, s), 1.77-1.92 (2H, m), 2.07-2.28 (2H, m), 2.40 (3H, s), 2.67-2.80 (2H, m), 2.98 (1H, d, J=10.3 Hz), 3.14-3.21 (2H, m), 3.50-3.60 (1H, m), 3.73-3.78 (5H, m), 4.15-4.35 (3H, m), 4.36-4.48 (2H, m), 5.24 (2H, s), 5.38 (1H, d, J=17.2 Hz), 5.43 (1H, d, J=17.2 Hz), 5.54-5.60 (1H, m), 6.53 (1H, d, J=1.8 Hz), 7.10-7.27 (5H, m), 7.30-7.37 (3H, m), 7.39 (2H, t, J=7.3 Hz), 7.69 (3H, t, J=7.3 Hz), 7.81 (1H, d, J=10.9 Hz), 7.87 (2H, d, J=7.9 Hz), 7.97-8.02 (1H, m), 8.08-8.13 (1H, m), 8.13-8.20 (1H, m), 8.32 (1H, d, J=1.8 Hz), 8.42 (1H, d, J=8.5 Hz).

MS (ESI) m/z: 1147 (M+H)$^+$.

Process 2: tert-Butyl (5S,14R)-14-amino-5-benzyl-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,4,7,10,13-pentaoxo-3,6,9,12-tetraazahexadecan-16-oate The compound (182 mg, 0.158 mmol) obtained in Process 1 above was reacted in the same manner as Process 2 of Example 73 to yield the titled compound (132 mg, 91%).

$^1$H-NMR (400 MHz, DMSO-$d_6$) δ: 0.87 (3H, t, J=7.0 Hz), 1.06 (1H, t, J=6.7 Hz), 1.37 (9H, s), 1.78-2.04 (4H, m), 2.04-2.26 (2H, m), 2.34 (1H, dd, J=16.3, 7.3 Hz), 2.41 (3H, s), 2.56-2.60 (1H, m), 2.77 (1H, dd, J=9.1, 13.9 Hz), 2.99 (1H, dd, J=13.9, 4.2 Hz), 3.15-3.21 (2H, m), 3.40-3.58 (3H, m), 3.64-3.76 (4H, m), 4.39-4.46 (1H, m), 5.22 (1H, d, J=19.6 Hz), 5.28 (1H, d, J=19.6 Hz), 5.38 (1H, d, J=16.6 Hz), 5.44 (1H, d, J=16.6 Hz), 5.54-5.61 (1H, m), 6.53 (1H, s), 7.13-7.26 (5H, m), 7.31 (1H, s), 7.81 (1H, d, J=10.9 Hz), 8.01 (1H, t, J=5.7 Hz), 8.08 (1H, d, J=7.9 Hz), 8.21-8.33 (2H, m), 8.41 (1H, d, J=9.1 Hz).

MS (ESI) m/z: 925 (M+H)$^+$.

Process 3: tert-Butyl (5S,14R)-5-benzyl-14-{[6-(2,5-dioxo-2,5-dihydro-1H-pyrrol-1-yl)hexanoyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,4,7,10,13-pentaoxo-3,6,9,12-tetraazahexadecan-16-oate The compound (130 mg, 0.140 mmol) obtained in Process 2 above was reacted in the same manner as Process 3 of Example 73 to yield the titled compound (85.0 mg, 54%).

$^1$H-NMR (400 MHz, DMSO-$d_6$) δ: 0.87 (3H, t, J=7.5 Hz), 1.12-1.23 (2H, m), 1.35 (9H, s), 1.40-1.50 (4H, m), 1.80-1.91 (2H, m), 2.04-2.18 (3H, m), 2.18-2.21 (1H, m), 2.41 (3H, s), 2.63-2.71 (1H, m), 2.77 (1H, dd, J=14.2, 9.7 Hz), 2.98 (1H, dd, J=14.2, 4.5 Hz), 3.15-3.20 (2H, m), 3.26-3.38 (3H, m), 3.54 (1H, dd, J=16.3, 5.4 Hz), 3.64-3.75 (4H, m), 4.39-4.46 (1H, m), 4.55-4.62 (1H, m), 5.22 (1H, d, J=19.3 Hz), 5.28 (1H, d, J=19.3 Hz), 5.38 (1H, d, J=16.0 Hz), 5.44 (1H, d, J=16.0 Hz), 5.54-5.61 (1H, m), 6.53 (1H, s), 6.99 (2H, t, J=14.8 Hz), 7.13-7.25 (5H, m), 7.31 (1H, s), 7.81 (1H, d, J=10.9 Hz), 7.95 (1H, t, J=5.7 Hz), 8.04-8.15 (3H, m), 8.27-8.33 (1H, m), 8.42 (1H, d, J=9.1 Hz).

MS (ESI) m/z: 1147 (M+H)$^+$.

Process 4: N-[6-(2,5-Dioxo-2,5-dihydro-1H-pyrrol-1-yl)hexanoyl]-D-α-aspartylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (85.0 mg, 0.0760 mmol) obtained in Process 3 above was reacted in the same manner as Process 2 of Example 1 to yield the titled compound as a pale yellow solid (20.0 mg, 25%).

$^1$H-NMR (400 MHz, DMSO-$d_6$) δ: 0.87 (3H, t, J=7.3 Hz), 1.11-1.21 (2H, m), 1.39-1.50 (4H, m), 1.80-1.91 (2H, m), 2.05-2.16 (3H, m), 2.17-2.25 (1H, m), 2.40 (3H, s), 2.44-2.47 (2H, m), 2.81 (1H, dd, J=13.4, 10.4 Hz), 2.99 (1H, dd, J=13.4, 4.3 Hz), 3.15-3.20 (2H, m), 3.57-3.78 (6H, m), 4.30-4.40 (1H, m), 4.51 (1H, q, J=6.9 Hz), 5.27 (2H, s), 5.38 (1H, d, J=16.5 Hz), 5.43 (1H, d, J=16.5 Hz), 5.53-5.60 (1H, m), 6.53 (1H, s), 6.97 (2H, s), 7.13-7.27 (7H, m), 7.31 (1H, s), 7.80 (1H, d, J=11.0 Hz), 8.00-8.10 (4H, m), 8.49 (2H, d, J=7.9 Hz), 12.40 (1H, brs).

MS (ESI) m/z: 1062 (M+H)$^+$.

Process 5: Antibody-Drug Conjugate (133)

By using the trastuzumab produced in Reference Example 1 and the compound obtained in Process 4 above, the compound of interest was obtained in the same manner as Process 6 of Example 2.

Antibody concentration: 1.63 mg/mL, antibody yield: 9.8 mg (78%), and average number of conjugated drug molecules (n) per antibody molecule: 3.8.

Example 134 Antibody-Drug Conjugate (134)

[Formula 187]

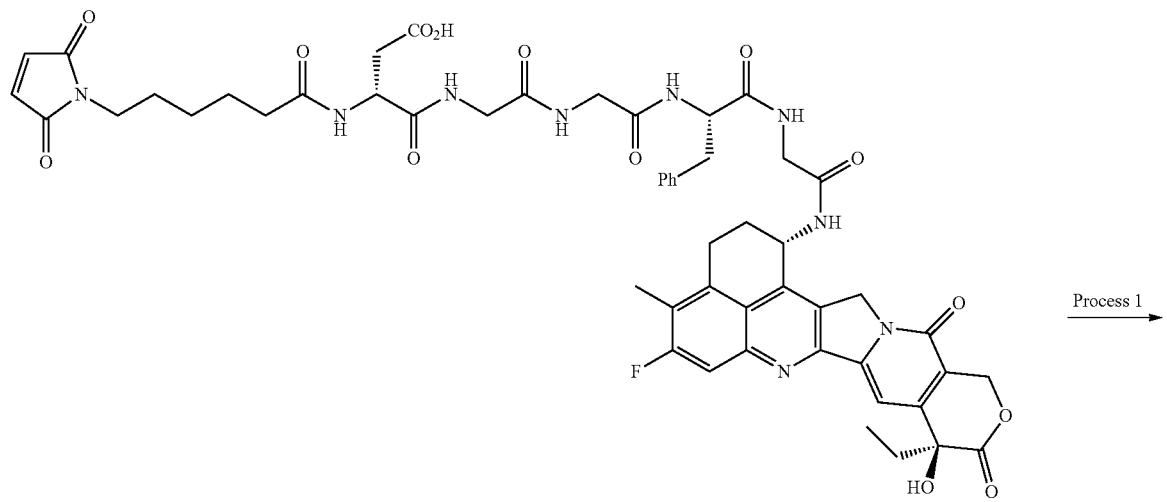

Process 1

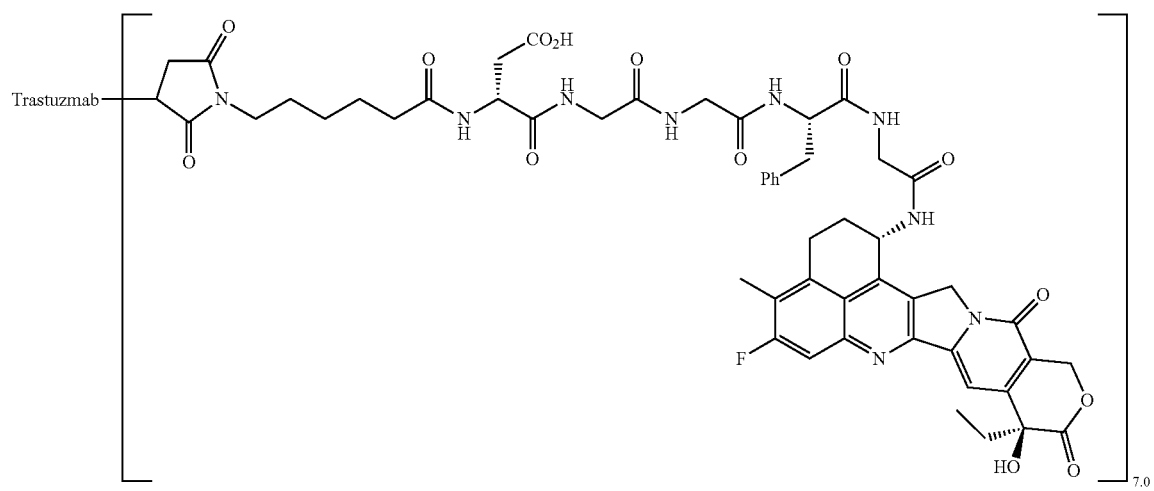

Process 1: Antibody-Drug Conjugate (134)

By using the trastuzumab produced in Reference Example 1 and the compound obtained in Process 4 of Example 133, the compound of interest was obtained in the same manner as Process 1 of Example 3.

Antibody concentration: 1.66 mg/mL, antibody yield: 10 mg (80%), and average number of conjugated drug molecules (n) per antibody molecule: 7.0.

Example 135 Antibody-Drug Conjugate (135)
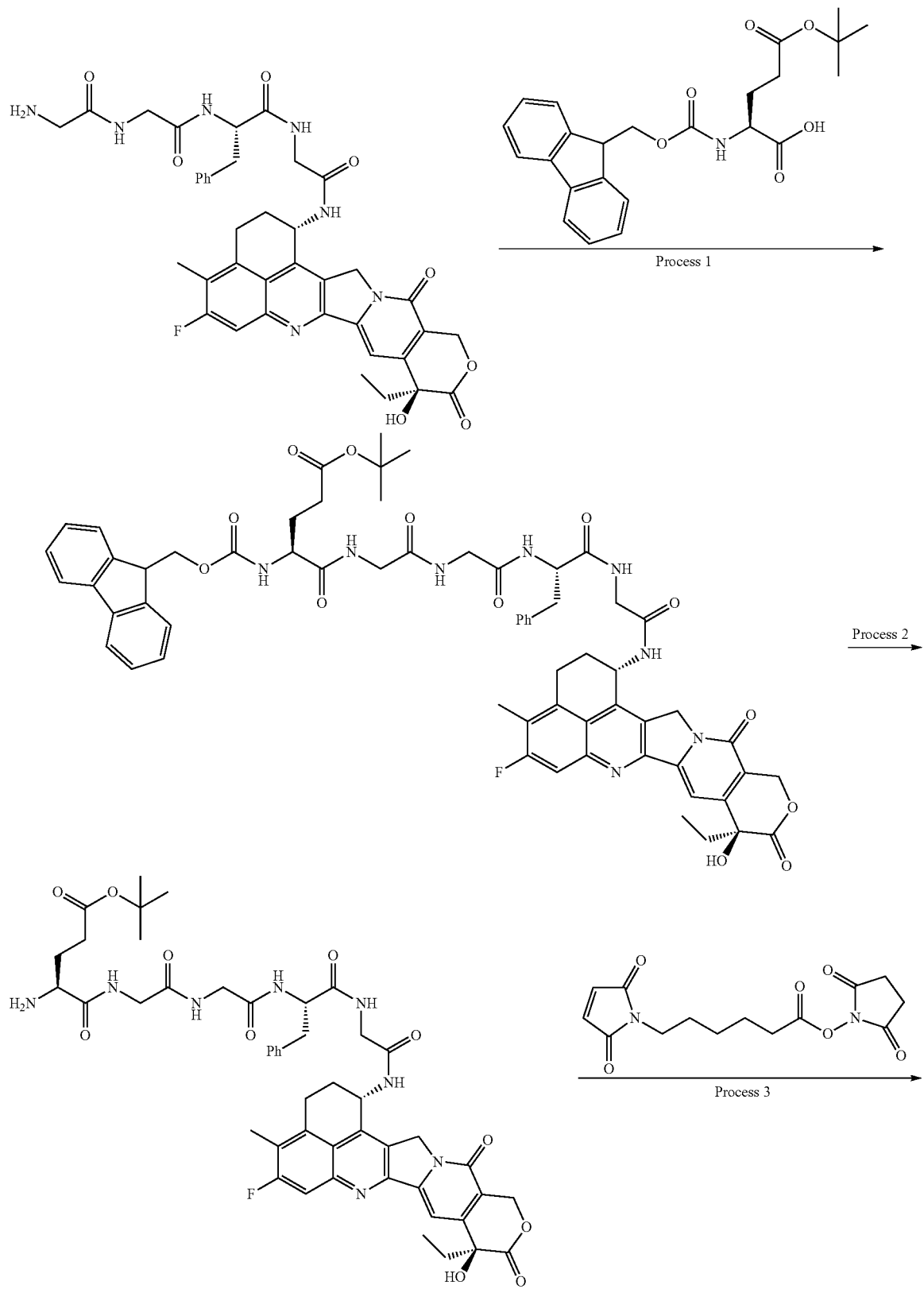
[Formula 188]

547
548
-continued
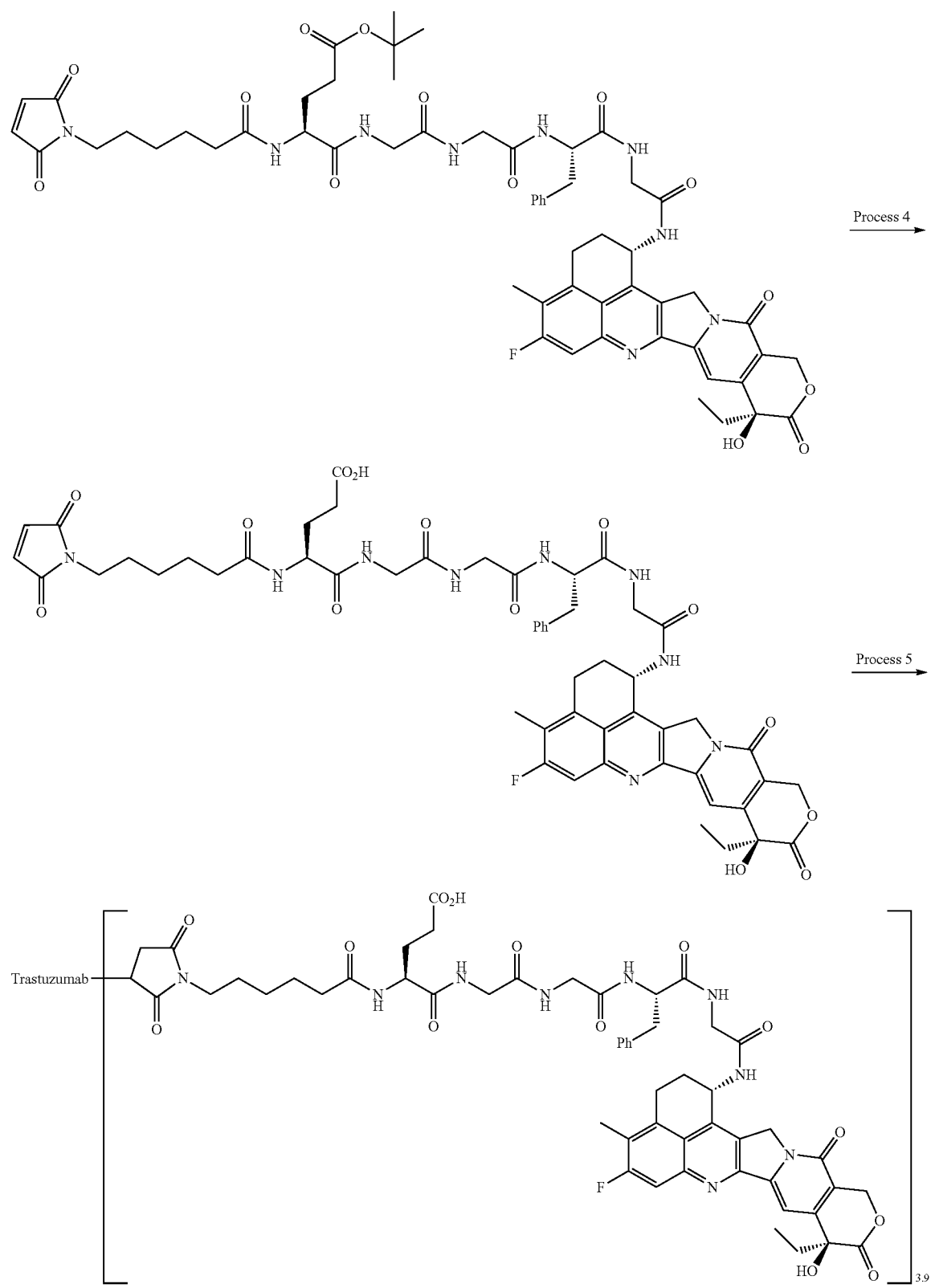

Process 1: tert-Butyl (5S,14S)-5-benzyl-1-{[(1S, 9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-14-{[(9H-fluoren-9-ylmethoxy)carbonyl]amino}-1,4,7,10,13-pentaoxo-3,6,9,12-tetraazaheptadecan-17-oate To an N,N-dimethylformamide (5.00 mL) solution of a free form of glycylglycyl-L-phenylalanyl-N-[(1S,9S)-9-ethyl-5-fluoro-9-hydroxy-4-methyl-10,13-dioxo-2,3,9,10, 13,15-hexahydro-1H,12H-benzo[de]pyrano[3',4':6,7]indolizino[1,2-b]quinolin-1-yl]glycinamide (International Publication No. WO 97/46260; 0.316 g, 0.360 mmol), 1-hydroxybenzotriazole (61.4 mg, 0.400 mmol), N-[(9H-fluoren-9-ylmethoxy)carbonyl]-L-glutamic acid 5-tert-butyl (0.175 g, 0.400 mmol), and triethylamine (0.178 mL, 1.28 mmol), 1-ethyl-3-(3-dimethylaminopropyl)carbodiimide hydrochloride (76.8 mg, 0.400 mmol) was added and stirred overnight at room temperature. The solvent was removed under reduced pressure and the residues obtained were purified by silica gel column chromatography [chloroform-chloroform:methanol=9:1 (v/v)] to yield the titled compound (0.215 g, 51%).

$^1$H-NMR (400 MHz, DMSO-$d_6$) δ: 0.89 (3H, t, J=7.3 Hz), 1.40 (9H, s), 1.74-2.03 (4H, m), 2.08-2.17 (1H, m), 2.19-2.30 (3H, m), 2.43 (3H, s), 2.81 (1H, dd, J=13.9, 9.5 Hz), 3.01 (1H, dd, J=13.7, 4.4 Hz), 3.17-3.22 (2H, m), 3.57 (1H, dd, J=16.6, 5.4 Hz), 3.66-3.78 (5H, m), 3.88-3.95 (1H, m), 4.21-4.34 (3H, m), 4.42-4.48 (1H, m), 5.26 (2H, s), 5.41 (1H, d, J=16.1 Hz), 5.45 (1H, d, J=16.1 Hz), 5.57-5.62 (1H, m), 6.57 (1H, s), 7.16-7.27 (5H, m), 7.32-7.36 (3H, m), 7.42 (2H, td, J=7.4, 2.8 Hz), 7.74 (3H, d, J=7.3 Hz), 7.83 (1H, d, J=11.2 Hz), 7.90 (2H, d, J=7.3 Hz), 8.05-8.12 (2H, m), 8.19 (1H, t, J=5.6 Hz), 8.34 (1H, t, J=5.9 Hz), 8.45 (1H, d, J=8.8 Hz).

MS (ESI) m/z: 1161 (M+H)$^+$.

Process 2: tert-Butyl (5S,14S)-14-amino-5-benzyl-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,4,7,10,13-pentaoxo-3,6,9,12-tetraazaheptadecan-17-oate The compound (185 mg, 0.160 mmol) obtained in Process 1 above was reacted in the same manner as Process 2 of Example 73 to yield the titled compound (110 mg, 73%).

$^1$H-NMR (400 MHz, DMSO-$d_6$) δ: 0.87 (3H, t, J=7.0 Hz), 1.05 (1H, td, J=7.1, 1.6 Hz), 1.40 (9H, s), 1.57-1.69 (1H, m), 1.76-1.92 (3H, m), 2.06-2.15 (1H, m), 2.16-2.25 (3H, m), 2.41 (3H, s), 2.54 (3H, d, J=1.2 Hz), 2.77 (1H, dd, J=13.9, 9.7 Hz), 2.98 (1H, dd, J=13.9, 4.2 Hz), 3.23-3.28 (1H, m), 3.44 (1H, ddd, J=13.9, 6.7, 1.2 Hz), 3.53 (1H, dd, J=17.2, 5.1 Hz), 3.62-3.68 (2H, m), 3.69-3.75 (2H, m), 4.38-4.46 (1H, m), 5.21 (1H, d, J=19.3 Hz), 5.28 (1H, d, J=19.3 Hz), 5.38 (1H, d, J=16.3 Hz), 5.43 (1H, d, J=16.3 Hz), 5.54-5.60 (1H, m), 6.54 (1H, brs), 7.13-7.26 (5H, m), 7.32 (1H, s), 7.81 (1H, d, J=10.9 Hz), 8.02-8.09 (2H, m), 8.21-8.15 (3H, m), 8.29-8.34 (1H, m), 8.42 (1H, d, J=8.5 Hz).

MS (ESI) m/z: 939 (M+H)$^+$.

Process 3: tert-Butyl (5S,14S)-5-benzyl-14-{[6-(2,5-dioxo-2,5-dihydro-1H-pyrrol-1-yl)hexanoyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,4,7,10,13-pentaoxo-3,6,9,12-tetraazaheptadecan-17-oate The compound (110 mg, 0.117 mmol) obtained in Process 2 above was reacted in the same manner as Process 3 of Example 73 to yield the titled compound (113 mg, 85%).

$^1$H-NMR (400 MHz, DMSO-$d_6$) δ: 0.86 (3H, t, J=7.3 Hz), 1.13-1.24 (2H, m), 1.36 (9H, s), 1.41-1.53 (4H, m), 1.67-1.79 (1H, m), 1.79-1.95 (3H, m), 2.03-2.10 (3H, m), 2.13-2.22 (3H, m), 2.41 (3H, s), 2.45-2.48 (1H, m), 2.77 (1H, dd, J=13.9, 9.1 Hz), 2.98 (1H, dd, J=13.6, 4.5 Hz), 3.14-3.22 (2H, m), 3.34-3.38 (2H, m), 3.53 (1H, dd, J=16.6, 5.7 Hz), 3.65 (2H, d, J=5.4 Hz), 3.71 (2H, dd, J=12.4, 5.7 Hz), 4.01-4.08 (1H, m), 4.38-4.45 (1H, m), 5.22 (1H, d, J=19.0 Hz), 5.28 (1H, d, J=19.0 Hz), 5.38 (1H, d, J=16.3 Hz), 5.44 (1H, d, J=16.3 Hz), 5.54-5.60 (1H, m), 6.53 (1H, s), 6.99 (2H, s), 7.13-7.25 (5H, m), 7.31 (1H, s), 7.81 (1H, d, J=10.9 Hz), 8.00-8.09 (3H, m), 8.14 (1H, t, J=5.7 Hz), 8.28-8.33 (1H, m), 8.41 (1H, d, J=8.5 Hz).

MS (ESI) m/z: 1133 (M+H)$^+$.

Process 4: N-[6-(2,5-Dioxo-2,5-dihydro-1H-pyrrol-1-yl)hexanoyl]-L-α-glutamylglycylglycyl-L-phenylalanyl-N-[(1S,9S)-9-ethyl-5-fluoro-9-hydroxy-4-methyl-10,13-dioxo-2,3,9,10,13,15-hexahydro-1H, 12H-benzo[de]pyrano[3',4':6,7]indolizino[1,2-b]quinolin-1-yl]glycinamide The compound (113 mg, 0.0998 mmol) obtained in Process 3 above was reacted in the same manner as Process 2 of Example 1 to yield the titled compound as a pale yellow solid (85.0 mg, 80%).

$^1$H-NMR (400 MHz, DMSO-$d_6$) δ: 0.89 (3H, t, J=7.2 Hz), 1.15-1.24 (2H, m), 1.44-1.53 (4H, m), 1.70-2.02 (4H, m), 2.10 (2H, t, J=7.4 Hz), 2.21 (2H, t, J=7.8 Hz), 2.43 (3H, s), 2.79 (1H, dd, J=13.7, 9.4 Hz), 3.00 (1H, dd, J=13.7, 4.3 Hz), 3.16-3.23 (2H, m), 3.40-3.44 (1H, m), 3.55 (1H, dd, J=16.8, 5.5 Hz), 3.67 (2H, d, J=5.5 Hz), 3.73 (2H, dd, J=14.1, 5.9 Hz), 4.12-4.19 (1H, m), 4.40-4.47 (1H, m), 5.24 (1H, d, J=19.2 Hz), 5.30 (1H, d, J=19.2 Hz), 5.40 (1H, d, J=16.2 Hz), 5.46 (1H, d, J=16.2 Hz), 5.57-5.63 (1H, m), 6.52-6.58 (1H, m), 7.01 (2H, s), 7.15-7.27 (5H, m), 7.34 (1H, s), 7.83 (1H, d, J=11.0 Hz), 8.03 (1H, t, J=5.9 Hz), 8.08 (2H, d, J=7.8 Hz), 8.15 (1H, t, J=5.7 Hz), 8.32 (1H, t, J=6.1 Hz), 8.43 (1H, d, J=8.2 Hz), 12.54 (1H, s).

MS (ESI) m/z: 1076 (M+H)$^+$.

Process 5: Antibody-Drug Conjugate (135)

By using the trastuzumab produced in Reference Example 1 and the compound obtained in Process 4 above, the compound of interest was obtained in the same manner as Process 6 of Example 2.

Antibody concentration: 1.61 mg/mL, antibody yield: 9.7 mg (78%), and average number of conjugated drug molecules (n) per antibody molecule: 3.9.

Example 136 Antibody-Drug Conjugate (136)

[Formula 189]

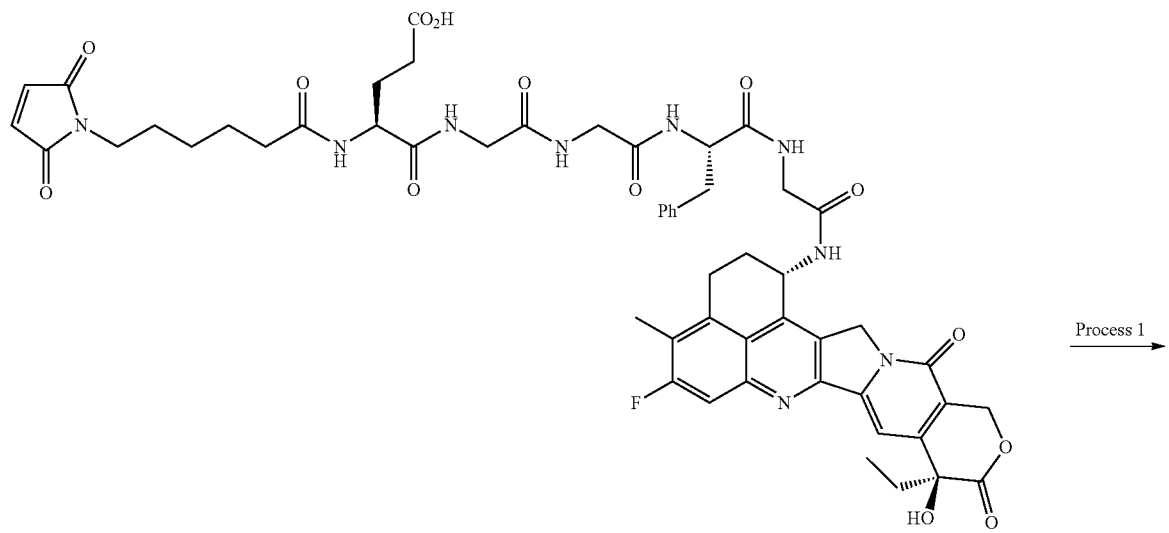

Process 1 →

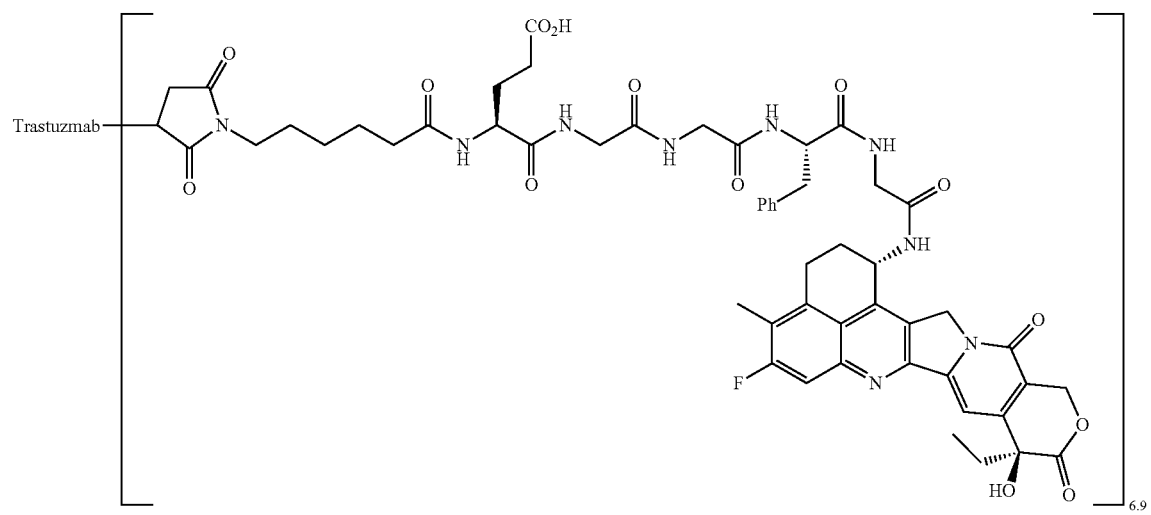

Process 1: Antibody-Drug Conjugate (136)

By using the trastuzumab produced in Reference Example 1 and the compound obtained in Process 4 of Example 135, the compound of interest was obtained in the same manner as Process 1 of Example 3.

Antibody concentration: 1.60 mg/mL, antibody yield: 9.6 mg (77%), and average number of conjugated drug molecules (n) per antibody molecule: 6.9.

Example 137 Antibody-Drug Conjugate (137)
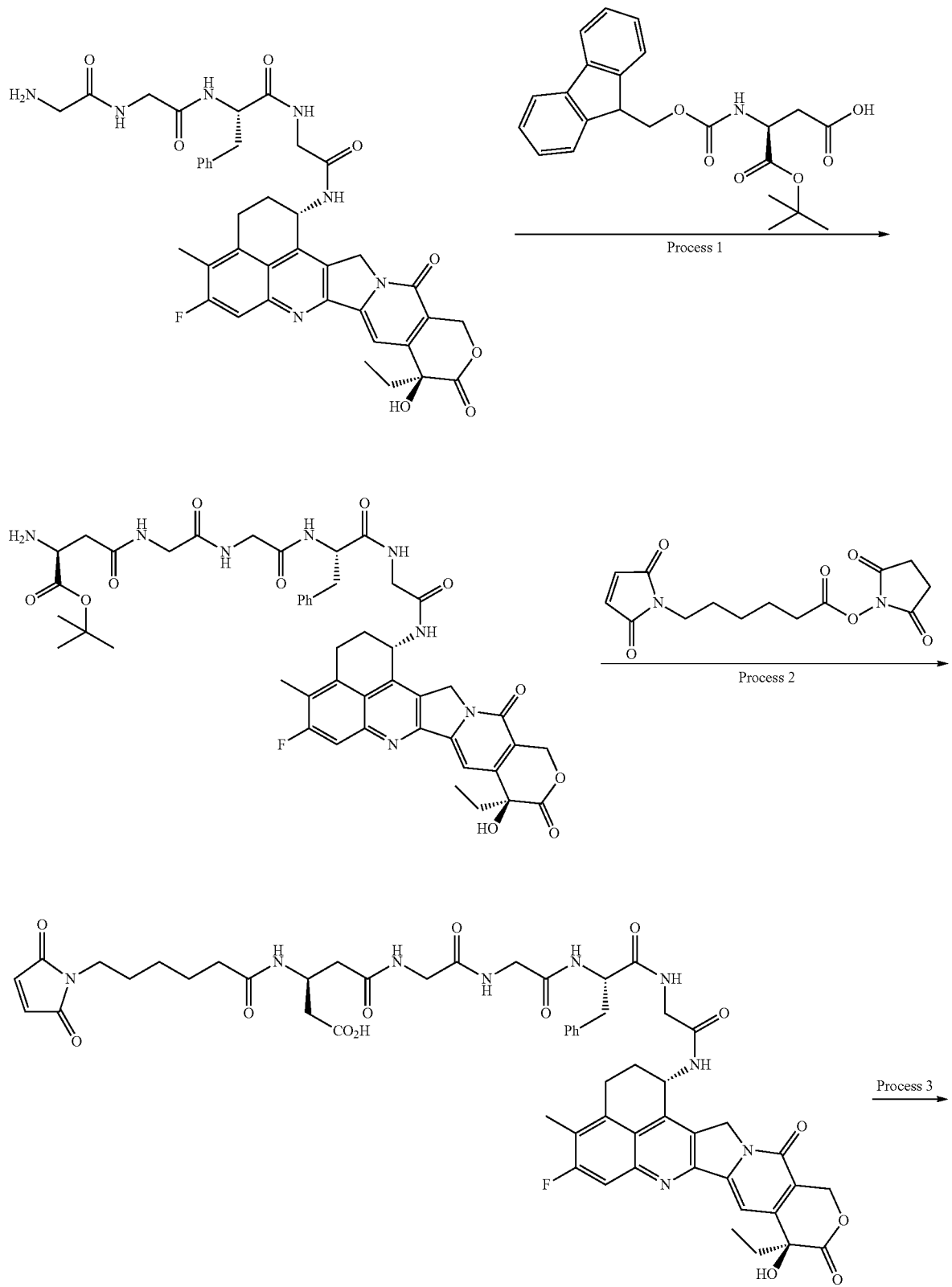
[Formula 190]

-continued

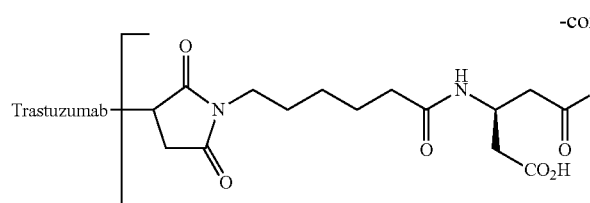
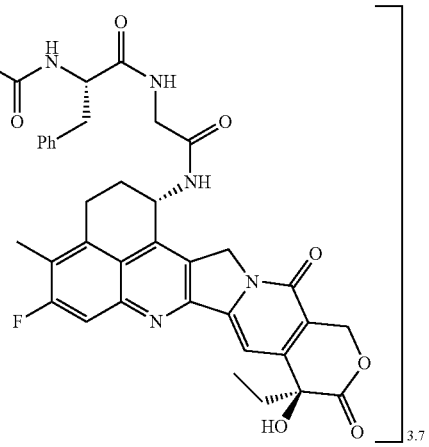

Process 1: tert-Butyl (5S,15S)-15-amino-5-benzyl-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,4,7,10,13-pentaoxo-3,6,9,12-tetraazahexadecan-16-oate A free form of glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (International Publication No. WO 97/46260; 150 mg, 0.199 mmol) was reacted in the same manner as Process 1 of Example 73 by using N-[(9H-fluoren-9-ylmethoxy)carbonyl]-L-aspartic acid 1-tert-butyl instead of N-[(9H-fluoren-9-ylmethoxy)carbonyl]-L-aspartic acid 4-tert-butyl and the crude product obtained was reacted in the same manner as Process 2 of Example 73 to yield the titled compound (72.0 mg, 39%).

$^1$H-NMR (400 MHz, DMSO-$d_6$) δ: 0.87 (3H, t, J=6.5 Hz), 1.38 (9H, s), 1.79-1.92 (2H, m), 2.06-2.15 (1H, m), 2.15-2.24 (1H, m), 2.25-2.35 (1H, m), 2.41 (3H, br.s.), 2.45-2.58 (2H, m), 2.71-2.82 (1H, m), 2.93-3.04 (1H, m), 3.10-3.23 (2H, m), 3.29-3.37 (2H, m), 3.41-3.79 (6H, m), 4.32-4.48 (1H, m), 5.16-5.33 (1H, m), 5.36-5.46 (2H, m), 5.53-5.63 (1H, m), 6.55 (1H, s), 7.12-7.26 (5H, m), 7.31 (1H, s), 7.81 (1H, d, J=10.6 Hz), 7.94-8.04 (1H, m), 8.24-8.39 (3H, m), 8.43 (1H, d, J=7.4 Hz).

Process 2: N-[6-(2,5-Dioxo-2,5-dihydro-1H-pyrrol-1-yl)hexanoyl]-L-β-aspartylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-yl]glycinamide The compound (72.0 mg, 0.0778 mol) obtained in Process 1 above was reacted in the same manner as Process 3 of Example 73, and the crude product obtained was reacted in the same manner as Process 1 of Example 2 to yield the titled compound as a solid (31.0 mg, 37%).

$^1$H-NMR (400 MHz, DMSO-$d_6$) δ: 0.87 (3H, t, J=7.4 Hz), 1.11-1.22 (2H, m), 1.34-1.52 (4H, m), 1.85 (2H, m, J=8.2 Hz), 1.94-2.02 (2H, m), 2.03-2.13 (1H, m), 2.15-2.25 (1H, m), 2.31-2.60 (2H, m), 2.38 (3H, s), 2.77-2.88 (1H, m), 2.99 (1H, dd, J=13.3, 3.5 Hz), 3.12-3.21 (2H, m), 3.28-3.41 (2H, m), 3.41-3.83 (6H, m), 4.05-4.33 (2H, m), 5.20 (1H, d, J=19.6 Hz), 5.26 (1H, d, J=19.2 Hz), 5.41 (2H, dd, J=19.6, 16.4 Hz), 5.51-5.59 (1H, m), 6.52 (1H, s), 7.00 (2H, s), 7.12-7.27 (5H, m), 7.30 (1H, s), 7.77 (1H, d, J=10.2 Hz), 7.83-8.06 (2H, m), 8.28-9.04 (3H, m), 8.47 (1H, d, J=8.6 Hz), 12.39-12.69 (1H, m).

MS (ESI) m/z: 1062 (M+H)$^+$.

Process 3: Antibody-Drug Conjugate (137)

By using the trastuzumab produced in Reference Example 1 and the compound obtained in Process 2 above, the compound of interest was obtained in the same manner as Process 6 of Example 2.

Antibody concentration: 1.52 mg/mL, antibody yield: 9.1 mg (73%), and average number of conjugated drug molecules (n) per antibody molecule: 3.7.

Example 138 Antibody-Drug Conjugate (138)

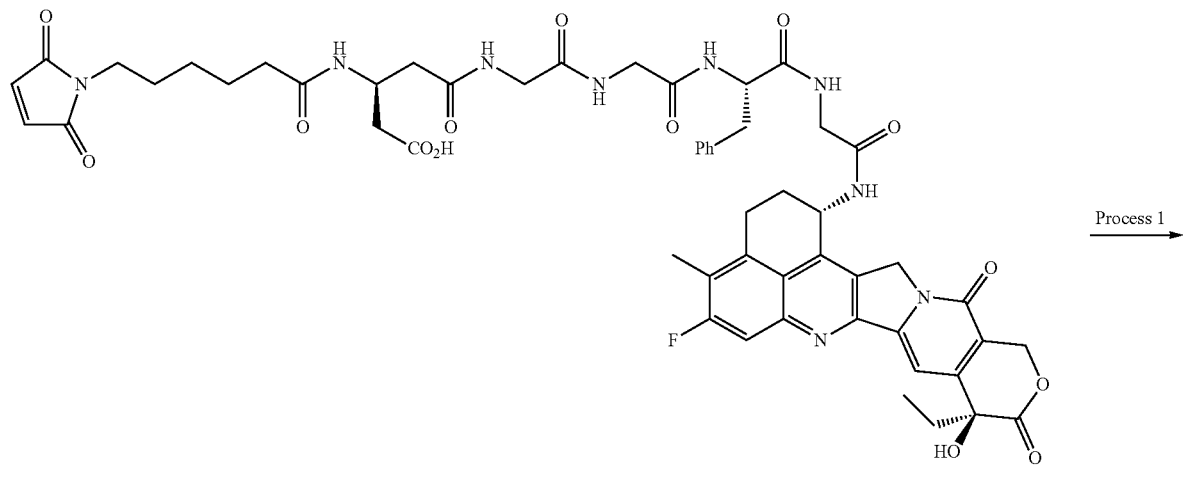

[Formula 191]

Process 1

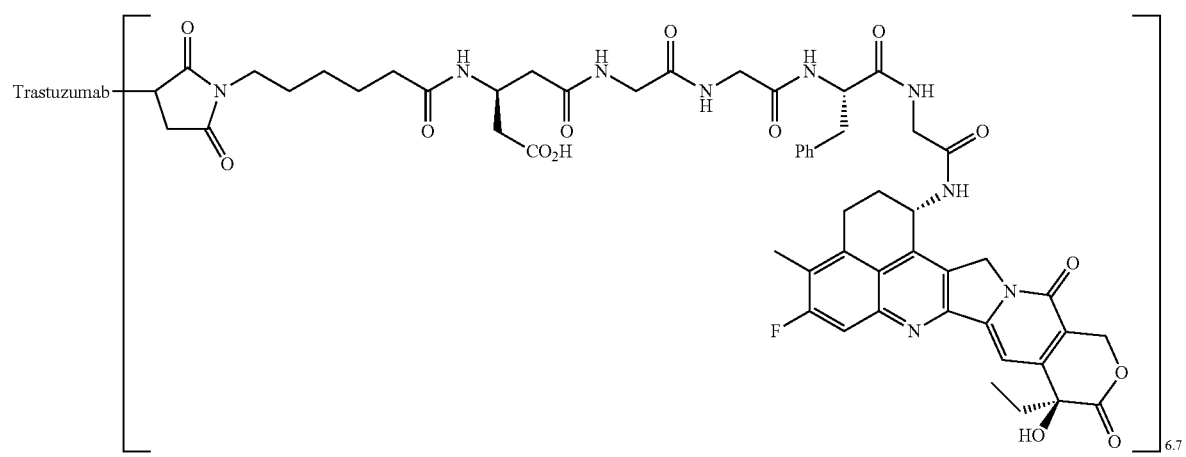

Process 1: Antibody-Drug Conjugate (138)

By using the trastuzumab produced in Reference Example 1 and the compound obtained in Process 2 of Example 137, the compound of interest was obtained in the same manner as Process 1 of Example 3.

Antibody concentration: 1.51 mg/mL, antibody yield: 9.1 mg (73%), and average number of conjugated drug molecules (n) per antibody molecule: 6.7.

Example 139 Antibody-Drug Conjugate (139)
[Formula 192]
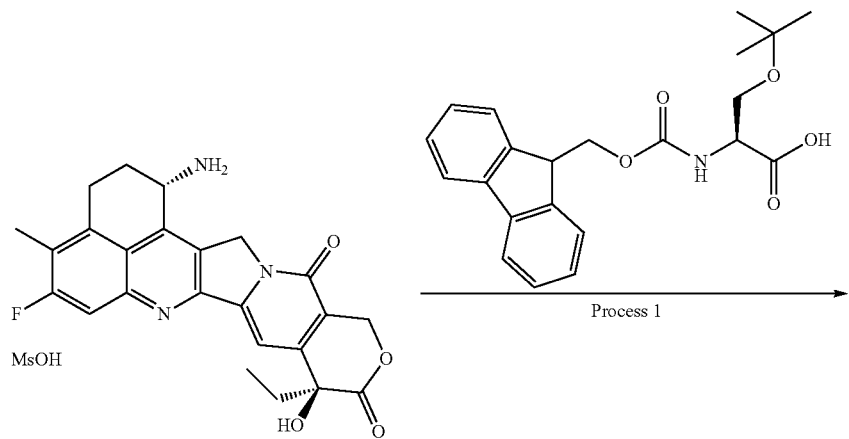
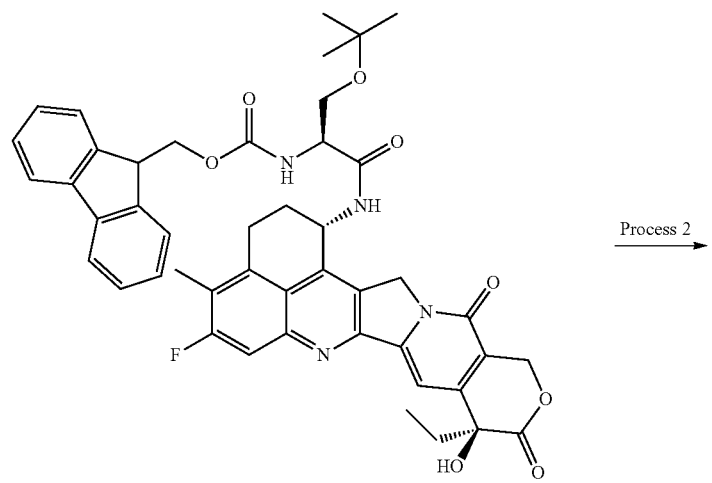
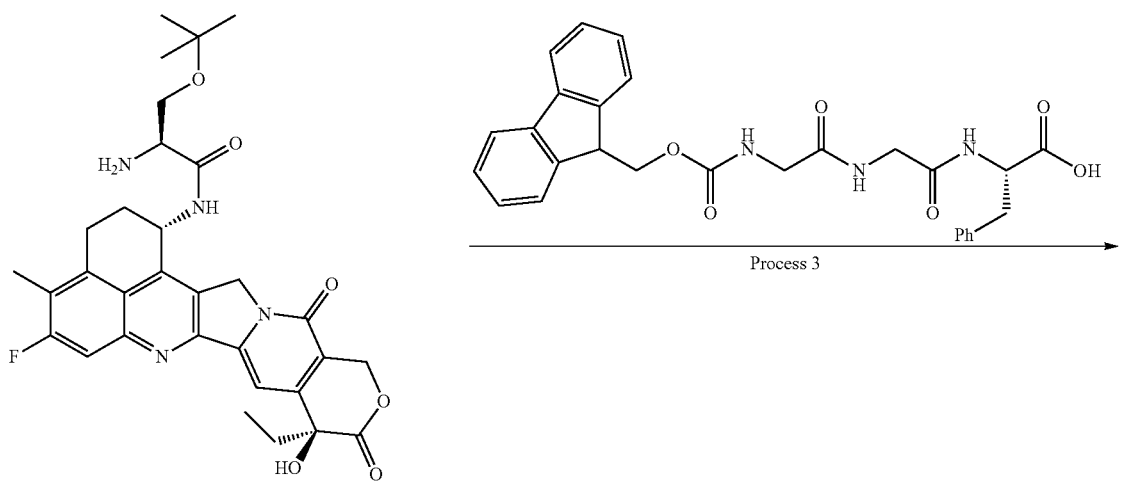

561
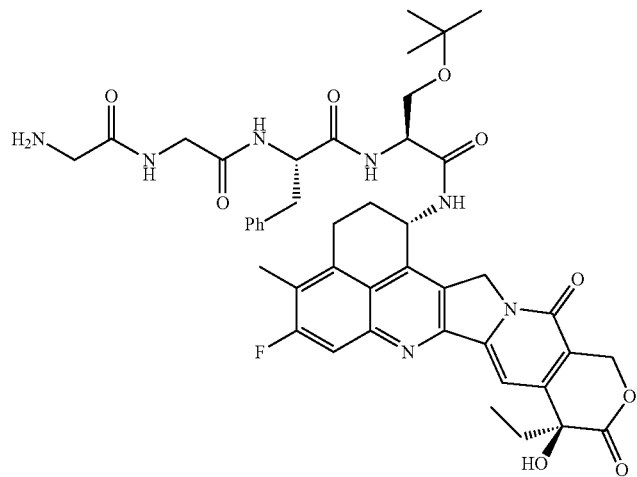
562
-continued
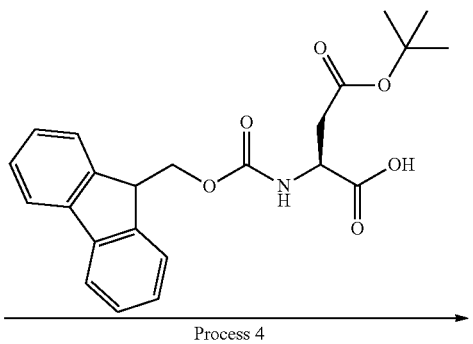
Process 4
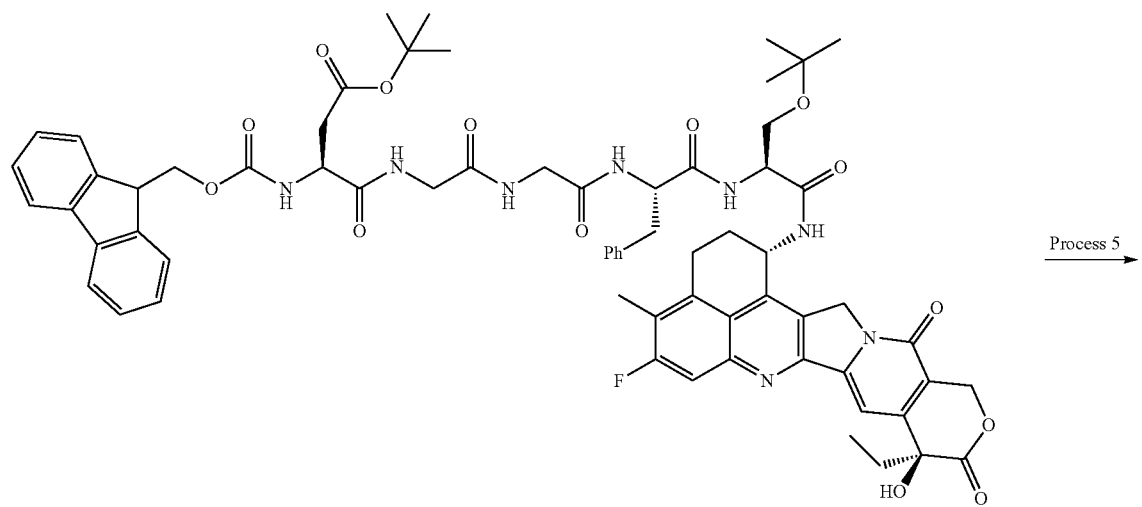
Process 5
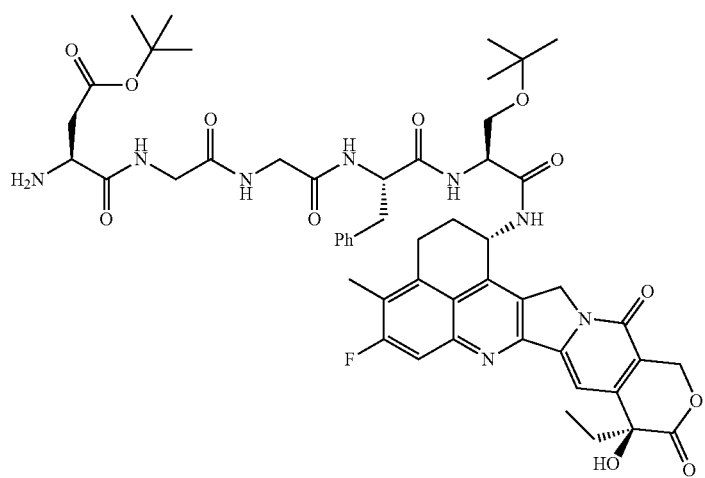
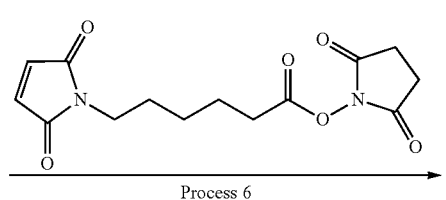
Process 6

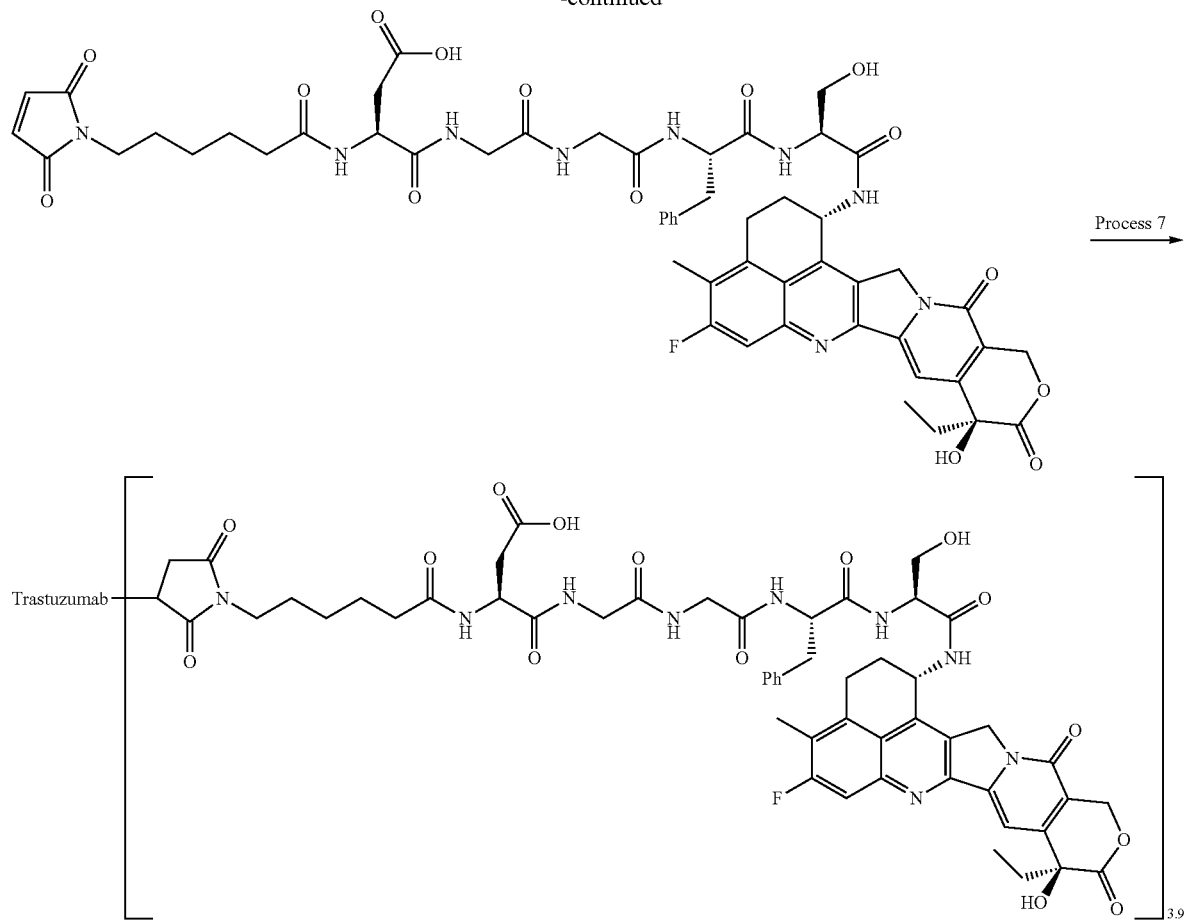

Process 1: 9H-Fluoren-9-ylmethyl[(2S)-3-tert-butoxy-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1-oxopropan-2-yl]carbamate Methanesulfonic acid salt of exatecan (0.750 g, 1.41 mmol) was reacted in the same manner as Process 1 of Example 80 by using O-tert-butyl-N-[(9H-fluoren-9-ylmethoxy)carbonyl]-L-serine instead of N-(tert-butoxycarbonyl)-glycine to yield the titled compound as a pale yellow solid (1.10 g, 97%).
MS(ESI) m/z: 801 (M+H)$^+$.

Process 2: O-tert-Butyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-serinamide The compound (659 mg, 0.823 mmol) obtained in Process 1 above was reacted in the same manner as Process 2 of Example 73 to yield the titled compound (395 mg, 83%).
$^1$H-NMR (400 MHz, DMSO-$d_6$) δ: 0.84 (3H, t, J=7.0 Hz), 0.90 (9H, s), 1.02-1.11 (1H, m), 1.71-1.94 (4H, m), 2.06-2.16 (1H, m), 2.17-2.27 (1H, m), 2.40 (3H, s), 3.14-3.22 (2H, m), 3.23-3.29 (1H, m), 5.22 (1H, d, J=19.2 Hz), 5.29 (1H, d, J=19.2 Hz), 5.42 (2H, s), 5.56-5.64 (1H, m), 6.54 (1H, s), 7.29 (1H, s), 7.80 (1H, d, J=10.9 Hz), 8.34-8.46 (1H, m).

Process 3: Glycylglycyl-L-phenylalanyl-O-tert-butyl-N-[(1S,9S)-9-ethyl-5-fluoro-9-hydroxy-4-methyl-10,13-dioxo-2,3,9,10,13,15-hexahydro-1H,12H-yl]-L-serinamide The compound (362 mg, 0.626 mmol) obtained in Process 2 above was reacted in the same manner as Process 1 of Example 58 by using N-[(9H-fluoren-9-ylmethoxy)carbonyl]glycylglycyl-L-phenylalanine (Japanese Patent Laid-Open No. 2002-60351) instead of N-[(9H-fluoren-9-ylmethoxy)carbonyl]-L-aspartic acid 4-tert-butyl and 3H-1,2,3-triazolo[4,5-b]pyridin-3-ol instead of N-hydroxysuccinimide, and the crude product obtained was reacted in the same manner as Process 2 of Example 73 to yield the titled compound (257 mg, 49%).
MS(ESI) m/z: 840 (M+H)$^+$.

Process 4: tert-Butyl (5S,8S,17S)-8-benzyl-5-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamoyl}-17-{[(9H-fluoren-9-ylmethoxy)carbonyl]amino}-2,2-dimethyl-7,10,13,16-tetraoxo-3-oxa-6,9,12,15-tetraazanonadecan-19-oate The compound (249 mg, 0.297 mmol) obtained in Process 3 above was reacted in the same manner as Process 1 of Example 73 to yield the titled compound (259 mg, 71%).
MS(ESI) m/z: 1234 (M+H)$^+$.

Process 5: tert-Butyl (5S,8S,17S)-17-amino-8-benzyl-5-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamoyl}-2,2-dimethyl-7,10,13,16-tetraoxo-3-oxa-6,9,12,15-tetraazanonadecan-19-oate The compound (259 mg, 0.210 mmol) obtained in Process 4 above was reacted in the same manner as Process 2 of Example 73 to yield the titled compound (99.0 mg, 47%).
$^1$H-NMR (400 MHz, DMSO-$d_6$) δ: 0.76-0.92 (3H, m), 0.85 (9H, br.s.), 1.00-1.12 (2H, m), 1.37 (9H, br.s.), 1.73-1.92 (1H, m), 2.03-2.17 (1H, m), 2.19-2.29 (1H, m), 2.30-2.60 (2H, m), 2.41 (3H, br.s.), 2.65-2.77 (1H, m), 2.81-2.92 (1H, m), 3.15-3.25 (2H, m), 3.27-3.36 (2H, m), 3.37-3.42 (1H, m), 3.45-3.57 (2H, m), 3.62-3.77 (3H, m), 4.27-4.39 (1H, m), 4.46-4.56 (1H, m), 5.17 (1H, d, J=19.9 Hz), 5.28-5.45 (3H, m), 5.54-5.64 (1H, m), 6.54 (1H, br.s.), 7.08-7.24 (5H, m), 7.28 (1H, br.s.), 7.81 (1H, d, J=9.4 Hz), 7.93-8.10 (3H, m), 8.20-8.31 (1H, m), 8.44-8.54 (1H, m).
MS (ESI) m/z: 1011 (M+H)$^+$.

Process 6: N-[6-(2,5-Dioxo-2,5-dihydro-1H-pyrrol-1-yl)hexanoyl]-L-α-aspartylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-yl]-L-serinamide The compound (94.0 mg, 0.0930 mol) obtained in Process 5 above was reacted in the same manner as Process 3 of Example 73, and the crude product obtained was reacted in the same manner as Process 2 of Example 1 to yield the titled compound as a solid (51.0 mg, 50%).
$^1$H-NMR (400 MHz, DMSO-$d_6$) δ: 0.85 (3H, t, J=7.4 Hz), 1.17 (2H, quin, J=7.7 Hz), 1.38-1.52 (4H, m), 1.76-1.91 (2H, m), 2.08 (3H, t, J=7.2 Hz), 2.18-2.36 (1H, m), 2.37-2.53 (1H, m), 2.41 (3H, s), 2.60-2.75 (2H, m), 2.85 (1H, dd, J=13.7, 3.9 Hz), 3.14-3.22 (2H, m), 3.29-3.39 (2H, m), 3.47-3.72 (6H, m), 4.28 (1H, dd, J=12.9, 5.5 Hz), 4.43-4.61 (2H, m), 4.88-5.01 (1H, m), 5.19 (1H, d, J=18.4 Hz), 5.29 (1H, d, J=18.8 Hz), 5.40 (2H, dd, J=21.9, 16.8 Hz), 5.51-5.60 (1H, m), 6.52 (1H, s), 6.94-7.03 (2H, m), 7.10-7.24 (5H, m), 7.29 (1H, m), 7.80 (1H, d, J=10.6 Hz), 7.92-7.99 (1H, m), 7.99-8.08 (2H, m), 8.09-8.16 (2H, m), 8.41 (1H, d, J=9.4 Hz), 12.29 (1H, brs).
MS (ESI) m/z: 1092 (M+H)$^+$.

Process 7: Antibody-Drug Conjugate (139)

By using the trastuzumab produced in Reference Example 1 and the compound obtained in Process 6 above, the compound of interest was obtained in the same manner as Process 6 of Example 2.
Antibody concentration: 1.61 mg/mL, 9.7 mg (78%), and average number of conjugated drug molecules (n) per antibody molecule: 3.9.

Example 140 Antibody-Drug Conjugate (140)

[Formula 193]

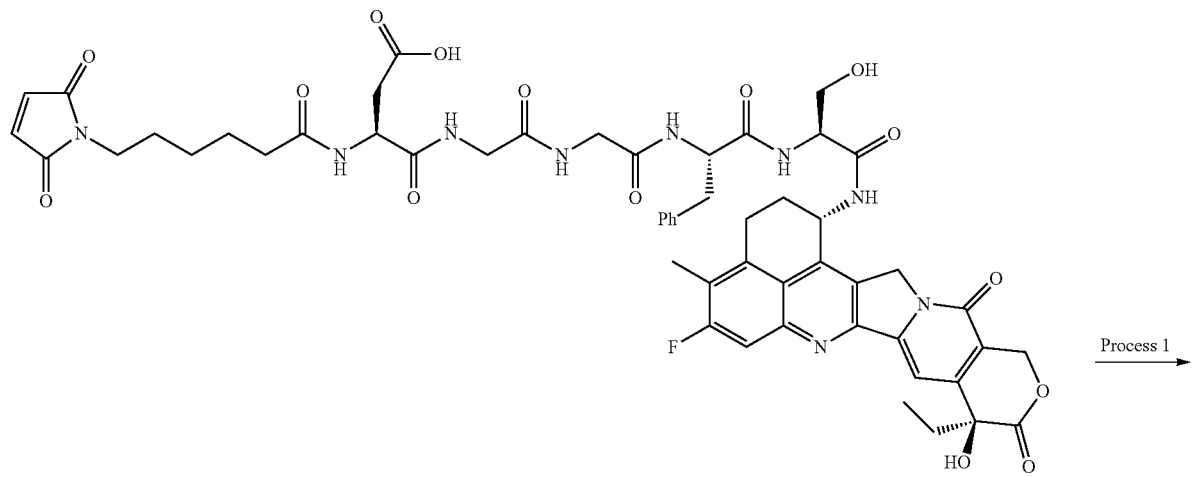

Process 1

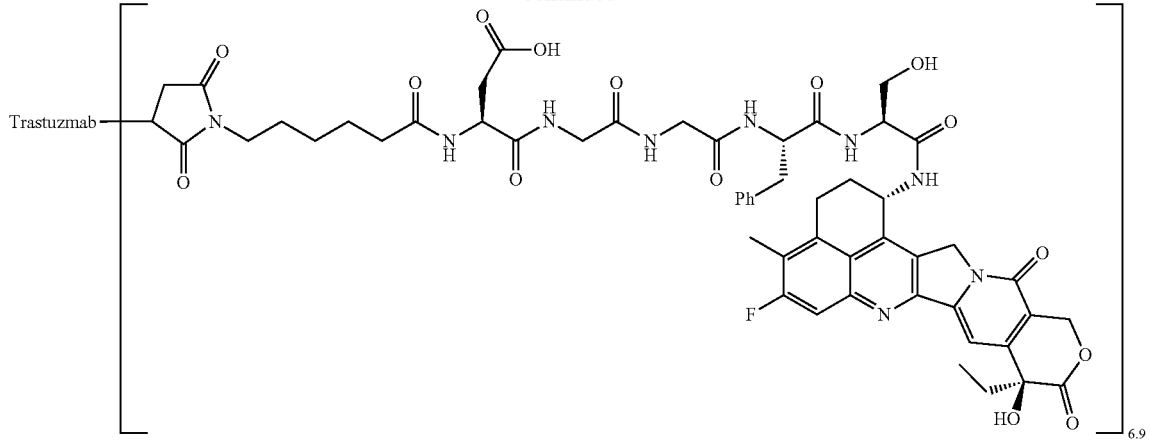

Process 1: Antibody-Drug Conjugate (140)

By using the trastuzumab produced in Reference Example 1 and the compound obtained in Process 6 of Example 139, the compound of interest was obtained in the same manner as Process 1 of Example 3.
Antibody concentration: 1.52 mg/mL, antibody yield: 9.1 mg (73%), and average number of conjugated drug molecules (n) per antibody molecule: 6.9.

Example 141 Antibody-Drug Conjugate (141)

[Formula 194]

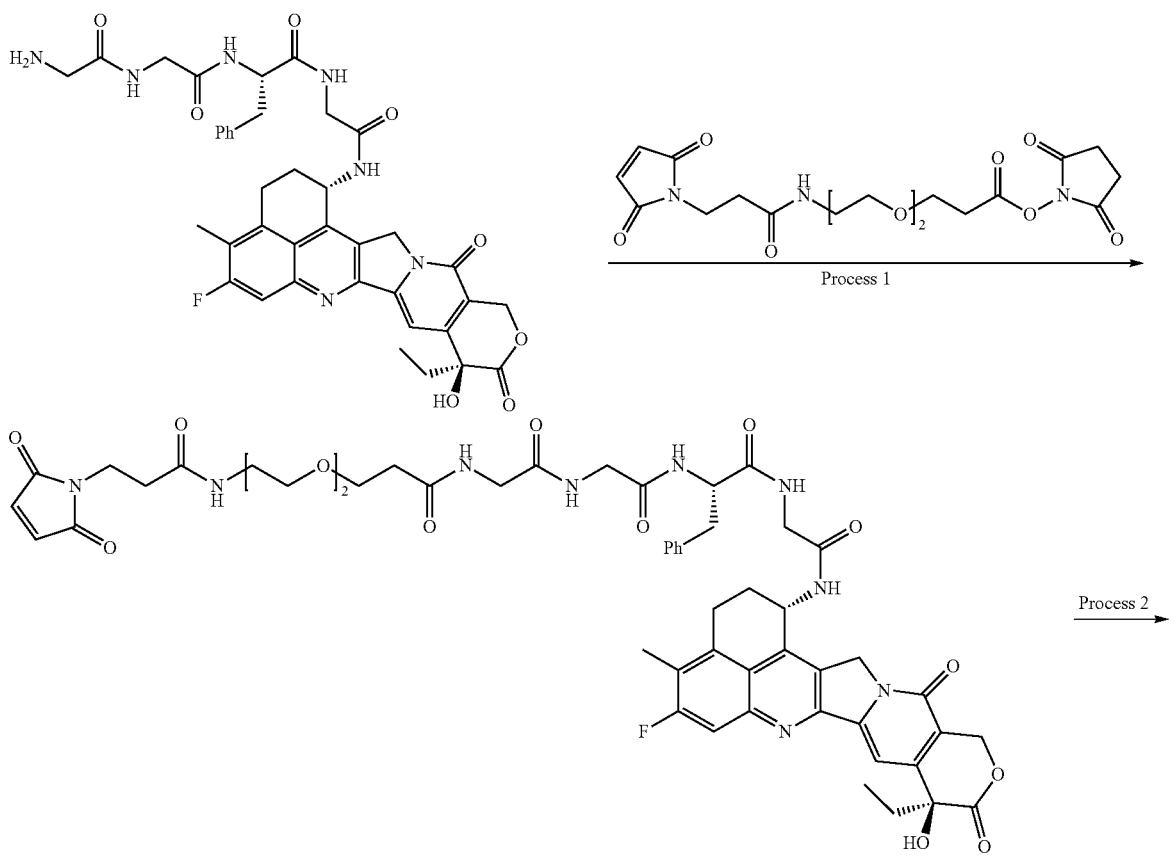

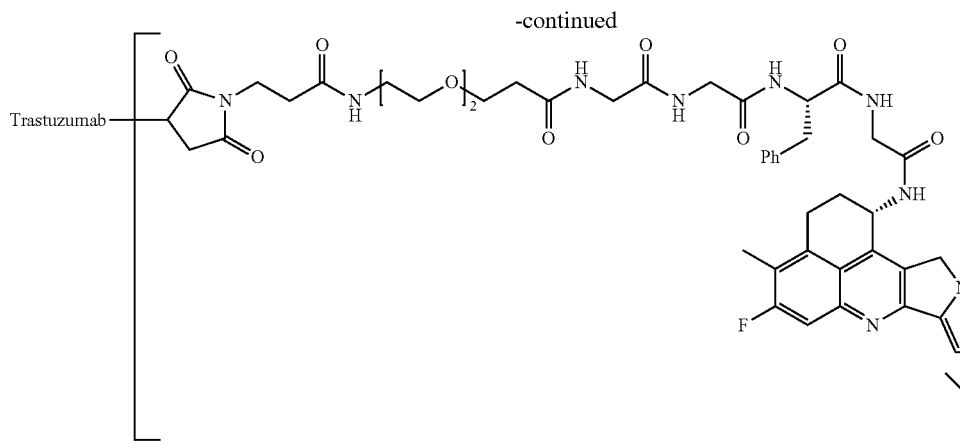
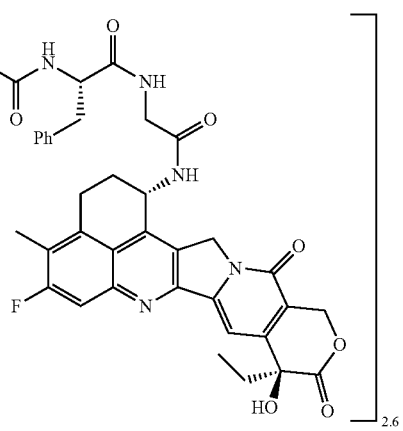

Process 1: N-{3-[2-(2-{[3-(2,5-Dioxo-2,5-dihydro-1H-pyrrol-1-yl)propanoyl]amino}ethoxy)ethoxy]propanoyl}-glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide N-Succinimidyl 3-(2-(2-(3-maleimidopropanamide)ethoxy)ethoxy)propanoate was used instead of N-succinimidyl 6-maleimidohexanoate and reacted in the same manner as Process 1 of Example 86 to yield the titled compound as a solid (39 mg, 55%).

$^1$H-NMR (400 MHz, DMSO-d$_6$) δ: 0.87 (3H, t, J=7.3 Hz), 1.79-1.91 (2H, m), 2.06-2.15 (1H, m), 2.16-2.24 (1H, m), 2.29-2.34 (2H, m), 2.37-2.43 (2H, m), 2.41 (3H, s), 2.54-2.58 (2H, m), 2.77 (1H, dd, J=14.2, 9.6 Hz), 2.98 (1H, dd, J=14.2, 4.6 Hz), 3.10-3.15 (2H, m), 3.15-3.20 (2H, m), 3.44-3.47 (4H, m), 3.55-3.61 (6H, m), 3.62-3.69 (2H, m), 3.70-3.75 (2H, m), 4.39-4.46 (1H, m), 5.22 (1H, d, J=18.8 Hz), 5.28 (1H, d, J=18.8 Hz), 5.39 (1H, d, J=16.5 Hz), 5.44 (2H, d, J=16.5 Hz), 5.54-5.61 (1H, m), 6.53 (1H, s), 6.99 (2H, s), 7.14-7.25 (5H, m), 7.32 (1H, s), 7.81 (1H, d, J=11.0 Hz), 7.97-8.03 (2H, m), 8.08 (1H, d, J=7.8 Hz), 8.17 (1H, t, J=5.7 Hz), 8.31 (1H, t, J=6.0 Hz), 8.42 (1H, d, J=8.7 Hz). MS (APCI) m/z: 1064 (M+H)$^+$.

Process 2: Antibody-Drug Conjugate (141)

The compound obtained in Process 1 above was used as the drug linker. The amount of the aqueous solution of 10 mM TCEP added was adjusted such that the molar ratio of TCEP to the antibody at the antibody reduction was 2.3. And the amount of the 10 mM drug linker solution added was adjusted such that the molar ratio of the drug linker to the antibody at the drug linker conjugation was 4.6. Then the amount of the aqueous solution of 100 mM NAC added was adjusted such that the molar ratio of NAC to the antibody at the termination of the reaction was 9.2. By the same procedures as Process 6 of Example 2, 6 mL of a solution containing the compound of interest was obtained, and the following characteristic values were obtained.
Antibody concentration: 1.28 mg/mL, antibody yield: 7.68 mg (77%), and average number of conjugated drug molecules (n) per antibody molecule: 2.6.

Example 142 Antibody-Drug Conjugate (142)

[Formula 195]

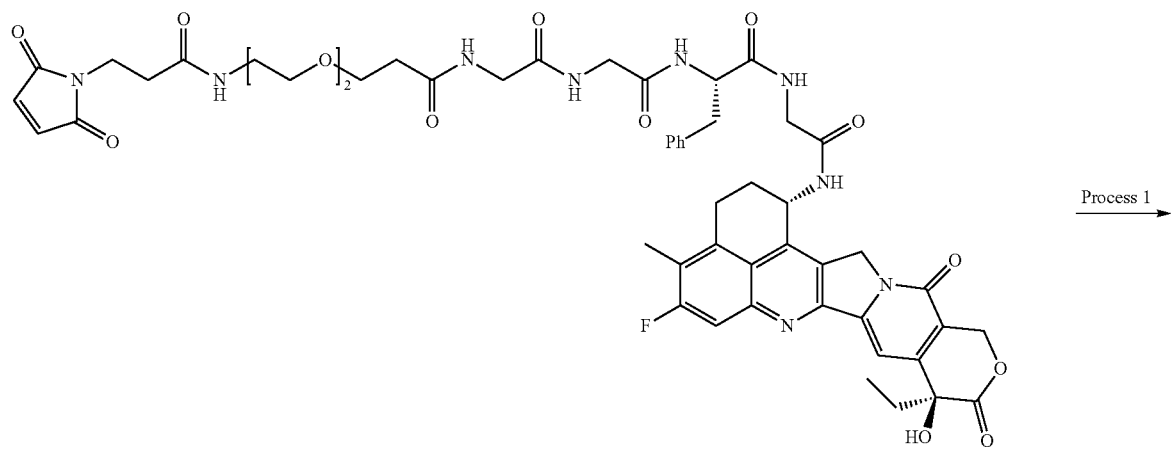

-continued

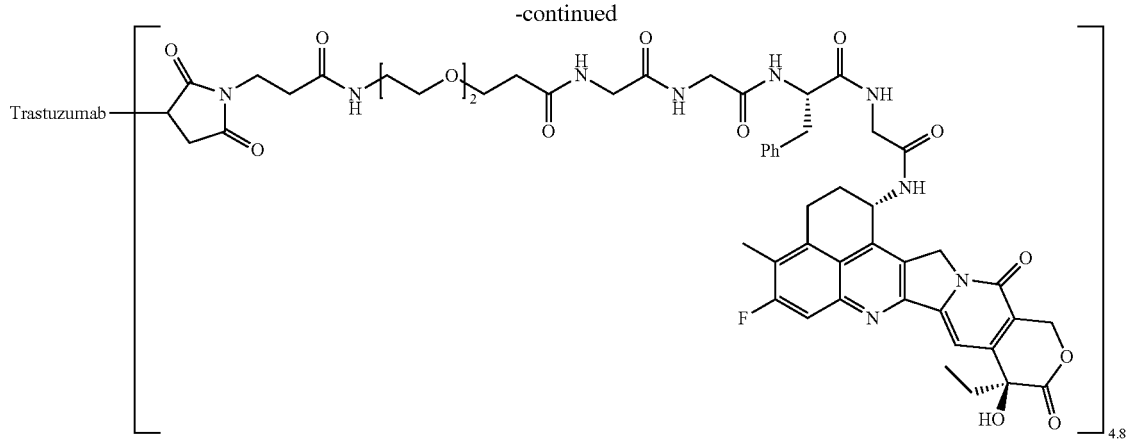

Process 1: Antibody-Drug Conjugate (142)

The compound obtained in Process 1 of Example 141 was used as the drug linker. The amount of the aqueous solution of 10 mM TCEP added was adjusted such that the molar ratio of TCEP to the antibody at the antibody reduction was 4.6. And the amount of the 10 mM drug linker solution added was adjusted such that the molar ratio of the drug linker to the antibody at the drug linker conjugation was 9.2. Then the amount of the aqueous solution of 100 mM NAC added was adjusted such that the molar ratio of NAC to the antibody at the termination of the reaction was 18.4. By the same procedures as Process 1 of Example 3, 6 mL of a solution containing the compound of interest was obtained, and the following characteristic values were obtained. Antibody concentration: 1.14 mg/mL, antibody yield: 6.84 mg (68%), and average number of conjugated drug molecules (n) per antibody molecule: 4.8.

Example 143 Antibody-Drug Conjugate (143)

[Formula 196]

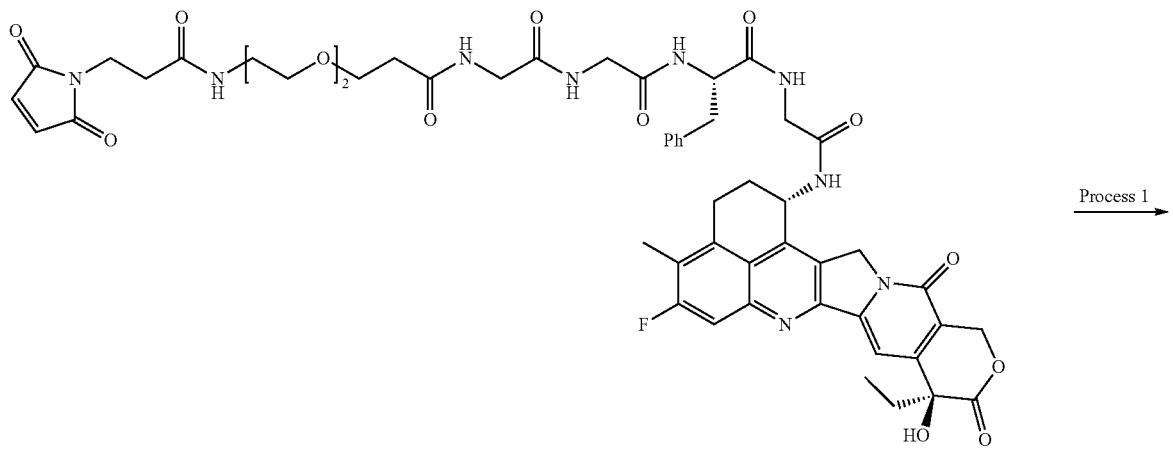

Process 1

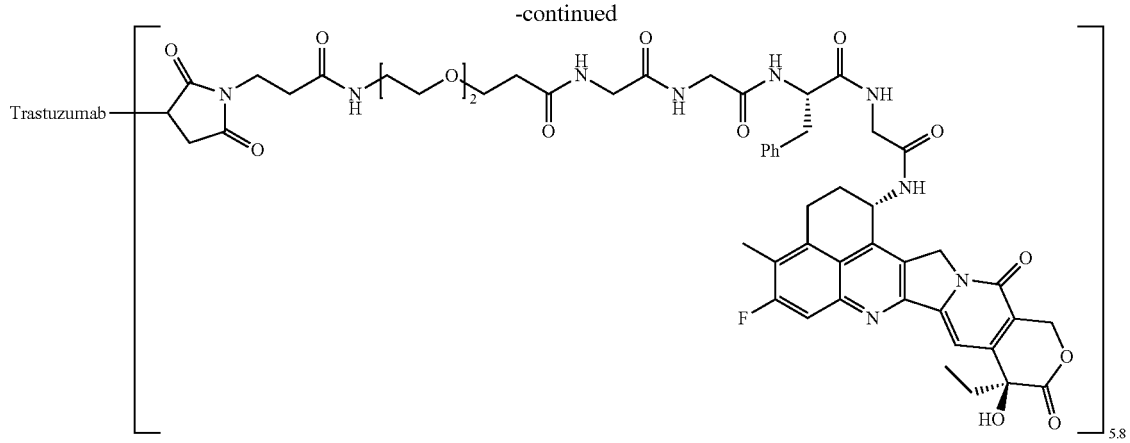

Process 1: Antibody-Drug Conjugate (143)

The compound obtained in Process 1 of Example 141 was used as the drug linker. The amount of the aqueous solution of 10 mM TCEP added was adjusted such that the molar ratio of TCEP to the antibody at the antibody reduction was 4.6. And the amount of the 10 mM drug linker solution added was adjusted such that the molar ratio of the drug linker to the antibody at the drug linker conjugation was 9.2. Then the amount of the aqueous solution of 100 mM NAC added was adjusted such that the molar ratio of NAC to the antibody at the termination of the reaction was 18.4. By the same procedures as Process 1 of Example 3, 6 mL of a solution containing the compound of interest was obtained, and the following characteristic values were obtained. Antibody concentration: 1.60 mg/mL, antibody yield: 9.12 mg (73%), and average number of conjugated drug molecules (n) per antibody molecule: 5.8.

Example 144 Antibody-Drug Conjugate (144)

[Formula 197]

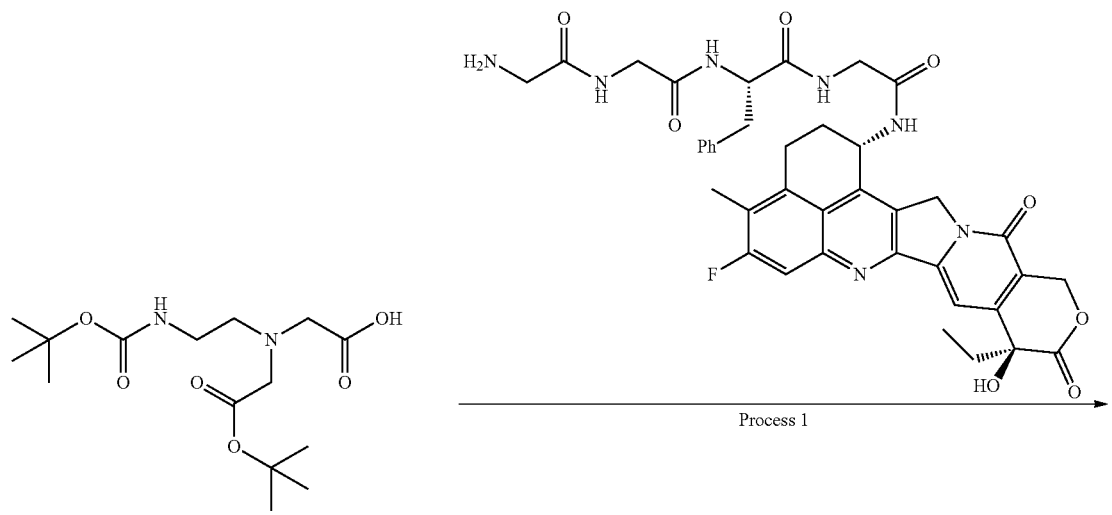

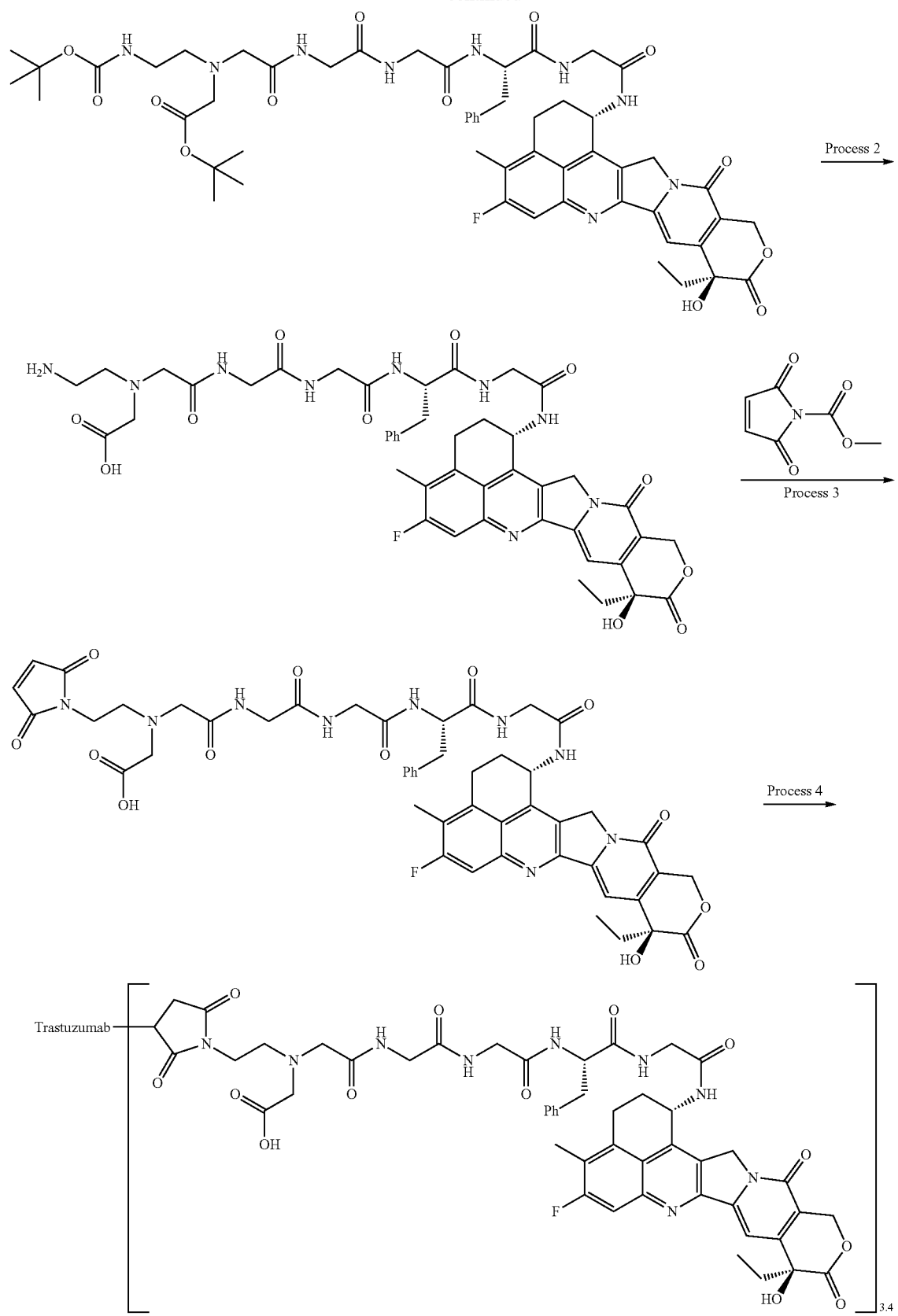

Process 1: N-{2-[(tert-Butoxycarbonyl)amino]ethyl}-N-(2-tert-butoxy-2-oxoethyl)glycylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.198 g, 0.597 mmol) obtained in Process 2 of Example 51 was used instead of (2S)-4-tert-butoxy-2-{[(9H-fluoren-9-ylmethoxy)carbonyl]amino}-4-oxobutanoic acid and reacted in the same manner as Process 1 of Example 58 to yield the titled compound as a pale yellow solid (0.380 g, 89%).

$^1$H-NMR (400 MHz, DMSO-$d_6$) δ: 0.87 (3H, t, J=7.2 Hz), 1.35 (9H, s), 1.39 (9H, s), 1.84-1.86 (2H, m), 2.09-2.11 (1H, m), 2.18-2.21 (1H, m), 2.41 (3H, s), 2.97-2.99 (5H, m), 3.18-3.23 (4H, m), 3.38-3.40 (3H, m), 3.55-3.73 (6H, m), 4.43 (1H, s), 5.22 (1H, d, J=19.2 Hz), 5.28 (1H, d, J=19.2 Hz), 5.39 (1H, d, J=16.4 Hz), 5.44 (1H, d, J=16.4 Hz), 5.59 (1H, s), 6.54 (1H, s), 6.59 (1H, s), 6.78 (1H, s), 7.15-7.23 (5H, m), 7.32 (1H, s), 7.81 (1H, d, J=10.9 Hz), 8.05-8.09 (2H, m), 8.32 (1H, s), 8.42 (1H, d, J=8.6 Hz).

MS (APCI) m/z: 1068 (M+H)$^+$.

Process 2: N-(2-Aminoethyl)-N-(carboxymethyl)glycylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-yl]glycinamide The compound (0.366 g, 0.338 mmol) obtained in Process 1 above was reacted in the same manner as Process 2 of Example 1 to yield the titled compound as a pale yellow solid (0.180 g, 58%).

$^1$H-NMR (400 MHz, DMSO-$d_6$) δ: 0.87 (3H, t, J=7.0 Hz), 1.82-1.89 (2H, m), 2.11-2.13 (1H, m), 2.18-2.20 (1H, m), 2.41 (3H, s), 2.77-2.81 (5H, m), 2.98-3.00 (1H, m), 3.16-3.18 (3H, m), 3.39-3.43 (3H, m), 3.58 (1H, dd, J=16.8, 5.5 Hz), 3.71-3.73 (5H, m), 4.45-4.46 (1H, m), 5.22 (1H, d, J=18.0 Hz), 5.28 (1H, d, J=18.0 Hz), 5.39 (1H, d, J=17.6 Hz), 5.44 (1H, d, J=15.6 Hz), 5.58-5.59 (1H, m), 6.55 (1H, s), 7.18-7.23 (6H, m), 7.32 (1H, s), 7.80 (2H, br.s), 7.82 (1H, d, J=10.9 Hz), 8.10 (1H, d, J=5.5 Hz), 8.19 (1H, d, J=7.8 Hz), 8.36 (1H, s), 8.43 (1H, s), 8.49 (1H, d, J=8.6 Hz).

MS (APCI) m/z: 912 (M+H)$^+$.

Process 3: N-(Carboxymethyl)-N-[2-(2,5-dioxo-2,5-dihydro-1H-pyrrol-1-yl)ethyl]glycylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide Under ice cooling, the compound (81.0 mg, 88.8 μmol) obtained in Process 2 above was dissolved in a saturated sodium hydrogen carbonate aqueous solution (1.00 mL) and 1,4-dioxane (4.00 mL) and stirred for 10 minutes. Under ice cooling, after adding methyl 2,5-dioxopyrrole-1-carboxylate (13.8 mg, 88.8 μmol), it was stirred for 20 minutes. It was further stirred at room temperature for 30 minutes. After adding an aqueous solution of 10% citric acid, it was stirred overnight. The reaction solution was extracted with chloroform and the organic layer obtained was dried over sodium sulfate and filtered. The solvent in the filtrate was removed under reduced pressure. The residues obtained were purified by silica gel column chromatography [chloroform-partitioned organic layer of chloroform:methanol:water=7:3:1 (v/v/v)] to yield the titled compound as a pale yellow solid (14.9 mg, 17%).

$^1$H-NMR (400 MHz, DMSO-$d_6$) δ: 0.87 (3H, t, J=7.2 Hz), 1.80-1.91 (2H, m), 2.09-2.11 (1H, m), 2.17-2.20 (1H, m), 2.38 (3H, s), 2.63-2.68 (2H, m), 2.84-3.00 (2H, m), 3.12-3.16 (3H, m), 3.40-3.45 (6H, m), 3.63-3.76 (5H, m), 4.33-4.35 (1H, m), 5.24 (2H, s), 5.38 (1H, d, J=16.8 Hz), 5.43 (1H, d, J=16.4 Hz), 5.56-5.57 (1H, m), 6.52 (1H, s), 6.95 (2H, s), 7.14-7.21 (6H, m), 7.31 (1H, s), 7.78 (1H, d, J=11.0 Hz), 8.10 (1H, s), 8.54 (1H, d, J=7.8 Hz), 8.72 (3H, br.s).

MS (APCI) m/z: 992 (M+H)$^+$.

Process 4: Antibody-Drug Conjugate (144)

By using the trastuzumab produced in Reference Example 1 and the compound obtained in Process 3 above, the compound of interest was obtained in the same manner as Process 6 of Example 2.
Antibody concentration: 10.55 mg/mL, antibody yield: 7.4 mg (59%), and average number of conjugated drug molecules (n) per antibody molecule: 3.4.

Example 145 Antibody-Drug Conjugate (145)

[Formula 198]

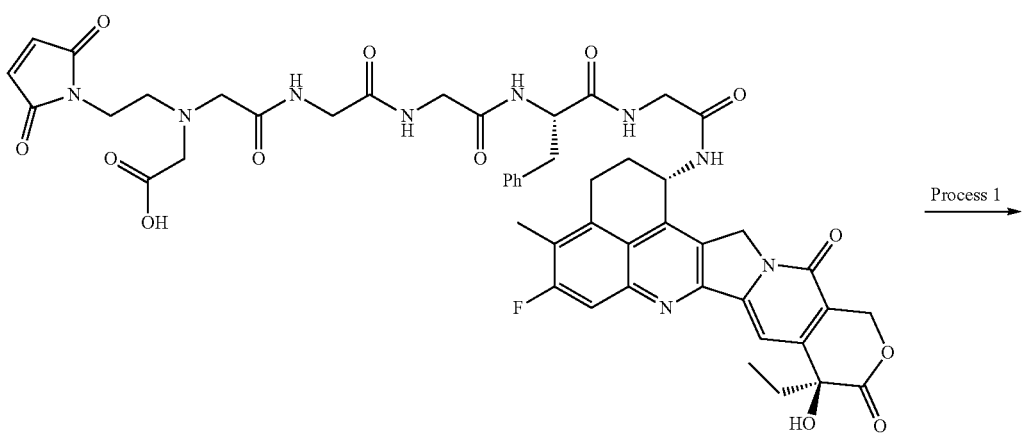

Process 1 →

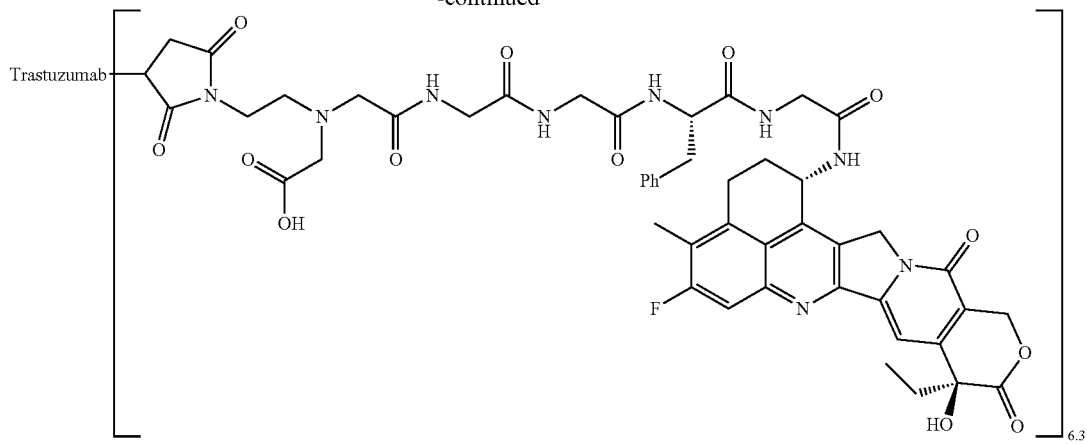

Process 1: Antibody-Drug Conjugate (145)

By using the trastuzumab produced in Reference Example 1 and the compound obtained in Process 3 of Example 144, the Example compound of interest was obtained in the same manner as Process 1 of Example 3.
Antibody concentration: 9.91 mg/mL, antibody yield: 6.9 mg (55%), and average number of conjugated drug molecules (n) per antibody molecule: 6.3.

Example 146 Antibody-Drug Conjugate (146)

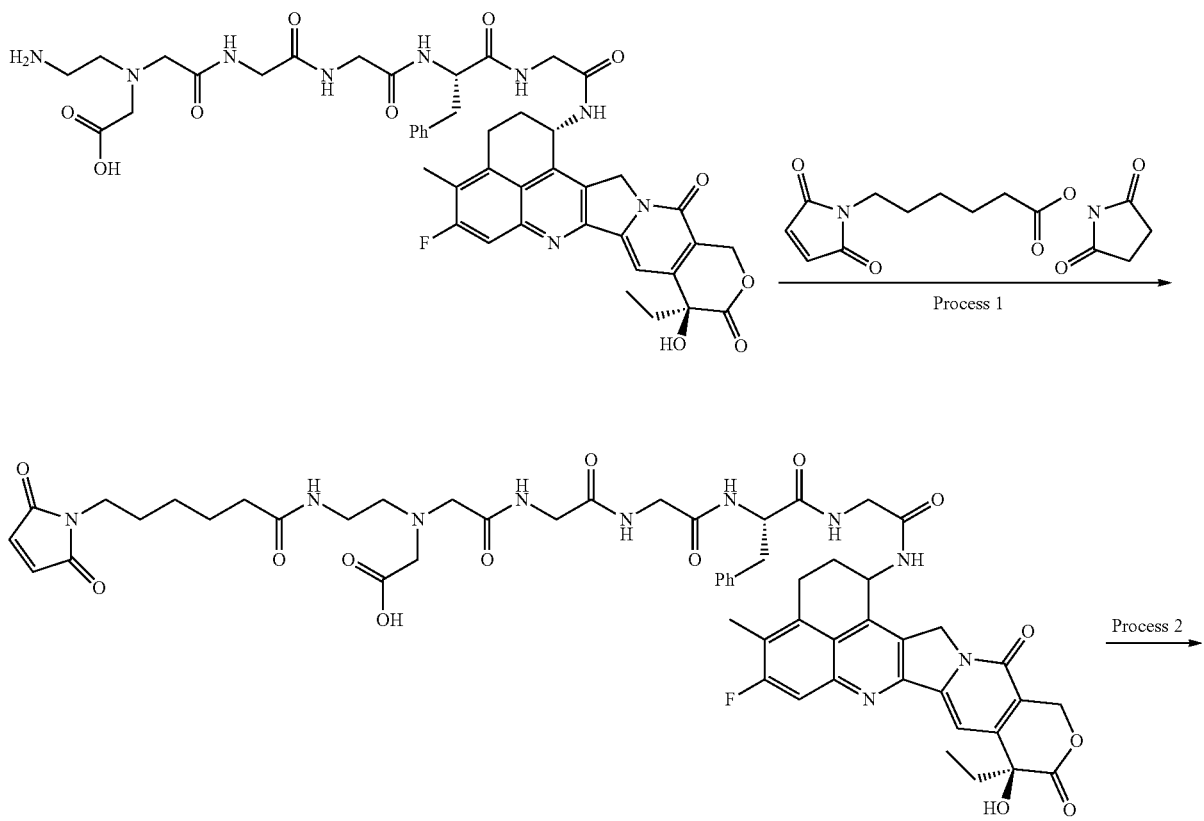

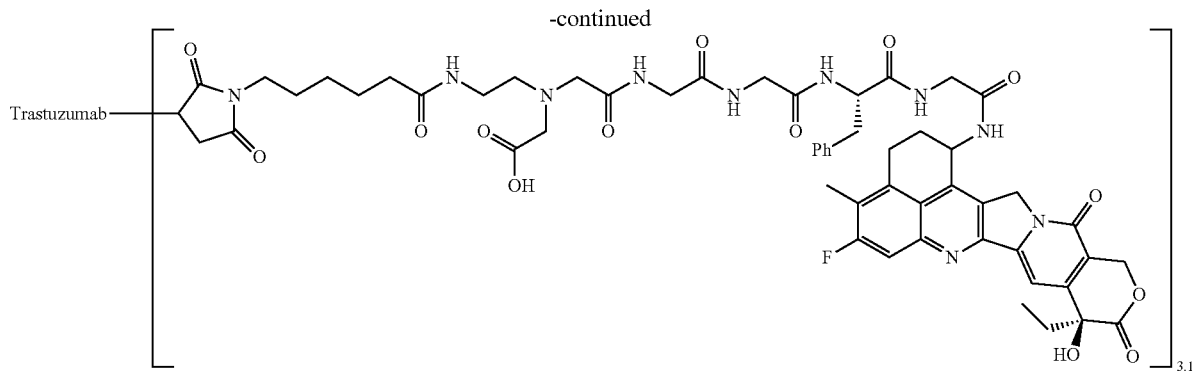

Process 1: N-(Carboxymethyl)-N-(2-{[6-(2,5-dioxo-2,5-dihydro-1H-pyrrol-1-yl)hexanoyl]amino}ethyl)glycylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (49.0 mg, 53.7 μmol) obtained in Process 2 of Example 144 was reacted in the same manner as Process 1 of Example 121 to yield the titled compound as a pale yellow solid (14.9 g, 25%).

$^1$H-NMR (400 MHz, DMSO-d$_6$) δ: 0.87 (3H, t, J=7.2 Hz), 1.07-1.16 (2H, m), 1.41-1.43 (4H, m), 1.85-1.87 (2H, m), 1.96-1.98 (2H, m), 2.09-2.12 (1H, m), 2.17-2.19 (1H, m), 2.37-2.42 (3H, m), 2.38 (3H, s), 2.48-2.60 (4H, m), 2.87-3.48 (8H, m), 3.63-3.82 (5H, m), 4.30 (1H, s), 5.22 (1H, d, J=20.3 Hz), 5.29 (1H, d, J=19.2 Hz), 5.41 (2H, s), 5.56-5.58 (1H, m), 6.53 (1H, s), 6.99 (2H, s), 7.20 (6H, d, J=10.6 Hz), 7.32 (1H, s), 7.78-7.80 (3H, m), 8.14-8.16 (2H, m), 8.32 (1H, s), 8.53 (1H, d, J=8.2 Hz).

MS (APCI) m/z: 1105 (M+H)$^+$.

Process 2: Antibody-Drug Conjugate (146)

By using the trastuzumab produced in Reference Example 1 and the compound obtained in Process 1 above, the compound of interest was obtained in the same manner as Process 6 of Example 2.

Antibody concentration: 1.48 mg/mL, antibody yield: 8.9 mg (71%), and average number of conjugated drug molecules (n) per antibody molecule: 3.1.

Example 147 Antibody-Drug Conjugate (147)

[Formula 200]

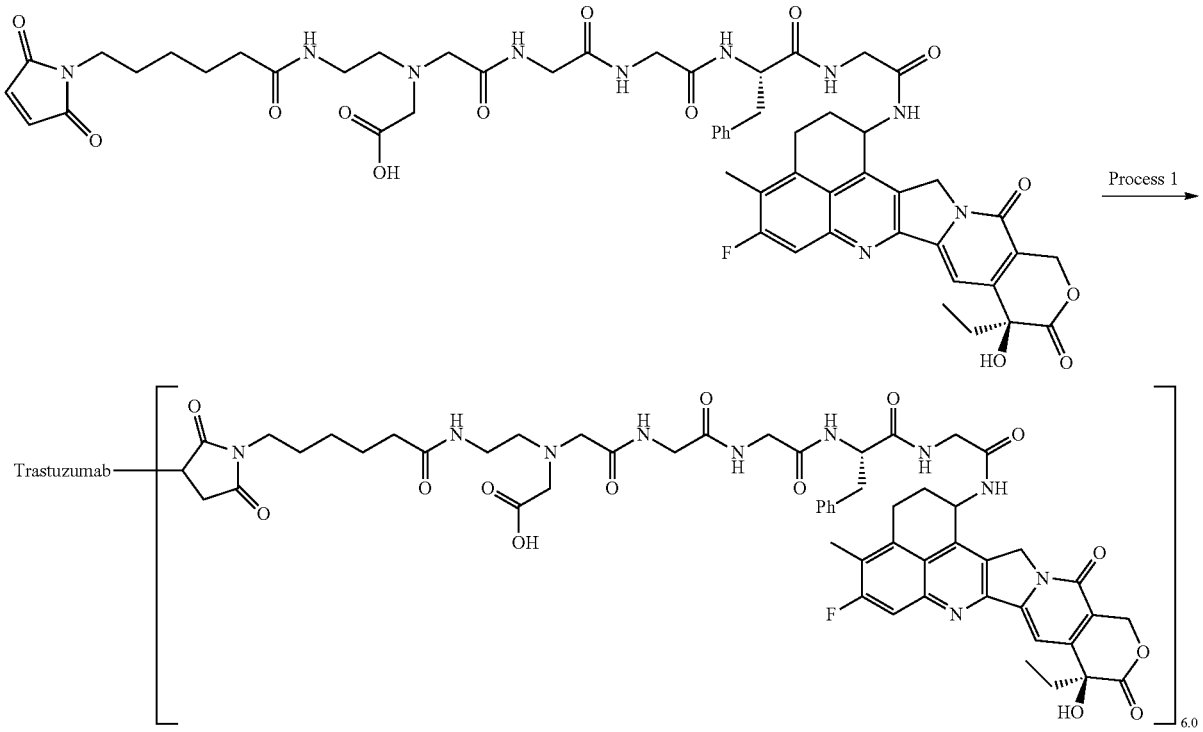

Process 1: Antibody-Drug Conjugate (147)

By using the trastuzumab produced in Reference Example 1 and the compound obtained in Process 1 of Example 146, the compound of interest was obtained in the same manner as Process 1 of Example 3.

Antibody concentration: 1.49 mg/mL, antibody yield: 8.9 mg (71%), and average number of conjugated drug molecules (n) per antibody molecule: 6.0.

Example 148 Antibody-Drug Conjugate (148)

[Formula 201]

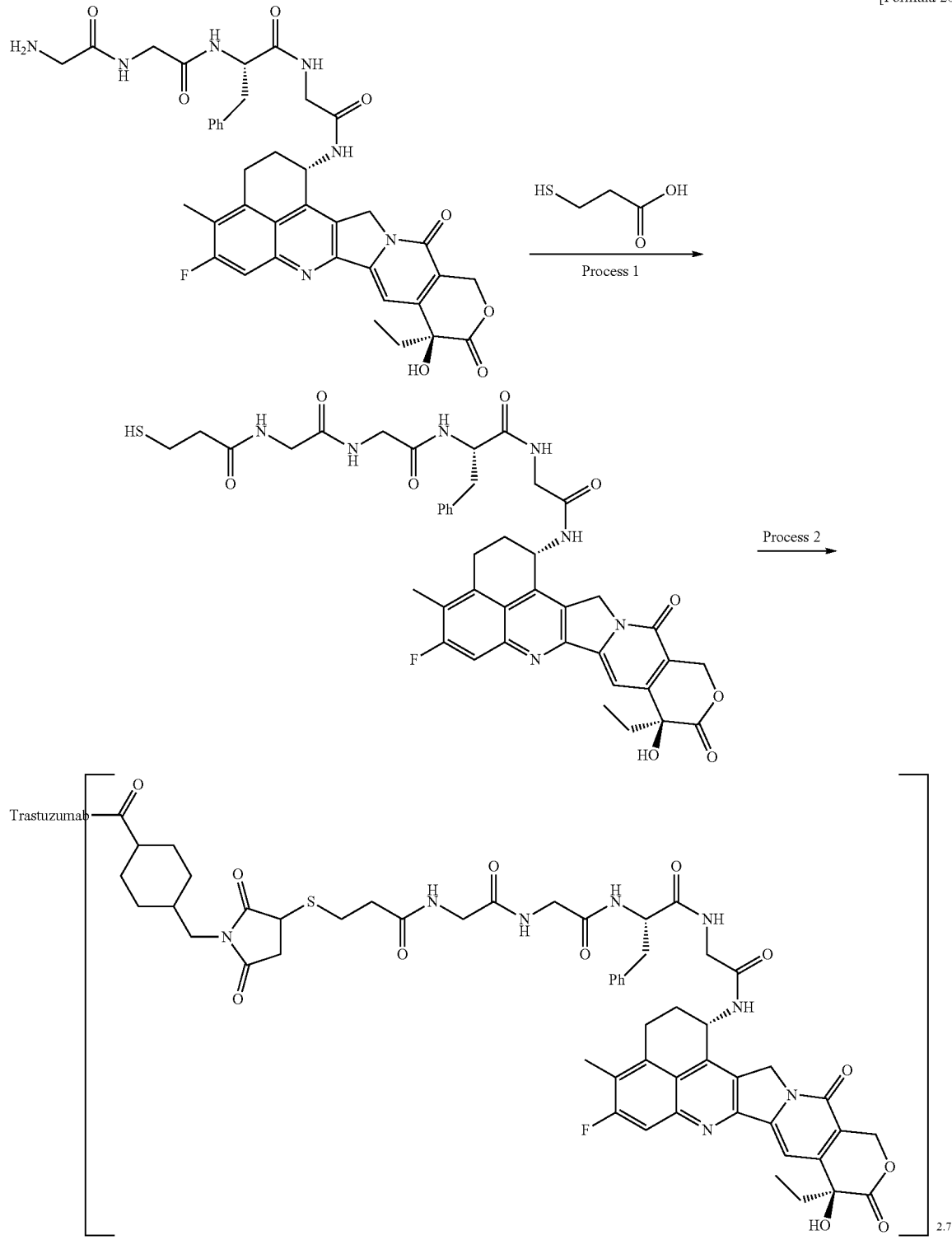

Process 1: N-(3-Sulfonylpropanoyl)glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide A free form of glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (International Publication No. WO 97/46260; 0.200 g, 0.27 mmol) was reacted in the same manner as Process 1 of Example 73 by using 3-mercaptopropionic acid (62.0 mg, 0.58 mmol) instead of N-[(9H-fluoren-9-ylmethoxy)carbonyl]-L-aspartic acid 4-tert-butyl to yield the titled compound as a pale yellow solid (55.0 mg, 25%).

$^1$H-NMR (400 MHz, DMSO-$d_6$) δ: 0.88 (3H, t, J=7.4 Hz), 1.82-1.93 (2H, m), 2.03-2.29 (2H, m), 2.35-2.57 (3H, m), 2.43 (3H, s), 2.66 (2H, q, J=7.0 Hz), 2.79 (1H, dd, J=13.7, 9.4 Hz), 3.00 (1H, dd, J=13.5, 4.5 Hz), 3.12-3.25 (2H, m), 3.56 (1H, dd, J=16.8, 5.5 Hz), 3.63-3.79 (5H, m), 4.42-4.48 (1H, m), 5.27 (2H, dd, J=23.9, 19.2 Hz), 5.43 (2H, dd, J=20.9, 16.2 Hz), 5.54-5.64 (1H, m), 6.55 (1H, s), 7.13-7.28 (5H, m), 7.33 (1H, s), 7.83 (1H, d, J=11.0 Hz), 8.03 (1H, t, J=5.9 Hz), 8.10 (1H, d, J=8.2 Hz), 8.24 (1H, t, J=5.5 Hz), 8.34 (1H, t, J=5.7 Hz), 8.45 (1H, d, J=8.6 Hz).

MS (ESI) m/z: 842 (M+H)$^+$.

Process 2: Antibody-Drug Conjugate (148)

SMCC derivatization of antibody: The trastuzumab produced in Reference Example 1 was prepared to have an antibody concentration of 20 mg/mL by replacing the medium with PBS6.5/EDTA by using the Common procedure C-2 and Common procedure B (as absorption coefficient at 280 nm, 1.37 mLmg$^{-1}$ cm$^{-1}$ was used). The solution (0.5 mL) was placed in a 1.5 mL tube, charged with a dimethyl sulfoxide solution (0.0125 mL; which corresponds to about 5.1 equivalents per antibody molecule) containing 27.6 mM of SMCC and dimethyl sulfoxide (0.0125 mL) at room temperature, and reacted at room temperature for 2 hours. This reaction solution was subjected to purification according to the Common procedure D-2 to yield 1.2 mL of a solution containing about 10 mg of the SMCC-derivatized antibody.

Conjugation between antibody and drug linker: After adding a dimethylacetamide solution containing 10 mM of the compound obtained in Process 1 above (0.03 mL; which corresponds to 5.8 equivalents per antibody molecule) to the above solution at room temperature, it was stirred by using a tube rotator for conjugating the drug linker to the antibody at room temperature for 16 hours.

Purification: The above solution was subjected to purification using the Common procedure D-1 (ABS was used as a buffer solution) to yield 6 mL of a solution containing the compound of interest.

Physicochemical characterization: By using the Common procedure B and Common procedure E, the following characteristic values were obtained.

Antibody concentration: 1.22 mg/mL, antibody yield: 7.3 mg (73%), and average number of conjugated drug molecules (n) per antibody molecule: 2.7.

Example 149 Antibody-Drug Conjugate (149)

[Formula 202]

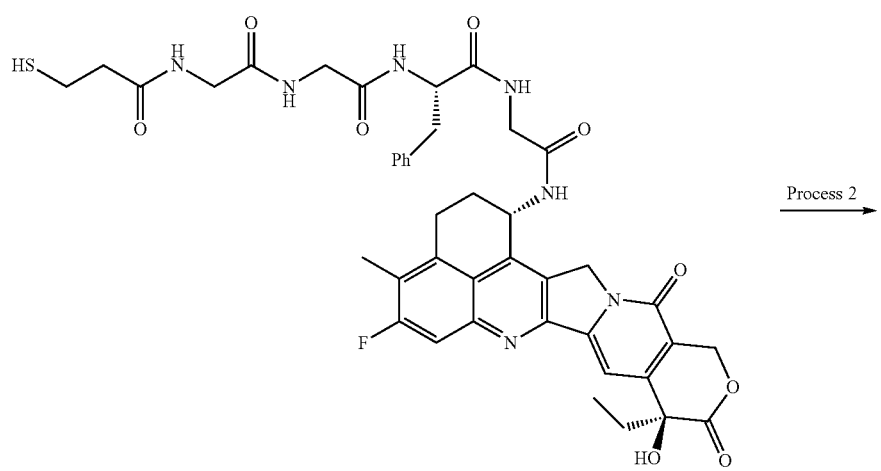

Process 2

-continued

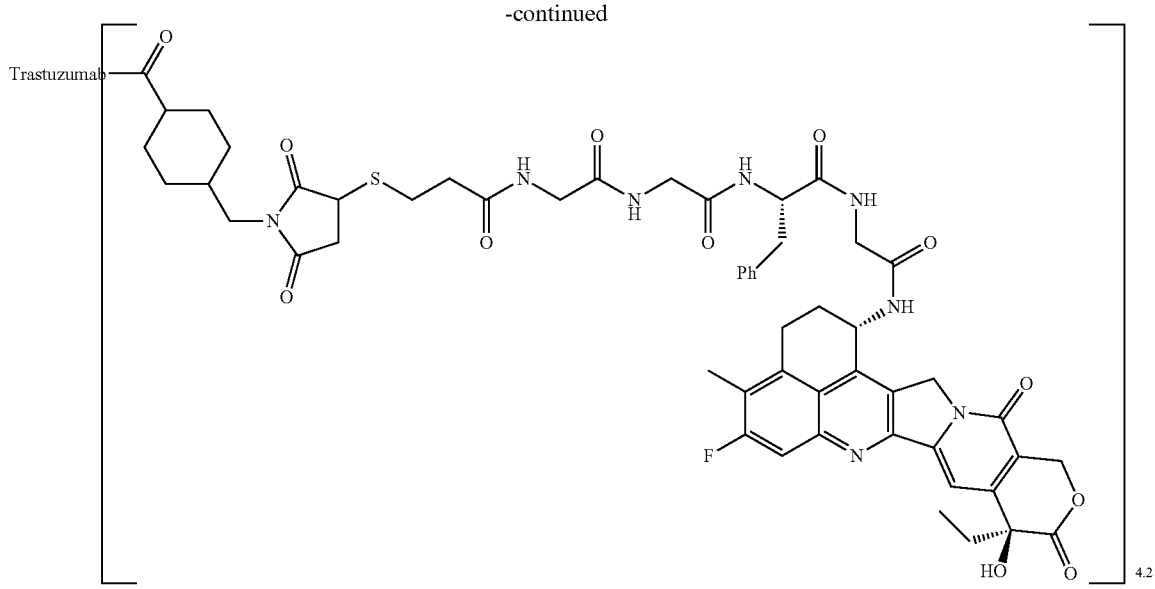

Process 1: Antibody-Drug Conjugate (149)

The amount of the DMSO solution of 27.6 mM SMCC added was adjusted such that the amount of SMCC added per antibody molecule was 10.2 equivalents. And the amount of the dimethylacetamide solution of 10 mM drug linker added was adjusted such that the amount of the compound obtained in Process 1 of Example 148 added per antibody molecule was 11.6 equivalents. By the same procedures as Process 2 of Example 148, 6 mL of a solution containing the compound of interest was obtained, and the following characteristic values were obtained.
Antibody concentration: 1.10 mg/mL, antibody yield: 6.6 mg (66%), and average number of conjugated drug molecules (n) per antibody molecule: 4.2.

Example 150 Antibody-Drug Conjugate (150)

[Formula 203]

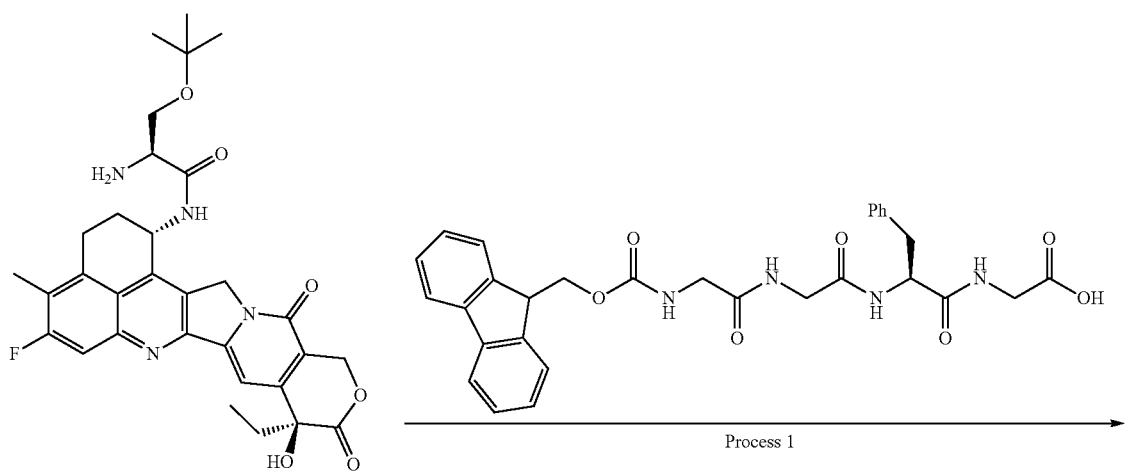

Process 1

-continued
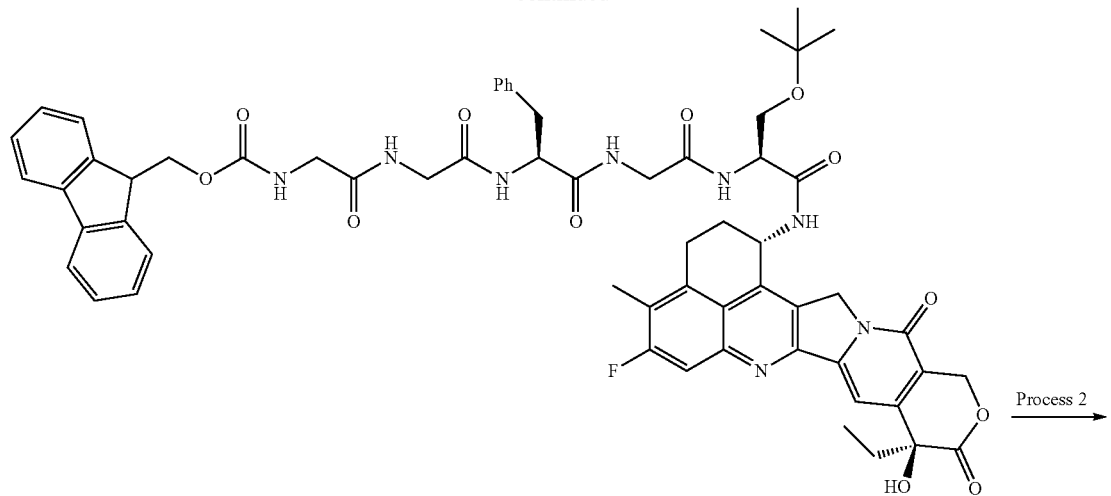
Process 2 →
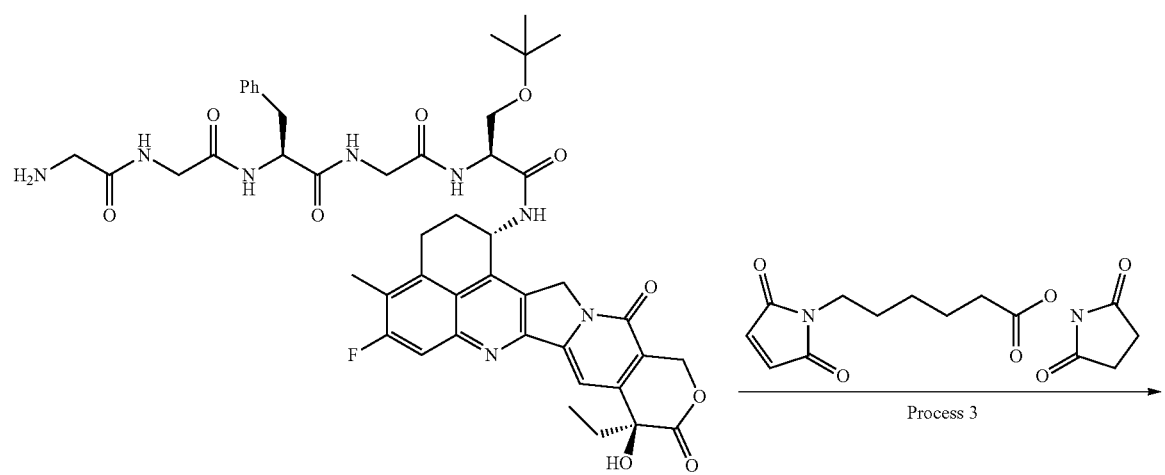
Process 3 →
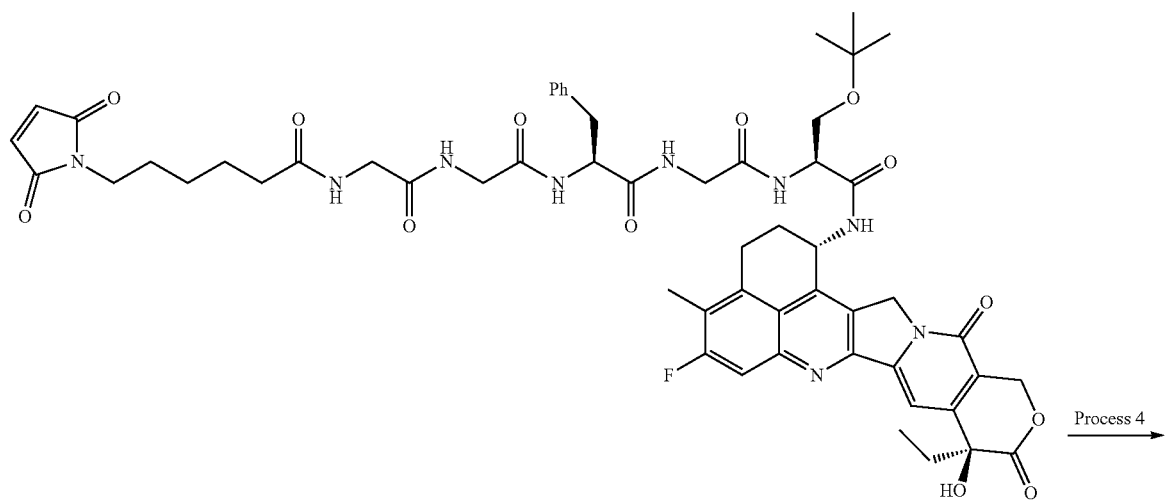
Process 4 →

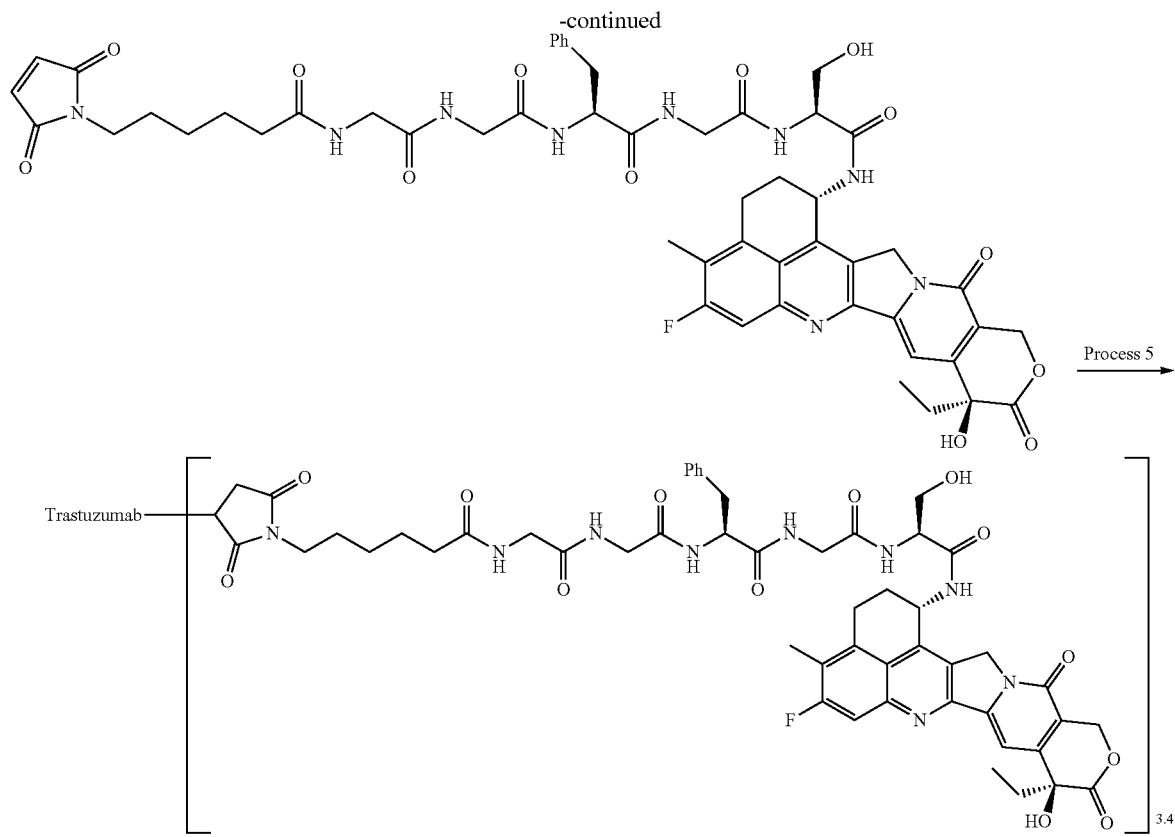

Process 1: N-[(9H-Fluoren-9-ylmethoxy)carbonyl]glycylglycyl-L-phenylalanylglycyl-O-tert-butyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-serinamide The compound (0.27 g, 0.46 mmol) obtained in Process 2 of Example 139 was reacted in the same manner as Process 1 of Example 1 by using the compound (0.39 g, 0.69 mmol) obtained in Process 2 of Example 34 instead of 4-(tert-butoxycarbonylamino)butanoic acid to yield the titled compound as a pale yellow solid (0.313 g, 72%).
MS(ESI) m/z: 1119 (M+H)$^+$.

Process 2: Glycylglycyl-L-phenylalanylglycyl-O-tert-butyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-serinamide The compound (0.31 g, 0.28 mol) obtained in Process 1 above was reacted in the same manner as Process 2 of Example 73. After concentrating the solvent, the residues were used for the next reaction without purification.

Process 3: N-[6-(2,5-Dioxo-2,5-dihydro-1H-pyrrol-1-yl)hexanoyl]glycylglycyl-L-phenylalanylglycyl-O-tert-butyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-serinamide The compound (0.28 mol) obtained in Process 2 above was reacted in the same manner as Process 3 of Example 73 to yield the titled compound as an orange solid (0.306 g, quantitative, 2 steps).
MS(ESI) m/z: 1090 (M+H)$^+$.

Process 4: N-[6-(2,5-Dioxo-2,5-dihydro-1H-pyrrol-1-yl)hexanoyl]glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-serinamide The compound (0.31 g, 0.28 mol) obtained in Process 3 above was reacted in the same manner as Process 2 of Example 1 to yield the titled compound as a pale yellow solid (0.12 g, 41%).
$^1$H-NMR (400 MHz, DMSO-d$_6$) δ: 0.86 (3H, t, J=7.4 Hz), 1.13-1.23 (2H, m), 1.39-1.52 (6H, m), 1.74-1.90 (2H, m), 2.03-2.14 (4H, m), 2.39 (3H, s), 2.60-2.95 (2H, m), 3.49-3.81 (10H, m), 4.15-4.59 (3H, m), 5.15-5.31 (2H, m), 5.40 (2H, s), 5.53-5.61 (1H, m), 6.52 (1H, brs), 6.99 (2H, s), 7.12-7.29 (6H, m), 7.76 (1H, d, J=11.0 Hz), 7.94-8.16 (4H, m), 8.25 (1H, t, J=5.5 Hz), 8.50 (1H, d, J=8.6 Hz).
MS (ESI) m/z: 1034 (M+H)$^+$.

Process 5: Antibody-Drug Conjugate (150)

By using the trastuzumab produced in Reference Example 1 and the compound obtained in Process 4 above, the compound of interest was obtained in the same manner as Process 6 of Example 2.
Antibody concentration: 1.57 mg/mL, antibody yield: 9.4 mg (75%), and average number of conjugated drug molecules (n) per antibody molecule: 3.4.

Example 151 Antibody-Drug Conjugate (151)

[Formula 204]

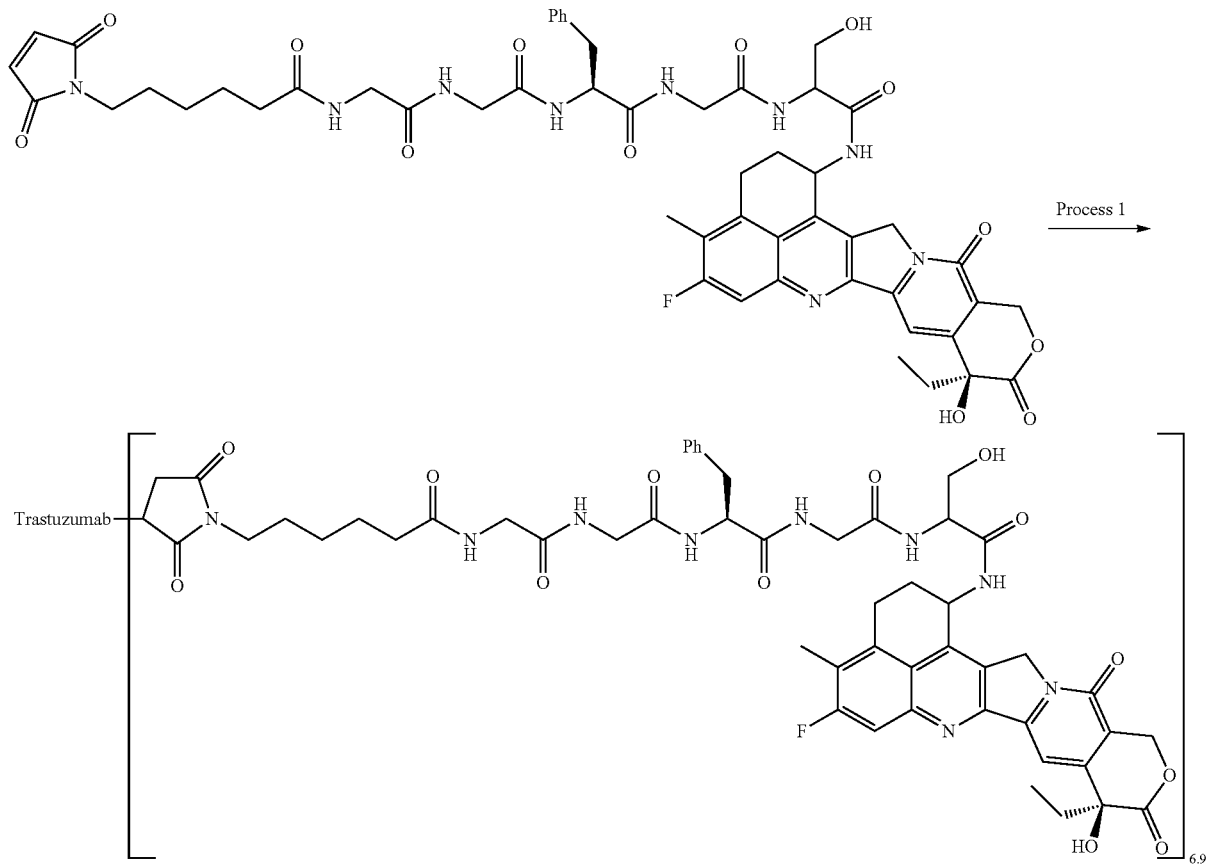

Process 1: Antibody-Drug Conjugate (151)

By using the trastuzumab produced in Reference Example 1 and the compound obtained in Process 4 of Example 150, the compound of interest was obtained in the same manner as Process 1 of Example 3.

Antibody concentration: 1.76 mg/mL, antibody yield: 10.6 mg (85%), and average number of conjugated drug molecules (n) per antibody molecule: 6.9.

Example 152 Antibody-Drug Conjugate (152)

[Formula 205]

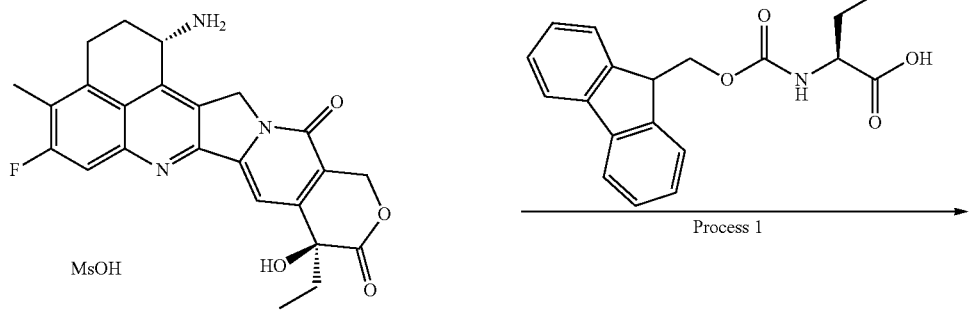

-continued
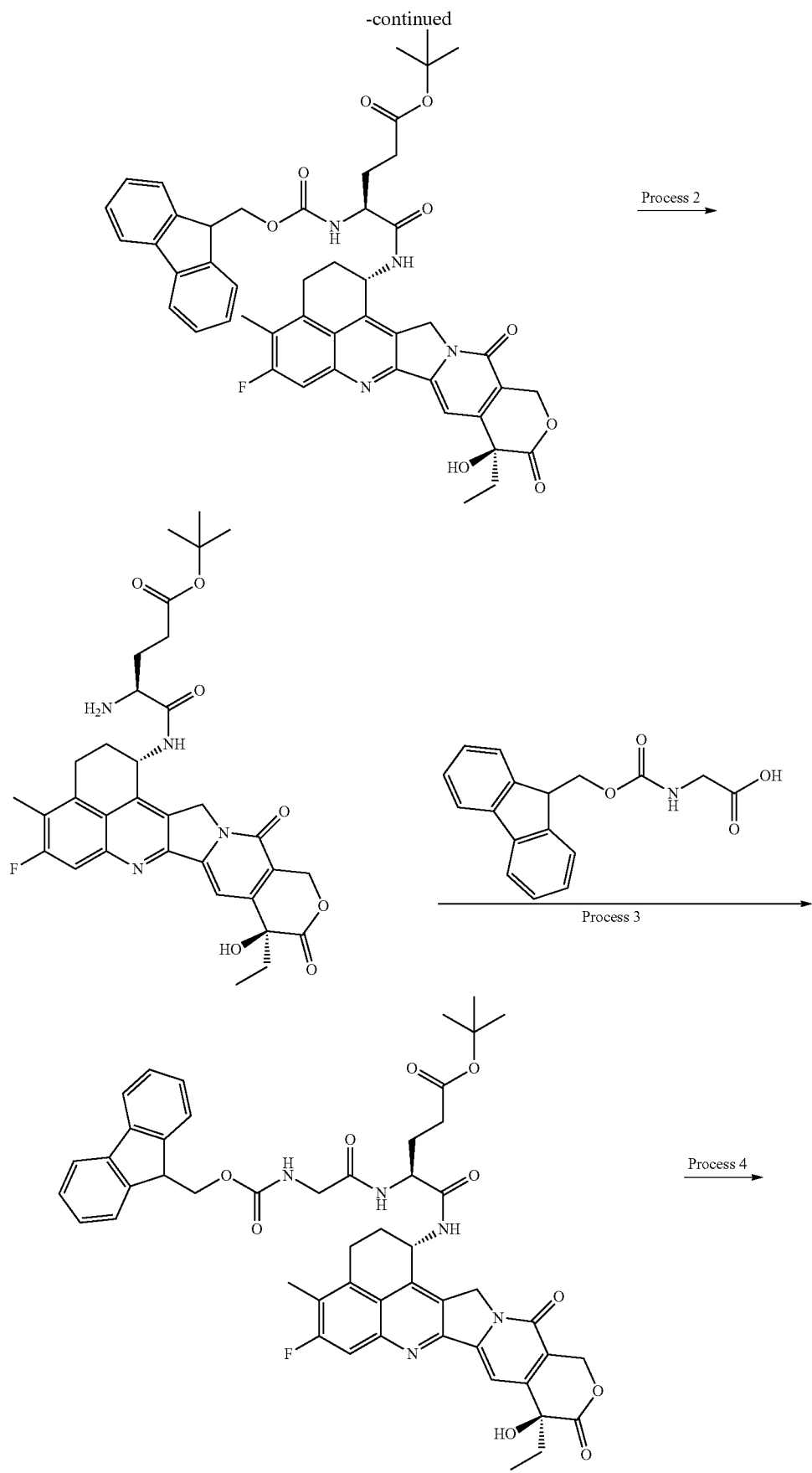

597
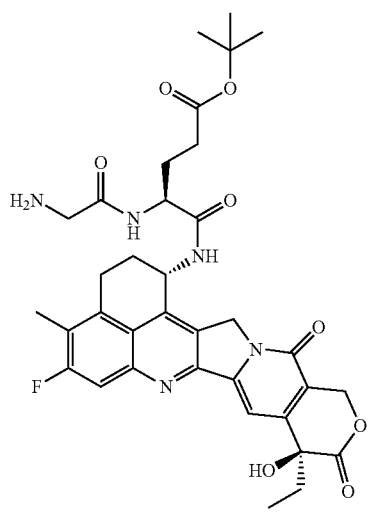
-continued
598
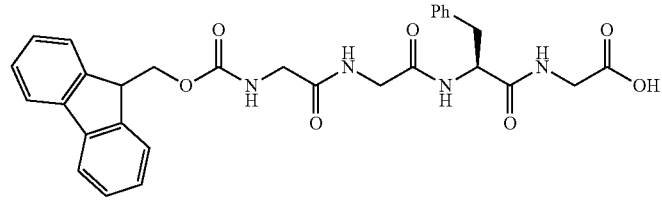
Process 5 →
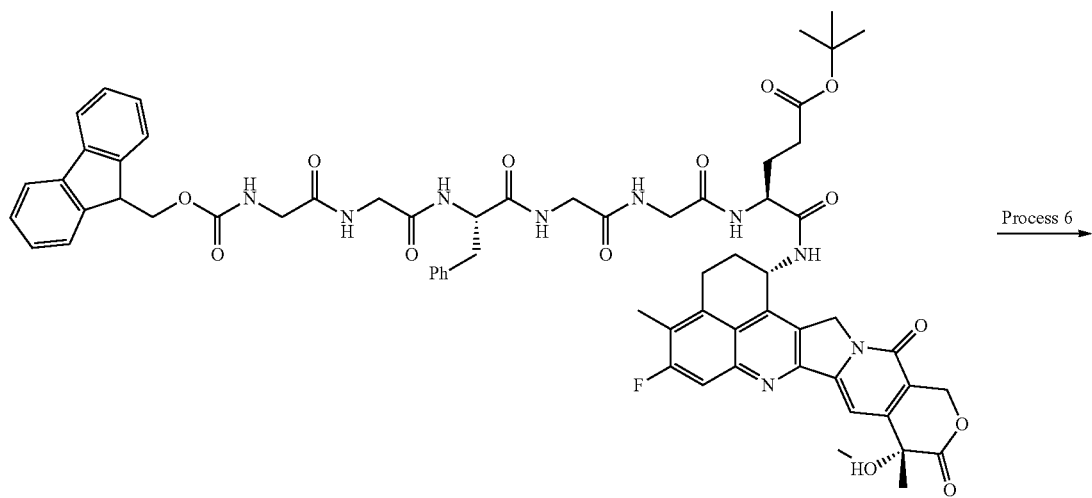
Process 6 →
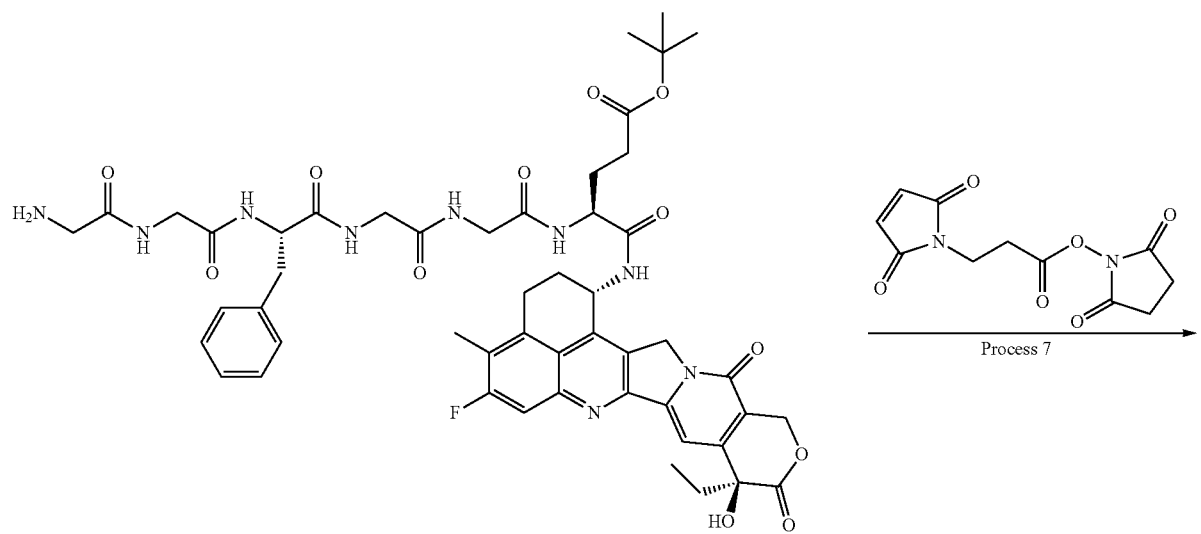
Process 7 →

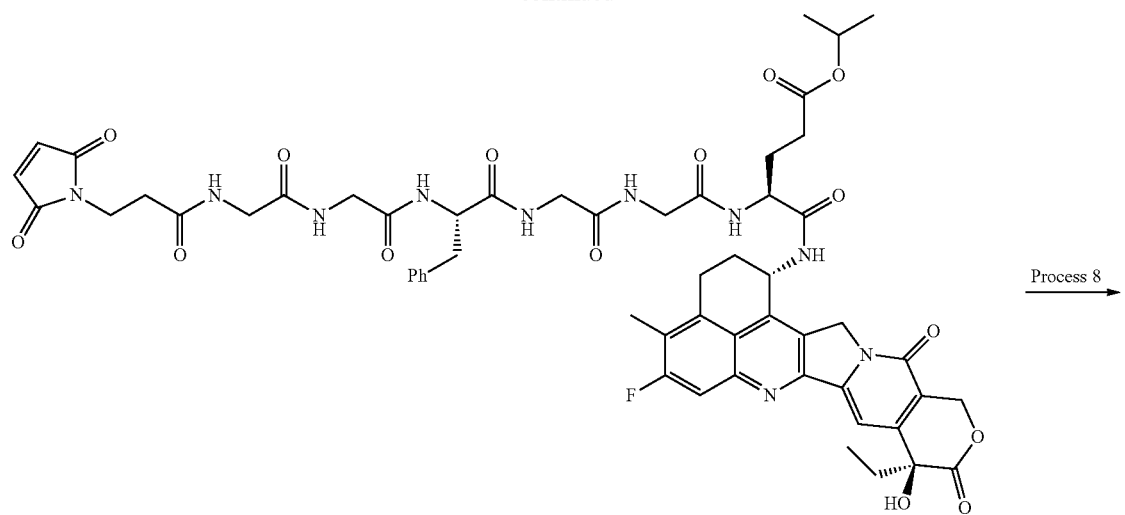
Process 8 →
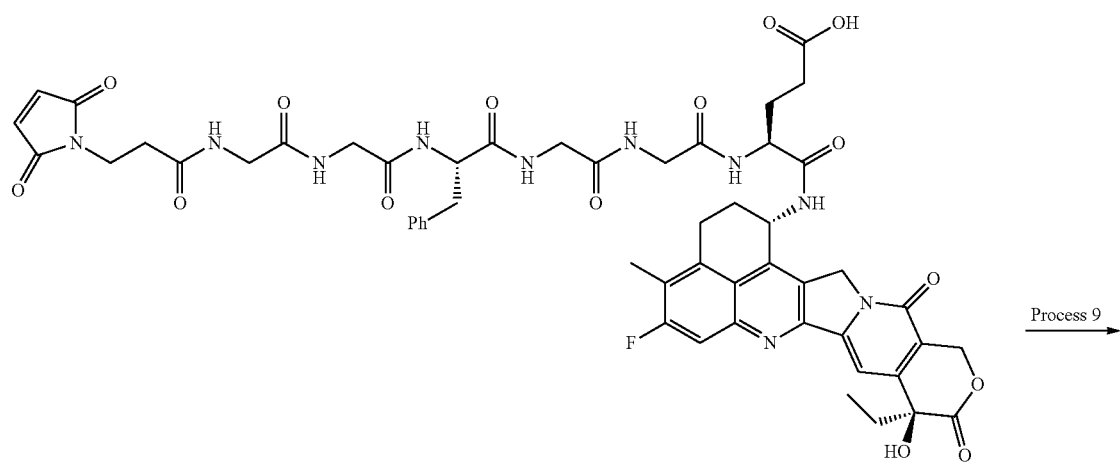
Process 9 →
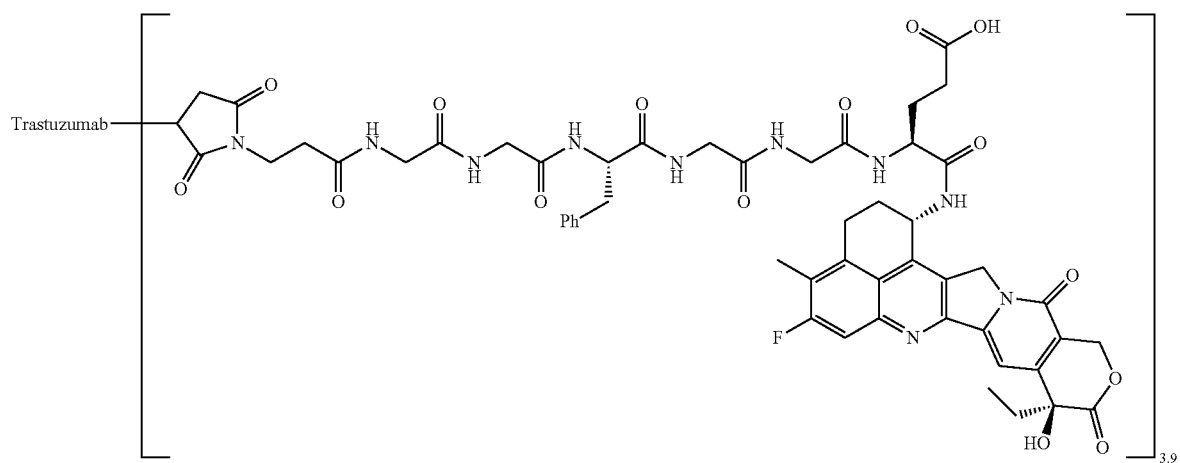

Process 1: tert-Butyl N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-N²-[(9H-fluoren-9-ylmethoxy)carbonyl]-L-α-glutaminate Methanesulfonic acid salt of exatecan (532 mg, 1.00 mmol) was reacted in the same manner as Process 1 of Example 80 by using N-[(9H-fluoren-9-ylmethoxy)carbonyl]-L-glutamic acid 5-tert-butyl (511 mg, 1.20 mmol) instead of N-(tert-butoxycarbonyl)-glycine, and the crude product obtained was used for the next reaction without purification.

Process 2: tert-Butyl N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-α-glutaminate The crude product obtained in Process 1 above was reacted in the same manner as Process 2 of Example 73 to yield the titled compound as a pale yellow solid (411 mg, 66%).

$^1$H-NMR (400 MHz, DMSO-$d_6$) δ: 0.87 (3H, t, J=7.4 Hz), 1.32 (9H, s), 1.51-2.35 (8H, m), 2.41 (3H, s), 3.13-3.22 (3H, m), 5.21 (2H, dd, J=57.7, 19.0 Hz), 5.42 (2H, dd, J=18.4, 16.4 Hz), 5.51-5.59 (1H, m), 6.54 (1H, s), 7.30 (1H, s), 7.81 (1H, d, J=10.9 Hz), 8.34-8.42 (1H, m).

Process 3: tert-Butyl N-[(9H-fluoren-9-ylmethoxy)carbonyl]glycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-α-glutaminate The compound (411 mg, 0.662 mmol) obtained in Process 2 above was reacted in the same manner as Process 1 of Example 80 by using N-[(9H-fluoren-9-ylmethoxy)carbonyl]glycine (236 mg, 0.795 mmol) instead of N-(tert-butoxycarbonyl)-glycine, and the crude product obtained was used for the next reaction without purification.

Process 4: tert-Butyl glycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-α-glutaminate The crude product obtained in Process 3 above was reacted in the same manner as Process 2 of Example 73 to yield the titled compound as a pale yellow solid (219 mg, 49%).

$^1$H-NMR (400 MHz, DMSO-$d_6$) δ: 0.87 (3H, t, J=7.4 Hz), 1.27 (9H, s), 1.66-2.45 (8H, m), 2.41 (3H, s), 3.11-3.45 (4H, m), 4.30-4.37 (1H, m), 5.19 (2H, dd, J=109.1, 18.8 Hz), 5.41 (2H, dd, J=16.4, 19.9 Hz), 5.50-5.58 (1H, m), 6.55 (1H, s), 7.31 (1H, s), 7.81 (1H, d, J=10.9 Hz), 8.14 (1H, s), 8.65 (1H, d, J=8.2 Hz).

Process 5: tert-Butyl N-[(9H-fluoren-9-ylmethoxy)carbonyl]glycylglycyl-L-phenylalanylglycylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-α-glutaminate The compound (219 mg, 0.323 mmol) obtained in Process 4 above was reacted in the same manner as Process 1 of Example 80 by using N-[(9H-fluoren-9-ylmethoxy)carbonyl]glycylglycyl-L-phenylalanylglycine (217 mg, 0.388 mmol) instead of N-(tert-butoxycarbonyl)-glycine, and the crude product obtained was used for the next reaction without purification.

Process 6: tert-Butyl glycylglycyl-L-phenylalanylglycylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-α-glutaminate The crude product obtained in Process 5 above was reacted in the same manner as Process 2 of Example 73 to yield the titled compound as a pale yellow solid (131 mg, 41%).

$^1$H-NMR (400 MHz, DMSO-$d_6$) δ: 0.87 (3H, t, J=7.2 Hz), 1.28 (9H, s), 1.66-2.29 (8H, m), 2.40 (3H, s), 2.72-2.80 (1H, m), 3.00-3.08 (1H, m), 3.37-3.10 (4H, m), 3.55-3.84 (6H, m), 4.23-4.31 (1H, m), 4.49-4.55 (1H, m), 5.19 (2H, dd, J=104.4, 18.8 Hz), 5.42 (2H, dd, J=19.9, 16.4 Hz), 5.50-5.58 (1H, m), 6.55 (1H, s), 7.16-7.28 (5H, m), 7.31 (1H, s), 7.81 (1H, d, J=10.9 Hz), 7.96-8.01 (1H, m), 8.09 (1H, d, J=7.4 Hz), 8.12-8.19 (1H, m), 8.24 (1H, d, J=8.2 Hz), 8.34-8.40 (1H, m), 8.52 (1H, d, J=8.6 Hz).

Process 7: tert-Butyl N-[3-(2,5-dioxo-2,5-dihydro-1H-pyrrol-1-yl)propanoyl]glycylglycyl-L-phenylalanylglycylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-α-glutaminate The compound (131 mg, 0.132 mol) obtained in Process 6 above was reacted in the same manner as Process 3 of Example 73 by using N-succinimidyl 3-maleimidopropionate instead of N-succinimidyl 6-maleimidohexanoate to yield the titled compound as a pale yellow solid (102 mg, 68%).

$^1$H-NMR (400 MHz, DMSO-$d_6$) δ: 0.87 (3H, t, J=7.4 Hz), 1.28 (9H, s), 2.87-2.86 (10H, m), 2.40 (3H, s), 2.73-2.82 (1H, m), 2.99-3.07 (1H, m), 3.11-3.20 (2H, m), 3.54-3.80 (10H, m), 4.23-4.31 (1H, m), 4.45-4.52 (1H, m), 5.19 (2H, dd, J=104.1, 18.8 Hz), 5.41 (2H, dd, J=16.4, 20.0 Hz), 5.50-5.58 (1H, m), 6.54 (1H, s), 6.99 (2H, s), 7.14-7.26 (5H, m), 7.31 (1H, s), 7.81 (1H, d, J=11.0 Hz), 7.92-7.97 (1H, m), 8.00-8.05 (1H, m), 8.06-8.13 (2H, m), 8.26-8.32 (2H, m), 8.50 (1H, d, J=8.6 Hz).

Process 8: N-[3-(2,5-Dioxo-2,5-dihydro-1H-pyrrol-1-yl)propanoyl]glycylglycyl-L-phenylalanylglycylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-L-α-glutamine The compound (102 mg, 0.0889 mol) obtained in Process 7 above was reacted in the same manner as Process 2 of Example 1 to yield the titled compound as a pale yellow solid (74.0 mg, 76%).

$^1$H-NMR (400 MHz, DMSO-$d_6$) δ: 0.88 (3H, t, J=7.4 Hz), 2.56-1.74 (10H, m), 2.40 (3H, s), 2.74-2.83 (1H, m), 2.99-3.08 (1H, m), 3.12-3.19 (2H, m), 3.55-3.78 (10H, m), 4.22-4.33 (1H, m), 4.44-4.53 (1H, m), 5.19 (2H, dd, J=83.1, 19.0 Hz), 5.43 (2H, s), 5.49-5.56 (1H, m), 6.53 (1H, s), 6.99 (2H, s), 7.15-7.29 (5H, m), 7.31 (1H, s), 7.80 (1H, d, J=11.3 Hz), 7.93-8.19 (4H, m), 8.24-8.36 (2H, m), 8.44-8.53 (1H, m), 12.08 (1H, s).

MS (APCI) m/z: 1091 (M+H)$^+$.

Process 9: Antibody-Drug Conjugate (152)

By using the trastuzumab produced in Reference Example 1 and the compound obtained in Process 8 above, the compound of interest was obtained in the same manner as Process 6 of Example 2.
Antibody concentration: 1.58 mg/mL, antibody yield: 9.5 mg (76%), and average number of conjugated drug molecules (n) per antibody molecule: 3.9.

Example 153 Antibody-Drug Conjugate (153)

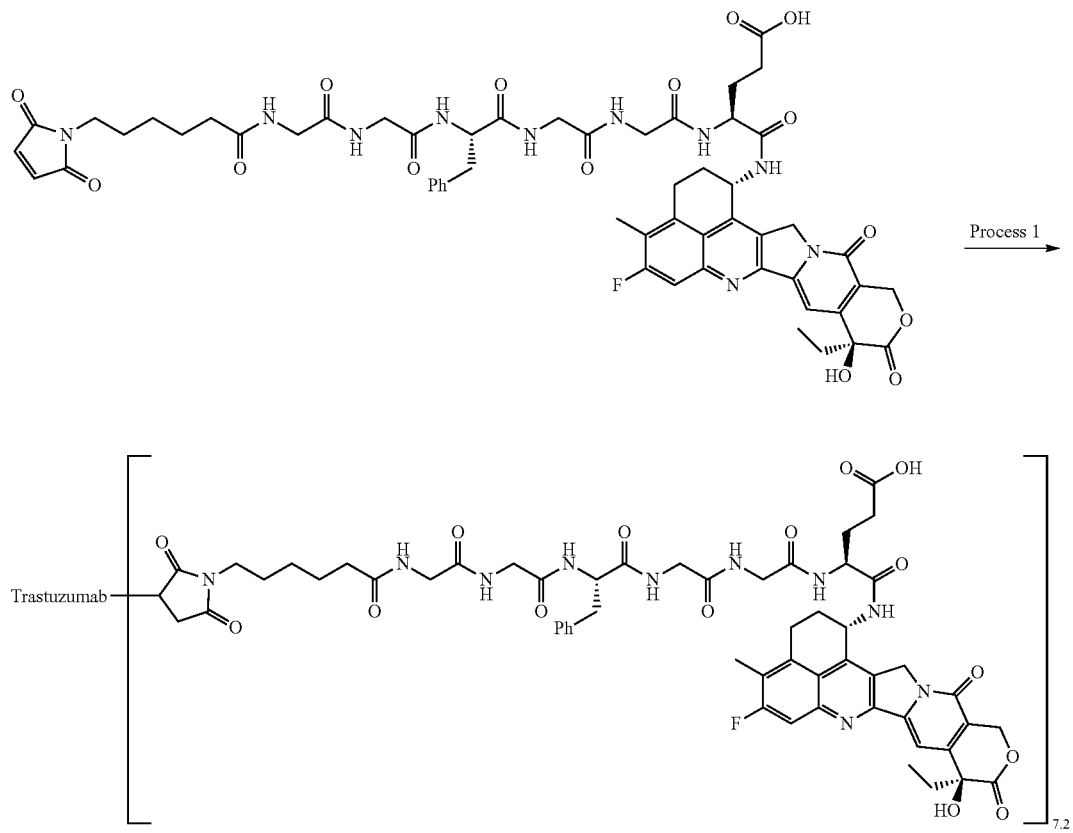

[Formula 206]

Process 1: Antibody-Drug Conjugate (153)

By using the trastuzumab produced in Reference Example 1 and the compound obtained in Process 8 of Example 152, the Example compound of interest was obtained in the same manner as Process 1 of Example 3.

Antibody concentration: 1.45 mg/mL, antibody yield: 8.7 mg (70%), and average number of conjugated drug molecules (n) per antibody molecule: 7.2.

Example 154 Antibody-Drug Conjugate (154)

[Formula 207]

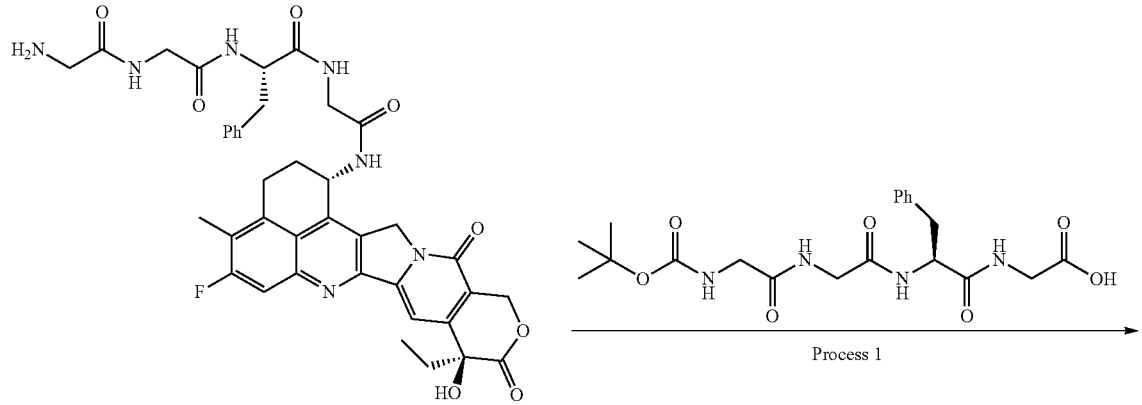

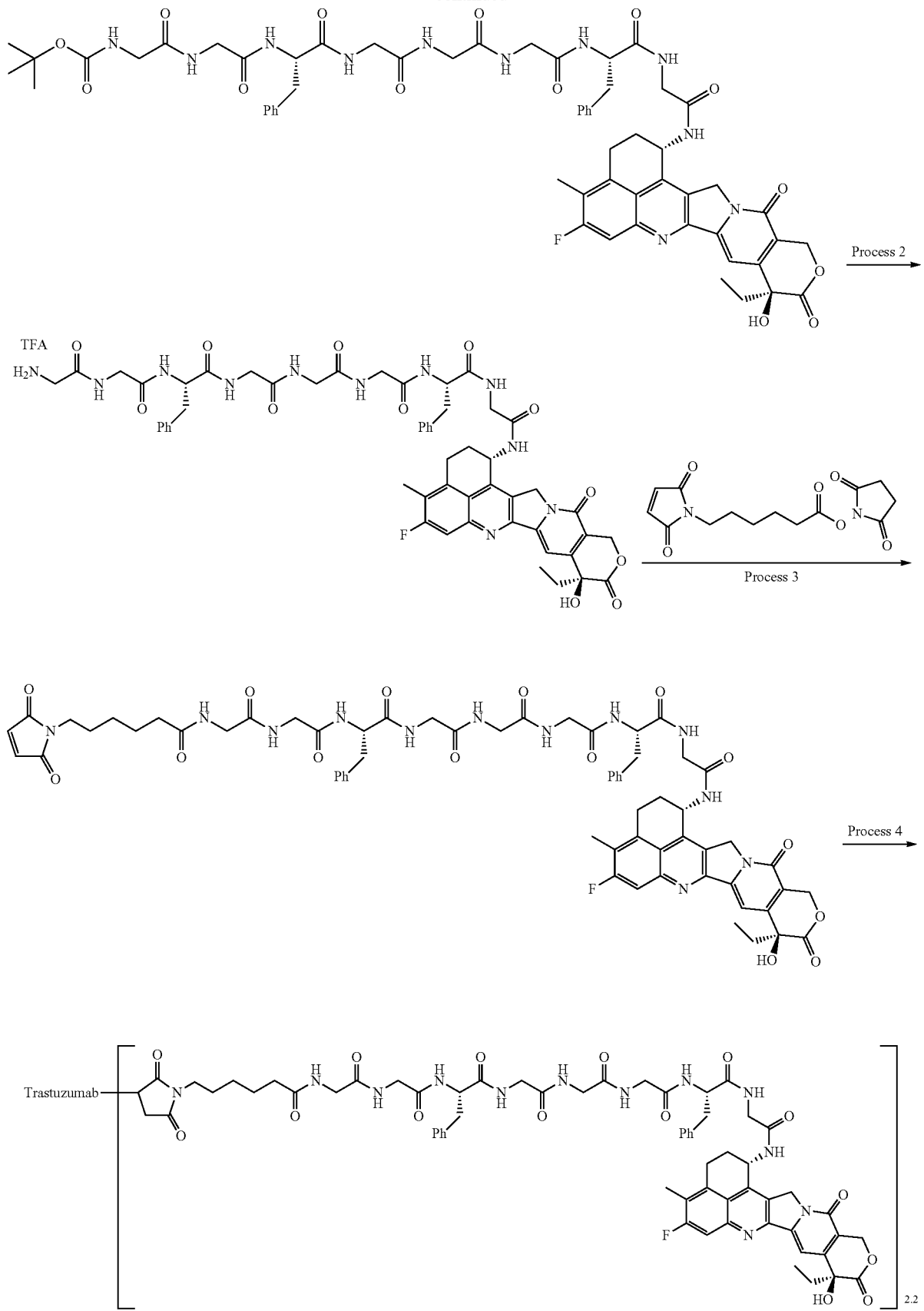

607

Process 1: N-(tert-Butoxycarbonyl)glycylglycyl-L-phenylalanylglycylglycylglycylphenylalanyl-N-[(1S,9S)-9-ethyl-5-fluoro-9-hydroxy-4-methyl-10,13-dioxo-2,3,9,10,13,15-hexahydro-1H,12H-yl]glycinamide Glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (0.550 g, 0.730 mmol) was reacted in the same manner as Process 1 of Example 73 by using N-(tert-butoxycarbonyl)-glycylglycyl-L-phenylalanylglycine (0.382 g, 0.876 mmol) instead of N-[(9H-fluoren-9-ylmethoxy)carbonyl]-L-aspartic acid 4-tert-butyl to yield the titled compound as a pale yellow solid (0.566 g, 66%).

$^1$H-NMR (400 MHz, DMSO-$d_6$) δ: 0.86 (3H, t, J=7.2 Hz), 1.37 (9H, s), 1.79-1.90 (2H, m), 2.10-2.13 (1H, m), 2.18-2.21 (1H, m), 2.41 (3H, s), 2.77-2.80 (2H, m), 2.98 (1H, dd, J=13.9, 4.5 Hz), 3.04 (1H, dd, J=13.7, 3.9 Hz), 3.17-3.19 (2H, m), 3.54-3.61 (4H, m), 3.70-3.74 (8H, m), 4.44 (1H, td, J=8.4, 4.7 Hz), 4.52 (1H, td, J=8.8, 4.0 Hz), 5.22 (1H, d, J=19.6 Hz), 5.28 (1H, d, J=19.6 Hz), 5.38 (1H, d, J=16.4 Hz), 5.44 (1H, d, J=16.4 Hz), 5.56-5.60 (1H, m), 6.53 (1H, s), 6.99 (1H, t, J=5.7 Hz), 7.17-7.23 (10H, m), 7.31 (1H, s), 7.81 (1H, d, J=11.0 Hz), 7.89 (1H, t, J=6.1 Hz), 8.03-8.05 (2H, m), 8.10 (1H, d, J=7.8 Hz), 8.15 (1H, d, J=8.2 Hz), 8.32-8.33 (2H, m), 8.44 (1H, d, J=8.2 Hz).

MS (APCI) m/z: 1172 (M+H)$^+$.

Process 2: Glycylglycyl-L-phenylalanylglycylglycylglycylphenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.440 g, 0.376 mmol) obtained in Process 1 above was reacted in the same manner as Process 2 of Example 1 to yield the titled compound as a yellow solid (0.264 g, 66%).

$^1$H-NMR (400 MHz, DMSO-$d_6$) δ: 0.86 (3H, t, J=7.2 Hz), 1.79-1.90 (2H, m), 2.14-2.20 (2H, m), 2.41 (3H, s), 2.73-2.80 (2H, m), 2.98 (1H, dd, J=13.7, 4.3 Hz), 3.05 (1H, dd, J=13.9, 4.5 Hz), 3.17-3.18 (2H, m), 3.55-3.88 (12H, m), 4.45 (1H, dd, J=13.1, 8.8 Hz), 4.56 (1H, td, J=8.9, 4.3 Hz), 5.22 (1H, d, J=19.9 Hz), 5.27 (1H, t, J=10.9 Hz), 5.38 (1H, d, J=16.0 Hz), 5.44 (1H, d, J=16.4 Hz), 5.58 (1H, t, J=4.1 Hz), 6.55 (1H, s), 7.16-7.32 (10H, m), 7.32 (1H, s), 7.81 (1H, d, J=10.9 Hz), 7.99 (3H, brs), 8.07-8.12 (2H, m), 8.34-8.38 (3H, m), 8.47-8.51 (2H, m).

MS (APCI) m/z: 1072 (M+H)$^+$.

Process 3: N-[6-(2,5-Dioxo-2,5-dihydro-1H-pyrrol-1-yl)hexanoyl]glycylglycyl-L-phenylalanylglycylglycylglycylphenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.229 g, 0.213 mmol) obtained in Process 2 above was reacted in the same manner as Process 8 of Example 5 to yield the titled compound as a pale yellow solid (0.0282 g, 11%).

$^1$H-NMR (400 MHz, DMSO-$d_6$) δ: 0.87 (3H, t, J=7.2 Hz), 1.17-1.63 (8H, m), 2.08-2.10 (3H, m), 2.31-2.35 (1H, m), 2.40 (3H, s), 2.76 (1H, dd, J=10.6, 3.1 Hz), 2.95-3.11 (2H, m), 3.13-3.24 (3H, m), 3.36-3.41 (2H, m), 3.59-3.79 (12H, m), 4.50-4.52 (2H, m), 5.23-5.25 (2H, m), 5.40-5.41 (2H, m), 5.57-5.58 (1H, m), 6.53 (1H, s), 6.99 (2H, s), 7.14-7.26 (10H, m), 7.32 (1H, s), 7.81 (1H, d, J=11.0 Hz), 7.97-8.13 (6H, m), 8.28-8.32 (2H, m), 8.42-8.47 (1H, m).

MS (APCI) m/z: 1265 (M+H)$^+$.

Process 4: Antibody-Drug Conjugate (154)

The compound obtained in Process 3 above was used as the drug linker. The amount of the aqueous solution of 10 mM TCEP added was adjusted such that the molar ratio of TCEP to the antibody at the antibody reduction was 2.3. And the amount of the 10 mM drug linker solution added was adjusted such that the molar ratio of the drug linker to the antibody at the drug linker conjugation was 4.6. Then the amount of the aqueous solution of 100 mM NAC added was adjusted such that the molar ratio of NAC to the antibody at the termination of the reaction was 9.2. By the same procedures as Process 5 of Example 78, 6 mL of a solution containing the Example compound of interest was obtained, and the following characteristic values were obtained.
Antibody concentration: 1.16 mg/mL, antibody yield: 7.0 mg (70%), and average number of conjugated drug molecules (n) per antibody molecule: 2.2.

Example 155 Antibody-Drug Conjugate (155)

[Formula 208]

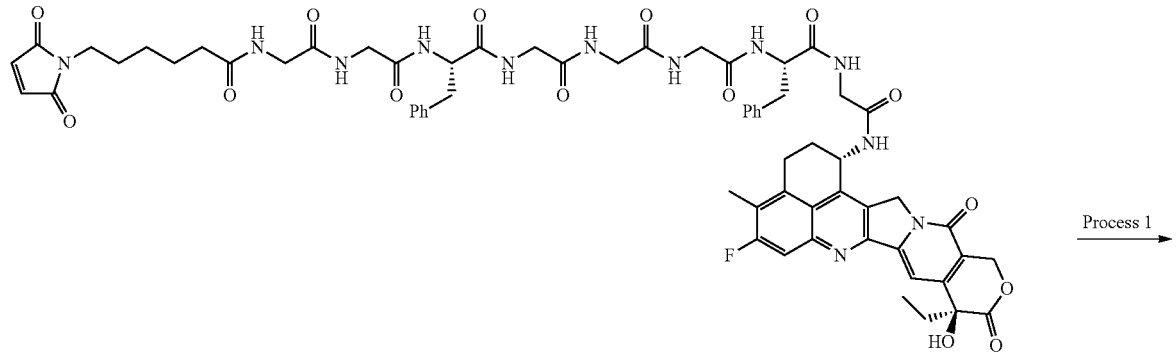

Process 1

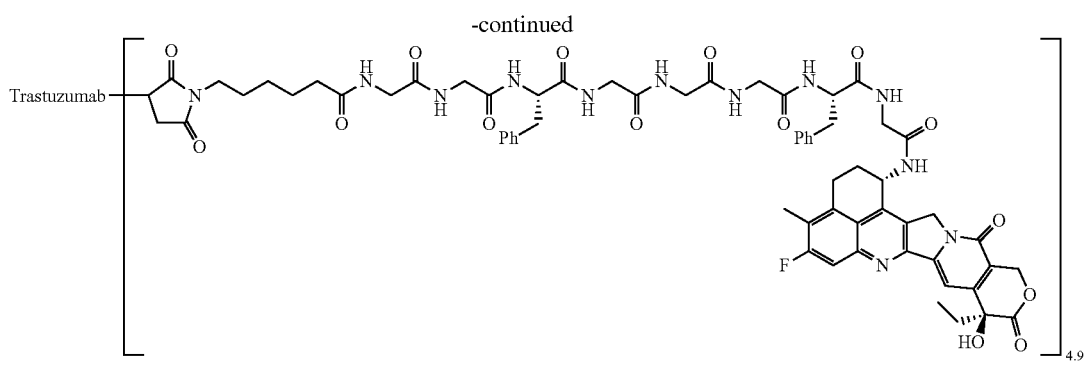

Process 1: Antibody-Drug Conjugate (155)

The compound obtained in Process 3 of Example 154 was used as the drug linker. The amount of the aqueous solution of 10 mM TCEP added was adjusted such that the molar ratio of TCEP to the antibody at the antibody reduction was 4.6. And the amount of the 10 mM drug linker solution added was adjusted such that the molar ratio of the drug linker to the antibody at the drug linker conjugation was 9.2. Then the amount of the aqueous solution of 100 mM NAC added was adjusted such that the molar ratio of NAC to the antibody at the termination of the reaction was 18.4. By the same procedures as Process 5 of Example 78, 6 mL of a solution containing the compound of interest was obtained, and the following characteristic values were obtained.
Antibody concentration: 1.36 mg/mL, antibody yield: 8.2 mg (82%), and average number of conjugated drug molecules (n) per antibody molecule: 4.9.

Example 156 Antibody-Drug Conjugate (156)

[Formula 209]

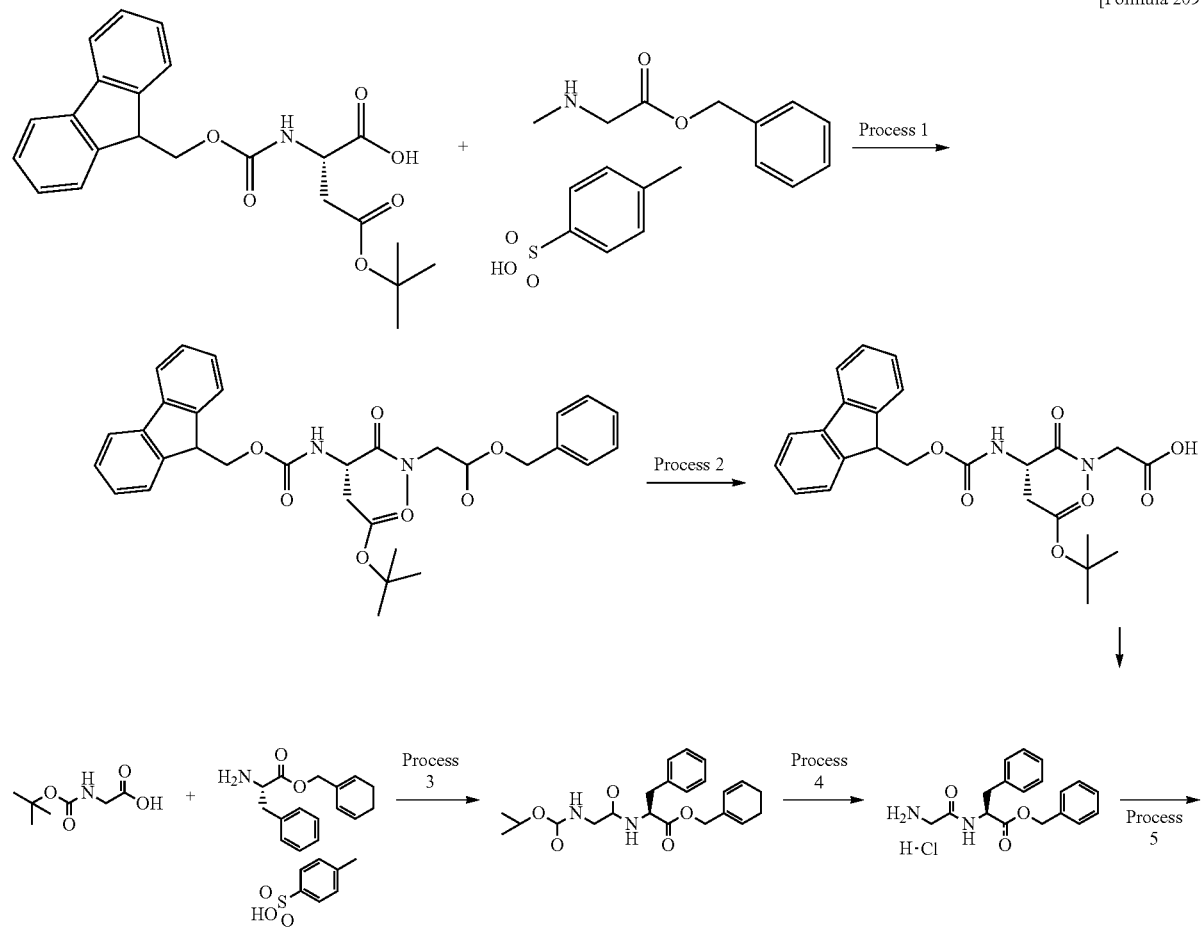

611                                                      612
-continued
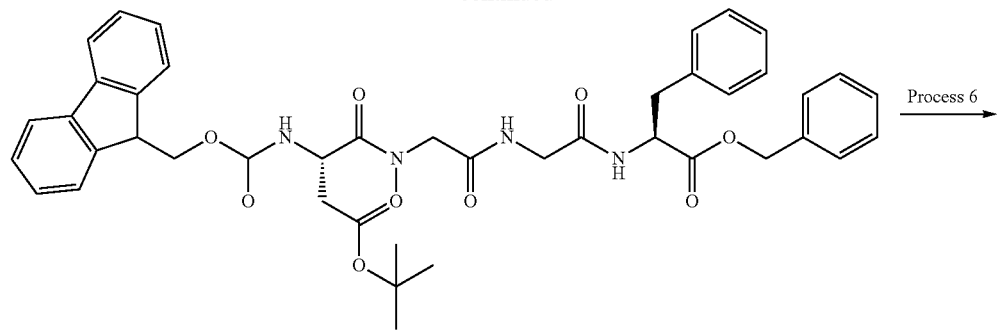
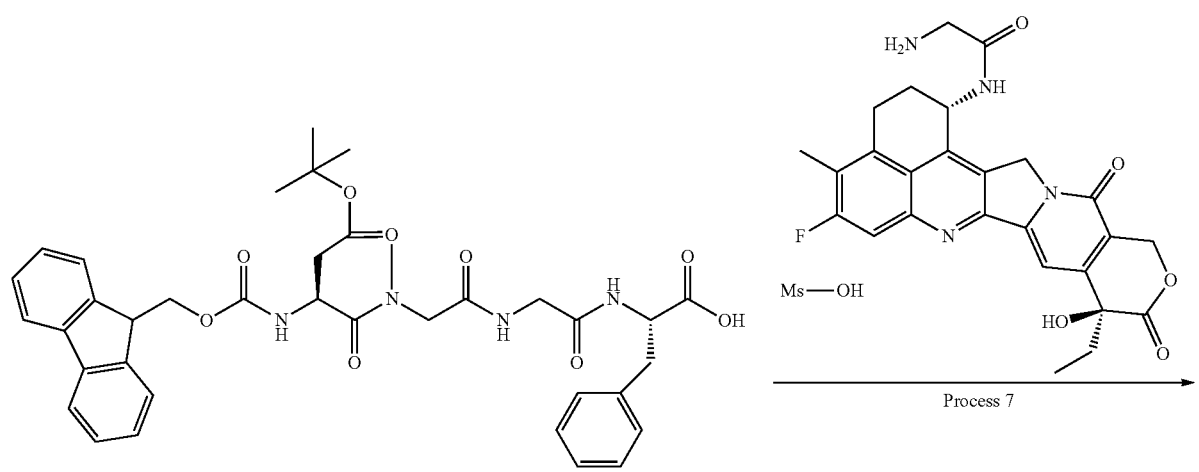
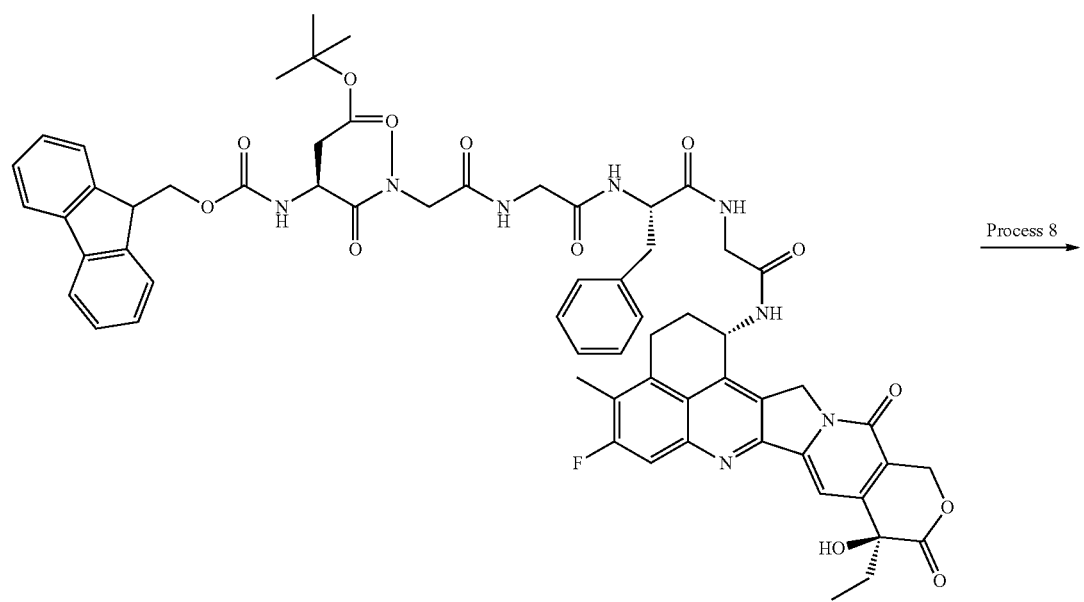

613 614
-continued
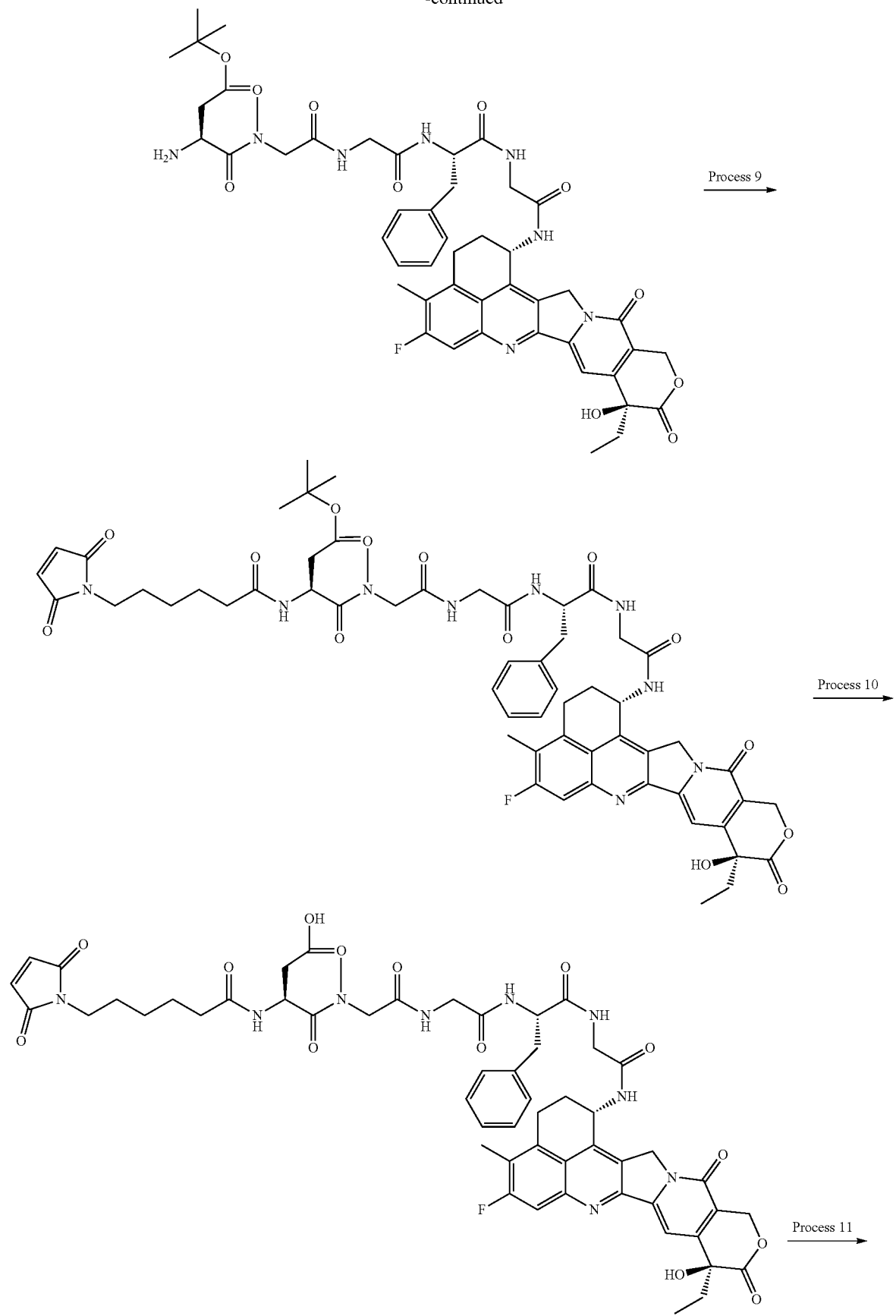
Process 9 →
Process 10 →
Process 11 →

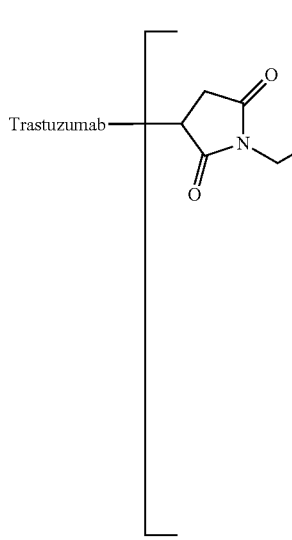
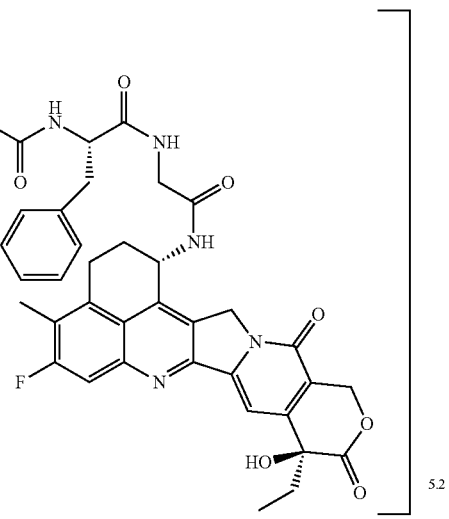

Process 1: tert-Butyl (3S)-4-{[2-(benzyloxy)-2-oxo-ethyl](methyl)amino}-3-{[(9H-fluoren-9-ylmethoxy)carbonyl]amino}-4-oxobutanate (2S)-4-tert-Butoxy-2-{[(9H-fluoren-9-ylmethoxy)carbonyl]amino}-4-oxobutanoic acid (9.00 g, 21.9 mmol) was dissolved in N,N-dimethylformamide (30.0 mL), charged with 1-hydroxybenzotriazole (2.96 g, 21.9 mmol) and 1-ethyl-3-(3-dimethylaminopropyl)carbodiimide hydrochloride (8.39 g, 43.8 mmol), and stirred at room temperature for 1 hour. After adding benzyl N-methylglycinate 4-methylbenzenesulfonate (7.69 g, 21.9 mmol) and triethylamine (3.05 mL, 21.88 mmol), it was stirred at room temperature for 21 hours. After adding water (200 mL), it was extracted with 150 mL of ethyl acetate 3 times, and the organic layer was dried over anhydrous sodium sulfate. The solvent was removed under reduced pressure to yield a mixture of a colorless solid containing the titled compound (11.9 g). The mixture was used for the next reaction without further purification.

Process 2: {[(2S)-4-tert-Butoxy-2-{[(9H-fluoren-9-ylmethoxy)carbonyl]amino}-4-oxobutanoyl](methyl)amino}acetic acid The mixture (11.9 g) obtained in Process 2 above was dissolved in methanol (200 mL). After adding palladium on carbon catalyst (500 mg), it was stirred under a hydrogen atmosphere at room temperature for 7 hours. The insolubles were removed by filtration through celite, and the solvent was removed under reduced pressure to yield a mixture of a colorless solid containing the titled compound (9.21 g). The mixture was used for the next reaction without further purification.

Process 3: Benzyl N-(tert-butoxycarbonyl)glycyl-L-phenylalanate

N-(tert-Butoxycarbonyl)glycine (5.00 g, 28.5 mmol) was dissolved in N,N-dimethylformamide (30 mL), charged with 1-hydroxybenzotriazole (3.86 g, 28.5 mmol) and 1-ethyl-3-(3-dimethylaminopropyl)carbodiimide hydrochloride (10.9 g, 57.1 mmol), and stirred at room temperature for 1 hour. After adding benzyl L-phenylalanate 4-methylbenzenesulfonate (12.2 g, 28.5 mmol) and triethylamine (3.98 mL, 28.5 mmol), it was stirred at room temperature for 17 hours. The reaction solution was poured to water and stirred, and then the deposited insolubles were collected by filtration. The solid was washed with water to yield the titled compound as a colorless solid (11.7 g, 99%).

$^1$H-NMR (400 MHz, DMSO-$d_6$) δ: 1.38 (9H, s), 2.96 (1H, dd, J=13.7, 8.5 Hz), 3.03 (1H, dd, J=13.8, 6.0 Hz), 3.52 (1H, dd, J=17.0, 6.2 Hz), 3.58 (1H, dd, J=16.8, 6.3 Hz), 4.54 (1H, dd, J=14.2, 7.6 Hz), 5.06 (1H, d, J=12.4 Hz), 5.10 (1H, d, J=12.4 Hz), 6.93 (1H, t, J=6.0 Hz), 7.17-7.37 (10H, m), 8.27 (1H, d, J=7.8 Hz).

MS (ESI) m/z: 413 (M+H)$^+$.

Process 4: Benzyl glycyl-L-phenylalanate

The compound (11.7 g, 28.2 mmol) obtained in Process 3 above was dissolved in a 4 N hydrogen chloride dioxane solution (100 mL) and stirred at room temperature for 2 hours. The solvent was removed under reduced pressure to yield hydrochloric acid salt of the titled compound as a colorless solid (9.98 g, quantitative).

$^1$H-NMR (400 MHz, DMSO-$d_6$) δ: 2.96 (1H, dd, J=13.8, 8.7 Hz), 3.08 (1H, dd, J=13.9, 5.9 Hz), 3.51-3.57 (2H, m), 4.62 (1H, q, J=7.2 Hz), 5.07 (1H, d, J=12.4 Hz), 5.13 (1H, d, J=12.7 Hz), 7.21-7.38 (10H, m), 8.10 (3H, s), 9.00 (1H, s).

MS (ESI) m/z: 313 (M+H)$^+$.

Process 5: Benzyl (5S,14S)-14-benzyl-5-(2-tert-butoxy-2-oxoethyl)-1-(9H-fluoren-9-yl)-7-methyl-3,6,9,12-tetraoxo-2-oxa-4,7,10,13-tetraazapantadecan-15-oate The mixture (2.8 g) obtained in Process 2 was dissolved in N,N-dimethylformamide (20 mL), charged with 1-hydroxybenzotriazole (780 mg, 5.80 mmol), 1-ethyl-3-(3-dimethylaminopropyl)carbodiimide hydrochloride (10.9 g, 11.6 mmol), the compound (2.02 g, 5.80 mmol) obtained in Process 4, and triethylamine (590 μL, 5.80 mmol), and stirred at room temperature for 13 hours. The reaction solution was poured to water and stirred, and then the deposited insolubles were collected by filtration. The solid was washed with water to yield the titled compound as a colorless solid (4.51 g, 87%, 3 steps).

$^1$H-NMR (400 MHz, DMSO-$d_6$) δ: 1.36 (9H, s), 2.43-2.48 (1H, m), 2.60-2.66 (1H, m), 2.79-2.81 (1H, m), 2.93-2.97 (1H, m), 3.03 (3H, s), 3.63-4.07 (4H, m), 4.17-4.35 (3H, m), 4.51-4.57 (1H, m), 4.69-4.80 (1H, m), 5.05-5.09 (2H, m), 7.18-7.46 (14H, m), 7.58-7.83 (2H, m), 7.82-8.03 (4H, m), 8.26-8.44 (1H, m).

MS (ESI) m/z: 111 (M+H)$^+$.

Process 6: (5S,14S)-14-Benzyl-5-(2-tert-butoxy-2-oxoethyl)-1-(9H-fluoren-9-yl)-7-methyl-3,6,9,12-tetraoxo-2-oxa-4,7,10,13-tetraazapantadecan-15-acid The compound (4.49 g, 5.78 mmol) obtained in Process 5 above was dissolved in methanol (50.0 mL). After adding a catalytic amount of palladium on carbon catalyst, it was stirred under a hydrogen atmosphere at room temperature for 1.5 hours. The insolubles were removed by filtration through celite, and the solvent was removed under reduced pressure to yield the titled compound as a colorless solid (3.99 g, quantitative).

$^1$H-NMR (400 MHz, DMSO-$d_6$) δ: 1.35 (9H, s), 2.42-2.45 (1H, m), 2.62-2.67 (1H, m), 2.77 (1H, s), 2.85-2.90 (1H, m), 3.00 (3H, s), 3.03-3.06 (1H, m), 3.61-4.06 (3H, m), 4.25-4.29 (3H, m), 4.40-4.42 (1H, m), 4.79-4.80 (1H, m), 7.19-7.43 (9H, m), 7.64-7.70 (2H, m), 7.81-7.89 (3H, m), 7.99 (1H, t, J=5.7 Hz), 8.12 (1H, d, J=8.1 Hz), 8.21 (1H, d, J=7.3 Hz).

MS (ESI) m/z: 687 (M+H)$^+$.

Process 7: tert-Butyl (5S,14S)-5-benzyl-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-14-{[(9H-fluoren-9-ylmethoxy)carbonyl]amino}-12-methyl-1,4,7,10,13-pentaoxo-3,6,9,12-tetraazapantadecan-16-oate Methanesulfonic acid salt of the compound (400 mg, 0.659 mmol) of Process 2 of Example 80 was dissolved in N,N-dimethylformamide (10 mL), charged with 1-hydroxybenzotriazole (90.0 mg, 0.659 mmol), 1-ethyl-3-(3-dimethylaminopropyl)carbodiimide hydrochloride (250 mg, 1.32 mmol), the compound (450 mg, 0.659 mmol) obtained in Process 6 above, and triethylamine (90.0 μL, 0.0659 mmol), and stirred at room temperature for 19 hours. The solvent was removed under reduced pressure and the residues obtained were purified by silica gel column chromatography [chloroform-chloroform:methanol=4:1 (v/v)] to yield the titled compound as a pale yellow solid (595 mg, 78%).

$^1$H-NMR (400 MHz, DMSO-$d_6$) δ: 0.86 (3H, t, J=7.3 Hz), 1.35 (9H, s), 1.80-1.89 (2H, m), 2.10-2.11 (1H, m), 2.17-2.19 (1H, m), 2.39 (3H, s), 2.40-2.45 (1H, m), 2.58-2.82 (3H, m), 2.99 (3H, s), 3.17 (2H, s), 3.53-4.01 (5H, m), 4.25-4.40 (5H, m), 4.65-4.79 (1H, m), 5.22 (2H, s), 5.37 (1H, d, J=16.4 Hz), 5.42 (1H, d, J=16.4 Hz), 5.56-5.58 (1H, m), 6.52 (1H, s), 7.14-7.40 (9H, m), 7.66-7.68 (2H, m), 7.79-7.84 (4H, m), 7.96-8.22 (2H, m), 8.34-8.43 (3H, m).

MS (ESI) m/z: 1161 (M+H)$^+$.

Process 8: tert-Butyl (5S,14S)-14-amino-5-benzyl-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-12-methyl-1,4,7,10,13-pentaoxo-3,6,9,12-tetraazapantadecan-16-oate The compound (520 mg, 0.448 mmol) obtained in Process 7 above was dissolved in N,N-dimethylformamide (8.00 mL), charged with piperidine (2.00 mL), and stirred at room temperature for 1 hour. The solvent was removed under reduced pressure and the residues obtained were purified by silica gel column chromatography [chloroform-partitioned organic layer of chloroform:methanol:water=7:3:1 (v/v/v)] to yield the titled compound as a pale yellow solid (350 mg, 83%).

$^1$H-NMR (400 MHz, DMSO-$d_6$) δ: 0.86 (3H, t, J=7.1 Hz), 1.36 (9H, s), 1.82-1.88 (3H, m), 2.12-2.22 (3H, m), 2.40 (3H, s), 2.54 (1H, s), 2.76-2.81 (1H, m), 2.98-3.03 (1H, m), 3.04 (3H, s), 3.16-3.17 (2H, m), 3.33 (2H, s), 3.50-4.16 (6H, m), 4.47 (1H, t, J=17.1 Hz), 5.24 (2H, s), 5.39 (1H, d, J=16.6 Hz), 5.43 (1H, d, J=16.4 Hz), 5.57-5.59 (1H, m), 6.53 (1H, s), 7.17-7.22 (5H, m), 7.31 (1H, s), 7.79-7.81 (1H, m), 7.89-8.01 (1H, m), 8.18-8.46 (3H, m).

MS (ESI) m/z: 939 (M+H)$^+$.

Process 9: tert-Butyl (5S,14S)-5-benzyl-14-{[6-(2,5-dioxo-2,5-dihydro-1H-pyrrol-1-yl)hexanoyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-12-methyl-1,4,7,10,13-pentaoxo-3,6,9,12-tetraazapantadecan-16-oate The compound (351 mg, 0.374 mmol) obtained in Process 8 above was dissolved in N,N-dimethylformamide (6.00 mL). After adding N-succinimidyl 6-maleimidohexanoate (115 mg, 0.374 mmol), it was stirred at room temperature for 16.5 hours. The solvent was removed under reduced pressure and the residues obtained were purified by silica gel column chromatography [chloroform-chloroform:methanol=4:1 (v/v)] to yield the titled compound as a pale yellow solid (403 mg, 95%).

$^1$H-NMR (400 MHz, DMSO-$d_6$) δ: 0.86 (3H, t, J=7.3 Hz), 1.15-1.18 (2H, m), 1.35 (9H, s), 1.41-1.44 (4H, m), 1.83-1.88 (2H, m), 1.99-2.00 (1H, m), 2.03-2.06 (1H, m), 2.10-2.12 (1H, m), 2.19-2.21 (1H, m), 2.33 (1H, dd, J=15.9, 6.8 Hz), 2.40 (3H, s), 2.61 (1H, dq, J=26.1, 6.5 Hz), 2.78 (1H, dd, J=13.8, 9.6 Hz), 2.97-2.99 (1H, m), 2.98 (3H, s), 3.17-3.19 (2H, m), 3.35-3.37 (2H, m), 3.67-3.83 (6H, m), 4.41-4.49 (1H, m), 4.90-5.02 (1H, m), 5.24 (2H, s), 5.39 (1H, d, J=16.1 Hz), 5.43 (1H, d, J=16.4 Hz), 5.57 (1H, dd, J=8.4, 4.3 Hz), 6.53 (1H, s), 6.99 (2H, s), 7.19 (5H, dq, J=26.7, 6.8 Hz), 7.32 (1H, d, J=7.6 Hz), 7.80 (1H, d, J=10.7 Hz), 7.92 (1H, dd, J=21.0, 15.4 Hz), 8.09 (1H, dt, J=20.1, 5.9 Hz), 8.22 (1H, dd, J=14.5, 8.4 Hz), 8.32-8.45 (2H, m).

MS (ESI) m/z: 1132 (M+H)$^+$.

Process 10: N-[6-(2,5-Dioxo-2,5-dihydro-1H-pyrrol-1-yl)hexanoyl]-L-α-aspartyl-N-methylglycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (343 mg, 0.302 mmol) obtained in Process 9 above was dissolved in trifluoroacetic acid (6.00 mL) and stirred at room temperature for 22 hours. The solvent was removed under reduced pressure and the residues obtained were purified by silica gel column chromatography [chloroform-chloroform:methanol=4:1 (v/v)] to yield the titled compound as a pale yellow solid (42.2 mg, 13%).

$^1$H-NMR (400 MHz, DMSO-$d_6$) δ: 0.87 (3H, t, J=7.2 Hz), 1.16-1.17 (2H, m), 1.45-1.48 (4H, m), 1.81-1.91 (2H, m), 2.00-2.02 (2H, m), 2.11-2.17 (2H, m), 2.38 (3H, s), 2.71-3.17 (8H, m), 3.11 (3H, s), 3.37-3.38 (3H, m), 3.63-3.80 (3H, m), 4.24-4.32 (1H, m), 4.86-4.90 (1H, m), 5.26 (2H, s), 5.39 (1H, d, J=16.6 Hz), 5.44 (1H, d, J=16.4 Hz), 5.57-5.58 (1H, m), 6.51 (1H, s), 7.00 (2H, s), 7.16-7.25 (5H, m), 7.31 (1H, d, J=3.2 Hz), 7.76-7.78 (2H, m), 8.05-8.14 (3H, m), 8.54 (1H, d, J=7.6 Hz), 8.73 (1H, s).

MS (ESI) m/z: 1077 (M+H)$^+$.

Process 11: Antibody-Drug Conjugate (156)

By using the trastuzumab produced in Reference Example 1 and the compound obtained in Process 10 above, the titled antibody-drug conjugate was obtained in the same manner as Process 1 of Example 3.

Antibody concentration: 1.82 mg/mL, antibody yield: 15.5 mg (78%), and average number of conjugated drug molecules (n) per antibody molecule: 5.2.

Example 157 Antibody-Drug Conjugate (157)

[Formula 210]

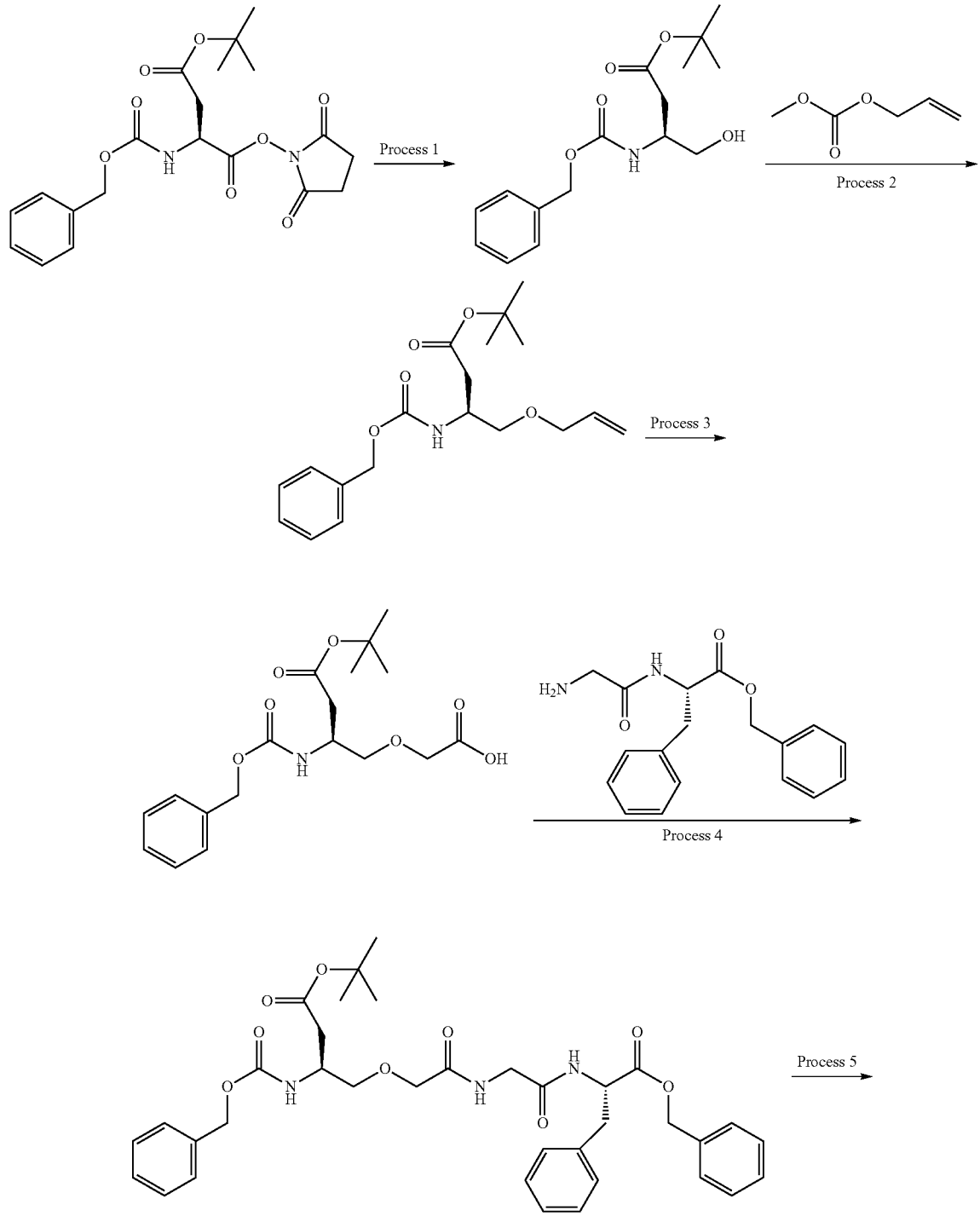

621     622
-continued
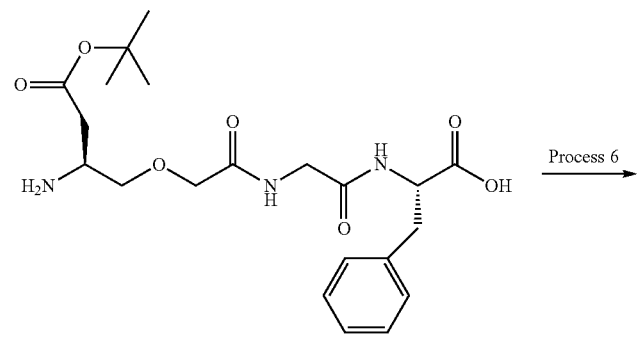
Process 6 →
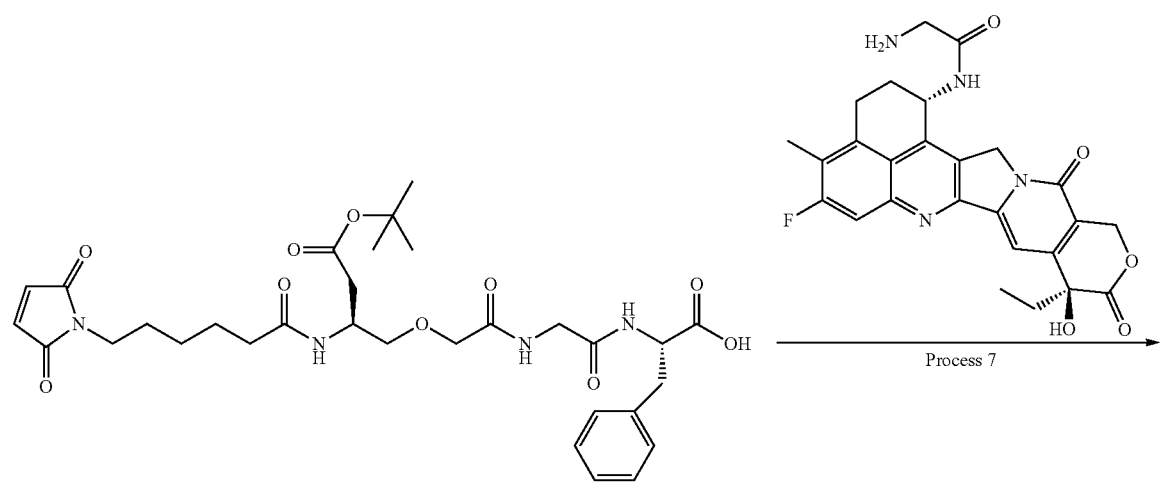
Process 7 →
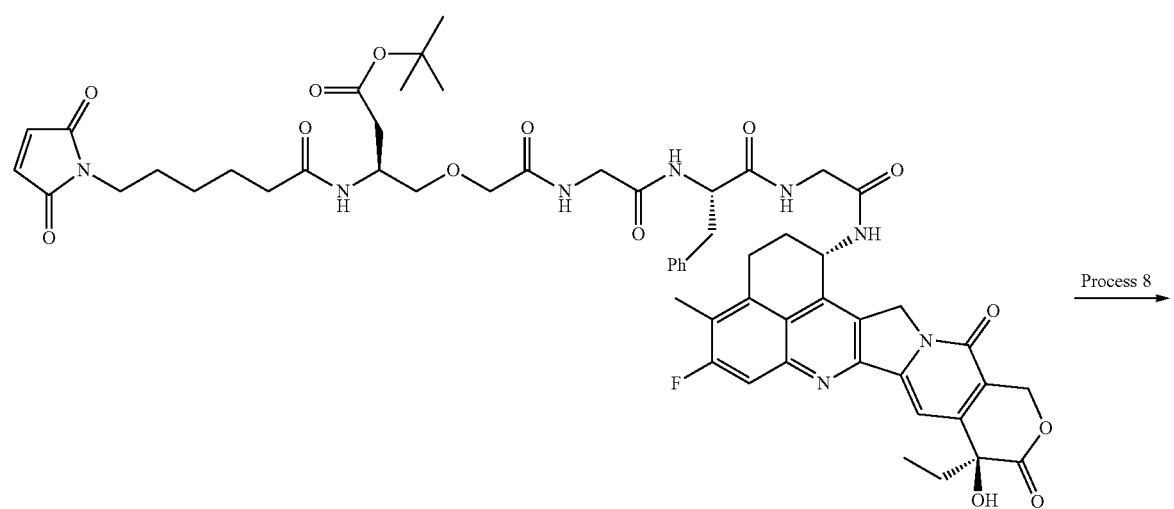
Process 8 →

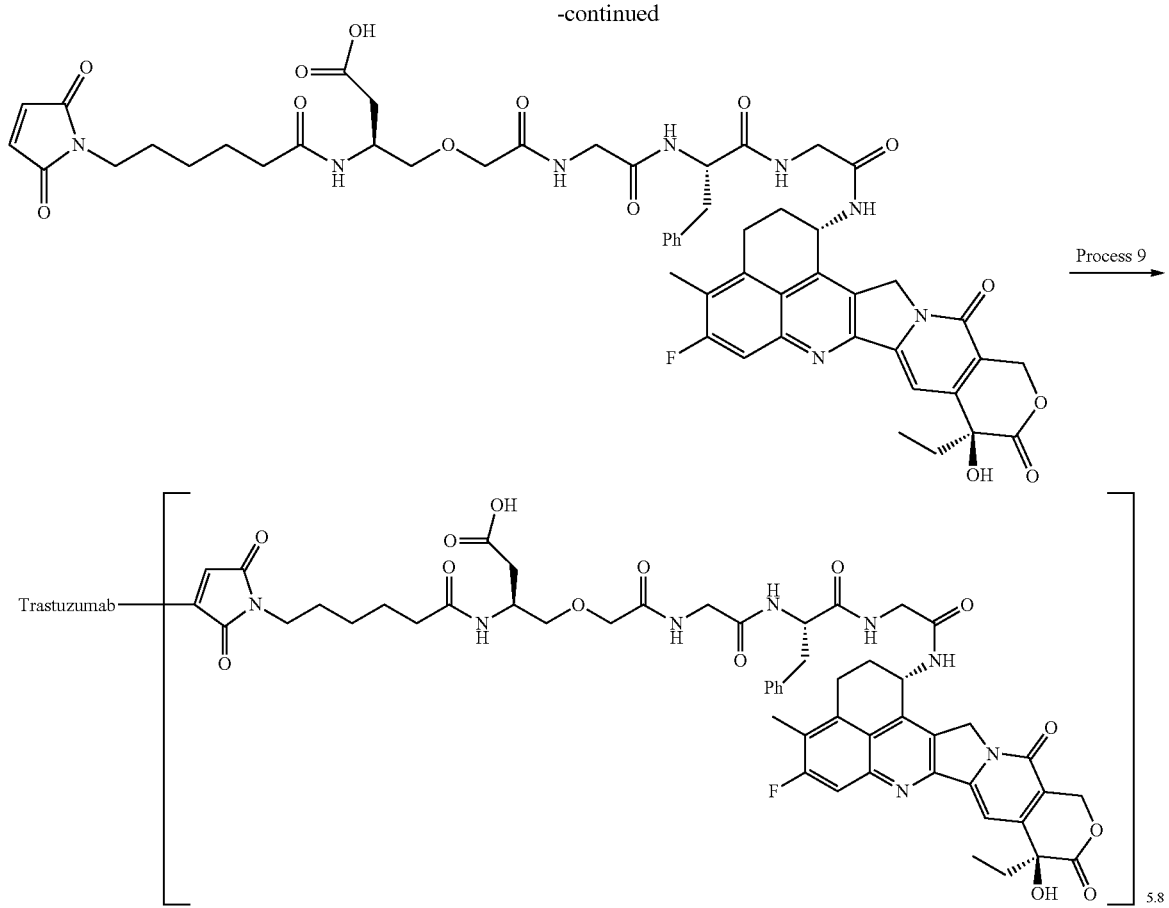

Process 1: tert-Butyl (3S)-3-{[(benzyloxy)carbonyl]amino}-4-hydroxybutanoate

To a tetrahydrofuran (50.0 mL) solution of N-α-benzyloxycarbonyl-L-aspartic acid α-(N-hydroxysuccinimidyl)β-t-butyl ester (10.0 g, 5.29 mmol) and benzyl glycolate (1.16 g, 7.93 mmol), an aqueous solution (10.0 mL) of sodium borohydride (1.47 g, 35.7 mmol) was added at 0° C. and stirred at the same temperature as above for 1 hour. The reaction solution was diluted with ethyl acetate and washed with water, and then the organic layer was dried over sodium sulfate. The solvent was removed under reduced pressure and the residues obtained were purified by silica gel column chromatography [hexane:ethyl acetate=4:1 (v/v) -ethyl acetate] to yield the titled compound as a clear colorless oily substance (7.91 g, quantitative).

$^1$H-NMR (400 MHz, CDCl$_3$) δ: 1.44 (9H, s), 2.41 (1H, brs), 2.48-2.62 (2H, m), 3.72 (2H, t, J=5.4 Hz), 3.99-4.08 (1H, m), 5.11 (2H, s), 5.42-5.53 (1H, m), 7.28-7.40 (5H, m).

MS (API) m/z: 310 (M+H)$^+$.

Process 2: tert-Butyl (3S)-3-{[(benzyloxy)carbonyl]amino}-4-(prop-2-en-1-yloxy)butanoate To a tetrahydrofuran (50.0 mL) solution of the compound (3.75 g, 12.1 mmol) obtained in the process above and allyl methyl carbonate (2.05 mL, 18.1 mmol), tetrakis(triphenylphosphine)palladium (0.700 g, 0.600 mmol) was added, and heated and stirred at 60° C. for 13 hours. The solvent was removed under reduced pressure and the residues obtained were purified by silica gel column chromatography [hexane-hexane:ethyl acetate=2:1 (v/v)] to yield the titled compound as a yellow oily substance (2.08 g, 49%).

$^1$H-NMR (400 MHz, CDCl$_3$) δ: 1.43 (9H, s), 2.54 (2H, d, J=6.0 Hz), 3.43-3.57 (2H, m), 3.97 (2H, d, J=5.4 Hz), 4.10-4.22 (1H, m), 5.10 (2H, s), 5.17 (1H, dd, J=10.3, 1.2 Hz), 5.24 (1H, dd, J=17.2, 1.2 Hz), 5.32-5.43 (1H, m), 5.80-5.91 (1H, m), 7.30-7.36 (5H, m).

MS (API) m/z: 350 (M+H)$^+$.

Process 3: {[(2S)-2-{[(Benzyloxy)carbonyl]amino}-4-tert-butoxy-4-oxobutyl]oxy}acetic acid To an aqueous solution (15.0 mL) of sodium periodate (3.06 g, 14.3 mmol), an ethyl acetate (10.0 mL) solution of acetonitrile (10.0 mL), ruthenium chloride hydrate (15.0 mg), and the compound (0.500 g, 1.43 mmol) obtained in the process above was added and stirred at room temperature for 1.5 hours. The reaction solution was charged with water and extracted with ethyl acetate and the organic layer obtained was dried over sodium sulfate. The solvent was removed under reduced pressure and the residues obtained were purified by silica gel column chromatography [chloroform-partitioned organic layer of chloroform:methanol:water=7:3:1 (v/v/v)] to yield the titled compound as a colorless oily substance (0.187 g, 36%).

$^1$H-NMR (400 MHz, DMSO-d$_6$) δ: 1.36 (9H, s), 2.29 (1H, dd, J=15.4, 8.8 Hz), 2.43-2.54 (1H, m), 3.36 (1H, dd, J=9.7, 6.0 Hz), 3.43 (1H, dd, J=9.7, 6.0 Hz), 3.93-4.03 (1H, m), 4.00 (2H, s), 4.98 (1H, d, J=12.7 Hz), 5.03 (1H, d, J=12.7 Hz), 7.25-7.39 (6H, m), 12.63 (1H, brs).

MS (API) m/z: 368 (M+H)$^+$.

Process 4: Benzyl N-({[(2S)-2-{[(benzyloxy)carbonyl]amino}-4-tert-butoxy-4-oxobutyl]oxy}acetyl) glycyl-L-phenylalanate To an N,N-dimethylformamide (10.0 mL) solution of the compound (0.266 g, 0.760 mmol) obtained in Process 4 of Example 156, N-hydroxysuccinimide (89.4 mg, 0.660 mmol), and the compound (0.187 g, 0.510 mmol) obtained in the process above, N,N-diisopropylethylamine (0.124 mL, 0.710 mmol) and 1-ethyl-3-(3-dimethylaminopropyl) carbodiimide hydrochloride (0.127 g, 0.660 mmol) was added and stirred at room temperature for 22 hours. The reaction solution was diluted with chloroform:methanol=9:1 (v/v) and washed with an aqueous solution of 10% citric acid, a saturated sodium hydrogen carbonate aqueous solution, and a saturated sodium chloride aqueous solution, and then the organic layer was dried over sodium sulfate. The solvent was removed under reduced pressure and the residues obtained were purified by silica gel column chromatography [chloroform-chloroform:methanol=9:1 (v/v)] to yield the titled compound as a pale orange oily substance (0.373 g, quantitative).

$^1$H-NMR (400 MHz, DMSO-d$_6$) δ: 1.35 (9H, s), 2.33 (1H, dd, J=15.1, 9.1 Hz), 2.47-2.53 (1H, m), 2.93 (1H, dd, J=13.9, 8.5 Hz), 3.03 (1H, dd, J=13.9, 6.0 Hz), 3.37 (1H, dd, J=9.1, 5.4 Hz), 3.44 (1H, dd, J=9.7, 4.8 Hz), 3.69 (1H, dd, J=16.3, 6.0 Hz), 3.79 (1H, dd, J=16.3, 6.0 Hz), 3.87 (2H, s), 3.99-4.09 (1H, m), 4.53 (1H, dd, J=14.2, 8.2 Hz), 4.94-5.12 (4H, m), 7.16-7.40 (15H, m), 7.92-7.99 (2H, m), 8.41 (1H, d, J=7.9 Hz).

MS (API) m/z: 662 (M+H)$^+$.

Process 5: N-({[(2S)-2-Amino-4-tert-butoxy-4-oxobutyl]oxo}acetyl)glycyl-L-phenylalanine The compound (0.373 g, 0.560 mmol) obtained in the process above was dissolved in N,N-dimethylformamide (30.0 mL). After adding palladium on carbon catalyst (0.400 g), it was stirred under a hydrogen atmosphere at room temperature for 4 days. The insolubles were removed by filtration through celite, and the solvent was removed under reduced pressure to yield the titled compound. The compound was used for the next reaction without further purification.

MS(API) m/z: 438 (M+H)$^+$.

Process 6: N-({[(2S)-4-tert-Butoxy-2-{[6-(2,5-dioxo-2,5-dihydro-1H-pyrrol-1-yl) hexanoyl]amino}-4-oxobutyl]oxy}acetyl)glycyl-L-phenylalanine To an N,N-dimethylformamide (10.0 mL) solution of the mixture (0.560 mmol) obtained in the process above, N-succinimidyl 6-maleimidohexanoate (0.261 g, 0.850 mmol) and N, N-diisopropylethylamine (98.2 µL, 0.560 mmol) were added and stirred at room temperature for 2 days. The solvent was removed under reduced pressure and the residues obtained were diluted with ethyl acetate and washed with an aqueous solution of 10% citric acid and a saturated sodium chloride aqueous solution. Then, the organic layer was dried over sodium sulfate. The solvent was removed under reduced pressure and the residues obtained were purified by silica gel column chromatography [chloroform-chloroform:methanol=9:1 (v/v)] to yield the titled compound as a pale yellow solid (0.246 g, 69%).

$^1$H-NMR (400 MHz, CDCl$_3$) δ: 1.23-1.34 (2H, m), 1.44 (9H, s), 1.53-1.67 (4H, m), 2.16 (2H, t, J=7.6 Hz), 2.43-2.55 (2H, m), 3.03-3.28 (2H, m), 3.46-3.59 (4H, m), 3.81-4.06 (4H, m), 4.38-4.49 (1H, m), 4.69-4.78 (1H, m), 6.61-6.73 (1H, m), 6.67 (2H, s), 6.99 (1H, brs), 7.11-7.33 (5H, m), 7.51 (1H, brs).

MS (API) m/z: 631 (M+H)$^+$.

Process 7: N-({[(2S)-4-tert-Butoxy-2-{[6-(2,5-dioxo-2,5-dihydro-1H-pyrrol-1-yl)hexanoyl]amino}-4-oxobutyl]oxy}acetyl)glycyl-L-phenylalanyl-N-[(1S, 9S)-9-ethyl-5-fluoro-9-hydroxy-4-methyl-10,13-dioxo-2,3,9,10,13,15-hexahydro-1H,12H-benzo[de] pyrano[3',4':6,7]indolizino[1,2-b]quinolin-1-yl] glycinamide To an N,N-dimethylformamide (10.0 mL) solution of methanesulfonic acid salt of the compound (0.101 g, 0.170 mmol) of Process 2 of Example 80, 1-hydroxybenzotriazole (25.7 mg, 0.190 mmol), and the compound (0.100 g, 0.160 mmol) obtained in the process above, N,N-diisopropylethylamine (29.0 µL, 0.170 mmol) and 1-ethyl-3-(3-dimethylaminopropyl)carbodiimide hydrochloride (39.5 mg, 0.210 mmol) were added and stirred at room temperature for 18 hours. The solvent was removed under reduced pressure and the residues obtained were purified by silica gel column chromatography [chloroform -chloroform:methanol=9:1 (v/v)] to yield the titled compound as a pale yellow solid (90.0 mg, 51%).

$^1$H-NMR (400 MHz, DMSO-d$_6$) δ: 0.87 (3H, t, J=7.3 Hz), 1.11-1.19 (2H, m), 1.35 (9H, s), 1.41-1.48 (4H, m), 1.82-1.89 (2H, m), 2.00 (2H, t, J=7.3 Hz), 2.06-2.35 (3H, m), 2.41 (3H, s), 2.76 (1H, dd, J=13.9, 9.7 Hz), 2.98 (1H, dd, J=13.6, 4.5 Hz), 3.14-3.22 (2H, m), 3.24-3.49 (5H, m), 3.58 (1H, dd, J=16.9, 5.4 Hz), 3.73-3.80 (3H, m), 3.82 (2H, s), 4.16-4.28 (1H, m), 4.41-4.51 (1H, m), 5.25 (2H, s), 5.35-5.47 (2H, m), 5.54-5.62 (1H, m), 6.52 (1H, s), 6.99 (2H, s), 7.12-7.26 (5H, m), 7.31 (1H, s), 7.74-7.84 (3H, m), 8.17 (1H, d, J=8.5 Hz), 8.36 (1H, t, J=5.4 Hz), 8.42 (1H, d, J=8.5 Hz).

MS (API) m/z: 1106 (M+H)$^+$.

Process 8: N-{[(2S) -3-Carboxy-2-{[6-(2,5-dioxo-2, 5-dihydro-1H-pyrrol-1-yl)hexanoyl]amino}propoxy] acetyl}glycyl-L-phenylalanyl-N-[(1S,9S)-9-ethyl-5-fluoro-9-hydroxy-4-methyl-10,13-dioxo-2,3,9,10,13, 15-hexahydro-1H,12H-yl]glycinamide Under ice cooling, to the compound (85.0 mg, 80.0 µmol) obtained in the process above, trifluoroacetic acid (6.00 mL) was added and stirred at room temperature for 1.5 hours. The solvent was removed under reduced pressure to yield the titled compound as a pale yellow solid (60.0 mg, 74%).

$^1$H-NMR (400 MHz, DMSO-d$_6$) δ: 0.87 (3H, t, J=7.6 Hz), 1.12-1.20 (2H, m), 1.41-1.48 (4H, m), 1.80-1.91 (2H, m), 2.00 (2H, t, J=7.3 Hz), 2.05-2.26 (2H, m), 2.34 (1H, dd, J=15.7, 7.9 Hz), 2.41 (3H, s), 2.76 (1H, dd, J=13.6, 9.4 Hz), 2.98 (1H, dd, J=13.6, 4.5 Hz), 3.13-3.22 (2H, m), 3.29-3.47 (5H, m), 3.59 (1H, dd, J=16.9, 5.4 Hz), 3.71-3.81 (3H, m), 3.83 (2H, s), 4.15-4.25 (1H, m), 4.41-4.51 (1H, m), 5.25 (2H, s), 5.35-5.47 (2H, m), 5.54-5.62 (1H, m), 6.52 (1H, brs), 6.99 (2H, s), 7.12-7.26 (5H, m), 7.31 (1H, s), 7.75-7.84 (3H, m), 8.17 (1H, d, J=7.9 Hz), 8.36 (1H, t, J=5.7 Hz), 8.42 (1H, d, J=9.1 Hz), 12.17 (1H, brs).

HRMS (FAB) m/z: (M+H)$^+$: Calcd for C$_{53}$H$_{58}$FN$_8$O$_{14}$: 1049.40564; Found: 1049.40646.

Process 9: Antibody-Drug Conjugate (157)

By using the trastuzumab produced in Reference Example 1 and the compound obtained in Process 8 above, the titled antibody-drug conjugate was obtained in the same manner as Process 1 of Example 3.

Antibody concentration: 1.90 mg/mL, antibody yield: 16.2 mg (81%), and average number of conjugated drug molecules (n) per antibody molecule: 5.8.

Example 158 Antibody-Drug Conjugate (158)

[Formula 211]

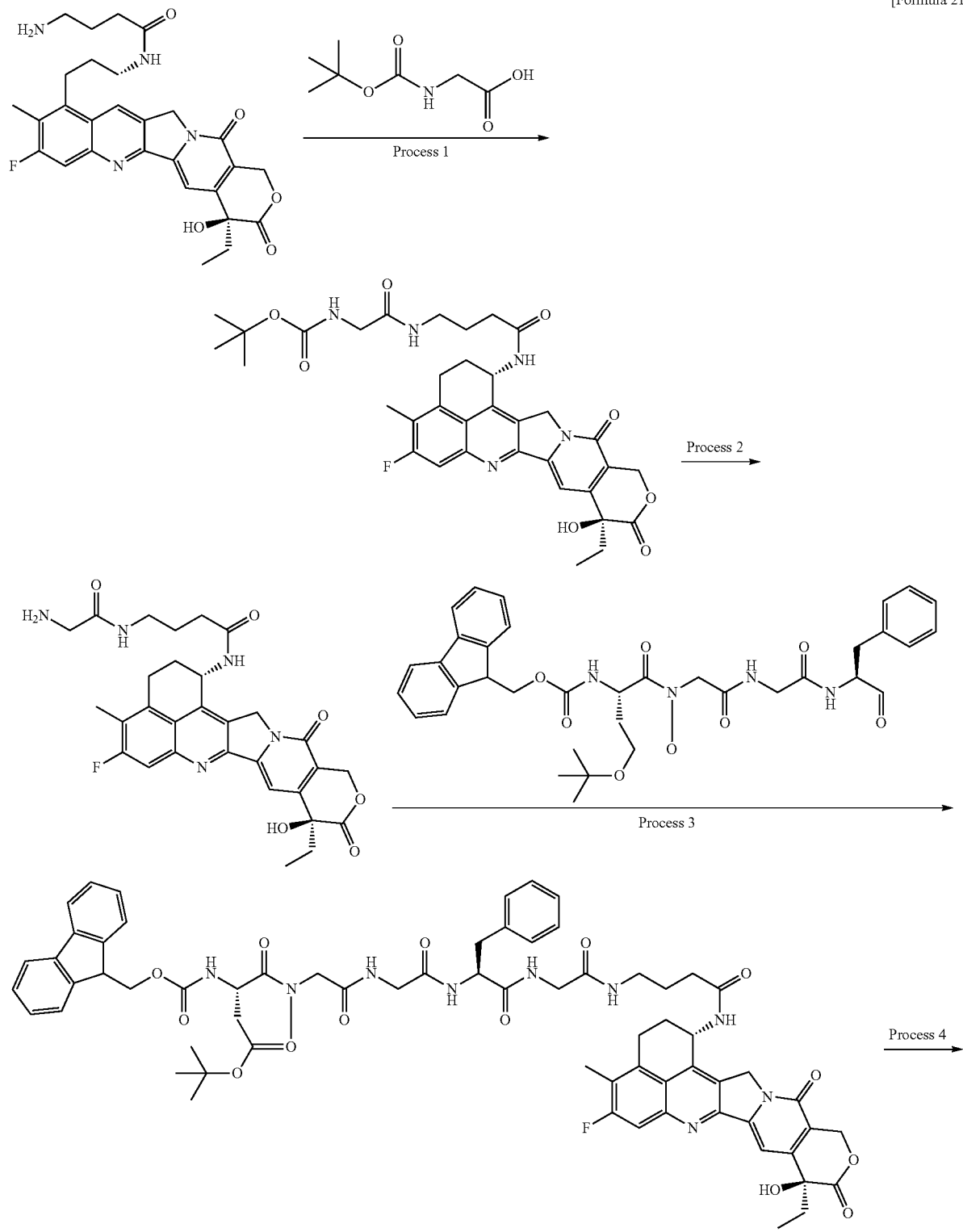

629
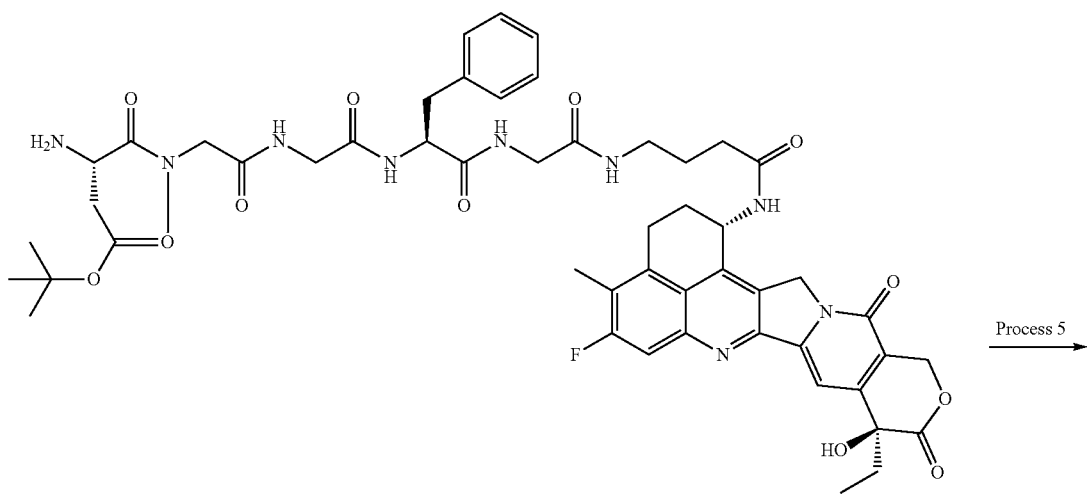
-continued
630
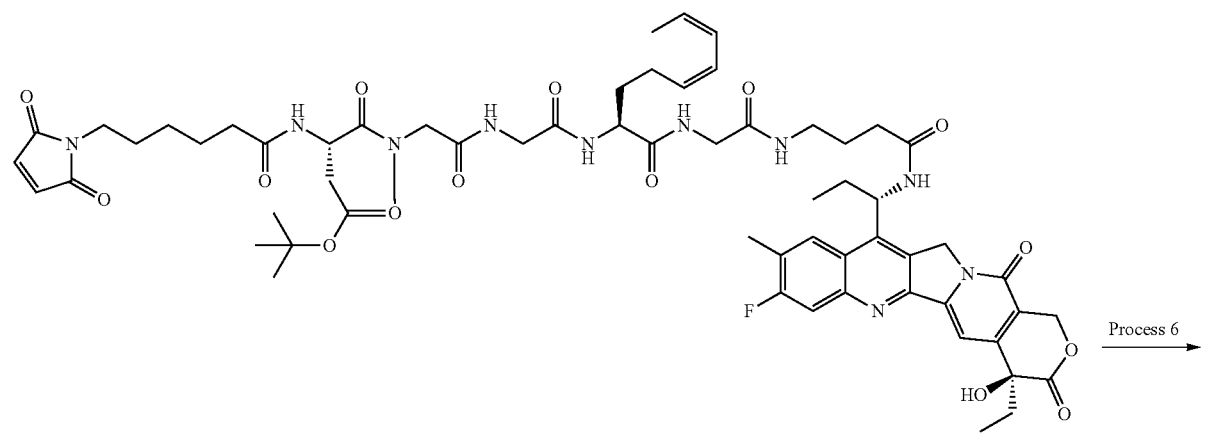
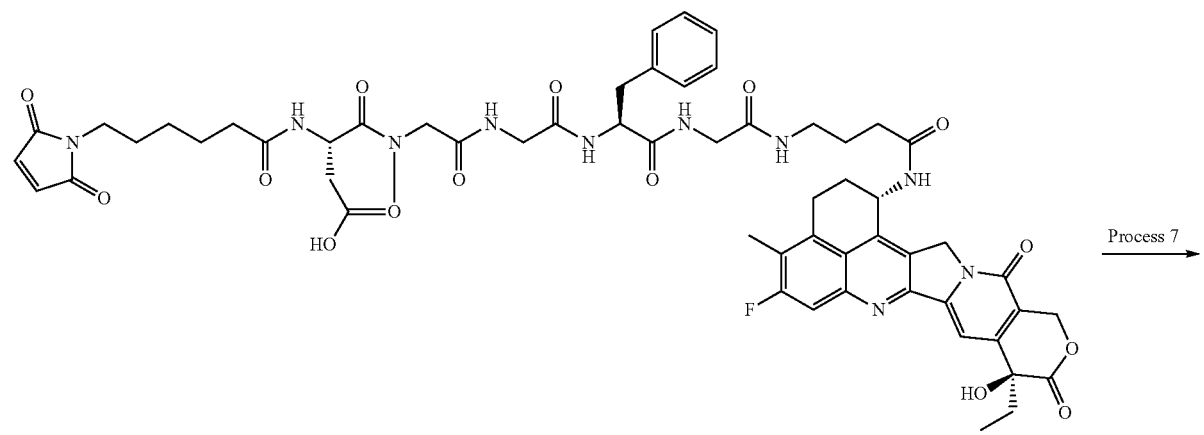

-continued

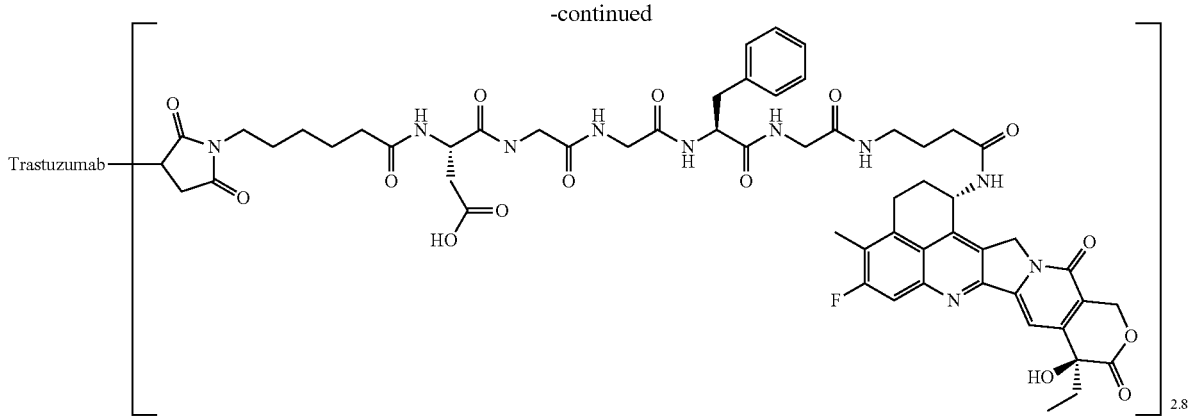

Process 1: tert-Butyl {2-[(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)amino]-2-oxoethyl}carbamate The compound (1.70 g, 2.68 mmol) of Process 1 of Example 1 was dissolved in N,N-dimethylformamide (10.0 mL), charged with 1-hydroxybenzotriazole (362 mg, 2.68 mmol) and 1-ethyl-3-(3-dimethylaminopropyl)carbodiimide hydrochloride (1.03 g, 5.36 mmol), and stirred at room temperature for 30 minutes. After adding N-(tert-butoxycarbonyl)glycine (469 mg, 2.68 mmol) and triethylamine (373 μL, 2.68 mmol), it was stirred at room temperature for 4 hours. The solvent was removed under reduced pressure and the residues obtained were purified by silica gel column chromatography [chloroform -chloroform:methanol=4:1 (v/v)] to yield the titled compound as a pale yellow solid (1.82 g, 91%).

$^1$H-NMR (400 MHz, CD$_3$OD) δ: 0.94 (3H, t, J=6.6 Hz), 1.37 (9H, s), 1.88-1.90 (4H, m), 2.07-2.08 (1H, m), 2.23 (3H, s), 2.33-2.36 (3H, m), 3.16-3.30 (4H, m), 3.66-3.73 (2H, m), 4.54 (1H, d, J=18.8 Hz), 4.95-4.98 (1H, m), 5.25 (1H, d, J=16.0 Hz), 5.47 (1H, d, J=16.0 Hz), 5.54-5.57 (1H, m), 7.29 (1H, d, J=10.6 Hz), 7.38 (1H, s).

MS (APCI) m/z: 678 (M+H)$^+$.

Process 2: N-[(1S,9S)-9-Ethyl-5-fluoro-9-hydroxy-4-methyl-10,13-dioxo-2,3,9,10,13,15-hexahydro-1H,12H-yl]-4-(glycylamino)butanamide The compound (1.66 g, 2.45 mmol) obtained in Process 1 above was dissolved in dichloromethane (6.00 mL), charged with trifluoroacetic acid (6.00 mL), and stirred at room temperature for 30 minutes. The solvent was removed under reduced pressure and the residues obtained were purified by silica gel column chromatography [[chloroform-partitioned organic layer of chloroform:methanol:water=7:3:1 (v/v/v)] to yield the titled compound as a yellow solid (1.69 g, 93%).

$^1$H-NMR (400 MHz, CD$_3$OD) δ: 0.97 (3H, t, J=6.8 Hz), 1.95-2.04 (5H, m), 2.31 (3H, s), 2.35-2.43 (3H, m), 3.07 (1H, s), 3.22 (1H, d, J=17.2 Hz), 3.35-3.37 (2H, m), 3.78 (2H, s), 4.74-5.01 (1H, m), 5.10 (1H, d, J=18.8 Hz), 5.30 (1H, d, J=16.4 Hz), 5.51 (1H, d, J=16.0 Hz), 5.61-5.63 (1H, m), 7.43 (1H, d, J=10.6 Hz), 7.47 (1H, s).

MS (APCI) m/z: 578 (M+H)$^+$.

Process 3: tert-Butyl (3S,12S)-12-benzyl-21-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-{[(9H-fluoren-9-ylmethoxy)carbonyl]amino}-5-methyl-4,7,10,13,16,21-hexaoxo-5,8,11,14,17-pentaazaheneicosan-1-oate The compound (1.56 g, 2.27 mmol) obtained in Process 6 of Example 156 was dissolved in N,N-dimethylformamide (20 mL), charged with 1-hydroxybenzotriazole (307 mg, 2.27 mmol) and 1-ethyl-3-(3-dimethylaminopropyl)carbodiimide hydrochloride (870 mg, 4.54 mmol), and stirred at room temperature for 1 hour and 30 minutes. After adding the compound (1.57 g, 2.27 mmol) obtained in Process 2 above and triethylamine (316 μL, 2.27 mmol), it was stirred at room temperature for 17 hours. The solvent was removed under reduced pressure and the residues obtained were purified by silica gel column chromatography [chloroform-chloroform:methanol=4:1 (v/v)] to yield the titled compound as a pale yellow solid (2.65 g, 94%).

$^1$H-NMR (400 MHz, DMSO-d$_6$) δ: 0.86 (3H, t, J=7.0 Hz), 1.35 (9H, s), 1.71-1.73 (2H, m), 1.80-1.91 (2H, m), 2.09-2.12 (2H, m), 2.18 (2H, t, J=7.2 Hz), 2.37 (3H, s), 2.40-2.48 (1H, m), 2.64-2.77 (2H, m), 3.01 (3H, s), 3.02-3.13 (5H, m), 3.59-3.68 (3H, m), 3.75-3.80 (2H, m), 3.98-4.07 (1H, m), 4.17-4.30 (3H, m), 4.47-4.48 (1H, m), 4.65-4.83 (1H, m), 5.14 (1H, d, J=19.2 Hz), 5.20 (1H, d, J=18.8 Hz), 5.39 (1H, d, J=17.2 Hz), 5.44 (1H, d, J=17.2 Hz), 5.53-5.56 (1H, m), 6.53 (1H, s), 7.18-7.24 (9H, m), 7.39-7.41 (2H, m), 7.65-7.87 (5H, m), 7.98-8.00 (1H, m), 8.13-8.14 (1H, m), 8.23-8.30 (2H, m), 8.45 (1H, d, J=7.8 Hz).

MS (ESI) m/z: 1247 (M+H)$^+$.

Process 4: tert-Butyl (3S,12S)-3-amino-12-benzyl-21-{[(1S,9S)-9-ethyl-5-fluoro-9-hydroxy-4-methyl-10,13-dioxo-2,3,9,10,13,15-hexahydro-1H,12H-yl]amino}-5-methyl-4,7,10,13,16,21-hexaoxo-5,8,11,14,17-pentaazaheneicosan-1-oate The compound (1.85 g, 1.48 mmol) obtained in Process 3 above was dissolved in N,N-dimethylformamide (16.0 mL), charged with piperidine (4.00 mL), and stirred at room temperature for 1 hour. The solvent was removed under reduced pressure and the residues obtained were purified by silica gel column chromatography [chloroform -partitioned organic layer of chloroform:methanol:water=7:3:1 (v/v/v)] to yield the titled compound as a yellow solid (1.15 g, 76%).

$^1$H-NMR (400 MHz, DMSO-d$_6$) δ: 0.87 (3H, t, J=7.2 Hz), 1.37 (9H, s), 1.72-1.73 (2H, m), 1.80-1.92 (2H, m), 2.17-2.22 (5H, m), 2.37 (3H, s), 2.53-2.56 (1H, m), 2.73-2.82 (1H, m), 2.99-3.15 (7H, m), 3.30-3.32 (2H, m), 3.57-4.00 (6H, m), 4.39-4.45 (1H, m), 5.14 (1H, d, J=19.0 Hz), 5.20 (1H, d, J=19.0 Hz), 5.40 (1H, d, J=19.3 Hz), 5.43 (1H, d, J=16.4 Hz), 5.55-5.56 (1H, m), 6.53 (1H, s), 7.16-7.21 (7H, m), 7.30 (1H, s), 7.69-7.72 (1H, m), 7.77 (1H, d, J=11.0 Hz), 8.02-8.09 (1H, m), 8.25-8.31 (2H, m), 8.47 (1H, d, J=8.5 Hz).

MS (ESI) m/z: 1025 (M+H)$^+$.

Process 5: tert-Butyl (3S,12S)-12-benzyl-3-{[6-(2,5-dioxo-2,5-dihydro-1H-pyrrol-1-yl)hexanoyl]amino}-21-{[(1S,9S)-9-ethyl-5-fluoro-9-hydroxy-4-methyl-10,13-dioxo-2,3,9,10,13,15-hexahydro-1H,12H-yl]amino}-5-methyl-4,7,10,13,16,21-hexaoxo-5,8,11,14,17-pentaazaheneicosan-1-oate The compound (1.09 g, 1.06 mmol) obtained in Process 4 above was dissolved in N,N-dimethylformamide (6.00 mL). After adding N-succinimidyl 6-maleimidohexanoate (328 mg, 1.06 mmol), it was stirred at room temperature for 17.5 hours. The solvent was removed under reduced pressure and the residues obtained were purified by silica gel column chromatography [chloroform-chloroform:methanol=4:1 (v/v)] to yield the titled compound as a pale yellow solid (730 mg, 56%).

$^1$H-NMR (400 MHz, DMSO-d$_6$) δ: 0.87 (3H, t, J=7.0 Hz), 1.14-1.16 (2H, m), 1.34 (9H, s), 1.44 (4H, d, J=7.0 Hz), 1.71-1.73 (2H, m), 1.83-1.86 (2H, m), 1.98-2.18 (6H, m), 2.31-2.35 (1H, m), 2.38 (3H, s), 2.56-2.66 (1H, m), 2.74-2.78 (1H, m), 3.00 (3H, s), 3.03-3.09 (3H, m), 3.16-3.18 (4H, m), 3.58-4.22 (6H, m), 4.45-4.48 (1H, m), 4.89-5.07 (1H, m), 5.15 (1H, d, J=18.8 Hz), 5.23 (1H, d, J=19.2 Hz), 5.42 (2H, s), 5.55-5.58 (1H, m), 6.53 (1H, s), 6.99 (2H, s), 7.18-7.23 (5H, m), 7.30 (1H, s), 7.70-7.73 (1H, m), 7.78 (1H, d, J=11.0 Hz), 7.97-7.99 (1H, m), 8.10-8.14 (1H, m), 8.21-8.27 (2H, m), 8.45 (1H, d, J=8.2 Hz).

MS (ESI) m/z: 1218 (M+H)$^+$.

Process 6: N-[6-(2,5-Dioxo-2,5-dihydro-1H-pyrrol-1-yl)hexanoyl]-L-α-aspartyl-N-methylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (690 mg, 0.567 mmol) obtained in Process 5 above was dissolved in dichloromethane (3.00 mL), charged with trifluoroacetic acid (6.00 mL), and stirred at room temperature for 1 hour. The solvent was removed under reduced pressure and the residues obtained were purified by silica gel column chromatography [chloroform-chloroform:methanol=4:1 (v/v)] to yield the titled compound as a pale yellow solid (346 mg, 53%).

$^1$H-NMR (400 MHz, DMSO-d$_6$) δ: 0.87 (3H, t, J=7.2 Hz), 1.14-1.16 (2H, m), 1.44-1.45 (4H, m), 1.71-1.73 (2H, m), 1.81-1.89 (2H, m), 1.99-2.03 (2H, m), 2.12-2.14 (2H, m), 2.17-2.19 (2H, m), 2.34-2.39 (1H, m), 2.39 (3H, s), 2.69-2.76 (2H, m), 3.01 (3H, s), 3.09-3.13 (2H, m), 3.16-3.18 (2H, m), 3.35-3.36 (2H, m), 3.58-3.89 (7H, m), 4.45-4.47 (1H, m), 4.91-4.99 (1H, m), 5.16 (1H, d, J=19.0 Hz), 5.23 (1H, d, J=19.0 Hz), 5.42 (2H, s), 5.56-5.58 (1H, m), 6.52 (1H, s), 6.99 (2H, s), 7.17-7.25 (5H, m), 7.31 (1H, s), 7.70-7.72 (1H, m), 7.79 (2H, d, J=11.0 Hz), 7.94-7.96 (1H, m), 8.10-8.12 (1H, m), 8.19-8.28 (2H, m), 8.47 (1H, d, J=7.1 Hz).

MS (ESI) m/z: 1162 (M+H)$^+$.

Process 7: Antibody-Drug Conjugate (158)

By using the trastuzumab produced in Reference Example 1 and the compound obtained in Process 6 above, the titled antibody-drug conjugate was obtained in the same manner as Process 6 of Example 2.

Antibody concentration: 1.76 mg/mL, antibody yield: 15.0 mg (75%), and average number of conjugated drug molecules (n) per antibody molecule: 2.8.

Example 159 Antibody-Drug Conjugate (159)

[Formula 212]

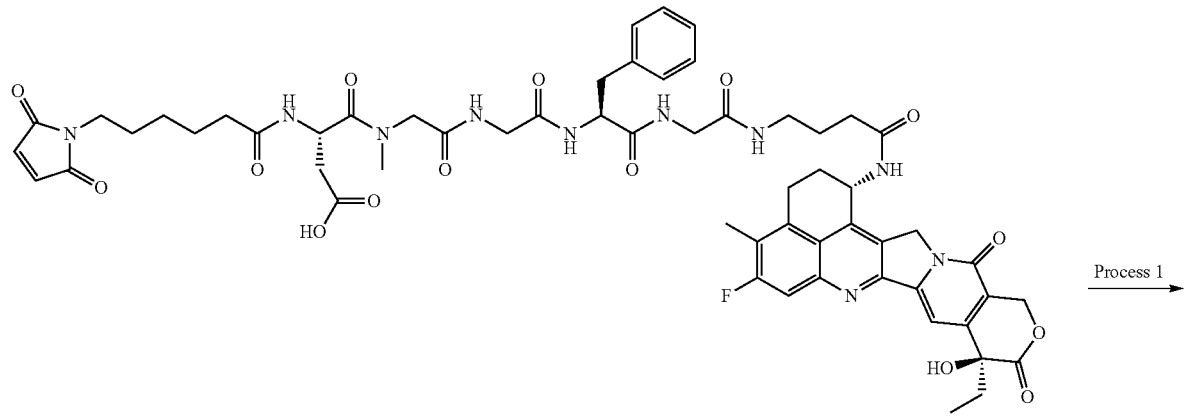

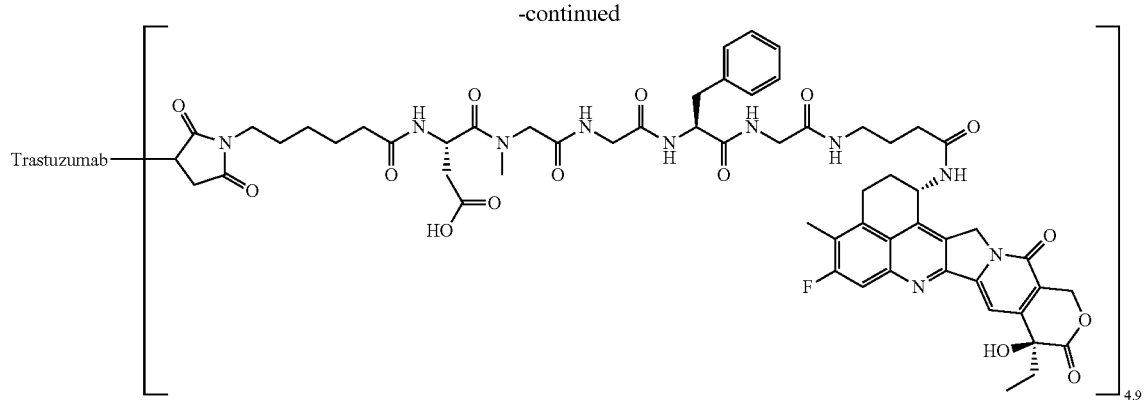

Process 1: Antibody-Drug Conjugate (159)

By using the trastuzumab produced in Reference Example 1 and the compound obtained in Process 6 of Example 158, the titled antibody-drug conjugate was obtained in the same manner as Process 1 of Example 3.
Antibody concentration: 1.75 mg/mL, antibody yield: 15.0 mg (75%), and average number of conjugated drug molecules (n) per antibody molecule: 4.9.

Example 160 Antibody-Drug Conjugate (160)

[Formula 213]

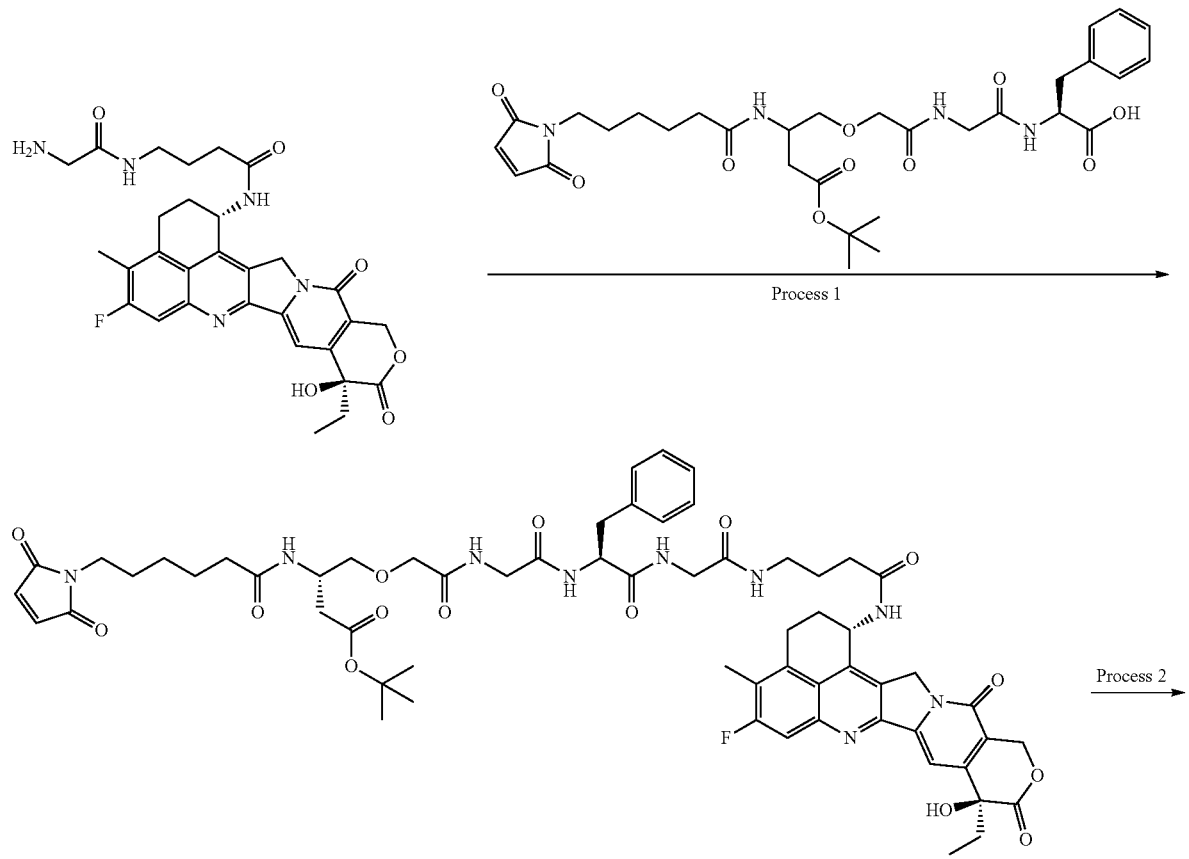

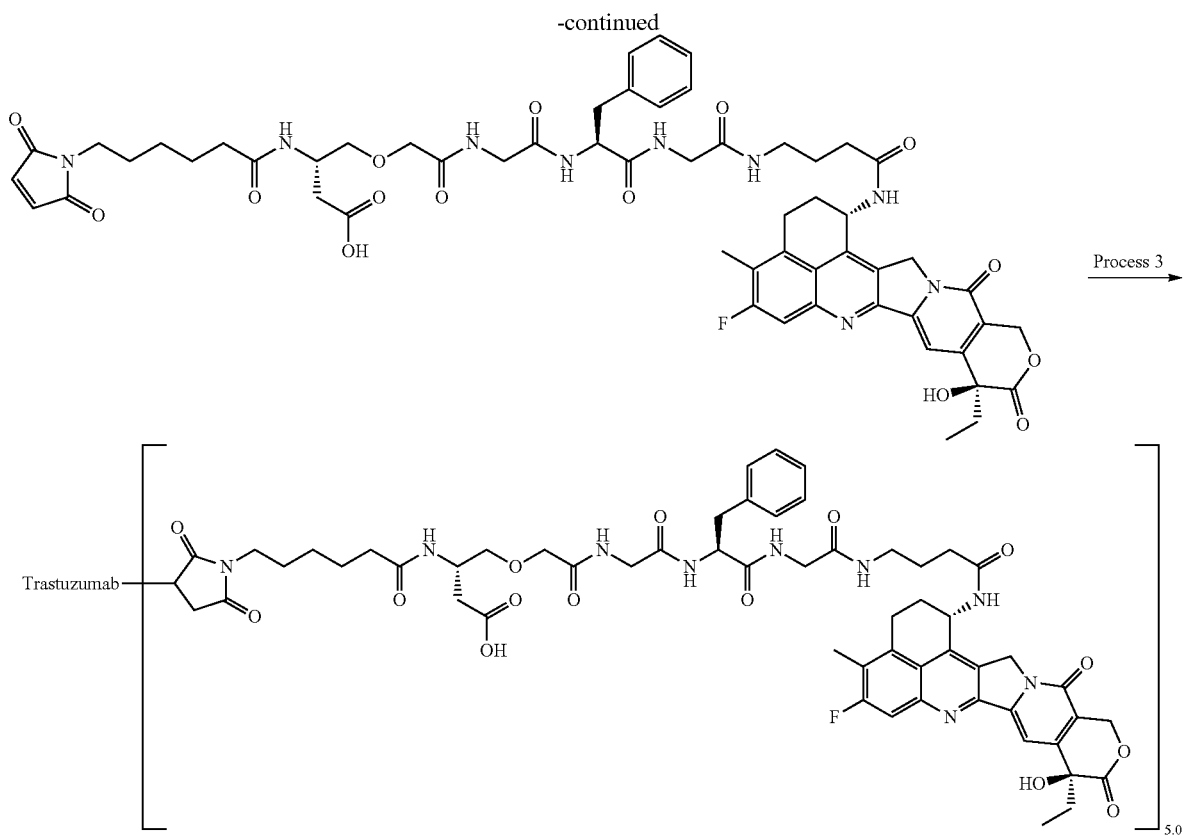

Process 1: N-({[(2S)-4-tert-Butoxy-2-{[6-(2,5-di-oxo-2,5-dihydro-1H-pyrrol-1-yl)hexanoyl]amino}-4-oxobutyl]oxy}acetyl)glycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (21.8 mg, 34.6 μmol) of Process 6 of Example 157 was dissolved in N,N-dimethylformamide (3.00 mL) and charged with 1-hydroxybenzotriazole (4.68 mg, 34.6 μmol) and 1-ethyl-3-(3-dimethylaminopropyl)carbodiimide hydrochloride (9.96 mg, 51.9 μmol). After further adding the compound (20.0 mg, 34.6 μmol) of Process 2 of Example 158, it was stirred at room temperature for 21 hours. The solvent was removed under reduced pressure and the residues obtained were purified by silica gel column chromatography [chloroform-chloroform:methanol=4:1 (v/v)] to yield the titled compound as a pale yellow solid (15.1 mg, 37%).

$^1$H-NMR (400 MHz, DMSO-$d_6$) δ: 0.87 (3H, t, J=7.2 Hz), 1.11-1.19 (2H, m), 1.35 (9H, s), 1.40-1.48 (4H, m), 1.67-1.75 (2H, m), 1.80-1.91 (2H, m), 1.99 (2H, t, J=7.4 Hz), 2.15-2.18 (4H, m), 2.27-2.32 (2H, m), 2.40 (3H, s), 2.67 (1H, s), 2.77 (1H, dd, J=13.7, 9.8 Hz), 3.01 (1H, dd, J=13.9, 4.5 Hz), 3.06-3.11 (2H, m), 3.17 (2H, t, J=2.5 Hz), 3.36-3.47 (3H, m), 3.58-3.67 (3H, m), 3.80 (1H, t, J=8.2 Hz), 3.85 (2H, s), 4.20-4.24 (1H, m), 4.45-4.50 (1H, m), 5.16 (1H, d, J=18.8 Hz), 5.25 (1H, d, J=18.8 Hz), 5.42 (2H, s), 5.55-5.59 (1H, m), 6.53 (1H, s), 6.99 (2H, s), 7.17-7.23 (5H, m), 7.31 (1H, s), 7.71 (1H, d, J=5.9 Hz), 7.78 (1H, s), 7.81 (1H, d, J=3.5 Hz), 7.86 (1H, t, J=5.7 Hz), 8.21 (1H, d, J=7.8 Hz), 8.30 (1H, t, J=5.9 Hz), 8.45 (1H, d, J=8.6 Hz).

MS (ESI) m/z: 1190 (M+H)$^+$.

Process 2: N-{[(2S)-3-Carboxy-2-{[6-(2,5-dioxo-2,5-dihydro-1H-pyrrol-1-yl)hexanoyl]amino}propxy]acetyl}glycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (14.3 mg, 0.120 μmol) obtained in Process 1 above was dissolved in dichloromethane (1.00 mL), charged with trifluoroacetic acid (1.00 mL), and stirred at room temperature for 1 hour. The solvent was removed under reduced pressure, and the insolubles deposited with ethanol and diethyl ether were collected by filtration to yield the titled compound as a pale yellow solid (11.8 mg, 87%).

$^1$H-NMR (400 MHz, DMSO-$d_6$) δ: 0.87 (3H, t, J=7.2 Hz), 1.15 (2H, t, J=7.2 Hz), 1.40-1.48 (4H, m), 1.68-1.75 (2H, m), 1.80-1.91 (2H, m), 2.00 (2H, t, J=7.4 Hz), 2.12-2.19 (4H, m), 2.34 (2H, dd, J=16.0, 7.8 Hz), 2.40 (3H, s), 2.77 (1H, dd, J=13.5, 9.6 Hz), 3.01 (1H, dd, J=13.7, 4.7 Hz), 3.05-3.11 (2H, m), 3.16-3.18 (2H, m), 3.33-3.35 (3H, m), 3.44-3.47 (2H, m), 3.61-3.68 (2H, m), 3.80 (1H, dd, J=16.6, 6.1 Hz), 3.85 (1H, s), 4.22-4.25 (1H, m), 4.47-4.50 (1H, m), 5.16 (1H, d, J=18.8 Hz), 5.25 (1H, d, J=19.2 Hz), 5.42 (2H, s), 5.57 (1H, s), 6.99 (2H, s), 7.15-7.26 (6H, m), 7.31 (1H, s), 7.71 (1H, t, J=5.5 Hz), 7.78-7.81 (2H, m), 7.84 (1H, t, J=5.7 Hz), 8.21 (1H, d, J=7.8 Hz), 8.30 (1H, t, J=6.8 Hz), 8.45 (1H, d, J=8.6 Hz).

MS (ESI) m/z: 1134 (M+H)$^+$.

639

Process 1: Antibody-Drug Conjugate (160)

By using the trastuzumab produced in Reference Example 1 and the compound obtained in Process 2 above, the titled antibody-drug conjugate was obtained in the same manner as Process 1 of Example 3.

640

Antibody concentration: 1.75 mg/mL, antibody yield: 14.7 mg (74%), and average number of conjugated drug molecules (n) per antibody molecule: 5.0.

Example 161 Antibody-Drug Conjugate (161)

[Formula 214]

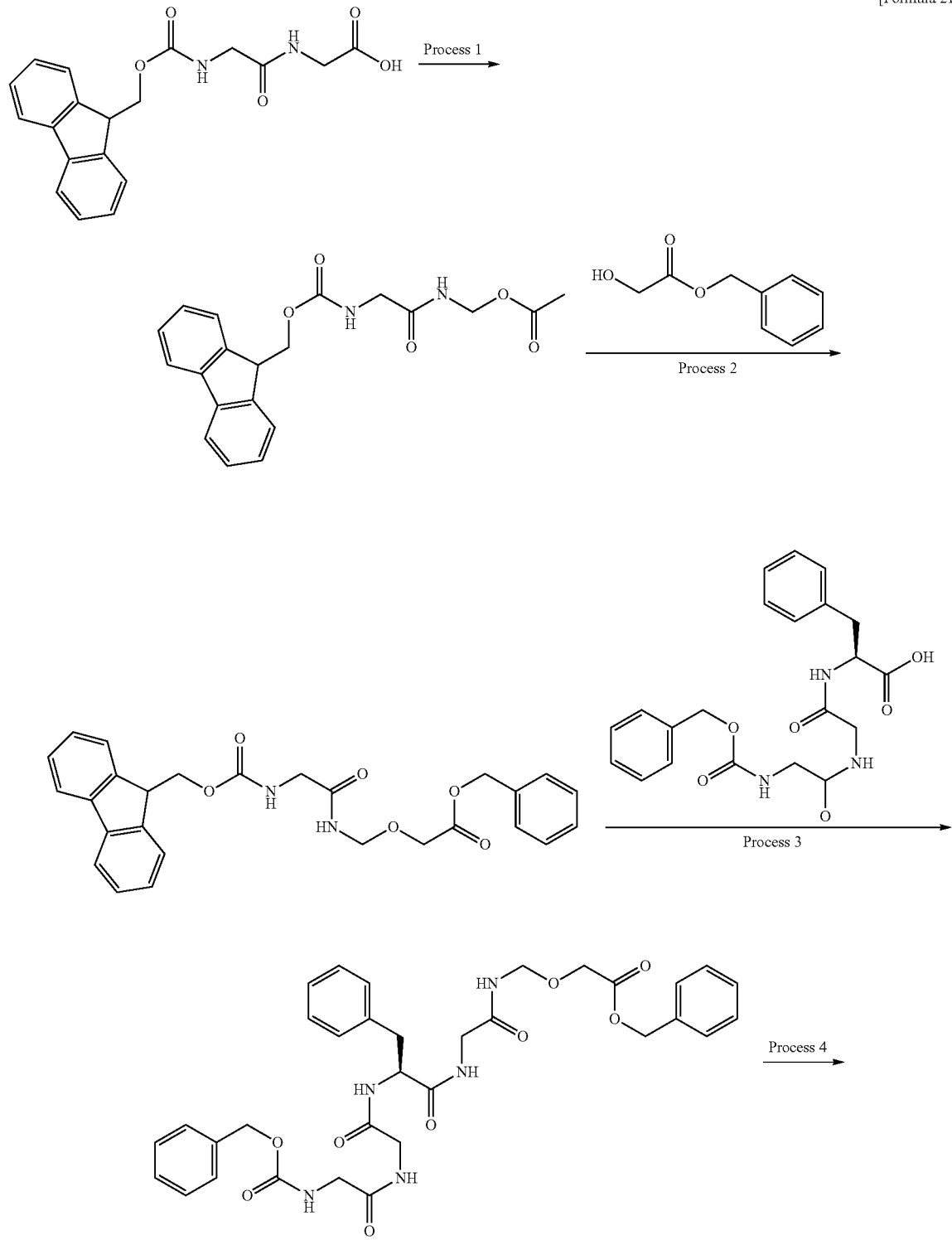

641
642
-continued
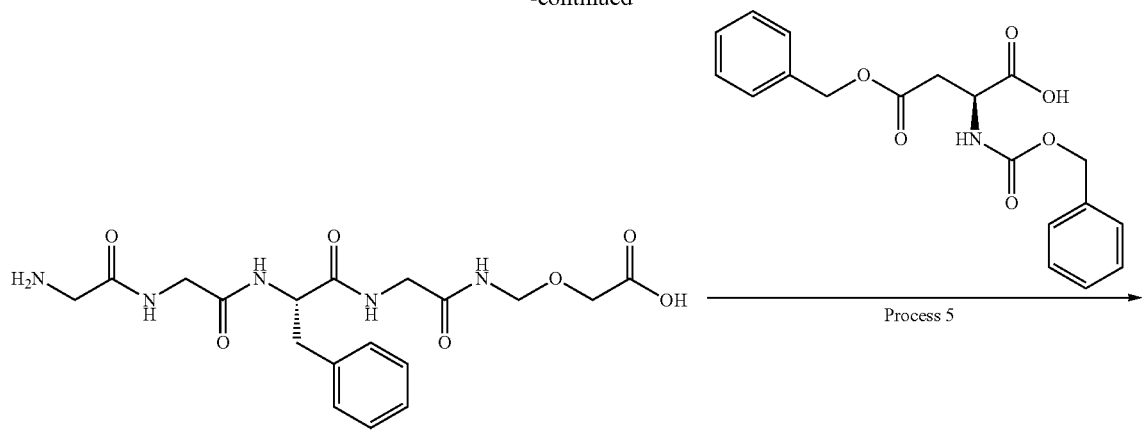
Process 5
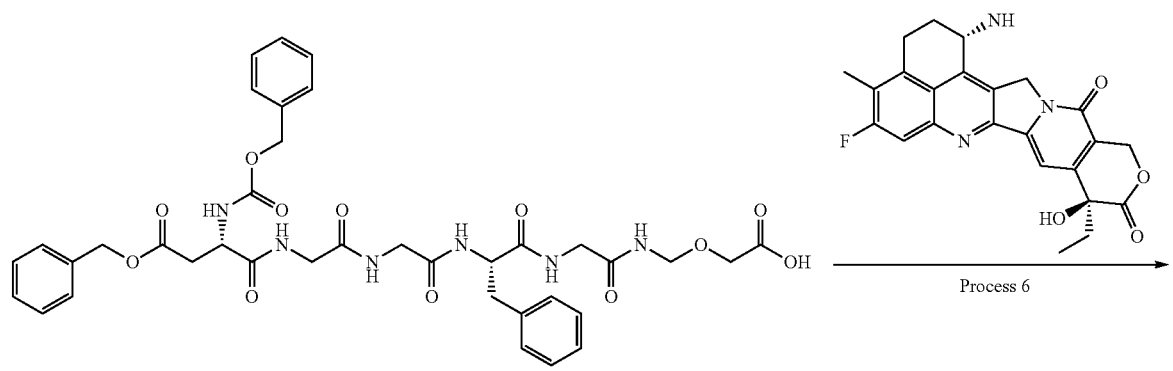
Process 6
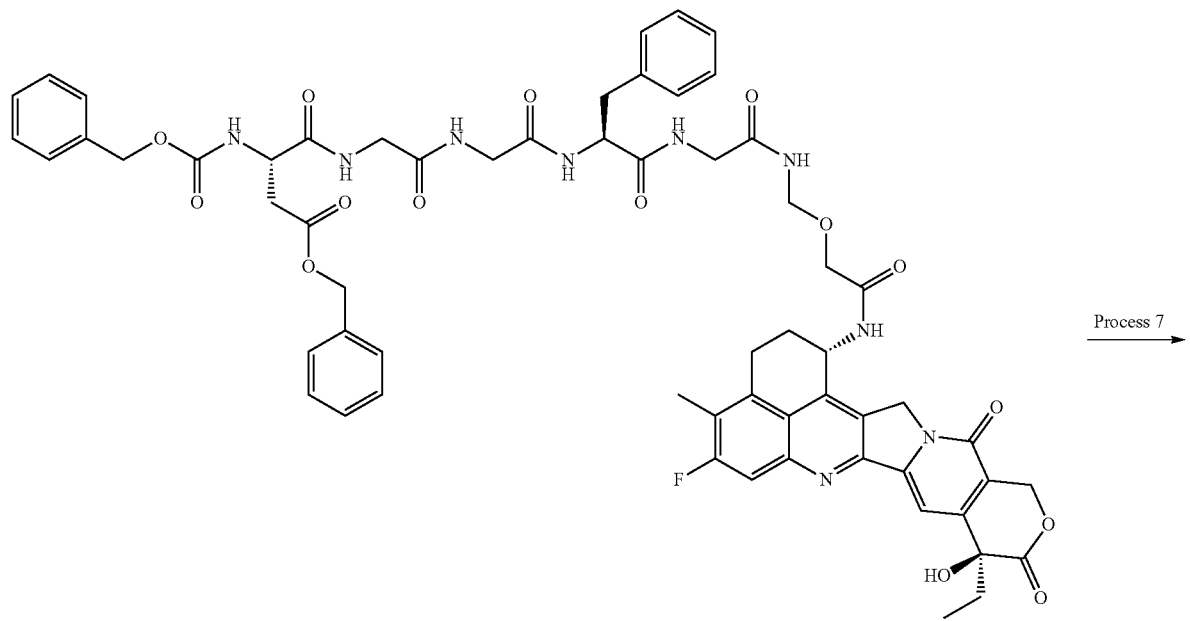
Process 7

643
644
-continued
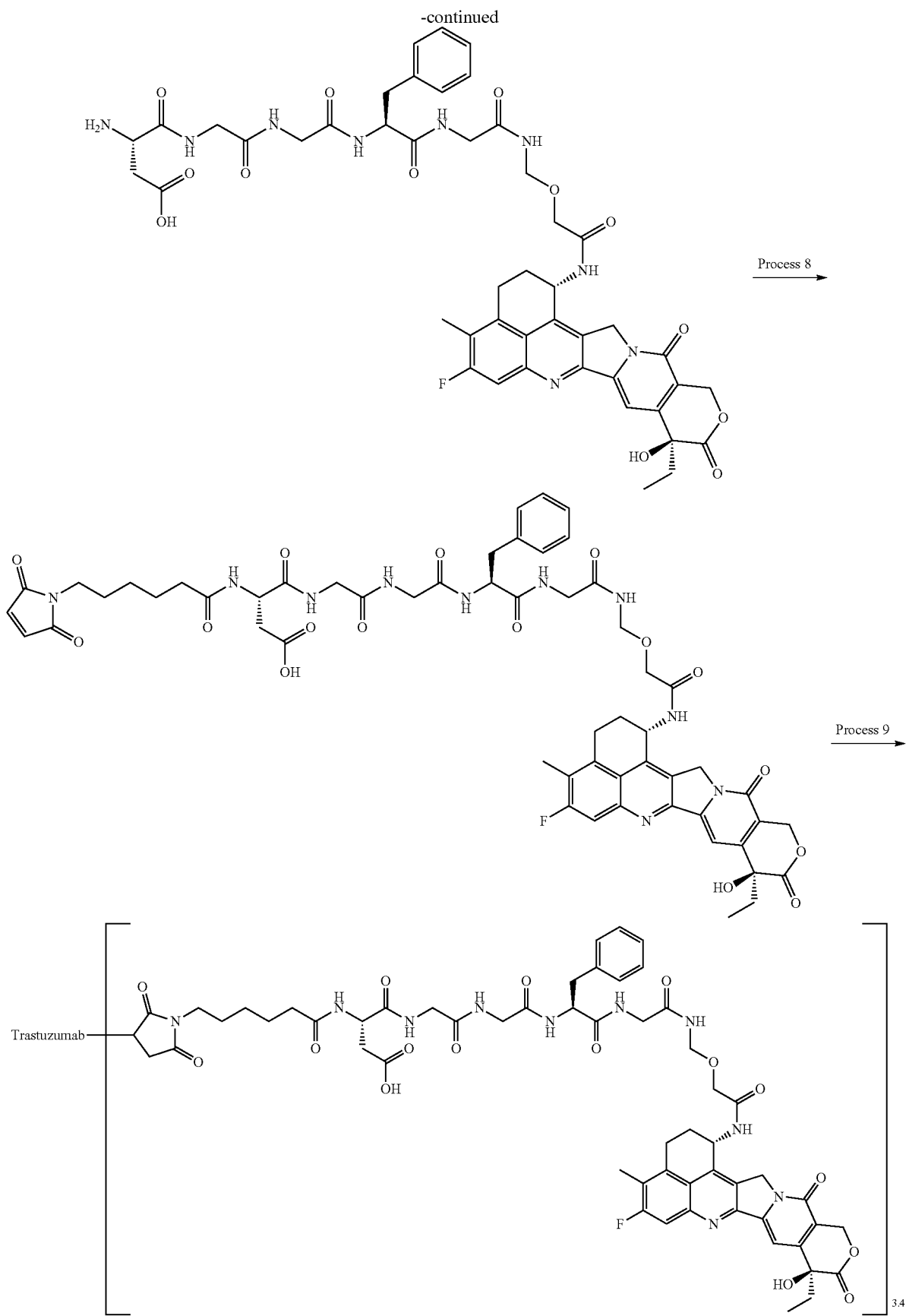
Process 8
Process 9

Process 1: ({N-[(9H-Fluoren-9-ylmethoxy)carbonyl]glycyl}amino)methylacetate

To a mixture consisting of N-9-fluorenylmethoxycarbonylglycylglycine (4.33 g, 12.2 mmol), tetrahydrofuran (120 mL), and toluene (40.0 mL), pyridine (1.16 mL, 14.7 mmol) and lead tetraacetate (6.84 g, 14.7 mmol) were added and heated under reflux for 5 hours. After the reaction solution was cooled to room temperature, the insolubles were removed by filtration through celite, and concentrated under reduced pressure. The residues obtained were dissolved in ethyl acetate and washed with water and a saturated sodium chloride aqueous solution, and then the organic layer was dried over anhydrous magnesium sulfate. After removing the solvent under reduced pressure, the residues obtained were purified by silica gel column chromatography [hexane:ethyl acetate=9:1 (v/v)-ethyl acetate] to yield the titled compound as a colorless solid (3.00 g, 67%).

$^1$H-NMR (400 MHz, CDCl$_3$) δ: 2.07 (3H, s), 3.90 (2H, d, J=5.1 Hz), 4.23 (1H, t, J=7.0 Hz), 4.46 (2H, d, J=6.6 Hz), 5.26 (2H, d, J=7.0 Hz), 5.32 (1H, brs), 6.96 (1H, brs), 7.32 (2H, t, J=7.3 Hz), 7.41 (2H, t, J=7.3 Hz), 7.59 (2H, d, J=7.3 Hz), 7.77 (2H, d, J=7.3 Hz).

Process 2: Benzyl [({N-[(9H-fluoren-9-ylmethoxy)carbonyl]glycyl}amino)methoxy]acetate To a tetrahydrofuran (200 mL) solution of the compound (7.37 g, 20.0 mmol) obtained in Process 1 above, benzyl glycolate (6.65 g, 40.0 mmol) and p-toluenesulfonic acid monohydrate (0.381 g, 2.00 mmol) were added at 0° C. and stirred at room temperature for 2 hours and 30 minutes. The reaction solution was charged with a saturated sodium hydrogen carbonate aqueous solution and extracted with ethyl acetate and the organic layer obtained was dried over sodium sulfate and filtered. The solvent was removed under reduced pressure and the residues obtained were purified by silica gel column chromatography [hexane:ethyl acetate=100:0 (v/v)-0:100] to yield the titled compound as a colorless solid (6.75 g, 71%).

$^1$H-NMR (400 MHz, CDCl$_3$) δ: 3.84 (2H, d, J=5.5 Hz), 4.24 (3H, t, J=6.5 Hz), 4.49 (2H, d, J=6.7 Hz), 4.88 (2H, d, J=6.7 Hz), 5.15-5.27 (1H, m), 5.19 (2H, s), 6.74 (1H, brs), 7.31-7.39 (7H, m), 7.43 (2H, t, J=7.4 Hz), 7.61 (2H, d, J=7.4 Hz), 7.79 (2H, d, J=7.4 Hz).

Process 3: N-[(Benzyloxy)carbonyl]glycylglycyl-L-phenylalanine-N-{[(2-(benzyloxy)-2-oxoethoxy]methyl}glycinamide To an N,N-dimethylformamide (140 mL) solution of the compound (6.60 g, 13.9 mmol) obtained in Process 2 above, 1,8-diazabicyclo[5.4.0]undec-7-ene (2.22 g, 14.6 mmol) was added at 0° C. and stirred at room temperature for 15 minutes. The reaction solution was charged with an N,N-dimethylformamide (140 mL) solution of N-[(benzyloxy)carbonyl]glycylglycyl-L-phenylalanine (6.33 g, 15.3 mmol), N-hydroxysuccinimide (1.92 g, 16.7 mmol), and 1-(3-dimethylaminopropyl)-3-ethylcarbodiimide hydrochloride (3.20 g, 16.7 mmol) stirred in advance at room temperature for 1 hour, and stirred at room temperature for 4 hours. The reaction solution was charged with 0.1 N hydrochloric acid and extracted with chloroform and the organic layer obtained was dried over sodium sulfate and filtered. The solvent was removed under reduced pressure and the residues obtained were purified by silica gel column chromatography [chloroform-chloroform:methanol=8:2 (v/v)] to yield the titled compound as a colorless solid (7.10 g, 79%).

$^1$h-nmr (dmso-D$_6$) δ: 2.78 (1H, DD, j=13.9, 9.6 hZ), 3.05 (1H, DD, j=13.9, 4.5 hZ), 3.56-3.80 (6h, M), 4.15 (2h, S), 4.47-4.55 (1h, M), 4.63 (2h, D, j=6.6 hZ), 5.03 (2h, S), 5.15 (2h, S), 7.16-7.38 (15h, M), 7.52 (1h, T, j=5.9 hZ), 8.03 (1h, T, j=5.5 hZ), 8.17 (1h, D, j=8.2 hZ), 8.36 (1h, T, j=5.7 hZ), 8.61 (1h, T, j=6.6 hZ).

Process 4: Glycylglycyl-L-phenylalanyl-N-[(carboxymethoxy)methyl]glycinamide

To an N,N-dimethylformamide (216 mL) solution of the compound (7.00 g, 10.8 mmol) obtained in Process 3 above, palladium on carbon catalyst (7.00 g) was added and stirred under a hydrogen atmosphere at room temperature for 24 hours. The insolubles were removed by filtration through celite, and the solvent was removed under reduced pressure. The residues obtained were dissolved in water, the insolubles were removed by filtration through celite, and the solvent was removed under reduced pressure. This procedure was repeated twice to yield the titled compound as a colorless solid (3.77 g, 82%).

$^1$H-NMR (DMSO-d$_6$) δ: 2.84 (1H, dd, J=13.7, 9.8 Hz), 3.08 (1H, dd, J=13.7, 4.7 Hz), 3.50-3.72 (4H, m), 3.77-3.86 (2H, m), 3.87 (2H, s), 4.52-4.43 (1H, m), 4.61 (2H, d, J=6.6 Hz), 7.12-7.30 (5H, m), 8.43 (1H, t, J=5.9 Hz), 8.54 (1H, d, J=7.8 Hz), 8.70 (1H, t, J=6.3 Hz), 8.79 (1H, t, J=5.5 Hz).

Process 5: (5S,14S)-14-Benzyl-5-[2-(benzyloxy)-2-oxoethyl]-3,6,9,12,15,18-hexaoxo-1-phenyl-2,21-dioxa-4,7,10,13,16,19-hexaazatricosan-23-acid (2S)-4-(Benzyloxy)-2-{[(benzyloxy)carbonyl]amino}-4-oxobutanoic acid (123 mg, 0.344 mmol) was dissolved in N,N-dimethylformamide, charged with N-hydroxysuccinimide (39.5 mg, 0.344 mmol) and 1-ethyl-3-(3-dimethylaminopropyl)carbodiimide hydrochloride (65.9 mg, 0.344 mmol), and stirred at room temperature for 30 minutes. After adding the compound (121 mg, 0.286 mmol) of Process 4 above and triethylamine (39.6 μL, 0.286 mmol), it was stirred at room temperature for 4 hours. The solvent was removed under reduced pressure and the residues obtained were purified by silica gel column chromatography [chloroform-partitioned organic layer of chloroform:methanol:water=7:3:1 (v/v/v)] to yield the titled compound as a colorless solid (66.2 mg, 30%).

$^1$H-NMR (400 MHz, DMSO-d$_6$) δ: 2.55 (1H, s), 2.62 (1H, dd, J=16.4, 7.4 Hz), 2.80 (1H, dd, J=13.9, 10.0 Hz), 2.86 (1H, dd, J=16.2, 4.9 Hz), 2.99 (1H, dd, J=14.3, 7.2 Hz), 3.63-3.73 (6H, m), 3.96 (2H, s), 4.46-4.52 (2H, m), 4.61 (2H, d, J=6.7 Hz), 5.00 (1H, d, J=12.5 Hz), 5.05 (1H, d, J=15.3 Hz), 5.07 (2H, s), 7.24-7.26 (5H, m), 7.31-7.35 (10H, m), 7.76 (1H, d, J=8.2 Hz), 8.07 (1H, t, J=5.1 Hz), 8.18 (1H, d, J=8.2 Hz), 8.30 (1H, t, J=5.3 Hz), 8.34 (1H, t, J=5.5 Hz), 8.60 (1H, t, J=6.7 Hz).

MS (ESI) m/z: 761 (M−H)$^−$.

Process 6: L-α-Aspartylglycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide The compound (85.6 mg, 0.112 mmol) obtained in Process 5 above and exatecan (63.7 mg, 0.112 mmol) were dissolved in a mixed solvent of N,N-dimethylformamide (1.50 mL) and methanol (0.500 mL), charged with triethylamine (15.6 μL, 0.112 mmol) and 4-(4,6-dimethoxy-1,3,5-triazin-2-yl)-4-methylmorpholinium chloriden hydrate (49.6 mg, 0.168 mmol), and stirred at room temperature for 17.5 hours. The solvent was removed under reduced pressure and the residues obtained were purified by silica gel column chromatography [chloroform-chloroform:methanol=4:1 (v/v)] to yield the titled compound as a pale yellow solid (59.8 mg, 45%).

$^1$H-NMR (400 MHz, DMSO-$d_6$) δ: 0.86 (3H, t, J=7.2 Hz), 1.80-1.90 (2H, m), 2.16-2.20 (2H, m), 2.38 (3H, s), 2.63 (1H, dd, J=16.4, 9.0 Hz), 2.76 (1H, dd, J=13.7, 9.8 Hz), 2.85 (1H, dd, J=16.2, 4.9 Hz), 3.01 (1H, dd, J=13.5, 4.5 Hz), 3.11-3.23 (2H, m), 3.58-3.76 (6H, m), 4.02 (2H, s), 4.45-4.50 (2H, m), 4.63 (2H, d, J=6.3 Hz), 4.98-5.01 (2H, m), 5.06 (2H, s), 5.20 (2H, s), 5.41 (2H, s), 5.58-5.61 (1H, m), 6.53 (1H, s), 7.16-7.22 (5H, m), 7.29-7.34 (11H, m), 7.70 (1H, d, J=8.2 Hz), 7.79 (1H, d, J=11.0 Hz), 7.99 (1H, t, J=5.7 Hz), 8.12 (1H, d, J=7.8 Hz), 8.23 (1H, d, J=5.5 Hz), 8.32 (1H, t, J=5.7 Hz), 8.52 (1H, d, J=9.0 Hz), 8.64 (1H, t, J=6.7 Hz).

MS (ESI) m/z: 1180 (M+H)$^+$.

Process 7: Benzyl (10S,19S)-10-benzyl-19-{[(benzyloxy)carbonyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,6,9,12,15,18-hexaoxo-3-oxa-5,8,11,14,17-pentaazahenicosane-21-oate The compound (57.3 mg, 48.6 μmol) obtained in Process 6 above was dissolved in N,N-dimethylformamide (6.00 mL). After adding palladium on carbon catalyst (10.0 mg), it was stirred under a hydrogen atmosphere at room temperature for 6 days. The insolubles were removed by filtration through celite, and the solvent was removed under reduced pressure to yield a mixture of a pale yellow solid containing the titled compound (46.8 mg). The mixture was used for the next reaction without further purification.

Process 8: N-[6-(2,5-Dioxo-2,5-dihydro-1H-pyrrol-1-yl)hexanoyl]-L-α-aspartylglycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide The mixture (43.6 mg, 1.06 mmol) obtained in Process 7 above was dissolved in N,N-dimethylformamide (0.500 mL). After adding N-succinimidyl 6-maleimidohexanoate (28.1 mg, 91.2 μmol), it was stirred at room temperature for 23 hours. The residues obtained were purified by silica gel column chromatography [chloroform-partitioned organic layer of chloroform:methanol:water=7:3:1 (v/v/v)] to yield the titled compound as a pale yellow solid (4.23 mg, 8.1%).

$^1$H-NMR (400 MHz, DMSO-$d_6$) δ: 0.86 (3H, t, J=7.2 Hz), 1.16 (2H, dt, J=18.9, 6.0 Hz), 1.45-1.50 (4H, m), 1.79-1.91 (2H, m), 2.09-2.14 (4H, m), 2.32 (2H, dd, J=5.3, 3.7 Hz), 2.36 (3H, s), 2.67-3.19 (4H, m), 3.43-3.48 (2H, m), 3.56-3.76 (6H, m), 4.01 (2H, s), 4.21-4.22 (1H, m), 4.35-4.37 (1H, m), 4.62-4.63 (2H, m), 5.21 (2H, s), 5.41 (2H, s), 5.56-5.59 (1H, m), 6.51 (1H, s), 6.99 (2H, s), 7.10-7.30 (9H, m), 7.75-7.78 (2H, m), 8.32-8.36 (1H, m), 8.55-8.70 (2H, m), 9.02-9.04 (1H, m).

MS (ESI) m/z: 1149 (M+H)$^+$.

Process 9: Antibody-Drug Conjugate (161)

By using the trastuzumab produced in Reference Example 1 and the compound obtained in Process 8 above, the titled antibody-drug conjugate was obtained in the same manner as Process 1 of Example 3.
Antibody concentration: 1.89 mg/mL, antibody yield: 15.9 mg (79%), and average number of conjugated drug molecules (n) per antibody molecule: 3.4.

Evaluation Example 1 Cell Growth Inhibitory Effect of Antibody-Drug Conjugate

Human breast cancer line KPL-4 of HER2 antigen-positive cells (Dr. Junichi Kurebayashi, Kawasaki Medical School, British Journal of Cancer, (1999) 79 (5/6). 707-717) or human breast cancer line MCF7 of HER2 antigen-negative cells (ECACC; European Collection of Cell Cultures) was cultured in RPMI1640 (GIBCO) containing 10% fetal bovine serum (MOREGATE) (hereinafter, referred to as medium). The KPL-4 or MCF7 was prepared to have a concentration of $2.5 \times 10^4$ cells/mL by using medium, added at a concentration of 100 μL/well to a 96-well microplate for cell culture, and cultured overnight. On the next day, trastuzumab or the antibody-drug conjugate diluted into 1000 nM, 200 nM, 40 nM, 8 nM, 1.6 nM, 0.32 nM, and 0.064 nM by using medium was added at a concentration of 10 μL/well to the microplate. Medium was added at a concentration of 10 μL/well to antibody non-supplemented wells. The cells were cultured under 5% $CO_2$ conditions at 37° C. for 5 to 7 days. After the culture, the microplate was taken out from the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, luminescence intensity of each well was measured by using a plate reader (PerkinElmer). The $IC_{50}$ value was calculated according to the following equation:

$$IC_{50} (nM) = \text{antilog}((50-d) \times (LOG_{10}(b) - LOG_{10}(a))/(d-c) + LOG_{10}(b))$$

a: Concentration of sample a
b: Concentration of sample b
c: Cell viability of sample a
d: Cell viability of sample b The cell viability at each concentration was calculated according to the following equation:

Cell viability (%)=$a/b \times 100$ a: Average luminescence intensity of the sample wells (n=2)
b: Average luminescence intensity of the antibody non-supplemented wells (n=10)

The results are shown in "Table 1". Trastuzumab exhibited a cell growth inhibitory effect against neither the KPL-4 cells nor the MCF7 cells (>100 (nM)).

TABLE 1

| | IC50 (nM) | |
| --- | --- | --- |
| Sample | KPL-4 | MCF7 |
| Reference Example 1 | >100 | >100 |
| Example 2 | 0.19 | >100 |
| Example 3 | 0.09 | >100 |

TABLE 1-continued

| Sample | IC50 (nM) KPL-4 | IC50 (nM) MCF7 |
|---|---|---|
| Example 5 | 0.10 | >100 |
| Example 6 | 0.07 | >100 |
| Example 11 | 0.18 | >100 |
| Example 12 | 0.09 | >100 |
| Example 13 | 0.08 | >100 |
| Example 14 | 0.10 | >100 |
| Example 15 | 0.14 | >100 |
| Example 16 | 0.09 | >100 |
| Example 19 | 0.29 | >100 |
| Example 20 | 0.09 | >100 |
| Example 22 | 0.59 | 66.00 |
| Example 23 | 0.13 | >100 |
| Example 25 | >100 | >100 |
| Example 26 | 0.30 | >100 |
| Example 27 | 0.18 | >100 |
| Example 28 | 0.08 | >100 |
| Example 29 | 0.35 | 1.90 |
| Example 30 | 0.09 | 3.10 |
| Example 31 | 7.30 | 2.20 |
| Example 32 | 1.80 | 3.00 |
| Example 34 | 0.47 | >100 |
| Example 35 | 0.11 | >100 |
| Example 37 | 0.19 | >100 |
| Example 38 | 0.09 | 81.00 |
| Example 40 | 0.21 | 26.00 |
| Example 41 | 0.08 | 13.00 |
| Example 43 | 0.21 | >100 |
| Example 44 | 0.07 | 74.00 |
| Example 46 | 0.53 | 18.00 |
| Example 47 | 0.11 | 10.00 |
| Example 49 | 1.30 | 17.00 |
| Example 50 | 0.24 | 10.00 |
| Example 52 | 1.48 | 26.00 |
| Example 53 | 0.23 | 12.00 |
| Example 54 | >100 | >100 |
| Example 55 | 0.76 | >100 |
| Example 56 | 0.41 | 67.00 |
| Example 57 | 0.11 | >100 |
| Example 58 | 0.08 | >100 |
| Example 59 | 0.39 | >100 |
| Example 60 | 0.11 | >100 |
| Example 61 | 0.15 | >100 |
| Example 62 | 0.03 | >100 |
| Example 63 | 0.20 | >100 |
| Example 64 | 0.08 | >100 |
| Example 65 | 0.23 | >100 |
| Example 66 | 0.08 | >100 |
| Example 67 | 0.09 | >100 |
| Example 68 | 0.07 | >100 |
| Example 69 | 0.10 | >100 |
| Example 70 | 0.05 | 73.00 |
| Example 71 | 0.24 | >100 |
| Example 72 | 0.08 | >100 |
| Example 73 | 0.05 | >100 |
| Example 74 | 0.08 | >100 |
| Example 75 | 0.15 | >100 |
| Example 76 | 0.02 | >100 |
| Example 78 | 0.34 | Not Tested |
| Example 79 | 0.16 | Not Tested |
| Example 81 | 0.39 | >100 |
| Example 82 | 0.12 | >100 |
| Example 84 | 0.17 | >100 |
| Example 85 | 0.06 | >100 |
| Example 86 | 0.32 | Not Tested |
| Example 87 | 0.33 | Not Tested |
| Example 89 | 0.12 | >100 |
| Example 90 | 0.07 | >100 |
| Example 91 | 0.11 | >100 |
| Example 92 | 0.07 | >100 |
| Example 93 | 0.10 | >100 |
| Example 94 | 0.06 | >100 |
| Example 95 | 0.12 | >100 |
| Example 96 | 0.07 | >100 |
| Example 97 | 0.16 | >100 |
| Example 98 | 0.07 | >100 |
| Example 99 | 0.10 | >100 |
| Example 100 | 0.06 | >100 |
| Example 101 | 0.21 | >100 |
| Example 102 | 0.09 | >100 |
| Example 103 | 0.24 | >100 |
| Example 104 | 0.09 | >100 |
| Example 105 | 0.21 | >100 |
| Example 106 | 0.08 | >100 |
| Example 107 | 0.13 | >100 |
| Example 108 | 0.08 | >100 |
| Example 109 | 0.16 | >100 |
| Example 110 | 0.05 | >100 |
| Example 111 | 100 | >100 |
| Example 112 | 0.35 | >100 |
| Example 113 | 0.30 | >100 |
| Example 114 | 0.77 | >100 |
| Example 115 | 0.24 | >100 |
| Example 116 | 0.09 | >100 |
| Example 117 | 0.21 | >100 |
| Example 118 | 0.08 | >100 |
| Example 119 | 0.26 | >100 |
| Example 120 | 0.09 | >100 |
| Example 121 | 2.6 | >100 |
| Example 122 | 0.20 | >100 |
| Example 123 | 0.37 | >100 |
| Example 124 | 0.11 | >100 |
| Example 125 | 0.26 | >100 |
| Example 126 | 0.12 | >100 |
| Example 127 | 0.30 | >100 |
| Example 128 | 0.10 | >100 |
| Example 129 | 0.32 | >100 |
| Example 130 | 0.11 | >100 |
| Example 131 | >100 | Not Tested |
| Example 132 | 0.54 | Not Tested |
| Example 133 | >100 | >100 |
| Example 134 | 0.44 | >100 |
| Example 135 | 0.56 | >100 |
| Example 136 | 0.24 | >100 |
| Example 137 | >100 | >100 |
| Example 138 | 0.74 | >100 |
| Example 139 | 0.48 | >100 |
| Example 140 | 0.11 | >100 |
| Example 141 | 1.5 | >100 |
| Example 142 | 0.18 | Not Tested |
| Example 144 | 0.59 | >100 |
| Example 145 | 0.12 | >100 |
| Example 146 | >100 | >100 |
| Example 147 | 0.60 | >100 |
| Example 148 | 1.6 | >100 |
| Example 149 | 0.35 | >100 |
| Example 150 | 0.58 | >100 |
| Example 151 | 0.13 | >100 |
| Example 152 | >100 | >100 |
| Example 153 | 0.45 | 82 |
| Example 154 | >100 | >100 |
| Example 155 | 2.00 | >100 |
| Example 156 | 0.40 | >100 |
| Example 157 | >100 | >100 |
| Example 158 | 0.34 | >100 |
| Example 159 | 0.11 | >100 |
| Example 160 | 0.05 | >100 |
| Example 161 | >100 | >100 |

Evaluation Example 2 Antitumor Test (1)

Mouse: 5- to 6-week-old female BALB/c nude mice (Charles River Laboratories Japan, Inc.) were acclimatized for 4 to 7 days under SPF conditions before use in the experiment. The mice were fed with sterilized solid feed (FR-2, Funabashi Farms Co., Ltd) and given sterilized tap water (prepared by the addition of 5 to 15 ppm sodium hypochlorite solution).

Assay and calculation expression: In all studies, the major axis and minor axis of a tumor were measured twice a week by using an electronic digital caliper (CD-15CX, Mitutoyo Corp.), and the tumor volume (mm³) was calculated. The calculation expression is as shown below.

Tumor volume (mm³)=½×Major axis (mm)×[Minor axis (mm)]²

All of the antibody-drug conjugates and the antibody were diluted with physiological saline (Otsuka Pharmaceutical Factory, Inc.) and used at a volume of 10 mL/kg for intravenous administration to the tail vein of each mouse. Human breast cancer line KPL-4 cells were suspended in physiological saline, and 1.5×10⁷ cells were subcutaneously transplanted to the right side of the body of each female nude mouse (Day 0), and the mice were randomly grouped on Day 15. The antibody-drug conjugate (61), (62), or (76), or the anti-HER2 antibody trastuzumab (Reference Example 1) for a control group was intravenously administered at a dose of 10 mg/kg to the tail vein of each mouse at Days 15 and 22. An untreated group was established as a control group.

The results are shown in FIG. 3. The administration of trastuzumab inhibited tumor growth, whereas the administration of the antibody-drug conjugate (61), (62), or (76) was found to have a stronger tumor growth inhibitory effect. Particularly, the administration of the antibody-drug conjugate (62) or (76) was found to have a significant tumor growth inhibitory effect. In the drawing, the abscissa depicts days after tumor inoculation, and the ordinate depicts tumor volume. In addition, the mice that received trastuzumab or the antibody-drug conjugate (61), (62), or (76) were free from notable signs such as weight loss, suggesting that the antibody-drug conjugate (61), (62), or (76) is highly safe.

Evaluation Example 3 Antitumor Test (2)

Human gastric cancer line NCI-N87 cells purchased from ATCC (American Type Culture Collection) were suspended in physiological saline, and 1×10⁷ cells were subcutaneously transplanted to the right side of the body of each female nude mouse (Day 0), and the mice were randomly grouped on Day 7. The antibody-drug conjugate (77), (143), or (88), or trastuzumab emtansine (Reference Example 2) was intravenously administered at a dose of 10 mg/kg to the tail vein of each mouse on Day 7. An untreated group was established as a control group.

Figure 4:
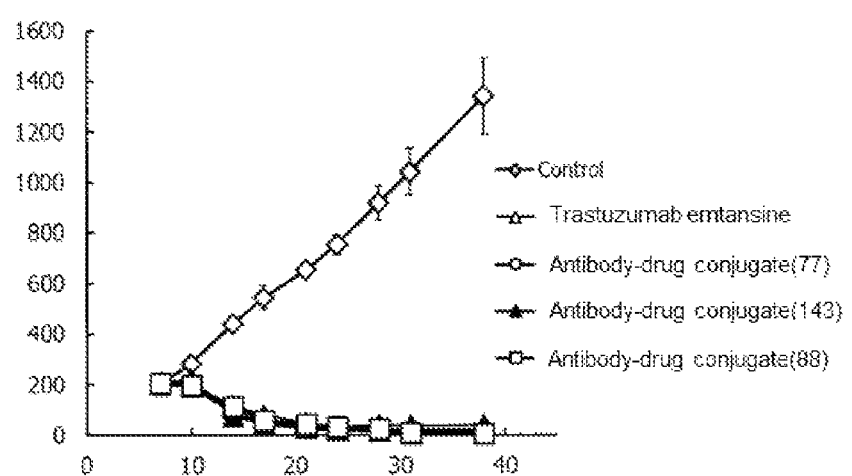
FIG. 4 is a diagram showing the antitumor effect of an antibody-drug conjugate (77), (88), (143), or trastuzumab emtansine on a nude mouse with subcutaneously transplanted human gastric cancer line NCI-N87 cells. In the drawing, the abscissa depicts days after tumor inoculation, and the ordinate depicts tumor volume.

The results are shown in FIG. 4. The antibody-drug conjugates (77), (143), and (88) were confirmed to have a strong antitumor effect with tumor regression equivalent to that of trastuzumab emtansine. In addition, the administration of the antibody-drug conjugate (77), (143), or (88), or trastuzumab emtansine was found to be free from weight loss of the mice.

Evaluation Example 4 Antitumor Test (3)

Human breast cancer line JIMT-1 cells purchased from DSMZ (Deutsche Sammlung von Mikroorganismen und Zellkulturen GmbH) were suspended in physiological saline, and 3×10⁶ cells were subcutaneously transplanted to the right side of the body of each female nude mouse (Day 0), and the mice were randomly grouped on Day 12. The antibody-drug conjugate (77), (88), or (143), trastuzumab, or trastuzumab emtansine was intravenously administered at a dose of 10 mg/kg to the tail vein of each mouse on Days 12 and 19. A physiological saline administration group was established as a control group.

Figure 5:
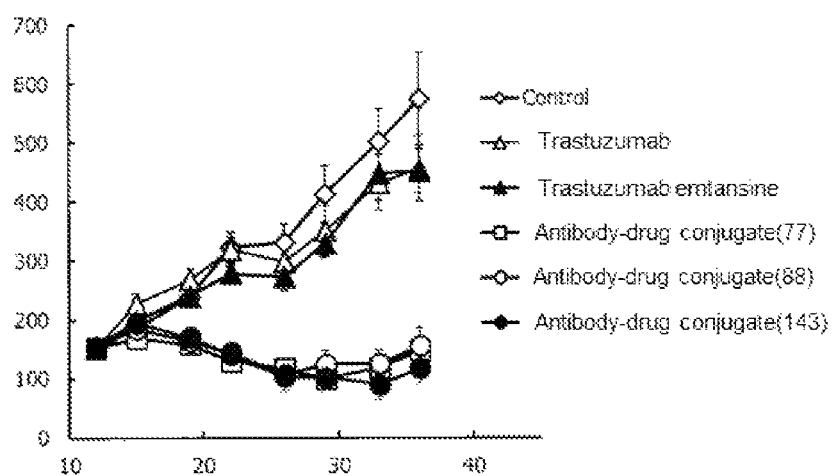
FIG. 5 is a diagram showing the antitumor effect of an antibody-drug conjugate (77), (88), (143), trastuzumab, or trastuzumab emtansine on a nude mouse with subcutaneously transplanted human breast cancer line JIMT-1 cells. In the drawing, the abscissa depicts days after tumor inoculation, and the ordinate depicts tumor volume.

The results are shown in FIG. 5. The administration of trastuzumab or trastuzumab emtansine did not inhibit the growth of the JIMT-1 tumor. On the other hand, the administration of the antibody-drug conjugate (11), (88), or (143) significantly inhibited the growth of the tumor. In addition, the administration of the antibody-drug conjugate (77), (88), or (143), trastuzumab, or trastuzumab emtansine was found to be free from weight loss of the mice.

Free Text of Sequence Listing
SEQ ID NO: 1—Amino acid sequence of a heavy chain of the humanized anti-HER2 monoclonal antibody
SEQ ID NO: 2—Amino acid sequence of a light chain of the humanized anti-HER2 monoclonal antibody

The invention claimed is:

1. An antibody-drug conjugate wherein an antitumor compound represented by the following formula:

[Formula 1]

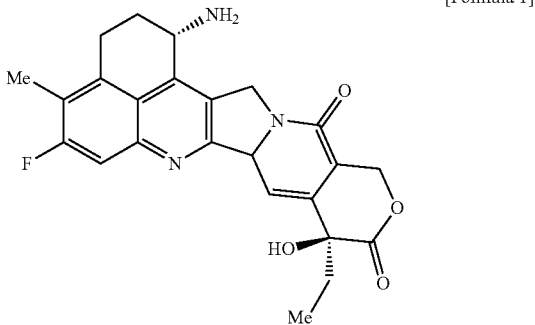

is conjugated to an anti-HER2 antibody via a linker having a structure represented by the following formula:

wherein
the anti-HER2 antibody is connected to the terminal $L^1$, the antitumor compound is connected to the terminal $L^c$ or $L^P$ with the nitrogen atom of the amino group at position 1 as the connecting position,
wherein
$n^1$ represents an integer of 0 to 6,
$L^1$ represents -(Succinimid-3-yl-N)—$(CH_2)n^2$-C(=O)—, wherein $n^2$ represents an integer of 2 to 8,
$L^2$ represents —NH—$(CH_2CH_2$—$O)n^6$-$CH_2CH_2$—C(=O)— or a single bond,
wherein $n^6$ represents an integer of 0 to 6,
$L^P$ represents a peptide residue consisting of DGGFG (SEQ ID NO: 10), DGGF (SEQ ID NO: 9), KGGFG (SEQ ID NO: 15), EGGFG (SEQ ID NO: 16), DDGGFG (SEQ ID NO: 13), KDGGFG (SEQ ID NO: 14), SGGFG (SEQ ID NO: 17), D$^d$GGFG, DGGFS (SEQ ID NO: 12), GGFGS (SEQ ID NO: 5), GGFGGE (SEQ ID NO: 7), or DG$^{Me}$GFG (SEQ ID NO: 11), wherein superscript of d indicates that the amino acid is in a D-form, and superscript of Me indicates that the amino acid is N-methylated at its α-amino group,
-(Succinimid-3-yl-N)— has a structure represented by the following formula:

[Formula 2]

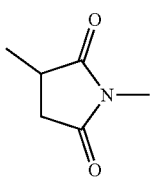

which is connected to the antibody at position 3 thereof and is connected to the methylene group in the linker structure containing this structure on the nitrogen atom at position 1.

2. The antibody-drug conjugate according to claim 1, wherein $L^P$ is DGGFG (SEQ ID NO: 10), D$^d$GGFG, or DG$^{Me}$GFG (SEQ ID NO: 11).

3. The antibody-drug conjugate according to claim 1, wherein the average number of units of the antitumor compound conjugated per antibody molecule is in the range of from 1 to 8.

4. The antibody-drug conjugate according to claim 1, wherein the average number of units of the antitumor compound conjugated per antibody molecule is in the range of from 3 to 8.

5. A drug containing the antibody-drug conjugate according to claim 1, a salt thereof, or a hydrate thereof.

6. An antitumor drug and/or anticancer drug containing the antibody-drug conjugate according to claim 1, a salt thereof, or a hydrate thereof.

7. A pharmaceutical composition containing the antibody-drug conjugate according to claim 1, a salt thereof, or a hydrate thereof as an active component, and a pharmaceutically acceptable formulation component.

8. The antibody-drug conjugate according to claim 1, wherein the drug-linker structure moiety, in which a drug is connected to -$L^1$-$L^2$-$L^P$-, is one drug-linker structure selected from the following group:

-(Succinimid-3-yl-N)—$CH_2CH_2CH_2CH_2CH_2$—C(=O)-DGGFG (SEQ ID NO: 10)-(NH-DX), -(Succinimid-3-yl-N)—$CH_2CH_2CH_2CH_2CH_2$—C(=O)—KGGFG (SEQ ID NO: 15)-(NH-DX), -(Succinimid-3-yl-N)—$CH_2CH_2$—C(=O)-DGGFG (SEQ ID NO: 10)-(NH-DX), -(Succinimid-3-yl-N)—$CH_2CH_2CH_2$—C(=O)-DGGFG (SEQ ID NO: 10)-(NH-DX), -(Succinimid-3-yl-N)—$CH_2CH_2$—C(=O)—NH—$CH_2CH_2$—O—$CH_2CH_2$—O—$CH_2CH_2$—C(=O)-DGGFG (SEQ ID NO: 10)-(NH-DX), -(Succinimid-3-yl-N)—$CH_2CH_2$—C(=O)—NH—$CH_2CH_2$—O—$CH_2CH_2$—O—$CH_2CH_2$—O—$CH_2CH_2$—O—$CH_2CH_2$—C(=O)-DGGFG (SEQ ID NO: 10)-(NH-DX), -(Succinimid-3-yl-N)—$CH_2CH_2CH_2CH_2CH_2$—C(=O)—SGGFG (SEQ ID NO: 17)-(NH-DX), -(Succinimid-3-yl-N)—$CH_2CH_2CH_2CH_2CH_2$—C(=O)-D$^d$GGFG-(NH-DX), -(Succinimid-3-yl-N)—$CH_2CH_2CH_2CH_2CH_2$—C(=O)-EGGFG (SEQ ID NO: 16)-(NH-DX), -(Succinimid-3-yl-N)—$CH_2CH_2CH_2CH_2CH_2$—C(=O)-DGGFS (SEQ ID NO: 12)-(NH-DX), -(Succinimid-3-yl-N)—$CH_2CH_2CH_2CH_2CH_2$—C(=O)-GGFGS (SEQ ID NO: 5)-(NH-DX), -(Succinimid-3-yl-N)—$CH_2CH_2$—C(=O)-GGFGGE (SEQ ID NO: 7)-(NH-DX), -(Succinimid-3-yl-N)—$CH_2CH_2CH_2CH_2CH_2$—C(=O)-GGFGGE (SEQ ID NO: 7)-(NH-DX), or -(Succinimid-3-yl-N)—$CH_2CH_2CH_2CH_2CH_2$—C(=O)-DG$^{Me}$GFG (SEQ ID NO: 11)-(NH-DX), wherein (NH-DX) is a group represented by the following formula:

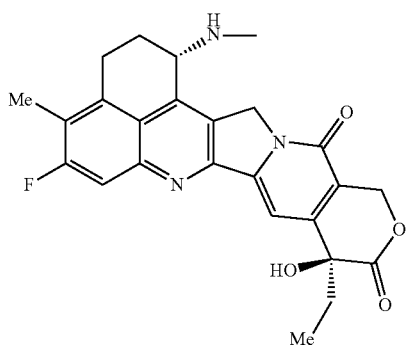 [SMILES: CC[C@@]1(O)C(=O)OCc2c1cc1n(c2=O)Cc2c-1nc1cc(F)c(C)c3c1c2[C@@H](NC)CC3]

wherein the nitrogen atom of the amino group at position 1 is the connecting position.

9. The antibody-drug conjugate according to claim 1, wherein the drug-linker structure moiety, in which a drug is connected to $L^1$-$L^2$-$L^P$- is -(Succinimid-3-yl-N)—$CH_2CH_2CH_2CH_2CH_2$—C(=O)-DGGFG(SEQ ID NO: 10)-(NH-DX)

wherein (NH-DX) is a group represented by the following formula:

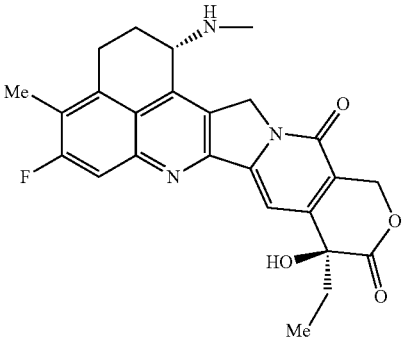 [SMILES: CC[C@@]1(O)C(=O)OCc2c1cc1n(c2=O)Cc2c-1nc1cc(F)c(C)c3c1c2[C@@H](NC)CC3]

wherein the nitrogen atom of the amino group at position 1 is the connecting position.

10. A method for treating a HER2 expressing tumor and/or cancer comprising administering the antibody-drug conjugate according to claim 1, a salt thereof, or a hydrate thereof.

11. The treatment method according to claim 10 which is for use against lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, endometrial cancer, uterine cancer, salivary gland cancer, kidney cancer, vulval cancer, penis cancer, leukemia, malignant lymphoma, plasmacytoma, myeloma, or sarcoma.

* * * * *

SEQUENCE LISTING

```
<160> NUMBER OF SEQ ID NOS: 21

<210> SEQ ID NO 1
<211> LENGTH: 450
<212> TYPE: PRT
<213> ORGANISM: Artificial Sequence
<220> FEATURE:
<223> OTHER INFORMATION: Description of Artificial Sequence: Synthetic
      amino acid sequence of the heavy chain of humanized
      anti-HER2 monoclonal antibody

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

```
                    85                  90                  95
Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      amino acid sequence of the light chain of humanized
``` anti-HER2 monoclonal antibody

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Phe Gly
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Phe Gly Gly
1               5

<210> SEQ ID NO 5
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 5

Gly Gly Phe Gly Ser
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Phe Gly Gly Gly
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Phe Gly Gly Glu
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Phe Gly Gly Gly Phe Gly
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Gly Gly Phe
1

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Gly Gly Phe Gly
1               5
```

```
<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methyl-Gly

<400> SEQUENCE: 11

Asp Gly Gly Phe Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Gly Gly Phe Ser
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Asp Gly Gly Phe Gly
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Asp Gly Gly Phe Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Gly Gly Phe Gly
1               5

<210> SEQ ID NO 16
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 16

Glu Gly Gly Phe Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Gly Gly Phe Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Asp Gly Gly Phe
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Asp Gly Gly Phe Gly
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Asp Gly Gly Phe Gly
1               5

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Phe
1
```